United States Patent
Bacani et al.

(10) Patent No.: US 9,745,328 B2
(45) Date of Patent: *Aug. 29, 2017

(54) FLAP MODULATORS

(71) Applicant: JANSSEN PHARMACEUTICA NV, Beerse (BE)

(72) Inventors: Genesis M. Bacani, San Diego, CA (US); Wendy Eccles, San Diego, CA (US); Anne E. Fitzgerald, San Diego, CA (US); Steven D. Goldberg, Encinitas, CA (US); Michael D. Hack, San Diego, CA (US); Natalie A. Hawryluk, San Diego, CA (US); William M. Jones, San Diego, CA (US); John M. Keith, San Diego, CA (US); Paul Krawczuk, San Diego, CA (US); Alec D. Lebsack, Ladera Ranch, CA (US); Alice Lee-Dutra, San Diego, CA (US); Jing Liu, San Diego, CA (US); Kelly J. McClure, Ramona, CA (US); Steven P. Meduna, San Diego, CA (US); Daniel J. Pippel, San Diego, CA (US); Mark D. Rosen, San Diego, CA (US); Zachary S. Sales, Escondido, CA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

This patent is subject to a terminal disclaimer.

(21) Appl. No.: 14/765,556

(22) PCT Filed: Jan. 31, 2014

(86) PCT No.: PCT/US2014/014111
§ 371 (c)(1),
(2) Date: Aug. 3, 2015

(87) PCT Pub. No.: WO2014/121055
PCT Pub. Date: Aug. 7, 2014

(65) Prior Publication Data
US 2015/0376212 A1    Dec. 31, 2015

Related U.S. Application Data

(60) Provisional application No. 61/760,627, filed on Feb. 4, 2013, provisional application No. 61/800,353, filed on Mar. 15, 2013.

(51) Int. Cl.
*C07F 7/08* (2006.01)
*C07D 491/107* (2006.01)
(Continued)

(52) U.S. Cl.
CPC .......... *C07F 7/0812* (2013.01); *C07D 209/08* (2013.01); *C07D 213/73* (2013.01);
(Continued)

(58) Field of Classification Search
CPC .......... C07F 7/0812; C07F 5/025; C07F 7/08; C07D 491/107; C07D 405/12; C07D 403/14; C07D 491/08; C07D 495/10; C07D 401/04; C07D 498/04; C07D 413/10; C07D 409/12; C07D 491/10; C07D 263/48; C07D 235/10; C07D 277/62; C07D 405/14; C07D 213/73; C07D 285/12; C07D 403/10;
(Continued)

(56) References Cited

U.S. PATENT DOCUMENTS

| 5,780,473 A | 7/1998 | Murugesan et al. |
| 6,040,327 A | 3/2000 | De Nanteuil et al. |

(Continued)

FOREIGN PATENT DOCUMENTS

| CA | 2137443 A1 | 6/1995 |
| CN | 105-2306 A | 6/1991 |

(Continued)

OTHER PUBLICATIONS

RN 1269234-42-5, [Database Registry Chemical Abstracts Service, Columbus, Ohio, Accession No. RN 1269234-42-5, Entered STN: Mar. 21, 2011]; p. 1.*

(Continued)

*Primary Examiner* — Samantha Shterengarts
*Assistant Examiner* — Matt Mauro

(57) ABSTRACT

The present invention relates to compounds of Formula (I), or a form thereof wherein ring $A_1$, $R_1$, $R_2$, $R_3$, $R_3'$, L, W, and V are as defined herein, useful as FLAP modulators. The invention also relates to pharmaceutical compositions comprising compounds of Formula (I). Methods of making and using the compounds of Formula (I) are also within the scope of the invention.

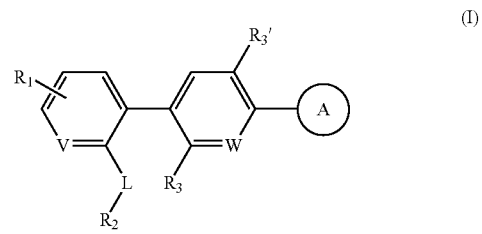

(I)

16 Claims, No Drawings

(51) Int. Cl.

| | | |
|---|---|---|
| C07D 491/08 | (2006.01) | |
| C07D 405/12 | (2006.01) | |
| C07D 403/14 | (2006.01) | |
| A61K 31/422 | (2006.01) | |
| A61K 31/55 | (2006.01) | |
| A61K 31/506 | (2006.01) | |
| C07D 403/10 | (2006.01) | |
| C07D 237/20 | (2006.01) | |
| C07D 409/12 | (2006.01) | |
| C07D 413/10 | (2006.01) | |
| C07D 241/20 | (2006.01) | |
| C07D 241/26 | (2006.01) | |
| C07D 401/12 | (2006.01) | |
| C07D 401/14 | (2006.01) | |
| C07D 403/12 | (2006.01) | |
| C07D 413/12 | (2006.01) | |
| C07D 487/04 | (2006.01) | |
| C07D 405/14 | (2006.01) | |
| C07D 413/14 | (2006.01) | |
| C07D 213/73 | (2006.01) | |
| C07D 401/04 | (2006.01) | |
| C07D 235/10 | (2006.01) | |
| C07D 401/10 | (2006.01) | |
| C07D 417/10 | (2006.01) | |
| C07D 471/04 | (2006.01) | |
| C07D 487/08 | (2006.01) | |
| C07D 263/48 | (2006.01) | |
| C07D 491/10 | (2006.01) | |
| C07D 498/04 | (2006.01) | |
| C07D 209/08 | (2006.01) | |
| C07D 277/62 | (2006.01) | |
| C07D 285/12 | (2006.01) | |
| C07F 5/02 | (2006.01) | |
| C07D 495/10 | (2006.01) | |

(52) U.S. Cl.
CPC ......... *C07D 235/10* (2013.01); *C07D 237/20* (2013.01); *C07D 241/20* (2013.01); *C07D 241/26* (2013.01); *C07D 263/48* (2013.01); *C07D 277/62* (2013.01); *C07D 285/12* (2013.01); *C07D 401/04* (2013.01); *C07D 401/10* (2013.01); *C07D 401/12* (2013.01); *C07D 401/14* (2013.01); *C07D 403/10* (2013.01); *C07D 403/12* (2013.01); *C07D 403/14* (2013.01); *C07D 405/12* (2013.01); *C07D 405/14* (2013.01); *C07D 409/12* (2013.01); *C07D 413/10* (2013.01); *C07D 413/12* (2013.01); *C07D 413/14* (2013.01); *C07D 417/10* (2013.01); *C07D 471/04* (2013.01); *C07D 487/04* (2013.01); *C07D 487/08* (2013.01); *C07D 491/08* (2013.01); *C07D 491/10* (2013.01); *C07D 491/107* (2013.01); *C07D 495/10* (2013.01); *C07D 498/04* (2013.01); *C07F 5/025* (2013.01); *C07F 7/08* (2013.01)

(58) Field of Classification Search
CPC .. C07D 413/14; C07D 471/04; C07D 209/08; C07D 487/08; C07D 237/20; C07D 401/10; C07D 417/10; C07D 401/12; C07D 241/26; C07D 401/14; C07D 241/20; C07D 487/04; C07D 413/12; C07D 403/12
See application file for complete search history.

(56) References Cited

U.S. PATENT DOCUMENTS

| | | |
|---|---|---|
| 7,314,849 B2 | 1/2008 | Balko et al. |
| 8,188,092 B2 | 5/2012 | Birch et al. |
| 8,586,754 B2 | 11/2013 | Bruncko et al. |
| 9,073,876 B2 | 7/2015 | Eccles et al. |
| 9,079,866 B2 | 7/2015 | Bacani et al. |
| 2005/0009894 A1 | 1/2005 | Babin et al. |
| 2007/0232620 A1 | 10/2007 | Dorsch et al. |
| 2007/0299074 A1 | 12/2007 | Netz et al. |
| 2009/0253735 A1 | 10/2009 | Almario-Garcia et al. |
| 2013/0267493 A1* | 10/2013 | Bhattacharya ....... C07D 405/14 514/210.18 |

FOREIGN PATENT DOCUMENTS

| | | |
|---|---|---|
| CN | 1013-56169 A | 1/2009 |
| EP | 0372934 A | 6/1990 |
| EP | 0562599 A1 | 9/1993 |
| EP | 0657459 A1 | 6/1995 |
| EP | 0894795 A1 | 2/1999 |
| EP | 1308441 A1 | 5/2003 |
| EP | 1354877 A1 | 10/2003 |
| EP | 1359139 A1 | 11/2003 |
| EP | 1389616 A1 | 2/2004 |
| EP | 247-1776 A1 | 7/2012 |
| EP | 2471776 A | 7/2012 |
| JP | 2009-023986 A | 2/2009 |
| WO | WO00/47578 A1 | 8/2000 |
| WO | WO01/74793 A2 | 10/2001 |
| WO | WO02/11724 A2 | 2/2002 |
| WO | WO02/22602 A2 | 3/2002 |
| WO | WO03/007955 A2 | 1/2003 |
| WO | WO03/035644 A1 | 5/2003 |
| WO | WO03/093248 A1 | 11/2003 |
| WO | WO2004/009017 A2 | 1/2004 |
| WO | WO2005/067923 A1 | 7/2005 |
| WO | WO2005/082871 A2 | 9/2005 |
| WO | WO2005/103022 A1 | 11/2005 |
| WO | WO2005/105744 A1 | 11/2005 |
| WO | WO2005/123688 A2 | 12/2005 |
| WO | WO2006/020767 A2 | 2/2006 |
| WO | WO 2006/038100 A1 | 4/2006 |
| WO | WO2006/063167 A1 | 6/2006 |
| WO | WO2006/074262 A1 | 7/2006 |
| WO | WO2006/132811 A2 | 12/2006 |
| WO | WO2007/034282 A2 | 3/2007 |
| WO | WO 2007/082076 A | 7/2007 |
| WO | WO 2007/082098 A | 7/2007 |
| WO | WO2007/126957 A2 | 11/2007 |
| WO | WO2008/018655 A1 | 2/2008 |
| WO | WO2008/034974 A1 | 3/2008 |
| WO | WO2008/104278 A1 | 9/2008 |
| WO | WO2008/150899 A1 | 12/2008 |
| WO | WO2008/152014 A2 | 12/2008 |
| WO | WO2009/100438 A2 | 8/2009 |
| WO | WO2009/121535 A2 | 10/2009 |
| WO | WO2009/129625 A1 | 10/2009 |
| WO | WO2010/012747 A1 | 2/2010 |
| WO | WO2010/019828 A1 | 2/2010 |
| WO | WO2010/115736 A2 | 10/2010 |
| WO | WO2011/047129 A1 | 4/2011 |
| WO | WO2011/053705 A1 | 5/2011 |
| WO | WO2011/072275 A2 | 6/2011 |
| WO | WO2011/106273 A1 | 9/2011 |
| WO | WO2012/006068 A2 | 1/2012 |
| WO | WO2012/064715 A1 | 5/2012 |
| WO | WO2012/116145 A1 | 8/2012 |
| WO | WO2012/119978 A1 | 9/2012 |
| WO | WO 2012/121939 A2 | 9/2012 |

OTHER PUBLICATIONS

Registry Database Chemical Abstracts Service, Columbus Ohio, Registry Nos. 1309199-07-2 (Entered STN: Jun. 13, 2011), 1269234-42-5 (Entered STN: Mar. 21, 2011), RN 1269159-98-9

(56) References Cited

OTHER PUBLICATIONS (Entered STN: Mar. 21, 2011), 1125448-01-2 (Entered STN: Mar. 23, 2009), and RN 1125444-06-5 (Entered STN: Mar. 23, 2009).*
International Search Report dated May 23, 2014, for corresponding international application PCT/US2014/014088.
Abramovitz et al, "5-lipoxygenase-activating protein stimulates the utilization of arachidonic acid by 5-lipoxygenase," *Eur. J. Biochem.*, 1993, 215:105-111.
Avis et al, editors, *Pharmaceutical Dosage Forms: Parenteral Medications*, 2$^{nd}$ Edition, vol. 1, published by Marcel Dekker, Inc., 1992, Table of Contents and Index.
Avis et al, editors, *Pharmaceutical Dosage Forms: Parenteral Medications*, vol. 2, published by Marcel Dekker, Inc., 1993, Table of Contents and Index.
Baldwin et al, "Kinase array design, back to front: Biaryl amides", *Bioorganic & Medicinal Chemistry Letters* (2008) 18(19):5285-5289.
Berge et al, "Pharmaceutical Salts," *Journal of Pharmaceutical Sciences*, 1997, 66(1):1-19.
Bundgaard, editor, *Design of Prodrugs*, published by Elsevier, 1985, Table of Contents.
Chi et al, "Interaction between ALOX5AP and CYP3A5 gene variants significantly increases the risk for cerebral infarctions in Chinese," *NeuroReport.*, 2014, 25(7):452-457.
Chu et al, "Involvement of 5-lipoxygenase activating protein in the amyloidotic phenotype of an Alzheimer's disease mouse model," *Journal of Neuroinflammation*, 2012, 9:127.
Chwieśko-Minarowska et al, "The role of leukotrienes in the pathogenesis of systemic sclerosis," *Folia Histochemica et Cytobiologica*, 2012, 50(2), 180-85.
Gould, "Salt selection for basic drugs," *International Journal of Pharmaceutics*, 1986, 33:201-217.
Greene et al, editors, *Protective Groups in Organic Synthesis*, 3$^{rd}$ Edition, published by John Wiley & Sons, 1999, Index.
Griffiths et al, "Collagen-induced Arthritis Is Reduced in 5-Lipoxygenase-activating Protein-deficient Mice," *J. Exp. Med.*, 1997, 185(6):1123-29.
Haeggström et al, "Lipoxygenase and Leukotriene Pathways: Biochemistry, Biology, and Roles in Disease," *Chemical Reviews*, 2011, 111(10):5866-98.
Helgadottir et al, "The gene encoding 5-lipoxygenase activating protein confers risk of myocardial infarction, atherosclerosis and stroke," *Nature Genetics*, Mar. 2004, 36(3):233-39.
Holloway et al, "The role of LTA4H and ALOX5AP polymorphism in asthma and allergy susceptibility," *Allergy*, 2008, 63(8):1046-53.
Ji et al, "Genetic Variants in the Promoter Region of the ALOX5AP Gene and Susceptibility of Ischemic Stroke," *Cerebrovascular Diseases*, 2011, 32(3), 261-68.
Krawiec et al, "Leukotriene inhibitors and non-steroidal therapies in the treatment of asthma," *Expert Opinion on Pharmacotherapy*, 2001, 2(1), 47-65.
Lieberman et al, editors, *Pharmaceutical Dosage Forms: Tablets*, Second Edition, vol. 1, published by Marcel Dekker, Inc., 1989, Table of Contents and Index.
Lieberman et al, editors, *Pharmaceutical Dosage Forms: Tablets*, Second Edition, vol. 2, published by Marcel Dekker, Inc., 1990, Table of Contents and Index.
Lieberman et al, editors, *Pharmaceutical Dosage Forms: Tablets*, Second Edition, vol. 3, published by Marcel Dekker, Inc., 1990, Table of Contents and Index.
Lieberman et al, editors, *Pharmaceutical Dosage Forms: Disperse Systems*, vol. 1, published by Marcel Dekker, Inc., 1996, Table of Contents and Index.
Lieberman et al, editors, *Pharmaceutical Dosage Forms: Disperse Systems*, vol. 2, published by Marcel Dekker, Inc., 1996, Table of Contents and Index.
Loell et al, "Activated LTB4 pathway in muscle tissue of patients with polymyositis or dermatomyositis," *Ann. Rheum. Dis.*, 2013, 72(2):293-99.

McComie, editor, *Protective Groups in Organic Chemistry*, published Plenum Press, 1973, Index and Table of Contents.
McMillan et al, "Designing therapeutically Effective 5-lipoxygenase Inhibitors", *Trends in Pharmacological Sciences*, 1992, 13:323-330.
Nair et al, "Expression Analysis of Leukotriene-Inflammatory Gene Interaction Network in Patients with Coronary Artery Disease," *Journal of Atherosclerosis and Thrombosis*, 2013, 20:000-000.
Queener, "Inhibition of Pneumocystis Dihydrofolate Reductase by Analogs of Pyrimethamine, Methotrexate and Trimetrexate", *Journal of Protozoology*, 1991, 38(6):1545-1575.
Reicin et al, "Montelukast, a Leukotriene Receptor Antagonist, in Combination with Loratadine, a Histamine Receptor Antagonist, in the Treatment of Chronic Asthma," *Arch. Intern. Med.*, 2000, 160(16):2418-88.
Rosnowska et al, "Leukotrienes C4 and B4 in cerebrospinal fluid of patients with multiple sclerosis," *Polski Merkuriusz Lekarski*, 1997, 2:254-55. (English Abstract).
Rowe et al, editors, *The Handbook of Pharmaceutical Excipients*, 5$^{th}$ Edition, published by the American Pharmaceutical Association and the Pharmaceutical Society of Great Britain, 2006, Table of Contents and Index.
Samuelsson, "Leukotrienes: Mediators of Immediate Hypersensitivity Reactions and Inflammation," *Science*, 1983, 220:568-75).
Sanada et al, "The effectiveness of montelukast for the treatment of anti-histamine-resistant chronic urticaria," *Arch. Dermatol. Res.*, 2005, 297(3):134-138.
Strid et al, "Distinct parts of leukotriene C(4) synthase interact with 5-lipoxygenase and 5-lipoxygenase activating protein," *Biochemical and Biophysical Research Communications*, 2009, 381(4):518-22.
Tulah et al, "The role of ALOX5AP, LTA4H and LTB4R polymorphisms in determining baseline lung function and COPD susceptibility in UK smokers," *BMC Medical Genetucs*, 2011, 29(12), 173.
Wang et al, "Eicosanoids and cancer," *Nature Reviews—Cancer*, 2010, 10(3), 181-93.
Yu et al, "Disruption of the 5-lipoxygenase pathway attenuates atherogenesis consequent to COX-2 deletion in mice," *Proc. Natl. Acad. Sci. (PNAS)*, 2012, 109(17):6727-32.
Yu et al, "Myeloid Cell 5-Lipoxygenase Activating Protein Modulates the Response to Vascular Injury," *Circulation Research*, 2013, 112:432-440.
International Search Report Dated Jul. 8, 2014, for Corresponding International Application PCT/US2014/014111.
International Search Report Dated Aug. 19, 2014, for Corresponding International Application PCT/US2014/014111.
U.S. Appl. No. 14/719,476, filed May 22, 2015, Eccles et al.
U.S. Appl. No. 14/765,552, filed Aug. 3, 2015, Eccles et al.
U.S. Appl. No. 14/728,128, filed Jun. 2, 2015, Bacani et al.
Abet at al "A New Class of Pyrazolopyridine Nucleus With Fluorescent Properties Obtained Through Either a Radical or a PD Arylation Pathway From N-Azinylpiridinium N- Aminides" The Journal of Organic Chemistry 2008 vol. 73(22) pp. 8800-8807.
Registry Database Chemical Abstracts Service, Columbus Ohio, Registry Nos. 1309199-07-2 (Entered STN: Jun. 13, 2011 ),1269234-42-5 (Entered STN: Mar. 21, 2011 ), RN 1269159-98-9 (Entered STN: Mar. 21, 2011 ), 1125448-01-2 (Entered STN:Mar. 23, 2009), and RN 1125444-06-5 (Entered STN: Mar. 23, 2009).
RN 1269234-42-5, [Database Registry Chemical Abstracts Service, Columbus, Ohio, Accession No. RN 1269234-42-5, Entered STN:Mar. 21, 2011];p. 1 .
Extended European Search Report for European Application No. EP16164934 8 dated Aug. 8, 2016.
Search Report for Chinese Application No. CN201480019599.1 dated Jul. 15, 2016.
U.S. Final Office Action for U.S. Appl. No. 14/765,552, dated Dec. 20, 2016.

* cited by examiner

FLAP MODULATORS

CROSS REFERENCE TO RELATED APPLICATIONS

This application is a national phase of International Application No. PCT/US2014/014111 filed on Jan. 31, 2014, which claims the benefit of U.S. Provisional Application No. 61/760,627 filed on Feb. 4, 2013 and U.S. Provisional Application No. 61/800,353 filed on Mar. 15, 2013, each of which is incorporated herein by reference in its entirety.

FIELD OF THE INVENTION

The present invention relates to substituted compounds useful as 5-lipoxygenase-activating protein (FLAP) modulators, pharmaceutical compositions of such compounds, methods of preparation and use thereof. More particularly, FLAP modulators are useful for preventing, treating or ameliorating FLAP-mediated diseases and/or disorders, including those inflammation diseases and/or disorders associated with dermatological and respiratory disorders, allergic disorders, autoimmunity, cancer, cardiovascular and metabolic disorders.

BACKGROUND OF THE INVENTION

FLAP is a key initiator of the leukotriene synthesis pathway that binds and then transfers arachidonic acid to 5-lipoxygenase (M. Abramovitz et al., "5-lipoxygenase-activating protein stimulates the utilization of arachidonic acid by 5-lipoxygenase," *Eur. J. Biochem.*, 1993, 215, 105-11). FLAP has been demonstrated to interact with $LTC_4$ synthase, and could putatively modulate the production of $LTC_4$ (T. Strid et al., "Distinct parts of leukotriene C(4) synthase interact with 5-lipoxygenase and 5-lipoxygenase activating protein," *Biochem. Biophys. Res. Comm.*, 2009, 381(4), 518-22). Modulation (including without limitation inhibition) or genetic deletion of FLAP blocks leukotriene production, specifically $LTB_4$, the cysteinyl leukotrienes ($LTC_4$, $LTD_4$ and $LTE_4$) as well as 5-oxo-ETE (J. Z. Haeggström et al., "Lipoxygenase and leukotriene pathways: biochemistry, biology, and roles in disease," *Chem Rev.*, 2011, 111(10), 5866-98).

Leukotrienes are immune-modulating lipids formed from arachidonic acid (reviewed in Samuelsson, "Leukotrienes: mediators of immediate hypersensitivity reactions and inflammation," *Science*, 1983, 220, 568-75). They are synthesized primarily by eosinophils, neutrophils, mast cells, basophils, dendritic cells, macrophages and monocytes. Leukotrienes mediate multiple biological effects including, by way of example only, smooth muscle contraction, leukocyte recruitment and activation, cytokine secretion, fibrosis, mucous secretion, and vascular function (J. Z. Haeggström, at 5866-98).

FLAP-deficient mice are healthy and reproduce normally. They do not produce leukotrienes and have decreased susceptibility in mouse models of arthritis (R. J. Griffiths et al., "Collagen-induced arthritis is reduced in 5-lipoxygenase-activating protein-deficient mice," *J. Exp. Med.*, 1997, 185, 1123-29). In humans, FLAP itself has been linked by genetic studies to respiratory disorders and cardiovascular disease, including myocardial infarction, atherosclerosis, cerebral infarctions, coronary artery disease and stroke (A. Helgadottir et al., "The gene encoding 5-lipoxygenase activating protein confers risk of myocardial infarction, atherosclerosis and stroke," *Nat. Genet.*, 2004, 36, 233-39; A. S. Tulah et al., "The role of ALOX5AP, LTA4H and LTB4R polymorphisms in determining baseline lung function and COPD susceptibility in UK smokers," *BMC Med. Genet.*, 2011, 29(12), 173; R. Ji et al., "Genetic variants in the promoter region of the ALOX5AP gene and susceptibility of ischemic stroke," *Cerebrovasc. Dis.*, 2011, 32(3), 261-68; J. W. Holloway et al., "The role of LTA4H and ALOX5AP polymorphism in asthma and allergy susceptibility," *Allergy.* 2008, 63(8), 1046-53; J. Nair et al., "Expression analysis of leukotriene-inflammatory gene interaction network in patients with coronary artery disease," *J Atheroscler. Thromb.*, 2013; L. F. Chi et al., "Interaction between ALOX5AP and CYP3A5 gene variants significantly increases the risk for cerebral infarctions in Chinese," *Neuroreport.*, 2013). In addition, studies using animal models support a causative role for leukotrienes in aortic aneurisms, atherosclerosis, pulmonary arterial hypertension, myocardial infarction, atherosclerosis, and stroke (reviewed in J. Z. Haeggström, at 5866-98).

Leukotrienes also play a role in autoimmune disorders such as rheumatoid arthritis, inflammatory bowel disease, nephritis, spondyloarthritis, polymyositis, dermatomyositis, gouty effusions, systemic lupus erythematosus, systemic sclerosis, Alzheimer's disease and multiple sclerosis (S. Chwieśko-Minarowska et al., "The role of leukotrienes in the pathogenesis of systemic sclerosis," *Folia Histochem. Cytobiol.*, 2012, 50(2), 180-85; M. Rosnowska et al., "Leukotrienes C4 and B4 in cerebrospinal fluid of patients with multiple sclerosis," *Pol. Merkuriusz Lek.*, 1997, 2, 254-55; and reviewed in J. Z. Haeggström, at 5866-98; I. Loell et al., "Activated LTB4 pathway in muscle tissue of patients with polymyositis or dermatomyositis," *Ann. Rheum. Dis.*, 2013, 72(2), 293-99; J. Chu et al., "Involvement of 5-lipoxygenase activating protein in the amyloidotic phenotype of an Alzheimer's disease mouse model," *J. Neuroinflammation*, 2012, 9, 127). Leukotrienes have also been implicated in several aspects of carcinogenesis including tumor cell proliferation, differentiation, and apoptosis, tumor-associated angiogenesis, as well as the migration and invasion of carcinoma cells (D. Wang and R. N. Dubois, "Eicosanoids and cancer," *Nat. Rev. Cancer,* 2010, 10(3), 181-93).

Leukotrienes play a key role in allergic disorders such as allergic rhinitis, allergic dermatitis and asthma, as well as respiratory disorders such as exacerbations, non-allergic asthma, aspirin exacerbated respiratory disease, fibrotic lung diseases, acute respiratory distress syndrome and chronic obstructive pulmonary disease (reviewed in J. Z. Haeggström at 5866-98). Approved antagonists of the $LTC_4$ receptor and leukotriene synthesis modulators such as zileuton have shown clinical efficacy in a variety of respiratory disorders (reviewed in M. E. Krawiec and S. E. Wenzel, "Leukotriene modulators and non-steroidal therapies in the treatment of asthma," *Expert. Opin. Pharmacotherapy,* 2001, 2(1), 47-65).

All the above evidence supports a key role of leukotrienes in a variety of human diseases and/or disorders, and FLAP modulation would be effective for the prevention, treatment, or amelioration of these immune-mediated inflammatory diseases and/or disorders. Furthermore, there still remains a need for FLAP modulator compounds that have pharmacokinetic and pharmacodynamic properties suitable for use as human pharmaceuticals.

SUMMARY OF THE INVENTION

In its many embodiments, the present invention provides novel compounds useful as, for example, FLAP modulators (including without limitation novel compounds that inhibit FLAP), methods of preparing such compounds, pharmaceutical compositions comprising one or more such compounds, methods of preparing pharmaceutical compositions comprising one or more such compounds, and methods of prophylaxis, treatment, amelioration, including without limitation inhibition, of one or more diseases and/or disorders associated with FLAP using such compounds or pharmaceutical compositions.

One aspect of the present invention is directed to compounds, methods, and compositions for the treatment or prophylaxis or amelioration of a variety of diseases and/or disorders that are mediated or sustained through the activity of leukotrienes, including pulmonary, allergic, fibrotic, neurological, inflammatory, autoimmune and cardiovascular diseases and cancer or associated symptoms or complications thereof. More specifically, this invention is directed to a method of treating exacerbations, non-allergic asthma, fibrotic lung diseases, acute respiratory distress syndrome and chronic obstructive pulmonary disease, or associated symptoms or complications thereof, in a subject afflicted with such a disease and/or disorder, wherein the method comprises administering a FLAP modulator.

Another aspect of the present invention is directed to compounds, methods, and compositions for the treatment or prophylaxis or amelioration of cardiac and cardiovascular diseases and/or disorders, or associated symptoms or complications thereof, that include but are not limited to myocardial infarction, atherosclerosis and stroke aortic aneurisms, atherosclerosis, or associated symptoms or complications thereof, in a subject afflicted with such a disease and/or disorder, wherein the method comprises administering a FLAP modulator.

Yet another aspect of the present invention is directed to compounds, methods, and compositions for the prophylaxis, treatment, or amelioration of autoimmune diseases and/or disorders, or associated symptoms or complications thereof, that include but are not limited to rheumatoid arthritis, inflammatory bowel disease, nephritis, spondyloarthritis, polymyositis, dermatomyositis, gouty effusions, systemic lupus erythematosus, systemic sclerosis, Alzheimer's disease, multiple sclerosis or allergic disorders that include but are not limited to allergic rhinitis, allergic dermatitis and asthma, or associated symptoms or complications thereof, in a subject afflicted with such a disease and/or disorder, wherein the method comprises administering a FLAP modulator.

Finally, one aspect of the present invention is directed to compounds, methods, and compositions for the prophylaxis, treatment, or amelioration of carcinogenesis including but not limited to tumor cell proliferation, differentiation, and apoptosis, tumor-associated angiogenesis, as well as the migration and invasion of carcinoma cells, or associated symptoms or complications thereof, in a subject afflicted with such a disease and/or disorder, wherein the method comprises administering a FLAP modulator.

Another aspect of the present invention features a compound of Formula (I)

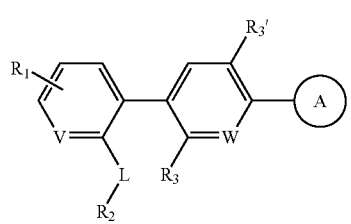

(I)

wherein
L is a bond, —CH$_2$—, —SO$_2$—, —CH$_2$—SO$_2$—, —SO$_2$—CH$_2$—, —SO$_2$—NR—, —SO$_2$—NR—CH$_2$—, —CH$_2$—SO$_2$—NR—, —NR—, —NR—SO$_2$—, —NR—SO$_2$—NR—, —S—, —S—CH$_2$—, —CH$_2$—S—, —C(=O)—, —C(=O)—O—, —O—, —O—CH$_2$—, —NR—C(=O)—, —NR—C(=O)—NR—, or —C(=O)—NR—, wherein R is H, C$_{1-2}$alkyl, C$_{1-2}$alkyl-OH or cyclopropyl;

R$_1$ is H, halo, methyl, CF$_3$, —O—CF$_3$, or —O—CH$_3$;

R$_2$ is H, cyano, halo, —SO$_2$—CH$_3$, 2-(trimethylsilyl)ethoxy, phenyl, C$_{1-6}$alkyl, heteroaryl, heterocyclyl, C$_{3-9}$cycloalkyl, provided R$_2$ is not H if L is a bond, and wherein said phenyl, C$_{1-6}$alkyl, heteroaryl, heterocycyl or C$_{3-9}$cycloalkyl is optionally and independently substituted with 1-4 substituents selected from the group consisting of:

methyl, ethyl, oxo, fluoro, hydroxyl, cyano, amino, methoxy, tert-butoxy, acetyl, cyclopropyl, cyclobutyl, cyclohexyl, phenyl, azetidin-1-yl, azetidin-3-yl, pyrrolidin-1-yl, 2,4-dihydro-3H-1,2,4-triazol-3-one-4-yl, 1H-imidazol-4-yl, pyrazin-2-yl, pyrimidin-2-yl, 1,3-oxazolidin-2-one-5-yl, N-benzamide, benzo[d]imidazol-2(3H)-one, 4-methylpiperazin-1-yl, morpholin-4-yl, CF$_3$, —SO$_2$—CH$_3$, —C(=O)-cyclopropyl, —SO$_2$-cyclohexyl, —NHCH$_3$, —N(CH$_3$)$_2$, —NHAc, —NHCO$_2$t-Bu, —CH$_2$—NH$_2$, —C(=O)—NH$_2$, —C(=O)—N(ethyl)$_2$, —NH—C(=O)—NH$_2$, —NH—C(=O)—CH$_3$, —C(=O)—(C$_1$-C$_4$alkyl), —C(=O—OH, —C(=O)—NH(C$_1$-C$_4$alkyl)-(CH$_2$)$_n$—OH, and —(CH$_2$)$_n$—CN, wherein n is 1 or 2;

V is CH, CR', or N, wherein R' is methyl or F;
W is CR" or N, wherein R" is H, F, hydroxyl, amino, CH$_3$ or —O—CH$_3$;
ring A is selected from the group consisting of:

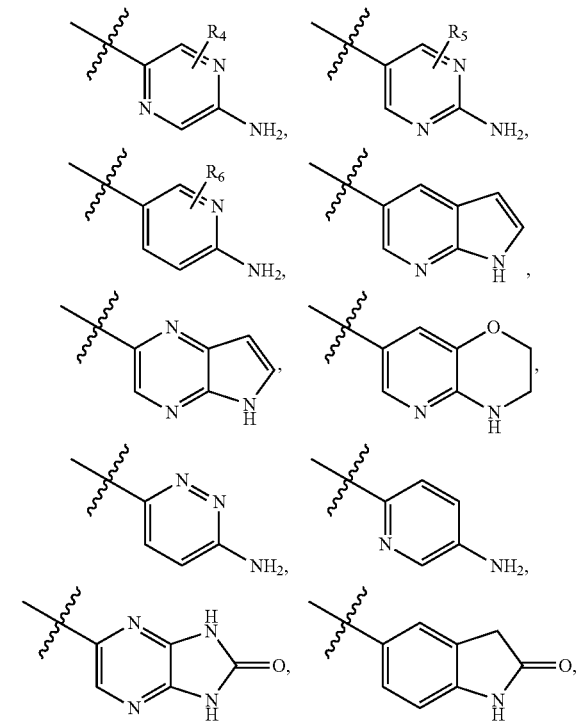

-continued

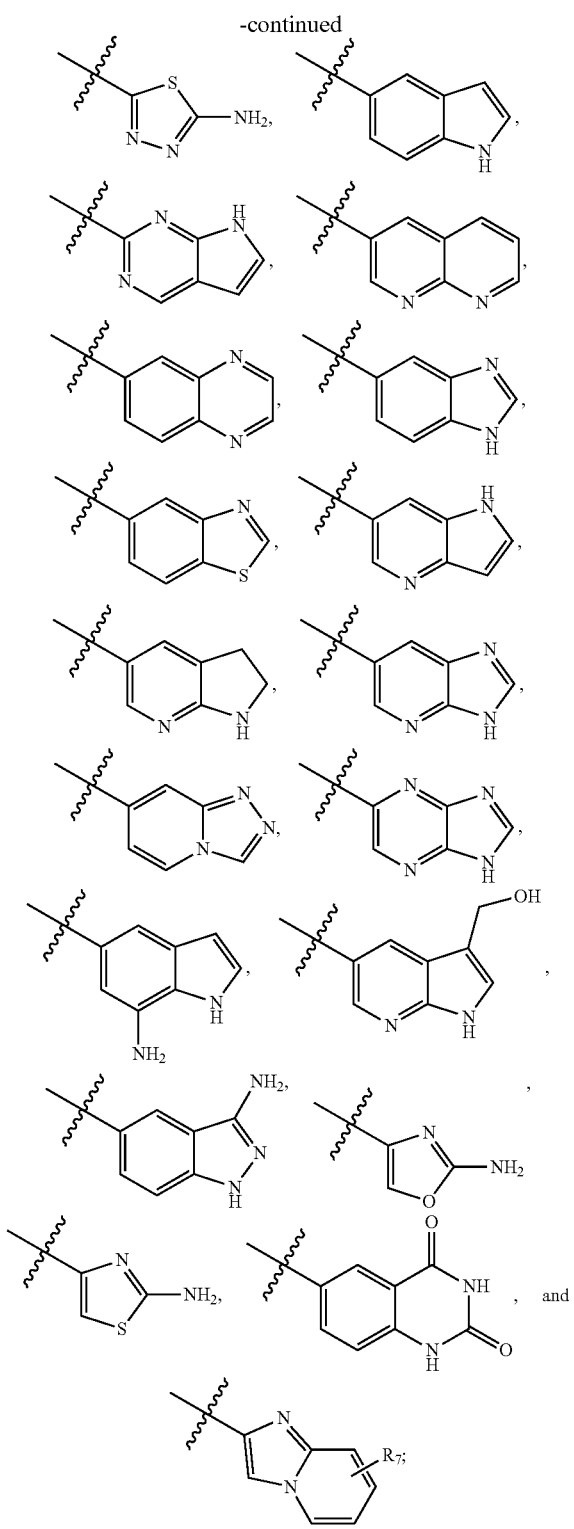

$R_3$ is H, F, methyl, or —O—CH$_3$;
$R_3'$ is H or F;
$R_4$ is H, methyl, cyano, amino, halo, —COOH, or —O—CH$_3$;
$R_5$ is H, methyl, cyano, or —CF$_3$;
$R_6$ is H, cyano, amino, halo, or —CF$_3$; and
$R_7$ is halo, amino, —CONH$_2$, cyano, —O—CH$_3$, —CF$_3$, or —COO-ethyl;

or an optical isomer, hydrate, metabolite, enantiomer, diastereomer, cis-trans isomer, racemate, prodrug or pharmaceutically acceptable salt thereof.

Another aspect of the present invention features a pharmaceutical composition comprising at least one compound of Formula (I) and at least one pharmaceutically acceptable carrier. The invention is also directed towards providing a process for formulating a pharmaceutical composition, comprising formulating a pharmaceutical composition of at least one compound of Formula (I) and at lease one pharmaceutically acceptable carrier. The present invention further relates to a process for making a pharmaceutical composition comprising mixing any of the compounds according to Formula (I) and a pharmaceutically acceptable carrier.

The present invention also features a method of treating a subject suffering from or diagnosed with a disease and/or disorder mediated by FLAP activity, comprising administering to the subject a therapeutically effective amount of at least one compound of Formula (I). Such a disease and/or disorder can include, but is not limited to respiratory disorders, cardiac and cardiovascular diseases, autoimmune disorders, carcinogenesis or associated symptoms or complications. More specifically, this invention is directed to a method of treating exacerbations, non-allergic asthma, fibrotic lung diseases, acute respiratory distress syndrome, chronic obstructive pulmonary disease myocardial infarction, atherosclerosis and stroke aortic aneurisms, atherosclerosis, rheumatoid arthritis, inflammatory bowel disease, nephritis, spondyloarthritis, polymyositis, dermatomyositis, gouty effusions, systemic lupus erythematosus, systemic sclerosis, Alzheimer's disease, multiple sclerosis, allergic rhinitis, allergic dermatitis and asthma, tumor cell proliferation, differentiation, and apoptosis, tumor-associated angiogenesis, as well as the migration and invasion of carcinoma cells, or associated symptoms or complications thereof, in a subject afflicted with such a disease and/or disorder, or associated symptoms or complications thereof, wherein the method comprises administering a FLAP modulator to a subject in need thereof, a therapeutically effective amount of at least one compound of Formula (I), preferably in a pharmaceutical composition comprising at least one compound of Formula (I).

Additional embodiments and advantages of the invention will become apparent from the detailed discussion, schemes, examples, and claims below.

DETAILED DESCRIPTION OF THE INVENTION

This invention relates to novel FLAP modulators and compositions thereof for the prophylaxis, treatment, or amelioration of numerous diseases and/or disorders, including but not limited to respiratory diseases and/or disorders, cardiac and cardiovascular diseases and/or disorders, autoimmune diseases and/or disorders, carcinogenesis, and associated symptoms or complications thereof.

One aspect of the present invention features a compound of Formula (I)

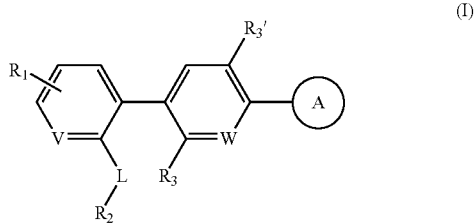

(I)

wherein

L is a bond, —CH₂—, —SO₂—, —CH₂—SO₂—, —SO₂—CH₂—, —SO₂—NR—, —SO₂—NR—CH₂—, —CH₂—SO₂—NR—, —NR—, —NR—SO₂—, —NR—SO₂—NR—, —S—, —S—CH₂—, —CH₂—S—, —C(=O)—, —C(=O)—O—, —O—, —O—CH₂—, —NR—C(=O)—, —NR—C(=O)—NR—, or —C(=O)—NR—, wherein R is H, C₁₋₂alkyl, C₁₋₂alkyl-OH or cyclopropyl;

R₁ is H, halo, methyl, CF₃, —O—CF₃, or —O—CH₃;

R₂ is H, cyano, halo, —SO₂—CH₃, 2-(trimethylsilyl)ethoxy, phenyl, C₁₋₆alkyl, heteroaryl, heterocyclyl, C₃₋₉cycloalkyl, provided R₂ is not H if L is a bond, and wherein said phenyl, C₁₋₆alkyl, heteroaryl, heterocyclyl or C₃₋₉cycloalkyl is optionally and independently substituted with 1-4 substituents selected from the group consisting of:

methyl, ethyl, oxo, fluoro, hydroxyl, cyano, amino, methoxy, tert-butoxy, acetyl, cyclopropyl, cyclobutyl, cyclohexyl, phenyl, azetidin-1-yl, azetidin-3-yl, pyrrolidin-1-yl, 2,4-dihydro-3H-1,2,4-triazol-3-one-4-yl, 1H-imidazol-4-yl, pyrazin-2-yl, pyrimidin-2-yl, 1,3-oxazolidin-2-one-5-yl, N-benzamide, benzo[d]imidazol-2(3H)-one, 4-methylpiperazin-1-yl, morpholin-4-yl, CF₃, —SO₂—CH₃, —C(=O)-cyclopropyl, —SO₂-cyclohexyl, —NHCH₃, —N(CH₃)₂, —NHAc, —NHCO₂t-Bu, —CH₂—NH₂, —C(=O)—NH₂, —C(=O)—N(ethyl)₂, —NH—C(=O)—NH₂, —NH—C(=O)—CH₃, —C(=O)—(C₁-C₄alkyl), —C(=O)—OH, —C(=O)—NH(C₁-C₄alkyl)-(CH₂)ₙ—OH, and —(CH₂)ₙ—CN, wherein n is 1 or 2;

V is CH, CR', or N, wherein R' is methyl or F;

W is CR'' or N, wherein R'' is H, F, hydroxyl, amino, CH₃ or —O—CH₃;

ring A is selected from the group consisting of:

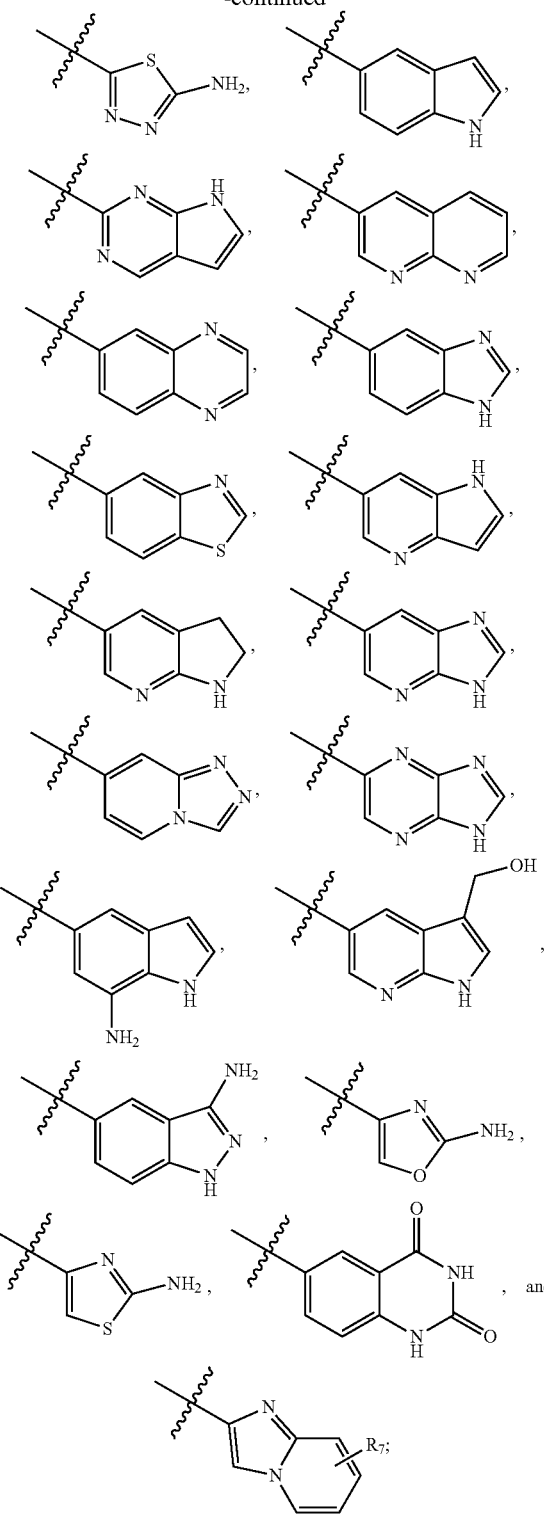

R₃ is H, F, methyl, or —O—CH₃;
R₃' is H or F;
R₄ is H, methyl, cyano, amino, halo, —COOH, or —O—CH₃;
R₅ is H, methyl, cyano, or —CF₃;
R₆ is H, cyano, amino, halo, or —CF₃; and
R₇ is halo, amino, —CONH₂, cyano, —O—CH₃, —CF₃, or —COO-ethyl.

Some embodiments are given by compounds of Formula (I), wherein ring A is

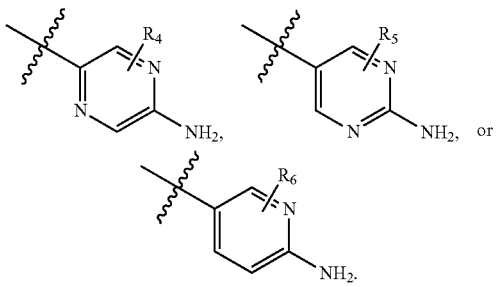

In some of these embodiments, wherein ring A is

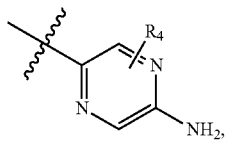

$R_4$ is H or cyano.

In some of these embodiments, wherein ring A is

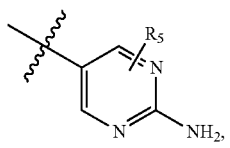

$R_5$ is H or —CF$_3$.

In some of these embodiments, wherein ring A is

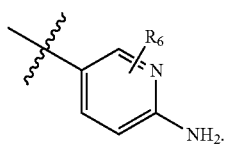

$R_6$ is H, fluoro, chloro, or cyano.

Some embodiments are given by compounds of Formula (I), wherein ring A is

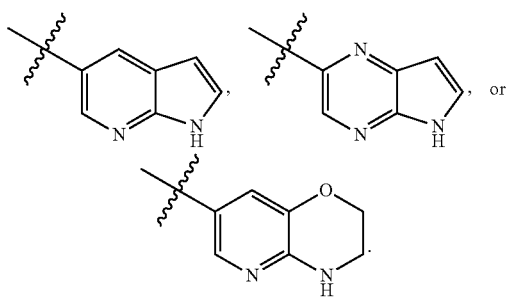

Some embodiments are given by compounds of Formula (I), wherein V is CH and $R_1$ is H, halo, methyl, or CF$_3$.

Some embodiments are given by compounds of Formula (I), wherein $R_3$' is H.

In some of these embodiments, wherein V is CH and $R_1$ is H, halo, methyl, or CF$_3$, the attachment point of $R_1$ to the phenyl ring is in the ortho position with regard to V.

Some embodiments are given by compounds of Formula (I), wherein W is CF, $R_3$ is H, and $R_3$' is H.

Some embodiments are given by compounds of Formula (I), wherein L is a bond, —CH$_2$—, —SO$_2$—, —SO$_2$—NH—, —SO$_2$—NR—CH$_2$—, —CH$_2$—SO$_2$—NR—, —S—, —CH$_2$—S—, —O—, or —O—CH$_2$—.

In another embodiment, the present invention includes a compound of Formula (I) wherein L is a bond, —O—, —SO$_2$—NH—, —NH—SO$_2$—, —SO$_2$—, —S—, —C(=O)—, fluoro or —C(=O)—NH—;

$R_1$ is H, bromo or CF$_3$;

$R_2$ is H, methyl, ethyl, propyl, isopropyl, tert-butyl, cyclopropyl, cyclohexyl, pyrrolidin-1-yl, pyrrolidin-3-yl, piperidin-1-yl, piperidin-2-yl, piperidin-3-yl, piperidin-4-yl, piperazin-1-yl, tetrahydro-2H-thiopyran-4-yl, morpholin-2-yl, morpholin-4-yl, thiomorpholin-4-yl, pyrazin-2-yl, pyrimidin-2-yl, or pyrimidin-4-yl, provided $R_2$ is not H if L is a bond, and wherein $R_2$ is optionally substituted with hydroxyl, fluoro, amino, oxo, methyl, or —CH$_2$—NH$_2$;

V is CH or N;

W is CR" or N, wherein R" is H or F;

ring A is

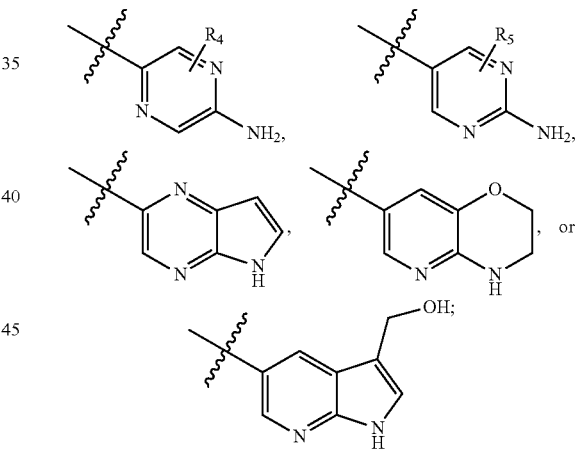

$R_3$' is H;

$R_4$ is H or cyano; and $R_5$ is H or cyano.

In yet another embodiment, the present invention includes a compound of Formula (I) wherein L is a bond, —O—, —SO$_2$—NH—, —NH—SO$_2$—, —SO$_2$—, —S—, or —C(=O)—;

$R_1$ is H or CF$_3$;

$R_2$ is H, methyl, ethyl, propyl, isopropyl, tert-butyl, cyclopropyl, cyclohexyl, pyrrolidin-1-yl, pyrrolidin-3-yl, piperidin-1-yl, piperidin-2-yl, piperidin-3-yl, piperidin-4-yl, piperazin-1-yl, tetrahydro-2H-thiopyran-4-yl, morpholin-2-yl, morpholin-4-yl, thiomorpholin-4-yl, pyrazin-2-yl, pyrimidin-2-yl, or pyrimidin-4-yl, provided $R_2$ is not H if L is a bond, and wherein $R_2$ is optionally substituted with hydroxyl, fluoro, amino, oxo, methyl, or —CH$_2$—NH$_2$;

V is CH or N;
W is CR" or N, wherein R" is H or F;
ring A is

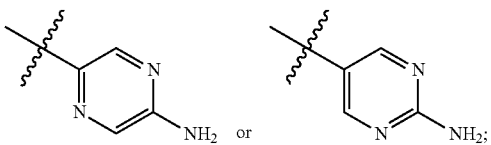 [SMILES: *c1cnc(N)cn1 ; "or" ; *c1cnc(N)nc1]

R_3 is H, and R_3' is H.

The embodiments of the present invention also include the optical isomers, hydrates, metabolites, enantiomers, diastereomers, cis-trans isomers, racemates, prodrugs or pharmaceutically acceptable salts thereof.

It is an embodiment of the present invention to provide a compound selected from the compounds listed in Table 1.

TABLE 1

5-(3-fluoro-2'-(methylsulfonyl)-[1,1'-biphenyl]-4-yl)pyrazin-2-amine,
N-[4'-(5-Aminopyrazin-2-yl)-3'-fluorobiphenyl-2-yl]methanesulfonamide,
6-Amino-3-[3-fluoro-2'-(methylsulfonyl)biphenyl-4-yl]pyrazine-2-carbonitrile,
4'-(5-Aminopyrazin-2-yl)-N-tert-butyl-3'-fluorobiphenyl-2-sulfonamide,
4'-(5-aminopyrazin-2-yl)-3'-fluoro-[1,1'-biphenyl]-2-sulfonamide,
4'-(5-Aminopyrazin-2-yl)-N-cyclohexyl-3'-fluorobiphenyl-2-sulfonamide,
4'-(5-Aminopyrazin-2-yl)-3'-fluoro-N-(2-methylpropyl)biphenyl-2-sulfonamide,
4'-(5-Aminopyrazin-2-yl)-3'-fluoro-N-(2,2,2-trifluoro-1-methylethyl)biphenyl-2-sulfonamide (racemic),
4'-(5-Aminopyrazin-2-yl)-N-(cyclobutylmethyl)-3'-fluorobiphenyl-2-sulfonamide,
(endo)-4'-(5-Aminopyrazin-2-yl)-N-bicyclo[2.2.1]hept-2-yl-3'-fluorobiphenyl-2-sulfonamide (racemic),
4'-(5-Aminopyrazin-2-yl)-3'-fluoro-N-(1-methylcyclobutyl)biphenyl-2-sulfonamide,
4'-(5-Aminopyrazin-2-yl)-N-(1,1-dimethylpropyl)-3'-fluorobiphenyl-2-sulfonamide,
4'-(5-Aminopyrazin-2-yl)-3'-fluoro-N-(2,2,2-trifluoro-1,1-dimethylethyl)biphenyl-2-sulfonamide,
4'-(5-Aminopyrazin-2-yl)-N-cyclopentyl-3'-fluorobiphenyl-2-sulfonamide,
4'-(5-Aminopyrazin-2-yl)-3'-fluoro-N-methylbiphenyl-2-sulfonamide,
4'-(5-Aminopyrazin-2-yl)-N-ethyl-3'-fluorobiphenyl-2-sulfonamide,
4'-(5-Aminopyrazin-2-yl)-3'-fluoro-N-(2-phenylethyl)biphenyl-2-sulfonamide,
(R)-4'-(5-Aminopyrazin-2-yl)-3'-fluoro-N-[(1R)-2,2,2-trifluoro-1-phenylethyl]biphenyl-2-sulfonamide,
(S)-4'-(5-Aminopyrazin-2-yl)-3'-fluoro-N-[(1S)-2,2,2-trifluoro-1-phenylethyl]biphenyl-2-sulfonamide,
(S)-4'-(5-Aminopyrazin-2-yl)-3'-fluoro-N-[(1S)-2,2,2-trifluoro-1-methylethyl]biphenyl-2-sulfonamide,
4'-(5-Aminopyrazin-2-yl)-N-(2,3-dihydro-1H-inden-2-yl)-3'-fluorobiphenyl-2-sulfonamide,
(S)-4'-(5-Aminopyrazin-2-yl)-N-[(1S)-2,3-dihydro-1H-inden-1-yl]-3'-fluorobiphenyl-2-sulfonamide,
(R)-4'-(5-Aminopyrazin-2-yl)-N-[(1R)-2,3-dihydro-1H-inden-1-yl]-3'-fluorobiphenyl-2-sulfonamide,
(R)-4'-(5-Aminopyrazin-2-yl)-3'-fluoro-N-[(1R)-1-phenylethyl]biphenyl-2-sulfonamide,
(R)-4'-(5-Aminopyrazin-2-yl)-3'-fluoro-N-[(1R)-2-hydroxy-1-methylethyl]biphenyl-2-sulfonamide,
4'-(5-Aminopyrazin-2-yl)-3'-fluoro-N-phenylbiphenyl-2-sulfonamide,
(S)-4'-(5-Aminopyrazin-2-yl)-N-[(3S)-1-ethyl-2-oxoazepan-3-yl]-3'-fluorobiphenyl-2-sulfonamide,
(S)-4'-(5-Aminopyrazin-2-yl)-3'-fluoro-N-[(3S)-2-oxoazepan-3-yl]biphenyl-2-sulfonamide,
(S)-4'-(5-Aminopyrazin-2-yl)-3'-fluoro-N-[(3S)-1-methyl-2-oxoazepan-3-yl]biphenyl-2-sulfonamide,
4'-(5-Aminopyrazin-2-yl)-3'-fluoro-N-(1,2,2,6,6-pentamethylpiperidin-4-yl)biphenyl-2-sulfonamide,
4'-(5-Aminopyrazin-2-yl)-3'-fluoro-N-pyridin-3-ylbiphenyl-2-sulfonamide, TABLE 1-continued 4'-(5-Aminopyrazin-2-yl)-3'-fluoro-N-[(1S)-2-hydroxy-1-methylethyl]biphenyl-2-sulfonamide,
N-[4'-(5-Aminopyrazin-2-yl)-3'-fluorobiphenyl-2-yl]sulfamide,
N-(4'-(5-aminopyrazin-2-yl)-3'-fluoro-[1,1'-biphenyl]-2-yl)propane-2-sulfonamide,
N-[4'-(5-Aminopyrazin-2-yl)-3'-fluorobiphenyl-2-yl]ethanesulfonamide,
N-[4'-(5-Aminopyrazin-2-yl)-3'-fluorobiphenyl-2-yl]propane-1-sulfonamide,
N-[4'-(5-Aminopyrazin-2-yl)-3'-fluorobiphenyl-2-yl]-2-methylpropane-1-sulfonamide,
N-(4'-(5-aminopyrazin-2-yl)-3'-fluoro-[1,1'-biphenyl]-2-yl)cyclopropanesulfonamide,
N-[4'-(5-Aminopyrazin-2-yl)-3'-fluorobiphenyl-2-yl]hexane-1-sulfonamide,
N-(4'-(5-aminopyrazin-2-yl)-3'-fluoro-[1,1'-biphenyl]-2-yl)cyclobutanesulfonamide,
N-[4'-(5-Aminopyrazin-2-yl)-3'-fluorobiphenyl-2-yl]-1,1,1-trifluoromethanesulfonamide,
4'-(5-Aminopyrazin-2-yl)-3'-fluoro-N,N-dimethylbiphenyl-2-sulfonamide,
5-[3-Fluoro-2'-(piperidin-1-ylsulfonyl)biphenyl-4-yl]pyrazin-2-amine,
5-[3-Fluoro-2'-(morpholin-4-ylsulfonyl)biphenyl-4-yl]pyrazin-2-amine,
5-{2'-[(1,1-Dioxidothiomorpholin-4-yl)sulfonyl]-3-fluorobiphenyl-4-yl}pyrazin-2-amine,
5-[3-Fluoro-2'-(piperazin-1-ylsulfonyl)biphenyl-4-yl]pyrazin-2-amine,
4'-(5-Aminopyrazin-2-yl)-N,N-diethyl-3'-fluorobiphenyl-2-sulfonamide,
5-[3-Fluoro-2'-(pyrrolidin-1-ylsulfonyl)biphenyl-4-yl]pyrazin-2-amine,
5-{2'-[(4,4-Difluoropiperidin-1-yl)sulfonyl]-3-fluorobiphenyl-4-yl}pyrazin-2-amine,
5-{2'-[(3,3-Difluoropiperidin-1-yl)sulfonyl]-3-fluorobiphenyl-4-yl}pyrazin-2-amine,
5-{2'-[(3,3-Difluoropyrrolidin-1-yl)sulfonyl]-3-fluorobiphenyl-4-yl}pyrazin-2-amine,
5-{2'-[(3,3-Difluoroazetidin-1-yl)sulfonyl]-3-fluorobiphenyl-4-yl}pyrazin-2-amine,
5-[2'-(Azepan-1-ylsulfonyl)-3-fluorobiphenyl-4-yl]pyrazin-2-amine,
5-{3-Fluoro-2'-[(4-methylpiperazin-1-yl)sulfonyl]biphenyl-4-yl}pyrazin-2-amine,
1-{[4'-(5-Aminopyrazin-2-yl)-3'-fluorobiphenyl-2-yl]sulfonyl}-4-(trifluoromethyl)piperidin-4-ol,
5-(3-Fluoro-2'-{[4-(methylsulfonyl)piperazin-1-yl]sulfonyl}biphenyl-4-yl)pyrazin-2-amine,
5-{2'-[(4-Acetylpiperazin-1-yl)sulfonyl]-3-fluorobiphenyl-4-yl}pyrazin-2-amine,
5-(2'-{[4-(Cyclopropylcarbonyl)piperazin-1-yl]sulfonyl}-3-fluorobiphenyl-4-yl)pyrazin-2-amine,
2-(4-{[4'-(5-Aminopyrazin-2-yl)-3'-fluorobiphenyl-2-yl]sulfonyl}piperazin-1-yl)ethanol,
5-{2'-[(4-Cyclopropylpiperazin-1-yl)sulfonyl]-3-fluorobiphenyl-4-yl}pyrazin-2-amine,
racemic 5-[3-Fluoro-2'-(hexahydropyrrolo[1,2-a]pyrazin-2(1H)-ylsulfonyl)biphenyl-4-yl]pyrazin-2-amine,
5-{2'-[(3,5-Dimethylpiperazin-1-yl)sulfonyl]-3-fluorobiphenyl-4-yl}pyrazin-2-amine,
racemic 1-{[4'-(5-Aminopyrazin-2-yl)-3'-fluorobiphenyl-2-yl]sulfonyl}piperidine-3-carbonitrile,
1-{[4'-(5-Aminopyrazin-2-yl)-3'-fluorobiphenyl-2-yl]sulfonyl}piperidine-4-carbonitrile,
5-{2'-[(4-Aminopiperidin-1-yl)sulfonyl]-3-fluorobiphenyl-4-yl}pyrazin-2-amine,
4-{[4'-(5-Aminopyrazin-2-yl)-3'-fluorobiphenyl-2-yl]sulfonyl}piperazin-2-one,
1-{[4'-(5-Aminopyrazin-2-yl)-3'-fluorobiphenyl-2-yl]sulfonyl}piperidin-4-ol,
(1-{[4'-(5-Aminopyrazin-2-yl)-3'-fluorobiphenyl-2-yl]sulfonyl}piperidin-4-yl)methanol,
2-(1-{[4'-(5-Aminopyrazin-2-yl)-3'-fluorobiphenyl-2-yl]sulfonyl}piperidin-4-yl)ethanol,
racemic 1-{[4'-(5-Aminopyrazin-2-yl)-3'-fluorobiphenyl-2-yl]sulfonyl}piperidin-3-ol,
racemic 2-(1-{[4'-(5-Aminopyrazin-2-yl)-3'-fluorobiphenyl-2-yl]sulfonyl}piperidin-3-yl)ethanol,
5-(3-Fluoro-2'-{[4-(methylamino)piperidin-1-yl]sulfonyl}biphenyl-4-yl)pyrazin-2-amine,
5-{2'-{[4-(Dimethylamino)piperidin-1-yl]sulfonyl}-3-fluorobiphenyl-4-yl)pyrazin-2-amine,
racemic 5-{2'-[(3-Aminopiperidin-1-yl)sulfonyl]-3-fluorobiphenyl-4-yl}pyrazin-2-amine, TABLE 1-continued N-(1-{[4'-(5-Aminopyrazin-2-yl)-3'-fluorobiphenyl-2-yl]sulfonyl}piperidin-4-yl)acetamide,
racemic (1-{[4'-(5-Aminopyrazin-2-yl)-3'-fluorobiphenyl-2-yl]sulfonyl}piperidin-3-yl)methanol,
racemic tert-Butyl (1-{[4'-(5-aminopyrazin-2-yl)-3'-fluorobiphenyl-2-yl]sulfonyl}piperidin-3-yl)carbamate,
4'-(5-Aminopyrazin-2-yl)-3'-fluoro-N-[(1S,2S)-2-hydroxy-1-(hydroxymethyl)-2-phenylethyl]biphenyl-2-sulfonamide,
4'-(5-Aminopyrazin-2-yl)-3'-fluoro-N-[(1S)-1-(hydroxymethyl)-3-methylbutyl]biphenyl-2-sulfonamide,
4'-(5-Aminopyrazin-2-yl)-3'-fluoro-N-(3-hydroxypropyl)biphenyl-2-sulfonamide,
4'-(5-Aminopyrazin-2-yl)-3'-fluoro-N-[(1S)-2-hydroxy-1-phenylethyl]biphenyl-2-sulfonamide,
4'-(5-Aminopyrazin-2-yl)-3'-fluoro-N-[(1R)-2-hydroxy-1-phenylethyl]biphenyl-2-sulfonamide,
4'-(5-Aminopyrazin-2-yl)-3'-fluoro-N-[(1S,2R)-2-hydroxy-1-methyl-2-phenylethyl]biphenyl-2-sulfonamide,
4'-(5-Aminopyrazin-2-yl)-3'-fluoro-N-[(1S,2S)-1-(hydroxymethyl)-2-methylbutyl]biphenyl-2-sulfonamide,
4'-(5-Aminopyrazin-2-yl)-3'-fluoro-N-[(1R,2R)-2-hydroxycyclohexyl]biphenyl-2-sulfonamide,
4'-(5-Aminopyrazin-2-yl)-3'-fluoro-N-[(1R)-1-(hydroxymethyl)propyl]biphenyl-2-sulfonamide,
4'-(5-Aminopyrazin-2-yl)-3'-fluoro-N-[(1R,2S)-2-hydroxycyclohexyl]biphenyl-2-sulfonamide,
4'-(5-Aminopyrazin-2-yl)-3'-fluoro-N-(2-hydroxyethyl)biphenyl-2-sulfonamide,
4'-(5-Aminopyrazin-2-yl)-N-cyclopropyl-3'-fluorobiphenyl-2-sulfonamide,
4'-(5-Aminopyrazin-2-yl)-N-(cyclopropylmethyl)-3'-fluorobiphenyl-2-sulfonamide,
(R)-(1-((4'-(5-aminopyrazin-2-yl)-3'-fluoro-[1,1'-biphenyl]-2-yl)sulfonyl)pyrrolidin-2-yl)methanol,
(R)-5-(2'-((3-aminopyrrolidin-1-yl)sulfonyl)-3-fluoro-[1,1'-biphenyl]-4-yl)pyrazin-2-amine,
(S)-5-(2'-((3-aminopyrrolidin-1-yl)sulfonyl)-3-fluoro-[1,1'-biphenyl]-4-yl)pyrazin-2-amine,
(R) 5-(2'-{[2-(Aminomethyl)pyrrolidin-1-yl]sulfonyl}-3-fluorobiphenyl-4-yl)pyrazin-2-amine,
(S)-(1-((4'-(5-aminopyrazin-2-yl)-3'-fluoro-[1,1'-biphenyl]-2-yl)sulfonyl)pyrrolidin-2-yl)methanol,
4'-(5-Aminopyrazin-2-yl)-3'-fluoro-N-(methylsulfonyl)biphenyl-2-sulfonamide,
(R)-4'-(5-aminopyrazin-2-yl)-3'-fluoro-N-(2-hydroxypropyl)-[1,1'-biphenyl]-2-sulfonamide,
(S)-4'-(5-aminopyrazin-2-yl)-3'-fluoro-N-(2-hydroxypropyl)-[1,1'-biphenyl]-2-sulfonamide,
4'-(5-Aminopyrazin-2-yl)-3'-fluoro-N-[(1-hydroxycyclohexyl)methyl]biphenyl-2-sulfonamide,
4'-(5-Aminopyrazin-2-yl)-3'-fluoro-N-(2-hydroxy-1,1-dimethylethyl)biphenyl-2-sulfonamide,
4'-(5-Aminopyrazin-2-yl)-3'-fluoro-N-(2-hydroxy-2-methylpropyl)biphenyl-2-sulfonamide,
4'-(5-Aminopyrazin-2-yl)-3'-fluoro-N-(3-hydroxy-1,1-dimethylpropyl)biphenyl-2-sulfonamide,
4'-(5-Aminopyrazin-2-yl)-3'-fluoro-N-(3-hydroxy-2,2-dimethylpropyl)biphenyl-2-sulfonamide,
(S)-4'-(5-aminopyrazin-2-yl)-N-(2,3-dihydroxypropyl)-3'-fluoro-[1,1'-biphenyl]-2-sulfonamide,
(R)-4'-(5-aminopyrazin-2-yl)-N-(2,3-dihydroxypropyl)-3'-fluoro-[1,1'-biphenyl]-2-sulfonamide,
(trans)-1-{[4'-(5-Aminopyrazin-2-yl)-3'-fluorobiphenyl-2-yl]sulfonyl}pyrrolidine-3,4-diol,
(S)-4'-(5-aminopyrazin-2-yl)-3'-fluoro-N-(2-oxopyrrolidin-3-yl)-[1,1'-biphenyl]-2-sulfonamide,
(S)-4'-(5-aminopyrazin-2-yl)-3'-fluoro-N-(2-oxopiperidin-3-yl)-[1,1'-biphenyl]-2-sulfonamide,
(R)-4'-(5-Aminopyrazin-2-yl)-3'-fluoro-N-[1-(hydroxymethyl)-2-methylpropyl]biphenyl-2-sulfonamide,
trans 4'-(5-Aminopyrazin-2-yl)-3'-fluoro-N-(4-hydroxycyclohexyl)biphenyl-2-sulfonamide,
(R)-(1-((4'-(5-aminopyrazin-2-yl)-3'-fluoro-[1,1'-biphenyl]-2-yl)sulfonyl)pyrrolidin-3-yl)methanol,
(S)-(1-{[4'-(5-Aminopyrazin-2-yl)-3'-fluorobiphenyl-2-yl]sulfonyl}pyrrolidin-3-yl)methanol,
(R)-4'-(5-Aminopyrazin-2-yl)-3'-fluoro-N-(2-oxopiperidin-3-yl)biphenyl-2-sulfonamide,
(R)-4'-(5-Aminopyrazin-2-yl)-3'-fluoro-N-methyl-N-piperidin-3-ylbiphenyl-2-sulfonamide,
(S)-4'-(5-Aminopyrazin-2-yl)-3'-fluoro-N-methyl-N-piperidin-3-ylbiphenyl-2-sulfonamide,
(S)-4'-(5-aminopyrazin-2-yl)-3'-fluoro-N-(1-hydroxy-3-phenylpropan-2-yl)-[1,1'-biphenyl]-2-sulfonamide,
(R)-4'-(5-Aminopyrazin-2-yl)-3'-fluoro-N-(2-hydroxy-2-phenylethyl)-[1,1'-biphenyl]-2-sulfonamide,
4'-(5-aminopyrazin-2-yl)-3'-fluoro-N-((1S,2S)-1-hydroxy-1-phenylpropan-2-yl)-N-methyl-[1,1'-biphenyl]-2-sulfonamide,
1-{[4'-(5-Aminopyrazin-2-yl)-3'-fluorobiphenyl-2-yl]sulfonyl}azetidin-3-ol,
racemic (trans)-4'-(5-Aminopyrazin-2-yl)-3'-fluoro-N-(2-hydroxycyclohexyl)biphenyl-2-sulfonamide,
racemic (trans)-4'-(5-Aminopyrazin-2-yl)-3'-fluoro-N-[2-(hydroxymethyl)cyclohexyl]biphenyl-2-sulfonamide,
racemic (cis)-4'-(5-Aminopyrazin-2-yl)-3'-fluoro-N-[2-(hydroxymethyl)cyclohexyl]biphenyl-2-sulfonamide,
4'-(5-Aminopyrazin-2-yl)-3'-fluoro-N-piperidin-4-ylbiphenyl-2-sulfonamide,
5-(2'-{[3-(Aminomethyl)azetidin-1-yl]sulfonyl}-3-fluorobiphenyl-4-yl)pyrazin-2-amine,
4'-(5-Aminopyrazin-2-yl)-N-(azetidin-3-ylmethyl)-3'-fluorobiphenyl-2-sulfonamide,
(R)-5-(3-Fluoro-2'-{[3-(methylamino)pyrrolidin-1-yl]sulfonyl}biphenyl-4-yl)pyrazin-2-amine,
(R)-4'-(5-Aminopyrazin-2-yl)-3'-fluoro-N-(2,2,2-trifluoro-1-methylethyl)biphenyl-2-sulfonamide,
5-[3-Fluoro-2'-(1,4,6,7-tetrahydro-5H-pyrazolo[4,3-c]pyridin-5-ylsulfonyl)biphenyl-4-yl]pyrazin-2-amine,
4-(1-{[4'-(5-Aminopyrazin-2-yl)-3'-fluorobiphenyl-2-yl]sulfonyl}piperidin-4-yl)-2,4-dihydro-3H-1,2,4-triazol-3-one,
5-(2'-((1R,4R)-2,5-diazabicyclo[2.2.1]heptan-2-ylsulfonyl)-3-fluoro-[1,1'-biphenyl]-4-yl)pyrazin-2-amine,
5-(2'-((1S,4S)-2,5-diazabicyclo[2.2.1]heptan-2-ylsulfonyl)-3-fluoro-[1,1'-biphenyl]-4-yl)pyrazin-2-amine,
4'-(5-Aminopyrazin-2-yl)-3'-fluoro-N-(5-hydroxypentyl)biphenyl-2-sulfonamide,
4'-(5-Aminopyrazin-2-yl)-3'-fluoro-N-(6-hydroxyhexyl)biphenyl-2-sulfonamide,
N-(4-Aminocyclohexyl)-4'-(5-aminopyrazin-2-yl)-3'-fluorobiphenyl-2-sulfonamide,
(S)-(1-{[4'-(5-Aminopyrazin-2-yl)-3'-fluorobiphenyl-2-yl]sulfonyl}-2,3-dihydro-1H-indol-2-yl)methanol,
4'-(5-Aminopyrazin-2-yl)-N-cyclohexyl-3'-fluoro-N-(2-hydroxyethyl)biphenyl-2-sulfonamide,
(S)-5-{2'-[(3-Aminopiperidin-1-yl)sulfonyl]-3-fluorobiphenyl-4-yl}pyrazin-2-amine,
4'-(5-Aminopyrazin-2-yl)-3'-fluoro-N,N-bis(2-hydroxyethyl)biphenyl-2-sulfonamide,
1-{[4'-(5-Aminopyrazin-2-yl)-3'-fluorobiphenyl-2-yl]sulfonyl}azetidine-2-carboxamide,
4'-(5-Aminopyrazin-2-yl)-N-cyclopropyl-3'-fluoro-N-(tetrahydro-2H-pyran-4-yl)biphenyl-2-sulfonamide,
4'-(5-Aminopyrazin-2-yl)-3'-fluoro-N-(2-hydroxyethyl)-N-(1-methylethyl)biphenyl-2-sulfonamide,
racemic (4-{[4'-(5-Aminopyrazin-2-yl)-3'-fluorobiphenyl-2-yl]sulfonyl}morpholin-2-yl)methanol,
(1R,5S)-3-((4'-(5-aminopyrazin-2-yl)-3'-fluoro-[1,1'-biphenyl]-2-yl)sulfonyl)-3-azabicyclo[3.1.0]hexan-6-amine,
(S)-5-(3-fluoro-2'-((2-methylpiperazin-1-yl)sulfonyl)-[1,1'-biphenyl]-4-yl)pyrazin-2-amine,
(R)-5-(3-fluoro-2'-((2-methylpiperazin-1-yl)sulfonyl)-[1,1'-biphenyl]-4-yl)pyrazin-2-amine,
(R)-(1-((4'-(5-aminopyrazin-2-yl)-3'-fluoro-[1,1'-biphenyl]-2-yl)sulfonyl)piperazin-2-yl)methanol,
4'-(5-Aminopyrazin-2-yl)-3'-fluoro-N-[2-hydroxy-1-(hydroxymethyl)-1-methylethyl]biphenyl-2-sulfonamide,
(S)-4'-(5-aminopyrazin-2-yl)-3'-fluoro-N-(1-hydroxy-3-methylbutan-2-yl)-[1,1'-biphenyl]-2-sulfonamide,
(S)-4'-(5-aminopyrazin-2-yl)-3'-fluoro-N-(1-hydroxy-3,3-dimethylbutan-2-yl)-[1,1'-biphenyl]-2-sulfonamide,
(R)-4'-(5-aminopyrazin-2-yl)-3'-fluoro-N-(1-hydroxy-3,3-dimethylbutan-2-yl)-[1,1'-biphenyl]-2-sulfonamide,
tert-Butyl [2-({[4'-(5-aminopyrazin-2-yl)-3'-fluorobiphenyl-2-yl]sulfonyl}amino)ethyl]carbamate,
N-(2-Aminoethyl)-4'-(5-aminopyrazin-2-yl)-3'-fluorobiphenyl-2-sulfonamide,
(S)-4'-(5-aminopyrazin-2-yl)-3'-fluoro-N-(1-hydroxybutan-2-yl)-[1,1'-biphenyl]-2-sulfonamide,
(S)-4'-(5-aminopyrazin-2-yl)-3'-fluoro-N-(pyrrolidin-3-yl)-[1,1'-biphenyl]-2-sulfonamide, TABLE 1-continued N-[2-({[4'-(5-Aminopyrazin-2-yl)-3'-fluorobiphenyl-2-yl]sulfonyl}amino)ethyl]acetamide,
(S)-2-(4'-(5-aminopyrazin-2-yl)-3'-fluoro-[1,1'-biphenyl]-2-ylsulfonamido)propanoic acid,
4'-(5-Aminopyrazin-2-yl)-N-[2-(carbamoylamino)ethyl]-3'-fluorobiphenyl-2-sulfonamide,
4'-(5-aminopyrazin-2-yl)-3'-fluoro-N-((1S,2S)-2-hydroxy-2,3-dihydro-1H-inden-1-yl)-[1,1'-biphenyl]-2-sulfonamide,
4'-(5-aminopyrazin-2-yl)-3'-fluoro-N-((1R,2R)-2-hydroxy-2,3-dihydro-1H-inden-1-yl)-[1,1'-biphenyl]-2-sulfonamide,
4'-(5-aminopyrazin-2-yl)-3'-fluoro-N-((1S,2R)-2-hydroxy-2,3-dihydro-1H-inden-1-yl)-[1,1'-biphenyl]-2-sulfonamide,
4'-(5-aminopyrazin-2-yl)-3'-fluoro-N-((1R,2S)-2-hydroxy-2,3-dihydro-1H-inden-1-yl)-[1,1'-biphenyl]-2-sulfonamide,
4'-(5-aminopyrazin-2-yl)-3'-fluoro-N-((1S,2S)-2-hydroxycyclohexyl)-[1,1'-biphenyl]-2-sulfonamide,
4'-(5-Aminopyrazin-2-yl)-3'-fluoro-N-[6-(trifluoromethyl)pyridin-3-yl]biphenyl-2-sulfonamide,
5-(3-Fluoro-2'-{[4-(1H-imidazol-4-yl)piperidin-1-yl]sulfonyl}biphenyl-4-yl)pyrazin-2-amine,
N-[(4-Amino-2-methylpyrimidin-5-yl)methyl]-4'-(5-aminopyrazin-2-yl)-3'-fluorobiphenyl-2-sulfonamide,
4'-(5-Aminopyrazin-2-yl)-N-(2,6-dimethoxypyrimidin-4-yl)-3'-fluorobiphenyl-2-sulfonamide,
4'-(5-Aminopyrazin-2-yl)-3'-fluoro-N-(5-methylpyrazin-2-yl)biphenyl-2-sulfonamide,
(S)-2-(4'-(5-aminopyrazin-2-yl)-3'-fluoro-[1,1'-biphenyl]-2-ylsulfonamido)-4-methylpentanamide,
4'-(5-Aminopyrazin-2-yl)-N-(2-cyanoethyl)-3'-fluorobiphenyl-2-sulfonamide,
(R)-4'-(5-aminopyrazin-2-yl)-N-(1-cyanopropan-2-yl)-3'-fluoro-[1,1'-biphenyl]-2-sulfonamide,
(S)-4'-(5-aminopyrazin-2-yl)-N-(1-cyanopropan-2-yl)-3'-fluoro-[1,1'-biphenyl]-2-sulfonamide,
4'-(5-Aminopyrazin-2-yl)-N-(2-cyanoethyl)-N-cyclopropyl-3'-fluorobiphenyl-2-sulfonamide,
4'-(5-Aminopyrazin-2-yl)-3'-fluoro-N-(3-methyloxetan-3-yl)biphenyl-2-sulfonamide,
3-(4-{[4'-(5-Aminopyrazin-2-yl)-3'-fluorobiphenyl-2-yl]sulfonyl}piperazin-1-yl)propanenitrile,
(S)-4'-(5-aminopyrazin-2-yl)-3'-fluoro-N-(1-methoxypropan-2-yl)-[1,1'-biphenyl]-2-sulfonamide,
5-{3-Fluoro-2'-[(4-pyrazin-2-ylpiperazin-1-yl)sulfonyl]biphenyl-4-yl}pyrazin-2-amine,
5-{3-Fluoro-2'-[(4-pyrimidin-2-ylpiperazin-1-yl)sulfonyl]biphenyl-4-yl}pyrazin-2-amine,
5-(2'-Amino-3-fluorobiphenyl-4-yl)pyrazin-2-amine,
4'-(5-Aminopyrazin-2-yl)-3'-fluoro-N-[1-(hydroxymethyl)cyclopentyl]biphenyl-2-sulfonamide,
1-{[4'-(5-Aminopyrazin-2-yl)-3'-fluorobiphenyl-2-yl]sulfonyl}-3-phenylpyrrolidin-3-ol,
N-[4'-(5-Aminopyrazin-2-yl)-3'-fluorobiphenyl-2-yl]pyrrolidine-1-sulfonamide,
N'-[4'-(5-Aminopyrazin-2-yl)-3'-fluorobiphenyl-2-yl]-N,N-dimethylsulfamide,
N-[4'-(5-Aminopyrazin-2-yl)-3'-fluorobiphenyl-2-yl]morpholine-4-sulfonamide,
(3S)-1-{[4'-(5-Aminopyrazin-2-yl)-3'-fluorobiphenyl-2-yl]sulfonyl}pyrrolidin-3-ol,
(3R)-1-{[4'-(5-Aminopyrazin-2-yl)-3'-fluorobiphenyl-2-yl]sulfonyl}pyrrolidin-3-ol,
(3'S,4'S)-1'-{[4'-(5-Aminopyrazin-2-yl)-3'-fluorobiphenyl-2-yl]sulfonyl}-1,3'-bipyrrolidin-4'-ol,
(3S,4S)-1-{[4'-(5-Aminopyrazin-2-yl)-3'-fluorobiphenyl-2-yl]sulfonyl}-4-morpholin-4-ylpyrrolidin-3-ol,
(3S,4S)-1-{[4'-(5-Aminopyrazin-2-yl)-3'-fluorobiphenyl-2-yl]sulfonyl}-4-(4-methylpiperazin-1-yl)pyrrolidin-3-ol,
5-{3-Fluoro-2'-[(trifluoromethyl)sulfanyl]biphenyl-4-yl}pyrazin-2-amine,
5-[2'-(tert-Butylsulfanyl)-3-fluorobiphenyl-4-yl]pyrazin-2-amine,
5-[2'-(Ethylsulfonyl)-3-fluorobiphenyl-4-yl]pyrazin-2-amine,
5-[3-Fluoro-2'-(propylsulfonyl)biphenyl-4-yl]pyrazin-2-amine,
5-{3,-Fluoro-2'-[(2-methylpropyl)sulfonyl]biphenyl-4-yl}pyrazin-2-amine,
5-[2'-(tert-Butylsulfonyl)-3-fluorobiphenyl-4-yl]pyrazin-2-amine,
5-[2'-(Cyclopentylsulfonyl)-3-fluorobiphenyl-4-yl]pyrazin-2-amine,
5-[2'-(Cyclobutylsulfonyl)-3-fluorobiphenyl-4-yl]pyrazin-2-amine,
5-[2'-(Cyclopropylsulfonyl)-3-fluorobiphenyl-4-yl]pyrazin-2-amine,
5-[3-Fluoro-2'-[(1-methylethyl)sulfonyl]biphenyl-4-yl]pyrazin-2-amine,
5-{3-Fluoro-2'-[(trifluoromethyl)sulfonyl]biphenyl-4-yl}pyrazin-2-amine,
2-{[4'-(5-Aminopyrazin-2-yl)-3'-fluorobiphenyl-2-yl]sulfanyl}acetamide,
2-{[4'-(5-Aminopyrazin-2-yl)-3'-fluorobiphenyl-2-yl]sulfanyl}-N,N-diethylacetamide,
5-{3-Fluoro-2'-[(2-morpholin-4-yl-2-oxoethyl)sulfanyl]biphenyl-4-yl}pyrazin-2-amine,
(racemic) 5-({[4'-(5-Aminopyrazin-2-yl)-3'-fluorobiphenyl-2-yl]sulfanyl}methyl)-1,3-oxazolidin-2-one,
N-(2-{[4'-(5-Aminopyrazin-2-yl)-3'-fluorobiphenyl-2-yl]sulfanyl}ethyl)benzamide,
5-(3-Fluoro-2'-{[4-(methylsulfonyl)benzyl]sulfanyl}biphenyl-4-yl)pyrazin-2-amine,
4'-(5-Aminopyrazin-2-yl)-3'-fluoro-4-(trifluoromethyl)biphenyl-2-sulfonamide,
5-[3-Fluoro-2'-(methylsulfonyl)-4'-(trifluoromethyl)biphenyl-4-yl]pyrazin-2-amine,
4'-(5-Aminopyrazin-2-yl)-3'-fluoro-N-methyl-4-(trifluoromethyl)biphenyl-2-sulfonamide,
4-{[4'-(5-Aminopyrazin-2-yl)-3'-fluoro-4-(trifluoromethyl)biphenyl-2-yl]sulfonyl}piperazin-2-one,
4'-(5-aminopyrazin-2-yl)-3'-fluoro-N-(2-hydroxyethyl)-4-(trifluoromethyl)biphenyl-2-sulfonamide,
4'-(5-Aminopyrazin-2-yl)-N-ethyl-3'-fluoro-4-(trifluoromethyl)biphenyl-2-sulfonamide,
5-[3-Fluoro-2'-[(4-methylpiperazin-1-yl)sulfonyl]-4'-(trifluoromethyl)biphenyl-4-yl]pyrazin-2-amine,
5-[3-Fluoro-2'-(pyrimidin-2-ylsulfanyl)biphenyl-4-yl]pyrazin-2-amine hydrochloride,
5-[3-Fluoro-2'-(pyrimidin-4-ylsulfanyl)biphenyl-4-yl]pyrimidin-2-amine formate salt,
6-{[4'-(5-Aminopyrazin-2-yl)-3'-fluorobiphenyl-2-yl]sulfanyl}pyrimidin-4-amine hydrochloride,
2-{[4'-(5-Aminopyrazin-2-yl)-3'-fluorobiphenyl-2-yl]sulfanyl}pyrimidin-4-amine hydrochloride,
4-{[4'-(5-Aminopyrazin-2-yl)-3'-fluorobiphenyl-2-yl]sulfanyl}pyrimidin-5-amine hydrochloride,
5-[3-Fluoro-2'-(pyrazin-2-ylsulfanyl)biphenyl-4-yl]pyrazin-2-amine hydrochloride,
2-{[4'-(5-Aminopyrazin-2-yl)-3'-fluorobiphenyl-2-yl]sulfanyl}pyrimidin-5-amine hydrochloride,
1-[4'-(5-Aminopyrazin-2-yl)-3'-fluorobiphenyl-2-yl]-N-methylmethanesulfonamide formic acid salt,
1-[4'-(5-Aminopyrazin-2-yl)-3'-fluorobiphenyl-2-yl]-N-(2-hydroxyethyl)methanesulfonamide formic acid salt,
1-({[4'-(5-Aminopyrazin-2-yl)-3'-fluorobiphenyl-2-yl]methyl}sulfonyl)azetidin-3-ol formic acid salt,
4-({[4'-(5-Aminopyrazin-2-yl)-3'-fluorobiphenyl-2-yl]methyl}sulfonyl)piperazin-2-one formic acid salt,
(S)-1-(4'-(5-Aminopyrazin-2-yl)-3'-fluoro-[1,1'-biphenyl]-2-yl)-N-(1-hydroxypropan-2-yl)methanesulfonamide,
(R)-1-(4'-(5-Aminopyrazin-2-yl)-3'-fluoro-[1,1'-biphenyl]-2-yl)-N-(1-hydroxypropan-2-yl)methanesulfonamide hydrochloride,
1-[4'-(5-Aminopyrazin-2-yl)-3'-fluorobiphenyl-2-yl]-N-(trans-4-hydroxycyclohexyl)methanesulfonamide,
(S)-1-[4'-(5-Aminopyrazin-2-yl)-3'-fluorobiphenyl-2-yl]-N-[(2S)-2-hydroxypropyl]methanesulfonamide hydrochloride,
(R)-1-[4'-(5-Aminopyrazin-2-yl)-3'-fluorobiphenyl-2-yl]-N-[(2S)-2-hydroxypropyl]methanesulfonamide,
5-(2'-{[(4-Aminopiperidin-1-yl)sulfonyl]methyl}-3-fluorobiphenyl-4-yl)pyrazin-2-amine hydrochloride,
1-[4'-(5-Aminopyrazin-2-yl)-3'-fluorobiphenyl-2-yl]methanesulfonamide hydrochloride,
1-[4'-(5-Aminopyrazin-2-yl)-3'-fluorobiphenyl-2-yl]-N-ethylmethanesulfonamide formate salt,
1-[1-({[4'-(5-Aminopyrazin-2-yl)-3-fluorobiphenyl-2-yl]methyl}sulfonyl)piperidin-4-yl]urea hydrochloride,
N-[1-({[4'-(5-Aminopyrazin-2-yl)-3'-fluorobiphenyl-2-yl]methyl}sulfonyl)piperidin-4-yl]acetamide formate salt,
5-{2'-[(Ethylsulfanyl)methyl]-3-fluorobiphenyl-4-yl}pyrazin-2-amine formate salt,
5-{3-Fluoro-2'-[(methylsulfanyl)methyl]biphenyl-4-yl}pyrazin-2-amine hydrochloride,
5-(3-Fluoro-2'-{[(1-methylethyl)sulfanyl]methyl}biphenyl-4-yl)pyrazin-2-amine hydrochloride,
2-(((4'-(5-Aminopyrazin-2-yl)-3'-fluoro-[1,1'-biphenyl]-2-yl)methyl)thio)pyrimidin-4-amine hydrochloride,
6-(((4'-(5-aminopyrazin-2-yl)-3'-fluoro-[1,1'-biphenyl]-2-yl)methyl)thio)pyrimidin-4-amine hydrochloride,
5-(3-fluoro-2'-((pyridazin-3-ylthio)methyl)-[1,1'-biphenyl]-4-yl)pyrazin-2-amine hydrochloride, TABLE 1-continued 6-(((4'-(5-aminopyrazin-2-yl)-3'-fluoro-[1,1'-biphenyl]-2-yl)methyl)thio)pyridazin-3-amine hydrochloride,
5-{2'-[(1,1-Dioxidotetrahydro-2H-thiopyran-4-yl)sulfonyl]-3-fluorobiphenyl-4-yl}pyrazin-2-amine,
4-{[4'-(5-Aminopyrazin-2-yl)-3'-fluorobiphenyl-2-yl]sulfanyl}pyrimidin-2-amine hydrochloride,
5-(3-fluoro-2'-((pyrimidin-4-ylthio)methyl)-[1,1'-biphenyl]-4-yl)pyrazin-2-amine hydrochloride,
5-[3-Fluoro-2'-({[2-(trimethylsilyl)ethoxy]methyl}sulfanyl)biphenyl-4-yl]pyrazin-2-amine,
5-[3-Fluoro-2'-({[2-(trimethylsilyl)ethoxy]methyl}sulfonyl)biphenyl-4-yl]pyrazin-2-amine hydrochloride,
5-(3-Fluoro-2'-{[3-(methylsulfonyl)propyl]sulfonyl}biphenyl-4-yl)pyrazin-2-amine hydrochloride,
5-(3-Fluoro-2'-{[(2R)-2-methylpiperazin-1-yl]sulfonyl}biphenyl-4-yl)pyrimidin-2-amine,
4'-(2-Aminopyrimidin-5-yl)-3'-fluoro-N-[(1S)-1-(hydroxymethyl)propyl]biphenyl-2-sulfonamide,
4'-(2-Aminopyrimidin-5-yl)-N-(2-cyanoethyl)-N-cyclopropyl-3'-fluorobiphenyl-2-sulfonamide,
4'-(2-Aminopyrimidin-5-yl)-N-(2-cyanoethyl)-3'-fluorobiphenyl-2-sulfonamide,
4'-(2-Aminopyrimidin-5-yl)-3'-fluoro-N-(3-hydroxy-2,2-dimethylpropyl)biphenyl-2-sulfonamide,
racemic (4-{[4'-(2-Aminopyrimidin-5-yl)-3'-fluorobiphenyl-2-yl]sulfonyl}morpholin-2-yl)methanol,
5-(3-Fluoro-2'-{[(2S)-2-methylpiperazin-1-yl]sulfonyl}biphenyl-4-yl)pyrimidin-2-amine,
5-[2'-(Cyclopropylsulfonyl)-3-fluorobiphenyl-4-yl]pyrimidin-2-amine,
4'-(2-Aminopyrimidin-5-yl)-3-fluoro-N-[2-hydroxy-1-(hydroxymethyl)-1-methylethyl]biphenyl-2-sulfonamide,
4'-(2-aminopyrimidin-5-yl)-3'-fluoro-N-methyl-N-[(3S)-piperidin-3-yl]biphenyl-2-sulfonamide,
4'-(2-aminopyrimidin-5-yl)-3'-fluoro-N-methyl-N-[(3R)-piperidin-3-yl]biphenyl-2-sulfonamide,
[(2R)-1-{[4'-(2-Aminopyrimidin-5-yl)-3'-fluorobiphenyl-2-yl]sulfonyl}piperazin-2-yl]methanol,
racemic cis 4'-(2-Aminopyrimidin-5-yl)-3'-fluoro-N-[(cis)-2-hydroxycyclohexyl]biphenyl-2-sulfonamide,
racemic trans 4'-(2-Aminopyrimidin-5-yl)-3'-fluoro-N-[(trans)-2-hydroxycyclohexyl]biphenyl-2-sulfonamide,
4'-(2-Aminopyrimidin-5-yl)-3'-fluoro-N-(2-hydroxyethyl)-N-(1-methylethyl)biphenyl-2-sulfonamide,
4'-(2-Aminopyrimidin-5-yl)-3'-fluoro-N-(trans-4-hydroxycyclohexyl)biphenyl-2-sulfonamide,
4'-(2-Aminopyrimidin-5-yl)-3'-fluoro-N-[(3S)-2-oxopyrrolidin-3-yl]biphenyl-2-sulfonamide,
5-{2'-[(1,1-Dioxidothiomorpholin-4-yl)sulfonyl]-3-fluorobiphenyl-4-yl}pyrimidin-2-amine,
4'-(2-Aminopyrimidin-5-yl)-3'-fluoro-N-[(2R)-2-hydroxypropyl]biphenyl-2-sulfonamide,
1-{[4'-(2-Aminopyrimidin-5-yl)-3'-fluorobiphenyl-2-yl]sulfonyl}azetidin-3-ol trifluoroacetic acid salt,
4'-(2-Aminopyrimidin-5-yl)-3'-fluoro-N-[(3R)-2-oxopiperidin-3-yl]biphenyl-2-sulfonamide trifluoroacetic acid salt,
4'-(2-Aminopyrimidin-5-yl)-3'-fluoro-N-[(3S)-2-oxopiperidin-3-yl]biphenyl-2-sulfonamide trifluoroacetic acid salt,
4'-(2-Aminopyrimidin-5-yl)-3'-fluoro-N-[(1R)-2,2,2-trifluoro-1-methylethyl]biphenyl-2-sulfonamide trifluoroacetic acid salt,
4'-(2-Aminopyrimidin-5-yl)-3'-fluoro-N-[(1R)-1-(hydroxymethyl)-2,2-dimethylpropyl]biphenyl-2-sulfonamide trifluoroacetic acid salt,
4'-(2-Aminopyrimidin-5-yl)-3'-fluoro-N-[(1S)-1-(hydroxymethyl)-2,2-dimethylpropyl]biphenyl-2-sulfonamide trifluoroacetic acid salt,
4'-(2-Aminopyrimidin-5-yl)-3'-fluoro-N-[(1S)-1-(hydroxymethyl)-2-methylpropyl]biphenyl-2-sulfonamide trifluoroacetic acid salt,
4'-(2-Aminopyrimidin-5-yl)-3'-fluoro-N-(2-hydroxy-2-methylpropyl)biphenyl-2-sulfonamide trifluoroacetic acid salt,
4'-(2-Aminopyrimidin-5-yl)-3'-fluoro-N-[(1R)-1-(hydroxymethyl)-2-methylpropyl]biphenyl-2-sulfonamide trifluoroacetic acid salt,
4'-(2-Aminopyrimidin-5-yl)-N-[(2S)-2,3-dihydroxypropyl]-3'-fluorobiphenyl-2-sulfonamide trifluoroacetic acid salt,
4'-(2-Aminopyrimidin-5-yl)-3'-fluoro-N-(2-hydroxyethyl)biphenyl-2-sulfonamide trifluoroacetic acid salt,
[(2R)-1-{[4'-(2-Aminopyrimidin-5-yl)-3'-fluorobiphenyl-2-yl]sulfonyl}pyrrolidin-2-yl]methanol trifluoroacetic acid salt,
[(2S)-1-{[4'-(2-Aminopyrimidin-5-yl)-3'-fluorobiphenyl-2-yl]sulfonyl}pyrrolidin-2-yl]methanol trifluoroacetic acid salt,
4'-(2-Aminopyrimidin-5-yl)-3'-fluoro-N-[(2S)-2-hydroxypropyl]biphenyl-2-sulfonamide trifluoroacetic acid salt,
4'-(2-Aminopyrimidin-5-yl)-3'-fluoro-N-(2-hydroxy-1,1-dimethylethyl)biphenyl-2-sulfonamide trifluoroacetic acid salt,
5-{2'-[(4-Cyclopropylpiperazin-1-yl)sulfonyl]-3-fluorobiphenyl-4-yl}pyrimidin-2-amine trifluoroacetic acid salt,
2-(4-{[4'-(2-Aminopyrimidin-5-yl)-3'-fluorobiphenyl-2-yl]sulfonyl}piperazin-1-yl)ethanol trifluoroacetic acid salt,
4'-(2-Aminopyrimidin-5-yl)-N-(cyclopropylmethyl)-3'-fluorobiphenyl-2-sulfonamide trifluoroacetic acid,
4'-(2-Aminopyrimidin-5-yl)-N-cyclopropyl-3'-fluorobiphenyl-2-sulfonamide trifluoroacetic acid salt,
4'-(2-Aminopyrimidin-5-yl)-3'-fluoro-N-phenylbiphenyl-2-sulfonamide trifluoroacetic acid salt,
4'-(2-Aminopyrimidin-5-yl)-3'-fluoro-N-[(1S)-2-hydroxy-1-methylethyl]biphenyl-2-sulfonamide trifluoroacetic acid salt,
4'-(2-Aminopyrimidin-5-yl)-N-tert-butyl-3'-fluoro-3-methylbiphenyl-2-sulfonamide trifluoroacetic acid salt,
4'-(2-Aminopyrimidin-5-yl)-3'-fluoro-N-methylbiphenyl-2-sulfonamide trifluoroacetic acid salt,
4'-(2-Aminopyrimidin-5-yl)-3'-fluoro-N-[(1R)-2-hydroxy-1-methylethyl]biphenyl-2-sulfonamide trifluoroacetic acid salt,
5-[3-Fluoro-2'-(piperazin-1-ylsulfonyl)biphenyl-4-yl]pyrimidin-2-amine trifluoroacetic acid salt,
4'-(2-Aminopyrimidin-5-yl)-3'-fluoro-N-[(1R)-2,2,2-trifluoro-1-phenylethyl]biphenyl-2-sulfonamide trifluoroacetic acid salt,
4'-(2-Aminopyrimidin-5-yl)-3'-fluoro-N-[(1S)-2,2,2-trifluoro-1-phenylethyl]biphenyl-2-sulfonamide trifluoroacetic acid salt,
5-[2'-(tert-Butylsulfonyl)-3-fluorobiphenyl-4-yl]pyrimidin-2-amine trifluoroacetic acid salt,
4'-(2-Aminopyrimidin-5-yl)-3'-fluoro-N-(2-methylpropyl)biphenyl-2-sulfonamide trifluoroacetic acid salt,
4'-(2-Aminopyrimidin-5-yl)-N-ethyl-3'-fluorobiphenyl-2-sulfonamide trifluoroacetic acid salt,
4'-(2-Aminopyrimidin-5-yl)-3'-fluoro-N-(2,2,2-trifluoro-1,1-dimethylethyl)biphenyl-2-sulfonamide trifluoroacetic acid salt,
4'-(2-Aminopyrimidin-5-yl)-3'-fluoro-N-[(1S)-2,2,2-trifluoro-1-methylethyl]biphenyl-2-sulfonamide trifluoroacetic acid salt,
5-[3-Fluoro-2'-(pyrrolidin-1-ylsulfonyl)biphenyl-4-yl]pyrimidin-2-amine trifluoroacetic acid salt,
4'-(2-Aminopyrimidin-5-yl)-3'-fluoro-N,N-dimethylbiphenyl-2-sulfonamide trifluoroacetic acid salt,
4'-(2-Aminopyrimidin-5-yl)-N,N-diethyl-3'-fluorobiphenyl-2-sulfonamide trifluoroacetic acid salt,
5-[3-Fluoro-2'-(piperidin-1-ylsulfonyl)biphenyl-4-yl]pyrimidin-2-amine trifluoroacetic acid salt,
4'-(2-Aminopyrimidin-5-yl)-3'-fluorobiphenyl-2-sulfonamide trifluoroacetic acid salt,
5-[3-Fluoro-2'-(morpholin-4-ylsulfonyl)biphenyl-4-yl]pyrimidin-2-amine trifluoroacetic acid salt,
5-[3-Fluoro-2'-(methylsulfonyl)biphenyl-4-yl]pyrimidin-2-amine trifluoroacetic acid salt,
4'-(2-aminopyrimidin-5-yl)-N-(tert-butyl)-3'-fluoro-[1,1'-biphenyl]-2-sulfonamide trifluoroacetic acid salt,
4-{[4'-(2-Aminopyrimidin-5-yl)-3'-fluorobiphenyl-2-yl]sulfonyl}piperazin-2-one trifluoroacetic acid salt,
tert-Butyl N-{[4'-(2-aminopyrimidin-5-yl)-3'-fluorobiphenyl-2-yl]sulfonyl}-L-alaninate,
N-{[4'-(2-Aminopyrimidin-5-yl)-3'-fluorobiphenyl-2-yl]sulfonyl}-L-alanine,
N-[4'-(2-Aminopyrimidin-5-yl)-3'-fluorobiphenyl-2-yl]pyrrolidine-1-sulfonamide,
N-[4'-(2-Aminopyrimidin-5-yl)-3'-fluorobiphenyl-2-yl]morpholine-4-sulfonamide,
N'-[4'-(2-Aminopyrimidin-5-yl)-3'-fluorobiphenyl-2-yl]-N,N-dimethylsulfamide,
5-(2'-(2-oxa-6-azaspiro[3.3]heptan-6-ylsulfonyl)-3-fluoro-[1,1'-biphenyl]-4-yl)pyrimidin-2-amine,
6-((4'-(2-aminopyrimidin-5-yl)-3'-fluoro-[1,1'-biphenyl]-2-yl)sulfonyl)-2-thia-6-azaspiro[3.3]heptane 2,2-dioxide,
1-((4'-(2-aminopyrimidin-5-yl)-3'-fluoro-[1,1'-biphenyl]-2-yl)sulfonyl)azetidine-3-carbonitrile,
1-((4'-(2-aminopyrimidin-5-yl)-3'-fluoro-[1,1'-biphenyl]-2-yl)sulfonyl)-3-(trifluoromethyl)azetidin-3-ol,
5-{2'-[(1,1-Dioxidotetrahydro-2H-thiopyran-4-yl)sulfonyl]-3-fluorobiphenyl-4-yl}pyrimidin-2-amine hydrochloride,
2-(((4'-(2-aminopyrimidin-5-yl)-3'-fluoro-[1,1'-biphenyl]-2-yl)sulfonyl)methyl)quinazolin-4(3H)-one,
1-(3-((4'-(2-aminopyrimidin-5-yl)-3'-fluoro-[1,1'-biphenyl]-2-yl)sulfonyl)propyl)-1H-benzo[d]imidazol-2(3H)-one,
5-(2'-{[3-(Cyclohexylsulfonyl)propyl]sulfonyl}-3-fluorobiphenyl-4-yl)pyrimidin-2-amine, TABLE 1-continued 5-{3-Fluoro-2'-[(1-methyl-1H-benzimidazol-2-yl)sulfonyl]biphenyl-4-yl}pyrimidin-2-amine,
5-(2'-{[(3-Cyclopropyl-1,2,4-oxadiazol-5-yl)methyl]sulfonyl}-3-fluorobiphenyl-4-yl)pyrimidin-2-amine,
4'-(2-aminopyrimidin-5-yl)-3'-fluoro-4-(trifluoromethyl)biphenyl-2-sulfonamide,
5-[3-fluoro-2'-(methylsulfonyl)-4'-(trifluoromethyl)biphenyl-4-yl]pyrimidin-2-amine,
4-{[4'-(2-aminopyrimidin-5-yl)-3'-fluoro-4-(trifluoromethyl)biphenyl-2-yl]sulfonyl}piperazin-2-one,
4'-(2-aminopyrimidin-5-yl)-3'-fluoro-N-methyl-4-(trifluoromethyl)biphenyl-2-sulfonamide,
4'-(2-Aminopyrimidin-5-yl)-3'-fluoro-N-(2-hydroxyethyl)-4-(trifluoromethyl)biphenyl-2-sulfonamide,
4'-(2-Aminopyrimidin-5-yl)-N-ethyl-3'-fluoro-4-(trifluoromethyl)biphenyl-2-sulfonamide,
5-{3-Fluoro-2'-[(4-methylpiperazin-1-yl)sulfonyl]-4'-(trifluoromethyl)biphenyl-4-yl}pyrimidin-2-amine,
5-{2'-[(5-Aminopyrimidin-2-yl)sulfanyl]-3-fluorobiphenyl-4-yl}pyrimidin-2-amine formate salt,
5-{2'-[(4-Aminopyrimidin-2-yl)sulfanyl]-3-fluorobiphenyl-4-yl}pyrimidin-2-amine formate salt,
5-{2'-[(5-Aminopyrimidin-4-yl)sulfanyl]-3-fluorobiphenyl-4-yl}pyrimidin-2-amine formate salt,
5-[3-Fluoro-2'-(pyrimidin-2-ylsulfanyl)biphenyl-4-yl]pyrimidin-2-amine hydrochloride,
5-[3-Fluoro-2'-(pyrazin-2-ylsulfanyl)biphenyl-4-yl]pyrimidin-2-amine hydrochloride,
5-{2'-[(6-Aminopyrimidin-4-yl)sulfanyl]-3-fluorobiphenyl-4-yl}pyrimidin-2-amine formate salt,
4-{[4'-(2-Aminopyrimidin-5-yl)-3'-fluorobiphenyl-2-yl]sulfonyl}pyrimidin-2-amine formate salt,
5-{2'-[(6-Aminopyrazin-2-yl)sulfanyl]-3-fluorobiphenyl-4-yl}pyrimidin-2-amine formate salt,
5-{2'-[(5-Aminopyrimidin-4-yl)sulfonyl]-3-fluorobiphenyl-4-yl}pyrimidin-2-amine hydrochloride,
5-[3-Fluoro-2'-({[2-(trimethylsilyl)ethoxy]methyl}sulfonyl)biphenyl-4-yl]pyrimidin-2-amine formate salt,
5-{2'-[(5-Aminopyrimidin-4-yl)sulfonyl]-3-fluorobiphenyl-4-yl}pyrimidin-2-amine hydrochloride,
5-[3-Fluoro-2'-({[2-(trimethylsilyl)ethoxy]methyl}sulfanyl)biphenyl-4-yl]pyrimidin-2-amine,
5-(3-Fluoro-2'-(methylsulfonyl)-[1,1'-biphenyl]-4-yl)pyridin-2-amine,
4'-(6-aminopyridin-3-yl)-N-(tert-butyl)-3'-fluoro-[1,1'-biphenyl]-2-sulfonamide,
4'-(6-aminopyridin-3-yl)-N,N-diethyl-3'-fluoro-[1,1'-biphenyl]-2-sulfonamide,
5-(3-fluoro-2'-(pyrrolidin-1-ylsulfonyl)-[1,1'-biphenyl]-4-yl)pyridin-2-amine,
5-(3-fluoro-2'-(piperidin-1-ylsulfonyl)-[1,1'-biphenyl]-4-yl)pyridin-2-amine,
4'-(6-aminopyridin-3-yl)-N-cyclohexyl-3'-fluoro-[1,1'-biphenyl]-2-sulfonamide,
(S)-4'-(6-aminopyridin-3-yl)-3'-fluoro-N-(1-hydroxypropan-2-yl)-[1,1'-biphenyl]-2-sulfonamide,
4'-(6-aminopyridin-3-yl)-3'-fluoro-N-isobutyl-[1,1'-biphenyl]-2-sulfonamide,
4'-(6-aminopyridin-3-yl)-3'-fluoro-N-(tert-pentyl)-[1,1'-biphenyl]-2-sulfonamide,
4'-(6-aminopyridin-3-yl)-3'-fluoro-N-(1,1,1-trifluoro-2-methylpropan-2-yl)-[1,1'-biphenyl]-2-sulfonamide,
(S)-4'-(6-aminopyridin-3-yl)-3'-fluoro-N-(2,2,2-trifluoro-1-phenylethyl)-[1,1'-biphenyl]-2-sulfonamide,
(R)-4'-(6-aminopyridin-3-yl)-3'-fluoro-N-(1-hydroxypropan-2-yl)-[1,1'-biphenyl]-2-sulfonamide,
4'-(6-aminopyridin-3-yl)-3'-fluoro-N-(1-methylcyclobutyl)-[1,1'-biphenyl]-2-sulfonamide,
4-((4'-(6-aminopyridin-3-yl)-3'-fluoro-[1,1'-biphenyl]-2-yl)sulfonyl)thiomorpholine 1,1-dioxide,
(S)-4'-(6-aminopyridin-3-yl)-3'-fluoro-N-(1,1,1-trifluoropropan-2-yl)-[1,1'-biphenyl]-2-sulfonamide,
5-(2'-((1S,4S)-2-oxa-5-azabicyclo[2.2.1]heptan-5-ylsulfonyl)-3-fluoro-[1,1'-biphenyl]-4-yl)pyridin-2-amine,
tert-butyl 3-((4'-(6-aminopyridin-3-yl)-3'-fluoro-[1,1'-biphenyl]-2-ylsulfonamido)methyl)-3-hydroxyazetidine-1-carboxylate,
4'-(6-aminopyridin-3-yl)-3'-fluoro-N-((3-hydroxyazetidin-3-yl)methyl)-[1,1'-biphenyl]-2-sulfonamide,
2-(1-((4'-(6-aminopyridin-3-yl)-3'-fluoro-[1,1'-biphenyl]-2-yl)sulfonyl)piperidin-4-yl)ethanol,
1-((4'-(6-aminopyridin-3-yl)-3'-fluoro-[1,1'-biphenyl]-2-yl)sulfonyl)piperidin-4-ol,
(1-((4'-(6-aminopyridin-3-yl)-3'-fluoro-[1,1'-biphenyl]-2-yl)sulfonyl)piperidin-4-yl)methanol,
3'-Fluoro-N-[(1S)-2-hydroxy-1-methylethyl]-4'-(1H-pyrrolo[2,3-b]pyridin-5-yl)biphenyl-2-sulfonamide,
3'-Fluoro-N-[(1R)-2-hydroxy-1-methylethyl]-4'-(1H-pyrrolo[2,3-b]pyridin-5-yl)biphenyl-2-sulfonamide,
3'-Fluoro-N-[(3S)-2-oxopyrrolidin-3-yl]-4'-(1H-pyrrolo[2,3-b]pyridin-5-yl)biphenyl-2-sulfonamide,
5-[2'-(Cyclopropylsulfonyl)-3-fluorobiphenyl-4-yl]-1H-pyrrolo[2,3-b]pyridine,
3'-Fluoro-N-(2-hydroxyethyl)-4'-(1H-pyrrolo[2,3-b]pyridin-5-yl)biphenyl-2-sulfonamide,
N-tert-Butyl-3'-fluoro-4'-(1H-pyrrolo[2,3-b]pyridin-5-yl)biphenyl-2-sulfonamide,
3'-Fluoro-4'-(1H-pyrrolo[2,3-b]pyridin-5-yl)biphenyl-2-sulfonamide,
N-[3'-Fluoro-4'-(5H-pyrrolo[2,3-b]pyrazin-2-yl)biphenyl-2-yl]methanesulfonamide,
3'-Fluoro-N,N-dimethyl-4'-(5H-pyrrolo[2,3-b]pyrazin-2-yl)biphenyl-2-sulfonamide,
N-tert-Butyl-3'-fluoro-4'-(5H-pyrrolo[2,3-b]pyrazin-2-yl)biphenyl-2-sulfonamide,
2-[3-Fluoro-2'-(pyrrolidin-1-ylsulfonyl)biphenyl-4-yl]-5H-pyrrolo[2,3-b]pyrazine,
N,N-Diethyl-3'-fluoro-4'-(5H-pyrrolo[2,3-b]pyrazin-2-yl)biphenyl-2-sulfonamide,
2-[3-Fluoro-2'-(piperidin-1-ylsulfonyl)biphenyl-4-yl]-5H-pyrrolo[2,3-b]pyrazine,
2-[3-Fluoro-2'-(morpholin-4-ylsulfonyl)biphenyl-4-yl]-5H-pyrrolo[2,3-b]pyrazine,
3'-Fluoro-4'-(5H-pyrrolo[2,3-b]pyrazin-2-yl)-N-(2,2,2-trifluoro-1-methylethyl)biphenyl-2-sulfonamide,
2-[3-Fluoro-2'-(methylsulfonyl)biphenyl-4-yl]-5H-pyrrolo[2,3-b]pyrazine,
3'-Fluoro-N-[(1R)-2-hydroxy-1-methylethyl]-4'-(5H-pyrrolo[2,3-b]pyrazin-2-yl)biphenyl-2-sulfonamide,
3'-Fluoro-N-methyl-4'-(5H-pyrrolo[2,3-b]pyrazin-2-yl)biphenyl-2-sulfonamide,
3'-Fluoro-N-[(1S)-2-hydroxy-1-methylethyl]-4'-(5H-pyrrolo[2,3-b]pyrazin-2-yl)biphenyl-2-sulfonamide,
1-{[3'-Fluoro-4'-(5H-pyrrolo[2,3-b]pyrazin-2-yl)biphenyl-2-yl]sulfonyl}piperidin-4-amine,
2-{2'-[(1,1-Dioxidothiomorpholin-4-yl)sulfonyl]-3-fluorobiphenyl-4-yl}-5H-pyrrolo[2,3-b]pyrazine,
2-[3,5'-Difluoro-2'-(methylsulfanyl)biphenyl-4-yl]-5H-pyrrolo[2,3-b]pyrazine,
2-[2'-(Ethylsulfanyl)-3-fluorobiphenyl-4-yl]-5H-pyrrolo[2,3-b]pyrazine,
7-[3-Fluoro-2'-(methylsulfonyl)biphenyl-4-yl]-3,4-dihydro-2H-pyrido[3,2-b][1,4]oxazine,
7-[3-Fluoro-2'-(piperidin-1-ylsulfonyl)biphenyl-4-yl]-3,4-dihydro-2H-pyrido[3,2-b][1,4]oxazine,
4'-(3,4-Dihydro-2H-pyrido[3,2-b][1,4]oxazin-7-yl)-3'-fluorobiphenyl-2-sulfonamide,
4'-(3,4-Dihydro-2H-pyrido[3,2-b][1,4]oxazin-7-yl)-3'-fluoro-N-[(1S)-2-hydroxy-1-methylethyl]biphenyl-2-sulfonamide,
1-{[4'-(3,4-Dihydro-2H-pyrido[3,2-b][1,4]oxazin-7-yl)-3'-fluorobiphenyl-2-yl]sulfonyl}piperidin-4-amine,
4'-(3,4-Dihydro-2H-pyrido[3,2-b][1,4]oxazin-7-yl)-3'-fluoro-N-[(1R)-2-hydroxy-1-methylethyl]biphenyl-2-sulfonamide,
4'-(3,4-Dihydro-2H-pyrido[3,2-b][1,4]oxazin-7-yl)-N,N-diethyl-3'-fluorobiphenyl-2-sulfonamide,
7-{2'-[(1,1-Dioxidothiomorpholin-4-yl)sulfonyl]-3-fluorobiphenyl-4-yl}-3,4-dihydro-2H-pyrido[3,2-b][1,4]oxazine,
N-tert-Butyl-4'-(3,4-dihydro-2H-pyrido[3,2-b][1,4]oxazin-7-yl)-3'-fluorobiphenyl-2-sulfonamide,
2-(2-Fluoro-4-{2-[(1-methylethyl)sulfanyl]-5-(trifluoromethyl)pyridin-3-yl}phenyl)-5H-pyrrolo[2,3-b]pyrazine,
5-(2-Fluoro-4-{2-[(1-methylethyl)sulfonyl]pyridin-3-yl}phenyl)pyrazin-2-amine,
5-(2-Fluoro-4-{2-[(1-methylethyl)sulfanyl]pyridin-3-yl}phenyl)pyrazin-2-amine,
2-{2-Fluoro-4-[2-(2,2,2-trifluoroethoxy)pyridin-3-yl]phenyl}-5H-pyrrolo[2,3-b]pyrazine,
2-{2-Fluoro-4-[2-(2-methylpropoxy)pyridin-3-yl]phenyl}-5H-pyrrolo[2,3-b]pyrazine,
2-{2-Fluoro-4-[2-(1-methylethoxy)pyridin-3-yl]phenyl}-5H-pyrrolo[2,3-b]pyrazine,
2-{4-[2-(Cyclopropylmethoxy)pyridin-3-yl]-2-fluorophenyl}-5H-pyrrolo[2,3-b]pyrazine, TABLE 1-continued 5-{2-Fluoro-4-[2-(1-methylethoxy)pyridin-3-yl]phenyl}pyrazin-2-amine,
5-{4-[2-(Cyclopentyloxy)pyridin-3-yl]-2-fluorophenyl}pyrazin-2-amine,
5-{4-[2-(Cyclohexyloxy)pyridin-3-yl]-2-fluorophenyl}pyrazin-2-amine,
5-[2-Fluoro-4-(2-methoxypyridin-3-yl)phenyl]pyrazin-2-amine,
5-{4-[2-(Cyclobutyloxy)pyridin-3-yl]-2-fluorophenyl}pyrazin-2-amine,
tert-Butyl 3-[({3-[4-(5-aminopyrazin-2-yl)-3-fluorophenyl]pyridin-2-yl}oxy)methyl]pyrrolidine-1-carboxylate,
5-{2-Fluoro-4-[2-(pyrrolidin-3-ylmethoxy)pyridin-3-yl]phenyl}pyrazin-2-amine,
5-{2-Fluoro-4-[2-(1-methylethoxy)pyridin-3-yl]phenyl}pyrimidin-2-amine,
5-[4-(2-Aminopyridin-3-yl)-2-fluorophenyl]pyrimidin-2-amine,
4'-(5-amino-6-cyanopyrazin-2-yl)-3'-fluoro-N-[(1R)-2-hydroxy-1-methylethyl]biphenyl-2-sulfonamide,
3-Amino-6-[2'-(cyclopropylsulfonyl)-3-fluorobiphenyl-4-yl]pyrazine-2-carbonitrile,
4'-(5-Amino-6-cyanopyrazin-2-yl)-3'-fluoro-N-[(1S)-2-hydroxy-1-methylethyl]biphenyl-2-sulfonamide,
4'-(5-Amino-6-cyanopyrazin-2-yl)-3'-fluoro-N-(2-hydroxyethyl)biphenyl-2-sulfonamide,
3-Amino-6-{3-fluoro-2'-[(3-oxopiperazin-1-yl)sulfonyl]biphenyl-4-yl}pyrazine-2-carbonitrile,
4'-(5-Amino-6-cyanopyrazin-2-yl)-3'-fluoro-N-[(2R)-2-hydroxypropyl]biphenyl-2-sulfonamide,
3-Amino-6-[3-fluoro-2'-(morpholin-4-ylcarbonyl)biphenyl-4-yl]pyrazine-2-carbonitrile,
4'-(6-Aminopyridazin-3-yl)-N-tert-butyl-3'-fluorobiphenyl-2-sulfonamide,
N-tert-Butyl-3'-fluoro-4'-(7H-pyrrolo[2,3-d]pyrimidin-2-yl)biphenyl-2-sulfonamide,
N-tert-Butyl-3'-fluoro-4'-(1,8-naphthyridin-3-yl)biphenyl-2-sulfonamide,
N-tert-Butyl-3'-fluoro-4'-quinoxalin-6-ylbiphenyl-2-sulfonamide,
N-tert-Butyl-3'-fluoro-4'-(1H-indol-5-yl)biphenyl-2-sulfonamide,
4'-(1H-Benzimidazol-5-yl)-N-tert-butyl-3'-fluorobiphenyl-2-sulfonamide,
4'-(1H-Benzimidazol-5-yl)-3'-fluoro-N-methylbiphenyl-2-sulfonamide,
4'-(1,3-Benzothiazol-5-yl)-N-tert-butyl-3'-fluorobiphenyl-2-sulfonamide,
N-tert-Butyl-3'-fluoro-4'-(1H-pyrrolo[3,2-b]pyridin-6-yl)biphenyl-2-sulfonamide,
3'-Fluoro-N-methyl-4'-(1H-pyrrolo[2,3-b]pyridin-5-yl)biphenyl-2-sulfonamide,
4'-(5-Aminopyridin-2-yl)-N-tert-butyl-3'-fluorobiphenyl-2-sulfonamide,
N-tert-Butyl-4'-(5,6-diaminopyrazin-2-yl)-3'-fluorobiphenyl-2-sulfonamide,
N-tert-Butyl-3'-fluoro-4'-(2-oxo-2,3-dihydro-1H-imidazo[4,5-b]pyrazin-5-yl)biphenyl-2-sulfonamide,
4'-(6-Amino-5-fluoropyridin-3-yl)-N-tert-butyl-3'-fluorobiphenyl-2-sulfonamide,
N-tert-Butyl-4'-(2,3-dihydro-1H-pyrrolo[2,3-b]pyridin-5-yl)-3'-fluorobiphenyl-2-sulfonamide,
N-tert-Butyl-3'-fluoro-4'-(3H-imidazo[4,5-b]pyridin-6-yl)biphenyl-2-sulfonamide,
4'-(5-Amino-6-methoxypyrazin-2-yl)-N-tert-butyl-3'-fluorobiphenyl-2-sulfonamide,
4'-(5-Amino-6-cyanopyrazin-2-yl)-N-tert-butyl-3'-fluorobiphenyl-2-sulfonamide,
4'-(5-Amino-3-cyanopyrazin-2-yl)-N-tert-butyl-3'-fluorobiphenyl-2-sulfonamide,
4'-(6-Amino-4-cyanopyridin-3-yl)-N-tert-butyl-3'-fluorobiphenyl-2-sulfonamide,
4'-(6-amino-2-cyanopyridin-3-yl)-N-(tert-butyl)-3'-fluoro-[1,1'-biphenyl]-2-sulfonamide,
4'-(5-amino-1,3,4-thiadiazol-2-yl)-N-(tert-butyl)-3'-fluoro-[1,1'-biphenyl]-2-sulfonamide,
(R)-4'-(5-amino-1,3,4-thiadiazol-2-yl)-3'-fluoro-N-(1-hydroxypropan-2-yl)-[1,1'-biphenyl]-2-sulfonamide,
4-((4'-(5-amino-1,3,4-thiadiazol-2-yl)-3'-fluoro-[1,1'-biphenyl]-2-yl)sulfonyl)thiomorpholine 1,1-dioxide,
4'-(5-Amino-6-chloropyrazin-2-yl)-N-tert-butyl-3'-fluorobiphenyl-2-sulfonamide,
4'-(5-Amino-6-bromopyrazin-2-yl)-N-tert-butyl-3'-fluorobiphenyl-2-sulfonamide,
6-amino-3-(2'-(cyclopropylsulfonyl)-3-fluoro-[1,1'-biphenyl]-4-yl)picolinonitrile,
N-tert-Butyl-3'-fluoro-4'-[1,2,4]triazolo[4,3-a]pyridin-7-ylbiphenyl-2-sulfonamide,
4'-(5-Amino-6-methylpyrazin-2-yl)-N-tert-butyl-3'-fluorobiphenyl-2-sulfonamide,
4'-(5-Amino-6-methylpyrazin-2-yl)-3'-fluorobiphenyl-2-sulfonamide,
N-tert-Butyl-3'-fluoro-4'-(1H-imidazo[4,5-b]pyrazin-5-yl)biphenyl-2-sulfonamide,
N-tert-Butyl-4'-(5,6-diaminopyridin-3-yl)-3'-fluorobiphenyl-2-sulfonamide,
4'-(5-Amino-6-methylpyrazin-2-yl)-3'-fluoro-N-methylbiphenyl-2-sulfonamide,
4'-(6-Amino-5-cyanopyridin-3-yl)-N-tert-butyl-3'-fluorobiphenyl-2-sulfonamide trifluoroacetic acid salt,
4'-(6-Amino-5-chloropyridin-3-yl)-N-tert-butyl-3'-fluorobiphenyl-2-sulfonamide trifluoroacetic acid salt,
4'-[6-Amino-5-(trifluoromethyl)pyridin-3-yl]-N-tert-butyl-3'-fluorobiphenyl-2-sulfonamide trifluoroacetic acid salt,
4'-[2-Amino-4-(trifluoromethyl)pyrimidin-5-yl]-N-tert-butyl-3'-fluorobiphenyl-2-sulfonamide trifluoroacetic acid salt,
4'-(2-Amino-4-methylpyrimidin-5-yl)-N-tert-butyl-3'-fluorobiphenyl-2-sulfonamide trifluoroacetic acid salt,
N-tert-Butyl-3'-fluoro-4'-[3-(hydroxymethyl)-1H-pyrrolo[2,3-b]pyridin-5-yl]biphenyl-2-sulfonamide,
4'-(7-Amino-1H-indol-5-yl)-3'-fluoro-N-[1-(hydroxymethyl)cyclopentyl]biphenyl-2-sulfonamide,
3'-Fluoro-4'-[3-(hydroxymethyl)-1H-pyrrolo[2,3-b]pyridin-5-yl]-N-methylbiphenyl-2-sulfonamide,
4'-(7-Amino-1H-indol-5-yl)-N-tert-butyl-3'-fluorobiphenyl-2-sulfonamide,
N-[4'-(5-Aminopyrazin-2-yl)-3'-fluorobiphenyl-2-yl]acetamide,
1-[4'-(5-Aminopyrazin-2-yl)-3'-fluorobiphenyl-2-yl]urea,
5-[2,3-Difluoro-2'-(methylsulfonyl)biphenyl-4-yl]pyrazin-2-amine,
4'-(5-Aminopyrazin-2-yl)-N-tert-butyl-2',3'-difluorobiphenyl-2-sulfonamide,
N-[4'-(5-Aminopyrazin-2-yl)-3'-fluoro-2'-methylbiphenyl-2-yl]methanesulfonamide,
4'-(5-Aminopyrazin-2-yl)-2',3'-difluorobiphenyl-2-sulfonamide,
4'-(2-Aminopyrimidin-5-yl)-2',3'-difluoro-N-methylbiphenyl-2-sulfonamide trifluoroacetic acid salt,
4'-(2-Aminopyrimidin-5-yl)-N-tert-butyl-2',3'-difluorobiphenyl-2-sulfonamide trifluoroacetic acid salt,
5-[2',3-Difluoro-4'-(trifluoromethoxy)biphenyl-4-yl]pyrazin-2-amine,
5-(2',3-Difluorobiphenyl-4-yl)pyrazin-2-amine,
5-(2'-Chloro-3-fluorobiphenyl-4-yl)pyrazin-2-amine,
5-(3-Fluoro-2'-methylbiphenyl-4-yl)pyrazin-2-amine,
5-[2',3-Difluoro-4'-(trifluoromethyl)biphenyl-4-yl]pyrazin-2-amine,
5-(3-Fluoro-2'-(trifluoromethyl)biphenyl-4-yl)pyrazin-2-amine,
5-(3-Fluoro-2'-methoxybiphenyl-4-yl)pyrazin-2-amine,
5-(3-Fluoro-2'-(methylsulfanyl)biphenyl-4-yl)pyrazin-2-amine,
5-[3-Fluoro-2'-(trifluoromethoxy)biphenyl-4-yl]pyrazin-2-amine,
4'-(5-Aminopyrazin-2-yl)-3'-fluorobiphenyl-2-ol,
5-[3-Fluoro-2'-(phenylsulfonyl)biphenyl-4-yl]pyrazin-2-amine,
5-(2',3,6'-Trifluorobiphenyl-4-yl)pyrazin-2-amine,
N-[4'-(5-Aminopyrazin-2-yl)-3'-fluorobiphenyl-2-yl]benzenesulfonamide,
5-(2'-Ethyl-3-fluorobiphenyl-4-yl)pyrazin-2-amine,
{[4'-(5-Aminopyrazin-2-yl)-3'-fluorobiphenyl-2-yl]oxy}acetic acid,
5-[3-Fluoro-2'-(1-methylethyl)biphenyl-4-yl]pyrazin-2-amine,
1-[4'-(5-Aminopyrazin-2-yl)-3'-fluorobiphenyl-2-yl]ethanone,
5-[3-Fluoro-2'-(2,2,2-trifluoroethoxy)biphenyl-4-yl]pyrazin-2-amine,
4'-(5-Aminopyrazin-2-yl)-3'-fluorobiphenyl-2-carboxylic acid,
4'-(5-Aminopyrazin-2-yl)-3'-fluorobiphenyl-2-carboxamide,
5-[3-Fluoro-2'-(1-methylethoxy)biphenyl-4-yl]pyrazin-2-amine,
5-{4-[2-(Cyclopropylmethoxy)pyridin-3-yl]-2-fluorophenyl}pyrazin-2-amine,
2-[3,4-Difluoro-2'-(methylsulfonyl)biphenyl-4-yl]-5H-pyrrolo[2,3-b]pyrazine,
N-[4'-(5-Aminopyrazin-2-yl)-3'-fluorobiphenyl-2-yl]-N-methylmethanesulfonmide,
N-[3'-Fluoro-4'-(5H-pyrrolo[2,3-b]pyrazin-2-yl)biphenyl-2-yl]ethanesulfonamide,
N-[3'-Fluoro-4'-(5H-pyrrolo[2,3-b]pyrazin-2-yl)biphenyl-2-yl]-N-methylmethanesulfonamide,
N-[3'-Fluoro-4'-(5H-pyrrolo[2,3-b]pyrazin-2-yl)biphenyl-2-yl]-N-methylethanesulfonamide,
N-[4'-(5-Aminopyrazin-2-yl)-3'-fluorobiphenyl-2-yl]-N-methylmethanesulfonamide,
N-[3'-Fluoro-4'-(5H-pyrrolo[2,3-b]pyrazin-2-yl)biphenyl-2-yl]-2-methylpropane-1-sulfonamide,
N-[4'-(5-Aminopyrazin-2-yl)-3'-fluorobiphenyl-2-yl]-N-ethylmethanesulfonamide,
N-[4'-(5-Aminopyrazin-2-yl)-3'-fluorobiphenyl-2-yl]-N,2-dimethylpropane-1-sulfonamide, TABLE 1-continued 5-[3-Fluoro-2'-(morpholin-4-ylcarbonyl)biphenyl-4-yl]-1H-pyrrolo[2,3-b]pyridine,
5-[3-Fluoro-2'-(morpholin-4-ylcarbonyl)biphenyl-4-yl]pyrimidin-2-amine,
2-[3-Fluoro-2'-(morpholin-4-ylcarbonyl)biphenyl-4-yl]-5H-pyrrolo[2,3-b]pyrazine,
4'-(5-Aminopyrazin-2-yl)-N-tert-butyl-3'-fluorobiphenyl-2-carboxamide,
4'-(5-Aminopyrazin-2-yl)-N-tert-butyl-3',4-difluorobiphenyl-2-carboxamide,
4'-(5-Aminopyrazin-2-yl)-N,N-diethyl-3'-fluorobiphenyl-2-carboxamide,
4'-(2-Aminopyrimidin-5-yl)-3'-fluoro-N-[(1S)-2,2,2-trifluoro-1-methylethyl]biphenyl-2-carboxamide,
4'-(5-Aminopyrazin-2-yl)-3'-fluoro-N-[(1S)-2,2,2-trifluoro-1-methylethyl]biphenyl-2-carboxamide,
5-[3-Fluoro-2'-(piperazin-1-ylcarbonyl)biphenyl-4-yl]pyrazin-2-amine,
5-{2'-[(4-Acetylpiperazin-1-yl)carbonyl]-3-fluorobiphenyl-4-yl}pyrazin-2-amine,
4'-(5-Aminopyrazin-2-yl)-N-cyclohexyl-3'-fluorobiphenyl-2-carboxamide,
5-{2'-[(1,1-Dioxidothiomorpholin-4-yl)carbonyl]-3-fluorobiphenyl-4-yl}pyrazin-2-amine,
4'-(5-Aminopyrazin-2-yl)-3'-fluoro-N-methylbiphenyl-2-carboxamide,
4'-(5-Aminopyrazin-2-yl)-3'-fluoro-N-[(1R)-2,2,2-trifluoro-1-methylethyl]biphenyl-2-carboxamide,
4'-(5-Aminopyrazin-2-yl)-3'-fluoro-N-[(1R)-2-hydroxy-1-methylethyl]biphenyl-2-carboxamide,
4'-(5-Aminopyrazin-2-yl)-3'-fluoro-N-[(1S)-2-hydroxy-1-methylethyl]biphenyl-2-carboxamide,
1-{[4'-(5-Aminopyrazin-2-yl)-3'-fluorobiphenyl-2-yl]carbonyl}piperidin-4-ol,
5-{2'-[(4-Aminopiperidin-1-yl)carbonyl]-3-fluorobiphenyl-4-yl}pyrazin-2-amine,
5-{2'-[(1,1-Dioxidothiomorpholin-4-yl)carbonyl]-3-fluorobiphenyl-4-yl}pyrimidin-2-amine,
4'-(2-Aminopyrimidin-5-yl)-3'-fluoro-N-[(1S)-2-hydroxy-1-methylethyl]biphenyl-2-carboxamide,
4'-(2-Aminopyrimidin-5-yl)-3'-fluoro-N-[(1R)-2,2,2-trifluoro-1-methylethyl]biphenyl-2-carboxamide,
4-{[4'-(5-Aminopyrazin-2-yl)-3'-fluorobiphenyl-2-yl]carbonyl}piperazin-2-one,
4-{[4'-(2-Aminopyrimidin-5-yl)-3'-fluorobiphenyl-2-yl]carbonyl}piperazin-2-one,
5-[3-Fluoro-2'-(morpholin-4-ylcarbonyl)-4'-(trifluoromethyl)biphenyl-4-yl]pyrazin-2-amine,
5-[3-Fluoro-2'-(morpholin-4-ylcarbonyl)-4'-(trifluoromethyl)biphenyl-4-yl]pyrimidin-2-amine,
4-{[3'-Fluoro-4'-(1H-pyrrolo[2,3-b]pyridin-5-yl)biphenyl-2-yl]oxy}pyrimidin-2-amine,
2-{[3'-Fluoro-4'-(1H-pyrrolo[2,3-b]pyridin-5-yl)biphenyl-2-yl]oxy}pyrimidin-4-amine,
5-[3-Fluoro-2'-(pyrimidin-2-yloxy)biphenyl-4-yl]-1H-pyrrolo[2,3-b]pyridine,
5-[3-Fluoro-2'-(pyrimidin-2-yloxy)biphenyl-4-yl]pyrazin-2-amine,
5-[3-Fluoro-2'-(pyrimidin-2-yloxy)biphenyl-4-yl]pyrimidin-2-amine,
2-{[4'-(5-Aminopyrazin-2-yl)-3'-fluorobiphenyl-2-yl]oxy}pyrimidin-4-amine,
5-{2'-[(4-Aminopyrimidin-2-yl)oxy]-3-fluorobiphenyl-4-yl}pyrimidin-2-amine,
6-({[4'-(5-Aminopyrazin-2-yl)-3'-fluorobiphenyl-2-yl]oxy}methyl)pyridine-2-carbonitrile,
2-({[4'-(5-Aminopyrazin-2-yl)-3'-fluorobiphenyl-2-yl]oxy}methyl)pyridine-3-carbonitrile,
2-{[4'-(5-Aminopyrazin-2-yl)-3'-fluorobiphenyl-2-yl]oxy}pyridine-3-carbonitrile,
4-{[4'-(5-Aminopyrazin-2-yl)-3'-fluorobiphenyl-2-yl]oxy}pyrimidin-2-amine,
4-{[4'-(2-Aminopyrimidin-5-yl)-3'-fluorobiphenyl-2-yl]oxy}pyrimidin-2-amine,
6-{[4'-(5-Aminopyrazin-2-yl)-3'-fluorobiphenyl-2-yl]oxy}pyrimidin-4-amine,
5-{2'-[(6-Aminopyrimidin-4-yl)oxy]-3-fluorobiphenyl-4-yl}pyrimidin-2-amine,
4-{[4'-(5-Aminopyrazin-2-yl)-3'-fluorobiphenyl-2-yl]oxy}pyridine-2-carbonitrile,
4-{[4'-(2-Aminopyrimidin-5-yl)-3'-fluorobiphenyl-2-yl]oxy}pyridine-2-carbonitrile,
5-{2'-[(6-Azetidin-1-ylpyrimidin-4-yl)oxy]-3-fluorobiphenyl-4-yl}pyrazin-2-amine,
5-{2'-[(6-Azetidin-1-ylpyrimidin-4-yl)oxy]-3-fluorobiphenyl-4-yl}pyrimidin-2-amine,
5-{3-Fluoro-2'-[(2-methylpyrimidin-4-yl)oxy]biphenyl-4-yl}pyrazin-2-amine,
5-{3-Fluoro-2'-[(2-methylpyrimidin-4-yl)oxy]biphenyl-4-yl}pyrimidin-2-amine,
5-[3-Fluoro-2'-(pyrimidin-2-yloxy)biphenyl-4-yl]-1H-benzimidazole,
6-[3-Fluoro-2'-(pyrimidin-2-yloxy)biphenyl-4-yl]-3H-imidazo[4,5-b]pyridine,
5-{3-Fluoro-2'-[(4-methylpyrimidin-2-yl)oxy]biphenyl-4-yl}pyrazin-2-amine,
5-{3-Fluoro-2'-[(4-methylpyrimidin-2-yl)oxy]biphenyl-4-yl}pyrimidin-2-amine,
5-(3-Fluoro-2'-{[2-(trifluoromethyl)pyrimidin-4-yl]oxy}biphenyl-4-yl)pyrazin-2-amine,
5-(3-Fluoro-2'-{[2-(trifluoromethyl)pyrimidin-4-yl]oxy}biphenyl-4-yl)pyrimidin-2-amine,
5-{3-Fluoro-2'-[(5-methoxypyrimidin-2-yl)oxy]biphenyl-4-yl}pyrazin-2-amine,
5-{3-Fluoro-2'-[(5-methoxypyrimidin-2-yl)oxy]biphenyl-4-yl}pyrimidin-2-amine,
5-[3-Fluoro-2'-(pyrimidin-2-yloxy)-4'-(trifluoromethyl)biphenyl-4-yl]pyrazin-2-amine,
5-[3-Fluoro-2'-(pyrimidin-2-yloxy)-4'-(trifluoromethyl)biphenyl-4-yl]pyrimidin-2-amine,
5-[3-Fluoro-2'-methoxy-4'-(trifluoromethyl)biphenyl-4-yl]pyrazin-2-amine,
4'-(5-Aminopyrazin-2-yl)-3'-fluoro-4-(trifluoromethyl)biphenyl-2-ol,
4-{[4'-(5-Aminopyrazin-2-yl)-3'-fluoro-4-(trifluoromethyl)biphenyl-2-yl]oxy}pyrimidin-2-amine,
2-{[4'-(5-Aminopyrazin-2-yl)-3'-fluoro-4-(trifluoromethyl)biphenyl-2-yl]oxy}pyrimidin-4-amine,
5-[3-Fluoro-4'-(trifluoromethyl)-2'-{[2-(trimethylsilyl)ethoxy]methoxy}biphenyl-4-yl]pyrimidin-2-amine,
4'-(2-Aminopyrimidin-5-yl)-3'-fluoro-4-(trifluoromethyl)biphenyl-2-ol,
5-{2'-[(4-Aminopyrimidin-2-yl)oxy]-3-fluoro-4'-(trifluoromethyl)biphenyl-4-yl}pyrimidin-2-amine,
4-{[4'-(2-Aminopyrimidin-5-yl)-3'-fluoro-4-(trifluoromethyl)biphenyl-2-yl]oxy}pyrimidin-2-amine,
5-{2'-[(6-Aminopyrimidin-4-yl)oxy]-3-fluoro-4'-(trifluoromethyl)biphenyl-4-yl}pyrimidin-2-amine,
5-[3-Fluoro-2',4'-bis(trifluoromethyl)biphenyl-4-yl]pyrazin-2-amine,
4'-(5-Aminopyrazin-2-yl)-3'-fluoro-4-(trifluoromethyl)biphenyl-2-carbonitrile,
5-{5-[2-(Pyrimidin-2-yloxy)-4-(trifluoromethyl)phenyl]pyridin-2-yl}pyrimidin-2-amine,
4-{2-[6-(2-Aminopyrimidin-5-yl)pyridin-3-yl]-5-(trifluoromethyl)phenoxy}pyrimidin-2-amine,
5-{5-[2-(Pyrimidin-2-yloxy)phenyl]pyridin-2-yl}pyrimidin-2-amine,
4-{2-[6-(2-Aminopyrimidin-5-yl)pyridin-3-yl]phenoxy}pyrimidin-2-amine,
5-(5-{2-[(4-Aminopyrimidin-2-yl)oxy]phenyl}pyridin-2-yl)pyrimidin-2-amine,
4'-(5-Aminopyrazin-2-yl)-N-tert-butyl-3'-methylbiphenyl-2-sulfonamide,
4'-(5-Aminopyrazin-2-yl)-N-tert-butyl-3'-methoxybiphenyl-2-sulfonamide,
4'-(5-Aminopyrazin-2-yl)-N-tert-butylbiphenyl-2-sulfonamide,
4'-(5-Aminopyrazin-2-yl)-N,N-dimethylbiphenyl-2-sulfonamide,
5-[2'-(Morpholin-4-ylsulfonyl)biphenyl-4-yl]pyrazin-2-amine,
4'-(5-Aminopyrazin-2-yl)-N-tert-butyl-2'-fluorobiphenyl-2-sulfonamide,
4'-(5-Aminopyrazin-2-yl)-2'-fluoro-N,N-dimethylbiphenyl-2-sulfonamide,
4'-(2-Amino-1,3-oxazol-4-yl)-N-tert-butyl-3'-fluorobiphenyl-2-sulfonamide,
4'-(2-Amino-1,3-thiazol-4-yl)-N-tert-butyl-3'-fluorobiphenyl-2-sulfonamide,
4'-(2-Amino-1,3-thiazol-4-yl)-N,N-diethyl-3'-fluorobiphenyl-2-sulfonamide,
4-[3-Fluoro-2'-(pyrrolidin-1-ylsulfonyl)biphenyl-4-yl]-1,3-thiazol-2-amine,
N-tert-Butyl-3'-fluoro-4'-(8-fluoroimidazo[1,2-a]pyridin-2-yl)biphenyl-2-sulfonamide,
4'-(5-Aminoimidazo[1,2-a]pyridin-2-yl)-N-tert-butyl-3'-fluorobiphenyl-2-sulfonamide,
2-[2'-(tert-Butylsulfamoyl)-3-fluorobiphenyl-4-yl]imidazo[1,2-a]pyridine-6-carboxamide,
2-[2'-(tert-Butylsulfamoyl)-3-fluorobiphenyl-4-yl]imidazo[1,2-a]pyridine-6-carboxamide,
N-tert-Butyl-4'-(5-cyanoimidazo[1,2-a]pyridin-2-yl)-3'-fluorobiphenyl-2-sulfonamide,
N-tert-Butyl-4'-(6-cyanoimidazo[1,2-a]pyridin-2-yl)-3'-fluorobiphenyl-2-sulfonamide, N-tert-Butyl-3'-fluoro-4'-[6-(trifluoromethyl)imidazo[1,2-a]pyridin-2-yl]biphenyl-2-sulfonamide,
Ethyl 2-[2'-(tert-butylsulfamoyl)-3-fluorobiphenyl-4-yl]imidazo[1,2-a]pyridine-5-carboxylate, and
N-tert-Butyl-3'-fluoro-4'-(5-methoxyimidazo[1,2-a]pyridin-2-yl)biphenyl-2-sulfonamide.
5-[2'-(Methylsulfonyl)biphenyl-4-yl]pyrazin-2-amine.
5-[3-Methyl-2'-(methylsulfonyl)biphenyl-4-yl]pyrazin-2-amine.
4'-(5-Aminopyrazin-2-yl)-N,N,3'-trimethylbiphenyl-2-sulfonamide.
4'-(5-Aminopyrazin-2-yl)-3'-hydroxybiphenyl-2-sulfonamide.
N-[4'-(5-Aminopyrazin-2-yl)biphenyl-2-yl]methanesulfonamide.
4'-(5-Aminopyrazin-2-yl)biphenyl-2-sulfonamide.
N-tert-Butyl-3'-fluoro-4'-(2-oxo-2,3-dihydro-1H-indol-5-yl)biphenyl-2-sulfonamide.
N-tert-Butyl-4'-(2,4-dioxo-1,2,3,4-tetrahydroquinazolin-6-yl)-3'-fluorobiphenyl-2-sulfonamide.
4'-(3-Amino-1H-indazol-5-yl)-N-tert-butyl-3'-fluorobiphenyl-2-sulfonamide.
3-Amino-6-[2'-(tert-butylsulfamoyl)-3-fluorobiphenyl-4-yl]pyrazine-2-carboxylic acid.
2-{[4'-(2-Aminopyrimidin-5-yl)-3'-fluorobiphenyl-2-yl]sulfonyl}acetamide.
2-{[4'-(2-Aminopyrimidin-5-yl)-3'-fluorobiphenyl-2-yl]sulfonyl}-N,N-diethylacetamide.
5-{3-Fluoro-2'-[(2-morpholin-4-yl-2-oxoethyl)sulfonyl]biphenyl-4-yl}pyrimidin-2-amine.
5,5'-(3,3''-Difluoro-1,1':2',1''-terphenyl-4,4''-diyl)dipyrazin-2-amine.
4'-(5-Aminopyrazin-2-yl)-3'-fluoro-4-(trifluoromethyl)biphenyl-2-carboxylic acid.
4'-(5-Aminopyrazin-2-yl)-3'-fluoro-4-(trifluoromethyl)biphenyl-2-carbaldehyde.
5-[3-Fluoro-2'-(morpholin-4-ylmethyl)-4'-(trifluoromethyl)biphenyl-4-yl]pyrazin-2-amine.
5-{2'-[(4-Aminopiperidin-1-yl)methyl]-3-fluoro-4'-(trifluoromethyl)biphenyl-4-yl}pyrazin-2-amine.
2-(([4'-(5-Aminopyrazin-2-yl)-3'-fluoro-4-(trifluoromethyl)biphenyl-2-yl]methyl}amino)ethanol.
5-{2'-[(4,6-Dimethylpyrimidin-2-yl)oxy]-3-fluorobiphenyl-4-yl}pyrazin-2-amine.
5-{2'-[(4,6-Dimethylpyrimidin-2-yl)oxy]-3-fluorobiphenyl-4-yl}pyrimidin-2-amine.
5-(3-Fluoro-2'-{[2-(trifluoromethyl)pyridin-4-yl]oxy}biphenyl-4-yl)pyrazin-2-amine.
5-(3-Fluoro-2'-{[2-(trifluoromethyl)pyridin-4-yl]oxy}biphenyl-4-yl)pyrimidin-2-amine.
5-(3-Fluoro-2'-{[4-(trifluoromethyl)pyrimidin-2-yl]oxy}biphenyl-4-yl)pyrazin-2-amine.
5-(3-Fluoro-2'-{[4-(trifluoromethyl)pyrimidin-2-yl]oxy}biphenyl-4-yl)pyrimidin-2-amine.
2-{[4'-(5-Aminopyrazin-2-yl)-3'-fluorobiphenyl-2-yl]oxy}pyrimidin-5-amine.
5-{2'-[(5-Aminopyrimidin-2-yl)oxy]-3-fluorobiphenyl-4-yl}pyrimidin-2-amine.
2-{[4'-(5-Aminopyrazin-2-yl)-3'-fluorobiphenyl-2-yl]oxy}-6-methylpyrimidin-4-amine.
5-{2'-[(4-Amino-6-methylpyrimidin-2-yl)oxy]-3-fluorobiphenyl-4-yl}pyrimidin-2-amine.
6-{[4'-(2-Aminopyrimidin-5-yl)-3'-fluorobiphenyl-2-yl]oxy}pyridine-2-carbonitrile.
6-{[4'-(5-Aminopyrazin-2-yl)-3'-fluorobiphenyl-2-yl]oxy}pyridine-2-carbonitrile.
5-{2'-[(5-Aminopyridin-2-yl)oxy]-3-fluorobiphenyl-4-yl}pyrazin-2-amine.
5-{2'-[(5-Aminopyridin-2-yl)oxy]-3-fluorobiphenyl-4-yl}pyrimidin-2-amine.
5-{2'-[(6-Amino-2-methylpyrimidin-4-yl)oxy]-3-fluorobiphenyl-4-yl}pyrimidin-2-amine.
6-{[4'-(5-Aminopyrazin-2-yl)-3'-fluorobiphenyl-2-yl]oxy}-2-methylpyrimidin-4-amine.
5-(3-Fluoro-2'-{[6-(trifluoromethyl)pyridin-2-yl]oxy}biphenyl-4-yl)pyrimidin-2-amine.
5-(3-Fluoro-2'-{[6-(trifluoromethyl)pyridin-2-yl]oxy}biphenyl-4-yl)pyrazin-2-amine.
6-{[4'-(5-Aminopyrazin-2-yl)-3'-fluorobiphenyl-2-yl]oxy}pyridine-3-carbonitrile.
6-{[4'-(2-Aminopyrimidin-5-yl)-3'-fluorobiphenyl-2-yl]oxy}pyridine-3-carbonitrile.
2-{[4'-(5-Aminopyrazin-2-yl)-3'-fluorobiphenyl-2-yl]oxy}ethanol.
2-{[4'-(2-Aminopyrimidin-5-yl)-3'-fluorobiphenyl-2-yl]oxy}ethanol.
5-[3-Fluoro-2'-(piperidin-4-yloxy)biphenyl-4-yl]pyrazin-2-amine.
5-[3-Fluoro-2'-(piperidin-4-yloxy)biphenyl-4-yl]pyrimidin-2-amine.
5-{3-Fluoro-2'-[(3R)-piperidin-3-yloxy]biphenyl-4-yl}pyrazin-2-amine.
5-{3-Fluoro-2'-[(3R)-piperidin-3-yloxy]biphenyl-4-yl}pyrimidin-2-amine.
5-{3-Fluoro-2'-[(3S)-piperidin-3-yloxy]biphenyl-4-yl}pyrazin-2-amine.
5-{3-Fluoro-2'-[(3S)-piperidin-3-yloxy]biphenyl-4-yl}pyrimidin-2-amine.
5-{2'-[(6-Cyclopropylpyrimidin-4-yl)oxy]-3-fluorobiphenyl-4-yl}pyrazin-2-amine.
5-{2'-[(6-Cyclopropylpyrimidin-4-yl)oxy]-3-fluorobiphenyl-4-yl}pyrimidin-2-amine.
5-{2'-[(2-Aminopyridin-4-yl)oxy]-3-fluorobiphenyl-4-yl}pyrazin-2-amine.
5-{2'-[(2-Aminopyridin-4-yl)oxy]-3-fluorobiphenyl-4-yl}pyrimidin-2-amine.
5-[2'-(2-Aminoethoxy)-3-fluorobiphenyl-4-yl]pyrazin-2-amine.
5-[2'-(2-Aminoethoxy)-3-fluorobiphenyl-4-yl]pyrimidin-2-amine.
{[4'-(5-Aminopyrazin-2-yl)-3'-fluorobiphenyl-2-yl]oxy}acetonitrile.
{[4'-(2-Aminopyrimidin-5-yl)-3'-fluorobiphenyl-2-yl]oxy}acetonitrile.
{[4'-(2-Aminopyrimidin-5-yl)-3'-fluorobiphenyl-2-yl]oxy}acetic acid.
5-{2-Fluoro-4-[2-(piperidin-4-yloxy)pyridin-3-yl]phenyl}pyrazin-2-amine.
5-{2-Fluoro-4-[2-(piperidin-4-yloxy)pyridin-3-yl]phenyl}pyrimidin-2-amine.
5-(4-{2-[(1,1-Dioxidotetrahydro-2H-thiopyran-4-yl)oxy]pyridin-3-yl}-2-fluorophenyl)pyrazin-2-amine.
5-(4-{2-[(1,1-Dioxidotetrahydro-2H-thiopyran-4-yl)oxy]pyridin-3-yl}-2-fluorophenyl)pyrimidin-2-amine.
2-({3-[4-(2-Aminopyrimidin-5-yl)-3-fluorophenyl]pyridin-2-yl}oxy)ethanol.
2-({3-[4-(5-Aminopyrazin-2-yl)-3-fluorophenyl]pyridin-2-yl}oxy)ethanol.
5-(4-{2-[(trans-4-Aminocyclohexyl)oxy]pyridin-3-yl}-2-fluorophenyl)pyrimidin-2-amine.
5-(4-{2-[(trans-4-Aminocyclohexyl)oxy]pyridin-3-yl}-2-fluorophenyl)pyrazin-2-amine formic acid salt.
5-{2-Fluoro-4-[2-(tetrahydro-2H-pyran-4-yloxy)pyridin-3-yl]phenyl}pyrazin-2-amine.
5-{2-Fluoro-4-[2-(tetrahydro-2H-pyran-4-yloxy)pyridin-3-yl]phenyl}pyrimidin-2-amine.
(2R)-2-({3-[4-(5-Aminopyrazin-2-yl)-3-fluorophenyl]pyridin-2-yl}oxy)propan-1-ol.
(2R)-2-({3-[4-(2-Aminopyrimidin-5-yl)-3-fluorophenyl]pyridin-2-yl}oxy)propan-1-ol.
(2S)-2-({3-[4-(5-Aminopyrazin-2-yl)-3-fluorophenyl]pyridin-2-yl}oxy)propan-1-ol.
(2I)-2-({3-[4-(2-Aminopyrimidin-5-yl)-3-fluorophenyl]pyridin-2-yl}oxy)propan-1-ol.
N-(4'-(6-Aminopyridin-3-yl)-3'-fluoro-[1,1'-biphenyl]-2-yl)methanesulfonamide
5-(3-Fluoro-2'-(morpholinosulfonyl)-[1,1'-biphenyl]-4-yl)pyridin-2-amine
4'-(6-Aminopyridin-3-yl)-3'-fluoro-N-methyl-[1,1'-biphenyl]-2-sulfonamide
4'-(6-Aminopyridin-3-yl)-3'-fluoro-[1,1'-biphenyl]-2-sulfonamide trifluoroacetate
5-(2'-((1S,4S)-2-Oxa-5-azabicyclo[2.2.1]heptan-5-ylsulfonyl)-3-fluoro-[1,1'-biphenyl]-4-yl)pyridin-2-amine
4'-(6-Aminopyrazin-3-yl)-3'-fluoro-N-((3-hydroxyazetidin-3-yl)methyl)-[1,1'-biphenyl]-2-sulfonamide
4'-(6-Aminopyridin-3-yl)-3'-fluoro-N-(1-hydroxy-2-methylpropan-2-yl)-[1,1'-biphenyl]-2-sulfonamide
4'-(6-Aminopyridin-3-yl)-3'-fluoro-N-((1S,2S)-1-hydroxy-1-phenylpropan-2-yl)-N-methyl-[1,1'-biphenyl]-2-sulfonamide
4'-(6-Amino-5-fluoropyridin-3-yl)-3'-fluoro-N-(1-hydroxy-2-methylpropan-2-yl)-[1,1'-biphenyl]-2-sulfonamide
(racemic)-1-((4'-(6-Amino-5-fluoropyridin-3-yl)-3'-fluoro-[1,1'-biphenyl]-2-yl)sulfonyl)piperidin-3-ol
4'-(6-Amino-5-fluoropyridin-3-yl)-3'-fluoro-N-((1S,2S)-1-hydroxy-1-phenylpropan-2-yl)-N-methyl-[1,1'-biphenyl]-2-sulfonamide
N-(1-((4'-(6-Amino-5-fluoropyridin-3-yl)-3'-fluoro-[1,1'-biphenyl]-2-yl)sulfonyl)piperidin-4-yl)acetamide
racemic 2-(1-((4'-(6-Amino-5-fluoropyridin-3-yl)-3'-fluoro-[1,1'-biphenyl]-2-yl)sulfonyl)piperidin-3-yl)ethanol.
racemic 1-((4'-(6-Amino-5-fluoropyridin-3-yl)-3'-fluoro-[1,1'-biphenyl]-2-yl)sulfonyl)piperidin-3-yl)methanol.
2-[6-(2-Aminopyrimidin-5-yl)-5-fluoropyridin-3-yl]-N-[(2R)-2-hydroxypropyl]benzenesulfonamide.
2-[6-(2-Aminopyrimidin-5-yl)-5-fluoropyridin-3-yl]-N-ethyl-5-(trifluoromethyl)benzenesulfonamide.
2-[6-(2-Aminopyrimidin-5-yl)-5-fluoropyridin-3-yl]-N-tert-butylbenzenesulfonamide.
5-{5-[2-(Morpholin-4-ylmethyl)-4-(trifluoromethyl)phenyl]pyridin-2-yl}pyrimidin-2-amine.
5-{5-[2-(Morpholin-4-ylcarbonyl)phenyl]pyridin-2-yl}pyrimidin-2-amine.
5-[5-(2-Methoxyphenyl)pyridin-2-yl]pyrimidin-2-amine.

TABLE 1-continued 5-(5-{2-[(3,3-Difluoropiperidin-1-yl)sulfonyl]phenyl}pyridin-2-yl)pyrimidin-2-amine trifluoroacetic acid salt.
5-(5-{2-[(3,3-Difluoropyrrolidin-1-yl)sulfonyl]phenyl}pyridin-2-yl)pyrimidin-2-amine trifluoroacetic acid salt.
5-{5-[2-(Azepan-1-ylsulfonyl)phenyl]pyridin-2-yl}pyrimidin-2-amine trifluoroacetic acid salt.
5-(5-{2-[(4,4-Difluoropiperidin-1-yl)sulfonyl]phenyl}pyridin-2-yl)pyrimidin-2-amine trifluoroacetic acid salt.
2-[6-(2-Aminopyrimidin-5-yl)pyridin-3-yl]-N-ethylbenzenesulfonamide trifluoroacetic acid salt.
2-[6-(2-Aminopyrimidin-5-yl)pyridin-3-yl]-N-(dicyclopropylmethyl)benzenesulfonamide trifluoroacetic acid salt.
2-[6-(2-Aminopyrimidin-5-yl)pyridin-3-yl]-N-[(1S)-2,2,2-trifluoro-1-methylethyl]benzenesulfonamide trifluoroacetic acid salt.
2-[6-(2-Aminopyrimidin-5-yl)pyridin-3-yl]-N-[(1R)-2,2,2-trifluoro-1-methylethyl]benzenesulfonamide trifluoroacetic acid salt.
4-({2-[6-(2-Aminopyrimidin-5-yl)pyridin-3-yl]phenyl}sulfonyl)piperazin-2-one.
2-[6-(2-Aminopyrimidin-5-yl)pyridin-3-yl]-N-[(2S)-2-hydroxypropyl]benzenesulfonamide.
2-[6-(2-Aminopyrimidin-5-yl)pyridin-3-yl]-N-[(2R)-2-hydroxypropyl]benzenesulfonamide.
2-[6-(2-Aminopyrimidin-5-yl)pyridin-3-yl]-N-(2-hydroxyethyl)-5-(trifluoromethyl)benzenesulfonamide.
5-{5-[2-(Cyclopropylsulfonyl)phenyl]pyridin-2-yl}pyrimidin-2-amine trifluoroacetic acid salt.
2-[6-(2-Aminopyrimidin-5-yl)pyridin-3-yl]-N-ethyl-5-(trifluoromethyl)benzenesulfonamide trifluoroacetic acid salt.
2-[6-(2-Aminopyrimidin-5-yl)pyridin-3-yl]N-tert-butylbenzenesulfonamide.
2-[6-(2-Aminopyrimidin-5-yl)pyridin-3-yl]-N-[(1R)-2-hydroxy-1-methylethyl]benzenesulfonamide.
3-Amino-6-{2'-[(4-aminopyrimidin-2-yl)oxy]-3-fluorobiphenyl-4-yl}pyrazine-2-carbonitrile trifluoroacetic acid salt.
5-(4'-Bromo-2',3-difluorobiphenyl-4-yl)pyrazin-2-amine.
5-(4'-Bromo-2',3-difluorobiphenyl-4-yl)-1H-pyrrolo[2,3-b]pyridine.
5-(3-fluoro-2-methoxy-4'-(trifluoromethyl)-[1,1'-biphenyl]-4-yl)pyrazin-2-amine.
5-(2',3,4'-Trifluorobiphenyl-4-yl)pyrazin-2-amine
racemic 5-[3-Fluoro-2'-(methylsulfinyl)biphenyl-4-yl]pyrazin-2-amine
4'-(5-Aminopyrazin-2-yl)-3'-fluorobiphenyl-2-carbonitrile
1-(4'-(5-Aminopyrazin-2-yl)-3'-fluoro-[1,1'-biphenyl]-2-yl)imidazolidin-2-one
4'-(2-Amino-4-cyanopyrimidin-5-yl)-N-tert-butyl-3'-fluorobiphenyl-2-sulfonamide
6-Amino-3-{2'-[(1,1-dioxidothiomorpholin-4-yl)sulfonyl]-3-fluorobiphenyl-4-yl}pyrazine-2-carbonitrile
1-{[4'-(2-Aminopyrimidin-5-yl)-3'-fluorobiphenyl-2-yl]sulfonyl}-N-methylazetidine-3-carboxamide
4'-(5-Amino-3-cyanopyrazin-2-yl)-3'-fluoro-N-(2-hydroxyethyl)biphenyl-2-sulfonamide
4'-(5-Amino-3-cyanopyrazin-2-yl)-3'-fluoro-N-[(2S)-2-hydroxypropyl]biphenyl-2-sulfonamide
4'-(5-Amino-3-cyanopyrazin-2-yl)-3'-fluoro-N-[(2R)-2-hydroxypropyl]biphenyl-2-sulfonamide
1-((4'-(2-Aminopyrimidin-5-yl)-3'-fluoro-[1,1'-biphenyl]-2-yl)sulfonyl)piperidine-4-carboxamide
4'-(5-Amino-3-cyanopyrazin-2-yl)-3'-fluoro-N-[(1R)-2-hydroxy-1-methylethyl]biphenyl-2-sulfonamide
4'-(5-Amino-3-cyanopyrazin-2-yl)-3'-fluoro-N-[(1S)-2-hydroxy-1-methylethyl]biphenyl-2-sulfonamide
4'-(5-Amino-3-cyanopyrazin-2-yl)-3'-fluoro-N-(2-hydroxyethyl)-4-(trifluoromethyl)biphenyl-2-sulfonamide
4'-(5-Amino-3-cyanopyrazin-2-yl)-N-ethyl-3'-fluoro-4-(trifluoromethyl)-[1,1'-biphenyl]-2-sulfonamide
4'-(5-Amino-3-cyanopyrazin-2-yl)-3'-fluoro-N-(3-hydroxy-2,2-dimethylpropyl)biphenyl-2-sulfonamide
6-Amino-3-{3-fluoro-2'-[(3-oxopiperazin-1-yl)sulfonyl]-4'-(trifluoromethyl)biphenyl-4-yl}pyrazine-2-carbonitrile
N-(2-{[4'-(2-Aminopyrimidin-5-yl)-3'-fluorobiphenyl-2-yl]sulfonyl}ethyl)benzamide
1-{[4'-(2-Aminopyrimidin-5-yl)-3'-fluorobiphenyl-2-yl]sulfonyl}-3,3-dimethylbutan-2-one
5-[3-Fluoro-2'-(pyrimidin-2-ylsulfonyl)biphenyl-4-yl]pyrimidin-2-amine
5-[3-Fluoro-2'-(pyrazin-2-ylsulfonyl)biphenyl-4-yl]pyrimidin-2-amine
5-[3-Fluoro-2'-(pyrimidin-4-ylsulfonyl)biphenyl-4-yl]pyrimidin-2-amine
5-{2'-[(6-Aminopyrimidin-4-yl)sulfonyl]-3-fluorobiphenyl-4-yl}pyrimidin-2-amine
5-{2'-[(4-Aminopyrimidin-2-yl)sulfonyl]-3-fluorobiphenyl-4-yl}pyrimidin-2-amine
5-{2'-[(5-Aminopyrazin-2-yl)sulfonyl]-3-fluorobiphenyl-4-yl}pyrimidin-2-amine
4-{[4'-(2-Aminopyrimidin-5-yl)-3'-fluorobiphenyl-2-yl]sulfonyl}pyrimidin-2-amine
5-{2'-[(6-Aminopyrazin-2-yl)sulfonyl]-3-fluorobiphenyl-4-yl}pyrimidin-2-amine
6-{[4'-(5-Aminopyrazin-2-yl)-3'-fluorobiphenyl-2-yl]sulfonyl}pyrimidin-4-amine
2-{[4'-(5-Aminopyrazin-2-yl)-3'-fluorobiphenyl-2-yl]sulfonyl}pyrimidin-4-amine
5-{2'-[(Cyclopropylmethyl)sulfonyl]-3-fluorobiphenyl-4-yl}pyrimidin-2-amine
6-Amino-3-[2'-(cyclopropylsulfonyl)-3-fluorobiphenyl-4-yl]pyrazine-2-carbonitrile
1-{[4'-(5-Aminopyrazin-2-yl)-3'-fluorobiphenyl-2-yl]sulfonyl}cyclopentanecarbonitrile
1-{[4'-(5-Aminopyrazin-2-yl)-3'-fluorobiphenyl-2-yl]sulfonyl}cyclopentanecarboxamide
2-{[4'-(2-Aminopyrimidin-5-yl)-3'-fluorobiphenyl-2-yl]sulfonyl}-2-methylpropanenitrile
2-{[4'-(5-Aminopyrazin-2-yl)-3'-fluorobiphenyl-2-yl]sulfonyl}-2-methylpropanamide
5-{2'-[(2-Amino-1,1-dimethylethyl)sulfonyl]-3-fluorobiphenyl-4-yl}pyrimidin-2-amine
2-{[4'-(2-Aminopyrimidin-5-yl)-3'-fluorobiphenyl-2-yl]sulfonyl}-2-methylpropanenitrile
2-{[4'-(5-Aminopyrazin-2-yl)-3'-fluorobiphenyl-2-yl]sulfonyl}-2-methylpropanamide
5-{2'-[(2-Amino-1,1-dimethylethyl)sulfonyl]-3-fluorobiphenyl-4-yl}pyrazin-2-amine
1-{[4'-(2-Aminopyrimidin-5-yl)-3'-fluorobiphenyl-2-yl]sulfonyl}cyclopentanecarbonitrile
1-{[4'-(2-Aminopyrimidin-5-yl)-3'-fluorobiphenyl-2-yl]sulfonyl}cyclopentanecarboxamide
5-(2'-{[1-(Aminomethyl)cyclopentyl]sulfonyl}-3-fluorobiphenyl-4-yl)pyrimidin-2-amine
5-{[4'-(5-Aminopyrazin-2-yl)-3'-fluorobiphenyl-2-yl]sulfonyl}pyrazin-2-amine
5-{2'-[(6-Aminopyrimidin-2-yl)sulfonyl]-3-fluorobiphenyl-4-yl}pyrazin-2-amine
5-(3-Fluoro-2'-(pyrimidin-4-ylthio)-[1,1'-biphenyl]-4-yl)pyrazin-2-amine
5-{2'-[(5-Aminopyrazin-2-yl)sulfonyl]-3-fluorobiphenyl-4-yl}pyrazin-2-amine
6-Amino-3-{2'-[(4-aminopyrimidin-2-yl)oxy]-3-fluorobiphenyl-4-yl}pyrazine-2-carbonitrile
8-Amino-3-[3-fluoro-2'-(pyrimidin-2-yloxy)-4'-(trifluoromethyl)biphenyl-4-yl]pyrazine-2-carbonitrile
6-Amino-3-[3-fluoro-2'-(pyrimidin-2-yloxy)biphenyl-4-yl]pyrazine-2-carbonitrile
N-(tert-Butyl)-3'-fluoro-4'-(5-(methylsulfonamido)pyrazin-2-yl)-[1,1'-biphenyl]-2-sulfonamide
5-{2'-[(Ethylsulfonyl)methyl]-3-fluorobiphenyl-4-yl}pyrazin-2-amine hydrogen chloride salt
5-{3-Fluoro-2'-[(methylsulfonyl)methyl]biphenyl-4-yl}pyrazin-2-amine
5-(3-Fluoro-2'-{[(1-methylethyl)sulfonyl]methyl}biphenyl-4-yl)pyrazin-2-amine
5-{3-Fluoro-2'-[(pyrimidin-2-ylsulfonyl)methyl]biphenyl-4-yl}pyrazin-2-amine
2-({[4'-(5-Aminopyrazin-2-yl)-3'-fluorobiphenyl-2-yl]methyl}sulfonyl)pyrimidin-4-amine
racemic 5-(3-Fluoro-2'-{[2-(trifluoromethyl)morpholin-4-yl]carbonyl}biphenyl-4-yl)pyrazin-2-amine
1-{[4'-(5-Aminopyrazin-2-yl)-3'-fluorobiphenyl-2-yl]carbonyl}azetidin-3-ol
4'-(5-Aminopyrazin-2-yl)-3'-fluoro-N-(tetrahydro-2H-pyran-4-yl)biphenyl-2-carboxamide
5-{2'-[(1,1-Dioxidothiomorpholin-4-yl)carbonyl]-3-fluoro-4'-(trifluoromethyl)biphenyl-4-yl}pyrazin-2-amine
1-(4-{[4'-(5-Aminopyrazin-2-yl)-3'-fluorobiphenyl-2-yl]carbonyl}morpholin-2-yl)ethanol (diastereomeric mixture).
1-(4-{[4'-(2-Aminopyrimidin-5-yl)-3'-fluorobiphenyl-2-yl]carbonyl}morpholin-2-yl)ethanol (diastereomeric mixture).
4'-(5-Aminopyrazin-2-yl)-3'-fluoro-N-(2-hydroxyethyl)biphenyl-2-carboxamide
4'-(2-Aminopyrimidin-5-yl)-3'-fluoro-N-(2-hydroxyethyl)biphenyl-2-carboxamide
(3R)-1-{[4'-(5-Aminopyrazin-2-yl)-3'-fluorobiphenyl-2-yl]carbonyl}piperidin-3-ol
(cis/trans) 4'-(5-Aminopyrazin-2-yl)-3'-fluoro-N-(4-hydroxycyclohexyl)biphenyl-2-carboxamide TABLE 1-continued (3R)-1-{[4'-(2-Aminopyrimidin-5-yl)-3'-fluorobiphenyl-2-yl]carbonyl}piperidin-3-ol
(cis/trans) 4'-(2-Aminopyrimidin-5-yl)-3'-fluoro-N-(4-hydroxycyclohexyl)biphenyl-2-carboxamide
racemic 5-(3-Fluoro-2'-{[2-(trifluoromethyl)morpholin-4-yl]carbonyl}biphenyl-4-yl)pyrimidin-2-amine
(3S)-1-{[4'-(2-Aminopyrimidin-5-yl)-3'-fluorobiphenyl-2-yl]carbonyl}piperidin-3-ol
(3S)-1-{[4'-(5-Aminopyrazin-2-yl)-3'-fluorobiphenyl-2-yl]carbonyl}piperidin-3-ol
(3R)-1-{[4'-(5-Aminopyrazin-2-yl)-3'-fluorobiphenyl-2-yl]carbonyl}pyrrolidin-3-ol
(3R)-1-{[4'-(2-Aminopyrimidin-5-yl)-3'-fluorobiphenyl-2-yl]carbonyl}pyrrolidin-3-ol
(3S)-1-{[4'-(5-Aminopyrazin-2-yl)-3'-fluorobiphenyl-2-yl]carbonyl}pyrrolidin-3-ol
(3S)-1-{[4'-(2-Aminopyrimidin-5-yl)-3'-fluorobiphenyl-2-yl]carbonyl}pyrrolidin-3-ol
5-{2'-[(2,8-Dimethylmorpholin-4-yl)carbonyl]-3-fluorobiphenyl-4-yl}pyrazin-2-amine (diastereoisomeric mixture).
5-(3-Fluoro-2'-{[(3S)-3-methylmorpholin-4-yl]carbonyl}biphenyl-4-yl)pyrazin-2-amine
5-(3-Fluoro-2'-{[(3R)-3-methylmorpholin-4-yl]carbonyl}biphenyl-4-yl)pyrazin-2-amine
5-(3-Fluoro-2'-{[(2S)-2-methylmorpholin-4-yl]carbonyl}biphenyl-4-yl)pyrazin-2-amine
5-(3-Fluoro-2'-{[(2S)-2-methylmorpholin-4-yl]carbonyl}biphenyl-4-yl)pyrimidin-2-amine
5-(3-Fluoro-2'-{[(3S)-3-methylmorpholin-4-yl]carbonyl}biphenyl-4-yl)pyrimidin-2-amine
5-(3-Fluoro-2'-{[(3R)-3-methylmorpholin-4-yl]carbonyl}biphenyl-4-yl)pyrimidin-2-amine
5-{2'-[(2,6-Dimethylmorpholin-4-yl)carbonyl]-3-fluorobiphenyl-4-yl}pyrimidin-2-amine (diastereoisomeric mixture)
5-{2-Fluoro-4-[2-(morpholin-4-ylcarbonyl)pyridin-3-yl]phenyl}-1H-pyrrolo[2,3-b]pyridine
5-{2-Fluoro-4-[2-(morpholin-4-ylcarbonyl)pyridin-3-yl]phenyl}pyrimidin-2-amine
5-{2-Fluoro-4-[2-(morpholin-4-ylcarbonyl)pyridin-3-yl]phenyl}pyrazin-2-amine
2-[4-(5-Aminopyrazin-2-yl)-3-fluoro-phenyl]-N-tert-butyl-5-(trifluoromethyl)benzamide
2-[4-(5-Aminopyrazin-2-yl)-3-fluoro-phenyl]-N-[(1R)-2-hydroxy-1-methyl-ethyl]-5-(trifluoromethyl)benzamide
2-[4-(5-Aminopyrazin-2-yl)-3-fluoro-phenyl]-N-[(1S)-2-hydroxy-1-methyl-ethyl]-5-(trifluoromethyl)benzamide
2-[4-(5-Aminopyrazin-2-yl)-3-fluoro-phenyl]-5-(trifluoromethyl)-N-[(1R)-2,2,2-trifluoro-1-methyl-ethyl]benzamide
2-[4-(2-Aminopyrimidin-5-yl)-3-fluoro-phenyl]-5-(trifluoromethyl)-N-[(1S)-2,2,2-trifluoro-1-methyl-ethyl]benzamide
2-[4-(2-Aminopyrimidin-5-yl)-3-fluoro-phenyl]-5-(trifluoromethyl)-N-[(1R)-2,2,2-trifluoro-1-methyl-ethyl]benzamide
2-[4-(5-Aminopyrazin-2-yl)-3-fluoro-phenyl]-5-(trifluoromethyl)-N-[(1S)-2,2,2-trifluoro-1-methyl-ethyl]benzamide
[2-[4-(2-Aminopyrimidin-5-yl)-3-fluoro-phenyl]phenyl]-(3-hydroxyazetidin-1-yl)methanone
[2-[4-(2-Aminopyrimidin-5-yl)-3-fluoro-phenyl]phenyl]-[4-(methylamino)-1-piperidyl]methanone
[2-[4-(2-Aminopyrimidin-5-yl)-3-fluoro-phenyl]-5-(trifluoromethyl)phenyl]-(1,1-dioxo-1,4-thiazinan-4-yl)methanone
2-[4-(2-Aminopyrimidin-5-yl)-3-fluoro-phenyl]-N-tert-butyl-5-(trifluoromethyl)benzamide
[2-[4-(5-Aminopyrazin-2-yl)-3-fluoro-phenyl]-5-(trifluoromethyl)phenyl]-(4-hydroxy-1-piperidyl)methanone
[2-[4-(2-Aminopyrimidin-5-yl)-3-fluoro-phenyl]-5-(trifluoromethyl)phenyl]-(4-hydroxy-1-piperidyl)methanone
2-[4-(2-Aminopyrimidin-5-yl)-3-fluoro-phenyl]-N-tetrahydropyran-4-yl-benzamide
racemic [2-[4-(5-Aminopyrazin-2-yl)-3-fluoro-phenyl]phenyl]-[2-(hydroxymethyl)morpholin-4-yl]methanone
racemic [2-[4-(2-Aminopyrimidin-5-yl)-3-fluoro-phenyl]phenyl]-[2-(hydroxymethyl)morpholin-4-yl]methanone
N-{3-[4-(2-Aminopyrimidin-5-yl)-3-fluorophenyl]pyridin-2-yl}-2,2-dimethylpropanamide
N-{3-[4-(5-Aminopyrazin-2-yl)-3-fluorophenyl]pyridin-2-yl}-2,2-dimethylpropanamide
N-{3-[3-Fluoro-4-(1H-pyrrolo[2,3-b]pyridin-5-yl)phenyl]pyridin-2-yl}-2,2-dimethylpropanamide
racemic 5-(2-Fluoro-4-(2-(pyrrolidin-3-ylsulfonyl)pyridin-3-yl)phenyl)pyrazin-2-amine hydrochloride
5-(2-Fluoro-4-(2-(pyrrolidin-3-ylsulfonyl)pyridin-3-yl)phenyl)pyrimidin-2-amine formic acid salt.
5-(4-(2-(Cyclobutylsulfonyl)pyridin-3-yl)-2-fluorophenyl)pyrimidin-2-amine hydrochloride.
5-(4-(2-(Cyclobutylsulfonyl)pyridin-3-yl)-2-fluorophenyl)pyrazin-2-amine hydrochloride
5-(4-(2-(Cyclohexlsulfonyl)pyridin-3-yl)-2-fluorophenyl)pyrimidin-2-amine hydrochloride
5-(4-(2-(Cyclohexylsulfonyl)pyridin-3-yl)-2-fluorophenyl)pyrazin-2-amine hydrochloride
5-(4-(2-(Cyclopentylsulfonyl)pyridin-3-yl)-2-fluorophenyl)pyrimidine-2-amine hydrochloride
5-(4-(2-(Cyclopentylsulfonyl)pyridin-3-yl)-2-fluorophenyl)pyrazin-2-amine hydrochloride
5-(4-(2-(tert-Butylsulfonyl)pyridin-3-yl)-2-fluorophenyl)pyrimidin-2-amine formic acid salt.
5-(4-(2-(tert-Butylsulfonyl)pyridin-3-yl)-2-fluorophenyl)pyrazin-2-amine formic acid salt.
racemic 5-(4-(2-(sec-Butylsulfonyl)pyridin-3-yl)-2-fluorophenyl)pyrimidin-2-amine formate
racemic 5-(4-(2-(sec-Butylsulfonyl)pyridin-3-yl)-2-fluorophenyl)pyrazin-2-amine formate
1-((3-(4-(2-Aminopyrimidin-5-yl)-3-fluorophenyl)pyridine-2-yl)sulfonyl)piperidin-1-yl)ethanone
1-((3-(4-(2-Aminopyrazin-5-yl)-3-fluorophenyl)pyridine-2-yl)sulfonyl)piperidin-1-yl)ethanone hydrogen chloride salt
5-(2-Fluoro-4-(2-((3-methoxypropyl)sulfonyl)pyridine-3-yl)phenyl)pyrimidin-2-amine hydrogen chloride salt.
5-(2-Fluoro-4-(2-((3-methoxypropyl)sulfonyl)pyridine-3-yl)phenyl)pyrazin-2-amine hydrogen chloride salt.
4-((3-(4-(2-aminopyrimidin-5-yl)-3-fluorophenyl)pyridine-2-yl)sulfonyl)tetrahydro-2H-thiopyran 1,1-dioxide
4-((3-(4-(2-Aminopyrazin-5-yl)-3-fluorophenyl)pyridine-2-yl)sulfonyl)tetrahydro-2H-thiopyran 1,1-dioxide
5-(2-Fluoro-4-(2-((2-morpholinoethyl)sulfonyl)pyridine-3-yl)phenyl)pyrimidin-2-amine formic acid salt.
5-(2-Fluoro-4-(2-((2-morpholinoethyl)sulfonyl)pyridine-3-yl)phenyl)pyrazin-2-amine
5-(2-Fluoro-4-(2-(((tetrahydro-2H-pyran-4-yl)methyl)sulfonyl)pyridine-3-yl)pyrimidin-2-amine formic acid salt.
5-(2-Fluoro-4-(2-(((tetrahydro-2H-pyran-4-yl)methyl)sulfonyl)pyridine-3-yl)pyrazin-2-amine formic acid salt.
5-(2-Fluoro-4-{2-[(1-methylethyl)sulfonyl]pyridin-3-yl}phenyl)pyrimidin-2-amine
5-(2-Fluoro-4-(2-(isopropylsulfonyl)pyridine-3-yl)phenyl)-1H-pyrrolo[2,3-b]pyridine
5-{2-Fluoro-4-[2-(piperidin-4-ylsulfonyl)pyridin-3-yl]phenyl}pyrimidin-2-amine formic acid salt.
5-{4-[2-(Cyclopropylsulfonyl)pyridin-3-yl]-2-fluorophenyl}pyrimidin-2-amine formic acid salt.
5-{4-[2-(Cyclopropylsulfonyl)pyridin-3-yl]-2-fluorophenyl}pyrazin-2-amine formic acid salt.
5-{2-Fluoro-4-[2-(tetrahydro-2H-pyran-4-ylsulfonyl)pyridin-3-yl]phenyl}pyrazin-2-amine hydrochloride
5-{2-Fluoro-4-[2-(tetrahydro-2H-pyran-4-ylsulfonyl)pyridin-3-yl]phenyl}pyrimidin-2-amine formic acid salt.
5-{2-Fluoro-4-[2-(piperidin-4-ylsulfonyl)pyridin-3-yl]phenyl}pyrazin-2-amine hydrochloride
5-(2,3-Difluorobiphenyl-4-yl)pyrazin-2-amine.
5-(3-Fluoro-2-methoxybiphenyl-4-yl)pyrazin-2-amine.
5-[3-Fluoro-2-methoxy-2'-(methylsulfonyl)biphenyl-4-yl]pyrazin-2-amine.
4'-(5-Aminopyrazin-2-yl)-N-tert-butyl-3'-fluoro-2'-methoxybiphenyl-2-sulfonamide.
N-[4'-(5-Aminopyrazin-2-y)-3'-fluoro-2'-methoxybiphenyl-2-yl]methanesulfonamide.
5-(3-Fluoro-2'-(pyrazin-2-yl)-[1,1'-biphenyl]-4-yl)pyrazin-2-amine
5-(3-Fluoro-2'-pyrazin-2-ylbiphenyl-4-yl)pyrimidin-2-amine.
5,5'-(3'-Fluorobiphenyl-2,4'-diyl)dipyrazin-2-amine.
5-[2'-(5-Aminopyrazin-2-yl)-3-fluorobiphenyl-4-yl]pyrimidin-2-amine.
5-[2'-(6-Aminopyrazin-2-yl)-3-fluorobiphenyl-4-yl]pyrazin-2-amine.
5-[4'-(5-Aminopyrazin-2-yl)-3'-fluorobiphenyl-2-yl]pyrimidin-2-amine.
5,5'-(3'-Fluorobiphenyl-2,4'-diyl)dipyrimidin-2-amine.
5-[4'-(5-Aminopyrazin-2-yl)-3'-fluoro-5-(trifluoromethyl)biphenyl-2-yl]pyrimidin-2-amine.
5-[3-Fluoro-2'-(2-methoxypyrimidin-5-yl)biphenyl-4-yl]pyrazin-2-amine.
5-[3-Fluoro-2'-(1-methyl-1H-pyrazol-4-yl)bipheny-4-yl]pyrazin-2-amine.
5-(3-Fluoro-2'-pyrimidin-5-ylbiphenyl-4-yl)pyrazin-2-amine.
5-[4'-(5-Aminopyrazin-2-yl)-3'-fluorobiphenyl-2-yl]pyrimidine-2-carbonitrile.

TABLE 1-continued

5-[3-Fluoro-2'-(2-morpholin-4-ylpyrimidin-5-yl)biphenyl-4-yl]pyrazin-2-amine.
1-{4-[4'-(5-Aminopyrazin-2-yl)-3'-fluorobiphenyl-2-yl]-1H-pyrazol-1-yl}-2-methylpropan-2-ol.
5-[3-Fluoro-2'-(1,2,3,6-tetrahydropyridin-4-yl)-4'-(trifluoromethyl)biphenyl-4-yl]pyrazin-2-amine.
5-[4'-(5-Aminopyrazin-2-yl)-3'-fluoro-4-(trifluoromethyl)biphenyl-2-yl]pyrimidin-2-amine.
5-{2-[6-(2-Aminopyrimidin-5-yl)-5-fluoropyridin-3-yl]phenyl}pyrimidin-2-amine.
5-{5-[2-(2-Aminopyrimidin-5-yl)phenyl]pyridin-2-yl}pyrimidin-2-amine.
5-[2'-(1,1-Dioxidoisothiazolidin-2-yl)-3-fluorobiphenyl-4-yl]pyrazin-2-amine
5-[2'-(1,1-Dioxido-1,2-thiazinan-2-yl)-3-fluorobiphenyl-4-yl]pyrazin-2-amine
5-[2'-(1,1-Dioxidoisothiazolidin-2-yl)-3-fluorobiphenyl-4-yl]pyrimidin-2-amine
5-[2-Fluoro-4-(2-pyrrolidin-1-ylpyridin-3-y)phenyl]pyrazin-2-amine
1-[4'-(5-Aminopyrazin-2-yl)-3'-fluorobiphenyl-2-yl]pyrrolidin-2-one
5-(4'-Bromo-2',3-difluorobiphenyl-4-yl)-1H-pyrrolo[2,3-b]pyridine
5-(2'3,4'-Trifluorobiphenyl-4-yl)pyrazin-2-amine
5-[3-Fluoro-2'-(methylsulfonyl)biphenyl-4-yl]pyrazin-2-amine
5-[2'-(Methylsulfonyl)biphenyl-4-yl]pyrazin-2-amine
5-[3-Methyl-2'-(methylsulfonyl)biphenyl-4-yl]pyrazin-2-amine
4'-(5-Aminopyrazin-2-yl)-3'-hydroxybiphenyl-2-sulfonamide
N-[4'-(5-Aminopyrazin-2-yl)biphenyl-2-yl]methanesulfonamide
4'-(5-Aminopyrazin-2-yl)biphenyl-2-sulfonamide
4'-(6-Aminopyridazin-3-yl)-3'-fluorobiphenyl-2-sulfonamide
N-tert-Butyl-4'-(2,4-dioxo-1,2,3,4-tetrahydroquinazolin-6-yl)-3'-fluorobiphenyl-2-sulfonamide
3-Amino-6-[2'-(tert-butylsulfamoyl)-3-fluorobiphenyl-4-yl]pyrazine-2-carboxylic acid
4'-(5-Aminopyrazin-2-yl)-N-tert-butyl-3'-fluoro-5-(trifluoromethyl)biphenyl-2-sulfonamide
5-{5-[2-(Cyclopropylsulfonyl)phenyl]pyridin-2-yl}pyrimidin-2-amine
2-{[4'-(2-Aminopyrimidin-5-yl)-3'-fluorobiphenyl-2-yl]sulfonyl}acetamide
2-{[4'-(2-Aminopyrimidin-5-yl)-3'-fluorobiphenyl-2-yl]sulfonyl}-N,N-diethylacetamide
5-{3-Fluoro-2'-[(2-morpholin-4-yl-2-oxoethyl)sulfonyl]biphenyl-4-yl}pyrimidin-2-amine
5-[5-(2-Methoxyphenyl)pyridin-2-yl]pyrimidin-2-amine
5-{5-[2-(Morpholin-4-ylcarbonyl)phenyl]pyridin-2-yl}pyrimidin-2-amine
4'-(2-Amino-4-cyanopyrimidin-5-yl)-N-tert-butyl-3'-fluorobiphenyl-2-sulfonamide
5-[3-Fluoro-2'-(pyrimidin-2-ylsulfonyl)biphenyl-4-yl]pyrimidin-2-amine
5-[3-Fluoro-2'-(pyrazin-2-ylsulfonyl)biphenyl-4-yl]pyrimidin-2-amine
N-(2-{[4'-(2-Aminopyrimidin-5-yl)-3'-fluorobiphenyl-2-yl]sulfonyl}ethyl)benzamide
5-[3-Fluoro-2'-(pyrimidin-4-ylsulfonyl)biphenyl-4-yl]pyrimidin-2-amine
5-{2'-[(6-Aminopyrimidin-4-yl)sulfonyl]-3-fluorobiphenyl-4-yl}pyrimidin-2-amine
5-{2'-[(4-Aminopyrimidin-2-yl)sulfonyl]-3-fluorobiphenyl-4-yl}pyrimidin-2-amine
5-{2'-[(5-Aminopyrazin-2-yl)sulfonyl]-3-fluorobiphenyl-4-yl}pyrimidin-2-amine
5-(2-Fluoro-4-{2-[(2-morpholin-4-ylethyl)sulfonyl]pyridin-3-yl}phenyl)pyrimidin-2-amine
5-[4'-(5-Aminopyrazin-2-yl)-3'-fluoro-5-(trifluoromethyl)biphenyl-2-yl]pyrimidin-2-amine
5-{5-[2-(2-Aminopyrimidin-5-yl)phenyl]pyridin-2-yl}pyrimidin-2-amine
4-{[4'-(2-Aminopyrimidin-5-yl)-3'-fluorobiphenyl-2-yl]sulfonyl}pyrimidin-2-amine
5-{2-Fluoro-4-[2-(morpholin-4-ylcarbonyl)pyridin-3-yl]phenyl}pyrazin-2-amine
5-{2-Fluoro-4-[2-(morpholin-4-ylcarbonyl)pyridin-3-yl]phenyl}pyrimidin-2-amine
5-(3-Fluoro-2'-{[(3S)-3-methylmorpholin-4-yl]carbonyl}biphenyl-4-yl)pyrimidin-2-amine
5-{2-Fluoro-4-[2-(piperidin-4-ylsulfonyl)pyridin-3-yl]phenyl}pyrimidin-2-amine
(3S)-1-{[4'-(2-Aminopyrimidin-5-yl)-3'-fluorobiphenyl-2-yl]carbonyl}pyrrolidin-3-ol
(3S)-1-{[4'-(5-Aminopyrazin-2-yl)-3'-fluorobiphenyl-2-yl]carbonyl}pyrrolidin-3-ol
(3R)-1-{[4'-(2-Aminopyrimidin-5-yl)-3'-fluorobiphenyl-2-yl]carbonyl}pyrrolidin-3-ol
2-({3-[4-(2-Aminopyrimidin-5-yl)-3-fluorophenyl]pyridin-2-yl}oxy)ethanol TABLE 1-continued 5-{2'-[(2,6-Dimethylmorpholin-4-yl)carbonyl]-3-fluorobiphenyl-4-yl}pyrimidin-2-amine
(3S)-1-{[4'-(2-Aminopyrimidin-5-yl)-3'-fluorobiphenyl-2-yl]carbonyl}piperidin-3-ol
5-[3-Fluoro-2'-(piperidin-4-yloxy)biphenyl-4-yl]pyrimidin-2-amine
2-{[4'-(2-Aminopyrimidin-5-yl)-3'-fluorobiphenyl-2-yl]sulfonyl}-2-methylpropanamide
5-{3-Fluoro-2'-[(3R)-piperidin-3-yloxy]biphenyl-4-yl}pyrimidin-2-amine
5-(2'-{[1-(Aminomethyl)cyclopentyl]sulfonyl}-3-fluorobiphenyl-4-yl)pyrimidin-2-amine
4'-(2-Aminopyrimidin-5-yl)-3'-fluoro-N-(4-hydroxycyclohexyl)biphenyl-2-carboxamide
(3R)-1-{[4'-(2-Aminopyrimidin-5-yl)-3'-fluorobiphenyl-2-yl]carbonyl}piperidin-3-ol.
{[4'-(2-Aminopyrimidin-5-yl)-3'-fluorobiphenyl-2-yl]oxy}acetic acid.
4'-(2-Aminopyrimidin-5-yl)-3'-fluoro-N-(2-hydroxyethyl)biphenyl-2-carboxamid
4'-(5-Aminopyrazin-2-yl)-3'-fluoro-N-(2-hydroxyethyl)biphenyl-2-carboxamide
4'-(5-Aminopyrazin-2-yl)-3'-fluoro-N-(tetrahydro-2H-pyran-4-yl)biphenyl-2-carboxamide
5-[2'-(2-Aminoethoxy)-3-fluorobiphenyl-4-yl]pyrazin-2-amine
5-[2'-(2-Aminoethoxy)-3-fluorobiphenyl-4-yl]pyrimidin-2-amine
2-[3,5'-Difluoro-2'-(methylsulfanyl)biphenyl-4-yl]-5H-pyrrolo[2,3-b]pyrazine
N-[4'-(2-Aminopyrimidin-5-yl)-3'-fluorobiphenyl-2-yl]methanesulfonamide
4'-(5-Aminopyrazin-2-yl)-N,N,3'-trimethylbiphenyl-2-sulfonamide
4'-(6-Aminopyridin-3-yl)-3'-fluoro-N-methylbiphenyl-2-sulfonamide
N-tert-Butyl-3'-fluoro-4'-(2-oxo-2,3-dihydro-1H-indol-5-yl)biphenyl-2-sulfonamide
4'-(3-Amino-1H-indazol-5-yl)-N-tert-butyl-3'-fluorobiphenyl-2-sulfonamide
5-(3-Fluoro-2'-{[(3R)-3-methylmorpholin-4-yl]carbonyl}biphenyl-4-yl)pyrimidin-2-amine
5-(3-Fluoro-2'-{[2-(trifluoromethyl)morpholin-4-yl]carbonyl}biphenyl-4-yl)pyrimidin-2-amine
5-[3-Fluoro-2'-(piperidin-4-yloxy)biphenyl-4-yl]pyrazin-2-amine
N-[4'-(5-Aminopyrazin-2-yl)-3'-fluoro-2'-methoxybiphenyl-2-yl]methanesulfonamide
1-{[4'-(5-Aminopyrazin-2-yl)-3'-fluorobiphenyl-2-yl]carbonyl}azetidin-3-ol
(3R)-1-{[4'-(5-Aminopyrazin-2-yl)-3'-fluorobiphenyl-2-yl]carbonyl}pyrrolidin-3-ol
4'-(5-Aminopyrazin-2-yl)-3'-fluorobiphenyl-2-carbonitrile
(2R)-2-({3-[4-(2-Aminopyrimidin-5-yl)-3-fluorophenyl]pyridin-2-yl}oxy)propan-1-ol
5-{2-Fluoro-4-[2-(piperidin-4-ylsulfonyl)pyridin-3-yl]phenyl}pyrazin-2-amine
5-{2'-[(6-Aminopyrazin-2-yl)sulfonyl]-3-fluorobiphenyl-4-yl}pyrimidin-2-amine
4'-(6-Aminopyridin-3-yl)-3'-fluorobiphenyl-2-sulfonamide
5-{3-Fluoro-2'-[(methylsulfonyl)methyl]biphenyl-4-yl}pyrazin-2-amine
5-{3-Fluoro-2'-[(3S)-piperidin-3-yloxy]biphenyl-4-yl}pyrimidin-2-amine
4'-(5-Aminopyrazin-2-yl)-3'-fluoro-N-(4-hydroxycyclohexyl)biphenyl-2-carboxamide
1-{[4'-(2-Aminopyrimidin-5-yl)-3'-fluorobiphenyl-2-yl]sulfonyl}-3,3-dimethylbutan-2-one
6-{[4'-(5-Aminopyrazin-2-yl)-3'-fluorobiphenyl-2-yl]sulfonyl}pyridin-4-amine
2-{[4'-(2-Aminopyrimidin-5-yl)-3'-fluorobiphenyl-2-yl]oxy}ethanol
2-({3-[4-(5-Aminopyrazin-2-yl)-3-fluorophenyl]pyridin-2-yl}oxy)ethanol
5-{2'-[(Cyclopropylmethyl)sulfonyl]-3-fluorobiphenyl-4-yl}pyrimidin-2-amine
N-[4'-(6-Aminopyridin-3-yl)-3'-fluorobiphenyl-2-yl]methanesulfonamide
4-({2-[6-(2-Aminopyrimidin-5-yl)pyridin-3-yl]phenyl}sulfonyl)piperazin-2-one
5-{2-Fluoro-4-[2-(morpholin-4-ylcarbonyl)pyridin-3-yl]phenyl}-1H-pyrrolo[2,3-b]pyridine
2-[6-(2-Aminopyrimidin-5-yl)pyridin-3-yl]-N-[(2S)-2-hydroxypropyl]benzenesulfonamide
2-[6-(2-Aminopyrimidin-5-yl)pyridin-3-yl]-N-[(1R)-2-hydroxy-1-methylethyl]benzenesulfonamide
5-{2-Fluoro-4-[2-(pyrrolidin-3-ylsulfonyl)pyridin-3-yl]phenyl}pyrimidin-2-amine
5-(5-{2-[(3,3-Difluoropyrrolidin-1-yl)sulfonyl]phenyl}pyridin-2-yl)pyrimidin-2-amine
2-[6-(2-Aminopyrimidin-5-yl)pyridin-3-yl]-N-ethylbenzenesulfonamide
(3S)-1-{[4'-(5-Aminopyrazin-2-yl)-3'-fluorobiphenyl-2-yl]carbonyl}piperidin-3-ol.

TABLE 1-continued (2S)-2-({3-[4-(2-Aminopyrimidin-5-yl)-3-fluorophenyl]pyridin-2-yl}oxy)propan-1-ol
2-{[4'-(2-Aminopyrimidin-5-yl)-3'-fluorobiphenyl-2-yl]sulfonyl}-2-methylpropanenitrile
(2R)-2-({3-[4-(5-Aminopyrazin-2-yl)-3-fluorophenyl]pyridin-2-yl}oxy)propan-1-ol
2-[6-(2-Aminopyrimidin-5-yl)pyridin-3-yl]-N-[(2R)-2-hydroxypropyl]benzenesulfonamide
2-{[4'-(5-Aminopyrazin-2-yl)-3'-fluorobiphenyl-2-yl]sulfonyl}pyrimidin-4-amine
4'-(5-Aminopyrazin-2-yl)-N-tert-butyl-3'-fluoro-5-methoxybiphenyl-2-sulfonamide
5-(2-Fluoro-4-{2-[(3-methoxypropyl)sulfonyl]pyridin-3-yl}phenyl)pyrimidin-2-amine
1-{[4'-(2-Aminopyrimidin-5-yl)-3'-fluorobiphenyl-2-yl]sulfonyl}cyclopentanecarboxamide
5-[3-Fluoro-2-methoxy-2'-(methylsulfonyl)biphenyl-4-yl]pyrazin-2-amine
2-{[4'-(5-Aminopyrazin-2-yl)-3'-fluorobiphenyl-2-yl]oxy}ethanol
2-[6-(2-Aminopyrimidin-5-yl)pyridin-3-yl]-N-[(1R)-2,2,2-trifluoro-1-methylethyl]benzenesulfonamide
2-{[4'-(5-Aminopyrazin-2-yl)-3'-fluorobiphenyl-2-yl]sulfonyl}-2-methylpropanamide
{[4'-(2-Aminopyrimidin-5-yl)-3'-fluorobiphenyl-2-yl]oxy}acetonitrile
5-{4-[2-(tert-Butylsulfonyl)pyridin-3-yl]-2-fluorophenyl}pyrimidin-2-amine
5-{3-Fluoro-2'-[(3S)-piperidin-3-yloxy]biphenyl-4-yl}pyrazin-2-amine
5-(4-{2-[(trans-4-Aminocyclohexyl)oxy]pyridin-3-yl}-2-fluorophenyl)pyrimidin-2-amine
5-(2-Fluoro-4-{2-[(2-morpholin-4-ylethyl)sulfonyl]pyridin-3-yl}phenyl)pyrazin-2-amine
5-(2-Fluoro-4-{2-[(1-methylethyl)sulfonyl]pyridin-3-yl}phenyl)pyrimidin-2-amine
5-(4-{2-[(1-Acetylpiperidin-4-yl)sulfonyl]pyridin-3-yl}-2-fluorophenyl)pyrimidin-2-amine
5-(4'-Bromo-2',3-difluorobiphenyl-4-yl)pyrazin-2-amine
5-(3-Fluoro-2'-{[2-(trifluoromethyl)pyridin-4-yl]oxy}biphenyl-4-yl)pyrimidin-2-amine
5-{2'-[(4,6-Dimethylpyrimidin-2-yl)oxy]-3-fluorobiphenyl-4-yl}pyrimidin-2-amine
5-{2'-[(Ethylsulfonyl)methyl]-3-fluorobiphenyl-4-yl}pyrazin-2-amine
1-{[4'-(2-Aminopyrimidin-5-yl)-3'-fluorobiphenyl-2-yl]sulfonyl}cyclopentanecarbonitrile
(3S)-1-{[4'-(2-Aminopyrimidin-5-yl)-3'-fluorobiphenyl-2-yl]sulfonyl}pyrrolidine-3-carboxamide
5-{5-[2-(Morpholin-4-ylmethyl)-4-(trifluoromethyl)phenyl]pyridin-2-yl}pyrimidin-2-amine
5-(5-{2-[(4,4-Difluoropiperidin-1-yl)sulfonyl]phenyl}pyridin-2-yl)pyrimidin-2-amine
5-{2'-[(2,6-Dimethylmorpholin-4-yl)carbonyl]-3-fluorobiphenyl-4-yl}pyrazin-2-amine
5-(3-Fluoro-2'-{[4-(trifluoromethyl)pyrimidin-2-yl]oxy}biphenyl-4-yl)pyrimidin-2-amine
(3R)-1-{[4'-(2-Aminopyrimidin-5-yl)-3'-fluorobiphenyl-2-yl]sulfonyl}pyrrolidine-3-carboxamide
5-(2-Fluoro-4-{2-[(tetrahydro-2H-pyran-4-ylmethyl)sulfonyl]pyridin-3-yl}phenyl)pyrimidin-2-amine
2-[6-(2-Aminopyrimidin-5-yl)pyridin-3-yl]-N-(2-hydroxyethyl)-5-(trifluoromethyl)benzenesulfonamide
(3R)-1-{[4'-(5-Aminopyrazin-2-yl)-3'-fluorobiphenyl-2-yl]carbonyl}piperidin-3-ol
5-[3-Fluoro-2'-(morpholin-4-ylcarbonyl)biphenyl-4-yl]pyrazin-2-amine
2-({[4'-(5-Aminopyrazin-2-yl)-3'-fluoro-4-(trifluoromethyl)biphenyl-2-yl]methyl}amino)ethanol
5-{3-Fluoro-2'-[(pyrimidin-2-ylsulfonyl)methyl]biphenyl-4-yl}pyrazin-2-amine
2-[6-(2-Aminopyrimidin-5-yl)-5-fluoropyridin-3-yl]-N-[(2R)-2-hydroxypropyl]benzenesulfonamide
5-(5-{2-[(3,3-Difluoropiperidin-1-yl)sulfonyl]phenyl}pyridin-2-yl)pyrimidin-2-amine
5-{2-Fluoro-4-[2-(tetrahydro-2H-pyran-4-ylsulfonyl)pyridin-3-yl]phenyl}pyrimidin-2-amine
5-{2-Fluoro-4-[2-(tetrahydro-2H-pyran-4-yloxy)pyridin-3-yl]phenyl}pyrimidin-2-amine
5-[3-Fluoro-2'-(1,2,3,6-tetrahydropyridin-4-yl)-4'-(trifluoromethyl)biphenyl-4-yl]pyrazin-2-amine
5-{4-[2-(Cyclopropylsulfonyl)pyridin-3-yl]-2-fluorophenyl}pyrimidin-2-amine
5-{2-Fluoro-4-[2-(pyrrolidin-3-ylsulfonyl)pyridin-3-yl]phenyl}pyrazin-2-amine TABLE 1-continued 6-Amino-3-{2'-[(1,1-dioxidothiomorpholin-4-yl)sulfonyl]-3-fluorobiphenyl-4-yl}pyrazine-2-carbonitrile
N-(1-{[4'-(6-Amino-5-fluoropyridin-3-yl)-3'-fluorobiphenyl-2-yl]sulfonyl}piperidin-4-yl)acetamide
1-{[4'-(2-Aminopyrimidin-5-yl)-3'-fluorobiphenyl-2-yl]sulfonyl}-N-methylazetidine-3-carboxamide
5-[3-Fluoro-2'-(morpholin-4-ylsulfonyl)biphenyl-4-yl]pyridin-2-amine
5-(3-Fluoro-2'-{[(1-methylethyl)sulfonyl]methyl}biphenyl-4-yl)pyrazin-2-amine
4'-(5-Amino-3-cyanopyrazin-2-yl)-3'-fluoro-N-(2-hydroxyethyl)biphenyl-2-sulfonamide
{[4'-(5-Aminopyrazin-2-yl)-3'-fluorobiphenyl-2-yl]oxy}acetonitrile
(2S)-2-({3-[4-(5-Aminopyrazin-2-yl)-3-fluorophenyl]pyridin-2-yl}oxy)propan-1-ol
6-Amino-3-[2'-(cyclopropylsulfonyl)-3-fluorobiphenyl-4-yl]pyrazine-2-carbonitrile
5-(4-{2-[(trans-4-Aminocyclohexyl)oxy]pyridin-3-yl}-2-fluorophenyl)pyrazin-2-amine
2-[6-(2-Aminopyrimidin-5-yl)pyridin-3-yl]-N-ethyl-5-(trifluoromethyl)benzenesulfonamide
2-[6-(2-Aminopyrimidin-5-yl)pyridin-3-yl]-N-[(1S)-2,2,2-trifluoro-1-methylethyl]benzenesulfonamide
5-{5-[2-(Azepan-1-ylsulfonyl)phenyl]pyridin-2-yl}pyrimidin-2-amine
2-[6-(2-Aminopyrimidin-5-yl)pyridin-3-yl]-N-tert-butylbenzenesulfonamide
2-[6-(2-Aminopyrimidin-5-yl)pyridin-3-yl]-N-(dicyclopropylmethyl)benzenesulfonamide
5-{2'-[(4-Aminopiperidin-1-yl)methyl]-3-fluoro-4'-(trifluoromethyl)biphenyl-4-yl}pyrazin-2-amine
5-{2'-[(6-Amino-2-methylpyrimidin-4-yl)oxy]-3-fluorobiphenyl-4-yl}pyrimidin-2-amine
6-{[4'-(2-Aminopyrimidin-5-yl)-3'-fluorobiphenyl-2-yl]oxy}pyridine-3-carbonitrile
4'-(5-Amino-3-cyanopyrazin-2-yl)-3'-fluoro-N-[(1S)-2-hydroxy-1-methylethyl]biphenyl-2-sulfonamide
5-(4-{2-[(1,1-Dioxidotetrahydro-2H-thiopyran-4-yl)sulfonyl]pyridin-3-yl}-2-fluorophenyl)pyrimidin-2-amine
5-(2-Fluoro-4-{2-[(1-methylpropyl)sulfonyl]pyridin-3-yl}phenyl)pyrimidin-2-amine
4'-(5-Amino-3-cyanopyrazin-2-yl)-3'-fluoro-N-[(2S)-2-hydroxypropyl]biphenyl-2-sulfonamide
2-{[4'-(5-Aminopyrazin-2-yl)-3'-fluorobiphenyl-2-yl]sulfonyl}-2-methylpropanenitrile
5-{4-[2-(Cyclobutylsulfonyl)pyridin-3-yl]-2-fluorophenyl}pyrimidin-2-amine
5-{2'-[(4,6-Dimethylpyrimidin-2-yl)oxy]-3-fluorobiphenyl-4-yl}pyrazin-2-amine
5-{2'-[(Cyclopropylmethyl)sulfonyl]-3-fluorobiphenyl-4-yl}pyrazin-2-amine
4'-(5-Aminopyrazin-2-yl)-3'-fluoro-4-(trifluoromethyl)biphenyl-2-carboxylic acid
5-(3-Fluoro-2'-{[2-(trifluoromethyl)pyridin-4-yl]oxy}biphenyl-4-yl)pyrazin-2-amine
5-(2-Fluoro-4-{2-[(3-methoxypropyl)sulfonyl]pyridin-3-yl}phenyl)pyrazin-2-amine
6-Amino-3-[3-fluoro-2'-(pyrimidin-2-yloxy)biphenyl-4-yl]pyrazine-2-carbonitrile
4'-(5-Aminopyrazin-2-yl)-N-tert-butyl-3'-fluoro-2'-methoxybiphenyl-2-sulfonamide
4'-(5-Amino-3-cyanopyrazin-2-yl)-3'-fluoro-N-[(2R)-2-hydroxypropyl]biphenyl-2-sulfonamide
1-{[4'-(6-Amino-5-fluoropyridin-3-yl)-3'-fluorobiphenyl-2-yl]sulfonyl}piperidin-3-ol
5-(4-{2-[(1-Acetylpiperidin-4-yl)sulfonyl]pyridin-3-yl}-2-fluorophenyl)pyrazin-2-amine
5-{2'-[(6-Cyclopropylpyrimidin-4-yl)oxy]-3-fluorobiphenyl-4-yl}pyrimidin-2-amine
5-{2-Fluoro-4-[2-(tetrahydro-2H-pyran-4-yloxy)pyridin-3-yl]phenyl}pyrazin-2-amine
2-(1-{[4'-(6-Amino-5-fluoropyridin-3-yl)-3'-fluorobiphenyl-2-yl]sulfonyl}piperidin-3-yl)ethanol
5-{2'-[(5-Aminopyrazin-2-yl)sulfanyl]-3-fluorobiphenyl-4-yl}pyrimidin-2-amine
1-{[4'-(5-Aminopyrazin-2-yl)-3'-fluorobiphenyl-2-yl]sulfonyl}cyclopentanecarboxamide
6-{[4'-(2-Aminopyrimidin-5-yl)-3'-fluorobiphenyl-2-yl]oxy}pyridine-2-carbonitrile
5-(3-Fluoro-2'-{[4-(trifluoromethyl)pyrimidin-2-yl]oxy}biphenyl-4-yl)pyrazin-2-amine TABLE 1-continued 4'-(5-Amino-3-cyanopyrazin-2-yl)-3'-fluoro-N-[(1R)-2-hydroxy-1-methylethyl]biphenyl-2-sulfonamide
(1-{[4'-(6-Amino-5-fluoropyridin-3-yl)-3'-fluorobiphenyl-2-yl]sulfonyl}piperidin-3-yl)methanol
6-Amino-3-{2'-[(4-aminopyrimidin-2-yl)oxy]-3-fluorobiphenyl-4-yl}pyrazine-2-carbonitrile
5-[3-Fluoro-2'-(2-methoxypyrimidin-5-yl)biphenyl-4-yl]pyrazin-2-amine
5-(2-Fluoro-4-{2-[(tetrahydro-2H-pyran-4-ylmethyl)sulfonyl]pyridin-3-yl}phenyl)pyrazin-2-amine
5-{4-[2-(tert-Butylsulfonyl)pyridin-3-yl]-2-fluorophenyl}pyrazin-2-amine
3-Amino-6-{2'-[(4-aminopyrimidin-2-yl)oxy]-3-fluorobiphenyl-4-yl}pyrazine-2-carbonitrile
6-Amino-3-{3-fluoro-2'-[(3-oxopiperazin-1-yl)sulfonyl]-4'-(trifluoromethyl)biphenyl-4-yl}pyrazine-2-carbonitrile
4'-(5-Aminopyrazin-2-yl)-N-tert-butyl-3'-fluoro-4-(trifluoromethyl)biphenyl-2-carboxamide
5-(3-Fluoro-2'-{[6-(trifluoromethyl)pyridin-2-yl]oxy}biphenyl-4-yl)pyrazin-2-amine
5-{2'-[(2-Aminopyridin-4-yl)oxy]-3-fluorobiphenyl-4-yl}pyrimidin-2-amine
1-{[4'-(5-Aminopyrazin-2-yl)-3'-fluorobiphenyl-2-yl]sulfonyl}cyclopentanecarbonitrile
6-{[4'-(5-Aminopyrazin-2-yl)-3'-fluorobiphenyl-2-yl]oxy}pyridine-3-carbonitrile
4'-(6-Amino-5-fluoropyridin-3-yl)-3'-fluoro-N-(2-hydroxy-1,1-dimethylethyl)biphenyl-2-sulfonamide
5-{4-[2-(Cyclohexylsulfonyl)pyridin-3-yl]-2-fluorophenyl}pyrimidin-2-amine
5-{3-Fluoro-2'-[(1S,4S)-2-oxa-5-azabicyclo[2.2.1]hept-5-ylsulfonyl]biphenyl-4-yl}pyrazin-2-amine
1-{[4'-(2-Aminopyrimidin-5-yl)-3'-fluorobiphenyl-2-yl]sulfonyl}piperidine-4-carboxamide
4'-(5-Aminopyrazin-2-yl)-3'-fluoro-4-(trifluoromethyl)biphenyl-2-carbaldehyde
4'-(5-Aminopyrazin-2-yl)-3'-fluoro-N-[(3-hydroxyazetidin-3-yl)methyl]biphenyl-2-sulfonamide
5-{2'-[(5-Aminopyridin-2-yl)oxy]-3-fluorobiphenyl-4-yl}pyrimidin-2-amine
5-{[4'-(5-Aminopyrazin-2-yl)-3'-fluorobiphenyl-2-yl]sulfanyl}pyrazin-2-amine
5-{2'-[(6-Cyclopropylpyrimidin-4-yl)oxy]-3-fluorobiphenyl-4-yl}pyrazin-2-amine
2-({[4'-(5-Aminopyrazin-2-yl)-3'-fluorobiphenyl-2-yl]methyl}sulfanyl)pyrimidin-4-amine
4'-(6-Amino-5-fluoropyridin-3-yl)-3'-fluoro-N-[(1S,2S)-2-hydroxy-1-methyl-2-phenylethyl]-N-methylbiphenyl-2-sulfonamide
5-{4-[2-(Cyclopentylsulfonyl)pyridin-3-yl]-2-fluorophenyl}pyrimidin-2-amine
2-[3-Fluoro-2'-(methylsulfanyl)biphenyl-4-yl]-5H-pyrrolo[2,3-b]pyrazine
6-{[4'-(5-Aminopyrazin-2-yl)-3'-fluorobiphenyl-2-yl]oxy}pyridine-2-carbonitrile
5-(4-{2-[(1,1-Dioxidotetrahydro-2H-thiopyran-4-yl)sulfonyl]pyridin-3-yl}-2-fluorophenyl)pyrazin-2-amine
5-{4-[2-(Cyclopropylsulfonyl)pyridin-3-yl]-2-fluorophenyl}pyrazin-2-amine
4'-(6-Aminopyridin-3-yl)-3'-fluoro-N-[(1S,2S)-2-hydroxy-1-methyl-2-phenylethyl]-N-methylbiphenyl-2-sulfonamide
5-{2'-[(1,1-Dioxidothiomorpholin-4-yl)carbonyl]-3-fluoro-4'-(trifluoromethyl)biphenyl-4-yl}pyrazin-2-amine
N,N-Diethyl-3'-fluoro-4'-(1H-pyrrolo[2,3-b]pyridin-5-yl)biphenyl-2-sulfonamide
5-{2-Fluoro-4-[2-(tetrahydro-2H-pyran-4-ylsulfonyl)pyridin-3-yl]phenyl}pyrazin-2-amine
5-{2'-[(6-Aminopyrazin-2-yl)sulfanyl]-3-fluorobiphenyl-4-yl}pyrazin-2-amine
5-(2-Fluoro-4-{2-[(1-methylpropyl)sulfonyl]pyridin-3-yl}phenyl)pyrazin-2-amine
4'-(6-Aminopyridin-3-yl)-3'-fluoro-N-(2-hydroxy-1,1-dimethylethyl)biphenyl-2-sulfonamide
2-[6-(2-Aminopyrimidin-5-yl)-5-fluoropyridin-3-yl]-N-ethyl-5-(trifluoromethyl)benzenesulfonamide
4'-(5-Amino-3-cyanopyrazin-2-yl)-3'-fluoro-N-(3-hydroxy-2,2-dimethylpropyl)biphenyl-2-sulfonamide
6-Amino-3-[3-fluoro-2'-(pyrimidin-2-yloxy)-4'-(trifluoromethyl)biphenyl-4-yl]pyrazine-2-carbonitrile
5-[3-Fluoro-2'-(morpholin-4-ylmethyl)-4'-(trifluoromethyl)biphenyl-4-yl]pyrazin-2-amine
4'-(5-Amino-3-cyanopyrazin-2-yl)-3'-fluoro-N-(2-hydroxyethyl)-4-(trifluoromethyl)biphenyl-2-sulfonamide TABLE 1-continued 5-{2'-[(5-Aminopyridin-2-yl)oxy]-3-fluorobiphenyl-4-yl}pyrazin-2-amine
5-{4-[2-(Cyclobutylsulfonyl)pyridin-3-yl]-2-fluorophenyl}pyrazin-2-amine
4'-(5-Amino-3-cyanopyrazin-2-yl)-N-ethyl-3'-fluoro-4-(trifluoromethyl)biphenyl-2-sulfonamide
5-[3-Fluoro-2'-(pyrimidin-4-ylsulfanyl)biphenyl-4-yl]pyrazin-2-amine
1-{[4'-(2-Aminopyrimidin-5-yl)-3'-fluorobiphenyl-2-yl]sulfonyl}-4-(pentafluoroethyl)piperidin-4-ol
5-{2'-[(2-Aminopyrimidin-4-yl)oxy]-3-fluorobiphenyl-4-yl}pyrazin-2-amine
5-(2-Fluoro-4-{2-[(1-methylethyl)sulfonyl]pyridin-3-yl}phenyl)-1H-pyrrolo[2,3-b]pyridine
2-[6-(2-Aminopyrimidin-5-yl)-5-fluoropyridin-3-yl]-N-tert-butylbenzenesulfonamide
tert-Butyl (1-{[3'-fluoro-4'-(5H-pyrrolo[2,3-b]pyrazin-2-yl)biphenyl-2-yl]sulfonyl}piperidin-4-yl)carbamate
5-{4-[2-(Cyclopentylsulfonyl)pyridin-3-yl]-2-fluorophenyl}pyrazin-2-amine
4'-(5-Aminopyrazin-2-yl)-N-tert-butyl-3,3'-difluorobiphenyl-2-sulfonamide
5-{4-[2-(Cyclohexylsulfonyl)pyridin-3-yl]-2-fluorophenyl}pyrazin-2-amine
4'-(5-Aminopyrazin-2-yl)-N-tert-butyl-3',4-difluorobiphenyl-2-sulfonamide
5-(3-Fluoro-2'-{[(2S)-2-methylmorpholin-4-yl]carbonyl}biphenyl-4-yl)pyrimidin-2-amine
5-(3-Fluoro-2'-{[(2S)-2-methylmorpholin-4-yl]carbonyl}biphenyl-4-yl)pyrazin-2-amine
2-{[4'-(5-Aminopyrazin-2-yl)-3'-fluorobiphenyl-2-yl]oxy}pyrimidin-5-amine
5-{2'-[(5-Aminopyrimidin-2-yl)oxy]-3-fluorobiphenyl-4-yl}pyrimidin-2-amine
5-(2-fluoro-4-(2-(piperidin-4-yloxy)pyridin-3-yl)phenyl)pyrazin-2-amine
5-{2-Fluoro-4-[2-(piperidin-4-yloxy)pyridin-3-yl]phenyl}pyrimidin-2-amine
2-{[4'-(5-Aminopyrazin-2-yl)-3'-fluorobiphenyl-2-yl]oxy}-6-methylpyrimidin-4-amine
5-{2'-[(4-Amino-6-methylpyrimidin-2-yl)oxy]-3-fluorobiphenyl-4-yl}pyrimidin-2-amine
5-(3-Fluoro-2'-{[(3R)-3-methylmorpholin-4-yl]carbonyl}biphenyl-4-yl)pyrazin-2-amine
5-(4-{2-[(1,1-Dioxidotetrahydro-2H-thiopyran-4-yl)oxy]pyridin-3-yl}-2-fluorophenyl)pyrazin-2-amine
5-(3-Fluoro-2'-{[(3S)-3-methylmorpholin-4-yl]carbonyl}biphenyl-4-yl)pyrazin-2-amine
5-(4-{2-[(1,1-Dioxidotetrahydro-2H-thiopyran-4-yl)oxy]pyridin-3-yl}-2-fluorophenyl)pyrimidin-2-amine
5-(3-Fluoro-2'-{[6-(trifluoromethyl)pyridin-2-yl]oxy}biphenyl-4-yl)pyrimidin-2-amine
5-{3-Fluoro-2'-[(3R)-piperidin-3-yloxy]biphenyl-4-yl}pyrazin-2-amine
1-(4-{[4'-(5-Aminopyrazin-2-yl)-3'-fluorobiphenyl-2-yl]carbonyl}morpholin-2-yl)ethanol
1-(4-{[4'-(2-Aminopyrimidin-5-yl)-3'-fluorobiphenyl-2-yl]carbonyl}morpholin-2-yl)ethanol
5-(3-Fluoro-2'-{[2-(trifluoromethyl)morpholin-4-yl]carbonyl}biphenyl-4-yl)pyrazin-2-amine
N-{3-[4-(5-Aminopyrazin-2-yl)-3-fluorophenyl]pyridin-2-yl}-2,2-dimethylpropanamide
N-{3-[4-(2-Aminopyrimidin-5-yl)-3-fluorophenyl]pyridin-2-yl}-2,2-dimethylpropanamide
5-{2'-[(2-Amino-1,1-dimethylethyl)sulfonyl]-3-fluorobiphenyl-4-yl}pyrazin-2-amine
5-{2'-[(2-Amino-1,1-dimethylethyl)sulfonyl]-3-fluorobiphenyl-4-yl}pyrimidin-2-amine
N-{3-[3-Fluoro-4-(1H-pyrrolo[2,3-b]pyridin-5-yl)phenyl]pyridin-2-yl}-2,2-dimethylpropanamide Particularly, an embodiment of the present invention comprises a compound selected from the compounds listed in Table 2.

TABLE 2

N-[4'-(5-Aminopyrazin-2-yl)-3'-fluorobiphenyl-2-yl]methanesulfonamide,
5-(3-fluoro-2'-(methylsulfonyl)-[1,1'-biphenyl]-4-yl)pyrazin-2-amine,
4'-(5-Aminopyrazin-2-yl)-N-tert-butylbiphenyl-2-sulfonamide,
4'-(5-Aminopyrazin-2-yl)-3'-fluoro-N-methylbiphenyl-2-sulfonamide,
4'-(2-aminopyrimidin-5-yl)-N-(tert-butyl)-3'-fluoro-[1,1'-biphenyl]-2-sulfonamide trifluoroacetic acid salt, TABLE 2-continued (S)-4'-(5-Aminopyrazin-2-yl)-3'-fluoro-N-[(1S)-2,2,2-trifluoro-1-methylethyl]biphenyl-2-sulfonamide,
4'-(2-Aminopyrimidin-5-yl)-3'-fluoro-N-(2,2,2-trifluoro-1,1-dimethylethyl)biphenyl-2-sulfonamide trifluoroacetic acid salt,
4'-(2-Aminopyrimidin-5-yl)-N-ethyl-3'-fluorobiphenyl-2-sulfonamide trifluoroacetic acid salt,
4'-(2-Aminopyrimidin-5-yl)-3'-fluoro-N-methylbiphenyl-2-sulfonamide trifluoroacetic acid salt,
5-{2'-[(4-Aminopiperidin-1-yl)sulfonyl]-3-fluorobiphenyl-4-yl}pyrazin-2-amine,
4'-(5-Aminopyrazin-2-yl)-N-tert-butyl-3'-fluorobiphenyl-2-sulfonamide,
4'-(2-Aminopyrimidin-5-yl)-2',3'-difluoro-N-methylbiphenyl-2-sulfonamide trifluoroacetic acid salt,
4'-(5-Amino-6-cyanopyrazin-2-yl)-N-tert-butyl-3'-fluorobiphenyl-2-sulfonamide,
4-{[4'-(5-Aminopyrazin-2-yl)-3'-fluorobiphenyl-2-yl]sulfonyl}piperazin-2-one,
4-{[4'-(5-Aminopyrazin-2-yl)-3'-fluorobiphenyl-2-yl]oxy}pyrimidin-2-amine,
4'-(2-Aminopyrimidin-5-yl)-3'-fluoro-N-[(1S)-2-hydroxy-1-methylethyl]biphenyl-2-sulfonamide trifluroacetic acid salt,
4'-(5-Amino-3-cyanopyrazin-2-yl)-N-tert-butyl-3'-fluorobiphenyl-2-sulfonamide,
4'-(5-Aminopyrazin-2-yl)-3'-fluoro-N-[(1S)-2-hydroxy-1-methylethyl]biphenyl-2-sulfonamide,
(R)-4'-(5-Aminopyrazin-2-yl)-3'-fluoro-N-[(1R)-2-hydroxy-1-methylethyl]biphenyl-2-sulfonamide,
5-[2'-(Cyclopropylsulfonyl)-3-fluorobiphenyl-4-yl]pyrazin-2-amine,
5-[2,3-Difluoro-2'-(methylsulfonyl)biphenyl-4-yl]pyrazin-2-amine,
5-{2'-[(1,1-Dioxidothiomorpholin-4-yl)sulfonyl]-3-fluorobiphenyl-4-yl}pyrazin-2-amine,
2-{[4'-(5-Aminopyrazin-2-yl)-3'-fluorobiphenyl-2-yl]oxy}pyrimidin-4-amine,
5-{4-[2-(Cyclopentyloxy)pyridin-3-yl]-2-fluorophenyl}pyrazin-2-amine,
(R)-4'-(6-aminopyridin-3-yl)-3'-fluoro-N-(1-hydroxypropan-2-yl)-[1,1'-biphenyl]-2-sulfonamide,
4'-(6-aminopyridin-3-yl)-3'-fluoro-N-(1-methylcyclobutyl)-[1,1'-biphenyl]-2-sulfonamide,
4-((4'-(6-aminopyridin-3-yl)-3'-fluoro-[1,1'-biphenyl]-2-yl)sulfonyl)thiomorpholine 1,1-dioxide,
4'-(2-Aminopyrimidin-5-yl)-3'-fluoro-N-[(1R)-2-hydroxy-1-methylethyl]biphenyl-2-sulfonamide trifluoroacetic acid salt,
5-{3-Fluoro-2'-[(trifluoromethyl)sulfonyl]biphenyl-4-yl}pyrazin-2-amine,
N-[4'-(5-Aminopyrazin-2-yl)-3'-fluorobiphenyl-2-yl]-1,1,1-trifluoromethanesulfonamide,
1-{[4'-(5-Aminopyrazin-2-yl)-3'-fluorobiphenyl-2-yl]sulfonyl}piperidin-4-ol,
(1-{[4'-(5-Aminopyrazin-2-yl)-3'-fluorobiphenyl-2-yl]sulfonyl}piperidin-4-yl)methanol,
2-(1-{[4'-(5-Aminopyrazin-2-yl)-3'-fluorobiphenyl-2-yl]sulfonyl}piperidin-4-yl)ethanol,
racemic 1-{[4'-(5-Aminopyrazin-2-yl)-3'-fluorobiphenyl-2-yl]sulfonyl}piperidin-3-ol,
racemic 2-(1-{[4'-(5-Aminopyrazin-2-yl)-3'-fluorobiphenyl-2-yl]sulfonyl}piperidin-3-yl)ethanol,
racemic 5-{2'-[(3-Aminopiperidin-1-yl)sulfonyl]-3-fluorobiphenyl-4-yl}pyrazin-2-amine,
N-(1-{[4'-(5-Aminopyrazin-2-yl)-3'-fluorobiphenyl-2-yl]sulfonyl}piperidin-4-yl)acetamide,
(R)-(1-((4'-(5-aminopyrazin-2-yl)-3'-fluoro-[1,1'-biphenyl]-2-yl)sulfonyl)pyrrolidin-2-yl)methanol,
(S)-5-(2'-((3-aminopyrrolidin-1-yl)sulfonyl)-3-fluoro[1,1'-biphenyl]-4-yl)pyrazin-2-amine,
(S)-(1-((4'-(5-aminopyrazin-2-yl)-3'-fluoro-[1,1'-biphenyl]-2-yl)sulfonyl)pyrroidin-2-yl)methanol,
4'-(5-Aminopyrazin-2-yl)-3'-fluoro-N-(2-hydroxyethyl)biphenyl-2-sulfonamide,
4'-(5-Aminopyrazin-2-yl)-3'-fluoro-N-(3-hydroxypropyl)biphenyl-2-sulfonamide,
(R)-4'-(5-aminopyrazin-2-yl)-3'-fluoro-N-(2-hydroxypropyl)-[1,1'-biphenyl]-2-sulfonamide,
(S)-4'-(5-aminopyrazin-2-yl)-3'-fluoro-N-(2-hydroxypropyl)-[1,1'-biphenyl]-2-sulfonamide,
4'-(5-Aminopyrazin-2-yl)-3'-fluoro-N-(2-hydroxy-1,1-dimethylethyl)biphenyl-2-sulfonamide,
(R)-(1-((4'-(5-aminopyrazin-2-yl)-3'-fluoro-[1,1'-biphenyl]-2-yl)sulfonyl)pyrrolidin-3-yl)methanol,
N-tert-Butyl-3'-fluoro-4'-[3-(hydroxymethyl)-1H-pyrrolo[2,3-b]pyridin-5-yl]biphenyl-2-sulfonamide,
4'-(5-Aminopyrazin-2-yl)-3'-fluoro-N-[(1S,2S)-2-hydroxy-1-(hydroxymethyl)-2-phenylethyl]biphenyl-2-sulfonamide,
4'-(5-Aminopyrazin-2-yl)-3'-fluoro-N-[(1R)-2-hydroxy-1-phenylethyl]biphenyl-2-sulfonamide,
4'-(5-Aminopyrazin-2-yl)-3'-fluoro-N-[(1S,2R)-2-hydroxy-1-methyl-2-phenylethyl]biphenyl-2-sulfonamide,
4'-(2-Aminopyrimidin-5-yl)-3'-fluoro-N-[(2S)-2-hydroxypropyl]biphenyl-2-sulfonamide trifluoroacetic acid salt,
4'-(2-Aminopyrimidin-5-yl)-3'-fluoro-N-(2-hydroxyethyl)biphenyl-2-sulfonamide trifluoroacetic acid salt,
5-{2'-[(1,1-Dioxidothiomorpholin-4-yl)sulfonyl]-3-fluorobiphenyl-4-yl}pyrimidin-2-amine,
(R)-4'-(5-Aminopyrazin-2-yl)-3'-fluoro-N-(2-oxopiperidin-3-yl)biphenyl-2-sulfonamide,
trans 4'-(5-Aminopyrazin-2-yl)-3'-fluoro-N-(4-hydroxycyclohexyl)biphenyl-2-sulfonamide,
4'-(5-Aminopyrazin-2-yl)-3'-fluoro-N-(2-hydroxy-2-methylpropyl)biphenyl-2-sulfonamide,
1-{[4'-(5-Aminopyrazin-2-yl)-3'-fluorobiphenyl-2-yl]sulfonyl}azetidin-3-ol,
(R) 5-(2'-{[2-(Aminomethyl)pyrrolidin-1-yl]sulfonyl}-3-fluorobiphenyl-4-yl)pyrazin-2-amine,
4'-(2-Aminopyrimidin-5-yl)-3'-fluoro-N-(2-hydroxy-2-methylpropyl)biphenyl-2-sulfonamide trifluoroacetic acid salt,
N-(2-Aminoethyl)-4'-(5-aminopyrazin-2-yl)-3'-fluorobiphenyl-2-sulfonamide,
(S)-4'-(5-aminopyrazin-2-yl)-3'-fluoro-N-(pyrrolidin-3-yl)-[1,1'-biphenyl]-2-sulfonamide,
3'-Fluoro-N-[(1R)-2-hydroxy-1-methylethyl]-4'-(5H-pyrrolo[2,3-b]pyrazin-2-yl)biphenyl-2-sulfonamide,
(cis)-4'-(5-Aminopyrazin-2-yl)-3'-fluoro-N[2-(hydroxymethyl)cyclohexyl]biphenyl-2-sulfonamide,
4'-(2-Aminopyrimidin-5-yl)-3'-fluoro-N-[(3S)-2-oxopiperidin-3-yl]biphenyl-2-sulfonamide trifluoroacetic acid salt,
(S)-5-{2'-[(3-Aminopiperidin-1-yl)sulfonyl]-3-fluorobiphenyl-4-yl}pyrazin-2-amine,
4'-(3,4-Dihydro-2H-pyrido[3,2-b][1,4]oxazin-7-yl)-3'-fluoro-N-[(1S)-2-hydroxy-1-methylethyl]biphenyl-2-sulfonamide,
(1R,5S)-3-((4'-(5-aminopyrazin-2-yl)-3'-fluoro-[1,1'-biphenyl]-2-yl)sulfonyl)-3-azabicyclo[3.1.0]hexan-6-amine,
4'-(5-Aminopyrazin-2-yl)-3'-fluoro-N-[1-(hydroxymethyl)cyclopentyl]biphenyl-2-sulfonamide,
(S)-4'-(5-aminopyrazin-2-yl)-3'-fluoro-N-(2-oxopyrrolidin-3-yl)-[1,1'-biphenyl]-2-sulfonamide,
(S)-4'-(5-aminopyrazin-2-yl)-3'-fluoro-N-(2-oxopiperidin-3-yl)-[1,1'-biphenyl]-2-sulfonamide,
5-(2-Fluoro-4-{2-[(1-methylethyl)sulfonyl]pyridin-3-yl}phenyl)pyrazin-2-amine,
2-{2'-[(1,1-Dioxidothiomorpholin-4-yl)sulfonyl]-3-fluorobiphenyl-4-yl}-5H-pyrrolo[2,3-b]pyrazine,
4'-(5-aminopyrazin-2-yl)-3'-fluoro-N-((1R,2R)-2-hydroxy-2,3-dihydro-1H-inden-1-yl)-[1,1'-biphenyl]-2-sulfonamide,
4'-(5-aminopyrazin-2-yl)-3'-fluoro-N-((1S,2S)-2-hydroxycyclohexyl)-[1,1'-biphenyl]-2-sulfonamide,
4'-(5-aminopyrazin-2-yl)-3'-fluoro-N-((1R,2S)-2-hydroxy-2,3-dihydro-1H-inden-1-yl)-[1,1'-biphenyl]-2-sulfonamide,
(S)-2-(4'-(5-aminopyrazin-2-yl)-3'-fluoro-[1,1'-biphenyl]-2-ylsulfonamido)-4-methylpentanamide,
2-[3-Fluoro-2'-(morpholin-4-ylcarbonyl)biphenyl-4-yl]-5H-pyrrolo[2,3-b]pyrazine,
4'-(5-Aminopyrazin-2-yl)-N-(2-cyanoethyl)-3'-fluorobiphenyl-2-sulfonamide,
4'-(2-Aminopyrimidin-5-yl)-3'-fluoro-N-[(3S)-2-oxopyrrolidin-3-yl]biphenyl-2-sulfonamide,
4'-(5-Aminopyrazin-2-yl)-3'-fluoro-4-(trifluoromethyl)biphenyl-2-sulfonamide,
5-{2'-[(1,1-Dioxidothiomorpholin-4-yl)carbonyl]-3-fluorobiphenyl-4-yl}pyrazin-2-amine,
4'-(5-Aminopyrazin-2-yl)-3'-fluoro-N-(3-methyloxetan-3-yl)biphenyl-2-sulfonamide,
4'-(5-Aminopyrazin-2-yl)-3'-fluoro-N-[(1S)-2,2,2-trifluoro-1-methylethyl]biphenyl-2-carboxamide,
5-[3-Fluoro-2'-(methylsulfonyl)-4'-(trifluoromethyl)biphenyl-4-yl]pyrazin-2-amine,
5-[3-Fluoro-2'-(pyrimidin-2-yloxy)biphenyl-4-yl]pyrazin-2-amine,
5-[3-Fluoro-2'-(pyrimidin-2-yloxy)biphenyl-4-yl]pyrimidin-2-amine,
4-{[4'-(5-Aminopyrazin-2-yl)-3'-fluoro-4-(trifluoromethyl)biphenyl-2-yl]sulfonyl}piperazin-2-one, TABLE 2-continued 4'-(5-Aminopyrazin-2-yl)-3'-fluoro-N-methyl-4-(trifluoromethyl)biphenyl-2-sulfonamide,
4'-(2-Aminopyrimidin-5-yl)-3'-fluoro-N-(trans-4-hydroxycyclohexyl)biphenyl-2-sulfonamide,
4'-(5-aminopyrazin-2-yl)-3'-fluoro-N-(2-hydroxyethyl)-4-(trifluoromethyl)biphenyl-2-sulfonamide,
4'-(2-Aminopyrimidin-5-yl)-N-ethyl-3'-fluoro-4-(trifluoromethyl)biphenyl-2-Sulfonamide,
4'-(2-Aminopyrimidin-5-yl)-3'-fluoro-N-(2-hydroxyethyl)-4-(trifluoromethyl)biphenyl-2-sulfonamide,
4'-(5-Aminopyrazin-2-yl)-N-ethyl-3'-fluoro-4-(trifluoromethyl)biphenyl-2-sulfonamide,
5-{3-Fluoro-2'-[(2-methylpyrimidin-4-yl)oxy]biphenyl-4-yl}pyrazin-2-amine,
6-{[4'-(5-Aminopyrazin-2-yl)-3'-fluorobiphenyl-2-yl]oxy}pyrimidin-4-amine,
5-{2'-[(6-Aminopyrimidin-4-yl)oxy]-3-fluorobiphenyl-4-yl}pyrimidin-2-amine,
4'-(5-amino-6-cyanopyrazin-2-yl)-3'-fluoro-N-[(1R)-2-hydroxy-1-methylethyl]biphenyl-2-sulfonamide,
4'-(5-Amino-6-cyanopyrazin-2-yl)-3'-fluoro-N-[(2R)-2-hydroxypropyl]biphenyl-2-sulfonamide,
N'-[4'-(5-Aminopyrazin-2-yl)-3'-fluorobiphenyl-2-yl]-N,N-dimethylsulfamide,
5-{2'-[(4-Aminopyrimidin-2-yl)oxy]-3-fluorobiphenyl-4-yl}pyrimidin-2-amine,
4-{[4'-(2-Aminopyrimidin-5-yl)-3'-fluorobiphenyl-2-yl]oxy}pyrimidin-2-amine,
5-[3-Fluoro-2'-(pyrimidin-2-yloxy)-4'-(trifluoromethyl)biphenyl-4-yl]pyrimidin-2-amine,
4'-(2-Aminopyrimidin-5-yl)-3'-fluoro-N-[(2R)-2-hydroxypropyl]biphenyl-2-sulfonamide,
5,5'-(3'-Fluorobiphenyl-2,4'-diyl)dipyrazin-2-amine,
5-{2'-[(6-Aminopyrimidin-4-yl)oxy]-3-fluoro-4'-(trifluoromethyl)biphenyl-4-yl}pyrimidin-2-amine,
5-{3-Fluoro-2'-[(4-methylpyrimidin-2-yl)oxy]biphenyl-4-yl}pyrimidin-2-amine,
5-[3-Fluoro-2'-(morpholin-4-ylcarbonyl)-4'-(trifluoromethyl)biphenyl-4-yl]pyrazin-2-amine,
5-[4'-(5-Aminopyrazin-2-yl)-3'-fluorobiphenyl-2-yl]pyrimidin-2-amine,
5-{2'-[(1,1-Dioxidotetrahydro-2H-thiopyran-4-yl)sulfonyl]-3-fluorobiphenyl-4-yl}pyrazin-2-amine,
5-{3-Fluoro-2'-[(4-pyrimidin-2-ylpiperazin-1-yl)sulfonyl]biphenyl-4-yl}pyrazin-2-amine,
5-{2'-[(5-Aminopyrimidin-4-yl)sulfanyl]-3-fluorobiphenyl-4-yl}pyrimidin-2-amine formate salt,
4-{[4'-(2-Aminopyrimidin-5-yl)-3'-fluorobiphenyl-2-yl]sulfanyl}pyrimidin-2-amine formate salt,
4-{[4'-(5-Aminopyrazin-2-yl)-3'-fluorobiphenyl-2-yl]sulfanyl}pyrimidin-2-amine hydrochloride,
4'-(5-amino-1,3,4-thiadiazol-2-yl)-N-(tert-butyl)-3'-fluoro-[1,1'-biphenyl]-2-sulfonamide,
2-{[4'-(5-Aminopyrazin-2-yl)-3'-fluorobiphenyl-2-yl]sulfanyl}pyrimidin-5-amine hydrochloride,
4-((4'-(5-amino-1,3,4-thiadiazol-2-yl)-3'-fluoro-[1,1'-biphenyl]-2-yl)sulfonyl)thiomorpholine 1,1-dioxide,
4'-(2-aminopyrimidin-5-yl)-3'-fluoro-4-(trifluoromethyl)biphenyl-2-sulfonamide,
4'-(5-aminopyrazin-2-yl)-3'-fluoro-[1,1'-biphenyl]-2-sulfonamide, and
4'-(5-Amino-6-chloropyrazin-2-yl)-N-tert-butyl-3'-fluorobiphenyl-2-sulfonamide.

Further, an embodiment of the present invention comprises a compound selected from the compounds listed in Table 1A.

TABLE 1A

5-[2'-Amino-3-fluoro-4'-(trifluoromethyl)biphenyl-4-yl]pyrazin-2-amine
5-{2'-[(1,1-Dioxidotetrahydro-2H-thiopyran-4-yl)methoxy]-3-fluorobiphenyl-4-yl}pyrazin-2-amine
5-{2'-[(1,1-Dioxidotetrahydro-2H-thiopyran-4-yl)oxy]-3-fluorobiphenyl-4-yl}pyrazin-2-amine
4-({[4'-(5-Aminopyrazin-2-yl)-3'-fluorobiphenyl-2-yl]oxy}methyl)benzoic acid
4-({[4'-(2-Aminopyrimidin-5-yl)-3'-fluorobiphenyl-2-yl]oxy}methyl)benzoic acid
4-{[4'-(5-Aminopyrazin-2-yl)-3'-fluorobiphenyl-2-yl]oxy}benzoic acid
4-{[4'-(2-Aminopyrimidin-5-yl)-3'-fluorobiphenyl-2-yl]oxy}benzoic acid
2-[4-({3-[4-(5-Aminopyrazin-2-yl)-3-fluorophenyl]pyridin-2-yl}sulfonyl)piperidin-1-yl]ethanol
4-[4'-(5-Aminopyrazin-2-yl)-3'-fluorobiphenyl-2-yl]pyrimidin-2-amine
1-[4-({3-[4-(5-Aminopyrazin-2-yl)-3-fluorophenyl]pyridin-2-yl}sulfonyl)piperidin-1-yl]propan-2-ol
5-[3-Fluoro-2'-(1H-pyrazol-4-yl)biphenyl-4-yl]pyrazin-2-amine
5-[2'-(6-Aminopyridin-3-yl)-3-fluorobiphenyl-4-yl]pyrazin-2-amine
5-{3-Fluoro-2'-[1-(2-methoxyethyl)-1H-pyrazol-4-yl]biphenyl-4-yl}pyrazin-2-amine
5-{5-[2-(Cyclopropylsulfonyl)phenyl]-3-fluoropyridin-2-yl}pyrimidin-2-amine
4-{[4'-(2-Aminopyrimidin-5-yl)-3'-fluorobiphenyl-2-yl]oxy}benzamide
5-{2'-[(trans-4-Aminocyclohexyl)oxy]-3-fluorobiphenyl-4-yl}pyrazin-2-amine
5-{2-Fluoro-4-[2-(phenylsulfonyl)pyridin-3-yl]phenyl}pyrazin-2-amine
6-[4'-(5-Aminopyrazin-2-yl)-3'-fluorobiphenyl-2-yl]pyridazin-3-amine
{4-[4'-(5-Aminopyrazin-2-yl)-3'-fluorobiphenyl-2-yl]-1H-pyrazol-1-yl}acetonitrile
5-[4'-(5-Aminopyrazin-2-yl)-3'-fluorobiphenyl-2-yl]-N-methylpyrimidin-2-amine
2-[6-(2-Aminopyrimidin-5-yl)-5-fluoropyridin-3-yl]-N-[(1S)-2,2,2-trifluoro-1-methylethyl]benzenesulfonamide
5-{2-Fluoro-4-[2-(phenylsulfonyl)pyridin-3-yl]phenyl}pyrimidin-2-amine
5-[3-Fluoro-2'-(2-piperazin-1-ylpyrimidin-5-yl)biphenyl-4-yl]pyrazin-2-amine
5-{2'-[1-(2-Aminoethyl)-1H-pyrazol-4-yl]-3-fluorobiphenyl-4-yl}pyrazin-2-amine
2-[6-(2-Aminopyrimidin-5-yl)-5-fluoropyridin-3-yl]-N-[(2S)-2-hydroxypropyl]benzenesulfonamide
5-(3-Fluoro-2'-isothiazol-4-ylbiphenyl-4-yl)pyrazin-2-amine
5-[2-Fluoro-4-(2-phenoxypyridin-3-yl)phenyl]pyrazin-2-amine
5-[2-Fluoro-4-(2-phenoxypyridin-3-yl)phenyl]pyrimidin-2-amine
2-{4-[4'-(5-Aminopyrazin-2-yl)-3'-fluorobiphenyl-2-yl]-1H-pyrazol-1-yl}ethanol
5-(4-{2-[(1-Acetylpiperidin-3-yl)sulfonyl]pyridin-3-yl}-2-fluorophenyl)pyrazin-2-amine
5-(4-{2-[(1-Acetylpiperidin-4-yl)sulfonyl]-6-(trifluoromethyl)pyridin-3-yl}-2-fluorophenyl)pyrazin-2-amine
2-[6-(2-Aminopyrimidin-5-yl)-5-fluoropyridin-3-yl]-N-[(1S)-2-hydroxy-1-methylethyl]benzenesulfonamide
2-[6-(2-Aminopyrimidin-5-yl)-5-fluoropyridin-3-yl]-N-[(1R)-2-hydroxy-1-methylethyl]benzenesulfonamide
5-[2-Fluoro-4-(2-phenylpyridin-3-yl)phenyl]pyrazin-2-amine
5-(2-Fluoro-4-{2-[(1-methylpyrrolidin-3-yl)sulfonyl]pyridin-3-yl}phenyl)pyrazin-2-amine
5-{2-Fluoro-4-[2-(pyridin-3-ylsulfonyl)pyridin-3-yl]phenyl}pyrazin-2-amine
5-(2-Fluoro-4-{2-[(1-methylethyl)sulfonyl]-6-(trifluoromethyl)pyridin-3-yl}phenyl)pyrazin-2-amine
5-(4-{2-[(1-Acetylpiperidin-4-yl)sulfonyl]-6-(trifluoromethyl)pyridin-3-yl}-2-fluorophenyl)pyrimidin-2-amine
5-[2'-(6-Aminopyridin-3-yl)-3-fluorobiphenyl-4-yl]pyrimidin-2-amine
5-[4'-(2-Aminopyrimidin-5-yl)-3'-fluorobiphenyl-2-yl]-N-methylpyrimidin-2-amine
5-(2-Fluoro-4-{2-[(1-methylethyl)sulfonyl]-6-(trifluoromethyl)pyridin-3-yl}phenyl)pyrimidin-2-amine
{4-[4'-(2-Aminopyrimidin-5-yl)-3'-fluorobiphenyl-2-yl]-1H-pyrazol-1-yl}acetonitrile
5-[3-Fluoro-2'-(1H-pyrazol-4-yl)biphenyl-4-yl]pyrimidin-2-amine
4-[4'-(2-Aminopyrimidin-5-yl)-3'-fluorobiphenyl-2-yl]pyrimidin-2-amine
5-{2-Fluoro-4-[2-(pyridin-3-yloxy)pyridin-3-yl]phenyl}pyrazin-2-amine
5-(4-{2-[(1,1-Dioxidotetrahydro-2H-thiopyran-4-yl)sulfonyl]-6-(trifluoromethyl)pyridin-3-yl}-2-fluorophenyl)pyrimidin-2-amine
5-[2-Fluoro-4-(2-{[1-(methylsulfonyl)piperidin-4-yl]sulfonyl}pyridin-3-yl)phenyl]pyrazin-2-amine
5-(4-{2-[(1,1-Dioxidotetrahydro-2H-thiopyran-4-yl)sulfonyl]-6-(trifluoromethyl)pyridin-3-yl}-2-fluorophenyl)pyrazin-2-amine TABLE 1A-continued 5-{2-Fluoro-4-[2-(tetrahydro-2H-pyran-4-ylsulfonyl)-6-(trifluoromethyl)pyridin-3-yl]phenyl}pyrazin-2-amine
5-{2-Fluoro-4-[2-(tetrahydro-2H-pyran-4-ylsulfonyl)-6-(trifluoromethyl)pyridin-3-yl]phenyl}pyrimidin-2-amine
2-[6-(2-Aminopyrimidin-5-yl)-5-fluoropyridin-3-yl]-N-(2-hydroxyethyl)benzenesulfonamide
2-[6-(2-Aminopyrimidin-5-yl)-5-fluoropyridin-3-yl]-N-[(1R)-2,2,2-trifluoro-1-methylethyl]benzenesulfonamide
5-[2-Fluoro-4-(2-{[1-(methylsulfonyl)piperidin-4-yl]sulfonyl}pyridin-3-yl)phenyl]pyrimidin-2-amine Additionally, an embodiment of the present invention comprises a compound selected from the compounds listed in Table 1, Table 2 and Table 1A.

The invention is also directed to a pharmaceutical composition which include, without limitation, one or more of the disclosed compounds, and pharmaceutically acceptable carriers or excipients.

Another embodiment of the present invention is a pharmaceutical composition of the present invention that comprises at least a compound selected from the compounds listed in Table 1. Another embodiment of the present invention is a pharmaceutical composition of the present invention that comprises at least a compound selected from the compounds listed in Table 3.

Particularly, an embodiment of the present invention is a pharmaceutical composition of the present invention that comprises at least a compound selected from the compounds listed in Table 2.

The present invention also features a method of treating a subject suffering from or diagnosed with a disease and/or disorder mediated by FLAP activity, comprising administering to the subject a therapeutically effective amount of at least one compound of Formula (I).

The present invention also features a method for preventing, treating, ameliorating, including without limitation inhibiting, the progression of an FLAP-mediated disease and/or disorder in a subject in need thereof, comprising administering to said subject a therapeutically effective amount of at least one compound of Formula (I). Such a disease and/or disorder includes, but is not limited to diabetes, respiratory disorders, and associated symptoms or complications thereof. More specifically, this invention is directed to a method of treating, but not limited to, exacerbations, non-allergic asthma, fibrotic lung diseases, acute respiratory distress syndrome and chronic obstructive pulmonary disease, and their associated symptoms or complications, in a subject afflicted with such a disease and/or disorder.

In another embodiment, the compounds of the present invention are useful for the amelioration of symptoms associated with and/or the treatment of the following cardiac and cardiovascular diseases and/or disorders: myocardial infarction, atherosclerosis and stroke aortic aneurisms, atherosclerosis, or associated symptoms or complications thereof, in a subject afflicted with such a disease and/or disorder.

In another embodiment, the compounds of the present invention are useful for the amelioration of symptoms associated with and/or the treatment of autoimmune or allergic diseases and/or disorders, wherein said autoimmune or allergic diseases and/or disorders include, but are not limited to, rheumatoid arthritis, inflammatory bowel disease, nephritis, spondyloarthritis, polymyositis, dermatomyositis, gouty effusions, systemic lupus erythematosus, systemic sclerosis, Alzheimer's disease, multiple sclerosis, allergic rhinitis, allergic dermatitis and asthma, or associated symptoms or complications thereof, in a subject afflicted with such a disease and/or disorder. In a further embodiment, the compounds of the present invention are useful for the amelioration of symptoms associated with and/or the prophylaxis or treatment of carcinogenesis, wherein said carcinogenesis include, but is not limited to, tumor cell proliferation, differentiation, and apoptosis, tumor-associated angiogenesis, as well as the migration and invasion of carcinoma cells.

It is a further embodiment of the invention to provide a process for making a pharmaceutical composition comprising admixing any of the compounds according to Formula (I) and a pharmaceutically acceptable carrier.

In a further embodiment of the invention, a method for treating or ameliorating an FLAP-mediated disease and/or disorder in a subject in need thereof comprises administering to the subject a therapeutically effective amount of at least one compound of Formula (I), wherein the therapeutically effective amount of the compound of Formula (I) is from about 0.1 mg/dose to about 5 g/dose. In particular, the therapeutically effective amount of the compound of Formula (I) is from about 0.5 mg/dose to about 1000 mg/dose.

More particularly, the therapeutically effective amount of the compound of Formula (I) is from about 1 mg/dose to about 100 mg/dose. In a further embodiment of the invention, the number of doses per day of a compound of Formula (I) is from 1 to 3 doses. In a further embodiment of the invention, the therapeutically effective amount of the compound of Formula (I) is from about 0.001 mg/kg/day to about 30 mg/kg/day. More particularly, the therapeutically effective amount of the compound of Formula (I) is from about 0.01 mg/kg/day to about 2 mg/kg/day.

The invention is further described below.

A) Terms

Some terms are defined below and by their usage throughout this disclosure.

It should also be noted that any atom with unsatisfied valences in the text, schemes, examples, structural formulae and any tables herein is assumed to have the hydrogen atom or atoms to satisfy the valences.

As used herein, the following terms are intended to have the following definitions. The definitions herein may specify that a chemical term has an indicated formula. The particular formula provided is not intended to limit the scope of the invention, but is provided as an illustration of the term. The scope of the per se definition of the term is intended to include the plurality of variations expected to be included by one of ordinary skill in the art.

The term "$C_{1-6}$alkyl" means a saturated branched or straight-chain hydrocarbon radical having from 1 up to 6 carbon atoms in a linear or branched arrangement, selected from the group consisting of methyl, ethyl, propyl, butyl, pentyl, and hexyl. Examples include isopropyl, isobutyl, tert-butyl, sec-butyl, n-butyl, 1,1-dimethylpropyl, 2,2-dimethylpropyl, 1,2-dimethylpropyl, butan-2-yl, 2-methylbutyl, 2-methylbutan-2-yl, 1-methyl-3-methylbutyl, 3,3-dimethylbutan-2-yl, and the like, and all that are exemplified in the below examples. An alkyl radical may be attached to a core molecule by any atom where allowed by available valences. The term "$C_{1-4}$alkyl" means a saturated branched or straight-chain hydrocarbon radical having from 1 up to 4 carbon atoms in a linear or branched arrangement, The term "$C_{3-9}$cycloalkyl" means a saturated or partially unsaturated, monocyclic, polycyclic or benzofused hydrocarbon ring system radical. Examples include cyclopropyl, cyclobutyl, cyclopentyl, cyclohexyl, bicyclo[2.2.1]heptan-2-yl, 2,3-dihydro-1H-inden-2-yl, and the like, and all that are exemplified in the below examples. A $C_{3-9}$cycloalkyl radical may be attached to a core molecule by any ring atom where allowed by available valences.

The term "aryl" means an unsaturated, aromatic monocyclic or polycyclic hydrocarbon ring system radical. Examples include phenyl and the like, and all that are exemplified in the below examples. An aryl radical may be attached to a core molecule by any ring atom where allowed by available valences.

The term "hetero", when used as a prefix for a ring system, refers to the replacement of at least one carbon atom member in the ring system with a heteroatom selected from N, O, S, S(O), or $SO_2$. A hetero ring may have 1, 2, 3 or 4 carbon atom members replaced by a nitrogen atom. Alternatively, a ring may have 1, 2 or 3 nitrogen atom members and 1 oxygen or sulfur atom member. Alternatively, a ring may have 1 oxygen or sulfur atom member. Alternatively, up to two adjacent ring members may be heteroatoms, wherein one heteroatom is nitrogen and the other heteroatom is selected from N, S or O.

The term "heteroaryl" means an unsaturated monocyclic, polycyclic aromatic "hetero" ring system radical, selected from the group consisting of pyridinyl, pyrimidinyl, pyrazinyl, pyridazinyl, benzimidazolyl, and tetrazolyl. Examples include pyridin-2-yl, pyridin-3-yl, pyridin-4-yl, pyrimidin-4-yl, pyrazin-2-yl, pyrazin-4-yl, pyrimidin-2-yl, pyridazin-3-yl, 1H-benzimidazol-2-yl, 2H-tetrazol-5-yl, and the like, and all that are exemplied in the below examples. A heteroaryl radical may be attached to a core molecule by any ring atom where allowed by available valences.

The term "heterocycyl" means a saturated monocyclic or polycyclic "hetero" ring system radical, selected from the group consisting of azetidinyl, pyrrolidinyl, piperidinyl, piperazinyl, morpholinyl, pyrazoyl, thiomorpholinyl, azepanyl, hexahydropyrrolo[1,2-a]pyrazinyl, tetrahydropyrazolo[4,3-c]pyridinyl, diazabicyclo[2.2.1]-heptanyl, dihydro-indolyl, tetrahydropyranyl, azabicyclo[3.1.0]hexanyl, oxetanyl, isothiazolidinyl, thiazinanyl, thiopyranyl, thiaazaspiro[3.3]heptanyl, oxa-azaspiro[3.3]heptanyl, tetrahydro-thiopyranyl, dihydroquinazolinyl, oxadiazolyl, oxaazabicylco[2.2.1]heptanyl, piperazin-2-one-yl, 2-oxa-5-azabicyclo[2.2.1]heptanyl, pyrrolidin-2-one-yl, imidazolidin-2-one-yl, 1,2-thiazinane 1,1-dioxide-yl, isothiazolidine 1,1-dioxide-yl, 1,2,3,6-tetrahydropyridinyl, and imidazolidinyl. Examples include azetidin-1-yl, azetidin-3-yl, pyrrolidin-1-yl, pyrrolidin-3-yl, piperidin-1-yl, piperidin-2-yl, piperidin-3-yl, piperidin-4-yl, piperazin-1-yl, morpholin-2-yl, morpholin-4-yl, thiomorpholin-4-yl, azepan-1-yl, azepan-3-yl, hexahydro-1H-pyrrolo[1,2-a]pyrazin-2-yl, 1,4,6,7-tetrahydro-5H-pyrazolo[4,3-c]pyridine-5-yl, 2,5-diazabicyclo[2.2.1]heptan-2-yl, 2,3-dihydro-1H-indol-2-yl, tetrahydro-2H-pyran-4-yl, 3-azabicyclo[3.1.0]hexan-3-yl, oxetan-3-yl, isothiazolidin-2-yl, 1,2-thiazinan-2-yl, 2H-thiopyran-4-yl, 2-thia-6-azaspiro[3.3]heptan-6-yl, 2-oxa-6-azaspiro[3.3]heptan-6-yl, tetrahydro-2H-thiopyran-4-yl, 3,4-dihydroquinazolin-2-yl, 1,2,3-oxadiazol-5-yl, 2-oxa-5-azabicylco[2.2.1]heptan-5-yl, imidazolidin-1-yl, thiomorpholine 1,1-dioxide-yl, 4-amino-tetrahydro-2H-pyran-yl, tetrahydro-2H-thiopyran 1,1-dioxide-yl, and the like, and all that are exemplified in the below examples. A heterocyclyl radical may be attached to a core molecule by any ring atom where allowed by available valences.

The term "carboxy" means a radical of the formula: —C(O)OH.

The term "halogen" or "halo" means a radical selected from the group consisting of chloro, bromo, fluoro or iodo.

The term "oxo" means a radical of the formula: =O.

The term "substituted" refers to a radical in which one or more hydrogen atoms are each independently replaced with the same or different substituent(s). In a preferred embodiment, up to three hydrogen atoms are each independently replaced.

With reference to substituents, the term "independently" means that when more than one of such substituent is possible, such substituents may be the same or different from each other.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

In general, unless otherwise specified, IUPAC nomenclature rules are used herein.

The term "about," whether used explicitly or not in reference to a quantitative expression given herein, means that every quantity given herein qualified with the term or otherwise is meant to refer both to the actual given value and the approximation to such given value that would reasonably be inferred based on the ordinary skill in the art, including approximations due to experimental and/or measurement conditions for such given value.

The term "form" means, in reference to compounds of the present invention, such may exist as, without limitation in the following states, a salt, stereoisomer, tautomer, crystalline, polymorph, amorphous, solvate, hydrate, ester, prodrug or metabolite form. The present invention encompasses all such compound forms and mixtures thereof.

The term "isolated form" means, in reference to compounds of the present invention, such may exist in an essentially pure state such as, without limitation, an enantiomer, a racemic mixture, a geometric isomer (such as a cis or trans stereoisomer), a mixture of geometric isomers, and the like. The present invention encompasses all such compound forms and mixtures thereof.

The term "composition" is intended to encompass a product comprising the specified ingredients in the specified amounts, as well as any product which results, directly or indirectly, from combinations of the specified ingredients in the specified amounts.

The term "subject" as used herein, refers to a patient, such as an animal, a mammal or a human, who has been the object of treatment, observation or experiment and is at risk of (or susceptible to) developing an FLAP-mediated disorder.

The term "administering" further means that the individual ingredients to be combined may be administered at the same time or at different times during the treatment period, either as one preparation or as different preparations. Accordingly, the invention should be so interpreted that it encompasses any and every administration mode at the same time or at different times. The range of the combination of the compound of the invention and the other therapeutic agent useful for the above-mentioned disorders encompasses, in principle, all combinations of the compound of the invention and any and every pharmaceutical agent useful for the above-mentioned disorders.

The term "treating" refers, without limitation, to facilitating the eradication of, preventing, ameliorating or otherwise inhibiting the progression of or promoting stasis of an FLAP-mediated disease and/or disorder, or associated symptoms or complications thereof.

The term "prodrug" means a compound of Formula (I) or a form thereof that is converted in vivo into a functional derivative form that may contribute to therapeutic biological activity, wherein the converted form may be: 1) a relatively active form; 2) a relatively inactive form; 3) a relatively less active form; or, 4) any form which results, directly or indirectly, from such in vivo conversions. Prodrugs are useful when said compound may be either too toxic to administer systemically, absorbed poorly by the digestive tract or broken down by the body before it reaches its target. Conventional procedures for the selection and preparation of suitable prodrug derivatives are described in, for example, "*Design of Prodrugs*", ed. H. Bundgaard, Elsevier, 1985.

The term "metabolite" means a prodrug form of a compound of Formula (I) or a form thereof converted by in vivo metabolism or a metabolic process to a relatively less active functional derivative of said compound.

The term "medicament" or "medicine" refers to a product containing a compound of Formula (I) or a form thereof. The present invention includes use of such a medicament for treating an FLAP-mediated disorder.

The term "combination form" refers to the use of a combination product comprising a compound of Formula (I) or a form, pharmaceutical composition, medicine or medicament thereof and at least one therapeutic agent for treating an FLAP-mediated disorder.

Methods are known in the art for determining effective doses for therapeutic and prophylactic purposes for the disclosed pharmaceutical compositions or the disclosed drug combinations, whether or not formulated in the same composition.

For therapeutic purposes, the term "therapeutically effective amount" or "effective amount" as used herein, means that amount of each active compound or pharmaceutical agent, alone or in combination, that elicits the biological or medicinal response in a tissue system, animal or human that is being sought by a researcher, veterinarian, medical doctor or other clinician, which includes alleviation of the symptoms of the disease and/or disorder being treated. For prophylactic purposes (i.e., inhibiting the progression of a disorder), the term "therapeutically effective amount" refers to that amount of each active compound or pharmaceutical agent, alone or in combination, that treats or inhibits in a subject the progression of a disorder as being sought by a researcher, veterinarian, medical doctor or other clinician. Thus, the present invention provides combinations of two or more drugs wherein, for example, (a) each drug is administered in an independently therapeutically or prophylactically effective amount; (b) at least one drug in the combination is administered in an amount that is sub-therapeutic or sub-prophylactic if administered alone, but is therapeutic or prophylactic when administered in combination with the second or additional drugs according to the invention; or (c) both (or more) drugs are administered in an amount that is sub-therapeutic or sub-prophylactic if administered alone, but are therapeutic or prophylactic when administered together. The effective amount of said compound is from about 0.001 mg/kg/day to about 300 mg/kg/day.

Advantageously, the effective amount of a combination product for treating an FLAP-mediated disease and/or disorder, or associated symptoms or complications thereof, may be a reduced amount of either or both, the compound or therapeutic agent, compared to the effective amount of the compound or therapeutic agent otherwise recommended for treating the disease and/or disorder, or associated symptoms or complications thereof. Therefore, it is contemplated that the compound is administered to the subject before, during or after the time the agent is administered.

The term "pharmaceutically acceptable salt" refers to non-toxic pharmaceutically acceptable salts (*Ref. Int'l J. Pharm.*, 1986, 33: 201-217; *J. Pharm. Sci.*, 1997 (January), 66(1): 1). Other salts well known to those in the art may, however, be useful in the preparation of compounds according to this invention or of their pharmaceutically acceptable salts. Representative organic or inorganic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic acid. Representative organic or inorganic bases include, but are not limited to, basic or cationic salts such as benzathine, chloroprocaine, choline, diethanolamine, ethylenediamine, meglumine, procaine, aluminum, calcium, lithium, magnesium, potassium, sodium and zinc.

The compounds of the invention may be present in the form of pharmaceutically acceptable salts. For use in medicines, the "pharmaceutically acceptable salts" of the compounds of this invention refer to non-toxic acidic/anionic or basic/cationic salt forms.

Suitable salt forms include acid addition salts which may, for example, be formed by mixing a solution of the compound according to the invention with a solution of an acid such as acetic acid, adipic acid, benzoic acid, carbonic acid, citric acid, fumaric acid, glycolic acid, hydrochloric acid, maleic acid, malonic acid, phosphoric acid, saccharinic acid, succinic acid, sulphuric acid, tartaric acid, trifluoroacetic acid and the like.

Furthermore when the compounds of the present invention carry an acidic moiety, suitable salts thereof may include alkali metal salts, e.g. sodium or potassium salts; alkaline earth metal salts, e.g. calcium or magnesium salts; and salts formed with suitable organic ligands, e.g. quaternary ammonium salts.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*. 3$^{rd}$ Edition, John Wiley & Sons, 1999. The protecting groups may be removed at a convenient subsequent stage using methods known in the art. The scope of the present invention encompasses all such protected compound forms and mixtures thereof.

The invention includes compounds of various isomers and mixtures thereof. The term "isomer" refers to compounds that have the same composition and molecular weight but differ in physical and/or chemical properties. Such substances have the same number and kind of atoms but differ in structure. The structural difference may be in constitution (geometric isomers) or in an ability to rotate the plane of polarized light (optical isomers).

The term "stereoisomer" refers to isomers that have the same molecular formula and the same sequence of covalently bonded atoms but a different spatial orientation.

The term "optical isomer" means isomers of identical constitution that differ only in the spatial arrangement of their groups. Optical isomers rotate the plane of polarized light in different directions. The term "optical activity" means the degree to which an optical isomer rotates the plane of polarized light.

The term "racemate" or "racemic" means an equimolar mixture of two enantiomeric species, wherein each of the isolated species rotates the plane of polarized light in the opposite direction such that the mixture is devoid of optical activity.

The term "enantiomer" means an isomer having a non-superimposable mirror image. The term "diastereomer" means stereoisomers that are not enantiomers.

The term "chiral" means a molecule that, in a given configuration, cannot be superimposed on its mirror image. This is in contrast to achiral molecules that can be superimposed on their mirror images.

The two distinct mirror image versions of the chiral molecule are also known as levo (left-handed), abbreviated L, or dextro (right-handed), abbreviated D, depending on which way they rotate polarized light. The symbols "R" and "S" represent the configuration of groups around a stereogenic carbon atom(s).

The term "geometric isomer" means isomers that differ in the orientation of substituent atoms in relationship to a carbon-carbon double bond, to a cycloalkyl ring, or to a bridged bicyclic system. Substituent atoms (other than hydrogen) on each side of a carbon-carbon double bond may be in an E or Z configuration according to the Cahn-Ingold-Prelog priority rules. In the "E" configuration, the substituents having the highest priorities are on opposite sides in relationship to the carbon-carbon double bond. In the "Z" configuration, the substituents having the highest priorities are oriented on the same side in relationship to the carbon-carbon double bond.

Substituent atoms (other than hydrogen) attached to a ring system may be in a cis or trans configuration. In the "cis" configuration, the substituents are on the same side in relationship to the plane of the ring; in the "trans" configuration, the substituents are on opposite sides in relationship to the plane of the ring. Compounds having a mixture of "cis" and "trans" species are designated "cis/trans".

The isomeric descriptors ("R," "S," "E," and "Z") indicate atom configurations and are intended to be used as defined in the literature.

The compounds of the invention may be prepared as individual isomers by either isomer-specific synthesis or resolved from an isomeric mixture. Conventional resolution techniques include combining the free base (or free acid) of each isomer of an isomeric pair using an optically active acid (or base) to form an optically active salt (followed by fractional crystallization and regeneration of the free base), forming an ester or amide of each of the isomers of an isomeric pair by reaction with an appropriate chiral auxiliary (followed by fractional crystallization or chromatographic separation and removal of the chiral auxiliary), or separating an isomeric mixture of either an intermediate or a final product using various well known chromatographic methods.

Furthermore, compounds of the present invention may have one or more polymorph or amorphous crystalline forms and, as such, are intended to be included in the scope of the invention. In addition, some of the compounds may form solvates with water (i.e., hydrates) or common organic solvents (e.g., organic esters such as ethanolate and the like) and, as such, are also intended to be encompassed within the scope of this invention.

B) Compounds

Representative compounds of the present invention are listed in Table 3 below:

TABLE 3

| STRUCTURE | COMPOUND # | NAME |
|---|---|---|
| 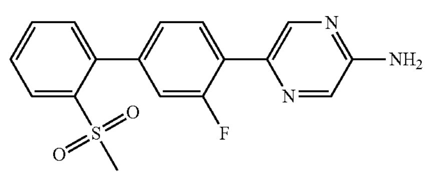 [SMILES: CS(=O)(=O)c1ccccc1-c1ccc(-c2cnc(N)cn2)c(F)c1] | 1 | 5-(3-fluoro-2'-(methylsulfonyl)-[1,1'-biphenyl]-4-yl)pyrazin-2-amine |
| 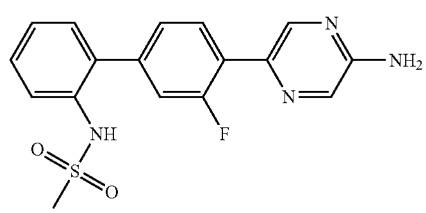 [SMILES: CS(=O)(=O)Nc1ccccc1-c1ccc(-c2cnc(N)cn2)c(F)c1] | 2 | N-[4'-(5-Aminopyrazin-2-yl)-3'-fluorobiphenyl-2-yl]methanesulfonamide |
| 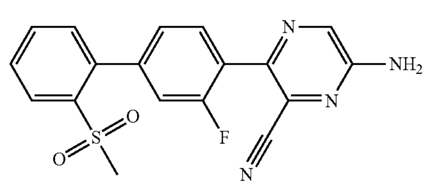 [SMILES: CS(=O)(=O)c1ccccc1-c1ccc(-c2ncc(N)nc2C#N)c(F)c1] | 3 | 6-Amino-3-[3.-fluoro-2'-(methylsulfonyl)biphenyl-4-yl]pyrazine-2-carbonitrile |

TABLE 3-continued

| STRUCTURE | COMPOUND # | NAME |
|---|---|---|
| 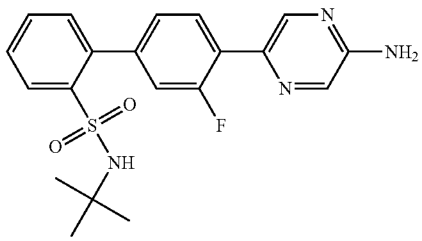 [SMILES: CC(C)(C)NS(=O)(=O)c1ccccc1-c1ccc(-c2cnc(N)cn2)c(F)c1] | 4 | 4'-(5-Aminopyrazin-2-yl)-N-tert-butyl-3'-fluorobiphenyl-2-sulfonamide |
| 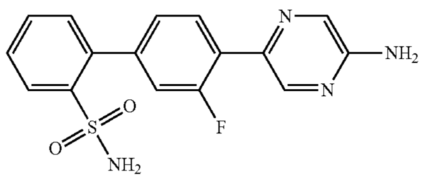 | 5 | 4'-(5-aminopyrazin-2-yl)-3'-fluoro-[1,1'-biphenyl]-2-sulfonamide |
| 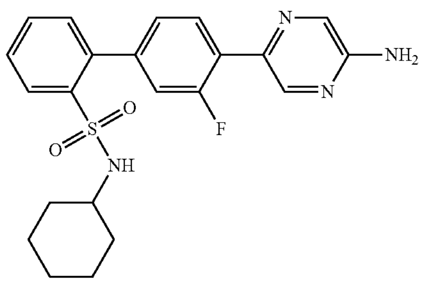 [SMILES: Nc1cnc(-c2ccc(-c3ccccc3S(=O)(=O)NC3CCCCC3)cc2F)cn1] | 6 | 4'-(5-Aminopyrazin-2-yl)-N-cyclohexyl-3'-fluorobiphenyl-2-sulfonamide |
| 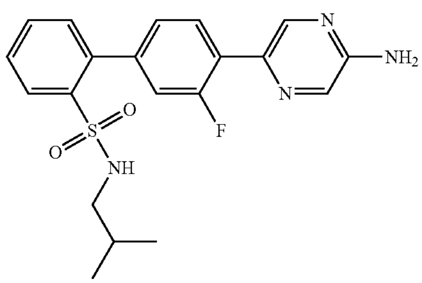 | 7 | 4'-(5-Aminopyrazin-2-yl)-3'-fluoro-N-(2-methylpropyl)biphenyl-2-sulfonamide |
| 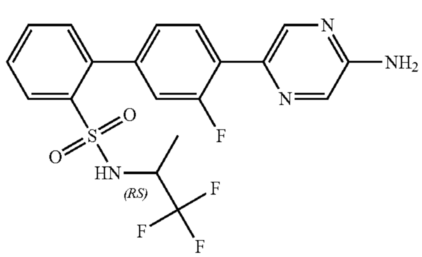 [SMILES: CC(NS(=O)(=O)c1ccccc1-c1ccc(-c2cnc(N)cn2)c(F)c1)C(F)(F)F] | 8 | (racemic)-4'-(5-Aminopyrazin-2-yl)-3'-fluoro-N-(2,2,2-trifluoro-1-methylethyl)biphenyl-2-sulfonamide racemic |
| 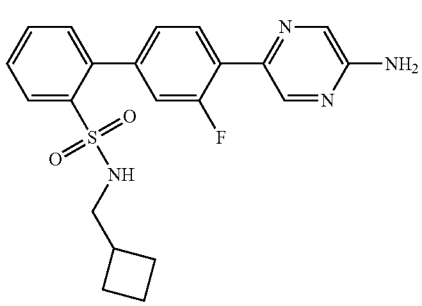 [SMILES: Nc1cnc(-c2ccc(-c3ccccc3S(=O)(=O)NCC3CCC3)cc2F)cn1] | 9 | 4'-(5-Aminopyrazin-2-yl)-N-(cyclobutylmethyl)-3'-fluorobiphenyl-2-sulfonamide |

TABLE 3-continued

| STRUCTURE | COMPOUND # | NAME |
|---|---|---|
| 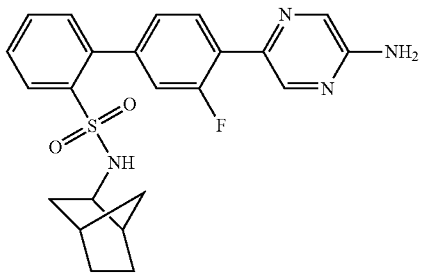 [SMILES: Nc1cnc(-c2ccc(-c3ccccc3S(=O)(=O)NC3CC4CCC3C4)cc2F)cn1] | 10 | (racemic)-(endo)-4'-(5-Aminopyrazin-2-yl)-N-bicyclo[2.2.1]hept-2-yl-3'-fluorobiphenyl-2-sulfonamide racemic |
| 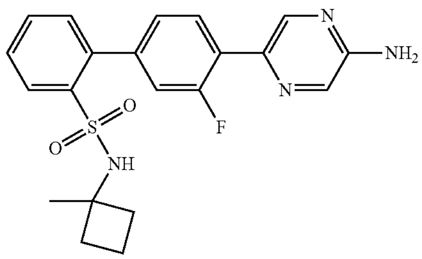 [SMILES: CC1(NS(=O)(=O)c2ccccc2-c2ccc(-c3cnc(N)cn3)c(F)c2)CCC1] | 11 | 4'-(5-Aminopyrazin-2-yl)-3'-fluoro-N-(1-methylcyclobutyl)biphenyl-2-sulfonamide |
| 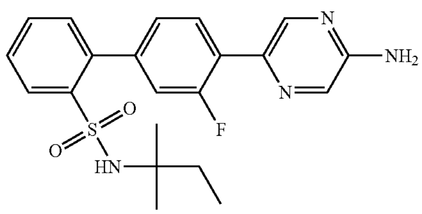 [SMILES: CCC(C)(C)NS(=O)(=O)c1ccccc1-c1ccc(-c2cnc(N)cn2)c(F)c1] | 12 | 4'-(5-Aminopyrazin-2-yl)-N-(1,1-dimethylpropyl)-3'-fluorobiphenyl-2-sulfonamide |
| 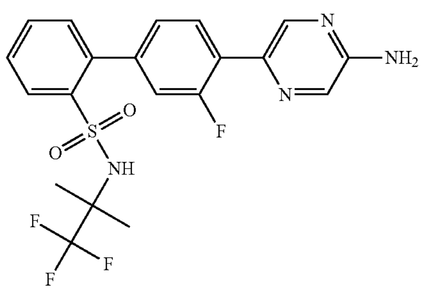 [SMILES: CC(C)(NS(=O)(=O)c1ccccc1-c1ccc(-c2cnc(N)cn2)c(F)c1)C(F)(F)F] | 13 | 4'-(5-4minopyrazin-2-yl)-3'-fluoro-N-(2,2,2-trifluoro-1,1-dimethylethyl)biphenyl-2-sulfonamide |
| 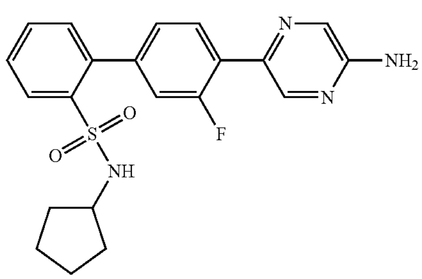 [SMILES: Nc1cnc(-c2ccc(-c3ccccc3S(=O)(=O)NC3CCCC3)cc2F)cn1] | 14 | 4'-(5-Aminopyrazin-2-yl)-N-cyclopentyl-3'-fluorobiphenyl-2-sulfonamide |
| 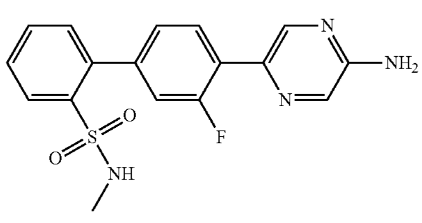 [SMILES: CNS(=O)(=O)c1ccccc1-c1ccc(-c2cnc(N)cn2)c(F)c1] | 15 | 4'-(5-Aminopyrazin-2-yl)-3'-fluoro-N-methylbiphenyl-2-sulfonamide |

TABLE 3-continued

| STRUCTURE | COMPOUND # | NAME |
|---|---|---|
| 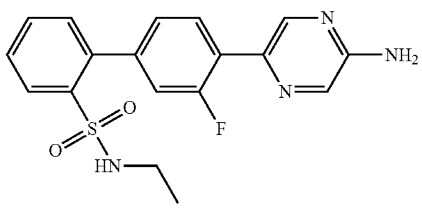 [SMILES: CCNS(=O)(=O)c1ccccc1-c1ccc(-c2cnc(N)cn2)c(F)c1] | 16 | 4'-(5-Aminopyrazin-2-yl)-N-ethyl-3'-fluorobiphenyl-2-sulfonamide |
| 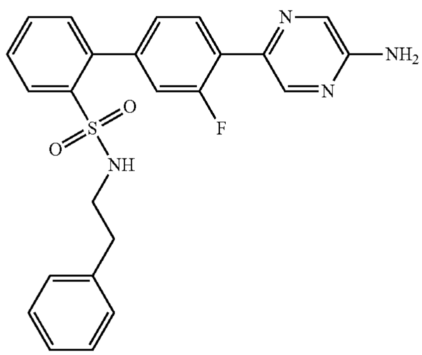 [SMILES: Nc1cnc(-c2ccc(-c3ccccc3S(=O)(=O)NCCc3ccccc3)cc2F)cn1] | 17 | 4'-(5-Aminopyrazin-2-yl)-3'-fluoro-N-(2-phenylethyl)biphenyl-2-sulfonamide |
| 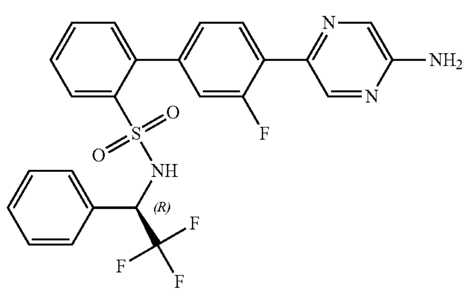 | 18 | (R)-4'-5-Aminopyrazin-2-yl)-3'-fluoro-N-[(1R)-2,2,2-trifluoro-1-phenylethyl]biphenyl-2-sulfonamide |
| 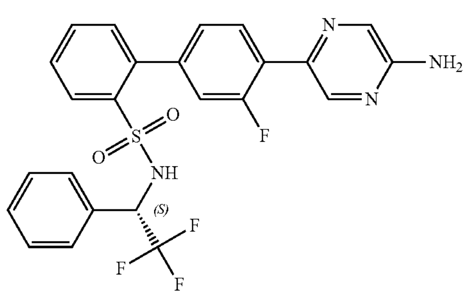 | 19 | (S)-4'-(5-Aminopyrazin-2-yl)-3'-fluoro-N-[(1S)-2,2,2-trifluoro-1-phenylethylibiphenyl-2-sulfonamide |
| 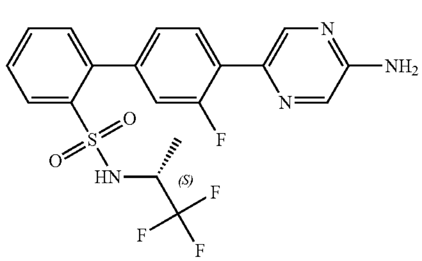 | 20 | (S)-4'-(5-Aminopyrazin-2-yl)-3'-fluoro-N-[(S)-2,2,2-trifluoro-1-methylethyl]biphenyl-2-sulfonamide |

TABLE 3-continued

| STRUCTURE | COMPOUND # | NAME |
|---|---|---|
| 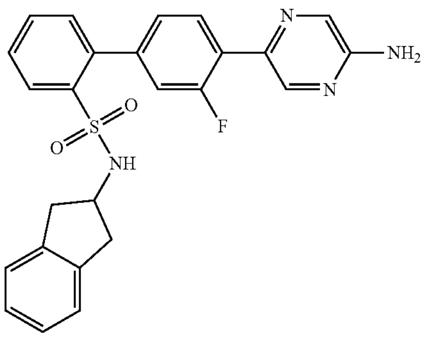 [SMILES: Nc1cnc(-c2ccc(-c3ccccc3S(=O)(=O)NC3Cc4ccccc4C3)cc2F)cn1] | 21 | 4'-(5-Aminopyrazin-2-yl)-N-(2,3-dihydro-1H-inden-2-yl)-3'-fluorobiphenyl-2-sulfonamide |
| 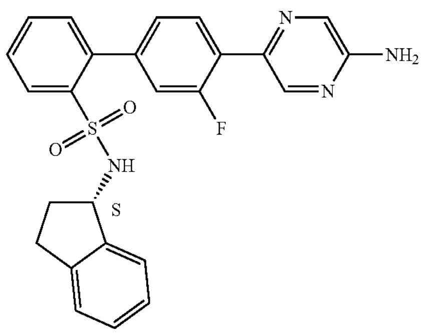 | 22 | (S)-4'-(5-Aminopyrazin-2-yl)-N-[(1S)-2,3-dihydro-1H-inden-1-yl]-3'-fluorobiphenyl-2-sulfonamide |
| | 23 | (R)-4'-(5-Aminopyrazin-2-yl)-N-[(1R)-2,3-dihydro-1H-inden-1-yl]-3'-fluorobiphenyl-2-sulfonamide |
| 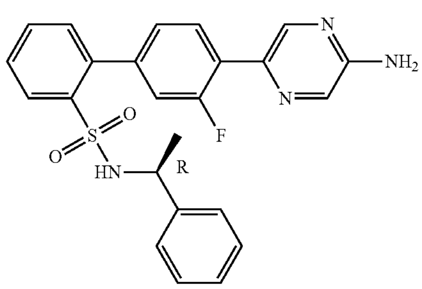 | 24 | (R)-4'-(5-Aminopyrazin-2-yl)-3'-fluoro-N-[(1R)-1-phenylethyl]biphenyl-2-sulfonamide |
| 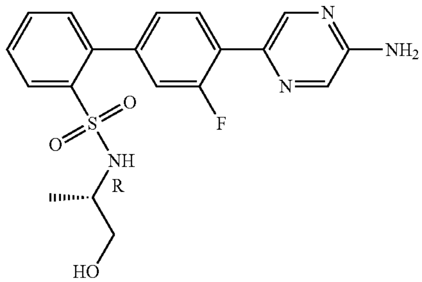 | 25 | (R)-4'-(5-Aminopyrazin-2-yl)-3'-fluoro-N-[(1R)-2-hydroxy-1-methylethyl]piphenyl-2-sulfonamicie |

TABLE 3-continued

| STRUCTURE | COMPOUND # | NAME |
|---|---|---|
| 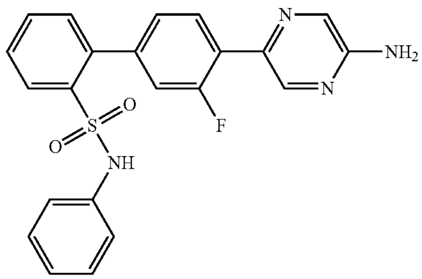 [SMILES: Nc1cnc(-c2ccc(-c3ccccc3S(=O)(=O)Nc3ccccc3)cc2F)cn1] | 26 | 4'-(5-Aminopyrazin-2-yl)-3'-fluoro-N-phenylbiphenyl-2-sulfonamide |
| 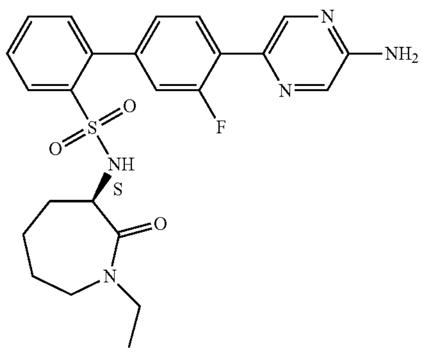 | 27 | (S)-4'-(5-Aminopyrazin-2-yl)-N-[((3S)-1-ethyl-2-oxoazepan-a-y]-3'-fluorobiphenyl-2-sulfonamide |
| 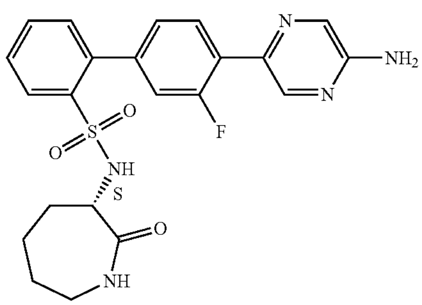 | 28 | (S)-4'-(5-Aminopyrazin-2-yl)-3'-fluoro-N-[(3S)-2-oxoazepan-3-yl]biphenyl-2-sulfonamide |
| 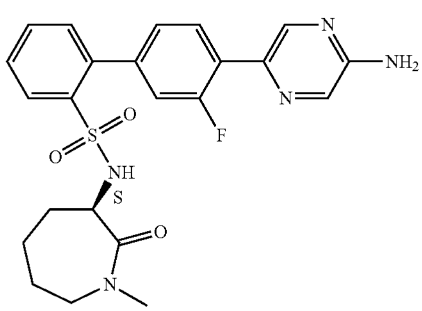 | 29 | (S)-4'-(5-Aminopyrazin-2-yl)-3'-fluoro-N-[(3S)-1-methyl-2-oxoazepan-3-yl]biphenyl-2-sulfonamide |

TABLE 3-continued

| STRUCTURE | COMPOUND # | NAME |
|---|---|---|
| 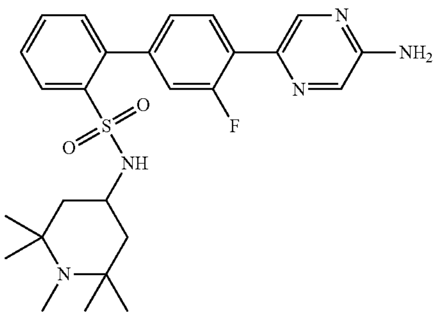 [SMILES: CN1C(C)(C)CC(NS(=O)(=O)c2ccccc2-c2ccc(-c3cnc(N)cn3)c(F)c2)CC1(C)C] | 30 | 4'-(5-Aminopyrazin-2-yl)-3'-fluoro-N-(1,2,2,6,6-pentamethylpiperidin-4-yl)biphenyl-2-sulfonamide |
| 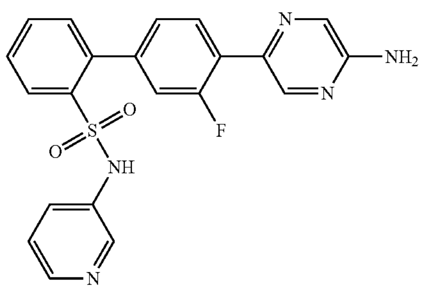 [SMILES: Nc1cnc(-c2ccc(-c3ccccc3S(=O)(=O)Nc3cccnc3)cc2F)cn1] | 31 | 4'-(5-Aminopyrazin-2-yl)-3'-fluoro-N-pyridin-3-ylbiphenyl-2-sulfonamide |
| 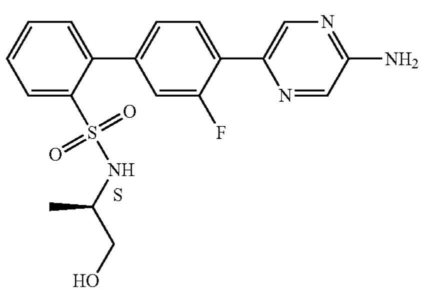 | 32 | 4'-(5-Aminopyrazin-2-yl)-3'-fluoro-N-[(1S)-2-hydroxy-1-methylethyl]piphenyl-2-sulfonamide |
| 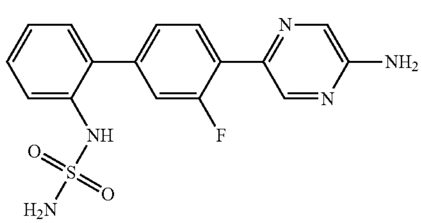 [SMILES: Nc1cnc(-c2ccc(-c3ccccc3NS(N)(=O)=O)cc2F)cn1] | 33 | N-[4'-(5-Aminopyrazin-2-yl)-3'-fluorobiphenyl-2-yl]sulfamide |
| 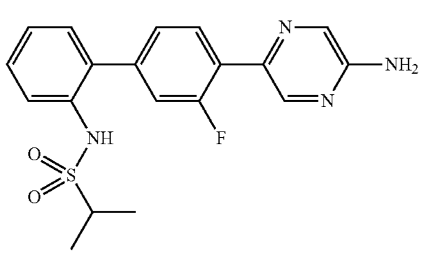 [SMILES: CC(C)S(=O)(=O)Nc1ccccc1-c1ccc(-c2cnc(N)cn2)c(F)c1] | 34 | N-(4'-(5-aminopyrazin-2-yl)-3'-fluoro-[1,1'-biphenyl]-2-yl)propane-2-sulfonamide |

TABLE 3-continued

| STRUCTURE | COMPOUND # | NAME |
|---|---|---|
| 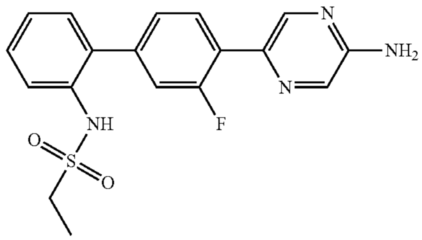 [SMILES: CCS(=O)(=O)Nc1ccccc1-c1ccc(-c2cnc(N)cn2)c(F)c1] | 35 | N-[4'-(5-Aminopyrazin-2-yl)-3'-fluorobiphenyl-2-yl]ethanesulfonamide |
| 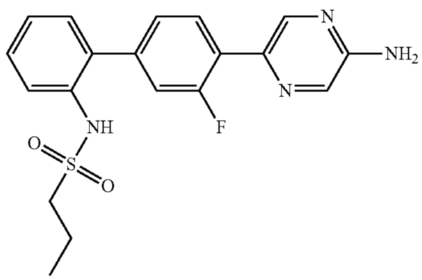 [SMILES: CCCS(=O)(=O)Nc1ccccc1-c1ccc(-c2cnc(N)cn2)c(F)c1] | 36 | N-[4'-(5-Aminopyrazin-2-yl)-3'-fluorobiphenyl-2-yl]propane-1-sulfonamide |
| 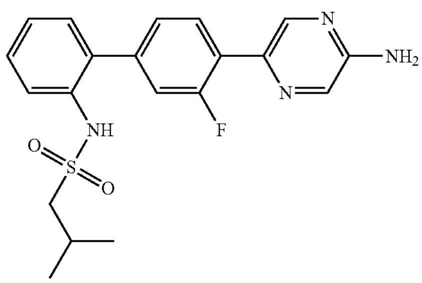 | 37 | N-[4'-(5-Aminopyrazin-2-yl)-3'-fluorobiphenyl-2-yl]-2-methylpropane-1-sulfonamide |
| 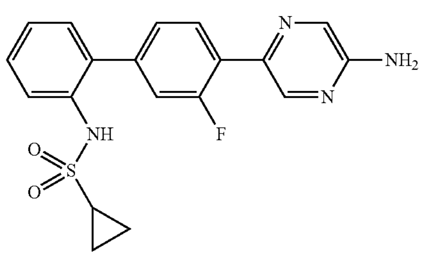 [SMILES: Nc1cnc(-c2ccc(-c3ccccc3NS(=O)(=O)C3CC3)cc2F)cn1] | 38 | N-(4'-(5-aminopyrazin-2-yl)-3'-fluoro-[1,1'-biphenyl]-2-yl)cyclopropanesulfonamide |
| 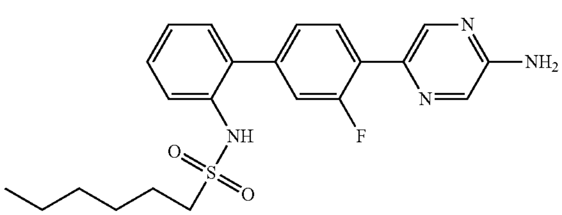 [SMILES: CCCCCCS(=O)(=O)Nc1ccccc1-c1ccc(-c2cnc(N)cn2)c(F)c1] | 39 | N-[4'-(5-Aminopyrazin-2-yl)-3'-fluorobiphenyl-2-yl]hexane-1-sulfonamide |
| 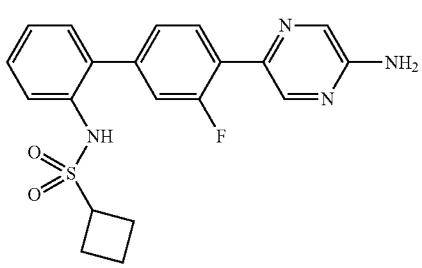 [SMILES: Nc1cnc(-c2ccc(-c3ccccc3NS(=O)(=O)C3CCC3)cc2F)cn1] | 40 | N-(4'-(5-aminopyrazin-2-yl)-3'-fluoro-[1,1'-biphenyl]-2-yl)cyclobutanesulfonamide |

TABLE 3-continued

| STRUCTURE | COMPOUND # | NAME |
|---|---|---|
| 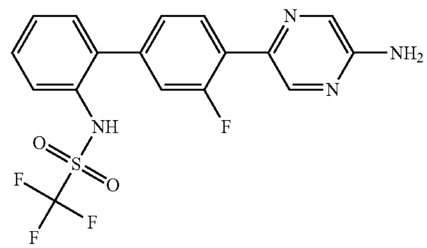 [SMILES: Nc1cnc(-c2ccc(-c3ccccc3NS(=O)(=O)C(F)(F)F)cc2F)cn1] | 41 | N-[4'-(5-Aminopyrazin-2-yl)-3'-fluorobiphenyl-2-yl]-1,1,1-trifluoromethanesulfonamide |
| 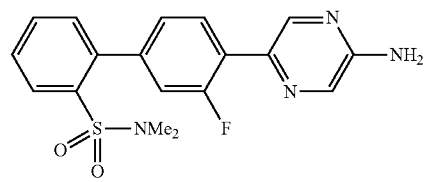 [SMILES: CN(C)S(=O)(=O)c1ccccc1-c1ccc(-c2cnc(N)cn2)c(F)c1] | 42 | 4'-(5-Aminopyrazin-2-yl)-3'-fluoro-N,N-dimethylbiphenyl-2-sulfonamide |
| 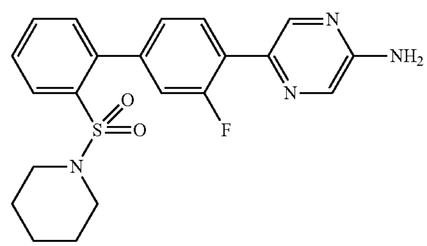 [SMILES: Nc1cnc(-c2ccc(-c3ccccc3S(=O)(=O)N3CCCCC3)cc2F)cn1] | 43 | 5-[3-fluoro-2'-(piperidin-1-ylsulfonyl)biphenyl-4-yl]pyrazin-2-amine |
| 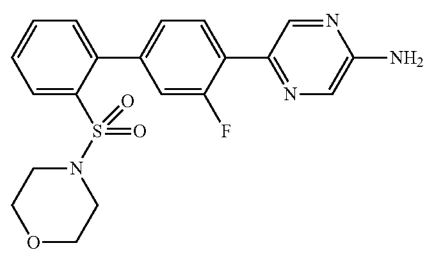 | 44 | 5-[3-Fluoro-2'-(morpholin-4-ylsulfonyl)biphenyl-4-yl]pyrazin-2-amine |
| 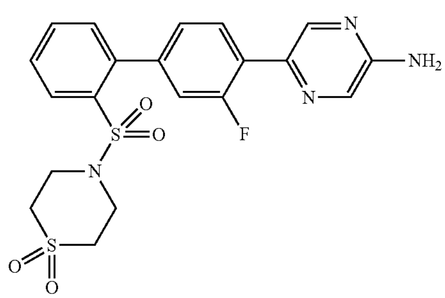 [SMILES: Nc1cnc(-c2ccc(-c3ccccc3S(=O)(=O)N3CCS(=O)(=O)CC3)cc2F)cn1] | 45 | 5-{2'-[(1,1-Dioxidothiomorpholin-4-yl)sulfonyl]-3-fluorobiphenyl-4-yl}pyrazin-2-amine |
| 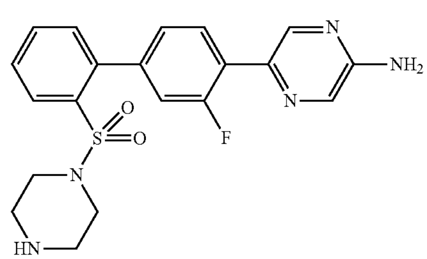 [SMILES: Nc1cnc(-c2ccc(-c3ccccc3S(=O)(=O)N3CCNCC3)cc2F)cn1] | 46 | 5-[3-Fluoro-2'-(piperazin-1-ylsulfonyl)biphenyl-4-yl]pyrazin-2-amine |

TABLE 3-continued

| STRUCTURE | COMPOUND # | NAME |
|---|---|---|
| 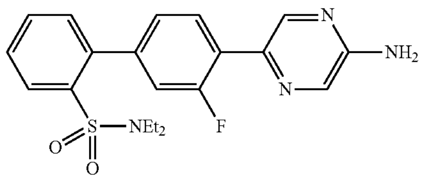 | 47 | 4'-(5-Aminopyrazin-2-yl)-N,N-diethyl-3'-fluorobiphenyl-2-sulfonamide |
| 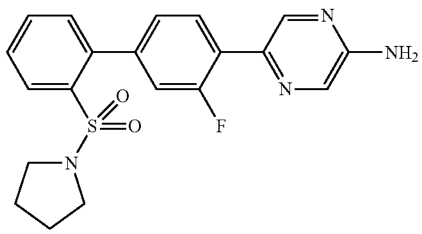 [SMILES: Nc1cnc(-c2ccc(-c3ccccc3S(=O)(=O)N3CCCC3)cc2F)cn1] | 48 | 5-[3-Fluoro-2'-(pyrrolidin-1-ylsulfonyl)biphenyl-4-yl]pyrazin-2-amine |
| 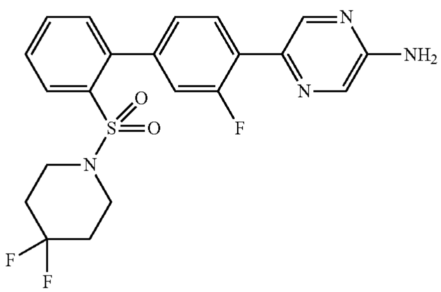 [SMILES: Nc1cnc(-c2ccc(-c3ccccc3S(=O)(=O)N3CCC(F)(F)CC3)cc2F)cn1] | 49 | 5-{2'-[(4,4-Difluoropiperidin-1-yl)sulfonyl]-3-fluorobiphenyl-4-yl}pyrazin-2-amine |
| 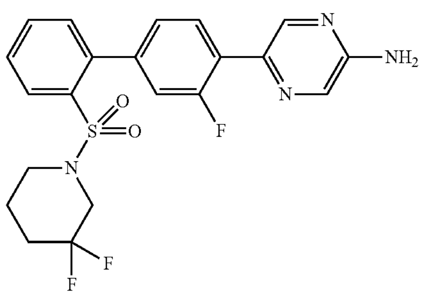 [SMILES: Nc1cnc(-c2ccc(-c3ccccc3S(=O)(=O)N3CCCC(F)(F)C3)cc2F)cn1] | 50 | 5-{2'-[(3,3-Difluoropiperidin-1-yl)sulfonyl)-3-fluorobiphenyl-4-yl}pyrazin-2-amine |
| 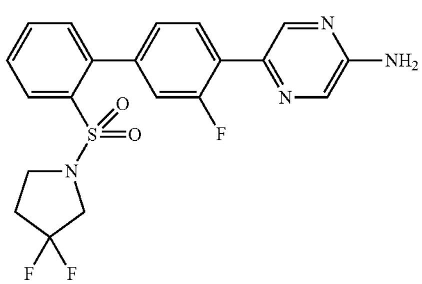 [SMILES: Nc1cnc(-c2ccc(-c3ccccc3S(=O)(=O)N3CCC(F)(F)C3)cc2F)cn1] | 51 | 5-{2'-[(3,3-Difluoropyrrolidin-1-yl)sulfonyl]-3-fluorobiphenyl-4-yl}pyrazin-2-amine |
| 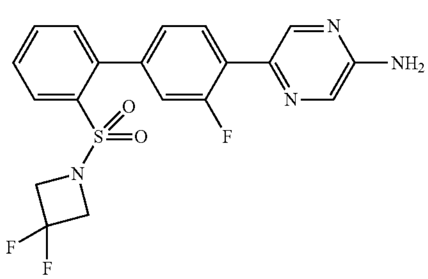 [SMILES: Nc1cnc(-c2ccc(-c3ccccc3S(=O)(=O)N3CC(F)(F)C3)cc2F)cn1] | 52 | 5-{2'-[(3,3-Difluoroazetidin-1-yl)sulfonyl]-3-fluorobiphenyl-4-yl}pyrazin-2-amine |

TABLE 3-continued

| STRUCTURE | COMPOUND # | NAME |
|---|---|---|
| 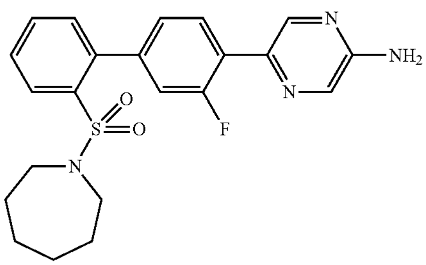 [SMILES: Nc1cnc(-c2ccc(-c3ccccc3S(=O)(=O)N3CCCCCC3)cc2F)cn1] | 53 | 5-[2'-(Azepan-1-ylsulfonyl)-3-fluorobiphenyl-4-yl]pyrazin-2-amine |
| 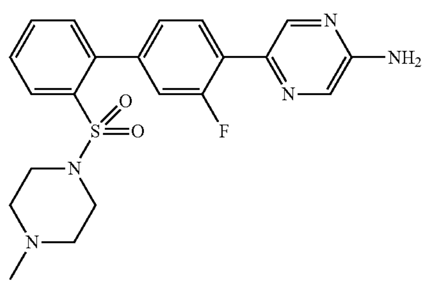 [SMILES: CN1CCN(S(=O)(=O)c2ccccc2-c2ccc(-c3cnc(N)cn3)c(F)c2)CC1] | 54 | 5-{3-Fluoro-2'-[(4-methylpiperazin-1-yl)sulfonyl]biphenyl4-yl}pyrazin-2-amine |
| 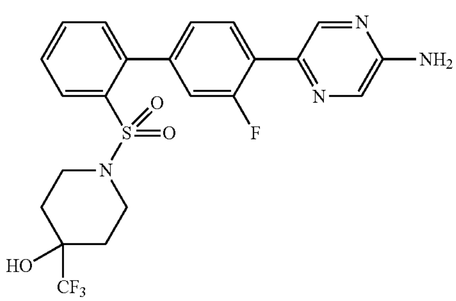 [SMILES: Nc1cnc(-c2ccc(-c3ccccc3S(=O)(=O)N3CCC(O)(C(F)(F)F)CC3)cc2F)cn1] | 55 | 1-{[4'-(5-Aminopyrazin-2-yl)-3'-fluorobiphenyl-2-yl]sulfonyl}-4-(trifluoromethyl)piperidin-4-ol |
| 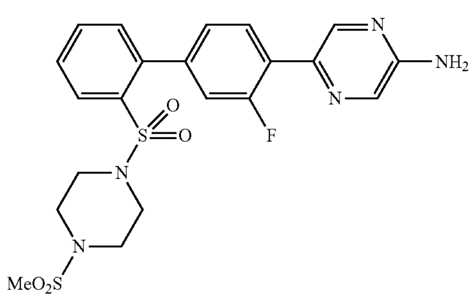 [SMILES: CS(=O)(=O)N1CCN(S(=O)(=O)c2ccccc2-c2ccc(-c3cnc(N)cn3)c(F)c2)CC1] | 56 | 5-(3-Fluoro-2'-{[4-(methylsulfonyl)piperazin-1-yl]sulfonyl}biphenyl-4-yl)pyrazin-2-amine |
| 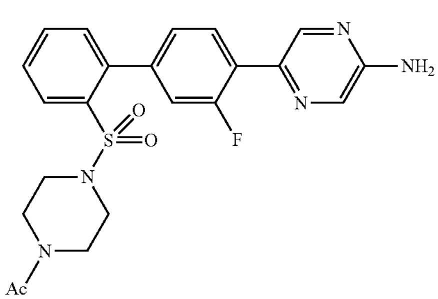 [SMILES: CC(=O)N1CCN(S(=O)(=O)c2ccccc2-c2ccc(-c3cnc(N)cn3)c(F)c2)CC1] | 57 | 5-{2'-[(4-Acetylpiperazin-1-yl)sulfonyl]-3-fluorobiphenyl-4-yl}pyrazin-2-amine |

TABLE 3-continued

| STRUCTURE | COMPOUND # | NAME |
|---|---|---|
| 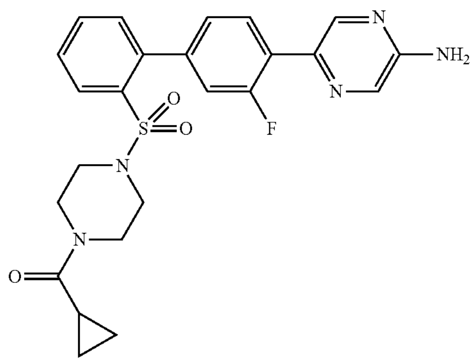 [SMILES: Nc1cnc(-c2ccc(-c3ccccc3S(=O)(=O)N3CCN(C(=O)C4CC4)CC3)cc2F)cn1] | 58 | 5-(2'-{[4-(Cyclopropylcarbonyl)piperazin-1-yl]sulfonyl}-3-fluorobiphenyl-4-yl)pyrazin-2-amine |
| 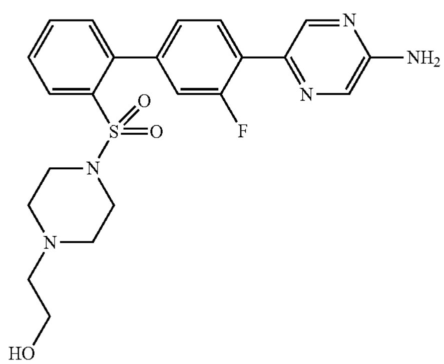 | 59 | 2-(4-{[4'-[5-Aminopyrazin-2-yl)-3'-fluorobiphenyl-2-yl]sulfonyl}piperazin-1-yl)ethanol |
| 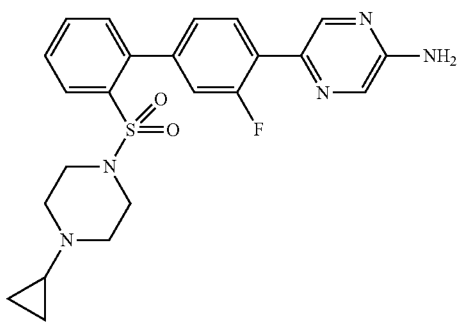 [SMILES: Nc1cnc(-c2ccc(-c3ccccc3S(=O)(=O)N3CCN(C4CC4)CC3)cc2F)cn1] | 60 | 5-{2'-[(4-Cyclopropylpiperazin-1-yl)sulfonyl]-3-fluorobiphenyl-4-yl}pyrazin-2-amine |
| 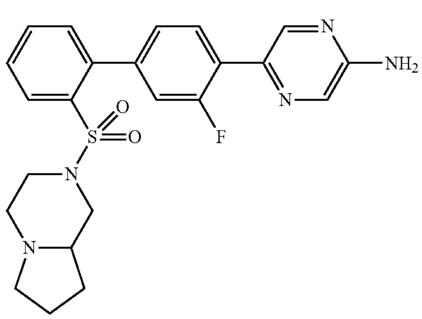 [SMILES: Nc1cnc(-c2ccc(-c3ccccc3S(=O)(=O)N3CCN4CCCC4C3)cc2F)cn1] | 61 | racemic 5-[3-Fluoro-2'-(hexahydropyrrolo[1,2-a]pyrazin-2(1H)-ylsulfonyl)biphenyl-4-yl]pyrazin-2-amine |

TABLE 3-continued

| STRUCTURE | COMPOUND # | NAME |
|---|---|---|
| 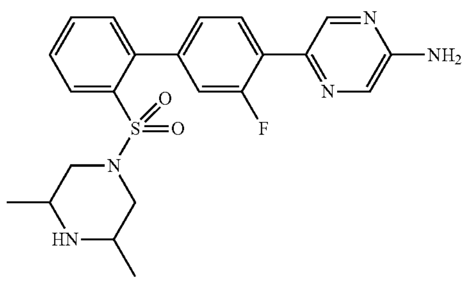 [SMILES: CC1CN(S(=O)(=O)c2ccccc2-c2ccc(-c3cnc(N)cn3)c(F)c2)CC(C)N1] | 62 | 5-{2'-[(3,5-Dimethylpiperazin-1-yl)sulfonyl]-3-fluorobiphenyl-4-yl}pyrazin-2-amine |
| 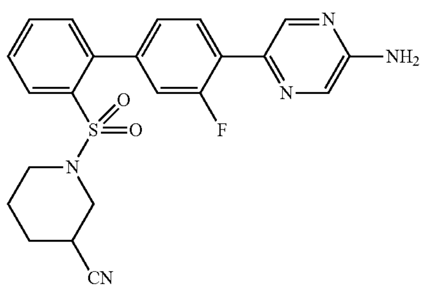 [SMILES: N#CC1CCCN(S(=O)(=O)c2ccccc2-c2ccc(-c3cnc(N)cn3)c(F)c2)C1] | 63 | racemic 1-{[4'-(5-Aminopyrazin-2-yl)-3'-fluorobiphenyl-2-yl]sulfonyl}piperidine-3-carbonitrile |
| 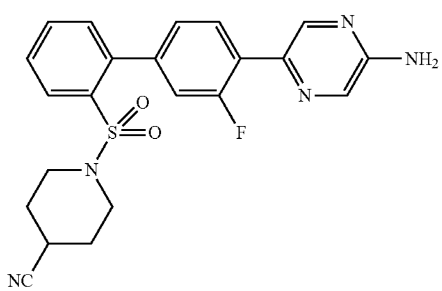 [SMILES: N#CC1CCN(S(=O)(=O)c2ccccc2-c2ccc(-c3cnc(N)cn3)c(F)c2)CC1] | 64 | 1-{[4'-(5-Aminopyrazin-2-yl)-3'-fluorobiphenyl-2-yl]sulfonyl}piperidine-4-carbonitrile |
| 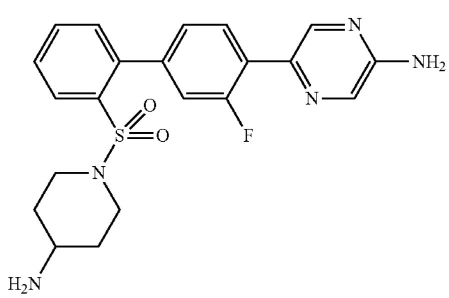 [SMILES: Nc1cnc(-c2ccc(-c3ccccc3S(=O)(=O)N3CCC(N)CC3)cc2F)cn1] | 65 | 5-{2'-[(4-Aminopiperidin-1-yl)sulfonyl]-3-fluorobiphenyl-4-yl}pyrazin-2-amine |
| 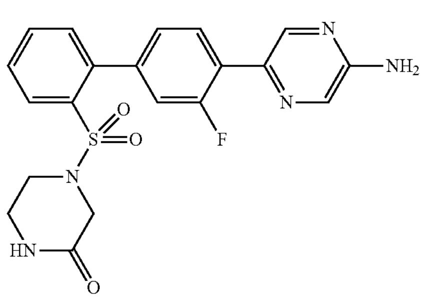 | 66 | 4-{1,4'-(5-Aminopyrazin-2-yl)-3'-fluorobiphenyl-2-ylisulfonyl}piperazin-2-one |

TABLE 3-continued
| STRUCTURE | COMPOUND # | NAME |
|---|---|---|
| 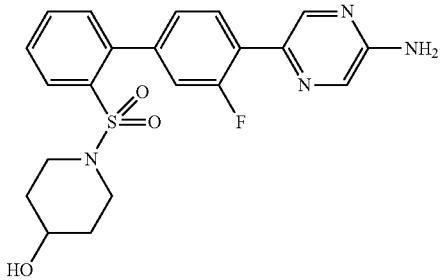 | 67 | 1-{[4'-(5-Aminopyrazin-2-yl)-3'-fluorobiphenyl-2-yl]sulfonyl}piperidin-4-ol |
| 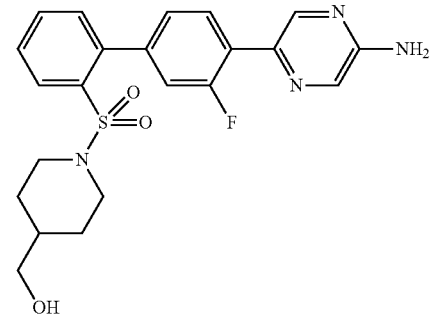 [SMILES: Nc1cnc(-c2ccc(-c3ccccc3S(=O)(=O)N3CCC(CO)CC3)cc2F)cn1] | 68 | (1-{[4'-(5-Aminopyrazin-2-yl)-3'-fluorobiphenyl-2-yl]sulfonyl}piperidin-4-yl)methanol |
| 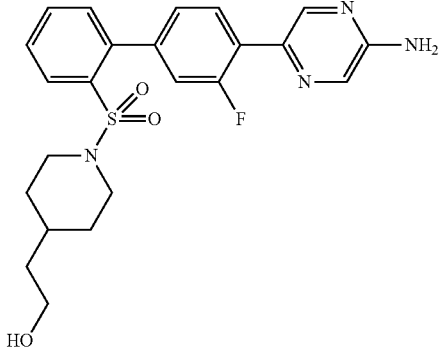 [SMILES: Nc1cnc(-c2ccc(-c3ccccc3S(=O)(=O)N3CCC(CCO)CC3)cc2F)cn1] | 69 | 2-(1-{[4'-(5-Aminopyrazin-2-yl)-3'-fluorobiphenyl-2-yl]sulfonyl}piperidin-4-yl)ethanol |
| 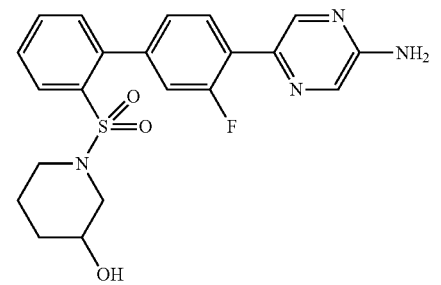 | 70 | racemic 1-{[4'-(5-Aminopyrazin-2-yl)-3'-fluorobiphenyl-2-yl]sulfonyl}piperidin-3-ol |

TABLE 3-continued

| STRUCTURE | COMPOUND # | NAME |
|---|---|---|
| 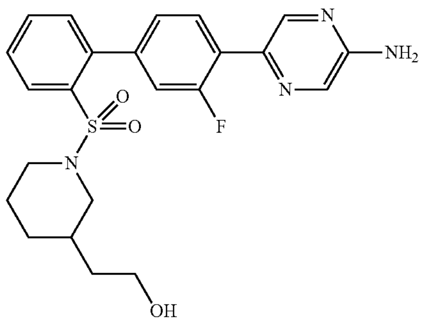 [SMILES: Nc1cnc(-c2ccc(-c3ccccc3S(=O)(=O)N3CCCC(CCO)C3)cc2F)cn1] | 71 | racemic 2-(1-{[4'-(5-Aminopyrazin-2-yl)-3'-fluorobiphenyl-2-yl]sulfonyl}piperidin-3-yl)ethanol |
| 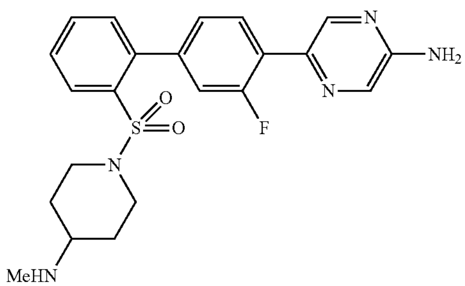 [SMILES: CNC1CCN(S(=O)(=O)c2ccccc2-c2ccc(-c3cnc(N)cn3)c(F)c2)CC1] | 72 | 5-{3-Fluoro-2'-{[4-(methylamino)piperidin-1-yl]sulfonyl}biphenyl-4-yl)pyrazin.-2-amine |
| 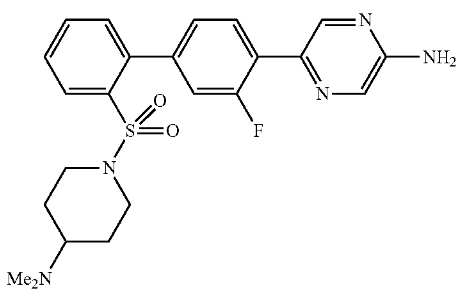 [SMILES: CN(C)C1CCN(S(=O)(=O)c2ccccc2-c2ccc(-c3cnc(N)cn3)c(F)c2)CC1] | 73 | 5-(2'-{[4-(Dimethylamino)piperidin-1-yl]sulfonyl}-3-fluorobiphenyl-4-yl)pyrazin-2-amine |
| 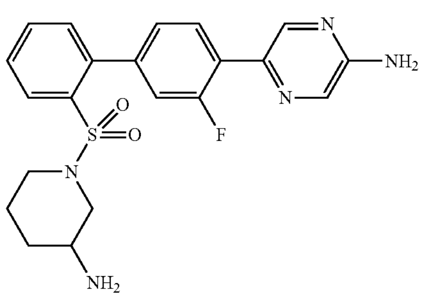 [SMILES: Nc1cnc(-c2ccc(-c3ccccc3S(=O)(=O)N3CCCC(N)C3)cc2F)cn1] | 74 | racemic 5-{2'-[(3-Aminopiperidin-1-yl)sulfonyl]-3-fluorobiphenyl-4-yl}pyrazin-2-amine |
| 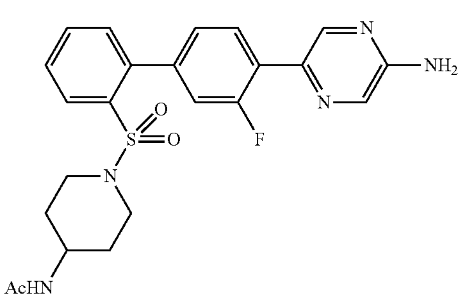 [SMILES: CC(=O)NC1CCN(S(=O)(=O)c2ccccc2-c2ccc(-c3cnc(N)cn3)c(F)c2)CC1] | 75 | N-(1-{[4'-(5-Aminopyrazin-2'yl)-3'-fluorobiphenyl-2-yl]sulfonyl}piperidin-4-yl)acetamide |

TABLE 3-continued

| STRUCTURE | COMPOUND # | NAME |
|---|---|---|
| 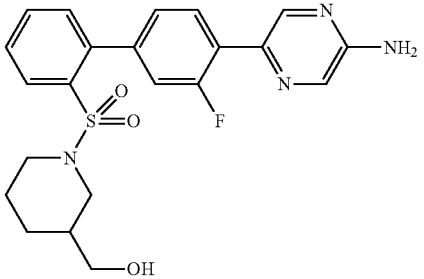 [SMILES: Nc1cnc(-c2ccc(-c3ccccc3S(=O)(=O)N3CCCC(CO)C3)cc2F)cn1] | 76 | racemic (1-{[4'-(5-Aminopyrazin-2-yl)-3'-fluorobiphenyl-2-yl]sulfonyl}piperldin-3-yl)methanol |
| 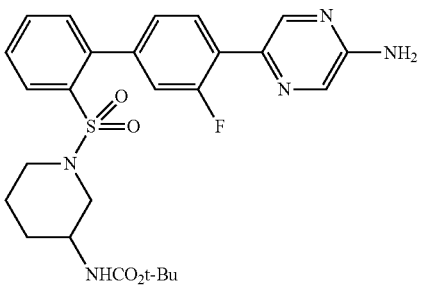 | 77 | racemic tert-Butyl (1-{[4'-(5-aminopyrazin-2-yl)-3'-fluorobiphenyl-2-yl]sulfonyl}piperidin-3-yl)carbamate |
| 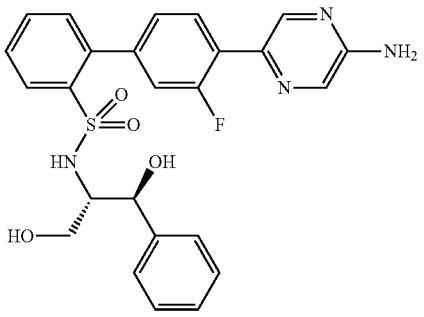 [SMILES: Nc1cnc(-c2ccc(-c3ccccc3S(=O)(=O)N[C@@H](CO)[C@@H](O)c3ccccc3)cc2F)cn1] | 78 | 4'-(5-Aminopyrazin-2-yl)-3'-fluoro-N-[(1S,2S)-2-hydroxy-1-(hydroxymethyl)-2-phenylethyl]biphenyl-2-sulfonamide |
| 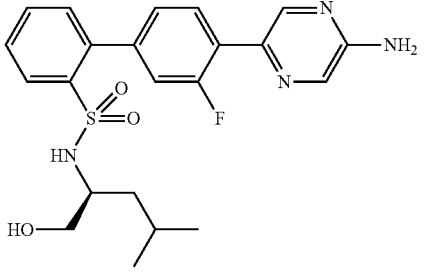 [SMILES: CC(C)C[C@@H](CO)NS(=O)(=O)c1ccccc1-c1ccc(-c2cnc(N)cn2)c(F)c1] | 79 | 4'-(5-Aminopyrazin-2-yl)-3'-fluoro-N-[(1S)-1-(hydroxymethyl)-3-methylbutyl]biphenyl-2-sulfonamide |
| 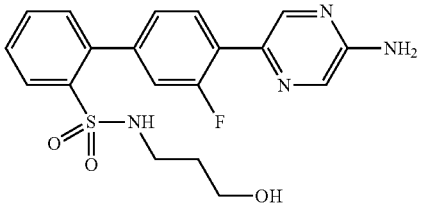 [SMILES: Nc1cnc(-c2ccc(-c3ccccc3S(=O)(=O)NCCCO)cc2F)cn1] | 80 | 4'-(5-Aminopyrazin-2-yl)-3'-fluoro-N-(3-hydroxypropyl)biphenyl-2-sulfonamide |

TABLE 3-continued

| STRUCTURE | COMPOUND # | NAME |
|---|---|---|
| 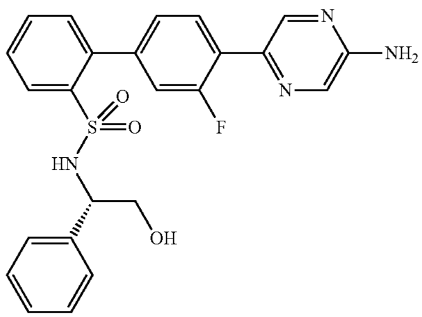 [SMILES: Nc1cnc(-c2ccc(-c3ccccc3S(=O)(=O)N[C@H](CO)c3ccccc3)cc2F)cn1] | 81 | 4'-(5-Aminopyrazin-2-yl)-3'-fluoro-N-[(1S)-2-hydroxy-1-phenylethyl]biphenyl-2-sulfonamide |
| 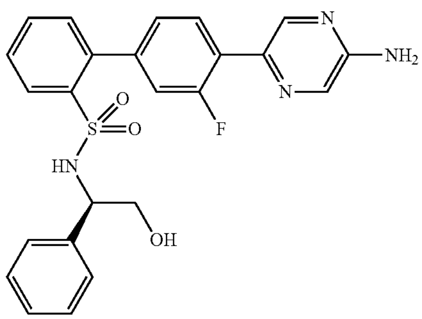 [SMILES: Nc1cnc(-c2ccc(-c3ccccc3S(=O)(=O)N[C@@H](CO)c3ccccc3)cc2F)cn1] | 82 | 4'-(5-Aminopyrazin-2-yl)-3'-fluoro-N-[(1R)-2-hydroxy-1-phenylethyl]biphenyl-2-sulfonamide |
| 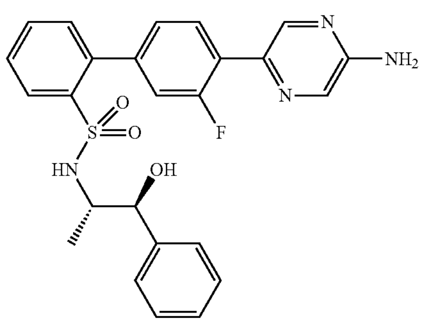 [SMILES: C[C@H](NS(=O)(=O)c1ccccc1-c1ccc(-c2cnc(N)cn2)c(F)c1)[C@@H](O)c1ccccc1] | 83 | 4'-(5-Aminopyrazin-2-yl)-3'-fluoro-N-[(1S,2R)-2-hydroxy-1-methyl-2-phenylethyl]biphenyl-2-sulfonamide |
| 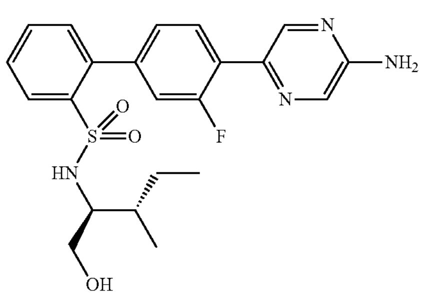 [SMILES: CC[C@H](C)[C@@H](CO)NS(=O)(=O)c1ccccc1-c1ccc(-c2cnc(N)cn2)c(F)c1] | 84 | 4'-(5-Aminopyrazin-2-yl)-3'-fluoro-N-[(1S,2S)-1-(hydroxymethyl)-2-methylbutyl]biphenyl-2-sulfonamide |
| 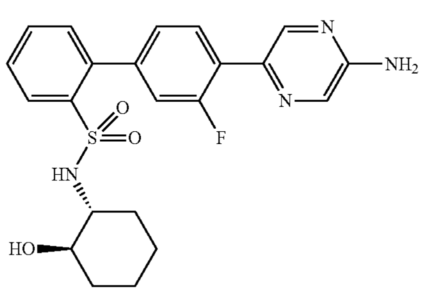 [SMILES: Nc1cnc(-c2ccc(-c3ccccc3S(=O)(=O)N[C@@H]3CCCC[C@H]3O)cc2F)cn1] | 85 | 4'-(5-Aminopyrazin-2-yl)-3'-fluoro-N-[(1R,2R)-2-hydroxycyclohexyl]biphenyl-2-sulfonamide |

TABLE 3-continued

| STRUCTURE | COMPOUND # | NAME |
|---|---|---|
| 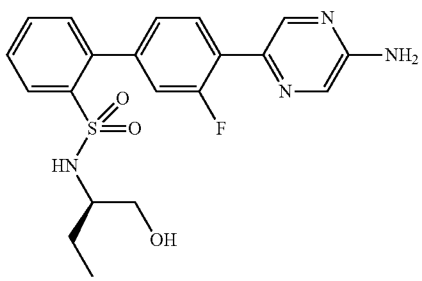 [SMILES: CC[C@H](CO)NS(=O)(=O)c1ccccc1-c1ccc(-c2cnc(N)cn2)c(F)c1] | 86 | 4'-(5-Aminopyrazin-2-yl)-3'-fluoro-N-[(1R)-1-(hydroxymethyl)propyl]biphenyl-2-sulfonamide |
| 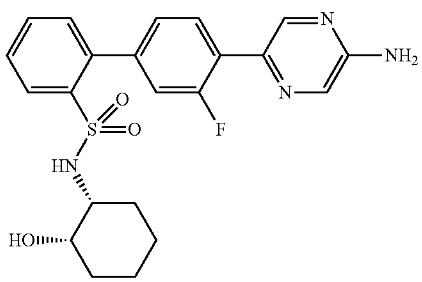 [SMILES: Nc1cnc(-c2ccc(-c3ccccc3S(=O)(=O)N[C@@H]3CCCC[C@@H]3O)cc2F)cn1] | 87 | 4'-(5-Aminopyrazin-2-yl)-3'-fluoro-N-[(1R,2S)-2-hydroxycyclohexyl]biphenyl-2-sulfonamide |
| 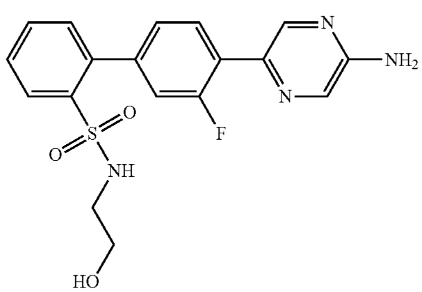 [SMILES: Nc1cnc(-c2ccc(-c3ccccc3S(=O)(=O)NCCO)cc2F)cn1] | 88 | 4'-(5-Aminopyrazin-2-yl)-3'-fluoro-N-(2-hydroxyethyl)biphenyl-2-sulfonamide |
| 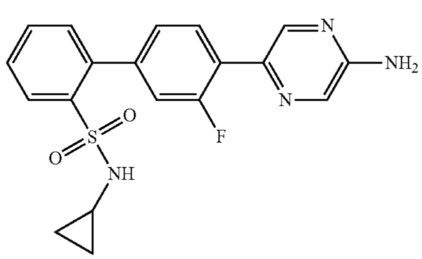 [SMILES: Nc1cnc(-c2ccc(-c3ccccc3S(=O)(=O)NC3CC3)cc2F)cn1] | 89 | 4'-(5-Aminopyrazin-2-yl)-N-cyclopropyl-3'-fluorobiphenyl-2-sulfonamide |
| 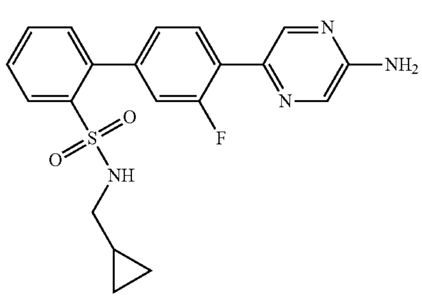 [SMILES: Nc1cnc(-c2ccc(-c3ccccc3S(=O)(=O)NCC3CC3)cc2F)cn1] | 90 | 4'-(5-Aminopyrazin-2-yl)-N-(cyclopropylmethyl)-3'-fluorobiphenyl-2-sulfonamide |

TABLE 3-continued

| STRUCTURE | COMPOUND # | NAME |
|---|---|---|
| 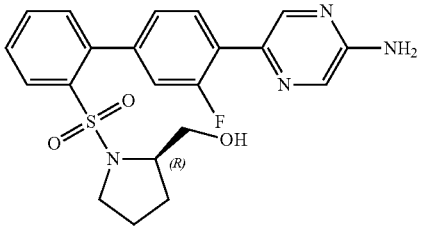 | 91 | (R)-(1-((4'-(5-aminopyrazin-2-yl)-3'-fluoro-[1,1'-biphenyl]-2-yl)sulfonyl)pyrrolidin-2-yl)methanol |
| 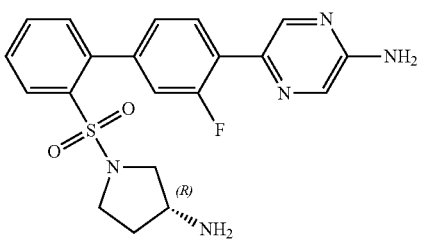 | 92 | (R)-5-(2'-((3-aminopyrrolidin-1-yl)sulfonyl)-3-fluoro-[1,1'-biphenyl]-4-yl)pyrazin-2-amine |
| 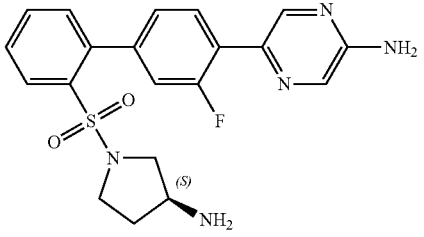 | 93 | (S)-5-(2'-((3-aminopyrrolidin-1-yl)sulfonyl)-3-fluoro-[1,1'-biphenyl]-4-yl)pyrazin-2-amine |
| 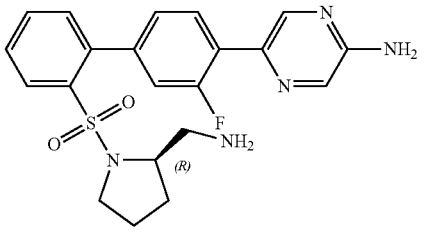 | 94 | (R) 5-(2'-{[2-(Aminomethyl)pyrrolidin-1-yl]sulfonyl}-3-fluorobiphenyl-4-yl)pyrazin-2-amine |
| 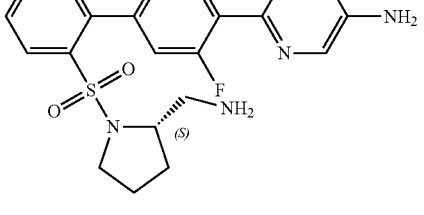 | 95 | (S)-(1-((4'-(5-aminopyrazin-2-yl)-3'-fluoro-[1,1'-biphenyl]-2'-yl)sulfonyl)pyrrolidin-2-yl)methanol |
| 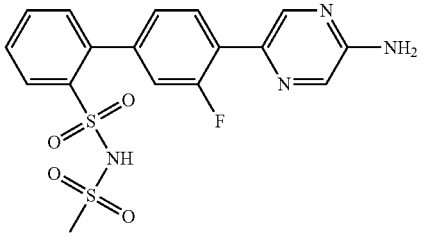 [SMILES: CS(=O)(=O)NS(=O)(=O)c1ccccc1-c1ccc(-c2cnc(N)cn2)c(F)c1] | 96 | 4'-(5-Aminopyrazin-2-yl)-3'-fluoro-N-(methylsulfonyl)biphenyl-2-sulfonamide |

TABLE 3-continued

| STRUCTURE | COMPOUND # | NAME |
|---|---|---|
| 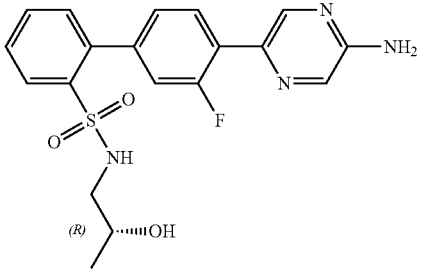 | 97 | (R)-4'-(5-aminopyrazin-2-yl)-3'-fluoro-N-(2-hydroxypropyl)-[1,1'-biphenyl]-2-sulfonamide |
| 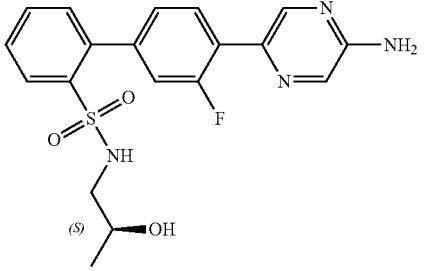 | 98 | (S)-4'-(5-aminopyrazin-2-yl)-3'-fluoro-N-(2-hydroxypropyl)-[1,1'-biphenyl]-2-sulfonamide |
| 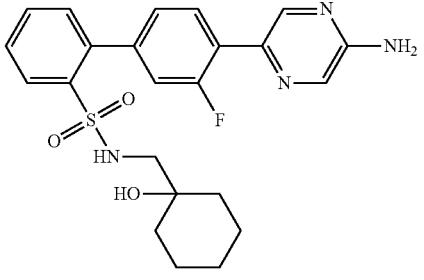 [SMILES: Nc1cnc(-c2ccc(-c3ccccc3S(=O)(=O)NCC3(O)CCCCC3)cc2F)cn1] | 99 | 4'-(5-Aminopyrazin-2-yl)-3'-fluoro-N-[(1-hydroxycyclohexyl)methyl]biphenyl-2-sulfonamide |
| 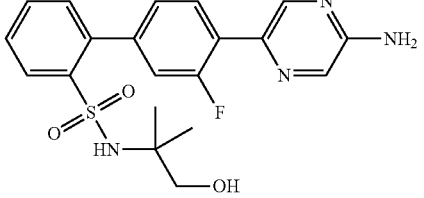 | 100 | 4'-(5-Aminopyrazin-2-yl)-3'-fluoro-N-(2-hydroxy-1,1-dimethylethyl)biphenyl-2-sulfonamide |
| 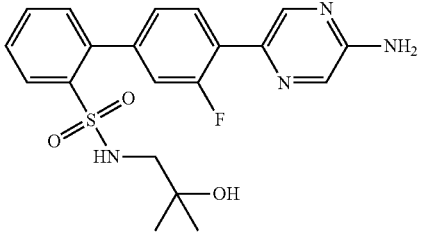 [SMILES: CC(C)(O)CNS(=O)(=O)c1ccccc1-c1ccc(-c2cnc(N)cn2)c(F)c1] | 101 | 4'-(5-Aminopyrazin-2-yl)-3'-fluoro-N-(2-hydroxy-2-methylpropyl)biphenyl-2-sulfonamide |

TABLE 3-continued

| STRUCTURE | COMPOUND # | NAME |
| --- | --- | --- |
| 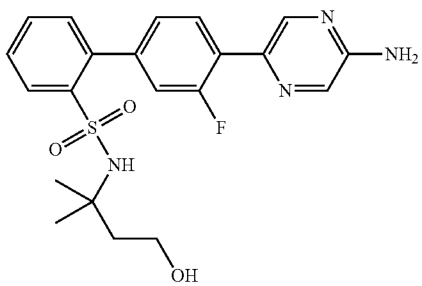 [SMILES: CC(C)(CCO)NS(=O)(=O)c1ccccc1-c1ccc(-c2cnc(N)cn2)c(F)c1] | 102 | 4'-(5-Aminopyrazin-2-yl)-3'-fluoro-N-(3-hydroxy-1,1-dimethylpropyl)biphenyl-2-sulfonamide |
| 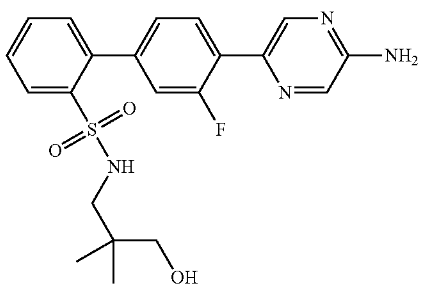 [SMILES: CC(C)(CO)CNS(=O)(=O)c1ccccc1-c1ccc(-c2cnc(N)cn2)c(F)c1] | 103 | 4'-(5-Aminopyrazin-2-yl)-3'-fluoro-N-(3-hydroxy-2,2-dimethylpropyl)biphenyl-2-sulfonamide |
| 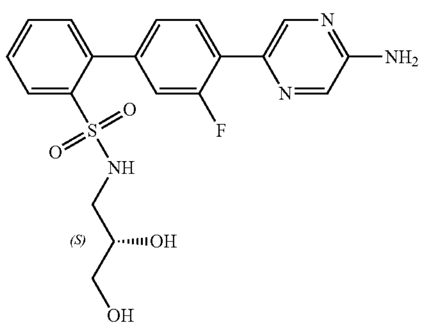 | 104 | (S)-4'-(5-aminopyrazin-2-yl)-N-(2,3-dihydroxypropyl)-3'-fluoro-[1,1'-biphenyl]-2-sulfonamide |
| | 105 | (R)-4'-(5-aminopyrazin-2-yl)-N-(2,3-dihydroxypropyl)-3'-fluoro-[1,1'-biphenyl]-2-sulfonamide |
| | 106 | (trans)-1-{[4'-(5-Aminopyrazin-2-yl)-3'-fluorobiphenyl-2-yl]sulfonyl}pyrrolidine-3,4-diol |

TABLE 3-continued

| STRUCTURE | COMPOUND # | NAME |
|---|---|---|
| 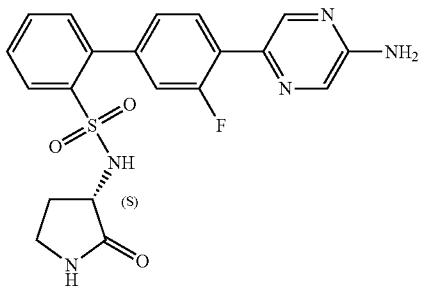 | 107 | (S)-4'-(5-aminopyrazin-2-yl)-3'-fluoro-N-(2-oxopyrrolidin-3-yl)-[1,1'-biphenyl]-2-sulfonamide |
| 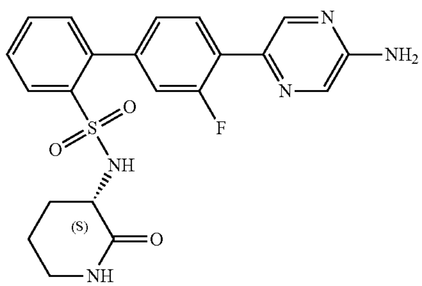 | 108 | (S)-4'-(5-aminopyrazin-2-yl)-3'-fluoro-N-(2-oxopiperidin-3-yl)-[1,1'-biphenyl]-2-sulfonamide |
| 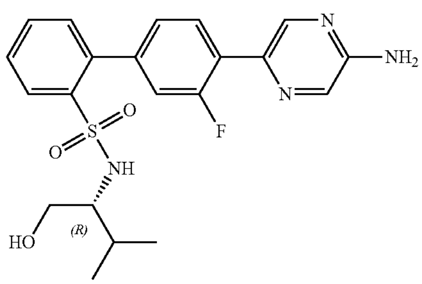 | 109 | (R)-4'-(5-Aminopyrazin-2-yl)-3'-fluoro-N-[1-(hydroxymethyl)-2'-methylpropyl]piphenyl-2-sulfonamide |
| 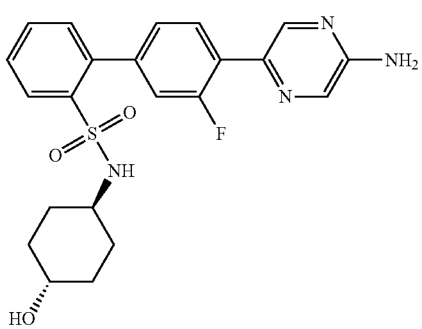 [SMILES: Nc1cnc(-c2ccc(-c3ccccc3S(=O)(=O)N[C@H]3CC[C@H](O)CC3)cc2F)cn1] | 110 | trans 4'-(5-Aminopyrazin-2-yl)-3'-fluoro-N-(4-hydroxycyclohexyl)biphenyl-2-sulfonamide |
| 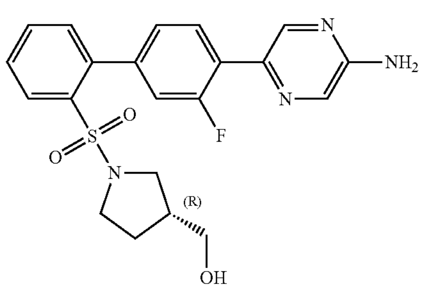 | 111 | (R)-(1-((4'-(5-aminopyrazin-2-yl)-3'-fluoro-[1,1'-biphenyl]-2-yl)sulfonyl)pyrrolidin-3-yl)methanol |

TABLE 3-continued

| STRUCTURE | COMPOUND # | NAME |
|---|---|---|
| 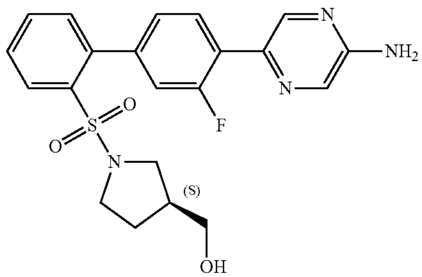 | 112 | (S)-(1-{[4'-(5-Aminopyrazin-2-yl)-3'-fluorobiphenyl-2-yl]sulfonyl}pyrrolidin-3-yl)methanol |
| 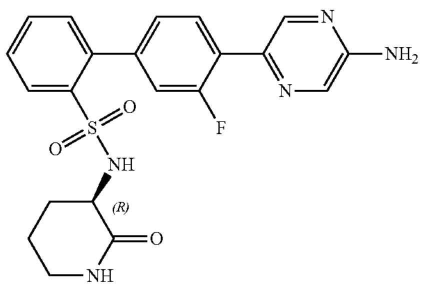 | 113 | (R)-4'-(5-Aminopyrazin-2-yl)-3'-fluoro-N-(2-oxopipendin-3-yl)biphenyl-2-sulfonamide |
| 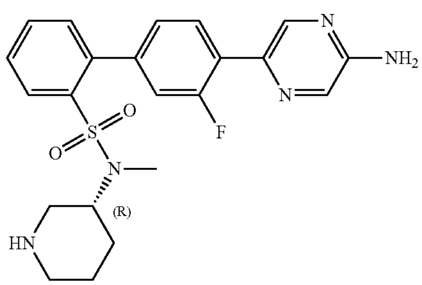 | 114 | (R)-4'-(5-Aminopyrazin-2-yl)-3'-fluoro-N-methyl-N-piperidin-3-ylbiphenyl-2-sulfonamide |
| 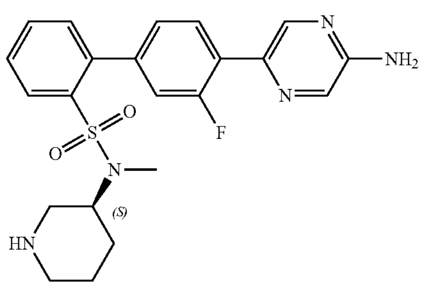 | 115 | (S)-4'-(5-Aminopyrazin-2-yl)-3'-fluoro-N-methyl-N-piperidin-3-ylbiphenyl-2'-sulfonamide |
| 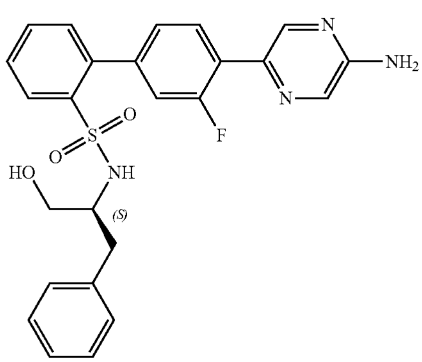 | 116 | (3),4-(5-aminopyrazin-2-yl)-3'-fluoro-N-(1-hydroxy-3-phenylpropan-2-yl)-[1,1'-biphenyl]-2-sulfonamide |

TABLE 3-continued

| STRUCTURE | COMPOUND # | NAME |
|---|---|---|
| 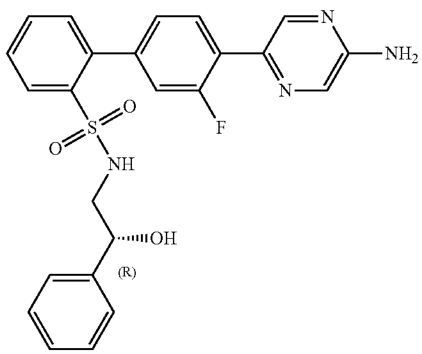 | 117 | (R)-4'-(5-aminopyrazin-2-yl)-3'-fluoro-N-(2-hydroxy-2-phenylethyl)-[1,1'-biphenyl]-2-sulfonamide |
| 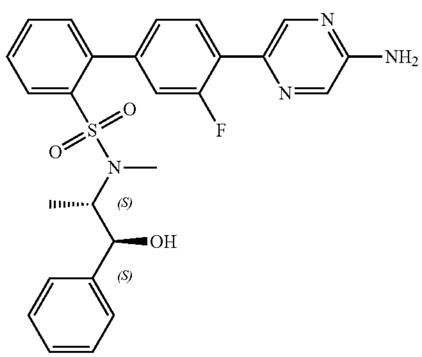 | 118 | 4'-(5-aminopyrazin-2-yl)-3'-fluoro-N-((1S,2S)-1-hydroxy-1-phenylpropan-2-yl)-N-methyl-[1,1'-biphenyl)-2-sulfonamide |
| 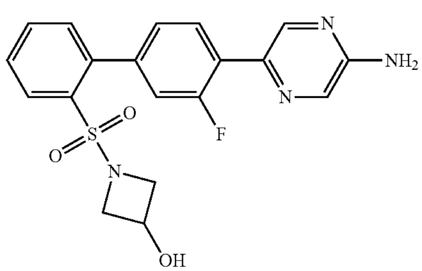 [SMILES: Nc1cnc(-c2ccc(-c3ccccc3S(=O)(=O)N3CC(O)C3)cc2F)cn1] | 119 | 1-{[4'-(5-Aminopyrazin-2-yl)-3'-fluorobiphenyl-2-yl]sulfonyl}azetidin-3-ol |
| 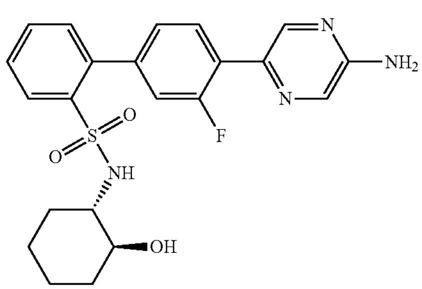 [SMILES: Nc1cnc(-c2ccc(-c3ccccc3S(=O)(=O)N[C@H]3CCCC[C@@H]3O)cc2F)cn1] | 120 | racemic (trans)-4'-(5-Aminopyrazin-2-yl)-3'-fluoro-N-(2-hydroxycyclohexyl)biphenyl-2-sulfonamide |
| 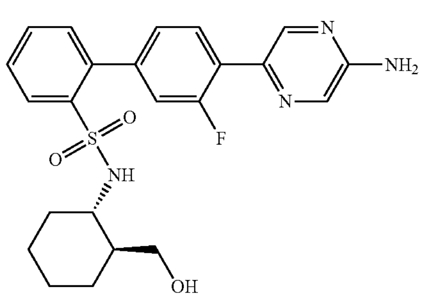 [SMILES: Nc1cnc(-c2ccc(-c3ccccc3S(=O)(=O)N[C@H]3CCCC[C@@H]3CO)cc2F)cn1] | 121 | racemic (trans)-4'-(5-Aminopyrazin-2-yl)-3'-fluoro-N-[2-(hydroxymethyl)cyclohexyl]biphenyl-2-sulfonamide |

TABLE 3-continued

| STRUCTURE | COMPOUND # | NAME |
|---|---|---|
| 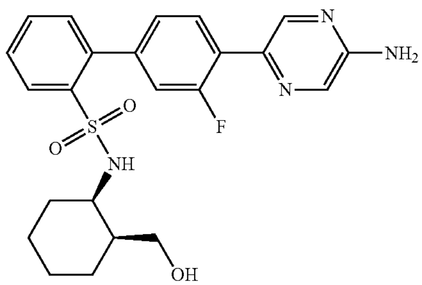 [SMILES: Nc1cnc(-c2ccc(-c3ccccc3S(=O)(=O)N[C@@H]3CCCC[C@@H]3CO)cc2F)cn1] | 122 | racemic (cis)-4'-(5-Aminopyrazin-2-yl)-3'-fluoro-N-[2-(hydroxymethyl)cyclohexyl]biphenyl-2-sulfonamide |
| 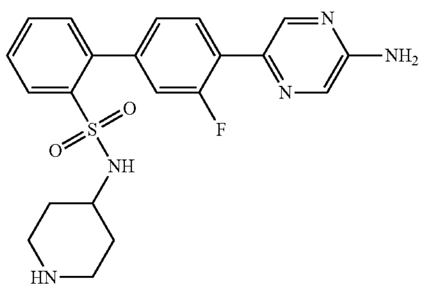 [SMILES: Nc1cnc(-c2ccc(-c3ccccc3S(=O)(=O)NC3CCNCC3)cc2F)cn1] | 123 | 4'-(5-Aminopyrazin-2-yl)-3'-fluoro-N-piperidin-4-ylbiphenyl-2-sulfonamide |
| 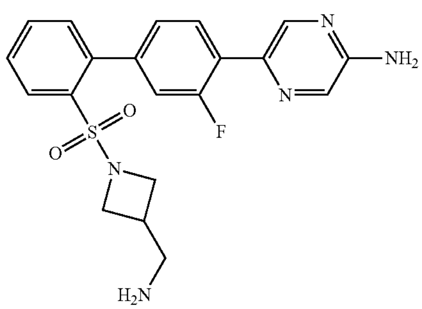 [SMILES: NCC1CN(S(=O)(=O)c2ccccc2-c2ccc(-c3cnc(N)cn3)c(F)c2)C1] | 124 | 5-(2'-{[3-(Aminomethyl)azetidin-1-yl]sulfonyl}-fluorobiphenyl-4-yl)pyrazin-2-amine |
| 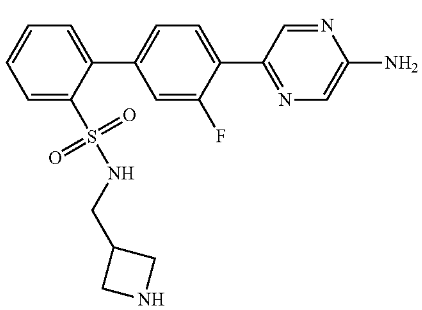 [SMILES: Nc1cnc(-c2ccc(-c3ccccc3S(=O)(=O)NCC3CNC3)cc2F)cn1] | 125 | 4'-(5-Aminopyrazin-2-yl)-N-(azetidin-3-ylmethyl)-3'-fluorobiphenyl-2-sulfonamide |
| 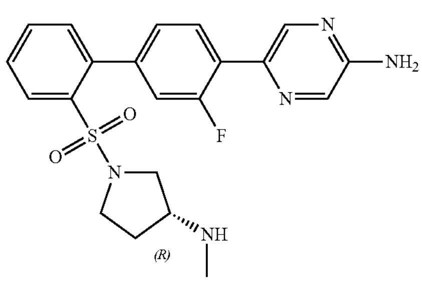 | 126 | (R)-5-(3-Fluoro-2'-{[3-(methylamino)pyrrolidin-1-yl]sulfonyl}biphenyl-4-yl)pyrazin-2-amine |

TABLE 3-continued

| STRUCTURE | COMPOUND # | NAME |
|---|---|---|
| 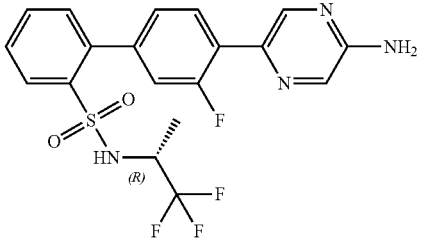 | 127 | (R)-4'-(5-Aminopyrazin-2-yl)-3'-fluoro-N-(2,2,2-trifluoro-1-methylethyl)biphenyl-2-sulfonamide |
| 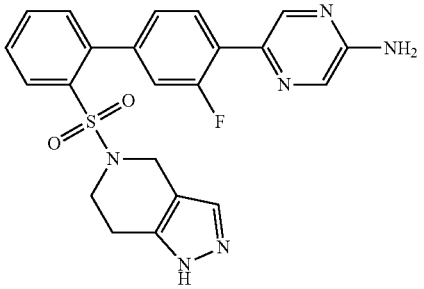 [SMILES: Nc1cnc(-c2ccc(-c3ccccc3S(=O)(=O)N3CCc4[nH]ncc4C3)cc2F)cn1] | 128 | 5-[3-Fluoro-2'-(1,4,6,7-tetrahydro-5H-pyrazolo[4,3-c]pyridin-5-ylsulfonyl)biphenyl-4-yl]pyrazin-2-amine |
| 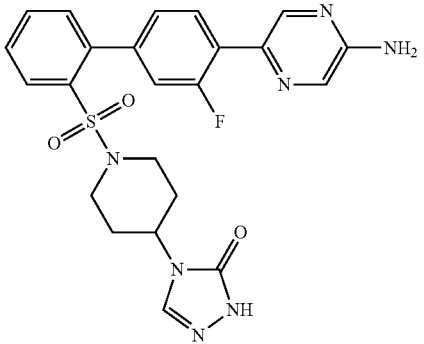 [SMILES: Nc1cnc(-c2ccc(-c3ccccc3S(=O)(=O)N3CCC(n4cn[nH]c4=O)CC3)cc2F)cn1] | 129 | 4-(1-{[4'-(5-Aminopyrazin-2-yl)-3'-fluorobiphenyl-2-yl]sulfonyl}piperidin-4-yl)-2,4-dihydro-3H-1,2,4-triazol-3-one |
| 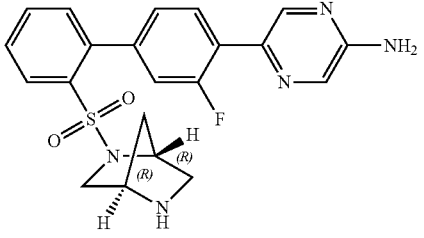 | 130 | 5-(2'-((1R,4R)-2,5-diazabicyclo[2.2.1]heptan-2-ylsulfonyl)-3-fluoro-[1,1'-biphenyl]-4-yl)pyrazin-2-amine |
| 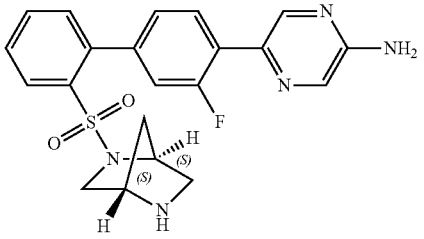 | 131 | 5-(2'-((1S,4S)-2,5-diazabicyclo[2.2.1]heptan-2-ylsulfonyl)-3-fluoro-[1,1'-biphenyl]-4-yl)pyrazin-2-amine |

TABLE 3-continued

| STRUCTURE | COMPOUND # | NAME |
|---|---|---|
| 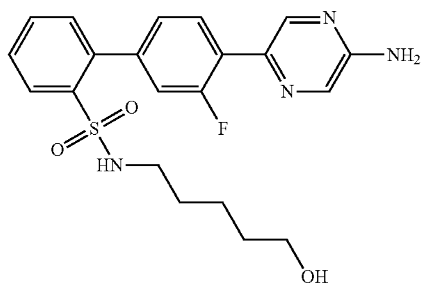 [SMILES: Nc1cnc(-c2ccc(-c3ccccc3S(=O)(=O)NCCCCCO)cc2F)cn1] | 132 | 4'-(5-Aminopyrazin-2-yl)-3'-fluoro-N-(5-hydroxypentyl)biphenyl-2'-sulfonamide |
| 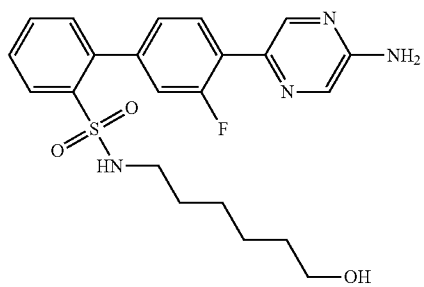 [SMILES: Nc1cnc(-c2ccc(-c3ccccc3S(=O)(=O)NCCCCCCO)cc2F)cn1] | 133 | 4'-(5-Aminopyrazin-2-yl)-3'-fluoro-N-(6-hydroxyhexyl)biphenyl-2'-sulfonamide |
| 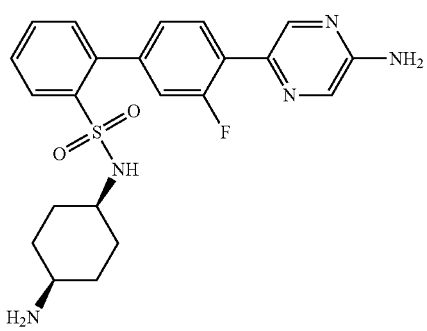 [SMILES: Nc1cnc(-c2ccc(-c3ccccc3S(=O)(=O)N[C@H]3CC[C@@H](N)CC3)cc2F)cn1] | 134 | N-(4-Aminocyclohexyl)-4'-(5-aminopyrazin-2-yl)-3'-fluorobiphenyl-2-sulfonamide |
| 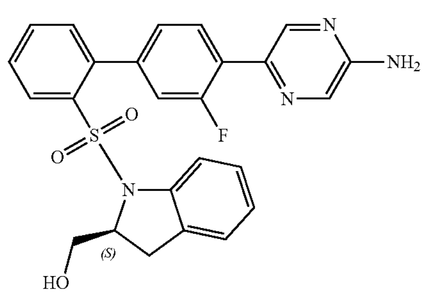 | 135 | (S)-(1-{[4'-(5-Aminopyrazin-2-yl)-3'-fluorobiphenyl-2-yl]sulfonyl}-2,3-dihydro-1H-indol-2-yl)methanol |
| 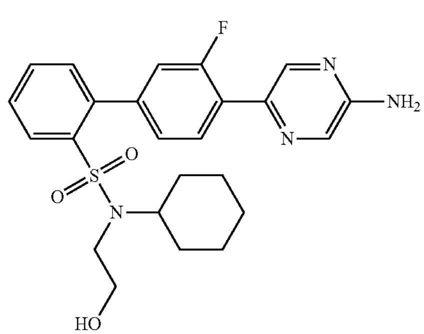 [SMILES: Nc1cnc(-c2ccc(-c3ccccc3S(=O)(=O)N(CCO)C3CCCCC3)cc2F)cn1] | 136 | 4'-(5-Aminopyrazin-2-yl)-N-cyclohexyl-3'-fluoro-N-(2-hydroxyethyl)biphenyl-2-sulfonamide |

TABLE 3-continued

| STRUCTURE | COMPOUND # | NAME |
|---|---|---|
| 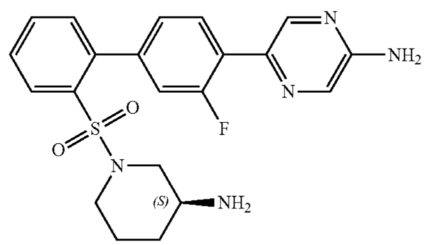 | 137 | (S)-5-{2'-[(3-Aminopiperidin-1-yl)sulfonyl]-3-fluorobiphenyl-4-yl}pyrazin-2-amine |
| 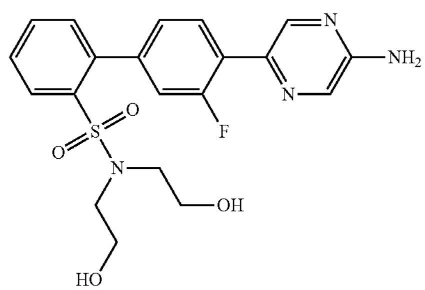 [SMILES: Nc1cnc(-c2ccc(-c3ccccc3S(=O)(=O)N(CCO)CCO)cc2F)cn1] | 138 | 4'-(5-Aminopyrazin-2-yl)-3'-fluoro-N,N-bis(2-hydroxyethyl)biphenyl-2-sulfonamide |
| 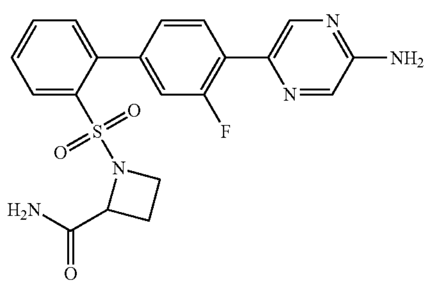 [SMILES: NC(=O)C1CCN1S(=O)(=O)c1ccccc1-c1ccc(-c2cnc(N)cn2)c(F)c1] | 139 | 1-{[4'-(5-Aminopyrazin-2-yl)-3'-fluorobiphenyl-2-yl)sulfonyl}azetidine-2-carboxamide |
| 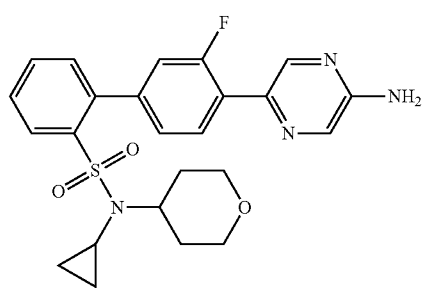 [SMILES: Nc1cnc(-c2ccc(-c3ccccc3S(=O)(=O)N(C3CCOCC3)C3CC3)cc2F)cn1] | 140 | 4'-(5-Aminopyrazin-2-yl)-N-cyclopropyl-3'-fluoro-N-(tetrahydro-2H-pyran-4-yl)biphenyl-2-sulfonamide |
| 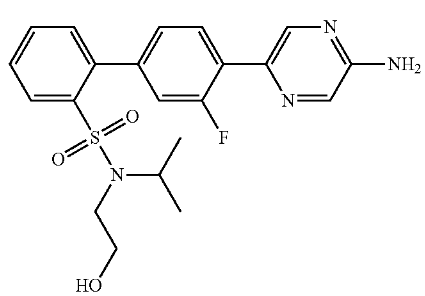 [SMILES: CC(C)N(CCO)S(=O)(=O)c1ccccc1-c1ccc(-c2cnc(N)cn2)c(F)c1] | 141 | 4'-(5-Aminopyrazin-2-yl)-3'-fluoro-N-(2-hydroxyethyl)-N-(1-methylethyl)biphenyl-2-sulfonamide |

TABLE 3-continued

| STRUCTURE | COMPOUND # | NAME |
| --- | --- | --- |
| 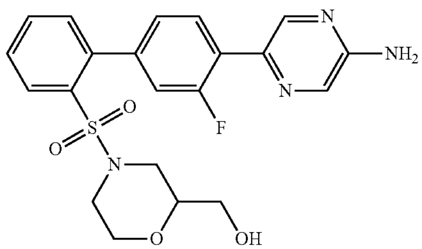 [SMILES: Nc1cnc(-c2ccc(-c3ccccc3S(=O)(=O)N3CCOC(CO)C3)cc2F)cn1] | 142 | racemic (4-{[4'-(5.-Aminopyrazin-2-yl)-3'-fluorobiphenyl-2-yl]sulfonyl}morpholin-2-yl)methanol |
| 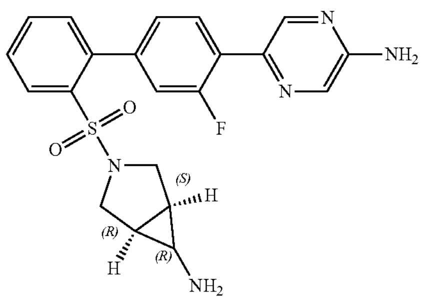 | 143 | (1R,5S)-3-((4'-(5-aminopyrazin-2-yl)-3'-fluoro-[1,1'-biphenyl]-2-yl)sulfonyl)-3-azabicyclo[3.1.0]hexan-6-amine |
| 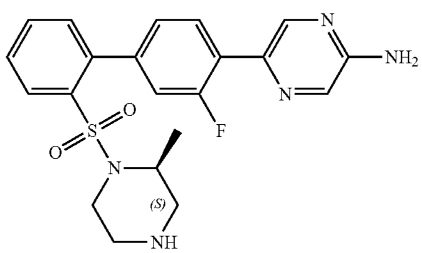 | 144 | (S)-5-(3-fluoro-2'-((2-methylpiperazin-1-yl)sulfonyl)-[1,1'-biphenyl]-4-yl)pyrazin-2-amine |
| 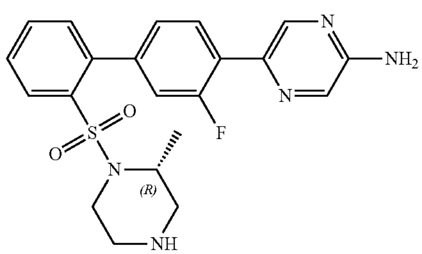 | 145 | (R)-5-(3-fluoro-2'-((2-methylpiperazin-1-yl)sulfonyl)-[1,1'-biphenyl]-4-yl)pyrazin-2-amine |
| 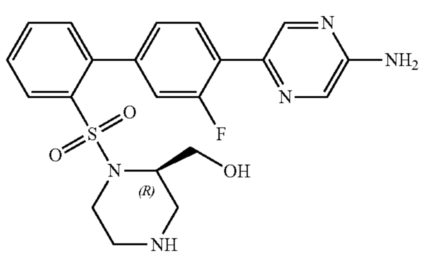 | 146 | (R)-(1-((4'-(5-aminopyrazin-2-yl)-3'-fluoro-[1,1'-biphenyl]-2-yl)sulfonyl)piperazin-2-yl)methanol |
| 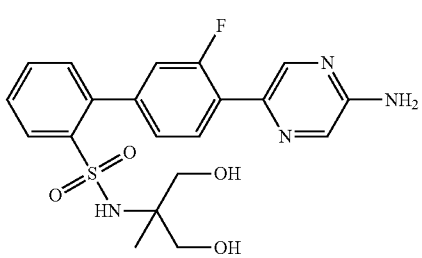 [SMILES: CC(CO)(CO)NS(=O)(=O)c1ccccc1-c1ccc(-c2cnc(N)cn2)c(F)c1] | 147 | 4'-(5-Aminopyrazin-2-yl)-3'-fluora-N-[2-hydroxy-1-(hydroxymethyl)-1-methylethyl]piphenyl-2-sulfonamide |

TABLE 3-continued

| STRUCTURE | COMPOUND # | NAME |
|---|---|---|
| 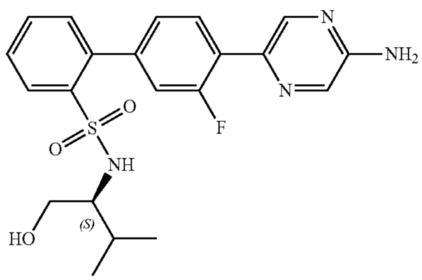 | 148 | (S)-4'-(5-aminopyrazin-2-yl)-3'-fluoro-N-(1-hydroxy-3-methylbutan-2-yl)-[1,1'-biphenyl]-2-sulfonamide |
| 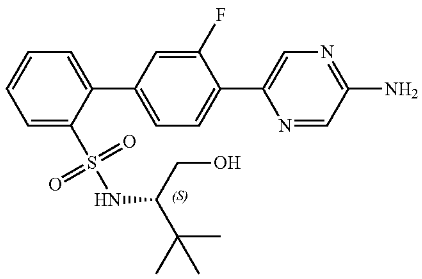 | 149 | (S)-4'-(5-aminopyrazin-2-yl)-3'-fluoro-N-(1-hydroxy-3,3-dimethylbutan-2-yl)-[1,1'-biphenyl]-2-sulfonamide |
| 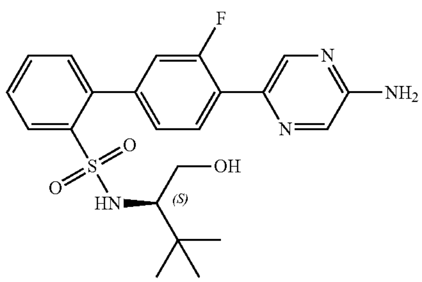 | 150 | (R)-4'-(5-aminopyrazin-2-yl)-3'-fluoro-N-(1-hydroxy-3,3-dimethylbutan-2-yl)-[1,1'-biphenyl]-2-sulfonamide |
| 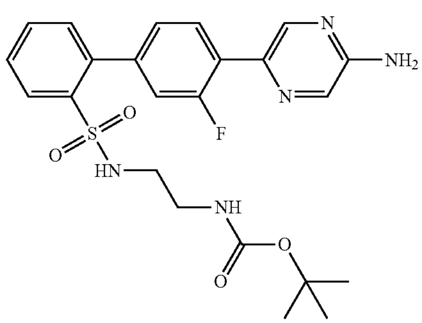 [SMILES: CC(C)(C)OC(=O)NCCNS(=O)(=O)c1ccccc1-c1ccc(-c2cnc(N)cn2)c(F)c1] | 151 | tert-Butyl [2-({4'-(5-aminopyrazin-2-yl)-3'-fluorobiphenyl-2-yl]sulfonyl}amino)ethyl]carbamate |
| 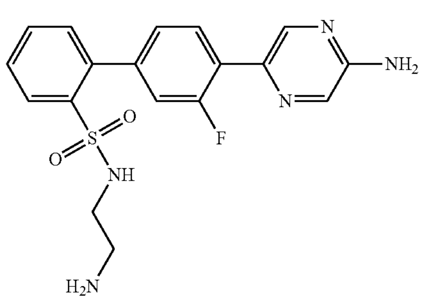 | 152 | N-(2-Aminoethyl)-4'-(5-aminopyrazin-2-yl)-3'-fluorobiphenyl-2-sulfonamide |

TABLE 3-continued

| STRUCTURE | COMPOUND # | NAME |
|---|---|---|
| 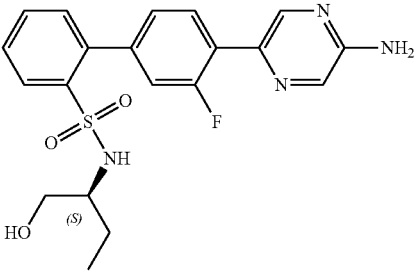 | 153 | (S)-4'-(5-aminopyrazin-2-yl)-3'-fluoro-N-(1-hydroxybutan-2-yl)-[1,1'-biphenyl]-2-sulfonamide |
| 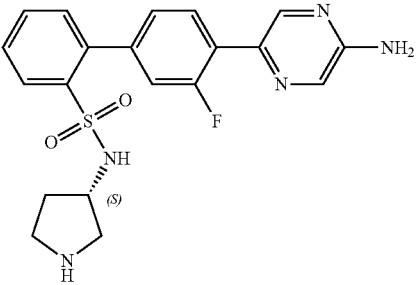 | 154 | (S)-4'-(5-aminopyrazin-2-yl)-3'-fluoro-N-(pyrrolidin-3-yl)-[1,1'-biphenyl]-2-sulfonamide |
| 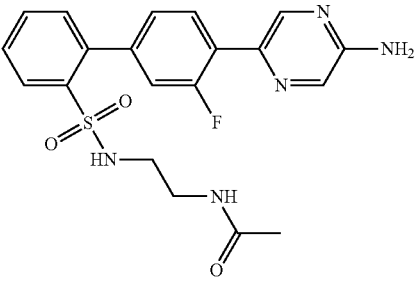 [SMILES: CC(=O)NCCNS(=O)(=O)c1ccccc1-c1ccc(-c2cnc(N)cn2)c(F)c1] | 155 | N-[2-({[4'-(5-Aminopyrazin-2-yl)-3'-fluorobiphenyl-2-yl]sulfonyl}amino)ethyl]acetamide |
| 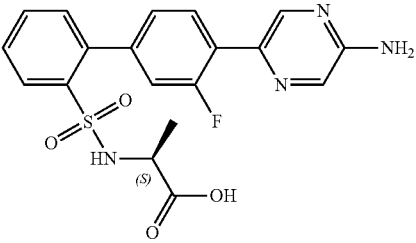 | 156 | (S)-2-(4'-(5-aminopyrazin-2-yl)-3'-fluoro-[1,1'-biphenyl]-2-ylsulfonamido)propanoic acid |
| 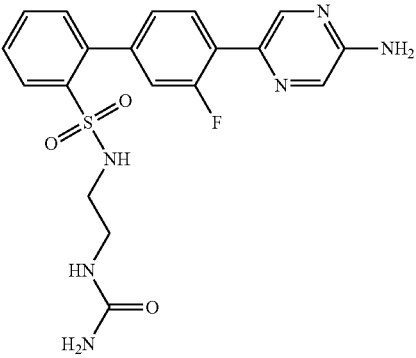 [SMILES: NC(=O)NCCNS(=O)(=O)c1ccccc1-c1ccc(-c2cnc(N)cn2)c(F)c1] | 157 | 4'-(5-Aminopyrazin-2-yl)-N-[2-(carbamoylamino)ethyl]-3'-fluorobiphenyl-2-sulfonamide |

TABLE 3-continued

| STRUCTURE | COMPOUND # | NAME |
|---|---|---|
| 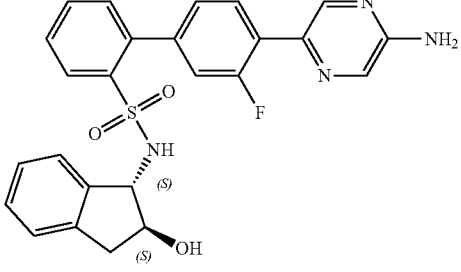 | 158 | 4'-(5-aminopyrazin-2-yl)-3'-fluoro-N-((1S,2S-2-hydroxy-2,3-dihydro-1H-inden-1-yl)-[1,1'-biphenyl]-2-sulfonamide |
| 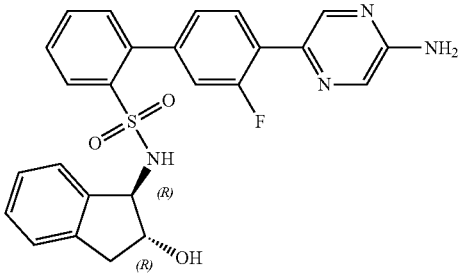 | 159 | 4'-(5-aminopyrazin-2-yl)-3'-fluoro-N-((1R,2R)-2-hydroxy-2,3-dihydro-1H-inden-1-yl)-[1,1'-biphenyl]-2-sulfonamide |
| 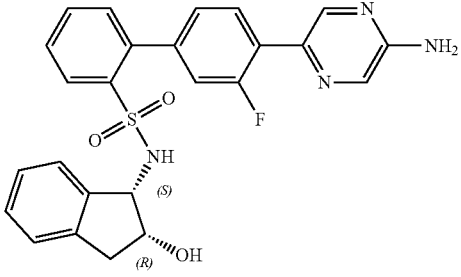 | 160 | 4'-(5-aminopyrazin-2-yl)-3'-fluoro-N-((1S,2R)-2-hydroxy-2,3-dihydro-1H-inden-1-yl)-[1,1'-biphenyl]-2-sulfonamide |
| 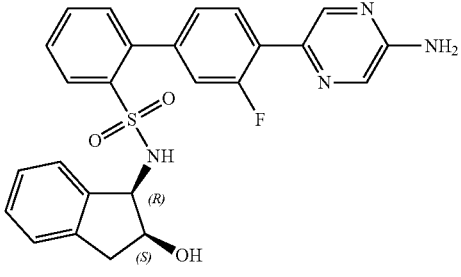 | 161 | 4'-(5-aminopyrazin-2-yl)-3'-fluoro-N-((1R,2S)-2-hydroxy-2,3-dihydro-1H-inden-1-yl)-[1,1'-biphenyl]-2-sulfonamide |
| 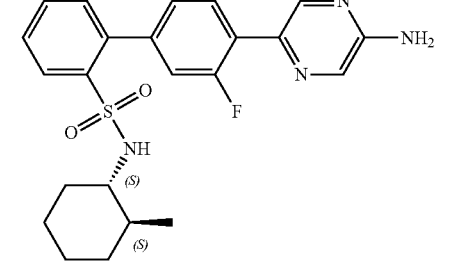 | 162 | 4'-(5-aminopyrazin-2-yl)-3'-fluoro-N-((1S,2S)-2-hydroxycyclohexyl)-[1,1'-biphenyl]-2-sulfonamide |

TABLE 3-continued

| STRUCTURE | COMPOUND # | NAME |
|---|---|---|
| 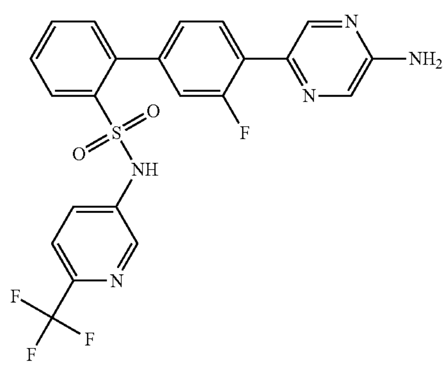 [SMILES: Nc1cnc(-c2ccc(-c3ccccc3S(=O)(=O)Nc3ccc(C(F)(F)F)nc3)cc2F)cn1] | 163 | 4'-(5-Aminopyrazin-2-yl)-3'-fluoro-N-[6-(trifluoromethyl)pyridin-3-yl]biphenyl-2-sulfonamide |
| 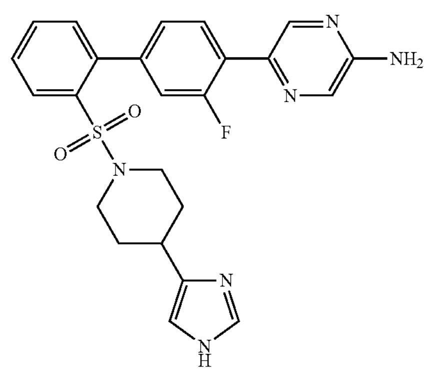 [SMILES: Nc1cnc(-c2ccc(-c3ccccc3S(=O)(=O)N3CCC(c4c[nH]cn4)CC3)cc2F)cn1] | 164 | 5-(3-Fluoro-2'-{[4-(1H-imidazol-4'-yl)piperidin-1-yl]sulfonyl}biphenyl-4-yl)pyrazin-2-amine |
| 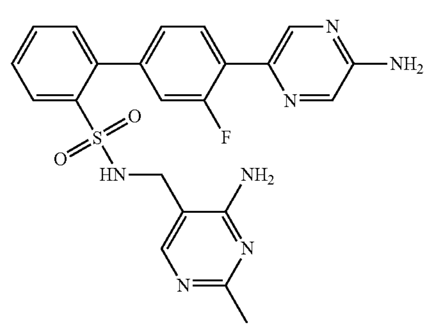 [SMILES: Cc1ncc(CNS(=O)(=O)c2ccccc2-c2ccc(-c3cnc(N)cn3)c(F)c2)c(N)n1] | 165 | N-[(4-Amino-2-methylpyrimidin-5-yl)methyl]-4'-(5-aminopyrazin-2-yl)-3'-fluorobiphenyl-2-sulfonamide |
| 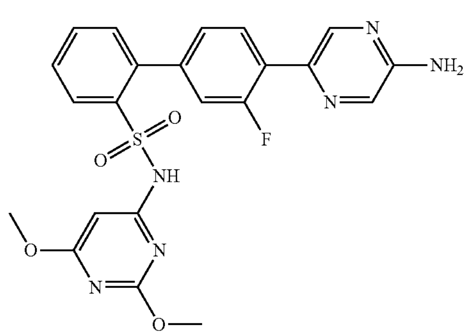 [SMILES: COc1cc(NS(=O)(=O)c2ccccc2-c2ccc(-c3cnc(N)cn3)c(F)c2)nc(OC)n1] | 166 | 4'-(5-Aminopyrazin-2-yl)-N-(2,6-dimethoxypyrimidin-4-yl)-3'-fluorobiphenyl-2-sulfonamide |

TABLE 3-continued

| STRUCTURE | COMPOUND # | NAME |
|---|---|---|
| 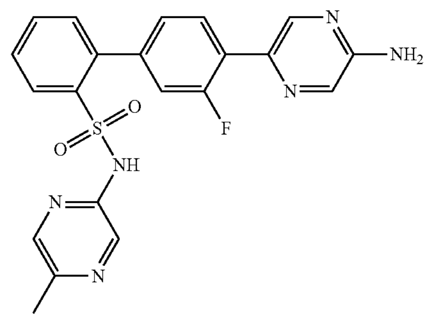 [SMILES: Cc1cnc(NS(=O)(=O)c2ccccc2-c2ccc(-c3cnc(N)cn3)c(F)c2)cn1] | 167 | 4'-(5-Aminopyrazin-2-yl)-3'-fluoro-N-(5-methylpyrazin-2-yl)biphenyl-2-sulfonamide |
| 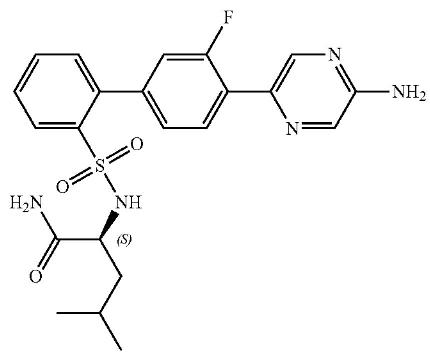 | 168 | (S)-2-(4'-(5-aminopyrazin-2-yl)-3'-fluoro-[1,1'-biphenyl]-2-ylsulfonamido)-4-methylpentanamide |
| 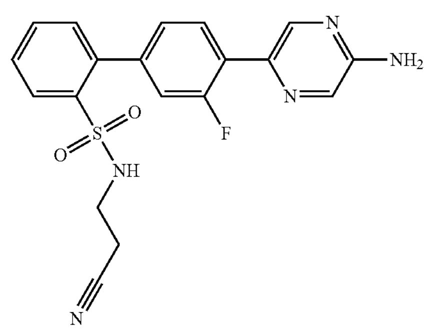 [SMILES: N#CCCNS(=O)(=O)c1ccccc1-c1ccc(-c2cnc(N)cn2)c(F)c1] | 169 | 4'-(5-Aminopyrazin-2-yl)-N-(2-cyanoethyl)-3'-fluorobiphenyl-2-sulfanamide |
| 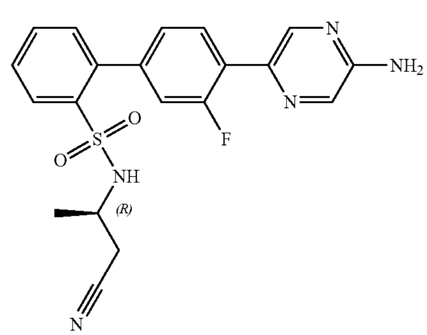 | 170 | (R)-4'-(5-aminopyrazin-2-yl)-N-(1-cyanopropan-2-yl)-3'-fluoro-[1,1'-biphenyl]-2-sulfonamide |

TABLE 3-continued

| STRUCTURE | COMPOUND # | NAME |
|---|---|---|
| 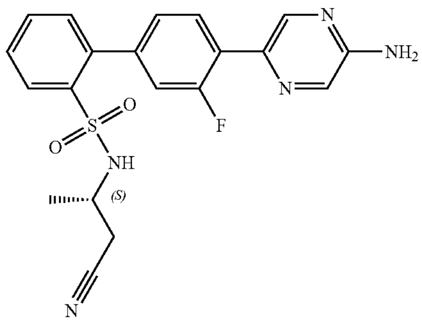 | 171 | (S)-4'-(5-aminopyrazin-2-yl)-N-(1-cyanopropan-2-yl)-3'-fluoro-[1,1'-biphenyl]-2-sulfonamide |
| 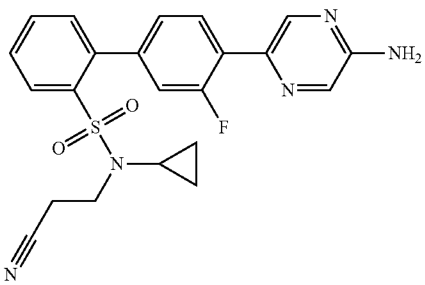 [SMILES: N#CCCN(C1CC1)S(=O)(=O)c1ccccc1-c1ccc(-c2cnc(N)cn2)c(F)c1] | 172 | 4'-(5-Aminopyrazin-2-yl)-N-(2-cyanoethyl)-N-cyclopropyl-3'-fluorobiphenyl-2-sulfonamide |
| 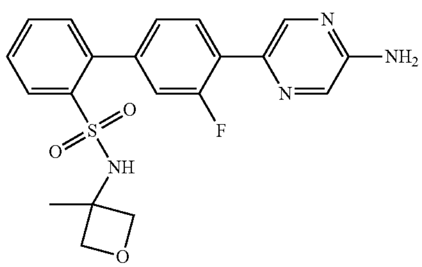 [SMILES: CC1(NS(=O)(=O)c2ccccc2-c2ccc(-c3cnc(N)cn3)c(F)c2)COC1] | 173 | 4'-(5-Aminopyrazin-2-yl)-3'-fluoro-N-(3-methyloxetan-3-yl)biphenyl-2-sulfonamide |
| 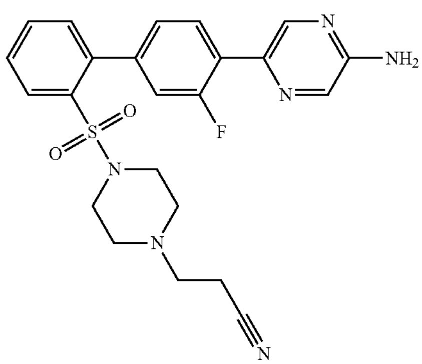 [SMILES: N#CCCN1CCN(S(=O)(=O)c2ccccc2-c2ccc(-c3cnc(N)cn3)c(F)c2)CC1] | 174 | 3-(4-{[4'-(5-Aminopyrazin-2-yl)-3'-fluorobiphenyl-2-yl]sulfonyl}piperazin-1-yl)propanenitrile |
| 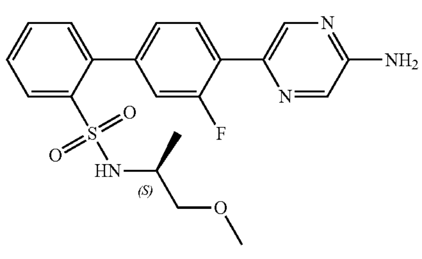 | 175 | (S)-4'-(5-aminopyrazin-2-yl)-3'-fluoro-N-(1-methoxypropan-2-yl)-[1,1'-biphenyl]-2-sulfonamide |

TABLE 3-continued

| STRUCTURE | COMPOUND # | NAME |
|---|---|---|
| 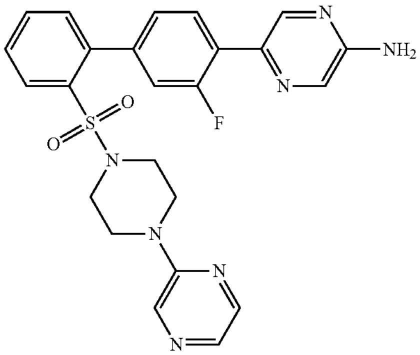 [SMILES: Nc1cnc(-c2ccc(-c3ccccc3S(=O)(=O)N3CCN(c4cnccn4)CC3)cc2F)cn1] | 176 | 5-{3-Fluoro-2'-[(4-pyrazin-2-ylpiperazin-1-yl)sulfonyl]biphenyl-4-yl}pyrazin-2-amine |
| 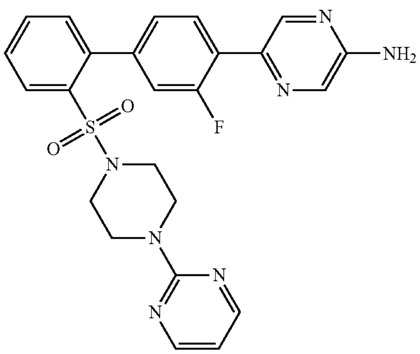 [SMILES: Nc1cnc(-c2ccc(-c3ccccc3S(=O)(=O)N3CCN(c4ncccn4)CC3)cc2F)cn1] | 177 | 5-{3-Fluoro-2'-(4-pyrimidin-2-ylpiperazin-1-yl)sulfonyl]biphenyl-4-yl}pyrazin-2-amine |
| 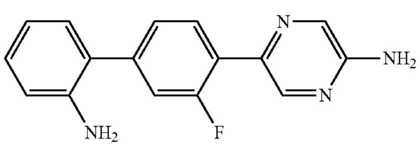 | 178 | 5-(2'-Amino-3-fluorobiphenyl-4-yl)pyrazin-2-amine |
| 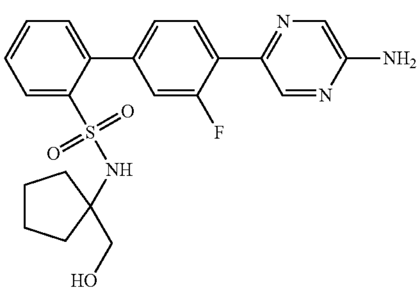 [SMILES: Nc1cnc(-c2ccc(-c3ccccc3S(=O)(=O)NC3(CO)CCCC3)cc2F)cn1] | 179 | 4'-(5-Aminepyrazin-2-yl)-3'-fluoro-N-[1-hydroxymethyl)cyclopentyl]biphenyl-2-sulfonamide |
| 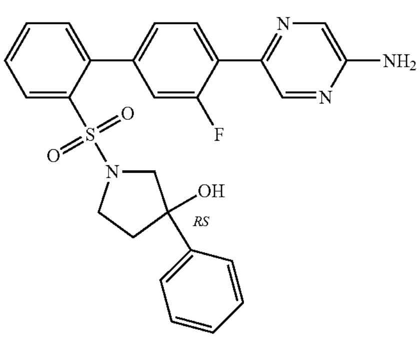 [SMILES: Nc1cnc(-c2ccc(-c3ccccc3S(=O)(=O)N3CCC(O)(c4ccccc4)C3)cc2F)cn1] | 180 | 1-{[4'-(5-Aminopyrazin-2-yl)-3'-fluorobiphenyl-2-yl]sulfonyl}-3-phenylpyrrolidin-3-ol |

TABLE 3-continued

| STRUCTURE | COMPOUND # | NAME |
|---|---|---|
| 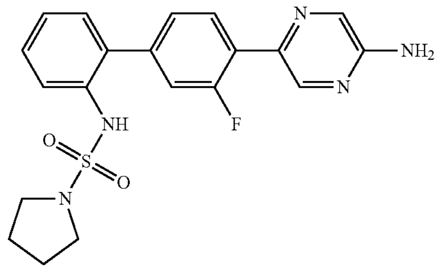 [SMILES: Nc1cnc(-c2ccc(-c3ccccc3NS(=O)(=O)N3CCCC3)cc2F)cn1] | 181 | N-[4'-(5-Aminopyrazin-2-yl)-3'-fluorobiphenyl-2-yl]pyrroildine-1-sulfonamide |
| 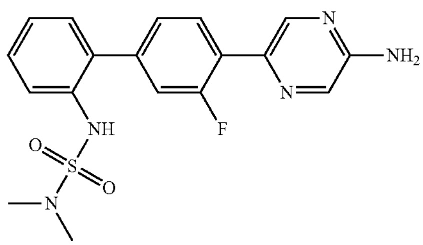 [SMILES: CN(C)S(=O)(=O)Nc1ccccc1-c1ccc(-c2cnc(N)cn2)c(F)c1] | 182 | N'-[4'-(5-Aminopyrazin-2-yl)-3'-fluorobiphenyl-2-yl]-N,N-dimethylsulfamide |
| 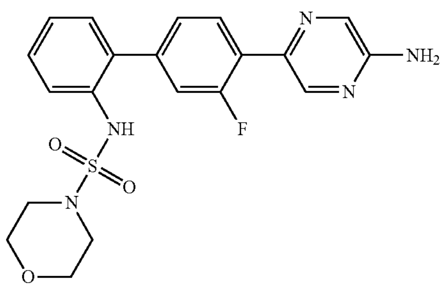 [SMILES: Nc1cnc(-c2ccc(-c3ccccc3NS(=O)(=O)N3CCOCC3)cc2F)cn1] | 183 | N-[4'-(5-Aminopyrazin-2-yl)-3'-fluorobiphenyl-2-yl]morpholine-4-sulfonamide |
| 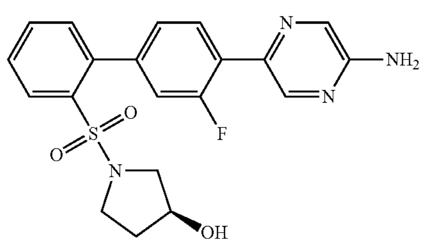 [SMILES: Nc1cnc(-c2ccc(-c3ccccc3S(=O)(=O)N3CC[C@H](O)C3)cc2F)cn1] | 184 | (3S)-1-{[4'-(5-Aminopyrazin-2-yl)-3'-fluorobiphenyl-2-yl]sulfonyl}pyrrolidin-3-ol |
| 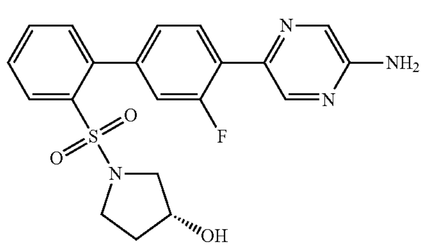 [SMILES: Nc1cnc(-c2ccc(-c3ccccc3S(=O)(=O)N3CC[C@@H](O)C3)cc2F)cn1] | 185 | (3R)-1-{[4'-(5-Aminopyrazin-2-yl)-3'-fluorobiphenyl-2-yl]sulfonyl}pyrrolidin-3-ol |
| 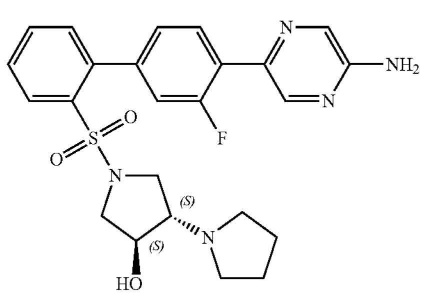 | 186 | (3'S,4'S)-1'-{[4'-(5-Aminopyrazin-2-yl)-3'-fluorobiphenyl-2-yl]sulfonyl}-1,3'-bipyrrolidin-4'-ol |

TABLE 3-continued

| STRUCTURE | COMPOUND # | NAME |
|---|---|---|
| 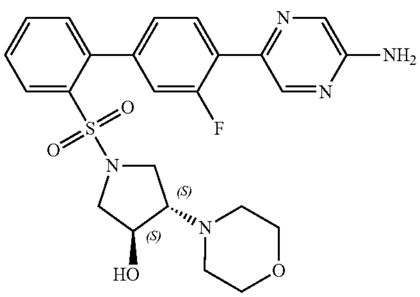 | 187 | (3S,4S)-1-{[4'-(5-Aminopyrazin-2-yl)-3'-fluorobiphenyl-2-yl]sulfonyl}-4-morpholin-4-ylpyrrolidin-3-ol |
| 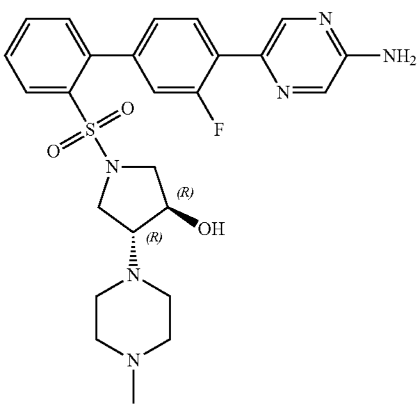 | 188 | (3S,4S)-1-{[4'-(5-Aminopyrazin-2-yl)-3'-fluorobiphenyl-2-yl]sulfonyl}-4-(4-methylpiperazin-1-yl)pyrrolidin-3-ol |
| 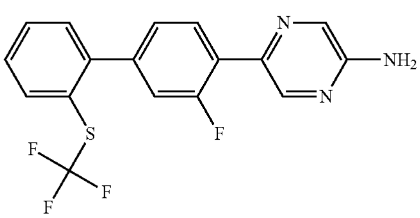 | 189 | 5-{3-Fluoro-2'-[(trifluoromethyl)sulfanyl]biphenyl-4-yl}pyrazin-2-amine |
| 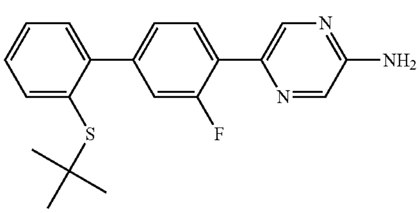 [SMILES: CC(C)(C)Sc1ccccc1-c1ccc(-c2cnc(N)cn2)c(F)c1] | 190 | 5-[2'-(tert-Butylsulfanyl)-3-fluorobiphenyl-4-yl]pyrazin-2-amine |
| 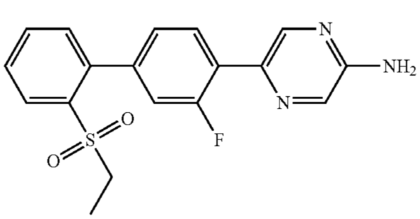 [SMILES: CCS(=O)(=O)c1ccccc1-c1ccc(-c2cnc(N)cn2)c(F)c1] | 191 | 5-[2'-(Ethylsulfonyl)-3-fluorobiphenyl-4-yl]pyrazin-2-amine |
| 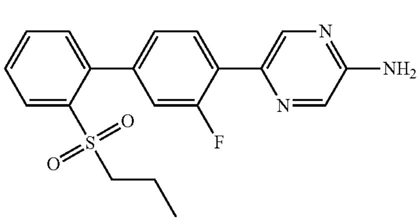 | 192 | 5-[3-Fluoro-2'-(propylsulfonyl)biphenyl-4-yl]pyrazin-2-amine |

TABLE 3-continued

| STRUCTURE | COMPOUND # | NAME |
|---|---|---|
| 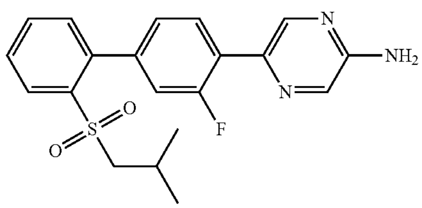 [SMILES: CC(C)CS(=O)(=O)c1ccccc1-c1ccc(-c2cnc(N)cn2)c(F)c1] | 193 | 5-{3-Fluoro-2'-[(2-methylpropyl)sulfonyyl]iphenyl-4-yl}pyrazin-2-amine |
| 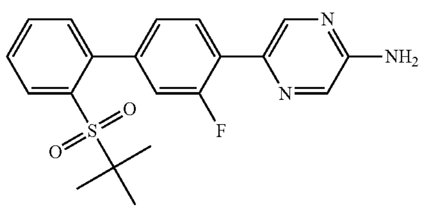 [SMILES: CC(C)(C)S(=O)(=O)c1ccccc1-c1ccc(-c2cnc(N)cn2)c(F)c1] | 194 | 5-[2'-(tert-Butylsulfonyl)-3-fluorobiphenyl-4-yl]pyrazin-2-amine |
| 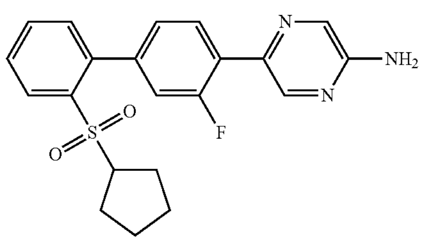 [SMILES: Nc1cnc(-c2ccc(-c3ccccc3S(=O)(=O)C3CCCC3)cc2F)cn1] | 195 | 5-[2'-(Cyclopentylsulfonyl)-3-fluorobiphenyl-4-yl]pyrazin-2-amine |
| 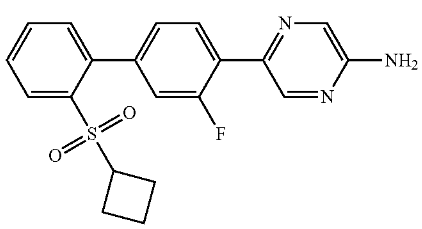 [SMILES: Nc1cnc(-c2ccc(-c3ccccc3S(=O)(=O)C3CCC3)cc2F)cn1] | 196 | 5-[2'-(Cyclobutylsulfonyl)-3-fluorobiphenyl-4-yl]pyrazin-2-amine |
| 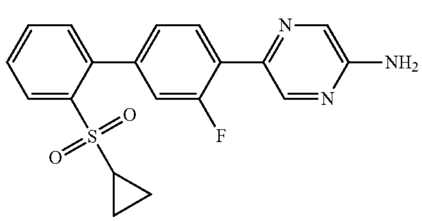 [SMILES: Nc1cnc(-c2ccc(-c3ccccc3S(=O)(=O)C3CC3)cc2F)cn1] | 197 | 5-[2'-(Cyclopropylsulfonyl)-3-fluorobiphenyl-4-yl]pyrazin-2-amine |
| 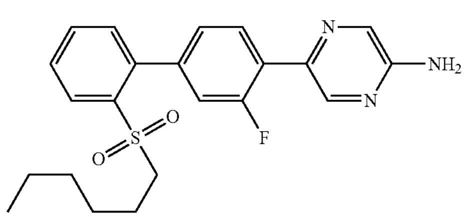 [SMILES: CCCCCCS(=O)(=O)c1ccccc1-c1ccc(-c2cnc(N)cn2)c(F)c1] | 198 | 5-[3-Fluoro-2'-(hexylsulfonyl)biphenyl-4-yl]pyrazin-2-amine |
| 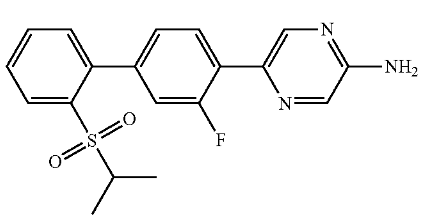 | 199 | 5{3Fluoro-2'-[(1-methylethyl)sulfonyl]biphenyl-4-yl}pyrazin-2-amine |

TABLE 3-continued

| STRUCTURE | COMPOUND # | NAME |
|---|---|---|
| 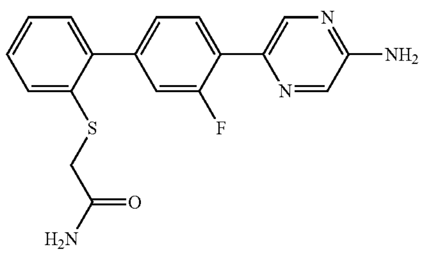 [SMILES: NC(=O)CSc1ccccc1-c1ccc(-c2cnc(N)cn2)c(F)c1] | 200 | 2-{[4'-(5-Aminopyrazin-2-yl)-3'-fluorobiphenyl-2-yl]sulfanyl}acetamide |
| 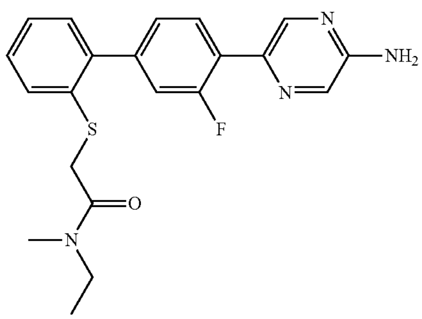 [SMILES: CCN(C)C(=O)CSc1ccccc1-c1ccc(-c2cnc(N)cn2)c(F)c1] | 201 | 2-{[4'-(5-Aminopyrazin-2-yl)-3'-fluorobiphenyl-2-yl]sulfanyl}-N,N-diethylacetemide |
| 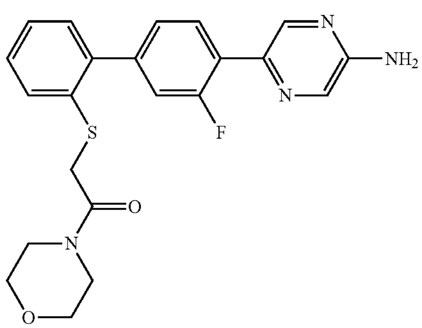 [SMILES: Nc1cnc(-c2ccc(-c3ccccc3SCC(=O)N3CCOCC3)cc2F)cn1] | 202 | 5-{3-Fluoro-2'-[(2-morpholin-4-yl-2-oxoethyl)sulfanyl]biphenyl-4-yl}pyrazin-2-amine |
| 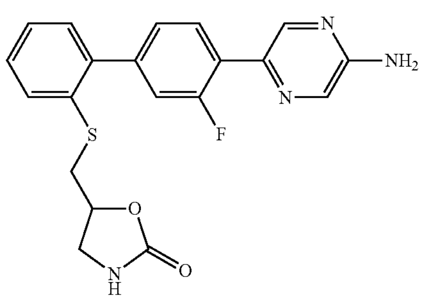 [SMILES: Nc1cnc(-c2ccc(-c3ccccc3SCC3CNC(=O)O3)cc2F)cn1] | 203 | (racemic) 5-({[4'-(5-Aminopyrazin-2-yl)-3'-fluorobiphenyl-2-yl]sulfanyl}methyly)-1,3-oxazolidin-2-one |
| 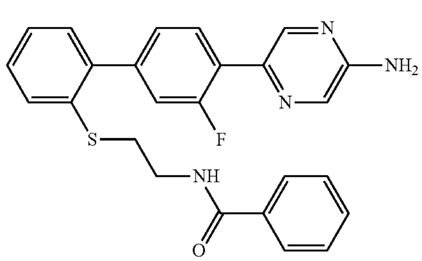 [SMILES: Nc1cnc(-c2ccc(-c3ccccc3SCCNC(=O)c3ccccc3)cc2F)cn1] | 204 | N-(2-{[4'-(5-Aminopyrazin-2-yl)-3'-fluorobiphenyl-2-yl]sulfanyl}ethyl)benzamide |

TABLE 3-continued

| STRUCTURE | COMPOUND # | NAME |
|---|---|---|
| 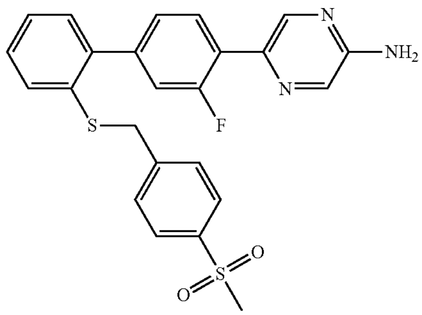 [SMILES: CS(=O)(=O)c1ccc(CSc2ccccc2-c2ccc(-c3cnc(N)cn3)c(F)c2)cc1] | 205 | 5-(3-Fluoro-2'-{[4-(methylsulfonyl)benzyl]sulfanyl}biphenyl-4-yl)pyrazin-2-amine |
| 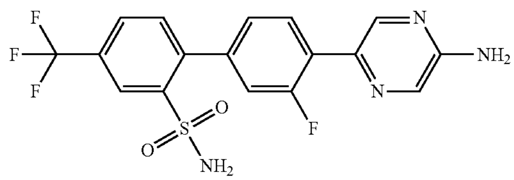 [SMILES: Nc1cnc(-c2ccc(-c3ccc(C(F)(F)F)cc3S(N)(=O)=O)cc2F)cn1] | 206 | 4'-(5-Aminopyrazin-2-yl)-3'-fluoro-4-(trifluoromethyl)biphenyl-2-sulfonamide |
| 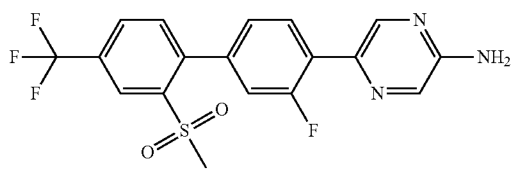 [SMILES: CS(=O)(=O)c1cc(C(F)(F)F)ccc1-c1ccc(-c2cnc(N)cn2)c(F)c1] | 207 | 5-[3-Fluoro-2'-(methylsulfonyl)-4'-(trifluoromethyl)biphenyl-4-yl]pyrazin-2-amine |
| 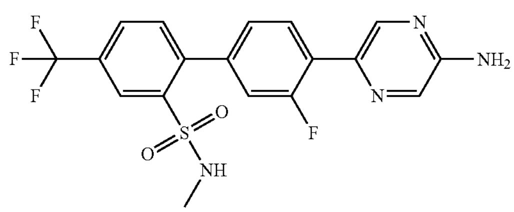 [SMILES: CNS(=O)(=O)c1cc(C(F)(F)F)ccc1-c1ccc(-c2cnc(N)cn2)c(F)c1] | 208 | 4'-(5-Aminopyrazin-2-yl)-3'-fluoro-N-methyl-4-(trifluoromethyl)biphenyl-2-sulfonamide |
| 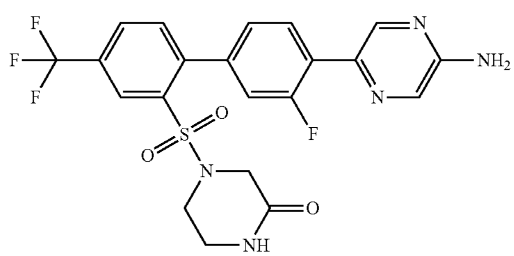 [SMILES: Nc1cnc(-c2ccc(-c3ccc(C(F)(F)F)cc3S(=O)(=O)N3CCNC(=O)C3)cc2F)cn1] | 209 | 4-{[4'-(5-Aminopyrazin-2-yl)-3'-fluoro-4-(trifluoromethyl)biphenyl-2-yl]sulfonyl}piperazin-2-one |
| 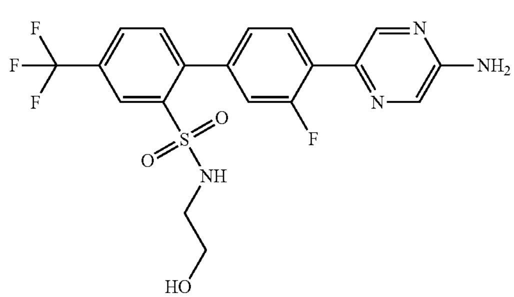 [SMILES: Nc1cnc(-c2ccc(-c3ccc(C(F)(F)F)cc3S(=O)(=O)NCCO)cc2F)cn1] | 210 | 4'-(5-aminopyrazin-2-yl)-3'-fluoro-N-(2-hydroxyethyl)-4-(trifluoromethyl)biphenyl-2-sulfonamide |

TABLE 3-continued

| STRUCTURE | COMPOUND # | NAME |
|---|---|---|
| 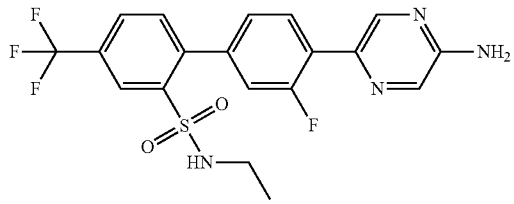 [SMILES: CCNS(=O)(=O)c1cc(C(F)(F)F)ccc1-c1ccc(-c2cnc(N)cn2)c(F)c1] | 211 | 4'-(5-Aminopyrazin-2-yl)-N-ethyl-3'-fluoro-4-(trifluoromethyl)biphenyl-2-sulfonamide |
| 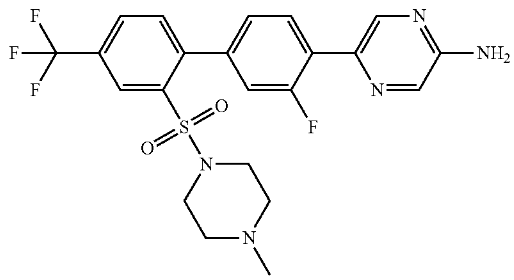 | 212 | 5-{3-Fluoro-2'-[(4-methylpiperazin-1-yl)sulfonyl]-4'-(trifluoromethyl)biphenyl-4-yl}pyrazin-2-amine |
| 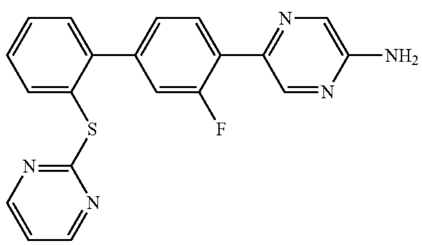 [SMILES: Nc1cnc(-c2ccc(-c3ccccc3Sc3ncccn3)cc2F)cn1] | 213 | 5-[3-Fluoro-2'-(pyrimidin-2-ylsulfanyl)biphenyl-4-yl]pyrazin-2-amine hydrochloride |
| 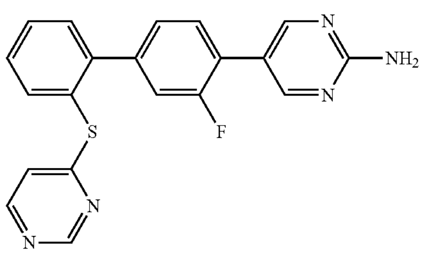 [SMILES: Nc1ncc(-c2ccc(-c3ccccc3Sc3ccncn3)cc2F)cn1] | 214 | 5-[3-Fluoro-2'-(pyrimidin-4-ylsulfanyl)biphenyl-4-yl]pyrimidin-2-amine formate salt |
| 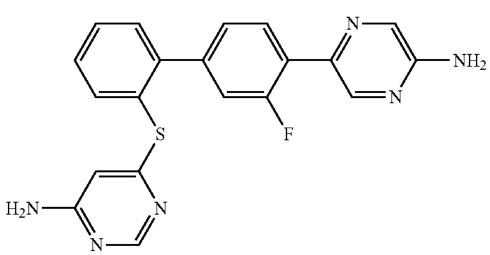 [SMILES: Nc1cnc(-c2ccc(-c3ccccc3Sc3cc(N)ncn3)cc2F)cn1] | 215 | 6-{[4'-(5-Aminopyrazin-2-yl)-3'-fluorobiphenyl-2-yl]sulfanyl}pyrimidin-4-amine hydrochloride |
| 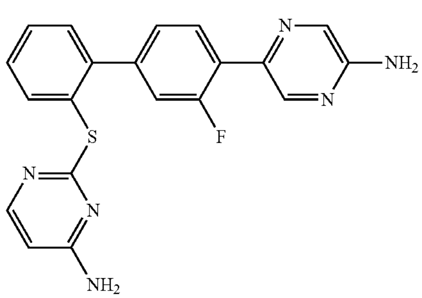 [SMILES: Nc1cnc(-c2ccc(-c3ccccc3Sc3nccc(N)n3)cc2F)cn1] | 216 | 2-{1,4'-(5-Aminopyrazin-2-yl)-3'-fluorobiphenyl-2-yl]sulfanyl}pyrimidin-4-amine hydrochloride |

TABLE 3-continued

| STRUCTURE | COMPOUND # | NAME |
|---|---|---|
| 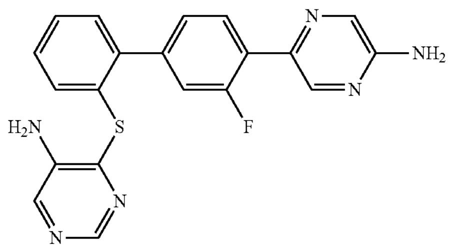 | 217 | 4-{[4'-(5-Aminopyrazin-2-yl)-3'-fluorobiphenyl-2-yl]sulfanyl}pyrimidin-5-amine hydrochloride |
| 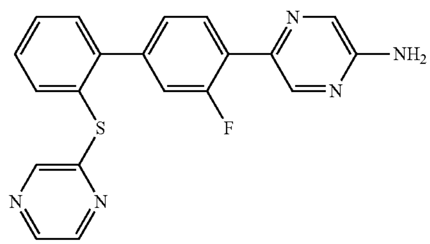 [SMILES: Nc1cnc(-c2ccc(-c3ccccc3Sc3cnccn3)cc2F)cn1] | 218 | 5-[3-Fluoro-2'-(pyrazin-2-ylsulfanyl)biphenyl-4-yl]pyrazin-2'-amine hydrochloride |
| 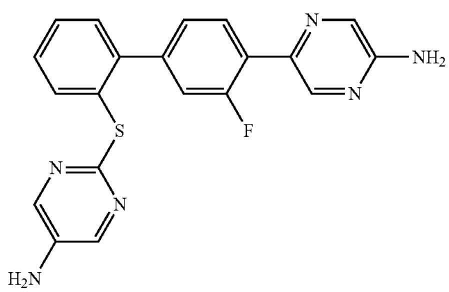 [SMILES: Nc1cnc(Sc2ccccc2-c2ccc(-c3cnc(N)cn3)c(F)c2)nc1] | 219 | 2-{[4'-(5-Aminopyrazin-2-yl)-3'-fluorobiphenyl-2-yl]sulfanyl}pyrimidin-5-amine hydrochloride |
| 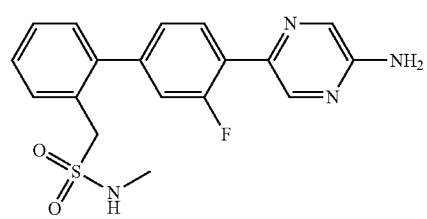 [SMILES: CNS(=O)(=O)Cc1ccccc1-c1ccc(-c2cnc(N)cn2)c(F)c1] | 220 | 1-[4'-(5-Aminopyrazin-2-yl)-3'-fluorotiphenyl-2-yl]-N-methylmethanesulfonamide formic acid salt |
| 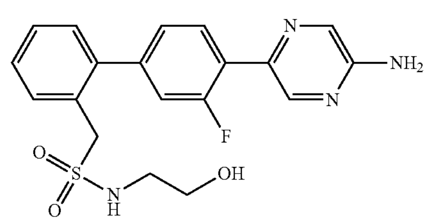 [SMILES: Nc1cnc(-c2ccc(-c3ccccc3CS(=O)(=O)NCCO)cc2F)cn1] | 221 | 1-[4'-(5-Aminopyrazin-2-yl)-3'-fluorobiphenyl-2-yl]-N-(2-hydroxyethyl)methanesulfonamide formic acid salt |
| 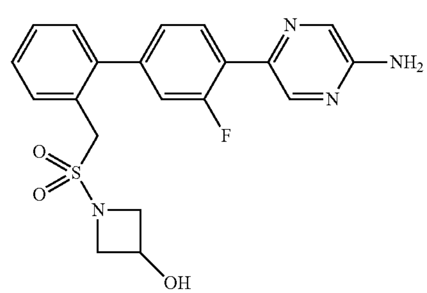 [SMILES: Nc1cnc(-c2ccc(-c3ccccc3CS(=O)(=O)N3CC(O)C3)cc2F)cn1] | 222 | 1-({[4'-(5-Aminopyrazin-2-yl)-3'-fluorobiphenyl-2-yl]methyl}sulfonyl)azetidin-3-ol formic acid salt |

TABLE 3-continued

| STRUCTURE | COMPOUND # | NAME |
|---|---|---|
| 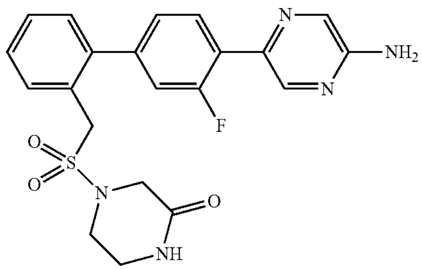 [SMILES: Nc1cnc(-c2ccc(-c3ccccc3CS(=O)(=O)N3CCNC(=O)C3)cc2F)cn1] | 223 | 4-({[4'-(5-Aminopyrazin-2-yl)-3'-fluorobiphenyl-2-yl]methyl}sulfonyl)piperazin-2-one formic acid salt |
| 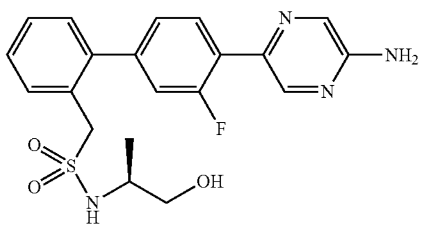 [SMILES: C[C@@H](CO)NS(=O)(=O)Cc1ccccc1-c1ccc(-c2cnc(N)cn2)c(F)c1] | 224 | (S)-1-(4'-(5-Aminopyrazin-2-yl)-3'-fluoro-[1,1'-biphenyl]-2-yl)-N-(1-hydroxypropan-2-yl)methanesulfonamide |
| 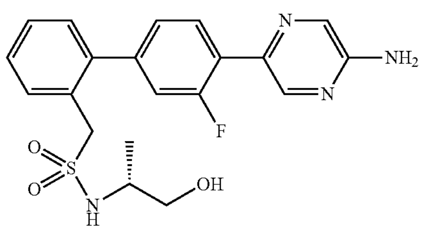 [SMILES: C[C@H](CO)NS(=O)(=O)Cc1ccccc1-c1ccc(-c2cnc(N)cn2)c(F)c1] | 225 | (R)-1-(4'-(5-Aminopyrazin-2-yl)-3'-fluoro-[1,1'-biphenyl]-2-yl)-N-(1-hydroxypropan-2-yl)methanesulfonamide hydrochloride |
| 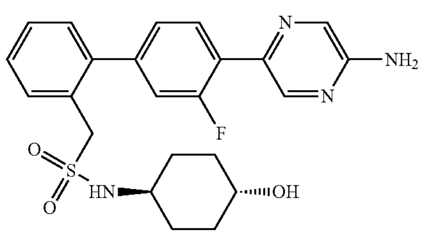 [SMILES: Nc1cnc(-c2ccc(-c3ccccc3CS(=O)(=O)N[C@H]3CC[C@H](O)CC3)cc2F)cn1] | 226 | 1-[4'-(5-Aminopyrazin-2-yl)-3'-fluorobiphenyl-2-yl]-N-(trans-4-hydroxycyclohexyl)methanesulfonamide |
| 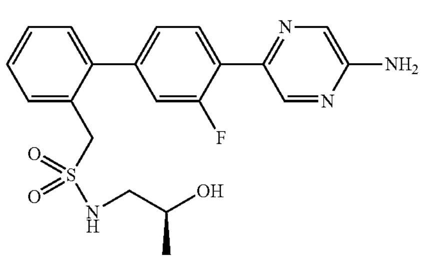 | 227 | (S)-1-[4'-(5-Aminopyrazin-2-yl)-3'-fluorobiphenyl-2-yl]-N-[(2S)-2-hydroxypropyl]methanesulfonamide hydrochloride |
| 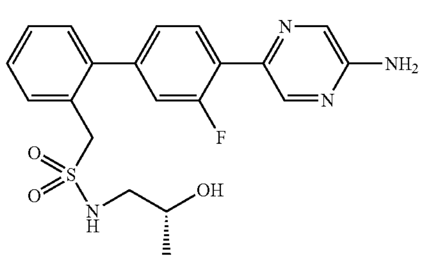 [SMILES: C[C@@H](O)CNS(=O)(=O)Cc1ccccc1-c1ccc(-c2cnc(N)cn2)c(F)c1] | 228 | (R)-1-[4'-(5-Aminopyrazin-2-yl)-3'-fluorobiphenyl-2-yl]-N-[(2S)-2-hydroxypropyl]methanesulfonamide |

TABLE 3-continued

| STRUCTURE | COMPOUND # | NAME |
|---|---|---|
| 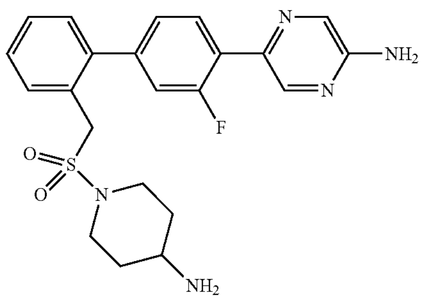 [SMILES: Nc1cnc(-c2ccc(-c3ccccc3CS(=O)(=O)N3CCC(N)CC3)cc2F)cn1] | 229 | 5-(2'-{[(4-Aminopiperidin.-1-yl)sulfonyl]methyl}-3-fluorobiphenyl-4-yl)pyrazin-2-amine hydrochloride |
| 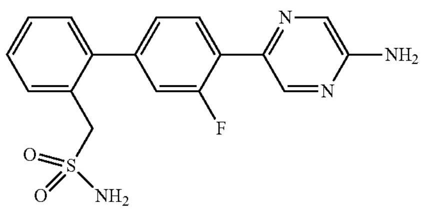 [SMILES: Nc1cnc(-c2ccc(-c3ccccc3CS(N)(=O)=O)cc2F)cn1] | 230 | 1-[4'-(5-Aminopyrazin-2-yl)-3'-fluorobiphenyl-2-yl]methanesulfonamide hydrochloride |
| 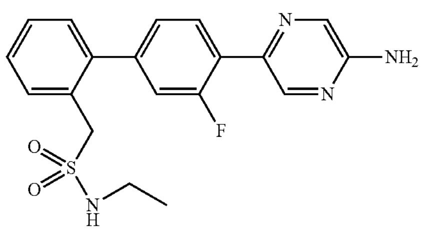 [SMILES: CCNS(=O)(=O)Cc1ccccc1-c1ccc(-c2cnc(N)cn2)c(F)c1] | 231 | 1-[4'-(5-Aminopyrazin-2-yl)-3'-fluorobiphenyl-2-yl]-N-ethylmethanesulfonamide formate salt |
| 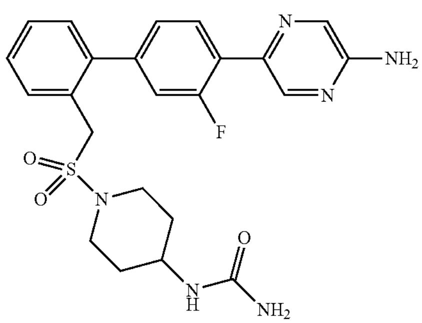 [SMILES: NC(=O)NC1CCN(S(=O)(=O)Cc2ccccc2-c2ccc(-c3cnc(N)cn3)c(F)c2)CC1] | 232 | 1-[1-({[4'-(5-Aminopyrazin-2-yl)-3'-fluorobiphenyl-2-yl]methyl}sulfonyl)piperidin4-yl]urea hydrochloride |
| 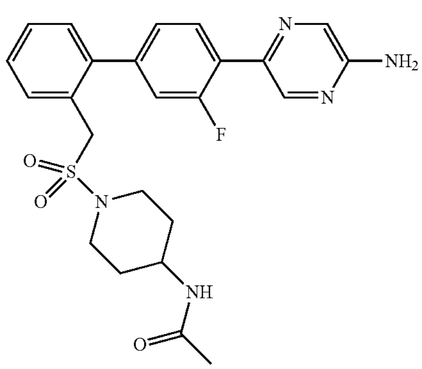 [SMILES: CC(=O)NC1CCN(S(=O)(=O)Cc2ccccc2-c2ccc(-c3cnc(N)cn3)c(F)c2)CC1] | 233 | N-[1-({[4'-(5-Aminopyrazin-2-yl)-3'-fluorobiphenyl-2-yl]methyl}sulfonyl)piperidin-4-yl]acetamide formate salt |

TABLE 3-continued

| STRUCTURE | COMPOUND # | NAME |
|---|---|---|
| 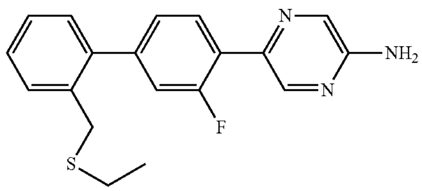 [SMILES: CCSCc1ccccc1-c1ccc(-c2cnc(N)cn2)c(F)c1] | 234 | 5-{2'-[(Ethylsulfanyl)methyl-3-fluorobiphenyl-4-yl}pyrazin-2-amine formate salt |
| 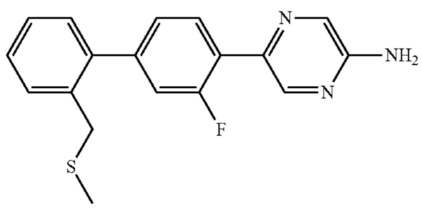 [SMILES: CSCc1ccccc1-c1ccc(-c2cnc(N)cn2)c(F)c1] | 235 | 5-{3-Fluoro-2'-[(methylsulfanyl)methyl]biphenyl-4-yl}pyrazin-2-amine hydrochloride |
| 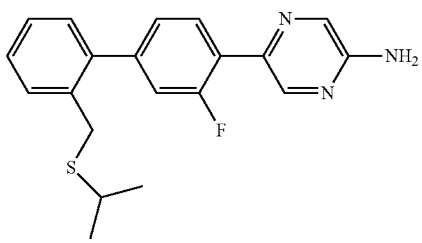 [SMILES: CC(C)SCc1ccccc1-c1ccc(-c2cnc(N)cn2)c(F)c1] | 236 | 5-(3-Fluoro-2-{[(1-methylethyl)sulfanyl]methyl}biphenyl-4-yl)pyrazin-2-amine hydrochloride |
| 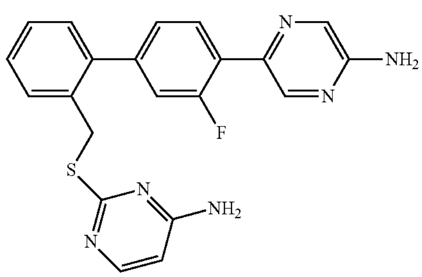 [SMILES: Nc1cnc(-c2ccc(-c3ccccc3CSc3nccc(N)n3)cc2F)cn1] | 237 | 2-(((4'-(5-Aminopyrazin-2-yl)-3'-fluoro-[1,1'-biphenyl]-2-yl)methyl)thio)pyrimidin-4-amine hydrochloride |
| 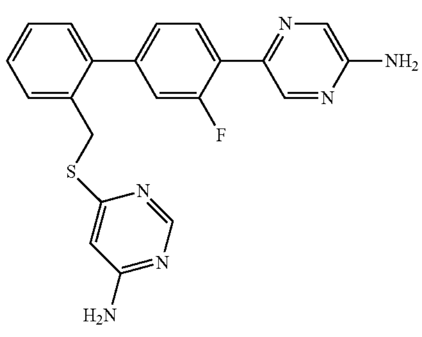 [SMILES: Nc1cnc(-c2ccc(-c3ccccc3CSc3cc(N)ncn3)cc2F)cn1] | 238 | 6-(((4'-(5-aminopyrazin-2-yl)-3'-fluoro-[1,1'-biphenyl]-2-yl)methyl)thio)pyrimidin-4-amine hydrochloride |
| 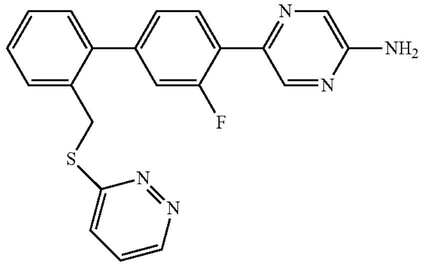 [SMILES: Nc1cnc(-c2ccc(-c3ccccc3CSc3cccnn3)cc2F)cn1] | 239 | 5-(3-fluoro-2'-((pyridazin-3-ylthio)methyl)-[1,1'-biphenyl]-4-yl)pyrazin-2-amine hydrochloride |

TABLE 3-continued

| STRUCTURE | COMPOUND # | NAME |
|---|---|---|
| 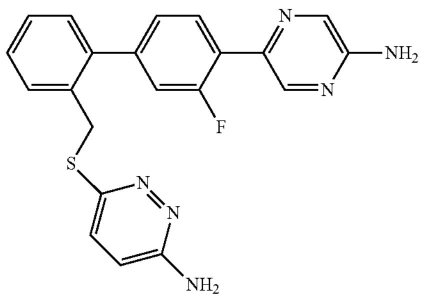 [SMILES: Nc1cnc(-c2ccc(-c3ccccc3CSc3ccc(N)nn3)cc2F)cn1] | 240 | 6-(((4'-(5-aminopyrazin-2-yl)-3'-fluoro-[1,1'-biphenyl]-2-yl)methyl)thio)pyridazin-3-amine hydrochloride |
| 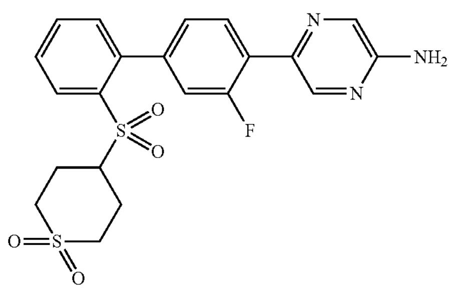 [SMILES: Nc1cnc(-c2ccc(-c3ccccc3S(=O)(=O)C3CCS(=O)(=O)CC3)cc2F)cn1] | 241 | 5-{2'-[(1,1-Dioxidotatrahydro-2H-thiopyran-4-yl)sulfonyl)-3-fluorobiphenyl-4-yl}pyrazin-2-amine |
| 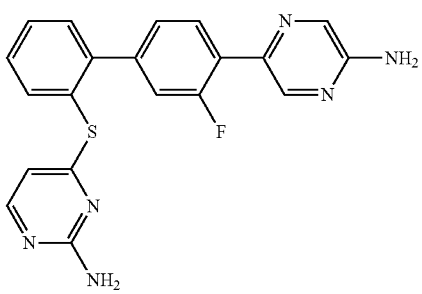 | 242 | 4-{[4'(5-Aminopyrazin-2-yl)-3'-fluorobiphenyl-2-yl]sulfanyl}pyrimidin-2-amine hydrochloride |
| 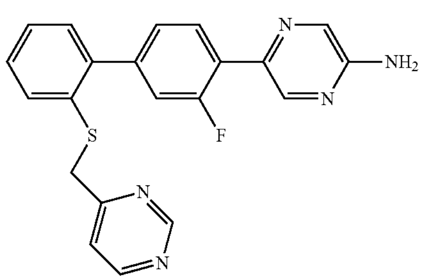 [SMILES: Nc1cnc(-c2ccc(-c3ccccc3SCc3ccncn3)cc2F)cn1] | 243 | 5-(3-fluoro-2'-((pyrimidin-4-ylthio)methyl)-[1,1'-biphenyl]-4-yl)pyrazin-2-amine hydrochloride |
| 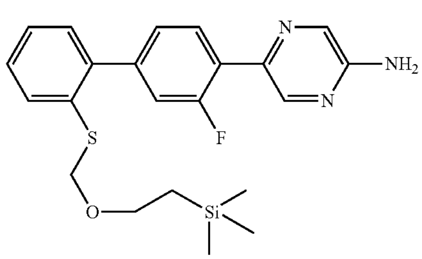 [SMILES: C[Si](C)(C)CCOCSc1ccccc1-c1ccc(-c2cnc(N)cn2)c(F)c1] | 244 | 5-[3-Fluoro-2'-({[2-(trimethylsilyl)ethoxy]methyl}sulfanyl)biphenyl-4-yl]pyrazin-2-amine |

TABLE 3-continued

| STRUCTURE | COMPOUND # | NAME |
|---|---|---|
| 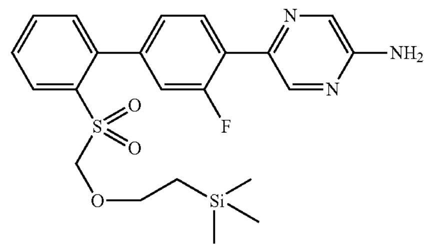 [SMILES: C[Si](C)(C)CCOCS(=O)(=O)c1ccccc1-c1ccc(-c2cnc(N)cn2)c(F)c1] | 245 | 5-[3-Fluoro-2'-({[2-(trimethylsilyl)ethoxy]methyl}sulfonyl)biphenyl-4-yl]pyrazin-2-amine hydrochloridee |
| 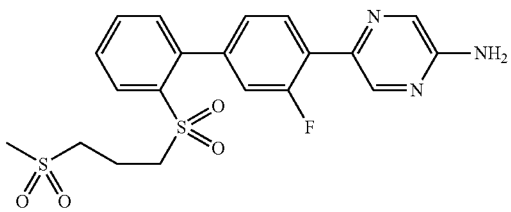 [SMILES: CS(=O)(=O)CCCS(=O)(=O)c1ccccc1-c1ccc(-c2cnc(N)cn2)c(F)c1] | 246 | 5-(3-Fluoro-2'-{[3-(methylsulfonyl)propyl]sulfonyl}biphenyl-4yl)pyrazin-2-amine hydrochloride |
| 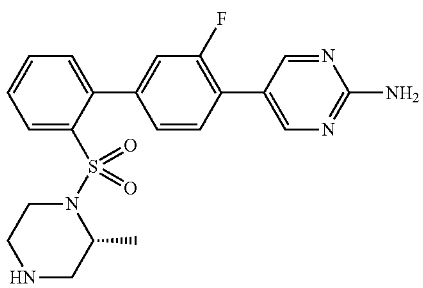 [SMILES: C[C@@H]1CNCCN1S(=O)(=O)c1ccccc1-c1ccc(-c2cnc(N)nc2)c(F)c1] | 247 | 5-(3-Fluoro-2'-{[(2R)-2-methylpiperazn-1-yl)sulfonyl)biphenyl-4-yl)pyrimidin-2-amine |
| 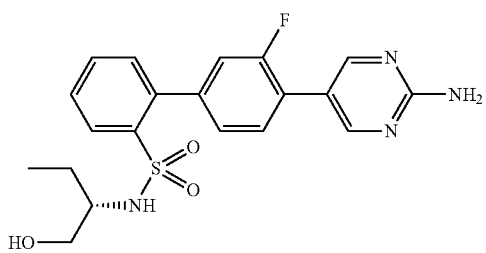 [SMILES: CC[C@@H](CO)NS(=O)(=O)c1ccccc1-c1ccc(-c2cnc(N)nc2)c(F)c1] | 248 | 4'-(2-Aminopyrimidin-5-yl)-3'-fluoro-N-[(1S)-1-(hydroxymethyl)propyl]biphenyl-2-sulfonamide |
| 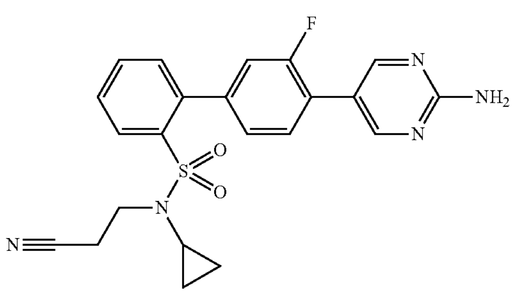 [SMILES: N#CCCN(C1CC1)S(=O)(=O)c1ccccc1-c1ccc(-c2cnc(N)nc2)c(F)c1] | 249 | 4'-(2-Aminopyrimidin-5-yl)-N-(2-cyanoethyl)-N-cyclopropyl-3'-fluorobiphenyl-2-sulfonamide |
| 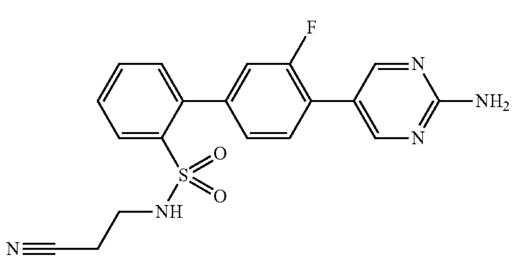 [SMILES: N#CCCNS(=O)(=O)c1ccccc1-c1ccc(-c2cnc(N)nc2)c(F)c1] | 250 | 4'-(2-Aminopyrimidin-5-yl)-N-(2-cyanoethyl)-3'-fluorobiphenyl-2-sulfonamide |

TABLE 3-continued

| STRUCTURE | COMPOUND # | NAME |
|---|---|---|
| 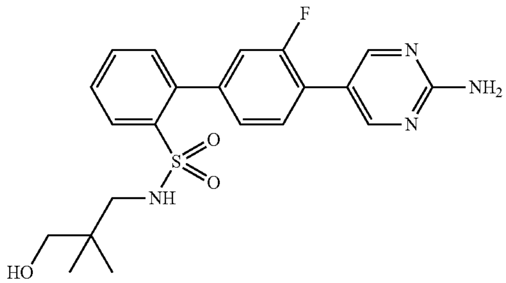 [SMILES: CC(C)(CO)CNS(=O)(=O)c1ccccc1-c1ccc(-c2cnc(N)nc2)c(F)c1] | 251 | 4'-(2-Aminopyrimidin-5-yl)-3'-fluoro-N-(3-hydroxy-2,2-dimethylpropyl)biphenyl-2-sulfonamide |
| 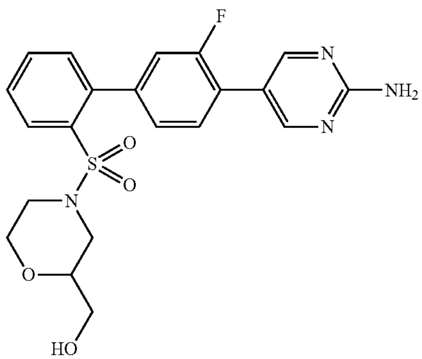 [SMILES: Nc1ncc(-c2ccc(-c3ccccc3S(=O)(=O)N3CCOC(CO)C3)cc2F)cn1] | 252 | racemic (4-{[4'-(2-Aminopyrimidin-5-yl)-3'-fluorobiphenyl-2-yl]sulfonyl}morpholin-2-yl)methanol |
| 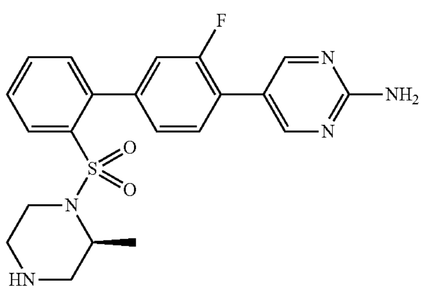 [SMILES: C[C@H]1CNCCN1S(=O)(=O)c1ccccc1-c1ccc(-c2cnc(N)nc2)c(F)c1] | 253 | 5-(3-Fluoro-2'-{[(2S)-2-methylpiperazin-1-yl]sulfonyl}biphenyl-4-yl)pyrimidin-2'-amine |
| 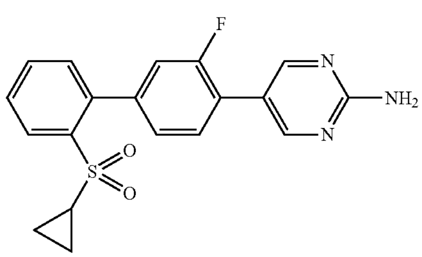 [SMILES: Nc1ncc(-c2ccc(-c3ccccc3S(=O)(=O)C3CC3)cc2F)cn1] | 254 | 5-[2'-(Cyclopropylsulfonyl)-3-fluorobiphenyl-4-yl]pyrimidin-2-amine |
| 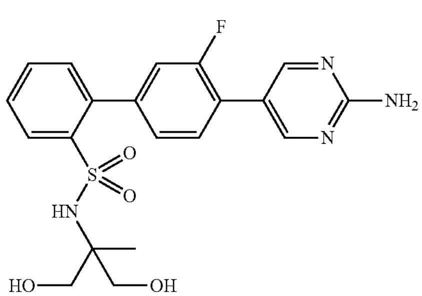 [SMILES: CC(CO)(CO)NS(=O)(=O)c1ccccc1-c1ccc(-c2cnc(N)nc2)c(F)c1] | 255 | 4'-(2-Aminopyrimidin-5-yl)-3'-fluoro-N-[2-hydroxy-1-(hydroxymethyl)-1-methylethyl]biphenyl-2-sulfonamide |

TABLE 3-continued

| STRUCTURE | COMPOUND # | NAME |
|---|---|---|
| 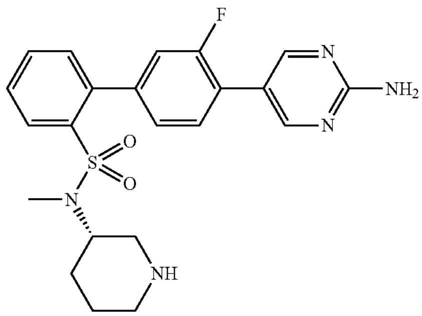 [SMILES: CN([C@H]1CCCNC1)S(=O)(=O)c1ccccc1-c1ccc(-c2cnc(N)nc2)c(F)c1] | 256 | 4'-(2-aminopyrimidin-5-yl)-3'-fluoro-N-methyl-N-[(3S)-piperidin-3-yl]biphenyl-2-sulfonamide |
| 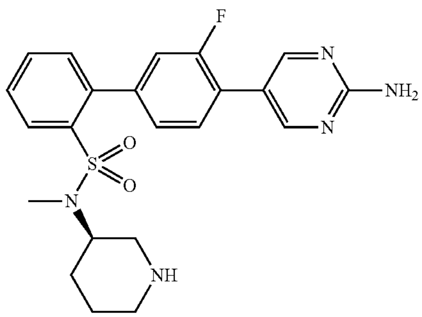 [SMILES: CN([C@@H]1CCCNC1)S(=O)(=O)c1ccccc1-c1ccc(-c2cnc(N)nc2)c(F)c1] | 257 | 4'-(2-aminopyrimidin-5-yl)-3'-fluoro-N-methyl-N-[(3R)-piperidin-3-yl]biphenyl-2-suifonamide |
| 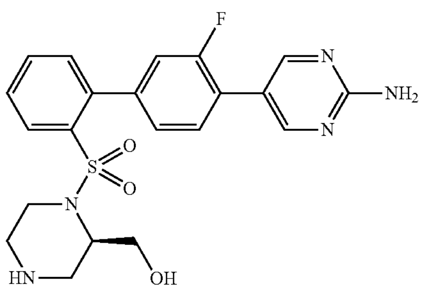 [SMILES: Nc1ncc(-c2ccc(-c3ccccc3S(=O)(=O)N3CCNC[C@@H]3CO)cc2F)cn1] | 258 | [(2R)-1-{[4'-(2-Aminopyrimidin-5-yl)-3'-fluorobiphenyl-2-yl]sulfonyl}piperazin-2-yl]methanol |
| 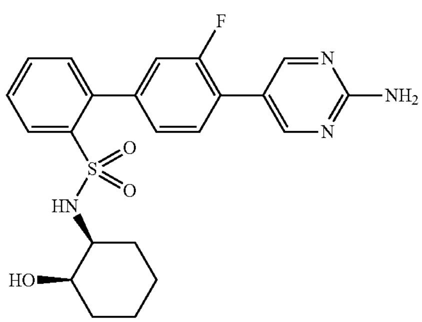 [SMILES: Nc1ncc(-c2ccc(-c3ccccc3S(=O)(=O)N[C@H]3CCCC[C@H]3O)cc2F)cn1] | 259 | racemic (cis) 4'-(2-Aminopyrimidin-5-yl)-3'-fluoro-N-[(cis)-2-hydroxycyclohexyl]biphenyl-2-sulfonamide |
| 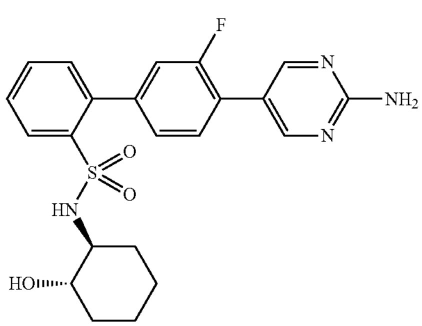 [SMILES: Nc1ncc(-c2ccc(-c3ccccc3S(=O)(=O)N[C@H]3CCCC[C@@H]3O)cc2F)cn1] | 260 | racemic (trans) 4'-(2-Aminopyrimidin-5-yl)-3'-fluoro-N-[(trans)-2-hydroxycyclohexyl]biphenyl-2-sulfonamide |

TABLE 3-continued

| STRUCTURE | COMPOUND # | NAME |
|---|---|---|
| 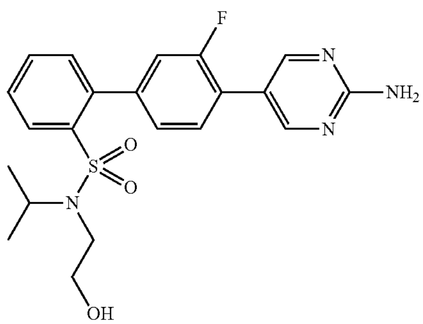 [SMILES: CC(C)N(CCO)S(=O)(=O)c1ccccc1-c1ccc(-c2cnc(N)nc2)c(F)c1] | 261 | 4'-(2-Aminopyrimidin-5-yl)-3'-fluoro-N-(2-hydroxyethyl)-N-(1-methylethyl)biphenyl-2-sulfonamide |
| 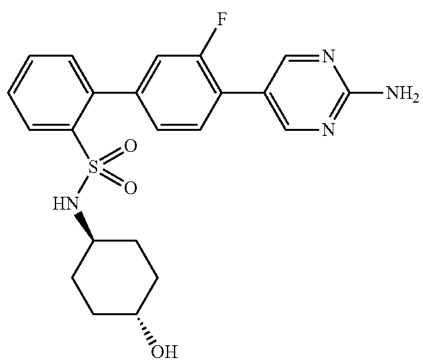 [SMILES: Nc1ncc(-c2ccc(-c3ccccc3S(=O)(=O)N[C@H]3CC[C@H](O)CC3)cc2F)cn1] | 262 | 4'-(2-Aminopyrimidin-5-yl)-3'-fluoro-N-(trans-4-hydroxycyclohexyl)biphenyl-2-sulfonamide |
| 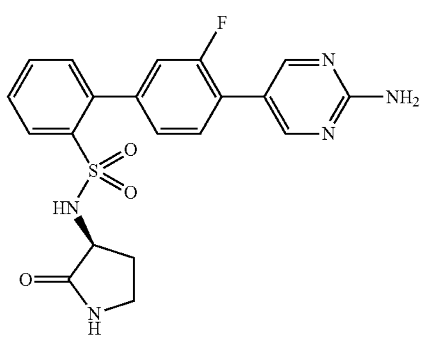 [SMILES: Nc1ncc(-c2ccc(-c3ccccc3S(=O)(=O)N[C@H]3CCNC3=O)cc2F)cn1] | 263 | 4'-(2-Aminopyrimidin-5-yl)-3'-fluoro-N-[(3S)-2-oxopyrrolidin-3-yl]biphenyl-2-sulfonamide |
| 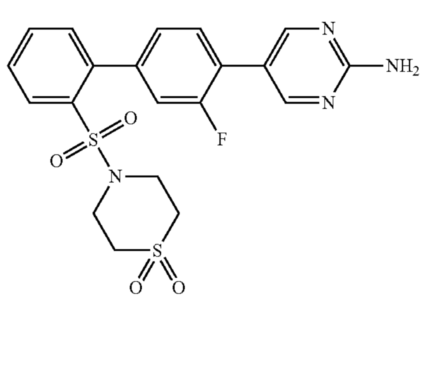 [SMILES: Nc1ncc(-c2ccc(-c3ccccc3S(=O)(=O)N3CCS(=O)(=O)CC3)cc2F)cn1] | 264 | 5-{2'-[(1,1-Dioxidothiomorpholin-4-yl)sulfonyl]-3-fluorobiphenyl-4-yl}pyrimidin-2-amine |

TABLE 3-continued

| STRUCTURE | COMPOUND # | NAME |
|---|---|---|
| 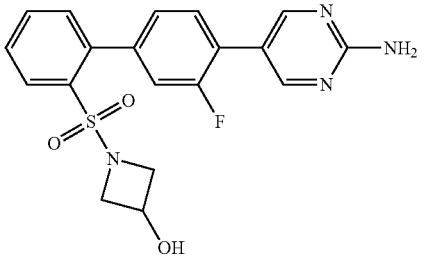 [SMILES: Nc1ncc(-c2ccc(-c3ccccc3S(=O)(=O)N3CC(O)C3)cc2F)cn1] | 265 | 1-{[4'-(2-Aminopyrimidin-5-yl)-3'-fluorobiphenyl-2-yl]sulfonyl}azetidin-3-ol trifluoroacetic acid salt |
| 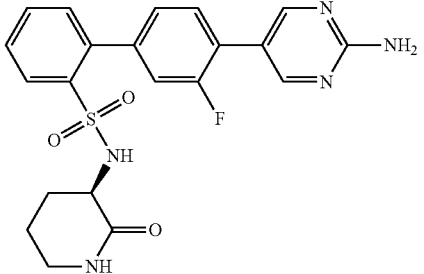 [SMILES: Nc1ncc(-c2ccc(-c3ccccc3S(=O)(=O)N[C@@H]3CCCNC3=O)cc2F)cn1] | 266 | 4'-(2-Aminopyrimidin-5-yl)-3'-fluoro-N-[(3R)-2-oxopiperidin-3-yl]biphenyl-2-sulfonamide trifluoroacetic acid salt |
| 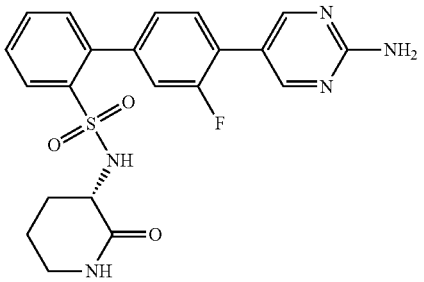 [SMILES: Nc1ncc(-c2ccc(-c3ccccc3S(=O)(=O)N[C@H]3CCCNC3=O)cc2F)cn1] | 267 | 4'-(2-Aminopyrimidin-5-yl)-3'-fluoro-N-[(3S)-2-oxopiperidin-3-yl]biphenyl-2-sulfonamide trifluoroacetic acid salt |
| 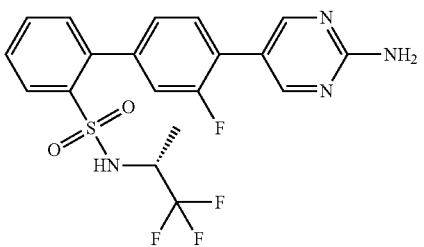 [SMILES: C[C@@H](NS(=O)(=O)c1ccccc1-c1ccc(-c2cnc(N)nc2)c(F)c1)C(F)(F)F] | 268 | 4'-(2-Aminopyrimidin-5-yl)-3'-fluoro-N-[(1R)-2,2,2-trifluoro-1-methylethyl]biphenyl-2-sulfonamide trifluoroacetic acid salt |
| 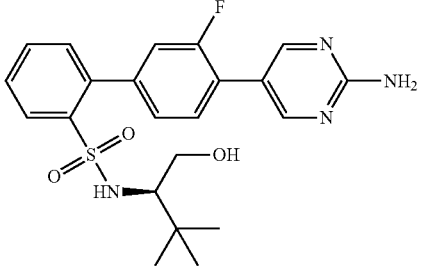 [SMILES: CC(C)(C)[C@H](CO)NS(=O)(=O)c1ccccc1-c1ccc(-c2cnc(N)nc2)c(F)c1] | 269 | 4'-(2-Aminopyrimidin-5-yl)-3'-fluoro-N[(R)-1-(hydroxymethyl)-2,2-dimethylpropyl]biphenyl-2-sulfonamide trifluoroacetic acid salt |

TABLE 3-continued

| STRUCTURE | COMPOUND # | NAME |
|---|---|---|
| 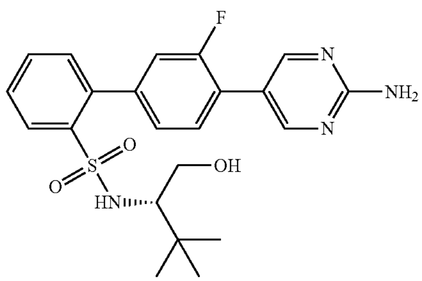 [SMILES: CC(C)(C)[C@@H](CO)NS(=O)(=O)c1ccccc1-c1ccc(-c2cnc(N)nc2)c(F)c1] | 270 | 4'-2-Aminopyrimidin-5-yl)-3'-fluoro-N-[(1S)-1-(hydroxymethyl)-2,2-dimethylpropyl]biphenyl-2-sulfonamide trifiuoroacetic acid salt |
| 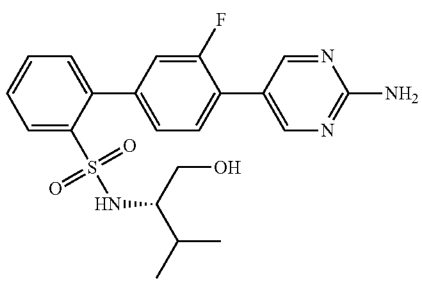 [SMILES: CC(C)[C@@H](CO)NS(=O)(=O)c1ccccc1-c1ccc(-c2cnc(N)nc2)c(F)c1] | 271 | 4'-(2-Aminopyrimidin-5-yl)-3'-fluoro-N-[(1S)-1-(hydroxymethyl)-2-methylpropyl]biphenyl-2-sulfonamide trifluoroacetic acid salt |
| 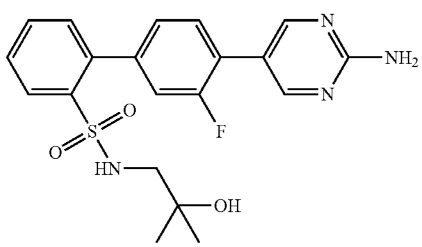 [SMILES: CC(C)(O)CNS(=O)(=O)c1ccccc1-c1ccc(-c2cnc(N)nc2)c(F)c1] | 272 | 4'-(2-Aminopyrimidin-5-y)-3'-fluoro-N-(2-hydroxy-2-methylpropyl)biphenyl-2-sulfonamide trifluoroacetic acid salt |
| 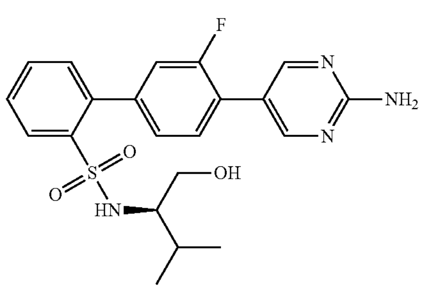 [SMILES: CC(C)[C@H](CO)NS(=O)(=O)c1ccccc1-c1ccc(-c2cnc(N)nc2)c(F)c1] | 273 | 4'-(2-Aminopyrimidin-5-yl)-3'-fluoro-N-[(1R)-1-(hydroxymethyl)-2-methylpropyl]biphenyl-2-sulfonamide trifluoroacetic acid salt |
| 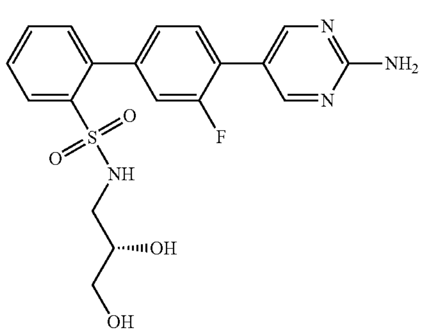 [SMILES: Nc1ncc(-c2ccc(-c3ccccc3S(=O)(=O)NC[C@H](O)CO)cc2F)cn1] | 274 | 4'-(2-Aminopyrimidin-5-yl)-N-[(2S)-2,3-dihydroxypropyl]-3'-fluorobiphenyl-2-sulfonamide trifluoroacetic acid salt |

TABLE 3-continued

| STRUCTURE | COMPOUND # | NAME |
|---|---|---|
| 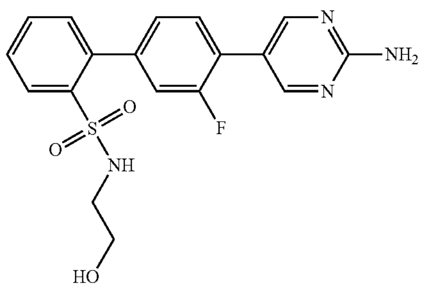 [SMILES: Nc1ncc(-c2ccc(-c3ccccc3S(=O)(=O)NCCO)cc2F)cn1] | 275 | 4'-(2-Aminopyrimidin-5-yl)-3'-fluoro-N-(2-hydroxyethyl)biphenyl-2'-sulfonamide trifluoroacetic acid salt |
| 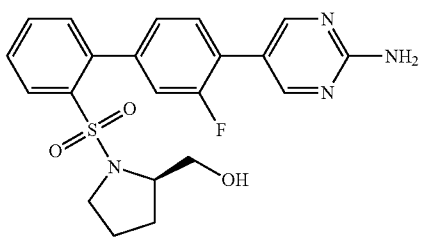 [SMILES: Nc1ncc(-c2ccc(-c3ccccc3S(=O)(=O)N3CCC[C@@H]3CO)cc2F)cn1] | 276 | [(2R)-1-{[4'-(2-Aminopyrimidin-5-yl)-3'-fluorobiphenyl-2-yl]sulfonyl}pyrrolidin-2-yl]methanol trifluoroacetic acid salt |
| 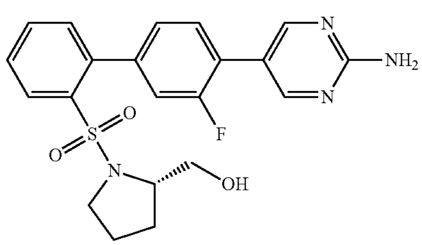 [SMILES: Nc1ncc(-c2ccc(-c3ccccc3S(=O)(=O)N3CCC[C@H]3CO)cc2F)cn1] | 277 | [(2S)-1-{[4'-(2-Aminopyrimidin-5-yl)-3'-fluorobiphenyl-2-ylisulfonyl}pyrrolidin-2-yl]methanol trifluoroacetic acid salt |
| 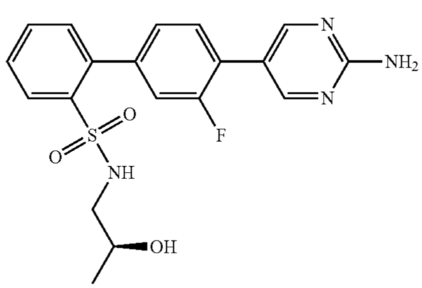 [SMILES: C[C@H](O)CNS(=O)(=O)c1ccccc1-c1ccc(-c2cnc(N)nc2)c(F)c1] | 278 | 4'-(2-Aminopyrimidin-5-yl)-3'-fluoro-N-[(2R)-2-hydroxypropyl]biphenyl-2-sulfonamide |
| 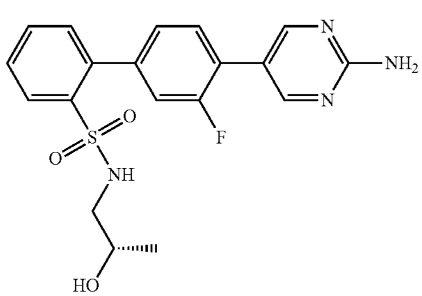 [SMILES: C[C@H](O)CNS(=O)(=O)c1ccccc1-c1ccc(-c2cnc(N)nc2)c(F)c1] | 279 | 4'-(2-Aminopyrimidin-5-yl)-3'-fluoro-N-[(2S)-2-hydroxypropyl]biphenyl-2-sulfonamide trifluoroacetic acid salt |

TABLE 3-continued

| STRUCTURE | COMPOUND # | NAME |
|---|---|---|
| 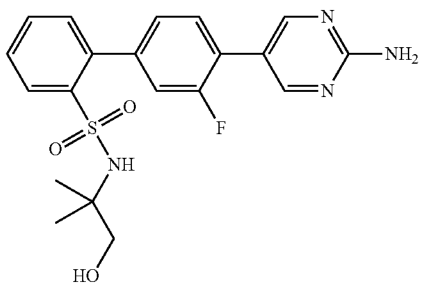 [SMILES: CC(C)(CO)NS(=O)(=O)c1ccccc1-c1ccc(-c2cnc(N)nc2)c(F)c1] | 280 | 4'-(2-Aminopyrimidin-5-yl)-3'-fluoro-N-(2-hydroxy-1,1-dimethylethyl)biphenyl-2-sulfonamide trifluoroacetic acid salt |
| 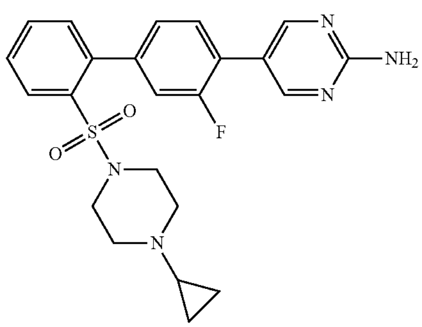 [SMILES: Nc1ncc(-c2ccc(-c3ccccc3S(=O)(=O)N3CCN(C4CC4)CC3)cc2F)cn1] | 281 | 5-{2'-[(4-Cyclopropylpiperazin-1-yl)sulfonyl]-3-fluorobiphenyl-4-yl}pyrimidin-2-amine trifluoroacetic acid salt |
| 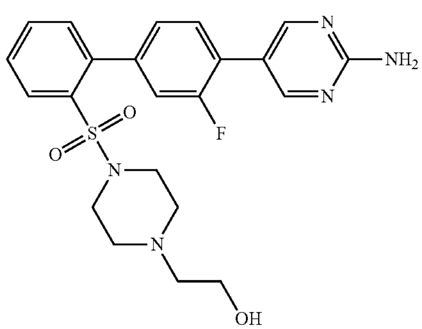 [SMILES: Nc1ncc(-c2ccc(-c3ccccc3S(=O)(=O)N3CCN(CCO)CC3)cc2F)cn1] | 282 | 2-(4-{(4'-[2-Aminopyrimidin-5-yl)-3'-fluorobiphenyl-2-yl]sulfonyl}piperazin-1-yl)ethanol trifluoroacetic acid salt |
| 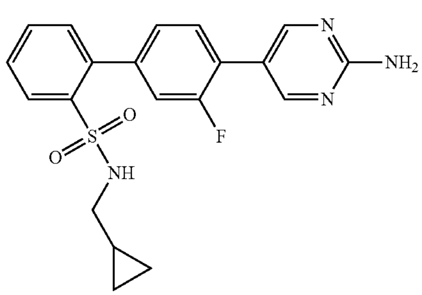 [SMILES: Nc1ncc(-c2ccc(-c3ccccc3S(=O)(=O)NCC3CC3)cc2F)cn1] | 283 | 4'-(2-Aminopyrimidin-5-yl)-N-(cyclopropylmethyl)-3'-fluorobiphenyl-2-sulfonamide trifluoroacetic acid |
| 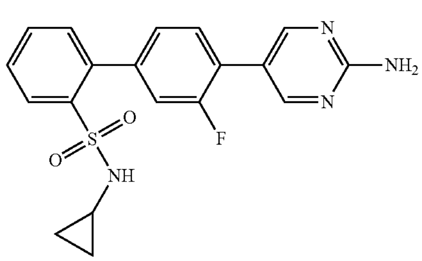 [SMILES: Nc1ncc(-c2ccc(-c3ccccc3S(=O)(=O)NC3CC3)cc2F)cn1] | 284 | 4'-(2-Aminopyrimidin-5-yl)-N-cyclopropyl-3'-fluorobiphenyl-2-sulfonamide trifluoroacetic acid salt |

TABLE 3-continued

| STRUCTURE | COMPOUND # | NAME |
|---|---|---|
| 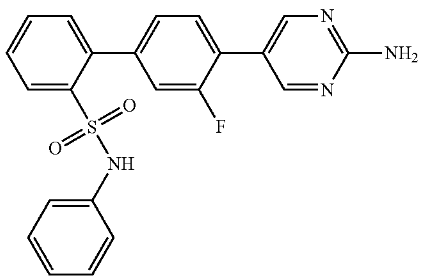 [SMILES: Nc1ncc(-c2ccc(-c3ccccc3S(=O)(=O)Nc3ccccc3)cc2F)cn1] | 285 | 4'-(2-Aminopyrimidin-5-yl)-3'-fluoro-N-phenylbiphenyl-2-sulfonamide trifluoroacetic acid salt |
| 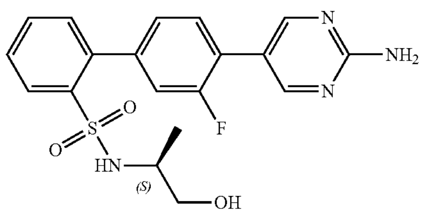 | 286 | 4'-(2-Aminopyrimidin-5-yl)-3'-fluoro-N-[(1S)-2-hydroxy-1-methylethyl]biphenyl-2-sulfonamide trifluoroacetic acid salt |
| 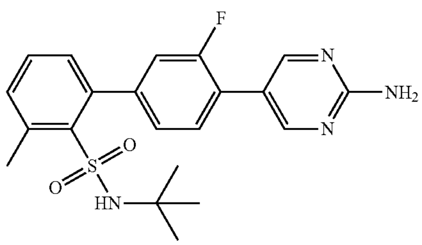 [SMILES: Cc1cccc(-c2ccc(-c3cnc(N)nc3)c(F)c2)c1S(=O)(=O)NC(C)(C)C] | 287 | 4'-(2-Aminopyrimidin-5-yl)-N-tert-butyl-3'-fluoro-3-methylbiphenyl-2-sulfonamide trifluoroacetic acid salt |
| 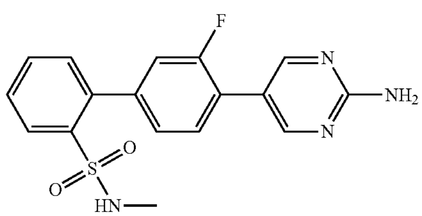 [SMILES: CNS(=O)(=O)c1ccccc1-c1ccc(-c2cnc(N)nc2)c(F)c1] | 288 | 4'-(2-Aminopyrimidin-5-yl)-3'-fluoro-N-methylbiphenyl-2-sulfonamide trifluoroacetic acid salt |
| 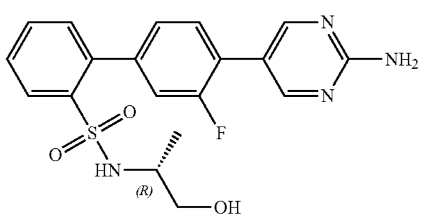 | 289 | 4'-(2-Aminopyrimidin-5-yl)-3'-fluoro-N-[(1R)-2-hydroxy-1-methylethyl]biphenyl-2-sulfonamide trifluoroacetic acid salt |
| 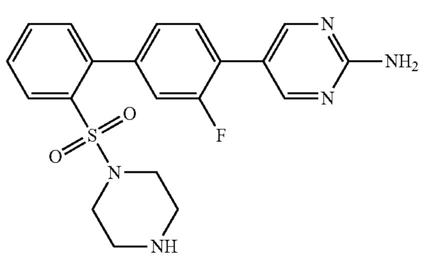 [SMILES: Nc1ncc(-c2ccc(-c3ccccc3S(=O)(=O)N3CCNCC3)cc2F)cn1] | 290 | 5-[3-Fluoro-2'-(piperazin-1-ylsulfonyl)biphenyl-4-yl]pyrimidin-2-amine trifluoroacetic acid salt |

TABLE 3-continued

| STRUCTURE | COMPOUND # | NAME |
|---|---|---|
| 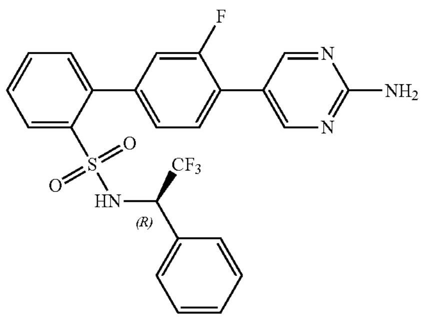 | 291 | 4'-(2-Aminopyrimidin-5-yl)-3'-fluoro-N-[(1R)-2,2,2-trifluoro-1-phanylethyl]biphenyl-2-sulfonamide trifluoroacetic acid salt |
| 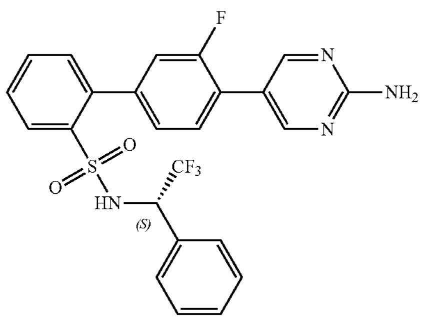 | 292 | 4'-(2-Aminopyrimidin-5-yl)-3'-fluoro-N-[(1S)-2,2,2-trifluoro-1-phenylethyl]biphenyl-2-sulfonamide trifluoroacetic acid salt |
| 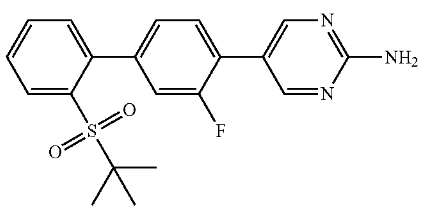 [SMILES: CC(C)(C)S(=O)(=O)c1ccccc1-c1ccc(-c2cnc(N)nc2)c(F)c1] | 293 | 5-[2'-(tert-Butylsulfonyl)-3-fluorobiphenyl-4-yl]pyrimidin-2-amine trifluoroacetic acid salt |
| 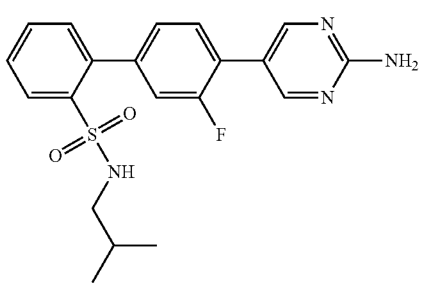 [SMILES: CC(C)CNS(=O)(=O)c1ccccc1-c1ccc(-c2cnc(N)nc2)c(F)c1] | 294 | 4'-(2-Aminopyrimidin-5-yl)-3'-fluoro-N-(2-methylpropyl)biphenyl-2-sulfonamide trifluoroacetic acid salt |
| 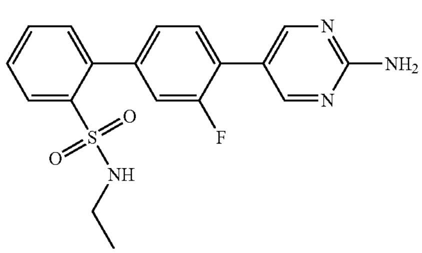 [SMILES: CCNS(=O)(=O)c1ccccc1-c1ccc(-c2cnc(N)nc2)c(F)c1] | 295 | 4'-(2-Aminopyrimidin-5-yl)-N-ethyl-3'-fluorobiphenyl-2-sulfonamide trifluoroacetic acid salt |

TABLE 3-continued

| STRUCTURE | COMPOUND # | NAME |
|---|---|---|
| 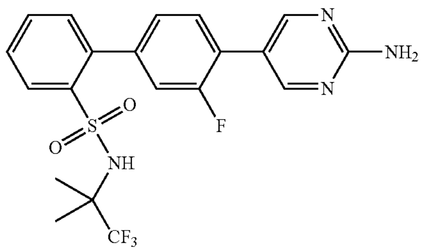 [SMILES: CC(C)(NS(=O)(=O)c1ccccc1-c1ccc(-c2cnc(N)nc2)c(F)c1)C(F)(F)F] | 296 | 4'-(2-Aminopyrimidin-5-yl)-3'-fluoro-N-(2,2,2-trifluoro-1,1-dimethylethyl)biphenyl-2-sulfonamide trifluoroacetic acid salt |
| 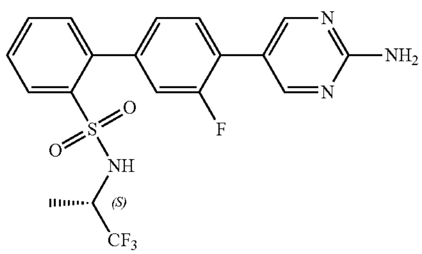 | 297 | 4'-(2-Aminopyrimidin-5-yl)-3'-fluoro-N-[(1S)-2,2,2-trifluoro-1-methylethyl]biphenyl-2-sulfonamide trifluoroacetic acid salt |
| 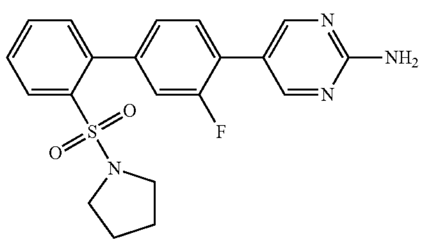 [SMILES: Nc1ncc(-c2ccc(-c3ccccc3S(=O)(=O)N3CCCC3)cc2F)cn1] | 298 | 5-[3-Fluoro-2'-(pyrrolidin-1-ylsulfonyl)biphenyl-4-yl]pyrimidin-2-amine trifluoroacetic acid salt |
| 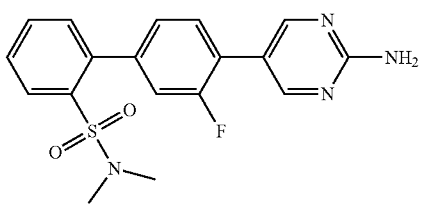 [SMILES: CN(C)S(=O)(=O)c1ccccc1-c1ccc(-c2cnc(N)nc2)c(F)c1] | 299 | 4'-(2-Aminopyrimidin-5-yl)-3'-fluoro-N,N-dimethylbiphenyl-2-sulfonamide trifluoroacetic acid salt |
| 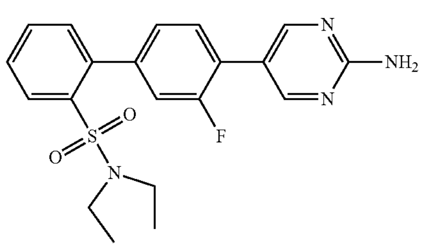 [SMILES: CCN(CC)S(=O)(=O)c1ccccc1-c1ccc(-c2cnc(N)nc2)c(F)c1] | 300 | 4'-(2-Aminopyrimidin-5-yl)-N,N-diethyl-3'-fluorobiphenyl-2-sulfonamide trifluoroacetic acid salt |
| 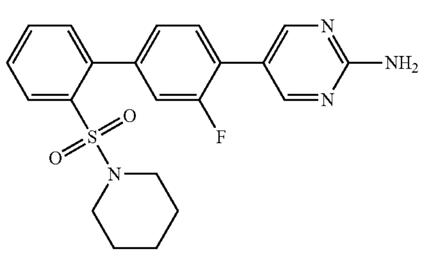 [SMILES: Nc1ncc(-c2ccc(-c3ccccc3S(=O)(=O)N3CCCCC3)cc2F)cn1] | 301 | 5-[3-Fluoro-2'-(piperidin-1-ylsulfonyl)biphenyl-4-yl]pyrimidin-2-amine trifluoroacetic acid salt |

TABLE 3-continued

| STRUCTURE | COMPOUND # | NAME |
|---|---|---|
| 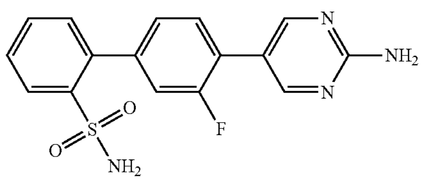 [SMILES: Nc1ncc(-c2ccc(-c3ccccc3S(N)(=O)=O)cc2F)cn1] | 302 | 4'-(2-Aminopyrimidin-5-yl)-3'-fluorobiphenyl-2-sulfonamide trifluoroacetic acid salt |
| 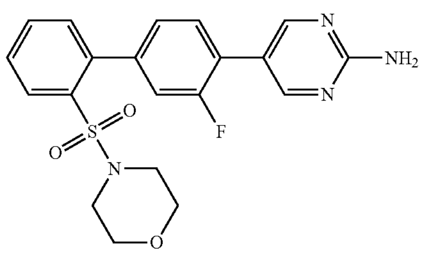 [SMILES: Nc1ncc(-c2ccc(-c3ccccc3S(=O)(=O)N3CCOCC3)cc2F)cn1] | 303 | 5-[3-Fluoro-2'-(morpholin-4-ylsulfonyl)biphenyl-4-yl]pyrimidin-2-amine trifluoroacetic acid salt |
| 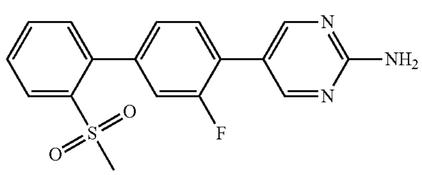 [SMILES: CS(=O)(=O)c1ccccc1-c1ccc(-c2cnc(N)nc2)c(F)c1] | 304 | 5-[3-Fluoro-2'-(methylsulfonyl)biphenyl-4-yl]pyrimidin-2-amine trifluoroacetic acid salt |
| 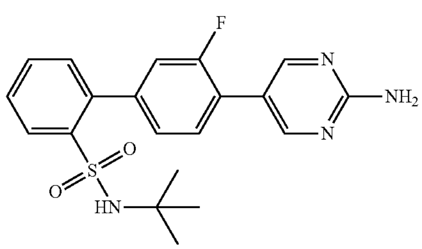 [SMILES: CC(C)(C)NS(=O)(=O)c1ccccc1-c1ccc(-c2cnc(N)nc2)c(F)c1] | 305 | 4'-(2-aminopyrimidin-5-yl)-N-(tert-butyl)-3'-fluoro[1,1'-biphenyl]-2-sulfonamide trifluoroacetic acid salt |
| 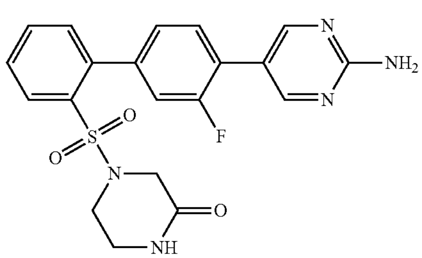 [SMILES: Nc1ncc(-c2ccc(-c3ccccc3S(=O)(=O)N3CCNC(=O)C3)cc2F)cn1] | 306 | 4-{[4'-(2-Aminopyrimidin-5-yl)-3'-fluorobiphenyl-2-yl]sulfonyl}piperazin-2-one trifluoroacetic acid salt |
| 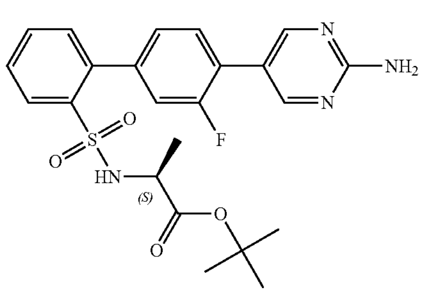 | 307 | tert-Butyl N-{[4'-(2-aminopyrimidin-5-yl)-3'-fluorobiphenyl-2-yl]sulfonyl}-L-alaninate |

TABLE 3-continued

| STRUCTURE | COMPOUND # | NAME |
|---|---|---|
| 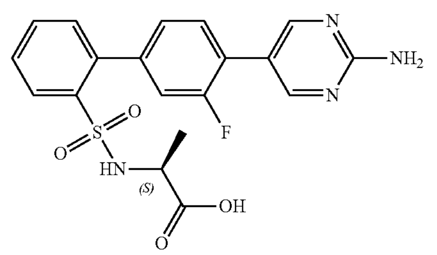 | 308 | N-{[4'-(2-Aminopyrimidin-5-yl)-3'-fluorobiphenyl-2-yl]sulfonyl}-L-alanine |
| 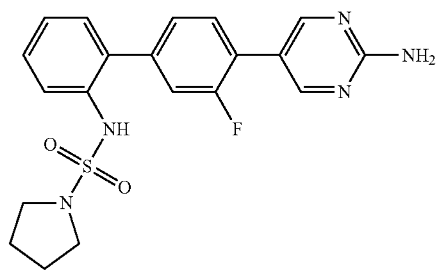 [SMILES: Nc1ncc(-c2ccc(-c3ccccc3NS(=O)(=O)N3CCCC3)cc2F)cn1] | 309 | N-[4'-(2-Aminopyrimidin-5-yl)-3'-fluorobiphenyl-2-yl]pyrrolidine-1-sulfonamide |
| 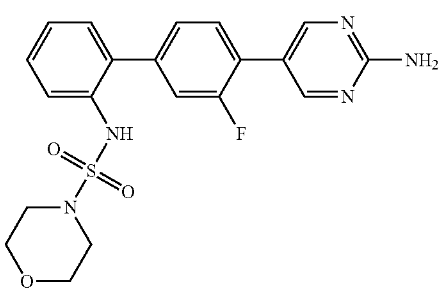 [SMILES: Nc1ncc(-c2ccc(-c3ccccc3NS(=O)(=O)N3CCOCC3)cc2F)cn1] | 310 | N-[4'-(2-Aminopyrimidin-5-yl)-3'-fluorobiphenyl-2-yl]morpholine-4-sulfonamide |
| 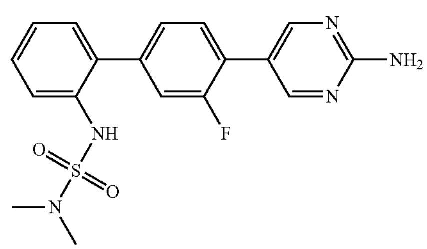 | 311 | N'-[4'-(2-Aminopyrimidin-5-yl)-3'-fluorobiphenyl-2-yl]-N,N-dimethylsulfamide |
| 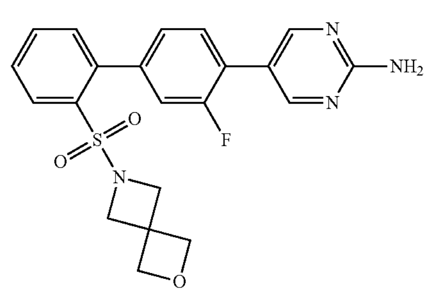 [SMILES: Nc1ncc(-c2ccc(-c3ccccc3S(=O)(=O)N3CC4(COC4)C3)cc2F)cn1] | 312 | 5-(2'-(2-oxa-6-azaspiro[3.3]heptan-6-ylsulfonyl)-3-fluoro-[1,1'-biphenyl]-4-yl)pyrimidin-2-amine |

TABLE 3-continued

| STRUCTURE | COMPOUND # | NAME |
| --- | --- | --- |
| 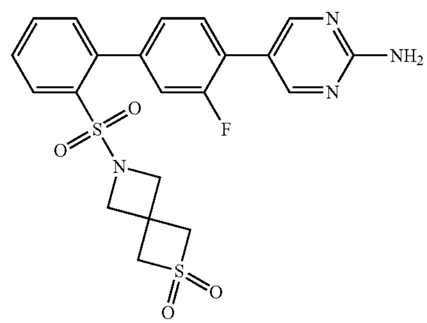 [SMILES: Nc1ncc(-c2ccc(-c3ccccc3S(=O)(=O)N3CC4(C3)CS(=O)(=O)C4)cc2F)cn1] | 313 | 6-((4'-(2-aminopyrimidin-5-yl)-3'-fluoro-[1,1'-biphenyl]-2-yl)sulfonyl)-2-thia-6-azaspiro[3.3]heptane 2,2-dioxide |
| 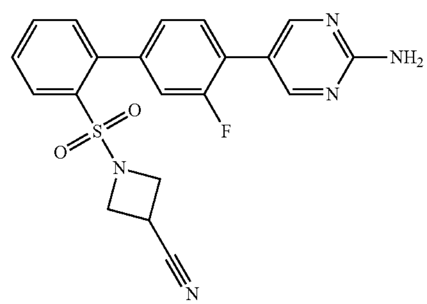 [SMILES: N#CC1CN(S(=O)(=O)c2ccccc2-c2ccc(-c3cnc(N)nc3)c(F)c2)C1] | 314 | 1-((4'-(2-aminopyrimidin-5-yl)-3'-fluoro-[1,1'-biphenyl]-2-yl)sulfonyl)azetidine-3-carbonitrile |
| 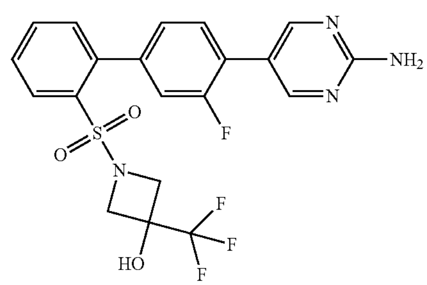 [SMILES: Nc1ncc(-c2ccc(-c3ccccc3S(=O)(=O)N3CC(O)(C(F)(F)F)C3)cc2F)cn1] | 315 | 1-((4-(2-aminopyrimidin-5-yl)-3'-fluoro-[1,1'-biphenyl]-2-yl)sulfonyl)-3-(trifluoromethyl)azetidin-3-ol |
| 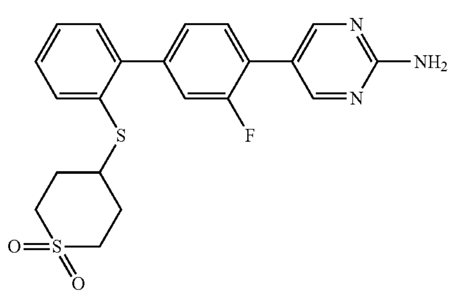 [SMILES: Nc1ncc(-c2ccc(-c3ccccc3SC3CCS(=O)(=O)CC3)cc2F)cn1] | 316 | 5-{2'-[(1,1-Dioxidotetrahydro-2H-thiopyran-4-yl)sulfonyl]-3-fluorobiphenyl-4-yl}pyrimidin.-2-amine hydrochloride |
| 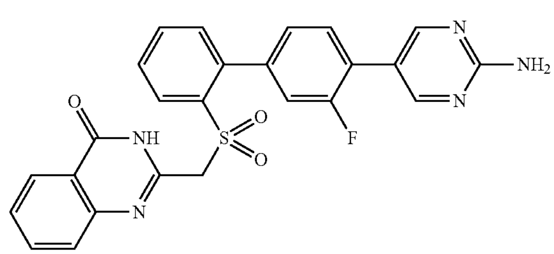 [SMILES: Nc1ncc(-c2ccc(-c3ccccc3S(=O)(=O)Cc3nc4ccccc4c(=O)[nH]3)cc2F)cn1] | 317 | 2-(((4'-(2-aminopyrimidin-5-yl)-3'-fluoro-[1,1'-biphenyl]-2-yl)sulfonyl)methyl)quinazolin-4(3H)-one |

TABLE 3-continued

| STRUCTURE | COMPOUND # | NAME |
|---|---|---|
| 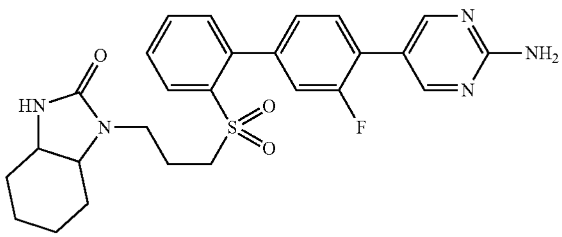 [SMILES: Nc1ncc(-c2ccc(-c3ccccc3S(=O)(=O)CCCN3C(=O)NC4CCCCC43)cc2F)cn1] | 318 | 1-(3-((4'-(2-aminopyrimidin-5-yl)-3'-fluoro-[1,1'-biphenyl]-2-yl)sulfonyl)propyl)-1H-benzo[d]imidazol-2(3H)-one |
| 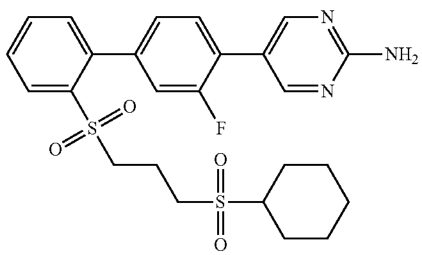 [SMILES: Nc1ncc(-c2ccc(-c3ccccc3S(=O)(=O)CCCS(=O)(=O)C3CCCCC3)cc2F)cn1] | 319 | 5-(2'-{[3-(Cyclohexylsulfonyl)propyl]sulfonyl}-3-fluorobiphenyl-4-yl)pyrimidin-2-amine |
| 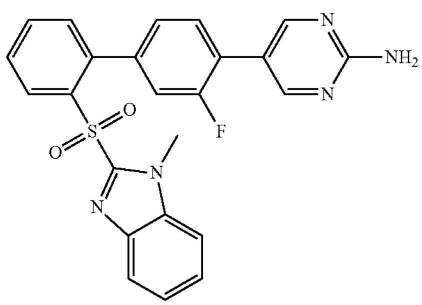 [SMILES: Cn1c(S(=O)(=O)c2ccccc2-c2ccc(-c3cnc(N)nc3)c(F)c2)nc2ccccc21] | 320 | 5-{3-Fluoro-2'-[(1-methyl-1H-benzimidazol-2-yl)sulfonyl]biphenyl-4-yl}pyrimidin-2-amine |
| 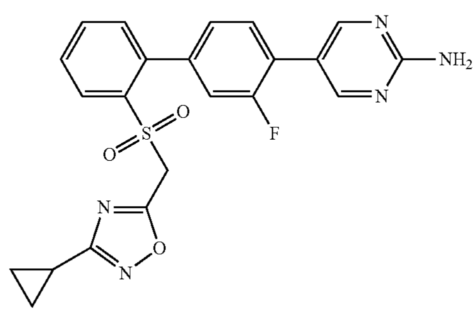 [SMILES: Nc1ncc(-c2ccc(-c3ccccc3S(=O)(=O)Cc3nc(C4CC4)no3)cc2F)cn1] | 321 | 5-(2'-{[(3-Cyclopropyl-1,2,4-oxadiazol-5-yl)methyl]sulfonyl}-3-fluorobiphenyl-4-yl)pyrimidin-2-amine |
| 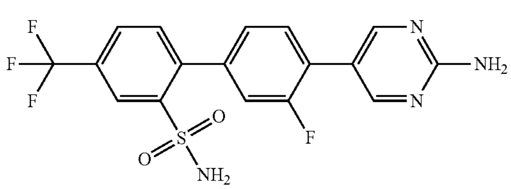 [SMILES: Nc1ncc(-c2ccc(-c3ccc(C(F)(F)F)cc3S(N)(=O)=O)cc2F)cn1] | 322 | 4'-(2-aminopyrimidin-5-yl)-3'-fuoro-4-(trifluoromethyl)biphenyl-2-sulfonamide |
| 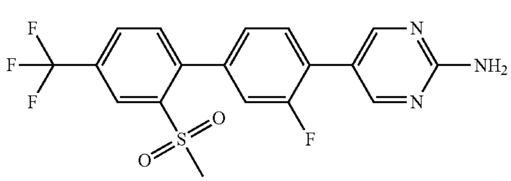 | 323 | 5-[3-fluoro-2'-(methylsulfonyl)-4'-(trifluoromethyl)biphenyl-4-yl]pyrimidin-2-amine |

TABLE 3-continued

| STRUCTURE | COMPOUND # | NAME |
|---|---|---|
| 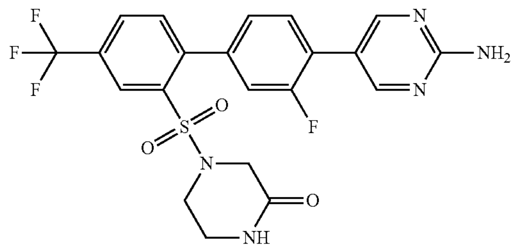 [SMILES: Nc1ncc(-c2ccc(-c3ccc(C(F)(F)F)cc3S(=O)(=O)N3CCNC(=O)C3)cc2F)cn1] | 324 | 4-{[4'-(2-aminopyrimidin-5-yl)-3'-fluoro-4-(trifluoromethyl)biphenyl-2-yl]sulfonyl}piperazin-2-one |
| 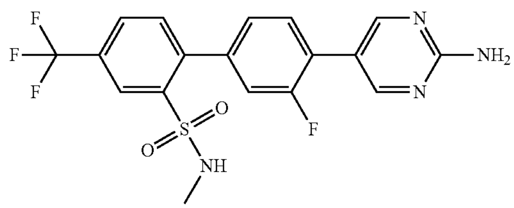 [SMILES: CNS(=O)(=O)c1cc(C(F)(F)F)ccc1-c1ccc(-c2cnc(N)nc2)c(F)c1] | 325 | 4'-(2-aminopyrimidin-5-yl)-3'-fluoro-N-methyl-4-(trifluoromethyl)biphenyl-2-sulfonamide |
| 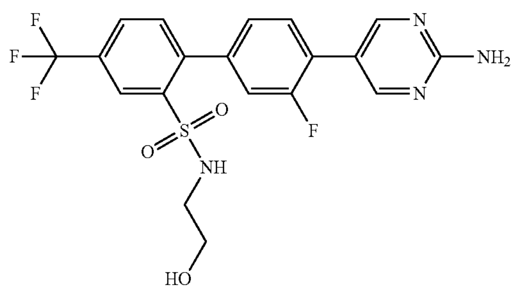 [SMILES: Nc1ncc(-c2ccc(-c3ccc(C(F)(F)F)cc3S(=O)(=O)NCCO)cc2F)cn1] | 326 | 4'-(2-Aminopyrimidin-5-yl)-3'-fluoro-N-(2-hydroxyethyl)-4-(trifluoromethyl)biphenyl-2-sulfonamide |
| 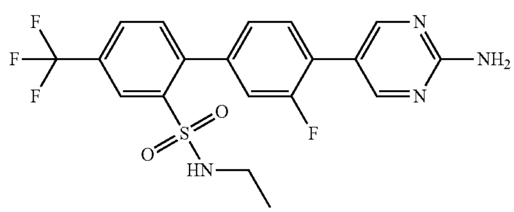 | 327 | 4'-(2-Aminopyrimidin-5-yl)-N-ethyl-3'-fluoro-4-(trifluoromethyl)biphenyl-2'-sulfonamide |
| 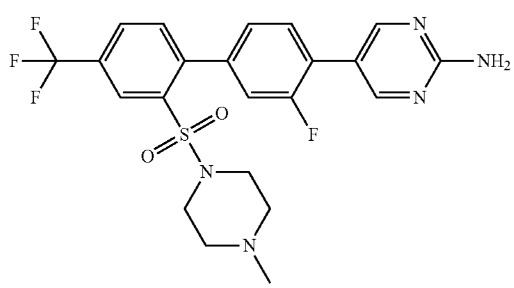 [SMILES: CN1CCN(S(=O)(=O)c2cc(C(F)(F)F)ccc2-c2ccc(-c3cnc(N)nc3)c(F)c2)CC1] | 328 | 5-{3-Fluoro-2'-[(4-methylpiperazin-1-yl)sulfonyl]-4'-(trifluoromethyl)biphenyl-4-yl}pyrimidin-2-amine |
| 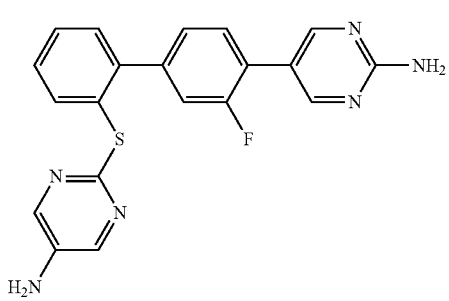 | 329 | 5-{2'-[(5-Aminopyrimidin-2-yl)sulfanyl]-3-fluorobiphenyl-4-yl}pyrimidin-2-amine formate salt |

TABLE 3-continued

| STRUCTURE | COMPOUND # | NAME |
|---|---|---|
| 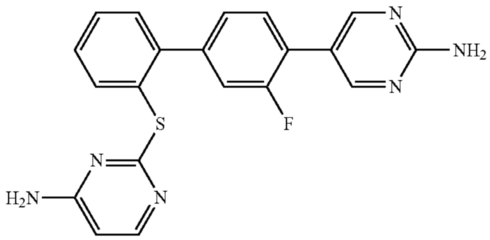 [SMILES: Nc1ccnc(Sc2ccccc2-c2ccc(-c3cnc(N)nc3)c(F)c2)n1] | 330 | 5-{2'-[(4-Aminopyrimidin-2-yl)sulfanyl]-3-fluorobiphenyl-4-yl}pyrimidin-2-amine formate salt |
| 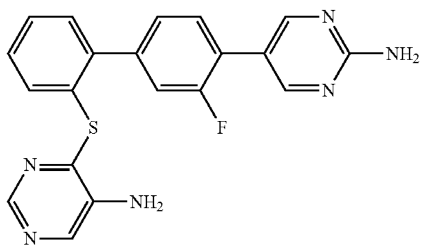 [SMILES: Nc1ncc(-c2ccc(-c3ccccc3Sc3ncncc3N)cc2F)cn1] | 331 | 5-{2'-[(5-Aminopyrimidin-4-yl)sulfanyl]-3-fluorobiphenyl-4-yl}pyrimidin-2-amine formate salt |
| 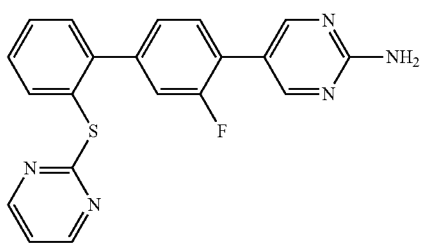 [SMILES: Nc1ncc(-c2ccc(-c3ccccc3Sc3ncccn3)cc2F)cn1] | 332 | 5-[3-Fluoro-2'-(pyrimidin-2-ylsulfanyl)biphenyl-4-yl]pyrimidin-2-amine hydrochloride |
| 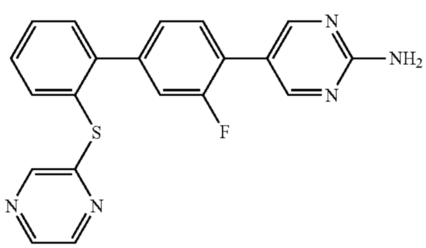 [SMILES: Nc1ncc(-c2ccc(-c3ccccc3Sc3cnccn3)cc2F)cn1] | 333 | 5-[3-Fluoro-2'-(pyrazin-2-ylsulfanyl)biphenyl-4-yl]pyrimidin-2-amine hydrochloride |
| 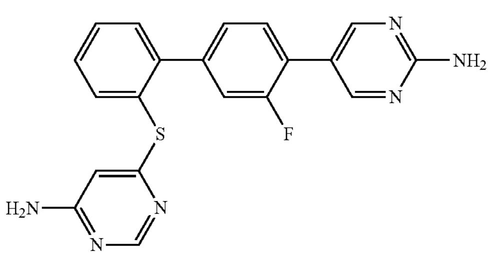 [SMILES: Nc1cc(Sc2ccccc2-c2ccc(-c3cnc(N)nc3)c(F)c2)ncn1] | 334 | 5-{2'-[(6-Aminopyrimidin-4-yl)sulfanyl)-3-fluorobiphenyl-4-yl}pyrimidin-2-amine formate salt |
| 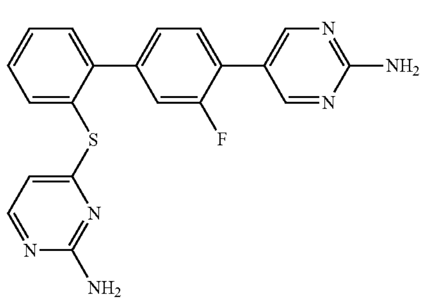 | 335 | 4-{[4'-(2-Aminopyrimidin-5-yl)-3'-fluorobiphenyl-2-yl]sulfanyl}pyrimidin-2-amine formate salt |

TABLE 3-continued

| STRUCTURE | COMPOUND # | NAME |
|---|---|---|
| 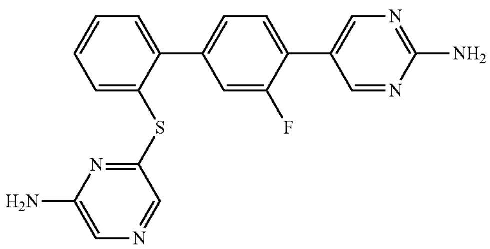 [SMILES: Nc1cncc(Sc2ccccc2-c2ccc(-c3cnc(N)nc3)c(F)c2)n1] | 336 | 5-{2'-[(6-Aminopyrazin-2-yl)sulfanyl]-3-fluorobiphenyl-4-yl}pyrimidin-2-amine formate salt |
| 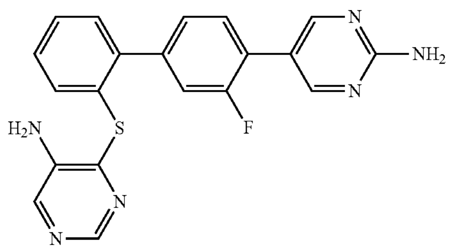 [SMILES: Nc1ncc(-c2ccc(-c3ccccc3Sc3ncncc3N)cc2F)cn1] | 337 | 5-{2'-[(5-Aminopyrimidin-4-yl)sulfonyl]-3-fluorobiphenyl-4-yl}pyrimidin-2-amine hydrochloride |
| 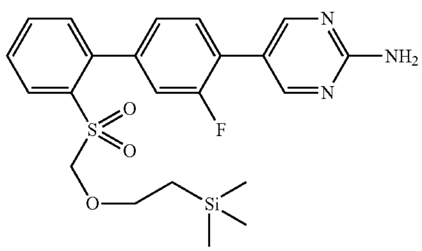 [SMILES: C[Si](C)(C)CCOCS(=O)(=O)c1ccccc1-c1ccc(-c2cnc(N)nc2)c(F)c1] | 338 | 5-[3-Fluoro-2'-({[2-trimethylsilyl)ethoxy]methyl}sulfonyl)biphenyl-4-yl]pyrimidin-2-amine formate salt |
| 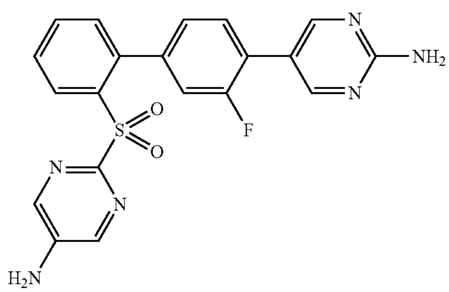 [SMILES: Nc1cnc(S(=O)(=O)c2ccccc2-c2ccc(-c3cnc(N)nc3)c(F)c2)nc1] | 339 | 5-{2'-[(5-Aminopyrimidin-2-yl)sulfonyl]-3-fluorobiphenyl-4-yl}pyrimidin-2-amine hydrochloride |
| 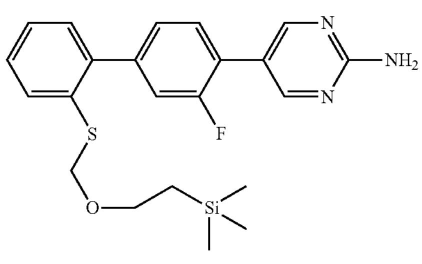 | 340 | 5-[3-Fluoro-2'-({[2-(trimethylsilyl)ethoxy]methyl}sulfanyl)biphanyl-4-yl]pyrimidin-2-amine |
| 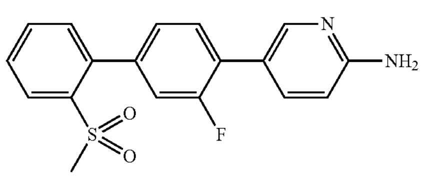 | 341 | 5-(3-Fluoro-2'-(methylsulfonyl)-[1,1'-biphenyl]-4-yl)pyridin-2-amine |

TABLE 3-continued

| STRUCTURE | COMPOUND # | NAME |
|---|---|---|
| 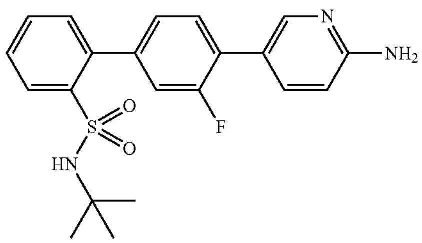 [SMILES: CC(C)(C)NS(=O)(=O)c1ccccc1-c1ccc(-c2ccc(N)nc2)c(F)c1] | 342 | 4'-(6-aminopyridin-3-yl)-N-((tert-butyl)-3'-fluoro-[1,1'-biphenyl]-2-sulfonamide |
| 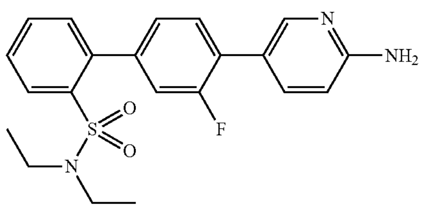 [SMILES: CCN(CC)S(=O)(=O)c1ccccc1-c1ccc(-c2ccc(N)nc2)c(F)c1] | 343 | 4'-(6-aminopyridin-3-yl)-N,N-diethyl-3'-fluoro-[1,1'-biphenyl]-2-sulfonamide |
| 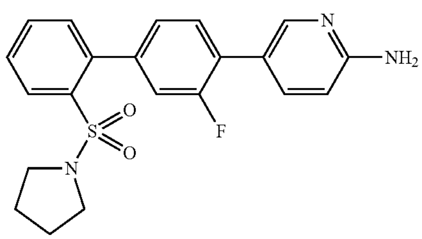 [SMILES: Nc1ccc(-c2ccc(-c3ccccc3S(=O)(=O)N3CCCC3)cc2F)cn1] | 344 | 5-(3-fluoro-2'-(pyrrolidin-1-ylsulfonyl)-[1,1'-biphenyl]-4-yl)pyridin-2-amine |
| 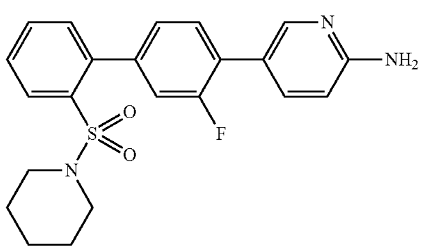 [SMILES: Nc1ccc(-c2ccc(-c3ccccc3S(=O)(=O)N3CCCCC3)cc2F)cn1] | 345 | 5-(3-fluoro-2'-(piperidin-1-ylsulfonyl)-[1,1'-biphenyl]-4-yl)pyridin-2-amine |
| 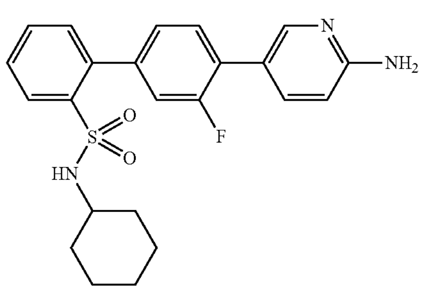 [SMILES: Nc1ccc(-c2ccc(-c3ccccc3S(=O)(=O)NC3CCCCC3)cc2F)cn1] | 346 | 4'-(6-aminopyridin-3-yl)-N-cyclohexyl-3'-fluoro-[1,1'-biphenyl]-2-sulfonamide |
| 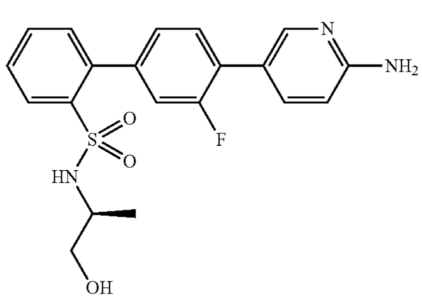 [SMILES: C[C@@H](CO)NS(=O)(=O)c1ccccc1-c1ccc(-c2ccc(N)nc2)c(F)c1] | 347 | (S)-4'-(6-aminopyridin-3-yl)-3'-fluoro-N-(1-hydroxypropan-2-yl)-[1,1'-biphenyl]-2-sulfonamide |

TABLE 3-continued

| STRUCTURE | COMPOUND # | NAME |
|---|---|---|
| 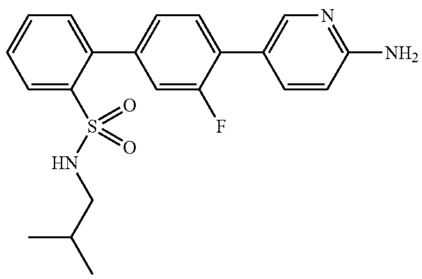 [SMILES: CC(C)CNS(=O)(=O)c1ccccc1-c1ccc(-c2ccc(N)nc2)c(F)c1] | 348 | 4'-(6-aminopyridin-3-yl)-3'-fluoro-N-isobutyl-[1,1'-biphenyl]-2-sulfonamide |
| 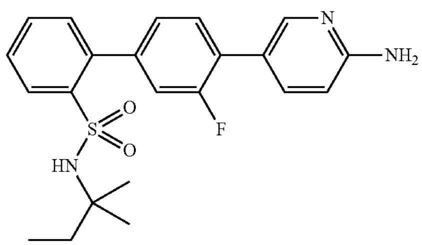 [SMILES: CCC(C)(C)NS(=O)(=O)c1ccccc1-c1ccc(-c2ccc(N)nc2)c(F)c1] | 349 | 4'-(6-aminopyridin-3-yl)-3'-fluoro-N-(tert-pentyl)-[1,1'-biphenyl]-2-sulfonamide |
| 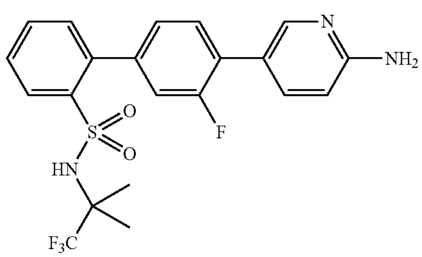 [SMILES: CC(C)(NS(=O)(=O)c1ccccc1-c1ccc(-c2ccc(N)nc2)c(F)c1)C(F)(F)F] | 350 | 4'-(6-aminopyridin-3-yl)-3'-fluoro-N-(1,1,1-trifluoro-2-methylpropan-2-yl)-[1,1'-biphenyl]-2-sulfonamide |
| 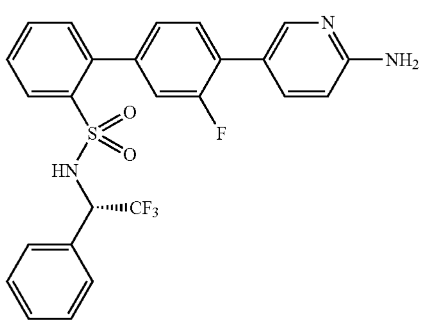 [SMILES: Nc1ccc(-c2ccc(-c3ccccc3S(=O)(=O)N[C@@H](c3ccccc3)C(F)(F)F)cc2F)cn1] | 351 | (S)-4'-(6-aminopyridin-3-yl)-3'-fluoro-N-(2,2,2-trifluoro-1-phenylethyl)-[1,1'-biphenyl]-2-sulfonamide |
| 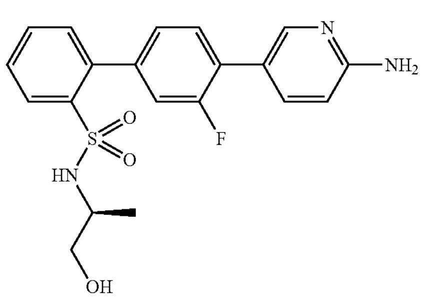 [SMILES: C[C@@H](CO)NS(=O)(=O)c1ccccc1-c1ccc(-c2ccc(N)nc2)c(F)c1] | 352 | (R)-4'-(6-aminopyridin-3-yl)-3-fluoro-N-(1-hydroxypropan-2-yl)-[1,1'-biphenyl]-2-sulfonamide |

TABLE 3-continued

| STRUCTURE | COMPOUND # | NAME |
|---|---|---|
| 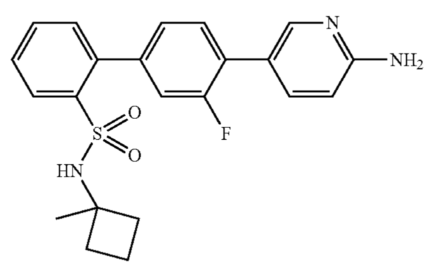 [SMILES: CC1(NS(=O)(=O)c2ccccc2-c2ccc(-c3ccc(N)nc3)c(F)c2)CCC1] | 353 | 4'-(6-aminopyridin-3-yl)-3'-fluoro-N-(1-methylcyclobutyl)-[1,1'-biphenyl]-2-sulfonamide |
| 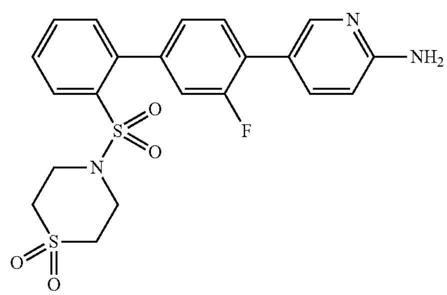 [SMILES: Nc1ccc(-c2ccc(-c3ccccc3S(=O)(=O)N3CCS(=O)(=O)CC3)cc2F)cn1] | 354 | 4-((4'-(6-aminopyridin-3-yl)-3'-fluoro-[1,1'-biphenyl]-2-yl)sulfonyl)thiomorpholine 1,1-dioxide |
| 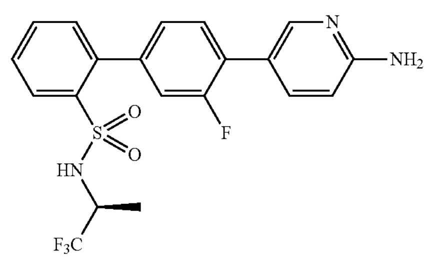 [SMILES: C[C@H](NS(=O)(=O)c1ccccc1-c1ccc(-c2ccc(N)nc2)c(F)c1)C(F)(F)F] | 355 | (S)-4'-(6-aminopyridin-3-yl)-3'-fluoro-N-(1,1,1-trifluoropropan-2-yl)-[1,1'-biphenyl]-2-sulfonamide |
| 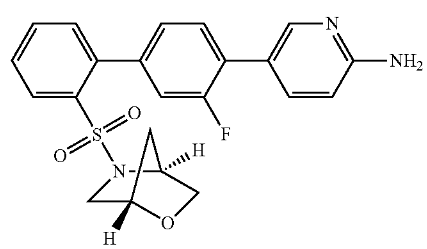 [SMILES: Nc1ccc(-c2ccc(-c3ccccc3S(=O)(=O)N3C[C@@H]4C[C@H]3CO4)cc2F)cn1] | 356 | 5-(2'-((1S,4S)-2-oxa-5-azabicyclo[2.2.1]heptan-5-ylsulfonyl)-3-fluoro-[1,1'-biphenyl]-4-yl)pyridin-2-amine |
| 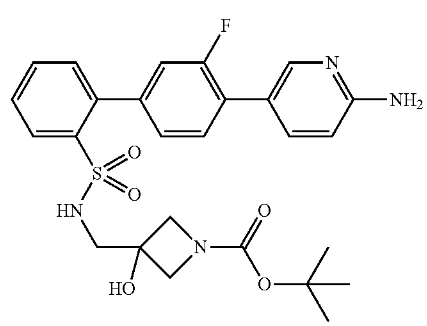 [SMILES: CC(C)(C)OC(=O)N1CC(O)(CNS(=O)(=O)c2ccccc2-c2ccc(-c3ccc(N)nc3)c(F)c2)C1] | 357 | tert-butyl 3-((4'-(6-aminopyridin-3-yl)-3'-fluoro-[1,1'-biphenyl]-2-ylsulfonamido)methyl)-3-hydroxyazetidine-1-carboxylate |

TABLE 3-continued

| STRUCTURE | COMPOUND # | NAME |
|---|---|---|
| 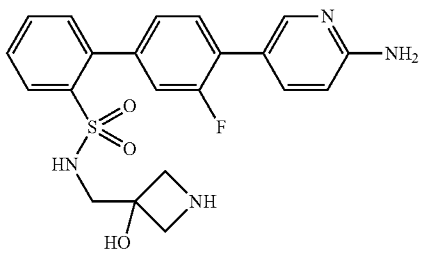 [SMILES: Nc1ccc(-c2ccc(-c3ccccc3S(=O)(=O)NCC3(O)CNC3)cc2F)cn1] | 358 | 4'-(6-aminopyridin-3-yl)-3'-fluoro-N-((3-hydroxyazetidin-3-yl)methyl)-[1,1'-biphenyl]-2-sulfonamide |
| 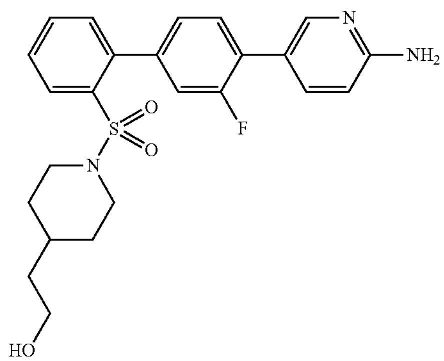 [SMILES: Nc1ccc(-c2ccc(-c3ccccc3S(=O)(=O)N3CCC(CCO)CC3)cc2F)cn1] | 359 | 2-(1-(4'-(6-aminopyridin-3-yl)-3'-fluoro-[1,1'-biphenyl]-2-yl)sulfonyl)piperidin-4-yl)ethanol |
| 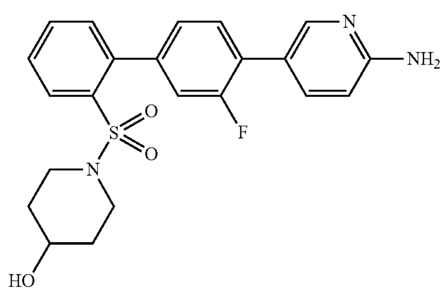 [SMILES: Nc1ccc(-c2ccc(-c3ccccc3S(=O)(=O)N3CCC(O)CC3)cc2F)cn1] | 360 | 1-((4'-(6-aminopyridin-3-yl)-3'-fluoro-[1,1'-biphenyl]-2-yl)sulfonyl)piperidin-4-ol |
| 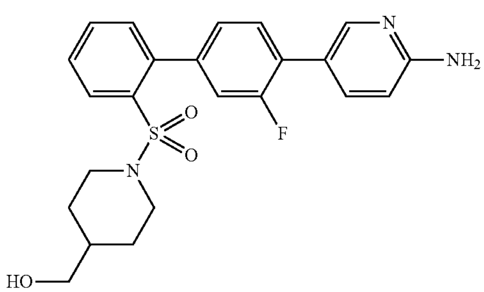 [SMILES: Nc1ccc(-c2ccc(-c3ccccc3S(=O)(=O)N3CCC(CO)CC3)cc2F)cn1] | 361 | (1-((4'-(6-aminopyridin-3-yl)-3'-fluoro-[1,1'-biphenyl]-2-yl)sulfonyl)piperidin-4-yl)methanol |
| 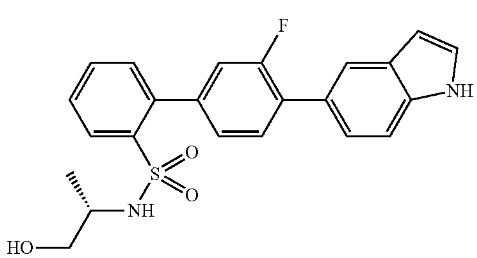 [SMILES: C[C@@H](CO)NS(=O)(=O)c1ccccc1-c1ccc(-c2ccc3[nH]ccc3c2)c(F)c1] | 362 | 3'-Fluoro-N-[(1S)-2-hydroxy-1-methylethyl]-4'-(1H-pyrrolo[2,3-b]pyridin-5-yl)biphenyl-2-sulfonamide |

TABLE 3-continued

| STRUCTURE | COMPOUND # | NAME |
|---|---|---|
| 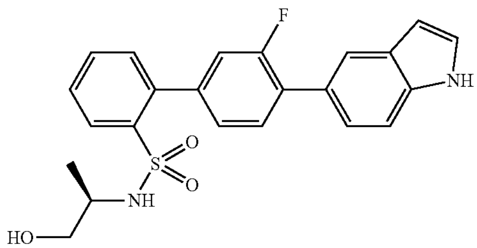 [SMILES: C[C@H](CO)NS(=O)(=O)c1ccccc1-c1ccc(-c2ccc3[nH]ccc3c2)c(F)c1] | 363 | 3'-Fluoro-N-[(1R)-2-hydroxy-1-methylethyl]-4'-(1H-pyrrolo[2,3-b]pyridin-5-yl)biphenyl-2-sulfonamide |
| 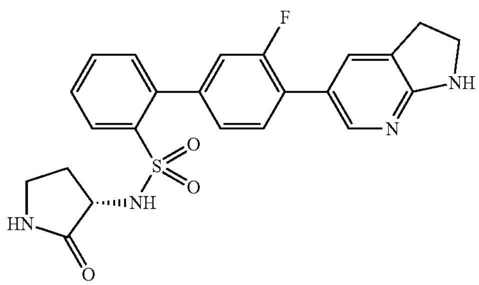 [SMILES: O=C1NCC[C@@H]1NS(=O)(=O)c1ccccc1-c1ccc(-c2cnc3c(c2)CCN3)c(F)c1] | 364 | 3'-Fluoro-N-[(3S)-2-oxopyrrolidin-3-yl]-4'-(1H-pyrrolo[2,3-b]pyridin-5-yl)biphenyl-2-sulfonamide |
| 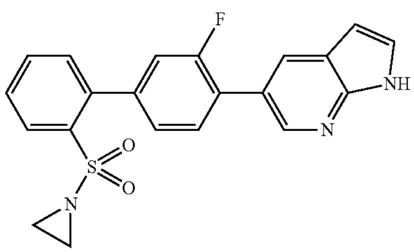 [SMILES: O=S(=O)(c1ccccc1-c1ccc(-c2cnc3[nH]ccc3c2)c(F)c1)N1CC1] | 365 | 5-[2'-(Cyclopropylsulfonyl)-3-fluorobiphenyl-4-yl]-1H-pyrrolo[2,3-b]pyridine |
| 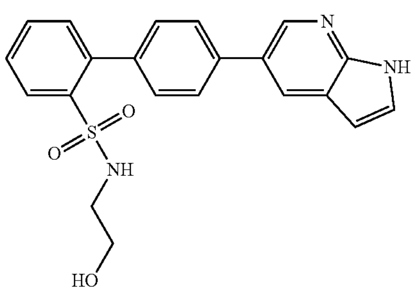 [SMILES: O=S(=O)(NCCO)c1ccccc1-c1ccc(-c2cnc3[nH]ccc3c2)cc1] | 366 | 3'-Fluoro-N-(2-hydroxyethyl)-4'-(1H-pyrrolo[2,3-b]pyridin-5-yl)biphenyl-2-sulfonamide |
| 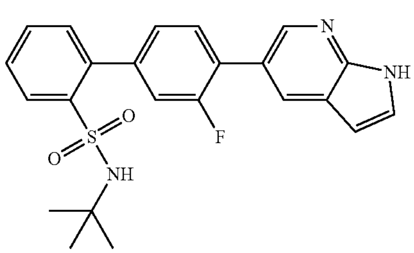 [SMILES: CC(C)(C)NS(=O)(=O)c1ccccc1-c1ccc(-c2cnc3[nH]ccc3c2)c(F)c1] | 367 | N-tert-Butyl-3'-fluoro-4'-(1H-pyrrolo[2,3-b]pyridin-5-yl)biphenyl-2-sulfonamide |
| 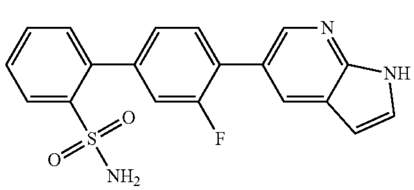 [SMILES: NS(=O)(=O)c1ccccc1-c1ccc(-c2cnc3[nH]ccc3c2)c(F)c1] | 368 | 3'-Fluoro-4'-(1H-pyrrolo[2,3-b]pyridin-5-yl)biphenyl-2-sulfonamide |

TABLE 3-continued

| STRUCTURE | COMPOUND # | NAME |
|---|---|---|
| 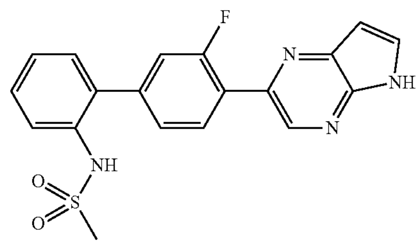 [SMILES: CS(=O)(=O)Nc1ccccc1-c1ccc(-c2cnc3[nH]ccc3n2)c(F)c1] | 369 | N-[3'-Fluoro-4'-(5H-pyrrolo[2,3-b]pyrazin-2-yl)biphenyl-2-yl]methanesulfonamide |
| 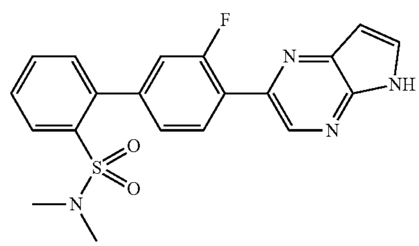 [SMILES: CN(C)S(=O)(=O)c1ccccc1-c1ccc(-c2cnc3[nH]ccc3n2)c(F)c1] | 370 | 3'-Fluoro-N,N-dimethyl-4'-(5H-pyrrolo[2,3-b]pyrazin-2-yl)biphenyl-2-sulfonamide |
| 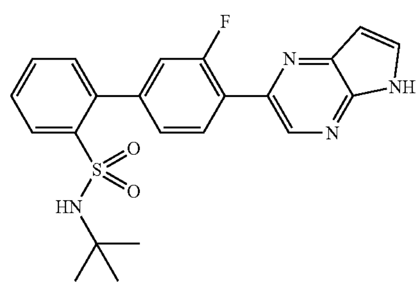 [SMILES: CC(C)(C)NS(=O)(=O)c1ccccc1-c1ccc(-c2cnc3[nH]ccc3n2)c(F)c1] | 371 | N-tert-Butyl-3'-fluoro-4'-(5H-pyrrolo[2,3-b]pyrazin-2-yl)biphenyl-2-sulfonamide |
| 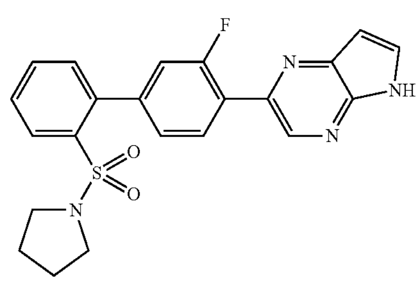 [SMILES: O=S(=O)(c1ccccc1-c1ccc(-c2cnc3[nH]ccc3n2)c(F)c1)N1CCCC1] | 372 | 2-[3-Fluoro-2'-(pyrrolidin-1-ylsulfonyl)biphenyl-4-yl]-5H-pyrrolo[2,3-b]pyrazine |
| 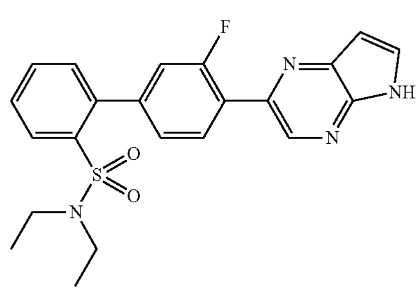 [SMILES: CCN(CC)S(=O)(=O)c1ccccc1-c1ccc(-c2cnc3[nH]ccc3n2)c(F)c1] | 373 | N-Diethyl-3'-fluoro-4'-(5H-pyrrolo[2,3-b]pyrazin-2-yl)biphenyl-2-sulfonamide |

TABLE 3-continued

| STRUCTURE | COMPOUND # | NAME |
|---|---|---|
| 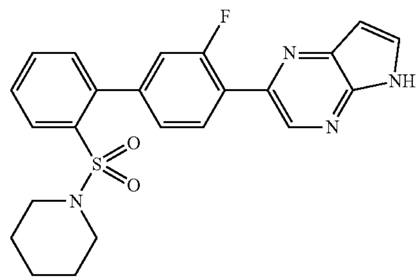 [SMILES: O=S(=O)(c1ccccc1-c1ccc(-c2cnc3[nH]ccc3n2)c(F)c1)N1CCCCC1] | 374 | 2-[3-Fluoro-2'-(piperidin-1-ylsulfonyl)biphenyl-4-yl]-5H-pyrrolo[2,3-b]pyrazine |
| 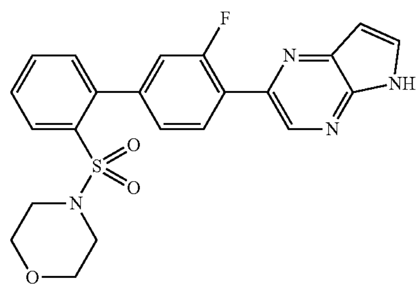 [SMILES: O=S(=O)(c1ccccc1-c1ccc(-c2cnc3[nH]ccc3n2)c(F)c1)N1CCOCC1] | 375 | 2-[3.-Fluoro-2'-(morpholin-4-ylsulfonyl)biphenyl-4-yl]-5H-pyrrolo[2,3-b]pyrazine |
| 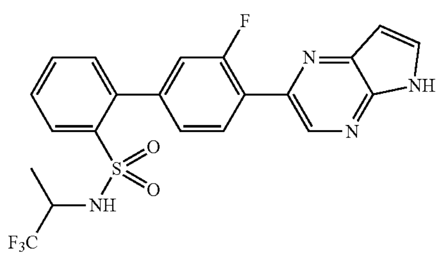 [SMILES: CC(NS(=O)(=O)c1ccccc1-c1ccc(-c2cnc3[nH]ccc3n2)c(F)c1)C(F)(F)F] | 376 | 3'-Fluoro-4'-(5H-pyrrolo[2,3-b]pyrazin-2-yl)N-N-(2,2,2-trifluoro-1-methylethyl)biphenyl-2-sulfonamide |
| 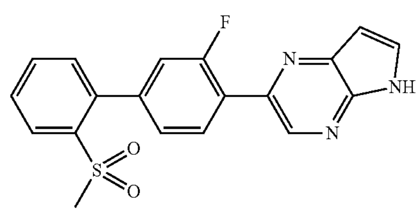 [SMILES: CS(=O)(=O)c1ccccc1-c1ccc(-c2cnc3[nH]ccc3n2)c(F)c1] | 377 | 2-[3-Fluoro-2'-(methylsulfonyl)biphenyl-4-yl]-5H-pyrrolo[2,3-b]pyrazine |
| 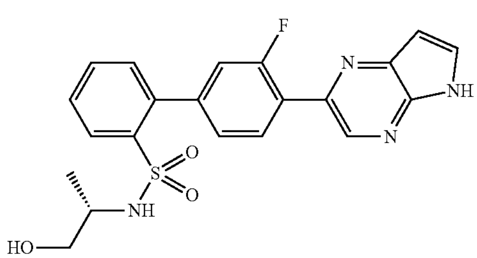 | 378 | 3'-Fluoro-N-[(1R)-2-hydroxy-1-methylethyl]-4'-(5H-pyrrolo[2,3-b]pyrazin-2-yl)biphenyl-2-sulfonamide |
| 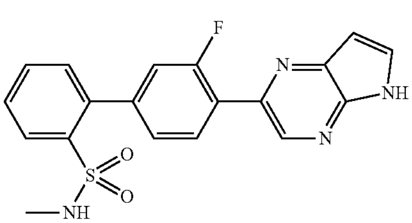 [SMILES: CNS(=O)(=O)c1ccccc1-c1ccc(-c2cnc3[nH]ccc3n2)c(F)c1] | 379 | 3'-Fluoro-N-methyl-4'-(5H-pyrrolo[2,3-b]pyrazin-2-yl)biphenyl-2-sulfonamide |

TABLE 3-continued

| STRUCTURE | COMPOUND # | NAME |
|---|---|---|
| 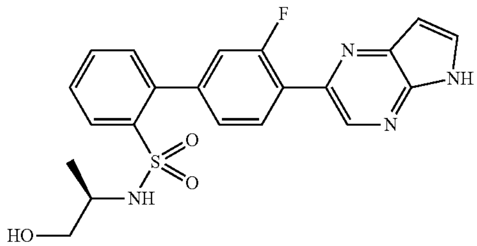 | 380 | 3'-Fluoro-N-[(1S)-2-hydroxy-1-methylethyl]4'-(5H-pyrrolo[2,3-b]pyrazin-2-yl)biphenyl-2-sulfonamide |
| 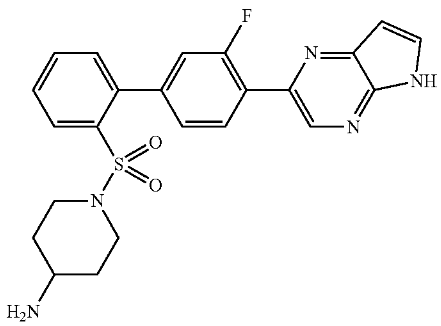 [SMILES: NC1CCN(S(=O)(=O)c2ccccc2-c2ccc(-c3cnc4[nH]ccc4n3)c(F)c2)CC1] | 381 | 1-{[3'-Fluoro-4'-(5H-pyrrolo[2,3-b]pyrazin-2-yl)biphenyl-2-yl]sulfonyl}piperidin-4-amine |
| 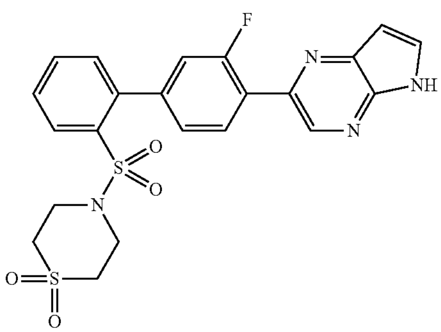 [SMILES: O=S1(=O)CCN(S(=O)(=O)c2ccccc2-c2ccc(-c3cnc4[nH]ccc4n3)c(F)c2)CC1] | 382 | 2-{2'-[(1,1-Dioxidothiomorpholin-4-yl)sulfonyl]-3-fluorobiphenyl-4-yl}-5H-pyrrolo[2,3-b]pyrazine |
| 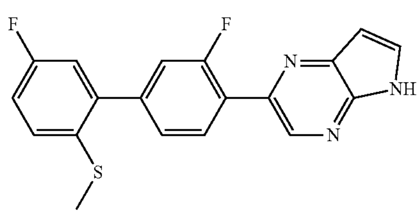 [SMILES: CSc1ccc(F)cc1-c1ccc(-c2cnc3[nH]ccc3n2)c(F)c1] | 383 | 2-[3,5-Difluoro-2'-(methylsulfanyl)biphenyl-4-yl]-5H-pyrrolo[2,3-b]pyrazine |
| 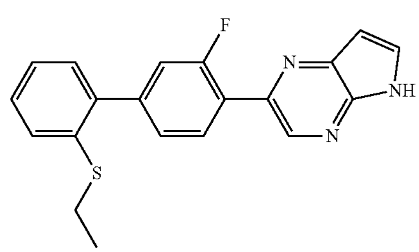 [SMILES: CCSc1ccccc1-c1ccc(-c2cnc3[nH]ccc3n2)c(F)c1] | 384 | 2-[2'-(Ethylsulfanyl)-3-fluorobiphenyl-4-yl]-5H-pyrrolo[2,3-b]pyrazine |
| 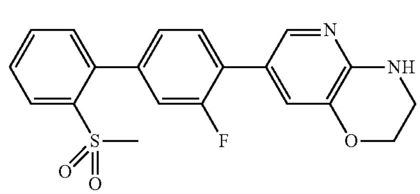 [SMILES: CS(=O)(=O)c1ccccc1-c1ccc(-c2cnc3c(c2)OCCN3)c(F)c1] | 385 | 7-[3-Fluoro-2'-(methylsulfonyl)biphenyl-4-yl]-3,4-dihydro-2H-pyrido[3,2-b][1,4]oxazine |

TABLE 3-continued

| STRUCTURE | COMPOUND # | NAME |
|---|---|---|
| 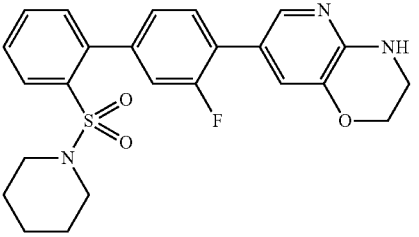 | 386 | 7-[3-Fluoro-2'-(piperidin-1-ylsulfonyl)biphenyl-4-yl]-3,4-dihydro-2H-pyrido[3,2-b][1,4]oxazine |
| 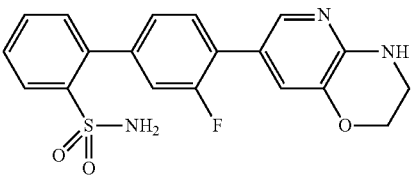 | 387 | 4'-(3,4-Dihydro-2H-pyrido[3,2-b][1,4]oxazin-7-yl)-3'-fluorobiphenyl-2-sulfonamide |
| 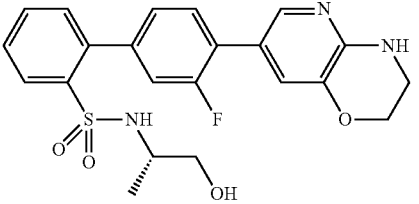 [SMILES: C[C@@H](CO)NS(=O)(=O)c1ccccc1-c1ccc(-c2cnc3c(c2)OCCN3)c(F)c1] | 388 | 4'-(3,4-Dihydro-2H-pyrido[3,2-b][1,4]oxazin-7-yl)-3'-fluoro-N-[(1S)-2-hydroxy-1-methylethyl]biphenyl-2-sulfonamide |
| 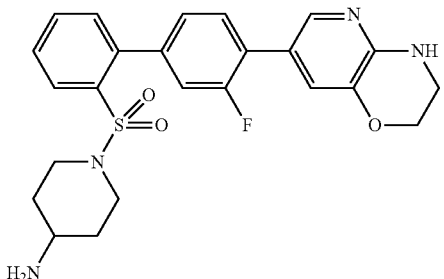 [SMILES: NC1CCN(S(=O)(=O)c2ccccc2-c2ccc(-c3cnc4c(c3)OCCN4)c(F)c2)CC1] | 389 | 1-{[4'-(3,4-Dihydro-2H-pyrido[3,2-b][1,4]oxazin-7-yl)-3'-fluorobiphenyl-2-yl]sulfonyl}piperidin-4-amine |
| 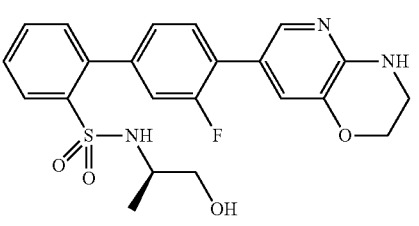 [SMILES: C[C@H](CO)NS(=O)(=O)c1ccccc1-c1ccc(-c2cnc3c(c2)OCCN3)c(F)c1] | 390 | 4'-(3,4-Dihydro-2H-pyrido[3,2-b][1,4]oxazin-7-yl)-3'-fluoro-N-[(1R)-2-hydroxy-1-methylethyl]biphenyl-2-sulfonamide |
| 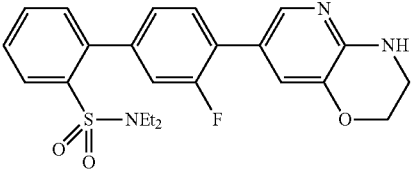 | 391 | 4'-(3,4-Dihydro-2H-pyrido[3,2-b][1,4]oxazin-7-yl)-N,N-diethyl-3'-fluorobiphenyl-2-sulfonamide |

TABLE 3-continued

| STRUCTURE | COMPOUND # | NAME |
|---|---|---|
| 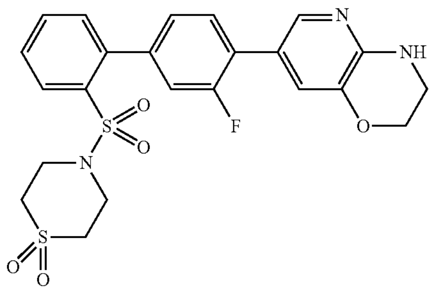 [SMILES: O=S1(=O)CCN(S(=O)(=O)c2ccccc2-c2ccc(-c3cnc4c(c3)OCCN4)c(F)c2)CC1] | 392 | 7-{2'-[(1,1-Dioxidothiomorpholin-4-yl)sulfonyl]-3-fluorobiphenyl-4-yl}-3,4-dihydro-2H-pyrido[3,2-b][1,4]oxazine |
| 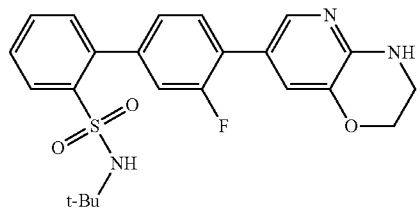 [SMILES: CC(C)(C)NS(=O)(=O)c1ccccc1-c1ccc(-c2cnc3c(c2)OCCN3)c(F)c1] | 393 | N-tert-Butyl-4'-(3,4-dihydro-2H-pyrido[3,2-b][1,4]oxazin-7-yl)-3'-fluorobiphenyl-2-sulfonamide |
| 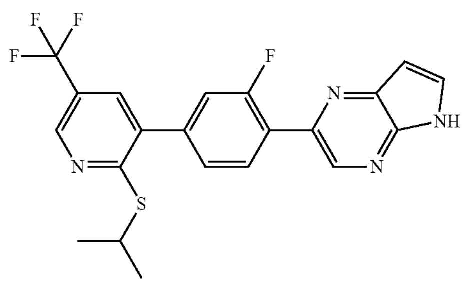 [SMILES: CC(C)Sc1ncc(C(F)(F)F)cc1-c1ccc(-c2cnc3[nH]ccc3n2)c(F)c1] | 394 | 2-(2-Fluoro-4-{2-[(1-methylethyl)sulfanyl]-5-(trifluoromethyl)pyridin-3-yl}phenyl)-5H-pyrrolo[2,3-b]pyrazine |
| 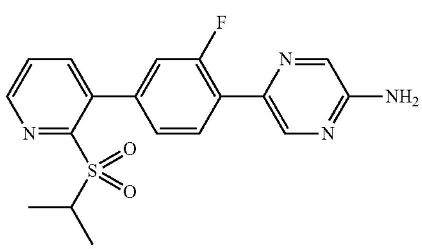 [SMILES: CC(C)S(=O)(=O)c1ncccc1-c1ccc(-c2cnc(N)cn2)c(F)c1] | 395 | 5-(2-Fluoro-4-{2-[(1-methylethyl)sulfonyl]pyridin-3-yl}phenyl)pyrazin-2-amine |
| 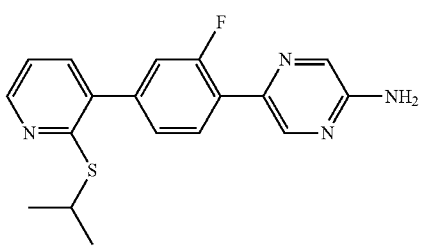 [SMILES: CC(C)Sc1ncccc1-c1ccc(-c2cnc(N)cn2)c(F)c1] | 396 | 5-(2-Fluoro-4-{2-[(1-methylethyl)sulfanyl]pyridin-3-yl}phenyl)pyrazin-2-amine |
| 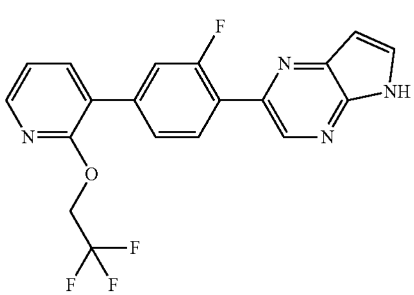 [SMILES: Fc1cc(-c2cccnc2OCC(F)(F)F)ccc1-c1cnc2[nH]ccc2n1] | 397 | 2-{2-Fluoro-4-[2-(2,2,2-trifluoroethoxy)pyridin-3-yl]phenyl}-5H-pyrrolo[2,3-b]pyrazine |

TABLE 3-continued

| STRUCTURE | COMPOUND # | NAME |
|---|---|---|
| 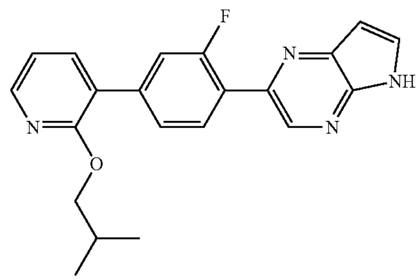 [SMILES: CC(C)COc1ncccc1-c1ccc(-c2cnc3[nH]ccc3n2)c(F)c1] | 398 | 2-{2-Fluoro-4-[2-(2-methylpropoxy)pyridin-3-yl]phenyl)-5H-pyrrolo[2,3-b]pyrazine |
| 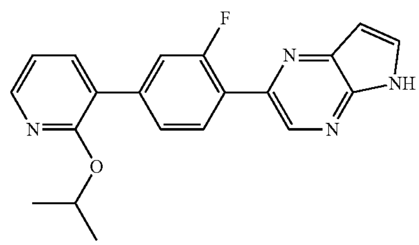 [SMILES: CC(C)Oc1ncccc1-c1ccc(-c2cnc3[nH]ccc3n2)c(F)c1] | 399 | 2-{2-Fluoro-4-[2-(1-methylethoxy)pyridin-3-yl]phenyl}-5H-pyrrolo[2,3-b]pyrazine |
| 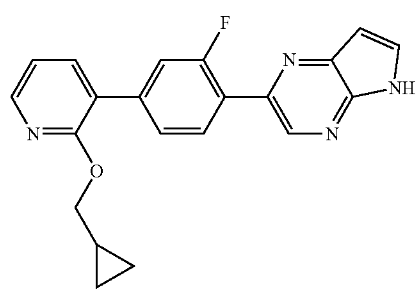 [SMILES: Fc1cc(-c2cccnc2OCC2CC2)ccc1-c1cnc2[nH]ccc2n1] | 400 | 2-{4-[2-(Cyclopropylmethoxy)pyridin-3-yl]-2-fluorophenyl}-5H-pyrrolo[2,3-b]pyrazine |
| 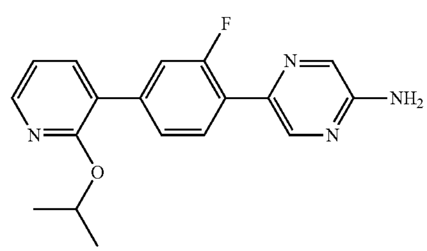 [SMILES: CC(C)Oc1ncccc1-c1ccc(-c2cnc(N)cn2)c(F)c1] | 401 | 5-{2-Fluoro-4-[2-(1-methylethoxy)pyridin-3-yl]phenyl}pyrazin-2-amine |
| 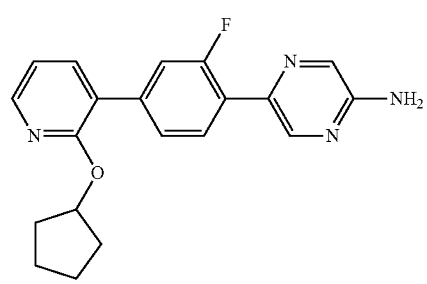 [SMILES: Nc1cnc(-c2ccc(-c3cccnc3OC3CCCC3)cc2F)cn1] | 402 | 5-{4-[2-(Cyclopentyloxy)pyridin-3-yl]-2-fluorophenyl}pyrazin-2-amine |

TABLE 3-continued
| STRUCTURE | COMPOUND # | NAME |
|---|---|---|
| 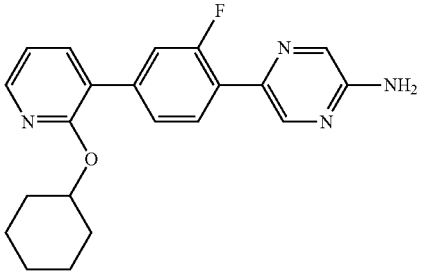 [SMILES: Nc1cnc(-c2ccc(-c3cccnc3OC3CCCCC3)cc2F)cn1] | 403 | 5-{4-[2-(Cyclohexyloxy)pyridin-3-yl]-2-fluorophenyl}pyrazin-2-amine |
| 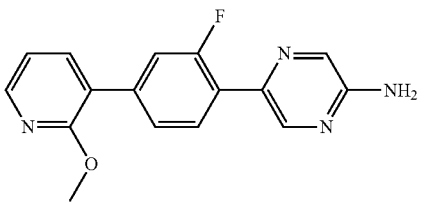 [SMILES: COc1ncccc1-c1ccc(-c2cnc(N)cn2)c(F)c1] | 404 | 5-[2-Fluoro-4-(2-methoxypyridin-3-yl)phenyl]pyrazin-2-amine |
| 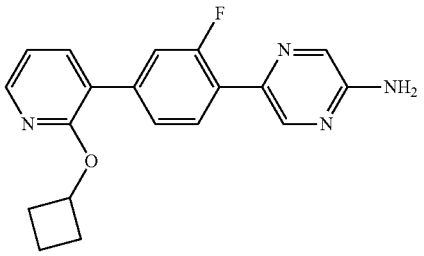 [SMILES: Nc1cnc(-c2ccc(-c3cccnc3OC3CCC3)cc2F)cn1] | 405 | 5-{4-[2-(Cyclobutyloxy)pyridin-3-yl]-2-fluorophenyl}pyrazin-2-amine |
| 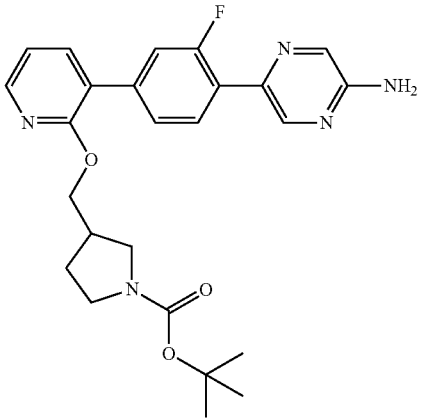 [SMILES: CC(C)(C)OC(=O)N1CCC(COc2ncccc2-c2ccc(-c3cnc(N)cn3)c(F)c2)C1] | 406 | tert-Butyl 3-[({3-[4-(5-aminopyrazin-2-yl)-3-fluorophenyl]pyridin-2-yl}oxy)methyl]pyrrolidine-1-carboxylate |
| 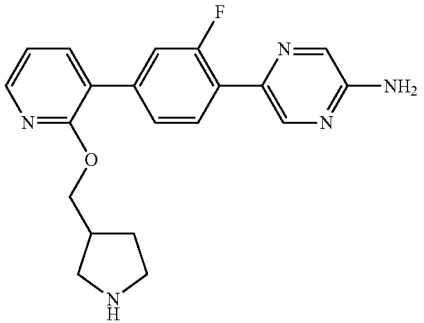 [SMILES: Nc1cnc(-c2ccc(-c3cccnc3OCC3CCNC3)cc2F)cn1] | 407 | 5-{2-Fluoro-4-[2-(pyrrolidin-3'-ylmethoxy)pyridin-3-yl]phenyl}pyrazin-2-amine |

TABLE 3-continued

| STRUCTURE | COMPOUND # | NAME |
|---|---|---|
| 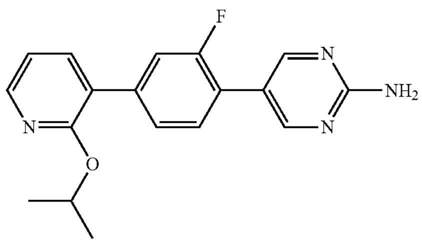 [SMILES: CC(C)Oc1ncccc1-c1ccc(-c2cnc(N)nc2)c(F)c1] | 408 | 5-{2-Fluoro-4-[2-(1-methylethoxy)pyridin-3-yl]phenyl}pyrimidin-2-amine |
| 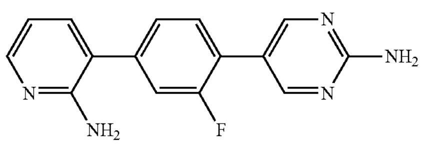 [SMILES: Nc1ncc(-c2ccc(-c3cccnc3N)cc2F)cn1] | 409 | 5-[4-(2-Aminopyridin-3-yl)-2-fluorophenyl]pyrimidin-2-amine |
| 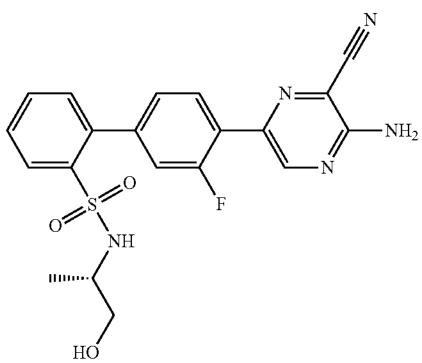 [SMILES: C[C@@H](CO)NS(=O)(=O)c1ccccc1-c1ccc(-c2cnc(N)c(C#N)n2)c(F)c1] | 410 | 4'-(5-amino-6-cyanopyrazin-2-yl)-3'-fluoro-N-[(1R)-2-hydroxy-1-methylethyl]piphenyl-2-sulfonamide |
| 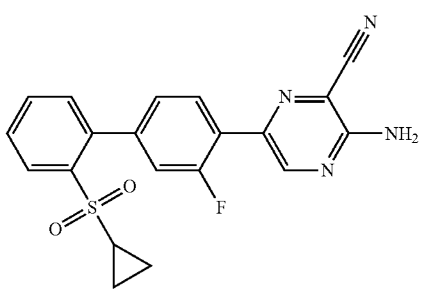 [SMILES: N#Cc1nc(-c2ccc(-c3ccccc3S(=O)(=O)C3CC3)cc2F)cnc1N] | 411 | 3-Amino-6-[2'-(cyclopropylsulfonyl)-3-fluorobiphenyl-4-yl]pyrazine-2-carbonitrile |
| 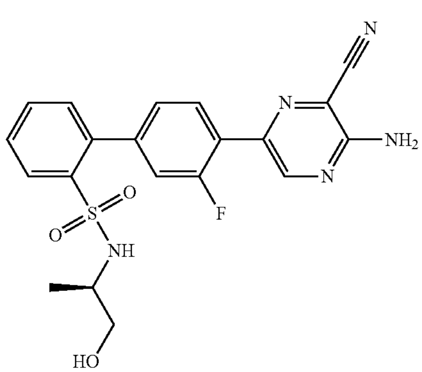 [SMILES: C[C@H](CO)NS(=O)(=O)c1ccccc1-c1ccc(-c2cnc(N)c(C#N)n2)c(F)c1] | 412 | 4'-(5-Amino-6-cyanopyrazin-2-yl)-3'-fluoro-N-[(1S)-2-hydroxy-1-methylethyl]biphenyl-2-sulfonamide |

TABLE 3-continued

| STRUCTURE | COMPOUND # | NAME |
|---|---|---|
| 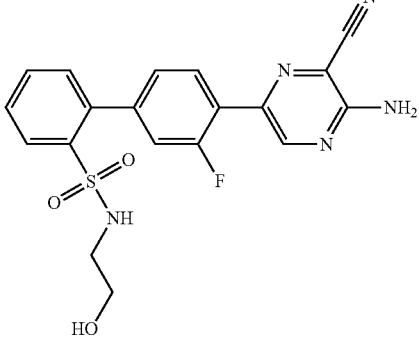 | 413 | 4'-(5-Amino-6-cyanopyrazin-2-yl)-3'-fluoro-N-(2-hydroxyethyl)biphenyl-2-sulfonamide |
| 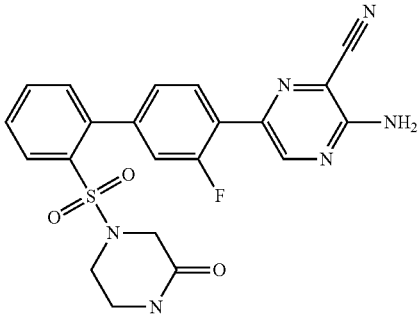 [SMILES: N#Cc1nc(-c2ccc(-c3ccccc3S(=O)(=O)N3CCNC(=O)C3)cc2F)cnc1N] | 414 | 3-Amino-6-{3-fluoro-2'-[(3-oxopiperazin-1-yl)sulfonyl]biphenyl-4-yl}pyrazine-2-carbontrile |
| 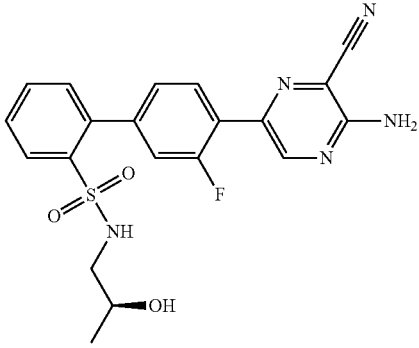 [SMILES: C[C@H](O)CNS(=O)(=O)c1ccccc1-c1ccc(-c2cnc(N)c(C#N)n2)c(F)c1] | 415 | 4'-(5-Amine-6-cyanopyrazin-2-yl)-3'-fluoro-N-[(R)-2-hydroxypropyl]biphenyl-2-sulfonamide |
| 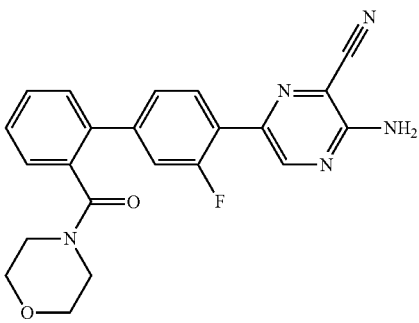 [SMILES: N#Cc1nc(-c2ccc(-c3ccccc3C(=O)N3CCOCC3)cc2F)cnc1N] | 416 | 3-Amino-6-[3-fluoro-2'-(morpholin-4-ylcarbonyl)biphenyl-4-yl]pyrazine-2-carbonitrile |
| 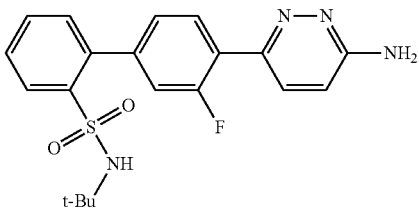 [SMILES: CC(C)(C)NS(=O)(=O)c1ccccc1-c1ccc(-c2ccc(N)nn2)c(F)c1] | 417 | 4'-(6-Aminopyridazin-3-yl)-N-tert-butyl-3'-fluorobiphenyl-2-sulfonamide |

TABLE 3-continued

| STRUCTURE | COMPOUND # | NAME |
|---|---|---|
| 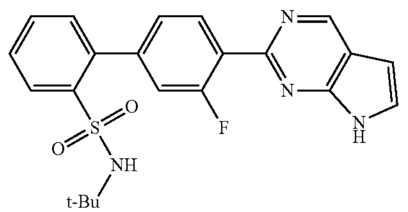 [SMILES: CC(C)(C)NS(=O)(=O)c1ccccc1-c1ccc(-c2ncc3cc[nH]c3n2)c(F)c1] | 418 | N-tert-Butyl-3'-fluoro-4'-(7H-pyrrolo[2,3-d]pyrimidin-2-yl)biphenyl-2-sulfonamide |
| 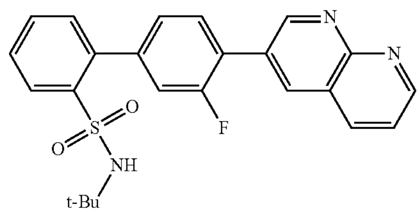 [SMILES: CC(C)(C)NS(=O)(=O)c1ccccc1-c1ccc(-c2cnc3ncccc3c2)c(F)c1] | 419 | N-tert-Butyl-3'-fluoro-4'-(1,8-naphthyridin-3-yl)biphenyl-2-sulfonamide |
| 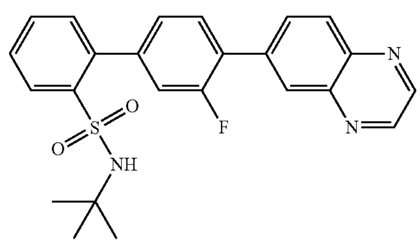 [SMILES: CC(C)(C)NS(=O)(=O)c1ccccc1-c1ccc(-c2ccc3nccnc3c2)c(F)c1] | 420 | N-tert-Butyl-3'-fluoro-4'-quinoxalin-6-ylbiphenyl-2-sulfonamide |
| 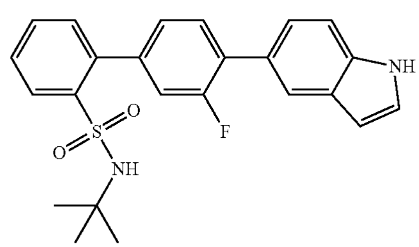 | 421 | N-tert-Butyl-3'-fluoro-4'-(1H-indol-5-yl)biphenyl-2-sulfonamide |
| 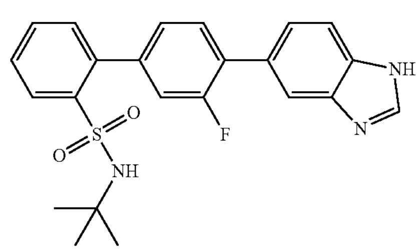 [SMILES: CC(C)(C)NS(=O)(=O)c1ccccc1-c1ccc(-c2ccc3[nH]ccc3c2)c(F)c1] | 422 | 4'-(1H-Benzimidazol-5-yl)-N-tert-butyl-3'-fluorobiphenyl-2-sulfonamide |
| 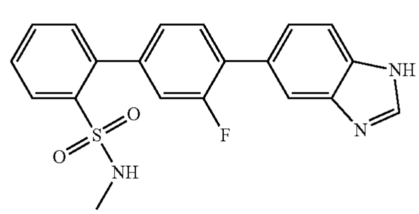 [SMILES: CNS(=O)(=O)c1ccccc1-c1ccc(-c2ccc3[nH]cnc3c2)c(F)c1] | 423 | 4'-1H-Benzimidazol-5-yl)-3'-fluoro-N-methylbiphenyl-2-sulfonamide |

TABLE 3-continued

| STRUCTURE | COMPOUND # | NAME |
|---|---|---|
| 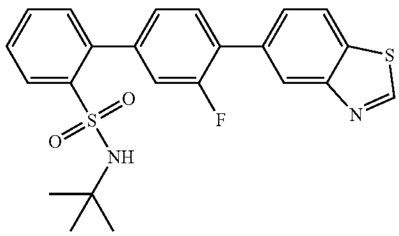 [SMILES: CC(C)(C)NS(=O)(=O)c1ccccc1-c1ccc(-c2ccc3scnc3c2)c(F)c1] | 424 | 4'-(1,3-Benzothiazol-5-yl)-N-tert-butyl-3'-fluorobiphenyl-2-sulfonamide |
| 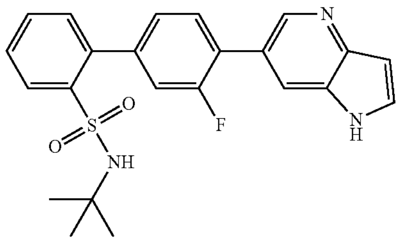 [SMILES: CC(C)(C)NS(=O)(=O)c1ccccc1-c1ccc(-c2cnc3cc[nH]c3c2)c(F)c1] | 425 | N-tert-Butyl-3'-fluoro-4'-(1H-pyrrolo[3,2-b]pyridin-6-yl)biphenyl-2-sulfonamide |
| 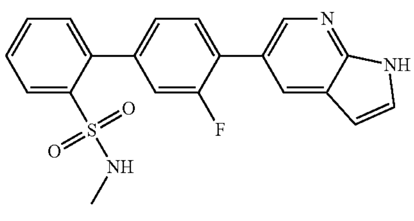 [SMILES: CNS(=O)(=O)c1ccccc1-c1ccc(-c2cnc3[nH]ccc3c2)c(F)c1] | 426 | 3'-Fluoro-N-methyl-4'-(1H-pyrrolo[2,3-b]pyridin-5-yl)biphenyl-2-sulfonamide |
| 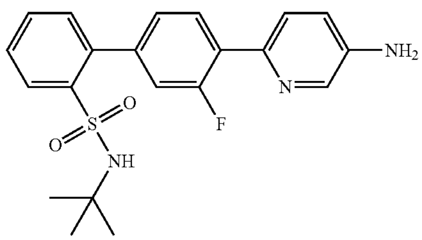 [SMILES: CC(C)(C)NS(=O)(=O)c1ccccc1-c1ccc(-c2ccc(N)cn2)c(F)c1] | 427 | 4'-(5-Aminepyridin-2-yl)-N-tert-butyl-3'-fluoro-biphenyl-2-sulfonamide |
| 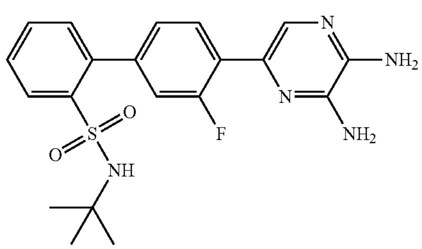 | 428 | N-tert-Butyl-4'-(5,6-diaminopyrazin-2-yl)-3'-fluorobiphenyl-2-sulfonamide |
| 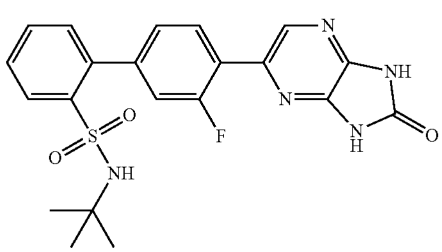 [SMILES: CC(C)(C)NS(=O)(=O)c1ccccc1-c1ccc(-c2cnc3[nH]c(=O)[nH]c3n2)c(F)c1] | 429 | N-tert-Butyl-3'-fluoro-4'-(2-oxo-2,3-dihydro-1H-imidazo[4,5-b]pyrazin-5-yl)biphenyl-2-sulfonamide |

TABLE 3-continued

| STRUCTURE | COMPOUND # | NAME |
|---|---|---|
| 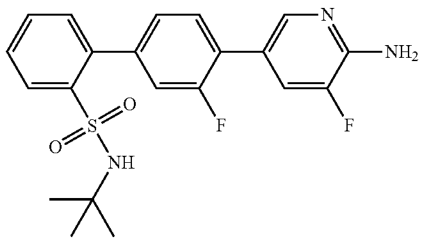 | 430 | 4'-(6-Amino-5-fluoropyridin-3-yl)-N-tert-butyl-3'-fluorobiphenyl-2-sulfonamide |
| 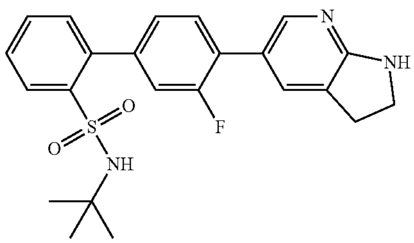 [SMILES: CC(C)(C)NS(=O)(=O)c1ccccc1-c1ccc(-c2cnc3c(c2)CCN3)c(F)c1] | 431 | N-tert-Butyl-4'-(2,3-dihydro-1H-pyrrolo[2,3-b]pyridin-5-yl)-3'-fluorobiphenyl-2-sulfonamide |
| 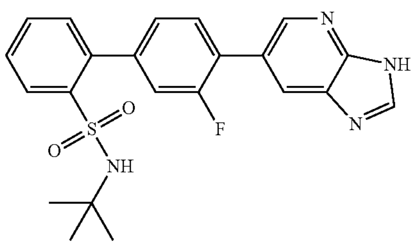 [SMILES: CC(C)(C)NS(=O)(=O)c1ccccc1-c1ccc(-c2cnc3[nH]cnc3c2)c(F)c1] | 432 | N-tert-Butyl-3'-fluoro-4'-(3H-imidazo[4,5-b]pyridin-6-yl)biphenyl-2-sulfonamide |
| 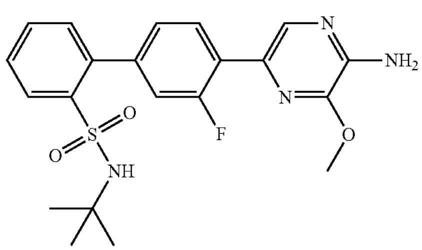 [SMILES: COc1nc(-c2ccc(-c3ccccc3S(=O)(=O)NC(C)(C)C)cc2F)cnc1N] | 433 | 4'-(5-Amino-6-methoxypyrazin-2-yl)-N-tert-butyl-3'-fluorobiphenyl-2-sulfonamide |
| 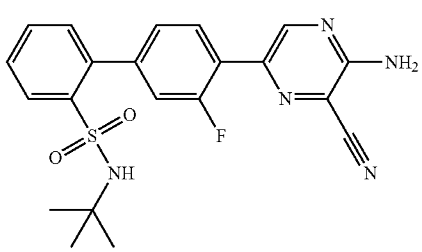 [SMILES: CC(C)(C)NS(=O)(=O)c1ccccc1-c1ccc(-c2cnc(N)c(C#N)n2)c(F)c1] | 434 | 4'-(5-Amino-6-cyanopyrazin-2-yl)-N-tert-butyl-3'-fluorobiphenyl-2-sulfonamide |
| 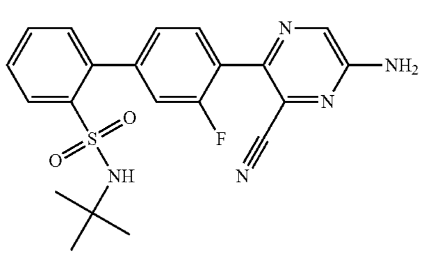 | 435 | 4'-(5-Amino-3-cyanopyrazin-2-yl)-N-tert-butyl-3'-fluorobiphenyl-2-sulfonamide |

TABLE 3-continued

| STRUCTURE | COMPOUND # | NAME |
|---|---|---|
| 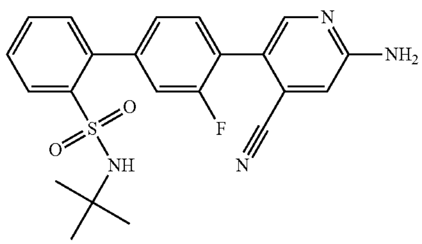 | 436 | 4'-(6-Amino-4-cyanopyridin-3-yl)-N-tert-butyl-3'-fluorobiphenyl-2-sulfonamide |
| 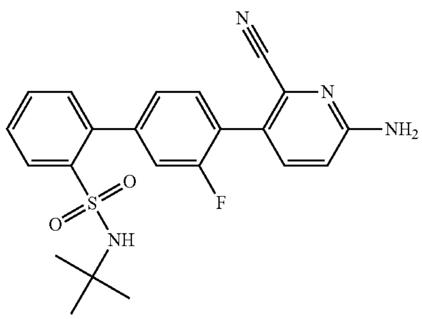 [SMILES: CC(C)(C)NS(=O)(=O)c1ccccc1-c1ccc(-c2ccc(N)nc2C#N)c(F)c1] | 437 | 4'-(6-amino-2-cyanopyridin-3-yl)-N-(tert-butyl)-3'-fluoro-[1,1'-biphenyl]-2-sulfonamide |
| 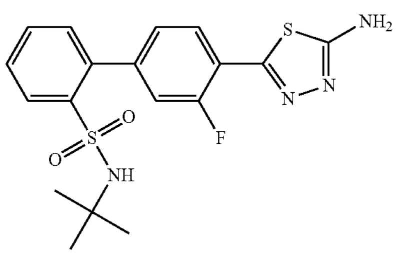 [SMILES: CC(C)(C)NS(=O)(=O)c1ccccc1-c1ccc(-c2nnc(N)s2)c(F)c1] | 438 | 4'-(5-amino-1,3,4-thiadiazol-2-yl)-N-(tert-butyl)-3'-fluoro-[1,1'-biphenyl]-2-sulfonamide |
| 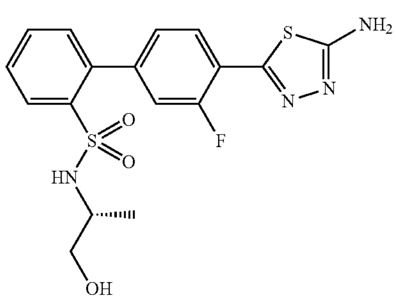 [SMILES: C[C@H](CO)NS(=O)(=O)c1ccccc1-c1ccc(-c2nnc(N)s2)c(F)c1] | 439 | (R)-4'-(5-amino-1,3,4-thiadiazol-2-yl)-3-fluoro-N-(1-hydroxypropan-2-yl)-[1,1'-biphenyl]-2-sulfonamide |
| 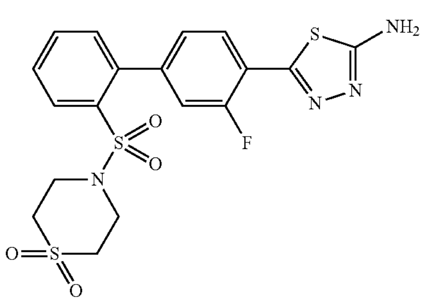 [SMILES: Nc1nnc(-c2ccc(-c3ccccc3S(=O)(=O)N3CCS(=O)(=O)CC3)cc2F)s1] | 440 | 4-((4'-(5-amino-1,3,4-thiadiazol-2-yl)-3'-fluoro-[1,1'-biphenyl]-2-yl)sulfonyl)thiomorpholine 1,1-dioxide |

TABLE 3-continued

| STRUCTURE | COMPOUND # | NAME |
|---|---|---|
| 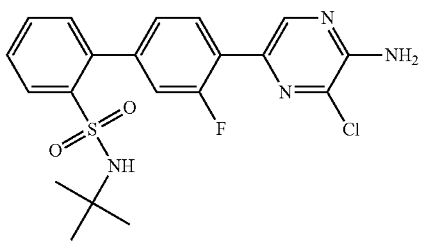 | 441 | 4'-(5-Amino-6-chloropyrazin-2-yl)-N-tert-butyl-3'-fluorobiphenyl-2-sulfonamide |
| 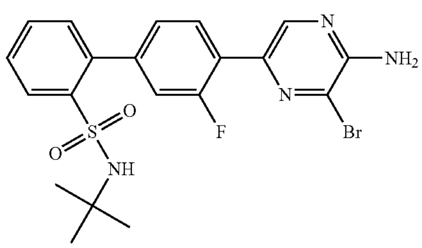 [SMILES: CC(C)(C)NS(=O)(=O)c1ccccc1-c1ccc(-c2cnc(N)c(Cl)n2)c(F)c1] | 442 | 4'-(5-Amino-6-bromopyrazin-2-yl)-N-tert-butyl-3'-fluorobiphenyl-2-sulfonamide |
| 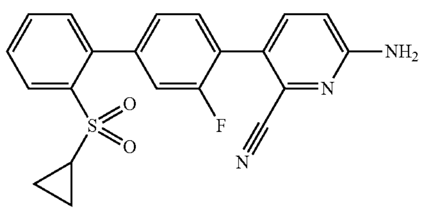 [SMILES: N#Cc1nc(N)ccc1-c1ccc(-c2ccccc2S(=O)(=O)C2CC2)cc1F] | 443 | 6-amino-3-(2'-(cyclopropylsulfonyl)-3-fluoro-[1,1'-biphenyl]-4-yl)picolinonitrile |
| 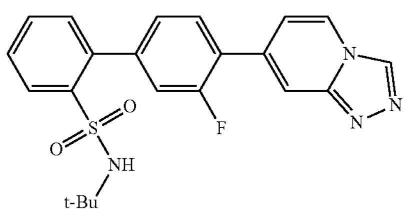 [SMILES: CC(C)(C)NS(=O)(=O)c1ccccc1-c1ccc(-c2ccn3cnnc3c2)c(F)c1] | 444 | N-tert-Butyl-3'-fluoro-4'-[1,2,4]triazolo[4,3-a]pyridin-7-ylbiphenyl-2-sulfonamide |
| 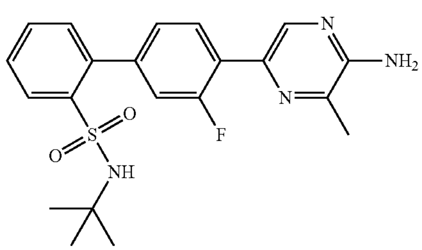 [SMILES: Cc1nc(-c2ccc(-c3ccccc3S(=O)(=O)NC(C)(C)C)cc2F)cnc1N] | 445 | 4'-(5-Amino-6-methylpyrazin-2-yl)-N-tert-butyl-3'-fluorobiphenyl-2-sulfonamide |
| 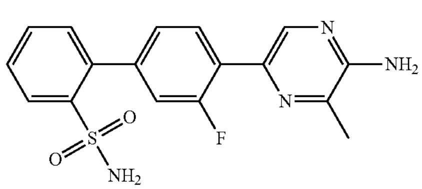 [SMILES: Cc1nc(-c2ccc(-c3ccccc3S(N)(=O)=O)cc2F)cnc1N] | 446 | 4'-(5-Amino-6-methylpyrazin-2-yl)-3'-fluorobiphenyl-2-sulfonamide |

TABLE 3-continued

| STRUCTURE | COMPOUND # | NAME |
|---|---|---|
| 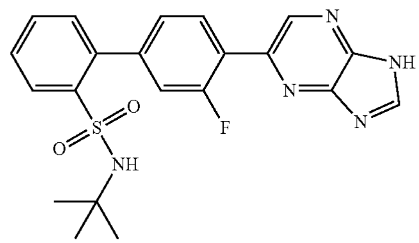 [SMILES: CC(C)(C)NS(=O)(=O)c1ccccc1-c1ccc(-c2cnc3[nH]cnc3n2)c(F)c1] | 447 | N-tert-Butyl-3'-fluoro-4'-(1H-imidazo[4,5-b]pyrazin-5-yl)biphenyl-2-sulfonamide |
| 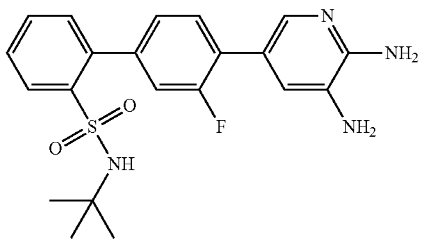 [SMILES: CC(C)(C)NS(=O)(=O)c1ccccc1-c1ccc(-c2cnc(N)c(N)c2)c(F)c1] | 448 | N-tert-Butyl-4'-(5,6-diaminopyridin-3-yl)-3'-fluorobiphenyl-2-sulfonamide |
| 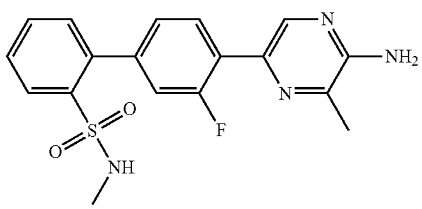 [SMILES: CNS(=O)(=O)c1ccccc1-c1ccc(-c2cnc(N)c(C)n2)c(F)c1] | 449 | 4'-(5-Amino-6-methylpyrazin-2-yl)-3'-fluoro-N-methylbiphenyl-2-sulfonamide |
| 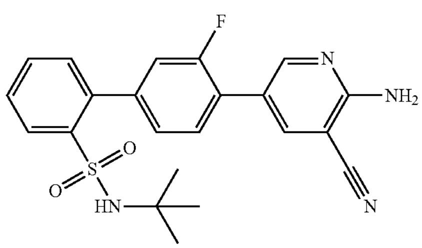 [SMILES: CC(C)(C)NS(=O)(=O)c1ccccc1-c1ccc(-c2cnc(N)c(C#N)c2)c(F)c1] | 450 | 4'-(6-Amino-5-cyanopyridin-3-yl)-N-tert-butyl-3'-fluorobiphenyl-2-sulfonamide trifluoroacetic acid salt |
| 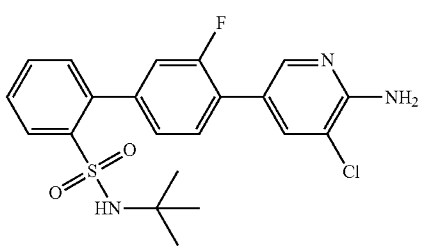 | 451 | 4'-(6-Amino-5-chloropyridin-3-yl)-N-tert-butyl-3'-fluorobiphenyl-2-sulfonamide trifluoroacetic acid salt |
| 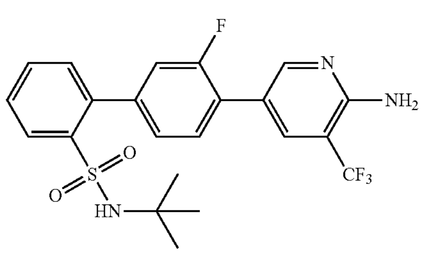 [SMILES: CC(C)(C)NS(=O)(=O)c1ccccc1-c1ccc(-c2cnc(N)c(C(F)(F)F)c2)c(F)c1] | 452 | 4'-[6-Amino-5-(trifluoromethyl)pyridin-3-yl]-N-tert-butyl-3'-fluorobiphenyl-2-sulfonamide trifluoroacetic acid salt |

TABLE 3-continued

| STRUCTURE | COMPOUND # | NAME |
|---|---|---|
| 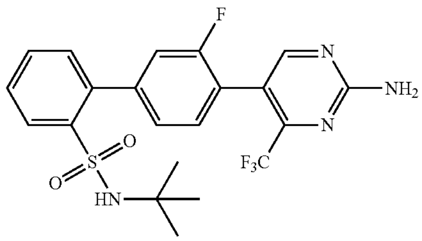 [SMILES: Cc1nc(N)ncc1-c1ccc(-c2ccccc2S(=O)(=O)NC(C)(C)C)cc1F] | 453 | 4'-[2-Amino-4-(trifluoromethyl)pyrimidin-5-yl]-N-tert-butyl-3'-fluorobiphenyl-2-sulfonamide trifluoroacetic acid salt |
| 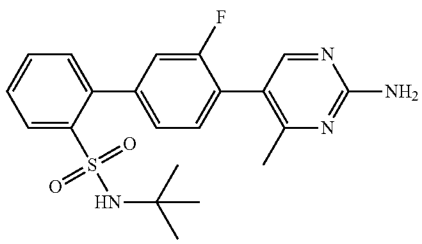 | 454 | 4'-(2-Amino-4-methylpyrimidin-5-yl)-N-tert-butyl-3'-fluorobiphenyl-2-sulfonamide trifluoroacetic acid salt |
| 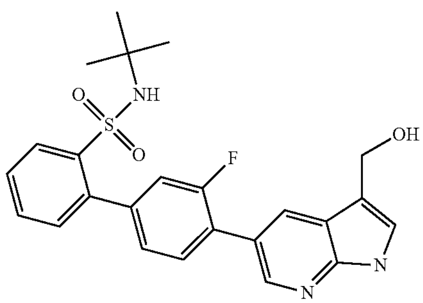 [SMILES: CC(C)(C)NS(=O)(=O)c1ccccc1-c1ccc(-c2cnc3[nH]cc(CO)c3c2)c(F)c1] | 455 | N-tert-Butyl-3'-fluoro-4'-[3-(hydroxymethyl)-1H-pyrrolo[2,3-b]pyridin-5-yl]biphenyl-2-sulfonamide |
| 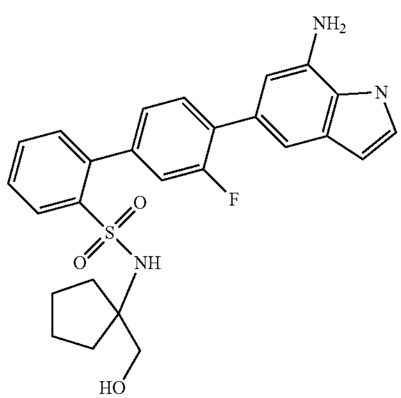 [SMILES: Nc1cc(-c2ccc(-c3ccccc3S(=O)(=O)NC3(CO)CCCC3)cc2F)cc2cc[nH]c12] | 456 | 4'-(7-Amino-1H-indol-5-yl)-3'-fluoro-N-[1-(hydroxymethyl)cyclopentyl]biphenyl-2-sulfonamide |
| 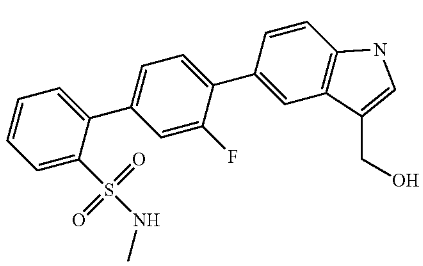 [SMILES: CNS(=O)(=O)c1ccccc1-c1ccc(-c2ccc3[nH]cc(CO)c3c2)c(F)c1] | 457 | 3'-Fluoro-4'-[3-(hydroxymethyl)-1H-pyrrolo[2,3-b]pyridin-5-yl]-N-methylbiphenyl-2-sulfonamide |

TABLE 3-continued

| STRUCTURE | COMPOUND # | NAME |
|---|---|---|
| 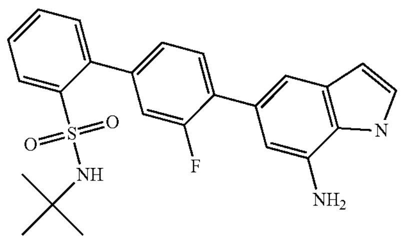 [SMILES: CC(C)(C)NS(=O)(=O)c1ccccc1-c1ccc(-c2cc(N)c3[nH]ccc3c2)c(F)c1] | 458 | 4'-(7-Amino-1H-indol-5-yl)-N-tert-butyl-3'-fluorobiphenyl-2-sulfonamide |
| 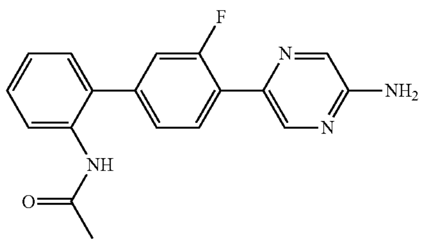 [SMILES: CC(=O)Nc1ccccc1-c1ccc(-c2cnc(N)cn2)c(F)c1] | 459 | N-[4'-(5-Aminopyrazin-2-yl)-3'-fluorobiphenyl-2-yl]acetamide |
| 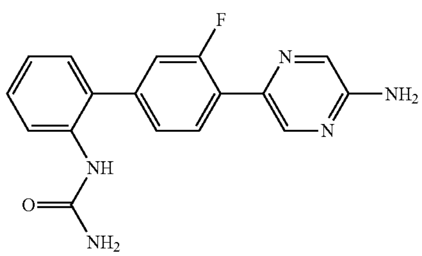 [SMILES: NC(=O)Nc1ccccc1-c1ccc(-c2cnc(N)cn2)c(F)c1] | 460 | 1-[4'-(5-Aminopyrazin-2-yl)-3'-fluorobiphenyl-2-yl]urea |
| 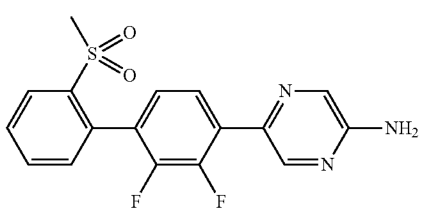 [SMILES: CS(=O)(=O)c1ccccc1-c1ccc(-c2cnc(N)cn2)c(F)c1F] | 461 | 5-[2,3-Difluoro-2'-(methylsulfonyl)biphenyl-4-yl]pyrazin-2-amine |
| 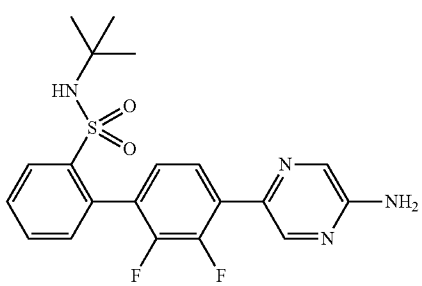 [SMILES: CC(C)(C)NS(=O)(=O)c1ccccc1-c1ccc(-c2cnc(N)cn2)c(F)c1F] | 462 | 4'-(5-Aminopyrazin-2-yl)-N-tert-butyl-2',3'-difluorobipnenyl-2-sulfonamide |
| 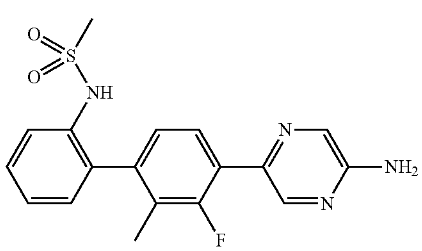 [SMILES: Cc1c(-c2ccccc2NS(C)(=O)=O)ccc(-c2cnc(N)cn2)c1F] | 463 | N-[4'-(5-Aminopyrazin-2-y)-3'-fluoro-2'-methylbiphenyl-2-yl]methanesulfonamide |

TABLE 3-continued

| STRUCTURE | COMPOUND # | NAME |
|---|---|---|
| 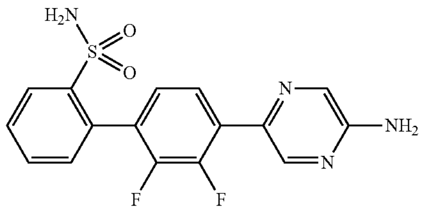 [SMILES: Nc1cnc(-c2ccc(-c3ccccc3S(N)(=O)=O)c(F)c2F)cn1] | 464 | 4'-(5-Aminopyrazin-2-yl)-2',3'-difluorobiphenyl-2-sulfonamide |
| 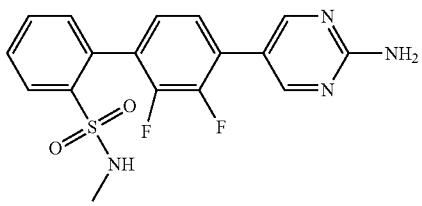 [SMILES: CNS(=O)(=O)c1ccccc1-c1ccc(-c2cnc(N)nc2)c(F)c1F] | 465 | 4'-(2-Aminopyrimidin-5-yl)-2',3'-difluoro-N-methylbiphenyl-2-sulfonamide trifluoroacetic acid salt |
| 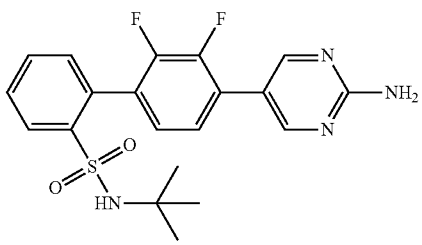 [SMILES: CC(C)(C)NS(=O)(=O)c1ccccc1-c1ccc(-c2cnc(N)nc2)c(F)c1F] | 466 | 4'-(2-Aminopyrimidin-5-yl)-N-tert-butyl-2',3'-difluorobipenyl-2-sulfonamide trifluoroacetic acid salt |
| 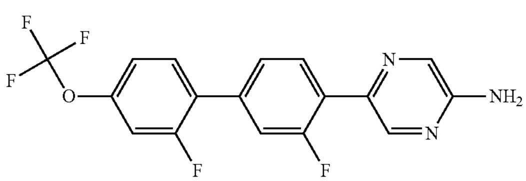 [SMILES: Nc1cnc(-c2ccc(-c3ccc(OC(F)(F)F)cc3F)cc2F)cn1] | 467 | 5-[2',3-Difluoro-4'-(trifluoromethoxy)biphenyl-4-yl]pyrazin-2-amine |
| 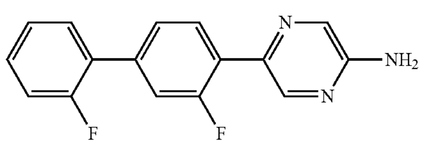 [SMILES: Nc1cnc(-c2ccc(-c3ccccc3F)cc2F)cn1] | 468 | 5-(2',3-Difluorobiphenyl-4-yl)pyrazin-2-amine |
| 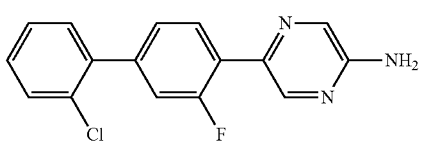 | 469 | 5-(2'-Chloro-3-fluorobiphenyl-4-yl)pyrazin-2-amine |
| 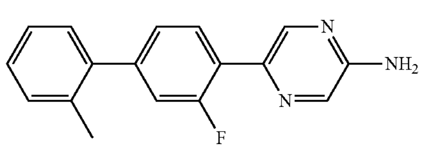 [SMILES: Cc1ccccc1-c1ccc(-c2cnc(N)cn2)c(F)c1] | 470 | 5-(3-Fluoro-2'-methylbiphenyl-4-yl)pyrazin-2-amine |
| 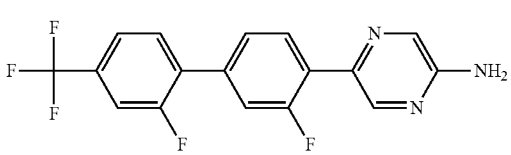 [SMILES: Nc1cnc(-c2ccc(-c3ccc(C(F)(F)F)cc3F)cc2F)cn1] | 471 | 5-[2',3-Difluoro-4'-(trifluoromethyl)biphenyl-4-yl]pyrazin-2-amine |

TABLE 3-continued

| STRUCTURE | COMPOUND # | NAME |
|---|---|---|
| 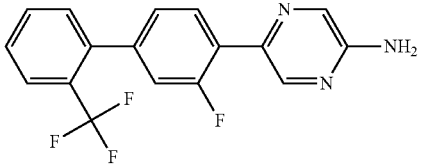 [SMILES: Nc1cnc(-c2ccc(-c3ccccc3C(F)(F)F)cc2F)cn1] | 472 | 5-[3-Fluoro-2'-(trifluoromethyl)biphenyl-4-yl]pyrazin-2-amine |
| 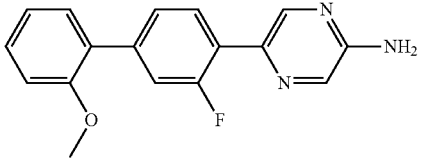 | 473 | 5-(3-Fluoro-2'-methoxybiphenyl-4-yl)pyrazin-2-amine |
| 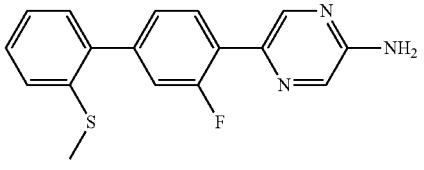 [SMILES: COc1ccccc1-c1ccc(-c2cnc(N)cn2)c(F)c1] | 474 | 5-[3-Fluoro-2'-(methylsulfanyl)biphenyl-4-yl]pyrazin-2-amine |
| 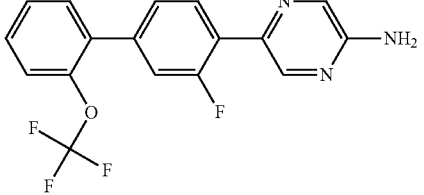 | 475 | 5-[3-Fluoro-2'-(trifluoromethoxy)biphenyl-4-yl]pyrazin-2-amine |
| 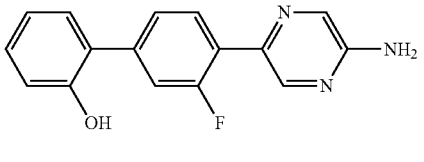 [SMILES: Nc1cnc(-c2ccc(-c3ccccc3O)cc2F)cn1] | 476 | 4'-(5-Aminopyrazin-2-yl)-3'-fluorobiphenyl-2-ol |
| 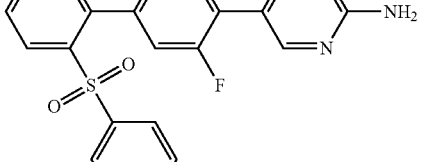 | 477 | 5-[3-Fluoro-2'-(phenylsulfonyl)biphenyl-4-yl]pyrazin-2-amine |
| 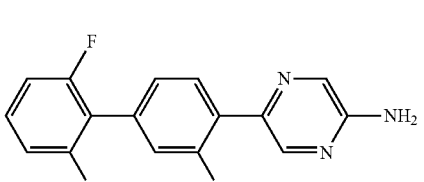 | 478 | 5-(2',3,6'-Trifluorobiphenyl-4-yl)pyrazin-2-amine |

TABLE 3-continued

| STRUCTURE | COMPOUND # | NAME |
|---|---|---|
| 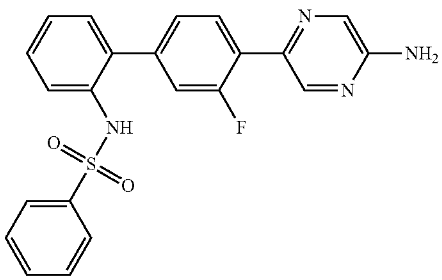 [SMILES: Nc1cnc(-c2ccc(-c3ccccc3NS(=O)(=O)c3ccccc3)cc2F)cn1] | 479 | N-[4'-(5-Aminopyrazin-2-yl)-3'-fluorobiphenyl-2-yl]benzenesulfonamide |
| 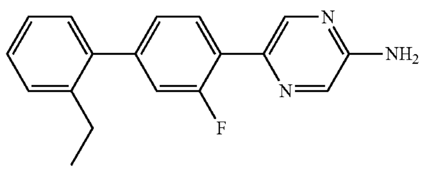 | 480 | 5-(2'-Ethyl-3-fluorobiphenyl-4-yl)pyrazin-2-amine |
| 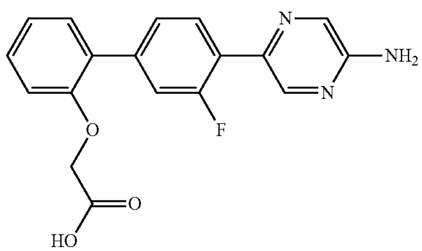 | 481 | {[4'-(5-Aminopyrazin-2-yl)-3'-fluorobiphenyl-2-yl]oxy}acetic acid |
| 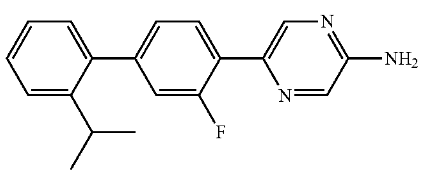 | 482 | 5-[3-Fluoro-2'-(1-methylethyl)biphenyl-4-yl]pyrazin-2-amine |
| 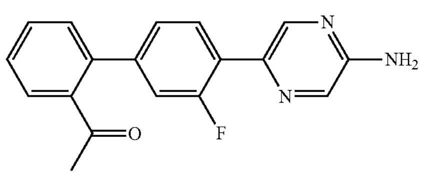 | 483 | 1-[4'-(5-Aminopyrazin-2-yl)-3'-fluorobiphenyl-2-yl]ethanone |
| 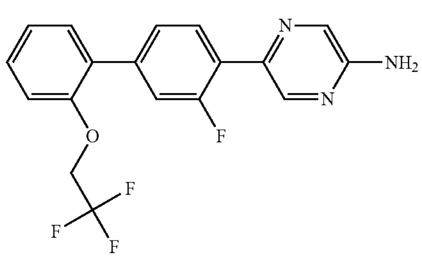 [SMILES: Nc1cnc(-c2ccc(-c3ccccc3OCC(F)(F)F)cc2F)cn1] | 484 | 5-[3-Fluoro-2'-(2,2,2-trifluoroethoxy)biphenyl-4-yl]pyrazin-2-amine |
| 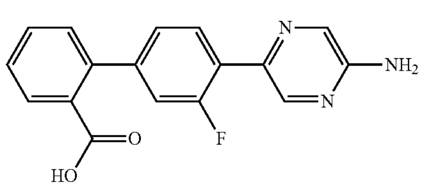 [SMILES: Nc1cnc(-c2ccc(-c3ccccc3C(=O)O)cc2F)cn1] | 485 | 4'-(5-Aminopyrazin-2-yl)-3'-fluorobiphenyl-2-carboxylic acid |

TABLE 3-continued

| STRUCTURE | COMPOUND # | NAME |
|---|---|---|
| 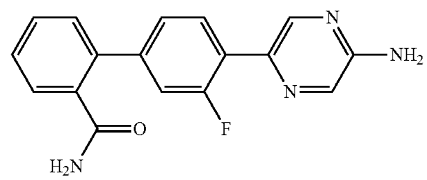 [SMILES: NC(=O)c1ccccc1-c1ccc(-c2cnc(N)cn2)c(F)c1] | 486 | 4'-(5-Aminopyrazin-2'-yl)-3'-fluorobiphenyl-2-carboxamide |
| 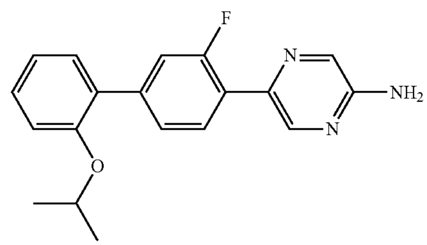 | 487 | 5-[3-Fluoro-2'-(1-methylethoxy)biphenyl-4-yl]pyrazin-2-amine |
| 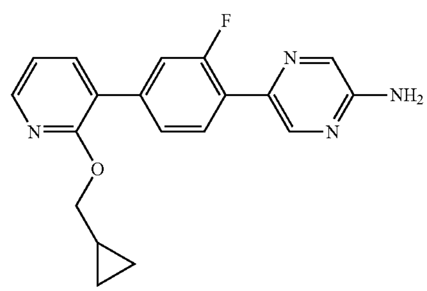 [SMILES: Nc1cnc(-c2ccc(-c3cccnc3OCC3CC3)cc2F)cn1] | 488 | 5-{4-[2-(Cyclopropylmethoxy)pyridin-3-yl]-2-fluorophenyl}pyrazin-2-amine |
| 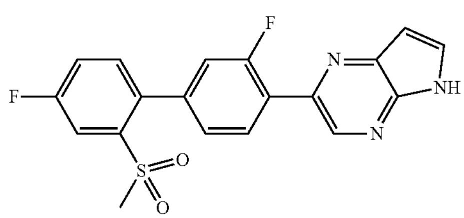 [SMILES: CS(=O)(=O)c1cc(F)ccc1-c1ccc(-c2cnc3[nH]ccc3n2)c(F)c1] | 489 | 2-[3,4'-Difluoro-2'-(methylsulfonyl)biphenyl-4-yl]-5H-pyrrolo[2,3-b]pyrazine |
| 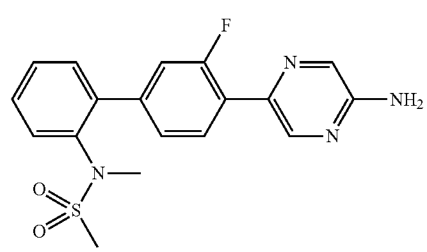 [SMILES: CN(c1ccccc1-c1ccc(-c2cnc(N)cn2)c(F)c1)S(C)(=O)=O] | 490 | N-[4'-(5-Aminopyrazin-2-yl)-3'-fluorobiphenyl-2-yl]-N-methylmethanesulfonmide |
| 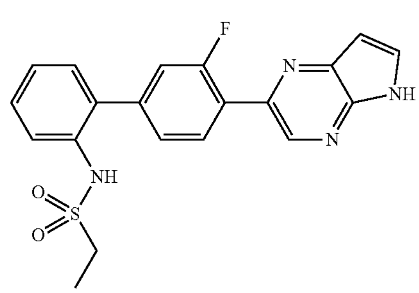 | 491 | N-[3'-Fluoro-4'-(5H-pyrrolo[2,3-b]pyrazin-2-yl)biphenyl-2-yl]ethanesulfonamide |

TABLE 3-continued

| STRUCTURE | COMPOUND # | NAME |
|---|---|---|
| 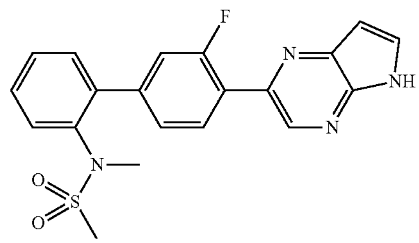 [SMILES: CN(c1ccccc1-c1ccc(-c2cnc3[nH]ccc3n2)c(F)c1)S(C)(=O)=O] | 492 | N-[3'-Fluoro-4'-(5H-pyrrolo[2,3-b]pyrazin-2-yl)biphenyl-2-yl]-N-N-methylmethanesulfonamide |
| 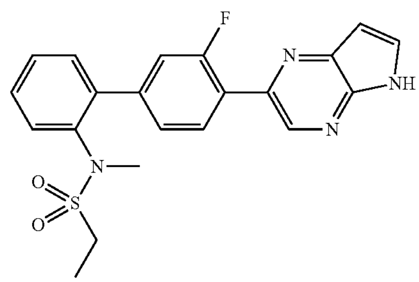 [SMILES: CCS(=O)(=O)N(C)c1ccccc1-c1ccc(-c2cnc3[nH]ccc3n2)c(F)c1] | 493 | N-[3'-Fluoro-4'-(5H-pyrrolo[2,3-b]pyrazin-2-yl)biphenyl-2-yl]-N-methylethanesulfonamide |
| 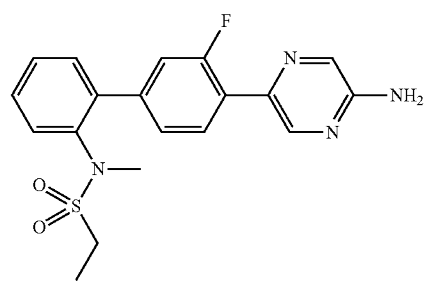 [SMILES: CCS(=O)(=O)N(C)c1ccccc1-c1ccc(-c2cnc(N)cn2)c(F)c1] | 494 | N-[4'-(5-Aminopyrazin-2-yl)-3'-fluorobiphenyl-2-yl]-N-methylethanesulfonamide |
| 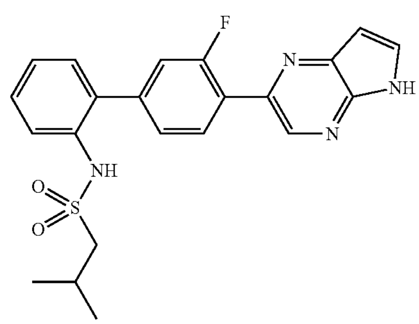 [SMILES: CC(C)CS(=O)(=O)Nc1ccccc1-c1ccc(-c2cnc3[nH]ccc3n2)c(F)c1] | 495 | N-[3'-Fluoro-4'-(5H-pyrrolo[2,3-b]pyrazin-2-yl)biphenyl-2-yl]-2-methylpropane-1-sulfonamide |
| 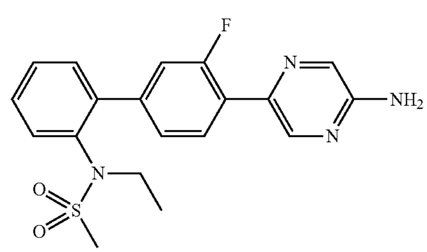 [SMILES: CCN(c1ccccc1-c1ccc(-c2cnc(N)cn2)c(F)c1)S(C)(=O)=O] | 496 | N-[4'-(5-Aminopyrazin-2-yl)-3'-fluorobiphenyl-2-yl]-N-ethylmethanesulfonamide |

TABLE 3-continued

| STRUCTURE | COMPOUND # | NAME |
|---|---|---|
| 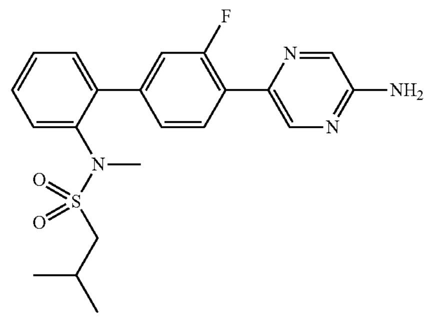 [SMILES: CC(C)CS(=O)(=O)N(C)c1ccccc1-c1ccc(-c2cnc(N)cn2)c(F)c1] | 497 | N-[4'-(5-Aminopyrazin-2-yl)-3'-fluorobiphenyl-2-yl]-N,2-dimethylpropane-1-sulfonamide |
| 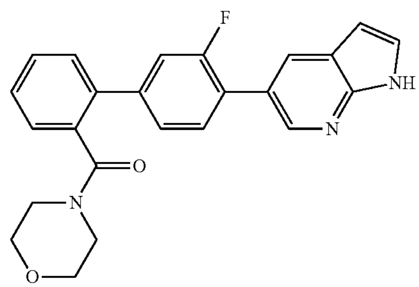 [SMILES: O=C(c1ccccc1-c1ccc(-c2cnc3[nH]ccc3c2)c(F)c1)N1CCOCC1] | 498 | 5-[3-Fluoro-2'-(morpholin-4-ylcarbonyl)biphenyl-4-yl]-1H-pyrrolo[2,3-b]pyridine |
| 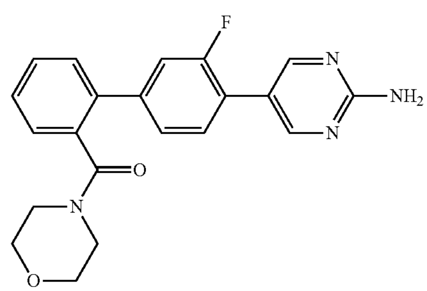 [SMILES: Nc1ncc(-c2ccc(-c3ccccc3C(=O)N3CCOCC3)cc2F)cn1] | 499 | 5-[3-Fluoro-2'-(morpholin-4-ylcarbonyl)biphenyl-4-yl]pyrimidin-2-amine |
| 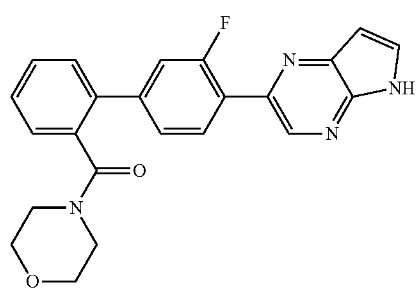 | 500 | 2-[3-Fluoro-2'-(morpholin-4-ylcarbonyl)biphenyl-4-yl]-5H-pyrrolo[2,3-b]pyrazine |
| 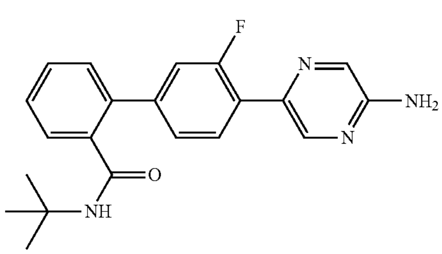 [SMILES: CC(C)(C)NC(=O)c1ccccc1-c1ccc(-c2cnc(N)cn2)c(F)c1] | 501 | 4'-(5-Aminopyrazin-2-yl)-N-tert-butyl-3'-fluorobiphenyl-2-carboxamide |

TABLE 3-continued

| STRUCTURE | COMPOUND # | NAME |
|---|---|---|
| 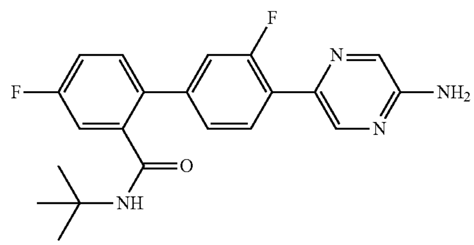 [SMILES: CC(C)(C)NC(=O)c1cc(F)ccc1-c1ccc(-c2cnc(N)cn2)c(F)c1] | 502 | 4'-(5-Aminopyrazin-2-yl)-N-tert-butyl-3',4-difluorobiphenyl-2-carboxamide |
| 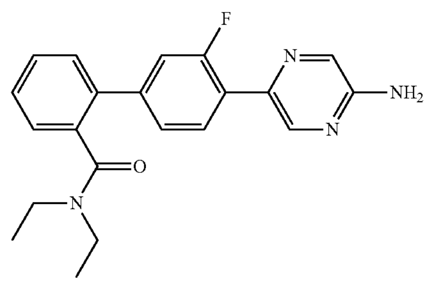 [SMILES: CCN(CC)C(=O)c1ccccc1-c1ccc(-c2cnc(N)cn2)c(F)c1] | 503 | 4'-(5-Aminopyrazin-2-yl)-N,N-diethyl-3'-fluorobiphenyl-2-carboxamide |
| 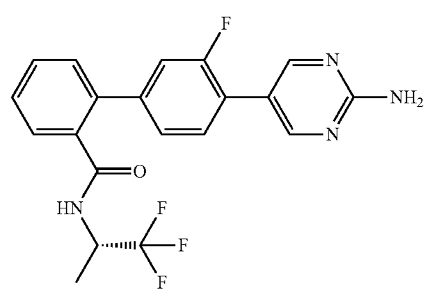 [SMILES: C[C@H](NC(=O)c1ccccc1-c1ccc(-c2cnc(N)nc2)c(F)c1)C(F)(F)F] | 504 | 4'-(2-Aminopyrimidin-5-yl)-3-fluoro-N-[(1S)-2,2,2-trifluoro-1-methylethyl]piphenyl-2-carboxamide |
| 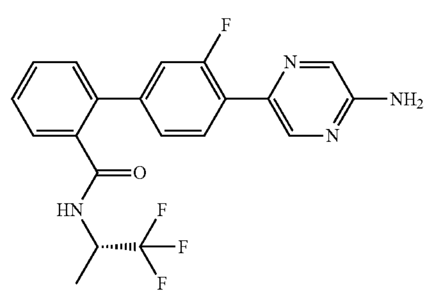 [SMILES: C[C@H](NC(=O)c1ccccc1-c1ccc(-c2cnc(N)cn2)c(F)c1)C(F)(F)F] | 505 | 4'-(5-Aminopyrazin-2-yl)-3'-fluoro-N-[(1S)-2,2,2-trifluoro-1-methylethyl]biphenyl-2-carboxamide |
| 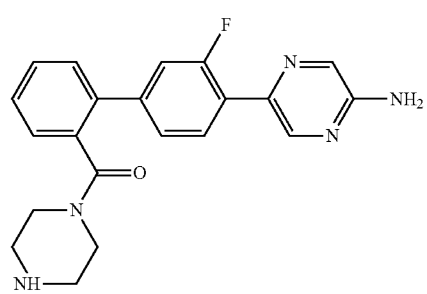 [SMILES: Nc1cnc(-c2ccc(-c3ccccc3C(=O)N3CCNCC3)cc2F)cn1] | 506 | 5-[3-Fluoro-2'-(piperazin-1-ylcarbonyl)biphenyl-4-yl]pyrazin-2-amine |

TABLE 3-continued

| STRUCTURE | COMPOUND # | NAME |
|---|---|---|
| 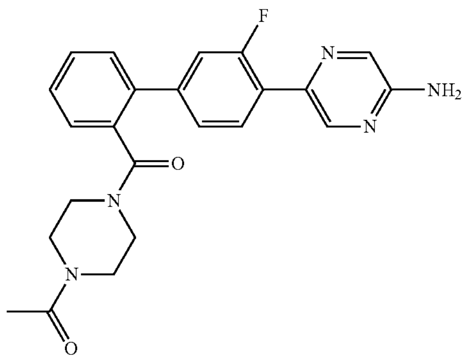 [SMILES: CC(=O)N1CCN(C(=O)c2ccccc2-c2ccc(-c3cnc(N)cn3)c(F)c2)CC1] | 507 | 5-{2'-[(4-Acetylpiperazin-1-yl)carbonyl]-3-fluorobiphenyl-4-yl}pyrazin-2-amine |
| 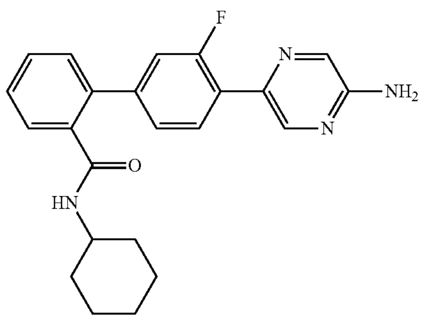 [SMILES: Nc1cnc(-c2ccc(-c3ccccc3C(=O)NC3CCCCC3)cc2F)cn1] | 508 | 4'-(5-Aminopyrazin-2-yl)-N-cyclohexyl-3'-fluorobiphenyl-2-carboxamide |
| 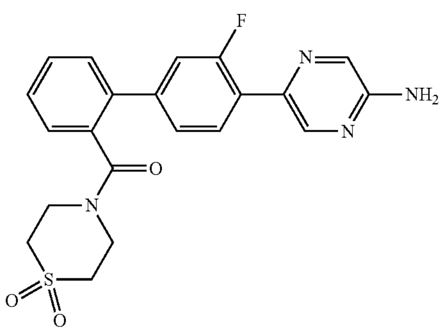 [SMILES: Nc1cnc(-c2ccc(-c3ccccc3C(=O)N3CCS(=O)(=O)CC3)cc2F)cn1] | 509 | 5-{2'-[(1,1-Dioxidathiomorpholin-4-yl)carbonyl]-3-fluorobiphenyl-4-yl}pyrazin-2-amine |
| 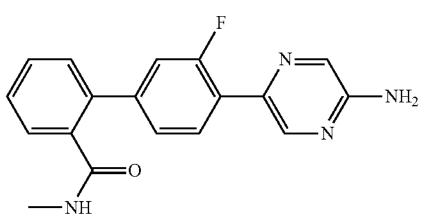 [SMILES: CNC(=O)c1ccccc1-c1ccc(-c2cnc(N)cn2)c(F)c1] | 510 | 4'-(5-Aminopyrazin-2-yl)-3'-fluoro-N-methylbiphenyl-2-carboxamide |
| 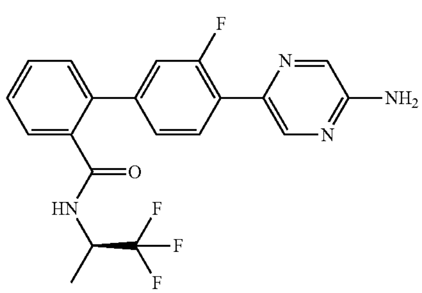 [SMILES: C[C@@H](NC(=O)c1ccccc1-c1ccc(-c2cnc(N)cn2)c(F)c1)C(F)(F)F] | 511 | 4'-(5-Aminopyrazin-2-yl)-3'-fluoro-N-[(1R)-2,2,2-trifluoro-1-methylethyl]biphenyl-2-carboxamide |

TABLE 3-continued

| STRUCTURE | COMPOUND # | NAME |
|---|---|---|
| 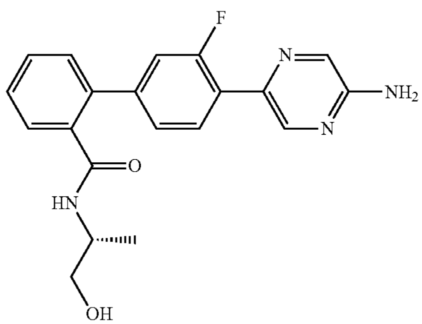 [SMILES: C[C@H](CO)NC(=O)c1ccccc1-c1ccc(-c2cnc(N)cn2)c(F)c1] | 512 | 4'-(5-Aminopyrazin-2-yl)-3'-fluoro-N-[(1R)-2-hydroxy-1-methylethyl]biphenyl-2-carboxamide |
| 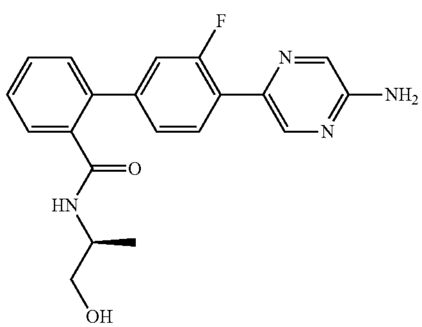 [SMILES: C[C@@H](CO)NC(=O)c1ccccc1-c1ccc(-c2cnc(N)cn2)c(F)c1] | 513 | 4'-(5-Aminopyrazin-2-yl)-3'-fluoro-N-[(1S)-2-hydroxy-1-methylethyl]biphenyl-2-carboxamide |
| 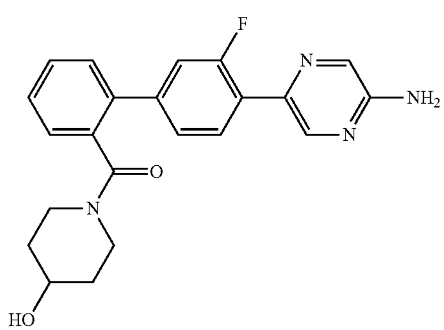 [SMILES: Nc1cnc(-c2ccc(-c3ccccc3C(=O)N3CCC(O)CC3)cc2F)cn1] | 514 | 1-{[4'-(5-Aminopyrazin-2-yl)-3'-fluorobiphenyl-2-yl]carbonyl)piperidin-4-ol |
| 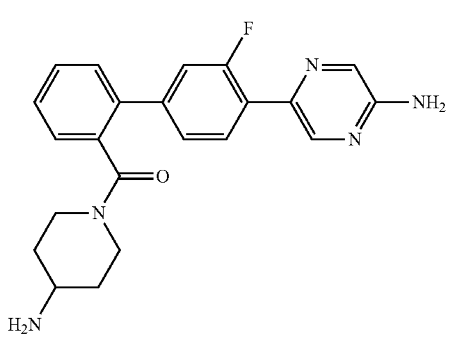 [SMILES: Nc1cnc(-c2ccc(-c3ccccc3C(=O)N3CCC(N)CC3)cc2F)cn1] | 515 | 5-{2'-[(4-Aminopiperidin-1-yl)carbonyl]-3-fluorobiphenyl-4-yl}pyrazin-2-amine |

TABLE 3-continued

| STRUCTURE | COMPOUND # | NAME |
|---|---|---|
| 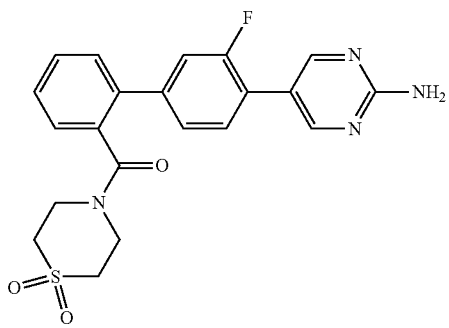 [SMILES: Nc1ncc(-c2ccc(-c3ccccc3C(=O)N3CCS(=O)(=O)CC3)cc2F)cn1] | 516 | 5-{2'-[(1,1-Dioxidothiomorpholin-4-yl)carbonyl]-3-fluorobiphenyl-4-yl}pyrimidin-2-amine |
| 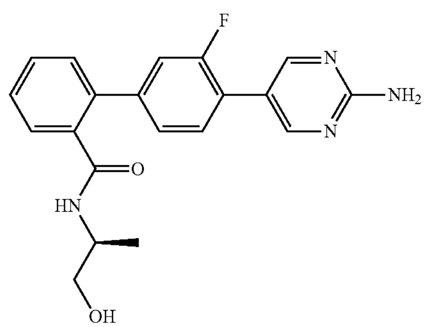 [SMILES: C[C@@H](CO)NC(=O)c1ccccc1-c1ccc(-c2cnc(N)nc2)c(F)c1] | 517 | 4'-(2-Aminopyrimidin-5-yl)-3'-fluoro-N-[(1S)-2-hydroxy-1-methylethyl]biphenyl-2-carboxamide |
| 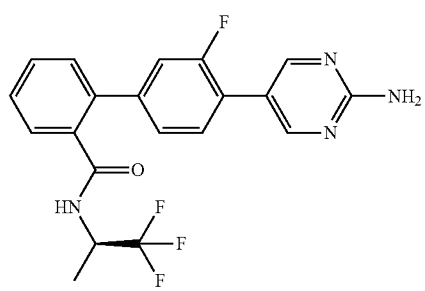 [SMILES: C[C@@H](NC(=O)c1ccccc1-c1ccc(-c2cnc(N)nc2)c(F)c1)C(F)(F)F] | 518 | 4'-(2-Aminopyrimidin-5-yl)-3'-fluoro-N[(1R)-2,2,2-trifluoro-1-methylethy]piphenyl-2-carboxamide |
| 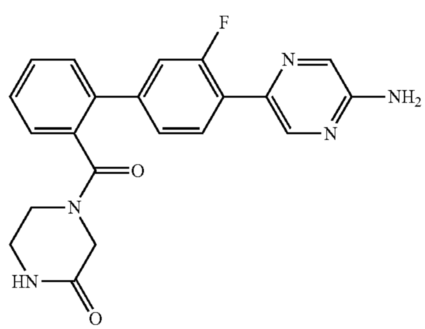 [SMILES: Nc1cnc(-c2ccc(-c3ccccc3C(=O)N3CCNC(=O)C3)cc2F)cn1] | 519 | 4-{[4'-(5-Aminopyrazin-2-yl)-3'-fluorobiphenyl-2-yl]carbonyl}piperazin-2-one |

TABLE 3-continued

| STRUCTURE | COMPOUND # | NAME |
|---|---|---|
| 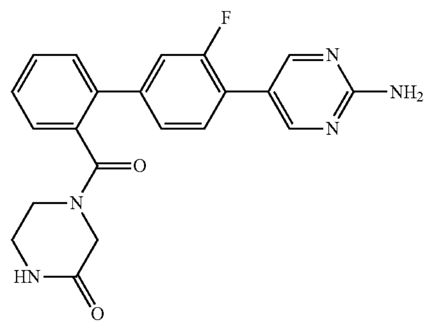 [SMILES: Nc1ncc(-c2ccc(-c3ccccc3C(=O)N3CCNC(=O)C3)cc2F)cn1] | 520 | 4-{[4'-(2-Aminopyrimidin-5-yl)-3'-fluorobiphenyl-2-yl]carbonyl}piperazin-2-one |
| 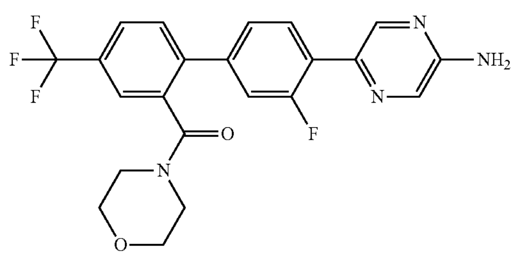 [SMILES: Nc1cnc(-c2ccc(-c3ccc(C(F)(F)F)cc3C(=O)N3CCOCC3)cc2F)cn1] | 521 | 5-[3-Fluoro-2'-(morpholin-4-ylcarbonyl)-4'-(trifluoromethyl)biphenyl-4-yl]pyrazin-2-amine |
| 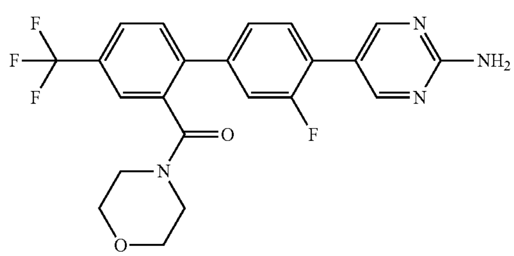 [SMILES: Nc1ncc(-c2ccc(-c3ccc(C(F)(F)F)cc3C(=O)N3CCOCC3)cc2F)cn1] | 522 | 5-[3-Fluoro-2'-(morpholin-4-ylcarbonyl)-4'-(trifluoromethyl)biphenyl-4-yl]pyrimidin-2-amine |
| 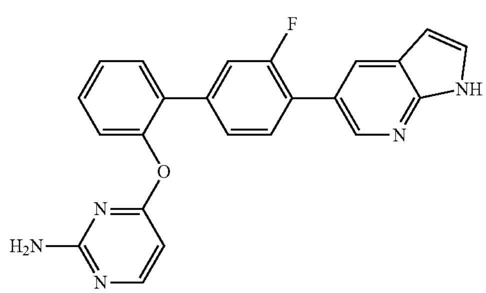 [SMILES: Nc1nccc(Oc2ccccc2-c2ccc(-c3cnc4[nH]ccc4c3)c(F)c2)n1] | 523 | 4-{[3'-Fluoro-4'-(1H-pyrrolo[2,3-b]pyridin-5-yl)biphenyl-2-yl]oxy}pyrimidin-2-amine |
| 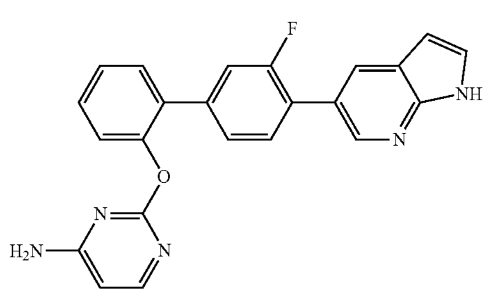 [SMILES: Nc1ccnc(Oc2ccccc2-c2ccc(-c3cnc4[nH]ccc4c3)c(F)c2)n1] | 524 | 2-{[3'-Fluoro-4'-(1H-pyrrolo[2,3-b]pyridin-5-yl)biphenyl-2-yl]oxy}pyrimidin-4-amine |

TABLE 3-continued

| STRUCTURE | COMPOUND # | NAME |
|---|---|---|
| 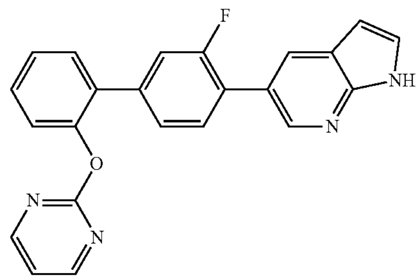 [SMILES: Fc1cc(-c2ccccc2Oc2ncccn2)ccc1-c1cnc2[nH]ccc2c1] | 525 | 5-[3-Fluoro-2'-(pyrimidin-2-yloxy)biphenyl-4-yl]-1H-pyrrolo[2,3-b]pyridine |
| 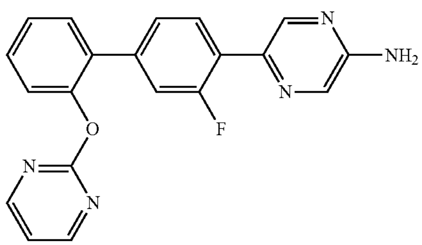 [SMILES: Nc1cnc(-c2ccc(-c3ccccc3Oc3ncccn3)cc2F)cn1] | 526 | 5-[3-Fluoro-2'-(pyrimidin-2-yloxy)biphenyl-4-yl]pyrazin-2-amine |
| 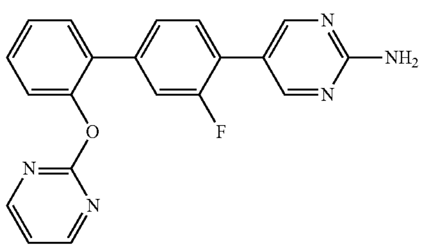 [SMILES: Nc1ncc(-c2ccc(-c3ccccc3Oc3ncccn3)cc2F)cn1] | 527 | 5-[3-Fluoro-2'-(pyrimidin-2-yloxy)biphenyl-4-yl]pyrimidin-2-amine |
| 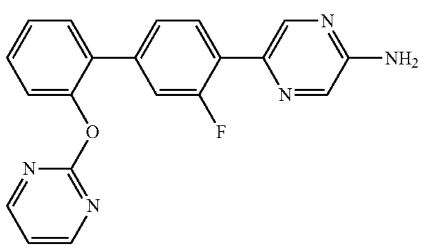 [SMILES: Nc1cnc(-c2ccc(-c3ccccc3Oc3ncccn3)cc2F)cn1] | 528 | 2-{[4'-(5-Aminopyrazin-2-yl)-3'-fluorobiphenyl-2-yl]oxy}pyrimidin-4-amine |
| 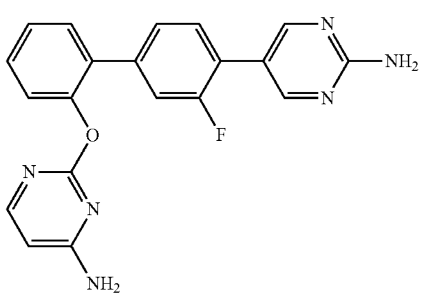 [SMILES: Nc1ccnc(Oc2ccccc2-c2ccc(-c3cnc(N)nc3)c(F)c2)n1] | 529 | 5-{2'-[(4-Aminopyrimidin-2-yl)oxy]-3-fluorobiphenyl-4-yl}pyrimidin-2-amine |
| 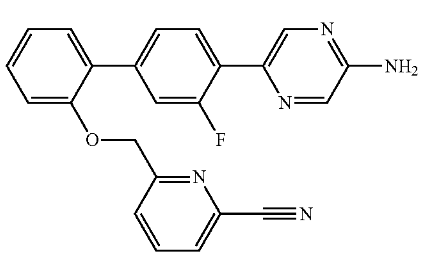 [SMILES: N#Cc1cccc(COc2ccccc2-c2ccc(-c3cnc(N)cn3)c(F)c2)n1] | 530 | 6-({[4'-(5-Aminopyrazin-2-yl)-3'-fluorobiphenyl-2-yl]oxy}methyl)pyridine-2-carbonitrile |

TABLE 3-continued

| STRUCTURE | COMPOUND # | NAME |
|---|---|---|
| 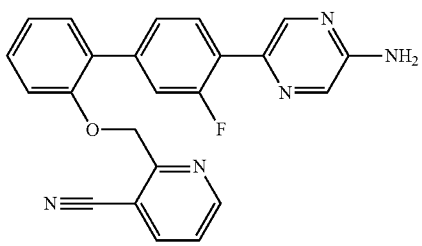 [SMILES: N#Cc1cccnc1COc1ccccc1-c1ccc(-c2cnc(N)cn2)c(F)c1] | 531 | 2-({[4'-(5-Aminopyrazin-2-yl)-3'-fluorobiphenyl-2-yl]oxy}methyl)pyridine-3-carbonitrile |
| 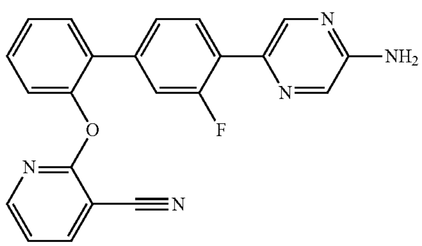 [SMILES: N#Cc1cccnc1Oc1ccccc1-c1ccc(-c2cnc(N)cn2)c(F)c1] | 532 | 2-{[4'-(5-Aminopyrazin-2-yl)-3'-fluorobiphenyl-2-yl]oxy}pyridine-3-carbonitrile |
| 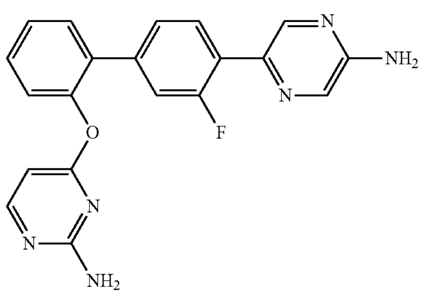 [SMILES: Nc1cnc(-c2ccc(-c3ccccc3Oc3ccnc(N)n3)cc2F)cn1] | 533 | 4-{[4'-(5-Aminopyrazin-2-yl)-3'-fluorobiphenyl-2-yl]oxy}pyrimidin-2-amine |
| 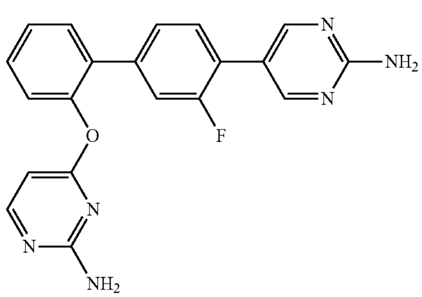 [SMILES: Nc1ncc(-c2ccc(-c3ccccc3Oc3ccnc(N)n3)cc2F)cn1] | 534 | 4-{[4'-(2-Aminopyrimidin-5-yl)-3'-fluorobiphenyl-2-yl]oxy}pyrimidin-2-amine |
| 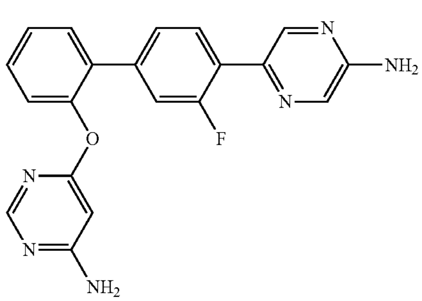 [SMILES: Nc1cnc(-c2ccc(-c3ccccc3Oc3cc(N)ncn3)cc2F)cn1] | 535 | 6-{[4'-(5-Aminopyrazin-2'yl)-3'-fluorobiphenyl-2-yl]oxy}pyrimidin-4'-amine |

TABLE 3-continued

| STRUCTURE | COMPOUND # | NAME |
|---|---|---|
| 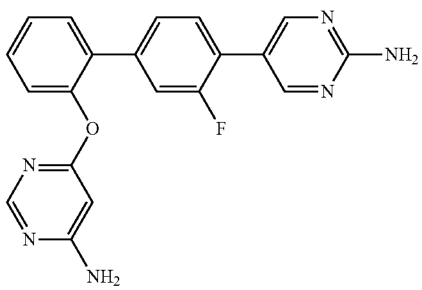 [SMILES: Nc1cc(Oc2ccccc2-c2ccc(-c3cnc(N)nc3)c(F)c2)ncn1] | 536 | 5-{2'-[(6-Aminopyrimidin-4-yl)oxy]-3-fluorobiphenyl-4-yl}pyrimidin-2-amine |
| 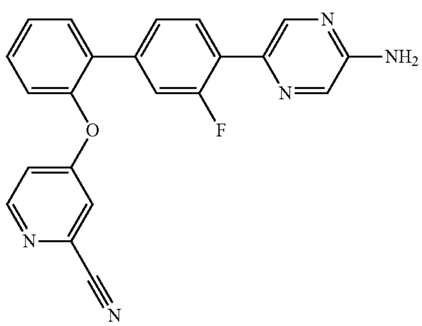 [SMILES: N#Cc1cc(Oc2ccccc2-c2ccc(-c3cnc(N)nc3)c(F)c2)ccn1] | 537 | 4-{[4'-(5-Aminopyrazin-2-yl)-3'-fluorobiphenyl-2-yl]oxy}pyridine-2-carbonitrile |
| 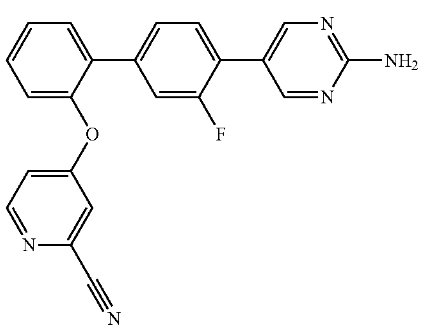 | 538 | 4-{[4'-(2-Aminopyrimidin-5-yl)-3'-fluorobiphenyl-2-yl]oxy}pyridine-2-carbonitrile |
| 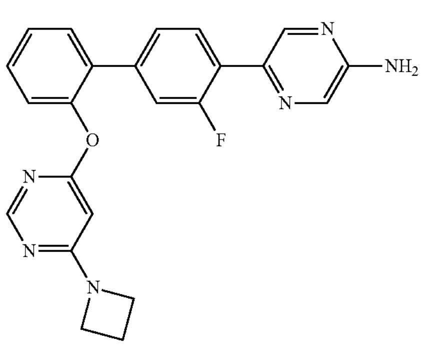 [SMILES: Nc1cnc(-c2ccc(-c3ccccc3Oc3cc(N4CCC4)ncn3)cc2F)cn1] | 539 | 5-{2'-[(6-Azetidin-1-ylpyrimidin-4-yl)oxy]-3-fluorobiphenyl-4-yl}pyrazin-2-amine |

TABLE 3-continued

| STRUCTURE | COMPOUND # | NAME |
|---|---|---|
| 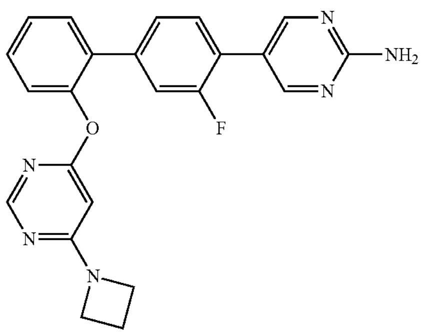 [SMILES: Nc1ncc(-c2ccc(-c3ccccc3Oc3cc(N4CCC4)ncn3)cc2F)cn1] | 540 | 5-{2'-[(6-Azetidin-1-ylpyrimidin-4-yl)oxy]-3-fluorobiphenyl-4-yl}pyrimidin-2-amine |
| 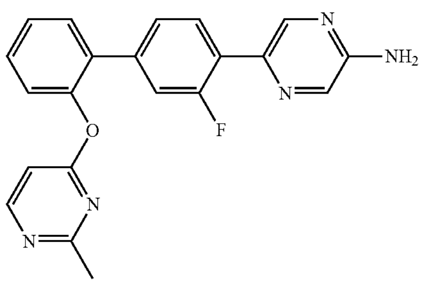 [SMILES: Cc1nccc(Oc2ccccc2-c2ccc(-c3cnc(N)cn3)c(F)c2)n1] | 541 | 5-{3-Fluoro-2'-[(2-methylpyrimidin-4-yl)oxy]biphenyl-4-yl}pyrazin-2-amine |
| 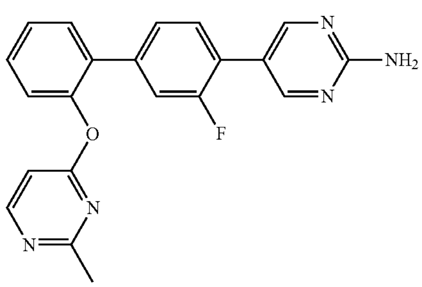 | 542 | 5-{3-Fluoro-2'-[(2-methylpyrimidin-4-yl)oxy]biphenyl-4-yl}pyrimidin-2-amine |
| 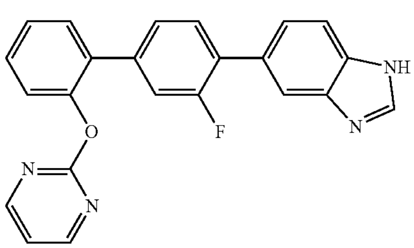 [SMILES: Fc1cc(-c2ccccc2Oc2ncccn2)ccc1-c1ccc2[nH]cnc2c1] | 543 | 5-[3-Fluoro-2'-(pyrimidin-2-yloxy)biphenyl-4-yl]-1H-benzimidazole |
| 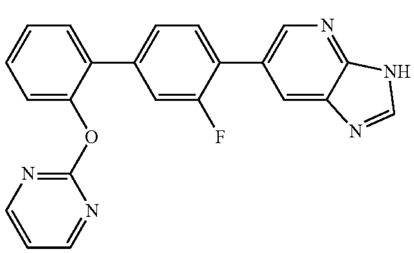 [SMILES: Fc1cc(-c2ccccc2Oc2ncccn2)ccc1-c1cnc2[nH]cnc2c1] | 544 | 6-[3-Fluoro-2'-(pyrimidin-2-yloxy)biphenyl-4-yl]-3H-imidazo[4,5-b]pyridine |

TABLE 3-continued

| STRUCTURE | COMPOUND # | NAME |
|---|---|---|
| 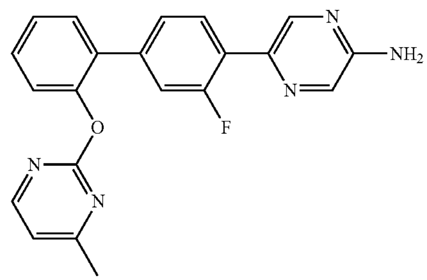 [SMILES: Cc1ccnc(Oc2ccccc2-c2ccc(-c3cnc(N)cn3)c(F)c2)n1] | 545 | 5-{3-Fluoro-2'-[(4-methylpyrimidin-2-yl)oxy]biphenyl-4-yl}pyrazin-2-amine |
| 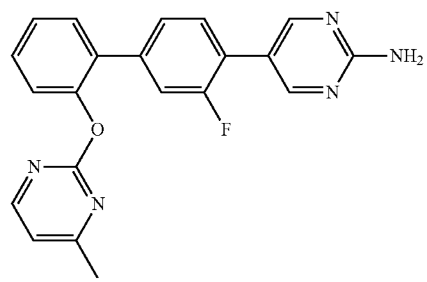 [SMILES: Cc1ccnc(Oc2ccccc2-c2ccc(-c3cnc(N)nc3)c(F)c2)n1] | 546 | 5-{3-Fluoro-2'-[(4-methylpyrimidin-2-yl)oxy]biphenyl-4-yl}pyrimidin-2-amine |
| 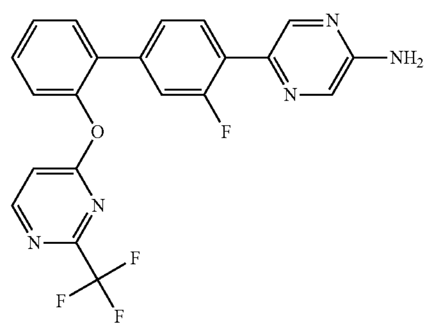 [SMILES: Nc1cnc(-c2ccc(-c3ccccc3Oc3ccnc(C(F)(F)F)n3)cc2F)cn1] | 547 | 5-(3-Fluoro-2'-{(2-(trifluoromethyl)pyrimidin-4-yl]oxy}biphenyl-4-yl)pyrazin-2-amine |
| 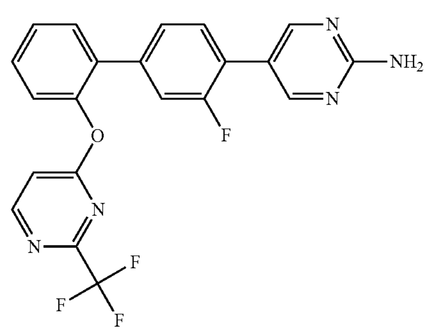 [SMILES: Nc1ncc(-c2ccc(-c3ccccc3Oc3ccnc(C(F)(F)F)n3)cc2F)cn1] | 548 | 5-(3-Fluoro-2'-{(2-(trifluoromethyl)pyrimidin-4-yl]oxylbiphenyl-4-yl)pyrimidin-2-amine |
| 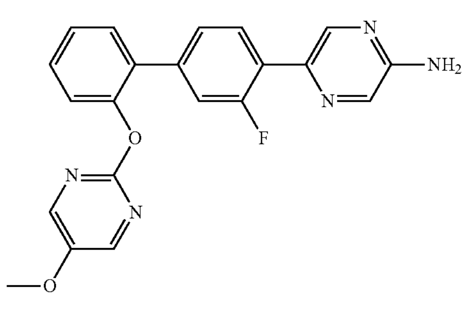 | 549 | 5-{3-Fluoro-2'-[(5-methoxypyrimidin-2-yl)oxy]biphenyl-4-yl}pyrazin-2-amine |

TABLE 3-continued

| STRUCTURE | COMPOUND # | NAME |
|---|---|---|
| 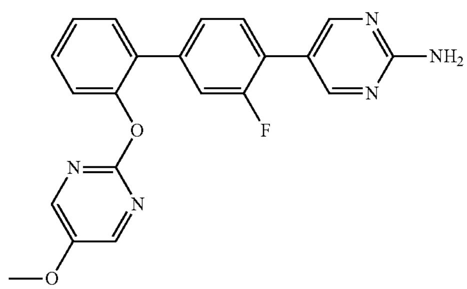 [SMILES: COc1cnc(Oc2ccccc2-c2ccc(-c3cnc(N)nc3)c(F)c2)nc1] | 550 | 5-{3-Fluoro-2'-[(5-methoxypyrimidin-2-yl)oxy]biphenyl-4-yl}pyrimidin-2-amine |
| 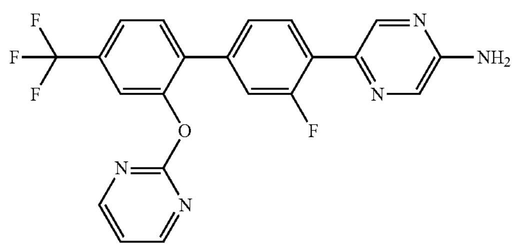 [SMILES: Nc1cnc(-c2ccc(-c3ccc(C(F)(F)F)cc3Oc3ncccn3)cc2F)cn1] | 551 | 5-[3-Fluoro-2'-(pyrimidin-2-yloxy)-4'-(trifluoromethyl)biphenyl-4-yl]pyrazin-2-amine |
| 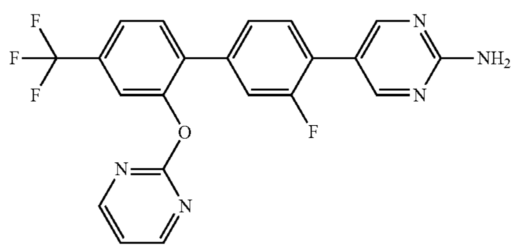 [SMILES: Nc1ncc(-c2ccc(-c3ccc(C(F)(F)F)cc3Oc3ncccn3)cc2F)cn1] | 552 | 5-[3-Fluoro-2'-(pyrimidin-2-yloxy)-4'-(trifluoromethyl)biphenyl-4-yl]pyrimidin-2-amine |
| 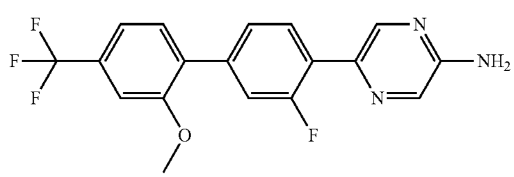 [SMILES: COc1cc(C(F)(F)F)ccc1-c1ccc(-c2cnc(N)cn2)c(F)c1] | 553 | 5-[3-Fluoro-2'-methoxy-4'-(trifluoromethyl)biphenyl-4-yl]pyrazin-2-amine |
| 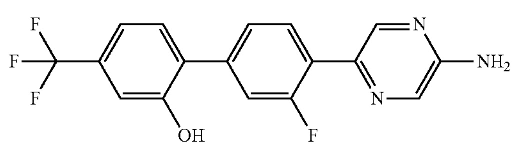 [SMILES: Nc1cnc(-c2ccc(-c3ccc(C(F)(F)F)cc3O)cc2F)cn1] | 554 | 4'-(5-Aminopyrazin-2-yl)-3'-fluoro-4-(trifluoromethyl)biphenyl-2-ol |
| 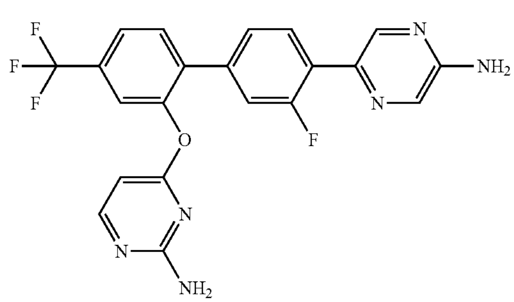 [SMILES: Nc1cnc(-c2ccc(-c3ccc(C(F)(F)F)cc3Oc3ccnc(N)n3)cc2F)cn1] | 555 | 4-{[4'-(5-Aminopyrazin-2-yl)-3'-fluoro-4-(trifluoromethyl)biphenyl-2-yl]oxy}pyrimidin-2-amine |

TABLE 3-continued

| STRUCTURE | COMPOUND # | NAME |
|---|---|---|
| 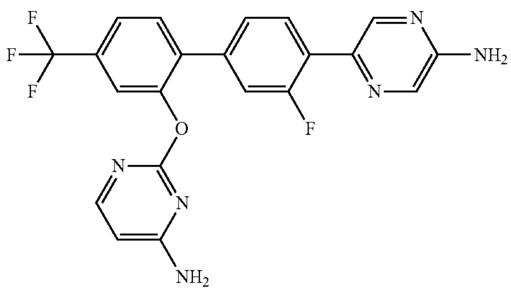 [SMILES: Nc1cnc(-c2ccc(-c3ccc(C(F)(F)F)cc3Oc3nccc(N)n3)cc2F)cn1] | 556 | 2-{[4'-(5-Aminopyrazin-2-yl)-3'-fluoro-4-(trifluoromethyl)biphenyl-2-yl]oxy}pyrimidin-4-amine |
| 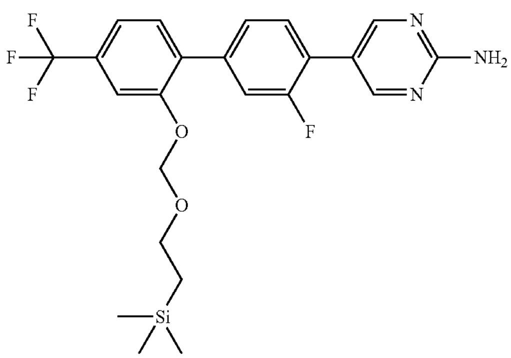 [SMILES: C[Si](C)(C)CCOCOc1cc(C(F)(F)F)ccc1-c1ccc(-c2cnc(N)nc2)c(F)c1] | 557 | 5-[3-Fluoro-4'-(trifluoromethyl)-2'-{[2-(trimethylsilyl)ethoxy]methoxy}biphenyl-yl-4-yl]pyrimidin-2-amine |
| 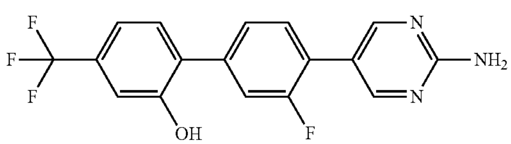 [SMILES: Nc1ncc(-c2ccc(-c3ccc(C(F)(F)F)cc3O)cc2F)cn1] | 558 | 4'-(2-Aminopyrimidin-5-yl)-3'-fluoro-4-(trifluoromethyl)biphenyl-2-ol |
| 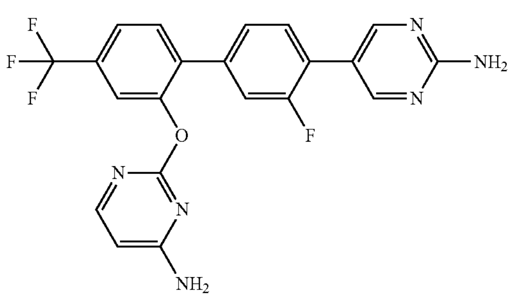 [SMILES: Nc1ccnc(Oc2cc(C(F)(F)F)ccc2-c2ccc(-c3cnc(N)nc3)c(F)c2)n1] | 559 | 5-{2'-[(4-Aminopyrimidin-2-yl)oxy]-3-fluoro-4'-(trifluoromethyl)biphenyl-4-yl}pyrimidin-2-amine |
| 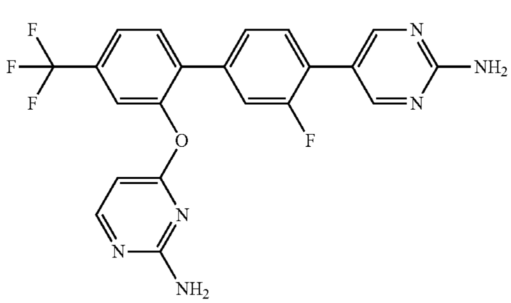 [SMILES: Nc1ncc(-c2ccc(-c3ccc(C(F)(F)F)cc3Oc3ccnc(N)n3)cc2F)cn1] | 560 | 4-{[4'-(2-Aminopyrimidin-5-yl)-3'-fluoro-4-(trifluoromethyl)biphenyl-2-yl]oxy}pyrimidin-2-amine |

TABLE 3-continued

| STRUCTURE | COMPOUND # | NAME |
|---|---|---|
| 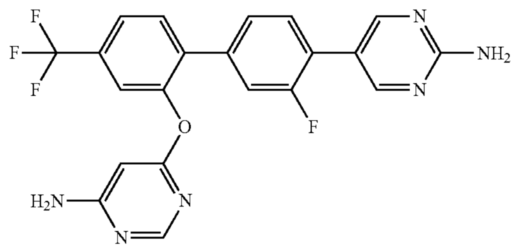 [SMILES: Nc1cc(Oc2cc(C(F)(F)F)ccc2-c2ccc(-c3cnc(N)nc3)c(F)c2)ncn1] | 561 | 5-{2'-[(6-Aminopyrimidin-4-yl)oxy]-3-fluoro-4'-(trifluoromethyl)biphenyl-4-yl}pyrimidin-2-amine |
| 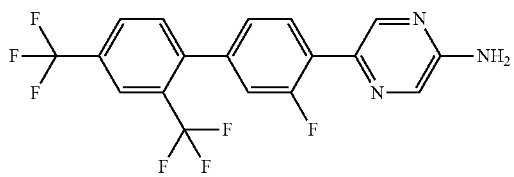 [SMILES: Nc1cnc(-c2ccc(-c3ccc(C(F)(F)F)cc3C(F)(F)F)cc2F)cn1] | 562 | 5-[3-Fluoro-2',4'-bis(trifluoromethyl)biphenyl-4-yl]pyrazin-2-amine |
| 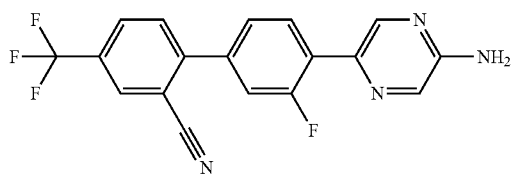 [SMILES: N#Cc1cc(C(F)(F)F)ccc1-c1ccc(-c2cnc(N)cn2)c(F)c1] | 563 | 4'-(5-Aminopyrazin-2-yl)-3'-fluoro-4-(trifluoromethyl)biphenyl-2-carbonitrile |
| 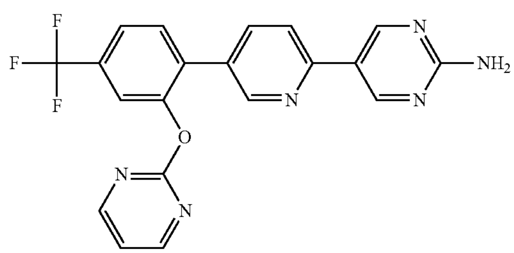 [SMILES: Nc1ncc(-c2ccc(-c3ccc(C(F)(F)F)cc3Oc3ncccn3)cn2)cn1] | 564 | 5-{5-[2-(Pyrimidin-2-yloxy)-4-(trifluoromethyl)phenyl]pyridin-2-yl}pyrimidin-2-amine |
| 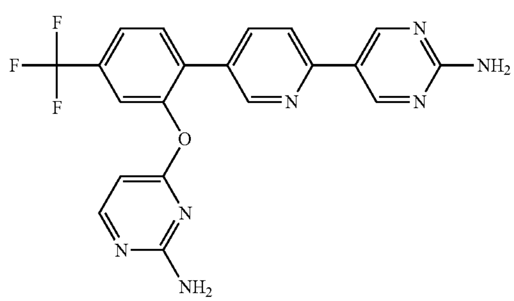 [SMILES: Nc1ncc(-c2ccc(-c3ccc(C(F)(F)F)cc3Oc3ccnc(N)n3)cn2)cn1] | 565 | 4-{2-[6-(2-Aminopyrimidin-5-yl)pyridin-3-yl]-5-(trifluoromethyl)phenoxy}pyrimidin-2-amine |
| 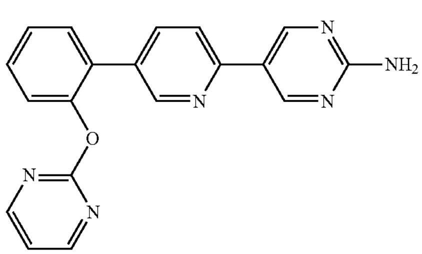 [SMILES: Nc1ncc(-c2ccc(-c3ccccc3Oc3ncccn3)cn2)cn1] | 566 | 5-{5-[2-(Pyrimidin-2-yloxy)phenyl]pyridin-2-yl}pyrimidin-2-amine |

TABLE 3-continued

| STRUCTURE | COMPOUND # | NAME |
|---|---|---|
| 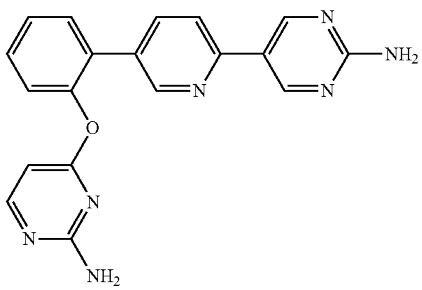 [SMILES: Nc1ncc(-c2ccc(-c3ccccc3Oc3ccnc(N)n3)cn2)cn1] | 567 | 4-{2-[6-(2-Aminopyrimidin-5-yl)pyridin-3-yl]phenoxy}pyrimidin-2-amine |
| 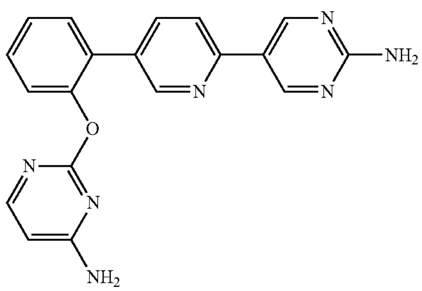 [SMILES: Nc1ccnc(Oc2ccccc2-c2ccc(-c3cnc(N)nc3)nc2)n1] | 568 | 5-(5-{2-[(4-Aminopyrimidin-2-yl)oxy]phenyl}pyridin-2-yl)pyrimidin-2-amine |
| 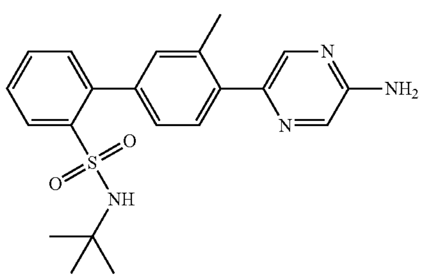 [SMILES: Cc1cc(-c2ccccc2S(=O)(=O)NC(C)(C)C)ccc1-c1cnc(N)cn1] | 569 | 4'-(5-Aminopyrazin-2-yl)-N-tert-butyl-3'-methylbiphenyl-2-sulfonamide |
| 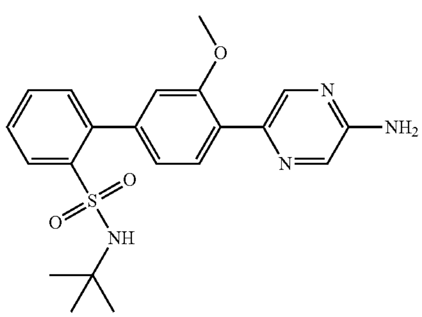 [SMILES: COc1cc(-c2ccccc2S(=O)(=O)NC(C)(C)C)ccc1-c1cnc(N)cn1] | 570 | 4'-(5-Aminopyrazin-2-yl)-N-tert-butyl-3'-methoxybiphenyl-2-sulfonamide |
| 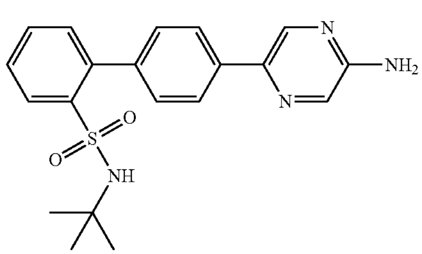 [SMILES: CC(C)(C)NS(=O)(=O)c1ccccc1-c1ccc(-c2cnc(N)cn2)cc1] | 571 | 4'-(5-Aminopyrazin-2-yl)-N-tert-butylbiphenyl-2-sulfonamide |

TABLE 3-continued

| STRUCTURE | COMPOUND # | NAME |
|---|---|---|
| 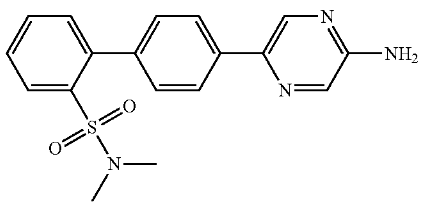 [SMILES: CN(C)S(=O)(=O)c1ccccc1-c1ccc(-c2cnc(N)cn2)cc1] | 572 | 4'-(5-Aminopyrazin-2-yl)-N,N-dimethylbiphenyl-2-sulfonamide |
| 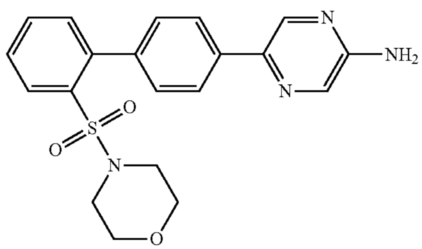 [SMILES: Nc1cnc(-c2ccc(-c3ccccc3S(=O)(=O)N3CCOCC3)cc2)cn1] | 573 | 5-[2'-(Morpholin-4-ylsulfonyl)biphenyl-4-yl]pyrazin-2'-amine |
| 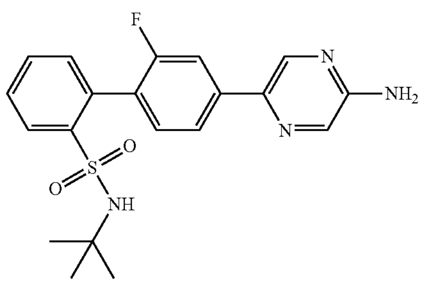 [SMILES: CC(C)(C)NS(=O)(=O)c1ccccc1-c1ccc(-c2cnc(N)cn2)cc1F] | 574 | 4'-(5-Aminopyrazin-2-yl)-N-tert-butyl-2'-fluorobiphenyl-sultonamide |
| 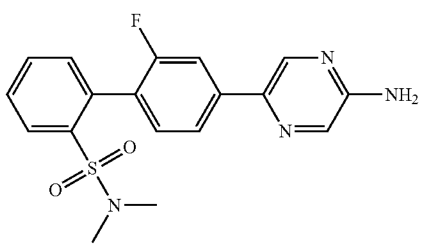 [SMILES: CN(C)S(=O)(=O)c1ccccc1-c1ccc(-c2cnc(N)cn2)cc1F] | 575 | 4'-(5-Aminopyrazin-2-yl)-2'-fluoro-N,N-dimethylbiphenyl-2-sulfonamide |
| 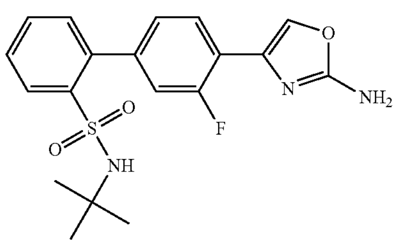 [SMILES: CC(C)(C)NS(=O)(=O)c1ccccc1-c1ccc(-c2coc(N)n2)c(F)c1] | 576 | 4'-(2-Amino-1,3-oxazol-4-yl)-N-tert-butyl-3'-fluorobiphenyl-2-sulfonamide |
| 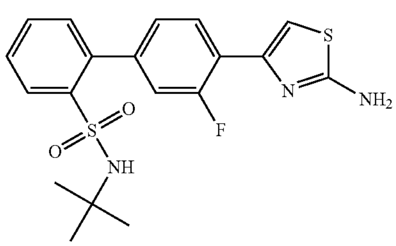 | 577 | 4'-(2-Amino-1,3-thiazol-4-yl)-N-tert-butyl-3'-fluorobiphenyl-2-sulfonamide |

TABLE 3-continued

| STRUCTURE | COMPOUND # | NAME |
|---|---|---|
| 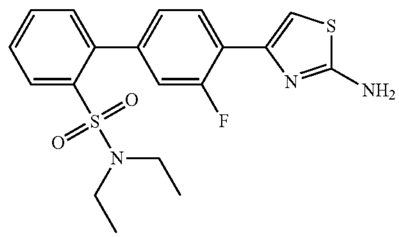 [SMILES: CCN(CC)S(=O)(=O)c1ccccc1-c1ccc(-c2csc(N)n2)c(F)c1] | 578 | 4'-(2-Amino-1,3-thiazol-4-yl)-N,N-diethyl-3'-fluorobiphenyl-2-sulfonamide |
| 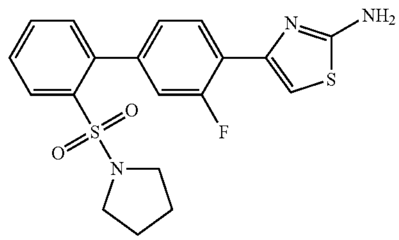 [SMILES: Nc1nc(-c2ccc(-c3ccccc3S(=O)(=O)N3CCCC3)cc2F)cs1] | 579 | 4-[3-Fluoro-2'-(pyrrolidin-1-ylsulfonyl)biphenyl-4-yl]-1,3-thiazol-2-amine |
| 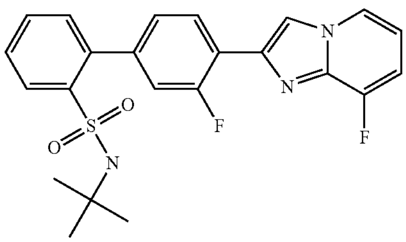 [SMILES: CC(C)(C)NS(=O)(=O)c1ccccc1-c1ccc(-c2cn3cccc(F)c3n2)c(F)c1] | 580 | N-tert-Butyl-3'-fluoro-4'-(8-fluoroimidazo[1,2-a]pyridin-2-yl)biphenyl-2-sulfonamide |
| 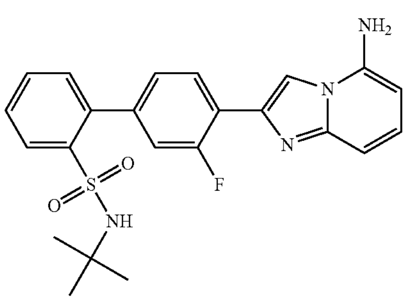 [SMILES: CC(C)(C)NS(=O)(=O)c1ccccc1-c1ccc(-c2cn3c(N)cccc3n2)c(F)c1] | 581 | 4'-(5-Aminoimidazo[1,2-a]pyridin-2-yl)-N-tert-butyl-3'-fluorobiphenyl-2-sulfonamide |
| 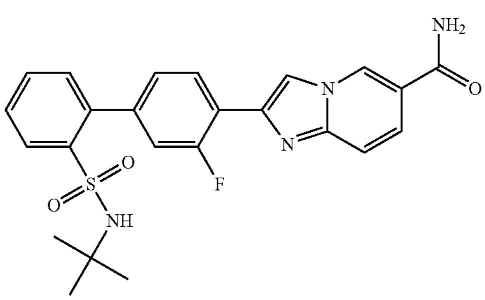 [SMILES: CC(C)(C)NS(=O)(=O)c1ccccc1-c1ccc(-c2cn3cc(C(N)=O)ccc3n2)c(F)c1] | 582 | 2-[2'-(tert-Butylsulfamoyl)-3-fluorobiphenyl-4-yl]imidazo[1,2-a]pyridine-6-carboxamide |

TABLE 3-continued

| STRUCTURE | COMPOUND # | NAME |
|---|---|---|
| 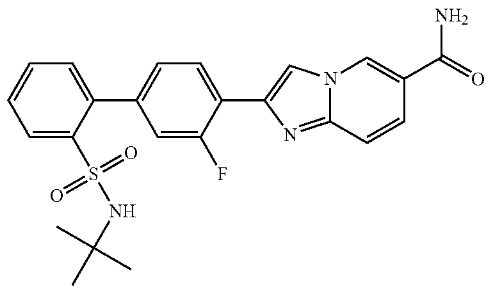 [SMILES: CC(C)(C)NS(=O)(=O)c1ccccc1-c1ccc(-c2cn3cc(C(N)=O)ccc3n2)c(F)c1] | 583 | 2-[2'-(tert-Butylsulfamoyl)-3-fluorobiphenyl-4-yl]imidazo[1,2-a]pyridine-6-carboxamide |
| 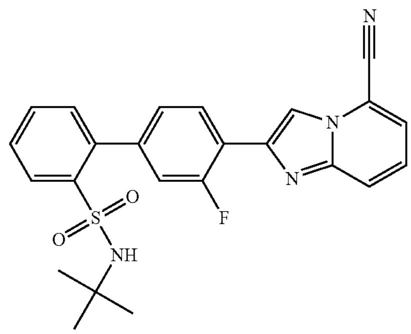 [SMILES: CC(C)(C)NS(=O)(=O)c1ccccc1-c1ccc(-c2cn3c(C#N)cccc3n2)c(F)c1] | 584 | N-tert-Butyl-4'-(5-cyanoimidazo[1,2-a]pyridin-2-yl)-3'-fluorobiphenyl-2-sulfonamide |
| 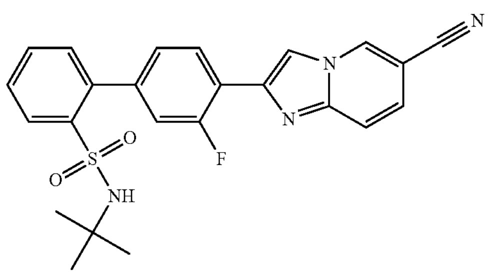 [SMILES: CC(C)(C)NS(=O)(=O)c1ccccc1-c1ccc(-c2cn3cc(C#N)ccc3n2)c(F)c1] | 585 | N-tert-Butyl-4'-(6-cyanoimidazo[1,2-a]pyridin-2-yl)-3'-fluorobiphenyl-2-sulfonamide |
| 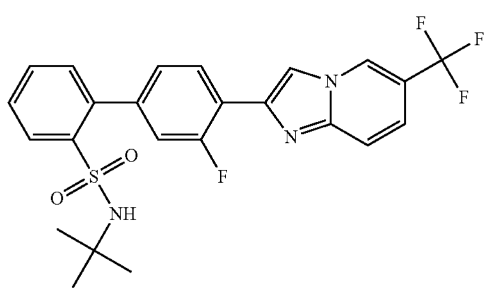 [SMILES: CC(C)(C)NS(=O)(=O)c1ccccc1-c1ccc(-c2cn3cc(C(F)(F)F)ccc3n2)c(F)c1] | 586 | N-tert-Butyl-3'-fluoro-4'-[6-(trifluoromethyl)imidazo[1,2-a]pyridin-2-yl]biphenyl-2-sulfonamide |
| 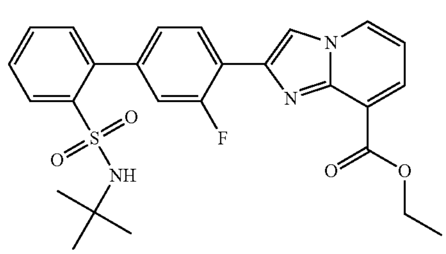 [SMILES: CCOC(=O)c1cccn2cc(-c3ccc(-c4ccccc4S(=O)(=O)NC(C)(C)C)cc3F)nc12] | 587 | Ethyl 2-[2'-(tert-butylsulfamoyl)-3-fluorobiphenyl-4-yl]imidazo[1,2-a]pyridine-5-carboxylate |

TABLE 3-continued

| STRUCTURE | COMPOUND # | NAME |
|---|---|---|
| 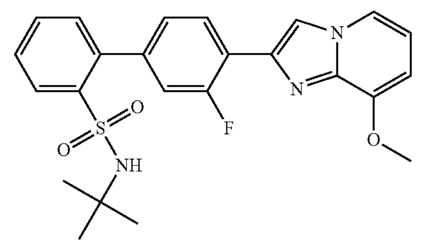 [SMILES: COc1cccn2cc(-c3ccc(-c4ccccc4S(=O)(=O)NC(C)(C)C)cc3F)nc12] | 588 | N-tert-Butyl-3-fluoro-4'-(5-methoxyimidazo[1,2-a]pyridin-2-yl)biphenyl-2-sulfonamide |
| 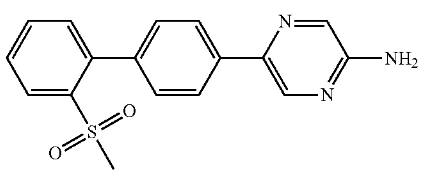 [SMILES: CS(=O)(=O)c1ccccc1-c1ccc(-c2cnc(N)cn2)cc1] | 589 | 5-[2'-(Methylsulfonyl)biphenyl-4-yl]pyrazin-2-amine. |
| 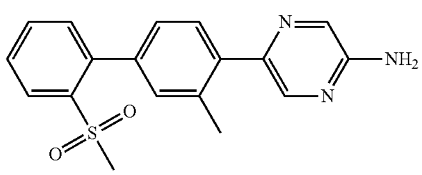 [SMILES: Cc1cc(-c2ccccc2S(C)(=O)=O)ccc1-c1cnc(N)cn1] | 590 | 5-[3-Methyl-2'-(methylsulfonyl)biphenyl-4-yl]pyrazin-2-amine. |
| 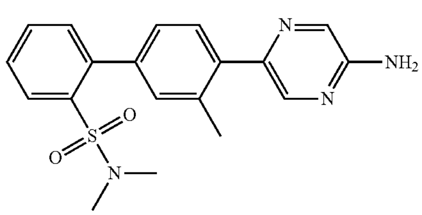 [SMILES: Cc1cc(-c2ccccc2S(=O)(=O)N(C)C)ccc1-c1cnc(N)cn1] | 591 | 4'-(5-Aminopyrazin-2-yl)-N,N,3'-trimethylbiphenyl-2-sulfonamide. |
| 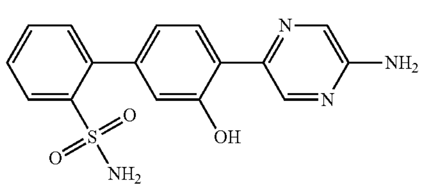 | 592 | 4'-(5-Aminopyrazin-2-yl)-3'-hydroxybiphenyl-2-sulfonamide. |
| 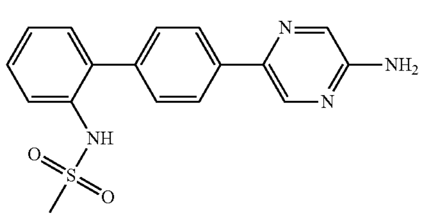 [SMILES: CS(=O)(=O)Nc1ccccc1-c1ccc(-c2cnc(N)cn2)cc1] | 593 | n-[4'-(5-Aminopyrazin-2-yl)biphenyl-2-yl]methanesulfonamide. |
| 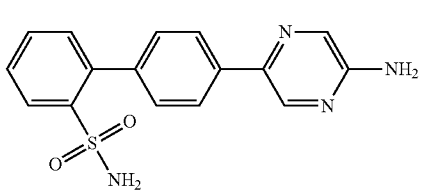 [SMILES: Nc1cnc(-c2ccc(-c3ccccc3S(N)(=O)=O)cc2)cn1] | 594 | 4'-(5-Aminopyrazin-2-yl)biphenyl-2-sulfonamide. |

TABLE 3-continued

| STRUCTURE | COMPOUND # | NAME |
|---|---|---|
| 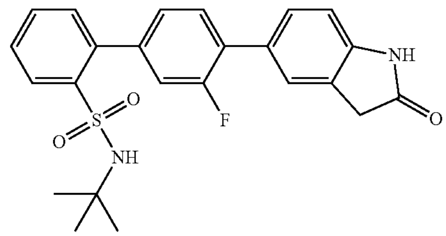 [SMILES: CC(C)(C)NS(=O)(=O)c1ccccc1-c1ccc(-c2ccc3c(c2)CC(=O)N3)c(F)c1] | 595 | N-tert-Butyl-3'-fluoro-4'-(2-oxo-2,3-dihydro-1H-indol-5-yl)biphenyl-2-sulfonamide. |
| 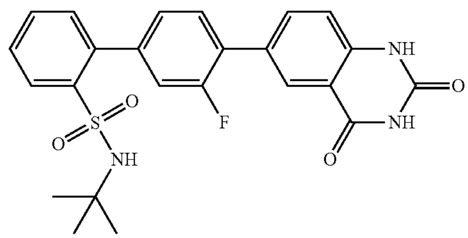 [SMILES: CC(C)(C)NS(=O)(=O)c1ccccc1-c1ccc(-c2ccc3[nH]c(=O)[nH]c(=O)c3c2)c(F)c1] | 596 | N-tert-Butyl-4'-(2,4-dioxo-1,2,3,4-tetrahydroquinazolin-6-yl)-3'-fluorobiphenyl-2-sulfonamide. |
| 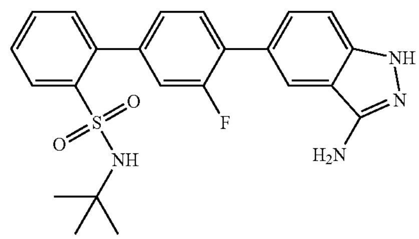 [SMILES: CC(C)(C)NS(=O)(=O)c1ccccc1-c1ccc(-c2ccc3[nH]nc(N)c3c2)c(F)c1] | 597 | 4'-(3-Amino-1H-indazol-5-yl)-N-tert-butyl-3'-fluorobiphenyl-2-sulfonamide. |
| 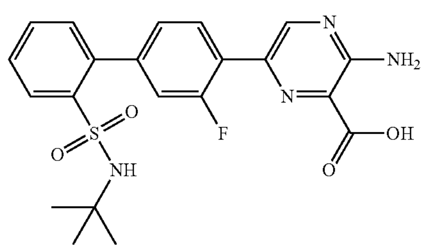 [SMILES: CC(C)(C)NS(=O)(=O)c1ccccc1-c1ccc(-c2cnc(N)c(C(=O)O)n2)c(F)c1] | 598 | 3-Amino-6-[2'-(tert-butylsulfamoyl)-3-fluorobiphenyl-4-yl]pyrazine-2-carboxylic acid. |
| 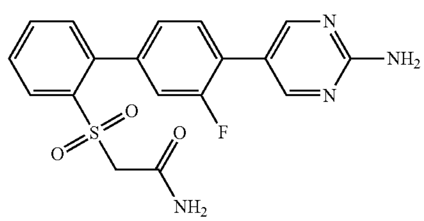 [SMILES: NC(=O)CS(=O)(=O)c1ccccc1-c1ccc(-c2cnc(N)nc2)c(F)c1] | 599 | 2-{[4'-(2-Aminopyrimidin-5-yl)-3'-fluorobiphenyl-2-yl]sulfonyl}acetamide. |
| 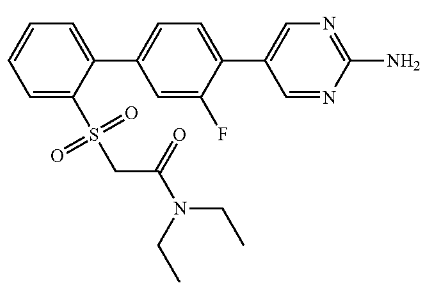 [SMILES: CCN(CC)C(=O)CS(=O)(=O)c1ccccc1-c1ccc(-c2cnc(N)nc2)c(F)c1] | 600 | 2-{4'-(2-Aminopyrimidin-5-yl)-3'-fluorobiphenyl-2-yl]sulfonyl}-N,N-diethylacetamide. |

TABLE 3-continued

| STRUCTURE | COMPOUND # | NAME |
|---|---|---|
| 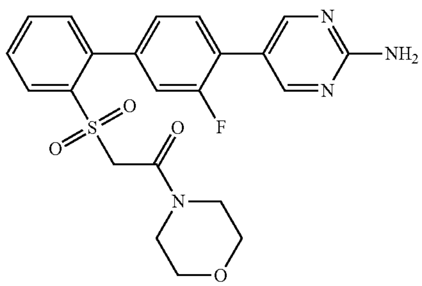 [SMILES: Nc1ncc(-c2ccc(-c3ccccc3S(=O)(=O)CC(=O)N3CCOCC3)cc2F)cn1] | 601 | 5-{3-Fluoro-2'-[(2-morpholin-4-yl-2-oxoethyl)sulfonyl]biphenyl-4-yl}pyrimidin-2-amine. |
| 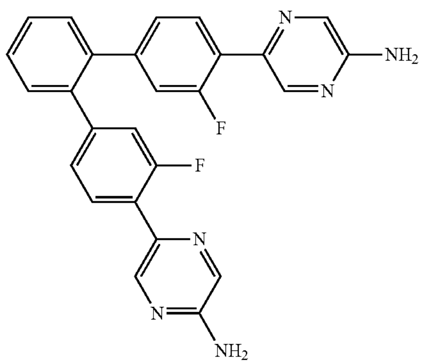 [SMILES: Nc1cnc(-c2ccc(-c3ccccc3-c3ccc(-c4cnc(N)cn4)c(F)c3)cc2F)cn1] | 602 | 5,5'-(3,3'-Difluoro-1,1':2',1''-terphenyl-4,4''-diyl)dipyrazin-2-amine. |
| 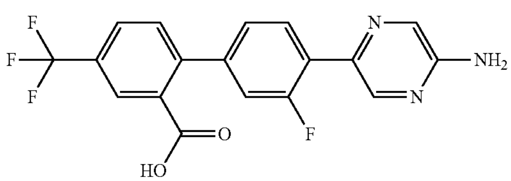 | 603 | 4'-(5-Aminopyrazin-2-yl)-3'-fluoro-4-(trifluoromethyl)biphenyl-2-carboxylic acid. |
| 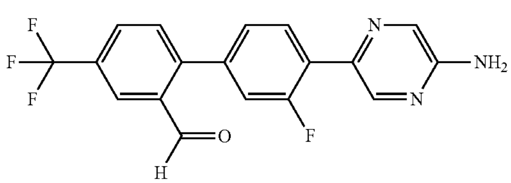 [SMILES: Nc1cnc(-c2ccc(-c3ccc(C(F)(F)F)cc3C=O)cc2F)cn1] | 604 | 4'-(5-Aminopyrazin-2-yl)-3'-fluoro-4-(trifluoromethyl)biphenyl-2-carbaldehyde. |
| 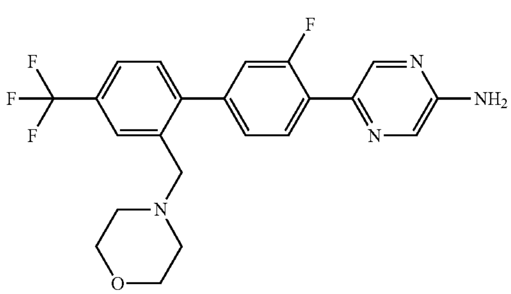 [SMILES: Nc1cnc(-c2ccc(-c3ccc(C(F)(F)F)cc3CN3CCOCC3)cc2F)cn1] | 605 | 5-[3-Fluoro-2'-(morpholin-4-ylmethyl)-4'-(trifluoromethyl)biphenyl-4-yl]pyrazin-2-amine. |

TABLE 3-continued

| STRUCTURE | COMPOUND # | NAME |
|---|---|---|
| 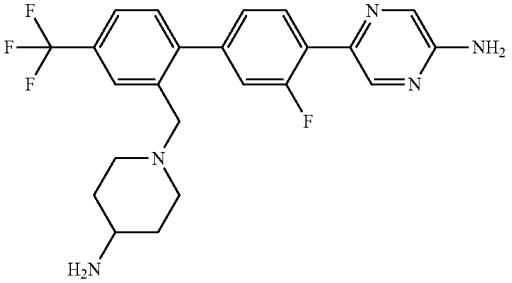 [SMILES: Nc1cnc(-c2ccc(-c3ccc(C(F)(F)F)cc3CN3CCC(N)CC3)cc2F)cn1] | 606 | 5-{2'-[(4-Aminopiperidin-1-yl)methyl]-3-fluoro-4'-(trifluoromethyl)biphenyl-4-yl}pyrazin-2-amine. |
| 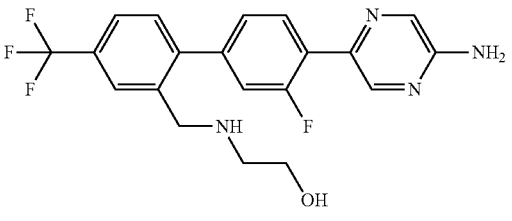 [SMILES: Nc1cnc(-c2ccc(-c3ccc(C(F)(F)F)cc3CNCCO)cc2F)cn1] | 607 | 2-({[4'-(5-Aminopyrazin-2-yl)-3'-fluoro-4-(trifluoromethyl)biphenyl-2-yl]methyl}amino)ethanol. |
| 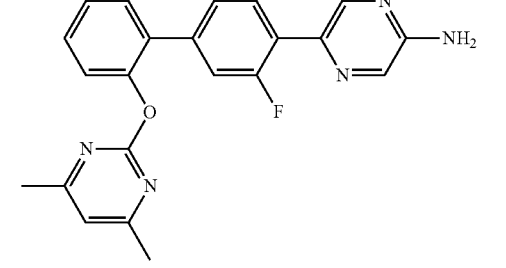 | 608 | 5-{2'-[(4,6-Dimethylpyrimidin-2-yl)oxy]-3-fluorobiphenyl-4-yl}pyrazin-2-amine. |
| 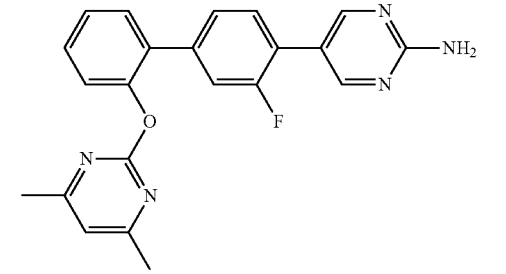 [SMILES: Cc1cc(C)nc(Oc2ccccc2-c2ccc(-c3cnc(N)nc3)c(F)c2)n1] | 609 | 5-{2'-[(4,6-Dimethylpyrimidin-2-yl)oxy]-3-fluorobiphenyl-4-yl}pyrimidin-2-amine. |
| 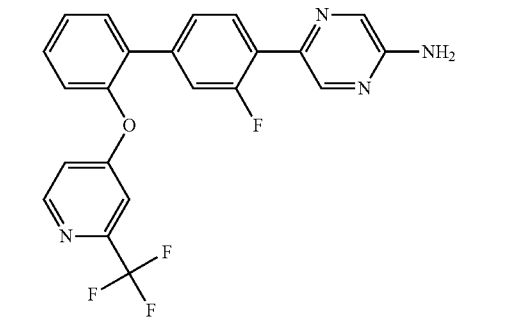 | 610 | 5-(3-Fluoro-2'-{[2-(trifluoromethyl)pyridin-4-yl]oxy}biphenyl-4-yl)pyrazin-2-amine. |

TABLE 3-continued

| STRUCTURE | COMPOUND # | NAME |
|---|---|---|
| 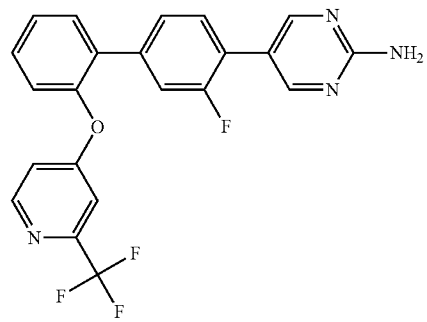 | 611 | 5-(3-Fluore-2'-{[2-(trifluoromethyl)pyridin-4-yl)oxy}biphenyl-4-yl)pyrimidin-2-amine. |
| 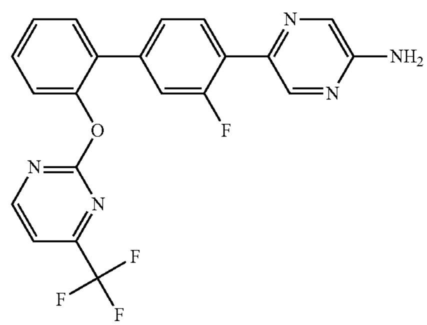 | 612 | 5-(3-Fluoro-2'-{[4-(trifluoromethyl)pyrimidin-2-yl]oxy}biphenyl-4-yl)pyrazin-2-amine. |
| 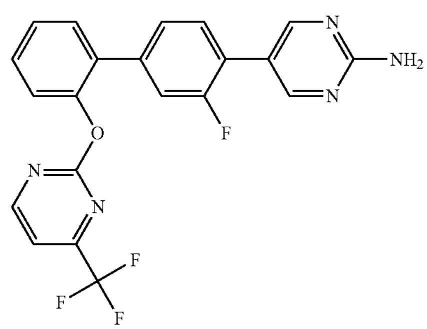 [SMILES: Nc1ncc(-c2ccc(-c3ccccc3Oc3nccc(C(F)(F)F)n3)cc2F)cn1] | 613 | 5-(3-Fluoro-2'-{[4-(trifluoromethyl)pyrimidin-2-yl]oxy}biphenyl-4-yl)pyrimidin-2-amine. |
| 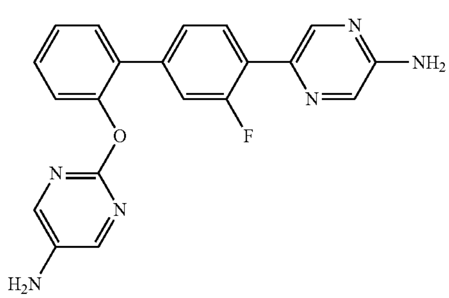 | 614 | 2-{[4'-(5-Aminopyrazin-2-yl)-3'-fluorobiphenyl-2-yl]oxy}pyrimidin-5-amine. |
| 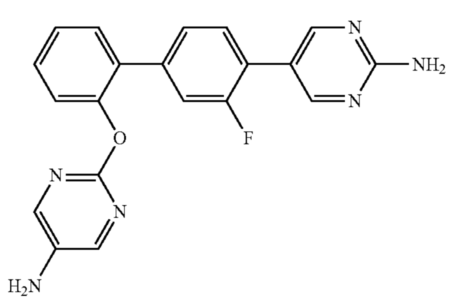 | 615 | 5-{2'-[(5-Aminopyrimidin-2-yl)oxy]-3-fluorobiphenyl-4-yl}pyrimidin-2-amine. |

TABLE 3-continued

| STRUCTURE | COMPOUND # | NAME |
|---|---|---|
| 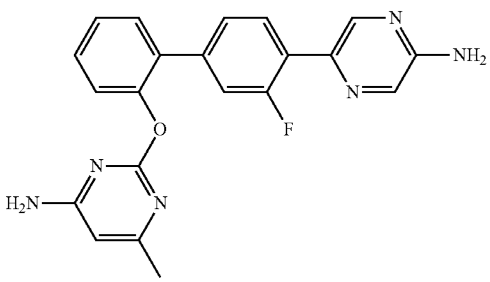 | 616 | 2-{[4'-(5-Aminopyrazin-2-yl)-3'-fluorobiphenyl-2-yl]oxy}-6-methylpyrimidin-4-amine. |
| 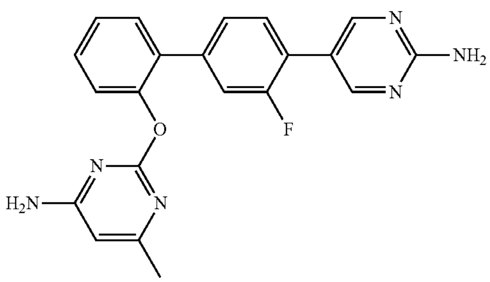 [SMILES: Cc1cc(N)nc(Oc2ccccc2-c2ccc(-c3cnc(N)nc3)c(F)c2)n1] | 617 | 5-{2'-[(4-Amino-6-methylpyrimidin-2-yl)oxy]-3-fluorobiphenyl-4-yl}pyrimidin-2-amine. |
| 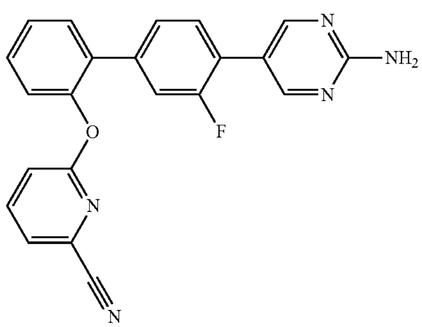 [SMILES: N#Cc1cccc(Oc2ccccc2-c2ccc(-c3cnc(N)nc3)c(F)c2)n1] | 618 | 6-{[4'-(2-Aminopyrimidin-5-yl)-3'-fluorobiphenyl-2-yl]oxy}pyridine-2-carbonitrile. |
| 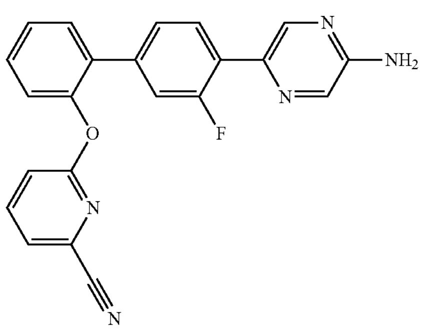 [SMILES: N#Cc1cccc(Oc2ccccc2-c2ccc(-c3cnc(N)cn3)c(F)c2)n1] | 619 | 6-{[4'-(5-Aminopyrazin-2-yl)-3'-fluorobiphenyl-2-yl]oxy}pyridine-2-carbonitrile. |
| 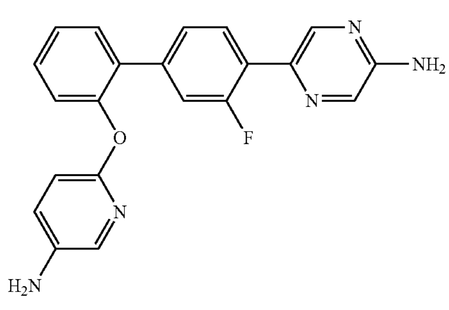 [SMILES: Nc1ccc(Oc2ccccc2-c2ccc(-c3cnc(N)cn3)c(F)c2)nc1] | 620 | 5-{2'-[(5-Aminopyridin-2-yl)oxy]-3-fluorobiphenyl-4-yl}pyrazin-2-amine. |

TABLE 3-continued

| STRUCTURE | COMPOUND # | NAME |
|---|---|---|
| 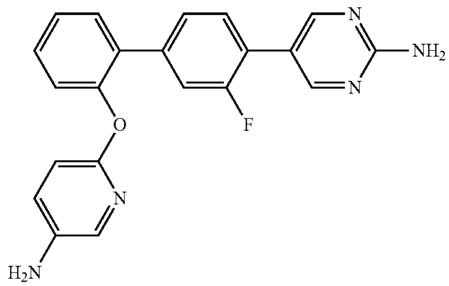 [SMILES: Nc1ccc(Oc2ccccc2-c2ccc(-c3cnc(N)nc3)c(F)c2)nc1] | 621 | 5-{2'-[(5-Aminopyridin-2-yl)oxy]-3-fluorobiphenyl-4-yl}pyrimidin-2-amine. |
| 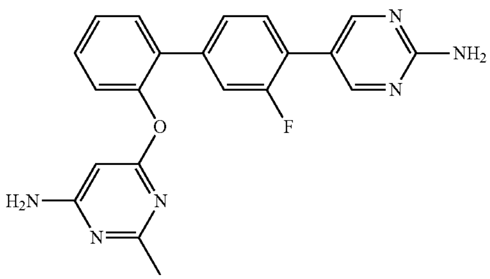 | 622 | 5-{2'-[(6-Amino-2-methylpyrimidin-4-yl)oxy]-3-fluorobiphenyl-4-yl}pyrimidin-2-amine. |
| 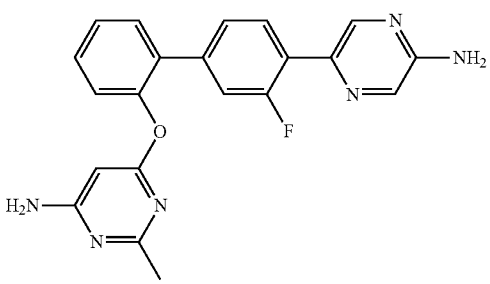 [SMILES: Cc1nc(N)cc(Oc2ccccc2-c2ccc(-c3cnc(N)cn3)c(F)c2)n1] | 623 | 6-{[4'-(5-Aminopyrazin-2-yl)-(3'fluorobiphenyl-2-yl]oxy}-2-methylpyrimidin4-amine. |
| 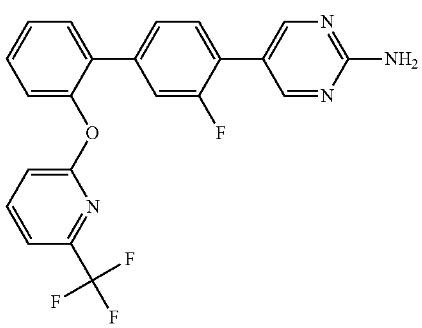 [SMILES: Nc1ncc(-c2ccc(-c3ccccc3Oc3cccc(C(F)(F)F)n3)cc2F)cn1] | 624 | 5-(3-Fluoro-2'-{[6-(trifluoromethyl)pyridin-2-yl]oxy}biphenyl-4-yl)pyrimidin-2-amine. |
| 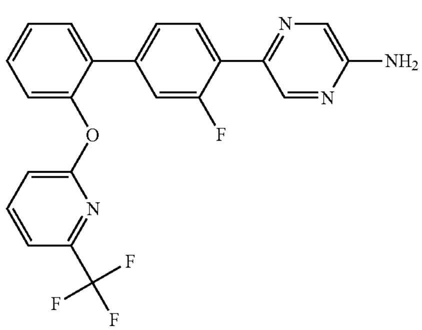 | 625 | 5-(3-Fluoro-2'-{[6-(trifluoromethyl)pyridin-2-yl]oxy}biphenyl-4-yl)pyrazin-2-amine. |

TABLE 3-continued

| STRUCTURE | COMPOUND # | NAME |
|---|---|---|
| 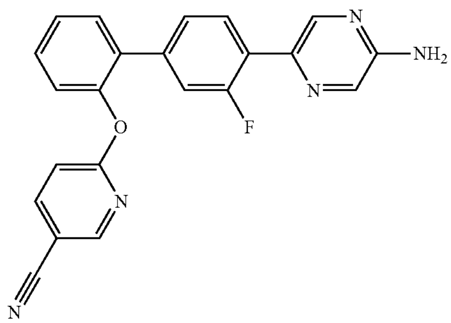 [SMILES: N#Cc1ccc(Oc2ccccc2-c2ccc(-c3cnc(N)cn3)c(F)c2)nc1] | 626 | 6-{[4'-(5-Aminopyrazin-2-yl)-3'-fluorobiphenyl-2-yl]oxy}pyridine-3-carbonitrile. |
| 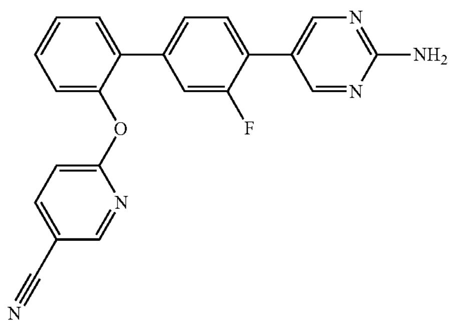 [SMILES: N#Cc1ccc(Oc2ccccc2-c2ccc(-c3cnc(N)nc3)c(F)c2)nc1] | 627 | 6-{[4'-(2-Aminopyrimidin-5-yl)-3'-fluorobiphenyl-2-yl]oxy}pyridine-3-carbonitrile. |
| 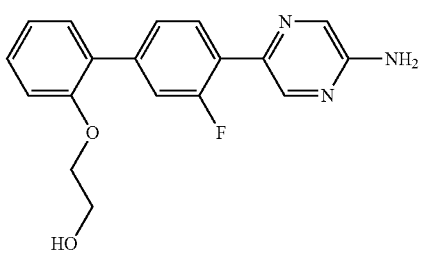 | 628 | 2-{[4'-(5-Aminopyrazin-2-yl)-3'-fluorobiphenyl-2-yl]oxy}ethanol. |
| 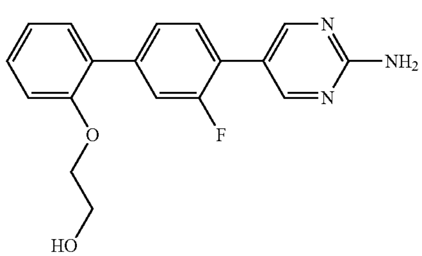 [SMILES: Nc1ncc(-c2ccc(-c3ccccc3OCCO)cc2F)cn1] | 629 | 2-{[4'-(2-Aminopyrimidin-5-yl)-3'-fluorobiphenyl-2-yl]oxy}ethanol. |
| 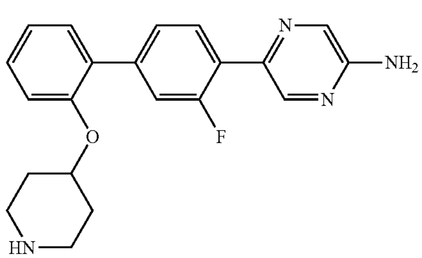 | 630 | 5-[3-Fluoro-2'-(piperidin-4-yloxy)biphenyl-4-yl]pyrazin-2-amine. |

TABLE 3-continued

| STRUCTURE | COMPOUND # | NAME |
|---|---|---|
| 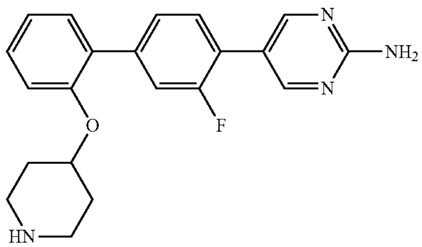 [SMILES: Nc1ncc(-c2ccc(-c3ccccc3OC3CCNCC3)cc2F)cn1] | 631 | 5-[3-fluoro-2'-(piperidin-4-yloxy)biphenyl-4-yl]pyrimidin-2-amine. |
| 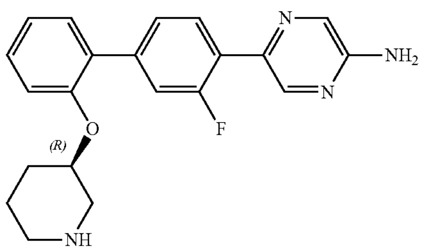 | 632 | 5-{3-Fluoro-2'-[(3R)-piperidin-3-yloxy]biphenyl-4-yl}pyrazin-2-amine |
| 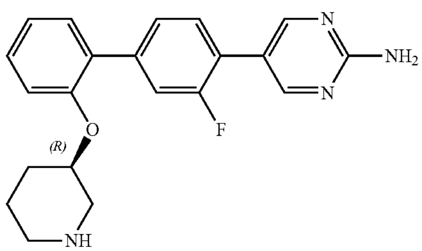 | 633 | 5-{3-Fluoro-2'-[(3R)-piperidin-3-yloxy]biphenyl-4-yl}pyrimidin-2-amine. |
| 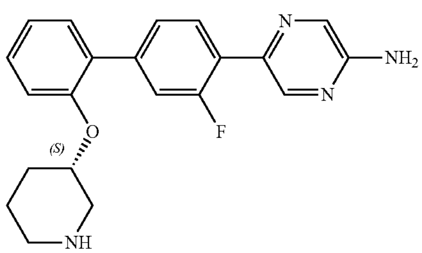 | 634 | 5-{3-Fluoro-2'-[(3S)-piperidin-3-yloxy]biphenyl-4-yl}pyrazin-2-amine. |
| 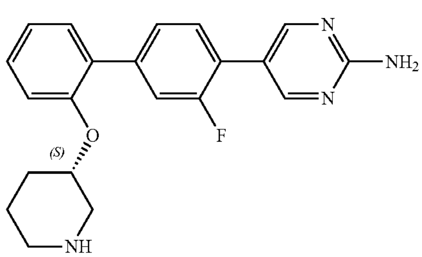 | 635 | 5-{3-Fluoro-2'-[(3S)-piperidin-3-yloxy]biphenyl-4-yl}pyrimidin-2-amine. |
| 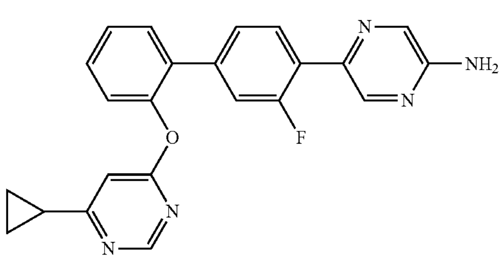 [SMILES: Nc1cnc(-c2ccc(-c3ccccc3Oc3cc(C4CC4)ncn3)cc2F)cn1] | 636 | 5-{2'-[(6-Cyclopropylpyrimidin-4-yl)oxy]-3-fluorobiphenyl-4-yl}pyrazin-2-amine. |

TABLE 3-continued

| STRUCTURE | COMPOUND # | NAME |
|---|---|---|
| 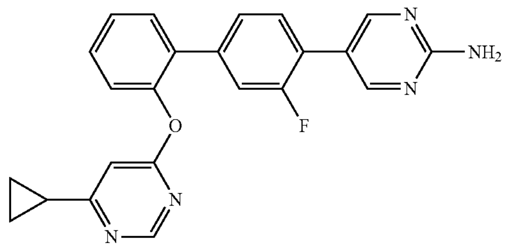 [SMILES: Nc1ncc(-c2ccc(-c3ccccc3Oc3cc(C4CC4)ncn3)cc2F)cn1] | 637 | 5-{2'-[(6-Cyclopropylpyrimidin-4-yl)oxy]-3-fluorobiphenyl-4-yl}pyrimidin-2-amine. |
| 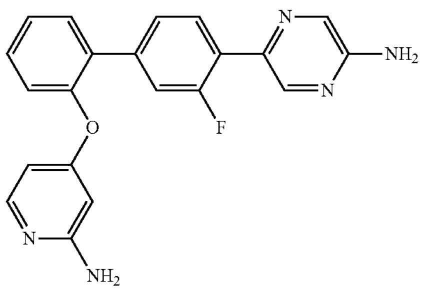 [SMILES: Nc1cnc(-c2ccc(-c3ccccc3Oc3ccnc(N)c3)cc2F)cn1] | 638 | 5-{2'-[(2-Aminopyridin-4-yl)oxy]-3-fluorobiphenyl-4-yl}pyrazin-2-amine. |
| 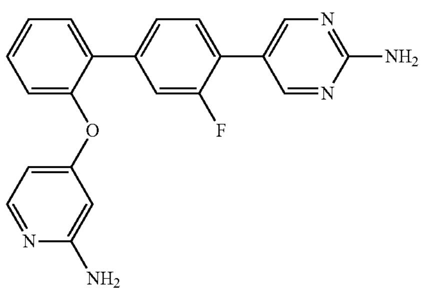 [SMILES: Nc1cc(Oc2ccccc2-c2ccc(-c3cnc(N)nc3)c(F)c2)ccn1] | 639 | 5-{2'-[(2-Aminopyridin-4-yl)oxy]-3-fluorobiphenyl-4-yl}pyrimidin-2-amine. |
| 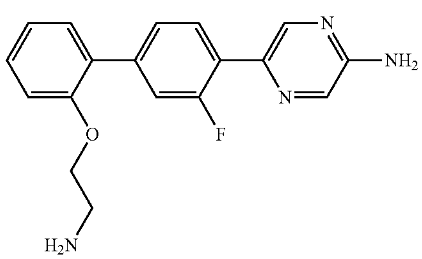 [SMILES: NCCOc1ccccc1-c1ccc(-c2cnc(N)cn2)c(F)c1] | 640 | 5-[2'-(2-Aminoethoxy)-3-fluorobiphenyl-4-yl]pyrazin-2-amine. |
| 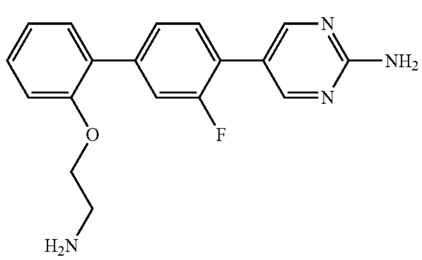 | 641 | 5-[2'-(2-Aminoethoxy)-3-fluorobiphenyl-4-yl]pyrimidin-2-amine. |
| 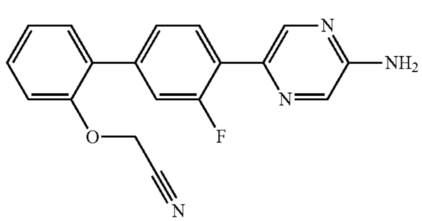 [SMILES: N#CCOc1ccccc1-c1ccc(-c2cnc(N)cn2)c(F)c1] | 642 | {[4'-(5-Aminopyrazin-2-yl)-3'-fluorobiphenyl-2-yl]oxy}acetonitrile. |

TABLE 3-continued

| STRUCTURE | COMPOUND # | NAME |
|---|---|---|
| 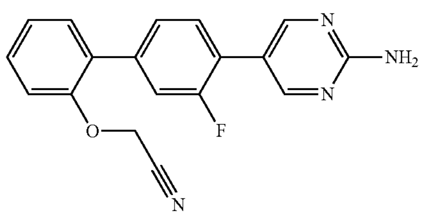 | 643 | {[4'-(2-Aminopyrimidin-5-yl)-3'-fluorobiphenyl-2-yl]oxy}acetonitrile. |
| 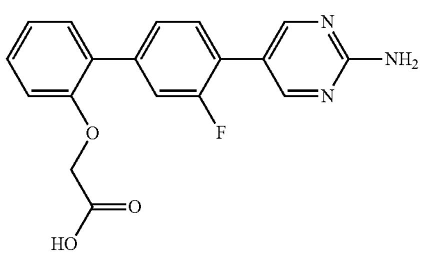 [SMILES: Nc1ncc(-c2ccc(-c3ccccc3OCC(=O)O)cc2F)cn1] | 644 | {[4'-(2-Aminopyrimidin-5-yl)-3'-fluorobiphenyl-2-yl]oxy}acetic acid. |
| 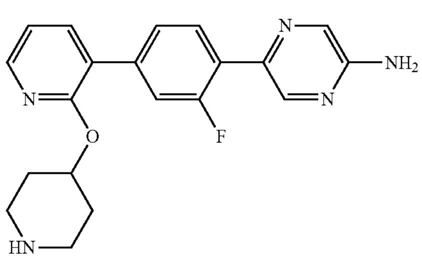 [SMILES: Nc1cnc(-c2ccc(-c3cccnc3OC3CCNCC3)cc2F)cn1] | 645 | 5-{2-Fluoro-4-[2-(piperidin-4-yloxy)pyridin-3-yl]phenyl}pyrazin-2-amine. |
| 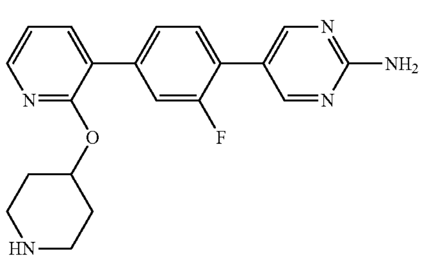 | 646 | 5-{2-Fluoro-4-[2-(piperidin-4-yloxy)pyridin-3-yl]phenyl}pyrimidin-2-amine. |
| 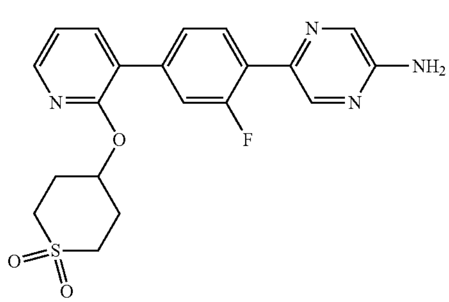 | 647 | 5-(4-{2-[(1,1-Dioxidotetrahydro-2H-thiopyran4-yl)oxy]pyridin-3-yl}-2-fluorophenyl)pyrazin-2-amine. |

TABLE 3-continued

| STRUCTURE | COMPOUND # | NAME |
|---|---|---|
| 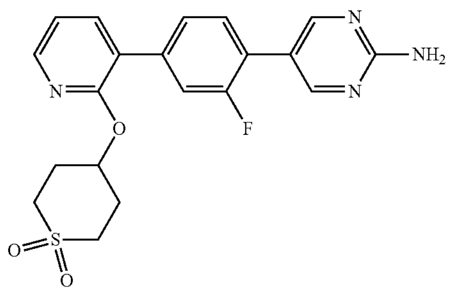 [SMILES: Nc1ncc(-c2ccc(-c3cccnc3OC3CCS(=O)(=O)CC3)cc2F)cn1] | 648 | 5-(4-{2-[(1,1-Dioxidotetranydro-2H-thiopyran-4-yl)oxy]pyridin-3-yl}-2-fluorophenyl)pyrimidin-2-amine. |
| 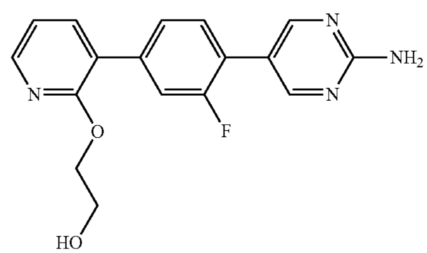 [SMILES: Nc1ncc(-c2ccc(-c3cccnc3OCCO)cc2F)cn1] | 649 | 2-({3-[4-(2-Aminopyrimidin-5-yl)-3-fluorophenyl]pyridin-2-yl}oxy)ethanol. |
| 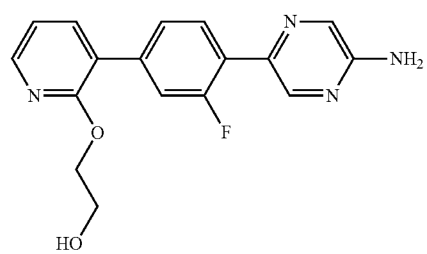 [SMILES: Nc1cnc(-c2ccc(-c3cccnc3OCCO)cc2F)cn1] | 650 | 2-({3-[4-(5-Aminopyrazin-2-yl)-3-fluorophenyl]pyridin-2-yl}oxy)ethanol. |
| 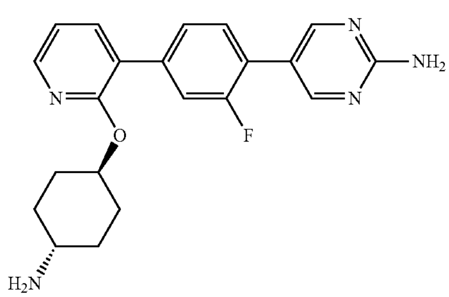 [SMILES: Nc1ncc(-c2ccc(-c3cccnc3O[C@H]3CC[C@H](N)CC3)cc2F)cn1] | 651 | 5-(4-{2-[(trans-4-Aminocyclohexyl)oxy]pyridin-3-yl}-2-fluorophenyl)pyrimidin-2-amine. |
| 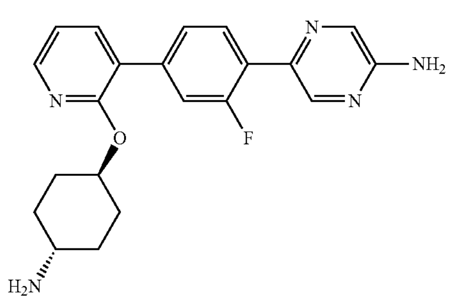 [SMILES: Nc1cnc(-c2ccc(-c3cccnc3O[C@H]3CC[C@H](N)CC3)cc2F)cn1] | 652 | 5-(4-{2-[(trans-4-Aminocyclohexyl)oxy]pyridin-3-yl}-2-fluorophenyl)pyrazin-2-amine formic acid salt |

TABLE 3-continued

| STRUCTURE | COMPOUND # | NAME |
|---|---|---|
| 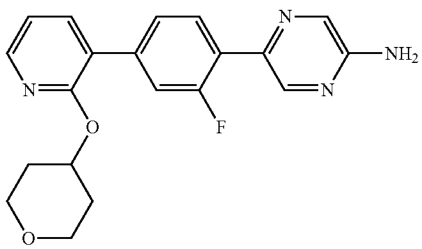 [SMILES: Nc1cnc(-c2ccc(-c3cccnc3OC3CCOCC3)cc2F)cn1] | 653 | 5-{2-Fluoro-4-[2-(tetrahydro-2H-pyran-4-yloxy)pyridin-3-yl]phenyl}pyrazin-2-amine. |
| 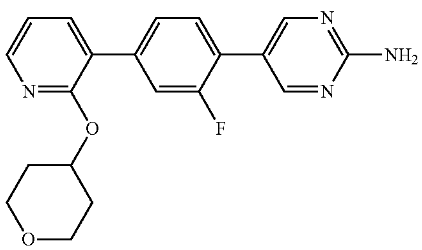 [SMILES: Nc1ncc(-c2ccc(-c3cccnc3OC3CCOCC3)cc2F)cn1] | 654 | 5-{2-Fluoro-4-[2-(tetrahydro-2H-pyran-4-yloxy)pyridin-3-yl]phenyl}pyrimidin-2-amine |
| 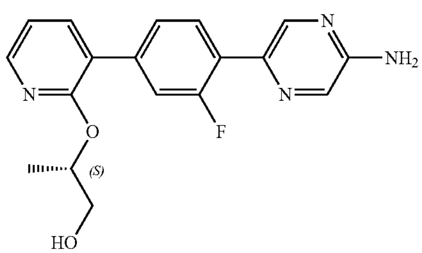 | 655 | (2R)-2-({3-[4-(5-Aminopyrazin-2-yl)-3-fluorophenyl]pyridin-2-yl}oxy)propan-1-ol. |
| 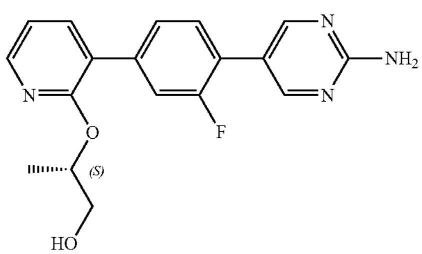 | 656 | (2R)-2-({3-[4-(2-Aminopyrimidin-5-yl)-3-fluorophenyl]pyridin-2-yl}oxy)propan-1-ol. |
| 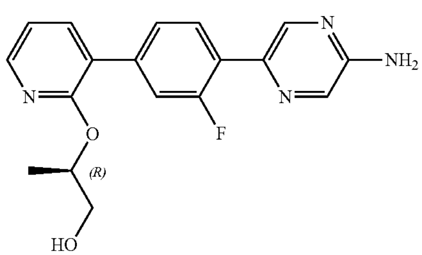 | 657 | (2S)-2-({3-[4-(5-Aminopyrazin-2-yl)-3-fluorophenyl]pyridin-2-yl}oxy)propan-1-ol. |
| 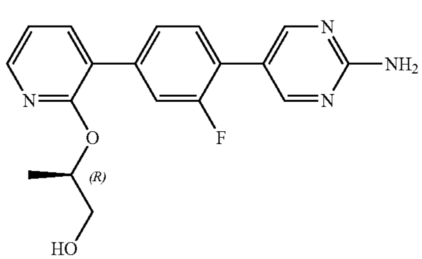 | 658 | (2I)-2-({3-[4-(2-Aminopyrimidin-5-yl)-3-fluorophenyl]pyridin-2-yl}oxy)propan-1-ol |

TABLE 3-continued

| STRUCTURE | COMPOUND # | NAME |
|---|---|---|
| 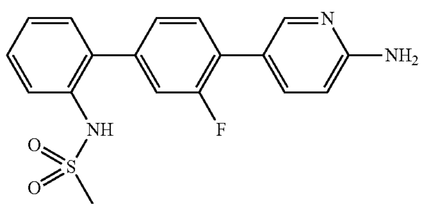 [SMILES: CS(=O)(=O)Nc1ccccc1-c1ccc(-c2ccc(N)nc2)c(F)c1] | 659 | N-(4'-(6-Aminopyridin-3-yl)-3'-fluoro-[1,1'-biphenyl]-2-yl)methanesulfonamide |
| 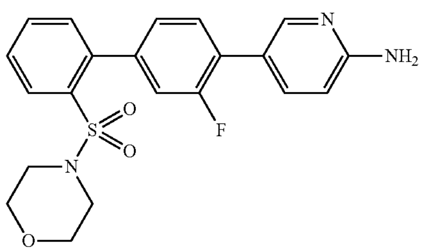 [SMILES: Nc1ccc(-c2ccc(-c3ccccc3S(=O)(=O)N3CCOCC3)cc2F)cn1] | 660 | 5-(3-Fluoro-2'-(morpholinosulfonyl)-[1,1'-biphenyl]-4-yl)pyridin-2-amine |
| 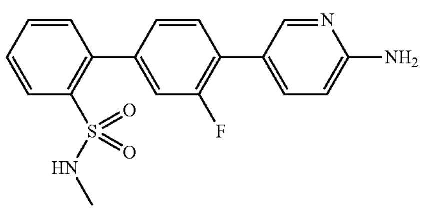 [SMILES: CNS(=O)(=O)c1ccccc1-c1ccc(-c2ccc(N)nc2)c(F)c1] | 661 | 4'-(6.-Aminopyridin-3-yl)-3'-fluoro-N-methyl-[1,1'-biphenyl]-2-sulfonamide |
| 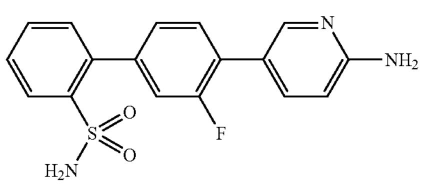 [SMILES: Nc1ccc(-c2ccc(-c3ccccc3S(N)(=O)=O)cc2F)cn1] | 662 | 4'-(6-Aminopyridin-3-yl)-3'-fluoro-[1,1'-biphenyl]-2-sulforiamide trifluoroacetate |
| 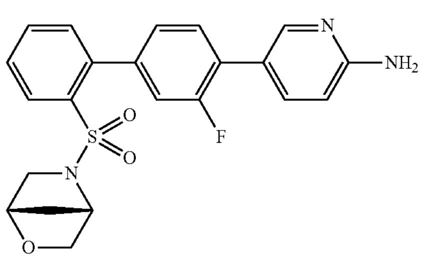 [SMILES: Nc1ccc(-c2ccc(-c3ccccc3S(=O)(=O)N3C[C@@H]4C[C@H]3CO4)cc2F)cn1] | 663 | 5-(2'-((1S,4S)-2-Oxa-5-azabicyclo[2.2.1]heptan-5-ylsulfonyl)-3-fluoro-[1,1'-biphenyl]-4-yl)pyridin-2-amine |
| 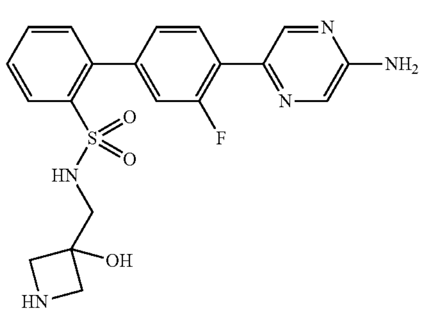 [SMILES: Nc1cnc(-c2ccc(-c3ccccc3S(=O)(=O)NCC3(O)CNC3)cc2F)cn1] | 664 | 4'-(6-Aminopyrazin-2-yl)-3'-fluoro-N-((3-hydroxyazetidin-3-yl)methyl)-[1,1'-biphenyl]-2-sulfonamide |

TABLE 3-continued

| STRUCTURE | COMPOUND # | NAME |
|---|---|---|
| 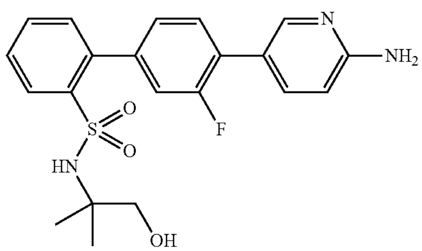 [SMILES: CC(C)(CO)NS(=O)(=O)c1ccccc1-c1ccc(-c2ccc(N)nc2)c(F)c1] | 665 | 4'-(6-Aminopyridin-3-yl)-3'-fluoro-N-(1-hydroxy-2-methylpropan-2-yl)-[1,1'-biphenyl]-2-sulfonamide |
| 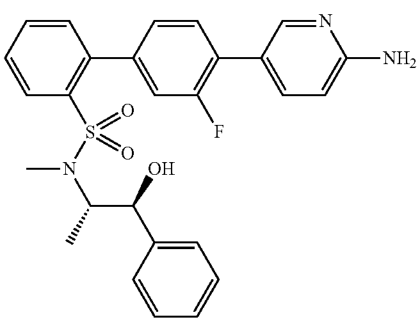 [SMILES: C[C@@H]([C@@H](O)c1ccccc1)N(C)S(=O)(=O)c1ccccc1-c1ccc(-c2ccc(N)nc2)c(F)c1] | 666 | 4'-(6-Aminopyridin-3-yl)-3'-fluoro-N-((1S,2S)-1-hydroxy-1-phenylpropan-2-yl)-N-methyl-[1,1'-biphenyl]-2-sulfonamide |
| 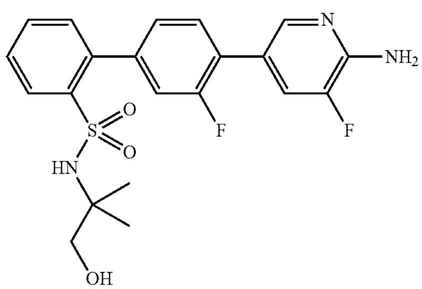 [SMILES: CC(C)(CO)NS(=O)(=O)c1ccccc1-c1ccc(-c2cnc(N)c(F)c2)c(F)c1] | 667 | 4'-(6-Amino-5-fluoropyridin-3-yl)-3'-fluoro-N-(1-hydroxy-2-methylpropan-2-yl)-[1,1'-biphenyl]-2-sulfonamide |
| 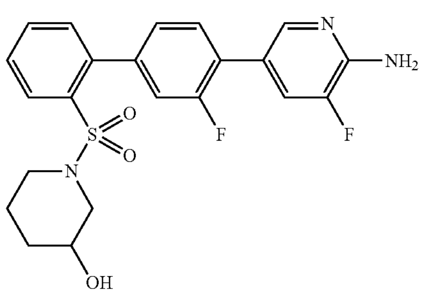 [SMILES: Nc1ncc(-c2ccc(-c3ccccc3S(=O)(=O)N3CCCC(O)C3)cc2F)cc1F] | 668 | (racemic)-1-((4'-(6-Amino-5-fluoropyridin-3-yl)-3'-fluoro-[1,1'-biphenyl]-2-yl)sulfonyl)piperidin-3-ol |
| 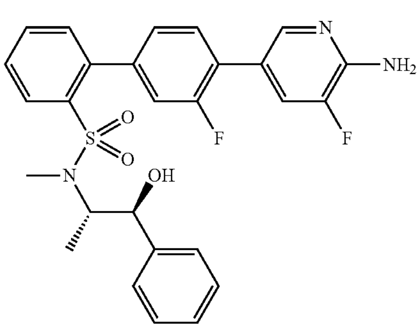 [SMILES: C[C@@H]([C@@H](O)c1ccccc1)N(C)S(=O)(=O)c1ccccc1-c1ccc(-c2cnc(N)c(F)c2)c(F)c1] | 669 | 4'-(6-Amino-5-fluoropyridin-3-yl)-3'-fluoro-N-((1S,2S)-1-hydroxy-1-phenylpropan-2-yl)-N-methyl-[1,1'-biphenyl]-2-sulfonamide |

TABLE 3-continued

| STRUCTURE | COMPOUND # | NAME |
|---|---|---|
| 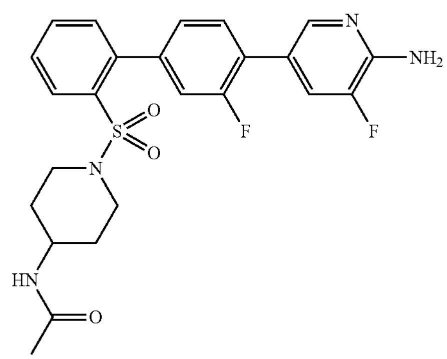 [SMILES: CC(=O)NC1CCN(S(=O)(=O)c2ccccc2-c2ccc(-c3cnc(N)c(F)c3)c(F)c2)CC1] | 670 | N-(1-((4'-(6-Amino-5-fluoropyridin-3-yl)-3'-fluoro-[1,1'-biphenyl]-2-yl)sulfonyl)piperidin-4-yl)acetamide |
| 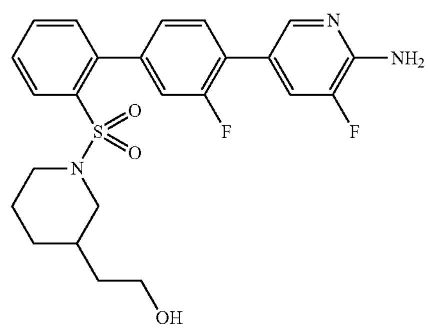 [SMILES: Nc1ncc(-c2ccc(-c3ccccc3S(=O)(=O)N3CCCC(CCO)C3)cc2F)cc1F] | 671 | racemic 2-(1-((4'-(6-Amino-5-fluoropyridin-3-yl)-3'-fluoro-[1,1'-biphenyl]-2-yl)sulfonyl)piperidin-3-yl)ethanol. |
| 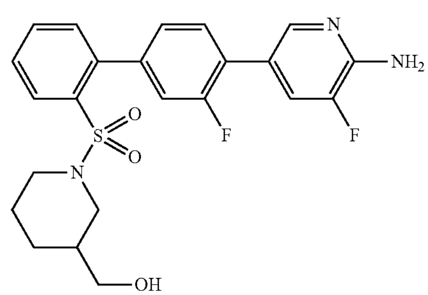 [SMILES: Nc1ncc(-c2ccc(-c3ccccc3S(=O)(=O)N3CCCC(CO)C3)cc2F)cc1F] | 672 | racemic 1-(4'-(6-Amino-5-fluoropyridin-3-yl)-3'-fluoro-[1,1'-biphenyl]-2-yl)sulfonyl)piperidin-3-yl)methanol. |
| 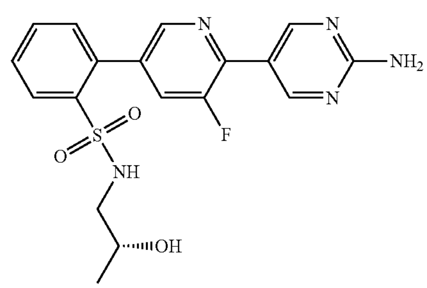 [SMILES: C[C@@H](O)CNS(=O)(=O)c1ccccc1-c1cnc(-c2cnc(N)nc2)c(F)c1] | 673 | 2-[6-(2-Aminopyrimidin-5-yl)-5-fluoropyridin-3-yl]-N-[(2R)-2-hydroxypropyl]benzenesulfonamide. |
| 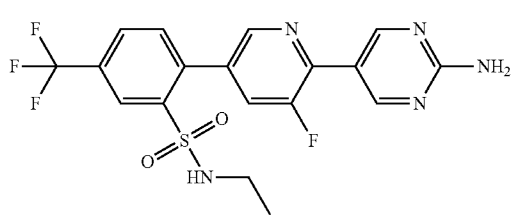 [SMILES: CCNS(=O)(=O)c1cc(C(F)(F)F)ccc1-c1cnc(-c2cnc(N)nc2)c(F)c1] | 674 | 2-[6-(2-Aminopyrimidin-5-yl)-5-fluoropyridin-3-yl]-N-ethyl-5-(trifluoromethyl)benzenesulfonamide. |

TABLE 3-continued

| STRUCTURE | COMPOUND # | NAME |
|---|---|---|
| 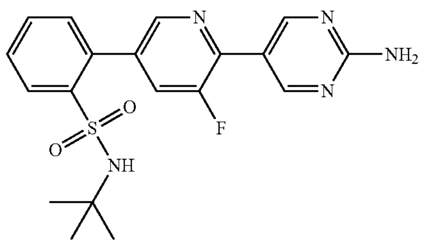 [SMILES: CC(C)(C)NS(=O)(=O)c1ccccc1-c1cnc(-c2cnc(N)nc2)c(F)c1] | 675 | 2-[6-(2-Aminopyrimidin-5-yl)-5-fluoropyridin-3-yl]-N-tert-butylbenzenesulfonamide. |
| 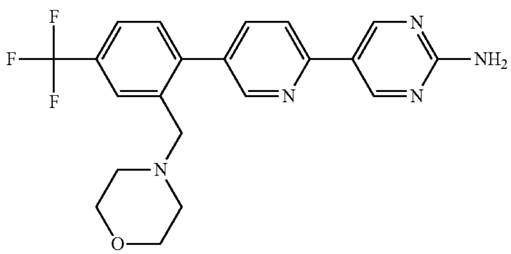 [SMILES: Nc1ncc(-c2ccc(-c3ccc(C(F)(F)F)cc3CN3CCOCC3)cn2)cn1] | 676 | 5-{5-[2-(Morpholin-4-ylmethyl)-4-(trifluoromethyl)phenyl]pyridin-2-yl}pyrimidin-2-amine. |
| 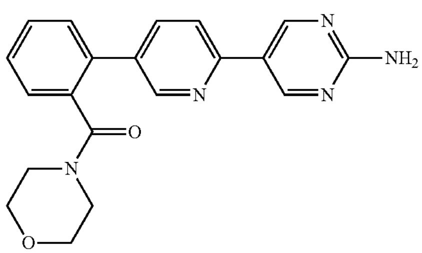 [SMILES: Nc1ncc(-c2ccc(-c3ccccc3C(=O)N3CCOCC3)cn2)cn1] | 677 | 5-{5-[2-(Morpholin-4-ylcarbonyl)phenyl]pyridin-2-yl}pyrimidin-2-amine. |
| 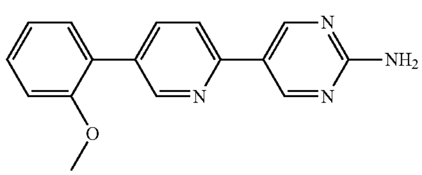 [SMILES: COc1ccccc1-c1ccc(-c2cnc(N)nc2)nc1] | 678 | 5-[5-(2-Methoxyphenyl)pyridin-2-yl]pyrimidin-2-amine. |
| 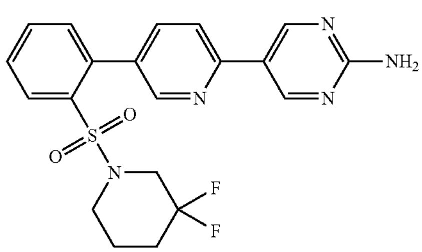 [SMILES: Nc1ncc(-c2ccc(-c3ccccc3S(=O)(=O)N3CCCC(F)(F)C3)cn2)cn1] | 679 | 5-(5-{2-[(3,3Difluoropiperidin-1-yl)sulfonyl]phenyl}pyridin-2-yl)pyrimidin-2-amine trifluoroacetic acid salt. |
| 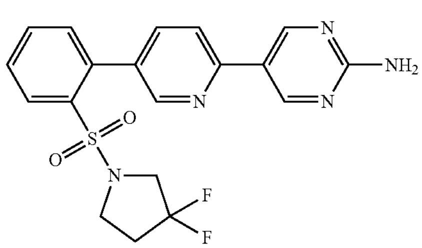 [SMILES: Nc1ncc(-c2ccc(-c3ccccc3S(=O)(=O)N3CCC(F)(F)C3)cn2)cn1] | 680 | 5-(5-{2-[(3,3-Difluoropyrrolidin-1-yl)sulfonyl]phenyl}pyridin-2-yl)pyrimidin-2-amine trifluoroacetic acid salt. |

TABLE 3-continued

| STRUCTURE | COMPOUND # | NAME |
|---|---|---|
| (structure) | 681 | 5-{5-[2-(Azepan-1-ylsulfonyl)phenyl]pyridin-2-yl}pyrimidin-2-amine trifluoroacetic acid salt. |
| (structure) | 682 | 5-(5-{2-[(4,4-Difluoropiperidin-1-yl)sulfonyl]phenyl}pyridin-2-yl)pyrimidin-2-amine trifluoroacetic acid salt. |
| (structure) | 683 | 2-[6-(2-Aminopyrimidin-5-yl)pyridin-3-yl]-N-ethylbenzenesulfonamide trifluoroacetic acid salt. |
| (structure) | 684 | 2-[6-(2-Aminopyrimidin-5-yl)pyridin-3-yl]-N-(dicyclopropylmethyl)benzenesulfonamide trifluoroacetic acid salt. |
| (structure) | 685 | 2-[6-(2-Aminopyrimidin-5-yl)pyridin-3-yl]-N-[(1S)-2,2,2-trifluoro-1-methylethyl]benzenesulfonamide trifluoroacetic acid salt. |
| (structure) | 686 | 2-[6-(2-Aminopyrimidin-5-yl)pyridin-3-yl]-N-[(1R)-2,2,2-trifluoro-1-methylethyl]benzenesulfonamide trifluoroacetic acid salt. |

TABLE 3-continued

| STRUCTURE | COMPOUND # | NAME |
|---|---|---|
| 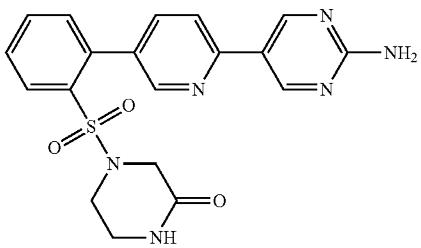 [SMILES: Nc1ncc(-c2ccc(-c3ccccc3S(=O)(=O)N3CCNC(=O)C3)cn2)cn1] | 687 | 4-({2-[6-(2-Aminopyrimidin-5-yl)pyridin-3-yl]phenyl}sulfonyl)piperazin-2-one. |
| 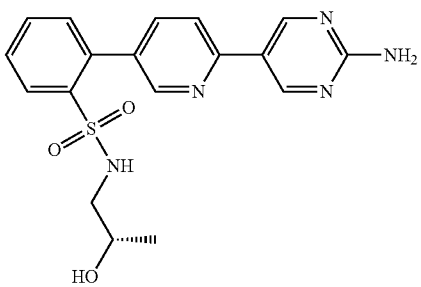 [SMILES: C[C@H](O)CNS(=O)(=O)c1ccccc1-c1ccc(-c2cnc(N)nc2)nc1] | 688 | 2-[6-(2-Aminopyrimidin-5-yl)pyridin-3-yl]-N-[(2S)-2-hydroxypropyl]benzenesulfonamide. |
| 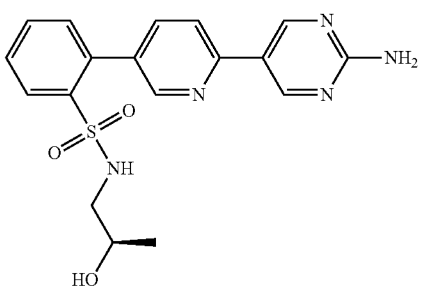 [SMILES: C[C@@H](O)CNS(=O)(=O)c1ccccc1-c1ccc(-c2cnc(N)nc2)nc1] | 689 | 2-[6-(2-Aminopyrimidin-5-yl)pyridin-3-yl]-N-[(2R)-2-hydroxypropyl]benzenesulfonamide. |
| 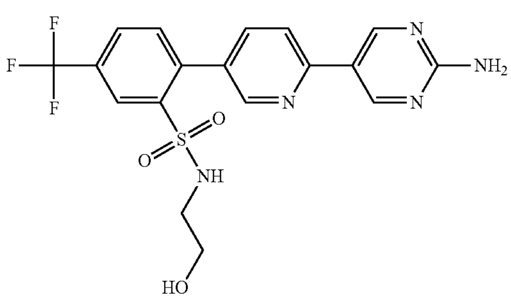 [SMILES: Nc1ncc(-c2ccc(-c3ccc(C(F)(F)F)cc3S(=O)(=O)NCCO)cn2)cn1] | 690 | 2-[6-(2-Aminopyrimidin-5-yl)pyridin-3-yl]-N-(2-hydroxyethyl)-5-(trifluoromethyl)benzenesulfonamide. |
| 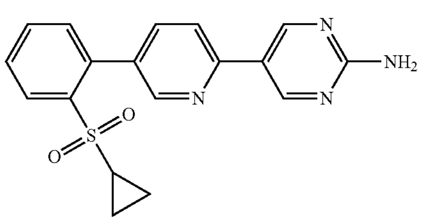 [SMILES: Nc1ncc(-c2ccc(-c3ccccc3S(=O)(=O)C3CC3)cn2)cn1] | 691 | 5-{5-[2-(Cyclopropylsulfonyl)phenyl]pyridin-2yl}pyrimidin-2-amine trifluoroacetic acid salt. |
| 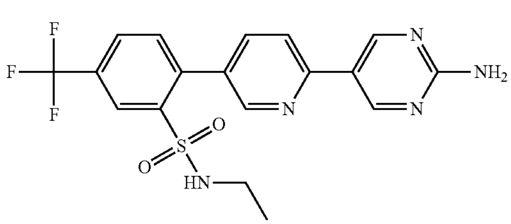 [SMILES: CCNS(=O)(=O)c1cc(C(F)(F)F)ccc1-c1ccc(-c2cnc(N)nc2)nc1] | 692 | 2-[6-(2-Aminopyrimidin-5-yl)pyridin-3-yl]-N-ethyl-5-(trifluoromethyl)benzenesulfonamide trifluoroacetic acid salt. |

TABLE 3-continued

| STRUCTURE | COMPOUND # | NAME |
|---|---|---|
| 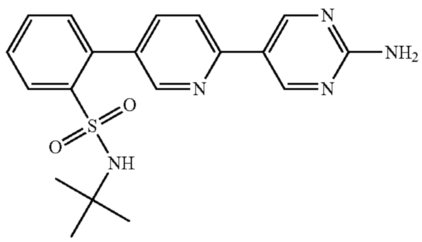 [SMILES: CC(C)(C)NS(=O)(=O)c1ccccc1-c1ccc(-c2cnc(N)nc2)nc1] | 693 | 2-[6-(2-Aminopyrimidin-5-yl)pyridin-3-yl]-N-tert-butylbenzenesulfonamide. |
| 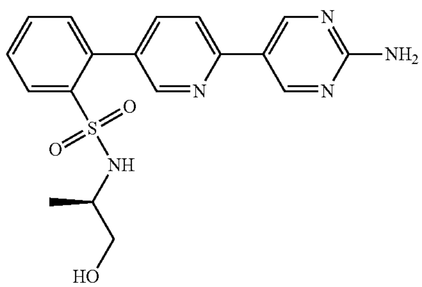 [SMILES: C[C@H](CO)NS(=O)(=O)c1ccccc1-c1ccc(-c2cnc(N)nc2)nc1] | 694 | 2-[6-(2-Aminopyrimidin-5-yl)pyridin-3-yl]-N-[(1R)-2-hydroxy-1-methylethyl]benzenesulfonamide. |
| 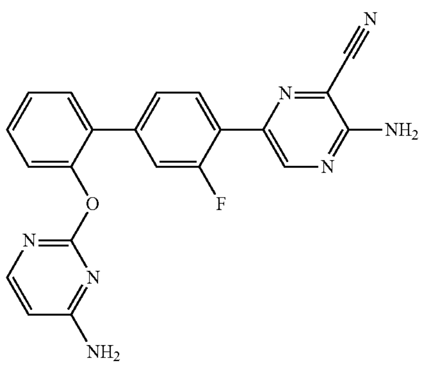 [SMILES: N#Cc1nc(-c2ccc(-c3ccccc3Oc3nccc(N)n3)cc2F)cnc1N] | 695 | 3-Amino-6-{2'-[(4-aminopyrimidin-2-yl)oxy]-3-fluorobiphenyl-4-yl}pyrazine-2-carbonitrile trifluoroacetic acid salt. |
| 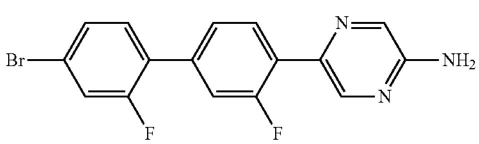 [SMILES: Nc1cnc(-c2ccc(-c3ccc(Br)cc3F)cc2F)cn1] | 696 | 5-(4'-Bromo-2',3-difluorobiphenyl-4-yl)pyrazin-2-amine. |
| 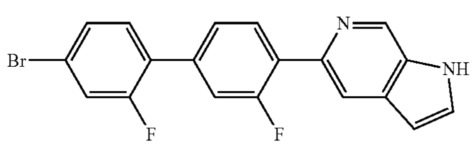 [SMILES: Fc1cc(Br)ccc1-c1ccc(-c2cc3cc[nH]c3cn2)c(F)c1] | 697 | 5-(4'-Bromo-2',3-difluorobiphenyl-4-yl)-1H-pyrrolo[2,3-b]pyridine. |
| 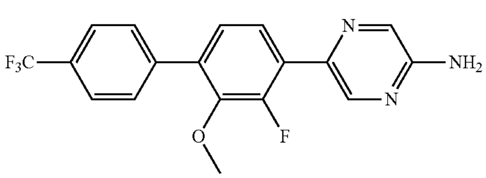 [SMILES: COc1c(-c2ccc(C(F)(F)F)cc2)ccc(-c2cnc(N)cn2)c1F] | 698 | 5-(3-fluoro-2-methoxy-4'-(trifluoromethyl)-[1,1'-biphenyl]-4-yl)pyrazin-2-amine. |
| 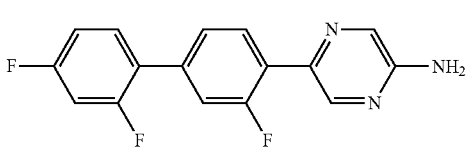 [SMILES: Nc1cnc(-c2ccc(-c3ccc(F)cc3F)cc2F)cn1] | 699 | 5-(2',3,4'-Trifluorobiphenyl-4-yl)pyrazin-2-amine |

TABLE 3-continued

| STRUCTURE | COMPOUND # | NAME |
|---|---|---|
| 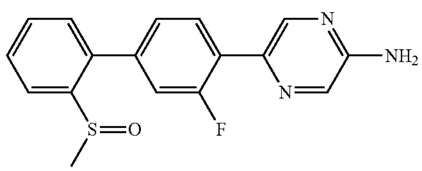 [SMILES: CS(=O)c1ccccc1-c1ccc(-c2cnc(N)cn2)c(F)c1] | 700 | racemic 5-[3-Fluoro-2'-(methylsulfinyl)biphenyl-4-yl]pyrazin-2-amine |
| 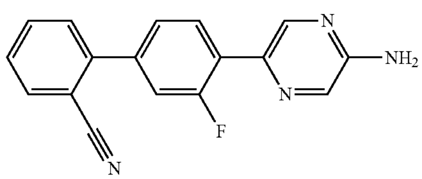 [SMILES: N#Cc1ccccc1-c1ccc(-c2cnc(N)cn2)c(F)c1] | 701 | 4'-(5-Aminopyrazin-2-yl)-3'-fluorobiphenyl-2-carbonitrile |
| 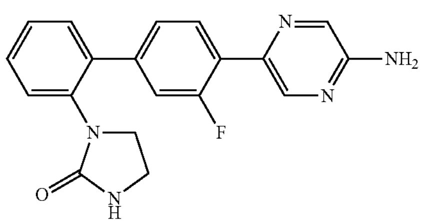 [SMILES: Nc1cnc(-c2ccc(-c3ccccc3N3CCNC3=O)cc2F)cn1] | 702 | 1-(4'-(5-Aminopyrazin-2-yl)-3'-fluoro-[1,1'-biphenyl]-2-yl)imidazolidin-2-one |
| 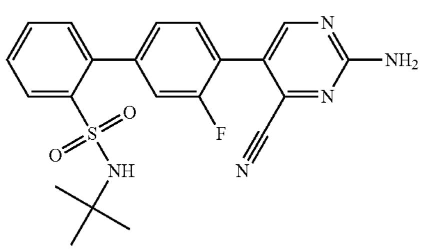 [SMILES: CC(C)(C)NS(=O)(=O)c1ccccc1-c1ccc(-c2cnc(N)nc2C#N)c(F)c1] | 703 | 4'-(2-Amino-4-cyanopyrimidin-5-yl)-N-tert-butyl-3'-fluorobiphanyl-2-sulfonamide |
| 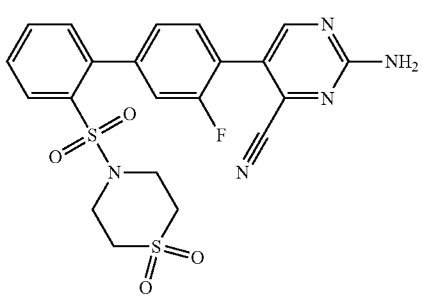 [SMILES: N#Cc1nc(N)ncc1-c1ccc(-c2ccccc2S(=O)(=O)N2CCS(=O)(=O)CC2)cc1F] | 704 | 6-Amino-3-{2'-[(1,1-dioxidothiomorpholin-4-yl)sulfonyl]-3-fluorobiphenyl4-yl}pyrazine-2-carbonitrile |
| 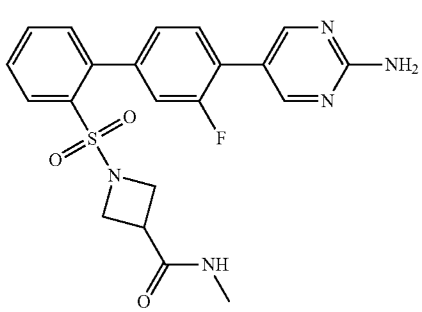 [SMILES: CNC(=O)C1CN(S(=O)(=O)c2ccccc2-c2ccc(-c3cnc(N)nc3)c(F)c2)C1] | 705 | 1-{[4'-(2-Aminopyrimidin-5-yl)-3'-fluorobiphenyl-2-yl]sulfonyl}-N-methylazetidine-3-carboxamide |

TABLE 3-continued

| STRUCTURE | COMPOUND # | NAME |
|---|---|---|
| 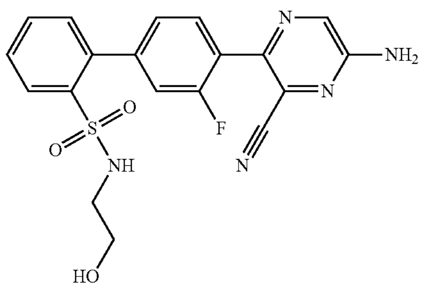 [SMILES: N#Cc1nc(N)cnc1-c1ccc(-c2ccccc2S(=O)(=O)NCCO)cc1F] | 706 | 4'-(5-Amino-3-cyanopyrazin-2-yl)-3'-fluoro-N-(2-hydroxyethyl)biphenyl-2-sulfonamide |
| 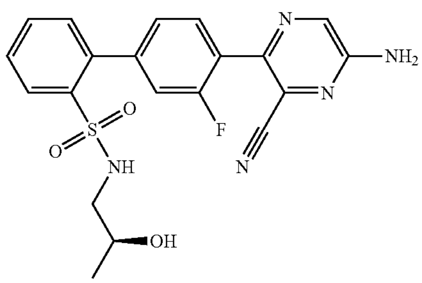 [SMILES: C[C@H](O)CNS(=O)(=O)c1ccccc1-c1ccc(-c2ncc(N)nc2C#N)c(F)c1] | 707 | 4'-(5-Amino-3-cyanopyrazin-2-yl)-3'-fluoro-N-[(2S)-2-hydroxypropyl]biphenyl-2-sulfonamide |
| 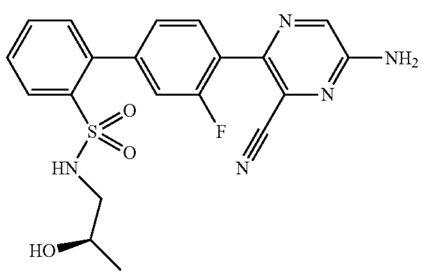 [SMILES: C[C@@H](O)CNS(=O)(=O)c1ccccc1-c1ccc(-c2ncc(N)nc2C#N)c(F)c1] | 708 | 4'-(5-Amino-3-cyanopyrazin-2-yl)-3'-fluoro-N-[(2R)-2-hydroxypropyl]biphenyl-2-sulfonamide |
| 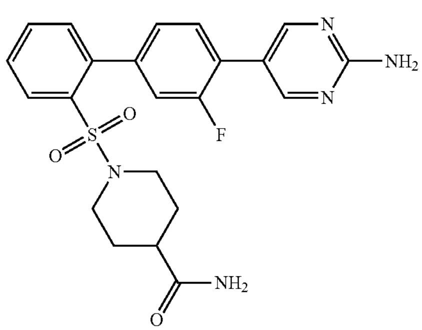 [SMILES: NC(=O)C1CCN(S(=O)(=O)c2ccccc2-c2ccc(-c3cnc(N)nc3)c(F)c2)CC1] | 709 | 1-((4'-(2-Aminopyrimidin-5-yl)-3'-fluoro-[1,1'-biphenyl]-2-yl)sulfonyl)piperidine-4-carboxamide |
| 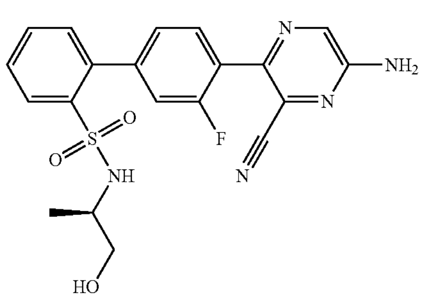 [SMILES: C[C@H](CO)NS(=O)(=O)c1ccccc1-c1ccc(-c2ncc(N)nc2C#N)c(F)c1] | 710 | 4'-(5-Amino-3-cyanopyrazin-2-yl)-3'-fluora-N-[(1R)-2-hydroxy-1-methylethyl]piphenyl-2-sulfonamide |

TABLE 3-continued

| STRUCTURE | COMPOUND # | NAME |
|---|---|---|
| 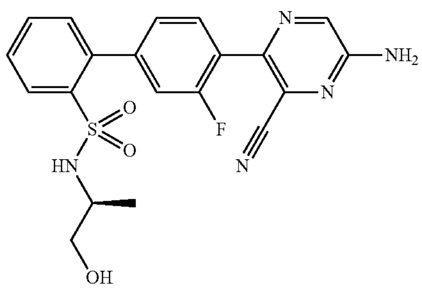 [SMILES: C[C@@H](CO)NS(=O)(=O)c1ccccc1-c1ccc(-c2ncc(N)nc2C#N)c(F)c1] | 711 | 4'-(5-Amino-3-cyanopyrazin-2-yl)-3'-fluoro-N-[(1S)-2-hydroxy-1-methylethyl)piphenyl-2-sulfonamide |
| 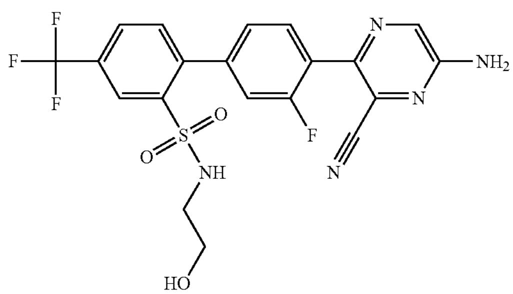 [SMILES: N#Cc1nc(N)cnc1-c1ccc(-c2ccc(C(F)(F)F)cc2S(=O)(=O)NCCO)cc1F] | 712 | 4'-(5-Amino-3-cyanopyrazin-2-yl)-3'-fluoro-N-(2-hydroxyethyl)-4-(trifluoromethyl)biphenyl-2-sulfonamide |
| 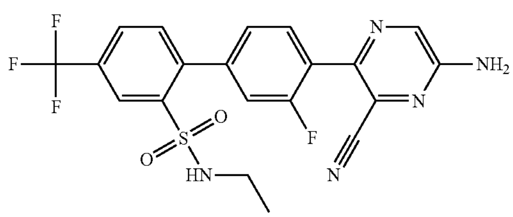 [SMILES: CCNS(=O)(=O)c1cc(C(F)(F)F)ccc1-c1ccc(-c2ncc(N)nc2C#N)c(F)c1] | 713 | 4'-(5-Amino-3-cyanopyrazin-2-yl)-N-ethyl-3'-fluoro-4-(trifluoromethyl)-[1,1'-biphenyl]-2-sulfonamide |
| 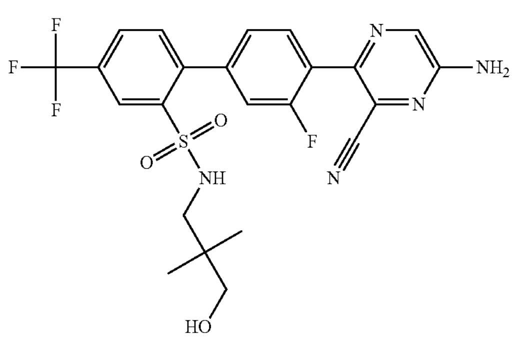 [SMILES: CC(C)(CO)CNS(=O)(=O)c1cc(C(F)(F)F)ccc1-c1ccc(-c2ncc(N)nc2C#N)c(F)c1] | 714 | 4'-(5-Amino-3-cyanopyrazin-2-yl)-3'-fluoro-N-(3-hydroxy-2,2-dimethylpropyl)biphenyl-2-sulfonamide |
| 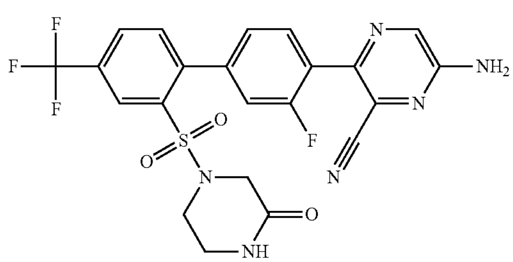 [SMILES: N#Cc1nc(N)cnc1-c1ccc(-c2ccc(C(F)(F)F)cc2S(=O)(=O)N2CCNC(=O)C2)cc1F] | 715 | 6-Amino-3-{3-fluoro-2'-[(3-oxopiperazin-1-yl)sulfonyl]-4'-(trifluoromethyl)biphenyl-4-yl}pyrazine-2-carbonitrile |

TABLE 3-continued
| STRUCTURE | COMPOUND # | NAME |
|---|---|---|
| 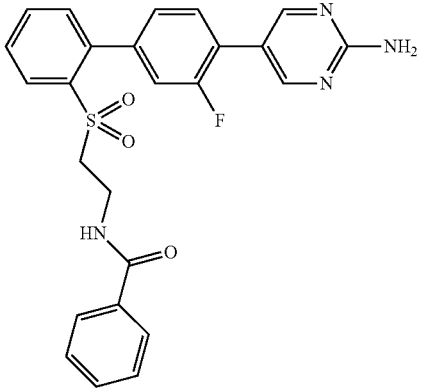 [SMILES: Nc1ncc(-c2ccc(-c3ccccc3S(=O)(=O)CCNC(=O)c3ccccc3)cc2F)cn1] | 716 | N-(2-{[4'-(2-Aminopyrimidin-5-yl)-3'-fluorobiphenyl-2-yl]sulfonyl}ethyl)benzamide |
| 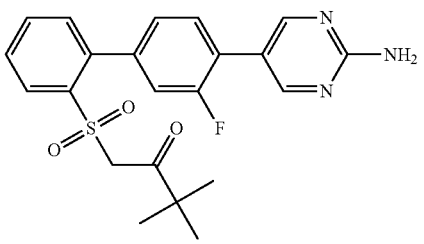 [SMILES: CC(C)(C)C(=O)CS(=O)(=O)c1ccccc1-c1ccc(-c2cnc(N)nc2)c(F)c1] | 717 | 1-{[4'-(2-Aminopyrimidin-5-yl)-3'-fluorobiphenyl-2-yl]sulfonyl)-3,3-dimethylbutan-2-one |
| 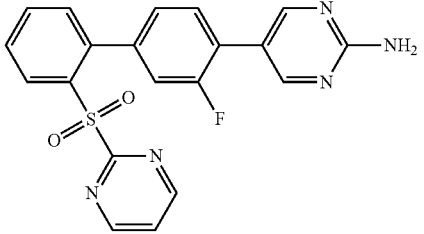 [SMILES: Nc1ncc(-c2ccc(-c3ccccc3S(=O)(=O)c3ncccn3)cc2F)cn1] | 718 | 5-[3-Fluoro-2'-(pyrimidin-2-ylsulfonyl)biphenyl-4-yl]pyrimidin-2-amine |
| 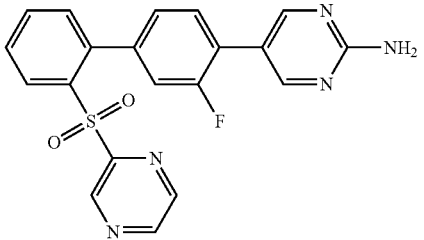 [SMILES: Nc1ncc(-c2ccc(-c3ccccc3S(=O)(=O)c3cnccn3)cc2F)cn1] | 719 | 5-[3-Fluoro-2'-(pyrazin-2-ylsulfonyl)biphenyl-4-yl]pyrimidin-2-amine |
| 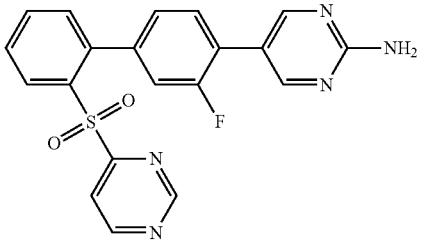 [SMILES: Nc1ncc(-c2ccc(-c3ccccc3S(=O)(=O)c3ccncn3)cc2F)cn1] | 720 | 5-[3-Fluoro-2'-(pyrimidin-4-ylsulfonyl)biphenyl-4-yl]pyrimidin-2-amine |

TABLE 3-continued

| STRUCTURE | COMPOUND # | NAME |
|---|---|---|
| 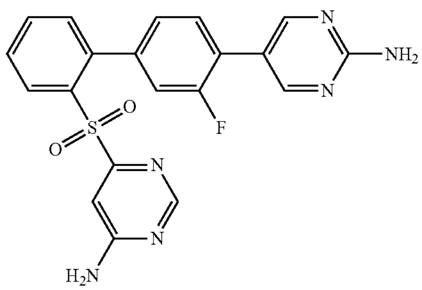 [SMILES: Nc1cc(S(=O)(=O)c2ccccc2-c2ccc(-c3cnc(N)nc3)c(F)c2)ncn1] | 721 | 5-{2'-[(6-Aminopyrimidin-4-yl)sulfonyl]-3-fluorobiphenyl-4-yl}pyrimidin-2-amine |
| 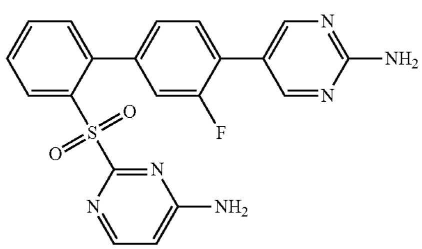 | 722 | 5-{2'-[(4-Aminopyrimidin-2-yl)sulfonyl]-3-fluorobiphenyl-4-yl}pyrimidin-2-amine |
| 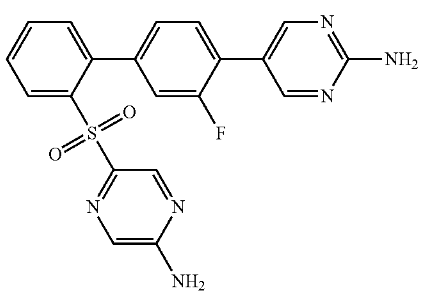 [SMILES: Nc1cnc(S(=O)(=O)c2ccccc2-c2ccc(-c3cnc(N)nc3)c(F)c2)cn1] | 723 | 5-{2'-[(5-Aminopyrazin-2-yl)sulfonyl]-3-fluorobiphenyl-4'-yl}pyrimidin-2-amine |
| 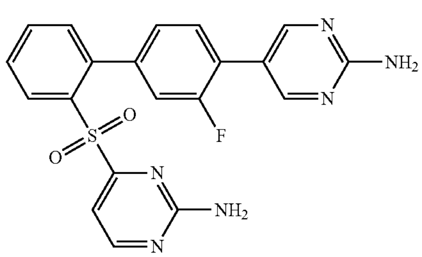 | 724 | 4-{[4'-(2-Aminopyrimidin-5-yl)-3'-fluorobiphenyl-2-yl]sulfonyl}pyrimidin-2-amine |
| 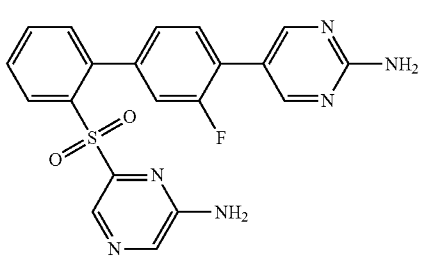 [SMILES: Nc1cncc(S(=O)(=O)c2ccccc2-c2ccc(-c3cnc(N)nc3)c(F)c2)n1] | 725 | 5-{2'-[(6-Aminopyrazin-2-yl)sulfonyl]-3-fluorobiphenyl-4-yl}pyrimidin-2-amine |

TABLE 3-continued

| STRUCTURE | COMPOUND # | NAME |
|---|---|---|
| 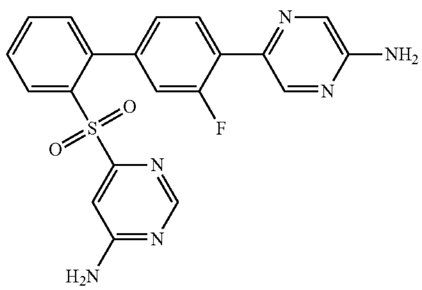 [SMILES: Nc1cnc(-c2ccc(-c3ccccc3S(=O)(=O)c3cc(N)ncn3)cc2F)cn1] | 726 | 6-{[4'-(5-Aminopyrazin-2-yl)-3'-fluorobiphenyl-2-yl]sulfonyl}pyrimidin-4-amine |
| 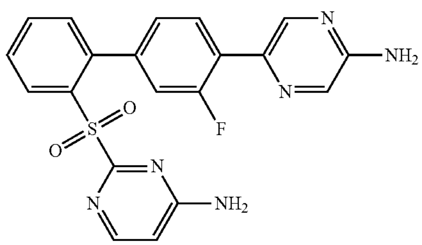 [SMILES: Nc1cnc(-c2ccc(-c3ccccc3S(=O)(=O)c3nccc(N)n3)cc2F)cn1] | 727 | 2.-{[4'-(5-Aminopyrazin-2-yl)-3'-fluorobiphenyl-2-yl]sulfonyl}pyrimidin-4-amine |
| 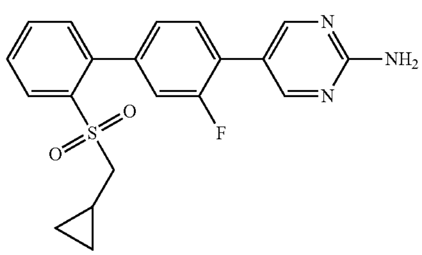 [SMILES: Nc1ncc(-c2ccc(-c3ccccc3S(=O)(=O)CC3CC3)cc2F)cn1] | 728 | 5-{2'-[(Cyclopropylmethyl)sulfonyl]-3-fluorobiphenyl-4-yl}pyrimidin-2-amine |
| 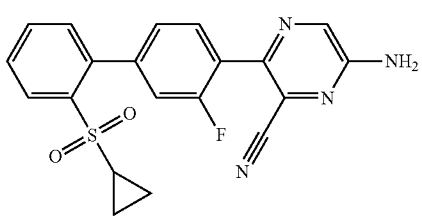 [SMILES: N#Cc1nc(N)cnc1-c1ccc(-c2ccccc2S(=O)(=O)C2CC2)cc1F] | 729 | 6-Amino-3-[2'-(cyclopropylsulfonyl)-3-fluorobiphenyl-4-yl]pyrazine-2-carbonitrile |
| 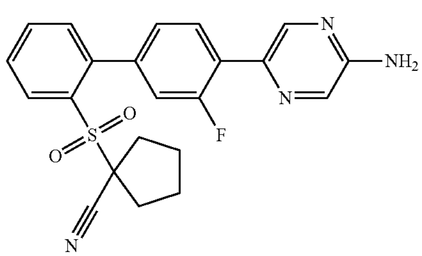 [SMILES: N#CC1(S(=O)(=O)c2ccccc2-c2ccc(-c3cnc(N)cn3)c(F)c2)CCCC1] | 730 | 1-{[4'-(5-Aminopyrazin-2-yl)-3'-fluorobiphenyl-2-yl]sulfonyl}cyclopentanecarbonitrile |
| 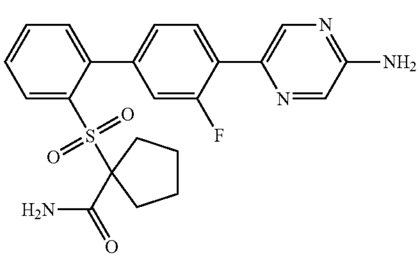 | 731 | 1-{[4'-(5-Aminopyrazin-2-yl)-3'-fluorobiphenyl-2-yl]sulfonyl}cyclopentanecarboxamide |

TABLE 3-continued

| STRUCTURE | COMPOUND # | NAME |
|---|---|---|
| 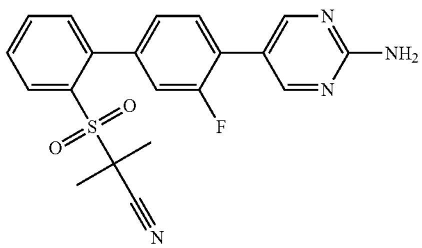 | 732 | 2-{[4'-(2-Aminopyrimidin-5-yl)-3'-fluorobiphenyl-2-yl]sulfonyl}-2-methylpropanenitrile |
| 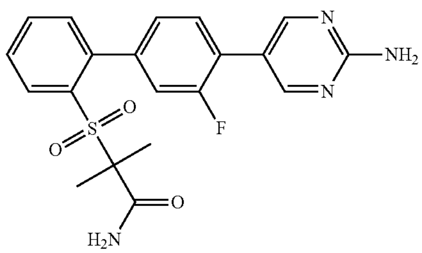 | 733 | 2-{[4'-(2-Aminopyridin-5-yl)-3'-fluorobiphenyl-2-yl]sulfonyl}-2-methylpropanamide |
| 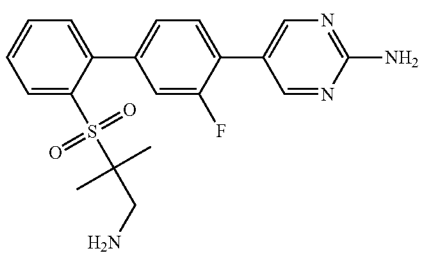 [SMILES: CC(C)(CN)S(=O)(=O)c1ccccc1-c1ccc(-c2cnc(N)nc2)c(F)c1] | 734 | 5-{2'-[(2-Amino-1,1-dimethylethyl)sulfonyl]-3-fluorobiphenyl-4-yl}pyrimidin-2-amine |
| 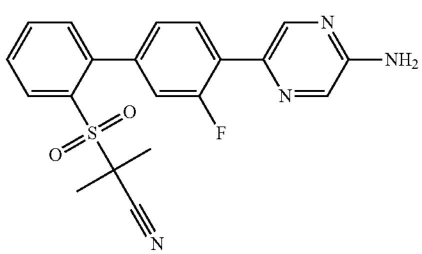 [SMILES: CC(C)(C#N)S(=O)(=O)c1ccccc1-c1ccc(-c2cnc(N)cn2)c(F)c1] | 735 | 2-{[4'-(5-Aminopyrazin-2-yl)-3'-fluorobiphenyl-2-yl]sulfonyl}-2-methylpropanenitrile |
| 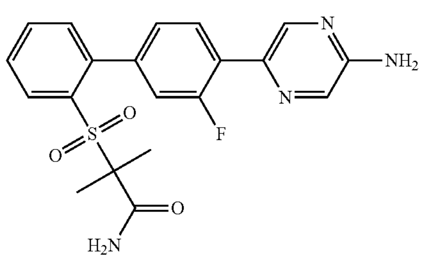 [SMILES: CC(C)(C(N)=O)S(=O)(=O)c1ccccc1-c1ccc(-c2cnc(N)cn2)c(F)c1] | 736 | 2-{[4'-(5-Aminopyrazin-2-yl)-3'-fluorobiphenyl-2-yl]sulfonyl}-2-methylpropanamide |
| 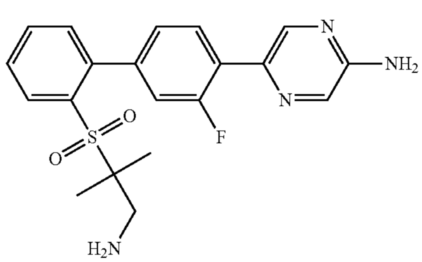 [SMILES: CC(C)(CN)S(=O)(=O)c1ccccc1-c1ccc(-c2cnc(N)cn2)c(F)c1] | 737 | 5-{2'-[(2-Amino-1,1-dimethylethyl)sulfonyl]-3-fluorobiphenyl-4-yl}pyrazin-2-amine |

TABLE 3-continued

| STRUCTURE | COMPOUND # | NAME |
|---|---|---|
| 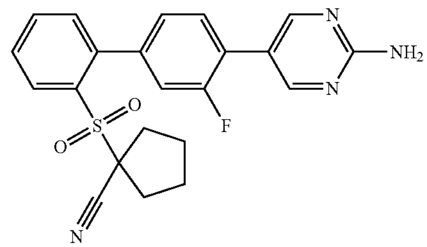 [SMILES: N#CC1(S(=O)(=O)c2ccccc2-c2ccc(-c3cnc(N)nc3)c(F)c2)CCCC1] | 738 | 1-{[4'-(2-Aminopyrimidin-5-yl)-3'-fluorobiphenyl-2-yl]sulfonyl}cyclopentanecarbonitrile |
| 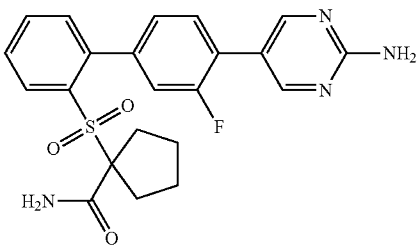 [SMILES: NC(=O)C1(S(=O)(=O)c2ccccc2-c2ccc(-c3cnc(N)nc3)c(F)c2)CCCC1] | 739 | 1-{[4'-(2-Aminopyrimidin-5-yl)-3'-fluorobiphenyl-2-yl]sulfonyl}cyclopentanecarboxamide |
| 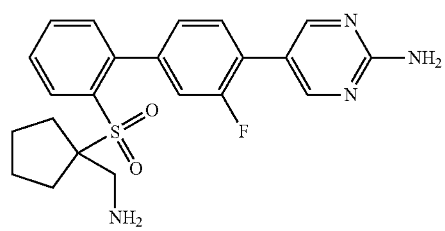 [SMILES: NCC1(S(=O)(=O)c2ccccc2-c2ccc(-c3cnc(N)nc3)c(F)c2)CCCC1] | 740 | 5-(2'-{[1-(Aminomethyl)cyclopentyl]sulfonyl}-3-fluorobiphenyl-4-yl)pyrimidin-2-amine |
| 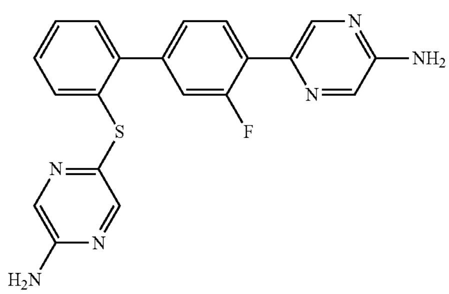 [SMILES: Nc1cnc(Sc2ccccc2-c2ccc(-c3cnc(N)cn3)c(F)c2)cn1] | 741 | 5-{[4'-(5-Aminopyrazin-2'-yl)-3'-fluorobiphenyl-2-yl]sulfanyl}pyrazin-2-amine |
| 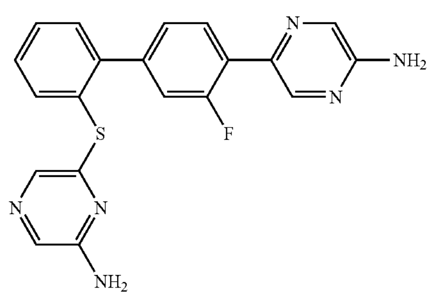 [SMILES: Nc1cnc(-c2ccc(-c3ccccc3Sc3cncc(N)n3)cc2F)cn1] | 742 | 5-{2'-[(6-Aminopyrazin-2-yl)sulfanyl]-fluorobiphenyl-4-yl}pyrazin-2-amine |
| 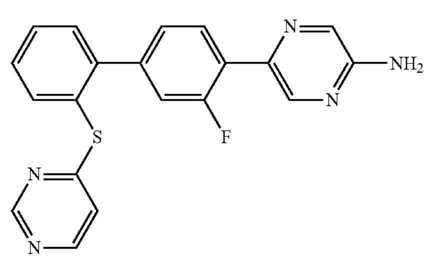 [SMILES: Nc1cnc(-c2ccc(-c3ccccc3Sc3ccncn3)cc2F)cn1] | 743 | 5-(3-Fluoro-2'-(pyrimidin-4-ylthio)-[1,1'-biphenyl]-4-yl)pyrazin-2-amine |

TABLE 3-continued

| STRUCTURE | COMPOUND # | NAME |
|---|---|---|
| 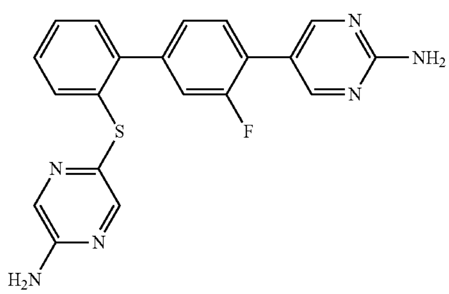 [SMILES: Nc1cnc(Sc2ccccc2-c2ccc(-c3cnc(N)nc3)c(F)c2)cn1] | 744 | 5-{2'-[(5-Aminopyrazin-2-yl)sulfanyl]-3-fluorobiphenyl-4-yl}pyrimidin-2-amine |
| 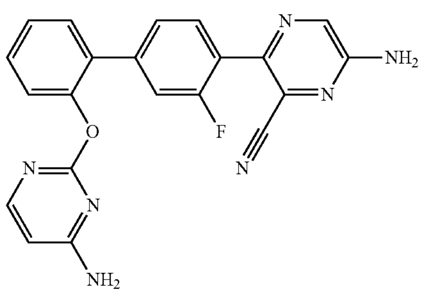 [SMILES: N#Cc1nc(N)cnc1-c1ccc(-c2ccccc2Oc2nccc(N)n2)cc1F] | 745 | 6-Amino-3-{2'-[(4-aminopyrimidin-2-yl)oxy]-3-fluorobiphenyl-4-yl}pyrazine-2-carbanitrile |
| 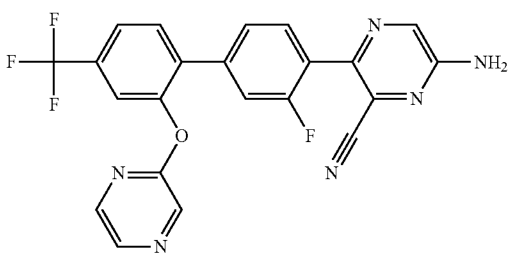 [SMILES: N#Cc1nc(N)cnc1-c1ccc(-c2ccc(C(F)(F)F)cc2Oc2cnccn2)cc1F] | 746 | 6-Amino-3-[3-fluoro-2'-(pyrimidin-2-yloxy)-4'-(trifluoramethyl)biphenyl-4-yl]pyrazine-2-carbonitrile |
| 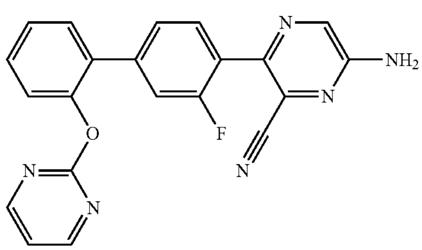 [SMILES: N#Cc1nc(N)cnc1-c1ccc(-c2ccccc2Oc2ncccn2)cc1F] | 747 | 6-Amino-3-[3-fluoro-2'-(pyrimidin-2-yloxy)biphenyl-4-yl]pyrazine-2-carbonitrile |
| 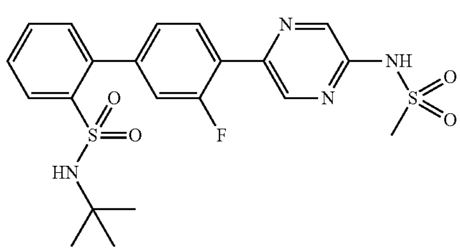 [SMILES: CC(C)(C)NS(=O)(=O)c1ccccc1-c1ccc(-c2cnc(NS(C)(=O)=O)cn2)c(F)c1] | 748 | N-(tert-Butyl)-3'-fluoro-4'-(5-(methylsulfonamido)pyrazin-2-yl)-[1,1'-biphenyl]-2-sulfonamide |

TABLE 3-continued

| STRUCTURE | COMPOUND # | NAME |
|---|---|---|
| 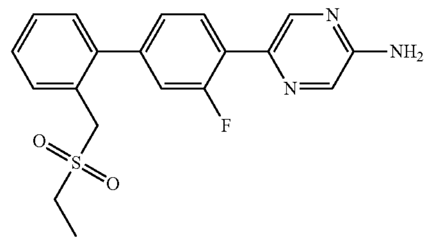 | 749 | 5-{2'-[(Ethylsulfonyl)methyl]-3-fluorobiphenyl-4-yl}pyrazin-2-amine hydrogen chloride salt |
| 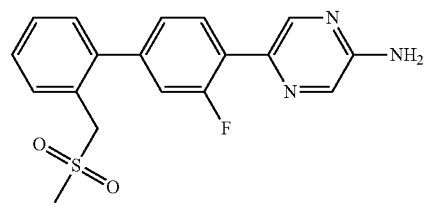 [SMILES: CS(=O)(=O)Cc1ccccc1-c1ccc(-c2cnc(N)cn2)c(F)c1] | 750 | 5-{3-Fluoro-2'-[(methylsulfonyl)methyl]biphenyl-4-yl}pyrazin-2-amine |
| 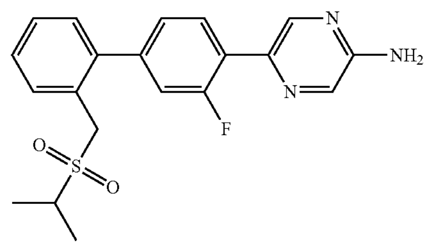 [SMILES: CC(C)S(=O)(=O)Cc1ccccc1-c1ccc(-c2cnc(N)cn2)c(F)c1] | 751 | 5-(3-Fluoro-2'-{[(1-methylethyl)sulfonyl]methyl}biphenyl-4-yl)pyrazin-2-amine |
| 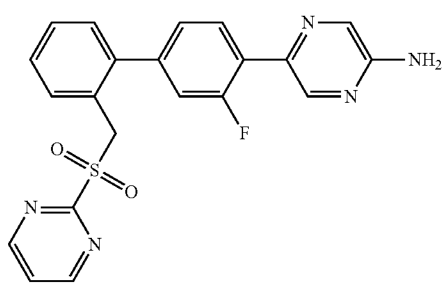 [SMILES: Nc1cnc(-c2ccc(-c3ccccc3CS(=O)(=O)c3ncccn3)cc2F)cn1] | 752 | 5-{3-Fluoro-2'-(pyrimidin-2-ylsulfonyl)methyl]biphenyl-4-yl}pyrazin-2-amine |
| 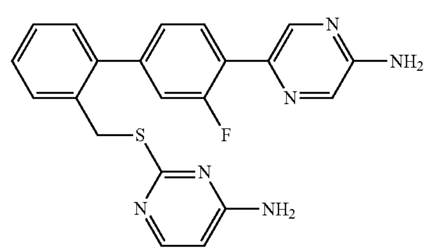 [SMILES: Nc1cnc(-c2ccc(-c3ccccc3CSc3nccc(N)n3)cc2F)cn1] | 753 | 2-({[(4'-(5-Aminopyrazin-2-yl)-3'-fluorobiphenyl-2-yl]methyl}sulfanyl)pyrimidin-4-amine |
| 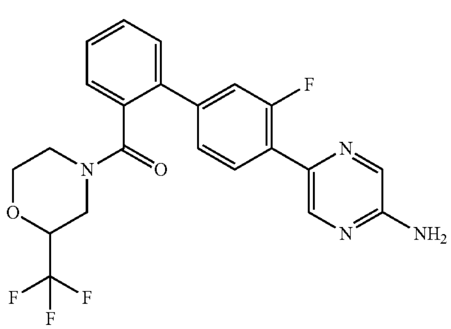 [SMILES: Nc1cnc(-c2ccc(-c3ccccc3C(=O)N3CCOC(C(F)(F)F)C3)cc2F)cn1] | 754 | racemic 5-(3-Fluoro-2'-{[2-{trifluoromethyl)morpholin-4-yl]carbonyl}biphenyl-4-yl)pyrazin-2-amine |

TABLE 3-continued

| STRUCTURE | COMPOUND # | NAME |
| --- | --- | --- |
| 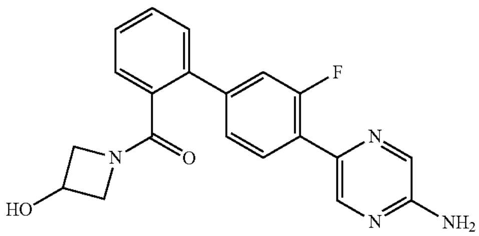 [SMILES: Nc1cnc(-c2ccc(-c3ccccc3C(=O)N3CC(O)C3)cc2F)cn1] | 755 | 1-{[4'-(5-Aminopyrazin-2-yl)-3'-fluorobiphenyl-2-yl]carbonyl}azetidin-3-ol |
| 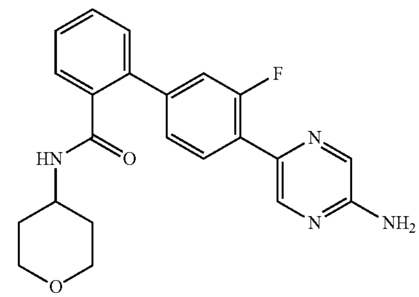 [SMILES: Nc1cnc(-c2ccc(-c3ccccc3C(=O)NC3CCOCC3)cc2F)cn1] | 756 | 4'-(5-Aminopyrazin-2-yl)-3'-fluoro-N-(tetrahydro-2H-pyran-4-yl)biphenyl-2-carboxamide |
| 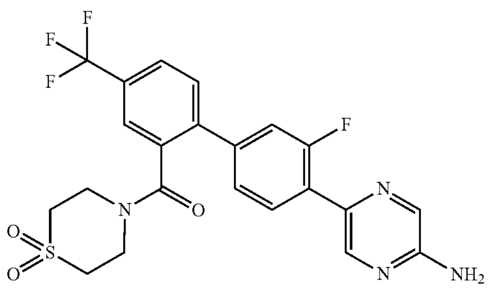 [SMILES: Nc1cnc(-c2ccc(-c3ccc(C(F)(F)F)cc3C(=O)N3CCS(=O)(=O)CC3)cc2F)cn1] | 757 | 5-{2'-[(1,1-Dioxidothiomorpholin-4-yl)carbonyl]-3-fluoro-4'-(trifluoromethyl)biphenyl-4-yl}pyrazin-2-amine |
| 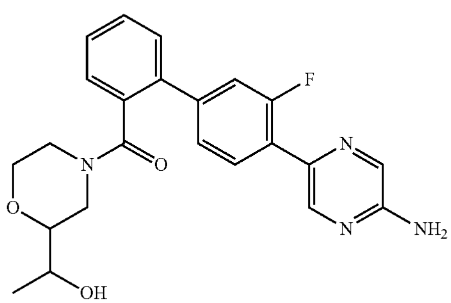 | 758 | 1-(4-{[4'-(5-Aminopyrazin-2-yl)-3'-fluorobiphenyl-2-yl]carbonyl)morpholin-2-yl)ethanol (diastereomeric mixture). |
| 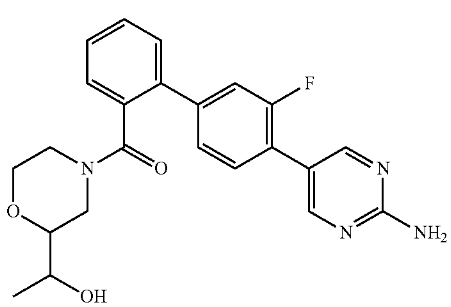 [SMILES: CC(O)C1CN(C(=O)c2ccccc2-c2ccc(-c3cnc(N)nc3)c(F)c2)CCO1] | 759 | 1-(4-{[4'-(2-Aminopyrimidin-5-yl)-3'-fluorobiphenyl-2-yl]carbonyl}morpholin-2-yl)ethanol (diastereomeric mixture). |

TABLE 3-continued

| STRUCTURE | COMPOUND # | NAME |
|---|---|---|
| 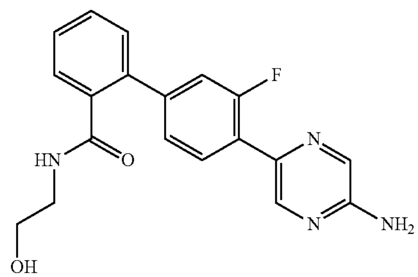 [SMILES: Nc1cnc(-c2ccc(-c3ccccc3C(=O)NCCO)cc2F)cn1] | 760 | 4'-(5-Aminopyrazin-2-yl)-3'-fluoro-N-(2-hydroxyethyl)biphenyl-2-carboxamide |
| 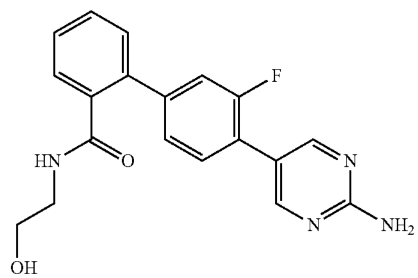 [SMILES: Nc1ncc(-c2ccc(-c3ccccc3C(=O)NCCO)cc2F)cn1] | 761 | 4'-(2-4minopyrimidin-5-yl)-3'-fluoro-N-(2-hydroxyethyl)biphenyl-2-carboxamide |
| 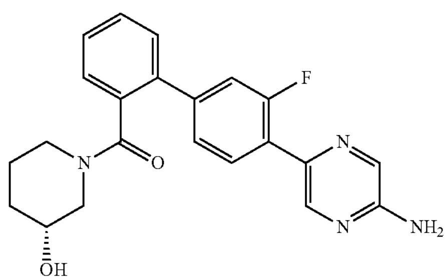 [SMILES: Nc1cnc(-c2ccc(-c3ccccc3C(=O)N3CCC[C@@H](O)C3)cc2F)cn1] | 762 | (3R)-1-{[4'-(5-Aminopyrazin-2-yl)-3'-fluorobiphenyl-2-yl]carbonyl}piperidin-3-ol |
| 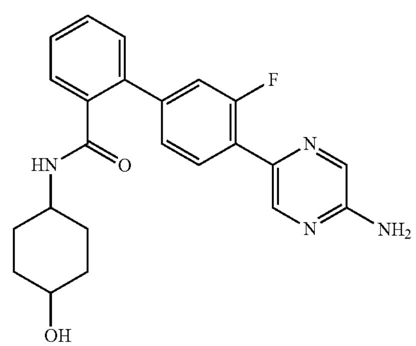 [SMILES: Nc1cnc(-c2ccc(-c3ccccc3C(=O)NC3CCC(O)CC3)cc2F)cn1] | 763 | (cis/trans) 4'-(5-Aminopyrazin-2-yl)-3'-fluoro-N-(4-hydroxycyclohexyl)biphenyl-2-carboxamide |
| 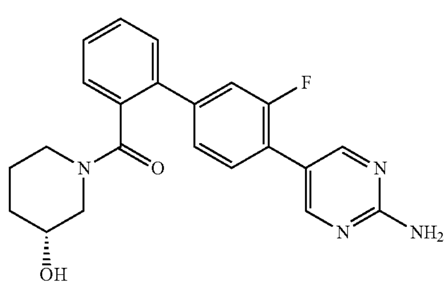 [SMILES: Nc1ncc(-c2ccc(-c3ccccc3C(=O)N3CCC[C@@H](O)C3)cc2F)cn1] | 764 | (3R)-1-{[4'-(2-Aminopyrimidin-5-yl)-3'-fluorobiphenyl-2-yl]carbonyl}piperidin-3-ol |

TABLE 3-continued

| STRUCTURE | COMPOUND # | NAME |
|---|---|---|
| 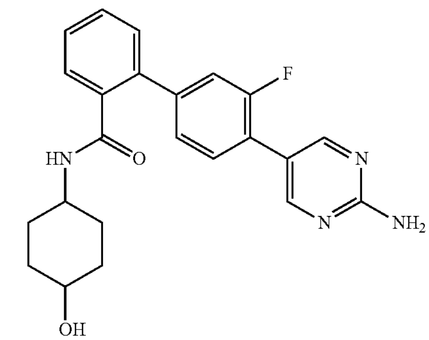 [SMILES: Nc1ncc(-c2ccc(-c3ccccc3C(=O)NC3CCC(O)CC3)cc2F)cn1] | 765 | (cis/trans) 4'-(2-Aminopyrimidin-5-yl)-3'-fluoro-N-(4-hydroxycyclohexyl)biphenyl-2-carboxamide |
| 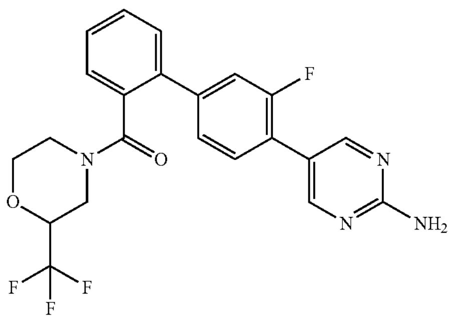 [SMILES: Nc1ncc(-c2ccc(-c3ccccc3C(=O)N3CCOC(C(F)(F)F)C3)cc2F)cn1] | 766 | racemic 5-(3-Fluoro-2'-{[2-(trifluoromethyl)morpholin-4-yl]carbonyl}biphenyl-4-yl)pyrimidin-2-amine |
| 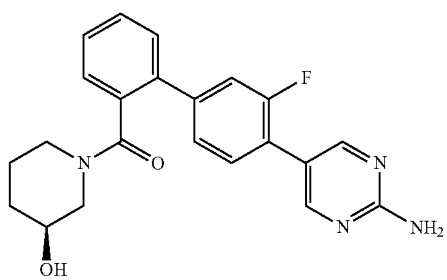 [SMILES: Nc1ncc(-c2ccc(-c3ccccc3C(=O)N3CCC[C@H](O)C3)cc2F)cn1] | 767 | (3S)-1-{[4'-(2-Aminopyrimidin-5-yl)-3'-fluorobiphenyl-2-yl]carbonyl}piperidin-3-ol |
| 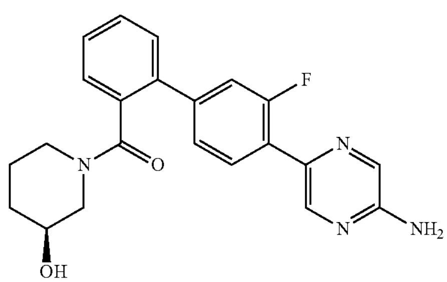 [SMILES: Nc1cnc(-c2ccc(-c3ccccc3C(=O)N3CCC[C@H](O)C3)cc2F)cn1] | 768 | (3S)-1-{[4-(5-Aminopyrazin-2-yl)-3'-fluorobiphenyl-2-yl]carbonyl}piperidin-3-ol |
| 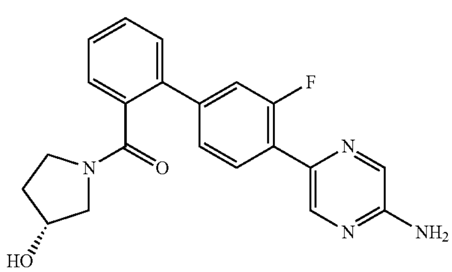 [SMILES: Nc1cnc(-c2ccc(-c3ccccc3C(=O)N3CC[C@@H](O)C3)cc2F)cn1] | 769 | (3R)-1-{[4'-(5-Aminopyrazin-2-yl)-3'-fluorobiphenyl-2-yl]carbonyl}pyrrolidin-3-ol |

TABLE 3-continued

| STRUCTURE | COMPOUND # | NAME |
|---|---|---|
| 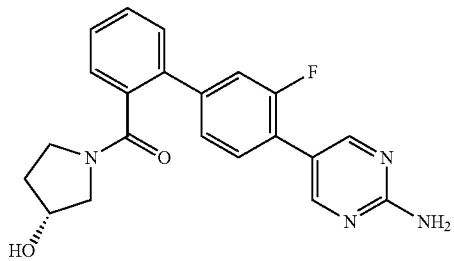 [SMILES: Nc1ncc(-c2ccc(-c3ccccc3C(=O)N3CC[C@@H](O)C3)cc2F)cn1] | 770 | (3R)-1-{[4'-(2-Aminopyrimidin-5-yl)-3'-fluorobiphenyl-2-yl]carbonyl}pyrrolidin-3-ol |
| 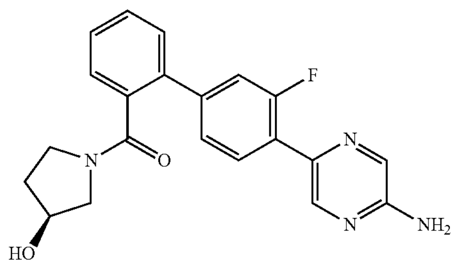 [SMILES: Nc1cnc(-c2ccc(-c3ccccc3C(=O)N3CC[C@H](O)C3)cc2F)cn1] | 771 | (3S)-1-{[4'-(5-Aminopyrazin-2-yl)-3'-fluorobiphenyl-2-yl]carbonyl}pyrrolidin-3-ol |
| 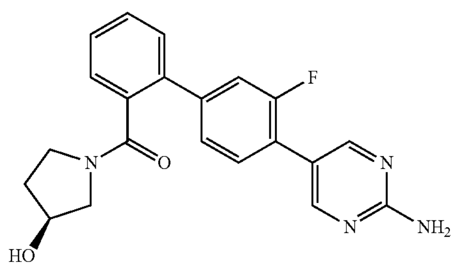 [SMILES: Nc1ncc(-c2ccc(-c3ccccc3C(=O)N3CC[C@H](O)C3)cc2F)cn1] | 772 | (3S)-1-{[4'-(2-Aminopyrimidin-5-yl)-3'-fluorobiphenyl-2-yl]carbonyl}pyrrolidin-3-ol |
| 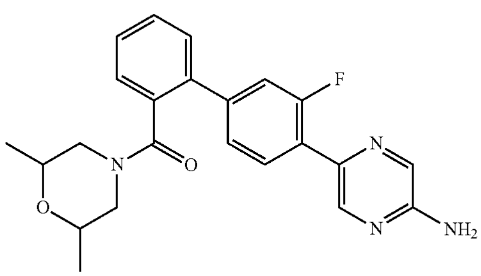 [SMILES: CC1CN(C(=O)c2ccccc2-c2ccc(-c3cnc(N)cn3)c(F)c2)CC(C)O1] | 773 | 5-{2'-[(2,6-Dimethylmorpholin-4-yl)carbonyl]-3-fluorobiphenyl-4-yl)pyrazin-2-amine (diastereoisomeric mixture). |
| 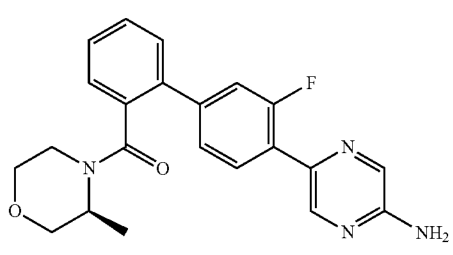 | 774 | 5-(3-Fluoro-2'-{[(3S)-3-methylmorpholin-4-yl]carbonyl}biphenyl-4-yl)pyrazin-2-amine |
| 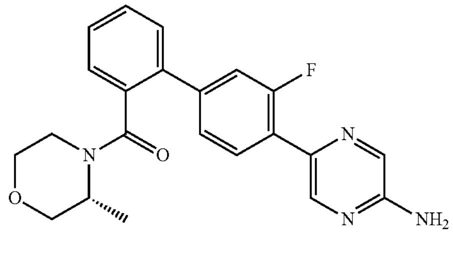 [SMILES: C[C@@H]1COCCN1C(=O)c1ccccc1-c1ccc(-c2cnc(N)cn2)c(F)c1] | 775 | 5-(3-Fluoro-2'-{[(3R)-3-methylmorpholin-4-yl]carbonyl}biphenyyl-4-yl)pyrazin-2-amine |

TABLE 3-continued

| STRUCTURE | COMPOUND # | NAME |
|---|---|---|
| 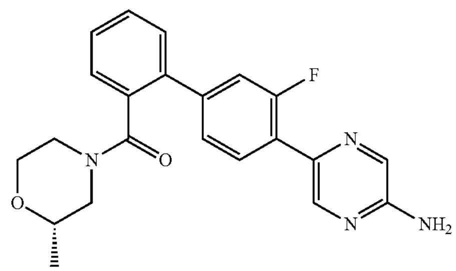 [SMILES: C[C@H]1CN(C(=O)c2ccccc2-c2ccc(-c3cnc(N)cn3)c(F)c2)CCO1] | 776 | 5-(3-Fluoro-2'-{[(2S)-2-methylmorpholin-4-yl]carbonyl}biphenyl-4-yl)pyrazin-2-amine |
| 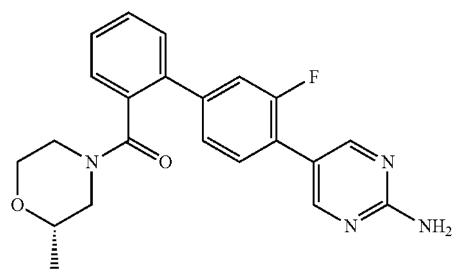 [SMILES: C[C@H]1CN(C(=O)c2ccccc2-c2ccc(-c3cnc(N)nc3)c(F)c2)CCO1] | 777 | 5-(3-Fluoro-2'-{[(2S)-2-methylmorpholin-4-yl]carbonyl}biphenyl-4-yl)pyrimidin-2-amine |
| 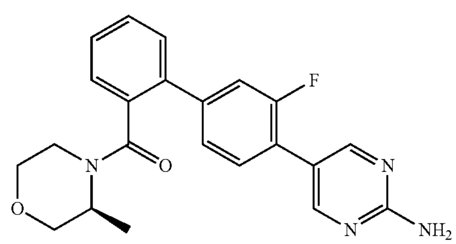 | 778 | 5-(3-Fluoro-2'-{[(3S)-3-methylmorpholin-4-yl]carbonyl}biphenyl-4-yl)pyrimidin-2'-amine |
| 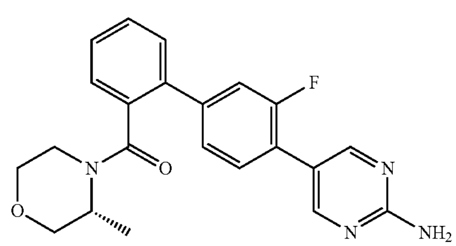 [SMILES: C[C@@H]1COCCN1C(=O)c1ccccc1-c1ccc(-c2cnc(N)nc2)c(F)c1] | 779 | 5-(3-Fluoro-2'-{[(3R)-3-methylmorpholin-4-yl]carbonyl}biphenyl-4-yl)pyrimidin-2-amine |
| 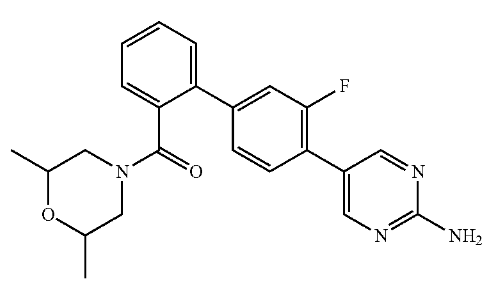 [SMILES: CC1CN(C(=O)c2ccccc2-c2ccc(-c3cnc(N)nc3)c(F)c2)CC(C)O1] | 780 | 5-{2'-[(2,6-Dimethylmorpholin-4-yl)carbonyl]-3-fluorobiphenyl-4-yl}pyrimidin-2-amine (diastereoisomeric mixture) |

TABLE 3-continued

| COMPOUND # | NAME |
|---|---|
| 781 | 5-{2-Fluoro-4-[2-(morpholin-4-ylcarbonyl)pyridin-3-yl]phenyl]-1H-pyrrolo[2,3-b]pyridine |
| 782 | 5-{2-Fluoro-4-[2-(morpholin-4-ylcarbonyl)pyridin-3-yl]phenyl}pyrimidin-2-amine |
| 783 | 5-{2-Fluoro-4-[2-(morpholin-4-ylcarbonyl)pyridin-3-yl]phenyl}pyrazin-2-amine |
| 784 | 2-[4-(5-Aminopyrazin-2-yl)-3-fluorophenyl]-N-tert-butyl-5-(trifluoromethyl)benzamide |
| 785 | 2-[4-(5-Aminopyrazin-2-yl)-3-fluorophenyl]-N-[(1R)-2-hydroxy-1-methylethyl]-5-(trifluoromethyl)benzamide |

TABLE 3-continued

| STRUCTURE | COMPOUND # | NAME |
|---|---|---|
| 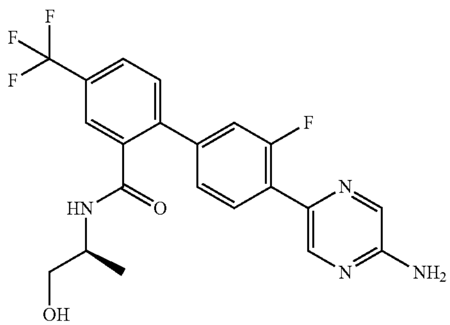 [SMILES: C[C@@H](CO)NC(=O)c1cc(C(F)(F)F)ccc1-c1ccc(-c2cnc(N)cn2)c(F)c1] | 786 | 2-[4-(5-Aminopyrazin-2-yl)-3-fluoro-phenyl]-N-[(1S)-2-hydroxy-1-methyl-ethyl]-5-(trifluoromethyl)benzamide |
| 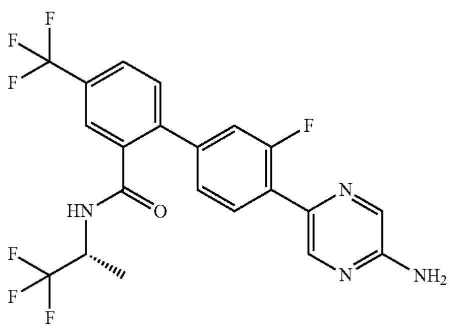 [SMILES: C[C@@H](NC(=O)c1cc(C(F)(F)F)ccc1-c1ccc(-c2cnc(N)cn2)c(F)c1)C(F)(F)F] | 787 | 2-[4-(5-Aminopyrazin-2-yl)-3-fluoro-phenyl]-5-(trifluoromethyl)-N-[(1R)-2,2,2-trifluoro-1-methyl-ethyl]enzamide |
| 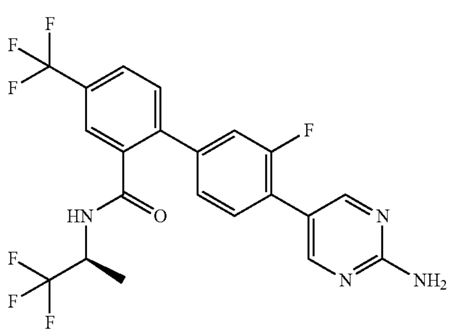 [SMILES: C[C@H](NC(=O)c1cc(C(F)(F)F)ccc1-c1ccc(-c2cnc(N)nc2)c(F)c1)C(F)(F)F] | 788 | 2-[4-(2-Aminopyrimidin-5-yl)-3-fluoro-phenyl]-5-(trifuoromethyl)-N-[(1S)-2,2,2-trifluoro-1-methyl-ethyl]enzamide |
| 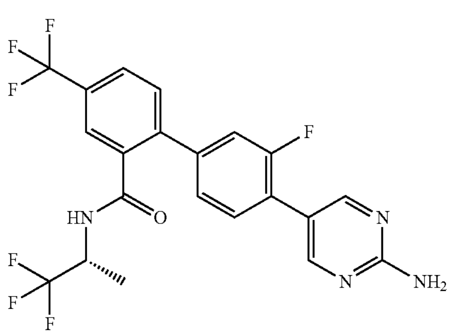 [SMILES: C[C@@H](NC(=O)c1cc(C(F)(F)F)ccc1-c1ccc(-c2cnc(N)nc2)c(F)c1)C(F)(F)F] | 789 | 2-[4-(2-Aminopyrimidin-5-yl)-3-fluoro-phenyl]-5-(trifluoromethyl)-N-(1R)-2,2,2-trifluoro-1-methyl-ethyl)benzamide |

TABLE 3-continued

| STRUCTURE | COMPOUND # | NAME |
|---|---|---|
| 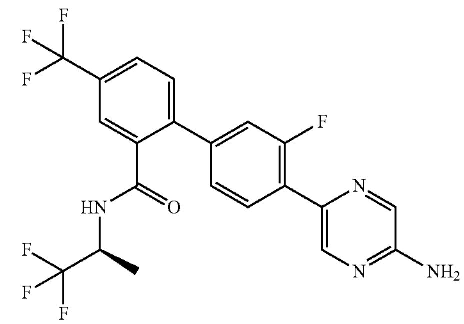 [SMILES: C[C@H](NC(=O)c1cc(C(F)(F)F)ccc1-c1ccc(-c2cnc(N)cn2)c(F)c1)C(F)(F)F] | 790 | 2-[4-(5-Aminopyrazin-2-yl)-3-fluoro-phenyl]-5-(trifluoromethyl)-N-[(1S)-2,2,2-trifluoro-1-methyl-ethyl]benzamide |
| 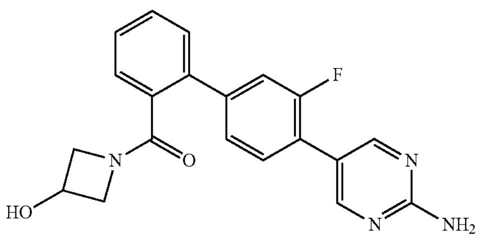 [SMILES: Nc1ncc(-c2ccc(-c3ccccc3C(=O)N3CC(O)C3)cc2F)cn1] | 791 | [2-[4-(2-Aminopyrimidin-5-yl)-3-fluoro-phenyl]phenyl]-(3-hydroxyazetidin-1-yl)methanone |
| 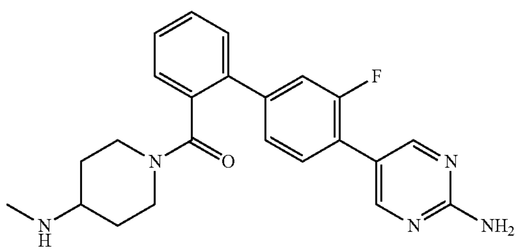 [SMILES: CNC1CCN(C(=O)c2ccccc2-c2ccc(-c3cnc(N)nc3)c(F)c2)CC1] | 792 | [2-[4-(2-Aminopyrimidin-5-yl)-3-fluoro-phenyl]phenyl]-[4-(methylamino)-1-piperidyl]methanone |
| 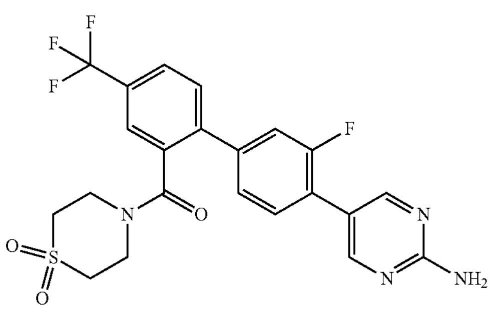 [SMILES: Nc1ncc(-c2ccc(-c3ccc(C(F)(F)F)cc3C(=O)N3CCS(=O)(=O)CC3)cc2F)cn1] | 793 | [2-[4-(2-Aminopyrimidin-5-yl)-3-fluoro-phenyl]-5-(trifluoromethyl)phenyl]-(1,1-dioxo-1,4-thiazinan-4-yl)methanone |
| 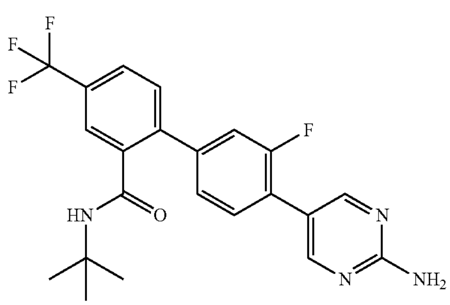 [SMILES: CC(C)(C)NC(=O)c1cc(C(F)(F)F)ccc1-c1ccc(-c2cnc(N)nc2)c(F)c1] | 794 | 2-[4-(2-Aminopyrimidin-5-yl)-3-fluoro-phenyl]-N-tert-butyl-5-(trifluoromethyl)benzamide |

TABLE 3-continued

| STRUCTURE | COMPOUND # | NAME |
|---|---|---|
| 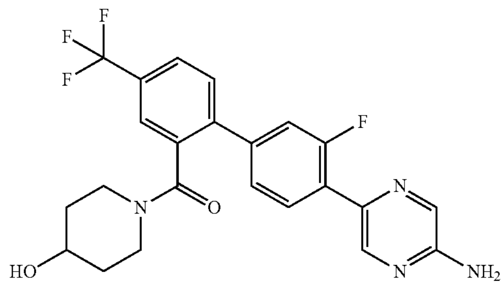 | 795 | [2-[4-(5-Aminopyrazin-2-yl)-3-fluoro-phenyl]-5-(trifluoromethyl)phenyl]-(4-hydroxy-1-piperidyl)methanone |
| 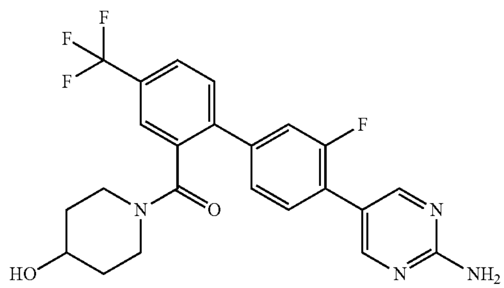 [SMILES: Nc1ncc(-c2ccc(-c3ccc(C(F)(F)F)cc3C(=O)N3CCC(O)CC3)cc2F)cn1] | 796 | [2-[4-(2-Aminopyrimidin-5-yl)-3-fluoro-phenyl]-5-(trifluoromethyl)phenyl]-(4-hydroxy-1-piperidyl)methanone |
| 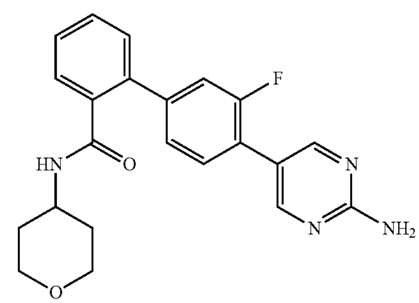 [SMILES: Nc1ncc(-c2ccc(-c3ccccc3C(=O)NC3CCOCC3)cc2F)cn1] | 797 | 2-[4-(2-Aminopyrimidin-5-yl)-3-fluoro-phenyl]-N-tetrahydropyran-4-yl-benzamide |
| 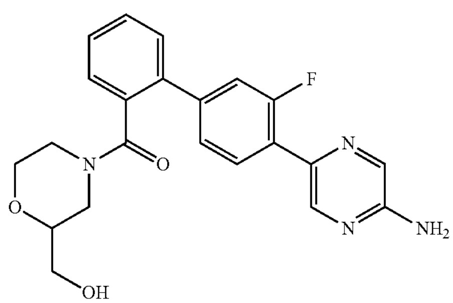 [SMILES: Nc1cnc(-c2ccc(-c3ccccc3C(=O)N3CCOC(CO)C3)cc2F)cn1] | 798 | racemic [2-]4-(5-Aminopyrazin-2-yl)-3-fluoro-phenyl]phenyl]-[2-(hydroxymethyl)morpholin-4-yl]methanone |
| 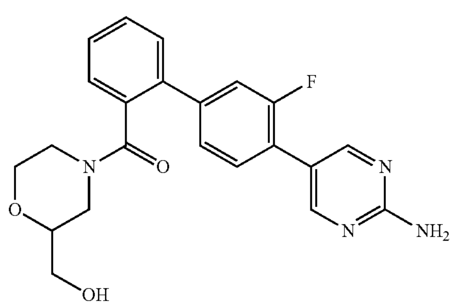 | 799 | racemic [2-[4-(2-Aminopyrimidin-5-yl)-3-fluoro-phenyl]phenyl]-2-(hydroxymethyl)morpholin-4-yl]methanone |

TABLE 3-continued

| STRUCTURE | COMPOUND # | NAME |
|---|---|---|
| 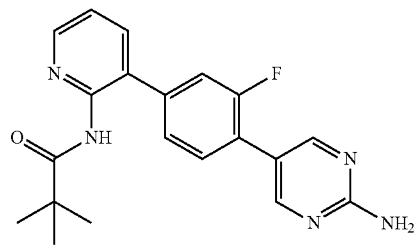 [SMILES: CC(C)(C)C(=O)Nc1ncccc1-c1ccc(-c2cnc(N)nc2)c(F)c1] | 800 | N-[3-[4-(2-Aminopyrimidin-5-yl)-3-fluorophenyl]pyridin-2-yl}-2,2-dimethylpropanamide |
| 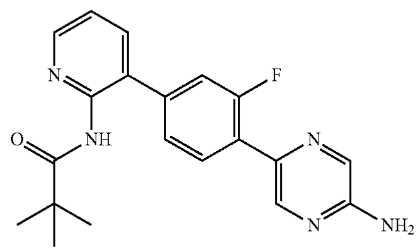 [SMILES: CC(C)(C)C(=O)Nc1ncccc1-c1ccc(-c2cnc(N)cn2)c(F)c1] | 801 | N-{3-[4-(5-Aminopyrazin-2-yl)-3-fluorophenyl]pyridin-2-yl}-2,2-dimethylpropanamide |
| 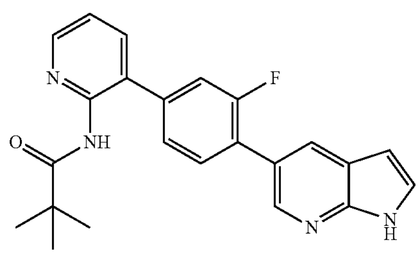 [SMILES: CC(C)(C)C(=O)Nc1ncccc1-c1ccc(-c2cnc3[nH]ccc3c2)c(F)c1] | 802 | N-{3-[3-Fluoro-4-(1H-pyrrolo[2,3-b]pyridin-5-yl)phenyl]pyridin-2-yl}-2,2-dimethylpropanamide |
| 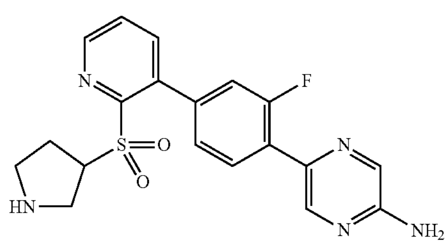 [SMILES: Nc1cnc(-c2ccc(-c3cccnc3S(=O)(=O)C3CCNC3)cc2F)cn1] | 803 | racemic 5-(2-Fluoro-4-(2-(pyrrolidin-3-ylsulfonyl)pyridin-3-yl)phenyl)pyrazin-2-amine hydrochloride |
| 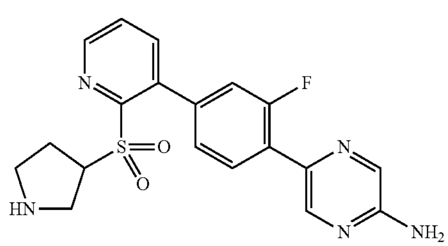 [SMILES: Nc1cnc(-c2ccc(-c3cccnc3S(=O)(=O)C3CCNC3)cc2F)cn1] | 804 | 5-(2-Fluoro-4-(2-(pyrrolidin-3-ylsulfonyl)pyridin-3-yl)phenyl)pyrimidin-2-amine formic acid salt. |
| 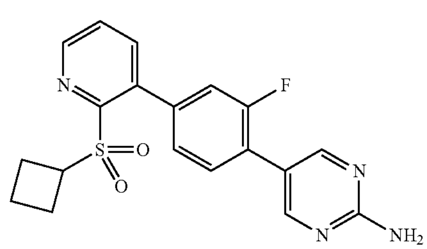 [SMILES: Nc1ncc(-c2ccc(-c3cccnc3S(=O)(=O)C3CCC3)cc2F)cn1] | 805 | 5-(4-(2-(Cyclobutylsulfonyl)pyridin-3-yl)-2-fluorophenyl)pyrimidin-2-amine hydrochloride. |

TABLE 3-continued

| STRUCTURE | COMPOUND # | NAME |
|---|---|---|
| 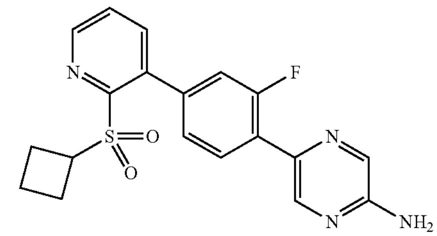 [SMILES: Nc1cnc(-c2ccc(-c3cccnc3S(=O)(=O)C3CCC3)cc2F)cn1] | 806 | 5-(4-(2-(Cyclobutylsulfonyl)pyridin-3-yl)-2-fluorophenyl)pyrazin-2-amine hydrochloride |
| 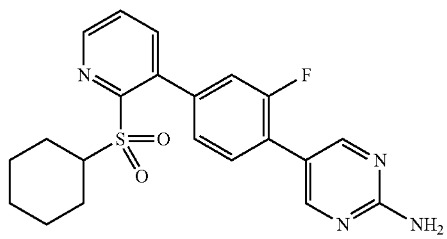 [SMILES: Nc1ncc(-c2ccc(-c3cccnc3S(=O)(=O)C3CCCCC3)cc2F)cn1] | 807 | 5-(4-(2-(Cyclohexylsulfonyl)pyridin-3-yl)-2-fluorophenyl)pyrimidin-2-amine hydrochloride |
| 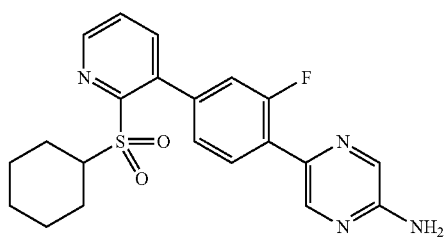 [SMILES: Nc1cnc(-c2ccc(-c3cccnc3S(=O)(=O)C3CCCCC3)cc2F)cn1] | 808 | 5-(4-(2-(Cyclohexylsulfonyl)pyridin-3-yl)-2-fluorophenyl)pyrazin-2-amine hydrochloride |
| 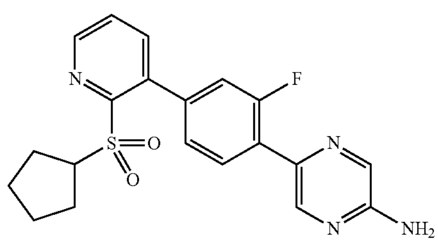 [SMILES: Nc1cnc(-c2ccc(-c3cccnc3S(=O)(=O)C3CCCC3)cc2F)cn1] | 809 | 5-(4-2-(Cyclopentylsulfonyl)pyridin-3-yl)-2-fluorophenyl)pyrimidine-2-amine hydrochloride |
| 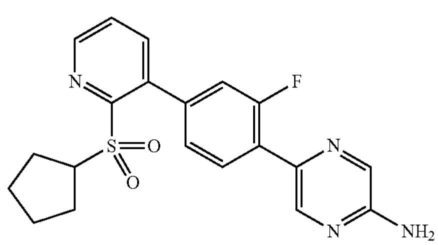 [SMILES: Nc1cnc(-c2ccc(-c3cccnc3S(=O)(=O)C3CCCC3)cc2F)cn1] | 810 | 5-(4-(2-(Cyclopentylsulfonyl)pyridin-3-yl)-2-fluorophenyl)pyrazin-2-amine hydrochloride |
| 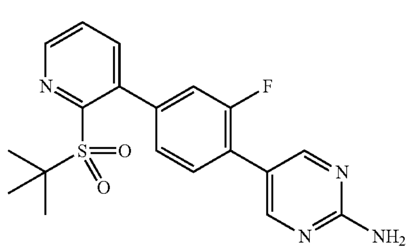 [SMILES: CC(C)(C)S(=O)(=O)c1ncccc1-c1ccc(-c2cnc(N)nc2)c(F)c1] | 811 | 5-(4-(2-(tert-Butylsulfonyl)pyridin-3-yl)-2-fluorophenyl)pyrimidin-2-amine formic acid salt. |

TABLE 3-continued

| STRUCTURE | COMPOUND # | NAME |
|---|---|---|
| 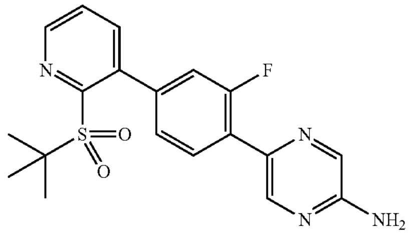 [SMILES: CC(C)(C)S(=O)(=O)c1ncccc1-c1ccc(-c2cnc(N)cn2)c(F)c1] | 812 | 5-(4-(2-(tert-Butylsulfonyl)pyridin-3-yl)-2-fluorophenyl)pyrazin-2-amine formic acid salt. |
| 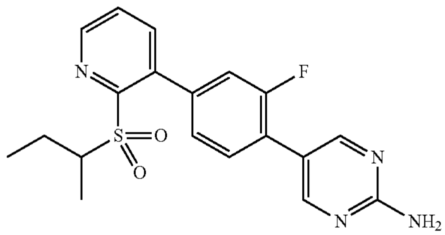 | 813 | racemic 5-(4-(2-(sec-Butylsulfonyl)pyridin-3-yl)-2-fluorophenyl)pyrimidin-2-amine formate |
| 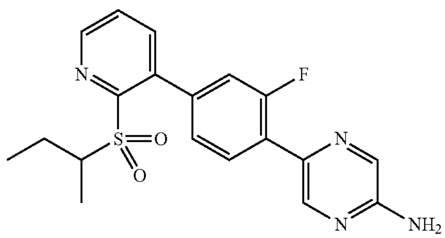 [SMILES: CCC(C)S(=O)(=O)c1ncccc1-c1ccc(-c2cnc(N)nc2)c(F)c1] | 814 | racemic 5-(4-(2-(sec-Butylsulfonyl)pyridin-3-yl)-2-fluorophenyl)pyrazin-2-amine formate |
| 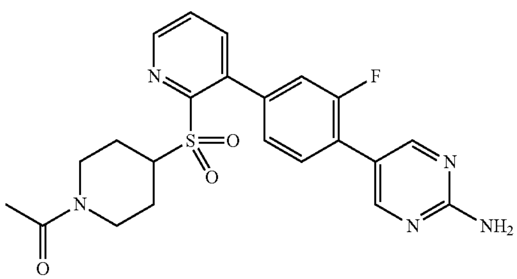 [SMILES: CC(=O)N1CCC(S(=O)(=O)c2ncccc2-c2ccc(-c3cnc(N)nc3)c(F)c2)CC1] | 815 | 1-((3-(4-(2-Aminopyrimidin-5-yl)-3-fluorophenyl)pyridine-2-yl)sulfonyl)piperidin-1-yl)ethanone |
| 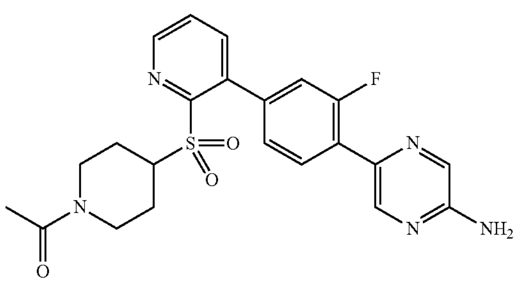 [SMILES: CC(=O)N1CCC(S(=O)(=O)c2ncccc2-c2ccc(-c3cnc(N)cn3)c(F)c2)CC1] | 816 | 1-((3-(4-(2-Aminopyrazin-5-yl)-3-fluorophenyl)pyridine-2-yl)sulfonyl)piperidin-1-yl)ethanone hydrogen chloride salt |
| 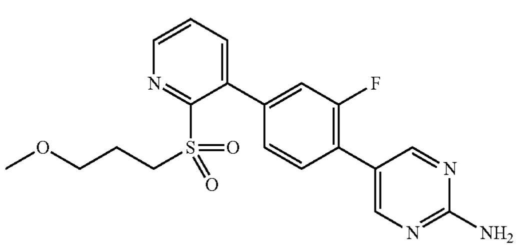 | 817 | 5-(2-Fluoro-4-(2-((3-methoxypropyl)sulfonyl)pyridine-3-yl)phenyl)pyrimidin-2-amine hydrogen chloride salt. |

TABLE 3-continued

| STRUCTURE | COMPOUND # | NAME |
|---|---|---|
| 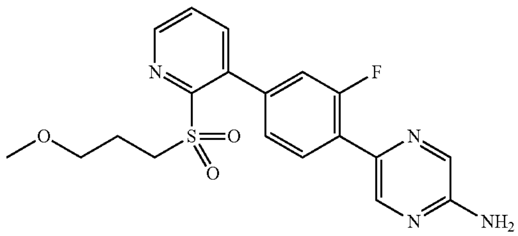 [SMILES: COCCCS(=O)(=O)c1ncccc1-c1ccc(-c2cnc(N)cn2)c(F)c1] | 818 | 5-(2-Fluoro-4-(2-((3-methoxypropyl)sulfonyl)pyridine-3-yl)phenyl)pyrazin-2-amine hydrogen chloride salt. |
| 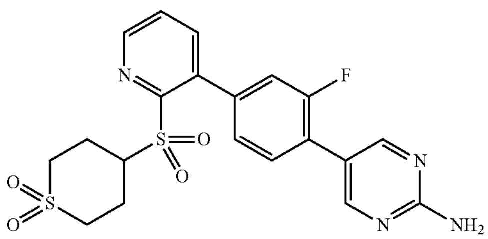 | 819 | 4-((3-(4-(2-aminopyrimidin-5-yl)-3-fluorophenyl)pyridine-2-yl)sulfonyl)tetrahydro-2H-thiopyran 1,1-dioxide |
| 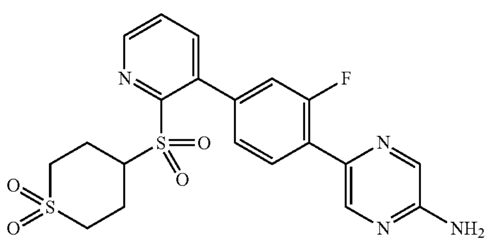 [SMILES: Nc1cnc(-c2ccc(-c3cccnc3S(=O)(=O)C3CCS(=O)(=O)CC3)cc2F)cn1] | 820 | 4-((3-(4-(2-Aminopyrazin-5-yl)-3-fluorophenyl)pyridine-2-yl)sulfonyl)tetrahydro-2H-thiopyran 1,1-dioxide |
| 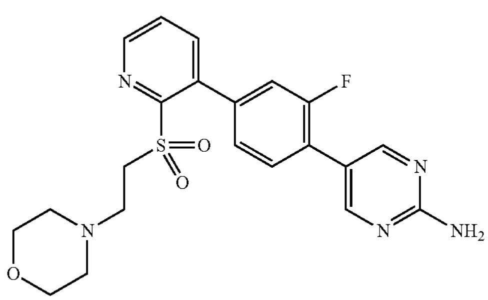 [SMILES: Nc1ncc(-c2ccc(-c3cccnc3S(=O)(=O)CCN3CCOCC3)cc2F)cn1] | 821 | 5-(2-Fluoro-4-(2-((2-morpholinoethyl)sulfonyl)pyridine-3-yl)phenyl)pyrimidin-2-amine formic acid salt. |
| 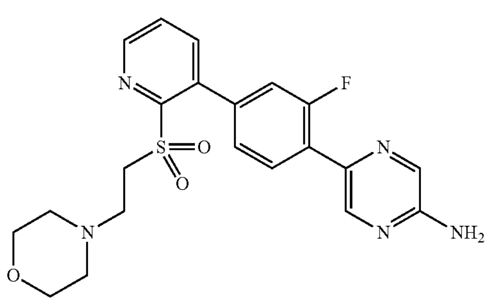 [SMILES: Nc1cnc(-c2ccc(-c3cccnc3S(=O)(=O)CCN3CCOCC3)cc2F)cn1] | 822 | 5-(2-Fluoro-4-(2-((2-morpholinoethyl)sulfonyl)pyridine-3-yl)phenyl)pyrazin-2-amine |

TABLE 3-continued

| STRUCTURE | COMPOUND # | NAME |
|---|---|---|
| 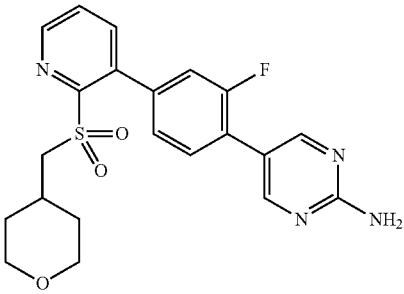 [SMILES: Nc1ncc(-c2ccc(-c3cccnc3S(=O)(=O)CC3CCOCC3)cc2F)cn1] | 823 | 5-(2-Fluoro-4-(2-(((tetrahydro-2H-pyran-4-yl)methyl)sulfonyl)pyridine-3-yl)pyrimidin-2-amine formic acid salt. |
| 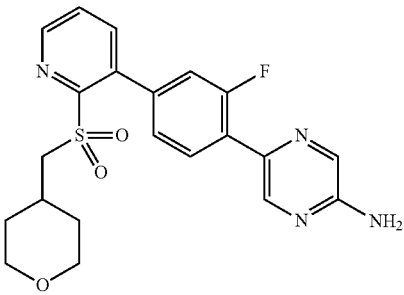 [SMILES: Nc1cnc(-c2ccc(-c3cccnc3S(=O)(=O)CC3CCOCC3)cc2F)cn1] | 824 | 5-(2-Fluoro-4-(2-(((tetrahydro-2H-pyran-4-yl)methyl)sulfonyl)pyridine-3-yl)pyrazin-2-amine formic acid salt. |
| 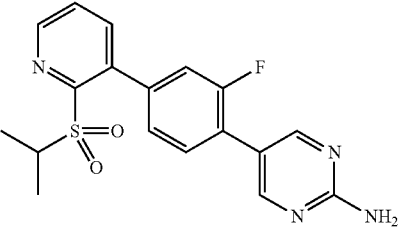 [SMILES: CC(C)S(=O)(=O)c1ncccc1-c1ccc(-c2cnc(N)nc2)c(F)c1] | 825 | 5-(2-Fluoro-4-{2-[(1-methylethyl)sulfonyl]pyridin-3-yl}phenyl)pyrimidin-2-amine |
| 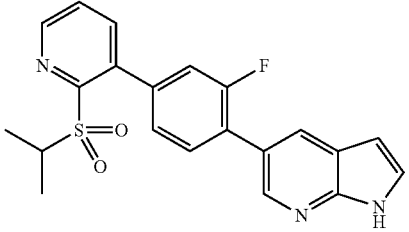 [SMILES: CC(C)S(=O)(=O)c1ncccc1-c1ccc(-c2cnc3[nH]ccc3c2)c(F)c1] | 826 | 5-(2-Fluoro-4-(2-(isopropylsulfonyl)pyridine-3-yl)phenyl)-1H-pyrrolo[2,3-b]pyridine |
| 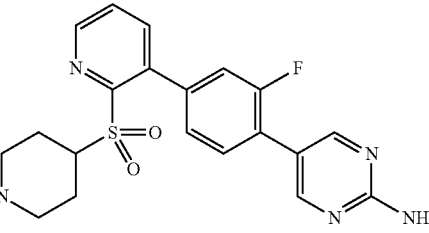 | 827 | 5-{2-Fluoro-4-[2-(piperidin-4-ylsulfonyl)pyridin-3-yl]phenyl)pyrimidin-2-amine formic acid salt. |
| 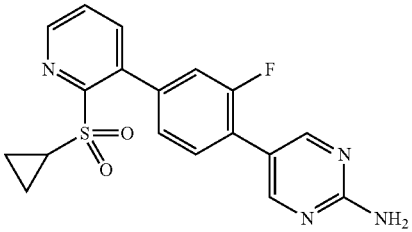 [SMILES: Nc1ncc(-c2ccc(-c3cccnc3S(=O)(=O)C3CC3)cc2F)cn1] | 828 | 5-{4-[2-(Cyclopropylsulfonyl)pyridin-3-yl]-2-fluorophenyl}pyrimidin-2-amine formic acid salt. |

TABLE 3-continued

| STRUCTURE | COMPOUND # | NAME |
|---|---|---|
| 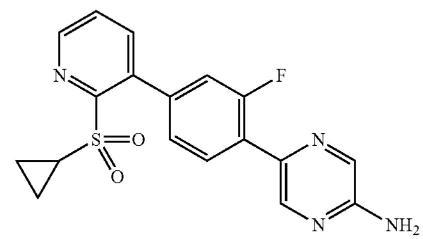 [SMILES: Nc1cnc(-c2ccc(-c3cccnc3S(=O)(=O)C3CC3)cc2F)cn1] | 829 | 5-{4-[2-(Cyclopropylsulfonyl)pyridin-3-yl]-2-fluorophenyl}pyrazin-2-amine formic acid salt. |
| 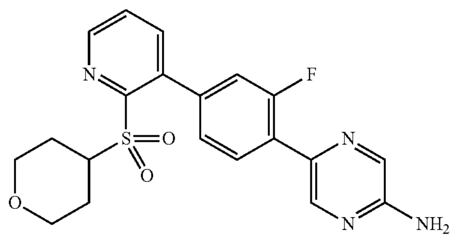 [SMILES: Nc1ncc(-c2ccc(-c3cccnc3S(=O)(=O)C3CCOCC3)cc2F)cn1] | 830 | 5-{2-Fluoro-4-[2-(tetrahydro-2H-pyran-4-ylsulfonyl)pyridin-3-yl]phenyl}pyrazin-2-amine hydrochloride |
| 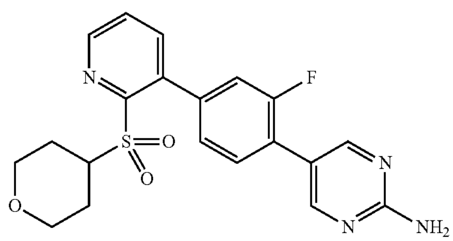 | 831 | 5-{2-Fluoro-4-[2-(tetrahydro-2H-pyran-4-ylsulfonyl)pyridin-3-yl]phenyl}pyrimidin-2-amine formic acid salt. |
| 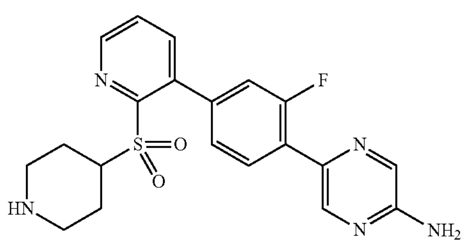 [SMILES: Nc1cnc(-c2ccc(-c3cccnc3S(=O)(=O)C3CCNCC3)cc2F)cn1] | 832 | 5-{2-Fluoro-4-[2-(piperidin-4-ylsulfonyl)pyridin-3-yl]phenyl}pyrazin-2-amine hydrochloride |
| 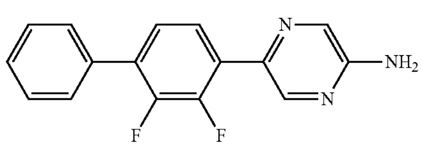 [SMILES: Nc1cnc(-c2ccc(-c3ccccc3)c(F)c2F)cn1] | 833 | 5-(2,3-Difluorobiphenyl-4-yl)pyrazin-2-amine. |
| 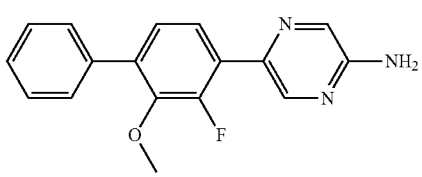 | 834 | 5-(3-Fluoro-2-methoxybiphenyl-4-yl)pyrazin-2-amine. |
| 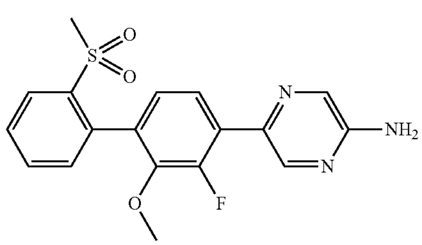 [SMILES: COc1c(-c2ccccc2S(C)(=O)=O)ccc(-c2cnc(N)cn2)c1F] | 835 | 5-[3-Fluoro-2-methoxy-2'-(methylsulfonyl)biphenyl-4-yl]pyrazin-2-amine. |

TABLE 3-continued

| STRUCTURE | COMPOUND # | NAME |
|---|---|---|
| 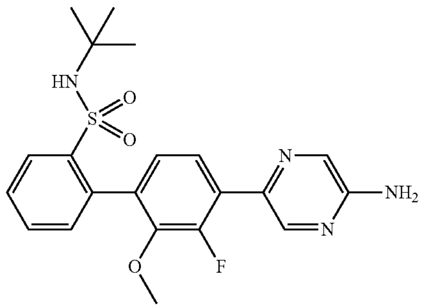 [SMILES: COc1c(-c2ccccc2S(=O)(=O)NC(C)(C)C)ccc(-c2cnc(N)cn2)c1F] | 836 | 4'-(5-Aminopyrazin-2-yl)-N-tert-butyl-3'-fluoro-2'-methoxybiphenyl-2-sulfonamide. |
| 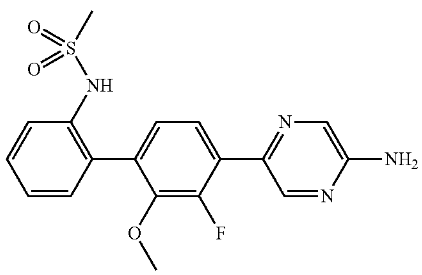 [SMILES: COc1c(-c2ccccc2NS(C)(=O)=O)ccc(-c2cnc(N)cn2)c1F] | 837 | N-[4'-(5-Aminopyrazin-2-yl)-3'-fluoro-2'-methoxybiphenyl-2-yl]methanesulfonamide. |
| 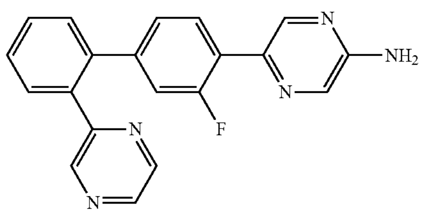 [SMILES: Nc1cnc(-c2ccc(-c3ccccc3-c3cnccn3)cc2F)cn1] | 838 | 5-(3-fluoro-2'-(pyrazin-2-yl-[1,1'-biphenyl]-4-yl)pyrazin-2-amine |
| 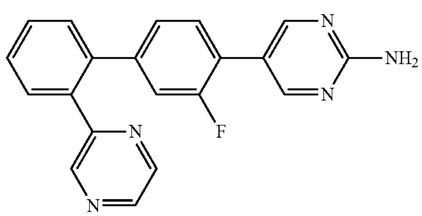 [SMILES: Nc1ncc(-c2ccc(-c3ccccc3-c3cnccn3)cc2F)cn1] | 839 | 5-(3-Fluoro-2'-pyrazin-2-ylbiphenyl-4-yl)pyrimidin-2-amine. |
| 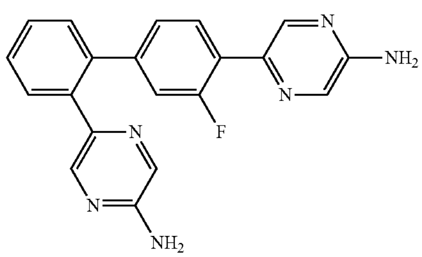 [SMILES: Nc1cnc(-c2ccc(-c3ccccc3-c3cnc(N)cn3)cc2F)cn1] | 840 | 5,5'-(3'-Fluorobiphenyl-2,4'-diyl)dipyrazin-2-amine. |
| 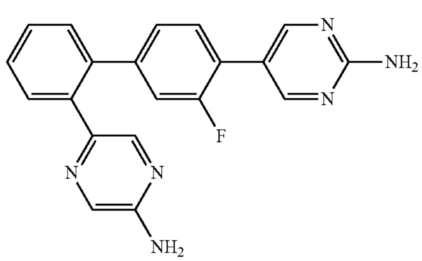 [SMILES: Nc1cnc(-c2ccccc2-c2ccc(-c3cnc(N)nc3)c(F)c2)cn1] | 841 | 5-[2'-(5-Aminopyrazin-2-yl)-3-fluorobiphenyl-4-yl]pyrimidin-2-amine. |

TABLE 3-continued

| STRUCTURE | COMPOUND # | NAME |
|---|---|---|
| 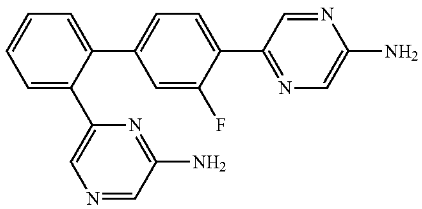 [SMILES: Nc1cnc(-c2ccc(-c3ccccc3-c3cncc(N)n3)cc2F)cn1] | 842 | 5-[2'-(6-Aminopyrazin-2-yl)-3-fluorobiphenyl-4-yl]pyrazin-2-amine. |
| 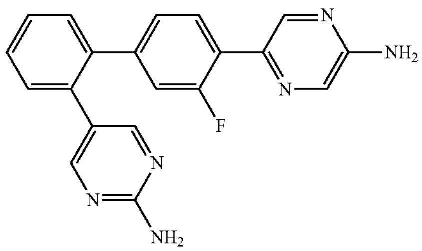 | 843 | 5-[4'-(5-Aminopyrazin-2-yl)-3'-fluorobiphenyl-2-yl]pyrimidin-2-amine. |
| 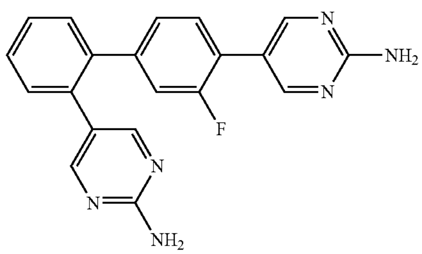 | 844 | 5-5'-(3'-Fluorobiphenyl-2,4'-diyl)dipyrimidin-2-amine. |
| 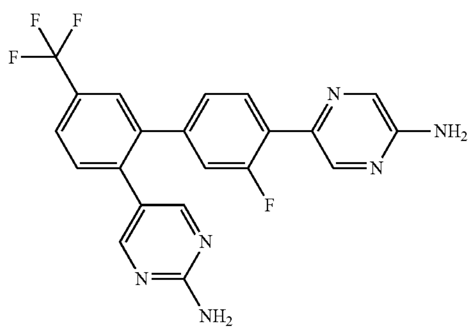 [SMILES: Nc1cnc(-c2ccc(-c3cc(C(F)(F)F)ccc3-c3cnc(N)nc3)cc2F)cn1] | 845 | 5-[4'-(5-Aminopyrazin-2-yl)-3'-fluoro-5-(trifluoromethyl)biphenyl-2-yl]pyrimidin-2-amine. |
| 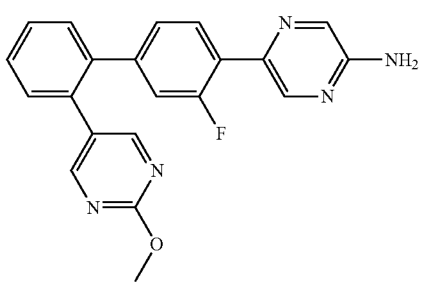 [SMILES: COc1ncc(-c2ccccc2-c2ccc(-c3cnc(N)cn3)c(F)c2)cn1] | 846 | 5-[3-Fluoro-2'-(2-methoxypyrimidin-5-yl)biphenyl-4-yl]pyrazin-2-amine. |
| 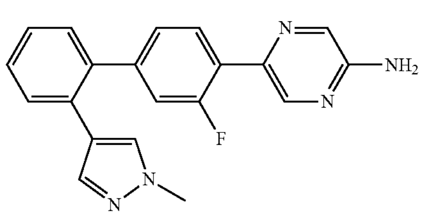 [SMILES: Cn1cc(-c2ccccc2-c2ccc(-c3cnc(N)cn3)c(F)c2)cn1] | 847 | 5-[3-Fluoro-2'-(1-methyl-1H-pyrazol-4-yl)biphenyl-4-yl]pyrazin-2-amine. |

TABLE 3-continued

| STRUCTURE | COMPOUND # | NAME |
|---|---|---|
| 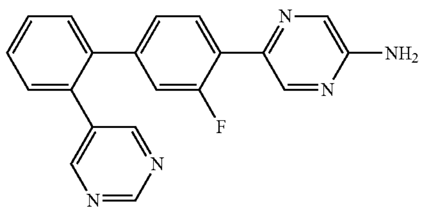 [SMILES: Nc1cnc(-c2ccc(-c3ccccc3-c3cncnc3)cc2F)cn1] | 848 | 5-(3-Fluoro-2'-pyrimidin-5-ylbiphenyl-4-yl)pyrazin-2-amine. |
| 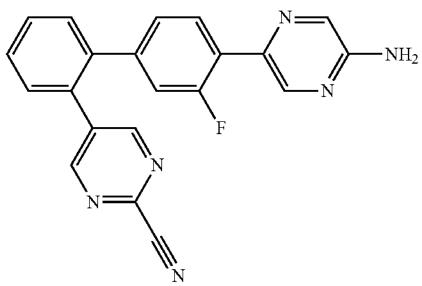 [SMILES: N#Cc1ncc(-c2ccccc2-c2ccc(-c3cnc(N)cn3)c(F)c2)cn1] | 849 | 5-[4'-(5-Aminopyrazin-2-yl)-3'-fluorobiphenyl-2-yl]pyrimidine-2-carbonitrile. |
| 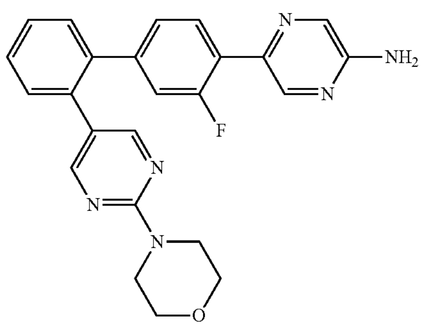 [SMILES: Nc1cnc(-c2ccc(-c3ccccc3-c3cnc(N4CCOCC4)nc3)cc2F)cn1] | 850 | 5-[3-Fluoro-2'-(2-morpholin-4-ylpyrimidin-5-yl)biphenyl-4-yl]pyrazin-2-amine. |
| 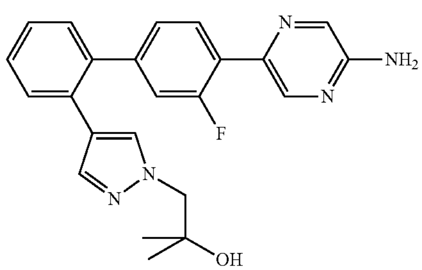 [SMILES: CC(C)(O)Cn1cc(-c2ccccc2-c2ccc(-c3cnc(N)cn3)c(F)c2)cn1] | 851 | 1-{4-[4-(5-Aminopyrazin-2-yl)-3'-fluorobiphenyl-2-yl]-1H-pyrazol-1-yl}-2-methylpropan-2-ol. |
| 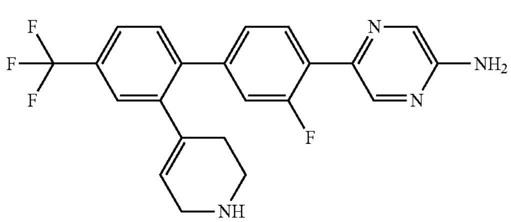 [SMILES: Nc1cnc(-c2ccc(-c3ccc(C(F)(F)F)cc3C3=CCNCC3)cc2F)cn1] | 852 | 5-[3-Fluoro-2'-(1,2,3,6-tetrahydropyridin-4-yl)-4'-(trifluoromethyl)biphenyl-4-yl]pyrazin-2-amine. |
| 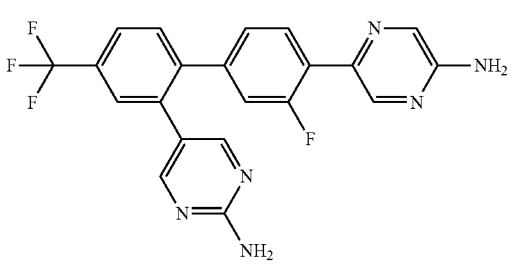 [SMILES: Nc1cnc(-c2ccc(-c3ccc(C(F)(F)F)cc3-c3cnc(N)nc3)cc2F)cn1] | 853 | 5-[4'-(5-Aminopyrazin-2-yl)-3'-fluoro-4-(trifluoromethyl)biphenyl-2-yl]pyrimidin-2-amine. |

TABLE 3-continued

| STRUCTURE | COMPOUND # | NAME |
|---|---|---|
| 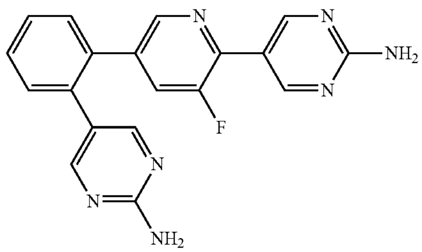 [SMILES: Nc1ncc(-c2ccccc2-c2cnc(-c3cnc(N)nc3)c(F)c2)cn1] | 854 | 5-{2-[6-(2-Aminopyrimidin-5-yl)-5-fluoropyridin-3-yl]phenyl}pyrimidin-2-amine. |
| 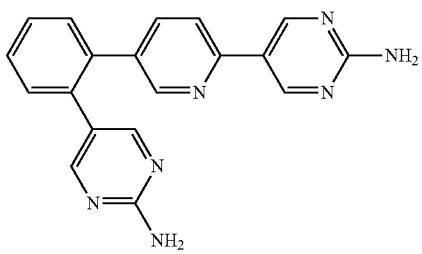 [SMILES: Nc1ncc(-c2ccc(-c3ccccc3-c3cnc(N)nc3)cn2)cn1] | 855 | 5-{5-[2-(2-Aminopyrimidin-5-yl)phenyl]pyridin-2-yl}pyrimidin-2-amine. |
| 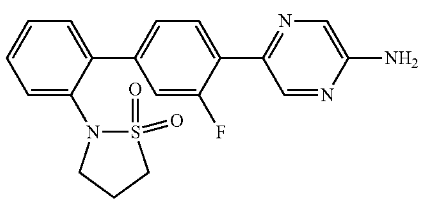 [SMILES: Nc1cnc(-c2ccc(-c3ccccc3N3CCCS3(=O)=O)cc2F)cn1] | 856 | 5-[2'-(1,1-Dioxidoisothiazolidin-2-yl)-3-fluorobiphenyl-4-yl]pyrazin-2-amine |
| 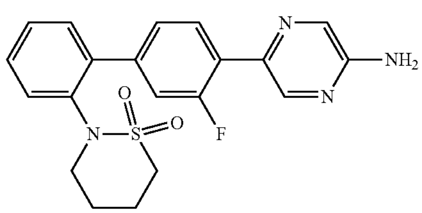 [SMILES: Nc1cnc(-c2ccc(-c3ccccc3N3CCCCS3(=O)=O)cc2F)cn1] | 857 | 5-[2'-(1,1-Dioxido-1,2-thiazinan-2-yl)-3-fluorobiphenyl-4-yl]pyrazin-2-amine |
| 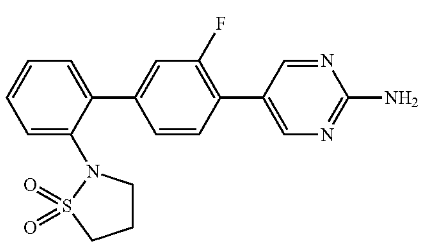 [SMILES: Nc1ncc(-c2ccc(-c3ccccc3N3CCCS3(=O)=O)cc2F)cn1] | 858 | 5-[2'-(1,1-Dioxidoisothiazolidin-2-yl)-3-fluorobiphenyl-4-yl]pyrimidin-2-amine |
| 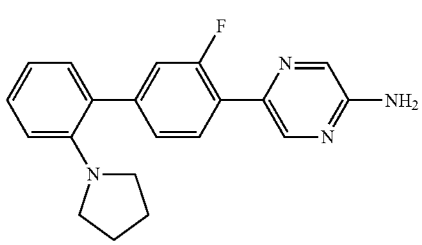 [SMILES: Nc1cnc(-c2ccc(-c3ccccc3N3CCCC3)cc2F)cn1] | 859 | 5-[2-Fluoro-4-(2-pyrrolidin-1-ylpyridin-3-yl)phenyl]pyrazin-2-amine |

TABLE 3-continued

| STRUCTURE | COMPOUND # | NAME |
|---|---|---|
| 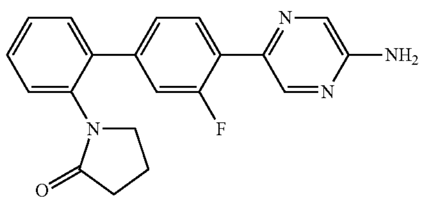 [SMILES: Nc1cnc(-c2ccc(-c3ccccc3N3CCCC3=O)cc2F)cn1] | 860 | 1-[4'-(5-Aminopyrazin-2-yl)-3'-fluorobiphenyl-2-yl]pyrrolidin-2-one |
| 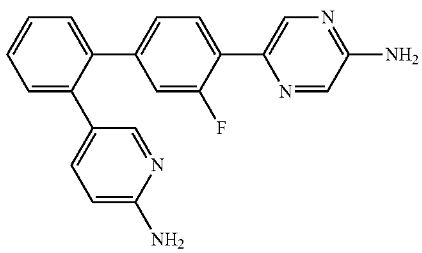 | 861 | 5-[2'-(6-Aminopyridin-3-yl)-3-fluorobiphenyl-4-yl]pyrazin-2-amine |
| 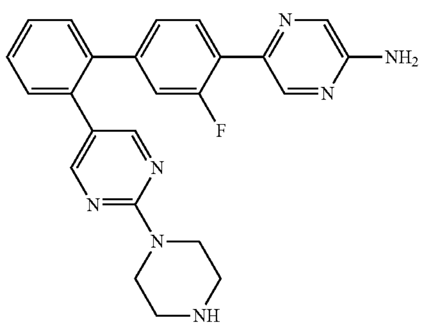 [SMILES: Nc1cnc(-c2ccc(-c3ccccc3-c3cnc(N4CCNCC4)nc3)cc2F)cn1] | 862 | 5-[3-Fluoro-2'-(2-piperazin-1-ylpyrimidin-5-yl)biphenyl-4-yl]pyrazin-2-amine |
| 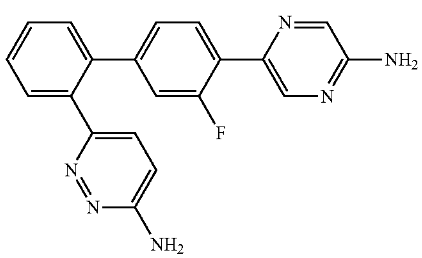 [SMILES: Nc1cnc(-c2ccc(-c3ccccc3-c3ccc(N)nn3)cc2F)cn1] | 863 | 6-[4-(5-Aminopyrazin-2-yl)-3'-fluorobiphenyl-2-yl]pyridazin-3-amine |
| 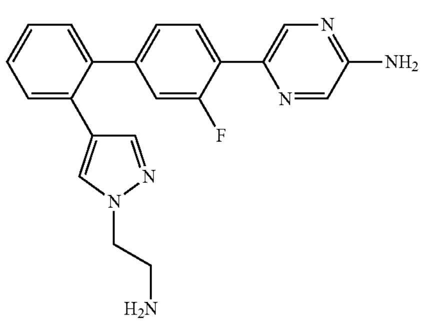 [SMILES: NCCn1cc(-c2ccccc2-c2ccc(-c3cnc(N)cn3)c(F)c2)cn1] | 864 | 5-{2'-[1-(2-Aminoethyl)-1H-pyrazol-4-yl]-3-fluorobiphenyl-4-yl}pyrazin-2-amine |

TABLE 3-continued

| STRUCTURE | COMPOUND # | NAME |
|---|---|---|
| 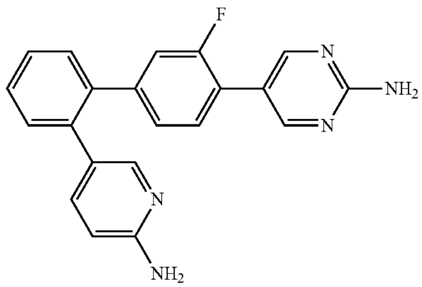 [SMILES: Nc1ccc(-c2ccccc2-c2ccc(-c3cnc(N)nc3)c(F)c2)cn1] | 865 | 5-[2'-(6-Aminopyridin-3-yl)-3-fluorobiphenyl-4-yl]pyrimidin-2-amine |
| 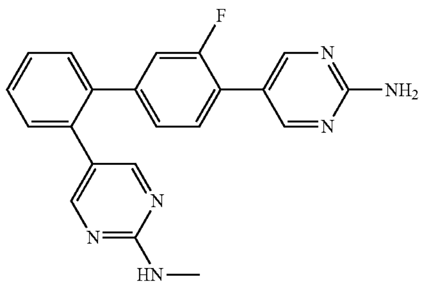 [SMILES: CNc1ncc(-c2ccccc2-c2ccc(-c3cnc(N)nc3)c(F)c2)cn1] | 866 | 5-[4'-(2-Aminopyrimidin-5-yl)-3'-fluorobiphenyl-2-yl]-N-methylpyrimidin-2-amine |
| 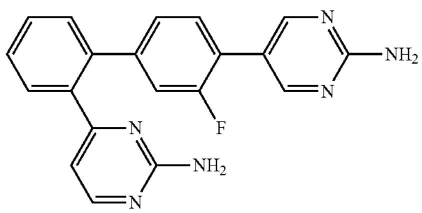 [SMILES: Nc1ncc(-c2ccc(-c3ccccc3-c3ccnc(N)n3)cc2F)cn1] | 867 | 4-[4'-(2-Aminopyrimidin-5-yl)-3'-fluorobiphenyl-2-yl]pyrimidin-2-amine |
| 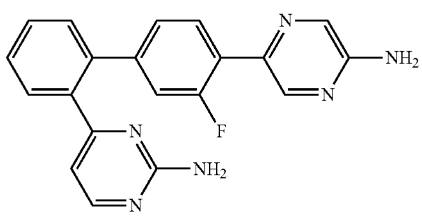 [SMILES: Nc1cnc(-c2ccc(-c3ccccc3-c3ccnc(N)n3)cc2F)cn1] | 868 | 4-[4'-(5-Aminopyrazin-2-yl)-3'-fluorobiphenyl-2-yl]pyrimidin-2-amine |
| 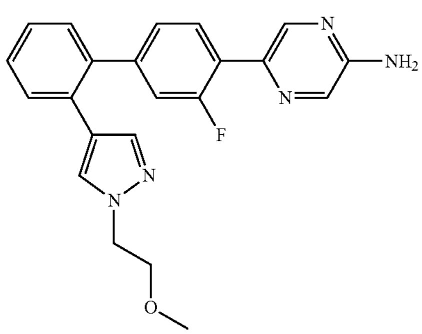 [SMILES: COCCn1cc(-c2ccccc2-c2ccc(-c3cnc(N)cn3)c(F)c2)cn1] | 869 | 5-{3-Fluoro-2'-[1-(2-methoxyethyl)-1H-pyrazol-4-yl]biphenyl-4-yl}pyrazin-2-amine |
| 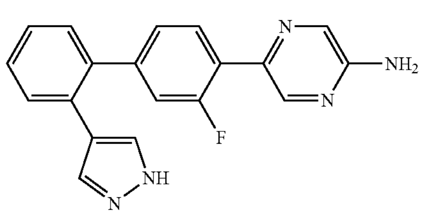 | 870 | 5-[3-Fluoro-2'-(1H-pyrazol-4-yl)biphenyl-4-yl]pyrazin-2-amine |

TABLE 3-continued

| STRUCTURE | COMPOUND # | NAME |
|---|---|---|
| 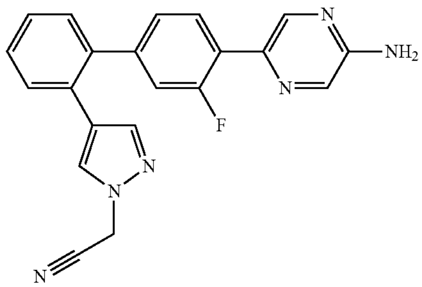 [SMILES: N#CCn1cc(-c2ccccc2-c2ccc(-c3cnc(N)cn3)c(F)c2)cn1] | 871 | {4-[4'-(5-Aminopyrazin-2-yl)-3'-fluorobiphenyl-2-yl]-1H-pyrazol-1-yl}acetonitrile |
| 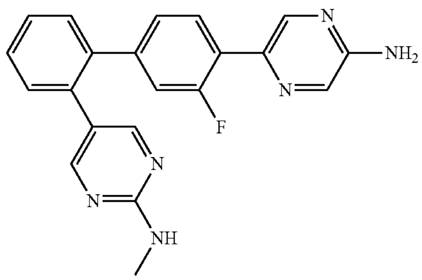 [SMILES: CNc1ncc(-c2ccccc2-c2ccc(-c3cnc(N)cn3)c(F)c2)cn1] | 872 | 5-[4'-(5-Aminopyrazin-2-yl)-3'-fluorobiphenyl-2-yl]-N-methylpyrimidin-2-amine |
| 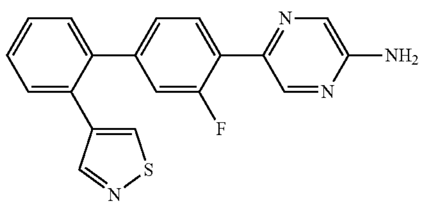 [SMILES: Nc1cnc(-c2ccc(-c3ccccc3-c3cnsc3)cc2F)cn1] | 873 | 5-(3-Fluoro-2'-isothiazol-4-ylbiphenyl-4-yl)pyrazin-2-amine |
| 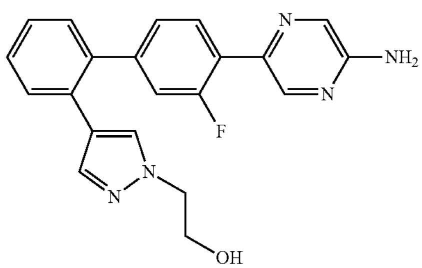 [SMILES: Nc1cnc(-c2ccc(-c3ccccc3-c3cnn(CCO)c3)cc2F)cn1] | 874 | 2-{4-[4'-(5-Aminopyrazin-2-yl)-3'-flluoroblphenyl-2-yl-1H-pyrazol-1-yl}ethanol |
| 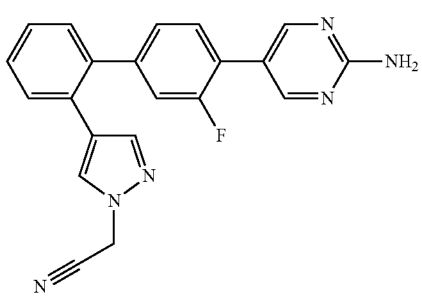 | 875 | {4-[4'-(2-Aminopyrimidin.-5-yl)-3'-fluorobiphenyl-2-yl]-1H-pyrazol-yl}acetonitrile |
| 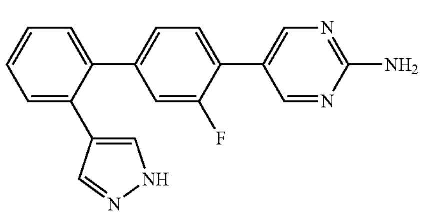 [SMILES: Nc1ncc(-c2ccc(-c3ccccc3-c3cn[nH]c3)cc2F)cn1] | 876 | 5-[3-Fluoro-2'-(1H-pyrazo-4-yl)biphenyl-4-yl]pyrimidin-2-amine |

TABLE 3-continued

| STRUCTURE | COMPOUND # | NAME |
|---|---|---|
| 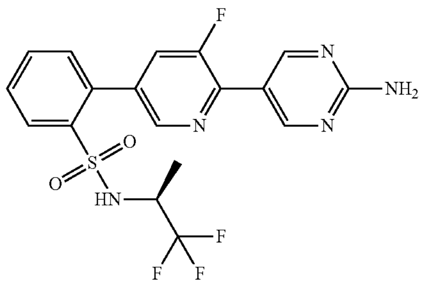 [SMILES: C[C@H](NS(=O)(=O)c1ccccc1-c1cnc(-c2cnc(N)nc2)c(F)c1)C(F)(F)F] | 877 | 2-[6-(2-Aminopyrimidin-5-yl)-5-fluoropyridin-3-yl]-N-[(1S)-2,2,2-trifluoro-1-methylethyl]penzenesulfonamide as the hydrochloride salt |
| 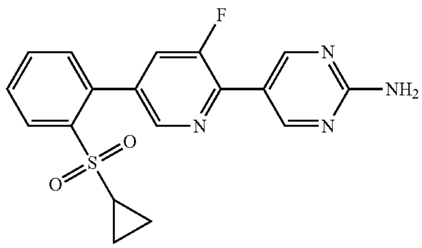 [SMILES: Nc1ncc(-c2ncc(-c3ccccc3S(=O)(=O)C3CC3)cc2F)cn1] | 878 | 5-{5-[2-(Cyclopropylsulfonyl)phenyl]-3-fluoropyridin-2-yl}pyrimidin-2-amine |
| 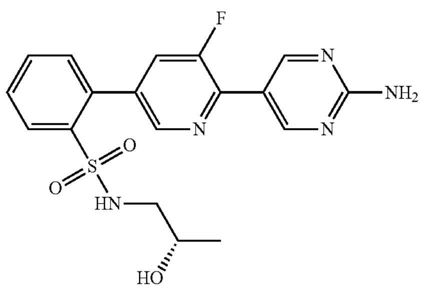 [SMILES: C[C@H](O)CNS(=O)(=O)c1ccccc1-c1cnc(-c2cnc(N)nc2)c(F)c1] | 879 | 2-[6-(2-Aminopyrimidin-5-yl)-5-fluoropyridin-3-yl]-N-[(2S)-2-hydroxypropyl]benzenesulfonamide |
| 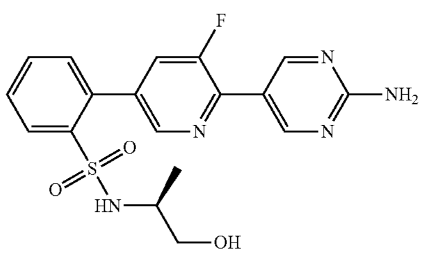 [SMILES: C[C@@H](CO)NS(=O)(=O)c1ccccc1-c1cnc(-c2cnc(N)nc2)c(F)c1] | 880 | 2-[6-(2-Aminopyrimidin-5-yl)-5-fluoropyridin-3-yl]-N-[(1S)-2-hydroxy-1-methylethyl]benzenesulfonamide |
| 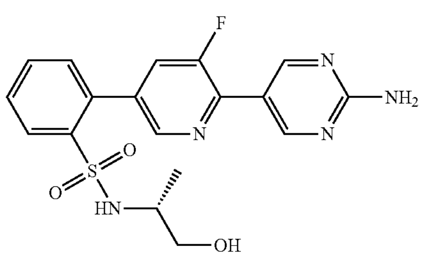 [SMILES: C[C@H](CO)NS(=O)(=O)c1ccccc1-c1cnc(-c2cnc(N)nc2)c(F)c1] | 881 | 2-[6-(2-Aminopyrimidin-5-yl)-5-fluoropyridin-a-yl]-N-[(1R)-2-hydroxy-1-methylethyl]benzenesulfonamide |
| 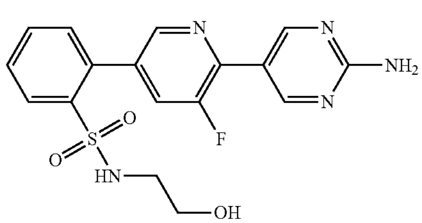 [SMILES: Nc1ncc(-c2ncc(-c3ccccc3S(=O)(=O)NCCO)cc2F)cn1] | 882 | 2-[6-(2-Aminopyrimidin-5-yl)-5-fluoropyridin-3-yl]-N-(2-hydroxyethyl)benzenesulfonamide. |

TABLE 3-continued

| STRUCTURE | COMPOUND # | NAME |
|---|---|---|
| 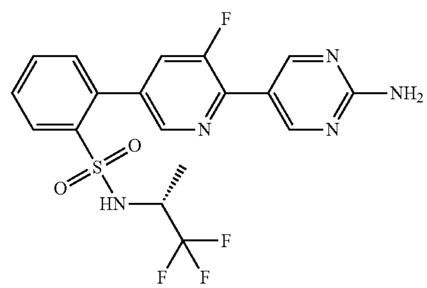 [SMILES: C[C@@H](NS(=O)(=O)c1ccccc1-c1cnc(-c2cnc(N)nc2)c(F)c1)C(F)(F)F] | 883 | 2-[6-(2-Aminopyrimidin-5-yl)-5-fluoropyridin-3yl]-N-[(1R)-2,2,2-trifluoro-1-methylethyl]benzenesulfonamide |
| 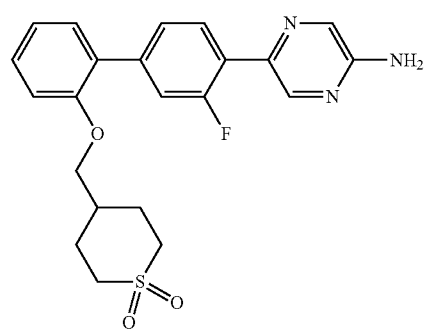 [SMILES: Nc1cnc(-c2ccc(-c3ccccc3OCC3CCS(=O)(=O)CC3)cc2F)cn1] | 884 | 5-{2'-[(1,1-Dioxidotetrahydro-2H-thiopyran-4-yl)methoxy]-3-fluorobiphenyl-4-yl}pyrazin-2-amine |
| 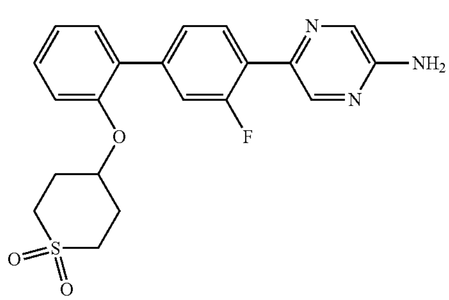 | 885 | 5-{2'-[(1,1-Dioxidotetrahydro-2H-thiopyran-4-yl)oxy]-3-fluorobiphenyl-4-yl}pyrazin-2-amine |
| 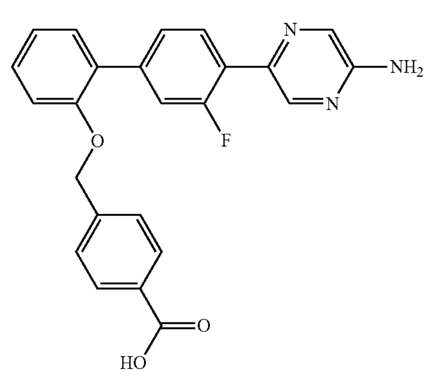 [SMILES: Nc1cnc(-c2ccc(-c3ccccc3OCc3ccc(C(=O)O)cc3)cc2F)cn1] | 886 | 4-(([4'-(5-Aminopyrazin-2-yl)-3'-fluorobiphenyl-2-yl]oxy}methyl)benzoic acid |

TABLE 3-continued

| STRUCTURE | COMPOUND # | NAME |
|---|---|---|
| 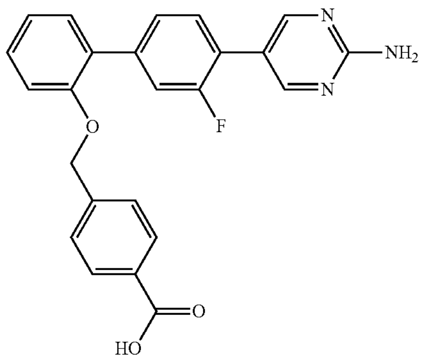 [SMILES: Nc1ncc(-c2ccc(-c3ccccc3OCc3ccc(C(=O)O)cc3)cc2F)cn1] | 887 | 4-({[4'-(2-Aminopyrimidin-5-yl)-3'-fluorobiphenyl-2-yl]oxy}methyl)benzoic acid |
| 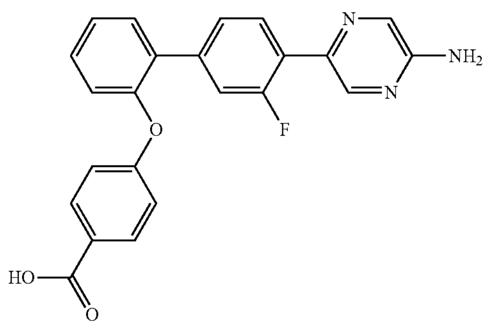 [SMILES: Nc1cnc(-c2ccc(-c3ccccc3Oc3ccc(C(=O)O)cc3)cc2F)cn1] | 888 | 4-{[4'-(5-Aminopyrazin-2-yl)-3'-fluorobiphenyl-2-yl]oxy}benzoic acid |
| 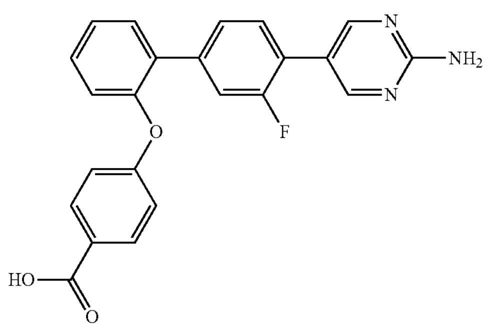 | 889 | 4-{[4'-(2-Aminopyrimidin-5-yl)-3'-fluorobiphenyl-2-yl]oxy}benzoic acid |
| 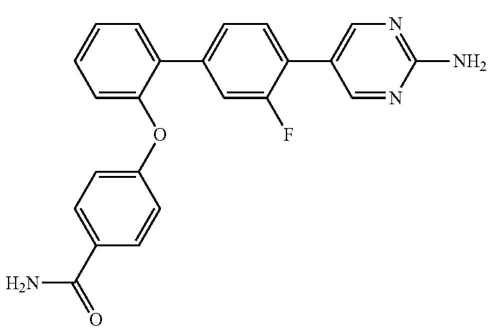 [SMILES: NC(=O)c1ccc(Oc2ccccc2-c2ccc(-c3cnc(N)nc3)c(F)c2)cc1] | 890 | 4-{[4'-(2-Aminopyrimidin-5-yl)-3'-fluorobiphenyl-2-yl]oxy)benzamide |

TABLE 3-continued

| STRUCTURE | COMPOUND # | NAME |
|---|---|---|
| 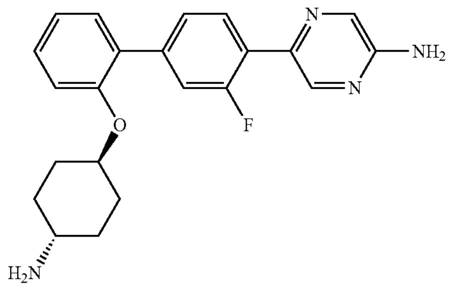 | 891 | 5-{2'-1(trans-4-Aminocyclohexyl)oxy]-3-fluorobiphenyl-4-yl}pyrazin-2-amine |
| 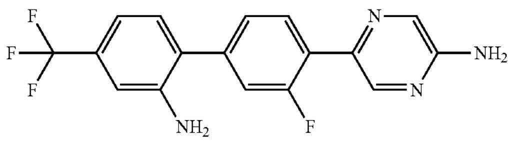 [SMILES: Nc1cnc(-c2ccc(-c3ccc(C(F)(F)F)cc3N)cc2F)cn1] | 892 | 5-[2'-Amino-3-fluoro-4'-(trifluoromethyl)biphenyl-4-yl]pyrazin-2-amine |
| 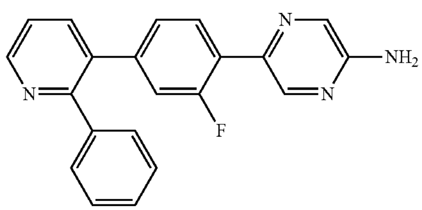 [SMILES: Nc1cnc(-c2ccc(-c3cccnc3-c3ccccc3)cc2F)cn1] | 893 | 5-[2-Fluoro-4-(2-phenylpyridin-3-yl)phenyl]pyrazin-2-amine |
| 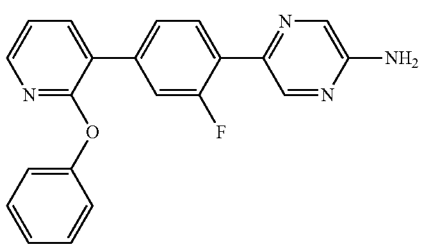 [SMILES: Nc1cnc(-c2ccc(-c3cccnc3Oc3ccccc3)cc2F)cn1] | 894 | 5-[2-Fluoro-4-(2-phenoxypyridin-3-yl)phenyl]pyrazin-2-amine |
| 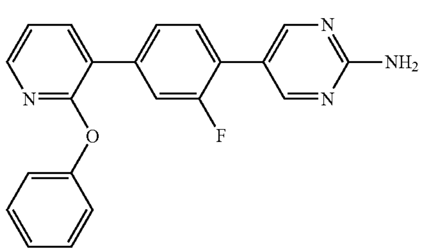 | 895 | 5-[2-Fluoro-4-(2-phenoxypyridin-3-yl)phenyl]pyrimidin-2-amine |
| 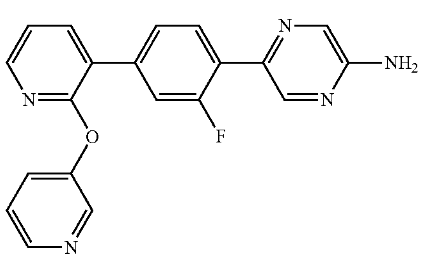 [SMILES: Nc1cnc(-c2ccc(-c3cccnc3Oc3cccnc3)cc2F)cn1] | 896 | 5-{2-Fluoro-4-[2-(pyridin-3-yloxy)pyridin-3-yl]phenyl}pyrazin-2-amine |

TABLE 3-continued

| STRUCTURE | COMPOUND # | NAME |
|---|---|---|
| 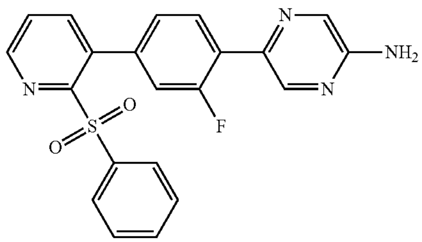 [SMILES: Nc1cnc(-c2ccc(-c3cccnc3S(=O)(=O)c3ccccc3)cc2F)cn1] | 897 | 5-{2-Fluoro-4-[2-(phenylsulfonyl)pyridin-3-yl]phenyl}pyrazin-2-amine |
| 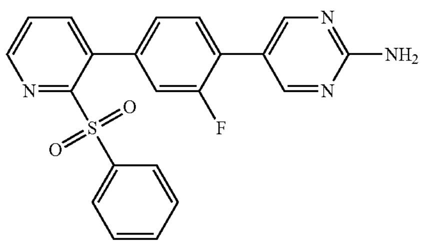 [SMILES: Nc1ncc(-c2ccc(-c3cccnc3S(=O)(=O)c3ccccc3)cc2F)cn1] | 898 | 5-{2-fluoro-4-[2-(phenylsulfonyl)pyridin-3-yl]phenyl}pyrimidin-2-amine |
| 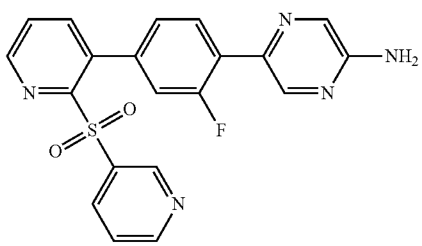 | 899 | 5-{2-Fluoro-4-[2-(pyridin-3-ylsulfonyl)pyridin-3-yl]phenyl}pyrazin-2-amine |
| 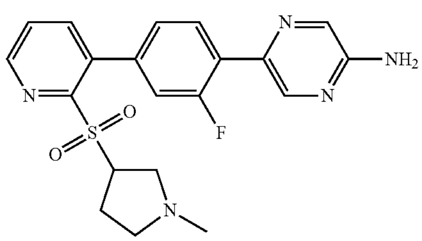 [SMILES: CN1CCC(S(=O)(=O)c2ncccc2-c2ccc(-c3cnc(N)cn3)c(F)c2)C1] | 900 | 5-(2-Fluoro-4-{2-[(1-methylpyrrolidin-3-yl)sulfonyl]pyridin-3-yl}phenyl)pyrazin-2-amine |
| 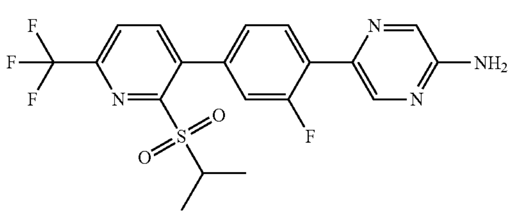 [SMILES: CC(C)S(=O)(=O)c1nc(C(F)(F)F)ccc1-c1ccc(-c2cnc(N)cn2)c(F)c1] | 901 | 5-(2-Fluoro-4-{2-[(1-methylethyl)sulfonyl]-6-(trifluoromethyl)pyridin-3-yl}phenyl)pyrazin-2-amine |
| 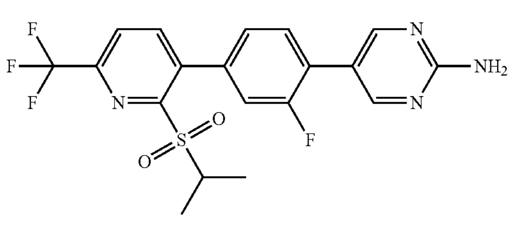 [SMILES: CC(C)S(=O)(=O)c1nc(C(F)(F)F)ccc1-c1ccc(-c2cnc(N)nc2)c(F)c1] | 902 | 5-(2-Fluoro-4-{2-[(1-methylethyl)sulfonyl]-6-(trifluoromethyl)pyridin-3-yl}phenyl)pyrimidin-2-amine |

US 9,745,328 B2

TABLE 3-continued

| STRUCTURE | COMPOUND # | NAME |
|---|---|---|
| 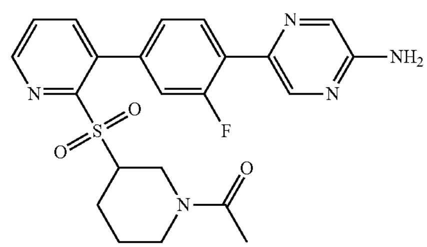 [SMILES: CC(=O)N1CCCC(S(=O)(=O)c2ncccc2-c2ccc(-c3cnc(N)cn3)c(F)c2)C1] | 903 | 5-(4-{2-[(1-Acetylpiperidin-3-yl)sulfonyl]pyridin-3-yl}-2-fluorophenyl)pyrazin-2-amine |
| 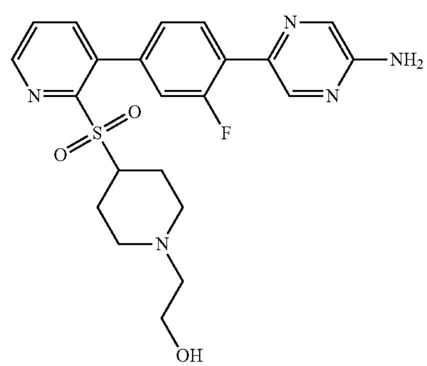 [SMILES: Nc1cnc(-c2ccc(-c3cccnc3S(=O)(=O)C3CCN(CCO)CC3)cc2F)cn1] | 904 | 2-[4-({3-[4-(5-Aminopyrazin-2-yl)-3-fluorophenyl]pyridin-2-yl}sulfonyl)pipendin-1-yl]ethanol |
| 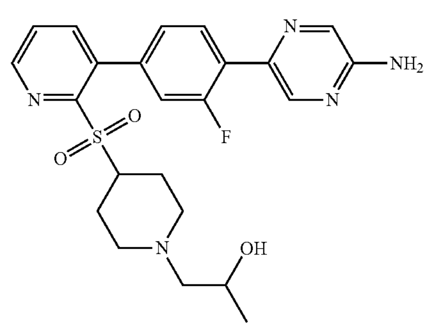 [SMILES: CC(O)CN1CCC(S(=O)(=O)c2ncccc2-c2ccc(-c3cnc(N)cn3)c(F)c2)CC1] | 905 | (racemic)-1-[4({3-[4-(5-Aminopyrazin-2-yl)-3-fluorophenyl]pyridin-2-yl}sulfonyl)piperidin-1-yl]propan-2-ol |
| 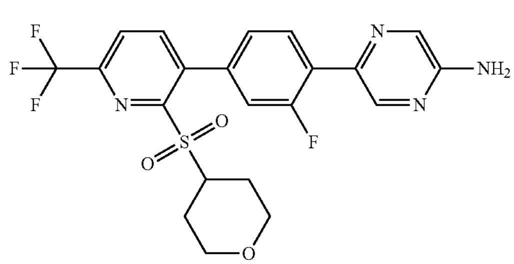 [SMILES: Nc1cnc(-c2ccc(-c3ccc(C(F)(F)F)nc3S(=O)(=O)C3CCOCC3)cc2F)cn1] | 906 | 5-{2-Fluoro-4-[2-tetrahydro-2H-pyran-4-ylsulfonyl)-6-(trifluoromethyl)pyridin-3-yl]phenyl}pyrazin-2-amine |
| 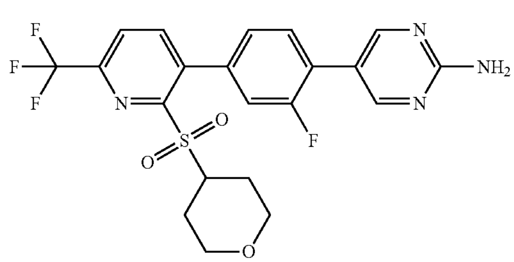 [SMILES: Nc1ncc(-c2ccc(-c3ccc(C(F)(F)F)nc3S(=O)(=O)C3CCOCC3)cc2F)cn1] | 907 | 5-{2-Fluoro-4-[2-(tetrahydro-2H-pyran-4-ylsulfonyl)-6-(trifluoromethyl)pyridin-3-yl]phenyl}pyrimidin-2-amine |

TABLE 3-continued

| STRUCTURE | COMPOUND # | NAME |
|---|---|---|
| 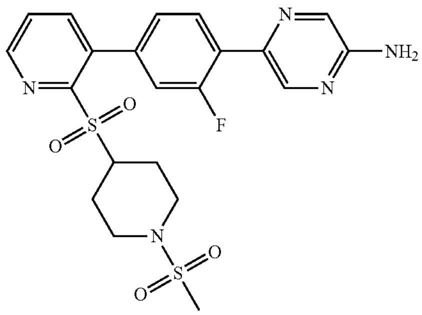 | 908 | 5-(2-Fluoro-4-(2-{[1-(methylsulfonyl)piperidin-4-yl]sulfonyl}pyridin-3-yl)phenyl]pyrazin-2-amine |
| 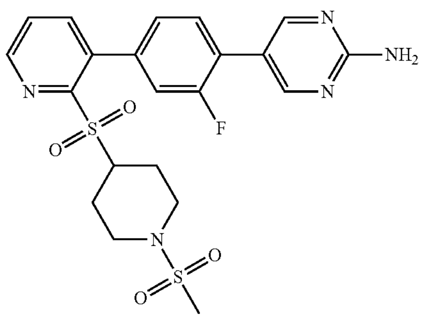 [SMILES: CS(=O)(=O)N1CCC(S(=O)(=O)c2ncccc2-c2ccc(-c3cnc(N)nc3)c(F)c2)CC1] | 909 | 5-(2-Fluoro-4-(2-{[1-(methylsulfonyl)piperidin-4-yl]sulfonyl}pyridin-3-yl)phenyl]pyrimidin-2-amine |
| 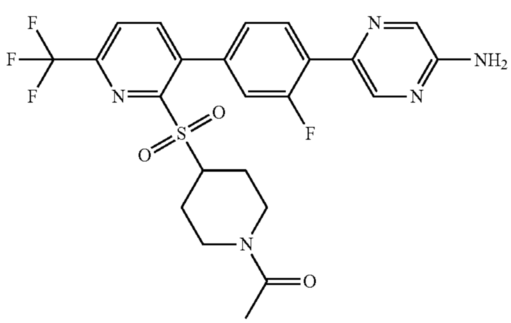 [SMILES: CC(=O)N1CCC(S(=O)(=O)c2nc(C(F)(F)F)ccc2-c2ccc(-c3cnc(N)cn3)c(F)c2)CC1] | 910 | 5-(4-{2-[(1-Acetylpiperidin-4-yl)sulfonyl]-6-(trifluoromethyl)pyridin-3-yl}-2-fluorophenyl)pyrazin-2-amine |
| 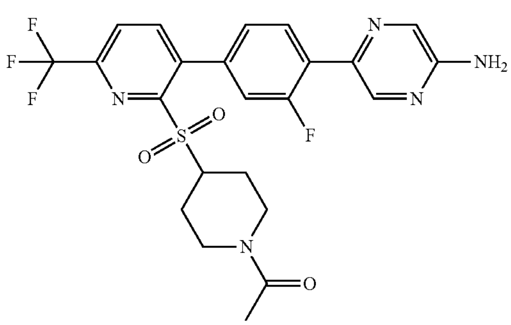 [SMILES: CC(=O)N1CCC(S(=O)(=O)c2nc(C(F)(F)F)ccc2-c2ccc(-c3cnc(N)cn3)c(F)c2)CC1] | 911 | 5-(4-{2-[(1-Acetylpiperidin-4-yl)sulfonyl]-6-(trifluoromethyl)pyridin-3-yl}-2-fluorophenyl)pyrimidin-2-amine |
| 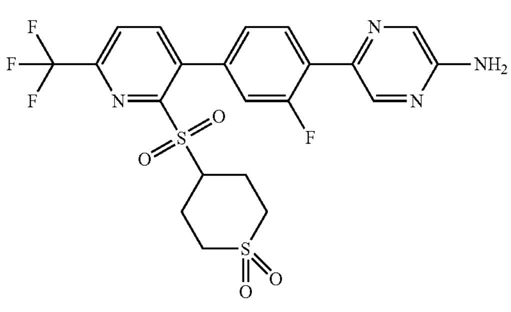 [SMILES: Nc1cnc(-c2ccc(-c3ccc(C(F)(F)F)nc3S(=O)(=O)C3CCS(=O)(=O)CC3)cc2F)cn1] | 912 | 5-(4-{2-[(1,1-Dioxidotetrahydro-2H-thiopyran-4-yl)sulfonyl]-6-(trifluoromethyl)pyridin-3-yl}-2-fluorophenyl)pyrazin-2-amine |

TABLE 3-continued

| STRUCTURE | COMPOUND # | NAME |
|---|---|---|
| (structure) | 913 | 5-(4-{2-[(1,1-Dioxidotetrahydro-2H-thiopyran-4-yl)sulfonyl]-6-(trifluoromethyl)pyridin-3-yl}-2-fluorophenyl)pyrimidin-2-amine |

C) Synthesis

The invention provides methods of making the disclosed compounds according to traditional organic synthetic methods as well as matrix or combinatorial synthetic methods. Scheme A described suggested synthetic routes. Using the schemes, the guidelines below, and the examples, a person of skill in the art may develop analogous or similar methods for a given compound that is within the invention. These methods are representative of the synthetic schemes, but are not to be construed as limiting the scope of the invention.

Where the compounds according to this invention have at least one chiral center, they may accordingly exist as enantiomers. Where the compounds possess two or more chiral centers, they may additionally exist as diastereomers. Where the processes for the preparation of the compounds according to the invention give rise to mixtures of stereoisomers, these isomers may be separated by conventional techniques such as preparative chromatography. The compounds may be prepared in racemic form or as individual enantiomers or diastereomers by either stereospecific synthesis or by resolution. The compounds may, for example, be resolved into their component enantiomers or diastereomers by standard techniques, such as the formation of stereoisomeric pairs by salt formation with an optically active base, followed by fractional crystallization and regeneration of the free acid. The compounds may also be resolved by formation of stereoisomeric esters or amides, followed by chromatographic separation and removal of the chiral auxiliary. Alternatively, the compounds may be resolved using a chiral HPLC column. It is to be understood that all stereoisomers, racemic and scalemic mixtures, diastereomers, geometric isomers, and enantiomers thereof are encompassed within the scope of the present invention.

Representative compounds of the present invention can be synthesized in accordance with the general synthetic schemes described below and are illustrated more particularly in the specific synthetic examples that follow. The general schemes are offered by way of illustration; the invention should not be construed as being limited by the chemical reactions and conditions expressed. The methods for preparing the various starting materials used in the schemes and examples are well within the skill of persons versed in the art. No attempt has been made to optimize the yields obtained in any of the example reactions. One skilled in the art would know how to increase such yields through routine variations in reaction times, temperatures, solvents and/or reagents.

General: $^1$H and $^{13}$C NMR spectra were measured on a Bruker AC-300 (300 MHz) spectrometer using tetramethylsilane and the deuterated solvent respectively as internal standards. Elemental analyses were obtained by Quantitative Technologies Inc. (Whitehouse, N.J.) and the results were within 0.4% of the calculated values unless otherwise mentioned. Melting points were determined in open capillary tubes with a Mel-Temp II apparatus (Laboratory Devices Inc.) and were uncorrected. Electrospray mass spectra (MS-ESI) were recorded in the positive mode on a Hewlett Packard 59987A spectrometer. High resolution mass spectra (HRMS) were obtained on a Micromass Autospec. E spectrometer by fast atom bombardment (FAB) technique.

Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

Examples of the described synthetic routes include Scheme A-G, Intermediates A-HZ. Examples 1-588 and prophetic Examples 1-247. Compounds analogous to the target compounds of these examples can be made according to similar routes. The disclosed compounds are useful as pharmaceutical agents as described herein.

Abbreviations or acronyms useful herein include:

| Abbreviation | Meaning |
|---|---|
| BOC/boc | tert-butyloxycarbonyl |
| BOP | benzotriazol-1-yloxy-tris(dimethylamino)phosphonium hexafluorophosphate |
| Cpd | compound |
| DCE | dichloroethane |
| DCM | dichloromethane |
| DIPEA | diisopropyl ethyl amine |
| DMA | N,N-dimethylacetamide |
| DMAP | N,N-dimethylaminopyridine |
| DMF | N,N-dimethylformamide |
| DMSO | dimethyl sulfoxide |
| DPBS | Dulbecco's phosphate buffered saline |
| EDC | 1-(3-dimethylaminopropyl)-3-ethylcarbodiimide hydrochloride |
| ESI | electrospray ionization |
| Et$_3$N or TEA | triethylamine |
| EtOAc | ethyl acetate |
| h/hr/hrs | hour(s) |
| HATU | 1-[bis(dimethylamino)methylene]-1H-1,2,3-triazolo[4,5-b]pyridinium 3-oxid hexafluorophosphate |

| Abbreviation | Meaning |
|---|---|
| HOBT | 1-hydroxybenzotriazole hydrate |
| HBTU | O-benzotriazol-1-yloxy-N,N,N',N'-tetramethyluronium hexafluorophosphate |
| I.D. | interior diameter |
| LG | Leaving group |
| LiOH | lithium hydroxide |
| m-CPBA | meta-chloroperoxybenzoic acid |
| min | minute(s) |
| MS | mass spectroscopy |
| NMR | nuclear magnetic resonance spectroscopy |
| OTf | Triflate |
| PG | protecting group |
| RT/rt | room temperature |
| TBME | tert-butyl methyl ether |
| THF | tetrahydrofuran |
| TLC | thin layer chromatography |
| Tos | p-toluenesulfonyl |
| dppf | 1,1'-Bis(diphenylphosphino)ferrocene |

General Guidance Representative compounds of the present invention can be synthesized in accordance with the general synthetic methods described below and are illustrated more particularly in the schemes that follow. Since the schemes are illustrations, the invention should not be construed as being limited by the chemical reactions and conditions expressed. The preparation of the various starting materials used in the schemes is well within the skill of persons versed in the art. The substituents for compounds of Formula (I) or a form thereof, represented in the schemes below, are as previously defined herein.

Unless otherwise specified, reaction solutions were stirred at room temperature under a $N_{2(g)}$ or $Ar_{(g)}$ atmosphere. When solutions were "concentrated to dryness", they were concentrated using a rotary evaporator under reduced pressure, when solutions were dried, they are typically dried over a drying agent such as $MgSO_4$ or $Na_2SO_4$.

Normal phase flash column chromatography (FCC) was performed on silica gel with RediSep® silica gel columns using ethyl acetate (EtOAc)/hexanes, $CH_2Cl_2$/MeOH, $CH_2Cl_2$/10% 2 N $NH_3$ in MeOH, $CH_2Cl_2$/i-PrOH, and the like as eluent, unless otherwise indicated.

Reverse phase high performance liquid chromatography (HPLC) was performed under the following conditions: 1) Instrument, Shimadzu; Column, Waters XBridge C18 10 μm (250×50 mm), Phenomenex Gemini column 5 μm C18 (150×21.2 mm) or Waters Xterra RP18 OBD 5 μm (100×30 mm); Gradient, 95:5 to 0:100 water (0.05% trifluoroacetic acid (TFA))/$CH_3CN$ (0.05% TFA); Flow rate, 30-80 mL/min; Detection, UV at λ=220-254 nM; 2) Instrument, Gilson; Column, Phenomenex LUNA column 5 μm C18 (250×50 mm) or Waters XBridge Prep C18 OBD 5 μm (30×150 mm); Gradient, 95:5 to 0:100 water (0.05% TFA)/$CH_3CN$ (0.05% TFA); Flow rate, 30-80 mL/min; Detection, UV at λ=220-254 nM; 3) Instrument. Gilson/Shimadzu: Column, Inertsil ODS-3 column (30×100 mm) or Inertsil ODS-3 (30×50 mm, 5 μm); Gradient, water-acetonitrile with both phases with 0.05% by volume trifluoroacetic acid; 1 min hold at 5% ACN, then 6 min gradient to 99% ACN followed by a hold at that concentration for 3 min. Flow rate, 80 ml/min; heated column at 46° Celsius with detection of UV light at λ=254 nm; and 4) Instrument, Dionex: UVD 170U Diode array detector and ThermoFinnegan Surveyor MSQ plus mass spectrometer for data collection. Waters XBridge C18 5 μm OBD 50×100 mm prep column.

All runs on the Dionex utilized water acetonitrile with 20 mM $NH_4OH$ added to the aqueous phase and a flow rate for all gradients was 80 mL/min using four possible gradients: 1) 5-60% MeCN over 12 min, then ramped to 100% MeCN and held for 6.3 min; 2) 30-70% MeCN over 12 min, then ramped to 100% MeCN and held for 6.3 min; 3) 50-80% MeCN over 12 min, then ramped to 100% MeCN and held for 6.3 min; and 4) 60-100% MeCN over 12 min, and then held for 6.3 min. The total run time for all gradient systems was 18.5 min.

Instances where solutions were filtered through a syringe filter, Pall 0.45 μM GHP membrane 13 mm and 25 mm diameter syringe filters were used Thin-layer chromatography was performed using Merck silica gel 60 $F_{254}$ 2.5 cm×7.5 cm 250 μm or 5.0 cm×10.0 cm 250 m pre-coated silica gel plates. Preparative thin-layer chromatography was performed using EM Science silica gel 60 $F_{254}$ 20 cm×20 cm 0.5 mm pre-coated plates with a 20 cm×4 cm concentrating zone. Microwave reactions were carried out in either a CEM Discover™ or a Biotage Initiator™ or Optimizer™ Microwave at specified temperatures. Mass spectra were obtained on an Agilent series 1100 MSD using electrospray ionization (ESI) in positive mode unless otherwise indicated. Calculated mass corresponds to the exact mass.

NMR spectra were obtained on either a Bruker model DPX400 (400 MHz), DPX500 (500 MHz), DRX600 (600 MHz) spectrometer. The format of the $^1$H NMR data below is: chemical shift in ppm down field of the tetramethylsilane reference (multiplicity, coupling constant J in Hz, integration).

Hydrochloride salts were obtained by treating the corresponding free bases with HCl (4 N in dioxane, 2 M in $Et_2O$, or 1.25 N in MeOH) at room temperature with mixtures either concentrated to obtain the HCl salt, or the resulting solid being isolated by filtration. Trifluoroacetic acid salts were obtained by purification of the crude reaction product by preparative reverse phase HPLC, whereby the final products were isolated as either mono-, di- or tri-fluoro acetic acid salts.

Chemical names were generated using ChemDraw Ultra 12.0 (CambridgeSoft Corp., Cambridge, Mass.) or ACD/Name Version 10.01 (Advanced Chemistry).

The compounds of Formula (I), wherein ring A, L, V, W, R, R', n, $R_1$, $R_2$, $R_3$, and $R_4$ are defined as in Formula (I), may be synthesized as outlined by the general synthetic route illustrated in Scheme A-G.

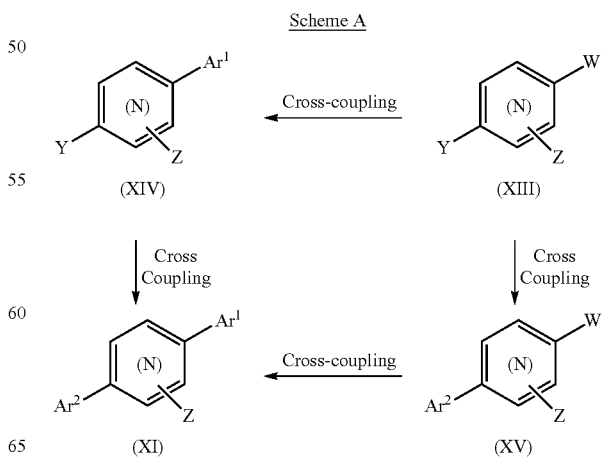

Referring to Scheme A, compounds of formulae (XI) can be obtained through a series of metal mediated cross coupling reactions starting from compound (XIII). Compounds of formulae (XIV) in which $Ar^1$ can be an amine substituted or des-amino 5-, 6-membered or 5/6- or 6/6-fused aromatic or heteroaromatic nitrogen containing ring system, can be prepared via Pd mediated cross coupling of either an aryl or heteroaryl boronic acid or ester, $Ar^1$—$B(OP)_2$, with intermediates of structure (XIII) in which W is bromo or chloro, Y is an alkyl, hetero-alkyl, aryl, or heteroaryl and Z is H, fluoro, alkyl or heteroalkyl. In instances where W is either bromo or chloro, the boronic acid or ester of compound (XIII) can be formed via palladium catalysis using bis (pinacolato)diboron and KOAc in the presence of [1,1'-bis (diphenylphosphino)ferrocene]-dichloro-palladium(II). $CH_2Cl_2$ ($Pd(dppf)Cl_2.CH_2Cl_2$) or the X-Phos pre-catalyst in solvents such as 1,4-dioxane or DMSO, at temperatures ranging from 0-100° Celsius. Alliteratively, compounds of Formulae (XIII) in which W is $B(OP)_2$ can be cross-coupled with an aryl or heteroaryl halide, $Ar^1$-X where X is either bromo or chloro to obtain compounds of formulae (XII). Preferably, in compounds of formulae (XII), Y is t-butyl, cyclobutyl, trifluoromethoxy, or $SF_5$, Z is H or -fluoro ortho to $Ar^1$, and $Ar^1$ is either amino-pyrazine, amino-pyrimidine, or amino-pyridine alliteratively substituted with or without CN, $CH_3$, $OCH_3$, $CF_3$, Cl, F, OH, and $NH_2$. Preferred solvents for cross coupling reactions include DME, DMSO, 1,4-dioxane, THF, EtOH DMF, water, and toluene or mixtures thereof, in the presence of a base, such as $Na_2CO_3$, $K_2CO_3$, KOAc, $KH_2PO_4$, and $K_3PO_4$ using catalysts such as $Pd(dppf)Cl_2.CH_2Cl_2$, palladium trifluoroacetate and $PhP_3$, chloro(2-dicyclohexylphosphino-2',4',6'-triisopropyl-1,1'-biphenyl)[2-(2-aminoethyl)phenyl)]-palladium(II), 1,1'-bis [di-t-butylphosphino)ferrocene]palladium chloride with temperatures ranging from rt to 100° Celsius.

Compounds of formulae (XI) can be prepared from compounds of formulae (XIII) via sequential (XIII→XIV→XI or XIII→XV→XI) Pd mediated cross-coupling using methods and intermediates, analogous to those described above compounds of formulae (XV) can be obtained via compounds of formulae (XIII), wherein Y is a boronic acid or ester and W is bromo or chloro, Compounds of formulae (XIII) in which Y is the boronic acid or ester can be obtained from the corresponding iodide wherein W is either bromo or chloro. Preferred methods for conversion of the iodo to the corresponding boronic acid or ester are analogous to the methods described above. In some cases, aryl and heteroaryl halides, boronic esters and acids are commercially available or can be prepared by known methods.

Compounds (XIV) in which Y is alkyl or cycloalykyl can be obtained from the corresponding bromide using alkylzinc bromides in solvents such as THF in the presence of palladium acetate and 2-dicyclohexylphosphine-2',6'-dimethoxy-1,1'-biphenyl at temperatures ranging from rt to 100° Celsius.

In further embodiments, compounds of formulae (XI) containing a pyridine core, where Z is H or -fluoro ortho to $Ar^1$, can be prepared using analogous Pd mediated cross coupling reactions described herein.

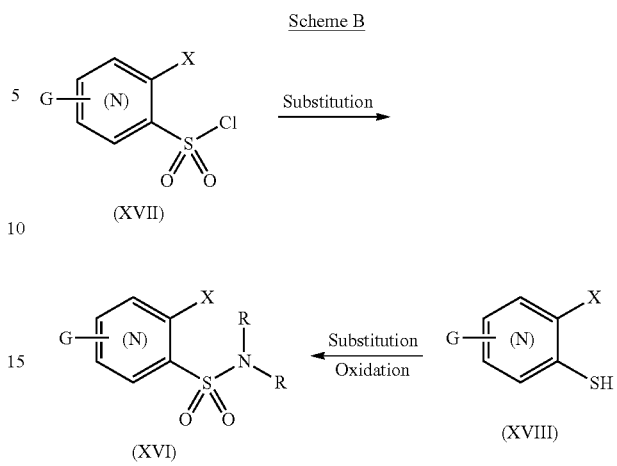

Referring to Scheme B, substituted aryl and heteroaryl sulfonamides (XVI) possessing from 0 to 3 G groups, where a G group is alkyl, cycloalkyl, heteroalkyl, $CF_3$, F, Cl, Br, or combinations thereof, and where X is bromo or chloro, can be prepared by addition of various primary and secondary amines to the aryl or heteroaryl sulfonyl chloride in solvents such as $CH_2Cl_2$, $CH_3CN$, THF, and DMF in the presences of bases such as pyridine, $Et_3N$ and i-$Pr_2EtNH$ at temperatures ranging from -20° to 1000 Celsius.

Alliteratively, sulfones (XVI) can be obtained from the corresponding bromo or chloro aryl thiol (XVIII). $S_N1$ substitution in the presence of a strong acid, such as $H_2SO_4$, with an appropriately reactive alcohol, such as tert-butanol, provides the desired aryl sulfide. Additionally, one can obtain substituted aryl sulfides via $S_N2$ or $S_NAr$ displacement of alkyl or aryl bromide, chloride, and fluorides (aryl only) under basic conditions using bases such as NaH or i-$Pr_2EtNH$ and the desired in solvents such as THF, DMSO, and DMF at temperatures ranging from rt to 1000 Celsius. Sulfone (XVI) can then be obtained via oxidation of the sulfide using an appropriate oxidant such as m-CPBA, oxone, or $RuCl_3/NaIO_4$.

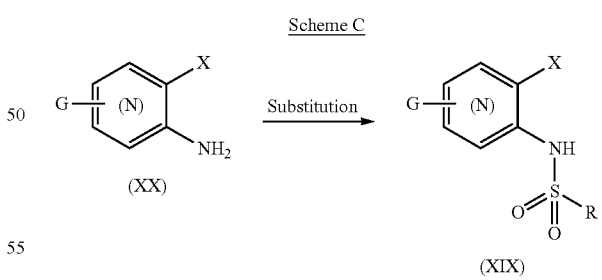

Referring to Scheme C, sulfonamides of formulae (XIX) can be prepared from an aniline (XX) possessing from 0 to 3 G groups G, where a G group can be a variety of alky, heteroalkyl, F, Cl, Br, $CF_3$, or combinations thereof, and X is bromo, chloro, $B(OH)_2$, or $B(OP)_2$, by treatment with an appropriate sulfonyl chloride on which R is alkyl, cycloalkyl, substituted aryl, substituted heteroaryl or $CF_3$, in a solvent, such as $CH_2Cl_2$, in the presence of a base, such as pyridine, at temperatures ranging from 0° to 100° Celsius.

Scheme D

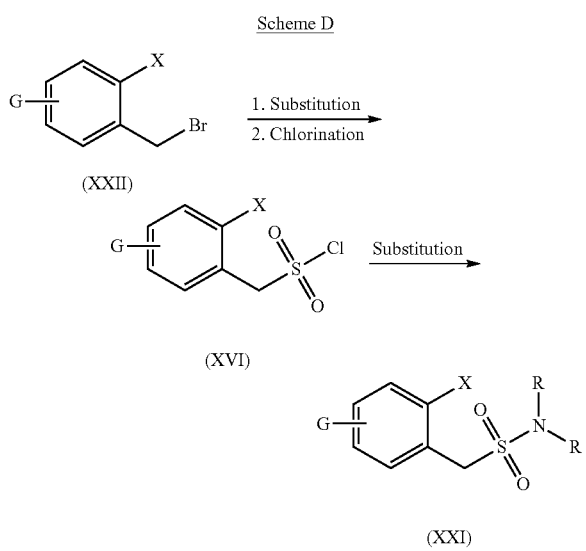

Referring to Scheme D, methanesulfonamides of formulae (XXI) can be prepared by treatment of a substituted (halomethyl)benzene, where X is bromo or chloro and possessing 0 to 3 G groups, which can be a variety of alkyl, cycloalkyl, heteroalkyl, F, Cl, Br, CF$_3$, or combinations thereof, with sodium sulfite to provide the desired arylmethyl sulfonate which can be subsequently treated with phosphorous pentachloride to provide the desired arylmethylsulfonyl chloride (XXIII). Sulfonyl chlorides (XXIII) can then be transformed to the corresponding sulfonamide (XXI) using methods described herein.

Scheme E

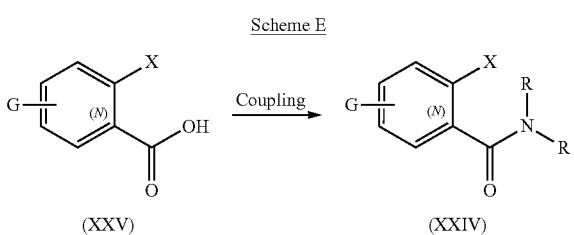

Referring to Scheme E, variously substituted amides (XXIV) can be prepared using standard amide coupling reactions. Substituted carboxylic acid (XXV), where X is bromo or chloro and possessing 0 to 3 G groups, which can be a variety of alkyl, cycloalkyl, heteroalkyl, F, Cl, Br, CF$_3$, or combinations thereof, can be treated with various primary and secondary amines using standard carbodiimide peptide coupling reagents, such as HATU or EDCl, in solvents such as DMF and CH$_2$Cl$_2$, at temperatures ranging from 0-60° Celsius, to provide amide (XXIV).

Scheme F

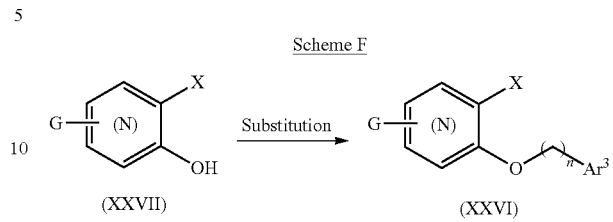

Referring to Scheme F, phenyl ethers of formulae (XXVI) can be prepared from the corresponding phenol (XXVII), where X is bromo or chloro, and possessing 0 to 3 G groups, which can be a variety of alkyl, cycloalkyl, heteroalkyl, F, Cl, Br, CF$_3$, or combinations thereof, and n=0, 1. Treatment of phenol (XXVII) with appropriately substituted halo aromatic heterocycles, where halo refers to F, Cl, and Br, or halomethyl aromatic heterocycles in which halo refers to Cl or Br, a base, such as Cs$_2$CO$_3$, K$_2$CO$_3$, or Na$_2$CO$_3$, In a polar solvent, such as DMSO, CH$_3$CN, or DMF at temperatures ranging from rt to 100° Celsius, provides ethers (XXVI).

Scheme G

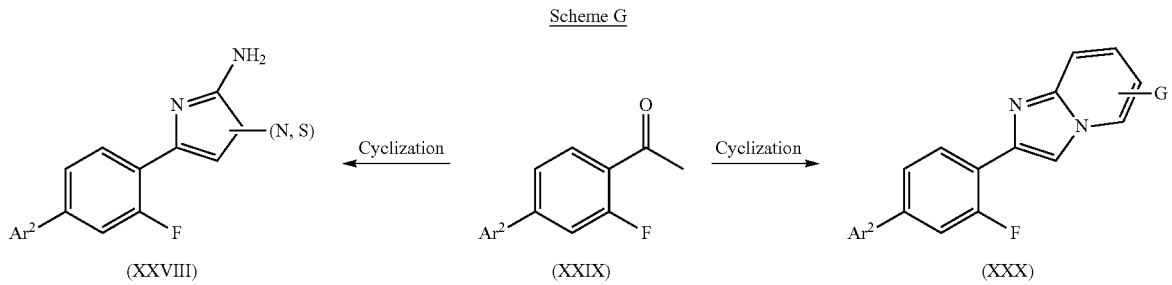

Referring to Scheme G, instances where Ar$^1$ in Scheme A is a 5-, 6-membered, or 5/5-, 5/6-fused heterocycle, compounds of formulae (XXVIII) and (XXX) can be obtained starting from methyl ketone (XXIX). Treatment of the ketone with either urea or thiourea in the presence of I$_2$ in EtOH at temperatures ranging from rt to 80° Celsius results in the corresponding five-membered amino heterocycle (XXVIII). Whereas, treatment of the ketone under analogous conditions with substituted 2-amino pyridines, possessing 0 to 3 G groups, which can be a variety of alkyl, cycloalkyl, heteroalkyl. F, Cl, Br, CF$_3$, or combinations thereof, results in a substituted fused 5/6 heterocycle (XXX).

EXAMPLES

The following examples are offered by way of illustration: the invention should not be construed as being limited by the chemical reactions and conditions expressed.

Intermediate A

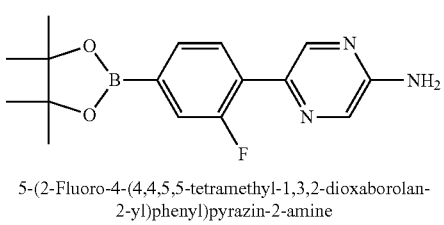 [SMILES: CC1(C)OB(c2ccc(-c3cnc(N)cn3)c(F)c2)OC1(C)C]

5-(2-Fluoro-4-(4,4,5,5-tetramethyl-1,3,2-dioxaborolan-2-yl)phenyl)pyrazin-2-amine

Method 1

To a 250 mL round-bottomed flask were added a stirbar, 5-(4-bromo-2-fluorophenyl)pyrazin-2-amine (3.07 g, 11.5 mmol), 4,4,4',4',5,5,5',5'-octamethyl-2,2'-bi(1,3,2-dioxaborolane) (5.82 g, 22.9 mmol), Pd(dppf)Cl$_2$.CH$_2$Cl$_2$ (512 mg, 0.623 mmol), and KOAc (2.30 g, 23.4 mmol). The flask was then thoroughly sparged with nitrogen and then charged with 1,4-dioxane (114 mL, sparged with N$_2$ for 30 min). The flask was then heated at 80° Celsius for 19.5 hours before cooling to rt, filtering the reaction mixture through Na$_2$SO$_4$ and concentrating the filtrate to dryness. The residue was purified by FCC to give the title compound. MS (ESI): mass calcd. for C$_{16}$H$_{19}$BFN$_3$O$_2$, 315.16; m/z found, 316.1 [M+H]$^+$. $^1$H NMR (500 MHz, DMSO-d$_6$) δ 8.38 (dd, J=2.4, 1.5, 1H), 8.02 (d, J=1.5, 1H), 7.96-7.89 (m, 1H), 7.56 (dd, J=7.7, 1.1, 1H), 7.42 (dd, J=11.8, 1.1, 1H), 6.77 (s, 2H), 1.31 (s, 12H).

Method 2

Step A: 5-(4-Bromo-2-fluorophenyl)pyrazin-2-amine

To a solution of 5-bromopyrazin-2-amine (1.74 g, 10.0 mmol) in 1,4-dioxane (40 mL) were added 4,4,4',4',5,5,5',5'-octamethyl-2,2'-bi(1,3,2-dioxaborolane) (2.65 g, 10.5 mmol) and KOAc (1.96 g, 20.0 mmol). The mixture was sparged with N$_2$ several times before adding Pd(dppf)Cl$_2$.CH$_2$Cl$_2$ (0.41 g, 0.5 mmol). The resultant mixture was stirred at 90° Celsius for 60 hours under N$_2$. After cooling to rt, 4-bromo-2-fluoro-1-iodobenzene (4.5 g, 15.0 mmol), K$_2$CO$_3$ (2.76 g, 20.0 mmol) and another portion of Pd(dppf)Cl$_2$.CH$_2$Cl$_2$ (0.41 g, 0.5 mmol) were added. The resultant mixture was sparged with N$_2$ again, and stirred at 80° Celsius for 48 hours under N$_2$. The mixture was then cooled to rt, diluted with THF (30 mL) and filtered. The filtrate was concentrated to dryness and the residue purified by FCC to give 5-(4-bromo-2-fluorophenyl)pyrazin-2-amine (0.4 g, 15%). $^1$H NMR (300 MHz, DMSO-d$_6$) δ 8.33 (s, 1H), 8.01 (s, 1H), 7.82 (m, 1H), 7.63 (dd, J=11.1, 2.1, 1H), 7.50 (dd, J=8.4, 2.1, 1H), 6.75 (s, 2H).

Step B

To a solution of 5-(4-bromo-2-fluorophenyl)pyrazin-2-amine (535 mg, 2.0 mmol) in 1,4-dioxane (20 mL) was added 4,4,4',4',5,5,5',5'-octamethyl-2,2'-bi(1,3,2-dioxaborolane) (1.1 g, 4.0 mmol) and KOAc (0.39 g, 4.0 mmol). The mixture was sparged by bubbling N$_2$ for 10 min. The mixture was treated with Pd(dppf)Cl$_2$.CH$_2$Cl$_2$ (82 mg, 0.1 mmol) and then stirred at 80° Celsius for 1 hour under N$_2$. After cooling to rt, the reaction mixture was filtered through Na$_2$SO$_4$ and the filtrate concentrated to dryness. The residue was purified by FCC to give the title compound (460 mg, 72%).

Intermediate B

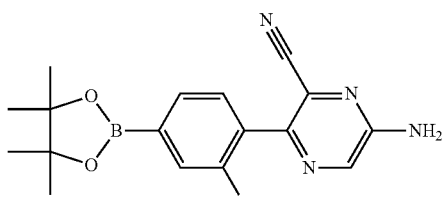

6-Amino-3-(2-fluoro-4-(4,4,5,5-tetramethyl-1,3,2-dioxaborolan-2-yl)phenyl)pyrazine-2-carbonitrile

Step A: 6-Amino-3-(4-chloro-2-fluorophenyl)pyrazine-2-carbonitrile

To a 200 mL round-bottomed flask were added a stirbar, 5-amino-3-cyano-2-bromopyrazine (4.09 g, 20.5 mmol), 4-chloro-2-fluorophenylboronic acid (3.90 g, 22.4 mmol), Pd(dppf)Cl$_2$.CH$_2$Cl$_2$ (839 mg, 1.03 mmol) and K$_2$CO$_3$ (8.36 g, 60.5 mmol). The flask was flushed with nitrogen and then charged with toluene (17.5 mL), water (17.5 mL) and DMF (10.5 mL), all of which were sparged with N$_2$. The flask was heated at 80° Celsius for 19 hours before cooling to rt and adding MgSO$_4$ until the mixture was a thick paste. The reaction mixture was then stirred with EtOAc and filtered through a thick pad of celite. The pad was rinsed with EtOAc until the filtrate was colorless. The filtrate was concentrated to dryness and subjected to FCC to give 6-amino-3-(4-chloro-2-fluorophenyl)pyrazine-2-carbonitrile. MS (ESI): mass calcd. for C$_{11}$H$_6$ClFN$_4$, 248.03; m/z found, 249.0 [M+H]$^+$. $^1$H NMR (500 MHz, DMSO-d) δ 8.22 (s, 1H), 7.67-7.60 (m, 2H), 7.46 (dd, J=8.4, 2.0, 1H), 7.37 (s, 2H).

Step B

To a 200 mL round-bottomed flask were added a stirbar, 6-amino-3-(4-chloro-2-fluorophenyl)pyrazine-2-carbonitrile (1.175 g, 4.73 mmol), 4,4,4',4',5,5,5',5'-octamethyl-2,2'-bi(1,3,2-dioxaborolane) 4,4,4',4',5,5,5',5'-octamethyl-2,2'-bi(1,3,2-dioxaborolane) (1.583 g, 6.23 mmol), chloro(2-dicyclohexylphosphino-2',4',6'-triisopropyl-1,1'-biphenyl)[2-(2'-amino-1,1'-biphenyl)]palladium(II) (194 mg, 0.247 mmol), and KOAc (1.43 g, 14.6 mmol). The flask was fitted with a septum and sparged with nitrogen for 30 min before adding 48 mL of thoroughly N$_2$ sparged THF via syringe. The mixture was then heated at 80° Celsius for 16.5 hours before cooling the mixture to rt and concentrating to dryness. The dark residue was taken up in DCM, filtered through a plug of celite, and concentrated to dryness. The residue was subjected to FCC to give the title compound. $^1$H NMR (600 MHz, DMSO-d$_6$) δ 8.23 (s, 1H), 7.66-7.58 (m, 2H), 7.53-7.46 (d, J=10.2, 1H), 7.40 (s, 2H), 1.34 (s, 12H).

Intermediate C

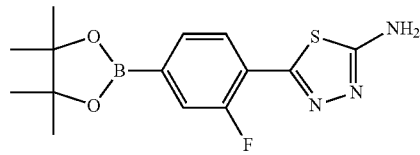

5-(2-Fluoro-4-(4,4,5,5-tetramethyl-1,3,2-dioxaborolan-2-yl)phenyl)-1,3,4-thiadiazol-2-amine

Step A: 4-Bromo-2-fluorobenzoyl chloride

A solution of 4-bromo-2-fluorobenzoic acid (10.8 g, 50.0 mmol) in SOCl$_2$ (50 mL) was stirred at 70° Celsius for 1 hour. After cooling to rt, the resulting mixture was concentrated to give 4-bromo-2-fluorobenzoyl chloride as colorless oil, which was used directly in the next step without purification.

Step B: 2-(4-Bromo-2-fluorobenzoyl)-hydrazinecarbothioamide

Hydrazinecarbothioamide (6.8 g, 75 mmol) was added to a solution of 4-bromo-2-fluorobenzoyl chloride (11.8 g, 50.0 mmol) in THF (50 mL) at rt and stirred for 1 hour. The reaction mixture was concentrated to give 2-(4-bromo-2-fluorobenzoyl)-hydrazinecarbothioamide as a white solid, which was used directly in the next step without purification. MS (ESI): mass calcd. for $C_8H_7BFN_3OS$, 290.95, m/z found, 292.1 [M+H]$^+$.

Step C: 5-(4-Bromo-2-fluorophenyl)-1,3,4-thiadiazol-2-amine $H_2SO_4$ (2 mL) was added to a solution of 2-(4-bromo-2-fluorobenzoyl)-hydrazinecarbothioamide (2.9 g, 10.0 mmol) in pentanoic acid (5 mL) and the resulting mixture was stirred at 110° Celsius for 2 hours. After cooling to rt, the reaction mixture was poured into ice-water (20 mL) and treated with $NH_3.H_2O$ (15 mL). 5-(4-Bromo-2-fluorophenyl)-1,3,4-thiadiazol-2-amine was then isolated via vacuum filtration and air dried. MS (ESI): mass calcd. for $C_8H_5BFN_3OS$, 272.94, m/z found, 274.1 [M+H]$^+$.

Step D

To a solution of 5-(4-bromo-2-fluorophenyl)-1,3,4-thiadiazol-2-amine (2.73 g, 10.0 mmol) in 1,4-dioxane (20 mL) were added 4,4,4',4',5,5,5',5'-octamethyl-2,2'-bi(1,3,2-dioxaborolane) (2.54 g, 10.0 mmol) and KOAc (1.5 g, 20.0 mmol). The mixture was sparged with $N_2$ for 10 min. Pd(dppf)Cl$_2$.CH$_2$Cl$_2$ (82 mg, 0.1 mmol) was then added, and the mixture, stirred at 80° Celsius for 1 hour under $N_2$. After cooling to rt, the reaction mixture was filtered through a pad of anhydrous Na$_2$SO$_4$ and the filtrate concentrated to dryness. The residue was purified by FCC to give the title compound. MS (ESI): mass calcd. for $C_{14}H_{17}N_3BO_2SBr$ 321.11, m/z found 322.1 [M+H]$^+$. $^1$H NMR (300 MHz, CDCl$_3$) δ 8.28-8.19 (m, 1H), 7.65 (dd, J=7.8, 1.0, 1H), 7.57 (d, J=11.3, 1H), 5.39 (s, 2H), 1.36 (s, 12H).

Intermediate D

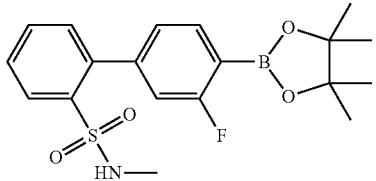

3'-Fluoro-N-methyl-4'-(4,4,5,5-tetramethyl-1,3,2-dioxaborolan-2-yl)-[1,1'-biphenyl]-2-sulfonamide

Step A: 4'-Bromo-3'-fluoro-N-methyl-[1,1'-biphenyl]-2-sulfonamide

1-Bromo-2-fluoro-4-iodobenzene (6.30 g, 20.9 mmol) and (2-(N-methyl-sulfamoyl)-phenyl) boronic acid (4.50 g, 20.9 mmol) were added to a 250 mL flask equipped with a stir bar and reflux condenser. 1,4-Dioxane (50 mL) and Na$_2$CO$_3$ (2 M, 50 mL) were added. Argon was bubbled through the solvent while it was rapidly stirred for 10 minutes before Pd(dppf)Cl$_2$.CH$_2$Cl$_2$ (766 mg, 1.05 mmol) was added and the reaction was stirred at 80° Celsius for 15 hours. The reaction was then diluted with 50 mL of water and extracted with ethyl acetate (1×50 mL, 3×100 mL). The combined organic extracts were dried with Na$_2$CO$_3$, filtered and concentrated to dryness. The crude product was purified by FCC to give 4'-bromo-3'-fluoro-N-methyl-[1,1'-biphenyl]-2-sulfonamide. $^1$H NMR (500 MHz, CDCl$_3$) δ 8.17-8.11 (m, 1H), 7.66-7.59 (m, 2H), 7.59-7.54 (m, 1H), 7.33-7.29 (m, 1H), 7.28-7.23 (m, 1H), 7.20-7.13 (m, 1H), 3.67-3.56 (dd, J=10.1, 4.5, 1H), 2.46-2.43 (d, J=5.3, 3H).

Step B: 3'-Fluoro-N-methyl-4'-(4,4,5,5-tetramethyl-1,3,2-dioxaborolan-2-yl)-[1,1'-biphenyl]-2-sulfonamide 4'-Bromo-3'-fluoro-N-methyl-[1,1'-biphenyl]-2-sulfonamide (2.0 g, 5.8 mmol), 4,4,4',4',5,5,5',5'-octamethyl-2,2'-bi(1,3,2-dioxaborolane) (2.95 g, 11.6 mmol) and anhydrous KOAc (1.71 g, 17.4 mmol) and 1,4-dioxane (50 mL) were added to a flask, equipped with a stir bar and reflux condenser. The reaction mixture was sparged with argon for 10 min, before adding Pd(dppf)Cl$_2$.CH$_2$Cl$_2$ (0.425 g, 0.58 mmol) was added. The flask was heated at 80° Celsius for 15 hours before cooling to rt, diluting with ethyl acetate (50 mL), filtering through Na$_2$SO$_4$ and concentrating to dryness. The crude product was purified by FCC to provide the title compound. $^1$H NMR (400 MHz, CDCl$_3$) δ 8.19-8.12 (dd, J=7.8, 1.4, 1H), 7.87-7.78 (dd, J=7.6, 6.2, 1H), 7.64-7.59 (dd, J=7.5, 1.5, 1H), 7.58-7.51 (m, 1H), 7.35-7.27 (m, 2H), 7.19-7.11 (dd, J=9.6, 1.5, 1H), 3.57-3.45 (d, J=5.5, 1H), 2.41-2.37 (d, J=5.4, 3H), 1.39 (s, 12H).

Intermediate E

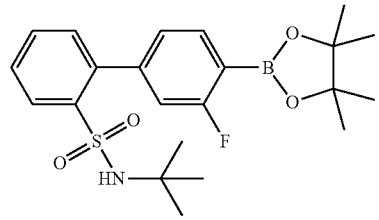

N-(tert-Butyl)-3'-fluoro-4'-(4,4,5,5-tetramethyl-1,3,2-dioxaborolan-2-yl)-[1,1'-biphenyl]-2-sulfonamide The title compound was prepared in a manner similar to that described for Intermediate D using (2-(N-(tert-butyl)sulfamoyl)phenyl)boronic acid in Step A. $^1$H NMR (400 MHz, CDCl$_3$) δ 8.17 (dd, J=7.9, 1.4, 1H), 7.81 (dd, J=7.6, 6.2, 1H), 7.62-7.53 (m, 1H), 7.53-7.46 (m, 1H), 7.36-7.30 (m, 1H), 7.29-7.27 (m, 1H), 7.19 (dd, J=9.9, 1.5, 1H), 3.61 (s, 1H), 1.39 (s, 12H), 1.04 (s, 9H).

Intermediate F

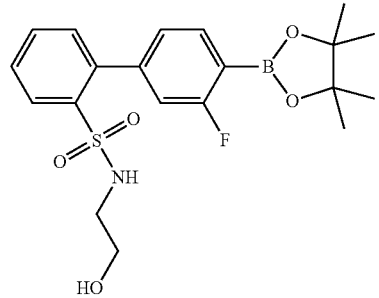

3'-Fluoro-N-(2-hydroxyethyl)-4'-(4,4,5,5-tetramethyl-1,3,2-dioxaborolan-2-yl)-[1,1'-biphenyl]-2-sulfonamide The title compound was prepared in a manner similar to that described for Intermediate D using 2-bromo-N-(2-hydroxyethyl)benzenesulfonamide in Step A. ¹H NMR (500 MHz, CD₃OD) δ 8.09-8.03 (dd, J=8.0, 1.3, 1H), 7.76-7.70 (dd, J=7.6, 6.2, 1H), 7.68-7.62 (m, 1H), 7.61-7.54 (dd, J=8.5, 7.1, 1H), 7.37-7.31 (dd, J=7.5, 1.4, 1H), 7.24-7.20 (dd, J=7.6, 1.5, 1H), 7.16-7.11 (dd, J=10.0, 1.5, 1H), 3.48-3.43 (t, J=5.9, 2H), 2.88-2.82 (t, J=5.9, 2H), 1.37 (s, 12H).

Intermediate G

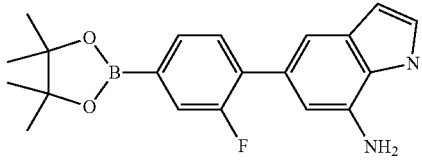

5-(2-Fluoro-4-(4,4,5,5-tetramethyl-1,3,2-dioxaborolan-2-yl)phenyl)-1H-indol-7-amine The title compound was prepared using analogous methods described in Intermediate D using 7-amino-5-bromoindole in Step A. MS (ESI): mass calcd. for C₂₀H₂₂BFN₂O₂, 352.18; m/z found, 353.3 [M+H]⁺.

Intermediate H

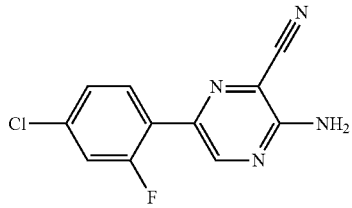

3-Amino-6-(4-chloro-2-fluorophenyl)pyrazine-2-carbonitrile

To a solution of 3-amino-6-bromopyrazine-2-carbonitrile (2.00 g, 9.55 mmol) in 1,4-dioxane (48 mL), were added (4-chloro-2-fluorophenyl)boronic acid (1.66 g, 9.55 mmol) and aqueous Na₂CO₃ (2 M, 24 mL, 48 mmol) and the reaction mixture sparged with N₂ gas for 10 min. Pd(dppf)Cl₂·CH₂Cl₂ (0.349 g, 0.477 mmol) was then added and the reaction mixture sparged for an additional 10 min with N₂ gas. The reaction vessel was sealed and heated for 3 hours at 80° Celsius. The mixture was cooled to rt, filtered through celite, and the filter cake washed with EtOAc (300 mL). The filtrate was washed with a 1:1 mixture of brine/H₂O (2×100 mL). The organic phase was concentrated to dryness and subjected to FCC to give the title compound (1.99 g, 84%). MS (ESI): mass calcd. for C₁₁H₆ClFN₄, 248.03; m/z found 249.0 [M+H]⁺. ¹H NMR (400 MHz, CDCl₃) δ 8.67 (d, J=2.0, 1H), 7.83 (m, 1H), 7.25-7.08 (m, 2H), 5.36 (s, 2H).

Intermediate I

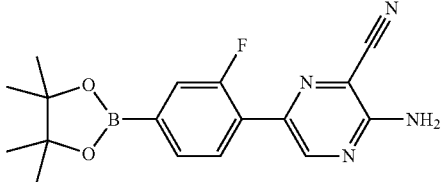

3-Amino-6-(2-fluoro-4-(4,4,5,5-tetramethyl-1,3,2-dioxaborolan-2-yl)phenyl)pyrazine-2-carbonitrile To a solution of 3-amino-6-(4-chloro-2-fluorophenyl)pyrazine-2-carbonitrile (0.290 g, 1.17 mmol) in 1,4-dioxane (12 mL), were added (4,4,4',4',5,5,5',5'-octamethyl-2,2'-bi(1,3,2-dioxaborolane) (0.370 g, 1.46 mmol) and KOAc (0.343 g, 3.50 mmol). The reaction mixture sparged with N₂ gas for 10 min, before adding chloro(2-dicyclohexylphosphino-2',4',6'-triisopropyl-1,1'-biphenyl)[2-(2'-amino-1,1'-biphenyl)]palladium(II) (18 mg, 0.023 mmol) and then sparged for an additional 10 min with N₂ gas. The reaction vessel was sealed, heated 3 hours at 80° Celsius and cooled to rt. The mixture was filtered through celite and the filter cake washed with EtOAc (30 mL). The filtrate was concentrated in vacuo onto silica gel and purified via FCC to give the product which was then triturated with hexanes to give 3-amino-6-(2-fluoro-4-(4,4,5,5-tetramethyl-1,3,2-dioxaborolan-2-yl)phenyl)pyrazine-2-carbonitrile (0.25 g, 63%). MS (ESI): mass calcd. for C₁₇H₁₈BFN₄O₂, 340.15; m/z found 341.1 [M+H]⁺. ¹H NMR (500 MHz, CDCl₃) δ 8.79 (d, J=1.8, 1H), 7.94 (m, 1H), 7.67 (dd, J=7.7, 1.1, 1H), 7.58 (dd, J=11.8, 1.1, 1H), 5.35 (s, 2H), 1.36 (s, 12H).

Intermediate K

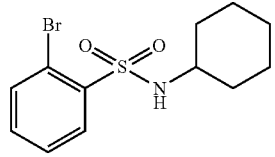

2-Bromo-N-cyclohexylbenzenesulfonamide

To a 20 mL vial were added a stirbar, 2-bromobenzene-1-sulfonyl chloride (1.053 g, 4.12 mmol), cyclohexylamine (431 mg, 4.34 mmol) and dry pyridine (5 mL). The mixture was stirred for 3 hours before adding it to a separatory funnel containing 1 N HCl and EtOAc. The layers were mixed thoroughly and then separated. The organic layer was then washed with water followed by sat. NaHCO₃, dried over MgSO₄, filtered and evaporated to dryness to give the title compound. MS (ESI): mass calcd. for C₁₂H₁₆NO₂SBr 317.01, m/z found 318.0 [M+H]⁺; ¹H NMR (500 MHz, CDCl₃) δ 8.14 (dd, J=7.9, 1.7, 1H), 7.71 (dd, J=7.9, 1.2, 1H), 7.49-7.42 (m, 1H), 7.42-7.35 (m, 1H), 5.05 (d, J=7.7, 1H), 3.19-3.04 (m, 1H), 1.79-1.66 (m, 2H), 1.66-1.57 (m, 2H), 1.52-1.44 (m, 1H), 1.28-1.04 (m, 5H).

Intermediate L

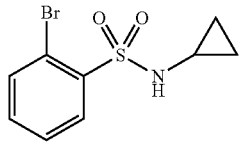

2-Bromo-N-cyclopropylbenzenesulfonamide

The title compound was prepared using analogous conditions to those described in Intermediate K using cyclopropylamine. ¹H NMR (500 MHz, CDCl₃) 8.19 (dd, J=7.8, 1.8, 1H), 7.73 (dd, J=7.8, 1.3, 1H), 7.51-7.45 (m, 1H), 7.44-7.39 (m, 1H), 5.46 (s, 1H), 2.21-2.08 (m, 1H), 0.69-0.60 (m, 2H), 0.60-0.51 (m, 2H).

Intermediate M

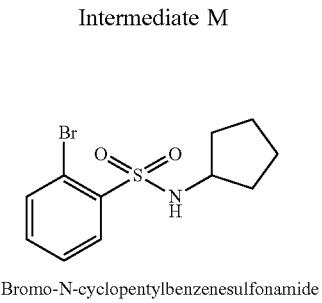

2-Bromo-N-cyclopentylbenzenesulfonamide

The title compound was prepared using analogous conditions to those described in Intermediate K using cyclopentylamine. ¹H NMR (500 MHz, DMSO-$d_6$) δ 8.02 (dd, J=7.7, 1.8, 1H), 7.84 (dd, J=7.8, 1.3, 2H), 7.61-7.55 (m, 1H), 7.55-7.50 (m, 1H), 3.51-3.40 (m, 1H), 1.64-1.49 (m, 4H), 1.45-1.30 (m, 4H).

Intermediate N

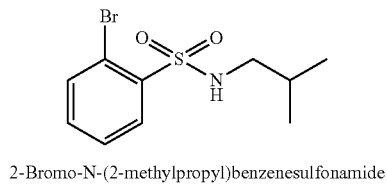

2-Bromo-N-(2-methylpropyl)benzenesulfonamide

The title compound was prepared using analogous conditions to those described in Intermediate K using isobutylamine. ¹H NMR (500 MHz, CDCl$_3$) δ 8.12 (dd, J=7.8, 1.8, 1H), 7.72 (dd, J=7.9, 1.3, 1H), 7.48-7.43 (m, 1H), 7.43-7.37 (m, 1H), 5.18-5.03 (m, 1H), 2.67 (t, J=6.6, 2H), 1.78-1.64 (m, 1H), 0.87 (d, J=6.7, 6H).

Intermediate O

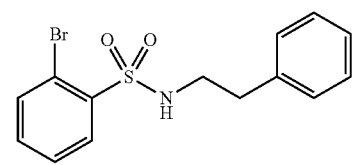

2-Bromo-N-(2-phenylethyl)benzenesulfonamide

The title compound was prepared using analogous conditions to those described in Intermediate K using 2-phenethylamine. ¹H NMR (600 MHz, CDCl$_3$) δ 8.14-8.09 (dd, J=7.9, 1.7, 1H), 7.69-7.63 (dd, J=7.8, 1.2, 1H), 7.47-7.42 (m, 1H), 7.42-7.36 (m, 1H), 7.29-7.24 (m, 2H), 7.24-7.17 (m, 1H), 7.12-7.06 (m, 2H), 5.16-5.00 (t, J=6.1, 1H), 3.23-3.10 (m, 2H), 2.84-2.73 (t, J=7.0, 2H).

Intermediate P

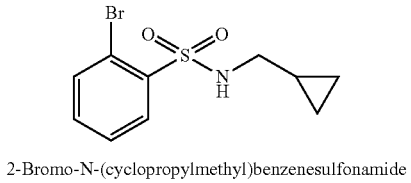 [SMILES: O=S(=O)(NCC1CC1)c1ccccc1Br]

2-Bromo-N-(cyclopropylmethyl)benzenesulfonamide

The title compound was prepared using analogous conditions to those described in Intermediate K using cyclopropylmethylamine. ¹H NMR (500 MHz, CDCl$_3$) δ 8.18 (dd, J=7.8, 1.7, 1H), 7.70 (dd, J=7.9, 1.2, 1H), 7.50-7.43 (m, 1H), 7.42-7.36 (m, 1H), 5.52 (s, 1H), 1.17-1.09 (m, 3H), 0.89-0.76 (m, 2H), 0.50-0.41 (m, 2H).

Intermediate Q

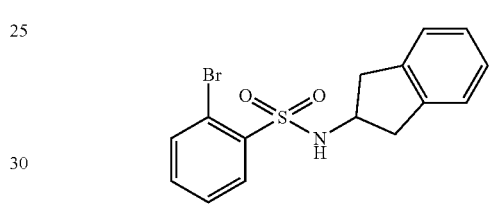

2-Bromo-N-(2,3-dihydro-1H-inden-2-yl)benzenesulfonamide

The title compound was prepared using analogous conditions to those described in Intermediate K using 2,3-dihydro-1H-inden-2-amine. ¹H NMR (600 MHz, DMSO-$d_6$) δ 8.34-8.27 (d, J=7.0, 1H), 8.09-8.04 (dd, J=7.7, 1.8, 1H), 7.91-7.85 (dd, J=7.8, 1.3, 1H), 7.64-7.54 (m, 2H), 7.17-7.06 (m, 4H), 4.01-3.92 (m, 1H), 2.98-2.89 (m, 2H), 2.87-2.79 (m, 2H).

Intermediate R

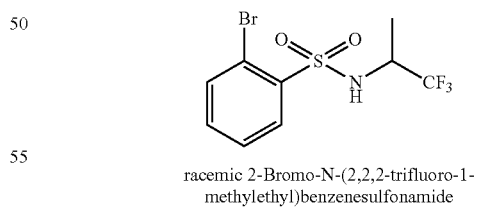

racemic 2-Bromo-N-(2,2,2-trifluoro-1-methylethyl)benzenesulfonamide

The title compound was prepared using analogous conditions to those described in Intermediate K using racemic 2-amino-1,1,1-trifluoropropane. ¹H NMR (500 MHz, CDCl$_3$) 8.10 (dd, J=7.7, 1.9, 1H), 7.74 (dd, J=7.7, 1.4, 1H), 7.49-7.38 (m, 2H), 5.33 (d, J=9.8, 1H), 4.03-3.88 (m, 1H), 1.29 (d, J=7.0, 3H).

Intermediate S

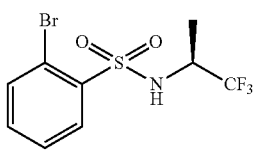

2-Bromo-N-[(1S)-2,2,2-trifluoro-1-methylethyl]benzenesulfonamide

The title compound was prepared using analogous conditions to those described in Intermediate K using (S)-2-amino-1,1,1-trifluoropropane.

Intermediate T

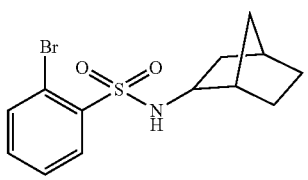

racemic (endo)-N-Bicyclo[2.2.1]hept-2-yl-2-bromobenzenesulfonamide

The title compound was prepared using analogous conditions to those described in Intermediate K using racemic (endo)-bicyclo[2.2.1]heptan-2-amine $^1$H NMR (500 MHz, CDCl$_3$) δ 8.13 (dd, J=7.8, 1.8, 1H), 7.71 (dd, J=7.9, 1.3, 1H), 7.49-7.42 (m, 1H), 7.42-7.37 (m, 1H), 4.98 (d, J=7.1, 1H), 3.17-3.04 (m, 1H), 2.27-2.14 (m, 1H), 2.05 (d, J=3.7, 1H), 1.62-1.50 (m, 1H), 1.45-1.28 (m, 3H), 1.28-1.17 (m, 1H), 1.17-1.08 (m, 1H), 1.05-0.91 (m, 2H).

Intermediate U

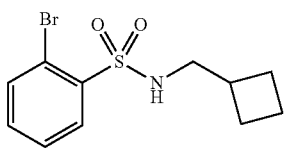

2-Bromo-N-(cyclobutylmethyl)benzenesulfonamide

The title compound was prepared using analogous conditions to those described in Intermediate K using cyclobutylmethylamine. $^1$H NMR (500 MHz, CDCl$_3$) δ 8.12 (dd, J=7.8, 1.8, 1H), 7.72 (dd, J=7.8, 1.3, 1H), 7.49-7.43 (m, 1H), 7.43-7.36 (m, 1H), 5.04 (d, J=6.0, 1H), 2.89 (dd, J=7.4, 6.1, 2H), 2.45-2.31 (m, 1H), 2.04-1.91 (m, 2H), 1.90-1.71 (m, 2H), 1.64-1.52 (m, 2H).

Intermediate V

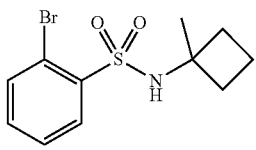

2-Bromo-N-(1-methylcyclobutyl)benzenesulfonamide

The title compound was prepared using analogous conditions to those described in Intermediate K using 1-amino-1-methylcyclobutane. $^1$H NMR (500 MHz, CDCl$_3$) δ 8.13 (dd, J=7.8, 1.7, 1H), 7.70 (dd, J=7.9, 1.3, 1H), 7.47-7.41 (m, 1H), 7.40-7.34 (m, 1H), 5.26 (s, 1H), 2.26-2.13 (m, 2H), 1.86-1.76 (m, 2H), 1.76-1.59 (m, 2H), 1.32 (t, J=0.8, 3H).

Intermediate W

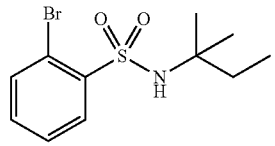

2-Bromo-N-(1,1-dimethylpropyl)benzenesulfonamide

The title compound was prepared using analogous conditions to those described in Intermediate K using 2-methylbutan-2-amine. $^1$H NMR (500 MHz, DMSO-d$_6$) δ 7.81 (dd, J=7.8, 1.7, 1H), 7.58 (dd, J=7.8, 1.3, 1H), 7.35-7.29 (m, 1H), 7.29-7.24 (m, 1H), 1.24 (q, J=7.4, 2H), 0.80 (s, 6H), 0.52 (t, J=7.4, 3H).

Intermediate X

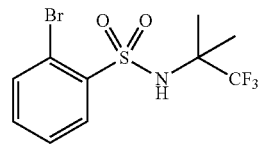

2-Bromo-N-(2,2,2-trifluoro-1,1-dimethylethyl)benzenesulfonamide

The title compound was prepared using analogous conditions to those described in Intermediate K using 1,1,1-trifluoro-2-methylpropan-2-amine. $^1$H NMR (500 MHz, DMSO-d$_6$) δ 8.61 (s, 1H), 8.05 (dd, J=7.7, 1.8, 1H), 7.86 (dd, J=7.7, 1.4, 1H), 7.62-7.57 (m, 1H), 7.57-7.52 (m, 1H), 1.30 (s, 6H).

Intermediate Y

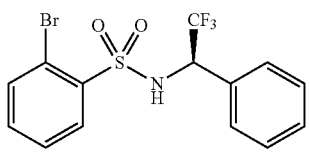

2-Bromo-N-([(1R)-2,2,2-trifluoro-1-phenylethyl]benzenesulfonamide

The title compound was prepared using analogous conditions to those described in Intermediate K using (R)-2,2,2-trifluoro-1-phenylethanamine. $^1$H NMR (600 MHz, DMSO-d$_6$) δ 9.64-9.53 (d, J=10.2, 1H), 8.03-7.91 (dd, J=7.8, 1.7, 1H), 7.68-7.62 (dd, J=7.8, 1.2, 1H), 7.53-7.39 (m, 4H), 7.34-7.23 (m, 3H), 5.25-5.11 (m, 1H).

Intermediate Z

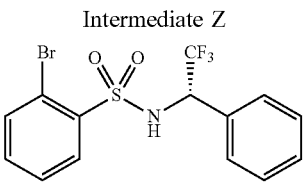

2-Bromo-N-([(1S)-2,2,2-trifluoro-1-phenylethyl]benzenesulfonamide

The title compound was prepared using analogous conditions to those described in Intermediate K using (S)-2,2,2-trifluoro-1-phenylethanamine.

Intermediate AA

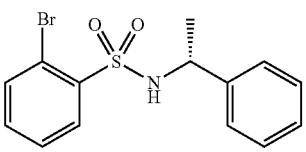

2-Bromo-N-([(1R)-1-phenylethyl]benzenesulfonamide

The title compound was prepared using analogous conditions to those described in Intermediate K using (R)-1-phenylethanamine $^1$H NMR (600 MHz, DMSO-$d_6$) δ 8.46-8.34 (d, J=8.4, 1H), 7.94-7.83 (dd, J=7.7, 1.9, 1H), 7.74-7.65 (dd, J=7.7, 1.4, 1H), 7.50-7.37 (m, 2H), 7.27-7.07 (m, 5H), 4.42-4.29 (m, 1H), 1.37-1.27 (d, J=7.0, 3H).

Intermediate AB

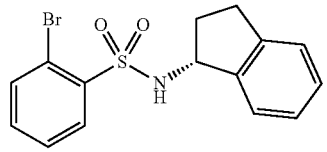

2-Bromo-N-([(1R)-2,3-dihydro-1H-inden-1-yl]benzenesulfonamide

The title compound was prepared using analogous conditions to those described in Intermediate K using (R)-2,3-dihydro-1H-inden-1-amine. $^1$H NMR (600 MHz, DMSO-$d_6$) δ 8.47-8.39 (d, J=9.0, 1H), 8.14-8.06 (dd, J=7.7, 1.8, 1H), 7.93-7.87 (dd, J=7.8, 1.3, 1H), 7.64-7.53 (m, 2H), 7.23-7.10 (m, 4H), 4.77-4.64 (m, 1H), 2.91-2.78 (m, 1H), 2.72-2.61 (m, 1H), 2.21-2.10 (m, 1H), 1.91-1.77 (m, 1H).

Intermediate AC

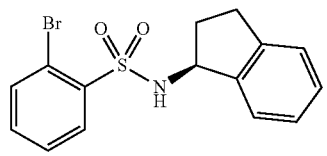

2-Bromo-N-([(1S)-2,3-dihydro-1H-inden-1-yl]benzenesulfonamide

The title compound was prepared using analogous conditions to those described in Intermediate K using (S)-2,3-dihydro-1H-inden-1-amine. NMR spectra as for Intermediate AB.

Intermediate AD

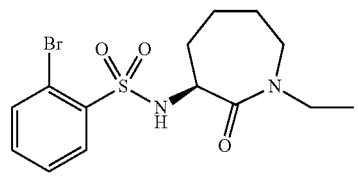

2-Bromo-N-([(3S)-1-ethyl-2-oxoazepan-3-yl]benzenesulfonamide

The title compound was prepared using analogous conditions to those described in Intermediate K using (S)-3-amino-1-ethylazepan-2-one. $^1$H NMR (600 MHz, DMSO-$d_6$) δ 8.04-7.99 (dd, J=7.8, 1.7, 1H), 7.84-7.80 (dd, J=7.9, 1.3, 1H), 7.58-7.53 (m, 2H), 7.53-7.49 (m, 1H), 4.13-4.04 (m, 1H), 3.40-3.31 (m, 1H), 3.30-3.15 (m, 3H), 1.85-1.73 (m, 2H), 1.73-1.63 (m, 1H), 1.62-1.52 (m, 1H), 1.50-1.40 (m, 1H), 1.28-1.16 (m, 1H), 0.96-0.88 (t, J=7.1, 3H).

Intermediate AE

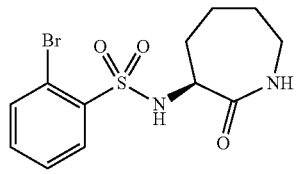

2-Bromo-N-([(3S)-2-oxoazepan-3-yl]benzenesulfonamide

The title compound was prepared using analogous conditions to those described in Intermediate K using (S)-3-aminoazepan-2-one. $^1$H NMR (600 MHz, DMSO-$d_6$) δ 8.05-8.01 (dd, J=7.8, 1.7, 1H), 7.96-7.91 (m, 1H), 7.85-7.81 (dd, J=7.8, 1.3, 1H), 7.60-7.55 (m, 1H), 7.55-7.50 (m, 1H), 7.47-7.43 (d, J=6.0, 1H), 3.95-3.86 (m, 1H), 3.04-2.93 (m, 2H), 1.89-1.79 (m, 2H), 1.71-1.62 (m, 1H), 1.59-1.44 (m, 2H), 1.20-1.07 (m, 1H).

Intermediate AF

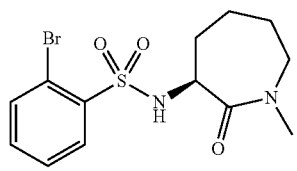

2-Bromo-N-[(3S)-1-methyl-2-oxoazepan-3-yl]benzenesulfonamide

The title compound was prepared using analogous conditions to those described in Intermediate K using (S)-3-amino-1-methylazepan-2-one. MS (ESI): mass calcd. for $C_{13}H_{17}BrN_2O_3S$ 360.01, m/z found 361.0 $[M+H]^+$; $^1H$ NMR (600 MHz, DMSO-$d_6$) δ 8.03-8.00 (dd, J=7.8, 1.8, 1H), 7.84-7.81 (dd, J=7.8, 1.3, 1H), 7.59-7.50 (m, 3H), 4.17-4.07 (m, 1H), 3.48-3.38 (m, 1H), 3.20-3.09 (m, 1H), 2.87-2.79 (s, 3H), 1.92-1.81 (dd, J=14.4, 3.4, 1H), 1.81-1.70 (m, 1H), 1.67-1.52 (m, 2H), 1.52-1.41 (m, 1H), 1.34-1.21 (m, 1H).

Intermediate AG

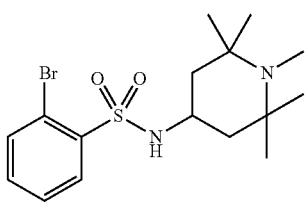

2-Bromo-N-(1,2,2,6,6-pentamethylpiperidin-4-yl)benzenesulfonamide

The title compound was prepared using analogous conditions to those described in Intermediate K using 1,2,2,6,6-pentamethylpiperidin-4-amine. MS (ESI): mass calcd. for $C_{16}H_{25}BrN_2O_2S$ 388.08, m/z found 389.1 $[M+H]^+$; $^1H$ NMR (600 MHz, DMSO-$d_6$) δ 8.07-8.03 (dd, J=7.8, 1.7, 1H), 7.87-7.81 (m, 2H), 7.61-7.56 (m, 1H), 7.56-7.51 (m, 1H), 3.32-3.21 (m, 1H), 2.11-2.02 (s, 3H), 1.46-1.37 (m, 2H), 1.35-1.26 (m, 2H), 1.01-0.92 (s, 6H), 0.83-0.74 (s, 6H).

Intermediate AH

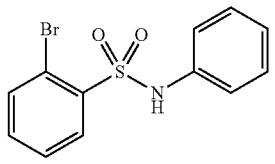

2-Bromo-N-phenylbenzenesulfonamide

The title compound was prepared using analogous conditions to those described in Intermediate K using aniline. $^1H$ NMR (600 MHz, DMSO-$d_6$) δ 10.68-10.56 (s, 1H), 8.13-8.02 (dd, J=7.9, 1.7, 1H), 7.85-7.75 (dd, J=7.8, 1.3, 1H), 7.62-7.46 (m, 2H), 7.25-7.16 (m, 2H), 7.12-7.04 (m, 2H), 7.02-6.93 (m, 1H).

Intermediate AI

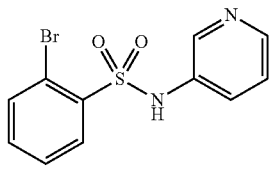

2-Bromo-N-pyridin-3-ylbenzenesulfonamide

The title compound was prepared using analogous conditions to those described in Intermediate K using 3-aminopyridine. MS (ESI): mass calcd. for $C_{11}H_9BrN_2O_2S$ 311.96, m/z found 312.9 $[M+H]^+$; $^1H$ NMR (600 MHz, DMSO-$d_6$) δ 11.05-10.87 (s, 1H), 8.40-8.29 (m, 1H), 8.25-8.17 (dd, J=4.7, 1.4, 1H), 8.15-8.06 (dd, J=7.8, 1.8, 1H), 7.93-7.78 (dd, J=7.8, 1.3, 1H), 7.66-7.52 (m, 2H), 7.47-7.44 (dd, J=2.7, 1.4, 1H), 7.32-7.23 (m, 2H).

Intermediate AJ

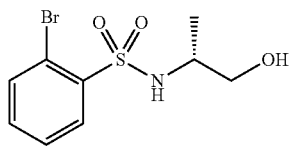

2-Bromo-N-[(1R)-2-hydroxy-1-methylethyl]benzenesulfonamide

The title compound was prepared using analogous conditions to those described in Intermediate K using (R)-2-aminopropan-1-ol. MS (ESI): mass calcd. for $C_9H_{12}NOSBr$ 292.97, m/z found 294.0 $[M+H]^+$; $^1H$ NMR (600 MHz, CDCl$_3$) δ 8.13 (dd, J=7.8, 1.8, 1H), 7.72 (dd, J=7.9, 1.3, 1H), 7.48-7.43 (m, 1H), 7.43-7.37 (m, 1H), 5.42 (d, J=7.4, 1H), 3.60-3.50 (m, 1H), 3.49-3.40 (m, 1H), 3.38-3.28 (m, 1H), 2.16 (t, J=5.4, 1H), 1.04 (d, J=6.8, 3H).

Intermediate AK

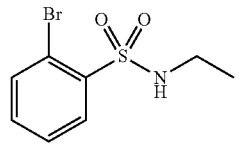

2-Bromo-N-ethylbenzenesulfonamide

To a 20 mL vial were added a stirbar, 2-bromobenzene-1-sulfonyl chloride (0.995 g, 3.89 mmol), and THF (5 mL). The vial was then charged with EtNH$_2$ in THF (5 mL, 2.0 M). The mixture was stirred for 24 hours before adding it to a separatory funnel containing 1 N HCl and EtOAc. The layers were mixed thoroughly and then separated. The organic layer was then washed with water followed by sat. NaHCO$_3$, dried over MgSO$_4$, filtered and concentrated to dryness to give the crude product. Subjecting the oil to FCC yielded the title compound (580 mg, 56%). $^1H$ NMR (600 MHz, CDCl$_3$) 8.17-8.10 (dd, J=7.8, 1.7, 1H), 7.75-7.69 (dd, J=7.8, 1.2, 1H), 7.48-7.43 (m, 1H), 7.43-7.37 (m, 1H), 5.16-4.91 (t, J=6.7, 1H), 3.06-2.87 (m, 2H), 1.19-1.00 (t, J=7.3, 3H).

Intermediate AL

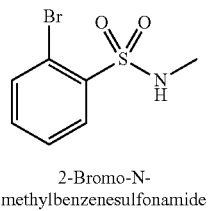

2-Bromo-N-methylbenzenesulfonamide

The title compound was prepared using analogous conditions to those described in Intermediate AK using 0.5 M methylamine in 1,4-dioxane. $^1$H NMR (600 MHz, CDCl$_3$) δ 8.15-8.11 (dd, J=7.8, 1.7, 1H), 7.75-7.70 (dd, J=7.8, 1.3, 1H), 7.49-7.45 (m, 1H), 7.44-7.39 (m, 1H), 5.11-5.00 (d, J=6.6, 1H), 2.66-2.55 (d, J=5.4, 3H).

Intermediate AM

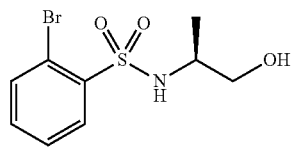

2-Bromo-N-[(1S)-2-hydroxy-1-methylethyl]benzenesulfonamide

To a 500 mL round-bottomed flask were added a stirbar, (S)-2-aminopropan-1-ol (2.151 g, 28.65 mmol), dry DCM (100 mL), and DIPEA (14.0 mL, 81.2 mmol). The mixture was then treated with 2-bromobenzene-1-sulfonyl chloride (6.981 g, 27.32 mmol) and stirred for 66.5 hours before concentrating to dryness and subjecting the residue to FCC to give the title compound. (7.31 g, 91%).

Intermediate AN

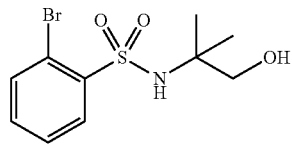

2-Bromo-N-(2-hydroxy-1,1-dimethylethyl)benzenesulfonamide

The title compound was prepared using analogous conditions to those described in Intermediate AM using 2-amino-2-methylpropan-1-ol. MS (ESI): mass calcd. for C$_{10}$H$_{14}$BrNO$_3$S 306.99, m/z found 330.0 [M+Na]$^+$; $^1$H NMR (600 MHz, CDCl$_3$) δ 8.14 (dd, J=7.8, 1.7, 1H), 7.72 (dd, J=7.9, 1.2, 1H), 7.50-7.42 (m, 1H), 7.42-7.35 (m, 1H), 5.33 (s, 1H), 3.46 (d, J=6.3, 2H), 1.11 (s, 6H).

Intermediate AO

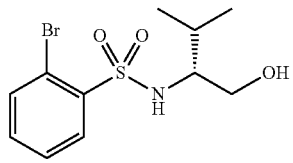

2-Bromo-N-[(1R)-1-(hydroxymethyl)-2-methylpropyl]benzenesulfonamide

The title compound was prepared using analogous conditions to those described in Intermediate AM using (R)-2-amino-3-methylbutan-1-ol. MS (ESI): mass calcd. for C$_{11}$H$_{16}$BrNO$_3$S 321.00, m/z found 322.0 [M+H]$^+$; $^1$H NMR (600 MHz, CDCl$_3$) δ 8.15-8.06 (m, 1H), 7.78-7.67 (m, 1H), 7.50-7.42 (m, 1H), 7.42-7.34 (m, 1H), 5.39 (s, 1H), 3.65-3.54 (m, 1H), 3.54-3.43 (m, 1H), 3.11-3.01 (m, 1H), 1.82 (d, J=5.7, 1H), 0.95-0.83 (m, 3H), 0.83-0.73 (m, 3H).

Intermediate AP

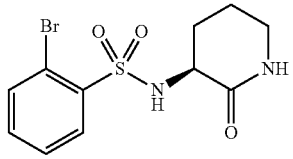

2-Bromo-N-[(3S)-2-oxopiperidin-3-yl]benzenesulfonamide

The title compound was prepared using analogous conditions to those described in Intermediate AM using (S)-3-aminopiperidin-2-one. MS (ESI): mass calcd. for C$_{11}$H$_{13}$BrN$_2$O$_3$S 331.98, m/z found 333.0 [M+H]$^+$; $^1$H NMR (600 MHz, CDCl$_3$) δ 8.08 (dd, J=7.8, 1.8, 1H), 7.71 (dd, J=7.8, 1.3, 1H), 7.46-7.40 (m, 1H), 7.40-7.36 (m, 1H), 6.77 (s, 1H), 6.52-6.41 (m, 1H), 3.61-3.49 (m, 1H), 3.34-3.18 (m, 2H), 2.43-2.32 (m, 1H), 1.96-1.84 (m, 1H), 1.81-1.69 (m, 2H).

Intermediate AQ

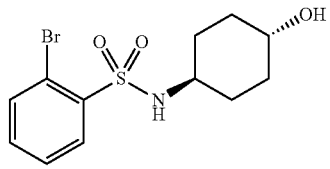

2-Bromo-N-(trans-4-hydroxycyclohexyl)benzenesulfonamide

To a 20 mL vial were added a stir-bar, trans-4-aminocyclohexanol (683 mg, 4.50 mmol), DMF (5 mL), and DIPEA (2.0 mL, 12 mmol). The mixture was then treated with 2-bromobenzene-1-sulfonyl chloride (1.00 g, 3.93 mmol) and the mixture stirred for 2 hours before subjecting the vial's content to FCC to give the title compound. (978 mg, 74%). MS (ESI): mass calcd. for $C_{12}H_{16}BrNO_3S$ 333.00, m/z found 334.0 [M+H]$^+$; $^1$H NMR (600 MHz, CDCl$_3$) δ 8.12 (dd, J=7.8, 1.7, 1H), 7.70 (dd, J=7.8, 1.2, 1H), 7.49-7.43 (m, 1H), 7.43-7.37 (m, 1H), 5.10 (d, J=7.5, 1H), 3.62-3.47 (m, 1H), 3.11-3.01 (m, 1H), 2.12 (s, 1H), 1.91-1.75 (m, 4H), 1.31-1.15 (m, 4H).

Intermediate AR

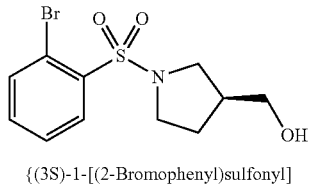

{(3S)-1-[(2-Bromophenyl)sulfonyl]pyrrolidin-3-yl}methanol

The title compound was prepared using analogous conditions to those described in Intermediate AQ using (S)-pyrrolidin-3-ylmethanol. $^1$H NMR (600 MHz, CDCl$_3$) δ 8.06 (dd, J=7.9, 1.7, 1H), 7.70 (dd, J=7.9, 1.2, 1H), 7.44-7.38 (m, 1H), 7.38-7.32 (m, 1H), 3.61-3.54 (m, 1H), 3.54-3.45 (m, 3H), 3.39-3.33 (m, 1H), 3.17 (dd, J=9.8, 6.4, 1H), 2.53-2.39 (m, 2H), 2.04-1.94 (m, 1H), 1.74-1.65 (m, 1H).

Intermediate AS

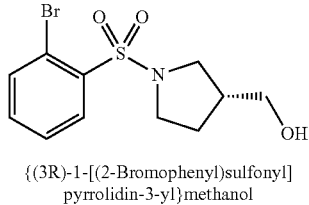 [SMILES: O=S(=O)(c1ccccc1Br)N1CC[C@@H](CO)C1]

{(3R)-1-[(2-Bromophenyl)sulfonyl]pyrrolidin-3-yl}methanol

The title compound was prepared using analogous conditions to those described in Intermediate AQ using (R)-pyrrolidin-3-ylmethanol.

Intermediate AT

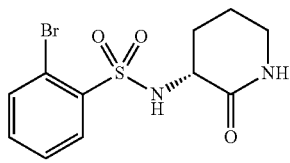

2-Bromo-N-[(3R)-2-oxopiperidin-3-yl]benzenesulfonamide

The title compound was prepared using analogous conditions to those described in Intermediate AQ using (R)-3-aminopiperidin-2-one.

Intermediate AU

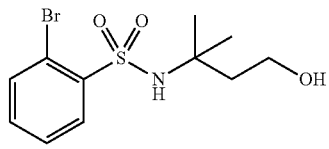

2-Bromo-N-(3-hydroxy-1,1-dimethylpropyl)benzenesulfonamide

To a 20 mL vial were added a stirbar, 3-amino-3-methylbutan-1-ol (428 mg, 4.15 mmol), ACN (5 mL), and DIPEA (2.0 mL, 12 mmol). The mixture was then treated with 2-bromobenzene-1-sulfonyl chloride (994 mg, 3.89 mmol) and stirred for 12.5 hours before concentrating to dryness and subjecting the residue to FCC to give the title compound. (676 mg, 54%). MS (ESI): mass calcd. for $C_{11}H_{16}BrNO_3S$ 321.00, m/z found 344.0 [M+Na]$^+$; $^1$H NMR (600 MHz, CDCl$_3$) δ 8.15 (dd, J=7.9, 1.7, 1H), 7.70 (dd, J=7.8, 1.2, 1H), 7.46-7.39 (m, 1H), 7.39-7.31 (m, 1H), 6.15 (s, 1H), 3.93-3.81 (m, 2H), 1.76 (t, J=6.0, 2H), 1.20 (s, 6H).

Intermediate AV

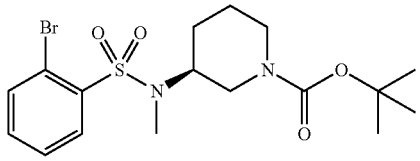

tert-Butyl(3S)-3-{[(2-bromophenyl)sulfonyl](methyl)amino}piperidine-1-carboxylate The title compound was prepared using analogous conditions to those described in Intermediate AU using (S)-tert-butyl 3-(methylamino)piperidine-1-carboxylate. MS (ESI): mass calcd. for $C_{17}H_{25}BrN_2O_4S$ 432.07, m/z found 455.0 [M+Na]$^+$; $^1$H NMR (600 MHz, CDCl$_3$) δ 8.14 (dd, J=7.9, 1.7, 1H), 7.72 (dd, J=7.9, 1.3, 1H), 7.46-7.40 (m, 1H), 7.40-7.35 (m, 1H), 4.06 (s, 2H), 3.67 (s, 1H), 2.85 (s, 3H), 2.72 (s, 1H), 2.47 (s, 1H), 1.86 (d, J=11.8, 1H), 1.75-1.65 (m, 1H), 1.65-1.55 (m, 1H), 1.54-1.46 (m, 1H), 1.38 (s, 9H).

Intermediate AW

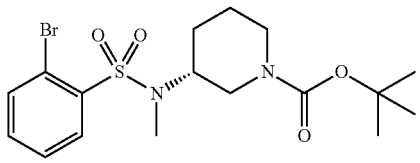

tert-Butyl(3R)-3-{[(2-bromophenyl)sulfonyl](methyl)amino}piperidine-1-carboxylate The title compound was prepared using analogous conditions to those described in Intermediate AU using (S)-tert-butyl 3-(methylamino)piperidine-1-carboxylate.

Intermediate AX

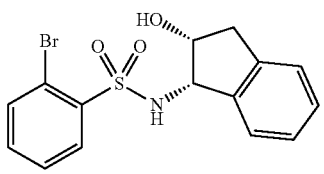

2-Bromo-N-[(1S,2R)-2-hydroxy-2,3-dihydro-1H-inden-1-yl]benzenesulfonamide

The title compound was prepared using analogous conditions to those described in Intermediate AU using (1S,2R)-1-amino-2,3-dihydro-1H-inden-2-ol. MS (ESI): mass calcd. for $C_{15}H_{14}BrNO_3S$ 366.99, m/z found 389.9 [M+Na]$^+$; $^1$H NMR (600 MHz, CDCl$_3$) δ 8.20 (dd, J=7.7, 1.9, 1H), 7.79 (dd, J=7.8, 1.4, 1H), 7.50-7.42 (m, 2H), 7.24-7.16 (m, 4H), 5.85 (d, J=8.2, 1H), 4.70-4.63 (m, 1H), 4.38-4.31 (m, 1H), 3.09-2.97 (m, 1H), 2.95-2.86 (m, 1H), 2.12 (d, J=5.2, 1H).

Intermediate AY

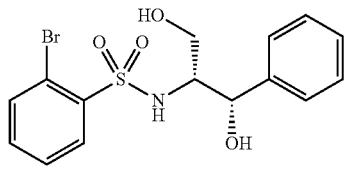

2-Bromo-N-[(1S,2S)-2-hydroxy-1-(hydroxymethyl)-2-phenylethyl]benzenesulfonamide

The title compound was prepared using analogous conditions to those described in Intermediate AU using (1S,2R)-2-amino-1-phenylpropane-1,3-diol. MS (ESI): mass calcd. for $C_{15}H_{16}BrNO_4S$ 384.00, m/z found 407.9 [M+Na]$^+$; $^1$H NMR (600 MHz, CDCl$_3$) δ 7.88 (dd, J=7.6, 1.9, 1H), 7.54 (dd, J=7.6, 1.5, 1H), 7.34-7.26 (m, 2H), 7.23-7.19 (m, 2H), 7.17-7.09 (m, 3H), 5.89 (d, J=6.4, 1H), 4.97 (dd, J=4.3, 2.4, 1H), 3.83-3.73 (m, 1H), 3.73-3.64 (m, 1H), 3.48-3.38 (m, 1H), 3.05 (d, J=2.6, 1H), 2.37-2.27 (m, 1H).

Intermediate AZ

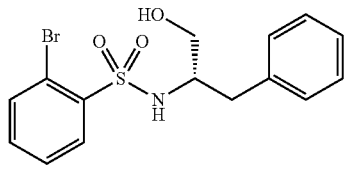

N-[(1S)-1-Benzyl-2-hydroxyethyl]-2-bromobenzenesulfonamide

The title compound was prepared using analogous conditions to those described in Intermediate AU using (S)-2-amino-3-phenylpropan-1-ol. MS (ESI): mass calcd. for $C_{15}H_{16}BrNO_3S$ 369.00, m/z found 392.0 [M+Na]$^+$; $^1$H NMR (600 MHz, CDCl$_3$) δ 8.07 (dd, J=7.8, 1.7, 1H), 7.62 (dd, J=7.9, 1.2, 1H), 7.45-7.39 (m, 1H), 7.38-7.32 (m, 1H), 7.20-7.10 (m, 3H), 7.05-6.95 (m, 2H), 5.46 (d, J=6.8, 1H), 3.63-3.54 (m, 1H), 3.54-3.43 (m, 2H), 2.88-2.78 (m, 1H), 2.78-2.68 (m, 1H), 2.14-1.97 (m, 1H).

Intermediate BA

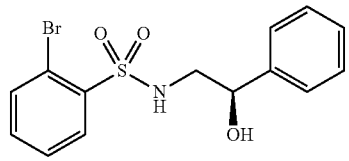

2-Bromo-N-[(2R)-2-hydroxy-2-phenylethyl]benzenesulfonamide

The title compound was prepared using analogous conditions to those described in Intermediate AU using (R)-2-amino-3-phenylpropan-1-ol. $^1$H NMR (600 MHz, CDCl$_3$) δ 8.10 (dd, J=7.8, 1.8, 1H), 7.71 (dd, J=7.8, 1.3, 1H), 7.47-7.42 (m, 1H), 7.42-7.37 (m, 1H), 7.33-7.28 (m, 2H), 7.28-7.25 (m, 3H), 5.68-5.57 (m, 1H), 4.78 (dd, J=8.7, 3.7, 1H), 3.26-3.15 (m, 1H), 3.04-2.94 (m, 1H), 2.41 (s, 1H).

Intermediate BB

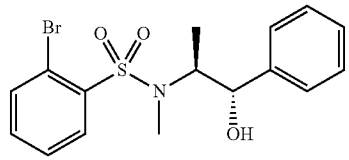

2-Bromo-N-[(1S,2S)-2-hydroxy-1-methyl-2-phenylethyl]-N-methylbenzenesulfonamide

The title compound was prepared using analogous conditions to those described in Intermediate AU using (1S,2S)-2-(methylamino)-1-phenylpropan-1-ol. MS (ESI): mass calcd. for $C_{16}H_{18}BrNO_3S$ 383.02, m/z found 406.0 [M+Na]$^+$; $^1$H NMR (600 MHz, CDCl$_3$) δ 8.19 (dd, J=7.9, 1.7, 1H), 7.73 (dd, J=7.8, 1.3, 1H), 7.49-7.44 (m, 1H), 7.41-7.36 (m, 1H), 7.34-7.29 (m, 2H), 7.29-7.25 (m, 3H), 4.45 (dd, J=9.4, 3.4, 1H), 3.95-3.85 (m, 1H), 3.05 (d, J=3.4, 1H), 2.98 (s, 3H), 0.97-0.86 (d, J=6.7, 3H).

Intermediate BC

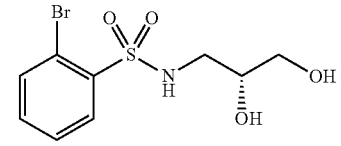

2-Bromo-N-[(2R)-2,3-dihydroxypropyl]benzenesulfonamide

The title compound was prepared using analogous conditions to those described in Intermediate AU using (R)-1-aminoethane-1,2-diol. MS (ESI): mass calcd. for C$_9$H$_{12}$BrNO$_4$S 308.97, m/z found 310.0 [M+H]$^+$; $^1$H NMR (600 MHz, CDCl$_3$) δ 8.05 (dd, J=7.8, 1.7, 1H), 7.68 (dd, J=7.9, 1.3, 1H), 7.49-7.40 (m, 1H), 7.40-7.32 (m, 1H), 6.18 (t, J=6.3, 1H), 3.95-3.75 (m, 3H), 3.64 (dd, J=11.8, 3.6, 1H), 3.54 (dd, J 11.6, 6.0, 1H), 3.06-2.97 (m, 1H), 2.97-2.85 (m, 1H).

Intermediate BD

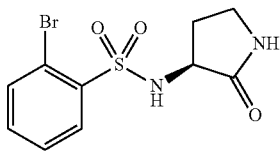

2-Bromo-N-[(3S)-2-oxopyrrolidin-3-yl]benzenesulfonamide

The title compound was prepared using analogous conditions to those described in Intermediate AU using (S)-3-aminopyrrolidin-2-one. MS (ESI): mass calcd. for C$_{10}$H$_{11}$BrN$_2$O$_3$S 317.97, m/z found 318.9 [M+H]$^+$; $^1$H NMR (600 MHz, CDCl$_3$) δ 8.14-8.05 (m, 1H), 7.71 (dd, J=7.8, 1.3, 1H), 7.49-7.36 (m, 2H), 7.06 (s, 1H), 6.22 (d, J=4.7, 1H), 3.81-3.68 (m, 1H), 3.41-3.29 (m, 1H), 3.29-3.18 (m, 1H), 2.47-2.34 (m, 1H), 2.12-2.00 (m, 1H).

Intermediate BE

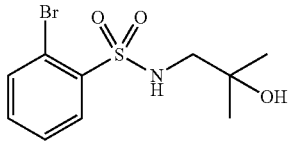

2-Bromo-N-(2-hydroxy-2-methylpropyl)benzenesulfonamide

The title compound was prepared using analogous conditions to those described in Intermediate AU using 1-amino-2-methylpropan-2-ol. MS (ESI): mass calcd. for C$_{10}$H$_{14}$BrNO$_3$S 306.99, m/z found 290.0 [M−OH]$^+$; $^1$H NMR (600 MHz, CDCl$_3$) δ 8.11 (dd, J=7.8, 1.7, 1H), 7.72 (dd, J=7.8, 1.3, 1H), 7.48-7.43 (m, 1H), 7.43-7.38 (m, 1H), 5.53 (t, J=6.0, 1H), 2.79 (d, J=6.6, 2H), 1.22 (s, 6H).

Intermediate BF

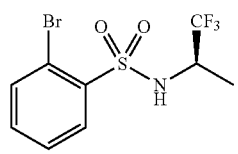

2-Bromo-N-[(1R)-2,2,2-trifluoro-1-methylethyl]benzenesulfonamide

The title compound was prepared using analogous conditions to those described in Intermediate AU using (R)-2-amino-1,1,1-trifluoropropane.

Intermediate BG

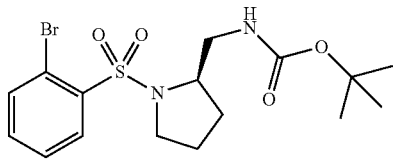

tert-Butyl ({[(2R)-1-[(2-bromophenyl)sulfonyl]pyrrolidin-2-yl}methyl)carbamate

The title compound was prepared using analogous conditions to those described in Intermediate AU using (R)-tert-butyl (pyrrolidin-2-ylmethyl)carbamate. MS (ESI): mass calcd. for C$_{16}$H$_{23}$BrN$_2$O$_4$S 418.06, m/z found 319.0 [M-Boc+H]$^+$; $^1$H NMR (600 MHz, CDCl$_3$) δ 8.10 (dd, J=7.9, 1.7, 1H), 7.73 (dd, J=7.9, 1.3, 1H), 7.46-7.41 (m, 1H), 7.41-7.36 (m, 1H), 4.99 (t, J=6.5, 1H), 4.05-3.95 (m, 1H), 3.50-3.40 (m, 1H), 3.40-3.34 (m, 1H), 3.32-3.17 (m, 2H), 1.98-1.86 (m, 2H), 1.86-1.71 (m, 2H), 1.40 (s, 9H).

Intermediate BH

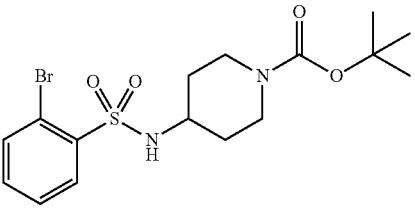

tert-Butyl 4-{[(2-bromophenyl)sulfonyl]amino}piperidine-1-carboxylate

The title compound was prepared using analogous conditions to those described in Intermediate AU using tert-butyl 4-aminopiperidine-1-carboxylate. MS (ESI): mass calcd. for C$_{16}$H$_{23}$BrN$_2$O$_4$S 418.06, m/z found 441.0 [M+Na]$^+$; $^1$H NMR (600 MHz, CDCl$_3$) δ 8.13 (dd, J=7.8, 1.7, 1H), 7.72 (dd, J=7.8, 1.3, 1H), 7.49-7.43 (m, 1H), 7.43-7.38 (m, 1H), 5.15 (d, J=7.5, 1H), 3.86 (s, 2H), 3.32-3.20 (m, 1H), 2.75 (s, 2H), 1.69 (d, J=12.2, 2H), 1.40 (s, 9H), 1.38-1.29 (m, 2H).

Intermediate BI

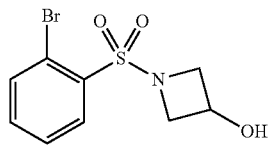

1-[(2-Bromophenyl)sulfonyl]azetidin-3-ol

The title compound was prepared using analogous conditions to those described in Intermediate AU using azetidin- 3-ol. MS (ESI): mass calcd. for $C_9H_{10}BrNO_3S$ 290.96, m/z found 292.0 [M+H]$^+$; $^1$H NMR (600 MHz, CDCl$_3$) δ 8.02 (dd, J=7.8, 1.8, 1H), 7.72 (dd, J=7.8, 1.3, 1H), 7.44-7.40 (m, 1H), 7.40-7.35 (m, 1H), 4.61-4.51 (m, 1H), 4.18-4.10 (m, 2H), 3.97-3.91 (m, 2H), 2.92 (d, J=6.3, 1H).

Intermediate BJ

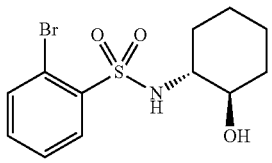

racemic 2-Bromo-N-[(1,2-trans)-2-hydroxycyclohexyl]benzenesulfonamide

The title compound was prepared using analogous conditions to those described in Intermediate AU using racemic-(1,2-trans)-1R-2-aminocyclohexanol. MS (ESI): mass calcd. for $C_{12}H_{16}BrNO_3S$ 333.00, m/z found 334.0 [M+H]$^+$; $^1$H NMR (600 MHz, CDCl$_3$) δ 8.15 (dd, J=7.8, 1.7, 1H), 7.73 (dd, J=7.8, 1.3, 1H), 7.50-7.44 (m, 1H), 7.44-7.39 (m, 1H), 5.29 (d, J=7.4, 1H), 3.38-3.28 (m, 1H), 2.88-2.77 (m, 1H), 2.58 (d, J=3.0, 1H), 2.04-1.96 (m, 1H), 1.77-1.69 (m, 1H), 1.59-1.51 (m, 1H), 1.27-1.12 (m, 3H), 1.12-1.01 (m, 1H).

Intermediate BK

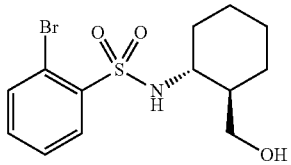

racemic 2-Bromo-N-[(1,2-trans)-2-(hydroxymethyl)cyclohexyl]benzenesulfonamide

The title compound was prepared using analogous conditions to those described in Intermediate AU using racemic-(1,2-trans)-1R-2-aminocyclohexyl)methanol. MS (ESI): mass calcd. for $C_{13}H_{18}BrNO_3S$ 347.02, m/z found 348.0 [M+H]$^+$; $^1$H NMR (600 MHz, CDCl$_3$) δ 8.13 (dd, J=7.8, 1.7, 1H), 7.73 (dd, J=7.8, 1.3, 1H), 7.49-7.44 (m, 1H), 7.44-7.38 (m, 1H), 5.19-5.06 (m, 1H), 4.10-4.00 (m, 1H), 3.51-3.41 (m, 1H), 3.08-2.97 (m, 1H), 2.45-2.36 (m, 1H), 1.72-1.66 (m, 1H), 1.66-1.60 (m, 1H), 1.59-1.53 (m, 1H), 1.52-1.46 (m, 1H), 1.41-1.32 (m, 1H), 1.31-1.24 (m, 1H), 1.20-1.07 (m, 2H), 1.05-0.96 (m, 1H).

Intermediate BL

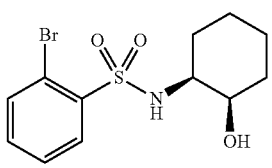

racemic 2-Bromo-N-[(1,2-cis)-2-hydroxycyclohexyl]benzenesulfonamide

The title compound was prepared using analogous conditions to those described in Intermediate AU using racemic-(1,2-cis)-1R-2-aminocyclohexanol. MS (ESI): mass calcd. for $C_{12}H_{16}BrNO_3S$ 333.00, m/z found 334.0 [M+H]$^+$; $^1$H NMR (600 MHz, CDCl$_3$) δ 8.13 (dd, J=7.8, 1.7, 1H), 7.72 (dd, J=7.8, 1.3, 1H), 7.47-7.42 (m, 1H), 7.42-7.38 (m, 1H), 5.52 (d, J=7.7, 1H), 3.80-3.72 (m, 1H), 3.27-3.15 (m, 1H), 1.80 (d, J=4.8, 1H), 1.74-1.63 (m, 1H), 1.63-1.51 (m, 2H), 1.51-1.43 (m, 2H), 1.43-1.36 (m, 1H), 1.36-1.26 (m, 1H), 1.26-1.11 (m, 1H).

Intermediate BM

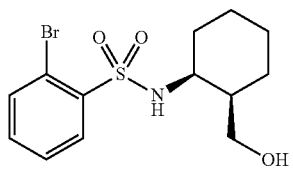

racemic 2-Bromo-N-[(1,2-cis)-2-hydroxymethyl)cyclohexyl]benzenesulfonamide

The title compound was prepared using analogous conditions to those described in Intermediate AU using racemic-(1,2-cis)-1R-2-aminocyclohexyl)methanol. MS (ESI): mass calcd. for $C_{13}H_{18}BrNO_3S$ 347.02, m/z found 348.0 [M+H]$^+$; $^1$H NMR (600 MHz, CDCl$_3$) δ 8.13 (dd, J=7.8, 1.8, 1H), 7.73 (dd, J=7.8, 1.3, 1H), 7.49-7.44 (m, 1H), 7.44-7.39 (m, 1H), 5.43 (d, J=9.3, 1H), 3.76-3.65 (m, 1H), 3.65-3.54 (m, 1H), 3.45-3.33 (m, 1H), 2.82 (dd, J=8.9, 5.2, 1H), 1.73-1.60 (m, 2H), 1.58-1.51 (m, 1H), 1.42-1.35 (m, 1H), 1.35-1.16 (m, 4H), 1.10-0.97 (m, 1H).

Intermediate BN

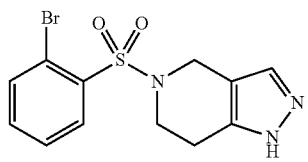

5-[(2-Bromophenyl)sulfonyl]-4,5,6,7-tetrahydro-1H-pyrazolo[4,3-c]pyridine

The title compound was prepared using analogous conditions to those described in Intermediate AU using 4,5,6,7-tetrahydro-1H-pyrazolo[4,3-c]pyridine. MS (ESI): mass calcd. for $C_{12}H_{12}BrN_3O_2S$ 340.98, m/z found 341.9 [M+H]$^+$; $^1$H NMR (600 MHz, CDCl$_3$) δ 8.15 (dd, J=7.8, 1.7, 1H), 7.71 (dd, J=7.9, 1.2, 1H), 7.47-7.42 (m, 1H), 7.41-7.36 (m, 1H), 7.33 (s, 1H), 4.45 (s, 2H), 3.66 (t, J=5.8, 2H), 2.83 (t, J=5.8, 2H).

Intermediate BO

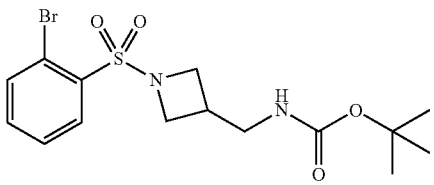

tert-Butyl ({1-[(2-bromophenyl)sulfonyl]azetidin-3-yl}methyl)carbamate

The title compound was prepared using analogous conditions to those described in Intermediate AU using tert-butyl (azetidin-3-ylmethyl)carbamate. MS (ESI): mass calcd. for $C_{15}H_{21}BrN_2O_4S$ 404.04, m/z found 349.0 [M-tBu+H]$^+$; $^1$H NMR (600 MHz, CDCl$_3$) δ 8.04 (dd, J=7.8, 1.8, 1H), 7.73 (dd, J=7.7, 1.3, 1H), 7.44-7.40 (m, 1H), 7.40-7.35 (m, 1H), 4.71 (s, 1H), 4.13-4.03 (m, 2H), 3.70 (dd, J=7.9, 5.4, 2H), 3.35-3.22 (m, 2H), 2.78-2.64 (m, 1H), 1.40 (s, 9H).

Intermediate BP

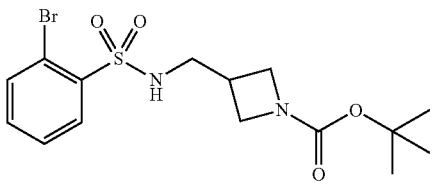

tert-Butyl 3-({[(2-bromophenyl)sulfonyl]amino}methyl)azetidine-1-carboxylate

The title compound was prepared using analogous conditions to those described in Intermediate AU using tert-butyl 3-(aminomethyl)azetidine-1-carboxylate. $^1$H NMR (600 MHz, CDCl$_3$) δ 8.12 (dd, J=7.8, 1.7, 1H), 7.73 (dd, J=7.8, 1.3, 1H), 7.50-7.45 (m, 1H), 7.45-7.39 (m, 1H), 5.42-5.30 (m, 1H), 3.96-3.85 (m, 2H), 3.52 (d, J=9.3, 2H), 3.17-3.02 (m, 2H), 2.69-2.54 (m, 1H), 1.39 (s, 9H).

Intermediate BQ

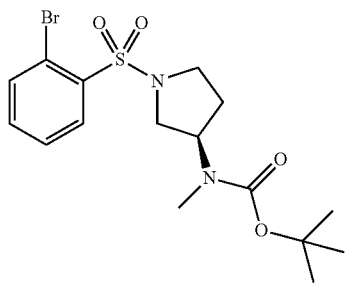

tert-Butyl {(3R)-1-[(2-bromophenyl)sulfonyl]pyrrolidin-3-yl}methylcarbamate

The title compound was prepared using analogous conditions to those described in Intermediate AU using (R)-tert-butyl methyl(pyrrolidin-3-yl)carbamate. MS (ESI): mass calcd. for $C_{16}H_{23}BrN_2O_4S$ 418.06, m/z found 441.0 [M+Na]$^+$; $^1$H NMR (600 MHz, CDCl$_3$) δ 8.08 (dd, J=7.9, 1.8, 1H), 7.73 (dd, J=7.8, 1.3, 1H), 7.46-7.40 (m, 1H), 7.40-7.34 (m, 1H), 4.80 (s, 1H), 3.61 (s, 1H), 3.51 (s, 1H), 3.38-3.30 (m, 1H), 3.19 (dd, J=9.9, 7.4, 1H), 2.73 (s, 3H), 2.12-2.03 (m, 1H), 2.03-1.93 (m, 1H), 1.41 (s, 9H).

Intermediate BR

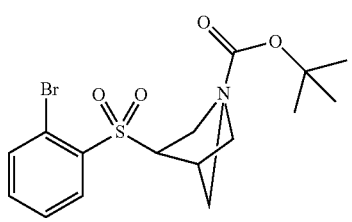

tert-Butyl (1R,4R)-5-[(2-bromophenyl)sulfonyl]-2,5-diazabicyclo[2.2.1]heptane-2-carboxylate The title compound was prepared using analogous conditions to those described in Intermediate AU using tert-butyl 2,5-diazabicyclo[2.2.1]heptane-2-carboxylate. MS (ESI): mass calcd. for $C_{16}H_{21}BrN_2O_4S$ 416.04, m/z found 439.0 [M+Na]$^+$; $^1$H NMR (600 MHz, CDCl$_3$) 8.10 (dd, J=7.9, 1.8, 1H), 7.73 (dd, J=8.0, 1.2, 1H), 7.46-7.40 (m, 1H), 7.40-7.34 (m, 1H), 4.63-4.39 (m, 2H), 3.59-3.39 (m, 2H), 3.33-3.22 (m, 2H), 1.88-1.76 (m, 2H), 1.42 (d, J=5.0, 9H).

Intermediate BS

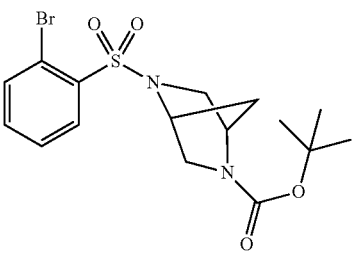

tert-Butyl (1S,4S)-5-[(2-bromophenyl)sulfonyl]-2,5-diazabicyclo[2.2.1]heptane-2-carboxylate The title compound was prepared using analogous conditions to those described in Intermediate AU (1S,4S)-tert-butyl 2,5-diazabicyclo[2.2.]heptane-2-carboxylate.

Intermediate BT

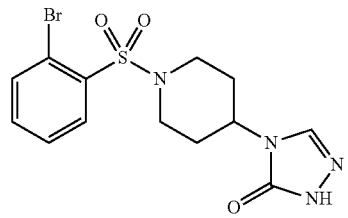

4-{1-[(2-Bromophenyl)sulfonyl]piperidin-4-yl}-2,4-dihydro-3H-1,2,4-triazol-3-one The title compound was prepared using analogous conditions to those described in Intermediate AU using 4-(piperidin-4-yl)-1H-1,2,4-triazol-5(4H)-one. MS (ESI): mass calcd. for $C_{13}H_{15}BrN_4O_3S$ 386.00, m/z found 387.0 [M+H]$^+$; $^1$H NMR (600 MHz, CDCl$_3$) δ 9.63 (s, 1H), 8.10 (dd, J=7.8, 1.8, 1H), 7.75 (dd, J=7.9, 1.3, 1H), 7.49-7.43 (m, 1H), 7.43-7.37 (m, 2H), 4.05-3.97 (m, 3H), 2.97-2.89 (m, 2H), 2.09-2.03 (m, 2H), 1.89-1.79 (m, 2H).

Intermediate BU

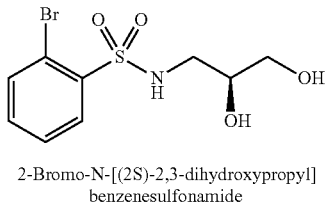 [SMILES: O=S(=O)(NC[C@H](O)CO)c1ccccc1Br]

2-Bromo-N-[(2S)-2,3-dihydroxypropyl]
benzenesulfonamide

The title compound was prepared using analogous conditions to those described in Intermediate AU using (S)-3-aminopropane-1,2-diol.

Intermediate BV

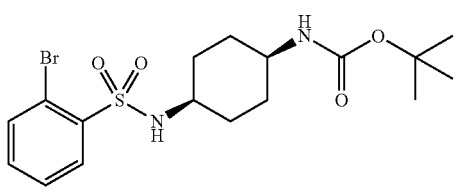

tert-Butyl (cis-4-{[(2-bromophenyl)sulfonyl]amino}
cyclohexyl)carbamate

The title compound was prepared using analogous conditions to those described in Intermediate AU using tert-butyl ((cis)-4-aminocyclohexyl)carbamate. MS (ESI): mass calcd. for $C_{17}H_{25}BrN_2O_4S$ 432.07, m/z found 455.0 [M+Na]$^+$; $^1$H NMR (600 MHz, CDCl$_3$) δ 8.13 (dd, J=7.8, 1.7, 1H), 7.72 (dd, J=7.8, 1.2, 1H), 7.48-7.43 (m, 1H), 7.43-7.38 (m, 1H), 5.17 (s, 1H), 4.45 (s, 1H), 3.47 (s, 1H), 3.30-3.20 (m, 1H), 1.66 (s, 2H), 1.60-1.49 (m, 4H), 1.45 (d, J=7.3, 1H), 1.41 (s, 9H).

Intermediate BW

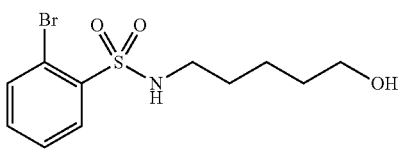

2-Bromo-N-(5-hydroxypentyl)benzenesulfonamide

The title compound was prepared using analogous conditions to those described in Intermediate AU using 5-aminopentan-1-ol. MS (ESI): mass calcd. for $C_{11}H_{16}BrNO_3S$ 321.00, m/z found 322.0 [M+H]$^+$; $^1$H NMR (600 MHz, CDCl$_3$) b 8.10 (dd. J=7.8, 1.7, 1H), 7.71 (dd, J=7.9, 1.3, 1H), 7.48-7.42 (m, 1H), 7.42-7.35 (m, 1H), 5.23 (t, J=6.3, 1H), 3.62-3.50 (m, 2H), 2.93-2.83 (m, 2H), 1.55 (s, 1H), 1.52-1.42 (m, 4H), 1.39-1.29 (m, 2H).

Intermediate BX

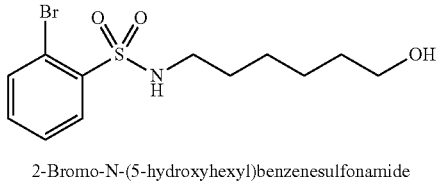 [SMILES: O=S(=O)(NCCCCCCO)c1ccccc1Br]

2-Bromo-N-(5-hydroxyhexyl)benzenesulfonamide

The title compound was prepared using analogous conditions to those described in Intermediate AU using 6-aminohexan-1-ol. MS (ESI): mass calcd. for $C_{12}H_{18}BrNO_3S$ 335.02, m/z found 336.0 [M+H]$^+$; $^1$H NMR (600 MHz, CDCl$_3$) δ 8.11 (dd, J=7.8, 1.8, 1H), 7.71 (dd, J=7.9, 1.3, 1H), 7.48-7.42 (m, 1H), 7.42-7.36 (m, 1H), 5.15 (t, J=6.2, 1H), 3.57 (t, J=6.6, 2H), 2.94-2.81 (m, 2H), 1.56-1.35 (m, 5H), 1.33-1.21 (m, 4H).

Intermediate BY

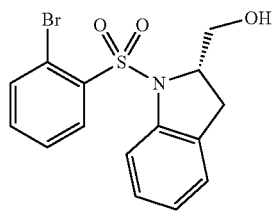

{(2S)-1-[(2-Bromophenyl)
sulfonyl]-2,3-dihydro-1H-
indol-2-yl}methanol

The title compound was prepared using analogous conditions to those described in Intermediate AU using (S)-indolin-2-ylmethanol. MS (ESI): mass calcd. for $C_{15}H_{14}BrNO_3S$ 366.99, m/z found 389.9 [M+Na]$^+$; $^1$H NMR (600 MHz, CDCl$_3$) δ 8.12 (dd, J=7.9, 1.7, 1H), 7.65 (dd, J=7.9, 1.3, 1H), 7.42-7.36 (m, 1H), 7.36-7.31 (m, 1H), 7.27 (d, J=8.1, 1H), 7.14-7.09 (m, 1H), 7.09-7.04 (m, 1H), 6.98-6.93 (m, 1H), 4.86-4.78 (m, 1H), 3.81-3.68 (m, 2H), 3.28 (dd, J=16.2, 9.6, 1H), 2.88-2.79 (m, 1H), 2.20 (s, 1H).

Intermediate BZ

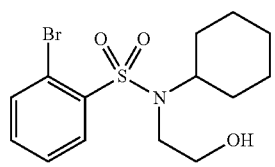

2-Bromo-N-cyclohexyl-N-(2-
hydroxyethyl)
benzenesulfonamide

The title compound was prepared using analogous conditions to those described in Intermediate AU using 2-(cyclohexylamino)ethanol. MS (ESI): mass calcd. for $C_{14}H_{20}BrNO_3S$ 361.03, m/z found 362.0 [M+H]$^+$; $^1$H NMR (600 MHz, CDCl$_3$) δ 8.14 (dd, J=7.9, 1.7, 1H), 7.71 (dd, J=7.8, 1.3, 1H), 7.46-7.40 (m, 1H), 7.40-7.34 (m, 1H), 3.71 (m, 2H), 3.65-3.57 (m, 1H), 3.47 (t, J=6.1, 2H), 2.22 (t, J=5.9, 1H), 1.80-1.67 (m, 4H), 1.62-1.53 (m, 1H), 1.44-1.32 (m, 2H), 1.27-1.15 (m, 2H), 1.07-0.94 (m, 1H).

Intermediate CA

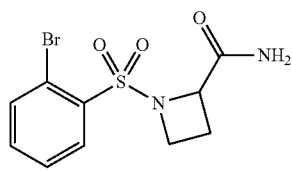

(racemic) 1-[(2-Bromophenyl)
sulfonyl]azetidine-2-carboxamide

The title compound was prepared using analogous conditions to those described in Intermediate AU using racemic-azetidine-2-carboxamide. MS (ESI): mass calcd. for $C_{10}H_{11}BrN_2O_3S$ 319.97, m/z found 319.0 [M+H]$^+$; $^1$H NMR (600 MHz, CDCl$_3$) δ 8.11-8.07 (m, 1H), 7.83-7.79 (m, 1H), 7.53-7.46 (m, 2H), 6.91 (s, 1H), 5.53 (s, 1H), 4.75 (t, J=8.8, 1H), 4.02-3.94 (m, 1H), 3.75-3.67 (m, 1H), 2.49-2.39 (m, 2H).

Intermediate CB

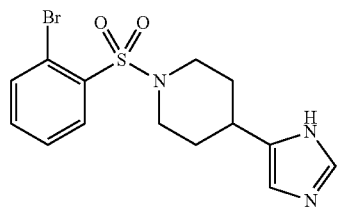

1-[(2-Bromophenyl)sulfonyl]-4-(1H-
imidazol-4-yl)piperidine

Step A: 1-[(2-Bromophenyl)sulfonyl]-4-{1-[(2-bromophenyl)sulfonyl]-1H-imidazol-4-yl}piperidine To a 20 mL vial were added a stirbar, 4-(1H-imidazol-4-yl)piperidine.HCl (696 mg, 3.71 mmol), ACN (5 mL), and DIPEA (2.0 mL, 12 mmol). The mixture was then treated with 2-bromobenzene-1-sulfonyl chloride (900 mg, 3.52 mmol) and the mixture was stirred for 15.5 hours before concentrating to dryness and subjecting the residue to FCC to give the title compound (950 mg, 92%). MS (ESI): mass calcd. for $C_{20}H_{19}Br_2N_3O_4S_2$ 586.92 m/z found 587.9 [M+H]$^+$; $^1$H NMR (600 MHz, CDCl$_3$) δ 8.20 (dd, J=7.9, 1.8, 1H), 8.08 (dd, J=7.8, 1.7, 1H), 8.06 (d, J=1.3, 1H), 7.75 (dd, J=7.7, 1.3, 1H), 7.72 (dd, J=7.9, 1.2, 1H), 7.58-7.53 (m, 1H), 7.53-7.49 (m, 1H), 7.45-7.40 (m, 1H), 7.39-7.34 (m, 1H), 6.93-6.91 (m, 1H), 3.90-3.82 (m, 2H), 2.93-2.83 (m, 2H), 2.68-2.59 (m, 1H), 2.02 (dd, J=13.9, 3.0, 2H), 1.70-1.59 (m, 2H).

Step B

To a 20 mL vial containing 1-[(2-bromophenyl)sulfonyl]-4-{1-[(2-bromophenyl)-sulfonyl]-1H-imidazol-4-yl}piperidine (884 mg, 1.50 mmol) were added a stirbar and DMSO (10 mL). Once the DMSO solution was homogeneous, LiOH (3 mL, 1.0 M) was added slowly. After 30 min the reaction mixture was diluted with EtOAc, washed with water (×4) and brine (×1), dried over MgSO$_4$, filtered and concentrated to dryness to give the title compound (522 mg, 94%). MS (ESI): mass calcd. for $C_{14}H_{16}BrN_3O_2S$ 369.01 m/z found 370.0 [M+H]$^+$; $^1$H NMR (600 MHz, CDCl$_3$) δ 8.08 (dd, J=7.9, 1.7, 1H), 7.72 (dd, J=7.8, 1.3, 1H), 7.62 (s, 1H), 7.45-7.41 (m, 1H), 7.40-7.35 (m, 1H), 6.76 (s, 1H), 3.88 (d, J=12.8, 1H), 2.90 (m, 2H), 2.76-2.69 (m, 1H), 2.09-2.01 (m, 2H), 1.77-1.67 (m, 2H).

Intermediate CC

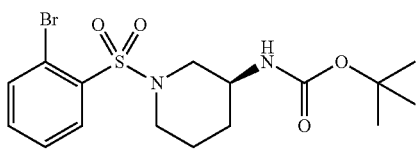

tert-Butyl {(3S)-1-[(2-bromophenyl)sulfonyl]
piperidin-3-yl}carbamate

The title compound was prepared using analogous conditions to those described in Intermediate AU using (S)-tert-butyl piperidin-3-ylcarbamate. MS (ESI): mass calcd. for $C_{16}H_{23}BrN_2O_4S$ 418.06 m/z found 441.0 [M+Na]$^+$; $^1$H NMR (600 MHz, CDCl$_3$) δ 8.10-8.06 (m, 1H), 7.73 (dd, J=7.7, 1.3, 1H), 7.46-7.40 (m, 1H), 7.40-7.35 (m, 1H), 4.88 (d, J=8.5, 1H), 3.77 (s, 1H), 3.44 (s, 1H), 3.28 (d, J=11.8, 1H), 3.23-3.03 (m, 2H), 1.85-1.55 (m, 4H), 1.39 (s, 9H).

Intermediate CD

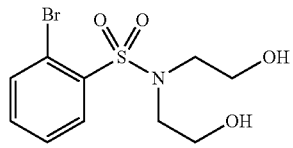

2-Bromo-N,N-bis(2-hydroxyethyl)
benzenesulfonamide

The title compound was prepared using analogous conditions to those described in Intermediate AU using 2,2'-azanediyldiethanol. MS (ESI): mass calcd. for $C_{10}H_{14}BrNO_4S$ 322.98 m/z found 324.0 [M+H]$^+$; $^1$H NMR (600 MHz, CDCl$_3$) δ 8.10-8.05 (m, 1H), 7.74 (dd, J=7.8, 1.3, 1H), 7.47-7.42 (m, 1H), 7.42-7.37 (m, 1H), 3.83 (dd, J=7.3, 3.8, 4H), 3.48 (t, J=5.0, 4H), 3.38 (s, 2H).

Intermediate CE

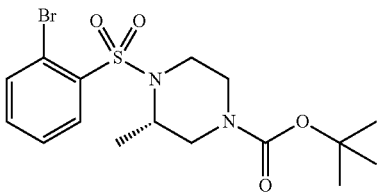

tert-Butyl (3S)-4-[(2-bromophenyl)sulfonyl]-3-methylpiperazine-1-carboxylate

The title compound was prepared using analogous conditions to those described in Intermediate AU using (S)-tert-butyl 3-methylpiperazine-1-carboxylate. MS (ESI): mass calcd. for $C_{16}H_{23}BrN_2O_4S$ 418.06 m/z found 319.0 [M-Boc+H]$^+$; $^1$H NMR (600 MHz, CDCl$_3$) δ 8.14 (dd, J=7.8, 1.8, 1H), 7.72 (dd, J=7.8, 1.3, 1H), 7.45-7.40 (m, 1H), 7.40-7.35 (m, 1H), 4.16-3.73 (m, 3H), 3.63-3.42 (m, 1H), 3.32-3.22 (m, 1H), 3.17-2.68 (m, 2H), 1.42 (s, 9H), 1.25-1.09 (m, 3H).

Intermediate CF

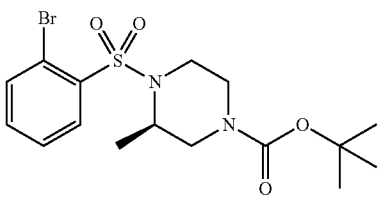

tert-Butyl (3R)-4-[(2-bromophenyl)sulfonyl]-3-methylpiperazine-1-carboxylate

The title compound was prepared using analogous conditions to those described in Intermediate AU using (R)-tert-butyl 3-methylpiperazine-1-carboxylate.

Intermediate CG

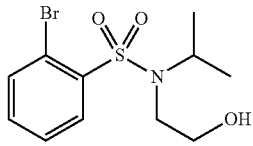

2-Bromo-N-(2-hydroxyethyl)-N-(1-methylethyl)benzenesulfonamide

The title compound was prepared using analogous conditions to those described in Intermediate AU using 2-(isopropylamino)ethanol. MS (ESI): mass calcd. for $C_{11}H_{16}BrNO_3S$ 321.00 m/z found 322.0 [M+H]$^+$; $^1$H NMR (600 MHz, CDCl$_3$) δ 8.15 (dd, J=7.9, 1.7, 1H), 7.71 (dd, J=7.9, 1.3, 1H), 7.46-7.41 (m, 1H), 7.39-7.34 (m, 1H), 4.01 (hept, J=6.7, 1H), 3.74 (m, 2H), 3.47 (t, J=6.1, 2H), 2.27 (t, J=5.8, 1H), 1.13 (d, J=6.8, 6H).

Intermediate CH

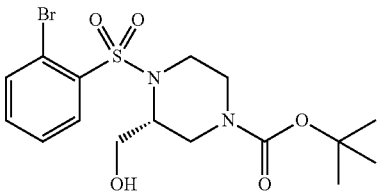

tert-Butyl (3R)-4-[(2-bromophenyl)sulfonyl]-3-(hydroxymethyl)piperazine-1-carboxylate The title compound was prepared using analogous conditions to those described in Intermediate AU using (R)-tert-butyl 3-(hydroxymethyl)piperazine-1-carboxylate. MS (ESI): mass calcd. for $C_{16}H_{23}BrN_2O_5S$ 434.05 m/z found 335.0 [M-Boc+H]$^+$; $^1$H NMR (600 MHz, CDCl$_3$) δ 8.16 (dd, J=7.8, 1.8, 1H), 7.73 (dd, J=7.9, 1.3, 1H), 7.47-7.42 (m, 1H), 7.42-7.37 (m, 1H), 4.32-3.43 (m, 6H), 3.27-3.15 (m, 1H), 3.15-2.66 (m, 3H), 1.44 (s, 9H).

Intermediate CI

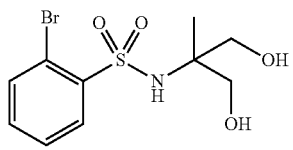

2-Bromo-N-[2-hydroxy-1-(hydroxymethyl)-1-methylethyl]benzenesulfonamide

The title compound was prepared using analogous conditions to those described in Intermediate AU using 2-amino-2-methylpropane-1,3-diol. $^1$H NMR (600 MHz, CDCl$_3$) δ 8.14 (dd, J=7.8, 1.7, 1H), 7.73 (dd, J=7.9, 1.3, 1H), 7.48-7.43 (m, 1H), 7.43-7.37 (m, 1H), 5.93 (s, 1H), 3.72-3.56 (m, 4H), 2.53-2.44 (m, 2H), 0.93 (s, 3H).

Intermediate CJ

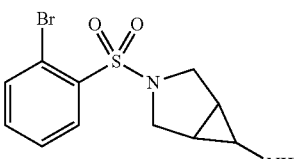

endo-3-[(2-Bromophenyl)sulfonyl]-3-azabicyclo[3.1.0]hexan-6-amine

The title compound was prepared using analogous conditions to those described in Intermediate AU using endo-3-azabicyclo[3.1.0]hexan-6-amine. MS (ESI): mass calcd. for $C_{11}H_{13}BrN_2O_2S$ 315.99 m/z found 317.0 [M+H]$^+$; $^1$H NMR (600 MHz, DMSO-d$_6$) δ 7.97 (dd, J=7.7, 1.9, 1H), 7.88 (dd, J=7.7, 1.4, 1H), 7.62-7.58 (m, 1H), 7.58-7.54 (m, 1H), 3.42-3.38 (m, 2H), 3.37-3.29 (m, 4H), 2.02 (t, J=2.2, 1H), 1.46-1.41 (m, 2H).

Intermediate CK

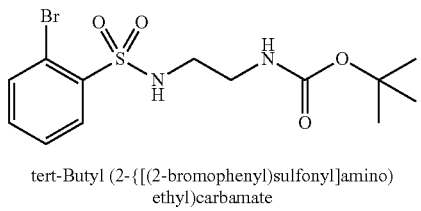 [SMILES: CC(C)(C)OC(=O)NCCNS(=O)(=O)c1ccccc1Br]

tert-Butyl (2-{[(2-bromophenyl)sulfonyl]amino)ethyl)carbamate

The title compound was prepared using analogous conditions to those described in Intermediate AU using tert-butyl(2-aminoethyl)carbamate. ¹H NMR (600 MHz, CDCl₃) δ 8.10 (dd, J=7.7, 1.7, 1H), 7.71 (dd, J=7.9, 1.3, 1H), 7.47-7.43 (m, 1H), 7.43-7.37 (m, 1H), 5.66 (t, J=5.8, 1H), 4.86 (s, 1H), 3.21 (t, J=5.8, 2H), 3.03-2.95 (m, 2H), 1.40 (s, 9H).

Intermediate CL

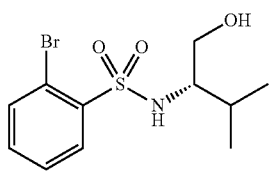

2-Bromo-N-[(1S)-1-(hydroxymethyl)-2-methylpropyl]benzenesulfonamide

The title compound was prepared using analogous conditions to those described in Intermediate AU using (S)-2-amino-3-methylbutan-1-ol. ¹H NMR (600 MHz, CDCl₃) δ 8.11 (dd, J=7.8, 1.7, 1H), 7.72 (dd, J=7.9, 1.2, 1H), 7.47-7.42 (m, 1H), 7.41-7.36 (m, 1H), 5.35 (d, J=8.6, 1H), 3.63-3.54 (m, 1H), 3.54-3.43 (m, 1H), 3.11-3.01 (m, 1H), 1.88-1.75 (m, 2H), 0.86 (d, J=6.9, 3H), 0.80 (d, J=6.8, 3H).

Intermediate CM

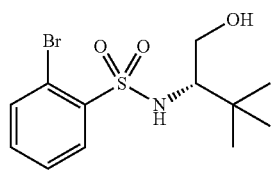

2-Bromo-N-[(1S)-1-(hydroxymethyl)-2,2-dimethylpropyl]benzenesulfonamide

The title compound was prepared using analogous conditions to those described in Intermediate AU using (S)-2-amino-3,3-dimethylbutan-1-ol. MS (ESI): mass calcd. for C₁₂H₁₈BrNO₃S 335.02 m/z found 336.0 [M+H]⁺; ¹H NMR (600 MHz, CDCl₃) δ 8.09 (dd, J=7.7, 1.7, 1H), 7.71 (dd, J=7.9, 1.3, 1H), 7.46-7.41 (m, 1H), 7.40-7.35 (m, 1H), 5.40 (d, J=9.4, 1H), 3.66-3.55 (m, 2H), 3.11-3.01 (m, 1H), 1.81 (t, J=5.6, 1H), 0.85 (s, 9H).

Intermediate CN

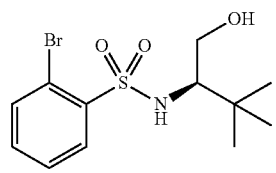

2-Bromo-N-[(1R)-1-(hydroxymethyl)-2,2-dimethylpropyl]benzenesulfonamide

The title compound was prepared using analogous conditions to those described in Intermediate AU using (R)-2-amino-3,3-dimethylbutan-1-ol.

Intermediate CO

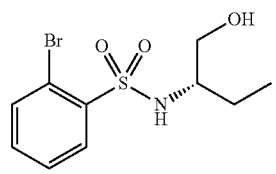

2-Bromo-N-[(1S)-1-(hydroxymethyl)propyl]benzenesulfonamide

The title compound was prepared using analogous conditions to those described in Intermediate AU using (S)-2-aminobutan-1-ol. MS (ESI): mass calcd. for C₁₀H₁₄BrNO₃S 306.99 m/z found 308.0 [M+H]⁺; ¹H NMR (600 MHz, CDCl₃) δ 8.11 (dd, J=7.8, 1.7, 1H), 7.72 (dd, J=7.9, 1.3, 1H), 7.47-7.42 (m, 1H), 7.42-7.37 (m, 1H), 5.41 (d, J=7.9, 1H), 3.59-3.46 (m, 2H), 3.19-3.10 (m, 1H), 2.15-1.99 (m, 1H), 1.56-1.38 (m, 2H), 0.78 (t, J=7.5, 3H).

Intermediate CP

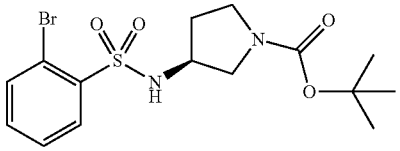

tert-Butyl (3S)-3-{[2-bromophenyl)sulfonyl]amino}pyrrolidine-1-carboxylate

The title compound was prepared using analogous conditions to those described in Intermediate AU using (S)-tert-butyl 3-aminopyrrolidine-1-carboxylate. MS (ESI): mass calcd. for C₁₅H₂₁BrN₂O₄S 404.04 m/z found 427.0 [M+Na]⁺; ¹H NMR (600 MHz, CDCl₃) δ 8.17-8.11 (m, 1H), 7.77-7.69 (m, 1H), 7.51-7.45 (m, 1H), 7.45-7.39 (m, 1H), 5.38-5.29 (m, 1H), 3.87-3.75 (m, 1H), 3.46-3.32 (m, 2H), 3.32-3.21 (m, 1H), 3.16-3.05 (m, 1H), 2.05-1.68 (m, 2H), 1.39 (s, 9H).

Intermediate CQ

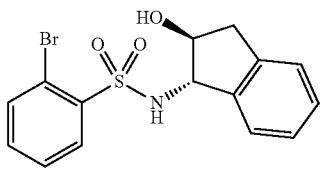

2-Bromo-N-[(1S,2S)-2-hydroxy-2,3-dihydro-1H-inden-1-yl]benzenesulfonamide

The title compound was prepared using analogous conditions to those described in Intermediate AU using (1S,2S)-1-amino-2,3-dihydro-1H-inden-2-ol. MS (ESI): mass calcd. for $C_{15}H_{14}BrNO_3S$ 366.99 m/z found 390.0 [M+Na]$^+$; $^1$H NMR (600 MHz, CDCl$_3$) δ 8.21 (dd, J=7.7, 1.8, 1H), 7.80 (dd, J=7.8, 1.3, 1H), 7.52-7.47 (m, 1H), 7.47-7.43 (m, 1H), 7.25-7.21 (m, 1H), 7.21-7.13 (m, 3H), 5.61 (d, J=6.8, 1H), 4.58-4.47 (m, 1H), 4.44-4.37 (m, 1H), 3.26 (dd, J=15.9, 7.7, 1H), 3.13 (d. J=2.7, 1H), 2.84-2.73 (m, 1H).

Intermediate CR

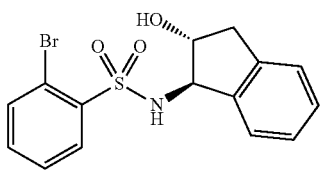

2-Bromo-N-[(1R,2R)-2-hydroxy-2,3-dihydro-1H-inden-1-yl]benzenesulfonamide

The title compound was prepared using analogous conditions to those described in Intermediate AU using (1R,2R)-1-amino-2,3-dihydro-1H-inden-2-ol.

Intermediate CS

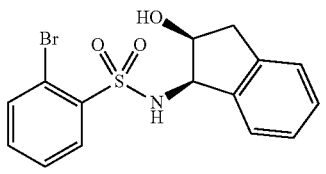

2-Bromo-N-[(1R,2R)-2-hydroxy-2,3-dihydro-1H-inden-1-yl]benzenesulfonamide

The title compound was prepared using analogous conditions to those described in Intermediate AU using (1R,2S)-1-amino-2,3-dihydro-1H-inden-2-ol.

Intermediate CT

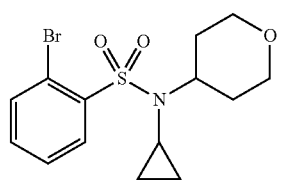

2-Bromo-N-cyclopropyl-N-(tetrahydro-2H-pyran-4-yl)benzenesulfonamide

The title compound was prepared using analogous conditions to those described in Intermediate AU using N-cyclopropyltetrahydro-2H-pyran-4-amine. MS (ESI): mass calcd. for $C_{14}H_{18}BrNO_3S$ 359.02 m/z found 392.0 [M+Na]$^+$; $^1$H NMR (600 MHz, CDCl$_3$) δ 8.16 (dd, J=7.9, 1.7, 1H), 7.69 (dd, J=7.9, 1.2, 1H), 7.47-7.40 (m, 1H), 7.40-7.34 (m, 1H), 4.40-4.30 (m, 1H), 4.05-3.96 (m, 2H), 3.52-3.39 (m, 2H), 2.34-2.25 (m, 1H), 2.16-2.06 (m, 2H), 1.85-1.75 (m, 2H), 0.64-0.56 (m, 2H), 0.54-0.46 (m, 2H).

Intermediate CU

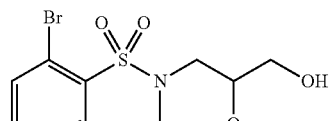

racemic {4-[(2-Bromophenyl)sulfonyl]morpholin-2-yl}methanol

The title compound was prepared using analogous conditions to those described in Intermediate AU using racemic morpholin-2-ylmethanol. MS (ESI): mass calcd. for $C_{11}H_{14}BrNO_4S$ 334.98 m/z found 357.9 [M+Na]$^+$; $^1$H NMR (600 MHz, CDCl$_3$) δ 8.06 (dd, J=7.8, 1.8, 1H), 7.74 (dd, J=7.8, 1.3, 1H), 7.47-7.42 (m, 1H), 7.42-7.36 (m, 1H), 3.93 (m, 1H), 3.70-3.58 (m, 5H), 3.58-3.51 (m, 1H), 2.94 (m, 1H), 2.77 (m, 1H), 1.96-1.83 (m, 1H).

Intermediate CV

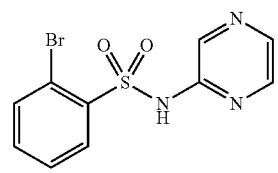

2-Bromo-N-pyrazin-2-ylbenzenesulfonamide

The title compound was prepared using analogous conditions to those described in Intermediate AU using 2-aminopyrazine. MS (ESI): mass calcd. for $C_{10}H_8BrN_3O_2S$ 312.95 m/z found 313.9 [M+H]$^+$; $^1$H NMR (600 MHz, DMSO-d$_6$) δ 11.94 (s, 1H), 8.34 (s, 1H), 8.25-8.16 (m, 2H), 8.11 (dd, J=2.7, 1.5, 1H), 7.81 (dd, J=7.9, 1.2, 1H), 7.68-7.59 (m, 1H), 7.59-7.51 (m, 1H).

Intermediate CW

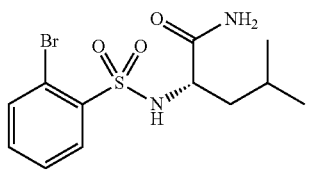

N~2~-[(2-Bromophenyl)sulfonyl]-L-leucinamide

The title compound was prepared using analogous conditions to those described in Intermediate AU using (S)-2-amino-4-methylpentanamide. MS (ESI): mass calcd. for $C_{12}H_{17}BrN_2O_3S$ 348.01 m/z found 349.0 [M+H]$^+$; $^1$H NMR (600 MHz, DMSO-$d_6$) δ 8.01 (dd, J=7.7, 1.8, 1H), 7.92 (d, J=8.3, 1H), 7.82 (dd, J=7.8, 1.3, 1H), 7.58-7.49 (m, 2H), 7.24 (d, J=2.3, 1H), 6.97 (d, J=2.2, 1H), 3.67-3.56 (m, 1H), 1.65-1.53 (m, 1H), 1.51-1.40 (m, 1H), 1.35-1.25 (m, 1H), 0.79 (d, J=6.6, 3H), 0.61 (d, J=6.5, 3H).

Intermediate CX

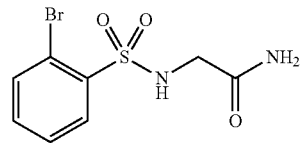

N~2~-[(2-Bromophenyl)sulfonyl]glycinamide

The title compound was prepared using analogous conditions to those described in Intermediate AU using 2-aminoacetamide. MS (ESI): mass calcd. for $C_8H_9BrN_2O_3S$ 291.95 m/z found 293.0 [M+H]$^+$; $^1$H NMR (600 MHz, DMSO-$d_6$) δ 8.00 (dd, J=7.7, 1.8, 1H), 7.88 (s, 1H), 7.84 (dd, J=7.8, 1.3, 1H), 7.59-7.54 (m, 1H), 7.54-7.50 (m, 1H), 7.27 (s, 1H), 7.13 (s, 1H), 3.51 (s, 2H).

Intermediate CY

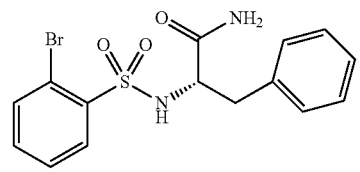

N-α-[(2-Bromophenyl)sulfonyl]-L-phenylalaninamide

The title compound was prepared using analogous conditions to those described in Intermediate AU using (S)-2-amino-3-phenylpropanamide. MS (ESI): mass calcd. for $C_{15}H_{15}BrN_2O_3S$ 382.00 m/z found 382.9 [M+H]$^+$; $^1$H NMR (600 MHz, DMSO-$d_6$) δ 7.95 (d, J=8.8, 1H), 7.71-7.65 (m, 2H), 7.44-7.35 (m, 2H), 7.20-7.12 (m, 5H), 7.06 (d, J=2.2, 1H), 3.93 (m, 1H), 2.91 (dd, J=13.7, 4.9, 1H), 2.77 (dd, J=13.7, 9.4, 1H).

Intermediate CZ

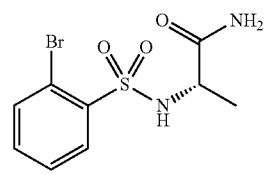

N~2~-[(2-Bromophenyl)sulfonyl]-L-alaninamide

The title compound was prepared using analogous conditions to those described in Intermediate AU using (S)-2-aminopropanamide. MS (ESI): mass calcd. for $C_9H_{11}BrN_2O_3S$ 305.97 m/z found 307.0 [M+H]$^+$; $^1$H NMR (600 MHz, DMSO-$d_6$) δ 8.01 (dd, J=7.7, 1.8, 1H), 7.86 (d, J=5.2, 1H), 7.84 (dd, J=7.7, 1.3, 1H), 7.60-7.55 (m, 1H), 7.55-7.50 (m, 1H), 7.24 (s, 1H), 7.07 (s, 1H), 3.78-3.69 (m, 1H), 1.17 (d, J=7.1, 3H).

Intermediate DA

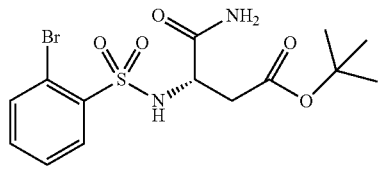

tert-Butyl N~2~-[(2-bromophenyl)sulfonyl]-L-alpha-asparaginate

The title compound was prepared using analogous conditions to those described in Intermediate AU using (S)-tert-butyl 3,4-diamino-4-oxobutanoate. MS (ESI): mass calcd. for $C_{14}H_{19}BrN_2O_5S$ 406.02 m/z found 429.0 [M+Na]$^+$; $^1$H NMR (600 MHz, DMSO-$d_6$) δ 8.04-7.99 (m, 2H), 7.80 (dd, J=7.7, 1.3, 1H), 7.58-7.53 (m, 1H), 7.53-7.49 (m, 1H), 7.24 (s, 1H), 7.16 (s, 1H), 4.00 (m, 1H), 2.56-2.51 (m, 1H), 2.45-2.39 (m, 1H), 1.32 (s, 9H).

Intermediate DB

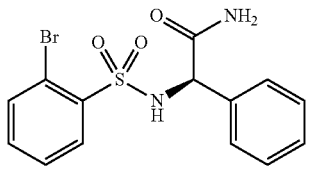

(2R)-2-{[(2-Bromophenyl)sulfonyl]amino}-2-phenylethanamide

The title compound was prepared using analogous conditions to those described in Intermediate AU using (R)-2-amino-2-phenylacetamide. MS (ESI): mass calcd. for $C_{14}H_{13}BrN_2O_3S$ 367.98 m/z found 369.0 [M+H]$^+$; $^1$H NMR (600 MHz, DMSO-$d_6$) δ 8.20 (d, J=8.8, 1H), 7.91-7.86 (m, 1H), 7.76-7.71 (m, 1H), 7.58 (d, J=2.0, 1H), 7.49-7.43 (m, 2H), 7.35-7.29 (m, 2H), 7.26-7.20 (m, 4H), 4.94 (d, J=8.8, 1H).

Intermediate DC

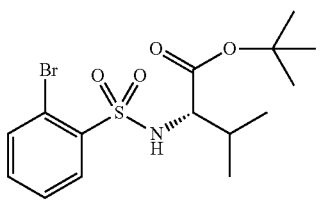

tert-Butyl-N-[(Bromophenyl)sulfonyl]-L-valinate

The title compound was prepared using analogous conditions to those described in Intermediate AU using (S)-tert-butyl-2-amino-3-methylbutanoate. $^1$H NMR (600 MHz, DMSO-d$_6$) δ 8.24 (d, J=9.6, 1H), 8.00 (dd, J=7.8, 1.7, 1H), 7.82 (dd, J=7.9, 1.3, 1H), 7.58-7.54 (m, 1H), 7.54-7.48 (m, 1H), 3.45 (dd, J=9.5, 7.1, 1H), 1.97 (h, J=6.8, 1H), 1.22 (s, 9H), 0.87 (d, J=6.7, 3H), 0.82 (d, J=6.8, 3H).

Intermediate DD

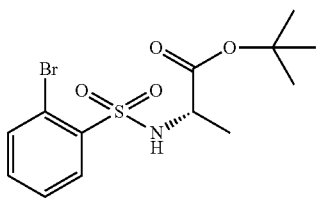

tert-Butyl-N-[(2-Bromophenyl)sulfonyl]-L-alaninate

The title compound was prepared using analogous conditions to those described in Intermediate AU using (S)-tert-butyl 2-aminopropanoate. MS (ESI): mass calcd. for C$_{13}$H$_{18}$BrNO$_4$S 363.01 m/z found 386.0 [M+Na]$^+$; $^1$H NMR (600 MHz, DMSO-d$_6$) δ 8.36 (d, J=8.6, 1H), 7.99 (dd, J=7.8, 1.8, 1H), 7.83 (dd, J=7.8, 1.3, 1H), 7.58-7.53 (m, 1H), 7.53-7.49 (m, 1H), 3.87-3.78 (m, 1H), 1.30-1.21 (m, 12H).

Intermediate DE

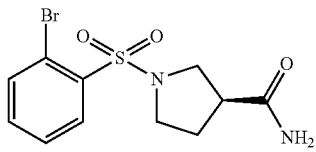

(S)-1-((2-Bromophenyl)sulfonyl)pyrrolidine-3-carboxamide

The title compound was prepared using analogous conditions to those described in Intermediate AU using (S)-pyrrolidine-3-carboxamide. MS (ESI): mass calcd. for C$_{11}$H$_{13}$BrN$_2$O$_3$S 331.98, m/z found 333.0 [M+H]+; $^1$H NMR (500 MHz, DMSO-d$_6$) δ 8.05-7.97 (dd, J=7.7, 1.9, 1H), 7.92-7.85 (dd, J=7.7, 1.5, 1H), 7.64-7.53 (m, 2H), 7.43 (s, 1H), 6.96 (s, 1H), 3.57-3.50 (dd, J=9.5, 8.0, 1H), 3.46-3.39 (m, 1H), 3.37-3.27 (m, 2H), 3.02-2.94 (p, J=7.8, 1H), 2.12-2.02 (m, 1H), 2.02-1.91 (m, 1H).

Intermediate DF

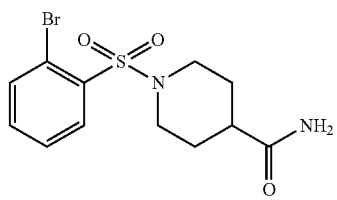

1-((2-Bromophenyl)sulfonyl)piperidine-4-carboxamide

The title compound was prepared using analogous conditions to those described in Intermediate AU using piperidine-4-carboxamide. MS (ESI): mass calcd. for C$_{12}$H$_{15}$BrN$_2$O$_3$S 346.00, m/z found 347.0 [M+H]$^+$; $^1$H NMR (600 MHz, DMSO-d$_6$) δ 8.03-7.97 (dd, J=7.8, 1.8, 1H), 7.91-7.86 (dd, J=7.8, 1.3, 1H), 7.63-7.53 (m, 2H), 7.28 (s, 1H), 6.82 (s, 1H), 3.72-3.62 (m, 2H), 2.83-2.73 (m, 2H), 2.27-2.17 (m, 1H), 1.79-1.70 (m, 2H), 1.57-1.44 (m, 2H).

Intermediate DG

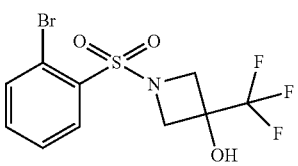

1-((2-Bromophenyl)sulfonyl)-3-(trifluoromethyl)azetidin-3-ol

The title compound was prepared using analogous conditions to those described in Intermediate AU using 3-(trifluoromethyl)azetidin-3-ol. MS (ESI): mass calcd. for C$_{10}$H$_9$BrF$_3$NO$_3$S 358.94; m/z found 359.9 [M+H]$^+$; $^1$H NMR (600 MHz, DMSO-d$_6$) δ 8.03-8.00 (m, 1H), 7.94-7.91 (dd, J=7.4, 1.7, 1H), 7.65-7.58 (m, 3H), 4.20-4.15 (m, 2H), 4.09-4.04 (m, 2H).

Intermediate DH

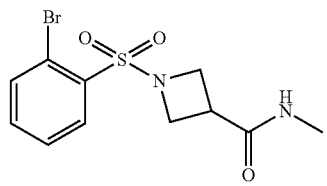

1-((2-Bromophenyl)sulfonyl)-N-methylazetidine-3-carboxamide

The title compound was prepared using analogous conditions to those described in Intermediate AU using N-methylazetidine-3-carboxamide. MS (ESI): mass calcd. for C$_{11}$H$_{13}$BrN$_2$O$_3$S 331.98; m/z found 333.0 [M+H]$^+$; $^1$H NMR (600 MHz, CDCl$_3$) δ 8.09-8.04 (dd, J=7.8, 1.8, 1H), 7.79-7.74 (dd, J=7.8, 1.3, 1H), 7.49-7.44 (m, 1H), 7.44-7.37 (m, 1H), 5.72 (s, 1H), 4.25-4.13 (m, 4H), 3.29-3.16 (m, 1H), 2.89-2.77 (d, J=4.8, 3H).

Intermediate DI

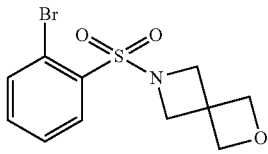

6-((2-Bromophenyl)sulfonyl)-2-oxa-6-azaspiro[3.3]heptane

The title compound was prepared using analogous conditions to those described in Intermediate AU using 2-oxa-6-azaspiro[3.3]heptane. MS (ESI): mass calcd. for $C_{11}H_{12}BrNO_3S$ 316.97; m/z found 317.9 [M+H]$^+$; $^1$H NMR (600 MHz, DMSO-d$_6$) δ 8.00-7.96 (m, 1H), 7.91-7.88 (m, 1H), 7.63-7.56 (m, 2H), 4.62 (s, 4H), 4.11 (s, 4H).

Intermediate DJ

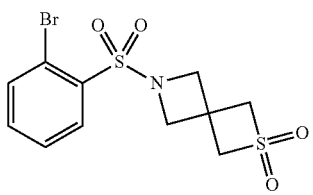

6-((2-Bromophenyl)sulfonyl)-2-thia-6-azaspiro[3.3]heptane 2,2-dioxide

The title compound was prepared using analogous conditions to those described in Intermediate AU using 2-thia-6-azaspiro[3.3]heptane 2,2-dioxide. MS (ESI): mass calcd. for $C_{11}H_{12}BrNO_4S_2$ 364.94; m/z found 365.9 [M+H]$^+$; $^1$H NMR (600 MHz, DMSO-d$_6$) δ 8.02-7.98 (m, 1H), 7.93-7.89 (m, 1H), 7.64-7.58 (m, 2H), 4.46 (s, 4H), 4.17 (s, 4H).

Intermediate DL

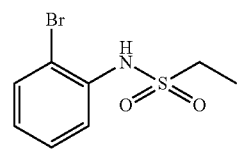

N-(2-Bromophenyl)ethanesulfonamide

To a solution of 2-bromoaniline (344 mg, 2.0 mmol) in pyridine (5 mL) was slowly added ethyl-sulfonyl chloride (257 mg, 2.0 mmol) at rt and the mixture was stirred at rt for 16 hours. The pyridine was removed under reduced pressure and resulting residue diluted with water (30 mL) and extracted with DCM (10 mL×2). The combined organic extracts were washed with brine, dried over Na$_2$SO$_4$, filtered and concentrated to dryness. The residue was purified by FCC to give the title compound (240 mg, 45%). MS (ESI): mass calcd. for $C_8H_{10}BrNO_2S$ 262.96 m/z found 264.1 [M+H]$^+$. $^1$H NMR (300 MHz, CDCl$_3$) 7.71 (dd, J=4.8, 1.5, 1H), 7.59 (dd, J=4.8, 1.5, 1H), 7.32-7.28 (m, 1H), 7.08-7.05 (m, 1H), 6.77 (bs, 1H), 3.14 (q, J=7.2, 2H), 1.41 (t, J=7.5, 3H).

Intermediate DM

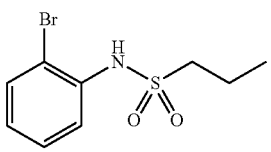

N-(2-bromophenyl)propane-1-sulfonamide

The title compound was prepared using analogous conditions described for Intermediate DL utilizing n-propylsulfonyl chloride. MS (ESI): mass calcd. for $C_9H_{12}BrNO_2S$, 276.98; m/z found, 278.1 [M+H]$^+$. $^1$H NMR (300 MHz, CDCl$_3$) δ 7.70 (dd, J=4.8, 1.5, 1H), 7.59 (dd, J=4.8, 1.5, 1H), 7.32-7.28 (m, 1H), 7.08-7.05 (m, 1H), 6.72 (br s, 1H), 3.15-2.94 (m, 2H), 1.93-1.73 (m, 2H), 1.00 (t, J=7.4, 3H).

Intermediate DN

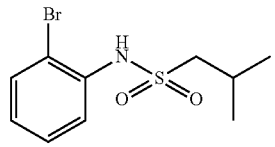

N-(2-Bromophenyl)-2-methylpropane-1-sulfonamide

The title compound was prepared using analogous conditions described for Intermediate DL utilizing iso-butylsulfonyl chloride. MS (ESI): mass calcd. for $C_{10}H_{14}BrNO_2S$, 290.99; m/z found, 292.1 [M+H]$^+$. $^1$H NMR (300 MHz, CDCl$_3$) δ 7.69 (dd, J=4.8, 1.5, 1H), 7.59 (dd, J=4.8, 1.5, 1H), 7.32-7.28 (m, 1H), 7.08-7.05 (m, 1H), 6.77 (br s, 1H), 2.99 (d, J=4.2, 2H), 2.38-2.25 (m, 1H), 1.07 (d, J=6.9, 6H).

Intermediate DO

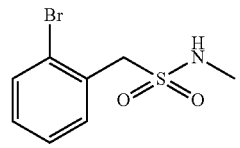

1-(2-Bromophenyl)-N-methylmethanesulfonamide

Step A: Sodium (2-bromophenyl)methanesulfonate

A mixture of 1-bromo-2-(bromomethyl)benzene (20 g, 0.08 mol) and Na$_2$SO$_3$ (15 g, 0.12 mol) in methanol/H$_2$O (100 mL/100 mL) was stirred at 85° Celsius for 2.5 hours, concentrated to dryness and dried to give sodium (2-bromophenyl)methanesulfonate (34 g, crude). $^1$H NMR (300 MHz, DMSO-d$_6$) δ 7.54 (m, 2H), 7.27 (m, 1H), 7.12 (m, 1H), 3.91 (s, 2H).

Step B: (2-Bromophenyl)methanesulfonyl chloride

To a suspension of crude sodium (2-bromophenyl)methanesulfonate (34 g) in toluene (500 mL) was added PCl$_5$ (34 g, 0.16 mol). The resulting mixture was stirred at 100° Celsius for 4 hours before concentrating to dryness and pouring the residue onto crushed ice (150 g), stirring for 5 min, and extracting with DCM (3×50 mL). The combined organic extracts were dried over MgSO$_4$, filtered and concentrated to dryness to give (2-bromophenyl)methanesulfonyl chloride (16.8 g, 77%). $^1$H NMR (300 MHz, DMSO-d$_6$) δ 7.62-7.45 (m, 2H), 7.29 (m, 1H), 7.18-7.01 (m, 1H), 3.97 (s, 2H).

Step C

To a solution of (2-bromophenyl)methanesulfonyl chloride (2 g, 7 mmol) in THF (15 mL) was added CH$_3$NH$_2$/H$_2$O (25%, 2 g, 20 mmol) at 0° Celsius. The resulting mixture was warmed up to rt, stirred for 16 hours, concentrated to dryness and purified by HPLC to give the title compound (0.8 g, 41%). MS (ESI): mass calcd. for C$_8$H$_8$BrO$_2$S, 262.96; m/z found, 264.0 [M+H]$^+$; $^1$H NMR (300 MHz, CDCl$_3$) δ 7.65-7.54 (m, 2H), 7.35 (m, 1H), 7.22 (dd, J=7.6, 1.7, 1H), 4.53 (s, 2H), 4.10 (s, 1H), 2.72 (s, 3H).

Intermediate DP

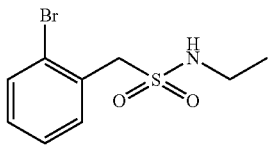

1-(2-Bromophenyl)-N-ethylmethanesulfonamide

The title compound was prepared using analogous conditions described for Intermediate DO utilizing ethylamine. MS (ESI): mass calcd. for C$_9$H$_{12}$BrNO$_2$S, 276.98; m/z found, 277.9 [M+H]$^+$; $^1$H NMR (300 MHz, CD$_3$OD) δ 7.64 (dd, J=8.0, 1.0, 1H), 7.57 (dd, J=7.6, 1.6, 1H), 7.37 (m, 1H), 7.25 (m, 1H), 4.54 (s, 2H), 3.03 (q, J=7.2, 2H), 1.12 (t, J=7.2, 3H).

Intermediate DQ

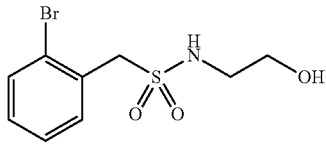

1-(2-Bromophenyl)-N-(2-hydroxyethyl)methanesulfonamide

The title compound was prepared using analogous conditions described for Intermediate DO utilizing ethanolamine. MS (ESI): mass calcd. for C$_9$H$_{12}$BrNO$_3$S, 292.97; m/z found, 294.0 [M+H]$^+$; $^1$H NMR (300 MHz, CDCl$_3$) δ 7.69-7.52 (m, 2H), 7.35 (m, 1H), 7.26-7.19 (m, 1H), 4.77 (t, J=6, 1H), 4.56 (s, 2H), 3.65 (t, J=6, 2H), 3.12 (t, J=6, 2H), 2.13 (br s, 1H).

Intermediate DR

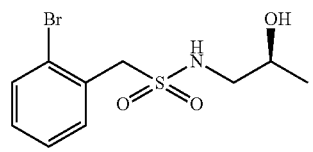

(S)-1-(2-Bromophenyl)-N-(2-hydroxypropyl)methanesulfonamide

The title compound was prepared using analogous conditions described for Intermediate DO utilizing (S)-3-amino-2-propanol. The product was isolated as a x. MS (ESI): mass calcd. for C$_7$H$_4$BrF$_3$O$_2$S, 306.99; m/z found, 307.9 [M+H]$^+$. $^1$H NMR (300 MHz, CDCl$_3$) δ 7.69-7.52 (m, 2H), 7.35 (m, 1H), 7.29-7.20 (m, 1H), 4.67 (s, 1H), 3.96-3.76 (m, 1H), 3.17-2.96 (m, 1H), 2.95-2.74 (m, 1H), 1.90-1.63 (m, 2H), 1.15 (d, J=6.3, 3H).

Intermediate DS

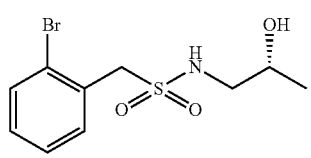

(R)-1-(2-Bromophenyl)-N-(2-hydroxypropyl)methanesulfonamide

The title compound was prepared using analogous conditions described for Intermediate DO utilizing (R)-3-amino-2-propanol.

Intermediate DT

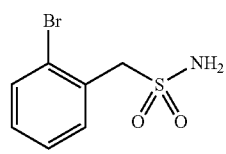

(2-Bromophenyl)methanesulfonamide

The title compound was prepared using analogous conditions described for Intermediate DO using ammonia. $^1$H NMR (300 MHz, DMSO-d$_6$) δ 7.65 (d, J=7.9, 1H), 7.52 (dd, J=7.6, 1.6, 1H), 7.41 (m, 1H), 7.28 (m, 1H), 7.04 (s, 2H), 4.46 (s, 2H).

Intermediate DU

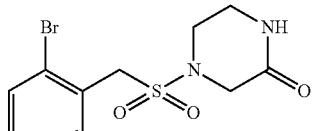

4-((2-Bromobenzyl)sulfonyl)piperazin-2-one

The title compound was prepared using analogous conditions described for Intermediate DO utilizing piperazin-2-one. The product was isolated as a white solid. MS (ESI): mass calcd. for $C_{11}H_{13}BrN_2O_3S$, 331.98; m/z found, 333.0 [M+H]+; $^1$H NMR (300 MHz, CDCl$_3$) δ 7.68-7.57 (m, 2H), 7.37 (m, 1H), 7.29-7.21 (m, 1H), 6.93 (s, 1H), 4.55 (s, 2H), 3.90 (s, J=18.1, 2H), 3.43-3.17 (m, 4H).

Intermediate DV

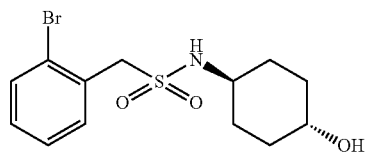

(1,4)-trans-1-(2-Bromophenyl)-N-(1R-4-hydroxycyclohexyl)
methanesulfonamide

The title compound was prepared using analogous conditions described for Intermediate DO utilizing trans-4-aminocyclohexanol. The product was isolated as a white solid. MS (ESI): mass calcd. for $C_7H_4BrF_3O_2S$, 347.02; m/z found, 348.0 [M+H]+. $^1$H NMR (300 MHz, CD$_3$OD) δ 7.70-7.56 (m, 2H), 7.37 (m, 1H), 7.26 (m, 1H), 4.55 (s, 2H), 3.54-3.42 (m, 1H), 3.10-2.93 (m, 1H), 2.05-1.82 (m, 4H), 1.40-1.16 (m, 4H).

Intermediate DW

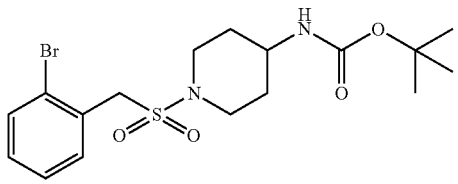

tert-Butyl (1-((2-bromobenzyl)sulfonyl)piperidin-4-yl)carbamate

The title compound was prepared using analogous conditions described for Intermediate DO utilizing tert-butyl piperazine-1-carboxylate. The product was isolated as a white solid. MS (ESI): mass calcd. for $C_{17}H_{25}BrN_2O_4S$, 432.07; m/z found, 454.9 [M+Na]+. $^1$H NMR (300 MHz, DMSO-d$_6$) δ 7.67 (dd, J=7.9, 1.2, 1H), 7.52 (dd, J=7.7, 1.7, 1H), 7.41 (m, 1H), 7.36-7.26 (m, 1H), 6.92 (d, J=7.8, 1H), 4.51 (s, 2H), 3.50 (d, J=12.2, 2H), 3.45-3.35 (m, 1H), 2.92 (t, J=11.3, 2H), 1.77 (d, J=12.5, 2H), 1.45-1.30 (m, 11H).

Intermediate DX

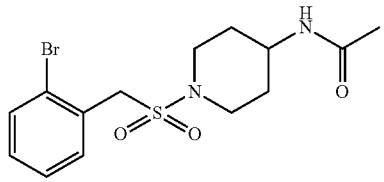

N-(1-((2-Bromobenzyl)sulfonyl)piperidin-4-yl)
acetamide

Step A:
1-(2-Bromobenzylsulfonyl)piperidin-4-amine.HCl

A mixture of tert-butyl (1-((2-bromobenzyl)sulfonyl)piperidin-4-yl)carbamate (500 mg, 1.15 mmol) in HCl methanol (6 N, 20 mL) was stirred at rt for 24 hours, and then concentrated to dryness to give 1-(2-bromobenzylsulfonyl)piperidin-4-amine.HCl (400 mg, 94%), which was directly used for next step without any further purification. MS (ESI): mass calcd. for $C_{14}H_{19}BrN_2O_3S$, 332.02; m/z found, 332.9 [M+H]+.

Step B

To a mixture of 1-(2-bromobenzylsulfonyl)piperidin-4-amine.HCl (200 mg, 0.54 mmol) and Et$_3$N (164 mg, 1.62 mmol) in dry DCM (20 mL) was added acetyl chloride (85 mg, 1.1 mmol) drop-wise at rt. The reaction mixture was stirred at rt for 2 hours before concentrating to dryness and purifying the residue by HPLC to give the title compound (180 mg, 89%). MS (ESI): mass calcd. for $C_{14}H_{19}BrN_2O_3S$, 374.03; m/z found, 374.8 [M+H]+.

Intermediate DY

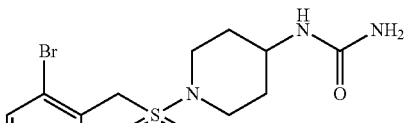

1-(1-((2-Bromobenzyl)sulfonyl)piperidin-4-yl)
urea

To a mixture of 1-(2-bromobenzylsulfonyl)piperidin-4-amine.HCl (200 mg, 0.54 mmol) and Et$_3$N (164 mg, 1.62 mmol) in dry THF (20 mL) was added (COCl$_2$)$_3$ (160 mg, 0.54 mmol) at rt. The reaction mixture was stirred at rt for 1 hour, and then a solution of NH$_3$ in THF (4 N, 10 mL) was added drop-wise. The resulting mixture was stirred at rt for 5 hours, concentrated to dryness and purified by HPLC to give the title compound (140 mg, 69%). MS (ESI): mass calcd. for $C_{13}H_{18}BrN_3O_3S$, 375.03; m/z found, 376.0 [M+H]+.

Intermediate DZ

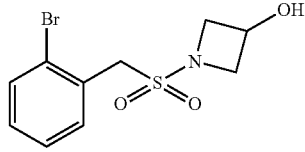

1-((2-Bromobenzyl)sulfonyl)azetidin-3-ol

The title compound was prepared using analogous conditions described for Intermediate DO utilizing 3-hydroxyazetidine. The product was isolated as a white solid. MS (ESI): mass calcd. for $C_7H_4BrF_3O_2S$, 304.97; m/z found 306.0 [M+H]+; $^1$H NMR (300 MHz, CDCl$_3$) δ 7.59 (dd, J=17.3, 7.8, 2H), 7.33 (m, 1H), 7.24-7.17 (m, 1H), 4.61-4.37 (m, 3H), 4.04-3.90 (m, 2H), 3.87-3.75 (m, 2H), 2.13 (br s, 1H).

Intermediate EA

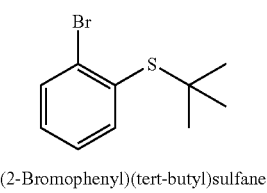

(2-Bromophenyl)(tert-butyl)sulfane

To a 50 mL round-bottomed flask were added a stirbar, water (3.5 mL) and H$_2$SO$_4$ (5.0 mL, 18 M). The flask was then cooled to approximately −10° Celsius and treated with t-BuOH (0.70 mL, 7.5 mmol) followed by 2-bromo-thiophenol (0.60 mL, 5.0 mmol) (drop-wise over three minutes). The resulting mixture was stirred for 24 hours with gradual warming to rt. The reaction mixture was then added to a separatory funnel containing Et$_2$O and sat. NaHCO$_3$. The layers were mixed thoroughly and then separated. The organic layer was washed with 1 N NaOH, dried over MgSO$_4$, filtered and concentrated to dryness. The resulting residue was subjected to FCC gave the title compound (686 mg, 56%). $^1$H NMR (500 MHz, DMSO-d$_6$) δ 7.75 (dd, J=7.8, 1.4, 1H), 7.68 (dd, J=7.6, 1.6, 1H), 7.43-7.37 (m, 1H), 7.36-7.29 (m, 1H), 1.28 (s, 9H).

Intermediate EB

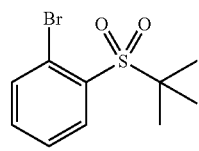

1-Bromo-2-(tert-butylsulfonyl)benzene

To a 20 mL vial containing 411 mg (1.43 mmol) 2-bromophenyl)(tert-butyl)sulfane were added DCM (6.0 mL) and a stirbar. The vial was cooled to 0° Celsius and then charged with m-CPBA (77%, 922 mg, 4.43 mmol). The resultant mixture was stirred for 22 hours with gradual warming to rt. The mixture was diluted with EtOAc, washed with aq Na$_2$S$_2$O$_3$ followed by 1 N NaOH, dried over MgSO$_4$, filtered and concentrated to dryness. The residue was subjected to FCC to give the title compound (304 mg, 77%). $^1$H NMR (500 MHz, CDCl$_3$) δ 8.09-8.02 (dd, J=7.9, 1.8, 1H), 7.79-7.74 (dd, J=7.9, 1.3, 1H), 7.50-7.45 (m, 1H), 7.45-7.39 (m, 1H), 1.42-1.37 (s, 9H).

Intermediate EC

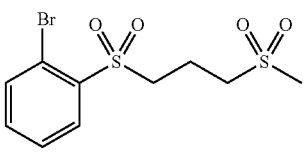

1-Bromo-2-((3-(methylsulfonyl)propyl)sulfonyl)benzene

Step A:
(2-Bromophenyl)(3-(methylthio)propyl)sulfane

To a solution of 1-bromo-3-chloropropane (1.2 mL, 12.0 mmol), DIPEA (2.1 mL, 12.0 mmol) in DCM (50 mL) was added 2-bromobenzenethiol (1.08 mL, 6.0 mmol) at 5° Celsius. The reaction mixture was warmed to rt and stirred for 4 hours. The reaction mixture was concentrated to dryness and the residue dissolved in ethanol (50 mL) and treated with NaSCH$_3$ (1.26 g, 18.0 mmol). The resulting mixture was stirred at rt for 18 h. The ethanol was then removed under reduced pressure and the residue taken up in DCM (100 mL) and washed with water (3×20 mL). The organic phase was dried over Na$_2$SO$_4$, filtered and concentrated to dryness to give (2-bromophenyl)(3-(methylthio)propyl)sulfane (2.3 g, crude).

Step B

The procedure to make 1-bromo-2-(3-(methylsulfonyl)propylsulfonyl)benzene is analogous to the one used to make Intermediate EB utilizing (2-bromophenyl)(3-(methylthio)propyl)sulfane. MS (ESI): mass calcd. for C$_{10}$H$_{13}$BrO$_4$S$_2$, 339.94; m/z found, 340.9 [M+H]$^+$; $^1$H NMR (300 MHz, CDCl$_3$) δ 8.19-8.12 (m, 1H), 7.83-7.75 (m, 1H), 7.59-7.46 (m, 2H), 3.65 (t, J=7.1, 2H), 3.34-3.23 (m, 2H), 2.94 (s, 3H), 2.43-2.30 (m, 2H).

Intermediate ED

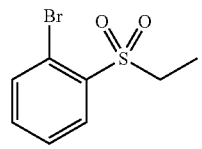

1-Bromo-2-(ethylsulfonyl)benzene

To a suspension of NaH (135 mg, 3.40 mmol, 60% in mineral oil) in anhydrous DMF (5 mL) was added 2-bromobenzenethiol (580 mg, 3.10 mmol) drop-wise at rt. After the resultant mixture was stirred at 20° Celsius for 10 min, bromoethane (670 mg, 6.10 mmol) was slowly added into the mixture. The reaction mixture was stirred at 30° Celsius for 14 hours in an oil bath. The reaction was diluted with water (60 mL) and extracted with petroleum ether (20 mL×2). The combined organic extracts were washed with brine, dried over Na$_2$SO$_4$, filtered, and concentrated to dryness. The residue was dissolved in a mixture of methanol (10 mL) and water (15 mL) then treated with oxone (10 g, 15 mmol) portion-wise. The reaction mixture was stirred at 80° Celsius for 16 hours. The mixture was cooled to rt and the methanol removed. The remaining aqueous mixture was further diluted with water (50 mL) and extracted with DCM (20 mL×2). The combined organic extracts were washed with brine, dried over Na$_2$SO$_4$, filtered, concentrated to dryness and purified by FCC to give the title compound (570 mg, 75%). $^1$H NMR (300 MHz, CDCl$_3$) δ 8.18-8.12 (m, 1H), 7.76 (dd, J=7.8, 1.5, 1H), 7.52-7.43 (m, 2H), 3.46 (q, J=7.5, 2H), 1.26 (t, J=7.5, 3H).

Intermediate EE

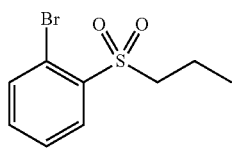

1-Bromo-2-(propylsulfonyl)benzene

The title compound was prepared using analogous conditions described for Intermediate ED utilizing 1-bromopropane. MS (ESI): mass calcd. for $C_9H_{11}BrO_2S$, 261.97; m/z found, 263.1 [M+H]$^+$. $^1$H NMR (300 MHz, CDCl$_3$) δ 8.15 (dd, J=7.8, 2.1, 1H), 7.78-7.74 (m, 1H), 7.54-7.42 (m, 2H), 3.45-3.37 (m, 2H), 1.80-1.67 (m, 2H), 1.02 (t, J=7.5, 3H).

Intermediate EF

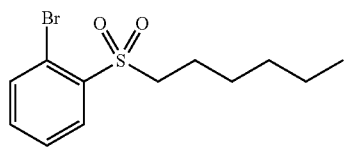

1-Bromo-2-(hexylsulfonyl)benzene

The title compound was prepared using analogous conditions described for Intermediate ED utilizing 1-bromohexane. MS (ESI): mass calcd. for $C_{12}H_{17}BrO_2S$, 304.01; m/z found, 305.1 [M+H]$^+$. $^1$H NMR (300 MHz, CDCl$_3$) δ 8.20-8.12 (m, 1H), 7.82-7.73 (m, 1H), 7.58-7.44 (m, 2H), 3.49-3.38 (m, 2H), 1.77-1.63 (m, 2H), 1.43-1.24 (m, 6H), 0.86 (t, J=6.6, 3H).

Intermediate EG

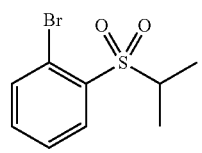

1-Bromo-2-(isopropylsulfonyl)benzene

The title compound was prepared using analogous conditions described for Intermediate ED utilizing isopropyl bromide. MS (ESI): mass calcd. for $C_9H_{11}BrO_2S$, 261.97; m/z found, 263.1 [M+H]$^+$. $^1$H NMR (300 MHz, CDCl$_3$) δ 8.14-8.10 (m, 1H), 7.77-7.72 (m, 1H), 7.50-7.43 (m, 2H), 3.93-3.83 (m, 1H), 1.30 (d, J=6.9, 6H).

Intermediate EH

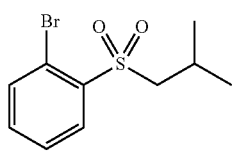

1-Bromo-2-(isobutylsulfonyl)benzene

The title compound was prepared using analogous conditions described for Intermediate ED utilizing isobutyl bromide. MS (ESI): mass calcd. for $C_{10}H_{13}BrO_2S$, 275.98; m/z found, 277.1 [M+H]$^+$. $^1$H NMR (300 MHz, CDCl$_3$) δ 8.19-8.14 (m, 1H), 7.78-7.73 (m, 1H), 7.55-7.42 (m, 2H), 3.34 (d, J=6.6, 2H), 2.30-2.19 (m, 1H), 1.07 (d, J=6.6, 6H).

Intermediate EI

1-Bromo-2-(cyclopropylsulfonyl)benzene

The title compound was prepared using analogous conditions described for Intermediate ED utilizing bromocyclopropane. MS (ESI): mass calcd. for $C_9H_9BrO_2S$, 259.95; m/z found, 261.1 [M+H]$^+$. $^1$H NMR (300 MHz, CDCl$_3$) δ 8.11-8.04 (m, 1H), 7.76 (dd, J=7.8, 1.5, 1H), 7.52-7.43 (m, 2H), 3.22-3.14 (m, 1H), 1.36-1.31 (m, 2H), 1.08-1.03 (m, 2H).

Intermediate EJ

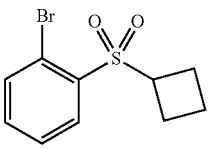

1-Bromo-2-(cyclobutylsulfonyl)benzene

The title compound was prepared using analogous conditions described for Intermediate ED utilizing bromocyclobutane. MS (ESI): mass calcd. for $C_{10}H_{11}BrO_2S$, 273.97; m/z found, 275.1 [M+H]$^+$. $^1$H NMR (300 MHz, CDCl$_3$) δ 8.13 (dd, J=7.8, 2.1, 1H), 7.73 (dd, J=7.8, 1.5, 1H), 7.53-7.38 (m, 2H), 4.46 (p, J=8.1, 1H), 2.65-2.46 (m, 2H), 2.25-2.12 (m, 2H), 2.08-1.98 (m, 2H).

Intermediate EK

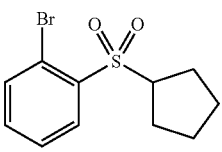

1-Bromo-2-(cyclopentylsulfonyl)benzene

The title compound was prepared using analogous conditions described for Intermediate ED utilizing bromocyclopentane. MS (ESI): mass calcd. for $C_{11}H_{13}BrO_2S$, 287.98; m/z found, 289.1 [M+H]$^+$. $^1$H NMR (300 MHz, CDCl$_3$) δ 8.20-8.10 (m, 1H), 7.80-7.72 (m, 1H), 7.58-7.39 (m, 2H), 4.27-4.12 (m, 1H), 2.12-1.97 (m, 2H), 1.93-1.75 (m, 4H), 1.70-1.57 (m, 2H).

Intermediate EL

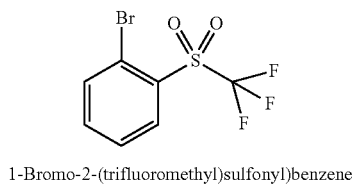 [SMILES: O=S(=O)(c1ccccc1Br)C(F)(F)F]

1-Bromo-2-(trifluoromethyl)sulfonyl)benzene

The title compound was prepared using analogous conditions described for Intermediate ED utilizing trifluoroiodomethane. MS (ESI): mass calcd. for $C_7H_4BrF_3O_2S$, 287.91; m/z found, 289.1 [M+H]$^+$. $^1$H NMR (300 MHz, CDCl$_3$) δ 8.15-8.07 (m, 1H), 7.80-7.72 (m, 1H), 7.52-7.43 (m, 2H).

Intermediate EM

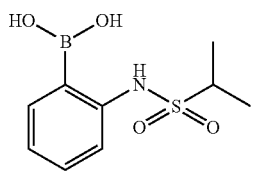

(2-(1-Methylethylsulfonamido)phenyl)boronic acid

To a solution of 2-aminophenylboronic acid hydrochloride (347 mg, 2.0 mmol) in pyridine (5 mL) was slowly added chlorosulfonylisopropane (300 mg, 2.1 mmol). The mixture was stirred below 20° Celsius for 14 hours, concentrated to dryness and the residue purified by FCC to give the title compound (280 mg, 57% yield). $^1$H NMR (300 MHz, D$_2$O+DMSO-d$_6$) δ 8.57-8.55 (m, 1H), 7.82-7.79 (m, 1H), 7.49-7.46 (m, 1H), 7.40-7.37 (m, 2H), 7.08-7.05 (m, 1H), 3.31-3.27 (m, 1H), 1.26 (d, J=6.9, 6H).

Intermediate EN

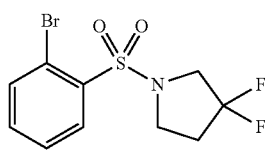

1-((2-bromophenyl)sulfonyl)-3,3-difluoropyrrolidine

A solution of 2-bromobenzene-1-sulfonyl chloride (0.300 g, 1.17 mmol) and 3,3-difluoropyrrolidine hydrochloride (0.169 g, 1.17 mmol) in pyridine (5 mL) was stirred for 16 hours at 60° Celsius. The reaction was then cooled to rt, diluted with EtOAc (25 mL), washed with 1 N HCl (2×25 mL), and brine (50 mL). The organic layer was isolated, dried over MgSO$_4$, filtered and concentrated to dryness to yield the title compound (0.335 g, 86%), The product was used without further purification. $^1$H NMR (500 MHz, CDCl$_3$) δ 8.13-8.09 (m, 1H), 7.80-7.76 (m, 1H), 7.50-7.41 (m, 2H), 3.74 (t, J=12.8, 2H), 3.67 (t, J=7.2, 2H), 2.44-2.35 (m, 2H).

Intermediate EO

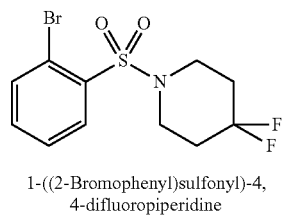 [SMILES: O=S(=O)(c1ccccc1Br)N1CCC(F)(F)CC1]

1-((2-Bromophenyl)sulfonyl)-4,4-difluoropiperidine

The title compound was prepared in a manner similar to that described in Intermediate EN using 4,4-difluoropiperidine. $^1$H NMR (500 MHz, CDCl$_3$) δ 8.13-8.11 (m, 1H), 7.78-7.75 (m, 1H), 7.50-7.45 (m, 1H), 7.44-7.39 (m, 1H), 3.53-3.44 (m, 4H), 2.12-2.03 (m, 4H).

Intermediate EP

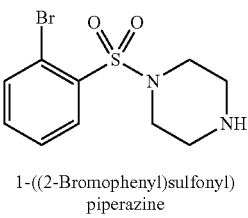 [SMILES: O=S(=O)(c1ccccc1Br)N1CCNCC1]

1-((2-Bromophenyl)sulfonyl) piperazine

The title compound was prepared in a manner similar to that described in Intermediate EN using piperazine.

Intermediate EQ

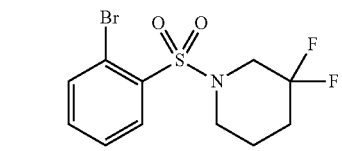

1-((2-Bromophenyl)sulfonyl)-3,3-difluoropiperidine

The title compound was prepared in a manner similar to that described in Intermediate EN using 3,3-difluoropiperidine. $^1$H NMR (500 MHz, CDCl$_3$) δ 8.14-8.11 (m, 1H), 7.77-7.74 (m, 1H), 7.49-7.44 (m, 1H), 7.44-7.39 (m, 1H), 3.54 (t, J=11.2, 2H), 3.32 (t, J=5.5, 2H), 2.04-1.94 (m, 2H), 1.91-1.85 (m, 2H).

Intermediate ER

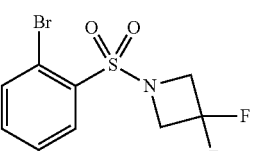

1-((2-Bromophenyl)sulfonyl)-3,3-difluoroazetidine

The title compound was prepared in a manner similar to that described in Intermediate EN using 3,3-difluoroazetidine. $^1$H NMR (500 MHz, CDCl$_3$) 8.11-8.06 (m, 1H), 7.80-7.76 (m, 1H), 7.50-7.42 (m, 2H), 4.42 (t, J=12.1, 4H).

Intermediate ES

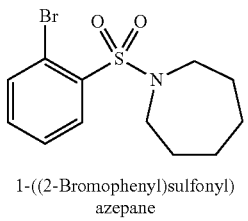 [SMILES: O=S(=O)(c1ccccc1Br)N1CCCCCC1]

1-((2-Bromophenyl)sulfonyl) azepane

The title compound was prepared in a manner similar to that described in Intermediate EN using azepane.

Intermediate ET

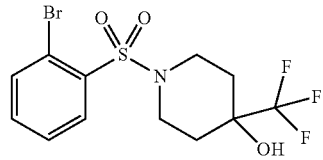

1-((2-Bromophenyl)sulfonyl)-4-trifluoromethyl) piperidin-4-ol

The title compound was prepared in a manner similar to that described in Intermediate EN using 4-(trifluoromethyl) piperidin-4-ol.

Intermediate EU

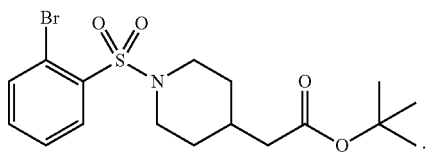

tert-Butyl (1-((2-bromophenyl)sulfonyl)piperidin-4-yl) carbamate

A solution of 2-bromobenzene-1-sulfonyl chloride (50 mg, 0.20 mmol), tert-butyl piperidin-4-ylcarbamate (49 mg, 0.25 mmol), and diisopropylethyl amine (0.101 mL, 0.59 mmol) in CH$_2$Cl$_2$ was stirred for 90 min at rt. The reaction mixture was then concentrated to dryness to give the title compound in quantitative yield. The product was used without further purification.

Intermediate EV

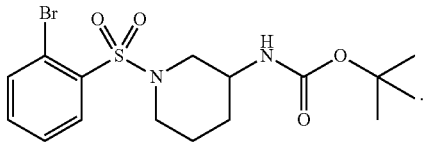

racemic tert-butyl (1-((2-Bromophenyl)sulfonyl)piperidin-3-yl) carbamate

The title compound was prepared in a manner similar to that described in Intermediate EU using racemic tert-butyl piperidin-3-ylcarbamate. $^1$H NMR (400 MHz, CDCl$_3$) δ 8.12-8.09 (m, 1H), 7.77-7.74 (m, 1H), 7.48-7.38 (m, 2H), 4.91 (d, J=8.0, 1H), 3.79 (s, 1H), 3.45 (s, 1H), 3.32 (d, J=12.4, 1H), 3.23-3.07 (m, 2H), 1.86-1.59 (m, 4H), 1.45 (s, 9H).

Intermediate EW

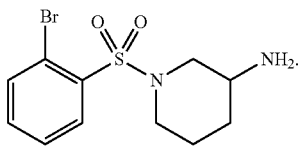

racemic-1-((2-Bromophenyl)sulfonyl) piperidin-3-amine hydrochloride salt

A solution of racemic tert-butyl (1-((2-bromophenyl)sulfonyl)piperidin-3-yl)carbamate (82 mg, 0.20 mmol) in CH$_2$Cl$_2$ (5 mL) was treated with 2 N HCl/Et$_2$O (1 mL, 2 mmol) and stirred 16 hours at rt. The reaction mixture was then concentrated to dryness to give the title compound in quantitative yield. The product was used without further purification.

Intermediate EX

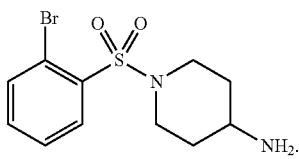

1-((2-Bromophenyl)sulfonyl)piperidin-4-amine hydrochloride

The title compound was prepared in a manner similar to that described in Intermediate EW using tert-butyl (1-((2-bromophenyl)sulfonyl)piperidin-4-yl)carbamate.

Intermediate EY

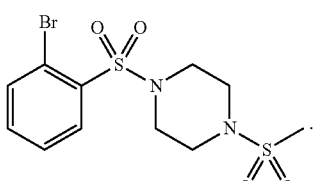

1-((2-Bromophenyl)sulfonyl)-4-(methylsulfonyl)piperazine

The title compound was prepared in a manner similar to that described in Intermediate EU using 1-(methylsulfonyl)piperazine.

Intermediate EZ

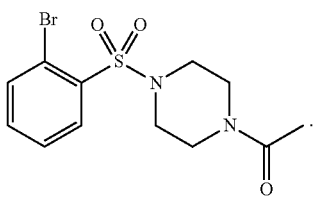

1-(4-((2-Bromophenyl)sulfonyl)piperazin-1-yl)ethanone

The title compound was prepared in a manner similar to that described in Intermediate EU using 1-(piperazin-1-yl)ethanone.

Intermediate FA

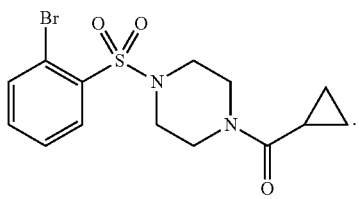

(4-((2-Bromophenyl)sulfonyl)piperazin-1-yl)(cyclopropyl)methanone

The title compound was prepared in a manner similar to that described in Intermediate EU using cyclopropyl(piperazin-1-yl)methanone.

Intermediate FB

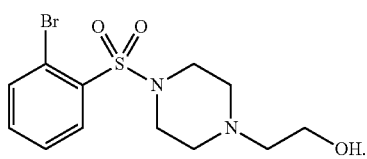

2-(4-((2-Bromophenyl)sulfonyl)piperazin-1-yl)ethanol

The title compound was prepared in a manner similar to that described in Intermediate EU using 2-(piperazin-1-yl)ethanol.

Intermediate FC

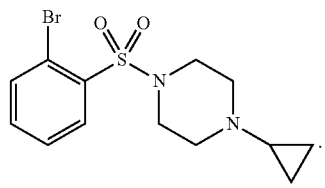

1-((2-Bromophenyl)sulfonyl)-4-cyclopropylpiperazine

The title compound was prepared in a manner similar to that described in Intermediate EU using 1-cyclopropylpiperazine.

Intermediate FD

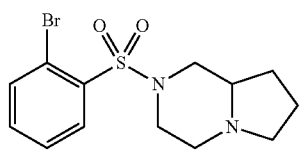

Racemic-2-((2-Bromophenyl)sulfonyl)octahydropyrrolo[1,2-a]pyrazine

The title compound was prepared in a manner similar to that described in Intermediate EU using racemic-octahydropyrrolo[1,2-a]pyrazine.

Intermediate FE

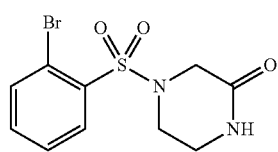

4-((2-Bromophenyl)sulfonyl)piperazin-2-one

The title compound was prepared in a manner similar to that described in Intermediate EU using piperazin-2-one.

Intermediate FF

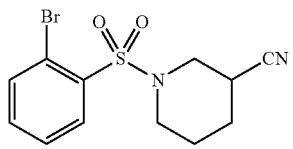

Racemic-1-((2-bromophenyl)sulfonyl)piperidine-3-carbonitrile.

The title compound was prepared in a manner similar to that described in Intermediate EU using racemic-piperidine-3-carbonitrile.

Intermediate FG

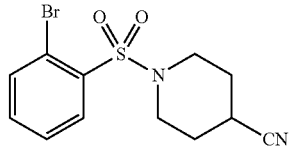

1-((2-Bromophenyl)sulfonyl)piperidine-4-carbonitrile.

The title compound was prepared in a manner similar to that described in Intermediate EU using piperidine-4-carbonitrile.

Intermediate FH

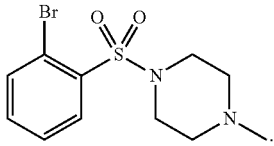

1-((2-Bromophenyl)sulfonyl)-4-methylpiperazine.

The title compound was prepared in a manner similar to that described in Intermediate EU using 1-methylpiperazine.

Intermediate FI

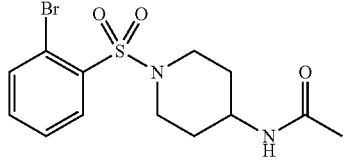

N-(1-((2-Bromophenyl)sulfonyl)piperidin-4-yl)acetamide.

A solution of 2-bromobenzene-1-sulfonyl chloride (0.500 g, 1.96 mmol), 4-acetamidopiperidine (0.335 g, 2.45 mmol), and diisopropylethyl amine (1.0 mL, 5.8 mmol) in $CH_2Cl_2$ (5 mL) was stirred for 15 min at rt. The reaction mixture was then washed with 1 N HCl (2×5 mL) followed by brine (10 mL). The organic layer was isolated, dried over $MgSO_4$, filtered, and concentrated to dryness to give the title compound (0.672 g, 95%). The product was used without further purification. $^1$H NMR (400 MHz, $CDCl_3$) δ 8.09-8.05 (m, 1H), 7.77-7.74 (m, 1H), 7.49-7.38 (m, 2H), 6.08 (d, J=8.0, 1H), 3.87-3.79 (m, 2H), 2.93-2.85 (m, 2H), 2.00-1.93 (m, 5H), 1.59-1.51 (m, 3H).

Intermediate FJ

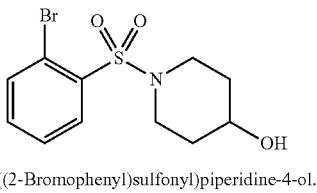

1-((2-Bromophenyl)sulfonyl)piperidine-4-ol.

The title compound was prepared in a manner similar to that described in Intermediate FI using piperidin-4-ol. $^1$H NMR (400 MHz, $CDCl_3$) δ 8.11-8.07 (m, 1H), 7.77-7.73 (m, 1H), 7.48-7.36 (m, 2H), 3.92-3.84 (m, 1H), 3.65-3.55 (m, 2H), 3.18-3.11 (m, 2H), 1.99-1.88 (m, 2H), 1.69-1.59 (m, 2H).

Intermediate FK

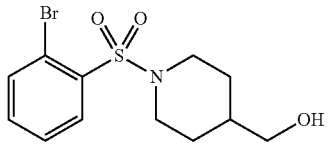

1-((2-Bromophenyl)sulfonyl)piperidine-4-yl)methanol.

The title compound was prepared in a manner similar to that described in Intermediate FI using piperidin-4-ylmethanol. $^1$H NMR (400 MHz, $CDCl_3$) δ 8.11-8.07 (m, 1H), 7.76-7.73 (m, 1H), 7.47-7.36 (m, 2H), 3.90-3.84 (m, 2H), 3.50 (d, J=6.4, 2H), 2.82-2.73 (m, 2H), 1.79-1.84 (m, 2H), 1.67-1.56 (m, 1H), 1.37-1.24 (m, 2H).

Intermediate FL

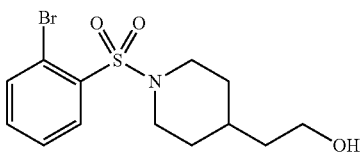

2-(1-((2-Bromophenyl)sulfonyl)piperidine-4-yl)ethanol.

The title compound was prepared in a manner similar to that described in Intermediate FI using 2-(piperidin-4-yl)ethanol. $^1$H NMR (400 MHz, $CDCl_3$) δ 8.10-8.06 (m, 1H), 7.76-7.72 (m, 1H), 7.47-7.36 (m, 2H), 3.86-3.79 (m, 2H), 3.68 (t, J=6.3, 2H), 2.80-2.72 (m, 2H), 1.78-1.71 (m, 2H), 1.56-1.51 (m, 3H), 1.37-1.23 (m, 2H).

Intermediate FM

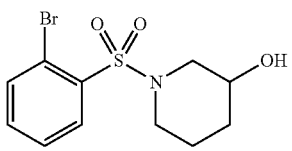

Racemic-1-((2-Bromophenyl)sulfonyl)piperidin-3-ol.

The title compound was prepared in a manner similar to that described in Intermediate FI using racemic piperidin-3-ol. ¹H NMR (400 MHz, CDCl₃) δ 8.13-8.09 (m, 1H), 7.77-7.73 (m, 1H), 7.50-7.37 (m, 2H), 3.89-3.82 (m, 1H), 3.57-3.51 (m, 1H), 3.40-3.32 (m, 1H), 3.24-3.16 (m, 1H), 3.06-3.00 (m, 1H), 2.16 (s, 1H), 1.94-1.80 (m, 2H), 1.70-1.50 (m, 2H).

Intermediate FN

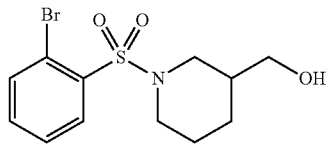

racemic (1-((2-Bromophenyl)sulfonyl)piperidin-3-yl)methanol.

The title compound was prepared in a manner similar to that described in Intermediate FI using racemic piperidin-3-ylmethanol. ¹H NMR (400 MHz, CDCl₃) δ 8.11-8.07 (m, 1H), 7.76-7.72 (m, 1H), 7.47-7.36 (m, 2H), 3.76-3.51 (m, 4H), 3.02-2.94 (m, 1H), 2.83-2.75 (m, 1H), 1.94-1.84 (m, 1H), 1.82-1.71 (m, 3H), 1.67-1.57 (m, 1H), 1.29-1.17 (m, 1H).

Intermediate FO

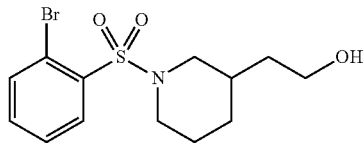

racemic 2-(1-((2-Bromophenyl)sulfonyl)piperidin-3-yl)ethanol.

The title compound was prepared in a manner similar to that described in Intermediate FI using racemic 2-(piperidin-3-yl)ethanol. ¹H NMR (400 MHz, CDCl₃) δ 8.10-8.06 (m, 1H), 7.76-7.72 (m, 1H), 7.47-7.36 (m, 2H), 3.72-3.62 (m, 4H), 2.88-2.80 (m, 1H), 2.60-2.53 (m, 1H), 1.89-1.39 (m, 7H), 1.16-1.03 (m, 1H).

Intermediate FP

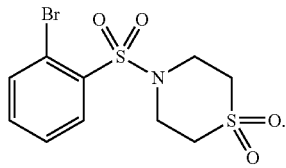

4-((2-Bromophenyl)sulfonyl) thiomorpholine 1,1-dioxide

The title compound was prepared in a manner similar to that described in Intermediate FI using thiomorpholine 1,1-dioxide. ¹H NMR (400 MHz, CDCl₃) δ 8.17-8.11 (m, 1H), 7.81-7.76 (m, 1H), 7.53-7.43 (m, 2H), 3.92-3.86 (m, 4H), 3.24-3.13 (m, 4H).

Intermediate FQ

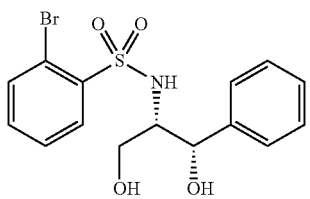

2-Bromo-N-((1S,2S)-1,3-dihydroxy-1-phenylpropan-2-yl)benzenesulfonamide.

The title compound was prepared in a manner similar to that described in Intermediate FI using (1S,2S)-2-amino-1-phenylpropane-1,3-diol.

Intermediate FR

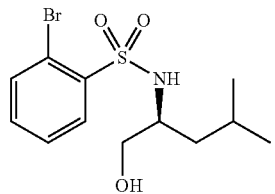

(S)-2-Bromo-N-(1-hydroxy-4-methylpentan-2-yl)benzenesulfonamide.

The title compound was prepared in a manner similar to that described in Intermediate FI using (S)-2-amino-4-methylpentan-1-ol.

Intermediate FS

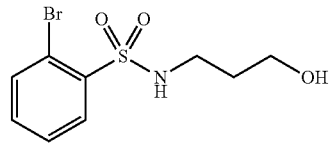

2-Bromo-N-(3-hydroxypropyl)benzenesulfonamide.

The title compound was prepared in a manner similar to that described in Intermediate FI using 3-aminopropan-1-ol Intermediate FT

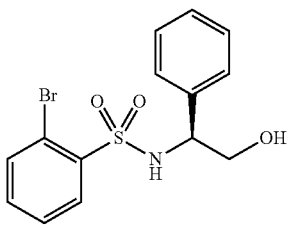

(S)-2-Bromo-N-(2-hydroxy-1-phenylethyl)benzenesulfonamide.

The title compound was prepared in a manner similar to that described in Intermediate FI using (S)-2-amino-2-phenylethanol.

Intermediate FU

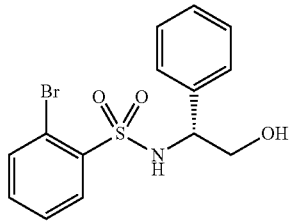

(R)-2-Bromo-N-(2-hydroxy-1-phenylethyl)benzenesulfonamide.

The title compound was prepared in a manner similar to that described in Intermediate FI using (R)-2-amino-2-phenylethanol Intermediate FV

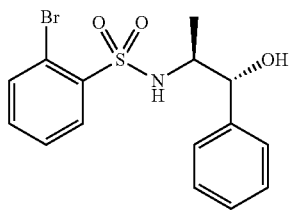

2-Bromo-N-((1R,2S)-1-hydroxy-1-phenylpropan-2-yl)benzenesulfonamide.

The title compound was prepared in a manner similar to that described in Intermediate FI using (1R,2S)-2-amino-1-phenylpropan-1-ol.

Intermediate FW

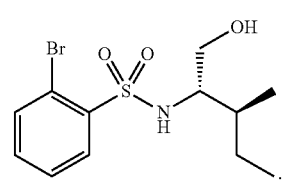

2-Bromo-N-((2S,3S)-1-hydroxy-3-methylpentan-2-yl)benzenesulfonamide

The title compound was prepared in a manner similar to that described in Intermediate FI using (2S,3S)-2-amino-3-methylpentan-1-ol.

Intermediate FX

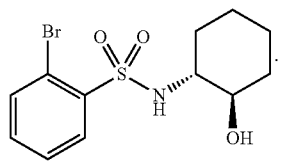

2-Bromo-N-((1R,2R)-2-hydroxycyclohexyl)benzenesulfonamide

The title compound was prepared in a manner similar to that described in Intermediate FI using (1R,2R)-2-aminocyclohexanol.

Intermediate FY

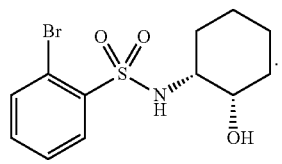

2-Bromo-N-((1R,2S)-2-hydroxycyclohexyl)benzenesulfonamide

The title compound was prepared in a manner similar to that described in Intermediate FI using (1S,2R)-2-aminocyclohexanol Intermediate FZ

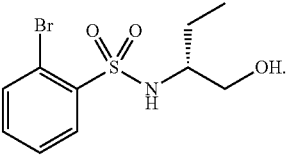

(R)-2-Bromo-N-(1-hyrdoxybutan-2-yl)benzenesulfonamide

The title compound was prepared in a manner similar to that described in Intermediate FI using (R)-2-aminobutan-1-ol.

Intermediate GA

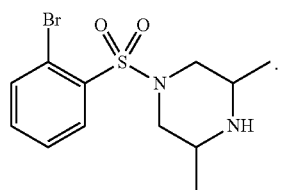

Racemic-1-((2-Bromophenyl)sulfonyl)-3,5-dimethylpiperazine

A solution of 2-bromobenzene-1-sulfonyl chloride (100 mg, 0.39 mmol), 2,6-dimethylpiperazine (56 mg, 0.49 mmol), and diisopropylethyl amine (0.202 mL, 1.17 mmol) in CH$_2$Cl$_2$ (2.5 mL) was allowed to stir for 15 min at rt. The reaction mixture was then directly subjected to FCC purification to give the title compound (0.105 g, 81%). $^1$H NMR (600 MHz, CDCl$_3$) δ 8.09-8.07 (m, 1H), 7.76-7.73 (m, 1H), 7.47-7.44 (m, 1H), 7.43-7.37 (m, 1H), 3.70-3.66 (m, 2H), 2.97-2.91 (m, 2H), 2.38-2.33 (m, 2H), 1.06-1.04 (m, 6H).

Intermediate GB

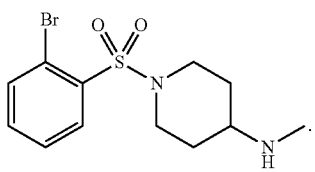

1-((2-Bromophenyl)sulfonyl)-
N-methylpiperidin-4-amine

The title compound was prepared in a manner similar to that described in Intermediate EU using N-methylpiperidin-4-amine.

Intermediate GC

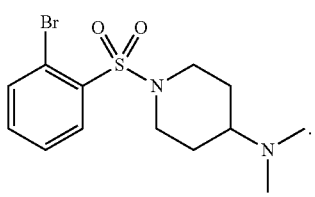

1-((2-Bromophenyl)sulfonyl)-N,N-
dimethylpiperidin-4-amine

The title compound was prepared in a manner similar to that described in Intermediate EU using N,N-dimethylpiperidin-4-amine.

Intermediate GD

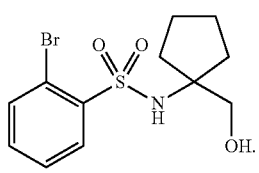

2-Bromo-N-(1-(hydroxymethyl)
cyclopentyl)benzenesulfonamide

The title compound was prepared using analogous conditions to those described in Intermediate AM using cycloleucinol. $^1$H NMR (500 MHz, CDCl$_3$) δ 8.16 (dd, J=7.8, 1.8, 1H), 7.75 (dd, J=7.9, 1.3, 1H), 7.51-7.45 (m, 1H), 7.44-7.39 (m, 1H), 5.25 (s, 1H), 4.23 (s, 1H), 3.59 (d. J=6.4, 2H), 2.36 (t, J=6.5, 1H), 1.90-1.78 (m, 1H), 1.77-1.60 (m, 4H), 1.56-1.49 (m, 2H).

Intermediate GE

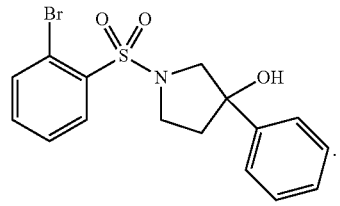

1-((2-Bromophenyl)sulfonyl)-3-
phenylpyrrolidin-3-ol

The title compound was prepared using analogous conditions to those described in Intermediate AM using 3-phenyl-3-pyrrolidinol. $^1$H NMR (500 MHz, CDCl$_3$) δ 8.17 (dd, J=7.8, 1.8, 1H), 7.77 (dd, J=7.8, 1.3, 1H), 7.49-7.43 (m, 3H), 7.43-7.34 (m, 3H), 7.34-7.27 (m, 1H), 3.82-3.75 (m, 3H), 3.71 (d, J=10.8, 1H), 2.46-2.37 (m, 1H), 2.29-2.23 (m, 1H), 2.15 (s, 1H).

Intermediate GF

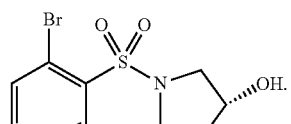

(R)-1-((2-Bromophenyl)sulfonyl)
pyrrolidin-3-ol

The title compound was prepared using analogous conditions to those described in Intermediate AM using (R)-3-hydroxypyrrolidine. $^1$H NMR (500 MHz, CDCl$_3$) δ 8.13 (dd, J=7.8, 1.7, 1H), 7.75 (dd, J=7.8, 1.3, 1H), 7.48-7.42 (m, 1H), 7.39 (m, 1H), 4.57-4.47 (m, 1H), 3.63-3.51 (m, 3H), 3.48-3.40 (m, 1H), 2.14-2.04 (m, 1H), 2.04-1.94 (m, 1H), 1.94-1.84 (m, 1H).

Intermediate GG

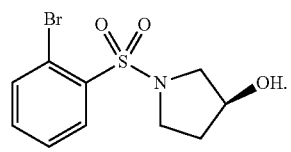

(S)-1-((2-Bromophenyl)
sulfonyl)pyrrolidin-3-ol

The title compound was prepared using analogous conditions to those described in Intermediate AM using (S)-3-hydroxypyrrolidine. $^1$H NMR (500 MHz, CDCl$_3$) δ 8.12 (dd, J=7.8, 1.7, 1H), 7.75 (dd, J=7.8, 1.3, 1H), 7.45 (m, 1H), 7.39 (m, 1H), 4.56-4.46 (m, 1H), 3.65-3.50 (m, 3H), 3.44 (m, 1H), 2.13-2.03 (m, 1H), 2.03-1.87 (m, 2H).

Intermediate GH

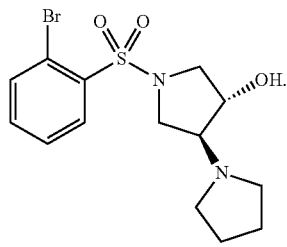

(Racemic)-1'-((2-Bromophenyl)
sulfonyl)-
[1,3'-bipyrrolidin]-4'-ol

The title compound was prepared using analogous conditions to those described in Intermediate AM using (racemic)-[1,3'-bipyrrolidin]-4'-ol. $^1$H NMR (500 MHz, CDCl$_3$) δ 8.12 (dd, J=7.8, 1.8, 1H), 7.75 (dd, J=7.8, 1.3, 1H), 7.48-7.34 (m, 2H), 4.42-4.29 (m, 1H), 3.74 (m, 2H), 3.36 (m, 2H), 2.83 (dd, J=10.9, 6.3, 1H), 2.70-2.43 (m, 4H), 1.83-1.66 (m, 4H).

Intermediate GI

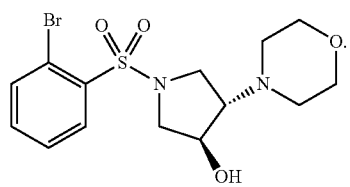

Racemic1-((2-Bromophenyl)sulfonyl)-4-
morpholinopyrrolidin-3-ol

The title compound was prepared using analogous conditions to those described in Intermediate AM using Racemic-4-morpholinopyrrolidin-3-ol. $^1$H NMR (500 MHz, CDCl$_3$) δ 8.11 (dd, J=7.8, 1.8, 1H), 7.76 (dd, J=7.8, 1.3, 1H), 7.49-7.44 (m, 1H), 7.44-7.38 (m, 1H), 4.35 (t, J=7.4, 1H), 3.78-3.70 (m, 2H), 3.70-3.67 (m, 4H), 3.35-3.26 (m, 2H), 2.89 (m, 1H), 2.65-2.56 (m, 2H), 2.52-2.44 (m, 2H).

Intermediate GJ

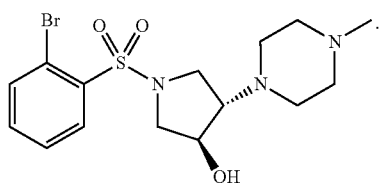

(Racemic)-1-((2-Bromophenyl)sulfonyl)-4-
(4-methylpiperazin-1-yl)
pyrrolidin-3-ol The title compound was prepared using analogous conditions to those described in Intermediate AM using Racemic-4-(4-methylpiperazin-1-yl)pyrrolidin-3-ol. $^1$H NMR (500 MHz, CDCl$_3$) δ 8.10 (dd, J=7.8, 1.8, 1H), 7.76 (dd, J=7.8, 1.3, 1H), 7.51-7.37 (m, 2H), 4.37 (dd, J=12.1, 5.8, 1H), 3.81-3.65 (m, 2H), 3.29 (m, 2H), 2.99 (dd, J=13.1, 7.3, 1H), 2.91-2.57 (m, 8H), 2.45 (s, 3H).

Intermediate GK

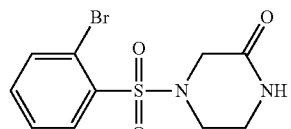

4-((2-Bomophenyl)sulfonyl)
piperazin-2-one

The title compound was prepared using analogous conditions to those described in Intermediate EU using 2-bromobenzene-1-sulfonyl chloride and piperazin-2-one. MS (ESI): mass calcd. for C$_{10}$H$_{11}$BrN$_2$O$_3$S, 317.96; m/z found, 319.0 [M+H]$^+$. $^1$H NMR (500 MHz, DMSO-d$_6$) δ 8.12 (s, 1H), 8.09-8.00 (m, 1H), 7.93-7.89 (m, 1H), 7.62 (m, 2H), 3.79 (s, 2H), 3.50-3.43 (m, 2H), 3.18 (m, 2H).

Intermediate GL

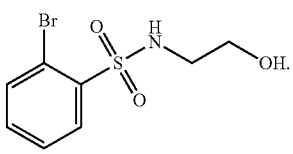

2-Bromo-N-(2-hydroxyethyl)
benzenesulfonamide

The title compound was prepared in a manner similar to that described for Intermediate EU using 2-aminoethanol. $^1$H NMR (500 MHz, CDCl$_3$) δ 8.17-8.11 (dd, J=7.8, 1.8, 1H), 7.79-7.72 (dd. J=7.8, 1.3, 1H), 7.52-7.46 (m, 1H), 7.46-7.40 (m, 1H), 5.79-5.66 (t, J=5.7, 1H), 3.73-3.65 (dd, J=5.6, 4.6, 2H), 3.13-3.03 (m, 2H), 2.14 (s, 1H).

Intermediate GM

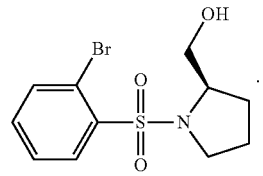

(R)-(1-((2-Bromophenyl)sulfonyl)pyrrolidin-2-yl)methanol

The title compound was prepared in a manner similar to that described for Intermediate EU using (R)-pyrrolidin-2-ylmethanol. $^1$H NMR (500 MHz, CDCl$_3$) δ 8.25-8.04 (m, 1H), 7.86-7.70 (m, 1H), 7.54-7.45 (m, 1H), 7.45-7.39 (m, 1H), 4.11-3.96 (m, 1H), 3.75-3.57 (m, 2H), 3.58-3.46 (dd, J=10.8, 4.5, 1H), 3.46-3.36 (m, 1H), 2.91-2.39 (m, 1H), 2.14-1.85 (m, 3H), 1.85-1.74 (dd, J=10.7, 5.3, 1H).

Intermediate GN

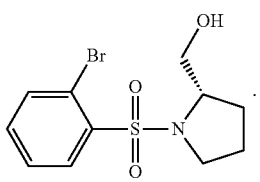

(S)-(1-((2-Bromophenyl)sulfonyl)pyrrolidin-2-yl)methanol

The title compound was prepared in a manner similar to that described for Intermediate EU using (S)-pyrrolidin-2-ylmethanol. $^1$H NMR (500 MHz, CDCl$_3$) δ 8.18-8.07 (dd, J=7.9, 1.8, 1H), 7.81-7.70 (dd, J=7.9, 1.3, 1H), 7.52-7.45 (m, 1H), 7.45-7.38 (m, 1H), 4.08-3.92 (m, 1H), 3.70-3.56 (m, 2H), 3.55-3.45 (m, 1H), 3.45-3.35 (m, 1H), 2.76-2.67 (t, J=6.1, 1H), 2.03-1.87 (m, 3H), 1.84-1.74 (m, 1H).

Intermediate GO

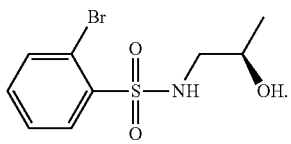

(R)-2-Bromo-N-(2-hydroxypropyl)benzenesulfonamide

The title compound was prepared in a manner similar to that described for Intermediate EU using (R)-1-aminopropan-2-ol. $^1$H NMR (500 MHz, CDCl$_3$) δ 8.17-8.09 (dd, J=7.8, 1.8, 1H), 7.81-7.71 (dd, J=7.8, 1.3, 1H), 7.51-7.46 (m, 1H), 7.46-7.40 (m, 1H), 5.65-5.60 (t, J=6.1, 1H), 3.98-3.81 (m, 1H), 3.08-2.96 (m, 1H), 2.85-2.58 (m, 1H), 2.04-2.02 (d, J=4.3, 1H), 1.18-1.14 (d, J=6.3, 3H).

Intermediate GP

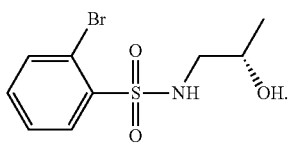

(S)-2-Bromo-N-(2-hydroxypropyl)benzenesulfonamide

The title compound was prepared in a manner similar to that described for Intermediate EU using (S)-1-aminopropan-2-ol. $^1$H NMR (500 MHz, CDCl$_3$) δ 8.21-8.04 (dd, J=7.8, 1.8, 1H), 7.78-7.72 (dd, J=7.8, 1.3, 1H), 7.53-7.46 (m, 1H), 7.46-7.38 (m, 1H), 5.71-5.54 (d, J=5.9, 1H), 3.97-3.84 (m, 1H), 3.07-2.96 (m, 1H), 2.80-2.69 (m, 1H), 2.03-1.95 (d, J=4.4, 1H), 1.19-1.07 (d, J=6.3, 3H).

Intermediate GQ

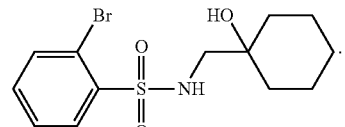

2-Bromo-N-((1-hydroxycyclohexyl)methyl)benzenesulfonamide

The title compound was prepared in a manner similar to that described for Intermediate EU using 1-(aminomethyl)cyclohexanol. $^1$H NMR (500 MHz, CDCl$_3$) δ 8.17-8.09 (dd, J=7.8, 1.8, 1H), 7.78-7.70 (dd, J=7.8, 1.3, 1H), 7.51-7.45 (m, 1H), 7.45-7.39 (m, 1H), 5.56-5.45 (t, J=6.3, 1H), 3.71 (s, 1H), 2.89-2.77 (d, J=6.4, 2H), 1.60-1.28 (m, 10H).

Intermediate GR

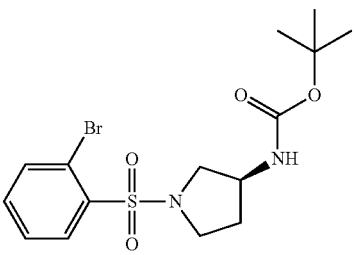

(S)-tert-Butyl (1-((2-bromophenyl)sulfonyl)pyrrolidin-3-yl)carbamate

The title compound was prepared in a manner similar to that described for Intermediate EU using (S)-tert-butyl pyrrolidin-3-ylcarbamate. $^1$H NMR (500 MHz, CDCl$_3$) δ 8.17-8.06 (dd, J=7.8, 1.8, 1H), 7.81-7.67 (dd, J=7.8, 1.3, 1H), 7.49-7.43 (m, 1H), 7.43-7.37 (m, 1H), 4.73 (s, 1H), 4.25 (s, 1H), 3.65-3.51 (d, J=8.8, 2H), 3.51-3.43 (m, 1H), 3.37-3.20 (dd, J=10.0, 3.8, 1H), 2.33-2.12 (m, 1H), 1.98-1.81 (dd, J=12.8, 6.9, 1H), 1.43 (s, 9H).

Intermediate GS

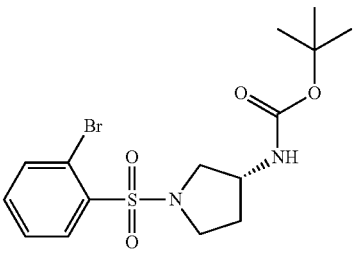

(R)-tert-Butyl (1-((2-bromophenyl)sulfonyl)pyrrolidin-3-yl)carbamate

The title compound was prepared in a manner similar to that described for Intermediate EU using (R)-tert-butyl pyrrolidin-3-ylcarbamate. $^1$H NMR (500 MHz, CDCl$_3$) δ 8.15-8.10 (dd, J=7.8, 1.8, 1H), 7.79-7.73 (dd, J=7.8, 1.3, 1H), 7.49-7.43 (m, 1H), 7.43-7.37 (m, 1H), 4.73 (s, 1H), 4.25 (s, 1H), 3.65-3.52 (m, 2H), 3.51-3.43 (m, 1H), 3.34-3.22 (m, 1H), 2.25-2.13 (m, 1H), 1.95-1.82 (dd, J=12.6, 7.0, 1H), 1.43 (s, 9H).

Intermediate GT

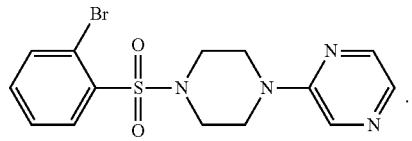

2-(4-((2-Bromophenyl)sulfonyl)piperizin-1-yl)pyrazine

The title compound was prepared in a manner similar to that described for Intermediate EU using 2-(piperazin-1-yl)pyrazine. ¹H NMR (500 MHz, CDCl₃) δ 8.16-8.09 (m, 2H), 8.07-8.02 (dd, J=2.6, 1.5, 1H), 7.90-7.87 (d, J=2.6, 1H), 7.78-7.74 (dd, J=7.9, 1.3, 1H), 7.51-7.45 (m, 1H), 7.44-7.37 (m, 1H), 3.74-3.58 (m, 4H), 3.48-3.38 (m, 4H).

Intermediate GU

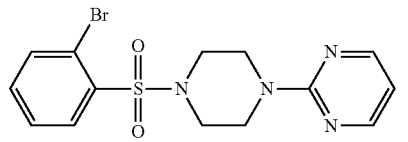

2-(4-((2-Bromophenyl)sulfonyl)piperizin-1-yl)pyrimidine

The title compound was prepared in a manner similar to that described for Intermediate EU using 2-(piperazin-1-yl)pyrimidine. ¹H NMR (500 MHz, CDCl₃) δ 8.33-8.27 (d, J=4.7, 2H), 8.15-8.06 (dd, J=7.9, 1.7, 1H), 7.78-7.71 (dd, J=7.9, 1.3, 1H), 7.50-7.43 (m, 1H), 7.43-7.36 (m, 1H), 6.57-6.43 (t, J=4.7, 1H), 3.98-3.78 (m, 4H), 3.42-3.31 (m, 4H).

Intermediate GV

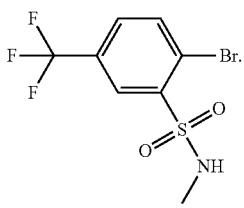

2-Bromo-N-methyl-5-(trifluoromethyl)benzenesulfonamide

The title compound was prepared in a manner similar to that described for Intermediate EU using methylamine and 2-bromo-5-(trifluoromethyl)benzene-1-sulfonyl chloride. ¹H NMR (500 MHz, CDCl₃) δ 8.46-8.29 (d, J=2.4, 1H), 7.99-7.79 (d, J=8.3, 1H), 7.79-7.59 (dd. J=8.3, 2.3, 1H), 5.20-5.01 (d, J=6.4, 1H), 2.80-2.56 (d, J=5.3, 3H).

Intermediate GW

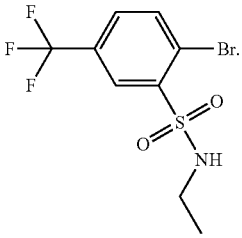

2-Bromo-N-ethyl-5-(trifluoromethyl)benzenesulfonamide

The title compound was prepared in a manner similar to that described for Intermediate EU using ethylamine and 2-bromo-5-(trifluoromethyl)benzene-1-sulfonyl chloride. ¹H NMR (500 MHz, CDCl₃) δ 8.43-8.38 (m, 1H), 7.93-7.86 (dd, J=8.3, 0.9, 1H), 7.70-7.62 (m, 1H), 5.08 (s, 1H), 3.11-2.96 (m, 2H), 1.19-1.09 (t, J=7.2, 3H).

Intermediate GX

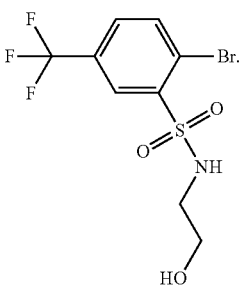

2-Bromo-N-(2-hydroxymethyl)-5-(trifluoromethyl)benzenesulfonamide

The title compound was prepared in a manner similar to that described for Intermediate EU using 2-aminoethanol and 2-bromo-5-(trifluoromethyl)benzene-1-sulfonyl chloride. ¹H NMR (500 MHz, CD₃OD) δ 8.35-8.30 (m, 1H), 8.07-7.98 (dd, J=8.2, 0.9, 1H), 7.82-7.76 (m, 1H), 3.59-3.50 (t, J=5.9, 2H), 3.10-3.02 (t, J=5.9, 2H).

Intermediate GY

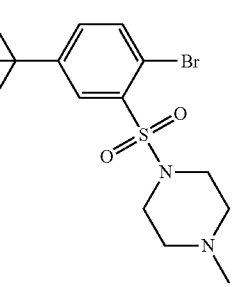

1-((2-Bromo-5-(trifluoromethyl)phenyl)sulfonyl)-4-methylpiperazine

The title compound was prepared in a manner similar to that described for Intermediate EU using 1-methylpiperazine and 2-bromo-5-(trifluoromethyl)benzene-1-sulfonyl chloride. ¹H NMR (500 MHz, CDCl₃) δ 8.37-8.28 (d, J=2.2, 1H), 7.98-7.86 (d, J=8.2, 1H), 7.73-7.59 (d, J=8.2, 1H), 3.45-3.31 (t, J=5.0, 4H), 2.60-2.42 (t, J=4.9, 4H), 2.40-2.20 (d, J=1.5, 3H).

Intermediate GZ

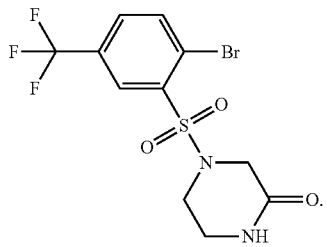

4-((2-Bromo-5-(trifluoromethyl)phenyl)sulfonyl)piperazin-2-one

The title compound was prepared in a manner similar to that described for Intermediate EU using piperazin-2-one and 2-bromo-5-(trifluoromethyl)benzene-1-sulfonyl chloride. ¹H NMR (400 MHz, CDCl₃) δ 8.43-8.35 (d, J=2.3, 1H), 7.99-7.89 (d, J=8.2, 1H), 7.77-7.65 (dd, J=8.3, 2.3, 2H), 6.95 (s, 2H), 3.99 (s, 3H), 3.73-3.58 (t, J=5.3, 3H), 3.51-3.42 (m, 3H), 1.36-1.04 (m, 1H).

Intermediate HA

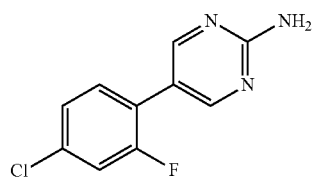

5-(4-Chloro-2-fluorophenyl)pyrimidin-2-amine

To a 500 mL round-bottomed flask were added 5-bromo-2-aminopyrimidine (4.0 g, 23 mmol), 4-chloro-2-fluorophenylboronic acid (3.9 g, 23 mmol), palladium(II)trifluoroacetate (240 mg, 0.72 mmol), and triphenylphoshine (373 mg, 1.40 mmol). The reaction vessel was fitted with a rubber septum, sparged with nitrogen and then charged with sparged toluene (75 mL), ethanol (75 mL), and a 2M solution of sodium carbonate (42 mL, 84 mmol) (solvents were sparged individually nitrogen gas for 30 minutes). The resulting mixture was stirred vigorously and heated at 50° Celsius. After 12 hours, the mixture was cooled to rt and treated with 100 mL of water. The precipitate was isolated via vacuum filtration, and the filtrate extracted with EtOAC. The EtOAc solution was dried, filtered and concentrated to dryness. The resultant solids were recrystallized from IPA (80 mL) to afford title compound (3.8 g, 74%). MS (ESI): mass calcd. for C₁₀H₇ClFN₃, 223.03; m/z found, 224.0 [M+H]⁺. ¹H NMR (500 MHz, DMSO-d₆) δ 8.44 (d, J=1.4, 2H), 7.59 (m, 1H), 7.54 (dd, J=10.7, 2.1, 1H), 7.37 (dd, J=8.3, 2.1, 1H), 6.94 (s, 2H).

Intermediate HB

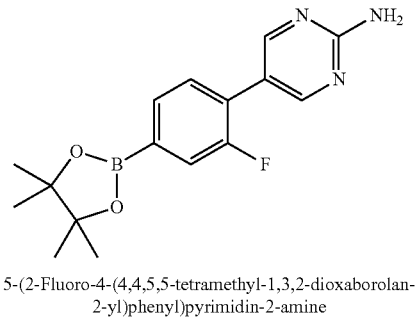 [SMILES: CC1(C)OB(c2ccc(-c3cnc(N)nc3)c(F)c2)OC1(C)C]

5-(2-Fluoro-4-(4,4,5,5-tetramethyl-1,3,2-dioxaborolan-2-yl)phenyl)pyrimidin-2-amine Nitrogen sparged 1,4-dioxane (80 mL) was added to a 250 mL round-bottomed flask containing 4,4,4',4',5,5,5',5'-octamethyl-2,2'-bi(1,3,2-dioxaborolane) (2.1 g, 8.4 mmol), 5-(4-chloro-2-fluorophenyl)pyrimidin-2-amine (1.5 g, 6.7 mmol), chloro(2-dicyclohexyl-phosphino-2',4',6'-triisopropyl-1-1'-biphenyl)[2-(2'-amino-1,1'-biphenyl)]palladium(II) (X-Phos pre-catalyst) (0.1 g, 0.13 mmol), and potassium acetate (1.9 g, 20 mmol). The reaction mixture was heated at 80° Celsius for 4 hours before cooling to rt, concentrating to dryness, and the residue subjected to FCC to provide the title compound (1.8 g, 83%). MS (ESI): mass calcd. for C₁₆H₁₉BFN₃O₂, 315.15; m/z found, 316.4 [M+H]⁺. ¹H NMR (500 MHz, CDCl₃) δ 8.53 (d, J=1.3 Hz, 2H), 7.64 (dd. J=7.6, 1.0 Hz, 1H), 7.58 (dd, J=11.0, 0.9 Hz, 1H), 7.38 (m, 1H), 5.23 (s, 2H), 1.36 (s, 12H).

Example 1

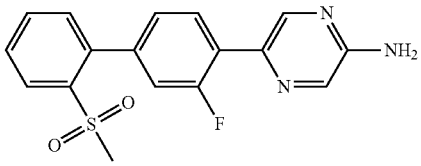

5-[3-Fluoro-2'-(methylsulfonyl)biphenyl-4-yl]pyrazin-2-amine

Method 1

To a 100 mL round-bottomed flask were added a stirbar, 5-(4-bromo-2-fluorophenyl)pyrazin-2-amine, (3.639 g, 13.57 mmol) (2-(methylsulfonyl)-phenyl)boronic acid (4.076 g, 20.38 mmol), Pd(dppf)Cl₂·CH₂Cl₂ (1.136 g, 1.391 mmol) and K₂CO₃ (5.663 g, 40.97 mmol). The flask was flushed with nitrogen and then charged with 56.0 mL thoroughly sparged (1 hour of bubbling N₂) DMSO. The flask was heated at 80° Celsius for 5.25 hours before cooling to room temperature, diluting the reaction mixture with EtOAc and filtering the mixture through a pad of celite. The filtrate was washed twice with 1 N NaOH and the organic layer dried over MgSO₄. Filtering and concentrating the filtrate to dryness gave the crude product. The soluble portion of the residue was then subjected to FCC to give the title compound. (3.80 g, 81%).

Method 2

Step A: 5-(4-Chloro-2-fluorophenyl)pyrazin-2-amine

To a nitrogen flushed flask containing 4-chloro-2-fluorobenzene boronic acid (40.0 g, 229 mmol), 2-amino-5-bromopyrazine (39.9 g, 229 mmol), palladium(II) trifluoroacetate (1.5 g, 4.6 mmol), and triphenylphosphine (2.4 g, 9.2 mmol) were added sparged toluene (750 mL), ethanol (750 mL), and 2 M $Na_2CO_{3(aq)}$ (418 mL, 836 mmol). The mixture was stirred and heated at 50° Celsius for 15 hours and then cooled to rt. Water (750 mL) was added and the layers were separated. The aqueous layer was washed with ethyl acetate (750 mL). The combined organic layers were washed with brine (500 mL), dried over $Na_2SO_4$, filtered, and concentrated to dryness to give 55.4 g of crude product. The crude solid was crystallized from toluene (450 mL) to provide the title compound (40.0 g, 78%). MS (ESI): mass calcd. for $C_{10}H_7ClFN_3$, 223.03; m/z found, 224.1 [M+H]$^+$. $^1$H NMR (400 MHz, DMSO-d$_6$) δ 8.34 (dd, J=2.6, 1.5, 1H), 8.03 (d, J=1.6, 1H), 7.89 (m, 1H), 7.52 (dd, J=11.3, 2.1, 1H), 7.38 (dd, J=8.5, 2.1, 1H), 6.79 (s, 2H).

Step B: 5-(3-Fluoro-2'-(methylsulfonyl)-[1,1'-biphenyl]-4-yl)pyrazin-2-amine To a nitrogen sparged flask containing 5-(4-chloro-2-fluorophenyl)pyrazin-2-amine (34.0 g, 152 mmol), 2-methylsulfonylphenylboronic acid (38.0 g, 190 mmol), and chloro(2-dicyclohexylphosphino-2',4',6'-triisopropyl-1,1'-biphenyl)[2-(2'-amino-1,1'-biphenyl)]palladium(II) (2.39 g, 3.0 mmol) were added sparged THF (300 mL) and $K_3PO_{4(aq)}$ (608 mL, 0.5 M). The mixture was stirred for 15 hours at rt and then concentrated under reduced pressure to remove the THF. The remaining portion was treated with toluene (325 mL) and THF (25 mL). The biphasic slurry was stirred for 20 h at rt and then filtered and the isolated solid washed with water (150 mL) and toluene (150 mL). The filter cake was dried to provide the title compound (47.1 g, 90%). MS (ESI): mass calcd. for $C_{17}H_{14}FN_3O_2S$, 343.08; m/z found, 344.1 [M+H]$^+$. $^1$H NMR (400 MHz, DMSO-d$_6$) δ 8.41 (dd, J=2.4, 1.5, 1H), 8.12 (dd, J=7.9, 1.4, 1H), 8.04 (d, J=1.5, 1H), 7.93 (m, 1H), 7.80 (m, 1H), 7.72 (m, 1H), 7.48 (dd, J=7.6, 1.4, 1H), 7.37 (dd, J=12.3, 1.7, 1H), 7.32 (dd, J=8.1, 1.7, 1H), 6.76 (s, 2H), 2.95 (s, 3H).

Example 2

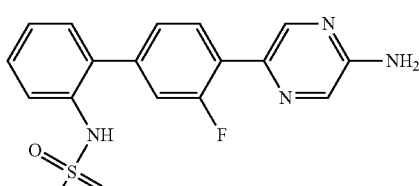

N-[4'-(5-Aminopyrazin-2-yl)-3'-fluorobiphenyl-2-yl]methanesulfonamide

The title compound was prepared using analogous conditions to those described in Example 1 using (2-(methylsulfonamido)phenyl)boronic acid. MS (ESI): mass calcd. for $C_{17}H_{15}FN_4O_2S$, 358.09; m/z found, 359.1 [M+H]$^+$. $^1$H NMR (500 MHz, DMSO-d$_6$) δ 9.11 (s, 1H), 8.40 (dd, J=2.3, 1.4, 1H), 8.04 (d, J=1.5, 1H), 7.97-7.89 (m, 1H), 7.50-7.34 (m, 6H), 6.71 (s, 2H), 2.84 (s, 3H).

Example 3

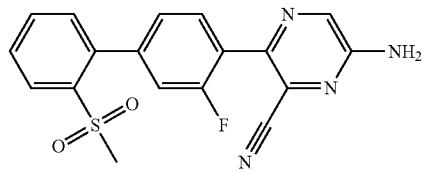

6-Amino-3-[3-fluoro-2'-(methylsulfonyl)biphenyl-4-yl]pyrazine-2-carbonitrile

The title compound was prepared using analogous conditions to those described in Example 1 using 2-(methylsulfonyl)phenylboronic acid and 5-(4-bromo-2-fluorophenyl)-6-cyanopyrazin-2-amine. MS (ESI): mass calcd. for $C_{18}H_{13}FN_4O_2S$, 368.07; m/z found, 369.0 [M+H]$^+$. $^1$H NMR (500 MHz, DMSO-d$_6$) δ 8.26 (s, 1H), 8.13 (dd, J=8.0, 1.4, 1H), 7.84-7.77 (m, 1H), 7.76-7.70 (m, 1H), 7.69-7.62 (m, 1H), 7.51 (dd, J=7.6, 1.4, 1H), 7.46 (dd, J=11.0, 1.6, 1H), 7.42-7.35 (m, 3H), 2.97 (s, 3H).

Example 4

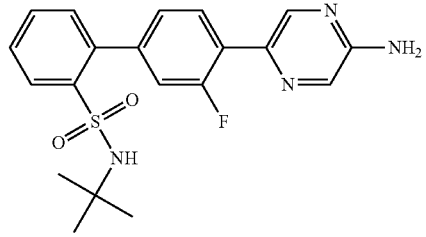

4'-(5-Aminopyrazin-2-yl)-N-tert-butyl-3'-fluorobiphenyl-2-sulfonamide

The title compound was prepared using analogous conditions to those described in Example 1 using (2-(N-(tert-butyl)sulfamoyl)phenyl)boronic acid. MS (ESI): mass calcd. for $C_{20}H_{21}FN_4O_2S$, 400.14; m/z found, 401.1 [M+H]$^+$. $^1$H NMR (500 MHz, DMSO-de) δ 8.39 (dd. J=2.2, 1.4, 1H), 8.09-8.02 (m, 2H), 7.93-7.87 (m, 1H), 7.68-7.63 (m, 1H), 7.63-7.57 (m, 1H), 7.38 (dd, J=7.5, 1.4, 1H), 7.33-7.26 (m, 2H), 6.94 (s, 1H), 6.71 (s, 2H), 1.02 (s, 9H).

Example 5

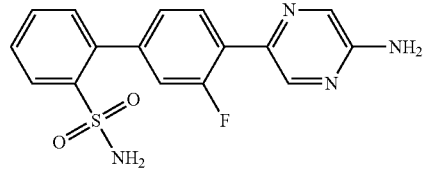

4'-(5-Aminopyrazin-2-yl)-3'-fluorobiphenyl-2-sulfonamide

Method 1

To a 50 mL round-bottomed flask were added 1.071 g (2.67 mmol) 4'-(5-aminopyrazin-2-yl)-N-tert-butyl-3'-fluorobiphenyl-2-sulfonamide, a stirbar and 20 mL TFA. The mixture was heated at 50° Celsius for 2 hours and then carefully and slowly added to 300 mL rapidly stirring sat. NaHCO$_3$. The resulting mixture was stirred for 30 min and then the solid was isolated via vacuum filtration. The solid was washed with 200 mL deionized water, air dried and then further dried under high vacuum with gentle heating to give the title compound (751 mg, 82%).

Method 2

Step A: 4'-(5-Aminopyrazin-2-yl)-N-(tert-butyl)-3'-fluoro-[1,1'-biphenyl]-2-sulfonamide To a nitrogen flushed flask containing 5-(4-chloro-2-fluorophenyl)pyrazin-2-amine (82.8 g, 370 mmol), (2-(N-(tert-butyl)sulfamoyl)phenyl)boronic acid (100.0 g, 388.9 mmol), and chloro(2-dicyclohexylphosphino-2',4',6'-triisopropyl-1,1'-biphenyl)[2-(2'-amino-1,1'-biphenyl)]palladium(II) (5.83 g, 7.41 mmol) were added N$_2$ sparged THF (926 mL) and sparged 0.5 M K$_3$PO$_{4(aq)}$ (1.65 L, 825 mmol). The mixture was stirred for 15 hours at room temperature. The layers were separated and the organic layer was washed with 600 mL brine, dried over MgSO$_4$, filtered, and concentrated to dryness to give a solid residue. The solid was dissolved in 900 mL DMA, stirred with 60 g activated charcoal at 80° Celsius for 2 hours, and then stirred at room temperature for an additional 16 hours. The charcoal was removed by filtration and then washed with 150 mL DMA. The combined filtrates were treated three times with fresh Silicycle brand SiliaMetS Thiol Pd Scavenger (30 g, 15 g, 7.5 g) in DMA at 80° Celsius for 8 hours to 16 hours. Upon cooling to rt the scavenger was filtered off and the filtrate was concentrated to dryness. The resulting solid was triturated in toluene (1.2 L) at 90° Celsius for 2 hours. Upon cooling to rt the solid was collected by filtration and washed twice with toluene (700 mL) and twice with hexanes (700 mL) yielding the title compound (120.0 g, 80.9%). MS (ESI): mass calcd. for C$_{20}$H$_{21}$FN$_4$O$_2$S, 400.14; m/z found, 401.1 [M+H]$^+$. $^1$H NMR (600 MHz, DMSO-d$_6$) δ 8.42-8.37 (m, 1H), 8.10-8.02 (m, 2H), 7.95-7.86 (m, 1H), 7.70-7.63 (m, 1H), 7.63-7.58 (m, 1H), 7.41-7.35 (m, 1H), 7.35-7.26 (m, 2H), 7.00-6.92 (s, 1H), 6.79-6.66 (s, 2H), 1.10-0.95 (s, 9H).

Step B: 4'-(5-Aminopyrazin-2-yl)-3'-fluoro-[1,1'-biphenyl]-2-sulfonamide

A solution of 4'-(5-aminopyrazin-2-yl)-N-(tert-butyl)-3'-fluoro-[1,1'-biphenyl]-2-sulfonamide (130.0 g, 298.0 mmol), anisole (97.4 mL, 894.0 mmol), and TFA (228.0 mL, 2.98 mol) was stirred at 60° Celsius for 16 hours. The reaction was cooled to rt, concentrated to dryness, and partitioned between 600 mL H$_2$O and 600 mL acetone. 750 mL sat. NaHCO$_{3(aq)}$ was added over 30 min. The resulting precipitate was isolated via filtration and rinsed with 300 mL H$_2$O then 300 mL acetone. The precipitate was triturated with 1.5 L acetone at 50° Celsius for 16 hours. After cooling to room temperature the solid was collected by filtration and rinsed twice with 250 mL acetone then dried in a vacuum oven at 50° Celsius for 16 hours yielding the title compound (74.3 g, 72.4%). MS (ESI): mass calcd. for C$_{16}$H$_{13}$FN$_4$O$_2$S, 344.07; m/z found, 345.1 [M+H]$^+$. $^1$H NMR (600 MHz, DMSO-d$_6$) δ 8.44-8.36 (s, 1H), 8.10-8.02 (m, 2H), 7.92-7.85 (m, 1H), 7.69-7.59 (m, 2H), 7.43-7.35 (m, 3H), 7.35-7.27 (m, 2H), 6.77-6.69 (s, 2H). Elemental analysis: calcd. for C$_{16}$H$_{13}$FN$_4$O$_2$S, C, 55.80; H, 3.81; N, 16.27; measured: C, 55.43; H, 3.54; N, 16.22.

Example 6

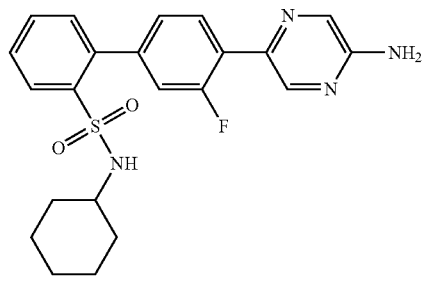

4'-(5-Aminopyrazin-2-yl)-N-cyclohexyl-3'-fluorobiphenyl-2-sulfonamide

To a 5 mL microwave vial were added a stirbar, 5-(2-fluoro-4-(4,4,5,5-tetramethyl-1,3,2-dioxaborolan-2-yl)phenyl)pyrazin-2-amine (54 mg, 0.17 mmol), 2-bromo-N-cyclohexylbenzenesulfonamide (58 mg, 0.18 mmol), Pd(dppf)Cl$_2$.CH$_2$Cl$_2$ (10 mg, 0.013 mmol), and K$_2$CO$_3$ (80 mg, 0.58 mmol). The vial was capped and flushed with nitrogen before adding 1 mL N$_2$ sparged DMSO and heating at 80° Celsius for 20 hours. The vial was cooled to rt and the reaction mixture subjected to FCC purification to give the title compound (45 mg, 62%). MS (ESI): mass calcd. for C$_{22}$H$_{23}$FN$_4$O$_2$S, 426.15; m/z found, 427.1 [M+H]$^+$. $^1$H NMR (500 MHz, DMSO-d$_6$) δ 8.43-8.35 (m, 1H), 8.05-8.03 (d, J=1.4, 1H), 8.03-7.99 (dd, J=7.9, 1.4, 1H), 7.92-7.84 (m, 1H), 7.70-7.64 (m, 1H), 7.64-7.58 (m, 1H), 7.44-7.37 (m, 2H), 7.32-7.24 (m, 2H), 6.72 (s, 2H), 2.85-2.72 (m, 1H), 1.69-1.52 (m, 5H), 1.48-1.39 (m, 1H), 1.19-0.93 (m, 5H).

Example 7

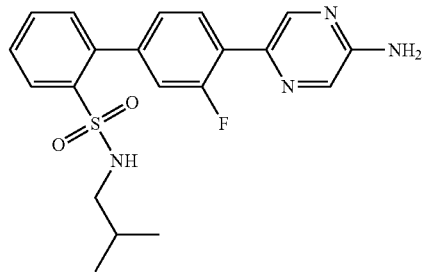

4'-(5-Aminopyrazin-2-yl)-3'-fluoro-N-(2-methylpropyl)biphenyl-2-sulfonamide

The title compound was prepared using analogous conditions to those described in Example 6 utilizing 2-bromo-N-(2-methylpropyl)benzenesulfonamide. MS (ESI): mass calcd. for C$_{20}$H$_{21}$FN$_4$O$_2$S, 400.14; m/z found, 401.1 [M+H]$^+$. $^1$H NMR (600 MHz, DMSO-d$_6$) δ 8.42-8.37 (m, 1H), 8.05-8.01 (d, J=1.5, 1H), 7.95-7.91 (dd, J=7.9, 1.3, 1H), 7.91-7.86 (m, 1H), 7.70-7.65 (m, 1H), 7.64-7.59 (m, 1H), 7.55-7.49 (m, 1H), 7.44-7.40 (dd, J=7.5, 1.4, 1H), 7.33-7.26 (m, 2H), 6.73 (s, 2H), 2.55-2.51 (m, 2H), 1.65-1.54 (m, 1H), 0.81-0.75 (d, J=6.7, 6H).

Example 8

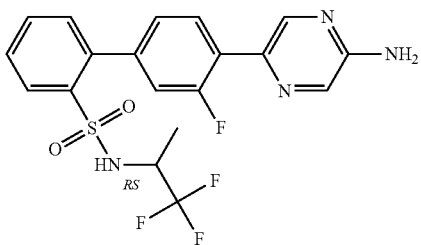

racemic 4'-(5-Aminopyrazin-2-yl)-3'-fluoro-N-(2,2,2-trifluoro-1-methylethyl)biphenyl-2-sulfonamide The title compound was prepared using analogous conditions to those described in Example 6 utilizing racemic 2-bromo-N-(2,2,2-trifluoro-1-methylethyl)-benzenesulfonamide. MS (ESI): mass calcd. for $C_{19}H_{16}F_4N_4O_2S$, 440.09; m/z found, 441.1 [M+H]+. $^1$H NMR (600 MHz, DMSO-$d_6$) δ 8.54-8.47 (d, J=8.9, 1H), 8.43-8.36 (m, 1H), 8.09-8.00 (m, 2H), 7.93-7.86 (m, 1H), 7.73-7.68 (m, 1H), 7.68-7.61 (m, 1H), 7.44-7.39 (dd, J=7.5, 1.4, 1H), 7.30-7.21 (m, 2H), 6.73 (s, 2H), 3.96-3.83 (m, 1H), 1.19-1.10 (d, J=6.9, 3H).

Example 9

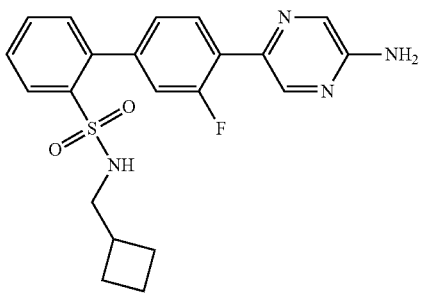

4'-(5-Aminopyrazin-2-yl)-N-(cyclobutylmethyl)-3'-fluorobiphenyl-2-sulfonamide

The title compound was prepared using analogous conditions to those described in Example 6 utilizing 2-bromo-N-(cyclobutylmethyl)benzenesulfonamide. MS (ESI): mass calcd. for $C_{21}H_{21}FN_4O_2S$, 412.14; m/z found, 413.1 [M+H]+. $^1$H NMR (600 MHz, DMSO-$d_6$) δ 8.41-8.36 (dd, J=2.2, 1.4, 1H), 8.06-8.01 (d, J=1.5, 1H), 7.97-7.91 (dd, J=7.9, 1.4, 1H), 7.91-7.85 (m, 1H), 7.71-7.65 (m, 1H), 7.65-7.59 (m, 1H), 7.52-7.47 (m, 1H), 7.44-7.39 (dd. J=7.5, 1.4, 1H), 7.33-7.24 (m, 2H), 6.73 (s, 2H), 2.79-2.69 (dd, J=7.2, 5.8, 2H), 2.35-2.24 (m, 1H), 1.93-1.82 (m, 2H), 1.81-1.67 (m, 2H), 1.59-1.50 (m, 2H).

Example 10

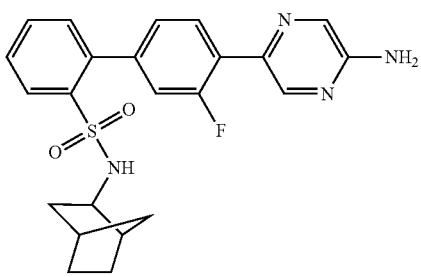

racemic (endo)-4'-(5-Aminopyrazin-2-yl)-N-bicyclo[2.2.1]hept-2-yl-3'-fluorobiphenyl-2-sulfonamide The title compound was prepared using analogous conditions to those described in Example 6 utilizing racemic (endo)-N-Bicyclo[2.2.1]hept-2-yl-2-bromobenzenesulfonamide. MS (ESI): mass calcd. for $C_{23}H_{23}FN_4O_2S$, 438.15; m/z found, 439.1 [M+H]+. $^1$H NMR (600 MHz, DMSO-$d_6$) δ 8.42-8.36 (m, 1H), 8.06-8.01 (d, J=1.5, 1H), 7.99-7.94 (dd, J=7.9, 1.3, 1H), 7.91-7.85 (m, 1H), 7.71-7.65 (m, 1H), 7.65-7.60 (m, 1H), 7.43-7.39 (dd, J=7.5, 1.4, 1H), 7.39-7.34 (d, J=6.9, 1H), 7.30-7.22 (m, 2H), 6.73 (s, 2H), 2.83-2.74 (m, 1H), 2.12-2.06 (m, 1H), 1.97-1.92 (m, 1H), 1.47-1.37 (m, 2H), 1.34-1.21 (m, 3H), 1.01-0.77 (m, 4H).

Example 11

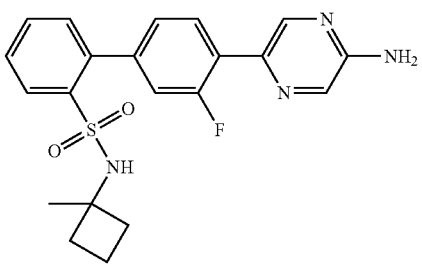

4'-(5-Aminopyrazin-2-yl)-3'-fluoro-N-(1-methylcyclobutyl)biphenyl-2-sulfonamide

The title compound was prepared using analogous conditions to those described in Example 6 utilizing 2-bromo-N-(1-methylcyclobutyl)benzenesulfonamide. MS (ESI): mass calcd. for $C_{21}H_{21}FN_4O_2S$, 412.14; m/z found, 413.1 [M+H]+. $^1$H NMR (600 MHz, CDCl$_3$) δ 8.52 (s, 1H), 8.26 (s, 1H), 8.16-8.11 (dd, J=7.9, 1.3, 1H), 8.11-8.05 (m, 1H), 7.62-7.58 (m, 1H), 7.56-7.51 (m, 1H), 7.40-7.37 (dd, J=8.1, 1.7, 1H), 7.34-7.28 (m, 2H), 4.37 (s, 1H), 2.13-2.00 (m, 2H), 1.82-1.73 (m, 2H), 1.69-1.59 (m, 2H), 1.24 (s, 3H).

Example 12

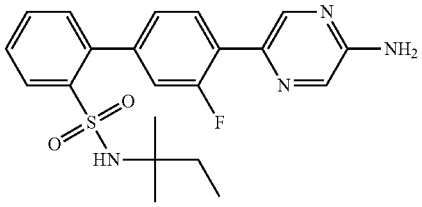

4'-(5-Aminopyrazin-2-yl)-N-(1,1-dimethylpropyl)-3'-fluorobiphenyl-2-sulfonamide

The title compound was prepared using analogous conditions to those described in Example 6 utilizing 2-bromo-N-(1,1-dimethylpropyl)benzenesulfonamide. MS (ESI): mass calcd. for $C_{21}H_{23}FN_4O_2S$, 414.15; m/z found, 415.1 [M+H]+. $^1$H NMR (600 MHz, CDCl$_3$) δ 8.56 (s, 1H), 8.28 (s, 1H), 8.18-8.13 (dd, J=7.9, 1.3, 1H), 8.12-8.06 (m, 1H), 7.62-7.56 (m, 1H), 7.55-7.49 (m, 1H), 7.44-7.39 (dd, J=8.1, 1.7, 1H), 7.35-7.28 (m, 2H), 3.90 (s, 1H), 1.50-1.39 (q, J=7.4, 2H), 1.01 (s, 6H), 0.78-0.68 (t, J=7.4, 3H).

Example 13

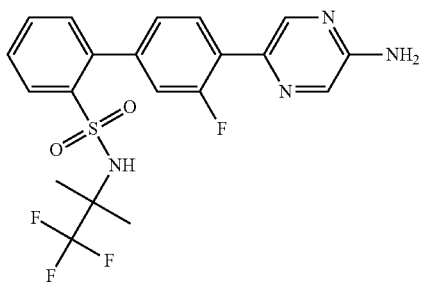

4'-(5-Aminopyrazin-2-yl)-3'-fluoro-N-(2,2,2-trifluoro-1,1-dimethylethyl)biphenyl-2-sulfonamide The title compound was prepared using analogous conditions to those described in Example 6 utilizing 2-bromo-N-(2,2,2-trifluoro-1,1-dimethylethyl)benzenesulfonamide. MS (ESI): mass calcd. for $C_{20}H_{18}F_4N_4O_2S$, 454.11; m/z found, 455.1 [M+H]$^+$. $^1$H NMR (600 MHz, CDCl$_3$) δ 8.54 (s, 1H), 8.27 (s, 1H), 8.15-8.10 (dd, J=8.0, 1.3, 1H), 8.10-8.04 (m, 1H), 7.66-7.59 (m, 1H), 7.57-7.52 (m, 1H), 7.40-7.27 (m, 3H), 4.49 (s, 1H), 1.33 (s, 6H).

Example 14

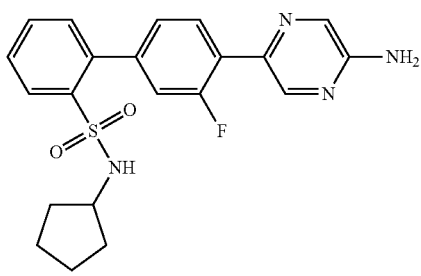

4'-(5-Aminopyrazin-2-yl)-N-cyclopentyl-3'-fluorobiphenyl-2-sulfonamide

The title compound was prepared using analogous conditions to those described in Example 6 utilizing 2-bromo-N-cyclopentylbenzenesulfonamide. MS (ESI): mass calcd. for $C_{21}H_{21}FN_4O_2S$, 412.14; m/z found, 413.1 [M+H]$^+$. $^1$H NMR (600 MHz, CDCl$_3$) δ 8.46 (s, 1H), 8.21 (s, 1H), 8.14-8.10 (dd, J=8.0, 1.4, 1H), 8.10-8.04 (m, 1H), 7.64-7.59 (m, 1H), 7.57-7.51 (m, 1H), 7.38-7.25 (m, 3H), 4.42-4.25 (d, J=6.6, 1H), 3.49-3.35 (m, 1H), 1.80-1.66 (m, 2H), 1.63-1.48 (m, 2H), 1.48-1.38 (m, 2H), 1.35-1.19 (m, 2H).

Example 15

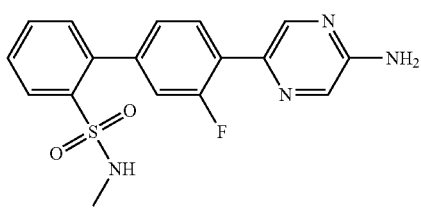

4'-(5-Aminopyrazin-2-yl)-3'-fluoro-N-methylbiphenyl-2-sulfonamide

The title compound was prepared using analogous conditions to those described in Example 6 utilizing 2-bromo-N-methylbenzenesulfonamide. MS (ESI): mass calcd. for $C_{17}H_{15}FN_4O_2S$, 358.09; m/z found, 359.0 [M+H]$^+$. $^1$H NMR (500 MHz, CD$_3$OD) δ 8.32 (s, 2H), 8.07-8.01 (dd, J=7.9, 1.4, 1H), 7.99-7.94 (m, 1H), 7.71-7.64 (m, 1H), 7.63-7.57 (m, 1H), 7.43-7.37 (dd, J=7.5, 1.4, 1H), 7.35-7.26 (m, 2H), 2.45 (s, 3H).

Example 16

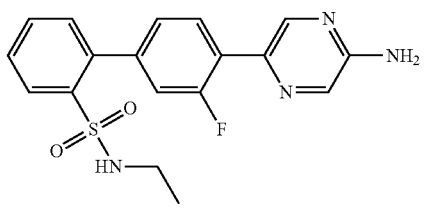

4'-(5-Aminopyrazin-2-yl)-N-ethyl-3'-fluorobiphenyl-2-sulfonamide

The title compound was prepared using analogous conditions to those described in Example 6 utilizing 2-bromo-N-ethylbenzenesulfonamide. MS (ESI): mass calcd. for $C_{18}H_{17}FN_4O_2S$, 372.11; m/z found, 373.1 [M+H]$^+$. $^1$H NMR (500 MHz, CD$_3$OD) δ 8.37 (s, 1H), 8.30 (s, 1H), 8.10-8.01 (dd, J=8.0, 1.5, 1H), 8.01-7.93 (m, 1H), 7.70-7.62 (m, 1H), 7.62-7.54 (m, 1H), 7.42-7.36 (dd, J=7.6, 1.5, 1H), 7.35-7.25 (m, 2H), 2.91-2.74 (q, J=7.2, 2H), 1.08-0.93 (t, J=7.2, 3H).

Example 17

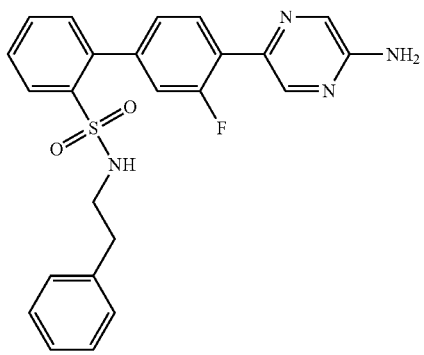

4'-(5-Aminopyrazin-2-yl)-3'-fluoro-N-(2-phenylethyl)biphenyl-2-sulfonamide

The title compound was prepared using analogous conditions to those described in Example 6 utilizing 2-bromo-N-(2-phenylethyl)benzenesulfonamide. MS (ESI): mass calcd. for $C_{24}H_{21}FN_4O_2S$, 448.14; m/z found, 449.1 [M+H]$^+$. $^1$H NMR (500 MHz, CDCl$_3$) δ 8.35 (s, 1H), 8.14 (s, 1H), 8.10-8.05 (dd, J=7.9, 1.3, 1H), 7.99-7.91 (m, 1H), 7.63-7.57 (m, 1H), 7.57-7.49 (m, 1H), 7.31-7.26 (dd, J=7.5, 1.4, 1H), 7.23-7.17 (m, 2H), 7.17-7.09 (m, 3H), 7.05-6.98 (m, 2H), 4.82-4.67 (m, 1H), 3.15-3.00 (m, 2H), 2.75-2.65 (t, J=7.1, 2H).

Example 18

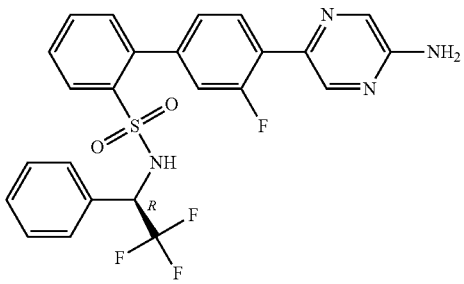

(R)-4'-(5-Aminopyrazin-2-yl)-3'-fluoro-N-[(1R)-2,2,2-trifluoro-1-phenylethyl]biphenyl-2-sulfonamide The title compound was prepared using analogous conditions to those described in Example 6 utilizing 2-bromo-N-[(1R)-2,2,2-trifluoro-1-phenylethyl]-benzenesulfonamide. MS (ESI): mass calcd. for $C_{24}H_{18}F_4N_4O_2S$, 502.08; m/z found, 503.1 [M+H]$^+$. $^1$H NMR (500 MHz, CDCl$_3$) δ 8.37-8.31 (s, 1H), 8.23-8.18 (dd, J=8.0, 1.4, 1H), 7.99-7.93 (d, J=1.6, 1H), 7.87-7.80 (m, 1H), 7.63-7.57 (m, 1H), 7.55-7.49 (m, 1H), 7.36-7.31 (d, J=7.4, 1H), 7.30-7.25 (m, 2H), 7.23-7.18 (d, J=7.6, 1H), 7.20-7.10 (m, 2H), 7.11-7.02 (m, 2H), 5.04-4.93 (s, 2H), 4.84-4.72 (m, 1H).

Example 19

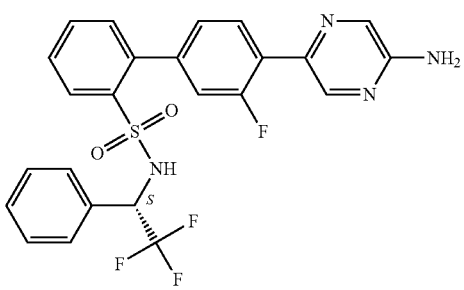

(S)-4'-(5-Aminopyrazin-2-yl)-3'-fluoro-N-[(1S)-2,2,2-trifluoro-1-phenylethyl]biphenyl-2-sulfonamide The title compound was prepared using analogous conditions to those described in Example 6 utilizing 2-bromo-N-[(1S)-2,2,2-trifluoro-1-phenylethyl]-benzenesulfonamide.

Example 20

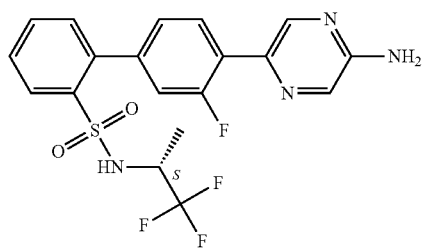

(S)-4'-(5-Aminopyrazin-2-yl)-3'-fluoro-N-[(1S)-2,2,2-trifluoro-1-methylethyl]biphenyl-2-sulfonamide The title compound was prepared using analogous conditions to those described in Example 6 utilizing 2-bromo-N-[(1S)-2,2,2-trifluoro-1-methylethyl]benzenesulfonamide. MS (ESI): mass calcd. for $C_{19}H_{16}F_4N_4O_2S$, 440.09; m/z found, 441.0 [M+H]$^+$. $^1$H NMR (500 MHz, CDCl$_3$) δ 8.21-8.12 (m, 2H), 7.92-7.85 (s, 1H), 7.85-7.79 (m, 1H), 7.62-7.55 (m, 1H), 7.54-7.47 (m, 1H), 7.43-7.36 (d, J=8.0, 1H), 7.33-7.27 (dd, J=7.5, 1.4, 1H), 7.19-7.07 (d, J=12.6, 1H), 5.45-5.13 (s, 2H), 4.04-3.90 (m, 1H), 1.31-1.22 (d, J=7.0, 3H).

Example 21

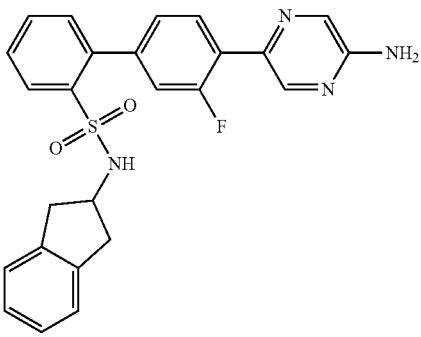

4'-(5-Aminopyrazin-2-yl)-N-(2,3-dihydro-1H-inden-2-yl)-3'-fluorobiphenyl-2-sulfonamide The title compound was prepared using analogous conditions to those described in Example 6 utilizing 2-bromo-N-(2,3-dihydro-1H-inden-2-yl)benzenesulfonamide. MS (ESI): mass calcd. for $C_{25}H_{21}FN_4O_2S$, 460.14; m/z found, 461.1 [M+H]$^+$. $^1$H NMR (500 MHz, CDCl$_3$) δ 8.44-8.39 (m, 1H), 8.24-8.18 (dd, J=8.0, 1.4, 1H), 8.05-8.00 (d, J=1.5, 1H), 7.91-7.84 (m, 1H), 7.65-7.58 (m, 1H), 7.58-7.51 (m, 1H), 7.34-7.29 (dd, J=7.5, 1.4, 1H), 7.27-7.21 (m, 1H), 7.15-7.04 (m, 5H), 4.89-4.74 (s, 2H), 4.74-4.61 (d, J=6.6, 1H), 4.00-3.89 (m, 1H), 3.06-2.92 (dd, J=15.9, 6.9, 2H), 2.70-2.58 (dd, J=15.9, 5.6, 2H).

Example 22

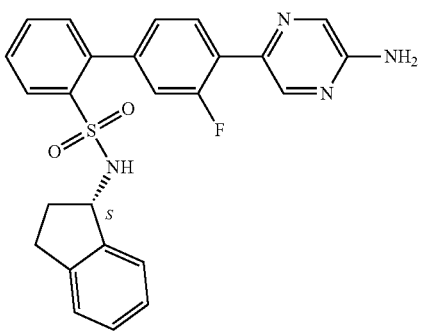

(S)-4'-(5-Aminopyrazin-2-yl)-N-[(1S)-2,3-dihydro-1H-inden-1-yl]-3'-fluorobiphenyl-2-sulfonamide The title compound was prepared using analogous conditions to those described in Example 6 utilizing 2-bromo-N-[(1S)-2,3-dihydro-1H-inden-1-yl]benzenesulfonamide.

MS (ESI): mass calcd. for C$_{25}$H$_{21}$FN$_4$O$_2$S, 460.14; m/z found, 461.1 [M+H]$^+$. $^1$H NMR (500 MHz, CDCl$_3$) δ 8.30-8.24 (dd, J=7.9, 1.4, 1H), 8.24-8.19 (m, 1H), 8.00-7.95 (d, J=1.5, 1H), 7.85-7.78 (m, 1H), 7.65-7.58 (m, 1H), 7.58-7.52 (m, 1H), 7.34-7.27 (dd, J=7.5, 1.4, 1H), 7.23-7.18 (d, J=7.7, 1H), 7.18-7.12 (dd, J=4.9, 1.1, 2H), 7.07-6.98 (m, 2H), 6.96-6.88 (d, J=7.6, 1H), 5.05-4.90 (d, J=8.7, 1H), 4.87-4.79 (s, 2H), 4.79-4.71 (m, 1H), 2.86-2.74 (m, 1H), 2.74-2.60 (m, 1H), 2.28-2.16 (m, 1H), 1.79-1.64 (m, 1H).

Example 23

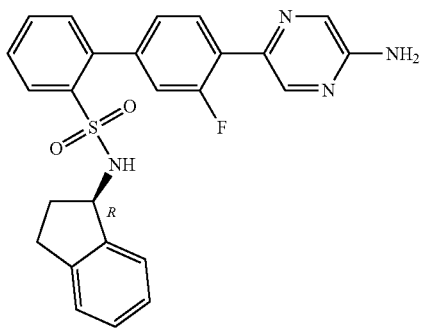

(R)-4'-(5-Aminopyrazin-2-yl)-N-[(1R)-2,3-dihydro-1H-inden-1-yl]-3'-fluorobiphenyl-2-sulfonamide The title compound was prepared using analogous conditions to those described in Example 6 utilizing 2-bromo-N-[(1R)-2,3-dihydro-1H-inden-1-yl]benzenesulfonamide.

Example 24

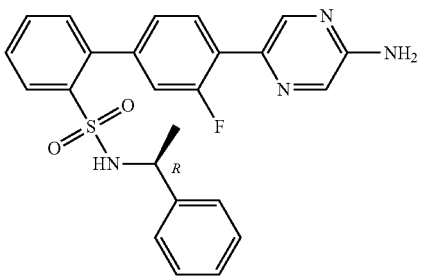

(R)-4'-(5-Aminopyrazin-2-yl)-3'-fluoro-N-[(1R)-1-phenylethyl]biphenyl-2-sulfonamide The title compound was prepared using analogous conditions to those described in Example 6 using 2-bromo-N-[(1R)-1-phenylethyl]benzenesulfonamide. MS (ESI): mass calcd. for C$_{24}$H$_{21}$FN$_4$O$_2$S, 448.14; m/z found, 449.1 [M+H]$^+$. $^1$H NMR (500 MHz, CDCl$_3$) δ 8.44-8.37 (d, J=1.4, 1H), 8.19-8.12 (m, 1H), 8.10-8.03 (dd, J=8.0, 1.3, 1H), 7.97-7.89 (m, 1H), 7.61-7.53 (m, 1H), 7.52-7.45 (m, 1H), 7.22-7.15 (m, 4H), 7.12-7.00 (s, 1H), 6.97-6.91 (m, 2H), 6.89-6.78 (s, 1H), 4.68-4.51 (d, J=7.0, 1H), 4.39-4.25 (m, 1H), 1.45-1.33 (d, J=6.9, 3H).

Example 25

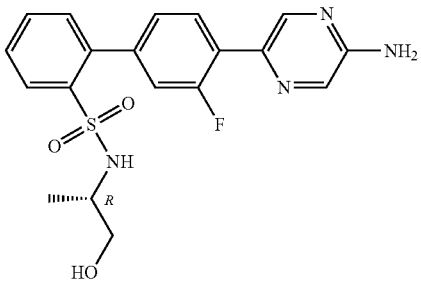

(R)-4'-(5-Aminopyrazin-2-yl)-3'-fluoro-N-[(1R)-2-hydroxy-1-methylethyl]biphenyl-2-sulfonamide The title compound was prepared using analogous conditions to those described in Example 6 utilizing 2-bromo-N-[(1R)-2-hydroxy-1-methylethyl]benzenesulfonamide.
MS (ESI): mass calcd. for C$_{19}$H$_{19}$FN$_4$O$_3$S, 402.12; m/z found, 403.1 [M+H]$^+$. $^1$H NMR (500 MHz, CD$_3$OD) δ 8.38-8.28 (m, 2H), 8.16-8.11 (dd, J=8.0, 1.3, 1H), 8.01-7.93 (m, 1H), 7.71-7.63 (m, 1H), 7.62-7.55 (m, 1H), 7.43-7.37 (dd, J=7.6, 1.4, 1H), 7.37-7.30 (m, 2H), 3.42-3.37 (m, 1H), 3.30-3.25 (dd, J=10.9, 6.3, 1H), 3.24-3.16 (m, 1H), 1.04-0.98 (d, J=6.6, 3H).

Example 26

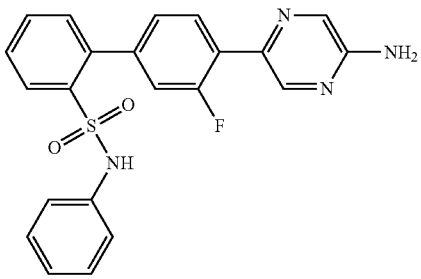

4'-(5-Aminopyrazin-2-yl)-3'-fluoro-N-phenylbiphenyl-2-sulfonamide

The title compound was prepared using analogous conditions to those described in Example 6 utilizing 2-bromo-N-phenylbenzenesulfonamide. MS (ESI): mass calcd. for C$_{22}$H$_{17}$FN$_4$O$_2$S, 420.11; m/z found, 421.1 [M+H]$^+$. $^1$H NMR (500 MHz, DMSO-d$_6$) δ 10.12 (s, 1H), 8.45-8.37 (m, 1H), 8.13-8.06 (d, J=1.5, 1H), 8.06-8.00 (dd, J=8.0, 1.4, 1H), 7.92-7.84 (t, J=8.3, 1H), 7.70-7.63 (m, 1H), 7.63-7.57 (m, 1H), 7.39-7.32 (dd, J=7.6, 1.4, 1H), 7.24-7.16 (dd, J=8.5, 7.3, 2H), 7.12 (s, 1H), 7.11-7.08 (dd, J=4.1, 1.6, 1H), 7.01-6.96 (m, 1H), 6.95-6.89 (m, 2H).

Example 27

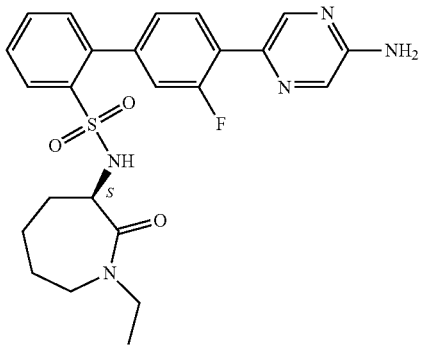

(S)-4'-(5-Aminopyrazin-2-yl)-N-[(3S)-1-ethyl-2-oxoazepan-3-yl]-3'-fluorobiphenyl-2-sulfonamide The title compound was prepared using analogous conditions to those described in Example 6 utilizing 2-bromo-N-[(3S)-1-ethyl-2-oxoazepan-3-yl]benzenesulfonamide. MS (ESI): mass calcd. for $C_{24}H_{26}FN_5O_3S$, 483.17; m/z found, 484.2 [M+H]$^+$. $^1$H NMR (500 MHz, CDCl$_3$) δ 8.39-8.33 (d, J=1.4, 1H), 8.25-8.20 (d, J=1.4, 1H), 8.10-8.05 (m, 1H), 8.05-8.00 (dd, J=8.0, 1.3, 1H), 7.61-7.55 (m, 1H), 7.53-7.47 (m, 1H), 7.43-7.38 (dd, J=8.1, 1.7, 1H), 7.34-7.30 (dd, J=7.5, 1.4, 1H), 7.30-7.25 (dd, J=12.3, 1.7, 1H), 6.02-5.93 (d, J=5.5, 1H), 3.91-3.83 (m, 1H), 3.45-3.20 (m, 3H), 3.18-3.10 (m, 1H), 2.04-1.94 (m, 1H), 1.92-1.81 (m, 1H), 1.81-1.70 (m, 1H), 1.66-1.53 (m, 1H), 1.52-1.42 (m, 1H), 1.34-1.21 (m, 1H), 1.09-0.99 (t, J=7.2, 3H).

Example 28

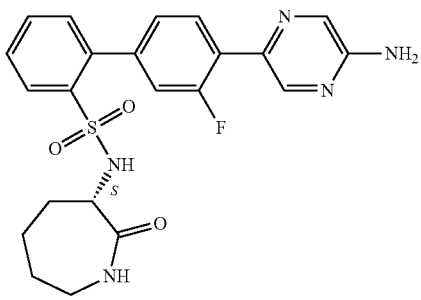

(S)-4'-(5-Aminopyrazin-2-yl)-3'-fluoro-N-[(3S)-2-oxoazepan-3-yl]biphenyl-2-sulfonamide The title compound was prepared using analogous conditions to those described in Example 6 utilizing 2-bromo-N-[(3S)-2-oxoazepan-3-yl]benzenesulfonamide. MS (ESI): mass calcd. for $C_{22}H_{22}FN_5O_3S$, 455.14; m/z found, 456.1 [M+H]$^+$. $^1$H NMR (500 MHz, CDCl$_3$) δ 8.46-8.33 (s, 1H), 8.24-8.14 (s, 1H), 8.10-8.00 (m, 2H), 7.63-7.56 (m, 1H), 7.56-7.48 (m, 1H), 7.41-7.35 (dd, J=8.0, 1.7, 1H), 7.35-7.29 (dd, J=7.4, 1.4, 1H), 7.29-7.25 (d, J=1.8, 1H), 7.00-6.82 (s, 1H), 5.88-5.71 (d, J=6.0, 1H), 3.89-3.73 (d, J=9.4, 1H), 3.24-3.11 (m, 1H), 3.11-2.97 (m, 1H), 2.09-1.98 (d, J=12.5, 1H), 1.98-1.85 (d, J=13.2, 1H), 1.81-1.67 (m, 1H), 1.64-1.44 (m, 2H), 1.37-1.21 (m, 1H).

Example 29

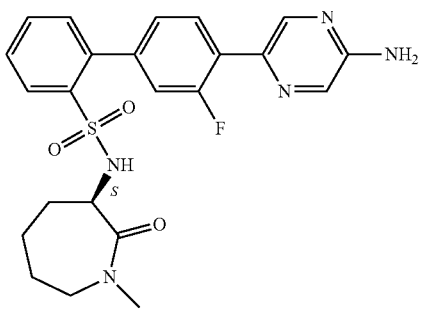

(S)-4'-(5-Aminopyrazin-2-yl)-3'-fluoro-N-[(3S)-1-methyl-2-oxoazepan-3-yl]biphenyl-2-sulfonamide The title compound was prepared using analogous conditions to those described in Example 6 utilizing 2-bromo-N-[(3S)-1-methyl-2-oxoazepan-3-yl]benzenesulfonamide. MS (ESI): mass calcd. for $C_{23}H_{24}FN_5O_3S$, 469.16; m/z found, 470.1 [M+H]$^+$. $^1$H NMR (500 MHz, CDCl$_3$) δ 8.44-8.38 (d, J=1.3, 1H), 8.22 (s, 1H), 8.10-8.05 (m, 1H), 8.05-8.00 (dd, J=7.9, 1.3, 1H), 7.63-7.56 (m, 1H), 7.54-7.47 (m, 1H), 7.43-7.37 (dd, J=8.1, 1.5, 1H), 7.34-7.29 (dd, J=7.6, 1.4, 1H), 7.28-7.24 (m, 1H), 6.00-5.85 (d, J=5.6, 1H), 3.98-3.86 (d, J=11.4, 1H), 3.39-3.28 (dd, J=15.2, 11.4, 1H), 3.16-3.05 (dd, J=15.3, 5.1, 1H), 2.95 (s, 3H), 2.04-1.93 (dd, J=17.1, 4.1, 1H), 1.91-1.81 (m, 1H), 1.77-1.66 (m, 1H), 1.65-1.53 (m, 1H), 1.53-1.42 (m, 1H), 1.38-1.26 (m, 1H).

Example 30

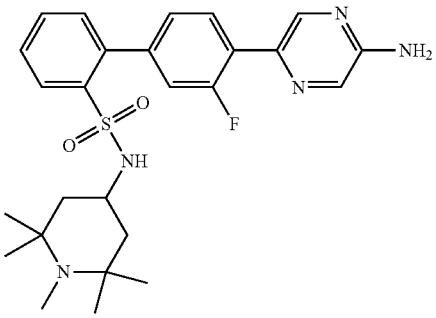

4'-(5-Aminopyrazin-2-yl)-3'-fluoro-N-[1,2,2,6,-pentamethylpiperidin-4-yl)]biphenyl-2-sulfonamide The title compound was prepared using analogous conditions to those described in Example 6 utilizing 2-bromo-N-(1,2,2,6,6-pentamethylpiperidin-4-yl)benzenesulfonamide. MS (ESI): mass calcd. for $C_{26}H_{32}FN_5O_2S$, 497.23; m/z found, 498.2 [M+H]$^+$. $^1$H NMR (500 MHz, CD$_3$OD) δ 8.39-8.35 (d, J=1.4, 1H), 8.35-8.30 (m, 1H), 8.18-8.13 (dd, J=8.0, 1.3, 1H), 8.05-7.99 (m, 1H), 7.73-7.67 (m, 1H), 7.65-7.59 (m, 1H), 7.45-7.40 (dd, J=7.6, 1.3, 1H), 7.39-7.36 (m, 1H), 7.36-7.32 (dd, J=2.9, 1.5, 1H), 3.49-3.39 (m, 1H), 2.75 (s, 3H), 1.95-1.87 (m, 2H), 1.75-1.64 (m, 2H), 1.38 (s, 6H), 1.30 (s, 6H).

Example 31

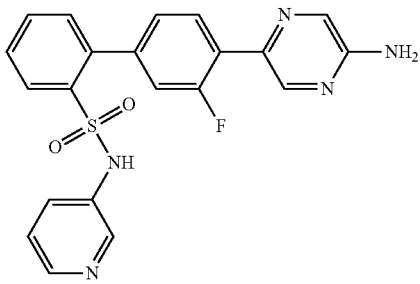

4'-(5-Aminopyrazin-2-yl)-3'-fluoro-N-pyridin-3-ylbiphenyl-2-sulfonamide

The title compound was prepared using analogous conditions to those described in Example 6 utilizing 2-bromo-N-pyridin-3-ylbenzenesulfonamide. MS (ESI): mass calcd. for $C_{21}H_{16}FN_5O_2S$, 421.10; m/z found, 422.1 [M+H]$^+$. $^1$H NMR (600 MHz. CD$_3$OD) δ 8.38-8.34 (d, J=1.5, 1H), 8.34-8.30 (m, 2H), 8.29-8.23 (m, 2H), 7.91-7.85 (m, 1H), 7.83-7.79 (m, 1H), 7.75-7.71 (m, 1H), 7.71-7.68 (dd, J=8.6, 5.4, 1H), 7.68-7.64 (m, 1H), 7.41-7.37 (dd, J=7.6, 1.3, 1H), 7.20-7.15 (dd, J=12.1, 1.7, 1H), 7.15-7.12 (dd, J=8.0, 1.7, 1H).

Example 32

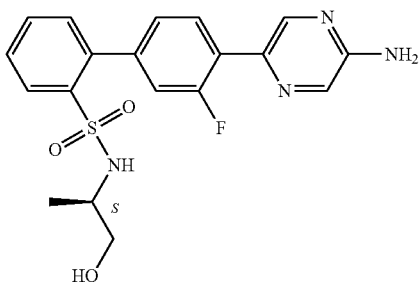

4'-(5-Aminopyrazin-2-yl)-3'-fluoro-N-[(1S)-2-hydroxy-1-methylethyl]biphenyl-2-sulfonamide The title compound was prepared using analogous conditions to those described in Example 6 utilizing 2-bromo-N-[(1S)-2-hydroxy-1-methylethyl]benzenesulfonamide.

Example 33

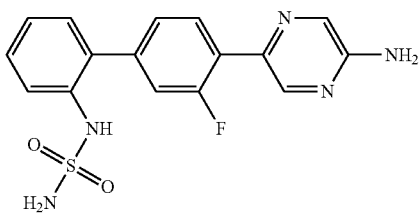

N-[4'-(5-Aminopyrazin-2-yl)-3'-fluorobiphenyl-2-yl]sulfamide

To a solution of tert-butanol (13 mg, 0.18 mmol) in DCM (5 mL) was added chlorosulfonylisocyanate (25 mg, 0.18 mmol) at 0° Celsius. The resulting solution containing N-(tert-butoxycarbonyl)sulfamoyl chloride was added to a reaction flask containing 5-(2'-amino-3-fluorobiphenyl-4-yl)pyrazin-2-amine (50 mg, 0.18 mmol) and triethylamine (36 mg, 0.36 mmol) in anhydrous DCM (10 mL) at 0° Celsius. The mixture was warmed to rt, stirred 2 hours, then concentrated to dryness, re-dissolved in TFA/DCM (5 mL/5 mL), stirred at rt for 1 hour, and concentrated to dryness. The residue was diluted with water (10 mL) and saturated NaHCO$_{3(aq)}$ (10 mL), extracted with DCM (10 mL×3) and the combined organic extracts washed with brine, dried over Na$_2$SO$_4$, filtered and concentrated to dryness. The residue was purified by HPLC to give the title compound (10 mg, 16%). MS (ESI): mass calcd. for $C_{16}H_{14}FN_5O_2S$, 359.09; m/z found, 360.0 [M+H]$^+$; $^1$H NMR (300 MHz, DMSO-d$_6$) δ 8.39 (s, 1H), 8.33 (s, 1H), 8.04 (d, J=1.3, 1H), 7.91 (m, 1H), 7.63 (d, J=7.8, 1H), 7.44-7.22 (m, 4H), 7.24 (m, 1H), 7.05 (s, 2H), 6.70 (s, 2H).

Example 34

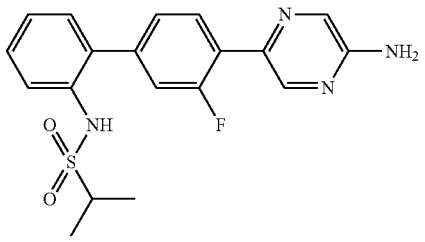

N-(4'-(5-Aminopyrazin-2-yl)-3'-fluoro-[1,1'-biphenyl]-2-yl)propane-2-sulfonamide To a solution of 5-(4-bromo-2-fluorophenyl)pyrazin-2-amine (309 mg, 1.15 mmol) in DMSO (5 mL) was added K$_2$CO$_3$ (317 mg, 2.3 mmol). The mixture was sparged with N$_2$ several times. Pd(PPh$_3$)$_4$ (66 mg, 0.058 mmol) and (2-(1-methylethylsulfonamido)-phenyl)boronic acid (280 mg, 1.15 mmol) were added and the resultant mixture sparged with N$_2$. The mixture was heated at 80° Celsius for 14 hours before cooling to rt and diluting with water (70 mL). The precipitate was collected, rinsed with water, air dried, and then purified by HPLC to give the title compound (40 mg, 9%). MS (ESI): mass calcd. for $C_{19}H_{19}FN_4O_2S$, 386.12; m/z found, 387.1 [M+H]$^+$. $^1$H NMR (300 MHz, CD$_3$OD) δ 8.72 (s, 1H), 8.25 (d, J=1.2, 1H), 8.16 (m, 1H), 7.50 (d, J=7.8, 1H), 7.47-7.34 (m, 5H), 3.15-3.03 (m, 1H), 1.23 (d, J=6.8, 6H).

Example 35

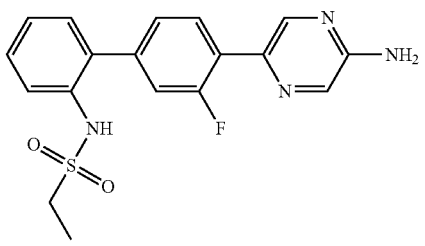

N-[4'-(5-Aminopyrazin-2-yl)-3'-fluorobiphenyl-2-yl]ethanesulfonamide

The title compound was prepared using analogous conditions to those described in Example 34 utilizing 5-(2-fluoro-4-(4,4,5,5-tetramethyl-1,3,2-dioxaborolan-2-yl)phenyl)-pyrazin-2-amine and N-(2-bromophenyl)ethanesulfonamide. MS (ESI): mass calcd. for $C_{18}H_{17}FN_4O_2S$, 372.11; m/z found, 372.9 [M+H]$^+$. $^1$H NMR (400 MHz, DMSO-$d_6$) δ 9.08 (s, 1H), 8.43-8.36 (m, 1H), 8.04 (d, J=1.0, 1H), 7.93 (m, 1H), 7.46-7.28 (m, 6H), 6.72 (s, 2H), 2.91 (q, J=7.4, 2H), 1.07 (t, J=7.3, 3H).

Example 36

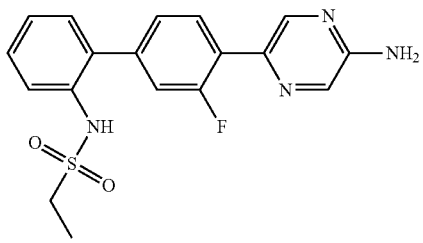

N-[4'-(5-Aminopyrazin-2-yl)-3'-fluorobiphenyl-2-yl]propane-1-sulfonamide

The title compound was prepared using analogous conditions to those described in Example 34 utilizing 5-(2-fluoro-4-(4,4,5,5-tetramethyl-1,3,2-dioxaborolan-2-yl)phenyl)-pyrazin-2-amine and 1-bromo-2-(propylsulfonyl)benzene. MS (ESI): mass calcd. for $C_{19}H_{19}FN_4O_2S$, 386.12; m/z found, 387.3 [M+H]$^+$. $^1$H NMR (400 MHz, DMSO-$d_6$) δ 9.09 (s, 1H), 8.38 (s, 1H), 8.04 (d, J=1.3, 1H), 7.93 (m, 1H), 7.42-7.35 (m, 6H), 6.71 (s, 2H), 2.87-2.74 (m, 2H), 1.59-1.44 (m, 2H), 0.81 (t, J=7.4, 3H).

Example 37

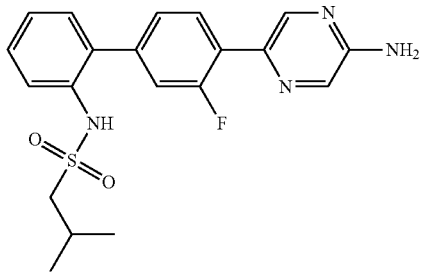

N-[4'-(5-Aminopyrazin-2-yl)-3'-fluorobiphenyl-2-yl]-2-methylpropane-1-sulfomaide The title compound was prepared using analogous conditions to those described in Example 34 utilizing 5-(2-fluoro-4-(4,4,5,5-tetramethyl-1,3,2-dioxaborolan-2-yl)phenyl)-pyrazin-2-amine and N-(2-bromophenyl)isobutylsulfonamide. MS (ESI): mass calcd. for $C_{20}H_{21}FN_4O_2S$, 400.14; m/z found, 401.2 [M+H]$^+$. $^1$H NMR (400 MHz, CD$_3$OD) δ 8.38 (s, 1H), 8.14 (s, 1H), 7.96 (m, 1H), 7.49 (d, J=7.0, 1H), 7.45-7.30 (m, 5H), 2.77 (d, J=6.5, 2H), 2.15-2.02 (m, 1H), 0.97 (d, J=6.7, 6H).

Example 38

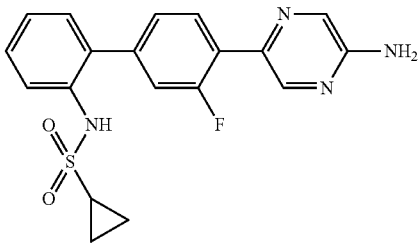

N-[4'-(5-aminopyrazin-2-yl)-3'-fluoro-[1,1'-biphenyl]-2-yl)cyclopropanesulfonamide

Step A: 2-(di-tert-Butyloxycarbonyl)amino-5-(4-bromo-2-fluorophenyl)pyrazine 2-Amino-5-(4-bromo-2-fluorophenyl)pyrazine (3.0 g, 11 mmol) was dissolved in pyridine (40 mL), and then slowly treated with (Boc)$_2$O (6.8 g, 34 mmol) at rt. The mixture was stirred at rt for 18 hours, concentrated to dryness and purified by FCC to give 2-(di-tert-butyloxycarbonyl)amino-5-(4-bromo-2-fluorophenyl)pyrazine (3.6 g, 68%) as a white solid. MS (ESI): mass calcd. for $C_{20}H_{23}FBrN_3O_4S$, 467.09; m/z found, 468.0 [M+H]$^+$.

Step B: 2-(di-tert-Butyloxycarbonyl)amino-5-(2'-amino-3-fluorobiphenyl-4-yl)pyrazine To a solution of 2-(di-tert-butyloxycarbonyl)amino-5-(4-bromo-2-fluorophenyl)-pyrazine (232 mg, 0.5 mmol) and 2-aminophenylboronic acid hydrochloride (174 mg, 1.0 mmol) in 1,4-dioxane/H$_2$O (10 mL/0.5 mL) was added Na$_2$CO$_3$ (232 mg, 2.0 mmol). The mixture was sparged with N$_2$ several times. Pd(PPh$_3$)$_4$ (29 mg, 0.025 mmol) was added and the resulted mixture was stirred at 80° Celsius for 14 hours under N$_2$. After cooling to rt, the mixture was diluted with water (50 mL) and extracted with DCM (15 mL×3). The combined organic extracts were washed with brine, dried over Na$_2$SO$_4$, filtered and concentrated to dryness to give 2-(di-tert-butyloxycarbonyl)amino-5-(2'-amino-3-fluorobiphenyl-4-yl)pyrazine, which was directly used in next step without any further purification. MS (ESI): mass calcd. for $C_{26}H_{29}FN_4O_4S$, 480.22; m/z found, 481.0 [M+H]$^+$.

Step C

To a solution of 2-(di-tert-butyloxycarbonyl)amino-5-(2'-amino-3-fluorobiphenyl-4-yl)pyrazine (280 mg crude, 0.5 mmol) in pyridine (5 mL) was slowly added cyclopropanesulfonyl chloride (105 mg, 0.75 mmol) at rt. The resultant mixture was stirred at 60° Celsius for 16 hours. The mixture was concentrated to dryness, the residue diluted with 40 mL of water and extracted with DCM (10 mL×2). The combined organic extracts were washed with brine, dried over Na$_2$SO$_4$, filtered and concentrated to dryness. The residue was purified by FCC to give 230 mg of impure product. The solid was dissolved in HCl (4 N) in EtOH (5 mL) and stirred at rt for 1 hour, then concentrated to dryness. The residue was purified by HPLC to give the title compound (55 mg, 37% yield). MS (ESI): mass calcd. for $C_{19}H_{17}FN_4O_4S$, 384.11; m/z found, 385.1 [M+H]$^+$. $^1$H NMR (300 MHz, DMSO-$d_6$) δ 9.14 (s, 1H), 8.39 (s, 1H), 8.05 (d, J=1.3, 1H), 7.92 (m, 1H), 7.51 (d, J=7.8, 1H), 7.48-7.34 (m, 5H), 6.81 (s, 2H), 2.48-2.42 (m, 1H), 0.89-0.75 (m, 4H).

Example 39

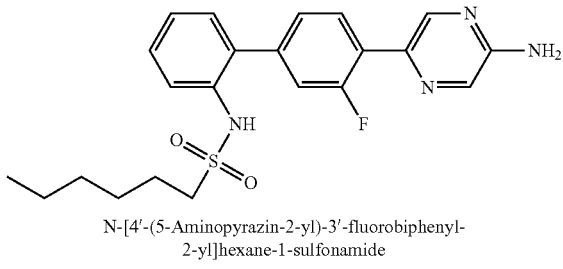 [SMILES: CCCCCCS(=O)(=O)Nc1ccccc1-c1ccc(-c2cnc(N)cn2)c(F)c1]

N-[4'-(5-Aminopyrazin-2-yl)-3'-fluorobiphenyl-2-yl]hexane-1-sulfonamide

The title compound was prepared using analogous conditions to those described in Example 38 utilizing hexane-1-sulfonyl chloride. MS (ESI): mass calcd. for $C_{22}H_{25}FN_4O_2S$, 428.17; m/z found, 429.1 [M+H]$^+$. $^1$H NMR (400 MHz, DMSO-$d_6$) δ 9.13 (s, 1H), 8.40 (s, 1H), 8.04 (d, J=1.1, 1H), 7.96 (m, 1H), 7.48-7.34 (m, 6H), 6.73 (s, 2H), 2.77-2.63 (m, 2H), 1.41-1.33 (m, 2H), 1.16-0.95 (m, 6H), 0.72 (t, J=6.9, 3H).

Example 40

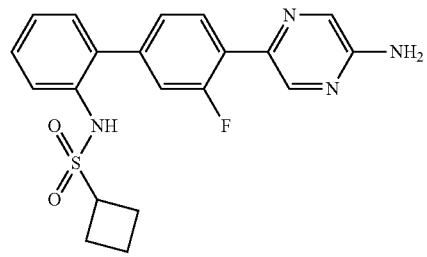

N-[4'-(5-Aminopyrazin-2-yl)-3'-fluoro-[1,1'-biphenyl]-2-yl)cyclobutanesulfonamide The title compound was prepared using analogous conditions to those described in Example 38 utilizing cyclobutanesulfonyl chloride. MS (ESI): mass calcd. for $C_{20}H_{19}FN_4O_2S$, 398.12; m/z found, 399.0 [M+H]$^+$. $^1$H NMR (300 MHz, DMSO-$d_6$) δ 9.07 (s, 1H), 8.38 (s, 1H), 8.04 (s, 1H), 7.92 (m, 1H), 7.47-7.31 (m, 6H), 6.71 (s, 2H), 3.66 (p, J=7.7, 1H), 2.21-2.08 (m, 2H), 2.03-1.92 (m, 2H), 1.86-1.70 (m, 2H).

Example 41

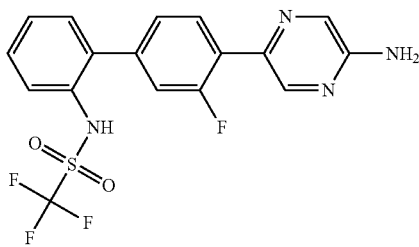

[4'-(5-Aminopyrazin-2-yl)-3'-fluorobiphenyl-2-yl]-1,1,1-trifluoromethanesulfonamide Trifluoromethanesulfonic anhydride (263 mg, 0.95 mmol) was added drop-wise to a solution consisting of 2-(di-tert-butyloxycarbonyl)amino-5-(2'-amino-3-fluorobiphenyl-4-yl)pyrazine (300 mg, 0.62 mmol) and Et$_3$N (190 mg, 1.86 mmol) and DCM (10 mL), at rt. The resulting mixture was stirred at rt for 16 hours, then quenched with sat. NaHCO$_3$ (20 mL), diluted with water (40 mL), and extracted with DCM (15 mL×3). The combined organic fractions were washed with brine, dried over Na$_2$SO$_4$ and concentrated to dryness. The solid was dissolved in 4 N HCl in EtOH (10 mL) and stirred at rt for 1 hour, concentrated to dryness and purified by HPLC to give the title compound. MS (ESI): mass calcd. for $C_1H_{12}F_4N_4O_2S$, 412.06; m/z found, 413.0 [M+H]$^+$. $^1$H NMR (400 MHz, DMSO-$d_6$) δ 8.41 (s, 1H), 8.06 (s, 1H), 7.96 (m, 1H), 7.56-7.45 (m, 3H), 7.44-7.32 (m, 3H), 6.77 (s, 2H).

Example 42

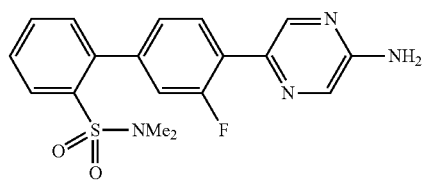

4'-(5-Aminopyrazin-2-yl)-3'-fluoro-N,N-dimethylbiphenyl-2-sulfonamide

To a 20 mL vial were 5-(4-bromo-2-fluorophenyl)pyrazin-2-amine (50 mg, 0.19 mmol), (2-(N,N-dimethylsulfamoyl)phenyl)boronic acid, K$_2$CO$_3$ (43 mg, 0.19 mmol), and Pd(dppf)Cl$_2$.CH$_2$Cl$_2$ (8 mg, 0.009 mmol), and a stir-bar. The vial was sealed with a teflon lined cap and sparged with N$_2$. The vial was then charged with freshly sparged DMSO (2 mL) and then stirred 16 hours at 80° Celsius. The reaction mixture was then cooled to rt, filtered, and purified by HPLC to give the title compound (36 mg, 40%). MS (ESI): mass calcd. for $C_{18}H_{17}FN_4O_2S$, 372.11; m/z found, 373.2 [M+H]$^+$. $^1$H NMR (400 MHz, CD$_3$OD) δ 8.33 (s, 2H), 8.06-7.96 (m, 2H), 7.72-7.67 (m, 1H), 7.64-7.59 (m, 1H), 7.43-7.39 (m, 1H), 7.32-7.26 (m, 2H), 2.49 (s, 6H).

Example 43

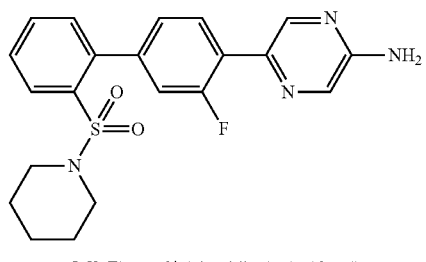

5-[3-Fluoro-2'-(piperidin-1-ylsulfonyl)biphenyl-4-yl]pyrazin-2-amine

The title compound was prepared in a manner similar to that described in Example 42 using 5-(4-bromo-2-fluorophenyl)pyrazin-2-amine and (2-(piperidin-1-ylsulfonyl)phenyl)boronic acid. MS (ESI): mass calcd. for $C_{21}H_{21}FN_4O_2S$, 412.14; m/z found, 413.3 [M+H]$^+$. $^1$H NMR (400 MHz, CD$_3$OD) δ 8.40-8.30 (m, 2H), 8.10-8.06 (m, 1H), 7.98 (m, 1H), 7.79-7.73 (m, 1H), 7.71-7.64 (m, 1H), 7.62-7.56 (m, 1H), 7.43-7.39 (m, 1H), 7.34-7.28 (m, 1H), 2.86 (d, J=5.3, 4H), 1.50-1.38 (m, 6H).

Example 44

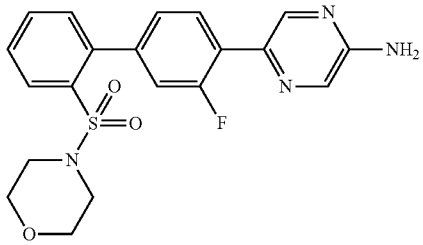

5-[3-Fluoro-2′-(morphloin-1-ylsulfonyl) biphenyl-4-yl]pyrazin-2-amine

The title compound was prepared in a manner similar to that described in Example 42 using 5-(4-bromo-2-fluorophenyl)pyrazin-2-amine and (2-(morpholinosulfonyl)phenyl)boronic acid. MS (ESI): mass calcd. for C$_{20}$H$_{19}$FN$_4$O$_3$S, 414.12; m/z found, 415.2 [M+H]$^+$. $^1$H NMR (400 MHz, CD$_3$OD) δ 8.38 (s, 1H), 8.31 (s, 1H), 8.13-8.09 (m, 1H), 7.99 (m, 1H), 7.75-7.69 (m, 1H), 7.65-7.60 (m, 1H), 7.46-7.43 (m, 1H), 7.37-7.31 (m, 2H), 3.54-3.46 (m, 4H), 2.91-2.84 (m, 4H).

Example 45

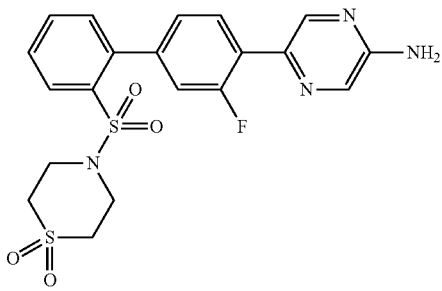

5-{2′-[(1,1-Dioxidothiomorpholin-4-yl)sulfonyl]-3-fluorobiphenyl-4-yl}pyrazin-2-amine The title compound was prepared in a manner similar to that described in Example 448 using 5-(2-fluoro-4-(4,4,5,5-tetramethyl-1,3,2-dioxaborolan-2-yl)phenyl)-pyrazin-2-amine and 4-((2-bromophenyl)sulfonyl)thiomorpholine 1,1-dioxide. MS (ESI): mass calcd. for C$_{20}$H$_{19}$FN$_4$O$_4$S$_2$, 462.08; m/z found, 463.0 [M+H]$^+$. $^1$H NMR (500 MHz, CDCl$_3$) δ 8.62-8.60 (m, 1H), 8.16-8.14 (m, 1H), 8.13-8.12 (m, 1H), 8.05 (t, J=8.1 Hz, 1H), 7.69-7.65 (m, 1H), 7.59-7.54 (m, 1H), 7.39-7.36 (m, 1H), 7.25-7.21 (m, 2H), 4.81 (s, 2H), 3.36-3.30 (m, 4H), 3.02-2.98 (m, 4H).

Example 46

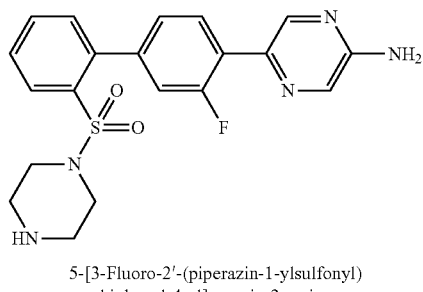

5-[3-Fluoro-2′-(piperazin-1-ylsulfonyl) biphenyl-4-yl]pyrazin-2-amine

The title compound was prepared in a manner similar to that described in Example 448 using 5-(2-fluoro-4-(4,4,5,5-tetramethyl-1,3,2-dioxaborolan-2-yl)phenyl)-pyrazin-2-amine and 1-((2-bromophenyl)sulfonyl)piperazine. MS (ESI): mass calcd. for C$_{20}$H$_{20}$FN$_5$O$_2$S, 413.13; m/z found, 414.1 [M+H]$^+$. $^1$H NMR (400 MHz, CD$_3$OD) δ 8.39 (m, 1H), 8.21-8.13 (m, 2H), 8.01-7.95 (m, 1H), 7.79-7.74 (m, 1H), 7.69-7.63 (m, 1H), 7.50-7.46 (m, 1H), 7.37-7.30 (m, 2H), 3.14-3.08 (m, 4H), 3.06-2.99 (m, 4H).

Example 47

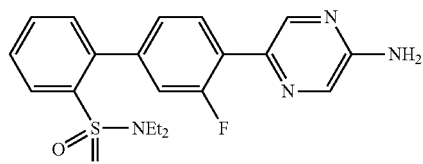

4′-(5-Aminopyrazin-2-yl)-N,N-diethyl-3′-fluorophenyl-2-sulfonamide

The title compound was prepared in a manner similar to that described in Example 448 using 5-(2-fluoro-4-(4,4,5,5-tetramethyl-1,3,2-dioxaborolan-2-yl)phenyl)-pyrazin-2-amine and 2-bromo-N,N-diethylbenzenesulfonamide. MS (ESI): mass calcd. for C$_{20}$H$_{21}$FN$_4$O$_2$S, 400.14; m/z found, 401.2 [M+H]$^+$. $^1$H NMR (400 MHz, CD$_3$OD) δ 8.37 (s, 1H), 8.29 (d, J=1.4, 1H), 8.08-8.04 (m, 1H), 8.0-7.94 (m, 1H), 7.70-7.64 (m, 1H), 7.61-7.55 (m, 1H), 7.41-7.36 (m, 1H), 7.32-7.25 (m, 2H), 2.96 (q, J=7.1, 4H), 1.00 (t, J=7.1, 6H).

Example 48

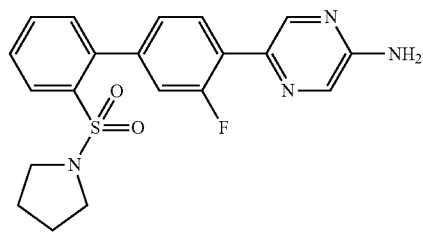

5-[3-Fluoro-2′-(pyrrolidin-1-ylsulfonyl)biphenyl-4-yl] pyrazin-2-amine

The title compound was prepared in a manner similar to that described in Example 448 using 5-(2-fluoro-4-(4,4,5,5-tetramethyl-1,3,2-dioxaborolan-2-yl)phenyl)-pyrazin-2-amine and 1-((2-bromophenyl)sulfonyl)pyrrolidine. MS (ESI): mass calcd. for $C_{20}H_{19}FN_4O_2S$, 398.12; m/z found, 399.2 [M+H]$^+$. $^1$H NMR (400 MHz, CD$_3$OD) δ 8.38 (s, 1H), 8.28 (d, J=1.4, 1H), 8.12-8.08 (m, 1H), 8.0-7.94 (m, 1H), 7.71-7.65 (m, 2H), 7.62-7.56 (m, 1H), 7.42-7.39 (m, 1H), 7.34-7.27 (m, 2H), 2.94 (t, J=6.7, 4H), 1.81-1.69 (m, 4H).

Example 49

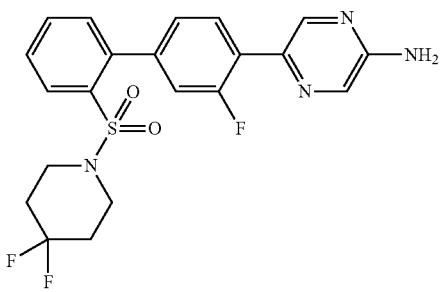

5-{2'-[(4,4-Difluoropiperidin-1-yl)sulfonyl]-3-fluorobiphenyl-4-yl}pyrazin-2-amine The title compound was prepared in a manner similar to that described in Example 448 using 5-(2-fluoro-4-(4,4,5,5-tetramethyl-1,3,2-dioxaborolan-2-yl)phenyl)-pyrazin-2-amine and 1-((2-bromophenyl)sulfonyl)-4,4-difluoropiperidine. MS (ESI): mass calcd. for $C_{21}H_{19}F_3N_4O_2S$, 448.12: m/z found, 449.2 [M+H]$^+$. $^1$H NMR (400 MHz, CD$_3$OD) δ 8.35 (s, 1H), 8.27 (d, J=1.4, 1H), 8.12 (d, J=8.0, 1H), 7.98 (m, 1H), 7.75-7.67 (m, 1H), 7.63 (m, 1H), 7.43 (d, J=7.6, 1H), 7.32 (d, J=10.6, 2H), 3.02-2.93 (m, 4H), 1.90-1.73 (m, 4H).

Example 50

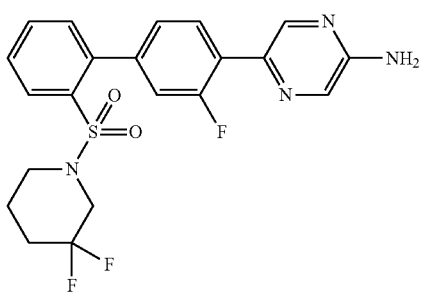

5-{2'-[(3,3-Difluoropiperidin-1-yl)sulfonyl]-3-fluorobiphenyl-4-yl}pyrazin-2-amine The title compound was prepared in a manner similar to that described in Example 448 using 5-(2-fluoro-4-(4,4,5,5-tetramethyl-1,3,2-dioxaborolan-2-yl)phenyl)-pyrazin-2-amine and 1-((2-bromophenyl)sulfonyl)-3,3-difluoropiperidine. MS (ESI): mass calcd. for $C_{21}H_{19}F_3N_4O_2S$, 448.12; m/z found, 449.2 [M+H]$^+$. $^1$H NMR (400 MHz, CD$_3$OD) δ 8.35-8.27 (m, 2H), 8.12-8.05 (m, 1H), 8.01-7.94 (m, 1H), 7.74-7.67 (m, 1H), 7.65-7.58 (m, 1H), 7.44-7.38 (m, 1H), 7.32-7.24 (m, 2H), 3.04-2.96 (m, 2H), 2.95-2.88 (m, 2H), 1.96-1.82 (m, 2H), 1.69-1.61 (m, 2H).

Example 51

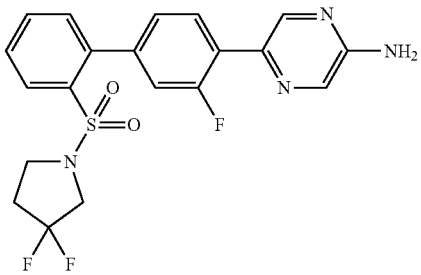

5-{2'-[(3,3-Difluoropyrrolidin-1-yl)sulfonyl]-3-fluorobiphenyl-4-yl}pyrazin-2-amine The title compound was prepared in a manner similar to that described in Example 448 using 5-(2-fluoro-4-(4,4,5,5-tetramethyl-1,3,2-dioxaborolan-2-yl)phenyl)-pyrazin-2-amine and 1-((2-bromophenyl)sulfonyl)-3,3-difluoropyrrolidine. MS (ESI): mass calcd. for $C_{20}H_{17}F_3N_4O_2S$, 434.10; m/z found, 435.2 [M+H]$^+$. $^1$H NMR (400 MHz, CD$_3$OD) δ 8.35 (d, J=1.3, 1H), 8.27 (d, J=1.4, 1H), 8.11 (d, J=7.9, 1H), 7.99 (m, 1H), 7.77-7.69 (m, 1H), 7.67-7.59 (m, 1H), 7.47-7.40 (m, 1H), 7.34-7.25 (m, 2H), 3.23 (t, J=12.9, 2H), 3.14 (t, J=7.3, 2H), 2.28-2.14 (m, 2H).

Example 52

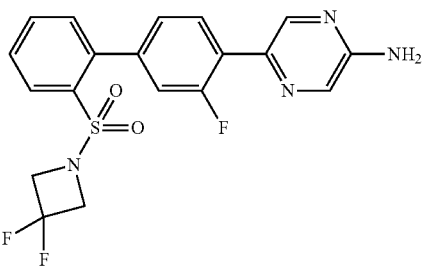

5-{2'-[(3,3-Difluoroazetidin-1-yl)sulfonyl]-3-fluorobiphenyl-4-yl}pyrazin-2-amine The title compound was prepared in a manner similar to that described in Example 448 using 5-(2-fluoro-4-(4,4,5,5-tetramethyl-1,3,2-dioxaborolan-2-yl)phenyl)-pyrazin-2-amine and 1-((2-bromophenyl)sulfonyl)-3,3-difluoroazetidine. MS (ESI): mass calcd. for $C_{19}H_{15}F_3N_4O_2S$, 420.09; m/z found, 421.2 [M+H]$^+$. $^1$H NMR (400 MHz, CD$_3$OD) δ 8.37-8.26 (m, 2H), 8.14-8.07 (m, 1H), 8.02-7.95 (m, 1H), 7.77-7.69 (m, 1H), 7.66-7.57 (m, 1H), 7.48-7.40 (m, 1H), 7.35-7.24 (m, 2H), 4.02-3.92 (m, 4H).

Example 53

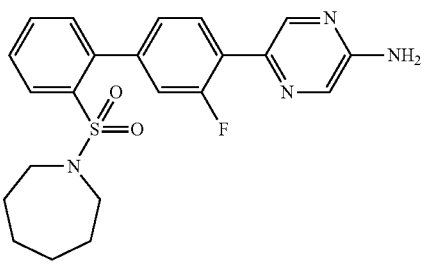

5-[2'-(Azepan-1-ylsulfonyl)-3-fluorobiphenyl-4-yl]pyrazin-2-amine

The title compound was prepared in a manner similar to that described in Example 448 using 5-(2-fluoro-4-(4,4,5,5-tetramethyl-1,3,2-dioxaborolan-2-yl)phenyl)-pyrazin-2-amine and 1-((2-bromophenyl)sulfonyl)azepane. MS (ESI): mass calcd. for $C_{22}H_{23}FN_4O_2S$, 426.15; m/z found, 427.2 [M+H]$^+$. $^1$H NMR (400 MHz, CD$_3$OD) δ 8.37 (s, 1H), 8.21 (s, 1H), 8.02 (d, J=7.9, 1H), 7.96 (t, J=8.2, 1H), 7.66 (m, 1H), 7.60-7.55 (m, 1H), 7.38 (d, J=6.5, 1H), 7.31-7.24 (m, 2H), 1.63-1.52 (m, 12H).

Example 54

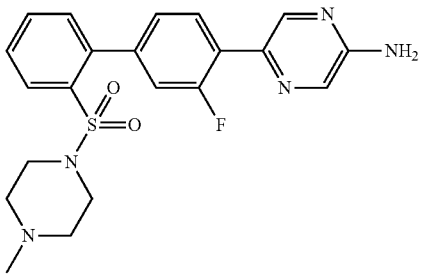

5-{3-Fluoro-2'-[(4-methylpiperazin-1-yl)sulfonyl]biphenyl-4-yl}pyrazin-2-amine

The title compound was prepared in a manner similar to that described in Example 448 using 5-(2-fluoro-4-(4,4,5,5-tetramethyl-1,3,2-dioxaborolan-2-yl)phenyl)-pyrazin-2-amine and 1-((2-bromophenyl)sulfonyl)-4-methylpiperazine. MS (ESI): mass calcd. for $C_{21}H_{22}FN_5O_2S$, 427.15; m/z found, 428.2 [M+H]$^+$. $^1$H NMR (400 MHz. CD$_3$OD) δ 8.37 (m, 1H), 8.23 (d, J=1.4, 1H), 8.16-8.12 (m, 1H), 8.02-7.96 (m, 1H), 7.78-7.73 (m, 1H), 7.68-7.62 (m, 1H), 7.48-7.45 (m, 1H), 7.34 (s, 1H), 7.32-7.30 (m, 1H), 3.61-3.33 (m, 4H), 3.01-2.70 (m, 7H).

Example 55

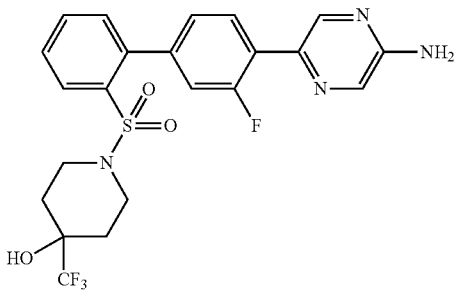

1-{[4'-(5-Aminopyrazin-2-yl)-3'-fluorobiphenyl-2-yl]sulfonyl}-4-(trifluoromethyl)piperidin-4-ol The title compound was prepared in a manner similar to that described in Example 448 using 5-(2-fluoro-4-(4,4,5,5-tetramethyl-1,3,2-dioxaborolan-2-yl)phenyl)-pyrazin-2-amine and 1-((2-bromophenyl)sulfonyl)-4-(trifluoromethyl)piperidin-4-d. MS (ESI): mass calcd. for $C_{22}H_{20}F_4N_4O_3S$, 496.12; m/z found, 497.1 [M+H]$^+$. $^1$H NMR (400 MHz, CD$_3$OD) δ 8.38 (s, 1H), 8.23 (d, J=1.1, 1H), 8.15-8.11 (m, 1H), 7.94 (m, 1H), 7.75-7.67 (m, 1H), 7.64-7.58 (m, 1H), 7.45-7.41 (m, 1H), 7.35-7.27 (m, 2H), 3.29-3.22 (m, 2H), 2.79-2.64 (m, 2H), 1.65-1.48 (m, 4H).

Example 56

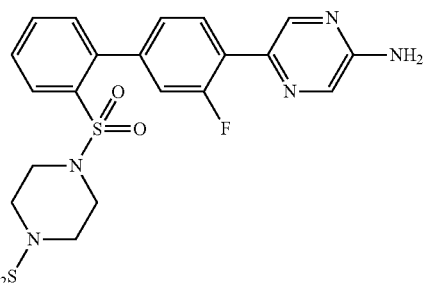

5-{3-Fluoro-2'-{[4-(methylsulfonyl)piperazin-1-yl)sulfonyl}biphenyl-4-yl)pyrazin-2-amine The title compound was prepared in a manner similar to that described in Example 448 using 5-(2-fluoro-4-(4,4,5,5-tetramethyl-1,3,2-dioxaborolan-2-yl)phenyl)-pyrazin-2-amine and 1-((2-bromophenyl)sulfonyl)-4-(methylsulfonyl)piperazine. MS (ESI): mass calcd. for $C_{21}H_{22}FN_5O_4S_2$, 491.11; m/z found, 492.1 [M+H]$^+$. $^1$H NMR (400 MHz, CD$_3$OD) δ 8.37 (s, 1H), 8.23 (s, 1H), 8.13 (d, J=7.0, 1H), 7.97 (m, 1H), 7.77-7.71 (m, 1H), 7.67-7.61 (m, 1H), 7.46 (d, J=6.4, 1H), 7.39-7.32 (m, 2H), 3.03-2.94 (m, 8H), 2.78 (s, 3H).

Example 57

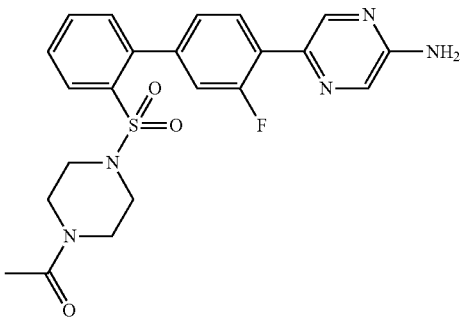

5-{2'-[(4-Acetylpiperazin-1-yl)sulfonyl]-3-fluorobiphenyl-4-yl}pyrazin-2-amine

The title compound was prepared in a manner similar to that described in Example 448 using 5-(2-fluor-4-(4,4,5,5-tetramethyl-1,3,2-dioxaborolan-2-yl)phenyl)pyrazin-2-amine and 1-(4-((2-bromophenyl)sulfonyl)piperazin-1-yl)ethanone. MS (ESI): mass calcd. for $C_{22}H_{22}FN_5O_3S$, 455.14; m/z found, 456.1 [M+H]$^+$. $^1$H NMR (400 MHz, CD$_3$OD) δ 8.34 (d, J=6.0, 2H), 8.11-8.08 (m, 1H), 8.00 (m, 1H), 7.75-7.70 (m, 1H), 7.65-7.60 (m, 1H), 7.45-7.41 (m, 1H), 7.37-7.29 (m, 2H), 3.43-3.34 (m, 4H), 2.96-2.81 (m, 4H), 2.02 (s, 3H).

Example 58

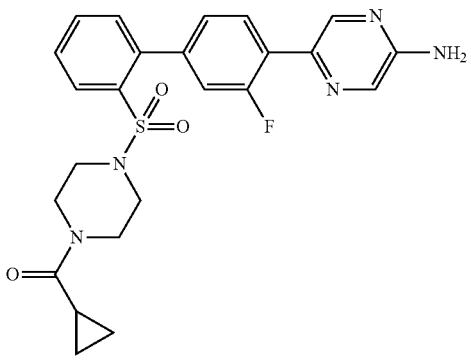

5-(2'-{[4-(Cyclopropylcarbonyl)piperazin-1-yl]sulfonyl}-3-fluorobiphenyl-4-yl)pyrazin-2-amine The title compound was prepared in a manner similar to that described in Example 448 using 5-(2-fluoro-4-(4,4,5,5-tetramethyl-1,3,2-dioxaborolan-2-yl)phenyl)-pyrazin-2-amine and (4-((2-bromophenyl)sulfonyl)piperazin-1-yl)(cyclopropyl)-methanone. MS (ESI): mass calcd. for $C_{24}H_{24}FN_5O_3S$, 481.16: m/z found, 482.1 [M+H]$^+$. $^1$H NMR (400 MHz, CDCl$_3$) δ 8.63-8.59 (m, 1H), 8.16-8.10 (m, 2H), 8.00 (m, 1H), 7.67-7.62 (m, 1H), 7.58-7.53 (m, 1H), 7.39-7.36 (m, 1H), 7.32-7.30 (m, 1H), 7.28 (s, 1H), 4.76 (s, 2H), 3.48 (s, 4H), 2.94-2.82 (m, 4H), 1.63-1.54 (m, 1H), 0.97-0.89 (m, 2H), 0.79-0.70 (m, 2H).

Example 59

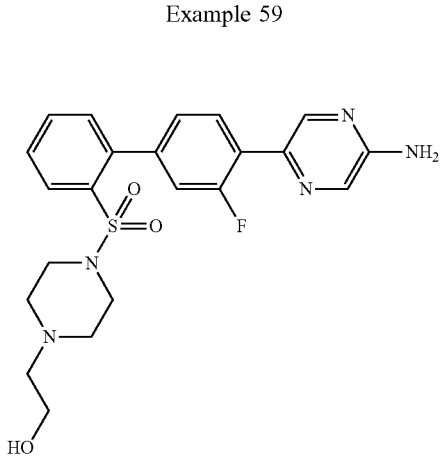

2-(4-{[4'-(5-Aminopyrazin-2-yl)-3'-fluorobiphenyl-2-yl]sulfonyl}piperazin-1-yl)ethanol The title compound was prepared in a manner similar to that described in Example 448 using 5-(2-fluoro-4-(4,4,5,5-tetramethyl-1,3,2-dioxaborolan-2-yl)phenyl)-pyrazin-2-amine and 2-(4-((2-bromophenyl)sulfonyl)piperazin-1-yl) ethanol. MS (ESI): mass calcd. for $C_{22}H_{24}FN_5O_3S$, 457.16; m/z found, 458.1 [M+H]$^+$. $^1$H NMR (400 MHz, CD$_3$OD) δ 8.38 (m, 1H), 8.21 (d, J=1.5, 1H), 8.16-8.13 (m, 1H), 7.98 (m, 1H), 7.79-7.73 (m, 1H), 7.68-7.63 (m, 1H), 7.49-7.45 (m, 1H), 7.36-7.30 (m, 2H), 3.86-3.78 (m, 2H), 3.66-3.32 (m, 4H), 3.24-3.20 (m, 2H), 3.15-2.72 (m, 4H).

Example 60

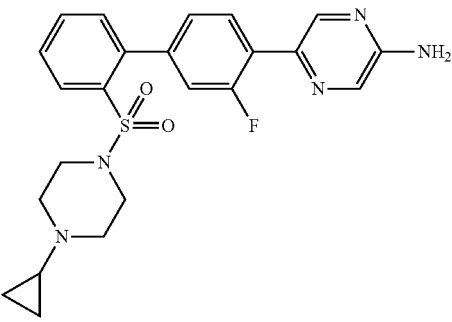

5-{2'-[(4-Cyclopropylpiperazin-1-yl)sulfonyl]-3-fluorobiphenyl-4-yl}pyrazin-2-amine The title compound was prepared in a manner similar to that described in Example 448 using 5-(2-fluoro-4-(4,4,5,5-tetramethyl-1,3,2-dioxaborolan-2-yl)phenyl)-pyrazin-2-amine and 1-((2-bromophenyl)sulfonyl)-4-cyclopropylpiperazine. MS (ESI): mass calcd. for $C_{23}H_{24}FN_5O_2S$, 453.16; m/z found, 454.1 [M+H]$^+$. $^1$H NMR (400 MHz, CD$_3$OD) δ 8.40 (s, 1H), 8.18-8.12 (m, 2H), 7.97 (m, 1H), 7.79-7.74 (m, 1H), 7.68-7.63 (m, 1H), 7.49-7.46 (m, 1H), 7.34-7.30 (m, 2H), 3.28-2.98 (d, J=1.6, 8H), 2.82-2.75 (m, 1H), 0.96-0.85 (m, 4H).

Example 61

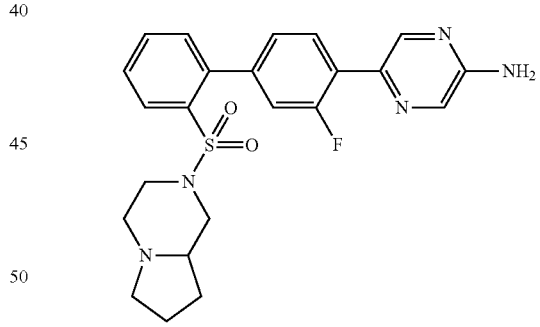

racemic 5-[3-Fluoro-2'-(hexahydropyrrolo[1,2-a]pyrazin-2(1H)-ylsulfonyl)biphenyl-4-yl]pyrazin-2-amine The title compound was prepared in a manner similar to that described in Example 448 using 5-(2-fluoro-4-(4,4,5,5-tetramethyl-1,3,2-dioxaborolan-2-yl)phenyl)-pyrazin-2-amine and racemic 2-((2-bromophenyl)sulfonyl)octahydropyrrolo[1,2-a]pyrazine. MS (ESI): mass calcd. for $C_{23}H_{24}FN_5O_2S$, 453.16; m/z found, 454.1 [M+H]$^+$. $^1$H NMR (400 MHz, CD$_3$OD) δ 8.37 (d, J=1.4, 1H), 8.24 (d, J=1.4, 1H), 8.17-8.13 (m, 1H), 7.99 (m, 1H), 7.78-7.73 (m, 1H), 7.68-7.63 (m, 1H), 7.48-7.45 (m, 1H), 7.36-7.30 (m, 2H), 3.89-3.35 (m, 4H), 3.26-2.53 (m, 6H), 2.18-1.97 (m, 3H).

Example 62

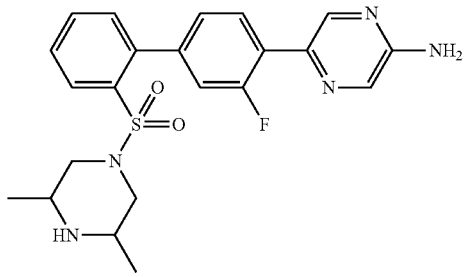

racemic 5-{2'-[(3,5-Dimethylpiperazin-1-yl)sulfonyl]-3-fluorobiphenyl-4-yl}pyrazin-2-amine The title compound was prepared in a manner similar to that described in Example 448 using 5-(2-fluoro-4-(4,4,5,5-tetramethyl-1,3,2-dioxaborolan-2-yl)phenyl)-pyrazin-2-amine and Racemic-1-((2-bromophenyl)sulfonyl)-3,5-dimethylpiperazine. MS (ESI): mass calcd. for $C_{22}H_{24}FN_5O_2S$, 441.16; m/z found, 442.1 [M+H]$^+$. $^1$H NMR (400 MHz, CD$_3$OD) δ 8.37 (s, 1H), 8.24 (d, J=1.4, 1H), 8.17-8.14 (m, 1H), 7.99 (m, 1H), 7.79-7.73 (m, 1H), 7.68-7.63 (m, 1H), 7.49-7.46 (m, 1H), 7.37-7.32 (m, 2H), 3.49-3.42 (m, 2H), 3.14-3.01 (m, 2H), 2.47-2.39 (m, 2H), 1.17 (d, J=6.6, 6H).

Example 63

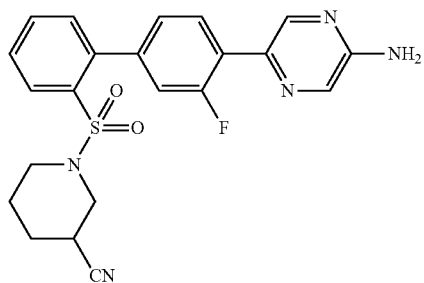

racemic 1-{[4'-(5-Aminopyrazin-2-yl)-3'-fluorobiphenyl-2-yl]sulfonyl}piperidine-3-carbonitrile The title compound was prepared in a manner similar to that described in Example 448 using 5-(2-fluoro-4-(4,4,5,5-tetramethyl-1,3,2-dioxaborolan-2-yl)phenyl)-pyrazin-2-amine and racemic 1-((2-bromophenyl)sulfonyl)piperidine-3-carbonitrile. MS (ESI): mass calcd. for $C_{22}H_{20}FN_5O_2S$, 437.13; m/z found, 438.1 [M+H]$^+$. $^1$H NMR (400 MHz, CD$_3$OD) δ 8.35 (s, 1H), 8.29 (d, J=1.1, 1H), 8.11-8.07 (m, 1H), 7.98 (m, 1H), 7.74-7.68 (m, 1H), 7.65-7.60 (m, 1H), 7.44-7.40 (m, 1H), 7.36-7.30 (m, 2H), 3.06-3.02 (m, 2H), 2.90-2.86 (m, 2H), 2.80-2.74 (m, 1H), 1.89-1.80 (m, 1H), 1.77-1.61 (m, 2H), 1.53-1.42 (m, 1H).

Example 64

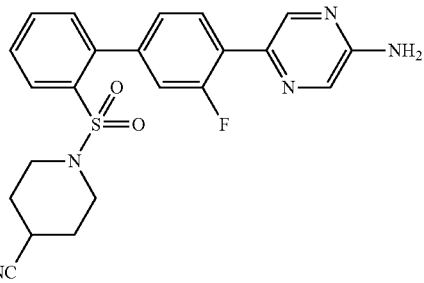

1-{[4'-(5-Aminopyrazin-2-yl)-3'-fluorobiphenyl-2-yl]sulfonyl}piperidine-4-carbonitrile The title compound was prepared in a manner similar to that described in Example 448 using 5-(2-fluoro-4-(4,4,5,5-tetramethyl-1,3,2-dioxaborolan-2-yl)phenyl)-pyrazin-2-amine and 1-((2-bromophenyl)sulfonyl)piperidine-4-carbonitrile. MS (ESI): mass calcd. for $C_{22}H_{20}FN_5O_2S$, 437.13; m/z found, 438.1 [M+H]$^+$. $^1$H NMR (400 MHz, CD$_3$OD) δ 8.35 (s, 1H), 8.29 (d, J=1.1, 1H), 8.12-8.09 (m, 1H), 7.99 (m, 1H), 7.74-7.69 (m, 1H), 7.65-7.60 (m, 1H), 7.45-7.42 (m, 1H), 7.34 (s, 1H), 7.32-7.30 (m, 1H), 3.10-3.02 (m, 2H), 2.86-2.73 (m, 3H), 1.82-1.73 (m, 2H), 1.64-1.53 (m, 2H).

Example 65

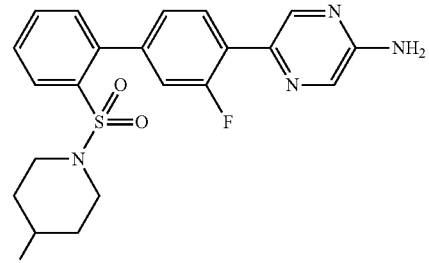

5-{2'-[(4-Aminopiperidin-1-yl)sulfonyl]-3-fluorobiphenyl-4-yl}pyrazin-2-amine

The title compound was prepared in a manner similar to that described in Example 448 using 5-(2-fluoro-4-(4,4,5,5-tetramethyl-1,3,2-dioxaborolan-2-yl)phenyl)-pyrazin-2-amine and 1-((2-bromophenyl)sulfonyl)piperidin-4-amine. MS (ESI): mass calcd. for $C_{21}H_{22}FN_5O_2S$, 427.15; m/z found, 428.1 [M+H]$^+$. $^1$H NMR (400 MHz, CD$_3$OD) δ 8.36 (s, 1H), 8.25-8.23 (d, J=1.4, 1H), 8.11-8.08 (m, 1H), 7.96 (m, 1H), 7.74-7.69 (m, 1H), 7.65-7.60 (m, 1H), 7.45-7.41 (m, 1H), 7.32-7.29 (m, 1H), 7.28 (s, 1H), 3.47-3.40 (m, 2H), 3.18-3.08 (m, 1H), 2.57-2.43 (m, 2H), 1.91-1.84 (m, 2H), 1.51-1.39 (m, 2H).

Example 66

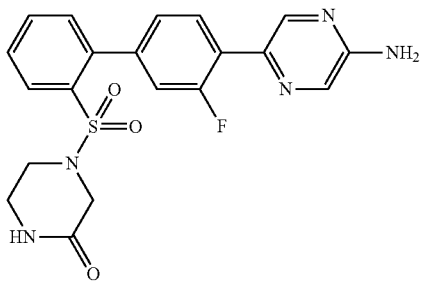

4-{[4'-(5-Aminopyrazin-2-yl)-3'-fluorobiphenyl-2-yl]sulfonyl}piperazin-2-one

The title compound was prepared in a manner similar to that described in Example 448 using 5-(2-fluoro-4-(4,4,5,5-tetramethyl-1,3,2-dioxaborolan-2-yl)phenyl)-pyrazin-2-amine and 4-((2-bromophenyl)sulfonyl)piperazin-2-one. MS (ESI): mass calcd. for $C_{20}H_{18}FN_5O_3S$, 427.11; m/z found, 428.2 [M+H]$^+$. $^1$H NMR (400 MHz, CD$_3$OD) δ 8.37 (s, 1H), 8.27 (d, J=1.4, 1H), 8.17-8.13 (m, 1H), 7.98 (m, 1H), 7.77-7.72 (m, 1H), 7.67-7.62 (m, 1H), 7.47-7.43 (m, 1H), 7.34-7.26 (m, 2H), 3.39 (s, 2H), 3.14 (s, 4H).

Example 67

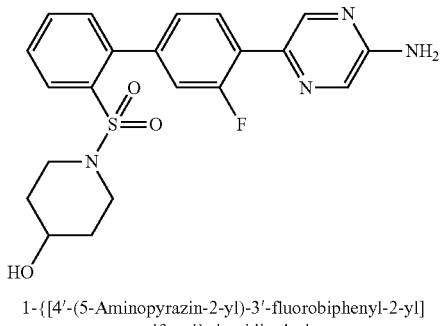

1-{[4'-(5-Aminopyrazin-2-yl)-3'-fluorobiphenyl-2-yl]sulfonyl}piperidin-4-ol

The title compound was prepared in a manner similar to that described in Example 448 using 5-(2-fluoro-4-(4,4,5,5-tetramethyl-1,3,2-dioxaborolan-2-yl)phenyl)-pyrazin-2-amine and 1-((2-bromophenyl)sulfonyl)piperidin-4-ol. MS (ESI): mass calcd. for $C_{21}H_{21}FN_4O_3S$, 428.13; m/z found, 429.1 [M+H]$^+$. $^1$H NMR (400 MHz, CD$_3$OD) δ 8.36-8.31 (m, 2H), 8.10-8.06 (m, 1H), 7.99 (m, 1H), 7.73-7.67 (m, 1H), 7.64-7.58 (m, 1H), 7.44-7.40 (m, 1H), 7.34-7.28 (m, 2H), 3.66-3.55 (m, 1H), 3.20-3.08 (m, 2H), 2.71-2.61 (m, 2H), 1.72-1.63 (m, 2H), 1.39-1.26 (m, 2H).

Example 68

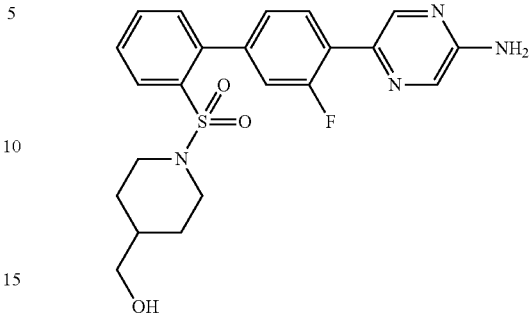

(1-{[4'-(5-Aminopyrazin-2-yl)-3'-fluorobiphenyl-2-yl]sulfonyl}piperidin-4-yl)methanol The title compound was prepared in a manner similar to that described in Example 448 using 5-(2-fluoro-4-(4,4,5,5-tetramethyl-1,3,2-dioxaborolan-2-yl)phenyl)-pyrazin-2-amine and (1-((2-bromophenyl)sulfonyl)piperidin-4-yl)methanol. MS (ESI): mass calcd. for $C_{22}H_{23}FN_4O_3S$, 442.15; m/z found, 443.1 [M+H]$^+$. $^1$H NMR (400 MHz, CD$_3$OD) δ 8.36-8.29 (m, 2H), 8.11-8.07 (m, 1H), 7.98 (m, 1H), 7.74-7.67 (m, 1H), 7.64-7.59 (m, 1H), 7.44-7.41 (m, 1H), 7.36-7.29 (m, 2H), 3.40-3.32 (m, 4H), 2.46-2.36 (m, 2H), 1.59 (d, J=10.5, 2H), 1.48-1.36 (m, 1H), 1.01-0.89 (m, 2H).

Example 69

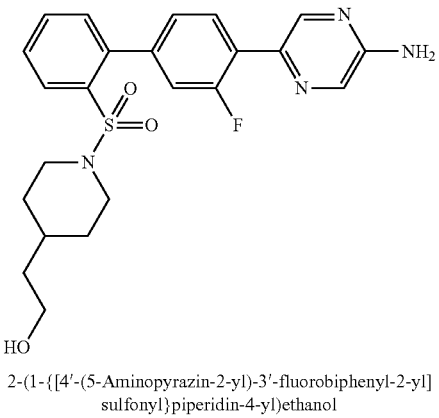 [SMILES: Nc1cnc(-c2ccc(-c3ccccc3S(=O)(=O)N3CCC(CCO)CC3)cc2F)cn1]

2-(1-{[4'-(5-Aminopyrazin-2-yl)-3'-fluorobiphenyl-2-yl]sulfonyl}piperidin-4-yl)ethanol The title compound was prepared in a manner similar to that described in Example 448 using 5-(2-fluoro-4-(4,4,5,5-tetramethyl-1,3,2-dioxaborolan-2-yl)phenyl)-pyrazin-2-amine and 2-(1-((2-bromophenyl)sulfonyl)piperidin-4-yl)ethanol. MS (ESI): mass calcd. for $C_{23}H_{25}FN_4O_3S$, 456.16; m/z found, 457.2 [M+H]$^+$. $^1$H NMR (400 MHz, CD$_3$OD) δ 8.34 (s, 1H), 8.31 (d, J=1.2, 1H), 8.10-8.07 (m, 1H), 7.98 (m, 1H), 7.73-7.67 (m, 1H), 7.64-7.58 (m, 1H), 7.44-7.41 (m, 1H), 7.34 (s, 1H), 7.32-7.30 (m, 1H), 3.56-3.48 (m, 2H), 3.32 (d, J=4.5, 2H), 2.45-2.36 (m, 2H), 1.61-1.54 (m, 2H), 1.46-1.34 (m, 3H), 1.01-0.87 (m, 2H).

Example 70

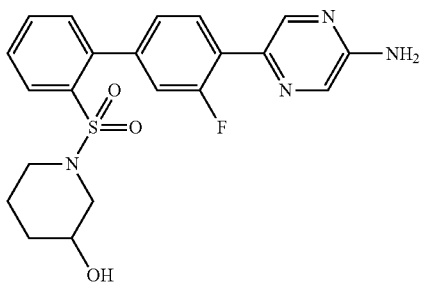

racemic 1-{[4'-(5-Aminopyrazin-2-yl)-3'-fluorobiphenyl-2-yl]sulfonyl}piperidin-3-ol The title compound was prepared in a manner similar to that described in Example 448 using 5-(2-fluoro-4-(4,4,5,5-tetramethyl-1,3,2-dioxaborolan-2-yl)phenyl)-pyrazin-2-amine and racemic-1-((2-bromophenyl)sulfonyl)piperidin-3-ol. MS (ESI): mass calcd. for $C_{21}H_{21}FN_4O_3S$, 428.13; m/z found, 429.1 [M+H]$^+$. $^1$H NMR (400 MHz, CD$_3$OD) δ 8.34 (s, 1H), 8.31 (d, J=1.4, 1H), 8.11-8.06 (m, 1H), 8.01-7.96 (m, 1H), 7.73-7.68 (m, 1H), 7.64-7.59 (m, 1H), 7.44-7.40 (m, 1H), 7.34-7.32 (m, 1H), 7.31-7.29 (m, 1H), 3.44-3.35 (m, 1H), 3.27-3.21 (m, 1H), 3.15-3.06 (m, 1H), 2.48-2.38 (m, 1H), 2.27-2.21 (m, 1H), 1.88-1.79 (m, 1H), 1.68-1.59 (m, 1H), 1.41-1.28 (m, 1H), 1.26-1.15 (m, 1H).

Example 71

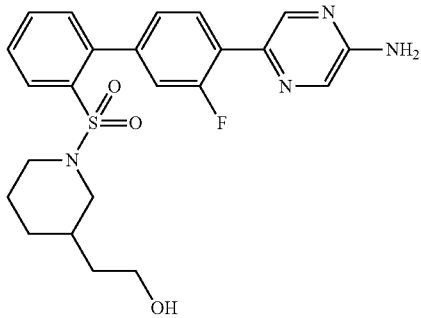

racemic-2-(1-{[4'-(5-Aminopyrazin-2-yl)-3'-fluorobiphenyl-2-yl]sulfonyl}piperidin-3-yl)ethanol The title compound was prepared in a manner similar to that described in Example 448 using 5-(2-fluoro-4-(4,4,5,5-tetramethyl-1,3,2-dioxaborolan-2-yl)phenyl)-pyrazin-2-amine and racemic-2-(1-((2-bromophenyl)sulfonyl)piperidin-3-yl)ethanol. MS (ESI): mass calcd. for $C_{23}H_{25}FN_4O_3S$, 456.16; m/z found, 457.1 [M+H]$^+$. $^1$H NMR (400 MHz, CD$_3$OD) δ 8.36-8.31 (m, 2H), 8.10-8.05 (m, 1H), 8.01-7.95 (m, 1H), 7.73-7.67 (m, 1H), 7.64-7.58 (m, 1H), 7.44-7.40 (m, 1H), 7.36-7.29 (m, 2H), 3.52-3.40 (m, 2H), 3.26-3.16 (m, 2H), 2.48-2.36 (m, 1H), 2.14-2.08 (m, 1H), 1.77-1.67 (m, 1H), 1.62-1.53 (m, 1H), 1.49-1.37 (m, 1H), 1.36-1.25 (m, 3H), 1.02-0.89 (m, 1H).

Example 72

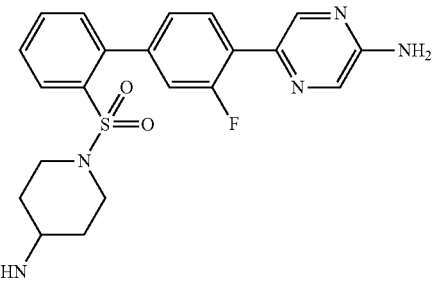

5-(3-Fluoro-2'-{[4-(methylamino)piperidin-1-yl]sulfonyl}biphenyl-4-yl)pyrazin-2-amine The title compound was prepared in a manner similar to that described in Example 448 using 5-(2-fluoro-4-(4,4,5,5-tetramethyl-1,3,2-dioxaborolan-2-yl)phenyl)-pyrazin-2-amine and 1-((2-bromophenyl)sulfonyl)-N-methylpiperidin-4-amine. MS (ESI): mass calcd. for $C_{22}H_{24}FN_5O_2S$, 441.16; m/z found, 442.1 [M+H]$^+$. $^1$H NMR (400 MHz, CD$_3$OD) δ 8.37 (s, 1H), 8.21 (d, J=1.4, 1H), 8.12-8.09 (m, 1H), 7.96 (m, 1H), 7.75-7.70 (m, 1H), 7.65-7.60 (m, 1H), 7.45-7.41 (m, 1H), 7.32-7.30 (m, 1H), 7.28 (s, 1H), 3.49-3.42 (m, 2H), 3.10-3.01 (m, 1H), 2.63 (s, 3H), 2.54-2.42 (m, 2H), 2.00-1.92 (m, 2H), 1.47-1.35 (m, 2H).

Example 73

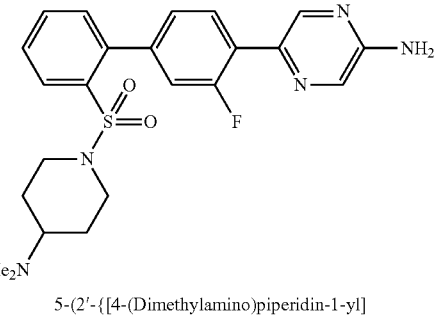

5-(2'-{[4-(Dimethylamino)piperidin-1-yl]sulfonyl}-3-fluorobiphenyl-4-yl)pyrazin-2-amine The title compound was prepared in a manner similar to that described in Example 448 using 5-(2-fluoro-4-(4,4,5,5-tetramethyl-1,3,2-dioxaborolan-2-yl)phenyl)-pyrazin-2-amine and 1-((2-bromophenyl)sulfonyl)-N,N-dimethylpiperidin-4-amine. MS (ESI): mass calcd. for $C_{23}H_{26}FN_5O_2S$, 455.18; m/z found, 456.2 [M+H]$^+$. $^1$H NMR (400 MHz, CD$_3$OD) δ 8.38 (m, 1H), 8.20 (d, J=1.5, 1H), 8.14-8.10 (m, 1H), 7.99-7.94 (m, 1H), 7.76-7.71 (m, 1H), 7.66-7.61 (m, 1H), 7.47-7.43 (m, 1H), 7.36-7.30 (m, 2H), 3.52-3.45 (m, 2H), 3.26-3.16 (m, 1H), 2.78 (s, 6H), 2.55-2.44 (m, 2H), 1.93 (d, J=11.6, 2H), 1.48-1.36 (m, 2H).

Example 74

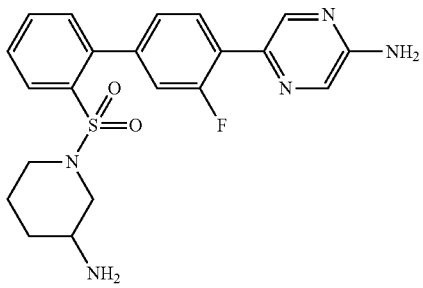

racemic 5-{2'-[(3-Aminopiperidin-1-yl)sulfonyl]-3-fluorobiphenyl-4-yl}pyrazin-2-amine The title compound was prepared in a manner similar to that described in Example 448 using 5-(2-fluoro-4-(4,4,5,5-tetramethyl-1,3,2-dioxaborolan-2-yl)phenyl)-pyrazin-2-amine and racemic-1-((2-bromophenyl)sulfonyl)piperidin-3-amine. MS (ESI): mass calcd. for $C_{26}H_{30}FN_5O_4S$, 427.15; m/z found, 428.1 [M+H]$^+$. $^1$H NMR (400 MHz, CD$_3$OD) δ 8.45 (s, 1H), 8.33 (s, 1H), 8.11-8.07 (m, 1H), 8.03 (m, 1H), 7.76-7.70 (m, 1H), 7.67-7.62 (m, 1H), 7.46-7.42 (m, 1H), 7.36-7.29 (m, 2H), 3.40-3.41 (m, 1H), 3.13-3.02 (m, 2H), 2.66-2.60 (m, 2H), 2.01-1.92 (m, 1H), 1.78-1.67 (m, 1H), 1.55-1.42 (m, 2H).

Example 75

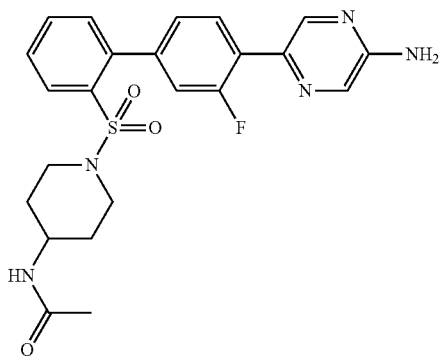

N-(1-{[4'-(5-Aminopyrazin-2-yl)-3'-fluorobiphenyl-2-yl]sulfonyl}piperidin-4-yl)acetamide The title compound was prepared in a manner similar to that described in Example 448 using 5-(2-fluoro-4-(4,4,5,5-tetramethyl-1,3,2-dioxaborolan-2-yl)phenyl)-pyrazin-2-amine and N-(1-((2-bromophenyl)sulfonyl)piperidin-4-yl)acetamide. MS (ESI): mass calcd. for $C_{23}H_{24}FN_5O_3S$, 469.16; m/z found, 470.1 [M+H]$^+$. $^1$H NMR (400 MHz, DMSO-d$_6$) δ 8.41-8.38 (m, 1H), 8.08 (d, J=1.4, 1H), 8.01-7.97 (m, 1H), 7.90 (m, 1H), 7.80 (d, J=7.6, 1H), 7.77-7.72 (m, 1H), 7.68-7.63 (m, 1H), 7.46-7.42 (m, 1H), 7.33-7.24 (m, 2H), 3.61-3.50 (m, 1H), 3.26-3.18 (m, 2H), 2.59-2.52 (m, 2H), 1.76 (s, 3H), 1.67-1.59 (m, 2H), 1.27-1.15 (m, 2H).

Example 76

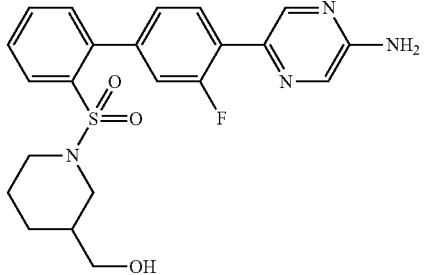

racemic (1-{[4'-(5-Aminopyrazin-2-yl)-3'-fluorobiphenyl-2-yl]sulfonyl}piperidin-3-yl)methanol The title compound was prepared in a manner similar to that described in Example 448 using 5-(2-fluoro-4-(4,4,5,5-tetramethyl-1,3,2-dioxaborolan-2-yl)phenyl)-pyrazin-2-amine and racemic (1-((2-bromophenyl)sulfonyl)piperidin-3-yl)methanol. MS (ESI): mass calcd. for $C_{22}H_{23}FN_4O_3S$, 442.15; m/z found, 443.1 [M+H]$^+$. $^1$H NMR (400 MHz, CD$_3$OD) δ 8.33 (d, J=8.7, 2H), 8.10-8.06 (m, 1H), 7.96 (m, 1H), 7.73-7.67 (m, 1H), 7.64-7.58 (m, 1H), 7.44-7.40 (m, 1H), 7.36-7.29 (m, 2H), 3.43-3.32 (m, 2H), 3.27-3.16 (m, 2H), 2.43-2.34 (m, 1H), 2.22-2.14 (m, 1H), 1.68-1.54 (m, 2H), 1.53-1.42 (m, 1H), 1.35-1.21 (m, 1H), 1.03-0.91 (m, 1H).

Example 77

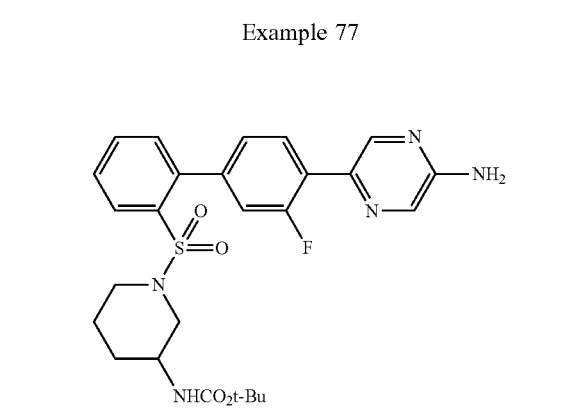

racemic tert-Butyl (1-{[4'-(5-aminopyrazin-2-yl)-3'-fluorobiphenyl-2-yl]sulfonyl}piperidin-3-yl)carbamate The title compound was prepared in a manner similar to that described in Example 448 using 5-(2-fluoro-4-(4,4,5,5-tetramethyl-1,3,2-dioxaborolan-2-yl)phenyl)-pyrazin-2-amine and racemic tert-butyl (1-((2-bromophenyl)sulfonyl)piperidin-3-yl)carbamate. MS (ESI): mass calcd. for $C_{26}H_{30}FN_5O_4S$, 527.20: m/z found, 528.3 [M+H]$^+$. $^1$H NMR (400 MHz, CD$_3$OD) δ 8.34 (d, J=9.1, 2H), 8.10-8.07 (m, 1H), 8.00 (m, 1H), 7.73-7.68 (m, 1H), 7.64-7.59 (m, 1H), 7.44-7.40 (m, 1H), 7.35-7.29 (m, 2H), 3.30-3.20 (m, 2H), 3.15-3.06 (m, 1H), 2.51-2.40 (m, 1H), 2.30-2.21 (m, 1H), 1.79-1.70 (m, 1H), 1.65-1.56 (m, 1H), 1.39-1.28 (m, 10H), 1.26-1.14 (m, 1H).

Example 78

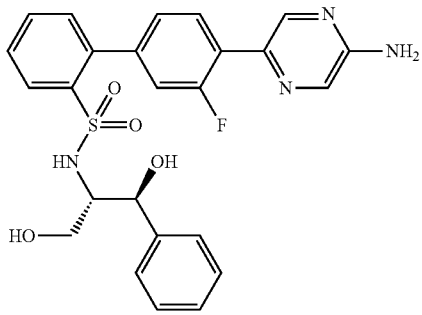

4'-(5-Aminopyrazin-2-yl)-3'-fluoro-N-[(1S,2S)-2-hydroxy-1-(hydroxymethyl)-2-phenylethyl]biphenyl-2-sulfonamide The title compound was prepared in a manner similar to that described in Example 448 using 5-(2-fluoro-4-(4,4,5,5-tetramethyl-1,3,2-dioxaborolan-2-yl)phenyl)-pyrazin-2-amine and 2-bromo-N-((1S,2S)-1,3-dihydroxy-1-phenylpropan-2-yl)benzenesulfonamide. MS (ESI): mass calcd. for $C_{25}H_{23}FN_4O_4S$, 494.14; m/z found, 495.2 $[M+H]^+$. $^1H$ NMR (400 MHz, CDCl$_3$) δ 8.45 (d, J=1.4, 1H), 8.10 (s, 1H), 7.87-7.80 (m, 2H), 7.55 (t, J=7.5, 1H), 7.43-7.36 (m, 2H), 7.30-7.14 (m, 8H), 4.89 (d, J=4.0, 1H), 3.65-3.57 (m, 1H), 3.36 (d, J=1.4, 2H).

Example 79

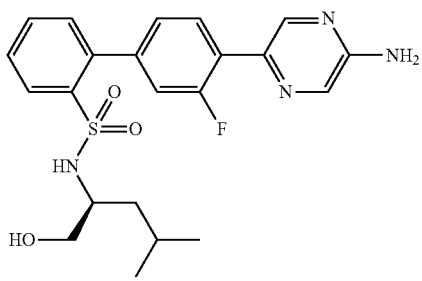

4'-(5-Aminopyrazin-2-yl)-3'-fluoro-N-[(1S)-1-(hydroxymethyl)-3-methylbutyl]biphenyl-2-sulfonamide The title compound was prepared in a manner similar to that described in Example 448 using 5-(2-fluoro-4-(4,4,5,5-tetramethyl-1,3,2-dioxaborolan-2-yl)phenyl)-pyrazin-2-amine and (S)-2-bromo-N-(1-hydroxy-4-methylpentan-2-yl)benzenesulfonamide. MS (ESI): mass calcd. for $C_{22}H_{25}FN_4O_3S$, 444.16; m/z found, 445.1 $[M+H]^+$. $^1H$ NMR (400 MHz, CD$_3$OD) δ 8.33 (s, 1H), 8.29 (d, J=1.4, 1H), 8.16-8.12 (m, 1H), 7.98-7.92 (m, 1H), 7.68-7.63 (m, 1H), 7.60-7.55 (m, 1H), 7.40-7.28 (m, 3H), 3.41-3.34 (m, 1H), 3.29-3.22 (m, 2H), 1.59-1.47 (m, 1H), 1.35-1.17 (m, 2H), 0.81 (d, J=6.7, 3H), 0.73 (d, J=6.5, 3H).

Example 80

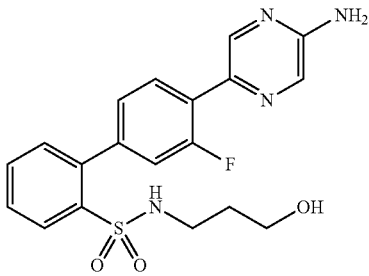

4'-(5-Aminopyrazin-2-yl)-3'-fluoro-N-(3-hydroxypropyl)biphenyl-2-sulfonamide

The title compound was prepared in a manner similar to that described in Example 448 using 5-(2-fluoro-4-(4,4,5,5-tetramethyl-1,3,2-dioxaborolan-2-yl)phenyl)-pyrazin-2-amine and 2-bromo-N-(3-hydroxypropyl)benzenesulfonamide. MS (ESI): mass calcd. for $C_{19}H_{19}FN_4O_3S$, 402.12; m/z found, 403.1 $[M+H]^+$. $^1H$ NMR (400 MHz, CD$_3$OD) δ 8.37 (d, J=1.2, 1H), 8.30 (s, 1H), 8.08-8.03 (m, 1H), 8.01-7.96 (m, 1H), 7.70-7.63 (m, 1H), 7.62-7.56 (m, 1H), 7.42-7.32 (m, 1H), 7.36-7.28 (m, 2H), 3.51 (t, J=6.2, 2H), 2.88 (t, J=7.0, 2H), 1.65-1.54 (m, 2H).

Example 81

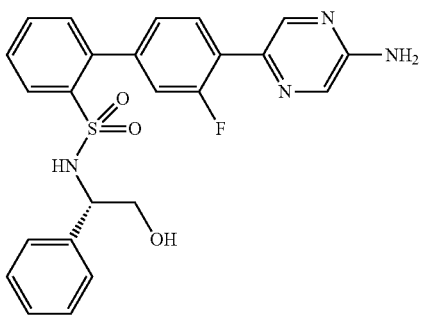

4'-(5-Aminopyrazin-2-yl)-3'-fluoro-N-[(1S)-2-hydroxy-1-phenylethyl]biphenyl-2-sulfonamide The title compound was prepared in a manner similar to that described in Example 448 using 5-(2-fluoro-4-(4,4,5,5-tetramethyl-1,3,2-dioxaborolan-2-yl)phenyl)-pyrazin-2-amine and (S)-2-bromo-N-(2-hydroxy-1-phenylethyl)benzenesulfonamide. MS (ESI): mass calcd. for $C_{24}H_{21}FN_4O_3S$, 464.13; m/z found, 465.1 $[M+H]^+$. $^1H$ NMR (400 MHz, CD$_3$OD) δ 8.30 (m, 2H), 8.05-8.01 (m, 1H), 7.85 (t, J=8.2, 1H), 7.61-7.56 (m, 1H), 7.50-7.44 (m, 1H), 7.26-7.19 (m, 4H), 7.10-6.97 (m, 4H), 4.20 (t, J=6.6, 1H), 3.69-3.58 (m, 2H).

Example 82

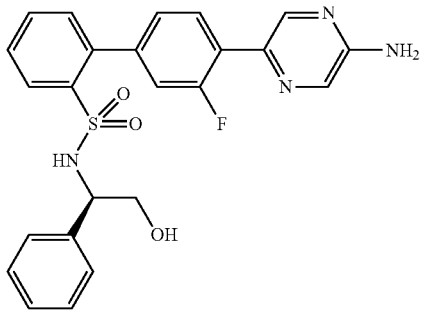

4'-(5-Aminopyrazin-2-yl)-3'-fluoro-N-[(1R)-2-hydroxy-1-phenylethyl]biphenyl-2-sulfonamide The title compound was prepared in a manner similar to that described in Example 448 using 5-(2-fluoro-4-(4,4,5,5-tetramethyl-1,3,2-dioxaborolan-2-yl)phenyl)-pyrazin-2-amine and (R)-2-bromo-N-(2-hydroxy-1-phenylethyl)benzenesulfonamide. MS (ESI): mass calcd. for $C_{24}H_{21}FN_4O_3S$, 464.13; m/z found, 465.1 [M+H]$^+$. $^1$H NMR (400 MHz, CD$_3$OD) δ 8.36-8.32 (m, 1H), 8.07-8.01 (m, 2H), 7.75 (t, J=8.2, 1H), 7.60-7.54 (m, 1H), 7.49-7.44 (m, 1H), 7.25-7.18 (m, 4H), 7.07-7.00 (m, 3H), 6.98-6.92 (m, 1H), 4.19 (t, J=6.6, 1H), 3.69-3.58 (m, 2H).

Example 83

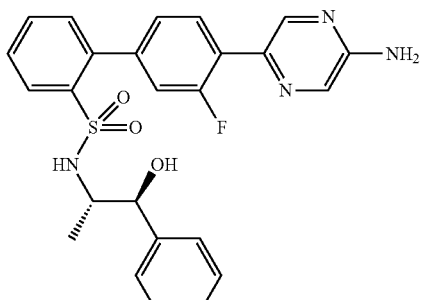

4'-(5-Aminopyrazin-2-yl)-3'-fluoro-N-[(1S,2R)-2-hydroxy-1-methyl-2-phenylethyl]biphenyl-2-sulfonamide The title compound was prepared in a manner similar to that described in Example 448 using 5-(2-fluoro-4-(4,4,5,5-tetramethyl-1,3,2-dioxaborolan-2-yl)phenyl)-pyrazin-2-amine and 2-bromo-N-((1S,2S)-1-hydroxy-1-phenylpropan-2-yl)benzenesulfonamide. MS (ESI): mass calcd. for $C_{25}H_{23}FN_4O_3S$, 478.15; m/z found, 479.1 [M+H]$^+$. $^1$H NMR (400 MHz, CD$_3$OD) δ 8.36 (s, 1H), 8.12-8.05 (m, 2H), 7.89-7.83 (m, 1H), 7.67-7.62 (m, 1H), 7.59-7.54 (m, 1H), 7.37-7.34 (m, 1H), 7.27-7.12 (m, 7H), 4.60 (t, J=4.4, 1H), 3.42-3.34 (m, 1H), 0.91-0.84 (m, 3H).

Example 84

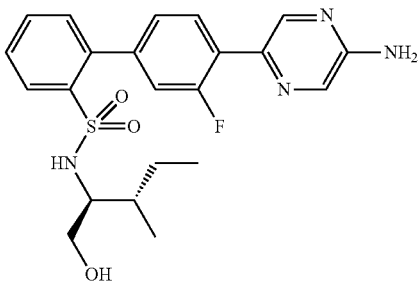

4'-(5-Aminopyrazin-2-yl)-3'-fluoro-N-[(1S,2S)-1-(hydroxymethyl)-2-methylbutyl]biphenyl-2-sulfonamide The title compound was prepared in a manner similar to that described in Example 448 using 5-(2-fluoro-4-(4,4,5,5-tetramethyl-1,3,2-dioxaborolan-2-yl)phenyl)-pyrazin-2-amine and 2-bromo-N-((2S,3S)-1-hydroxy-3-methylpentan-2-yl)benzenesulfonamide. MS (ESI): mass calcd. for $C_{22}H_{25}FN_4O_3S$, 444.16; m/z found, 445.2 [M+H]$^+$. $^1$H NMR (400 MHz, CD$_3$OD) δ 8.37 (s, 1H), 8.16-8.13 (m, 1H), 8.06 (d, J=1.4, 1H), 7.86 (m, 1H), 7.67-7.62 (m, 1H), 7.58-7.53 (m, 1H), 7.39-7.28 (m, 3H), 3.46-3.35 (m, 2H), 3.13 (q, J=5.4, 1H), 1.60-1.49 (m, 1H), 1.48-1.36 (m, 1H), 1.07-0.93 (m, 1H), 0.84-0.74 (m, 6H).

Example 85

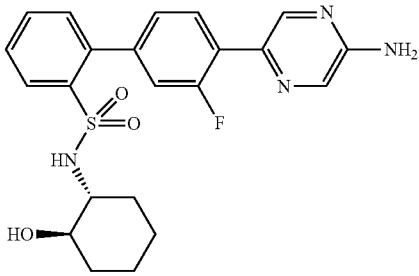

4'-(5-Aminopyrazin-2-yl)-3'-fluoro-N-[(1R,2R)-2-hydroxycyclohexyl]biphenyl-2-sulfonamide The title compound was prepared in a manner similar to that described in Example 448 using 5-(2-fluoro-4-(4,4,5,5-tetramethyl-1,3,2-dioxaborolan-2-yl)phenyl)-pyrazin-2-amine and 2-bromo-N-((1R,2R)-2-hydroxycyclohexyl)benzenesulfonamide. MS (ESI): mass calcd. for $C_{22}H_{23}FN_4O_3S$, 442.15; m/z found, 443.1 [M+H]$^+$. $^1$H NMR (400 MHz, CD$_3$OD) δ 8.37-8.30 (m, 2H), 8.21-8.16 (m, 1H), 7.97 (m, 1H), 7.68-7.62 (m, 1H), 7.60-7.54 (m, 1H), 7.40-7.32 (m, 3H), 3.26-3.18 (m, 1H), 2.87-2.79 (m, 1H), 1.94-1.77 (m, 2H), 1.67-1.50 (m, 2H), 1.26-1.09 (m, 4H).

Example 86

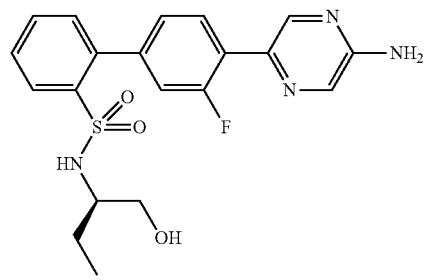

4′-(5-Aminopyrazin-2-yl)-3′-fluoro-N-[(1R)-1-(hydroxymethyl)propyl]biphenyl-2-sulfonamide The title compound was prepared in a manner similar to that described in Example 448 using 5-(2-fluoro-4-(4,4,5,5-tetramethyl-1,3,2-dioxaborolan-2-yl)phenyl)-pyrazin-2-amine and (R)-2-bromo-N-(1-hydroxybutan-2-yl)benzenesulfonamide. MS (ESI): mass calcd. for $C_{20}H_{21}FN_4O_3S$, 416.13; m/z found, 417.1 [M+H]$^+$. $^1$H NMR (400 MHz, CD$_3$OD) δ 8.32 (m, 2H), 8.16-8.12 (m, 1H), 7.96 (m, 1H), 7.68-7.63 (m, 1H), 7.60-7.55 (m, 1H), 7.40-7.30 (m, 3H), 3.43-3.35 (m, 1H), 3.33 (d, J=5.9, 1H), 3.12-3.05 (m, 1H), 1.60-1.48 (m, 1H), 1.42-1.28 (m, 1H), 0.79 (t, J=7.4, 3H).

Example 87

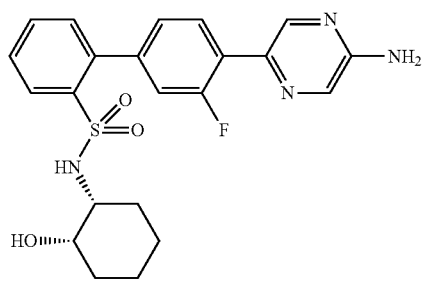

4′(5-Aminopyrazin-2-yl)-3′-fluoro-N-[(1R,2S)-2-hydroxycyclohexyl]biphenyl-2-sulfonamide The title compound was prepared in a manner similar to that described in Example 448 using 5-(2-fluoro-4-(4,4,5,5-tetramethyl-1,3,2-dioxaborolan-2-yl)phenyl)-pyrazin-2-amine and 2-bromo-N-((1R,2S)-2-hydroxycyclohexyl)benzenesulfonamide. MS (ESI): mass calcd. for $C_{22}H_{23}FN_4O_3S$, 442.15; m/z found, 443.2 [M+H]$^+$. $^1$H NMR (400 MHz, CD$_3$OD) δ 8.33 (s, 2H), 8.15-8.11 (m, 1H), 7.98 (m, 1H), 7.69-7.64 (m, 1H), 7.61-7.56 (m, 1H), 7.42-7.32 (m, 3H), 3.70-3.63 (m, 1H), 3.09-3.03 (m, 1H), 1.70-1.61 (m, 1H), 1.60-1.44 (m, 3H), 1.42-1.24 (m, 3H), 1.22-1.10 (m, 1H).

Example 88

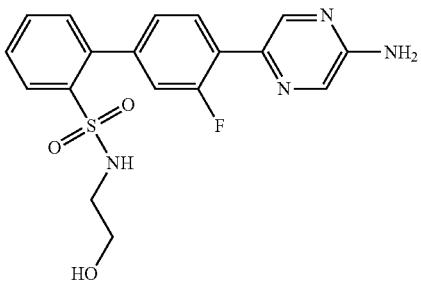

4′(5-Aminopyrazin-2-yl)-3′-fluoro-N-(2-hydroxyethyl)biphenyl-2-sulfonamide 5-(2-Fluoro-4-(4,4,5,5-tetramethyl-1,3,2-dioxaborolan-2-yl)phenyl)pyrazin-2-amine (40 mg, 0.13 mmol) and 2-bromo-N-(2-hydroxyethyl)benzenesulfonamide (53 mg, 0.19 mmol) were added to a 5 mL sealable vial equipped with a stir bar. 1,4-Dioxane (0.7 mL) and Na$_2$CO$_3$ (0.3 mL, 2 M) were added. Argon was bubbled through the solvent while it was rapidly stirred for 10 min before adding Pd(dppf)Cl$_2$.CH$_2$Cl$_2$ (5 mg, 0.006 mmol) and heating the mixture heated 15 hours at 80° Celsius. The reaction was cooled to rt, diluted with 2 mL of ethylacetate, 2 mL of water and extracted with of ethyl acetate (3×10 mL). The combined organic extracts were then dried with Na$_2$SO$_4$ and concentrated to dryness. The crude product was purified by HPLC to give the title compound. MS (ESI): mass calcd. for $C_{18}H_{17}FN_4O_3S$, 388.10; m/z found, 389.1 [M+H]$^+$. $^1$H NMR (500 MHz, CD$_3$OD) δ 8.43-8.37 (dd, J=2.2, 1.5, 1H), 8.11-8.06 (m, 2H), 7.93-7.86 (m, 1H), 7.70-7.64 (m, 1H), 7.62-7.56 (m, 1H), 7.44-7.38 (dd, J=7.6, 1.3, 1H), 7.35-7.27 (m, 2H), 3.49-3.44 (t, J=5.9, 2H), 2.90-2.84 (t, J=5.9, 2H).

Example 89

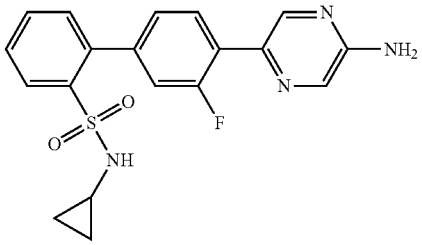

4′(5-Aminopyrazin-2-yl)-N-cyclopropyl-3′-fluorobiphenyl-2-sulfonamide

The title compound was prepared in a manner similar to that described in Example 88 using 2-bromo-N-cyclopropylbenzenesulfonamide. MS (ESI): mass calcd. for $C_{19}H_{17}FN_4O_2S$, 384.11; m/z found, 385.1 [M+H]$^+$. $^1$H NMR (500 MHz, CD$_3$OD) δ 8.39-8.31 (d, J=1.6, 1H), 8.26-8.18 (d, J=1.5, 1H), 8.14-8.08 (dd, J=8.0, 1.3, 1H), 7.97-7.89 (m, 1H), 7.73-7.66 (m, 1H), 7.65-7.57 (m, 1H), 7.46-7.37 (dd, J=7.6, 1.4, 1H), 7.33-7.23 (m, 3H), 2.22-2.13 (m, 1H), 0.50-0.43 (m, 2H), 0.41-0.34 (m, 2H).

Example 90

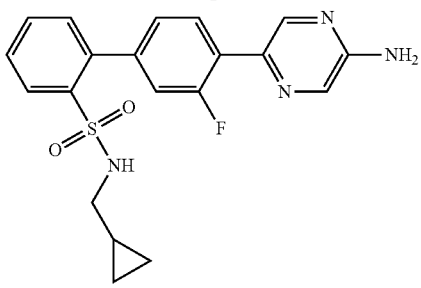

4'(5-Aminopyrazin-2-yl)-N-(cyclopropylmethyl)-3'-fluorobiphenyl-2-sulfonamide

The title compound was prepared in a manner similar to that described in Example 88 using 2-bromo-N-(cyclopropylmethyl)benzenesulfonamide. MS (ESI): mass calcd. for C$_{20}$H$_{19}$FN$_4$O$_2$S, 398.12; m/z found, 399.2 [M+H]$^+$. $^1$H NMR (500 MHz, CD$_3$OD) δ 8.42-8.33 (m, 1H), 8.15-8.10 (dd, J=8.0, 1.3, 1H), 8.09-8.06 (d, J=1.5, 1H), 7.91-7.82 (m, 1H), 7.70-7.63 (m, 1H), 7.61-7.53 (m, 1H), 7.40-7.35 (dd, J=7.6, 1.4, 1H), 7.25 (s, 1H), 7.24-7.21 (m, 1H), 1.21 (m, 3H), 0.50-0.46 (m, 2H), 0.39-0.28 (m, 2H).

Example 91

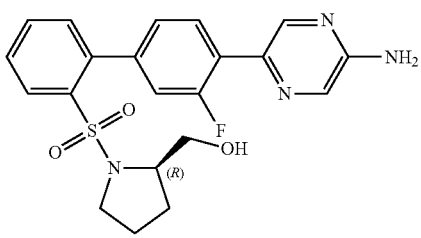

(R)-(1-((4'-(5-Aminopyrazin-2-yl)-3'-fluoro-[1,1'-biphenyl]-2-yl)sulfonyl)pyrrolidin-2-yl)methanol The title compound was prepared in a manner similar to that described in Example 88 using (R)-(1-((2-bromophenyl)sulfonyl)pyrrolidin-2-yl)methanol. MS (ESI): mass calcd. for C$_{21}$H$_{21}$FN$_4$O$_3$S, 428.13; m/z found, 429.2 [M+H]$^+$. $^1$H NMR (500 MHz, CD$_3$OD) δ 8.39-8.34 (m, 1H), 8.24-8.19 (d, J=1.5, 1H), 8.14-8.08 (dd, J=8.0, 1.3, 1H), 7.98-7.91 (m, 1H), 7.73-7.66 (m, 1H), 7.65-7.57 (m, 1H), 7.46-7.39 (dd, J=7.6, 1.3, 1H), 7.33-7.32 (m, 1H), 7.32-7.27 (dd, J=6.0, 1.6, 1H), 3.52-3.45 (m, 1H), 3.41-3.34 (dd, J=11.0, 3.9, 1H), 3.24-3.13 (m, 1H), 3.02-2.89 (m, 2H), 1.88-1.73 (m, 3H), 1.71-1.62 (dd, J=6.9, 4.6, 1H).

Example 92

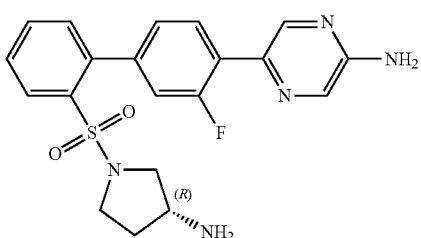

(R)-5-(2'-((3-Aminopyrrolidin-1-yl)sulfonyl)-3-fluoro-[1,1'-biphenyl]-4-yl)pyrazin-2-amine The title compound was prepared in a manner similar to that described in Example 88 using (R)-1-((2-bromophenyl)sulfonyl)pyrrolidin-3-amine, followed by removal of the Boc group with trifluoroacetic acid in dichloromethane at rt. MS (ESI): mass calcd. for C$_{20}$H$_{20}$FN$_5$O$_2$S, 413.13; m/z found, 414.2 [M+H]$^+$. $^1$H NMR (500 MHz, CD$_3$OD) δ 8.44-8.29 (m, 1H), 8.17-8.13 (d, J=1.5, 1H), 8.13-8.09 (dd, J=8.0, 1.3, 1H), 7.99-7.88 (m, 1H), 7.79-7.69 (m, 1H), 7.69-7.59 (m, 1H), 7.50-7.42 (dd, J=7.6, 1.4, 1H), 7.32 (s, 1H), 7.31-7.29 (dd, J=2.9, 1.5, 1H), 3.77-3.60 (m, 1H), 3.29-3.25 (m, 1H), 3.21-3.12 (dd. J=10.9, 6.7, 1H), 3.12-3.01 (dd, J=10.9, 5.0, 1H), 2.98-2.86 (m, 1H), 2.23-2.12 (m, 1H), 1.94-1.78 (m, 1H).

Example 93

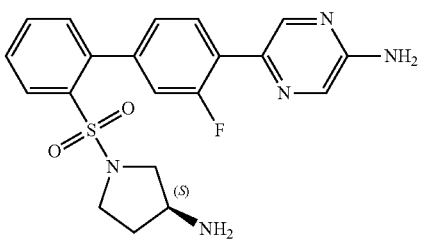

(S)-5-(2'-((3-Aminopyrrolidin-1-yl)sulfonyl)-3-fluoro-[1,1'-biphenyl]-4-yl)pyrazin-2-amine The title compound was prepared in a manner similar to that described in Example 88 using (S)-1-((2-bromophenyl)sulfonyl)pyrrolidin-3-amine, followed by removal of the Boc group with trifluoroacetic acid in dichloromethane at rt. MS (ESI): mass calcd. for C$_{20}$H$_{20}$FN$_5$O$_2$S, 413.13; m/z found, 414.2 [M+H]$^+$. $^1$H NMR (500 MHz, CD$_3$OD) δ 8.43-8.35 (m, 1H), 8.16-8.13 (d, J=1.4, 1H), 8.13-8.09 (dd, J=8.0, 1.3, 1H), 7.98-7.90 (m, 1H), 7.77-7.71 (m, 1H), 7.68-7.60 (m, 1H), 7.47-7.43 (dd, J=7.5, 1.3, 1H), 7.34-7.31 (m, 1H), 7.31-7.29 (q, J=1.5, 1H), 3.73-3.63 (p, J=6.1, 1H), 3.29-3.23 (m, 1H), 3.19-3.13 (dd, J=10.8, 6.7, 1H), 3.10-3.03 (dd, J=10.9, 5.0, 1H), 2.98-2.85 (m, 1H), 2.25-2.11 (m, 1H), 1.93-1.80 (m, 1H).

Example 94

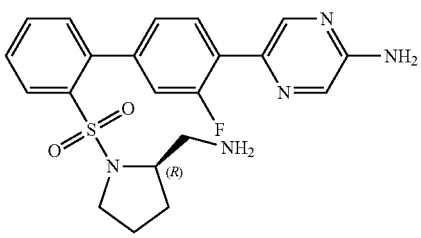

(R)5-(2'-{[2-(Aminomethyl)pyrrolidin-1-yl]sulfonyl}-3-fluorobiphenyl-4-yl)pyrazin-2-amine The title compound was prepared in a manner similar to that described in Example 88 using (R)-(1-((2-bromophenyl)sulfonyl)pyrrolidin-2-yl)-methan-amine. MS (ESI): mass calcd. for C$_{21}$H$_{22}$FN$_5$O$_2$S, 427.15; m/z found, 428.1 [M+H]$^+$. $^1$H NMR (500 MHz, CD$_3$OD) δ 8.42-8.38 (m, 1H), 8.16-8.13 (dd, J=8.1, 1.3, 1H), 8.13-8.12 (d, J=1.5, 1H), 7.94-7.89 (m, 1H), 7.78-7.73 (m, 1H), 7.69-7.63 (m, 1H), 7.48-7.45 (dd, J=7.6, 1.3, 1H), 7.36-7.30 (m, 2H), 3.71-3.62 (m, 1H), 3.15-3.08 (m, 1H), 3.05-2.98 (m, 1H), 2.86-2.74 (m, 2H), 1.92-1.76 (m, 2H), 1.73-1.62 (m, 2H).

Example 95

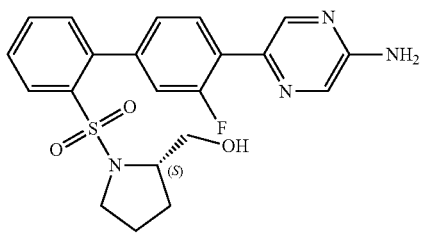

(S)-(1-((4'-(5-Aminopyrazin-2-yl)-3'-fluoro-[1,1'-biphenyl]-2-yl)sulfonyl)pyrrolidin-2-yl)methanol The title compound was prepared in a manner similar to that described in Example 88 using (S)-(1-((2-bromophenyl)sulfonyl)pyrrolidin-2-yl)methanol. MS (ESI): mass calcd. for $C_{21}H_{21}FN_4O_3S$, 428.13; m/z found, 429.2 [M+H]+. 1H NMR (500 MHz, CD3OD) δ 8.37-8.34 (m, 1H), 8.24-8.22 (d, J=1.4, 1H), 8.13-8.09 (dd, J=8.0, 1.3, 1H), 7.98-7.93 (m, 1H), 7.73-7.67 (m, 1H), 7.63-7.59 (m, 1H), 7.44-7.40 (dd, J=7.6, 1.3, 1H), 7.34-7.32 (m, 1H), 7.32-7.30 (dd, J=5.9, 1.6, 1H), 3.52-3.45 (dd, J=7.6, 4.0, 1H), 3.40-3.34 (m, 1H), 3.22-3.11 (dd, J=10.8, 7.9, 1H), 3.02-2.87 (m, 2H), 1.90-1.72 (m, 3H), 1.71-1.62 (dd, J=6.7, 4.5, 1H).

Example 96

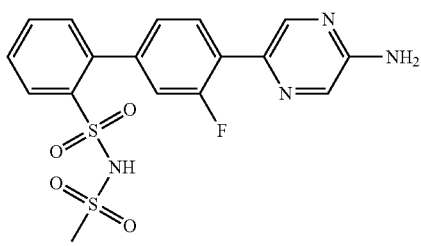

4'-(5-Aminopyrazin-2-yl)-3'-fluoro-N-(methylsulfonyl)biphenyl-2-sulfonamide

The title compound was prepared in a manner similar to that described in Example 88 using 2-bromo-N-(methylsulfonyl)benzenesulfonamide. MS (ESI): mass calcd. for $C_{17}H_{15}FN_4O_4S_2$, 422.05; m/z found, 423.0 [M+H]+. 1H NMR (500 MHz, acetone-d6) δ 8.56 (s, 1H), 8.25-8.18 (dd, J=7.9, 1.4, 1H), 8.16 (s, 1H), 7.90-7.84 (m, 1H), 7.64-7.57 (m, 1H), 7.57-7.50 (m, 1H), 7.46-7.40 (dd, J=8.2, 1.6, 1H), 7.38-7.31 (d, J=13.3, 1H), 7.31-7.26 (dd, J=7.4, 1.4, 1H), 2.96 (s, 3H).

Example 97

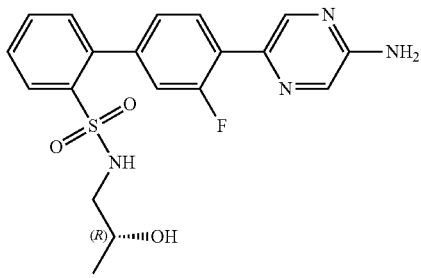

(R)-4'-(5-aminopyrazin-2-yl)-3'-fluoro-N-(2-hydroxypropyl)-[1,1'-biphenyl]-2-sulfonamide The title compound was prepared in a manner similar to that described in Example 88 using (R)-2-bromo-N-(2-hydroxypropyl)benzenesulfonamide. MS (ESI): mass calcd. for $C_{19}H_{19}FN_4O_3S$, 402.12; m/z found, 403.1 [M+H]+. 1H NMR (500 MHz, CD3OD) δ 8.37 (s, 1H), 8.27-8.19 (m, 1H), 8.11-8.03 (dd, J=8.0, 1.3, 1H), 7.99-7.91 (m, 1H), 7.72-7.64 (m, 1H), 7.64-7.55 (m, 1H), 7.45-7.38 (d, J=7.5, 1H), 7.37-7.27 (m, 2H), 3.74-3.61 (m, 1H), 2.80-2.72 (m, 1H), 2.72-2.64 (m, 1H), 1.10-0.99 (d, J=6.2, 3H).

Example 98

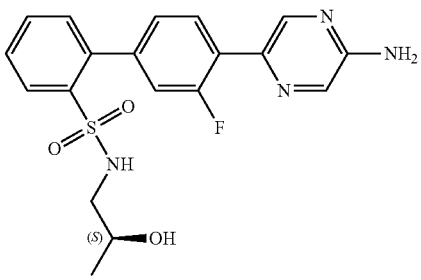

(S)-4'-(5-aminopyrazin-2-yl)-3'-fluoro-N-(2-hydroxypropyl)-[1,1'-biphenyl]-2-sulfonamide The title compound was prepared in a manner similar to that described in Example 88 using (S)-2-bromo-N-(2-hydroxypropyl)benzenesulfonamide. MS (ESI): mass calcd. for $C_{19}H_{19}FN_4O_3S$, 402.12; m/z found, 403.1 [M+H]+. 1H NMR (500 MHz, CD3OD) δ 8.41-8.35 (m, 1H), 8.21-8.17 (d, J=1.5, 1H), 8.10-8.04 (dd, J=8.0, 1.3, 1H), 7.96-7.91 (m, 1H), 7.71-7.65 (m, 1H), 7.62-7.57 (m, 1H), 7.44-7.39 (dd, J=7.5, 1.3, 1H), 7.36-7.29 (m, 2H), 3.73-3.60 (m, 1H), 2.77-2.72 (m, 1H), 2.71-2.65 (m, 1H), 1.08-1.03 (d, J=6.3, 3H).

Example 99

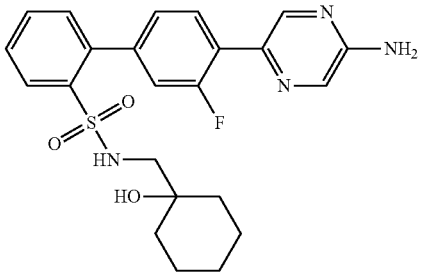

4'-(5-Aminopyrazin-2-yl)-3'-fluoro-N-[(1-hydroxycyclohexyl)methyl]biphenyl-2-sulfonamide The title compound was prepared in a manner similar to that described in Example 88 using 2-bromo-N-((1-hydroxycyclohexyl)methyl)-benzenesulfonamide. MS (ESI): mass calcd. for $C_{23}H_{25}FN_4O_3S$, 456.16; m/z found, 457.1 [M+H]+. 1H NMR (400 MHz, CD3OD) δ 8.44-8.37 (dd, J=2.2, 1.5, 1H), 8.10-8.04 (m, 2H), 7.96-7.87 (m, 1H), 7.71-7.64 (m, 1H), 7.63-7.56 (m, 1H), 7.46-7.39 (dd, J=7.6, 1.4, 1H), 7.37-7.28 (m, 2H), 2.67 (s, 2H), 1.61-1.22 (m, 10H).

Example 100

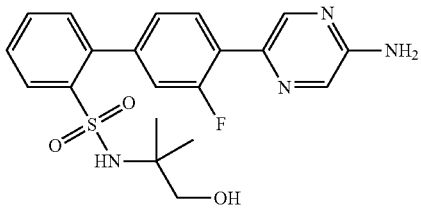

4'-(5-Aminopyrazin-2-yl)-3'-fluoro-N-(2-hydroxy-1,1-dimethylethyl)biphenyl-2-sulfonamide The title compound was prepared in a manner similar to that described in Example 88 using 2-bromo-N-(1-hydroxy-2-methylpropan-2-yl)benzenesulfonamide. MS (ESI): mass calcd. for $C_{20}H_{21}FN_4O_3S$, 416.13; m/z found, 417.0 [M+H]$^+$. $^1$H NMR (500 MHz, CD$_3$OD) δ 8.41-8.35 (m, 1H), 8.18-8.13 (m, 2H), 7.97-7.90 (m, 1H), 7.69-7.63 (m, 1H), 7.60-7.54 (m, 1H), 7.41-7.38 (dd, J=7.7, 1.4, 1H), 7.38-7.33 (m, 2H), 3.27 (s, 2H), 1.01 (s, 6H).

Example 101

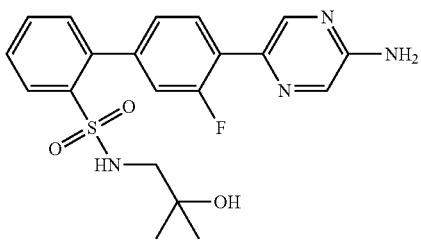

4'-(5-Aminopyrazin-2-yl)-3'-fluoro-N-(2-hydroxy-2-methylpropyl)biphenyl-2-sulfonamide The title compound was prepared in a manner similar to that described in Example 88 using 2-bromo-N-(2-hydroxy-2-methylpropyl)benzenesulfonamide. MS (ESI): mass calcd. for $C_{20}H_{21}FN_4O_3S$, 416.13; m/z found, 417.0 [M+H]$^+$. $^1$H NMR (500 MHz, CD$_3$OD) δ 8.42-8.38 (dd, J=2.2, 1.4, 1H), 8.10-8.07 (d, J=1.5, 1H), 8.07-8.03 (dd, J=7.9, 1.0, 1H), 7.93-7.88 (m, 1H), 7.70-7.64 (m, 1H), 7.62-7.57 (m, 1H), 7.44-7.40 (dd, J=7.5, 1.2, 1H), 7.36-7.28 (m, 2H), 2.67 (s, 2H), 1.09 (s, 6H).

Example 102

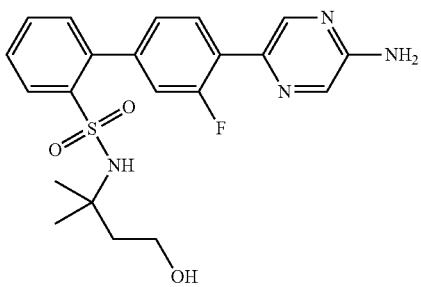

4'-(5-Aminopyrazin-2-yl)-3'-fluoro-N-(3-hydroxy-1,1-dimethylpropyl)biphenyl-2-sulfonamide The title compound was prepared in a manner similar to that described in Example 88 using 2-bromo-N-(4-hydroxy-2-methylbutan-2-yl)benzenesulfonamide. MS (ESI): mass calcd. for $C_{21}H_{23}FN_4O_3S$, 430.15; m/z found, 431.1 [M+H]$^+$. $^1$H NMR (500 MHz, CD$_3$OD) δ 8.40-8.36 (m, 1H), 8.18-8.16 (d, J=1.5, 1H), 8.16-8.12 (dd, J=8.0, 1.3, 1H), 7.96-7.89 (m, 1H), 7.68-7.62 (m, 1H), 7.60-7.54 (m, 1H), 7.42-7.37 (dd, J=7.6, 1.4, 1H), 7.37-7.35 (m, 1H), 7.35-7.32 (dd, J=3.9, 1.6, 1H), 3.61-3.53 (t, J=6.7, 2H), 1.67-1.62 (t, J=6.7, 2H), 1.08 (s, 6H).

Example 103

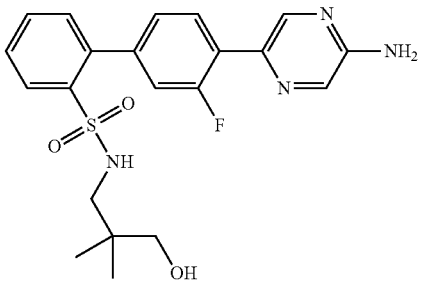

4'-(5-Aminopyrazin-2-yl)-3'-fluoro-N-(3-hydroxy-2,2-dimethylpropyl)biphenyl-2-sulfonamide The title compound was prepared in a manner similar to that described in Example 88 using 2-bromo-N-(3-hydroxy-2,2-dimethylpropyl)benzenesulfonamide. MS (ESI): mass calcd. for $C_{21}H_{23}FN_4O_3S$, 430.15; m/z found, 431.1 [M+H]$^+$. $^1$H NMR (500 MHz, CD$_3$OD) δ 8.43-8.35 (m, 1H), 8.10-8.06 (d, J=1.5, 1H), 8.05-8.02 (dd, J=8.0, 1.3, 1H), 7.95-7.85 (m, 1H), 7.71-7.63 (m, 1H), 7.63-7.54 (m, 1H), 7.45-7.39 (dd, J=7.6, 1.3, 1H), 7.38-7.28 (m, 2H), 3.19 (s, 2H), 2.62 (s, 2H), 0.77 (s, 6H).

Example 104

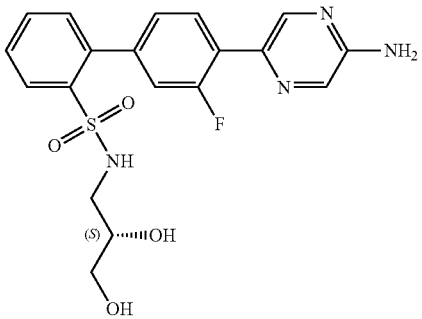

(S)-4'-(5-Aminopyrazin-2-yl)-N-(2,3-dihydroxypropyl)-3'-fluoro-[1,1'-biphenyl]-2-sulfonamide The title compound was prepared in a manner similar to that described in Example 88 using (S)-2-bromo-N-(2,3-dihydroxypropyl)benzenesulfonamide. MS (ESI): mass calcd. for $C_{19}H_{19}FN_4O_4S$, 418.11; m/z found, 419.1 [M+H]$^+$. $^1$H NMR (500 MHz, CD$_3$OD) δ 8.38-8.33 (m, 1H), 8.27-8.23 (d, J=1.4, 1H), 8.11-8.05 (dd, J=8.0, 1.3, 1H), 7.99-7.93 (m, 1H), 7.72-7.64 (m, 1H), 7.63-7.57 (m, 1H), 7.44-7.39 (dd, J=7.6, 1.4, 1H), 7.38-7.29 (m, 2H), 3.62-3.53 (m, 1H), 3.43-3.39 (m, 2H), 2.97-2.90 (dd, J=13.2, 4.8, 1H), 2.79-2.71 (dd, J=13.2, 7.0, 1H).

Example 105

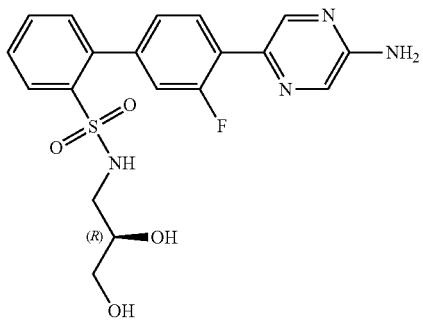

(R)-4'-(5-Aminopyrazin-2-yl)-
N-(2,3-dihydroxypropyl)-
3'-fluoro-[1,1'-biphenyl]-2-sulfonamide The title compound was prepared in a manner similar to that described in Example 88 using (R)-2-bromo-N-(2,3-dihydroxypropyl)benzenesulfonamide. MS (ESI): mass calcd. for $C_{19}H_{19}FN_4O_4S$, 418.11; m/z found, 419.0 [M+H]$^+$. $^1$H NMR (500 MHz, CD$_3$OD) δ 8.38-8.32 (m, 1H), 8.29-8.22 (d, J=1.4, 1H), 8.11-8.05 (dd, J=8.0, 1.3, 1H), 8.00-7.91 (m, 1H), 7.72-7.64 (m, 1H), 7.64-7.58 (m, 1H), 7.44-7.40 (dd, J=7.6, 1.3, 1H), 7.37-7.29 (m, 2H), 3.61-3.52 (m, 1H), 3.43-3.39 (m, 2H), 2.97-2.90 (dd, J=13.1, 4.8, 1H), 2.80-2.72 (dd, J=13.1, 7.0, 1H).

Example 106

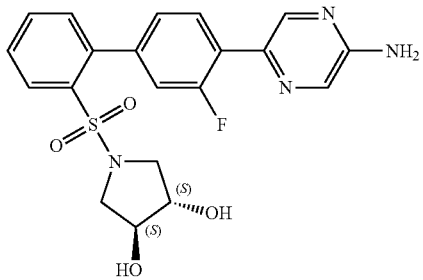

(trans)-1-{[4'-(5-Aminopyrazin-2-yl)-3'-fluorobiphenyl-2-yl]sulfonyl}pyrrolidine-3,4-diol The title compound was prepared in a manner similar to that described in Example 88 using (trans)-1-((2-bromophenyl)sulfonyl)pyrrolidine-3,4-diol. MS (ESI): mass calcd. for $C_{20}H_{19}FN_4O_4S$, 430.11; m/z found, 431.1 [M+H]$^+$. $^1$H NMR (500 MHz, CD$_3$OD) δ 8.39-8.34 (m, 1H), 8.24-8.20 (d, J=1.5 Hz, 1H), 8.15-8.08 (dd, J=8.0, 1.3 Hz, 1H), 7.97-7.88 (m, 1H), 7.70-7.64 (td, J=7.5, 1.4 Hz, 1H), 7.62-7.54 (td, J=7.7, 1.4 Hz, 1H), 7.47-7.38 (dd, J=7.6, 1.3 Hz, 1H), 7.34-7.31 (dd, J=8.0, 1.7 Hz, 1H), 7.31-7.27 (dd, J=12.3, 1.7 Hz, 1H), 4.00-3.97 (m, 2H), 3.29-3.27 (m, 2H), 3.07-3.03 (m, 2H).

Example 107

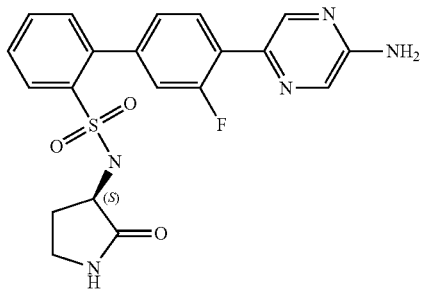

(S)-4'-(5-Aminopyrazin-2-yl)-3'-fluoro-N-
(2-oxopyrrolidin-3-yl)-[1,1'-biphenyl]-2-sulfonamide The title compound was prepared in a manner similar to that described in Example 88 using (S)-2-bromo-N-(2-oxopyrrolidin-3-yl)benzenesulfonamide. MS (ESI): mass calcd. for $C_{20}H_{18}FN_5O_3S$, 427.11; m/z found, 428.1 [M+H]$^+$. $^1$H NMR (500 MHz, CD$_3$OD) δ 8.42-8.38 (dd, J=2.2, 1.4, 1H), 8.26-8.22 (dd, J=8.2, 1.3, 1H), 8.08-8.06 (d, J=1.5, 1H), 7.91-7.84 (m, 1H), 7.70-7.64 (m, 1H), 7.61-7.55 (m, 1H), 7.41-7.38 (dd, J=7.6, 1.3, 1H), 7.38-7.32 (m, 2H), 3.88-3.81 (dd, J=10.3, 8.3, 1H), 3.28-3.22 (m, 1H), 3.22-3.15 (m, 1H), 2.38-2.30 (m, 1H), 1.96-1.86 (m, 1H).

Example 108

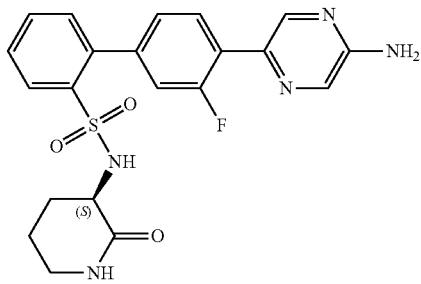

(S)-4'-(5-Aminopyrazin-2-yl)-3'-
fluoro-N-(2-oxopiperidin-3-yl)-
[1,1'-biphenyl]-2-sulfonamide The title compound was prepared in a manner similar to that described in Example 88 using (S)-2-bromo-N-(2-oxopiperidin-3-yl)benzenesulfonamide. MS (ESI): mass calcd. for $C_{21}H_{20}FN_5O_3S$, 441.13; m/z found, 442.1 [M+H]$^+$. $^1$H NMR (500 MHz, CD$_3$OD) δ 8.37 (s, 1H), 8.25-8.15 (m, 2H), 7.97-7.88 (m, 1H), 7.71-7.62 (m, 1H), 7.62-7.54 (m, 1H), 7.42-7.30 (m, 3H), 3.67-3.57 (dd, J=10.4, 5.8, 1H), 3.22-3.17 (m, 2H), 2.19-2.07 (d, J=10.6, 1H), 1.90-1.79 (m, 1H), 1.78-1.64 (m, 2H).

Example 109

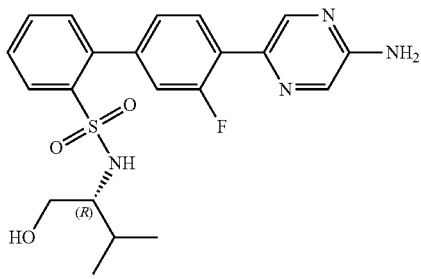

(R)-4'-(5-Aminopyrazin-2-yl)-3'-fluoro-
N-[1-(hydroxymethyl)-2-
methylpropyl]biphenyl-2-sulfonamide The title compound was prepared in a manner similar to that described in Example 88 using (R)-2-bromo-N-(1-hydroxy-3-methylbutan-2-yl)benzenesulfonamide. MS (ESI): mass calcd. for $C_{21}H_{23}FN_4O_3S$, 430.15; m/z found, 431.1 [M+H]$^+$. $^1$H NMR (500 MHz, CD$_3$OD) δ 8.42-8.37 (dd, J=2.2, 1.4, 1H), 8.16-8.11 (dd, J=8.0, 1.3, 1H), 8.10-8.06 (d, J=1.5, 1H), 7.91-7.84 (m, 1H), 7.68-7.61 (m, 1H), 7.60-7.53 (m, 1H), 7.39-7.35 (dd, J=7.7, 1.4, 1H), 7.36-7.28 (m, 2H), 3.45-3.39 (m, 1H), 3.38-3.33 (m, 1H), 3.10-3.03 (m, 1H), 1.89-1.75 (m, 1H), 0.86-0.75 (dd, J=6.9, 4.4, 6H).

Example 110

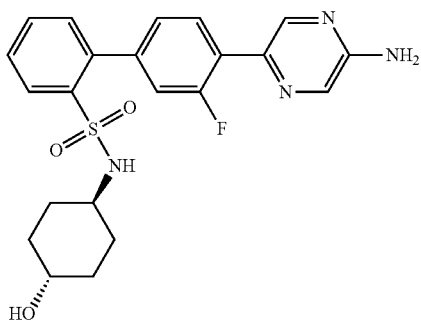

trans 4'-(5-Aminopyrazin-2-yl)-3'-fluoro-N-
(4-hydroxycyclohexyl)biphenyl-2-sulfonamide The title compound was prepared in a manner similar to that described in Example 88 using trans-2-bromo-N-(4-hydroxycyclohexyl)benzenesulfonamide. MS (ESI): mass calcd. for $C_{22}H_{23}FN_4O_3S$, 442.15; m/z found, 443.1 [M+H]$^+$. $^1$H NMR (500 MHz, CD$_3$OD) δ 8.40-8.34 (m, 1H), 8.22-8.17 (d, J=1.5, 1H), 8.14-8.08 (dd, J=7.9, 1.3, 1H), 7.96-7.90 (m, 1H), 7.69-7.64 (m, 1H), 7.62-7.56 (m, 1H), 7.43-7.38 (dd, J=7.7, 1.3, 1H), 7.35-7.28 (m, 2H), 3.43-3.36 (m, 1H), 2.89-2.77 (m, 1H), 1.87-1.77 (m, 2H), 1.77-1.68 (dd, J=8.3, 4.0, 2H), 1.27-1.05 (m, 4H).

Example 111

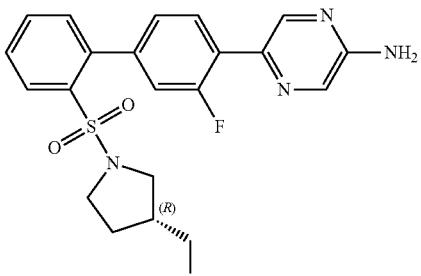

(R)-(1-((4'-(5-Aminopyrazin-2-yl)-3'-fluoro-
[1,1'-biphenyl]-2-yl)sulfonyl)pyrrolidin-3-yl)methanol The title compound was prepared in a manner similar to that described in Example 88 using (R)-(1-((2-bromophenyl)sulfonyl)pyrrolidin-3-yl)methanol. MS (ESI): mass calcd. for $C_{21}H_{21}FN_4O_3S$, 428.13; m/z found, 429.0 [M+H]$^+$. $^1$H NMR (500 MHz, CD$_3$OD) δ 8.37 (s, 1H), 8.22-8.19 (d, J=1.5, 1H), 8.14-8.08 (dd, J=8.1, 1.3, 1H), 7.97-7.93 (m, 1H), 7.75-7.66 (m, 1H), 7.65-7.57 (m, 1H), 7.45-7.39 (dd, J=7.6, 1.3, 1H), 7.37-7.25 (m, 2H), 3.42-3.36 (m, 1H), 3.09-3.03 (dd, J=9.5, 7.5, 1H), 3.03-2.97 (m, 1H), 2.95-2.85 (m, 1H), 2.75-2.64 (dd, J=9.6, 7.2, 1H), 2.29-2.17 (m, 1H), 1.86-1.76 (m, 1H), 1.54-1.41 (m, 1H).

Example 112

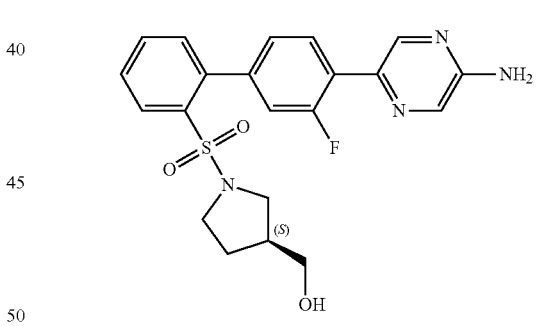

(S)-(1-{[4'-(5-Aminopyrazin-2-yl)-3'-fluorobiphenyl-2-yl]
sulfonyl}pyrrolidin-3-yl)methanol The title compound was prepared in a manner similar to that described in Example 88 using (S)-(1-((2-bromophenyl)sulfonyl)pyrrolidin-3-yl)methanol. MS (ESI): mass calcd. for $C_{21}H_{21}FN_4O_3S$, 428.13; m/z found, 429.0 [M+H]$^+$. $^1$H NMR (500 MHz, CD$_3$OD) δ 8.40-8.32 (m, 1H), 8.24-8.17 (d, J=1.5, 1H), 8.12-8.07 (dd, J=8.0, 1.3, 1H), 7.99-7.93 (m, 1H), 7.72-7.66 (m, 1H), 7.64-7.58 (m, 1H), 7.44-7.40 (dd, J=7.5, 1.3, 1H), 7.35-7.26 (m, 2H), 3.43-3.36 (m, 1H), 3.33-3.28 (m, 1H), 3.08-3.03 (dd, J=9.6, 7.6, 1H), 3.03-2.98 (m, 1H), 2.94-2.86 (m, 1H), 2.74-2.65 (dd, J=9.6, 7.1, 1H), 2.30-2.13 (m, 1H), 1.87-1.74 (m, 1H), 1.56-1.41 (m, 1H).

Example 113

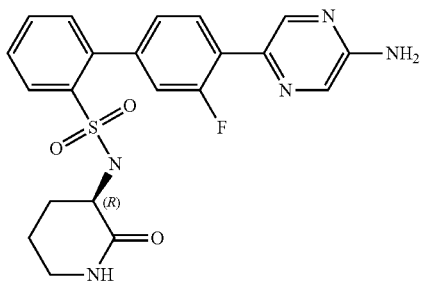

(R)-4'-(5-Aminopyrazin-2-yl)-3'-fluoro-N-(2-oxopiperidin-3-yl)biphenyl-2-sulfonamide The title compound was prepared in a manner similar to that described in Example 88 using (R)-2-bromo-N-(2-oxopiperidin-3-yl)benzenesulfonamide. MS (ESI): mass calcd. for $C_{21}H_{20}FN_5O_3S$, 441.13; m/z found, 442.1 [M+H]$^+$. $^1$H NMR (500 MHz, CD$_3$OD) δ 8.37-8.34 (m, 1H), 8.26-8.19 (m, 2H), 7.97-7.91 (m, 1H), 7.69-7.64 (m, 1H), 7.62-7.54 (m, 1H), 7.42-7.34 (m, 3H), 3.67-3.58 (dd, J=10.4, 5.9, 1H), 3.22-3.16 (m, 2H), 2.19-2.10 (m, 1H), 1.88-1.80 (m, 1H), 1.78-1.64 (m, 2H).

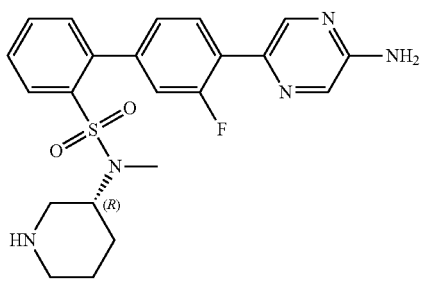

(R)-4'-(5-Aminopyrazin-2-yl)-3'-fluoro-N-methyl-N-piperidin-3-ylbiphenyl-2-sulfonamide The title compound was prepared in a manner similar to that described in Example 88 using (R)-2-bromo-N-methyl-N-(piperidin-3-yl)benzenesulfonamide. MS (ESI): mass calcd. for $C_2H_{24}FN_5O_2S$, 441.16; m/z found, 442.1 [M+H]$^+$. $^1$H NMR (500 MHz, CD$_3$OD) δ 8.41-8.37 (m, 1H), 8.20-8.16 (dd, J=8.1, 1.3, 1H), 8.16-8.14 (d, J=1.5, 1H), 8.00-7.92 (m, 1H), 7.78-7.71 (m, 1H), 7.68-7.61 (m, 1H), 7.48-7.43 (dd, J=7.6, 1.3, 1H), 7.37-7.35 (m, 1H), 7.35-7.32 (dd, J=7.0, 1.7, 1H), 3.64-3.53 (m, 1H), 3.23-3.17 (d, J=12.8, 1H), 3.06-3.00 (t, J=5.9, 1H), 3.00-2.93 (m, 1H), 2.78-2.70 (m, 1H), 2.42 (s, 3H), 1.92-1.81 (dd, J=16.5, 3.2, 1H), 1.68-1.57 (m, 1H), 1.57-1.44 (m, 1H), 1.44-1.33 (d, J=12.3, 1H).

Example 115

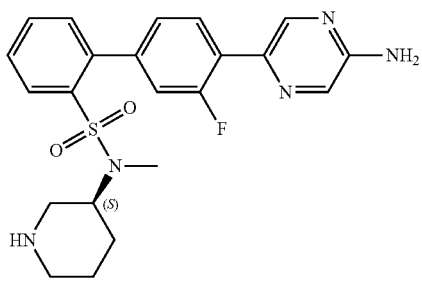

(S)-4'-(5-Aminopyrazin-2-yl)-3'-fluoro-N-methyl-N-piperidin-3-ylbiphenyl-2-sulfonamide The title compound was prepared in a manner similar to that described in Example 88 using (S)-2-bromo-N-methyl-N-(piperidin-3-yl)benzenesulfonamide. MS (ESI): mass calcd. for $C_{22}H_{24}FN_5O_2S$, 441.16; m/z found, 442.1 [M+H]$^+$. $^1$H NMR (500 MHz, CD$_3$OD) δ 8.43-8.36 (m, 1H), 8.21-8.15 (dd, J=8.1, 1.3, 1H), 8.14-8.09 (d, J=1.5, 1H), 7.99-7.90 (m, 1H), 7.78-7.72 (m, 1H), 7.67-7.61 (m, 1H), 7.49-7.43 (dd, J=7.6, 1.3, 1H), 7.36-7.35 (m, 1H), 7.35-7.32 (dd, J=7.1, 1.7, 1H), 3.64-3.52 (m, 1H), 3.22-3.17 (d, J=13.2, 1H), 3.05-3.00 (m, 1H), 3.00-2.93 (m, 1H), 2.79-2.69 (m, 1H), 2.42 (s, 3H), 1.93-1.82 (m, 1H), 1.67-1.56 (m, 1H), 1.56-1.45 (m, 1H), 1.43-1.34 (m, 1H).

Example 116

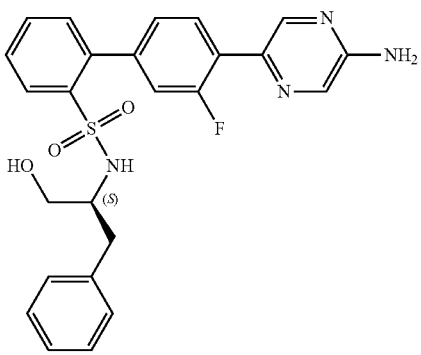

(S)-4'-(5-Aminopyrazin-2-yl)-3'-fluoro-N-(1-hydroxy-3-phenylpropan-2-yl)-[1,1'-biphenyl]-2-sulfonamide The title compound was prepared in a manner similar to that described in Example 88 using (S)-2-bromo-N-(1-hydroxy-3-phenylpropan-2-yl)benzenesulfonamide. MS (ESI): mass calcd. for $C_{25}H_{23}FN_4O_3S$, 478.15; m/z found, 479.1 [M+H]$^+$. $^1$H NMR (500 MHz, CD$_3$OD) δ 8.40-8.35 (m, 1H), 8.10-8.05 (d, J=1.5, 1H), 7.99-7.95 (dd, J=8.0, 1.3, 1H), 7.86-7.79 (t, J=8.1, 1H), 7.63-7.57 (m, 1H), 7.51-7.45 (m, 1H), 7.31-7.26 (dd, J=7.6, 1.3, 1H), 7.19-7.07 (m, 5H), 7.08-7.02 (dd, J=8.0, 1.5, 2H), 3.49-3.41 (m, 2H), 3.41-3.34 (m, 1H), 2.92-2.82 (dd, J=13.9, 6.3, 1H), 2.68-2.59 (dd, J=13.9, 6.8, 1H).

Example 117

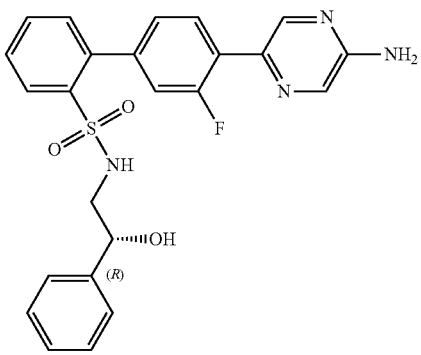

(R)-4'-(5-Aminopyrazin-2-yl)-3'-fluoro-N-(2-hydroxy-2-phenylethyl)-[1,1'-biphenyl]-2-sulfonamide The title compound was prepared in a manner similar to that described in Example 88 using (R)-2-bromo-N-(2-hydroxy-2-phenylethyl)benzenesulfonamide. MS (ESI): mass calcd. for $C_{24}H_{21}FN_4O_3S$, 464.13; m/z found, 465.0 [M+H]$^+$. $^1$H NMR (500 MHz, CD$_3$OD) δ 8.41-8.33 (m, 1H), 8.11-8.03 (m, 2H), 7.90-7.82 (t, J=8.2, 1H), 7.70-7.63 (m, 1H), 7.61-7.54 (m, 1H), 7.42-7.36 (dd, J=7.6, 1.3, 1H), 7.30-7.16 (m, 7H), 4.60-4.53 (dd, J=7.9, 4.8, 1H), 2.98-2.92 (m, 1H), 2.92-2.86 (m, 1H).

Example 118

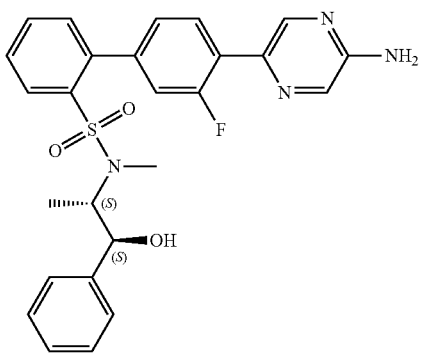

4'-(5-aminopyrazin-2-yl)-3'-fluoro-N-((1S,2S)-1-hydroxy-1-phenylpropan-2-yl)-N-methyl-[1,1'-biphenyl]-2-sulfonamide The title compound was prepared in a manner similar to that described in Example 88 using 2-bromo-N-((1S,2S)-1-hydroxy-1-phenylpropan-2-yl)-N-methylbenzenesulfonamide. MS (ESI): mass calcd. for $C_{26}H_{25}FN_4O_3S$, 492.16; m/z found, 493.1 [M+H]$^+$. $^1$H NMR (500 MHz, CD$_3$OD) δ 8.42-8.35 (m, 1H), 8.16-8.11 (dd, J=8.0, 1.3, 1H), 8.10-8.07 (d, J=1.5, 1H), 7.92-7.84 (t, J=8.0, 1H), 7.68-7.61 (m, 1H), 7.60-7.54 (m, 1H), 7.40-7.35 (dd, J=7.6, 1.4, 1H), 7.33-7.20 (m, 7H), 4.57-4.43 (d, J=8.4, 1H), 3.91-3.79 (m, 1H), 2.49 (s, 3H), 0.75-0.62 (d, J=6.8, 3H).

Example 119

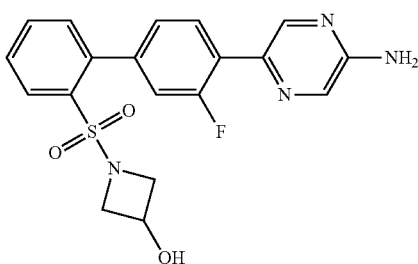

1-{[4'-(5-Aminopyrazin-2-yl)-3'-fluorobiphenyl-2-yl]sulfonyl}azetidin-3-ol

The title compound was prepared in a manner similar to that described in Example 88 using 1-((2-bromophenyl)sulfonyl)azetidin-3-ol. MS (ESI): mass calcd. for $C_{19}H_{17}FN_4O_3S$, 400.10; m/z found, 401.1 [M+H]$^+$. $^1$H NMR (500 MHz, CD$_3$OD) δ 8.40-8.29 (m, 1H), 8.22-8.17 (d, J=1.4, 1H), 8.10-8.05 (dd, J=8.0, 1.3, 1H), 7.97-7.91 (m, 1H), 7.75-7.67 (m, 1H), 7.64-7.56 (m, 1H), 7.46-7.40 (dd, J=7.5, 1.3, 1H), 7.36-7.27 (m, 2H), 4.37-4.25 (m, 1H), 3.70-3.60 (m, 2H), 3.60-3.53 (m, 2H).

Example 120

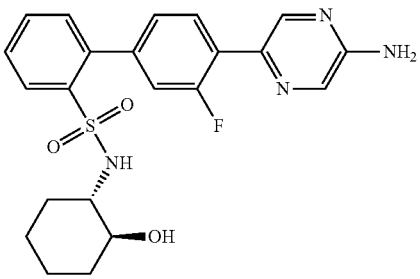

Racemic-(trans)-4'-(5-Aminopyrazin-2-yl)-3'-fluoro-N-(2-hydroxycyclohexyl)biphenyl-2-sulfonamide The title compound was prepared in a manner similar to that described in Example 88 using racemic-(trans)-2-bromo-N-(2-hydroxycyclohexyl)benzenesulfonamide. MS (ESI): mass calcd. for $C_{22}H_{23}FN_4O_3S$, 442.15; m/z found, 443.1 [M+H]$^+$. $^1$H NMR (500 MHz, CD$_3$OD) δ 8.37 (s, 1H), 8.21-8.16 (m, 2H), 7.95-7.90 (m, 1H), 7.68-7.62 (m, 1H), 7.60-7.55 (m, 1H), 7.40-7.36 (dd, J=7.6, 1.3, 1H), 7.36-7.35 (m, 1H), 7.35-7.32 (dd, J=6.2, 1.6, 1H), 3.25-3.19 (m, 1H), 2.86-2.79 (m, 1H), 1.94-1.86 (m, 1H), 1.85-1.77 (m, 1H), 1.66-1.58 (m, 1H), 1.58-1.51 (m, 1H), 1.26-1.09 (m, 4H).

Example 121

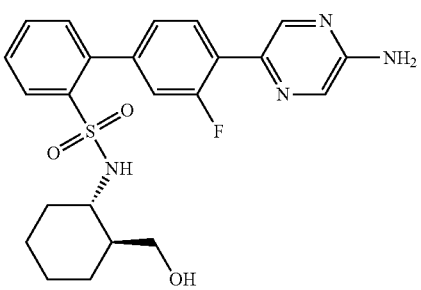

racemic (trans)-4'-(5-Aminopyrazin-2-yl)-3'-fluoro-N-[2-(hydroxymethyl)cyclohexyl]biphenyl-2-sulfonamide The title compound was prepared in a manner similar to that described in Example 88 using racemic (trans)-2-bromo-N-(2-(hydroxymethyl)cyclohexyl)benzenesulfonamide. MS (ESI): mass calcd. for $C_{23}H_{25}FN_4O_3S$, 456.16; m/z found, 457.2 [M+H]$^+$. $^1$H NMR (500 MHz, CD$_3$OD) δ 8.40-8.34 (m, 1H), 8.20-8.14 (d, J=1.5, 1H), 8.14-8.08 (dd, J=8.1, 1.3, 1H), 7.97-7.88 (m, 1H), 7.70-7.63 (m, 1H), 7.63-7.55 (m, 1H), 7.43-7.36 (dd, J=7.7, 1.4, 1H), 7.35-7.25 (m, 2H), 3.61-3.52 (dd, J=11.1, 3.7, 1H), 3.43-3.36 (dd, J=11.0, 6.4, 1H), 2.92-2.79 (m, 1H), 1.86-1.80 (m, 1H), 1.66-1.53 (m, 3H), 1.34-1.26 (m, 1H), 1.18-1.03 (m, 4H).

Example 122

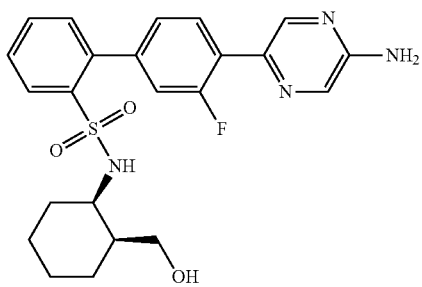

racemic (cis)-4'-(5-Aminopyrazin-2-yl)-3'-fluoro-
N-[2-(hydroxymethyl)cyclohexyl]biphenyl-2-sulfonamide The title compound was prepared in a manner similar to that described in Example 88 using racemic cis-2-bromo-N-(2-(hydroxymethyl)cyclohexyl)benzenesulfonamide. MS (ESI): mass calcd. for $C_{23}H_{25}FN_4O_3S$, 456.16; m/z found, 457.1 [M+H]$^+$. $^1$H NMR (500 MHz, CD$_3$OD) δ 8.43-8.37 (m, 1H), 8.16-8.10 (dd, J=8.0, 1.3, 1H), 8.09-8.07 (d, J=1.5, 1H), 7.92-7.85 (m, 1H), 7.70-7.63 (m, 1H), 7.62-7.55 (m, 1H), 7.43-7.37 (dd, J=7.5, 1.4, 1H), 7.34-7.26 (m, 2H), 3.58-3.51 (dd, J=11.1, 7.1, 1H), 3.47-3.39 (m, 1H), 3.38-3.33 (m, 1H), 1.69-1.59 (m, 1H), 1.58-1.50 (m, 1H), 1.47-1.16 (m, 7H).

Example 123

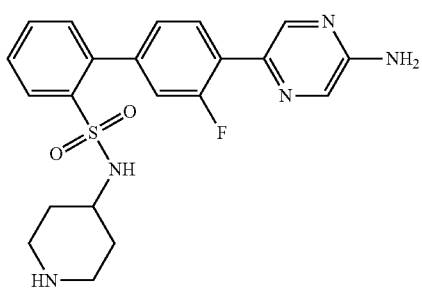

4'-(5-Aminopyrazin-2-yl)-3'-fluoro-
N-piperidin-4-ylbiphenyl-2-sulfonamide

The title compound was prepared in a manner similar to that described in Example 88 using 2-bromo-N-(piperidin-4-yl)benzenesulfonamide. MS (ESI): mass calcd. for $C_{21}H_{22}FN_5O_2S$, 427.15; m/z found, 428.1 [M+H]$^+$. $^1$H NMR (500 MHz, CD$_3$OD) δ 8.41-8.37 (m, 1H), 8.16-8.10 (m, 2H), 7.95-7.89 (m, 1H), 7.74-7.66 (m, 1H), 7.64-7.56 (m, 1H), 7.46-7.40 (dd, J=7.7, 1.3, 1H), 7.38-7.29 (m, 2H), 3.30-3.22 (m, 2H), 3.21-3.14 (m, 1H), 2.98-2.89 (m, 2H), 1.98-1.85 (dd, J=14.6, 3.9, 2H), 1.65-1.48 (m, 2H).

Example 124

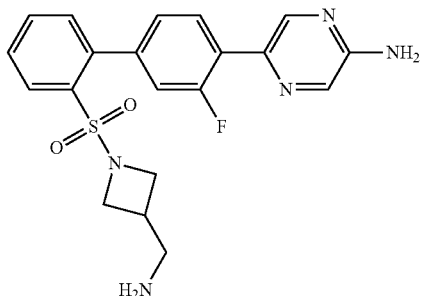

5-(2'-{[3-(Aminomethyl)azetidin-1-yl]sulfonyl}-3-
fluorobiphenyl-4-yl)pyrazin-2-amine The title compound was prepared in a manner similar to that described in Example 88 using (1-((2-bromophenyl)sulfonyl)azetidin-3-yl)methanamine. MS (ESI): mass calcd. for $C_{20}H_{20}FN_5O_2S$, 413.13; m/z found, 414.0 [M+H]$^+$. $^1$H NMR (500 MHz, CD$_3$OD) δ 8.42-8.37 (m, 1H), 8.14-8.11 (d, J=1.5, 1H), 8.11-8.07 (dd, J=8.0, 1.3, 1H), 7.97-7.90 (m, 1H), 7.76-7.70 (m, 1H), 7.65-7.57 (m, 1H), 7.52-7.42 (dd, J=7.7, 1.3, 1H), 7.39-7.25 (m, 2H), 3.81-3.67 (t, J=8.1, 2H), 3.42-3.36 (dd, J=8.1, 5.5, 2H), 3.07-3.00 (d, J=7.5, 2H), 2.72-2.59 (m, 1H).

Example 125

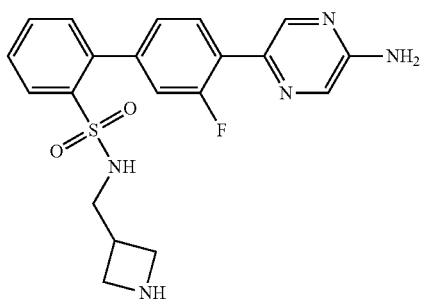

4'-(5-Aminopyrazin-2-yl)-N-(azetidin-3-ylmethyl)-3'-
fluorobiphenyl-2-sulfonamide The title compound was prepared in a manner similar to that described in Example 88 using N-(azetidin-3-ylmethyl)-2-bromobenzenesulfonamide. MS (ESI): mass calcd. for $C_{20}H_{20}FN_5O_2S$, 413.13; m/z found, 414.0 [M+H]$^+$. $^1$H NMR (500 MHz, CD$_3$OD) δ 8.41-8.37 (m, 1H), 8.17-8.12 (d, J=1.5, 1H), 8.09-8.05 (dd, J=8.0, 1.3, 1H), 7.97-7.88 (m, 1H), 7.73-7.66 (m, 1H), 7.65-7.58 (m, 1H), 7.47-7.41 (dd, J=7.6, 1.4, 1H), 7.36-7.28 (m, 2H), 4.02-3.95 (dd, J=11.2, 7.7, 2H), 3.91-3.78 (dd, J=11.3, 6.1, 2H), 3.04-2.91 (m, 3H).

Example 126

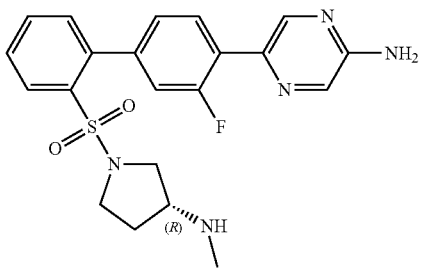

(R)-5-(3-Fluoro-2'-{[3-(methylamino)pyrrolidin-1-yl]sulfonyl}biphenyl-4-yl)pyrazin-2-amine The title compound was prepared in a manner similar to that described in Example 88 using (R)-1-((2-bromophenyl)sulfonyl)-N-methylpyrrolidin-3-amine. MS (ESI): mass calcd. for $C_{21}H_{22}FN_5O_2S$, 427.15; m/z found, 428.1 [M+H]$^+$. $^1$H NMR (500 MHz, CD$_3$OD) δ 8.44-8.35 (m, 1H), 8.15-8.08 (m, 2H), 7.98-7.91 (m, 1H), 7.78-7.71 (m, 1H), 7.68-7.61 (m, 1H), 7.48-7.43 (dd, J=7.7, 1.3, 1H), 7.34-7.27 (m, 2H), 3.69-3.57 (m, 1H), 3.29-3.23 (m, 1H), 3.22-3.16 (m, 1H), 3.16-3.11 (m, 1H), 2.99-2.85 (m, 1H), 2.65 (s, 3H), 2.28-2.14 (m, 1H), 1.99-1.87 (m, 1H).

Example 127

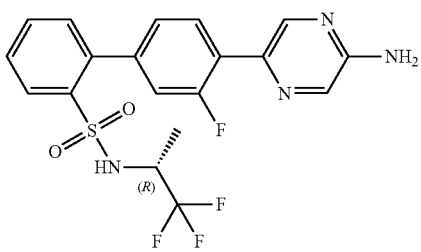

(R)-4'-(5-Aminopyrazin-2-yl)-3'-fluoro-N-(2,2,2-trifluoro-1-methylethyl)biphenyl-2-sulfonamide The title compound was prepared in a manner similar to that described in Example 88 using (R)-2-bromo-N-(1,1,1-trifluoropropan-2-yl)benzenesulfonamide. MS (ESI): mass calcd. for $C_{19}H_{16}F_4N_4O_2S$, 440.09; m/z found, 441.0 [M+H]$^+$. $^1$H NMR (500 MHz, CD$_3$OD) δ 8.42-8.38 (dd, J=2.1, 1.5, 1H), 8.13-8.09 (dd, J=8.1, 1.3, 1H), 8.09-8.07 (d, J=1.5, 1H), 7.90-7.85 (m, 1H), 7.70-7.64 (m, 1H), 7.61-7.55 (m, 1H), 7.41-7.36 (dd, J=7.7, 1.4, 1H), 7.30-7.27 (dd, J=8.0, 1.7, 1H), 7.27-7.22 (dd, J=12.3, 1.7, 1H), 3.91-3.79 (m, 1H), 1.24-1.16 (d, J=7.0, 3H).

Example 128

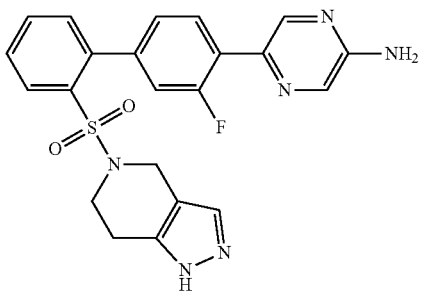

5-[3-Fluoro-2'-(1,4,6,7-tetrahydro-5H-pyrazolo[4,3-c]pyridin-5-ylsulfonyl)biphenyl-4-yl]pyrazin-2-amine The title compound was prepared in a manner similar to that described in Example 88 using 5-((2-bromophenyl)sulfonyl)-4,5,6,7-tetrahydro-1H-pyrazolo[4,3-c]pyridine. MS (ESI): mass calcd. for $C_{22}H_{19}FN_6O_2S$, 450.13; m/z found, 451.1 [M+H]$^+$. $^1$H NMR (500 MHz, CD$_3$OD) δ 8.40-8.35 (m, 1H), 8.21-8.14 (dd, J=8.1, 1.3, 1H), 8.11-8.07 (d, J=1.5, 1H), 7.85-7.79 (m, 1H), 7.76-7.68 (m, 1H), 7.65-7.59 (m, 1H), 7.45-7.37 (dd, J=7.5, 1.4, 1H), 7.31-7.14 (m, 3H), 4.02-3.88 (m, 2H), 3.28-3.22 (t, J=5.9, 2H), 2.59-2.48 (t, J=5.9, 2H).

Example 129

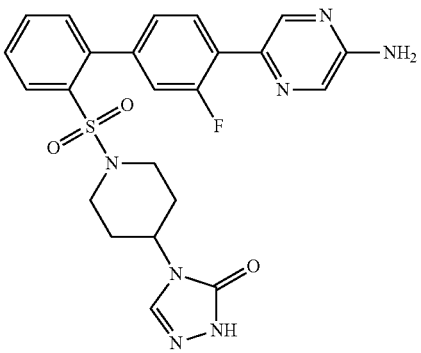

4-(1-{[4'-(5-Aminopyrazin-2-yl)-3'-fluorobiphenyl-2-yl]sulfonyl}piperidin-4-yl)-2,4-dihydro-3H-1,2,4-triazol-3-one The title compound was prepared in a manner similar to that described in Example 88 using 4-(1-((2-bromophenyl)sulfonyl)piperidin-4-yl)-1H-1,2,4-triazol-5(4H)-one. MS (ESI): mass calcd. for $C_{23}H_{22}FN_7O_3S$, 495.15; m/z found, 496.1 [M+H]$^+$. $^1$H NMR (500 MHz, CD$_3$OD) δ 8.38-8.35 (m, 1H), 8.24-8.22 (d, J=1.5, 1H), 8.15-8.11 (dd, J=8.1, 1.3, 1H), 8.01-7.96 (m, 1H), 7.78 (s, 1H), 7.76-7.70 (m, 1H), 7.66-7.60 (m, 1H), 7.48-7.43 (dd, J=7.6, 1.3, 1H), 7.41-7.33 (m, 2H), 3.88-3.76 (m, 1H), 3.51-3.42 (m, 2H), 2.64-2.53 (m, 2H), 1.88-1.79 (d, J=12.3, 2H), 1.68-1.50 (m, 2H).

Example 130

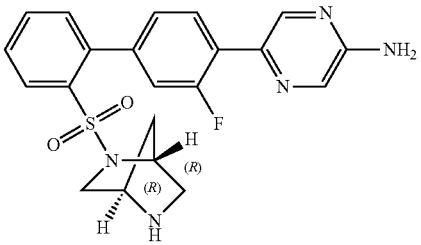

5-(2'-((1R,4R)-2,5-Diazabicyclo[2.2.1]heptan-2-ylsulfonyl)-3-fluoro-[1,1'-biphenyl]-4-yl)pyrazin-2-amine The title compound was prepared in a manner similar to that described in Example 88 using (1R,4R)-2-((2-bromophenyl)sulfonyl)-2,5-diazabicyclo[2.2.1]heptane. MS (ESI): mass calcd. for $C_{21}H_{20}FN_5O_2S$, 425.13; m/z found, 426.0 [M+H]$^+$. $^1$H NMR (500 MHz, CD$_3$OD) δ 8.42-8.38 (m, 1H), 8.19-8.14 (dd, J=8.1, 1.3, 1H), 8.14-8.10 (d, J=1.5, 1H), 7.99-7.91 (m, 1H), 7.79-7.72 (m, 1H), 7.68-7.60 (m, 1H), 7.51-7.43 (dd, J=7.6, 1.3, 1H), 7.38-7.35 (m, 1H), 7.33 (s, 1H), 4.32 (s, 1H), 4.05 (s, 1H), 3.38-3.33 (m, 1H), 3.30-3.25 (m, 1H), 3.21-3.14 (dd, J=11.6, 2.2, 1H), 3.04-2.98 (dd, J=11.0, 2.6, 1H), 1.85-1.72 (m, 2H).

Example 131

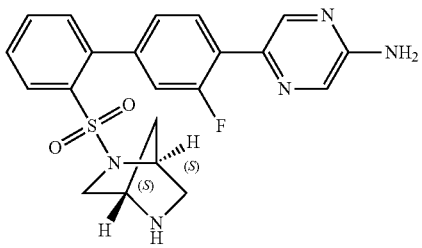

5-(2'-((1S,4S)-2,5-Diazabicyclo[2.2.1]heptan-2-ylsulfonyl)-3-fluoro-[1,1'-biphenyl]-4-yl)pyrazin-2-amine The title compound was prepared in a manner similar to that described in Example 88 using (1S,4S)-2-((2-bromophenyl)sulfonyl)-2,5-diazabicyclo[2.2.1]heptane. MS (ESI): mass calcd. for $C_{21}H_{20}FN_5O_2S$, 425.13; m/z found, 426.0 [M+H]$^+$. $^1$H NMR (500 MHz, CD$_3$OD) δ 8.42-8.36 (m, 1H), 8.17-8.14 (m, 2H), 8.00-7.92 (m, 1H), 7.79-7.72 (m, 1H), 7.68-7.61 (m, 1H), 7.49-7.45 (dd, J=7.6, 1.3, 1H), 7.39-7.35 (m, 1H), 7.34 (s, 1H), 4.38-4.28 (m1H), 4.05 (s, 1H), 3.38-3.32 (dd, J=11.6, 1.7, 1H), 3.30-3.26 (m, 1H), 3.23-3.12 (dd, J=11.6, 2.2, 1H), 3.08-2.95 (dd, J=11.0, 2.6, 1H), 1.85-1.74 (m, 2H).

Example 132

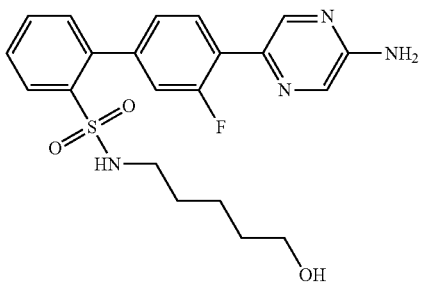

4'-(5-Aminopyrazin-2-yl)-3'-fluoro-N-(5-hydroxypentyl}biphenyl-2-sulfonamide

The title compound was prepared in a manner similar to that described in Example 88 using 2-bromo-N-(5-hydroxypentyl)benzenesulfonamide. MS (ESI): mass calcd. for $C_{21}H_{23}FN_4O_3S$, 430.15; m/z found, 431.1 [M+H]$^+$. $^1$H NMR (500 MHz, CD$_3$OD) δ 8.44-8.38 (m, 1H), 8.10-8.07 (d, J=1.5, 1H), 8.07-8.04 (dd, J=8.0, 1.3, 1H), 7.92-7.87 (m, 1H), 7.68-7.64 (m, 1H), 7.62-7.55 (m, 1H), 7.43-7.38 (dd, J=7.6, 1.4, 1H), 7.33-7.27 (m, 2H), 3.49-3.45 (t, J=6.6, 2H), 2.78-2.73 (t, J=7.1, 2H), 1.48-1.41 (m, 2H), 1.41-1.34 (m, 2H), 1.31-1.21 (m, 2H).

Example 133

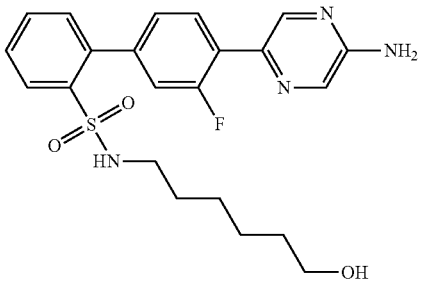

4'-(5-Aminopyrazin-2-yl)-3'-fluoro-N-(6-hydroxyhexyl)biphenyl-2-sulfonamide

The title compound was prepared in a manner similar to that described in Example 88 using 2-bromo-N-(6-hydroxyhexyl)benzenesulfonamide. MS (ESI): mass calcd. for $C_{22}H_{25}FN_4O_3S$, 444.16; m/z found, 445.1 [M+H]$^+$. $^1$H NMR (500 MHz, CD$_3$OD) δ 8.43-8.38 (m, 1H), 8.09-8.08 (d, J=1.5, 1H), 8.08-8.04 (dd, J=7.9, 1.3, 1H), 7.94-7.85 (m, 1H), 7.70-7.63 (m, 1H), 7.62-7.56 (m, 1H), 7.43-7.37 (dd, J=7.7, 1.4, 1H), 7.33-7.26 (m, 2H), 3.51-3.46 (t, J=6.6, 2H), 2.78-2.72 (t, J=7.1, 2H), 1.51-1.41 (m, 2H), 1.42-1.33 (p, J=7.2, 2H), 1.33-1.16 (m, 4H).

Example 134

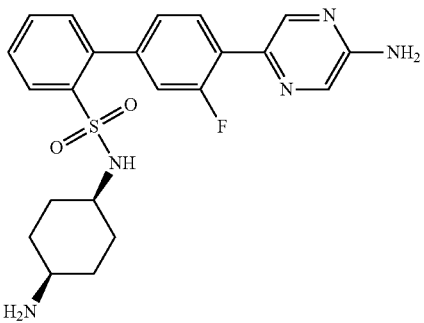

cis-N-(4-Aminocyclohexyl)-4'-(5-aminopryazin-2-yl)-3'-fluorobiphenyl-2-sulfonamide The title compound was prepared in a manner similar to that described in Example 88 using (cis)-N-(4-aminocyclohexyl)-2-bromobenzenesulfonamide. MS (ESI): mass calcd. for $C_{22}H_{24}FN_5O_2S$, 441.16; m/z found, 442.1 [M+H]$^+$. $^1$H NMR (500 MHz, CD$_3$OD) δ 8.41-8.36 (m, 1H), 8.19-8.14 (m, 1H), 8.13-8.07 (dd, J=8.0, 1.3, 1H), 7.97-7.91 (m, 1H), 7.73-7.67 (m, 1H), 7.65-7.58 (m, 1H), 7.46-7.41 (dd, J=7.5, 1.3, 1H), 7.35-7.33 (m, 1H), 7.33-7.31 (dd, J=6.2, 1.6, 1H), 3.15-3.00 (m, 2H), 1.80-1.69 (m, 4H), 1.68-1.57 (m, 2H), 1.58-1.48 (m, 2H).

Example 135

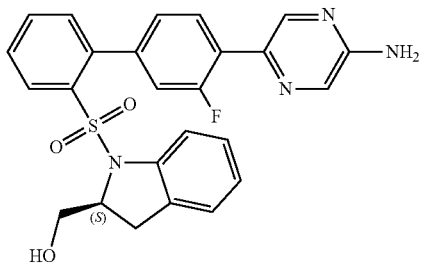

(S)-(1-{[4'-(5-Aminopyrazin-2-yl)-3'-fluorobiphenyl-2-yl]sulfonyl}-2,3-dihydro-1H-indol-2-yl)-methanol The title compound was prepared in a manner similar to that described in Example 88 using (S)-(1-((2-bromophenyl)sulfonyl)indolin-2-yl)methanol. MS (ESI): mass calcd. for $C_{25}H_{21}FN_4O_3S$, 476.13; m/z found, 477.0 $[M+H]^+$. $^1H$ NMR (400 MHz, $CD_3OD$) δ 8.36-8.33 (m, 1H), 8.22-8.20 (d, J=1.5, 1H), 8.19-8.14 (dd, J=8.0, 1.3, 1H), 7.85-7.79 (m, 1H), 7.69-7.63 (m, 1H), 7.61-7.56 (m, 1H), 7.32-7.28 (dd, J=7.5, 1.4, 1H), 7.11-7.06 (m, 2H), 7.01-6.95 (dd, J=12.2, 1.7, 1H), 6.91-6.80 (m, 3H), 3.85-3.74 (m, 1H), 3.67-3.58 (dd, J=10.9, 4.2, 1H), 3.40-3.33 (dd, J=11.0, 7.8, 1H), 2.89-2.72 (m, 2H).

Example 136

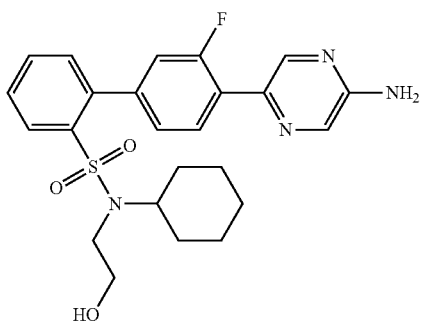

4'-(5-Aminopyrazin-2-yl)-N-cyclohexyl-3'-fluoro-N-(2-hydroxyethyl)biphenyl-2-sulfonamide The title compound was prepared in a manner similar to that described in Example 88 using 2-bromo-N-cyclohexyl-N-(2-hydroxyethyl)benzenesulfonamide. MS (ESI): mass calcd. for $C_{24}H_{27}FN_4O_3S$, 470.18; m/z found, 471.2 $[M+H]^+$. $^1H$ NMR (400 MHz, $CD_3OD$) δ 8.40-8.34 (m, 1H), 8.21-8.18 (d, J=1.5, 1H), 8.16-8.12 (dd, J=8.0, 1.4, 1H), 7.99-7.92 (m, 1H), 7.72-7.65 (m, 1H), 7.63-7.56 (m, 1H), 7.42-7.38 (dd, J=7.6, 1.4, 1H), 7.35-7.32 (m, 1H), 7.32-7.28 (dd, J=5.5, 1.6, 1H), 3.43-3.34 (dd, J=8.0, 6.9, 2H), 3.19-3.09 (m, 1H), 2.95-2.87 (dd, J=8.0, 6.9, 2H), 1.73-1.58 (d, J=12.6, 2H), 1.58-1.40 (m, 3H), 1.38-1.23 (m, 2H), 1.17-0.93 (m, 3H).

Example 137

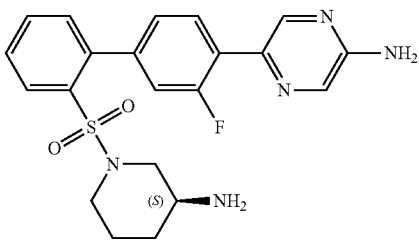

(S)-5-{2'-[(3-Aminopiperidin-1-yl)sulfonyl]-3-fluorobiphenyl-4-yl}pyrazin-2-amine The title compound was prepared in a manner similar to that described in Example 88 using (S)-1-((2-bromophenyl)sulfonyl)piperidin-3-amine. MS (ESI): mass calcd. for $C_{21}H_{22}FN_5O_2S$, 427.15; m/z found, 428.1 $[M+H]^+$. $^1H$ NMR (400 MHz, $CD_3OD$) δ 8.41-8.37 (m, 1H), 8.18-8.14 (d, J=1.5, 1H), 8.14-8.08 (dd, J=8.0, 1.3, 1H), 7.97-7.90 (m, 1H), 7.79-7.71 (m, 1H), 7.68-7.61 (m, 1H), 7.49-7.42 (dd, J=7.6, 1.4, 1H), 7.33-7.31 (m, 1H), 7.31-7.28 (dd, J=5.2, 1.6, 1H), 3.37-3.32 (m, 1H), 3.10-2.98 (m, 2H), 2.73-2.62 (m, 1H), 2.62-2.50 (dd, J=12.7, 8.9, 1H), 2.00-1.88 (m, 1H), 1.81-1.66 (m, 1H), 1.59-1.33 (m, 2H).

Example 138

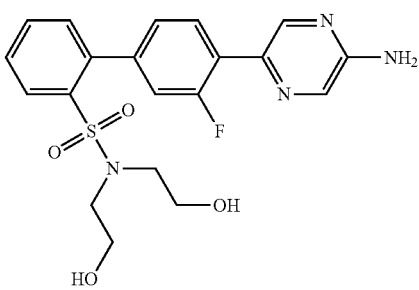

4'-(5-Aminopyrazin-2-yl)-3'-fluoro-N,N-bis(2-hydroxyethyl)biphenyl-2-sulfonamide The title compound was prepared in a manner similar to that described in Example 88 using 2-bromo-N,N-bis(2-hydroxyethyl)benzenesulfonamide. MS (ESI): mass calcd. for $C_{20}H_{21}FN_4O_4S$, 432.13; m/z found, 433.1 $[M+H]^+$. $^1H$ NMR (400 MHz, $CD_3OD$) δ 8.37-8.33 (m, 1H), 8.30-8.25 (d, J=1.4, 1H), 8.10-8.05 (dd, J=7.9, 1.3, 1H), 8.01-7.94 (m, 1H), 7.72-7.65 (m, 1H), 7.65-7.56 (m, 1H), 7.43-7.38 (dd, J=7.6, 1.4, 1H), 7.34-7.33 (m, 1H), 7.32-7.29 (dd, J=5.2, 1.6, 1H), 3.57-3.49 (t, J=6.0, 4H), 3.09-3.01 (t, J=6.0, 4H).

Example 139

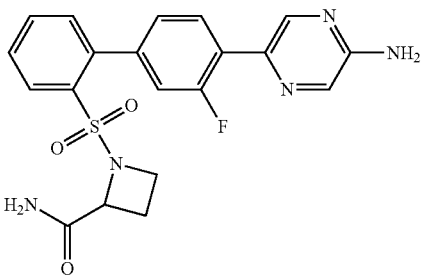

Racemic 1-{[4'-(5-Aminopyrazin-2-yl)-3'-fluorobiphenyl-2-yl]sulfonyl}azetidine-2-carboxamide The title compound was prepared in a manner similar to that described in Example 88 using racemic 1-((2-bromophenyl)sulfonyl)azetidine-2-carboxamide. MS (ESI): mass calcd. for $C_{20}H_{18}FN_5O_3S$, 427.11; m/z found, 428.1 [M+H]$^+$. $^1$H NMR (500 MHz, CD$_3$OD) δ 8.42-8.38 (m, 1H), 8.19-8.13 (m, 1H), 8.09-8.07 (d, J=1.5, 1H), 7.93-7.87 (m, 1H), 7.79-7.73 (m, 1H), 7.68-7.61 (m, 1H), 7.49-7.43 (dd, J=7.6, 1.3, 1H), 7.38-7.31 (m, 2H), 4.57-4.49 (dd, J=9.5, 7.8, 1H), 3.80-3.68 (m, 1H), 2.39-2.28 (m, 1H), 2.26-2.15 (m, 1H). (one proton obscured under methanol signal)

Example 140

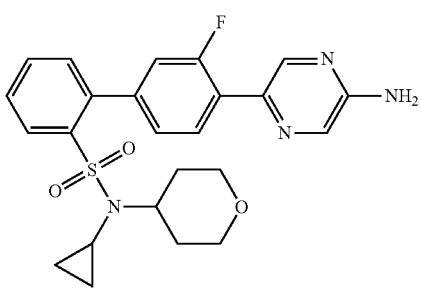

4'-(5-Aminopyrazin-2-yl)-N-cyclopropyl-3'-fluoro-N-(tetrahydro-2H-pyran-4-yl)biphenyl-2-sulfonamide The title compound was prepared in a manner similar to that described in Example 88 using 2-bromo-N-cyclopropyl-N-(tetrahydro-2H-pyran-4-yl)-benzenesulfonamide. MS (ESI): mass calcd. for $C_{24}H_{25}FN_4O_3S$, 468.16; m/z found, 469.1 [M+H]$^+$. $^1$H NMR (500 MHz, CD$_3$OD) δ 8.38-8.33 (m, 1H), 8.20-8.17 (dd, J=8.0, 1.3, 1H), 8.16-8.15 (d, J=1.5, 1H), 7.95-7.90 (m, 1H), 7.74-7.68 (m, 1H), 7.66-7.59 (m, 1H), 7.44-7.39 (dd, J=7.6, 1.3, 1H), 7.35-7.27 (m, 2H), 3.83-3.75 (m, 1H), 3.52-3.43 (m, 1H), 3.20-3.11 (m, 2H), 2.25-2.17 (m, 1H), 1.93-1.81 (m, 2H), 1.26-1.19 (d, J=12.0, 2H), 0.54-0.47 (m, 2H), 0.31-0.26 (dd, J=4.0, 2.3, 2H).

Example 141

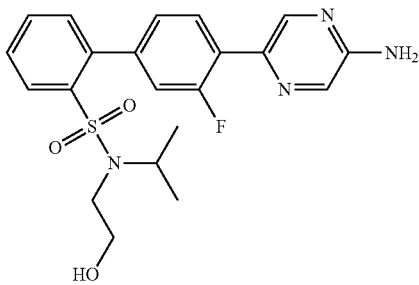

4'-(5-Aminopyrazin-2-yl)-3'-fluoro-N-(2-hydroxyethyl-N-(1-methylethyl)biphenyl-2-sulfonamide The title compound was prepared in a manner similar to that described in Example 88 using 2-bromo-N-(2-hydroxyethyl)-N-isopropylbenzenesulfonamide. MS (ESI): mass calcd. for $C_{21}H_{23}FN_4O_3S$, 430.15; m/z found, 431.1 [M+H]$^+$. $^1$H NMR (500 MHz, CD$_3$OD) δ 8.40-8.36 (m, 1H), 8.21-8.17 (d, J=1.5, 1H), 8.14-8.10 (dd, J=8.0, 1.3, 1H), 8.00-7.91 (m, 1H), 7.72-7.66 (m, 1H), 7.63-7.56 (m, 1H), 7.44-7.38 (dd, J=7.5, 1.3, 1H), 7.36-7.27 (m, 2H), 3.69-3.55 (m, 1H), 3.43-3.37 (dd, J=7.8, 6.9, 2H), 2.92-2.84 (t, J=7.3, 2H), 1.01-0.97 (d, J=6.7, 6H).

Example 142

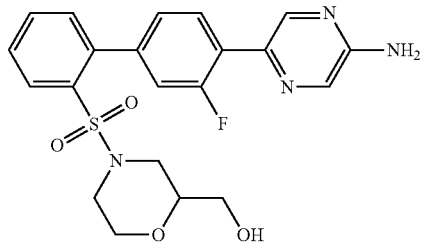

racemic (4-{[4'-(5-Aminopyrazin-2-yl)-3'-fluorobiphenyl-2-yl]sulfonyl}morpholin-2-yl)methanol The title compound was prepared in a manner similar to that described in Example 88 using racemic (4-((2-bromophenyl)sulfonyl)morpholin-2-yl)methanol. MS (ESI): mass calcd. for $C_{21}H_{21}FN_4O_4S$, 444.13; m/z found, 445.1 [M+H]$^+$. $^1$H NMR (500 MHz, CD$_3$OD) δ 8.38-8.34 (m, 1H), 8.24-8.18 (d, J=1.4, 1H), 8.14-8.07 (dd, J=8.0, 1.3, 1H), 7.98-7.92 (m, 1H), 7.76-7.69 (m, 1H), 7.69-7.60 (m, 1H), 7.49-7.43 (dd, J=7.6, 1.3, 1H), 7.35 (s, 1H), 7.34-7.31 (dd, J=3.6, 1.5, 1H), 3.78-3.70 (dd, J=11.3, 3.0, 1H), 3.45-3.39 (m, 1H), 3.38-3.33 (m, 1H), 3.29-3.25 (m, 1H), 3.22-3.16 (m, 2H), 3.12-3.04 (d, J=12.3, 1H), 2.62-2.49 (m, 1H), 2.45-2.31 (m, 1H).

Example 143

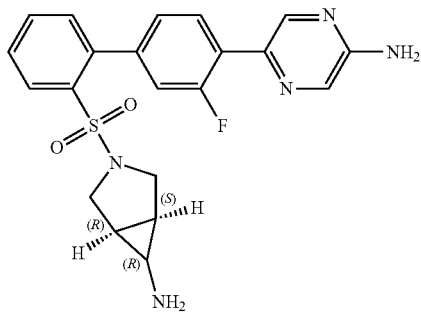

endo-3-((4'-(5-Aminopyrazin-2-yl)-3'-fluoro-[1,1'-biphenyl]-2-yl)sulfonyl)-3-azabicyclo[3.1.0]hexan-6-amine The title compound was prepared in a manner similar to that described in Example 88 using endo-3-((2-bromophenyl)sulfonyl)-3-azabicyclo[3.1.0]hexan-6-amine. MS (ESI): mass calcd. for $C_{21}H_{20}FN_5O_2S$, 425.13: m/z found, 426.2 [M+H]+. $^1$H NMR (500 MHz, CD$_3$OD) δ 8.42-8.38 (m, 1H), 8.16-8.14 (d, J=1.5, 1H), 8.11-8.06 (dd, J=8.1, 1.3, 1H), 7.98-7.91 (m, 1H), 7.75-7.69 (m, 1H), 7.65-7.59 (m, 1H), 7.46-7.42 (dd, J=7.7, 1.3, 1H), 7.35-7.28 (m, 2H), 3.28 (s, 1H), 2.99-2.90 (m, 2H), 2.25-2.16 (t, J=2.3, 1H), 1.90-1.80 (m, 2H).

Example 144

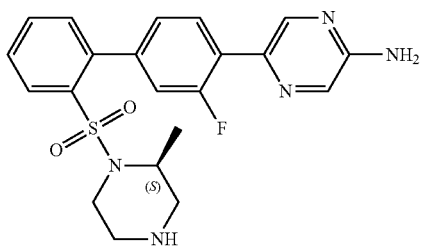

(S)-5-(3-Fluoro-2'-((2-methylpiperazin-1-yl)sulfonyl)-[1,1'-biphenyl]-4-yl)pyrazin-2-amine The title compound was prepared in a manner similar to that described in Example 88 using (S)-1-((2-bromophenyl)sulfonyl)-2-methylpiperazine. MS (ESI): mass calcd. for $C_{21}H_{22}FN_5O_2S$, 427.15; m/z found, 428.1 [M+H]+. $^1$H NMR (500 MHz. CD$_3$OD) δ 8.43-8.37 (m, 1H), 8.23-8.17 (dd, J=8.0, 1.3, 1H), 8.15-8.10 (d, J=1.5, 1H), 8.01-7.91 (m, 1H), 7.80-7.73 (m, 1H), 7.69-7.60 (m, 1H), 7.53-7.46 (dd, J=7.7, 1.3, 1H), 7.44-7.35 (d, J=9.9, 2H), 3.93-3.80 (m 1H), 3.23-3.15 (m, 1H), 3.15-3.03 (m, 3H), 2.79-2.63 (m, 2H), 1.21-1.14 (d, J=7.1, 3H).

Example 145

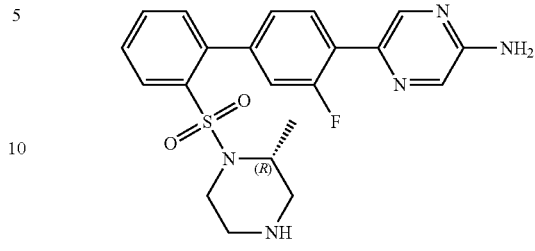

(R)-5-(3-Fluoro-2'-((2-methylpiperazin-1-yl)sulfonyl)-[1,1'-biphenyl]-4-yl)pyrazin-2-amine The title compound was prepared in a manner similar to that described in Example 88 using (R)-1-((2-bromophenyl)sulfonyl)-2-methylpiperazine. MS (ESI): mass calcd. for $C_{21}H_{22}FN_5O_2S$, 427.15; m/z found, 428.1 [M+H]+. $^1$H NMR (500 MHz, CD$_3$OD) δ 8.43-8.38 (m, 1H), 8.23-8.16 (dd, J=8.1, 1.3, 1H), 8.16-8.12 (d, J=1.5, 1H), 8.01-7.95 (m, 1H), 7.80-7.73 (m, 1H), 7.68-7.62 (m, 1H), 7.52-7.45 (dd, J=7.6, 1.3, 1H), 7.44-7.36 (m, 2H), 3.95-3.79 (dd, J=7.1, 4.4, 1H), 3.23-3.15 (m, 1H), 3.15-3.03 (m, 3H), 2.79-2.64 (m, 2H), 1.19-1.15 (d, J=7.1, 3H).

Example 146

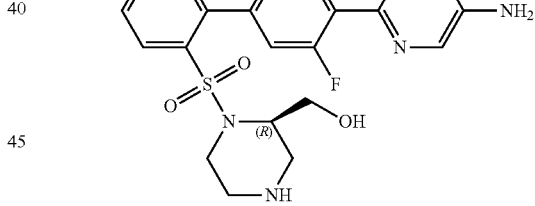

(R)-(1-((4'-(5-Aminopyrazin-2-yl)-3'-fluoro-[1,1'-biphenyl]-2-yl)sulfonyl)piperazin-2-yl)methanol The title compound was prepared in a manner similar to that described in Example 88 using (R)-(1-((2-bromophenyl)sulfonyl)piperazin-2-yl)methanol. MS (ESI): mass calcd. for $C_{21}H_{22}FN_5O_3S$, 443.14; m/z found, 444.1 [M+H]+. $^1$H NMR (500 MHz, CD$_3$OD) δ 8.43-8.37 (m, 1H), 8.24-8.17 (dd, J=8.0, 1.3, 1H), 8.16-8.11 (d, J=1.5, 1H), 8.01-7.94 (m, 1H), 7.82-7.74 (m, 1H), 7.69-7.61 (m, 1H), 7.53-7.46 (dd, J=7.7, 1.3, 1H), 7.41 (s, 1H), 7.40-7.36 (dd, J=4.3, 1.6, 1H), 3.79-3.64 (m, 3H), 3.49-3.43 (m, 1H), 3.43-3.35 (m, 1H), 3.29-3.25 (d, J=3.7, 1H), 3.21-3.11 (m, 1H), 2.81-2.70 (m, 1H), 2.70-2.62 (dd, J=13.1, 4.7, 1H).

Example 147

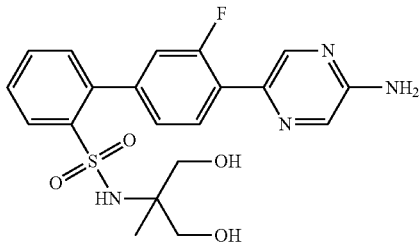

4'-(5-Aminopyrazin-2-yl)-3'-fluoro-N-[2-hydroxy-1-(hydroxymethyl)-1-methylethyl]biphenyl-2-sulfonamide The title compound was prepared in a manner similar to that described in Example 88 using 2-bromo-N-(1,3-dihydroxy-2-methylpropan-2-yl)-benzenesulfonamide. MS (ESI): mass calcd. for $C_{20}H_{21}FN_4O_4S$, 432.13; m/z found, 433.0 [M+H]$^+$. $^1$H NMR (500 MHz, CD$_3$OD) δ 8.43-8.37 (dd, J=2.2, 1.5, 1H), 8.20-8.14 (dd, J=8.0, 1.3, 1H), 8.10-8.06 (d, J=1.5, 1H), 7.93-7.84 (m, 1H), 7.69-7.63 (m, 1H), 7.60-7.54 (m, 1H), 7.42-7.38 (dd, J=7.5, 1.3, 1H), 7.38-7.32 (m, 2H), 3.45-3.39 (m, 2H), 3.39-3.33 (m, 2H), 0.97 (s, 3H).

Example 148

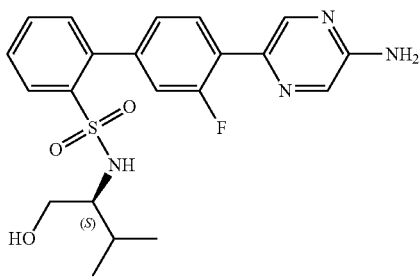

(S)-4'-(5-Aminopyrazin-2-yl)-3'-fluoro-N-(1-hydroxy-3-methylbutan-2-yl)-1,1'-biphenyl]-2-sulfonamide The title compound was prepared in a manner similar to that described in Example 88 using (S)-2-bromo-N-(1-hydroxy-3-methylbutan-2-yl)benzenesulfonamide. MS (ESI): mass calcd. for $C_{21}H_{23}FN_4O_3S$, 430.15; m/z found, 431.1 [M+H]$^+$. $^1$H NMR (500 MHz, CD$_3$OD) δ 8.41-8.38 (d, J=1.7, 1H), 8.15-8.12 (dd, J=8.0, 1.3, 1H), 8.09-8.06 (d, J=1.5, 1H), 7.90-7.84 (m, 1H), 7.67-7.61 (m, 1H), 7.60-7.54 (m, 1H), 7.39-7.35 (dd, J=7.6, 1.4, 1H), 7.35-7.29 (m, 2H), 3.46-3.39 (m, 1H), 3.39-3.33 (m, 1H), 3.09-3.02 (q, J=5.5, 1H), 1.90-1.75 (m, 1H), 0.83-0.76 (dd, J=6.9, 4.4, 6H).

Example 149

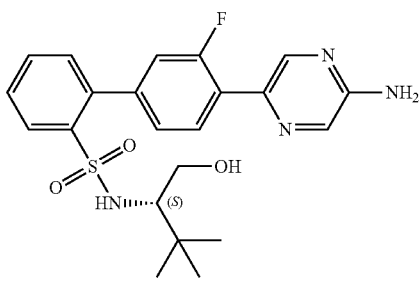

(S)-4'-(5-Aminopyrazin-2-yl)-3'-fluoro-N-(1-hydroxy-3,3-dimethylbutan-2-yl)-[1,1'-biphenyl]-2-sulfonamide The title compound was prepared in a manner similar to that described in Example 88 using (S)-2-bromo-N-(1-hydroxy-3,3-dimethylbutan-2-yl)benzenesulfonamide. MS (ESI): mass calcd. for $C_{22}H_{25}FN_4O_3S$, 444.16; m/z found, 445.0 [M+H]$^+$. $^1$H NMR (500 MHz, CD$_3$OD) δ 8.43-8.35 (dd, J=2.2, 1.5, 1H), 8.16-8.11 (dd, J=8.1, 1.3, 1H), 8.10-8.06 (d, J=1.5, 1H), 7.93-7.83 (m, 1H), 7.65-7.59 (m, 1H), 7.58-7.52 (m, 1H), 7.37-7.35 (dd, J=3.3, 1.6, 1H), 7.35-7.31 (m, 2H), 3.55-3.49 (m, 1H), 3.49-3.43 (m, 1H), 3.11-3.04 (dd, J=5.9, 4.2, 1H), 0.82 (s, 9H).

Example 150

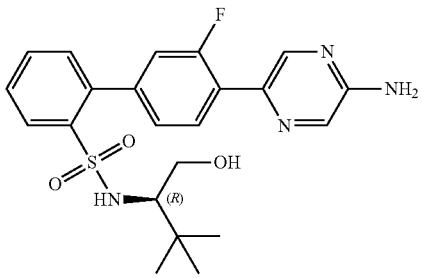

(R)-4'-(5-Aminopyrazin-2-yl)-3'-fluoro-N-[1-hydroxy-3,3-dimethylbutan-2-yl)-[1,1'-biphenyl]-2-sulfonamide The title compound was prepared in a manner similar to that described in Example 88 using (R)-2-bromo-N-(1-hydroxy-3,3-dimethylbutan-2-yl)benzenesulfonamide. MS (ESI): mass calcd. for $C_{22}H_{25}FN_4O_3S$, 444.16; m/z found, 445.0 [M+H]$^+$. $^1$H NMR (500 MHz, CD$_3$OD) δ 8.42-8.37 (m, 1H), 8.15-8.11 (dd, J=8.0, 1.3, 1H), 8.09-8.05 (d, J=1.5, 1H), 7.92-7.86 (m, 1H), 7.65-7.59 (m, 1H), 7.58-7.52 (m, 1H), 7.38-7.35 (dd, J=3.3, 1.5, 1H), 7.35-7.31 (m, 2H), 3.55-3.49 (m, 1H), 3.49-3.42 (m, 1H), 3.10-3.04 (dd, J=5.9, 4.2, 1H), 0.82 (s, 9H).

Example 151

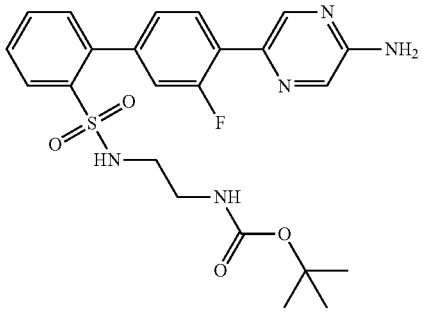

tert-Butyl [2-({[4'-(5-aminopyrazin-2-yl)-3'-fluorobiphenyl-2-yl]sulfonyl}amino)ethyl]carbamate The title compound was prepared in a manner similar to that described in Example 88 using tert-butyl-(2-(2-bromophenylsulfonamido)ethyl)carbamate. MS (ESI): mass calcd. for $C_{23}H_{26}FN_5O_4S$, 487.17; m/z found, 488.1 [M+H]$^+$. $^1$H NMR (500 MHz, CDCl$_3$) δ 8.57-8.54 (m, 1H), 8.18-8.13 (dd, J=8.0, 1.4, 1H), 8.11-8.08 (d, J=1.5, 1H), 8.05-7.98 (m, 1H), 7.65-7.59 (m, 1H), 7.58-7.52 (m, 1H), 7.37-7.33 (m, 2H), 7.32-7.29 (dd, J=11.8, 1.7, 1H), 4.78 (s, 3H), 4.46 (s, 1H), 3.17-3.04 (d, J=5.9, 2H), 2.97-2.77 (m, 2H), 1.38 (s, 9H).

Example 152

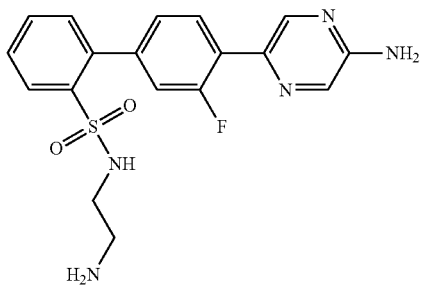

N-(2-Aminoethyl)-4'-(5-aminopyrazin-2-yl)-3'-fluorobiphenyl-2-sulfonamide

The title compound was prepared in a manner similar to that described in Example 88 using N-(2-aminoethyl)-2-bromobenzenesulfonamide. MS (ESI): mass calcd. for $C_{18}H_{18}FN_5O_2S$, 387.12; m/z found, 388.1 [M+H]$^+$. $^1$H NMR (500 MHz, CD$_3$OD) δ 8.41-8.38 (d, J=1.7, 1H), 8.15-8.11 (d, J=1.5, 1H), 8.10-8.06 (dd, J=8.0, 1.3, 1H), 7.98-7.91 (m, 1H), 7.74-7.69 (m, 1H), 7.65-7.59 (m, 1H), 7.47-7.43 (dd, J=7.6, 1.3, 1H), 7.33-7.32 (dd, J=4.1, 1.8, 1H), 7.31-7.29 (dd, J=8.2, 1.6, 1H), 3.05-2.98 (t, J=5.9, 2H), 2.97-2.92 (m, 2H).

Example 153

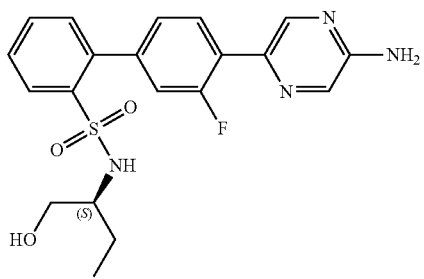

(S)-4'-(5-Aminopyrazin-2-yl)-3'-fluoro-N-(1-hydroxybutan-2-yl)-[1-1'-biphenyl]-2-sulfonamide The title compound was prepared in a manner similar to that described in Example 88 using (S)-2-bromo-N-(1-hydroxybutan-2-yl)benzenesulfonamide. MS (ESI): mass calcd. for $C_{20}H_{21}FN_4O_3S$, 416.13; m/z found, 417.1 [M+H]$^+$. $^1$H NMR (500 MHz, CD$_3$OD) δ 8.40-8.35 (d, J=1.6, 1H), 8.23-8.17 (d, J=1.5, 1H), 8.17-8.10 (dd, J=8.0, 1.3, 1H), 7.97-7.88 (m, 1H), 7.69-7.61 (m, 1H), 7.61-7.55 (m, 1H), 7.41-7.36 (dd, J=7.5, 1.4, 1H), 7.36-7.28 (m, 2H), 3.43-3.36 (m, 1H), 3.34-3.31 (m, 1H), 3.12-3.05 (m, 1H), 1.60-1.46 (m, 1H), 1.42-1.28 (m, 1H), 0.85-0.72 (t, J=7.4, 3H).

Example 154

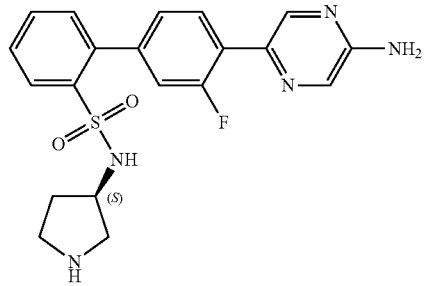

(S)-4'-(5-Aminopyrazin-2-yl)-3'-fluoro-N-(pyrrolidin-3-yl)-[1-1'-biphenyl]-2-sulfonamide The title compound was prepared in a manner similar to that described in Example 88 using (S)-2-bromo-N-(pyrrolidin-3-yl)benzenesulfonamide. MS (ESI): mass calcd. for $C_{20}H_{20}FN_5O_2S$, 413.13; m/z found, 414.1 [M+H]$^+$. $^1$H NMR (500 MHz, CD$_3$OD) δ 8.42-8.37 (m, 1H), 8.15-8.10 (m, 2H), 7.96-7.90 (m, 1H), 7.75-7.69 (m, 1H), 7.66-7.60 (m, 1H), 7.45 (dd, J=7.6, 1.3 Hz, 1H), 7.33 (s, 1H), 7.31 (dd, J=3.7, 1.6 Hz, 1H), 3.74-3.60 (m, 1H), 3.33-3.32 (m, 1H), 3.28-3.26 (m, 1H), 3.25-3.18 (m, 1H), 3.11 (dd, J=12.3, 5.4 Hz, 1H), 2.17-2.04 (m, 1H), 1.85-1.73 (m, 1H).

Example 155

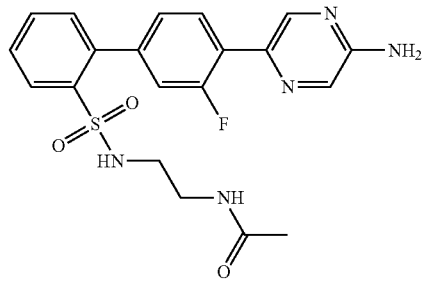

N-2-({[4'-(5-Aminopyrazin-2-yl)-3'-fluorobiphenyl-2-yl]sulfonyl}amino)ethyl]acetamide The title compound was prepared in a manner similar to that described in Example 88 using N-(2-(2-bromophenylsulfonamido)ethyl)acetamide. MS (ESI): mass calcd. for $C_{20}H_{20}FN_5O_3S$, 429.13; m/z found, 430.0 [M+H]$^+$. $^1$H NMR (500 MHz, CD$_3$OD) δ 8.39-8.33 (m, 1H), 8.28-8.25 (d, J=1.4, 1H), 8.09-8.03 (dd, J=8.0, 1.3, 1H), 8.00-7.93 (m, 1H), 7.70-7.65 (dd, J=7.5, 1.4, 1H), 7.63-7.56 (m, 1H), 7.43-7.39 (dd, J=7.5, 1.4, 1H), 7.36-7.28 (m, 2H), 3.19-3.12 (t, J=6.3, 2H), 2.89-2.83 (t, J=6.3, 2H), 1.86 (s, 3H).

Example 156

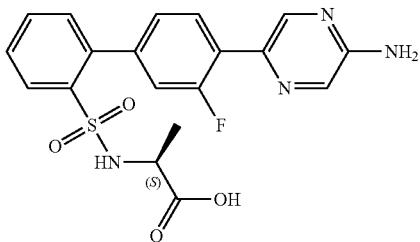

(S)-2-(4'-(5-Aminopyrazin-2-yl)-3'-fluoro-
[1,1'-biphenyl]-2-ylsulfonamido)propanoic acid The title compound was prepared in a manner similar to that described in Example 88 using (S)-2-(2-bromophenylsulfonamido)propanoic acid. MS (ESI): mass calcd. for $C_{19}H_{17}FN_4O_4S$, 416.10; m/z found, 417.0 [M+H]$^+$. $^1$H NMR (500 MHz, CD$_3$OD) δ 8.39-8.34 (m, 1H), 8.23-8.20 (d, J=1.4, 1H), 8.13-8.08 (dd, J=8.0, 1.3, 1H), 7.96-7.89 (m, 1H), 7.69-7.62 (m, 1H), 7.60-7.54 (m, 1H), 7.39-7.36 (dd, J=7.6, 1.3, 1H), 7.36-7.34 (dd, J=8.0, 1.7, 1H), 7.34-7.30 (dd, J=12.3, 1.7, 1H), 3.77-3.66 (q, J=7.2, 1H), 1.33-1.25 (d, J=7.2, 3H).

Example 157

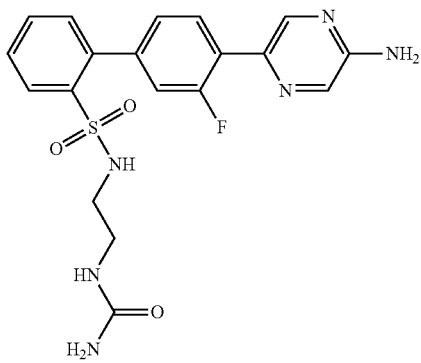

4'-(5-Aminopyrazin-2-yl)N-N-[2-carbamoylamino)ethyl]-
3'-fluorobiphenyl-2-sulfonamide The title compound was prepared in a manner similar to that described in Example 88 using 2-bromo-N-(2-ureidoethyl)benzenesulfonamide. MS (ESI): mass calcd. for $C_{19}H_{19}FN_6O_3S$, 430.12; m/z found, 431.1 [M+H]$^+$. $^1$H NMR (500 MHz, CD$_3$OD) δ 8.38-8.32 (m, 1H), 8.29 (s, 1H), 8.09-8.03 (dd, J=8.0, 1.3, 1H), 8.01-7.93 (m, 1H), 7.73-7.64 (m, 1H), 7.64-7.55 (m, 1H), 7.45-7.38 (dd, J=7.6, 1.4, 1H), 7.37-7.28 (m, 2H), 3.15-3.04 (t, J=6.2, 2H), 2.87-2.78 (t, J=6.2, 2H).

Example 158

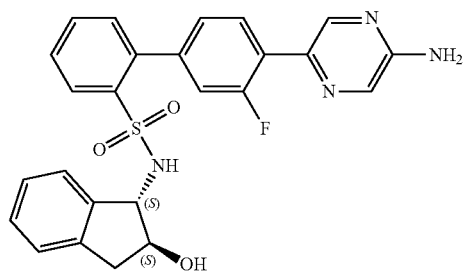

4'-(5-Aminopyrazin-2-yl)-3'-fluoro-N-((1S,2S)-2-hydroxy-2,3-
dihydro-1H-inden-1-yl)-[1,1'-biphenyl]-2-sulfonamide The title compound was prepared in a manner similar to that described in Example 88 using 2-bromo-N-((1S,2S)-2-hydroxy-2,3-dihydro-1H-inden-1-yl)benzenesulfonamide. MS (ESI): mass calcd. for $C_{25}H_{21}FN_4O_3S$, 476.13; m/z found, 477.0 [M+H]$^+$. $^1$H NMR (500 MHz, CD$_3$OD) δ 8.38-8.34 (m, 1H), 8.29-8.24 (dd, J=8.0, 1.3, 1H), 8.07-8.05 (d, J=1.5, 1H), 7.84-7.79 (m, 1H), 7.71-7.66 (m, 1H), 7.63-7.58 (m, 1H), 7.42-7.37 (dd, J=7.6, 1.3, 1H), 7.31-7.23 (m, 2H), 7.21-7.13 (m, 2H), 7.12-7.07 (m, 1H), 7.03-6.97 (m, 1H), 4.49-4.45 (d, J=5.3, 1H), 4.28-4.22 (m, 1H), 3.19-3.11 (dd, J=15.8, 6.7, 1H), 2.70-2.64 (dd, J=15.8, 5.9, 1H).

Example 159

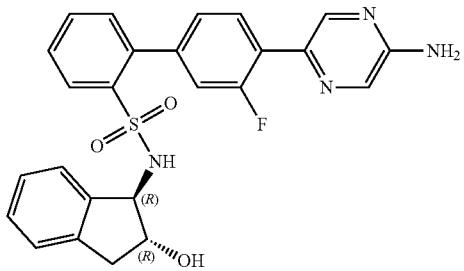

4'-(5-Aminopyrazin-2-yl)-3'-fluoro-N-((1R,2R)-2-hydroxy-2,3-
dihydro-1H-inden-1-yl)-[1,1'-biphenyl]-2-sulfonamide The title compound was prepared in a manner similar to that described in Example 88 using 2-bromo-N-((1R,2R)-2-hydroxy-2,3-dihydro-1H-inden-1-yl)benzenesulfonamide. MS (ESI): mass calcd. for $C_{25}H_{21}FN_4O_3S$, 476.13; m/z found, 477.0 [M+H]$^+$. $^1$H NMR (500 MHz, CD$_3$OD) δ 8.38-8.34 (m, 1H), 8.29-8.25 (dd, J=8.1, 1.3, 1H), 8.07-8.04 (d, J=1.5, 1H), 7.86-7.78 (m, 1H), 7.73-7.65 (m, 1H), 7.65-7.57 (m, 1H), 7.44-7.36 (dd, J=7.6, 1.3, 1H), 7.32-7.23 (m, 2H), 7.22-7.12 (m, 2H), 7.12-7.06 (m, 1H), 7.02-6.95 (d, J=7.6, 1H), 4.51-4.43 (d, J=5.4, 1H), 4.30-4.21 (m, 1H), 3.20-3.10 (dd, J=15.9, 6.7, 1H), 2.72-2.58 (dd, J=15.8, 6.0, 1H).

Example 160

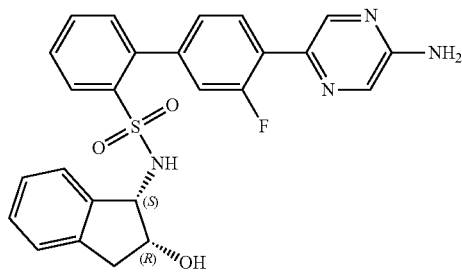

4'-(5-Aminopyrazin-2-yl)-3'-fluoro-N-((1S,2R)-2-hydroxy-2,3-dihydro-1H-inden-1-yl)-[1,1'-biphenyl]-2-sulfonamide The title compound was prepared in a manner similar to that described in Example 88 using 2-bromo-N-((1S,2R)-2-hydroxy-2,3-dihydro-1H-inden-1-yl)benzenesulfonamide. MS (ESI): mass calcd. for $C_{25}H_{21}FN_4O_3S$, 476.13; m/z found, 477.0 [M+H]$^+$. $^1$H NMR (500 MHz, CD$_3$OD) δ 8.39-8.33 (m, 1H), 8.27-8.22 (dd. J=8.0, 1.3, 1H), 8.08-8.04 (d, J=1.5, 1H), 7.88-7.80 (m, 1H), 7.72-7.67 (m, 1H), 7.65-7.58 (m, 1H), 7.42-7.37 (dd. J=7.7, 1.4, 1H), 7.31-7.26 (dd, J=8.0, 1.7, 1H), 7.26-7.21 (dd, J=12.2, 1.7, 1H), 7.20-7.16 (dd, J=4.7, 1.2, 2H), 7.12-7.05 (m, 1H), 7.06-7.01 (m, 1H), 4.64-4.56 (dd, J=5.1, 1.0, 1H), 4.30-4.24 (m, 1H), 3.01-2.93 (dd, J=16.2, 5.2, 1H), 2.80-2.72 (dd, J=16.2, 2.6, 1H).

Example 161

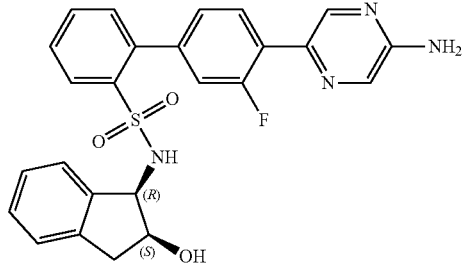

4'-(5-Aminopyrazin-2-yl)-3'-fluoro-N-((1R,2S)-2-hydroxy-2,3-dihydro-1H-inden-1-yl)-[1,1'-biphenyl]-2-sulfonamide The title compound was prepared in a manner similar to that described in Example 88 using 2-bromo-N-((1R,2S)-2-hydroxy-2,3-dihydro-1H-inden-1-yl)benzenesulfonamide. MS (ESI): mass calcd. for $C_{25}H_{21}FN_4O_3S$, 476.13; m/z found, 477.0 [M+H]$^+$. $^1$H NMR (500 MHz, CD$_3$OD) δ 8.38-8.32 (m, 1H), 8.28-8.21 (dd, J=8.0, 1.3, 1H), 8.09-8.02 (d, J=1.5, 1H), 7.88-7.79 (m, 1H), 7.73-7.66 (m, 1H), 7.65-7.57 (m, 1H), 7.42-7.38 (dd, J=7.6, 1.4, 1H), 7.30-7.26 (dd, J=8.0, 1.7, 1H), 7.26-7.21 (dd, J=12.2, 1.7, 1H), 7.20-7.16 (dd, J=4.7, 1.2, 2H), 7.11-7.05 (m, 1H), 7.06-7.01 (m, 1H), 4.62-4.55 (d, J=5.3, 1H), 4.30-4.21 (m, 1H), 3.04-2.92 (dd, J=16.2, 5.2, 1H), 2.81-2.72 (dd, J=16.1, 2.6, 1H).

Example 162

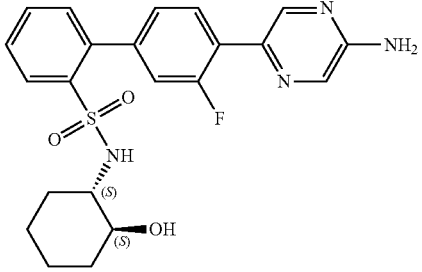

4'-(5-Aminopyrazin-2-yl)-3'-fluoro-N-((1S,2S)-2-hydroxycyclohexyl-[1,1'-biphenyl]-2-sulfonamide The title compound was prepared in a manner similar to that described in Example 88 using 2-bromo-N-((1S,2S)-2-hydroxycyclohexyl)benzenesulfonamide. MS (ESI): mass calcd. for $C_{22}H_{23}FN_4O_3S$, 442.15; m/z found, 443.1 [M+H]$^+$. $^1$H NMR (500 MHz, CD$_3$OD) δ 8.36 (s, 1H), 8.26-8.22 (d, J=1.5, 2H), 8.22-8.15 (dd, J=8.0, 1.3, 2H), 7.97-7.90 (m, 2H), 7.69-7.62 (m, 2H), 7.61-7.54 (m, 2H), 7.41-7.32 (m, 5H), 3.25-3.18 (m, 1H), 2.88-2.77 (m, 2H), 1.96-1.84 (m, 2H), 1.85-1.77 (m, 2H), 1.68-1.59 (m, 2H), 1.59-1.49 (m, 2H), 1.25-1.18 (m, 4H), 1.18-1.11 (m, 3H).

Example 163

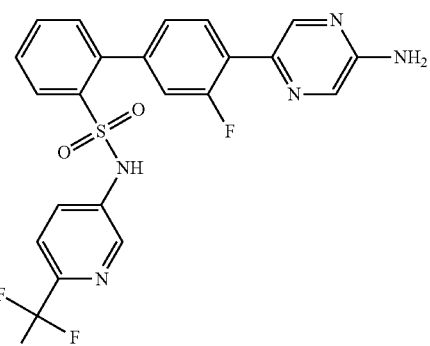

4'-(5-Aminopyrazin-2-yl)-3'-fluoro-N-[6-(trifluoromethyl)pyridin-3-yl]biphenyl-2-sulfonamide The title compound was prepared in a manner similar to that described in Example 88 using 2-bromo-N-(6-(trifluoromethyl)pyridin-3-yl)benzenesulfonamide. MS (ESI): mass calcd. for $C_{22}H_{15}F_4N_5O_2S$, 489.09; m/z found, 490.0 [M+H]$^+$. $^1$H NMR (500 MHz, CD$_3$OD) δ 8.43-8.38 (m, 1H), 8.29-8.24 (dd, J=8.0, 1.4, 1H), 8.11-8.08 (d, J=1.5, 1H), 8.08-8.06 (d, J=2.6, 1H), 7.87-7.80 (m, 1H), 7.72-7.67 (m, 1H), 7.67-7.61 (m, 1H), 7.58-7.52 (d, J=8.7, 1H), 7.46-7.42 (dd, J=8.7, 2.5, 1H), 7.38-7.33 (dd, J=7.5, 1.4, 1H), 7.16-7.10 (dd, J=12.1, 1.7, 1H), 7.10-7.05 (dd, J=8.0, 1.7, 1H).

Example 164

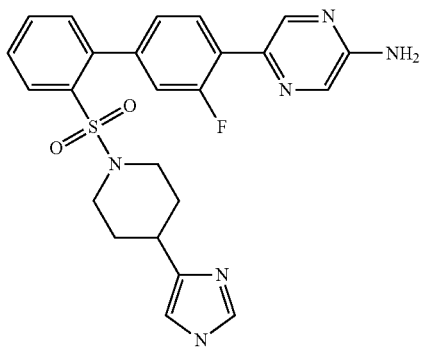

5-(3-Fluoro-2'-{[4-imidazol-4-yl)piperidin-
1-yl]sulfonyl}biphenyl-4-yl)pyrazin-
2-amine The title compound was prepared in a manner similar to that described in Example 88 using 1-((2-bromophenyl) sulfonyl)-4-(1H-imidazol-4-yl)piperidine. MS (ESI): mass calcd. for $C_{24}H_{23}FN_6O_2S$, 478.16; m/z found, 479.1 [M+H]$^+$. $^1$H NMR (500 MHz, CD$_3$OD) δ 8.83-8.76 (d, J=1.4, 1H), 8.39-8.33 (m, 1H), 8.16-8.08 (m, 2H), 7.98-7.85 (m, 1H), 7.75-7.68 (m, 1H), 7.65-7.60 (m, 1H), 7.48-7.41 (dd, J=7.5, 1.3, 1H), 7.34 (s, 1H), 7.32-7.31 (m, 1H), 7.30-7.26 (d, J=1.2, 1H), 3.48-3.39 (d, J=13.3, 2H), 2.84-2.69 (m, 1H), 2.64-2.48 (m, 2H), 1.93-1.80 (d, J=12.9, 2H), 1.52-1.33 (m, 2H).

Example 165

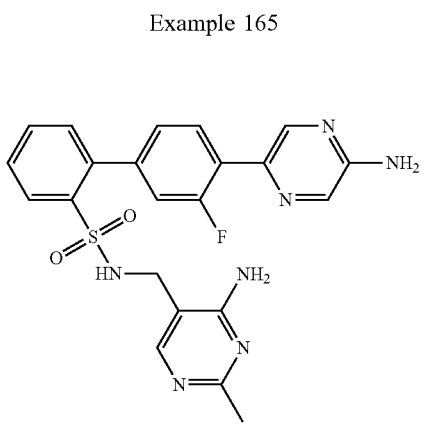

N-[(4-Amino-2-methylpyrimidin-5-yl)methyl]-
4'-(5-aminopyrazin-2-yl)-3'-fluorobiphenyl-2-
sulfonamide The title compound was prepared in a manner similar to that described in Example 88 using N-((4-amino-2-methyl-pyrimidin-5-yl)methyl)-2-bromobenzenesulfonamide. MS (ESI): mass calcd. for $C_{22}H_{20}FN_7O_2S$, 465.14; m/z found, 466.0 [M+H]$^+$. $^1$H NMR (500 MHz, CD$_3$OD) δ 8.36 (s, 1H), 8.26-8.18 (d, J=1.4, 1H), 8.12-8.06 (d, J=7.9, 1H), 7.98-7.92 (m, 1H), 7.90 (s, 1H), 7.76-7.69 (m, 1H), 7.68-7.59 (m, 1H), 7.48-7.41 (dd, J=7.6, 1.4, 1H), 7.39-7.29 (m, 2H), 3.88 (s, 2H), 2.50 (s, 3H).

Example 166

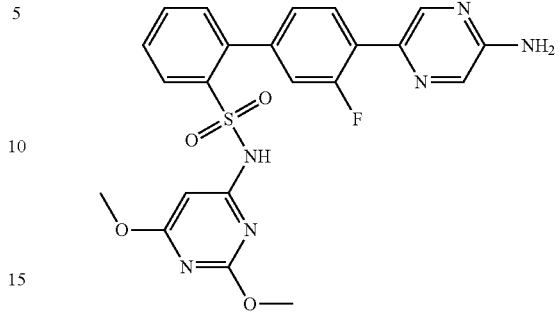

4'-(5-Aminopyrazin-2-yl)-N-(2,6-dimethoxypyrimidin-4-yl)-
3'-fluorobiphenyl-2-sulfonamide The title compound was prepared in a manner similar to that described in Example 88 using 2-bromo-N-(2,6-dimethoxypyrimidin-4-yl)benzenesulfonamide. MS (ESI): mass calcd. for $C_{22}H_{19}FN_6O_4S$, 482.12; m/z found, 483.0 [M+H]$^+$. $^1$H NMR (500 MHz, CD$_3$OD) δ 8.41-8.36 (m, 1H), 8.28-8.20 (d, J=8.0, 1H), 8.10-8.06 (d, J=1.5, 1H), 7.84-7.77 (m, 1H), 7.66-7.52 (m, 3H), 7.34-7.29 (d, J=7.3, 1H), 7.14-7.05 (m, 2H), 3.75 (s, 3H), 3.60 (s, 3H).

Example 167

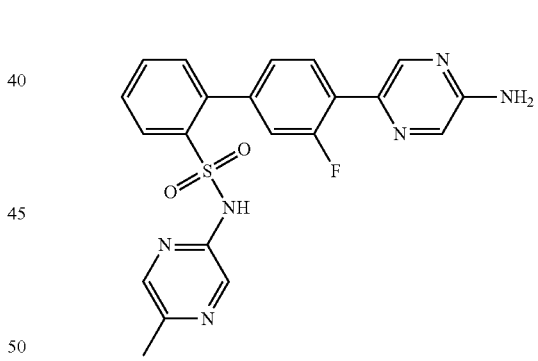

4'-(5-Aminopyrazin-2-yl)-3'-fluoro-N-(5-methylpyrazin-
2-yl)biphenyl-2-sulfonamide The title compound was prepared in a manner similar to that described in Example 88 using 2-bromo-N-(5-methyl-pyrazin-2-yl)benzenesulfonamide. MS (ESI): mass calcd. for $C_{21}H_{17}FN_6O_2S$, 436.11; m/z found, 437.1 [M+H]$^+$. $^1$H NMR (500 MHz, CD$_3$OD) δ 8.41-8.37 (m, 1H), 8.25-8.21 (dd, J=8.1, 1.0, 1H), 8.10-8.07 (d, J=1.5, 1H), 7.94-7.85 (m, 2H), 7.82-7.76 (m, 1H), 7.67-7.60 (m, 1H), 7.61-7.54 (m, 1H), 7.34-7.27 (m, 1H), 7.15-7.05 (m, 2H), 2.23 (s, 3H).

Example 168

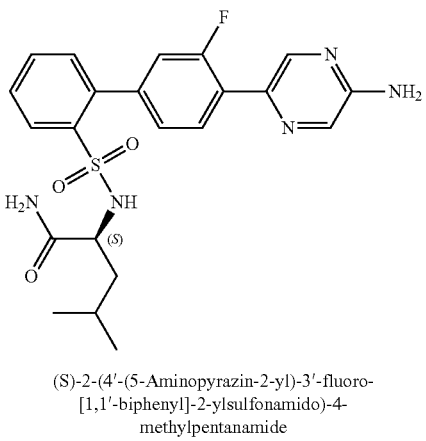

(S)-2-(4'-(5-Aminopyrazin-2-yl)-3'-fluoro-[1,1'-biphenyl]-2-ylsulfonamido)-4-methylpentanamide The title compound was prepared in a manner similar to that described in Example 88 using (S)-2-(2-bromophenylsulfonamido)-4-methylpentanamide. MS (ESI): mass calcd. for $C_{22}H_{24}FN_5O_3S$, 457.16; m/z found, 458.1 [M+H]$^+$. $^1$H NMR (500 MHz, CD$_3$OD) δ 8.42-8.37 (m, 1H), 8.13-8.09 (dd, J=8.0, 1.3, 1H), 8.09-8.06 (d, J=1.5, 1H), 7.90-7.85 (m, 1H), 7.69-7.62 (m, 1H), 7.59-7.53 (m, 1H), 7.40-7.36 (dd, J=7.6, 1.3, 1H), 7.36-7.29 (m, 2H), 3.79-3.73 (dd, J=9.1, 5.7, 1H), 1.72-1.54 (m, 1H), 1.51-1.34 (m, 2H), 0.88-0.84 (d, J=6.6, 3H), 0.81-0.78 (d, J=6.6, 3H).

Example 169

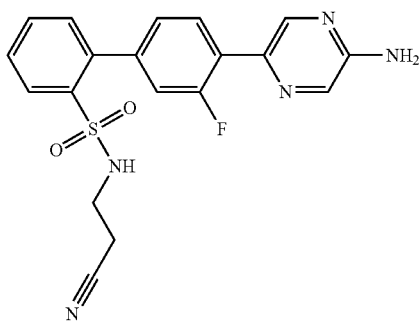

4'-(5-Aminopyrazin-2-yl)-N-(2-cyanoethyl)-3'-fluorobiphenyl-2-sulfonamide

The title compound was prepared in a manner similar to that described in Example 88 using 2-bromo-N-(2-cyanoethyl)benzenesulfonamide. MS (ESI): mass calcd. for $C_{19}H_{16}FN_5O_2S$, 397.10; m/z found, 398.1 [M+H]$^+$. $^1$H NMR (500 MHz, CD$_3$OD) δ 8.39-8.34 (m, 1H), 8.21-8.17 (d, J=1.5, 1H), 8.09-8.06 (dd, J=8.0, 1.3, 1H), 7.96-7.90 (m, 1H), 7.72-7.66 (m, 1H), 7.64-7.57 (m, 1H), 7.43-7.39 (dd, J=7.7, 1.4, 1H), 7.37-7.27 (m, 2H), 3.09-3.02 (t, J=6.6, 2H), 2.56-2.50 (t, J=6.6, 2H).

Example 170

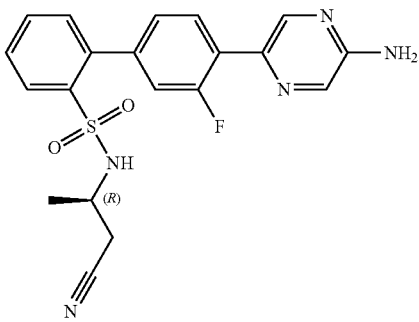

(R)-4'-(5-Aminopyrazin-2-yl)-N-(1-cyanopropan-2-yl)-3'-fluoro-[1,1'-biphenyl]-2-sulfonamide The title compound was prepared in a manner similar to that described in Example 88 using (R)-2-bromo-N-(1-cyanopropan-2-yl)benzenesulfonamide. MS (ESI): mass calcd. for $C_{20}H_{18}FN_5O_2S$, 411.12; m/z found, 412.0 [M+H]$^+$. $^1$H NMR (500 MHz, CD$_3$OD) δ 8.42-8.36 (m, 1H), 8.17-8.14 (d, J=1.4, 1H), 8.14-8.10 (dd, J=8.0, 1.3, 1H), 7.96-7.87 (m, 1H), 7.72-7.65 (m, 1H), 7.63-7.56 (m, 1H), 7.44-7.38 (dd, J=7.7, 1.4, 1H), 7.37-7.29 (m, 2H), 3.47-3.39 (dd, J=12.3, 6.1, 1H), 2.61-2.46 (m, 2H), 1.18-1.11 (d, J=6.7, 3H).

Example 171

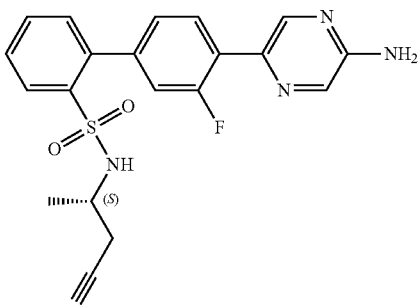

(S)-4'-(5-Aminopyrazin-2-yl)-N-(1-cyanopropan-2-yl)-3'-fluoro-[1,1'-biphenyl]-2-sulfonamide The title compound was prepared in a manner similar to that described in Example 88 using (S)-2-bromo-N-(1-cyanopropan-2-yl)benzenesulfonamide. MS (ESI): mass calcd. for $C_{20}H_{18}FN_5O_2S$, 411.12; m/z found, 412.0 [M+H]$^+$. $^1$H NMR (500 MHz, CD$_3$OD) δ 8.42-8.38 (dd, J=2.2, 1.5, 1H), 8.16-8.09 (dd, J=8.0, 1.3, 1H), 8.09-8.07 (d, J=1.5, 1H), 7.93-7.86 (m, 1H), 7.71-7.65 (m, 1H), 7.64-7.56 (m, 1H), 7.45-7.38 (dd, J=7.5, 1.3, 1H), 7.37-7.28 (m, 2H), 3.51-3.37 (m, 1H), 2.64-2.45 (m, 2H), 1.18-1.11 (d, J=6.7, 3H).

Example 172

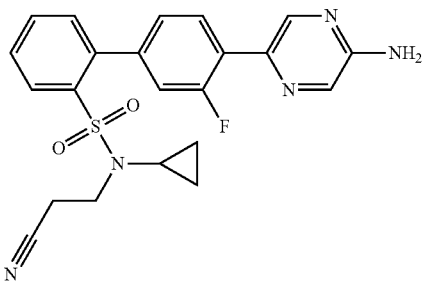

4'-(5-Aminopyrazin-2-yl)-N-(2-cyanoethyl)-N-cyclopropyl-3'-fluorobiphenyl-2-sulfonamide The title compound was prepared in a manner similar to that described in Example 88 using 2-bromo-N-(2-cyanoethyl)-N-cyclopropylbenzenesulfonamide. MS (ESI): mass calcd. for $C_{22}H_{20}FN_5O_2S$, 437.13; m/z found, 438.1 [M+H]$^+$. $^1$H NMR (500 MHz, CD$_3$OD) δ 8.41-8.34 (d, J=1.6, 1H), 8.23-8.18 (d, J=1.4, 1H), 8.18-8.13 (dd, J=8.0, 1.3, 1H), 8.00-7.92 (m, 1H), 7.76-7.71 (m, 1H), 7.68-7.60 (m, 1H), 7.43-7.38 (dd, J=7.6, 1.3, 1H), 7.22 (s, 1H), 7.21-7.19 (dd, J=4.4, 1.5, 1H), 3.02-2.95 (t, J=6.7, 2H), 2.62-2.55 (t, J=6.7, 2H), 2.52-2.35 (m, 1H), 0.63-0.52 (m, 2H), 0.42-0.34 (m, 2H).

Example 173

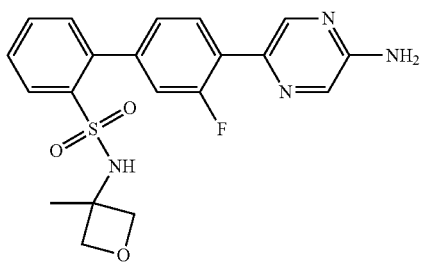

4'-(5-Aminopyrazin-2-yl)-3'-fluoro-N-(3-methyloxetan-3-yl)biphenyl-2-sulfonamide The title compound was prepared in a manner similar to that described in Example 88 using 2-bromo-N-(3-methyloxetan-3-yl)benzenesulfonamide. MS (ESI): mass calcd. for $C_{20}H_{19}FN_4O_3S$, 414.12; m/z found, 415.0 [M+H]$^+$. $^1$H NMR (500 MHz, CD$_3$OD) δ 8.38 (s, 1H), 8.17 (s, 1H), 8.14-8.08 (d, J=8.0, 1H), 7.97-7.88 (m, 1H), 7.73-7.65 (m, 1H), 7.65-7.55 (m, 1H), 7.47-7.38 (d, J=7.6, 1H), 7.37-7.25 (m, 2H), 4.57-4.49 (d, J=6.3, 2H), 4.20-4.13 (d, J=6.2, 2H), 1.46 (s, 3H).

Example 174

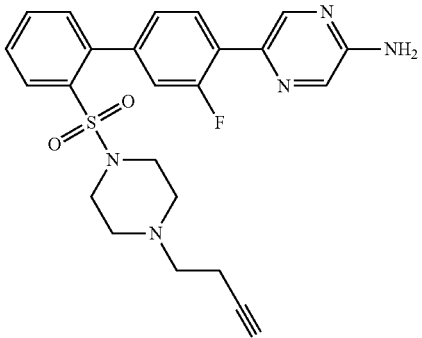

3-(4-{[4'-(5-Aminopyrazin-2-yl)-3'-fluorobiphenyl-2-yl]sulfonyl}piperazin-1-yl)propanenitrile The title compound was prepared in a manner similar to that described in Example 88 using 3-(4-((2-bromophenyl)sulfonyl)piperazin-1-yl)propanenitrile. MS (ESI): mass calcd. for $C_{23}H_{23}FN_6O_2S$, 466.16; m/z found, 467.1 [M+H]$^+$. $^1$H NMR (500 MHz, CD$_3$OD) δ 8.40-8.38 (m, 1H), 8.15-8.11 (m, 2H), 8.00-7.92 (m, 1H), 7.78-7.70 (m, 1H), 7.67-7.60 (m, 1H), 7.49-7.43 (dd, J=7.6, 1.3, 1H), 7.34-7.32 (d, J=0.9, 1H), 7.32-7.30 (dd, J=3.7, 1.6, 1H), 3.13-3.07 (t, J=7.1, 2H), 3.07-3.02 (t, J=4.7, 4H), 2.87-2.81 (d, J=4.8, 4H), 2.81-2.76 (t, J=7.0, 2H).

Example 175

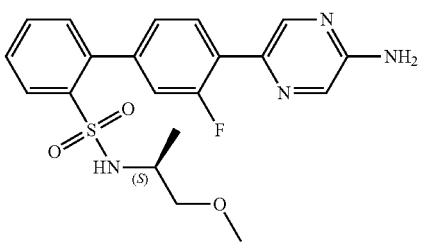

(S)-4'-(5-Aminopyrazin-2-yl)-3'-fluoro-N-(1-methoxypropan-2-yl)-[1,1'-biphenyl]-2-sulfonamide The title compound was prepared in a manner similar to that described in Example 88 using (S)-2-bromo-N-(1-methoxypropan-2-yl)benzenesulfonamide. MS (ESI): mass calcd. for $C_{20}H_{21}FN_4O_3S$, 416.13; m/z found, 417.1 [M+H]$^+$. $^1$H NMR (500 MHz, CD$_3$OD) δ 8.42-8.37 (m, 1H), 8.16-8.11 (dd, J=8.0, 1.3, 1H), 8.10-8.06 (d, J=1.5, 1H), 7.91-7.86 (m, 1H), 7.70-7.62 (m, 1H), 7.61-7.53 (m, 1H), 7.42-7.36 (dd, J=7.5, 1.4, 1H), 7.35-7.26 (m, 2H), 3.37-3.31 (m, 1H), 3.22-3.18 (m, 1H), 3.17 (s, 3H), 3.15-3.10 (m, 1H), 1.06-1.00 (d, J=6.7, 3H).

Example 176

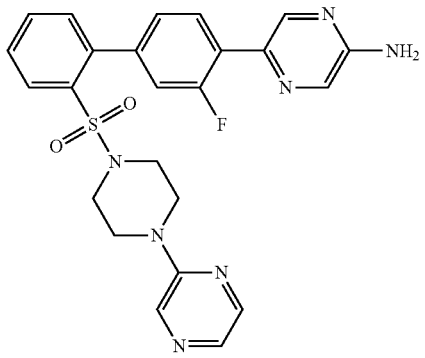

5-{3-Fluoro-2'-[(4-pyrazin-2-ylpiperazin-1-yl)sulfonyl]biphenyl-4-yl}pyrazin-2-amine The title compound was prepared in a manner similar to that described in Example 88 using 2-(4-((2-bromophenyl)sulfonyl)piperazin-1-yl)pyrazine. MS (ESI): mass calcd. for $C_{24}H_{22}FN_7O_2S$, 491.15; m/z found, 492.0 [M+H]$^+$. $^1$H NMR (500 MHz, CD$_3$OD) δ 8.38-8.32 (m, 1H), 8.23-8.17 (d, J=1.4, 1H), 8.16-8.10 (m, 2H), 8.09-8.05 (m, 1H), 7.97-7.90 (m, 1H), 7.80-7.76 (d, J=2.7, 1H), 7.75-7.70 (m, 1H), 7.67-7.60 (m, 1H), 7.47-7.42 (dd. J=7.6, 1.3, 1H), 7.36-7.33 (dd, J=5.1, 1.6, 1H), 7.33 (s, 1H), 3.53-3.39 (t, J=5.1, 4H), 3.02-2.95 (t, J=5.1, 4H).

Example 177

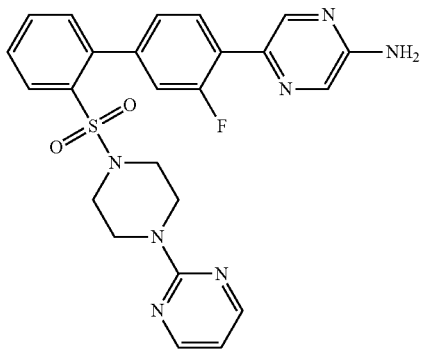

5-{3-Fluoro-2'-[(4-pyrimidin-2-ylpiperazin-1-yl)sulfonyl]biphenyl-4-yl}pyrazin-2-amine The title compound was prepared in a manner similar to that described in Example 88 using 2-(4-((2-bromophenyl)sulfonyl)piperazin-1-yl)pyrimidine. MS (ESI): mass calcd. for $C_{24}H_{22}FN_7O_2S$, 491.15; m/z found, 492.0 [M+H]$^+$. $^1$H NMR (500 MHz, CD$_3$OD) δ 8.39 (s, 1H), 8.29-8.23 (d, J=4.7, 2H), 8.16-8.10 (d, J=8.0, 1H), 8.08 (s, 1H), 7.95-7.87 (m, 1H), 7.76-7.68 (m, 1H), 7.66-7.57 (m, 1H), 7.50-7.42 (d, J=7.5, 1H), 7.34-7.32 (d, J=3.6, 1H), 7.31 (s, 1H), 6.68-6.51 (t, J=4.8, 1H), 3.73-3.56 (t, J=5.0, 4H), 2.97-2.85 (t, J=4.9, 4H).

Example 178

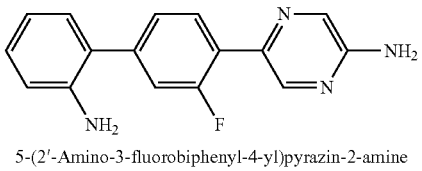 [SMILES: Nc1cnc(-c2ccc(-c3ccccc3N)cc2F)cn1]

5-(2'-Amino-3-fluorobiphenyl-4-yl)pyrazin-2-amine

The title compound was prepared using analogous conditions to those described in Example 6 utilizing 5-(2-fluoro-4-(4,4,5,5-tetramethyl-1,3,2-dioxaborolan-2-yl)phenyl)-pyrazin-2-amine and 2-bromoaniline. MS (ESI): mass calcd. for $C_{16}H_{13}FN_4$, 280.11; m/z found, 281.1 [M+H]$^+$. $^1$H NMR (400 MHz, DMSO-d$_6$) δ 8.36 (s, 1H), 8.02 (s, 1H), 7.91 (m, 1H), 7.31 (d, J=12.7, 2H), 7.04 (d, J=7.3, 2H), 6.82-6.58 (m, 4H), 4.94 (s, 2H).

Example 179

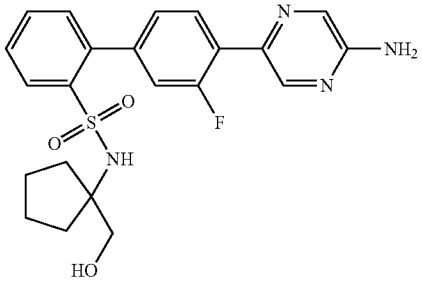

4'-(5-Aminopyrazin-2-yl)-3'-fluoro-N-[1-(hydroxymethyl)cyclopentyl]biphenyl-2-sulfonamide The title compound was prepared in a manner similar to that described in Example 584 using 5-(2-fluoro-4-(4,4,5,5-tetramethyl-1,3,2-dioxaborolan-2-yl)phenyl)pyrazin-2-amine and 2-bromo-N-(1-(hydroxymethyl)-cyclopentyl) benzenesulfonamide in Step B. MS (ESI): mass calcd. for $C_{22}H_{23}FN_4O_3S$, 442.15; m/z found, 443.2 [M+H]$^+$. $^1$H NMR (500 MHz, CDCl$_3$) δ 8.42 (s, 1H), 8.39 (s, 1H), 8.18 (d, J=7.3, 1H), 8.08 (m, 1H), 7.66-7.60 (m, 1H), 7.58-7.52 (m, 1H), 7.43 (dd, J=8.1, 1.8, 1H), 7.38-7.32 (m, 2H), 4.12 (s, 1H), 3.49 (s, 2H), 1.64-1.39 (m, 8H).

Example 180

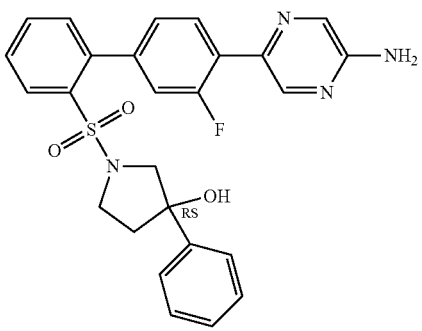

racemic 1-{[4'-(5-Aminopyrazin-2-yl)-3'-fluorobiphenyl-2-yl]sulfonyl}-3-phenylpyrrolidin-3-ol The title compound was prepared in a manner similar to that described in Example 584 using 5-(2-fluoro-4-(4,4,5,5-tetramethyl-1,3,2-dioxaborolan-2-yl)phenyl)-pyrazin-2-amine and racemic 1-((2-bromophenyl)sulfonyl)-3-phenylpyrrolidin-3-ol in Step B. MS (ESI): mass calcd. for $C_{26}H_{23}FN_4O_3S$, 490.15; m/z found, 491.2 [M+H]$^+$. $^1$H NMR (500 MHz, CDCl$_3$) δ 8.57 (s, 1H), 8.20 (d, J=9.2, 1H), 8.11 (d, J=1.5, 1H), 8.00 (t, J=8.1, 1H), 7.61 (dd, J=7.5, 6.2, 1H), 7.53 (m, 1H), 7.40-7.34 (m, 3H), 7.34-7.28 (m, 5H), 4.68 (s, 2H), 3.41-3.23 (m, 4H), 3.18 (d, J=10.8, 1H), 2.21-2.11 (m, 1H), 2.10-2.01 (m, 1H).

Example 181

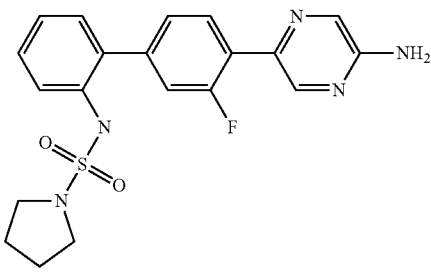

N-[4'-(5-Aminopyrazin-2-yl)-3'-fluorobiphenyl-2-yl]pyrrolidine-1-sulfonamide

The title compound was prepared in a manner similar to that described in Example 571 using 5-(2-fluoro-4-(4,4,5,5-tetramethyl-1,3,2-dioxaborolan-2-yl)phenyl)-pyrazin-2-amine and N-(2-bromophenyl)pyrrolidine-1-sulfonamide in Step B. MS (ESI): mass calcd. for $C_{20}H_{20}FN_5O_2S$, 413.13; m/z found, 414.2 [M+H]$^+$. $^1$H NMR (500 MHz, CDCl$_3$) δ 8.40 (dd, J=5.4, 1.4, 2H), 8.14 (m, 1H), 7.61 (dd, J=8.3, 1.1, 1H), 7.42-7.35 (m, 1H), 7.32 (dd, J=8.0, 1.7, 1H), 7.23 (dd, J=3.6, 1.6, 1H), 7.22-7.15 (m, 1H), 6.44 (s, 1H), 3.33-3.25 (m, 4H), 1.87 (dd, J=7.0, 0.9, 4H).

Example 182

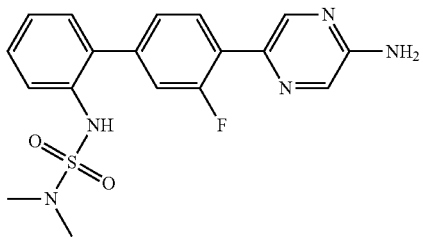

N-[4'-(5-Aminopyrazin-2-yl)-3'-fluorobiphenyl-2-yl]-N, N-dimethylsulfamide

The title compound was prepared in a manner similar to that described in Example 571 using 5-(2-fluoro-4-(4,4,5,5-tetramethyl-1,3,2-dioxaborolan-2-yl)phenyl)pyrazin-2-amine and N-(2-bromophenyl) N,N-dimethylsulfonamide in Step B. MS (ESI): mass calcd. for $C_{18}H_{18}FN_5O_2S$, 387.12; m/z found, 388.3 [M+H]$^+$. $^1$H NMR (500 MHz, CDCl$_3$) δ 8.60 (dd, J=2.3, 1.4, 1H), 8.12 (d, J=1.5, 1H), 8.07 (m, 1H), 7.61 (dd, J=8.3, 1.1, 1H), 7.40-7.34 (m, 1H), 7.29-7.26 (m, 1H), 7.25-7.24 (m, 1H), 7.21-7.16 (m, 2H), 6.42 (s, 1H), 4.72 (s, 2H), 2.79 (s, 6H).

Example 183

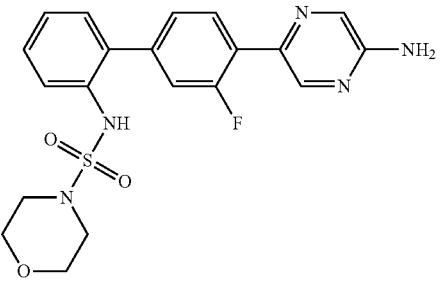

N-[4'-(5-Aminopyrazin-2-yl)-3'-fluorobiphenyl-2-yl]morpholine-4-sulfonamide

The title compound was prepared in a manner similar to that described in Example 571 using 5-(2-fluoro-4-(4,4,5,5-tetramethyl-1,3,2-dioxaborolan-2-yl)phenyl)pyrazin-2-amine and N-(2-bromophenyl)morpholine-4-sulfonamide. MS (ESI): mass calcd. for $C_{20}H_{20}FN_5O_3S$, 429.13; m/z found, 430.2 [M+H]$^+$. $^1$H NMR (500 MHz, CDCl$_3$) δ 8.45 (s, 1H), 8.34 (d, J=1.4, 1H), 8.14 (m, 1H), 7.63 (d, J=8.0, 1H), 7.43-7.35 (m, 1H), 7.31 (dd, J=8.0, 1.7, 1H), 7.24-7.19 (m, 2H), 6.39 (s, 1H), 3.67 (dd, J=5.8, 3.7, 4H), 3.23-3.14 (m, 4H).

Example 184

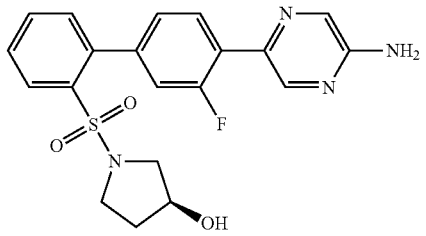

(3S)-1-{[4'-(5-Aminopyrazin-2-yl)-3'-fluorobiphenyl-2-yl]sulfonyl}pyrrolidin-3-ol trifluoroacetic acid salt The title compound was prepared in a manner similar to that described in Example 571 using 5-(2-fluoro-4-(4,4,5,5-tetramethyl-1,3,2-dioxaborolan-2-yl)phenyl)pyrazin-2-amine and (S)-1-((2-bromophenyl)sulfonyl)pyrrolidin-3-ol in Step B. MS (ESI): mass calcd. for $C_{20}H_{19}FN_4O_3S$, 414.12; m/z found, 415.2 [M+H]$^+$. $^1$H NMR (500 MHz, CDCl$_3$) δ 8.44 (d, J=1.3, 1H), 8.33 (d, J=1.5, 1H), 8.13 (dd, J=7.9, 1.3, 1H), 8.07 (m, 1H), 7.62 (m, 1H), 7.58-7.52 (m, 1H), 7.41-7.29 (m, 3H), 4.44-4.36 (m, 1H), 3.23-3.15 (m, 3H), 3.07-2.99 (m, 1H), 1.98-1.88 (m, 1H), 1.88-1.78 (m, 1H).

Example 185

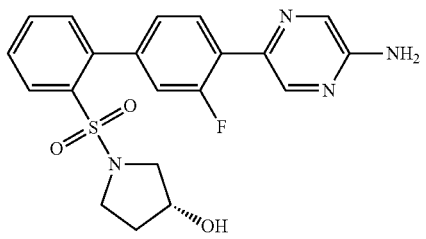

(3R)-1-{[4'-(5-Aminopyrazin-2-yl)-3'-fluorobiphenyl-2-yl]sulfonyl}pyrrolidin-3-ol trifluoroacetic acid salt The title compound was prepared in a manner similar to that described in Example 571 using 5-(2-fluoro-4-(4,4,5,5-tetramethyl-1,3,2-dioxaborolan-2-yl)phenyl)pyrazin-2-amine and (R)-1-((2-bromophenyl)sulfonyl)pyrrolidin-3-ol in Step B. MS (ESI): mass calcd. for $C_{20}H_{19}FN_4O_3S$, 414.12; m/z found, 415.2 $[M+H]^+$. $^1H$ NMR (500 MHz, CDCl$_3$) δ 8.43 (d, J=1.4, 1H), 8.33 (d, J=1.5, 1H), 8.13 (dd, J=7.7, 1.3, 1H), 8.07 (m, 1H), 7.62 (m, 1H), 7.55 (m, 1H), 1.98-1.88 (m, 1H), 7.42-7.29 (m, 3H), 3.24-3.15 (m, 3H), 3.04 (t, J=1.5, 1H), 1.86 (s, 1H), 4.44-4.35 (m, 1H).

Example 186

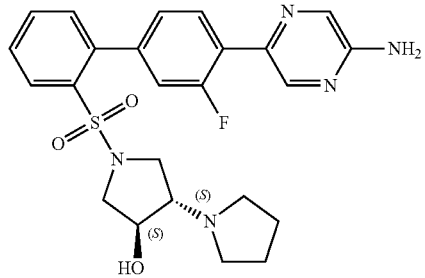

Racemic-1'-{[4'-(5-Aminopyrazin-2-yl)-3'-fluorobiphenyl-2-yl]sulfonyl}-1, 3'-bipyrrolidin-4'-ol The title compound was prepared in a manner similar to that described in Example 571 using 5-(2-fluoro-4-(4,4,5,5-tetramethyl-1,3,2-dioxaborolan-2-yl)phenyl)pyrazin-2-amine and Racemic-1'-((2-bromophenyl)sulfonyl)-[1,3'-bipyrrolidin]-4'-ol in Step B. MS (ESI): mass calcd. for $C_{24}H_{26}FN_5O_3S$, 483.17; m/z found, 484.2 $[M+H]^+$. $^1H$ NMR (500 MHz, CDCl$_3$) δ 8.60-8.57 (m, 1H), 8.15 (d, J=6.8, 1H), 8.11 (d, J=1.5, 1H), 7.97 (m, 1H), 7.61 (dd, J=7.5, 6.1, 1H), 7.55-7.49 (m, 1H), 7.38-7.28 (m, 3H), 4.68 (s, 2H), 4.18-4.12 (m, 1H), 3.30 (dd, J=10.5, 6.2, 1H), 3.23 (dd, J=10.1, 6.8, 1H), 2.95 (dd, J=10.0, 6.4, 1H), 2.88 (dd, J=10.4, 4.4, 1H), 2.63-2.57 (m, 1H), 2.52-2.38 (m, 5H), 1.74-1.67 (m, 4H).

Example 187

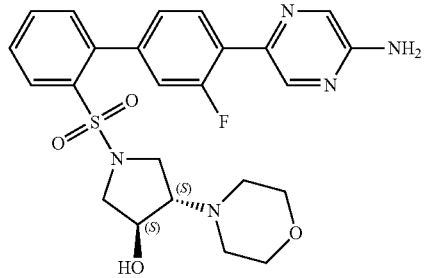

Racemic-1-{[4'-(5-Aminopyrazin-2-yl)-3'-fluorobiphenyl-2-yl]sulfonyl}-4-morpholin-4-ylpyrrolidin-3-ol trifluoroacetic acid salt The title compound was prepared in a manner similar to that described in Example 571 using 5-(2-fluoro-4-(4,4,5,5-tetramethyl-1,3,2-dioxaborolan-2-yl)phenyl)pyrazin-2-amine and Racemic-1-((2-bromophenyl)sulfonyl)-4-morpholinopyrrolidin-3-ol in Step B. MS (ESI): mass calcd. for $C_{24}H_{26}FN_5O_4S$, 499.17; m/z found, 500.3 $[M+H]^+$. $^1H$ NMR (500 MHz, CDCl$_3$) δ 8.41 (s, 1H), 8.32 (s, 1H), 8.13-8.09 (m, 1H), 7.99 (m, 1H), 7.70-7.64 (m, 1H), 7.61-7.56 (m, 1H), 7.38 (dd, J=7.5, 1.3, 1H), 7.35-7.30 (m, 2H), 4.72-4.63 (m, 2H), 3.94-3.85 (m, 3H), 3.40-3.25 (m, 3H), 3.22-3.10 (m, 3H), 3.05-2.94 (m, 2H), 2.92-2.84 (m, 2H), 2.08-2.02 (m, 2H).

Example 188

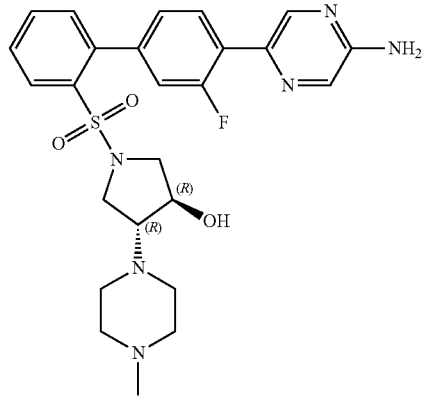

Racemic-1-{[4'-(5-Aminopyrazin-2-yl)-3'-fluorobiphenyl-2-yl]sulfonyl}-4-(4-methylpiperazin-1-yl)-pyrrolidin-3-ol trifluoroacetic acid salt The title compound was prepared in a manner similar to that described in Example 571 using 5-(2-fluoro-4-(4,4,5,5-tetramethyl-1,3,2-dioxaborolan-2-yl)phenyl)pyrazin-2-amine and Racemic-1-((2-bromophenyl)sulfonyl)-4-(4-methylpiperazin-1-yl)pyrrolidin-3-ol in Step B. MS (ESI): mass calcd. for $C_{25}H_{29}FN_6O_3S$, 512.20; m/z found, 513.3 $[M+H]^+$. $^1H$ NMR (500 MHz, CD$_3$OD) δ 6.90-6.87 (m, 1H), 6.63-6.57 (m, 2H), 6.45-6.40 (m, 1H), 6.23-6.17 (m, 1H), 6.12-6.07 (m, 1H), 5.95-5.89 (m, 1H), 5.83-5.76 (m, 2H), 2.58-2.50 (m, 1H), 2.46 (s, 2H), 1.84-1.81 (m, 2H), 1.77-1.72 (m, 2H), 1.63-1.58 (m, 1H), 1.32 (s, 3H), 1.31-1.26 (m, 1H), 1.23-1.13 (m, 3H), Example 189

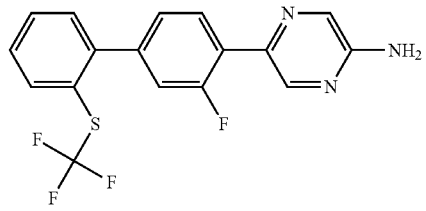

5-{3-Fluoro-2'-[(trifluoromethyl)sulfanyl]biphenyl-4-yl}pyrazin-2-amine

The title compound was prepared using analogous conditions to those described in Example 1 utilizing 5-(2-fluoro-4-(4,4,5,5-tetramethyl-1,3,2-dioxaborolan-2-yl)phenyl)pyrazin-2-amine and 2-trifluorothiomethylbromobenzene. MS (ESI): mass calcd. for $C_{17}H_{11}F_4N_3S$, 365.06; m/z found, 366.1 $[M+H]^+$. $^1H$ NMR (400 MHz, CD$_3$OD) δ 8.46-8.37 (m, 1H), 8.09 (d, J=1.3, 1H), 7.93 (m, 1H), 7.87 (d, J=7.7, 1H), 7.69-7.60 (m, 1H), 7.55-7.50 (m, 2H), 7.28-7.17 (m, 2H).

Example 190

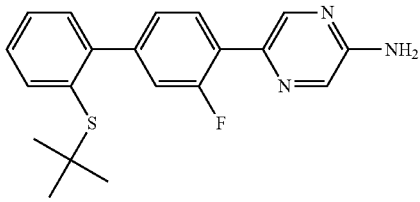

5-[2'-(tert-Butylsulfanyl)-3-fluorobiphenyl-4-yl]pyrazin-2-amine

The title compound was prepared using analogous conditions to those described in The title compound was prepared using analogous conditions to those described in Example 6 utilizing (2-bromophenyl)(tert-butyl)sulfane. MS (ESI): mass calcd. for $C_{20}H_{20}FN_3S$, 353.14; m/z found, 354.1 [M+H]$^+$. $^1$H NMR (600 MHz, DMSO-d$_6$) δ 8.44-8.36 (m, 1H), 8.10-8.03 (d, J=1.5, 1H), 7.93-7.86 (m, 1H), 7.73-7.65 (dd, J=7.8, 1.4, 1H), 7.56-7.49 (m, 1H), 7.49-7.41 (m, 2H), 7.34-7.25 (m, 2H), 1.99 (s, 1H), 1.02 (s, 9H).

Example 191

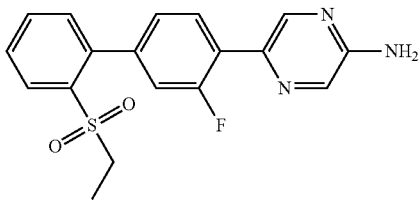

5-[2'-(Ethylsulfonyl)-3-fluorobiphenyl-4-yl]pyrazin-2-amine

The title compound was prepared using analogous conditions to those described in Example 1 utilizing 5-(2-fluoro-4-(4,4,5,5-tetramethyl-1,3,2-dioxaborolan-2-yl)phenyl)pyrazin-2-amine and N-(2-bromophenyl)ethane-1-sulfonamide. MS (ESI): mass calcd. for $C_{18}H_{16}FN_3O_2S$, 357.09; m/z found, 358.1 [M+H]$^+$. $^1$H NMR (400 MHz, CD$_3$OD) δ 8.48-8.36 (m, 1H), 8.16 (dd, J=7.9, 1.3, 1H), 8.09 (d, J=1.4, 1H), 7.94 (m, 1H), 7.78 (m, 1H), 7.68 (m, 1H), 7.48 (dd, J=7.5, 1.3, 1H), 7.34 (s, 1H), 7.31 (d, J=2.4, 1H), 2.84 (q, J=7.4, 2H), 1.06 (t, J=7.4, 3H).

Example 192

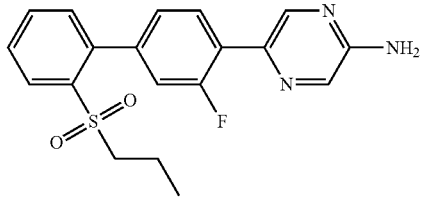

5-[3-Fluoro-2'-(propylsulfonyl)biphenyl-4-yl}pyrazin-2-amine

The title compound was prepared using analogous conditions to those described in Example 1 utilizing 5-(2-fluoro-4-(4,4,5,5-tetramethyl-1,3,2-dioxaborolan-2-yl)phenyl) pyrazin-2-amine and 1-bromo-2-(propylsulfonyl)benzene. MS (ESI): mass calcd. for $C_{19}H_{18}FN_3O_2S$, 371.11; m/z found, 372.1 [M+H]$^+$. $^1$H NMR (400 MHz, DMSO-d$_6$) δ 8.40 (s, 1H), 8.14 (d, J=1.2, 1H), 8.08 (dd, J=7.8, 1.1, 1H), 7.95 (m, 1H), 7.81 (m, 1H), 7.72 (m, 1H), 7.48 (dd, J=7.4, 1.1, 1H), 7.38 (dd, J=12.4, 1.4, 1H), 7.32 (dd, J=8.0, 1.6, 1H), 2.94-2.81 (m, 2H), 1.49-1.32 (m, 2H), 0.79 (t, J=7.4, 3H).

Example 193

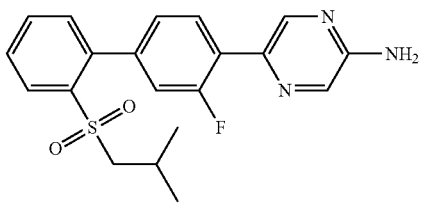

5-{3-Fluoro-2'-[(2-methylpropyl)sulfonyl]biphenyl-4-yl}pyrazin-2-amine

The title compound was prepared using analogous conditions to those described in Example 1 utilizing 5-(2-fluoro-4-(4,4,5,5-tetramethyl-1,3,2-dioxaborolan-2-yl)phenyl) pyrazin-2-amine and 1-bromo-2-(isobutylsulfonyl)benzene. MS (ESI): mass calcd. for $C_{20}H_{20}FN_3O_2S$, 385.13; m/z found, 386.2 [M+H]$^+$. $^1$H NMR (400 MHz, DMSO-d$_6$) δ 8.42 (s, 1H), 8.12 (dd, J=7.9, 1.1, 1H), 8.05 (d, J=1.4, 1H), 7.96 (m, 1H), 7.81 (m, 1H), 7.73 (m, 1H), 7.49 (dd, J=7.5, 1.0, 1H), 7.37 (dd, J=12.4, 1.5, 1H), 7.32 (dd, J=8.0, 1.6, 1H), 6.76 (s, 2H), 2.81 (d, J=6.4, 2H), 1.85-1.75 (m, 1H), 0.82 (d, J=6.7, 6H).

Example 194

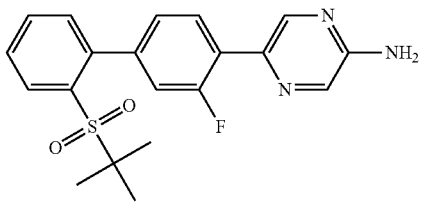

5-[2'-(tert-Butylsulfonyl)-3-fluorobiphenyl-4-yl]pyrazin-2-amine

The title compound was prepared using analogous conditions to those described in Example 1 utilizing 1-bromo-2-(tert-butylsulfonyl)benzene. MS (ESI): mass calcd. for $C_{20}H_{20}FN_3O_2S$, 385.13; m/z found, 386.1 [M+H]$^+$. $^1$H NMR (500 MHz, CDCl$_3$) δ 8.51-8.44 (d, J=1.4, 1H), 8.27-8.20 (d, J=1.4, 1H), 8.10-8.04 (dd, J=8.0, 1.4, 1H), 8.04-7.98 (m, 1H), 7.70-7.63 (m, 1H), 7.62-7.55 (m, 1H), 7.36-7.30 (dd, J=7.6, 1.4, 1H), 7.29-7.25 (dd, J=8.1, 1.7, 1H), 7.22-7.17 (dd, J=12.3, 1.7, 1H), 1.23-1.11 (s, 9H).

Example 195

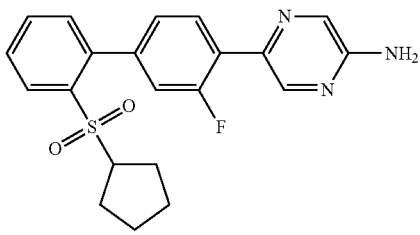

5-[2'-(Cyclopentylsulfonyl)-3-fluorobiphenyl-4-yl]pyrazin-2-amine

The title compound was prepared using analogous conditions to those described in Example 1 utilizing 5-(2-fluoro-4-(4,4,5,5-tetramethyl-1,3,2-dioxaborolan-2-yl)phenyl)pyrazin-2-amine and 1-bromo-2-(cyclopentylsulfonyl)benzene MS (ESI): mass calcd. for $C_{21}H_{2}FN_3O_2S$, 397.13; m/z found, 398.0 [M+H]$^+$. $^1$H NMR (400 MHz, CD$_3$OD) δ 8.65 (d, J=1.3, 1H), 8.30 (d, J=1.3, 1H), 8.19 (dd, J=7.9, 1.2, 1H), 8.14 (m, 1H), 7.79 (m, 1H), 7.71 (m, 1H), 7.48 (dd, J=7.5, 1.2, 1H), 7.42 (s, 1H), 7.41-7.38 (m, 1H), 3.23-3.15 (m, 1H), 1.92-1.81 (m, 2H), 1.77-1.63 (m, 4H), 1.60-1.51 (m, 2H).

Example 196

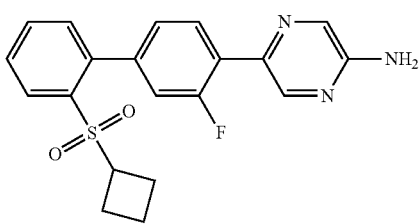

5-[2'-(Cyclopentylsulfonyl)-3-fluorobiphenyl-4-yl]pyrazin-2-amine

The title compound was prepared using analogous conditions to those described in Example 1 utilizing 5-(2-fluoro-4-(4,4,5,5-tetramethyl-1,3,2-dioxaborolan-2-yl)phenyl)pyrazin-2-amine and 1-bromo-2-(cyclobutylsulfonyl)benzene. MS (ESI): mass calcd. for $C_{20}H_{18}FN_3O_2S$, 383.11; m/z found, 384.2 [M+H]$^+$. $^1$H NMR (400 MHz, CD$_3$OD) δ 8.44 (s, 1H), 8.17 (dd, J=7.9, 1.1, 1H), 8.13 (d, J=1.4, 1H), 7.96 (m, 1H), 7.77 (m, 1H), 7.68 (m, 1H), 7.46 (dd, J=7.6, 1.1, 1H), 7.34 (s, 1H), 7.31 (dd, J=6.4, 1.5, 1H), 3.65-3.53 (m, 1H), 2.39-2.26 (m, 2H), 2.08-1.98 (m, 2H), 1.98-1.87 (m, 2H).

Example 197

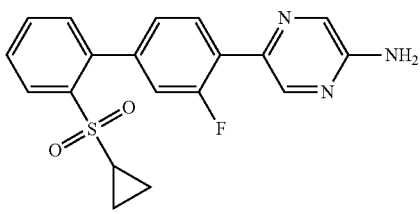

5-[2'-(Cyclopentylsulfonyl)-3-fluorobiphenyl-4-yl]pyrazin-2-amine

The title compound was prepared using analogous conditions to those described in Example 1 utilizing 5-(2-fluoro-4-(4,4,5,5-tetramethyl-1,3,2-dioxaborolan-2-yl)phenyl)pyrazin-2-amine and 1-bromo-2-(cyclopropylsulfonyl)benzene. MS (ESI): mass calcd. for $C_{19}H_{16}FN_3O_2S$, 369.09; m/z found, 370.0 [M+H]$^+$. $^1$H NMR (400 MHz, CD$_3$OD) δ 8.55-8.49 (m, 1H), 8.33 (s, 1H), 8.13 (dd, J=8.0, 1.2, 1H), 8.11-8.05 (m, 1H), 7.77 (m, 1H), 7.68 (m, 1H), 7.48 (dd, J=7.6, 1.1, 1H), 7.43-7.36 (m, 2H), 2.35-2.26 (m, 1H), 1.04-0.91 (m, 4H).

Example 198

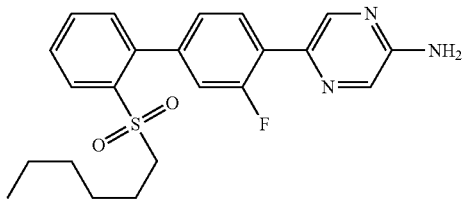

5-[3-Fluoro-2'-(hexylsulfonyl)biphenyl-4-yl]pyrazin-2-amine

The title compound was prepared using analogous conditions to those described in Example 1 utilizing 5-(2-fluoro-4-(4,4,5,5-tetramethyl-1,3,2-dioxaborolan-2-yl)phenyl)pyrazin-2-amine and 1-bromo-2-(hexylsulfonyl)benzene MS (ESI): mass calcd. for $C_{22}H_{24}FN_3O_2S$, 413.16; m/z found, 414.2 [M+H]$^+$. $^1$H NMR (400 MHz, CD$_3$OD) δ 8.66 (s, 1H), 8.31 (s, 1H), 8.21-8.13 (m, 2H), 7.81 (m, 1H), 7.72 (m, 1H), 7.49 (dd, J=7.6, 1.2, 1H), 7.43 (dd, J=3.6, 1.4, 1H), 7.40 (s, 1H), 2.89-2.80 (m, 2H), 1.50 (m, 2H), 1.31-1.11 (m, 6H), 0.85 (t, J=7.1, 3H).

Example 199

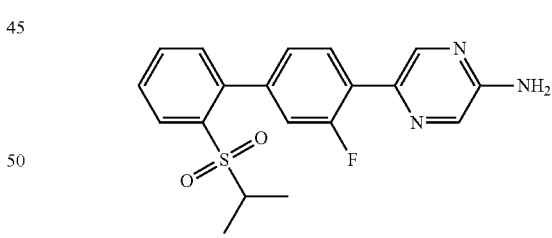

5-{3-Fluoro-2'-[(1-methylethyl)sulfonyl]biphenyl-4-yl}pyrazin-2-amine

The title compound was prepared using analogous conditions to those described in Example 1 utilizing 5-(2-fluoro-4-(4,4,5,5-tetramethyl-1,3,2-dioxaborolan-2-yl)phenyl)pyrazin-2-amine and 1-bromo-2-(isopropylsulfonyl)benzene. MS (ESI): mass calcd. for $C_{19}H_{18}FN_3O_2S$, 371.11; m/z found, 372.1 [M+H]$^+$. $^1$H NMR (400 MHz, CD$_3$OD) δ 8.42 (s, 1H), 8.15 (dd, J=8.0, 1.1, 1H), 8.09 (d, J=1.4, 1H), 7.93 (m, 1H), 7.78 (m, 1H), 7.68 (m, 1H), 7.51-7.44 (m, 1H), 7.37-7.28 (m, 2H), 2.90-2.77 (m, 1H), 1.09 (d, J=6.8, 6H).

Example 200

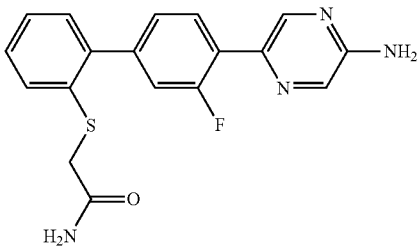

2-{[4′-(5-Aminopyrazin-2-yl)-3′-fluorobiphenyl-2-yl]sulfonyl}acetamide

The title compound was prepared in a manner similar to that described in Example 88 using 2-((2-bromophenyl)thio)acetamide. MS (ESI): mass calcd. for $C_{18}H_{15}FN_4OS$, 354.10; m/z found, 355.0 [M+H]$^+$. $^1$H NMR (500 MHz, CD$_3$OD) δ 8.41-8.36 (dd, J=2.2, 1.4, 1H), 8.10-8.06 (d, J=1.5, 1H), 7.93-7.87 (m, 1H), 7.53-7.48 (m, 1H), 7.39-7.34 (m, 1H), 7.33-7.25 (m, 4H), 3.52 (s, 2H).

Example 201

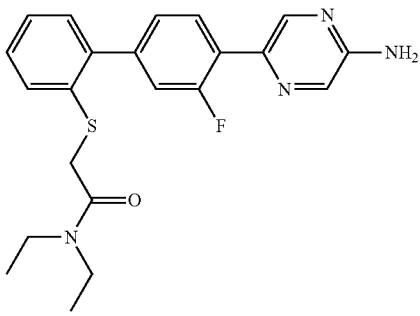

2-{[4′-(5-Aminopyrazin-2-yl)-3′-fluorobiphenyl-2-yl]sulfonyl}-N,N-diethylacetamide The title compound was prepared in a manner similar to that described in Example 88 using 2-((2-bromophenyl)thio)-N,N-diethylacetamide. MS (ESI): mass calcd. for $C_{22}H_{23}FN_4OS$, 410.16; m/z found, 411.1 [M+H]$^+$. $^1$H NMR (500 MHz, CD$_3$OD) δ 8.42-8.35 (d, J=1.9, 1H), 8.12-8.06 (d, J=1.5, 1H), 7.94-7.86 (m, 1H), 7.63-7.55 (dd, J=7.1, 2.1, 1H), 7.41-7.23 (m, 5H), 3.62 (s, 2H), 3.31-3.26 (m, 4H), 1.13-1.08 (t, J=7.1, 3H), 1.07-1.03 (t, J=7.1, 3H).

Example 202

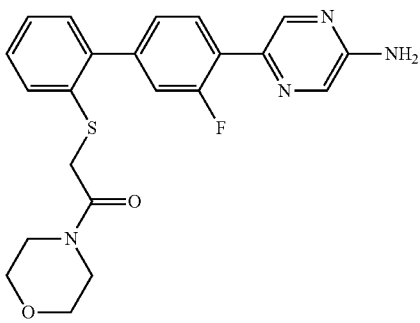

5-{3-Fluoro-2′-[(2-morpholin-4-yl-2-oxoethyl)sulfanyl]biphenyl-4-yl}pyrazin-2-amine The title compound was prepared in a manner similar to that described in Example 88 using 2-((2-bromophenyl)thio)-1-morpholinoethanone. MS (ESI): mass calcd. for $C_{22}H_{21}FN_4O_2S$, 424.14; m/z found, 425.1 [M+H]$^+$. $^1$H NMR (500 MHz, CD$_3$OD) δ 8.41-8.39 (m, 1H), 8.10-8.08 (d, J=1.5, 1H), 7.95-7.89 (m, 1H), 7.68-7.61 (m, 1H), 7.41-7.34 (m, 2H), 7.34-7.29 (m, 2H), 7.29-7.25 (dd, J=12.2, 1.7, 1H), 3.66 (s, 2H), 3.58-3.53 (t, J=4.9, 2H), 3.54-3.49 (t, J=4.8, 2H), 3.49-3.44 (m, 2H), 3.40-3.35 (t, J=4.8, 2H).

Example 203

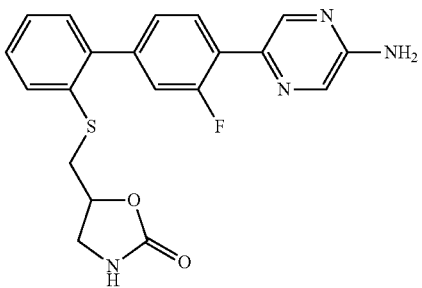

racemic 5-({[4′-(5-Aminopyrazin-2-yl)-3′-fluorobiphenyl-2-yl]sulfanyl}methyl)-1,3-oxazolidin-2-one The title compound was prepared in a manner similar to that described in Example 88 using racemic 5-(((2-bromophenyl)thio)methyl)oxazolidin-2-one. MS (ESI): mass calcd. for $C_{20}H_{17}FN_4O_2S$, 396.11; m/z found, 397.0 [M+H]$^+$. $^1$H NMR (500 MHz, CD$_3$OD) δ 8.41-8.37 (m, 1H), 8.09-8.07 (d, J=1.5, 1H), 7.94-7.88 (m, 1H), 7.65-7.59 (m, 1H), 7.43-7.37 (m, 1H), 7.37-7.29 (m, 3H), 7.28-7.23 (dd, J=12.2, 1.7, 1H), 4.68-4.54 (m, 1H), 3.56-3.48 (t, J=8.8, 1H), 3.29-3.22 (dd, J=9.2, 6.4, 1H), 3.20-3.13 (m, 1H), 3.07-3.01 (m, 1H).

Example 204

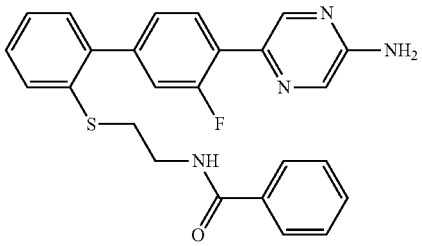

N-(2-{[4′-(5-Aminopyrazin-2-yl)-3′-fluorobiphenyl-2-yl]sulfanyl}ethylbenzamide

The title compound was prepared in a manner similar to that described in Example 88 using N-(2-((2-bromophenyl)thio)ethyl)benzamide. MS (ESI): mass calcd. for $C_{25}H_{21}FN_4OS$, 444.14; m/z found, 445.0 [M+H]$^+$. $^1$H NMR (500 MHz, CD$_3$OD) δ 8.38-8.32 (m, 1H), 8.09-8.03 (d, J=1.4, 1H), 7.89-7.83 (t, J=8.1, 1H), 7.73-7.67 (m, 2H), 7.67-7.63 (d, J=7.9, 1H), 7.52-7.45 (m, 1H), 7.44-7.34 (m, 3H), 7.30-7.26 (m, 3H), 7.26-7.21 (dd, J=12.4, 1.7, 1H), 3.53-3.46 (t, J=7.0, 2H), 3.11-3.03 (t, J=7.0, 2H).

Example 205

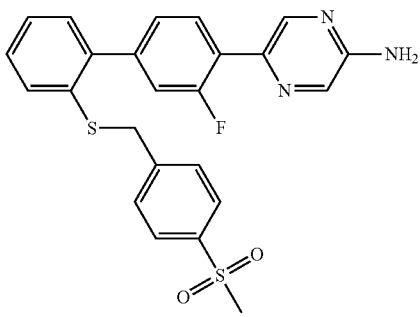

5-(3-Fluoro-2'-{[4-(methylsulfonyl)benzyl]sulfanyl}biphenyl-4-yl)pyrazin-2-amine The title compound was prepared in a manner similar to that described in Example 88 using (2-bromophenyl)(4-(methylsulfonyl)benzyl)sulfane. MS (ESI): mass calcd. for $C_{24}H_{20}FN_3O_2S_2$, 465.10; m/z found, 466.0 [M+H]+. 1H NMR (500 MHz, CD3OD) δ 8.41-8.35 (m, 1H), 8.12-8.04 (d, J=1.5, 1H), 7.87-7.81 (m, 1H), 7.79-7.73 (m, 2H), 7.59-7.48 (m, 1H), 7.39-7.30 (m, 4H), 7.29-7.24 (m, 1H), 7.18-7.12 (dd, J=8.0, 1.7, 1H), 7.11-7.03 (dd, J=12.3, 1.7, 1H), 4.04 (s, 2H), 3.08 (s, 3H).

Example 206

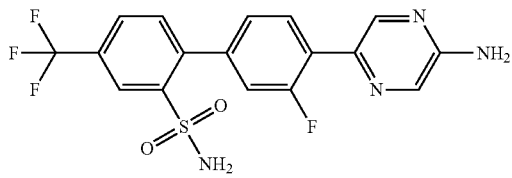

4'-(5-Aminopyrazin-2-yl)-3'-fluoro-4-(trifluoromethyl)biphenyl-2-sulfonamide

The title compound was prepared in a manner similar to that described in Example 88 using 2-bromo-5-(trifluoromethyl)benzenesulfonamide. MS (ESI): mass calcd. for $C_{17}H_{12}F_4N_4O_2S$, 412.06; m/z found, 413.0 [M+H]+. 1H NMR (500 MHz, CD3OD) δ 8.41 (s, 1H), 8.38 (s, 1H), 8.22-8.16 (m, 1H), 8.01-7.92 (m, 2H), 7.63-7.58 (d, J=8.0, 1H), 7.40-7.30 (m, 2H).

Example 207

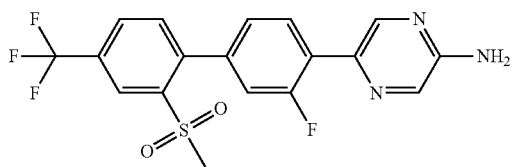

5-[3-Fluoro-2'-(methylsulfonyl)-4'-(trifluoromethyl)biphenyl-4-yl]pyrazin-2-amine The title compound was prepared in a manner similar to that described in Example 88 using 1-bromo-2-(methylsulfonyl)-4-(trifluoromethyl)benzene and 5-(2-fluoro-4-(4,4,5,5-tetramethyl-1,3,2-dioxaborolan-2-yl)phenyl)pyrimidin-2-amine. MS (ESI): mass calcd. for $C_{18}H_{13}F_4N_3O_2S$, 411.07; m/z found, 412.0 [M+H]+. 1H NMR (500 MHz, CD3OD) δ 8.45-8.44 (d, J=2.0, 1H), 8.43 (s, 1H), 8.10-8.09 (d, J=1.5, 1H), 8.09-8.06 (dd, J=7.8, 1.7, 1H), 8.02-7.97 (m, 1H), 7.71-7.68 (d, J=7.9, 1H), 7.41-7.39 (m, 1H), 7.39-7.37 (m, 1H), 2.88 (s, 3H).

Example 208

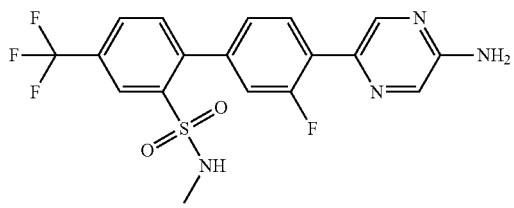

4'-(5-Aminopyrazin-2-yl)-3'-fluoro-N-methyl-4-(trifluoromethyl)biphenyl-2-sulfonamide The title compound was prepared in a manner similar to that described in Example 88 using 2-bromo-N-methyl-5-(trifluoromethyl)benzenesulfonamide. MS (ESI): mass calcd. for $C_{18}H_{14}F_4N_4O_2S$, 426.08; m/z found, 427.0 [M+H]+. 1H NMR (500 MHz, CD3OD) δ 8.43-8.36 (m, 1H), 8.34-8.27 (d, J=1.9, 1H), 8.21-8.14 (d, J=1.4, 1H), 8.02-7.92 (m, 2H), 7.66-7.61 (d, J=7.9, 1H), 7.35 (s, 1H), 7.34-7.32 (dd, J=4.3, 1.6, 1H), 2.46 (s, 3H).

Example 209

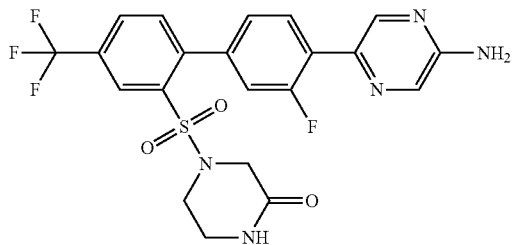

4-{[4'-(5-Aminopyrazin-2-yl)-3'-fluoro-4-(trifluoromethyl)biphenyl-2-yl]sulfonyl}piperazin-2-one The title compound was prepared in a manner similar to that described in Example 88 using 4-((2-bromo-5-(trifluoromethyl)phenyl)sulfonyl)piperazin-2-one. MS (ESI): mass calcd. for $C_{21}H_{17}F_4N_5O_3S$, 495.10; m/z found, 496.0 [M+H]+. 1H NMR (500 MHz, CD3OD) δ 8.43-8.37 (m, 2H), 8.24-8.21 (d, J=1.4, 1H), 8.08-8.04 (dd, J=8.0, 1.8, 1H), 8.04-7.99 (m, 1H), 7.69-7.65 (d, J=7.9, 1H), 7.38-7.35 (m, 1H), 7.35-7.32 (dd, J=5.8, 1.6, 1H), 3.38 (s, 2H), 3.15 (s, 4H).

Example 210

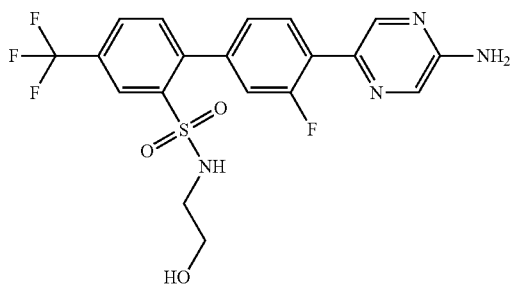

4'-(5-Aminopyrazin-2-yl)-3'-fluoro-N-(2-hydroxyethyl)-4-(trifluoromethyl)biphenyl-2-sulfonamide The title compound was prepared in a manner similar to that described in Example 88 using 2-bromo-N-(2-hydroxyethyl)-5-(trifluoromethyl)benzenesulfonamide. MS (ESI): mass calcd. for $C_{19}H_{16}F_4N_4O_3S$, 456.09; m/z found, 457.0 [M+H]$^+$. $^1$H NMR (500 MHz, CD$_3$OD) δ 8.41-8.39 (m, 1H), 8.36 (s, 1H), 8.16-8.13 (d, J=1.5, 1H), 7.99-7.93 (m, 1H), 7.64-7.61 (d, J=8.0, 1H), 7.38-7.36 (m, 1H), 7.36-7.33 (dd, J=5.0, 1.6, 1H), 3.49-3.45 (t, J=5.9, 2H), 2.93-2.86 (t, J=5.8, 2H).

Example 211

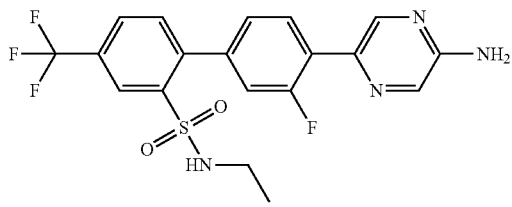

4'-(5-Aminopyrazin-2-yl)-N-ethyl-3'-fluoro-4-(trifluoromethyl)biphenyl-2-sulfonamide The title compound was prepared in a manner similar to that described in Example 88 using 2-bromo-N-ethyl-5-(trifluoromethyl)benzenesulfonamide. MS (ESI): mass calcd. for $C_{19}H_{16}F_4N_4O_2S$, 440.09; m/z found, 441.0 [M+H]$^+$. $^1$H NMR (500 MHz, CD$_3$OD) δ 8.41-8.37 (m, 1H), 8.34-8.31 (m, 1H), 8.20-8.16 (d, J=1.5, 1H), 8.01-7.94 (m, 2H), 7.65-7.59 (d, J=7.9, 1H), 7.37-7.34 (m, 1H), 7.34-7.31 (dd, J=2.9, 1.5, 1H), 2.88-2.76 (q, J=7.2, 2H), 1.07-0.94 (t, J=7.2, 3H).

Example 212

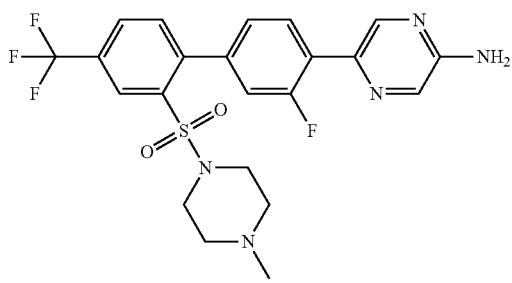

5-{3-Fluoro-2'-[(4-methylpiperazin-1-yl)sulfonyl]-4'-(trifluoromethyl)biphenyl-4-yl}pyrazin-2-amine The title compound was prepared in a manner similar to that described in Example 88 using 2-bromo-N-ethyl-5-(trifluoromethyl)benzenesulfonamide. MS (ESI): mass calcd. for $C_{22}H_{21}F_4N_5O_2S$, 495.14; m/z found, 496.0 [M+H]$^+$. $^1$H NMR (500 MHz, CD$_3$OD) δ 8.44-8.41 (m, 1H), 8.41-8.38 (d, J=2.0, 1H), 8.13-8.10 (d, J=1.5, 1H), 8.10-8.06 (m, 1H), 8.05-7.97 (m, 1H), 7.73-7.60 (d, J=8.0, 1H), 7.39-7.37 (dd, J=6.6, 1.6, 1H), 7.37-7.35 (dd, J=2.8, 1.7, 1H), 2.85 (s, 3H), 3.93-2.45 (br m, 8H).

Example 213

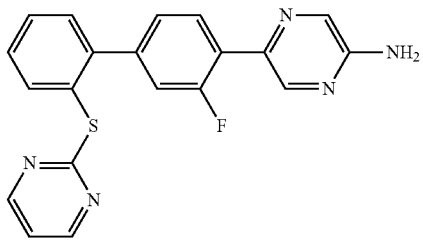

5-[3-Fluoro-2'-(pyrimidin-2-ylsulfanyl)biphenyl-4-yl]pyrazin-2-amine hydrochloride

Step A: Ethyl 3-(2-bromophenylthio)propanoate

A mixture of 2-bromobenzenethiol (6 g, 30 mmol), ethyl 3-chloropropanoate (13 g, 96 mmol), K$_2$CO$_3$ (8.8 g, 64 mmol) and acetone (150 mL) was refluxed for 15 h. The reaction mixture was filtered and the filter cake washed with acetone (50 mL). The filtrate was concentrated to dryness and subjected to FCC to give ethyl 3-(2-bromophenylthio)propanoate (7 g, 78%). MS (ESI): mass calcd. for $C_{11}H_{13}O_2S$, 287.98; m/z found, 288.8 [M+H]$^+$.

Step B: Ethyl 3-(4'-(5-aminopyrazin-2-yl)-5'-fluoro-biphenyl-2-ylthio) propanoate A mixture of ethyl 3-(2-bromophenylthio)propanoate (7 g, 24 mmol), 5-(2-fluoro-4-(4,4,5,5-tetramethyl-1,3,2-dioxaborolan-2-yl)phenyl)pyrazin-2-amine (7.6 g, 24 mmol), Pd(dppf)Cl$_2$.CH$_2$Cl$_2$ (378 mg, 0.52 mmol) and Na$_2$CO$_3$ (5 g, 48 mmol) in dioxane/water (20 mL/5 mL) was stirred at 80° Celsius for 5 hours under N$_2$, then poured into water (60 mL) and extracted with EtOAc (50 mL×3). The combined organic extracts were dried over Na$_2$SO$_4$, filtered, concentrated to dryness and purified by FCC to give ethyl 3-(4'-(5-aminopyrazin-2-yl)-5'-fluorobiphenyl-2-ylthio) propanoate (7.7 g, 80%) as a white solid. MS (ESI): mass calcd. for $C_{21}H_{20}FN_3O_2S$, 397.13; m/z found, 397.9 [M+H]$^+$.

Step C: 4'-(5-Aminopyrazin-2-yl)-5'-fluorobiphenyl-2-thiol

To a solution consisting of ethyl 3-(4'-(5-aminopyrazin-2-yl)-5'-fluorobiphenyl-2-ylthio) propanoate (7.7 g, 19.4 mmol) and THF (60 mL) was added t-BuOK (4.3 g, 38.8 mmol) and the mixture stirred for 1 hour at rt. The reaction mixture was poured into water (100 mL) and the system brought to a pH=5-6 with 1 M HCl. The mixture was, extracted with EtOAc (80 mL×3) and the combined extracts dried over Na$_2$SO$_4$, filtered and concentrated to dryness to give 4'-(5-aminopyrazin-2-yl)-5'-fluorobiphenyl-2-thiol (4.6 g, 80%). MS (ESI): mass calcd. for $C_{16}H_{12}FN_3S$, 297.07; m/z found, 298.0 $[M+H]^+$.

Step D

To a solution of 4'-(5-aminopyrazin-2-yl)-5'-fluorobiphenyl-2-thiol (400 mg, 1.34 mmol) and 2-chloropyrimidine (167 mg, 1.47 mmol) in DMF (8 mL) were added DIPEA (345 mg, 2.68 mmol) and $Ph_3P$ (351 mg, 1.34 mmol) and the resultant mixture heated at 80° Celsius for 1 hour under a $N_2$ atmosphere for 15 h. The mixture was cooled to rt, concentrated to dryness and the residue subjected to FCC to give the title compound (350 mg, 68%). MS (ESI): mass calcd. for $C_{20}H_{14}FN_5S.HCl$, 375.10; m/z found, 376.0 $[M+H]^+$. $^1H$ NMR (300 MHz, $CD_3OD$) δ 8.42 (d, J=4.9, 2H), 8.33-8.28 (m, 1H), 8.03 (d, J=1.4, 1H), 7.79-7.69 (m, 2H), 7.60-7.53 (m, 1H), 7.51-7.43 (m, 2H), 7.21 (dd, J=8.0, 1.7, 1H), 7.15 (dd, J=12.3, 1.6, 1H), 7.06 (m, 1H).

Example 214

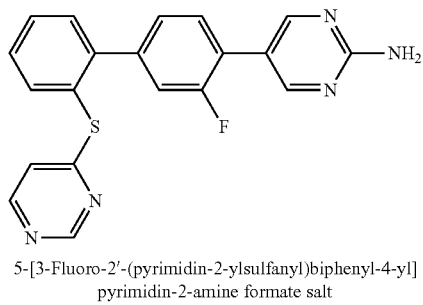 [SMILES: Nc1ncc(-c2ccc(-c3ccccc3Sc3ccncn3)cc2F)cn1]

5-[3-Fluoro-2'-(pyrimidin-2-ylsulfanyl)biphenyl-4-yl]pyrimidin-2-amine formate salt The title compound was prepared using analogous conditions to those described in Example 213 utilizing 4'-(5-aminopyrazin-2-yl)-3'-fluoro-[1,1'-biphenyl]-2-thiol and 4-chloropyrimidine. MS (ESI): mass calcd. for $C_{20}H_{14}FN_5S$, 375.10; m/z found, 375.9 $[M+H]^+$. $^1H$ NMR (400 MHz, $CD_3OD$); δ 8.84 (d, J=1.1, 1H), 8.46 (d, J=1.4, 2H), 8.44 (d, J=5.6, 1H), 7.81-7.75 (m, 1H), 7.73-7.65 (m, 1H), 7.62-7.51 (m, 3H), 7.30 (dd, J 20=11.8, 1.6, 1H), 7.24 (dd, J=7.9, 1.7, 1H), 6.96 (dd, J=5.6, 1.3, 1H), 6.90 (s, 2H).

Example 215

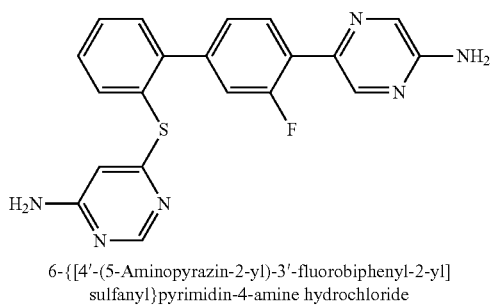 [SMILES: Nc1cnc(-c2ccc(-c3ccccc3Sc3cc(N)ncn3)cc2F)cn1]

6-{[4'-(5-Aminopyrazin-2-yl)-3'-fluorobiphenyl-2-yl]sulfanyl}pyrimidin-4-amine hydrochloride The title compound was prepared using analogous conditions to those described in Example 213 utilizing 4'-(5-aminopyrazin-2-yl)-3'-fluoro-[1,1'-biphenyl]-2-thiol and 4-amino-6-chloropyrimidine. MS (ESI): mass calcd. for $C_{20}H_{15}FN_6S$, 390.11; m/z found, 391.1 $[M+H]^+$. $^1H$ NMR (400 MHz, $CD_3OD$) δ 8.29-8.25 (m, 3H), 7.94 (m 1H), 7.82 (d, J=7.4, 1H), 7.74 (m, 1H), 7.67-7.58 (m, 2H), 7.34-7.23 (m, 2H), 5.94 (s, 1H).

Example 216

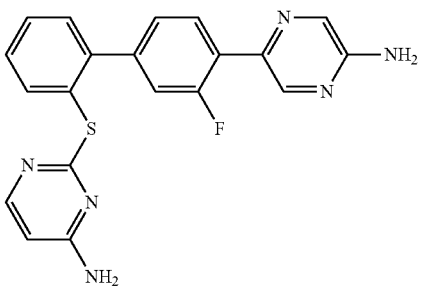

2-{[4'-(5-Aminopyrazin-2-yl)-3'-fluorobiphenyl-2-yl]sulfanyl}pyrimidin-4-amine hydrochloride The title compound was prepared using analogous conditions to those described in Example 213 utilizing 4'-(5-aminopyrazin-2-yl)-3'-fluoro-[1,1'-biphenyl]-2-thiol and 4-amino-2-chloropyrimidine. MS (ESI): mass calcd. for $C_{20}H_{15}FN_6S$, 390.11; m/z found, 390.9 $[M+H]^+$. $^1H$ NMR (400 MHz, $CD_3OD$) δ 8.31 (m, 1H), 8.16 (s, 1H), 7.88 (m, 1H), 7.83-7.75 (m, 2H), 7.71-7.63 (m, 1H), 7.58-7.52 (m, 2H), 7.32-7.21 (m, 2H), 6.37 (d, J=7.2, 1H).

Example 217

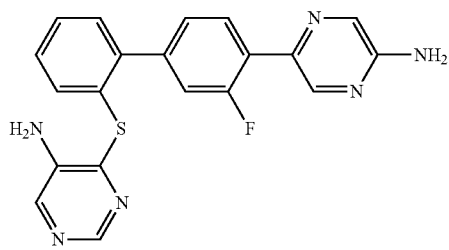

4-{[4'-(5-Aminopyrazin-2-yl)-3'-fluorobiphenyl-2-yl]sulfanyl}pyrimidin-5-amine hydrochloride The title compound was prepared using analogous conditions to those described in Example 213 utilizing 4'-(5-aminopyrazin-2-yl)-3'-fluoro-[1,1'-biphenyl]-2-thiol and 5-amino-4-chloropyrimidine. MS (ESI): mass calcd. for $C_{20}H_{15}FN_6S$, 390.11: m/z found, 391.0 $[M+H]^+$. $^1H$ NMR (400 MHz, DMSO-d) δ 8.35-8.30 (m, 1H), 8.22 (s, 1H), 8.02 (d, J=1.4, 1H), 7.90 (s, 1H), 7.80 (m, 1H), 7.59-7.54 (m, 2H), 7.52-7.44 (m, 2H), 7.24 (dd, J=6.5, 1.6, 1H), 7.21 (m, 1H).

Example 218

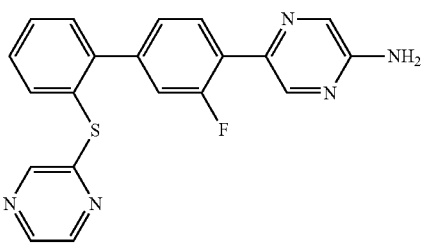

5-[3-Fluoro-2'-(pyrazin-2-ylsulfanyl)biphenyl-4-yl]pyrazin-2-amine hydrochloride The title compound was prepared using analogous conditions to those described in Example 213 utilizing 4'-(5-aminopyrazin-2-yl)-3'-fluoro-[1,1'-biphenyl]-2-thiol and 2-chloropyrazine. MS (ESI): mass calcd. for $C_{20}H_{14}FN_5S$, 375.10; m/z found, 375.9 [M+H]$^+$. $^1$H NMR (400 MHz, CD$_3$OD) δ 8.26-8.24 (m, 3H), 8.18 (d, J=2.6, 1H), 8.08 (d, J=1.4, 1H), 7.84 (m, 1H), 7.77-7.69 (m, 1H), 7.64-7.55 (m, 1H), 7.55-7.46 (m, 2H), 7.27-7.14 (m, 2H).

Example 219

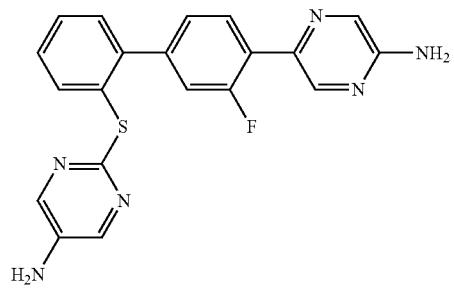

2-{[4'-(5-Aminopyrazin-2-yl)-3'-fluorobiphenyl-2-yl]sulfanyl}pyrimidin-5-amine hydrochloride The title compound was prepared using analogous conditions to those described in Example 213 utilizing 4'-(5-aminopyrazin-2-yl)-3'-fluoro-[1,1'-biphenyl]-2-thiol and 5-amino-2-chloropyrimidine. MS (ESI): mass calcd. for $C_{20}H_{15}FN_6S$, 390.11; m/z found, 391.1 [M+H]$^+$. $^1$H NMR (400 MHz, CD$_3$OD) δ 8.36 (s, 1H), 8.24 (s, 1H), 7.95 (s, 2H), 7.88 (m, 1H), 7.65-7.59 (m, 1H), 7.53-7.38 (m, 3H), 7.27-7.16 (m, 2H).

Example 220

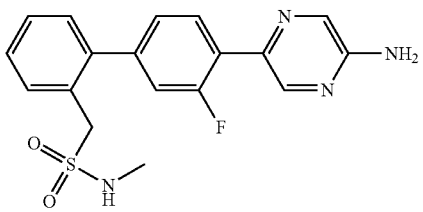

1-[4'-(5-Aminopyrazin-2-yl)-3'-fluorobiphenyl-2-yl]-N-methylmethanesulonamide formic acid salt The title compound was prepared using analogous conditions to those described in Example 1 utilizing 5-(2-fluoro-4-(4,4,5,5-tetramethyl-1,3,2-dioxaborolan-2-yl)phenyl)pyrazin-2-amine and 1-(2-bromophenyl)-N-methylmethanesulfonamide. MS (ESI): mass calcd. for $C_{16}H_{17}FN_4O_2S$, 372.11; m/z found, 373.1 [M+H]$^+$. $^1$H NMR (400 MHz, CD$_3$OD) δ 8.34 (s, 1H), 8.25 (s, 1H), 7.99 (m, 1H), 7.68-7.60 (m, 1H), 7.50-7.40 (m, 2H), 7.39-7.31 (m, 3H), 4.36 (s, 2H), 2.49 (s, 3H).

Example 221

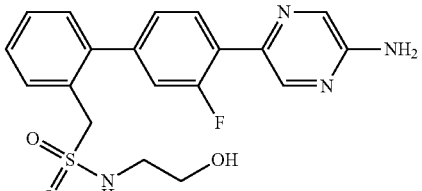

1-[4'-(5-Aminopyrazin-2-yl)-3'-fluorobiphenyl-2-yl]-N-methylmethanesulonamide formic acid salt The title compound was prepared using analogous conditions to those described in Example 1 utilizing 5-(2-fluoro-4-(4,4,5,5-tetramethyl-1,3,2-dioxaborolan-2-yl)phenyl)pyrazin-2-amine and 1-(2-bromophenyl)-N-(2-hydroxyethyl)methanesulfonamide. MS (ESI): mass calcd. for $C_{19}H_{19}FN_4O_3S$, 402.12; m/z found, 403.0 [M+H]$^+$. $^1$H NMR (400 MHz, CD$_3$OD) δ 8.38 (d, J=1.2, 1H), 8.31 (s, 1H), 8.02 (m, 1H), 7.70-7.63 (m, 1H), 7.49-7.40 (m, 2H), 7.40-7.30 (m, 3H), 4.40 (s, 2H), 3.51 (t, J=5.9, 2H), 2.95 (t, J=5.9, 2H), 2.66 (s, 1H).

Example 222

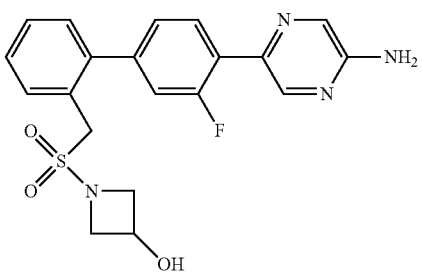

1-({[4'-(5-Aminopyrazin-2-yl)-3'-fluorobiphenyl-2-yl]methyl}sulfonyl)azetidin-3-ol formic acid salt The title compound was prepared using analogous conditions to those described in Example 1 utilizing 5-(2-fluoro-4-(4,4,5,5-tetramethyl-1,3,2-dioxaborolan-2-yl)phenyl)pyrazin-2-amine and 1-((2-bromobenzyl)sulfonyl)azetidin-3-ol. MS (ESI): mass calcd. for $C_{20}H_{19}FN_4O_3S$, 414.12; m/z found, 414.9 [M+H]$^+$. $^1$H NMR (400 MHz, CD$_3$OD) δ 8.43-8.38 (m, 1H), 8.08 (d, J=1.5, 1H), 7.95 (m, 1H), 7.68-7.60 (m, 1H), 7.49-7.41 (m, 2H), 7.39-7.28 (m, 3H), 4.45-4.36 (m, 3H), 3.79-3.70 (m, 2H), 3.67-3.59 (m, 2H).

Example 223

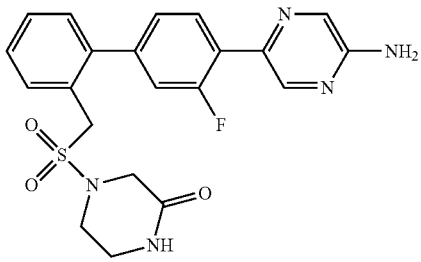

4-({[4'-(5-Aminopyrazin-2-yl)-3'-fluorobiphenyl-2-yl]methyl}sulfonyl)piperazin-2-one formic acid salt The title compound was prepared using analogous conditions to those described in Example 1 utilizing 5-(2-fluoro-4-(4,4,5,5-tetramethyl-1,3,2-dioxaborolan-2-yl)phenyl)pyrazin-2-amine and 4-((2-bromobenzyl)sulfonyl)piperazin-2-one. MS (ESI): mass calcd. for $C_{21}H_{20}FN_5O_3S$, 441.13; m/z found, 441.9 [M+H]$^+$. $^1$H NMR (400 MHz, CD$_3$OD) δ 8.41 (s, 1H), 8.08 (d, J=1.3, 1H), 7.96 (m, 1H), 7.70-7.62 (m, 1H), 7.52-7.28 (m, 5H), 4.48 (s, 2H), 3.63 (s, 2H), 3.25 (s, 4H).

Example 224

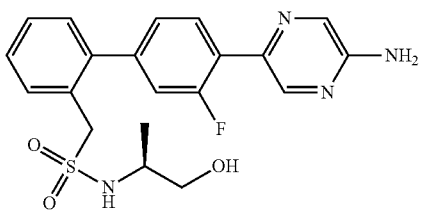

(S)-1-(4'-(5-Aminopyrazin-2-yl)-3'-fluoro-[1,1'-biphenyl]-2-yl)-N-(1-hydroxypropan-2-yl)-methanesulfonamide The title compound was prepared using analogous conditions to those described in Example 1 utilizing 5-(2-fluoro-4-(4,4,5,5-tetramethyl-1,3,2-dioxaborolan-2-yl)phenyl)pyrazin-2-amine and (S)-1-(2-bromophenyl)-N-(1-hydroxypropan-2-yl)methanesulfonamide. MS (ESI): mass calcd. for $C_{20}H_{21}FN_4O_3S$, 416.13; m/z found, 416.9 [M+H]$^+$. $^1$H NMR (400 MHz, DMSO-d) 8.43-8.36 (m, 1H), 8.03 (d, J=1.5, 1H), 7.92 (m, 1H), 7.70-7.59 (m, 1H), 7.47-7.28 (m, 5H), 7.12 (d, J=6.6, 1H), 6.71 (s, 2H), 4.75 (t, J=5.4, 1H), 4.35 (q, J=14.1, 2H), 3.31-3.11 (m, 3H), 1.01 (d, J=6.2, 3H).

Example 225

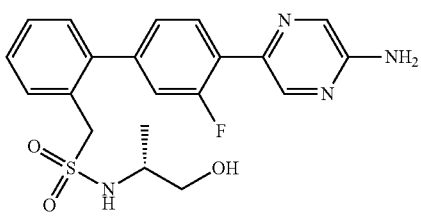

(R)-1-(4'-(5-Aminopyrazin-2-yl)-3'-fluoro-[1,1'-biphenyl]-2-yl)-N-(1-hydroxypropan-2-yl)-methanesulfonamide hydrohloride The title compound was prepared using analogous conditions to those described in Example 1 utilizing 5-(2-fluoro-4-(4,4,5,5-tetramethyl-1,3,2-dioxaborolan-2-yl)phenyl)pyrazin-2-amine and (R)-1-(2-bromophenyl)-N-(1-hydroxypropan-2-yl)methanesulfonamide. MS (ESI): mass calcd. for $C_{20}H_{21}FN_4O_3S$, 416.48; m/z found, 417.1 [M+H]$^+$. $^1$H NMR (400 MHz, CD$_3$OD) δ 8.32 (d, J=3.7, 2H), 7.99 (m, 1H), 7.77-7.66 (m, 1H), 7.50-7.39 (m, 2H), 7.39-7.28 (m, 3H), 4.41 (q, J=13.9, 2H), 3.49-3.33 (m, 3H), 1.11 (d, J=6.3, 3H).

Example 226

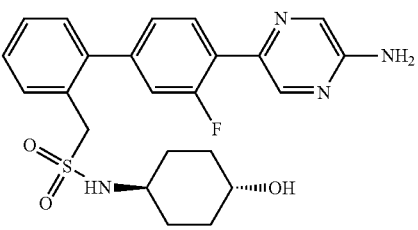

1-[4'-(5-Aminopyazin-2-yl)-3'-fluorobiphenyl-2-yl]-N-(trans-4-hydroxycyclohexyl)-methanesulfonamide formic acid salt The title compound was prepared using analogous conditions to those described in Example 1 utilizing 5-(2-fluoro-4-(4,4,5,5-tetramethyl-1,3,2-dioxaborolan-2-yl)phenyl)-pyrazin-2-amine and trans-1-(2-bromophenyl)-N-((trans)-4-hydroxycyclohexyl)-methane-sulfonamide. MS (ESI): mass calcd. for $C_{23}H_{25}FN_4O_3S \cdot HCO_2H$, 456.16; m/z found, 457.0 [M+H]$^+$. $^1$H NMR (400 MHz, CD$_3$OD) δ 8.40 (s, 1H), 8.08 (d, J=1.3, 1H), 7.94 (m, 1H), 7.72-7.63 (m, 1H), 7.47-7.38 (m, 1H), 7.38-7.27 (m, 3H), 4.36 (s, 2H), 3.42 (s, 1H), 2.97 (s, 1H), 1.84 (d, J=9.0, 4H), 1.38-1.10 (m, 4H).

Example 227

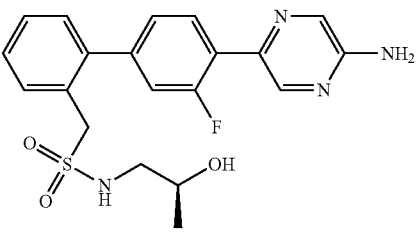

(S)-1-(4'-(5-Aminopyrazin-2-yl)-3'-fluorobiphenyl-2-yl]-N-[(2S)-2-hydroxypropyl]-methanesulfonamide hydrochloride The title compound was prepared using analogous conditions to those described in Example 1 utilizing 5-(2-fluoro-4-(4,4,5,5-tetramethyl-1,3,2-dioxaborolan-2-yl)phenyl)-pyrazin-2-amine and (S)-1-(2-bromophenyl)-N-(2-hydroxypropyl)-methane-sulfonamide. MS (ESI): mass calcd. for $C_{20}H_{21}FN_4O_3S$, 416.13; m/z found, 417.1 [M+H]$^+$. $^1$H NMR (400 MHz, CD$_3$OD) δ 8.67 (s, 1H), 8.28-8.23 (m, 1H), 8.13 (m, 1H), 7.70-7.62 (m, 1H), 7.49-7.30 (m, 5H), 4.40 (s, 2H), 3.77-3.65 (m, 1H), 2.80 (d. J=5.9, 2H), 1.09 (d, J=6.3, 3H).

Example 228

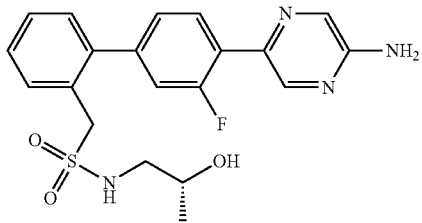

(R)-1-(4'-(5-Aminopyrazin-2-yl)-3'-fluorobiphenyl-2-yl]-N-[(2R)-2-hydroxypropyl]-methanesulfonamide The title compound was prepared using analogous conditions to those described in Example 1 utilizing 5-(2-fluoro-4-(4,4,5,5-tetramethyl-1,3,2-dioxaborolan-2-yl)phenyl)-pyrazin-2-amine and (R)-1-(2-bromophenyl)-N-(2-hydroxypropyl)methane-sulfonamide.

Example 229

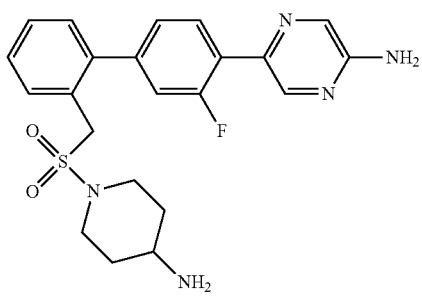

5-(2'-{[(4-Aminopiperidin-1-yl)sulfonyl]methyl}-3-fluorobiphenyl-4-yl)pyrazin-2-amine hydrochloride

Step A: tert-Butyl 1-((4'-(5-aminopyrazin-2-yl-5'-fluorobiphenyl-2-yl)methylsulfonyl)-piperidin-4-ylcarbamate A mixture of tert-butyl (1-((2-bromobenzyl)sulfonyl)piperidin-4-yl)carbamate (200 mg, 0.46 mmol), 5-(2-fluoro-4-(4,4,5,5-tetramethyl-1,3,2-dioxaborolan-2-yl)phenyl) pyrazin-2-amine (175 mg, 0.55 mmol), Pd(dppf)Cl$_2$·CH$_2$Cl$_2$ (34 mg, 0.046 mmol) and Na$_2$CO$_3$ (150 mg, 1.36 mmol) in dry DMF (15 mL) was stirred at 130° Celsius under N$_2$. After 5 hours, the solvent was removed under vacuum and the residue was subjected to FCC purification to give tert-butyl 1-((4'-(5-aminopyrazin-2-yl)-5'-fluorobiphenyl-2-yl)methylsulfonyl)piperidin-4-ylcarbamate (190 mg, 76%). MS (ESI): mass calcd. for C$_{27}$H$_{32}$FN$_5$O$_2$S, 541.22; m/z found, 542.1 [M+H]$^+$. $^1$H NMR (300 MHz, DMSO-d$_6$) δ 8.39 (s, 1H), 8.03 (s, 1H), 7.95 (s, 1H), 7.78-7.29 (m, 7H), 6.87 (d, J=5.2, 1H), 6.73 (s, 2H), 4.34 (s, 2H), 3.45-3.33 (m, 3H), 2.85-2.75 (m, 2H), 1.72 (d, J=12.4, 2H), 1.45-1.30 (m, 11H).

Step B

A mixture of tert-butyl 1-((4'-(5-aminopyrazin-2-yl)-5'-fluorobiphenyl-2-yl)methylsulfonyl)piperidin-4-ylcarbamate (190 mg, 0.35 mmol) in HCl (20 mL, 6 N in methanol) was stirred at rt for 24 hours. The solvent was removed under reduced pressure and the residue purified by HPLC to give the title compound (80 mg HCl salt, 61%). MS (ESI): mass calcd. for C$_{22}$H$_{24}$FN$_5$O$_2$S, 441.16; m/z found, 442.1 [M+H]$^+$. $^1$H NMR (300 MHz, DMSO-d$_6$) δ 8.38 (s, 1H), 8.10 (br, 4H), 7.95 (m, 1H), 7.64-7.55 (m, 1H), 7.52-7.32 (m, 4H), 4.80 (br, 4H), 4.37 (s, 2H), 3.50 (d, J=13.0, 2H), 3.10 (s, 1H), 2.76 (t. J=12.6, 2H), 1.91 (d. J=11.0, 3H), 1.58-1.41 (m, 2H).

Example 230

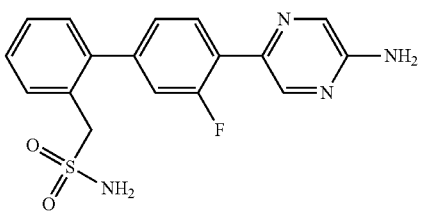

1-(4'-(5-Aminopyrazin-2-yl)-3'-fluorobiphenyl-2-yl] methanesulfonamide hydrochloride The title compound was prepared using analogous conditions to those described in Example 1 utilizing 5-(2-fluoro-4-(4,4,5,5-tetramethyl-1,3,2-dioxaborolan-2-yl)phenyl) pyrazin-2-amine and (2-bromophenyl)methanesulfonamide. MS (ESI): mass calcd. for C$_{17}$H$_{15}$FN$_4$O$_2$S, 358.09; m/z found, 359.1 [M+H]$^+$. $^1$H NMR (400 MHz, DMSO-d$_6$) δ 8.36 (s, 1H), 8.12 (s, 1H), 7.92 (m, 1H), 7.66-7.56 (m, 1H), 7.38 (m, 5H), 6.98 (s, 2H), 4.31 (s, 2H).

Example 231

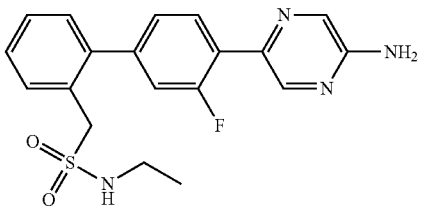

1-(4'-(5-Aminopyrazin-2-yl)-3'-fluorobiphenyl-2-yl]-N-ethylmethanesulfonamide formate salt The title compound was prepared using analogous conditions to those described in Example 1 utilizing 5-(2-fluoro-4-(4,4,5,5-tetramethyl-1,3,2-dioxaborolan-2-yl)phenyl) pyrazin-2-amine and 1-(2-bromophenyl)-N-ethylmethanesulfonamide. MS (ESI): mass calcd. for C$_{19}$H$_{19}$FN$_4$O$_2$S, 386.12; m/z found, 387.0 [M+H]$^+$. $^1$H NMR (400 MHz, CD$_3$OD) δ 8.39 (s, 1H), 8.08 (d, J=1.4, 1H), 7.93 (m, 1H), 7.71-7.61 (m, 1H), 7.49-7.27 (m, 5H), 4.36 (s, 2H), 2.85 (q, J=7.2, 2H), 1.06 (t, J=7.2, 3H).

Example 232

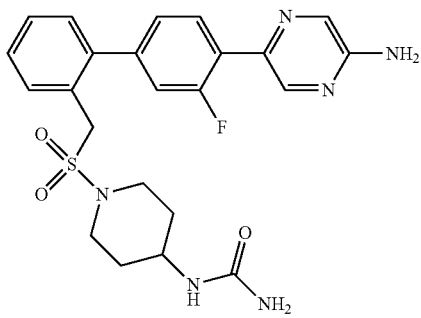

1-[1-({[4'-(5-Aminopyrazin-2-yl)-3'-fluorobiphenyl-2-yl]methyl}sulfonyl)piperidin-4-yl]urea hydrochloride The title compound was prepared using analogous conditions to those described in Example 1 utilizing 5-(2-fluoro-4-(4,4,5,5-tetramethyl-1,3,2-dioxaborolan-2-yl)phenyl)pyrazin-2-amine and 1-(1-((2-bromobenzyl)sulfonyl)piperidin-4-yl)urea. MS (ESI): mass calcd. for $C_{23}H_{25}FN_6O_3S$, 484.17; m/z found, 485.0 [M+H]$^+$. $^1$H NMR (400 MHz, DMSO-d$_6$) δ 8.37 (s, 1H), 8.16 (s, 1H), 7.96 (t, J=8.2, 1H), 7.66-7.28 (m, 6H), 4.35 (s, 2H), 3.41-3.32 (m, 2H), 2.85-2.70 (m, 2H), 1.83-1.70 (m, 2H), 1.33-1.19 (m, 2H).

Example 233

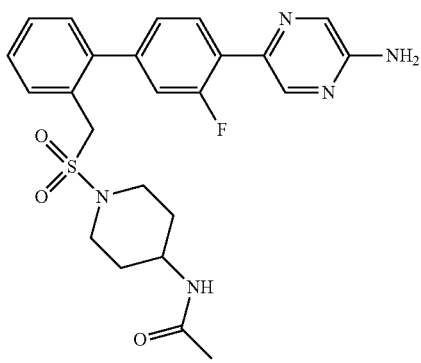

N-[1-({[4'-(5-Aminopyrazin-2-yl)-3'-fluorobiphenyl-2-yl]methyl}sulfonyl)piperidin-4-yl]-acetamide formate salt The title compound was prepared using analogous conditions to those described in Example 1 utilizing 5-(2-fluoro-4-(4,4,5,5-tetramethyl-1,3,2-dioxaborolan-2-yl)phenyl)pyrazin-2-amine and N-(1-((2-bromobenzyl)sulfonyl)piperidin-4-yl)acetamide. MS (ESI): mass calcd. for $C_{24}H_{26}FN_5O_3S$, 483.17; m/z found, 484.0 [M+H]$^+$. $^1$H NMR (400 MHz, DMSO-d$_6$) δ 8.39 (s, 1H), 8.03 (d, J=1.3, 1H), 7.95 (m, 1H), 7.81 (d, J=7.3, 1H), 7.64-7.55 (m, 1H), 7.50-7.31 (m, 5H), 6.73 (s, 2H), 4.35 (s, 2H), 3.71-3.56 (m, 1H), 3.39 (d, J=11.6, 2H), 2.79 (t, J=10.8, 2H), 1.82-1.67 (m, 5H), 1.41-1.24 (m, 3H).

Example 234

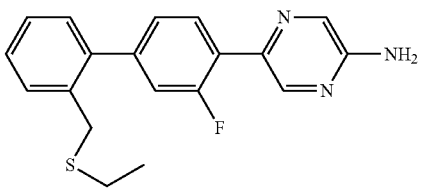

5-{2'-[(Ethylsulfanyl)methyl]-3-fluorobiphenyl-4-yl}pyrazin-2-amine formic acid salt

Step A: (4'-(5-Aminopyrazin-2-yl)-5'-fluorobiphenyl-2-yl)methanol

A mixture of 2-(hydroxymethyl)phenylboronic acid (1 g, 7 mmol), 5-(4-bromo-2-fluorophenyl)pyrazin-2-amine (1.76 g, 6.6 mmol), Pd(dppf)Cl$_2$·CH$_2$Cl$_2$ (483 mg, 0.66 mmol) and Na$_2$CO$_3$ (2.1 g, 20 mmol) in DMF (50 mL) was stirred at 110° Celsius overnight under N$_2$. The solution was concentrated to dryness and the residue purified by FCC to give (4'-(5-aminopyrazin-2-yl)-5'-fluorobiphenyl-2-yl)methanol (1.2 g, 62%). $^1$H NMR (300 MHz, DMSO-d$_6$) δ 8.38 (s, 1H), 8.02 (d, J=1.4, 1H), 7.90 (m, 1H), 7.57 (d, J=7.4, 1H), 7.49-7.26 (m, 5H), 6.69 (s, 2H), 5.20 (t, J=5.3, 1H), 4.44 (d, J=5.3, 2H).

Step B: 5-(6'-(Chloromethyl)-3-fluorobiphenyl-4-yl)pyrazin-2-amine

A mixture of (4'-(5-aminopyrazin-2-yl)-5'-fluorobiphenyl-2-yl)methanol (1.8 g, 6.1 mmol) and SOCl$_2$ (6 mL) in DCM (20 mL) was stirred at 70° Celsius for 4 hours. The reaction mixture was cooled to rt and concentrated to dryness to give 5-(6'-(chloromethyl)-3-fluorobiphenyl-4-yl)pyrazin-2-amine (1.86 g, 98%). $^1$H NMR (300 MHz, DMSO-d$_6$) δ 8.40 (s, 1H), 8.04 (s, 1H), 7.96 (m, 1H), 7.66-7.57 (m, 1H), 7.51-7.42 (m, 2H), 7.40-7.30 (m, 3H), 6.89-6.62 (br s, 2H), 4.73 (s, 2H).

Step C: S-(4'-(5-Aminopyrazin-2-yl)-5'-fluorobiphenyl-2-yl)methyl ethanethioate A mixture of 5-(6'-(chloromethyl)-3-fluorobiphenyl-4-yl)pyrazin-2-amine (1.86 g, 5.94 mmol) and KSAc (0.81 g, 7.1 mmol) in 1,4-dioxane/H$_2$O (30 mL/6 mL) was stirred at rt for 2 hours. Then the solvent was removed under vacuum and the residue purified by FCC to give S-(4'-(5-aminopyrazin-2-yl)-5'-fluorobiphenyl-2-yl)methyl ethanethioate (1.42 g, 68%). MS (ESI): mass calcd. for $C_{19}H_{18}FN_3OS$, 353.10; m/z found, 353.9 [M+H]$^+$.

Step D

To a solution of S-(4'-(5-aminopyrazin-2-yl)-5'-fluorobiphenyl-2-yl)methyl ethanethioate (100 mg, 0.28 mmol) in CH$_3$OH (30 mL) were added Ph$_3$P (147 mg, 0.56 mmol) and K$_2$CO$_3$ (78 mg, 0.56 mmol) followed by drop-wise addition of bromoethane (60 mg, 0.56 mmol). After 16 hours, the mixture was concentrated to dryness and the residue was purified by prep-TLC and followed by HPLC to give the title compound (70 mg HCOOH salt, 73%). MS (ESI): mass calcd. for $C_{19}H_{18}FN_3S$, 339.12; m/z found, 340.1 [M+H]$^+$.

$^1$H NMR (400 MHz, CD$_3$OD) δ 8.38 (m, 1H), 8.07 (d, J=1.5, 1H), 7.89 (m, 1H), 7.48-7.40 (m, 1H), 7.37-7.21 (m, 5H), 3.71 (s, 2H), 2.42 (q, J=7.4, 2H), 1.13 (t, J=7.4, 3H).

Example 235

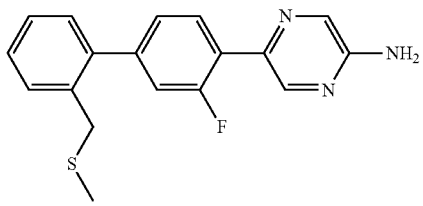

5-{3-Fluoro-2′-[(methylsulfanyl)methyl]biphenyl-4-yl}pyrazin-2-amine hydrochloride The title compound was prepared using analogous conditions to those described in Example 234 utilizing iodomethane. MS (ESI): mass calcd. for C$_{18}$H$_{16}$FN$_3$S, 325.10; m/z found, 326.1 [M+H]$^+$. $^1$H NMR (400 MHz, CD$_3$OD) δ 8.45 (s, 1H), 8.30 (d, J=1.0, 1H), 8.04 (m, 1H), 7.49-7.24 (m, 6H), 3.68 (s, 2H).

The title

Example 236

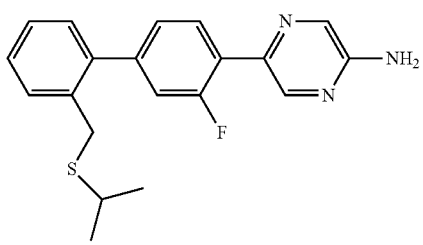

5-(3-Fluoro-2′-{[(1-methylethyl)sulfanyl]methyl}biphenyl-4-yl)pyrazin-2-amine hydrochloride The title compound was prepared using analogous conditions to those described in Example 234 utilizing 2-iodopropane. MS (ESI): mass calcd. for C$_{20}$H$_{20}$FN$_3$S, 353.14; m/z found, 354.0 [M+H]$^+$. $^1$H NMR (400 MHz, CD$_3$OD) δ 8.66 (s, 1H), 8.23 (d, J=1.2, 1H), 8.12 (m, 1H), 7.48-7.23 (m, 6H), 3.73 (s, 2H), 2.84-2.71 (m, 1H), 1.16 (d, J=6.7, 6H).

Example 237

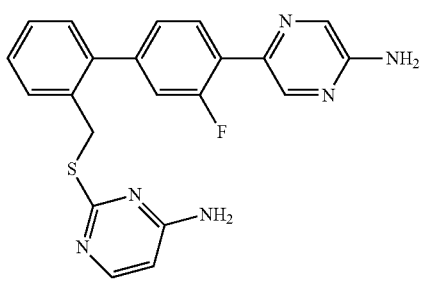

2-(((4′-(5-Aminopyrazin-2-yl)-3′-fluoro-[1,1′-biphenyl]-2-yl)methyl)thio)pyrimidin-4-amine hydrochloride The title compound was prepared using analogous conditions to those described in Example 234 utilizing 4-amino-2-chloropyrimidine. MS (ESI): mass calcd. for C$_{18}$H$_{16}$FN$_3$S, 404.12; m/z found, 404.9 [M+H]$^+$. $^1$H NMR (400 MHz, CD$_3$OD) δ 8.77-8.68 (m, 1H), 8.21 (d, J=1.3, 1H), 8.10 (m, 1H), 7.79 (d, J=6.9, 1H), 7.63-7.55 (m, 1H), 7.45-7.22 (m, 5H), 6.73 (d, J=6.8, 1H), 4.57 (s, 2H).

Example 238

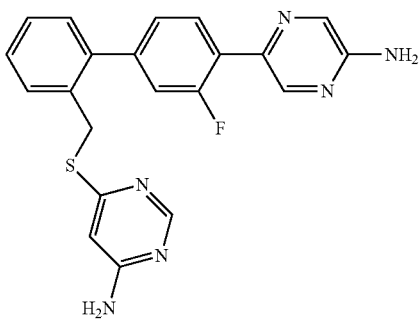

6-(((4′-(5-Aminopyrazin-2-yl)-3′-fluoro-[1,1′-biphenyl]-2-yl)methyl)thio)pyrimidin-4-amine hydrochloride The title compound was prepared using analogous conditions to those described in Example 6 utilizing 4-amino-6-chloropyrimidine. MS (ESI): mass calcd. for C$_{21}$H$_{17}$FN$_6$S, 404.12; m/z found, 405.1 [M+H]$^+$. $^1$H NMR (400 MHz, CD$_3$OD) δ 8.78-8.68 (m, 1H), 8.38 (d, J=0.6, 1H), 8.26 (d, J=1.3, 1H), 8.16 (m, 1H), 7.66-7.57 (m, 1H), 7.50-7.44 (m, 2H), 7.42-7.31 (m, 3H), 6.58 (d, J=3.4, 1H), 4.51 (s, 2H).

Example 239

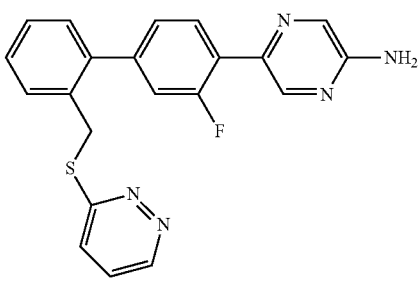

5-(3-Fluoro-2′-((pyridazin-3-ylthio)methyl)-[1,1′-biphenyl]-4-yl)pyrazin-2-amine hydrochloride The title compound was prepared using analogous conditions to those described in Example 6 utilizing 3-chloropyrazine. MS (ESI): mass calcd. for C$_{21}$H$_{16}$FN$_5$S, 389.11; m/z found, 390.1 [M+H]$^+$. $^1$H NMR (400 MHz. CD$_3$OD) δ 9.33-9.24 (m, 1H), 8.74 (s, 1H), 8.31-8.20 (m, 2H), 8.14 (m, 2H), 7.72-7.64 (m, 1H), 7.50-7.33 (m, 5H), 4.63 (s, 2H).

Example 240

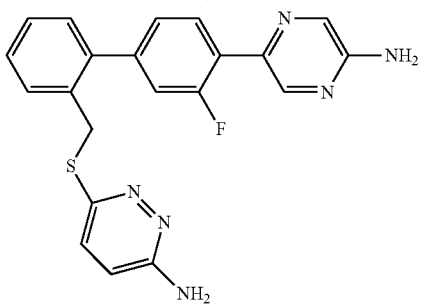

6-(((4'-(5-Aminopyrazin-2-yl)-3'-fluoro-[1,1'-biphenyl]-2-yl)methyl)thio)pyridazin-3-amine hydrochloride The title compound was prepared using analogous conditions to those described in Example 6 utilizing 3-chloropyrazine. MS (ESI): mass calcd. for $C_{21}H_{17}FN_6S$, 404.12; m/z found, 405.1 [M+H]$^+$. $^1$H NMR (400 MHz, CD$_3$OD) δ 8.70-8.63 (m, 1H), 8.28 (d, J=1.1, 1H), 8.12 (m, 1H), 7.65-7.57 (m, 2H), 7.46-7.41 (m, 2H), 7.39 (dd, J=8.1, 1.6, 1H), 7.36-7.30 (m, 3H), 4.43 (s, 2H).

Example 241

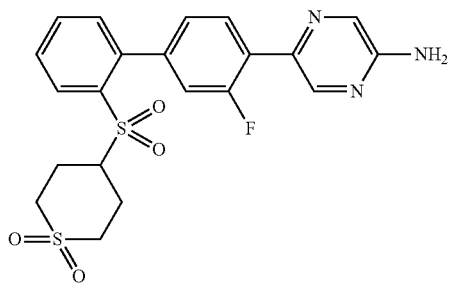

5-{2'-[(1,1-Dioxidotetrahydro-2H-thiopyran-4-yl)sulfonyl]-3-fluorobiphenyl-4-yl}pyrazin-2-amine The title compound was prepared using analogous conditions to those described in Example 6 utilizing 5-(2-fluoro-4-(4,4,5,5-tetramethyl-1,3,2-dioxaborolan-2-yl)phenyl)-pyrazin-2-amine and 4-((2-bromophenyl)sulfonyl)tetrahydro-2H-thiopyran 1,1-dioxide. MS (ESI): mass calcd. for $C_{21}H_{20}FN_3O_4S_2$, 461.09; m/z found, 462.1 [M+H]$^+$. $^1$H NMR (400 MHz, DMSO-d$_6$) δ 8.42 (s, 1H), 8.07-8.04 (m, 2H), 7.92 (m, 1H), 7.84 (m, 1H), 7.75 (m, 1H), 7.49 (dd, J=7.5, 1.0, 1H), 7.38-7.31 (m, 1H), 7.29 (dd, J=8.0, 1.6, 1H), 6.74 (s, 2H), 3.25-3.06 (m, 5H), 2.16-2.04 (m, 2H), 2.02-1.86 (m, 2H).

Example 242

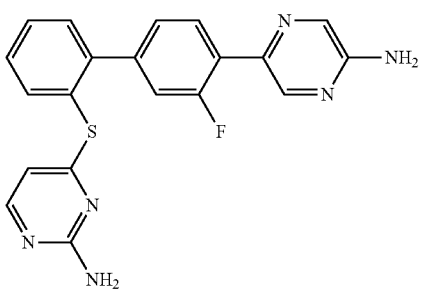

4-{[4'-(5-Aminopyrazin-2-yl)-3'-fluorobiphenyl-2-yl]sulfanyl}pyrimidin-2-amine hydrochloride The title compound was prepared using analogous conditions to those described in Example 234 utilizing 2-amino-4-chloropyrimidine. MS (ESI): mass calcd. for $C_{20}H_{15}FN_6S$, 390.11; m/z found, 391.1 [M+H]$^+$. $^1$H NMR (400 MHz, DMSO-d$_6$) δ 8.39-8.32 (m, 1H), 8.01 (d, J=1.5, 1H), 7.94 (d, J=6.1, 1H), 7.85 (m, 1H), 7.76 (d, J=7.8, 1H), 7.71-7.65 (m, 1H), 7.62-7.53 (m, 2H), 7.35-7.24 (m, 2H), 6.88 (s, 2H), 6.18 (d, J=6.4, 1H).

Example 243

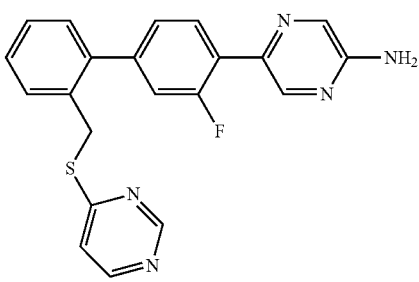

5-(3-Fluoro-2'-((pyrimidin-4-ylthio)methyl)-[1,1'-biphenyl]-4-yl)pyrazin-2-amine hydrochloride The title compound was prepared using analogous conditions to those described in Example 6 utilizing 4-chloropyrimidine. MS (ESI): mass calcd. for $C_{18}H_{16}FN_3S$, 389.11; m/z found, 390.0 [M+H]$^+$. $^1$H NMR (400 MHz, CD$_3$OD) δ 8.70 (d, J=1.4, 1H), 8.53 (d, J=4.9, 2H), 8.20 (d, J=1.3, 1H), 8.10 (m, 1H), 7.65-7.55 (m, 1H), 7.39-7.25 (m, 5H), 7.13 (m, 1H), 4.46 (s, 2H).

Example 244

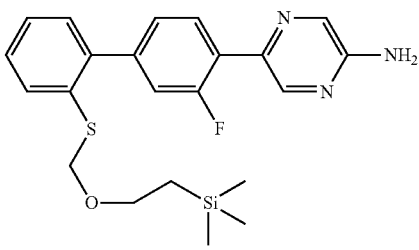

5-[3-Fluoro-2'-({[2-(trimethylsilyl)ethoxy]methyl}sulfanyl)biphenyl-4-yl]pyrazin-2-amine The title compound was prepared using analogous conditions to those described in Example 6 utilizing 5-(2-fluoro-4-(4,4,5,5-tetramethyl-1,3,2-dioxaborolan-2-yl)-phenyl)-pyrazin-2-amine and (2-(((2-bromophenyl)thio)methoxy)ethyl)trimethylsilane. MS (ESI): mass calcd. for $C_{22}H_{26}FN_3OSSi$, 427.16; m/z found, 428.1 [M+H]$^+$. $^1$H NMR (400 MHz, CD$_3$OD) δ 8.43-8.36 (m, 1H), 8.07 (d, J=1.5, 1H), 7.89 (m, 1H), 7.73 (dd, J=6.7, 1.4, 1H), 7.40-7.17 (m, 5H), 4.90 (s, 2H), 3.64-3.50 (m, 2H), 0.91-0.78 (m, 2H). 0.04 (s, 9H).

Example 245

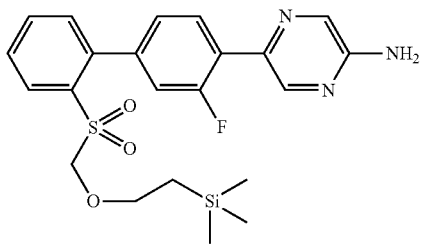

5-[3-Fluoro-2'-({[2-(trimethylsilyl)ethoxy]methyl}sulfonyl)
biphenyl-4-yl]pyrazin-2-amine hydrochloride The title compound was prepared using analogous conditions to those described in Example Example 244 utilizing 5-[3-fluoro-2'-({[2-(trimethylsilyl)ethoxy]methyl}sulfanyl-biphenyl-4-yl]-pyrazin-2-amine. MS (ESI): mass calcd. for $C_{22}H_{26}FN_3O_3SSi$, 459.14; m/z found, 459.9 [M+H]$^+$. $^1$H NMR (400 MHz, CD$_3$OD) δ 8.44-8.39 (m, 1H), 8.18 (dd, J=8.0, 1.3, 1H), 8.08 (d, J=1.4, 1H), 7.94 (m, 1H), 7.80-7.75 (m, 1H), 7.72-7.65 (m, 1H), 7.47 (dd, J=7.5, 1.4, 1H), 7.31 (dd, J=3.6, 1.7, 1H), 7.28 (dd, J=7.7, 1.5, 1H), 4.34 (s, 2H), 3.77-3.68 (m, 2H), 0.85-0.75 (m, 2H), 0.08 (s, 9H).

Example 246

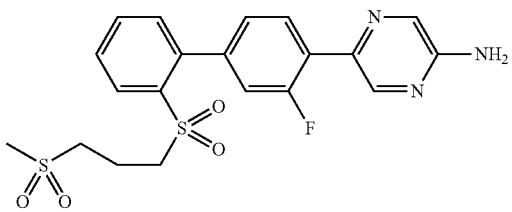

5-(3-Fluoro-2'-{[3-(methylsulfonyl)propyl]sulfonyl}
biphenyl-4-yl)pyrazin-2-amine hydrochloride The title compound was prepared using analogous conditions to those described in Example 6 utilizing 5-(2-fluoro-4-(4,4,5,5-tetramethyl-1,3,2-dioxaborolan-2-yl)phenyl)-pyrazin-2-amine and 1-bromo-2-((3-(methylsulfonyl)propyl)sulfonyl)benzene. MS (ESI): mass calcd. for $C_{20}H_{20}FN_3O_4S_2$, 449.53; m/z found, 450.0 [M+H]$^+$. $^1$H NMR (400 MHz, CD$_3$OD) δ 8.69 (d, J=1.3, 1H), 8.25 (d, J=1.3, 1H), 8.18 (dd, J=7.9, 1.3, 1H), 8.12 (m, 1H), 7.81 (m, 1H), 7.71 (m, 1H), 7.48 (dd, J=7.4, 1.3, 1H), 7.44-7.34 (m, 2H), 3.20-3.09 (m, 4H), 2.89 (s, 3H), 2.12-1.96 (m, 2H).

Example 247

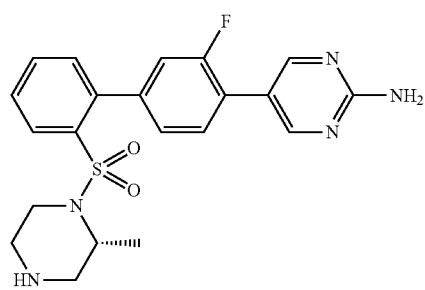

5-(3-Fluoro-2'-{[(2R)-2-methylpiperazin-1-yl]sulfonyl}biphenyl-4-yl)pyrimidin-2-amine Step A: (R)-tert-Butyl 4-((4'-(2-aminopyrimidin-5-yl)-3'-fluoro-[1,1'-biphenyl]-2-yl)sulfonyl-3-methyl-piperazine-1-carboxylate The title compound was prepared using methods analogous to those described in Example 376 using 5-(2-fluoro-4-(4,4,5,5-tetramethyl-1,3,2-dioxaborolan-2-yl)phenyl)pyrimidin-2-amine and (R)-tert-butyl 4-((2-bromophenyl)sulfonyl)-3-methylpiperazine-1-carboxylate. MS (ESI): mass calcd. for $C_{26}H_{30}FN_5O_4S$, 527.20; m/z found, 528.2 [M+H]$^+$.

Step B

The title compound was prepared by dissolving (R)-tert-butyl 4-((4'-(2-aminopyrimidin-5-yl)-3'-fluoro-[1,1'-biphenyl]-2-yl)sulfonyl)-3-methylpiperazine-1-carboxylate (42 mg, 0.08 mmol) in a 50/50 mixture of DCM/TFA (1 mL) and allowing it to stir at rt for 2 h. The reaction mixture was concentrated to dryness and the residue subjected to HPLC purification to give the title compound (29 mg, 85%). MS (ESI): mass calcd. for $C_{21}H_{22}FN_5O_2S$, 427.15; m/z found, 428.1 [M+H]$^+$. $^1$H NMR (400 MHz, CDCl$_3$) δ 8.56 (d, J=1.4, 2H), 8.16 (dd, J=8.0, 1.4, 1H), 7.65-7.58 (m, 1H), 7.56-7.49 (m, 1H), 7.48-7.39 (m, 1H), 7.38-7.31 (m, 3H), 5.18 (s, 2H), 3.64-3.52 (m, 1H), 2.99-2.87 (m, 2H), 2.81-2.69 (m, 1H), 2.61-2.41 (m, 4H), 1.18 (d, J=6.8, 3H).

Example 248

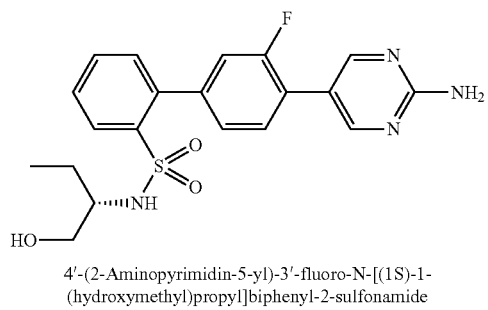 [SMILES: CC[C@@H](CO)NS(=O)(=O)c1ccccc1-c1ccc(-c2cnc(N)nc2)c(F)c1]

4'-(2-Aminopyrimidin-5-yl)-3'-fluoro-N-[(1S)-1-(hydroxymethyl)propyl]biphenyl-2-sulfonamide The title compound was prepared using methods analogous to those described in Example 376 using 5-(2-fluoro-4-(4,4,5,5-tetramethyl-1,3,2-dioxaborolan-2-yl)phenyl)pyrimidin-2-amine and (S)-2-bromo-N-(1-hydroxybutan-2-yl)benzenesulfonamide. MS (ESI): mass calcd. for $C_{20}H_{21}FN_4O_3S$, 416.13; m/z found, 417.0 [M+H]$^+$. $^1$H NMR (400 MHz, CDCl$_3$) δ 8.47 (d, J=1.3, 2H), 8.18 (dd, J=7.9, 1.4, 1H), 7.67-7.57 (m, 1H), 7.59-7.49 (m, 1H), 7.42-7.30 (m, 4H), 5.39 (s, 2H), 5.07 (d, J=8.0, 1H), 3.55-3.38 (m, 2H), 3.25-3.11 (m, 1H), 1.93 (s, 1H), 1.54-1.29 (m, 2H), 0.80 (t, J=7.4, 3H).

Example 249

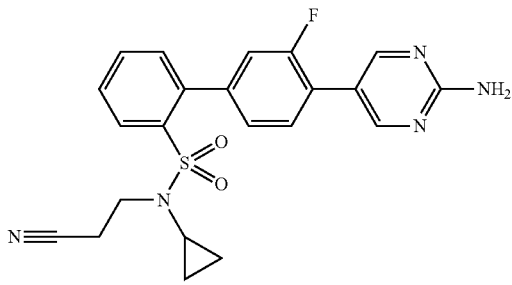

4'-(2-Aminopyrimidin-5-yl)-N-(2-cyanoethyl)-N-cyclopropyl-3'-fluorobiphenyl-2-sulfonamide The title compound was prepared using methods analogous to those described in Example 376 using 5-(2-fluoro-4-(4,4,5,5-tetramethyl-1,3,2-dioxaborolan-2-yl)phenyl)phenyl)pyrimidin-2-amine and 2-bromo-N-(2-cyanoethyl)-N-cyclopropylbenzenesulfonamide. MS (ESI): mass calcd. for $C_{22}H_{20}FN_5O_2S$, 437.13; m/z found, 438.0 [M+H]$^+$. $^1$H NMR (400 MHz, CDCl$_3$) δ 8.57 (d, J=1.4, 2H), 8.17 (dd, J=7.9, 1.3, 1H), 7.71-7.62 (m, 1H), 7.62-7.52 (m, 1H), 7.49-7.40 (m, 1H), 7.33 (dd, J=7.5, 1.4, 1H), 7.20 (dd, J=8.0, 1.7, 1H), 7.14 (dd, J=11.1, 1.7, 1H), 5.20 (s, 2H), 3.02 (t, J=7.0, 2H), 2.59-2.41 (m, 3H), 0.65-0.55 (m, 2H), 0.39-0.28 (m, 2H).

Example 250

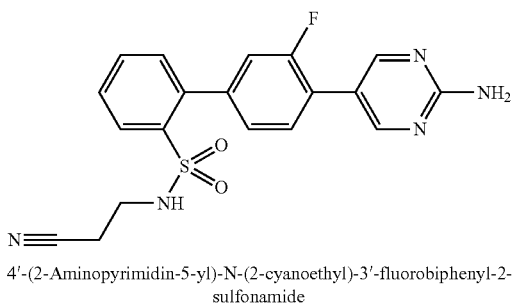 [SMILES: N#CCCNS(=O)(=O)c1ccccc1-c1ccc(-c2cnc(N)nc2)c(F)c1]

4'-(2-Aminopyrimidin-5-yl)-N-(2-cyanoethyl)-3'-fluorobiphenyl-2-sulfonamide

The title compound was prepared using methods analogous to those described in Example 376 using 5-(2-fluoro-4-(4,4,5,5-tetramethyl-1,3,2-dioxaborolan-2-yl)phenyl)phenyl)pyrimidin-2-amine and 2-bromo-N-(2-cyanoethyl)benzenesulfonamide. MS (ESI): mass calcd. for $C_{19}H_{16}FN_5O_2S$, 397.10; m/z found, 398.1 [M+H]$^+$. $^1$H NMR (400 MHz, CDCl$_3$) δ 8.50 (d, J=1.4, 2H), 8.18 (dd, J=7.9, 1.4, 1H), 7.70-7.64 (m, 1H), 7.62-7.55 (m, 1H), 7.49-7.42 (m, 1H), 7.40-7.32 (m, 3H), 5.36 (s, 2H), 5.24 (t, J=6.5, 1H), 3.07 (m, 2H), 2.50 (t, J=6.5, 2H).

Example 251

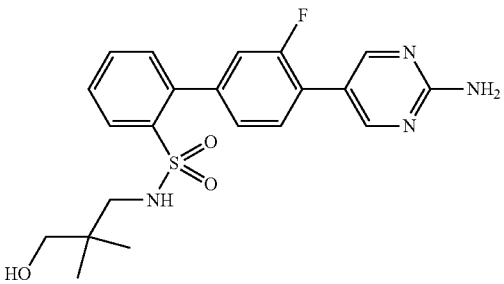

4'-(2-Aminopyrimidin-5-yl)-N-3'-fluoro-N-(3-hydroxy-2,2-dimethylpropyl)biphenyl-2-sulfonamide The title compound was prepared using methods analogous to those described in Example 376 using 5-(2-fluoro-4-(4,4,5,5-tetramethyl-1,3,2-dioxaborolan-2-yl)phenyl)phenyl)pyrimidin-2-amine and 2-bromo-N-(3-hydroxy-2,2-dimethylpropyl)-benzenesulfonamide. MS (ESI): mass calcd. for $C_{21}H_{23}FN_4O_3S$, 430.15; m/z found, 431.1 [M+H]$^+$. $^1$H NMR (400 MHz, CDCl$_3$) δ 8.53 (d, J=1.4, 2H), 8.12 (dd, J=7.8, 1.5, 1H), 7.62-7.55 (m, 1H), 7.55-7.48 (m, 1H), 7.48-7.38 (m, 1H), 7.38-7.27 (m, 3H), 5.08 (s, 2H), 4.23 (t, J=6.6, 1H), 3.33-3.21 (m, 2H), 2.61 (d, J=6.8, 2H), 1.40 (s, 6H).

Example 252

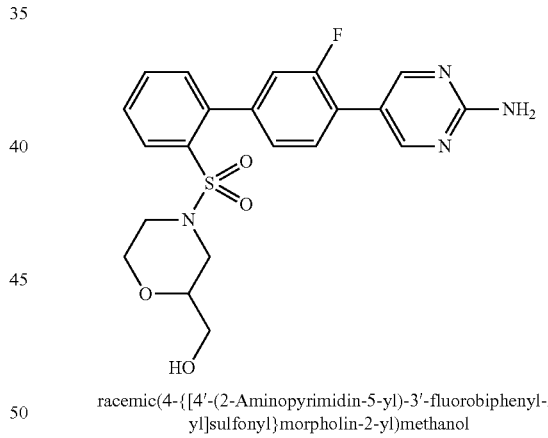

racemic(4-{[4'-(2-Aminopyrimidin-5-yl)-3'-fluorobiphenyl-2-yl]sulfonyl}morpholin-2-yl)methanol The title compound was prepared using methods analogous to those described in Example 376 using 5-(2-fluoro-4-(4,4,5,5-tetramethyl-1,3,2-dioxaborolan-2-yl)phenyl)phenyl)pyrimidin-2-amine and racemic (4-((2-bromophenyl)sulfonyl)morpholin-2-yl)methanol. MS (ESI): mass calcd. for $C_{21}H_{21}FN_4O_4S$, 444.13; m/z found, 445.0 [M+H]$^+$. $^1$H NMR (400 MHz, CDCl$_3$) δ 8.56 (d, J=1.4, 2H), 8.10 (dd, J=7.9, 1.4, 1H), 7.70-7.60 (m, 1H), 7.60-7.52 (m, 1H), 7.47-7.35 (m, 2H), 7.33-7.26 (m, 2H), 5.22 (s, 2H), 3.86-3.76 (m, 1H), 3.63-3.51 (m, 1H), 3.51-3.29 (m, 3H), 3.24-3.09 (m, 2H), 2.64-2.52 (m, 1H), 2.45 (dd, J=12.4, 10.5, 1H), 1.95 (s, 1H).

Example 253

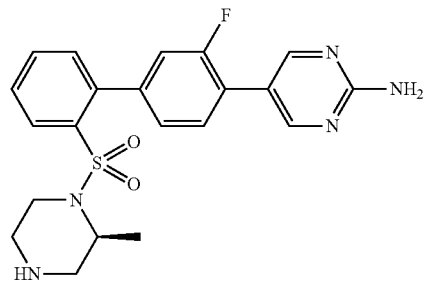

5-(3-Fluoro-2'-{[(2S)-2-methylpiperazin-1-yl]sulfonyl}biphenyl-4-yl)pyrimidin-2-amine

Step A: (S-tert-Butyl 4-((4'-(2-aminopyrimidin-5-yl)-3'-fluoro-[1,1'-biphenyl]-2-yl)sulfonyl-3-methyl-piperazine-1-carboxylate The title compound was prepared using methods analogous to those described in Example 376 using 5-(2-fluoro-4-(4,4,5,5-tetramethyl-1,3,2-dioxaborolan-2-yl)phenyl)pyrimidin-2-amine and (S)-tert-butyl 4-((2-bromophenyl)sulfonyl)-3-methypiperazine-1-carboxylate. MS (ESI): mass calcd. for $C_{26}H_{30}FN_5O_4S$, 527.20: m/z found, 528.2 [M+H]$^+$.

Step B

The title compound was prepared as described in the preparation of Example 252 using (S)-tert-butyl 4-((4'-(2-aminopyrimidin-5-yl)-3'-fluoro-[1,1'-biphenyl]-2-yl)sulfonyl)-3-methylpiperazine-1-carboxylate. MS (ESI): mass calcd. for $C_{21}H_{22}FN_5O_2S$, 427.15; m/z found, 428.1 [M+H]$^+$. $^1$H NMR (400 MHz, CDCl$_3$) b 8.56 (d, J=1.4, 2H), 8.16 (dd, J=7.9, 1.3, 1H), 7.65-7.58 (m, 1H), 7.56-7.49 (m, 1H), 7.48-7.39 (m, 1H), 7.38-7.31 (m, 3H), 5.16 (s, 2H), 3.64-3.51 (m, 1H), 3.02-2.86 (m, 2H), 2.81-2.70 (m, 1H), 2.63-2.41 (m, 4H), 1.18 (d, J=6.8, 3H).

Example 254

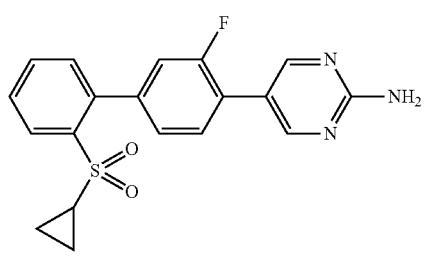

5-(3-Fluoro-2'-(Cyclopropylsulfonyl)-3-fluorobiphenyl-4-yl]pyrimidin-2-amine

The title compound was prepared using methods analogous to those described in Example 376 using 5-(2-fluoro-4-(4,4,5,5-tetramethyl-1,3,2-dioxaborolan-2-yl)phenyl)pyrimidin-2-amine and 1-bromo-2-(cyclopropylsulfonyl)benzene. MS (ESI): mass calcd. for $C_{19}H_{16}FN_3O_2S$, 369.10; m/z found, 370.0 [M+H]$^+$. $^1$H NMR (400 MHz, CDCl$_3$) δ 8.59 (d, J=1.5, 2H), 8.14 (dd, J=7.9, 1.5, 1H), 7.70-7.63 (m, 1H), 7.62-7.54 (m, 1H), 7.45 (m, 1H), 7.41-7.28 (m, 3H), 5.23 (s, 2H), 2.19-2.06 (m, 1H), 1.16-1.07 (m, 2H), 0.93-0.81 (m, 2H).

Example 255

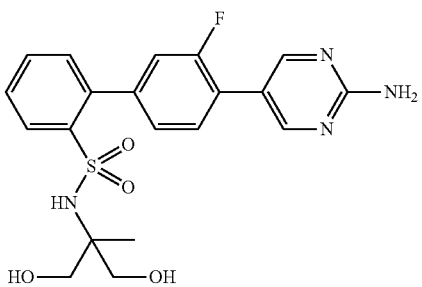

4'-(2-Aminopyrimidin-5-yl)-3'-fluoro-N-[2-hydroxy-1-(hydroxymethyl)-1-methylethyl]-1-methylethyl]
biphenyl-2-sulfonamide The title compound was prepared using methods analogous to those described in Example 376 using 5-(2-fluoro-4-(4,4,5,5-tetramethyl-1,3,2-dioxaborolan-2-yl)phenyl)pyrimidin-2-amine and 2-bromo-N-(1,3-dihydroxy-2-methylpropan-2-yl)benzenesulfonamide. MS (ESI): mass calcd. for $C_{20}H_{21}FN_4O_4S$, 432.13; m/z found, 433.1 [M+H]$^+$.

Example 256

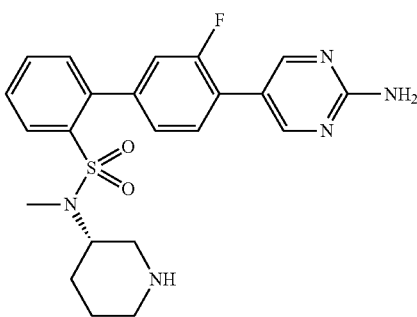

4'-(2-Aminopyrimidin-5-yl)-3'-fluoro-N-methyl-N-[(3S)-piperidin-3-yl]
biphenyl-2-sulfonamide

Step A: (S)-tert-Butyl 3-(4'-2-aminopyrimidin-5-yl)-3'-fluoro-N-methyl-[1,1'-biphenyl]-2-ylsulfonamido)piperidine-1-carboxylate The title compound was prepared using methods analogous to those described in Example 376 using 5-(2-fluoro-4-(4,4,5,5-tetramethyl-1,3,2-dioxaborolan-2-yl)phenyl)pyrimidin-2-amine and (S)-tert-butyl 3-(2-bromo-N-methylphenylsulfonamido)-piperidine-1-carboxylate yielding 41 mg (48%) of the title compound after HPLC purification. MS (ESI): mass calcd. for $C_{27}H_{32}FN_5O_4S$, 541.21; m/z found, 542.1 [M+H]$^+$.

Step B

The title compound was prepared as described in the preparation of Example 247 using (S)-tert-butyl 3-(4'-2- aminopyrimidin-5-yl)-3'-fluoro-N-methyl-[1,1'-biphenyl]-2-ylsulfonamido)piperidine-1-carboxylate. The crude product was purified by HPLC to give the title compound (35 mg, 91%). MS (ESI): mass calcd. for $C_{22}H_{24}FN_5O_2S$, 441.16; m/z found, 442.0 [M+H]$^+$. $^1$H NMR (400 MHz, CDCl$_3$) δ 8.56 (d, J=1.4, 2H), 8.14 (dd, J=7.9, 1.4, 1H), 7.65-7.57 (m, 1H), 7.56-7.49 (m, 1H), 7.48-7.38 (m, 1H), 7.37-7.24 (m, 3H), 5.19 (s, 2H), 3.43-3.24 (m, 1H), 2.96-2.74 (m, 2H), 2.51 (t, J=11.3, 1H), 2.42 (s, 4H), 2.38-2.27 (m, 1H), 1.78-1.21 (m, 4H).

Example 257

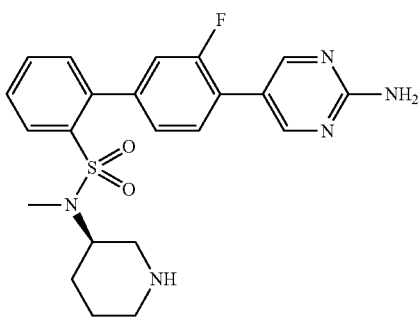

4'-(2-Aminopyrimidin-5-yl)-3'-fluoro-N-methyl-N-[(3R)-piperidin-3-yl]biphenyl-2-sulfonamide Step A: R)-tert-Butyl 3-(4'-2-aminopyrimidin-5-yl)-3'-fluoro-N-methyl-[1,1'-biphenyl]-2-ylsulfonamido)piperidine-1-carboxylate The title compound was prepared using methods analogous to those described in Example 376 using 5-(2-fluoro-4-(4,4,5,5-tetramethyl-1,3,2-dioxaborolan-2-yl)phenyl)pyrimidin-2-amine and (R)-tert-butyl 3-(2-bromo-N-methylphenylsulfonamido)piperidine-1-carboxylate. MS (ESI): mass calcd. for $C_{27}H_{32}FN_5O_4S$, 541.21; m/z found, 542.2 [M+H]$^+$.

Step B

The title compound was prepared as described in the preparation of Example 247 using (R)-tert-butyl 3-(4'-2-aminopyrimidin-5-yl)-3'-fluoro-N-methyl-[1,1'-biphenyl]-2-ylsulfonamido)piperidine-1-carboxylate. MS (ESI): mass calcd. for $C_{22}H_{24}FN_5O_2S$, 441.16; m/z found, 442.0 [M+H]$^+$. $^1$H NMR (400 MHz, CDCl$_3$) δ 8.56 (d, J=1.4, 2H), 8.14 (dd, J=8.0, 1.4, 1H), 7.65-7.57 (m, 1H), 7.56-7.49 (m, 1H), 7.47-7.36 (m, 1H), 7.37-7.25 (m, 3H), 5.18 (s, 2H), 3.42-3.26 (m, 1H), 2.93-2.73 (m, 2H), 2.57-2.46 (m, 1H), 2.42 (s, 3H), 2.38-2.27 (m, 2H), 1.73-1.23 (m, 4H).

Example 258

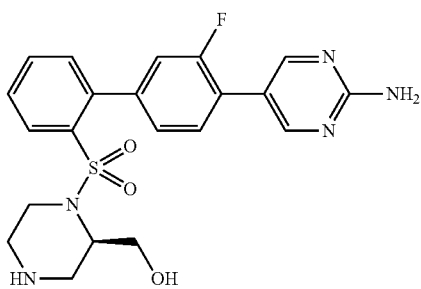

[(2R)-1-{[4'-(2-Aminopyrimidin-5-yl)-3'-fluorobiphenyl-2-yl]sulfonyl}piperazin-2-yl]methanol Step A: (R)-tert-Butyl 4-((4'-(2-aminopyrimidin-5-yl)-3'-fluoro-[1,1'-biphenyl]-2-yl)sulfonyl)-3-(hydroxymethyl)piperazine-1-carboxylate The title compound was prepared using methods analogous to those described in Example 376 using 5-(2-fluoro-4-(4,4,5,5-tetramethyl-1,3,2-dioxaborolan-2-yl)phenyl)pyrimidin-2-amine and (R)-tert-butyl 4-((2-bromophenyl)sulfonyl)-3-hydroxymethy)piperazine-1-carboxylate. MS (ESI): mass calcd. for $C_{26}H_{30}FN_5O_5S$, 543.20; m/z found, 544.2 [M+H]$^+$.

Step B

The title compound was prepared as described in the preparation of Example 247 using (R)-tert-butyl 4-((4'-(2-aminopyrimidin-5-yl)-3'-fluoro-[1,1'-biphenyl]-2-yl)sulfonyl)-3-(hydroxymethyl)piperazine-1-carboxylate. MS (ESI): mass calcd. for $C_{21}H_{22}FN_5O_3S$, 443.14; m/z found, 444.1 [M+H]$^+$. $^1$H NMR (400 MHz, CDCl$_3$) δ 8.56 (d, J=1.4, 2H), 8.18 (dd, J=8.0, 1.3, 1H), 7.66-7.59 (m, 1H), 7.57-7.49 (m, 1H), 7.47-7.40 (m, 1H), 7.39-7.31 (m, 3H), 5.19 (s, 2H), 3.94-3.77 (m, 2H), 3.52-3.39 (m, 1H), 3.34-3.18 (m, 1H), 3.17-2.99 (m, 2H), 2.88-2.77 (m, 1H), 2.65-2.46 (m, 2H), 1.65 (br s, 2H).

Example 259

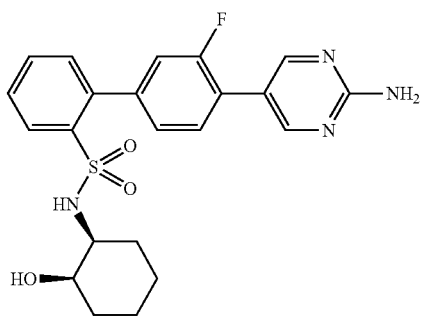

racemic cis 4'-(2-Aminopyrimidin-5-yl)-3'-fluoro-N-[(cis)-2-hydroxycyclohexyl]biphenyl-2-sulfonamide The title compound was prepared using methods analogous to those described in Example 376 using 5-(2-fluoro- 4-(4,5,5-tetramethyl-1,3,2-dioxaborolan-2-yl)phenyl)pyrimidin-2-amine and racemic 2-bromo-N-((cis)-2-hydroxycyclohexyl)-benzenesulfonamide. MS (ESI): mass calcd. for $C_{22}H_{23}FN_4O_3S$, 442.15; m/z found, 443.1 [M+H]$^+$. $^1$H NMR (500 MHz, CDCl$_3$) δ 8.51 (d, J=1.3, 2H), 8.17 (dd, J=8.0, 1.4, 1H), 7.64-7.59 (m, 1H), 7.57-7.51 (m, 1H), 7.44-7.31 (m, 4H), 5.30 (s, 2H), 4.83 (d, J 20=7.7, 1H), 3.78 (s, 1H), 3.20-3.11 (m, 1H), 1.72-1.65 (m, 1H), 1.57-1.10 (m, 8H).

Example 260

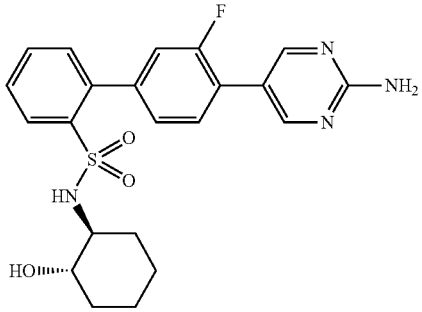

racemic 4'-(2-Aminopyrimidin-5-yl)-3'-fluoro-N-[(trans)-2-hydroxycyclohexyl]biphenyl-2-sulfonamide The title compound was prepared using methods analogous to those described in Example 376 using 5-(2-fluoro-4-(4,4,5,5-tetramethyl-1,3,2-dioxaborolan-2-yl)phenyl)pyrimidin-2-amine and 2-bromo-N-((trans)-2-hydroxycylohexyl)benzenesulfonamide. MS (ESI): mass calcd. for $C_{22}H_{23}FN_4O_3S$, 442.15; m/z found, 443.1 [M+H]$^+$. $^1$H NMR (500 MHz, CDCl$_3$) δ 8.51 (d, J=1.3, 2H), 8.17 (dd, J=8.0, 1.4, 1H), 7.64-7.59 (m, 1H), 7.57-7.51 (m, 1H), 7.44-7.31 (m, 4H), 5.30 (s, 2H), 4.83 (d, J=7.7, 1H), 3.78 (s, 1H), 3.20-3.11 (m, 1H), 1.72-1.65 (m, 1H), 1.57-1.10 (m, 8H).

Example 261

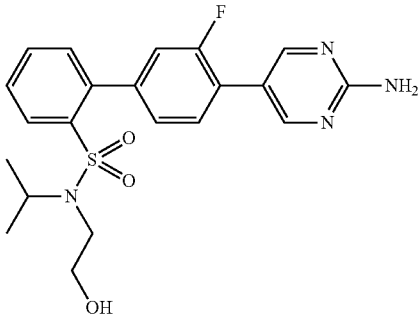

4'-(2-Aminopyrimidin-5-yl)-3'-fluoro-N-(2-hydroxyethyl)-N-(1-methylethyl)biphenyl-2-sulfonamide The title compound was prepared using methods analogous to those described in Example 376 using 5-(2-fluoro-4-(4,4,5,5-tetramethyl-1,3,2-dioxaborolan-2-yl)phenyl)pyrimidin-2-amine and 2-bromo-N-(2-hydroxyethyl)-N-isopropylbenzenesulfonamide. MS (ESI): mass calcd. for $C_{21}H_{23}FN_4O_3S$, 430.15; m/z found, 431.1 [M+H]$^+$. $^1$H NMR (400 MHz, CDCl$_3$) δ 8.56 (d, J=1.4, 2H), 8.10 (dd, J=8.0, 1.4, 1H), 7.65-7.57 (m, 1H), 7.58-7.49 (m, 1H), 7.49-7.38 (m, 1H), 7.37-7.28 (m, 3H), 5.22 (s, 2H), 3.72 (p, J=6.7, 1H), 3.65-3.50 (m, 2H), 2.99 (t, J=6.0, 2H), 2.19 (d, J=7.0, 1H), 1.04 (d, J=6.7, 6H).

Example 262

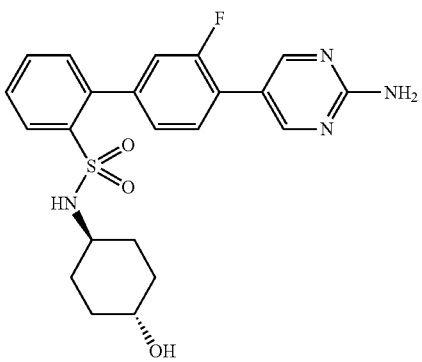

4'-(2-Aminopyrimidin-5-yl)-3'-fluoro-N-(trans-4-hydroxycyclohexyl)biphenyl-2-sulfonamide The title compound was prepared using methods analogous to those described in Example 376 using 5-(2-fluoro-4-(4,4,5,5-tetramethyl-1,3,2-dioxaborolan-2-yl)phenyl)pyrimidin-2-amine and trans-2-bromo-N-4-hydroxycyclohexyl)benzenesulfonamide. MS (ESI): mass calcd. for $C_{22}H_{23}FN_4O_3S$, 442.15; m/z found, 443.1 [M+H]$^+$. $^1$H NMR (400 MHz, CDCl$_3$) δ 8.53 (s, 1H), 8.22-8.15 (m, 1H), 7.67-7.60 (m, 1H), 7.59-7.51 (m, 1H), 7.48-7.39 (m, 1H), 7.39-7.31 (m, 3H), 5.26 (s, 2H), 4.11 (d, J=7.1, 1H), 3.60-3.43 (m, 1H), 3.10-2.94 (m, 1H), 1.93-1.73 (m, 4H), 1.38 (d, J=4.4, 1H), 1.34-1.00 (m, 5H).

Example 263

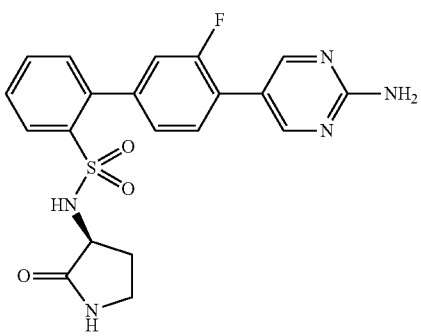

4'-(2-Aminopyrimidin-5-yl)-3'-fluoro-N-[(3S)-2-oxopyrrolidin-3-yl]biphenyl-2-sulfonamide The title compound was prepared using methods analogous to those described in Example 376 using 5-(2-fluoro-4-(4,4,5,5-tetramethyl-1,3,2-dioxaborolan-2-yl)phenyl)pyrimidin-2-amine and (S)-2-bromo-N-(2-oxopyrrolidin-3-yl)benzenesulfonamide. MS (ESI): mass calcd. for $C_{20}H_{18}FN_5O_3S$, 427.11; m/z found, 428.1 [M+H]$^+$. $^1$H NMR (400 MHz, CDCl$_3$) δ 8.51 (dd, J=2.2, 1.3, 2H), 8.18 (dd, J=7.9, 1.3, 1H), 7.67-7.60 (m, 1H), 7.58-7.51 (m, 1H), 7.45-7.31 (m, 4H), 6.05 (d, J=9.3, 1H), 5.51 (dd, J=9.8, 3.3, 1H), 5.35 (d, J=3.1, 2H), 3.67-3.55 (m, 1H), 3.39-3.19 (m, 2H), 2.65-2.50 (m, 1H), 2.16-1.99 (m, 1H).

Example 264

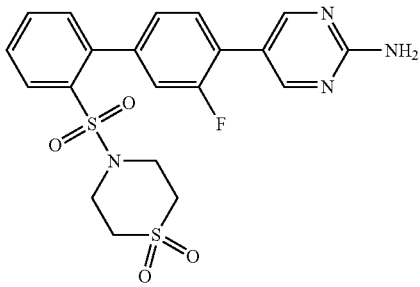

5-{2'-[(1,1-Dioxidothiomorpholin-4-yl)sulfonyl]-3-fluorobiphenyl-4-yl}pyrimidin-2-amine trifluoroacetic salt The title compound was prepared using analogous conditions to those described in Example 571 using 5-(2-fluoro-4-(4,4,5,5-tetramethyl-1,3,2-dioxaborolan-2-yl)phenyl)-pyrimidin-2-amine and 4-((2-bromophenyl)sulfonyl)thiomorpholine 1,1-dioxide. MS (ESI): mass calcd. for $C_{20}H_{19}FN_4O_4S_2$. 462.08; m/z found, 463.1 [M+H]$^+$. $^1$H NMR (600 MHz, CD$_3$OD) δ 8.78 (d, J=0.9, 2H), 8.15 (dd, J=8.0, 1.1, 1H), 7.75 (m, 1H), 7.71-7.62 (m, 2H), 7.44 (dd, J=7.6, 1.1, 1H), 7.40-7.31 (m, 2H), 3.34 (dd, J=7.8, 3.2, 4H), 3.04-2.99 (m, 4H).

Example 265

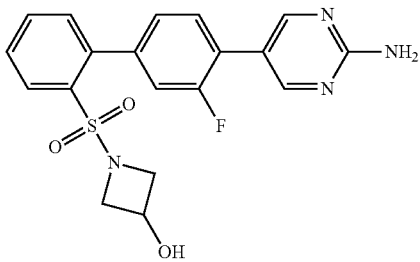

1-{[4'-(2-Aminopyrimidin-5-yl)-3'-fluorobiphenyl-2-yl]sulfonyl}azetidin-3-ol trifluoroacetic acid salt The title compound was prepared using analogous conditions to those described in Example 571 using 5-(2-fluoro-4-(4,4,5,5-tetramethyl-1,3,2-dioxaborolan-2-yl)phenyl)-pyrimidin-2-amine and 1-((2-bromophenyl)sulfonyl)azetidin-3-ol. MS (ESI): mass calcd. for $C_{19}H_{17}FN_4O_3S$, 400.10; m/z found, 401.1 [M+H]$^+$. $^1$H NMR (600 MHz, CD$_3$OD) δ 8.79 (d, J=0.7, 2H), 8.08 (dd, J=8.0, 1.1, 1H), 7.72 (m, 1H), 7.68-7.55 (m, 2H), 7.47-7.38 (m, 1H), 7.36 (dd, J=8.3, 1.5, 2H), 4.36 (m, 1H), 3.76-3.64 (m, 2H), 3.60-3.53 (m, 2H).

Example 266

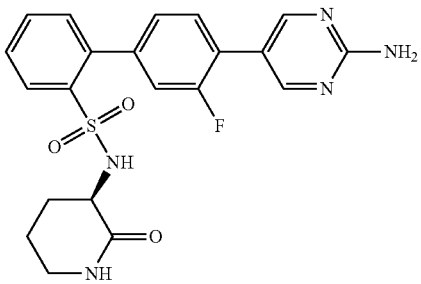

4'-(2-Aminopyrimidin-5-yl)-3'-fluoro-N-[(3R)-2-oxopiperidin-3-yl]biphenyl-2-sulfonamide trifluoroacetic acid salt The title compound was prepared using analogous conditions to those described in Example 571 using 5-(2-fluoro-4-(4,4,5,5-tetramethyl-1,3,2-dioxaborolan-2-yl)phenyl)-pyrimidin-2-amine and (R)-2-bromo-N-(2-oxopiperidin-3-yl)benzenesulfonamide. MS (ESI): mass calcd. for $C_{21}H_{20}FN_5O_3S$, 441.13; m/z found, 442.1 [M+H]$^+$. $^1$H NMR (600 MHz, CD$_3$OD) δ 8.71 (d, J=0.7, 2H), 8.24 (dd, J=8.0, 1.2, 1H), 7.67 (m, 1H), 7.58 (m, 2H), 7.42 (s, 1H), 7.41-7.39 (m, 1H), 7.38 (dd, J=7.6, 1.2, 1H), 3.63 (dd, J=10.5, 5.8, 1H), 3.20 (dd, J=8.9, 5.1, 2H), 2.17 (m, 1H), 1.89-1.80 (m, 1H), 1.78-1.64 (m, 2H).

Example 267

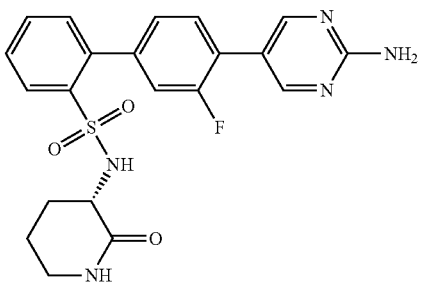

4'-(2-Aminopyrimidin-5-yl)-3'-fluoro-N-[(3S)-2-oxopiperidin-3-yl]biphenyl-2-sulfonamide trifluoroacetic acid salt The title compound was prepared using analogous conditions to those described in Example 571 using 5-(2-fluoro-4-(4,4,5,5-tetramethyl-1,3,2-dioxaborolan-2-yl)phenyl)-pyrimidin-2-amine and (S)-2-bromo-N-(2-oxopiperidin-3-yl)benzenesulfonamide. MS (ESI): mass calcd. for $C_{21}H_{20}FN_5O_3S$, 441.13; m/z found, 442.1 [M+H]$^+$. $^1$H NMR (600 MHz, CD$_3$OD) δ 8.74 (d, J=0.8, 2H), 8.24 (dd, J=8.0, 1.1, 1H), 7.67 (m, 1H), 7.62-7.54 (m, 2H), 7.42 (s, 1H), 7.42-7.40 (m, 1H), 7.38 (dd, J=7.6, 1.2, 1H), 3.64 (dd, J=10.5, 5.8, 1H), 3.20 (dd, J=8.7, 5.0, 2H), 2.17 (m, 1H), 1.89-1.80 (m, 1H), 1.80-1.65 (m, 2H).

Example 268

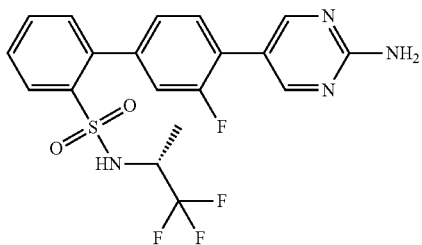

4'-(2-Aminopyrimidin-5-yl)-3'-fluoro-N-[(1R)-2,2,2-trifluoro-1-methylethyl]biphenyl-2-sulfonamide trifluoroacetic acid salt The title compound was prepared using analogous conditions to those described in Example 571 using 5-(2-fluoro-4-(4,4,5,5-tetramethyl-1,3,2-dioxaborolan-2-yl)phenyl)-pyrimidin-2-amine and (R)-2-bromo-N-(1,1,1-trifluoropropan-2-yl)benzenesulfonamide. MS (ESI): mass calcd. for $C_{19}H_{16}F_4N_4O_2S$, 440.09; m/z found, 441.0 [M+H]$^+$. $^1$H NMR (600 MHz, CD$_3$OD) δ 8.64 (d, J=0.9, 2H), 8.10 (dd, J=8.0, 1.1, 1H), 7.67 (m, 1H), 7.59 (m, 1H), 7.55 (m, 1H), 7.37 (dd, J=7.6, 1.2, 1H), 7.33-7.24 (m, 2H), 3.86 (m, 1H), 1.22 (m, 3H).

Example 269

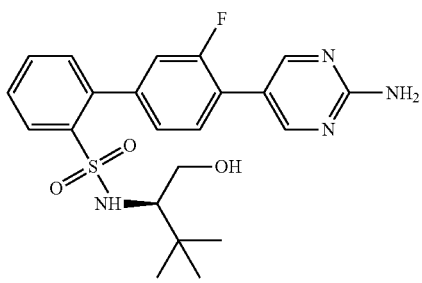

4'-(2-Aminopyrimidin-5-yl)-3'-fluoro-N-[(1R)-1-(hydroxymethyl)-2,2-dimethylpropyl]biphenyl-2-sulfonamide trifluoroacetic acid salt The title compound was prepared using analogous conditions to those described in Example 571 using 5-(2-fluoro-4-(4,4,5,5-tetramethyl-1,3,2-dioxaborolan-2-yl)phenyl)-pyrimidin-2-amine and (R)-2-bromo-N-(1-hydroxy-3,3-dimethylbutan-2-yl)benzenesulfonamide. MS (ESI): mass calcd. for $C_{22}H_{25}FN_4O_3S$, 444.16; m/z found, 445.2 [M+H]$^+$. $^1$H NMR (600 MHz, CD$_3$OD) δ 8.68 (d, J=1.0, 2H), 8.15 (dd, J=8.0, 1.1, 1H), 7.62 (m, 1H), 7.58-7.49 (m, 2H), 7.42-7.35 (m, 2H), 7.35-7.29 (m, 1H), 3.50 (m, 2H), 3.06 (dd, J=5.8, 4.3, 1H), 0.84 (s, 9H).

Example 270

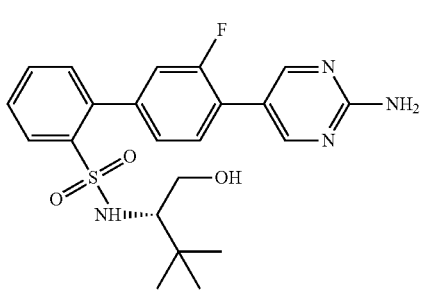

4'-(2-Aminopyrimidin-5-yl)-3'-fluoro-N-[(1S)-1-(hydroxymethyl)-2,2-dimethylpropyl]biphenyl-2-sulfonamide trifluoroacetic acid salt The title compound was prepared using analogous conditions to those described in Example 571 using 5-(2-fluoro-4-(4,4,5,5-tetramethyl-1,3,2-dioxaborolan-2-yl)phenyl)-pyrimidin-2-amine and (S)-2-bromo-N-(1-hydroxy-3,3-dimethylbutan-2-yl)benzenesulfonamide. MS (ESI): mass calcd. for $C_{22}H_{25}FN_4O_3S$, 444.16; m/z found, 445.2 [M+H]$^+$. $^1$H NMR (600 MHz, CD$_3$OD) δ 8.69 (d, J=1.0, 2H), 8.15 (dd, J=8.0, 1.1, 1H), 7.63 (m, 1H), 7.59-7.47 (m, 2H), 7.41-7.36 (m, 2H), 7.33 (m, 1H), 3.50 (m, 2H), 3.06 (dd, J=5.9, 4.2, 1H), 0.84 (s, 9H).

Example 271

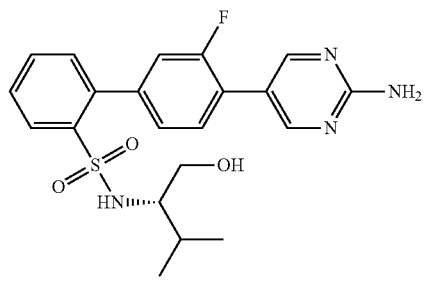

4'-(2-Aminopyrimidin-5-yl)-3'-fluoro-N-[(1S)-1-(hydroxymethyl)-2-methylpropyl]biphenyl-2-sulfonamide trifluoroacetic acid salt The title compound was prepared using analogous conditions to those described in Example 571 using 5-(2-fluoro-4-(4,4,5,5-tetramethyl-1,3,2-dioxaborolan-2-yl)phenyl)-pyrimidin-2-amine and (S)-2-bromo-N-(1-hydroxy-3-methylbutan-2-yl)benzenesulfonamide. MS (ESI): mass calcd. for $C_{21}H_{23}FN_4O_3S$, 430.15; m/z found, 431.1 [M+H]$^+$. $^1$H NMR (600 MHz, CD$_3$OD) δ 8.71 (d, J=0.9, 2H), 8.15 (dd, J=8.0, 1.1, 1H), 7.66-7.61 (m, 1H), 7.60-7.54 (m, 2H), 7.36 (m, 3H), 3.47-3.38 (m, 1H), 3.38-3.32 (m, 1H), 3.06 (q, J=5.5, 1H), 1.84 (m, 1H), 0.83-0.78 (m, 6H).

Example 272

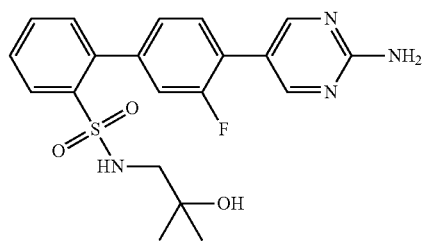

4'-(2-Aminopyrimidin-5-yl)-3'-fluoro-N-(2-hydroxy-2-methylpropyl)biphenyl-2-sulfonamide trifluoroacetic acid salt The title compound was prepared using analogous conditions to those described in Example 571 using 5-(2-fluoro-4-(4,4,5,5-tetramethyl-1,3,2-dioxaborolan-2-yl)phenyl)-pyrimidin-2-amine and 2-bromo-N-(2-hydroxy-2-methylpropyl)benzenesulfonamide. MS (ESI): mass calcd. for $C_{20}H_{21}FN_4O_3S$, 416.13; m/z found, 417.1 [M+H]$^4$. $^1$H NMR (600 MHz. CD$_3$OD) δ 8.75 (d, J=1.0 Hz, 2H), 8.04 (dd, J=8.0, 1.3 Hz, 1H), 7.70-7.65 (m, 1H), 7.64-7.58 (m, 2H), 7.41 (dd, J=7.6, 1.3 Hz, 1H), 7.39-7.35 (m, 2H), 2.71 (s, 2H), 1.11 (s, 6H).

Example 273

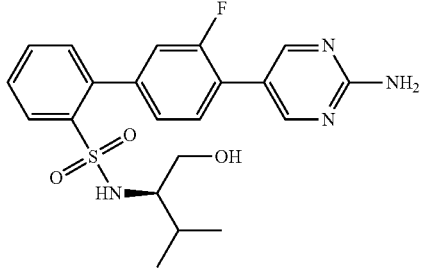

4'-(2-Aminopyrimidin-5-yl)-3'-fluoro-N-[(1R)-1-(hydroxymethyl)-2-methylpropyl]biphenyl-2-sulfonamide trifluoroacetic acid salt The title compound was prepared using analogous conditions to those described in Example 571 using 5-(2-fluoro-4-(4,4,5,5-tetramethyl-1,3,2-dioxaborolan-2-yl)phenyl)-pyrimidin-2-amine and (R)-2-bromo-N-(1-hydroxy-3-methylbutan-2-yl)benzenesulfonamide. MS (ESI): mass calcd. for $C_{21}H_{23}FN_4O_3S$, 430.15; m/z found, 431.1 [M+H]$^+$. $^1$H NMR (600 MHz, CD$_3$OD) δ 8.71 (d, J=0.9, 2H), 8.15 (dd, J=8.0, 1.1, 1H), 7.66-7.61 (m, 1H), 7.60-7.54 (m, 2H), 7.36 (m, 3H), 3.47-3.38 (m, 1H), 3.38-3.32 (m, 1H), 3.06 (q, J=5.5, 1H), 1.84 (m, 1H), 0.83-0.78 (m, 6H).

Example 274

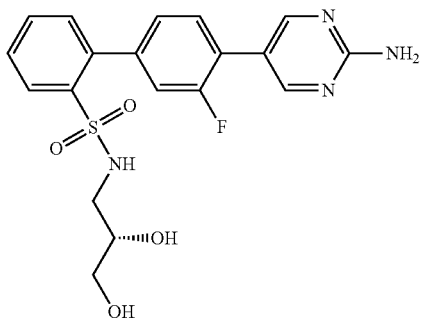

4'-(2-Aminopyrimidin-5-yl)-N-[(2S)-2,3-dihydroxypropyl]-3'-fluorobiphenyl-2-sulfonamide trifluoroacetic acid salt The title compound was prepared using analogous conditions to those described in Example 571 using 5-(2-fluoro-4-(4,4,5,5-tetramethyl-1,3,2-dioxaborolan-2-yl)phenyl)-pyrimidin-2-amine and (S)-2-bromo-N-(2,3-dihydroxypropyl)benzenesulfonamide. MS (ESI): mass calcd. for $C_{19}H_{19}FN_4O_4S$, 418.11; m/z found, 419.1 [M+H]$^+$.

Example 275

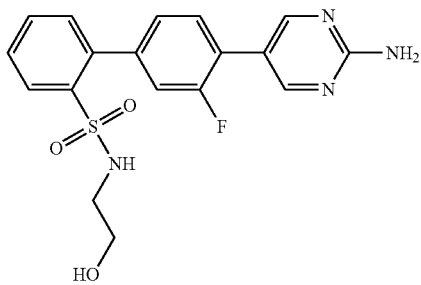

4'-(2-Aminopyrimidin-5-yl)-3'-fluoro-N-(2-hydroxyethyl)biphenyl-2-sulfonamide trifluoroacetic acid salt The title compound was prepared using analogous conditions to those described in Example 571 using 5-(2-fluoro-4-(4,4,5,5-tetramethyl-1,3,2-dioxaborolan-2-yl)phenyl)-pyrimidin-2-amine and 2-bromo-N-(2-hydroxyethyl)benzenesulfonamide. MS (ESI): mass calcd. for $C_{18}H_{17}FN_4O_3S$, 388.10; m/z found, 389.1 [M+H]$^+$. $^1$H NMR (600 MHz, CD$_3$OD) δ 8.75 (d, J=0.9, 2H), 8.07 (m, 1H), 7.71-7.66 (m, 1H), 7.63-7.59 (m, 2H), 7.40 (dd, J=7.6, 1.1, 1H), 7.37 (m, 2H), 3.49 (t, J=5.9, 2H), 2.90 (t, J=5.9, 2H).

Example 276

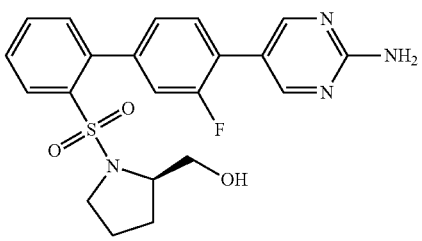

[(2R)-1-{[4'-(2-Aminopyrimidin-5-yl)-3'-fluorobiphenyl-2-yl]sulfonyl}pyrrolidin-2-yl]methanol trifluoroacetic acid salt The title compound was prepared using analogous conditions to those described in Example 571 using 5-(2-fluoro-4-(4,4,5,5-tetramethyl-1,3,2-dioxaborolan-2-yl)phenyl)-pyrimidin-2-amine and (R)-(1-((2-bromophenyl)sulfonyl)pyrrolidin-2-yl)methanol. MS (ESI): mass calcd. for $C_{21}H_{21}FN_4O_3S$, 428.13; m/z found, 429.1 [M+H]$^+$. $^1$H NMR (600 MHz, CD$_3$OD) G 8.70 (d, J=1.0, 2H), 8.10 (dd, J=8.0, 1.2, 1H), 7.70 (m, 1H), 7.64-7.61 (m, 1H), 7.59 (dd, J=10.9, 5.4, 1H), 7.41 (dd, J=7.6, 1.2, 1H), 7.37-7.32 (m, 2H), 3.50 (m, 1H), 3.37 (dd, J=10.8, 3.9, 1H), 3.21-3.15 (m, 1H), 3.03-2.95 (m, 2H), 1.88-1.75 (m, 3H), 1.73-1.66 (m, 1H).

Example 277

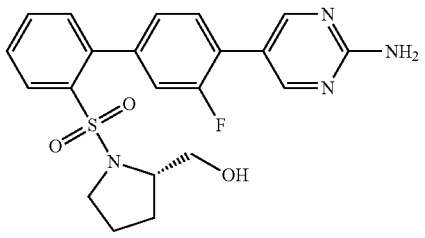

[(2S)-1-{[4'-(2-Aminopyrimidin-5-yl)-3'-fluorobiphenyl-2-yl]sulfonyl}pyrrolidin-2-yl]methanol trifluoroacetic acid salt The title compound was prepared using analogous conditions to those described in Example 571 using 5-(2-fluoro-4-(4,4,5,5-tetramethyl-1,3,2-dioxaborolan-2-yl)phenyl)pyrimidin-2-amine and (S)-(1-((2-bromophenyl)sulfonyl)pyrrolidin-2-yl)methanol. MS (ESI): mass calcd. for $C_{21}H_{21}FN_4O_3S$, 428.13; m/z found, 429.1 [M+H]$^+$. $^1$H NMR (600 MHz, CD$_3$OD) δ 8.70 (d, J=1.0, 2H), 8.10 (dd, J=8.0, 1.2, 1H), 7.70 (m, 1H), 7.64-7.61 (m, 1H), 7.59 (dd, J=10.9, 5.4, 1H), 7.41 (dd, J=7.6, 1.2, 1H), 7.37-7.32 (m, 2H), 3.50 (m, 1H), 3.37 (dd, J=10.8, 3.9, 1H), 3.21-3.15 (m, 1H), 3.03-2.95 (m, 2H), 1.88-1.75 (m, 3H), 1.73-1.66 (m, 1H).

Example 278

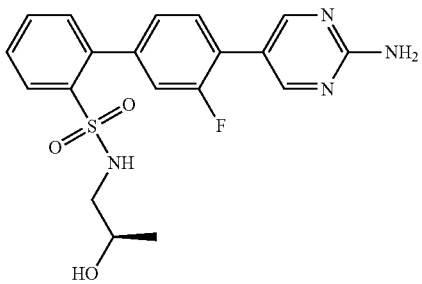

4'-(2-Aminopyrimidin-5-yl)-3'-fluoro-N-[(2R)-2-hydroxypropyl]biphenyl-2-sulfonamide-trifluoroacetic acid salt The title compound was prepared using analogous conditions to those described in Example 571 using 5-(2-fluoro-4-(4,4,5,5-tetramethyl-1,3,2-dioxaborolan-2-yl)phenyl)-pyrimidin-2-amine and (R)-2-bromo-N-(2-hydroxypropyl)benzenesulfonamide. MS (ESI): mass calcd. for $C_{19}H_{19}FN_4O_3S$, 402.12; m/z found, 403.1 [M+H]$^+$. $^1$H NMR (600 MHz, CD$_3$OD) δ 8.60 (d, J=1.2 Hz, 2H), 8.06 (dd, J=8.0, 1.3 Hz, 1H), 7.71-7.65 (m, 1H), 7.63-7.58 (m, 1H), 7.58-7.51 (m, 1H), 7.41 (dd, J=7.5, 1.4 Hz, 1H), 7.35 (s, 1H), 7.34-7.30 (m, 1H), 3.74-3.63 (m, 1H), 2.76 (dd, J=13.1, 5.0 Hz, 1H), 2.69 (dd, J=13.0, 6.8 Hz, 1H), 1.06 (d, J=6.3 Hz, 3H).

Example 279

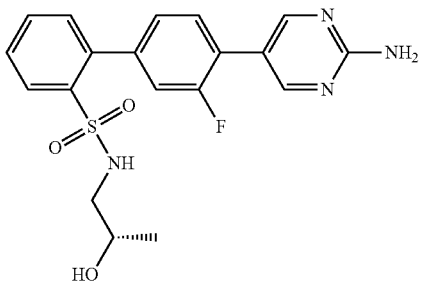

4'-(2-Aminopyrimidin-5-yl)-3'-fluoro-N-[(2S)-2-hydroxypropyl]biphenyl-2-sulfonamide trifluoroacetic acid salt The title compound was prepared using analogous conditions to those described in Example 571 using 5-(2-fluoro-4-(4,4,5,5-tetramethyl-1,3,2-dioxaborolan-2-yl)phenyl)-pyrimidin-2-amine and (S)-2-bromo-N-(2-hydroxypropyl)benzenesulfonamide. MS (ESI): mass calcd. for $C_{19}H_{19}FN_4O_3S$, 402.12; m/z found, 403.1 [M+H]$^+$. $^1$H NMR (600 MHz, CD$_3$OD) δ 8.60 (d, J=1.2 Hz, 2H), 8.06 (dd, J=8.0, 1.3 Hz, 1H), 7.71-7.65 (m, 1H), 7.63-7.58 (m, 1H), 7.58-7.51 (m, 1H), 7.41 (dd, J=7.5, 1.4 Hz, 1H), 7.35 (s, 1H), 7.34-7.30 (m, 1H), 3.74-3.63 (m, 1H), 2.76 (dd, J=13.1, 5.0 Hz, 1H), 2.69 (dd, J=13.0, 6.8 Hz, 1H), 1.06 (d, J=6.3 Hz, 3H)

Example 280

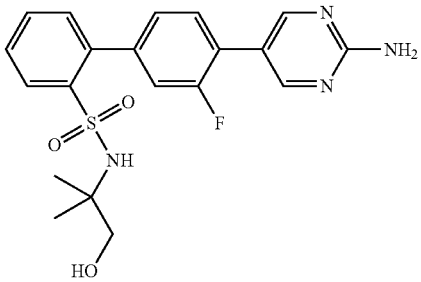

4'-(2-Aminopyrimidin-5-yl)-3'-fluoro-N-(2-hydroxy-1,1-dimethylethyl)biphenyl-2-sulfonamide-trifluoroacetic acid salt The title compound was prepared using analogous conditions to those described in Example 571 using 5-(2-fluoro-4-(4,4,5,5-tetramethyl-1,3,2-dioxaborolan-2-yl)phenyl)-pyrimidin-2-amine and 2-bromo-N-(1-hydroxy-2-methylpropan-2-yl)benzenesulfonamide. MS (ESI): mass calcd. for $C_{20}H_{21}FN_4O_3S$, 416.13; m/z found, 417.1 [M+H]$^+$. $^1$H NMR (600 MHz, CD$_3$OD) δ 8.69 (s, 2H), 8.16 (dd, J=8.0, 1.2, 1H), 7.66 (m, 1H), 7.61-7.55 (m, 2H), 7.38 (dd, J=7.8, 1.3, 3H), 3.27 (s, 2H), 1.03 (s, 6H).

Example 281

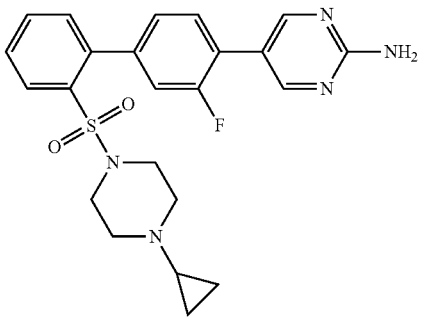

5-{2'-[(4-Cyclopropylpiperazin-1-yl)sulfonyl]-3-fluorobiphenyl-4-yl}pyrimidin-2-amine trifluoroacetic acid salt The title compound was prepared using analogous conditions to those described in Example 1 using 5-(2-fluoro-4-(4,4,5,5-tetramethyl-1,3,2-dioxaborolan-2-yl)phenyl)-pyrimidin-2-amine and 1-((2-bromophenyl)sulfonyl)-4-cyclopropylpiperazine. MS (ESI): mass calcd. for $C_{23}H_{24}FN_5O_2S$, 453.16; m/z found, 454.1 [M+H]$^+$. $^1$H NMR (600 MHz, CD$_3$OD) δ 8.75 (d, J=0.6, 2H), 8.13 (dd, J=8.0, 1.2, 1H), 7.79-7.74 (m, 1H), 7.69-7.59 (m, 2H), 7.45 (dd, J=7.6, 1.2, 1H), 7.37-7.32 (m, 2H), 3.59-3.33 (m, 4H), 3.28-3.00 (m, 4H), 2.82 (m, 1H), 1.00-0.86 (m, 4H).

Example 282

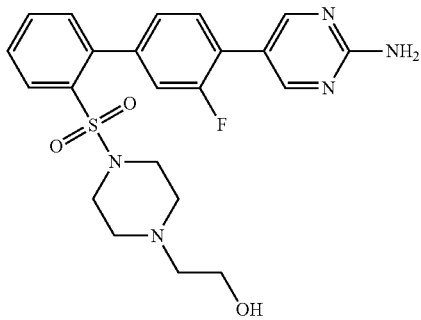

2-(4-{[4'-(2-Aminopyrimidin-5-yl)-3'-fluorobiphenyl-2-yl]sulfonyl}piperazin-1-yl)ethanol trifluoroacetic acid salt The title compound was prepared using analogous conditions to those described in Example 1 using 5-(2-fluoro-4-(4,4,5,5-tetramethyl-1,3,2-dioxaborolan-2-yl)phenyl)-pyrimidin-2-amine and 2-(4-((2-bromophenyl)sulfonyl)piperazin-1-yl)ethanol. MS (ESI): mass calcd. for $C_{22}H_{24}FN_5O_3S$, 457.16; m/z found, 458.1 [M+H]$^+$. $^1$H NMR (600 MHz, CD$_3$OD) δ 8.72 (s, 2H), 8.13 (dd, J=8.0, 1.2, 1H), 7.77 (m, 1H), 7.71-7.59 (m, 2H), 7.46 (dd, J=7.6, 1.2, 1H), 7.39-7.33 (m, 2H), 3.85-3.80 (m, 2H), 3.68-3.33 (m, 4H), 3.26-3.22 (m, 2H), 3.17-2.81 (m, 4H).

Example 283

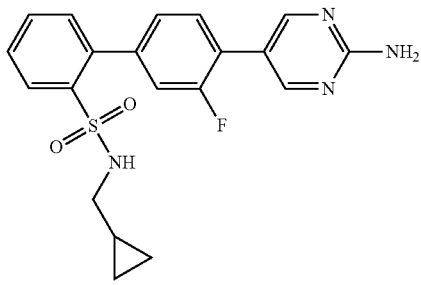

4'-(2-Aminopyrimidin-5-yl)-N-(cyclopropylmethyl)-3'-fluorobiphenyl-2-sulfonamide trifluoroacetic acid The title compound was prepared using analogous conditions to those described in Example 571 using 5-(2-fluoro-4-(4,4,5,5-tetramethyl-1,3,2-dioxaborolan-2-yl)phenyl)-pyrimidin-2-amine and 2-bromo-N-(cyclopropylmethyl)benzenesulfonamide. MS (ESI): mass calcd. for $C_{20}H_{19}FN_4O_2S$, 398.12; m/z found, 399.1 [M+H]$^+$. $^1$H NMR (500 MHz, CD$_3$OD) δ 8.67 (d, J=8.0, 1.4 Hz, 1H), 7.70-7.65 (m, 1H), 7.65-7.53 (m, 2H), 7.39-7.35 (m, 1H), 7.31-7.25 (m, 2H), 1.22 (s, 3H), 0.52-0.48 (m, 2H), 0.38-0.33 (m, 2H).

Example 284

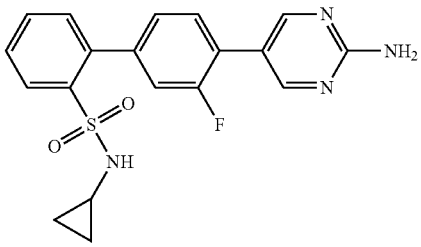

4'-(2-Aminopyrimidin-5-yl)-N-cyclopropyl-3'-fluorobiphenyl-2-sulfonamide trifluoroacetic acid salt The title compound was prepared using analogous conditions to those described in Example 571 using 5-(2-fluoro-4-(4,4,5,5-tetramethyl-1,3,2-dioxaborolan-2-yl)phenyl)-pyrimidin-2-amine and 2-bromo-N-cyclopropylbenzenesulfonamide. MS (ESI): mass calcd. for $C_{19}H_{17}FN_4O_2S$, 384.10; m/z found, 385.1 [M+H]$^+$. $^1$H NMR (500 MHz, CD$_3$OD) δ 8.68 (d, J=1.0, 2H), 8.11 (dd, J=8.0, 1.2, 1H), 7.69 (m, 1H), 7.62 (m, 1H), 7.56 (m, 1H), 7.40 (dd, J=7.6, 1.2, 1H), 7.35-7.22 (m, 2H), 2.20 (m, 1H), 0.55-0.34 (m, 4H).

Example 285

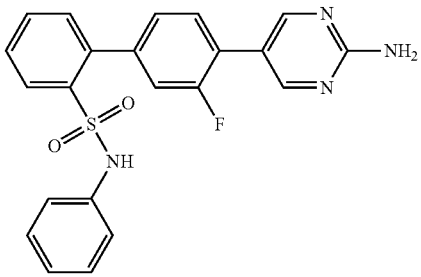

4'-(2-Aminopyrimidin-5-yl)-3'-fluoro-N-phenylbiphenyl-2-sulfonamide trifluoroacetic acid salt The title compound was prepared using analogous conditions to those described in Example 1 using 5-(2-fluoro-4-(4,4,5,5-tetramethyl-1,3,2-dioxaborolan-2-yl)phenyl)-pyrimidin-2-amine and 2-bromo-N-phenylbenzenesulfonamide. MS (ESI): mass calcd. for $C_{22}H_{17}FN_4O_2S$, 420.10; m/z found, 421.1 [M+H]$^+$. $^1$H NMR (500 MHz, CD$_3$OD) δ 8.66 (s, 1H), 8.14 (d, J=7.8, 1H), 7.57 (m, 3H), 7.33 (m, 2H), 7.12 (m, 4H), 7.02-6.75 (m, 3H).

Example 286

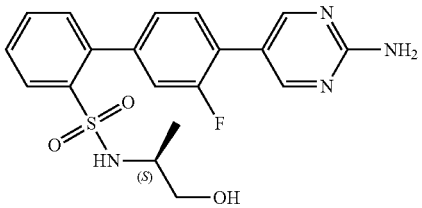

4'-(2-Aminopyrimidin-5-yl)-3'-fluoro-N-[(1S)-2-hydroxy-1-methylethyl]biphenyl-2-sulfonamide trifluoroacetic acid salt The title compound was prepared using analogous conditions to those described in Example 1 using 5-(2-fluoro-4-(4,4,5,5-tetramethyl-1,3,2-dioxaborolan-2-yl)phenyl)-pyrimidin-2-amine and (S)-2-bromo-N-(1-hydroxypropan-2-yl)benzenesulfonamide. MS (ESI): mass calcd. for $C_{19}H_{19}FN_4O_3S$, 402.11; m/z found, 403.1 [M+H]$^+$. $^1$H NMR (500 MHz, CD$_3$OD) δ 8.59 (d, J=1.3, 2H), 8.07 (dd, J=7.9, 1.4, 1H), 7.68 (td, J=7.5, 1.4, 1H), 7.65-7.58 (m, 2H), 7.39 (dd, J=7.5, 1.4, 1H), 7.35 (dd, J=11.8, 1.8, 1H), 7.29 (dd, J=7.9, 1.8, 1H), 7.25 (d, J=7.5, 1H), 3.30 (dd, J=10.3, 4.9, 1H), 3.14-3.09 (m, 1H), 3.09-3.01 (m, 1H), 0.96 (d. J=6.5, 3H).

Example 287

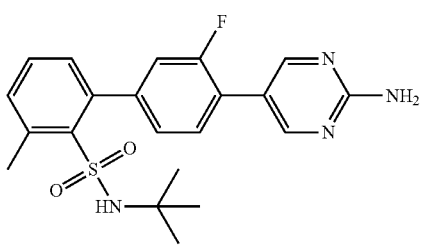

4'-(2-Aminopyrimidin-5-yl)-N-tert-butyl-3'-fluoro-3-methylbiphenyl-2-sulfonamide trifluoroacetic acid salt To a 6 mL microwave vial the following were added 5-(2-fluoro-4-(4,4,5,5-tetramethyl-1,3,2-dioxaborolan-2-yl)phenyl)pyrimidin-2-amine (60 mg, 0.19 mmol), N-(tert-butyl)-2-chloro-6-methylbenzenesulfonamide (62 mg, 0.24 mmol), and chloro(2-dicyclohexylphosphino-2',4',6'-triisopropyl-1-1'-biphenyl)[2-(2'-amino-1,1'-biphenyl)]palladium (II) (3 mg, 0.004 mmol). The vial was flushed with nitrogen and charged with N$_2$ sparged THF (0.3 mL) and N$_2$ sparged K$_3$PO$_4$ (0.8 mL, 0.5 M). The resulting biphasic mixture was stirred at rt for 1 h and at 45° C. for 1 h. The resulting mixture was concentrated to dryness and the resulting residue was purified by HPLC to provide the title compound. MS (ESI): mass calcd. for $C_{21}H_{23}FN_4O_2S$, 414.15: m/z found, 415.1 [M+H]$^+$.

Example 288

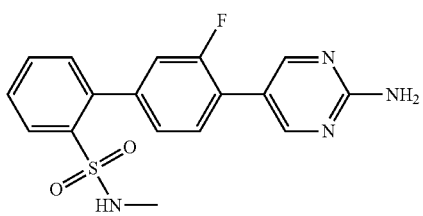

4'-(2-Aminopyrimidin-5-yl)-3'-fluoro-N-methylbiphenyl-2-sulfonamide trifluoroacetic acid salt The title compound was prepared using analogous conditions to those described in Example 1 using 5-(2-fluoro-4-(4,4,5,5-tetramethyl-1,3,2-dioxaborolan-2-yl)phenyl)-pyrimidin-2-amine and 2-bromo-N-methylbenzenesulfonamide. MS (ESI): mass calcd. for $C_{17}H_{15}FN_4O_2S$, 358.09; m/z found, 359.1 [M+H]$^+$. $^1$H NMR (500 MHz, DMSO-d$_6$) δ 8.59 (s, 2H), 7.93 (dd, J=7.8, 1.4, 1H), 7.70 (td, J=7.5, 1.4, 1H), 7.67-7.58 (m, 2H), 7.42 (dd, J=7.5, 1.5, 1H), 7.34 (dd, J=11.8, 1.8, 1H), 7.31-7.26 (m, 4H), 2.41 (d, J=4.8, 3H).

Example 289

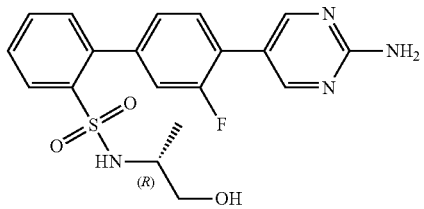

4'-(2-Aminopyrimidin-5-yl)-3'-fluoro-N-[(1R)-2-hydroxy-1-methylethyl]biphenyl-2-sulfonamide Method 1

The title compound was prepared using analogous conditions to those described in Example 1 using 5-(2-fluoro-4-(4,4,5,5-tetramethyl-1,3,2-dioxaborolan-2-yl)phenyl)-pyrimidin-2-amine and (R)-2-bromo-N-(1-hydroxypropan-2-yl)benzenesulfonamide.

Method 2

A mixture of 5-(2-fluoro-4-(4,4,5,5-tetramethyl-1,3,2-dioxaborolan-2-yl)phenyl)-pyrazin-2-amine (30.0 g, 95.2 mmol), K$_3$PO$_4$ (70.7 g, 333 mmol), (R)-2-bromo-N-(1-hydroxypropan-2-yl)benzenesulfonamide (28.0 g, 95.2 mmol), PdCl$_2$(dppf).CH$_2$Cl$_2$ (0.70 g, 0.95 mmol), acetonitrile (476 mL), and water (190 mL) was sparged with N$_2$ and stirred at 75° Celsius for 26 hours. After filtration, water was added and the reaction mixture was cooled to rt. Solid precipitate was collected by vacuum filtration and dried in a vacuum oven at 70° Celsius (24.0 g, 63%). The solid was recrystallized from EtOH and treated successively with activated charcoal and silica-supported thiol to remove residual Pd and afford the title compound (21.6 g, 57%). MS (ESI): mass calcd. for $C_{19}H_{19}FN_4O_3S$, 402.12; m/z found, 403.1 [M+H]$^+$. $^1$H NMR (500 MHz, DMSO-d$_6$) δ 8.52 (d, J=1.4, 2H), 8.12-7.99 (m, 1H), 7.73-7.65 (m, 1H), 7.65-7.53 (m, 2H), 7.39 (dd, J=7.5, 1.4, 1H), 7.36-7.31 (m, 1H), 7.28 (dd, J=7.9, 1.8, 1H), 7.23 (d, J=7.5, 1H), 6.92 (s, 2H), 4.75-4.67 (m, 1H), 3.33-3.27 (m, 1H), 3.16-3.01 (m, 2H), 0.96 (d, J=6.4, 3H). Chiral HPLC: Chiralpak IC 4.6×250 mm column, 30% EtOH+0.2% TEA, 70% CO$_2$, 2 mL/min, retention time 22.4 min, ee>99%.

Example 290

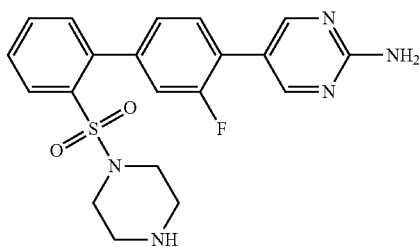

5-[3-Fluoro-2'-(piperazin-1-ylsulfonyl)biphenyl-4-yl]pyrimidin-2-amine trifluoroacetic acid salt The title compound was prepared using analogous conditions to those described in Example 1 using 5-(2-fluoro-4-(4,4,5,5-tetramethyl-1,3,2-dioxaborolan-2-yl)phenyl)-pyrimidin-2-amine and 1-((2-bromophenyl)sulfonyl)piperazine. MS (ESI): mass calcd. for $C_{20}H_{20}FN_5O_2S$, 413.13; m/z found, 414.1 [M+H]$^+$. $^1$H NMR (600 MHz, DMSO-d$_6$) δ 8.63 (s, 2H), 8.54 (d, J=1.0, 2H), 8.08-8.04 (m, 1H), 7.81 (m, 1H), 7.74-7.68 (m, 1H), 7.61 (m, 1H), 7.50 (d, J=7.6, 1H), 7.36 (dd, J=11.6, 1.5, 1H), 7.29 (dd, J=7.9, 1.7, 1H), 7.05 (s, 2H), 3.04-2.86 (m, 8H).

Example 291

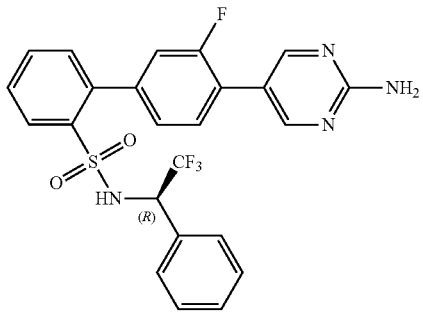

4'-(2-Aminopyrimidin-5-yl)-3'-fluoro-N-[(1R)-2,2,2-trifluoro-1-phenylethyl]biphenyl-2-sulfonamide trifluoroacetic acid salt The title compound was prepared using analogous conditions to those described in Example 1 using 5-(2-fluoro-4-(4,4,5,5-tetramethyl-1,3,2-dioxaborolan-2-yl)phenyl)-pyrimidin-2-amine and (R)-2-bromo-N-(2,2,2-trifluoro-1-phenylethyl)benzenesulfonamide. MS (ESI): mass calcd. for $C_{24}H_{18}F_4N_4O_2S$, 502.11; m/z found, 503.1 [M+H]$^+$. $^1$H NMR (600 MHz, DMSO-d$_6$) δ 9.28 (d, J=10.1, 1H), 8.54 (d, J=1.2, 2H), 7.88 (dd, J=8.1, 1.1, 1H), 7.59 (m, 1H), 7.53 (t, J=8.3, 1H), 7.46-7.40 (m, 3H), 7.41-7.30 (m, 3H), 7.27 (dd, J=7.6, 1.2, 1H), 7.12-6.97 (m, 4H), 5.14-4.96 (m, 1H).

Example 292

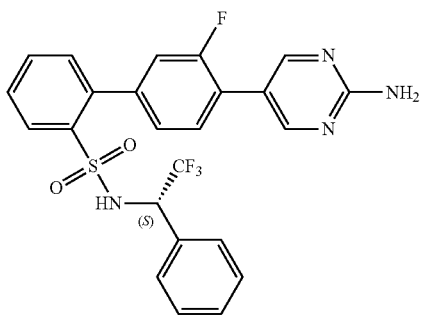

4'-(2-Aminopyrimidin-5-yl)-3'-fluoro-N-[(1S)-2,2,2-trifluoro-1-phenylethyl]biphenyl-2-sulfonamide trifluoroacetic acid salt The title compound was prepared using analogous conditions to those described in Example 1 using 5-(2-fluoro-4-(4,4,5,5-tetramethyl-1,3,2-dioxaborolan-2-yl)phenyl)-pyrimidin-2-amine and (S)-2-bromo-N-(2,2,2-trifluoro-1-phenylethyl)benzenesulfonamide. MS (ESI): mass calcd. for $C_{24}H_{18}F_4N_4O_2S$, 502.11; m/z found, 503.1 [M+H]$^+$. $^1$H NMR (600 MHz, DMSO-d) δ 9.29 (d, J=10.1, 1H), 8.59 (s, 2H), 7.88 (dd, J=8.0, 1.0, 1H), 7.60 (m, 1H), 7.54 (t, J=8.2, 1H), 7.47-7.42 (m, 3H), 7.38-7.31 (m, 3H), 7.27 (dd, J=7.6, 1.0, 1H), 7.11-7.04 (m, 2H), 5.11-5.03 (m, 1H).

Example 293

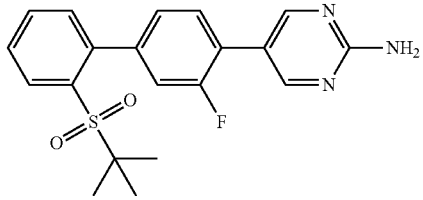

5-[2'-(tert-Butylsulfonyl)-3-fluorobiphenyl-4-yl]pyrimidin-2-amine trifluoroacetic acid salt The title compound was prepared using analogous conditions to those described in Example 1 using 5-(2-fluoro-4-(4,4,5,5-tetramethyl-1,3,2-dioxaborolan-2-yl)phenyl)-pyrimidin-2-amine and 1-bromo-2-(tert-butylsulfonyl)benzene. MS (ESI): mass calcd. for $C_{20}H_{20}FN_3O_2S$, 385.12; m/z found, 386.1 [M+H]$^+$. $^1$H NMR (600 MHz, DMSO-d$_6$) δ 8.57 (d, J=0.8, 2H), 8.03 (dd, J=8.0, 1.2, 1H), 7.81 (m, 1H), 7.72 (m, 1H), 7.56 (m, 1H), 7.41 (dd, J=7.6, 1.2, 1H), 7.32 (dd, J=11.9, 1.6, 1H), 7.25 (dd, J=7.9, 1.7, 1H), 7.14 (s, 2H), 1.08 (s, 9H).

Example 294

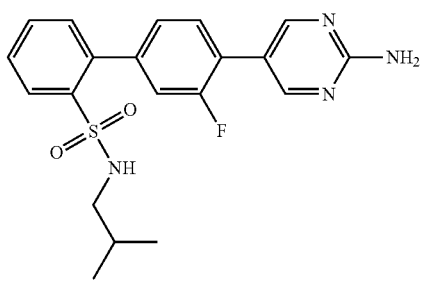

4'-(2-Aminopyrimidin-5-yl)-3'-fluoro-N-(2-methylpropyl)biphenyl-2-sulfonamide trifluoroacetic acid salt The title compound was prepared using analogous conditions to those described in Example 1 using 5-(2-fluoro-4-(4,4,5,5-tetramethyl-1,3,2-dioxaborolan-2-yl)phenyl)-pyrimidin-2-amine and 2-bromo-N-isobutylbenzenesulfonamide. MS (ESI): mass calcd. for $C_{20}H_{21}FN_4O_2S$, 400.14; m/z found, 401.1 [M+H]$^+$. $^1$H NMR (600 MHz, DMSO-d$_6$) δ 8.53 (s, 2H), 7.94 (dd, J=7.9, 1.0, 1H), 7.68 (m, 1H), 7.65-7.57 (m, 2H), 7.52 (m, 1H), 7.41 (dd, J=7.5, 1.1, 1H), 7.33 (dd, J=11.8, 1.4, 1H), 7.29 (dd, J=7.9, 1.6, 1H), 7.03 (s, 2H), 2.53 (t, J=6.4, 2H), 1.60 (m, 1H), 0.79 (d, J=6.7, 6H).

Example 295

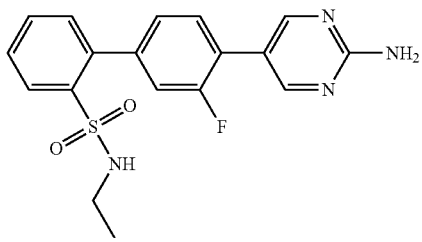

4′-(2-Aminopyrimidin-5-yl)-N-ethyl-3′-fluorobiphenyl-2-sulfonamide trifluoroacetic acid salt The title compound was prepared using analogous conditions to those described in Example 1 using 5-(2-fluoro-4-(4,4,5,5-tetramethyl-1,3,2-dioxaborolan-2-yl)phenyl)-pyrimidin-2-amine and 2-bromo-N-ethylbenzenesulfonamide. MS (ESI): mass calcd. for $C_{18}H_{17}FN_4O_2S$, 372.11; m/z found, 373.1 $[M+H]^+$. $^1H$ NMR (600 MHz, DMSO-$d_6$) δ 8.57 (d, J=1.3, 2H), 7.96 (dd, J=7.9, 1.4, 1H), 7.69 (td, J=7.5, 1.4, 1H), 7.66-7.58 (m, 2H), 7.44-7.40 (m, 2H), 7.34 (dd, J=11.8, 1.8, 1H), 7.29 (dd, J=7.9, 1.7, 1H), 7.18 (s, 2H), 2.77 (qd, J=7.2, 5.6, 2H), 0.97 (t. J=7.2, 3H).

Example 296

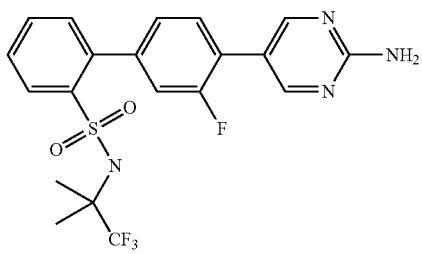

4′-(2-Aminopyrimidin-5-yl)-3′-fluoro-N-(2,2,2-trifluoro-1,1-dimethylethyl)biphenyl-2-sulfonamide trifluoroacetic acid salt The title compound was prepared using analogous conditions to those described in Example 1 using 5-(2-fluoro-4-(4,4,5,5-tetramethyl-1,3,2-dioxaborolan-2-yl)phenyl)-pyrimidin-2-amine and 2-bromo-N-(1,1,1-trifluoro-2-methylpropan-2-yl)benzenesulfonamide. MS (ESI): mass calcd. for $C_{20}H_{18}F_4N_4O_2S$, 454.11; m/z found, 455.1 $[M+H]^+$. $^1H$ NMR (500 MHz, CD$_3$OD) δ 8.65 (s, 2H), 8.12 (dd, J=8.0, 1.1, 1H), 7.67 (m, 1H), 7.60 (m, 1H), 7.55 (m, 1H), 7.39 (dd, J=7.5, 1.2, 1H), 7.32 (dd, J=6.0, 4.7, 2H), 1.29 (s, 6H).

Example 297

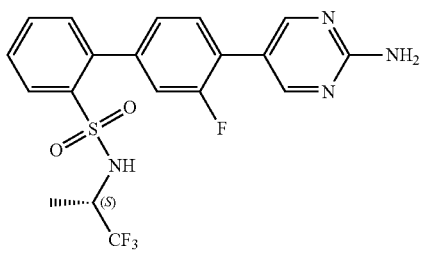

4′-(2-Aminopyrimidin-5-yl)-3′-fluoro-N-[(1S)-2,2,2-trifluoro-1-methylethyl]biphenyl-2-sulfonamide trifluoroacetic acid salt The title compound was prepared using analogous conditions to those described in Example 1 using 5-(2-fluoro-4-(4,4,5,5-tetramethyl-1,3,2-dioxaborolan-2-yl)phenyl)-pyrimidin-2-amine and (S)-2-bromo-N-(1,1,1-trifluoropropan-2-yl)benzenesulfonamide. MS (ESI): mass calcd. for $C_{19}H_{16}F_4N_4O_2S$, 440.09; m/z found, 441.0 $[M+H]^+$. $^1H$ NMR (500 MHz, CD$_3$OD) δ 8.71 (s, 2H), 8.10 (d, J=7.9, 1H), 7.68 (m, 1H), 7.63-7.53 (m, 2H), 7.40-7.34 (m, 1H), 7.33-7.26 (m, 2H), 3.87 (m, 1H), 1.23 (d, J=7.0, 3H).

Example 298

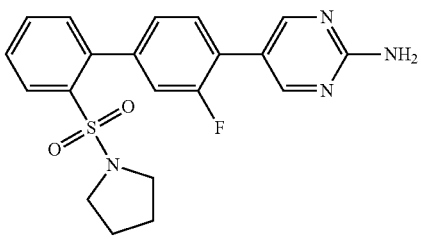

5-[3-Fluoro-2′-(pyrolidin-1-ylsulfonyl)biphenyl-4-yl]pyrimidin-2-amine trifluoroacetic acid salt The title compound was prepared using analogous conditions to those described in Example 287 using 5-(4-chloro-2-fluorophenyl)pyrimidin-2-amine and (2-(pyrrolidin-1-ylsulfonyl)phenyl)boronic acid. MS (ESI): mass calcd. for $C_{20}H_{19}FN_4O_2S$, 398.12; m/z found, 399.1 $[M+H]^+$. $^1H$ NMR (500 MHz, DMSO-$d_6$) δ 8.54 (d. J=1.2, 2H), 7.98 (dd, J=7.9, 1.1, 1H), 7.73 (m, 1H), 7.67-7.59 (m, 2H), 7.43 (dd, J=7.5, 1.1, 1H), 7.34 (dd, J=11.8, 1.6, 1H), 7.28 (dd. J=7.9, 1.7, 1H), 7.05 (s, 2H), 2.88 (t, J=6.7, 4H), 1.76-1.60 (m, 4H).

Example 299

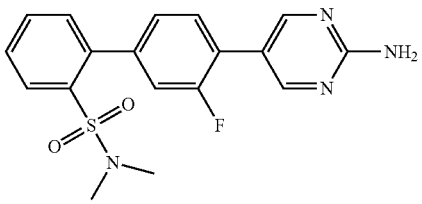

4′-(2-Aminopyrimidin-5-yl)-3′-fluoro-N,N-dimethylbiphenyl-2-sulfonamide trifluoroacetic acid salt The title compound was prepared using analogous conditions to those described in Example 287 using 5-(4-chloro-2-fluorophenyl)pyrimidin-2-amine and (2-(N,N-dimethylsulfamoyl)phenyl)boronic acid MS (ESI): mass calcd. for $C_{18}H_{17}FN_4O_2S$, 372.10; m/z found, 373.1 $[M+H]^+$. $^1H$ NMR (500 MHz, DMSO-$d_6$) δ 8.56 (d, J=1.1, 2H), 7.95 (dd, J=7.9, 1.2, 1H), 7.73 (m, 1H), 7.66 (m, 1H), 7.61 (m, 1H), 7.43 (dd, J=7.5, 1.2, 1H), 7.32 (dd, J=11.8, 1.6, 1H), 7.26 (dd, J=7.9, 1.7, 1H), 2.50 (s, 6H).

Example 300

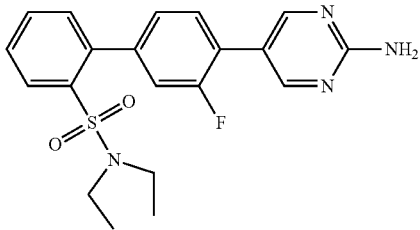

4'-(2-Aminopyrimidin-5-yl)-N,N-diethyl-3'-fluorobiphenyl-2-sulfonamide trifluoroacetic acid salt The title compound was prepared using analogous conditions to those described in Example 287 using 5-(4-chloro-2-fluorophenyl)pyrimidin-2-amine and (2-(N,N-diethyl-sulfamoyl)phenyl)boronic acid. MS (ESI): mass calcd. for $C_{20}H_{21}FN_4O_2S$, 400.14; m/z found, 401.1 [M+H]$^+$. $^1$H NMR (500 MHz, DMSO-d$_6$) δ 8.54 (d, J=1.3, 2H), 7.96 (dd, J=8.0, 1.2, 1H), 7.71 (m, 1H), 7.63 (m, 2H), 7.41 (dd, J=7.5, 1.2, 1H), 7.30 (m, 1H), 7.26 (m, 1H), 7.04 (s, 2H), 2.93 (q, J=7.1, 4H), 0.94 (t, J=7.1, 6H).

Example 301

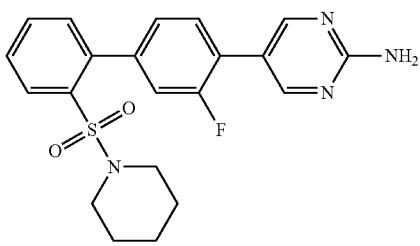

5-[3-Fluoro-2'-(piperidin-1-ylsulfonyl)biphenyl-4-yl]pyrimidin-2-amine trifluoroacetic acid salt The title compound was prepared using analogous conditions to those described in Example 287 using 5-(4-chloro-2-fluorophenyl)pyrimidin-2-amine and (2-(piperidin-1-ylsulfonyl)phenyl)boronic acid. MS (ESI): mass calcd. for $C_{21}H_{21}FN_4O_2S$, 412.14; m/z found, 413.1 [M+H]$^+$. $^1$H NMR (500 MHz, DMSO-d$_6$) δ 8.54 (d, J=1.2, 2H), 7.99 (dd, J=8.0, 1.2, 1H), 7.73 (m, 1H), 7.69-7.57 (m, 2H), 7.44 (dd, J=7.6, 1.2, 1H), 7.33 (m, 1H), 7.27 (dd, J=7.9, 1.7, 1H), 7.05 (s, 2H), 2.84-2.74 (m, 4H), 1.43-1.25 (m, 6H).

Example 302

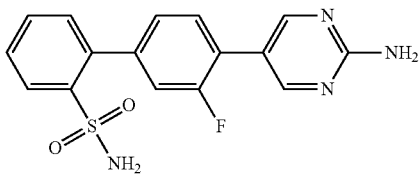

4'-(2-Aminopyrimidin-5-yl)-3'-fluorobiphenyl-2-sulfonamide trifluoroacetic acid salt Trifluoroacetic acid (1 mL) was added to neat 4'-(2-aminopyrimidin-5-yl)-N-(tert-butyl)-3'-fluoro-[1,1'-biphenyl]-2-sulfonamide (52 mg, 0.13 mmol). After 4 hours, the resulting solution was concentrated to dryness and purified by HPLC to provide the title compound (33 mg, 59%) as a clear glassy solid. MS (ESI): mass calcd. for $C_{16}H_{13}FN_4O_2S$, 344.07; m/z found, 345.0 [M+H]$^+$. $^1$H NMR (500 MHz, DMSO-d$_6$) δ 8.54 (d, J=1.3, 2H), 8.05 (dd, J=7.8, 1.4, 1H), 7.70-7.56 (m, 3H), 7.40-7.28 (m, 5H), 7.03 (s, 2H).

Example 303

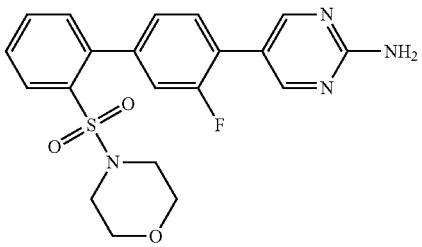

5-[3-Fluoro-2'-(morpholin-4-ylsulfonyl)biphenyl-4-yl]pyrimidin-2-amine trifluoroacetic acid salt The title compound was prepared using analogous conditions to those described in Example 287 using 5-(4-chloro-2-fluorophenyl)pyrimidin-2-amine and (2-(morpholino-sulfonyl)phenyl)boronic acid. MS (ESI): mass calcd. for $C_{20}H_{19}FN_4O_3S$, 414.12; m/z found, 415.1 [M+H]$^+$. $^1$H NMR (500 MHz, DMSO-d$_6$) δ 8.56 (d, J=1.3, 2H), 8.02 (dd, J=8.0, 1.2, 1H), 7.77 (m, 1H), 7.68 (m, 1H), 7.62 (m, 1H), 7.46 (dd, J=7.6, 1.2, 1H), 7.38 (dd, J=11.8, 1.6, 1H), 7.31 (dd, J=7.9, 1.7, 1H), 3.46-3.37 (m, 4H), 2.83-2.73 (m, 4H).

Example 304

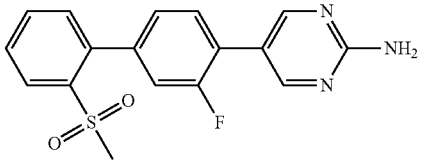

5-[3-Fluoro-2'-(methylsulfonyl)biphenyl-4-yl]pyrimidin-2-amine sulfonamide trifluoroacetic acid salt The title compound was prepared using analogous conditions to those described in Example 287 using 5-(4-chloro-2-fluorophenyl)pyrimidin-2-amine and (2-(methyl-sulfonyl)phenyl)boronic acid. MS (ESI): mass calcd. for $C_{17}H_{14}FN_3O_2S$, 343.08; m/z found, 344.1 [M+H]$^+$. $^1$H NMR (500 MHz, DMSO-d$_6$) δ 8.57 (d, J=1.3, 2H), 8.12 (dd, J=8.0, 1.2, 1H), 7.80 (m, 1H), 7.72 (m, 1H), 7.65 (m, 1H), 7.46 (dd, J=7.5, 1.2, 1H), 7.40 (dd, J=11.7, 1.7, 1H), 7.33 (dd, J=7.9, 1.7, 1H), 2.96 (s, 3H).

Example 305

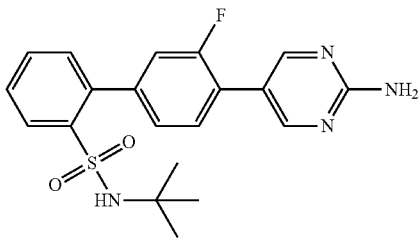

4'-(2-Aminopyrimidin-5-yl)N-(tert-butyl)-3'-fluoro-
[1,1'-biphenyl]-2-sulfonamide trifluoroacetic acid salt The title compound was prepared using analogous conditions to those described in Example 287 using 5-(4-chloro-2-fluorophenyl)pyrimidin-2-amine and (2-(N-(tert-butyl)sulfamoyl)phenyl)boronic acid. MS (ESI): mass calcd. for $C_{20}H_{21}FN_4O_2S$, 400.14; m/z found, 401.1 [M+H]$^+$. $^1$H NMR (500 MHz, DMSO-$d_6$) δ 8.55 (s, 2H), 8.06 (dd, J=7.9, 1.3, 1H), 7.66 (m, 1H), 7.63-7.57 (m, 2H), 7.38 (dd, J=7.5, 1.2, 1H), 7.33 (dd, J=11.9, 1.5, 1H), 7.28 (dd, J=7.9, 1.6, 1H), 6.99-6.88 (m, 1H), 1.03 (s, 9H).

Example 306

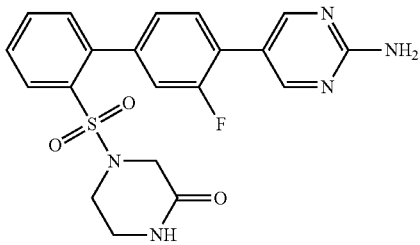

4-{[4'-(2-Aminopyrimidin-5-yl)-3'-fluorophenyl-2-yl]sulfonyl}piperazin-2-one trifluoroacetic acid salt The title compound was prepared using analogous conditions to those described in Example 571 using 5-(2-fluoro-4-(4,4,5,5-tetramethyl-1,3,2-dioxaborolan-2-yl)phenyl)-pyrimidin-2-amine and 4-((2-bromophenyl)sulfonyl)piperazin-2-one. MS (ESI): mass calcd. for $C_{20}H_{18}FN_5O_3S$, 427.11; m/z found, 428.1 [M+H]$^+$. $^1$H NMR (500 MHz, CD$_3$OD) δ 7.22 (d, J=0.7, 2H), 6.61 (m, 1H), 6.22 (m, 1H), 6.12 (m, 1H), 6.07 (dd, J=11.3, 4.9, 1H), 5.92 (dd, J=7.6, 1.2, 1H), 5.82 (t, J=1.8, 1H), 5.80 (dd, J=5.4, 1.4, 1H), 1.81 (s, 2H), 1.63 (m, 4H).

Example 307

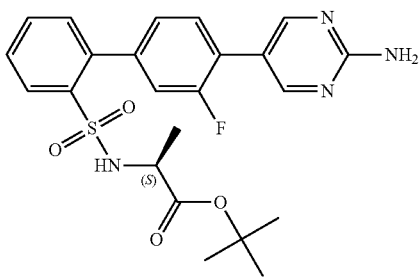

tert-Butyl N-{[4'-(2-aminopyrimidin-5-yl)-3'-fluorobiphenyl-2-yl]sulfonyl}-L-alaninate The title compound was prepared using analogous conditions to those described in Example 571 using 5-(2-fluoro-4-(4,4,5,5-tetramethyl-1,3,2-dioxaborolan-2-yl)phenyl)pyrimidin-2-amine and (S)-tert-butyl 2-(2-bromophenylsulfonamido)propanoate. MS (ESI): mass calcd. for $C_{23}H_{25}FN_4O_4S$, 472.16; m/z found, 473.1 [M+H]$^+$. $^1$H NMR (500 MHz, CD$_3$OD) δ 8.65 (d, J=1.1, 2H), 8.08 (dd, J=8.0, 1.2, 1H), 7.66 (m, 1H), 7.61-7.49 (m, 2H), 7.37 (m, 3H), 3.66 (q, J=7.2, 1H), 1.34 (s, 9H), 1.26 (d, J=7.2, 3H).

Example 308

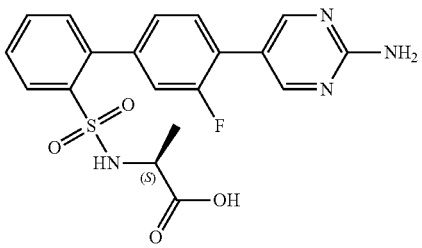

N-{[4'-(2-Aminopyrimidin-5-yl)-3'-fluorobiphenyl-2-yl]sulfonyl}-L-alanine

Trifluoroacetic acid (0.5 mL) was added to a solution of tert-butyl N-{[4'-(2-aminopyrimidin-5-yl)-3'-fluorobiphenyl-2-yl]sulfonyl}-L-alaninate (80 mg, 0.17 mmol) in DCM (1 mL) at rt. After 2 hours, the solution was concentrated to dryness and purified by HPLC to afford the title compound (70 mg, 89%). MS (ESI): mass calcd. for $C_{19}H_{17}FN_4O_4S$, 416.10; m/z found, 417.1 [M+H]$^+$. $^1$H NMR (500 MHz, CD$_3$OD) δ 8.72 (s, 2H), 8.10 (dd, J=8.0, 1.2, 1H), 7.66 (m, 1H), 7.61-7.53 (m, 2H), 7.37 (m, 3H), 3.73 (q, J=7.2, 1H), 1.31 (d, J=7.2, 3H).

Example 309

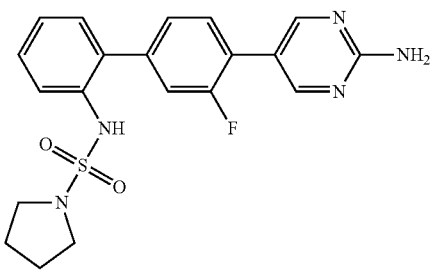

N-[4'-(2-Aminopyrimidin-5-yl)-3'-fluorobiphenyl-2-yl]pyrrolidine-1-sulfonamide

The title compound was prepared in a manner similar to that described in Example 571 using 5-(2-fluoro-4-(4,4,5,5-tetramethyl-1,3,2-dioxaborolan-2-yl)phenyl)pyrimidin-2-amine and N-(2-bromophenyl)pyrrolidine-1-sulfonamide MS (ESI): mass calcd. for $C_{20}H_{20}FN_5O_2S$, 413.13; m/z found, 414.4 [M+H]$^+$. $^1$H NMR (500 MHz, CDCl$_3$) 8.63 (s, 2H), 7.59 (d, J=8.4, 1H), 7.50 (m, 1H), 7.39 (m, 1H), 7.32-7.29 (m, 2H), 7.24-7.22 (m, 1H), 7.22-7.15 (m, 1H), 6.87-6.79 (m, 2H), 6.36 (s, 1H), 3.37-3.26 (m, 4H), 1.94-1.83 (m, 4H).

Example 310

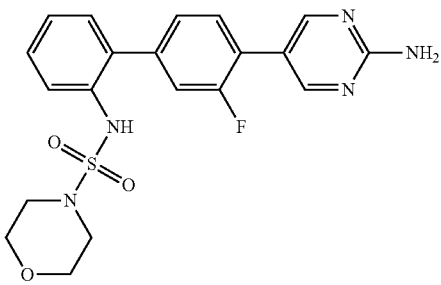

N-[4'-(2-Aminopyrimidin-5-yl)-3'-fluorobiphenyl-2-yl]morpholine-4-sulfonamide

The title compound was prepared in a manner similar to that described in Example 571 using 5-(2-fluoro-4-(4,4,5,5-tetramethyl-1,3,2-dioxaborolan-2-yl)phenyl)pyrimidin-2-amine and N-(2-bromophenyl)morpholine-4-sulfonamide. MS (ESI): mass calcd. for $C_{20}H_{20}FN_5O_3S$, 429.13; m/z found, 430.4 [M+H]$^+$. $^1$H NMR (500 MHz, CD$_3$OD) δ 8.63 (d, J=1.2, 2H), 7.70-7.54 (m, 2H), 7.48-7.25 (m, 5H), 3.70-3.55 (m, 4H), 3.05 (dd, J=5.7, 3.8, 4H).

Example 311

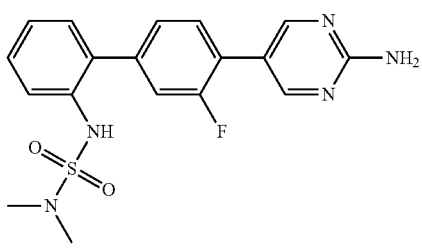

N'-[4'-(2-Aminopyrimidin-5-yl)-3'-fluorobiphenyl-2-yl]-N,N-dimethylsulfamide

The title compound was prepared in a manner similar to that described in Example 571 using 5-(2-fluoro-4-(4,4,5,5-tetramethyl-1,3,2-dioxaborolan-2-yl)phenyl)pyrimidin-2-amine and N-(2-bromophenyl)-N,N-dimethylsulfonamide. MS (ESI): mass calcd. for $C_{18}H_{18}FN_5O_2S$, 387.12; m/z found, 388.3 [M+H]$^+$. $^1$H NMR (500 MHz, CDCl$_3$) δ 8.57 (d, J=1.4, 2H), 7.61-7.55 (m, 1H), 7.50 (m, 1H), 7.42-7.35 (m, 1H), 7.24-7.21 (m, 1H), 7.21-7.17 (m, 2H), 6.36 (s, 1H), 5.17 (s, 2H), 2.82 (s, 6H).

Example 312

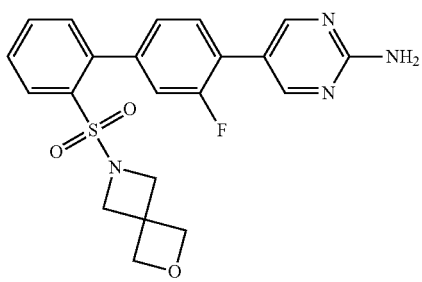

5-(2'-(2-Oxa-6-azaspiro[3.3]heptan-6-ylsulfonyl)-3-fluoro-[1,1'-biphenyl]-4-yl)pyrimidin-2-amine The title compound was prepared using analogous conditions to those described in Example 6 utilizing 6-((2-bromophenyl)sulfonyl)-2-oxa-6-azaspiro[3.3]heptanes and 5-(2-fluoro-4-(4,4,5,5-tetramethyl-1,3,2-dioxaborolan-2-yl)phenyl)pyrimidin-2-amine. MS (ESI): mass calcd. for $C_{21}H_{19}FN_4O_3S$, 426.12; m/z found, 426.9 [M+H]$^+$. $^1$H NMR (500 MHz, DMSO-d$_6$) δ 8.53 (s, 2H), 8.05-7.96 (d, J=7.9, 1H), 7.78-7.71 (m, 1H), 7.68-7.58 (m, 2H), 7.47-7.41 (d, J=7.5, 1H), 7.35-7.28 (m, 1H), 7.28-7.23 (m, 1H), 6.90 (s, 2H), 4.51 (d, J=1.3, 4H), 3.71 (d, J=1.4, 4H).

Example 313

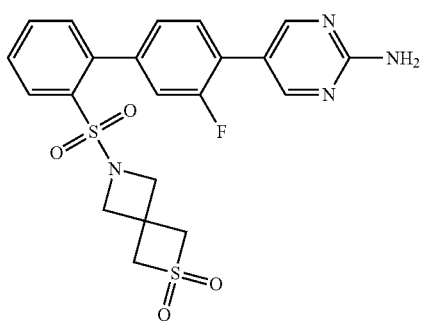

6-((4'-Aminopyrimidin-5-yl)-3'-fluoro-[1,1'-biphenyl]-2-yl)sulfonyl)-2-thia-6-azaspiro[3.3]heptane 2,2-dioxide The title compound was prepared using analogous conditions to those described in Example 6 utilizing 6-((2-bromophenyl)sulfonyl)-2-thia-6-azaspiro[3.3]heptane 2,2-dioxide and 5-(2-fluoro-4-(4,4,5,5-tetramethyl-1,3,2-dioxaborolan-2-yl)phenyl)pyrimidin-2-amine. MS (ESI): mass calcd. for $C_{21}H_{19}FN_4O_4S_2$, 474.08; m/z found, 474.8 [M+H]$^+$. $^1$H NMR (500 MHz, DMSO-d$_6$) δ 8.56-8.50 (d, J=1.4, 2H), 8.05-7.99 (dd, J=8.0, 1.3, 1H), 7.80-7.73 (m, 1H), 7.69-7.60 (m, 2H), 7.48-7.43 (dd, J=7.6, 1.3, 1H), 7.38-7.32 (dd, J=11.8, 1.8, 1H), 7.31-7.26 (dd, J=7.9, 1.7, 1H), 6.90 (s, 2H), 4.32 (s, 4H), 3.76 (s, 4H).

Example 314

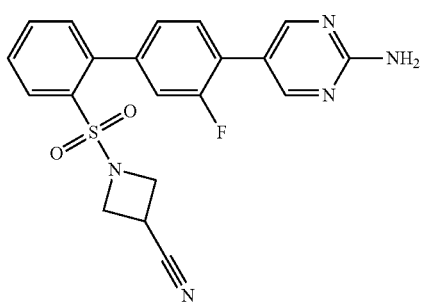

1-((4'-Aminopyrimidin-5-yl)-3'-fluoro-[1,1'-biphenyl]-2-yl)sulfonyl)azetidine-3-carbonitrile The title compound was prepared using analogous conditions to those described in Example 6 utilizing 1-((2-bromophenyl)sulfonyl)azetidine-3-carbonitrile and 5-(2-fluoro-4-(4,4,5,5-tetramethyl-1,3,2-dioxaborolan-2-yl)phenyl)pyrimidin-2-amine. MS (ESI): mass calcd. for $C_{20}H_{16}FN_5O_2S$, 409.10; m/z found, 409.9 [M+H]$^+$. $^1$H NMR (500 MHz, DMSO-d) δ 8.52 (s, 2H), 8.08-8.00 (d, J=8.0, 1H), 7.83-7.75 (m, 1H), 7.71-7.65 (m, 1H), 7.65-7.58 (m, 1H), 7.51-7.43 (d, J=7.5, 1H), 7.38-7.31 (d, J=11.7, 1H), 7.31-7.26 (m, 1H), 6.89 (s, 2H), 3.96-3.87 (m, 2H), 3.68-3.59 (m, 3H).

Example 315

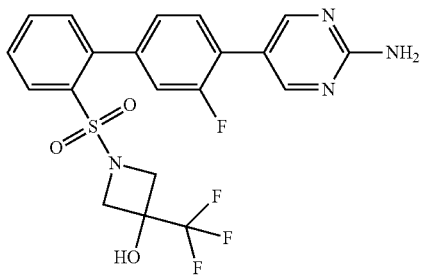

1-((4'-Aminopyrimidin-5-yl)-3'-fluoro-[1,1'-biphenyl]-2-yl)sulfonyl)-3-(trifluoromethyl)azetidine-3-ol The title compound was prepared using analogous conditions to those described in Example 6 utilizing 1-((2-bromophenyl)sulfonyl)-3-(trifluoromethyl)azetidin-3-ol and 5-(2-fluoro-4-(4,4,5,5-tetramethyl-1,3,2-dioxaborolan-2-yl)phenyl)pyrimidin-2-amine. MS (ESI): mass calcd. for $C_{20}H_{16}F_4N_4O_3S$, 468.09; m/z found, 469.0 [M+H]$^+$. $^1$H NMR (600 MHz, DMSO-d$_6$) δ 8.53-8.47 (d, J=1.4, 2H), 8.06-8.01 (dd, J=8.0, 1.3, 1H), 7.81-7.76 (m, 1H), 7.70-7.65 (m, 1H), 7.64-7.58 (m, 1H), 7.51-7.45 (m, 2H), 7.35-7.29 (dd, J=11.7, 1.8, 1H), 7.28-7.24 (dd, J=7.8, 1.7, 1H), 6.94 (s, 2H), 3.81-3.76 (d, J=9.3, 2H), 3.71-3.66 (m, 2H)

Example 316

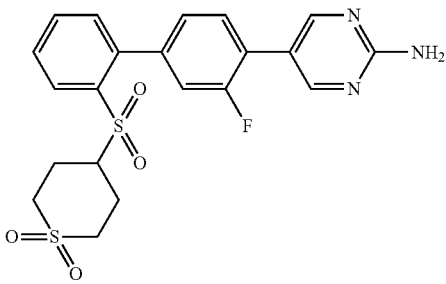

5-{2'-[(1,1-Dioxidotetrahydro-2H-thiopyran-4-yl)sulfonyl]-3-fluorobiphenyl-4-yl}pyrimidin-2-amine hydrochloride The title compound was prepared using analogous conditions to those described in Example 6 utilizing 5-(2-fluoro-4-(4,4,5,5-tetramethyl-1,3,2-dioxaborolan-2-yl)phenyl)-pyrimidin-2-amine and 4-((2-bromophenyl)sulfonyl) tetrahydro-2H-thiopyran 1,1-dioxide. MS (ESI): mass calcd. for $C_{21}H_{20}FN_3O_4S_2$, 461.09; m/z found, 461.9 [M+H]$^+$. $^1$H NMR (400 MHz, DMSO-d$_6$) δ 8.55 (s, 2H), 8.06 (d, J=7.9, 1H), 7.85 (m, 1H), 7.76 (m, 1H), 7.61 (m, 1H), 7.49 (d, J=7.5, 1H), 7.37 (d, J=11.6, 1H), 7.30 (d, J=8.0, 1H), 6.94 (s, 2H), 3.26-3.07 (m, 5H), 2.12-2.09 (m, 2H), 2.01-1.86 (m, 2H).

Example 317

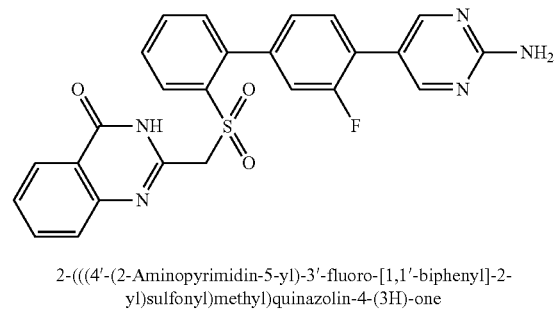 [SMILES: Nc1ncc(-c2ccc(-c3ccccc3S(=O)(=O)Cc3nc4ccccc4c(=O)[nH]3)cc2F)cn1]

2-(((4'-(2-Aminopyrimidin-5-yl)-3'-fluoro-[1,1'-biphenyl]-2-yl)sulfonyl)methyl)quinazolin-4-(3H)-one The title compound was prepared using analogous conditions to those described in Example 6 utilizing 5-(2-fluoro-4-(4,4,5,5-tetramethyl-1,3,2-dioxaborolan-2-yl)phenyl)-pyrimidin-2-amine and 2-(((2-bromophenyl)sulfonyl)methyl)quinazolin-4(3H)-one. MS (ESI): mass calcd. for $C_{25}H_{18}FN_5O_3S$, 487.11; m/z found, 487.9 [M+H]$^+$. $^1$H NMR (500 MHz, DMSO-d$_6$) δ 12.36 (s, 1H), 8.60-8.43 (d, J=1.4, 2H), 8.12-8.02 (dd, J=8.0, 1.5, 1H), 7.96-7.89 (dd, J=8.0, 1.3, 1H), 7.84-7.71 (m, 2H), 7.66-7.42 (m, 4H), 7.42-7.22 (m, 3H), 6.91 (s, 2H), 4.37 (s, 2H).

Example 318

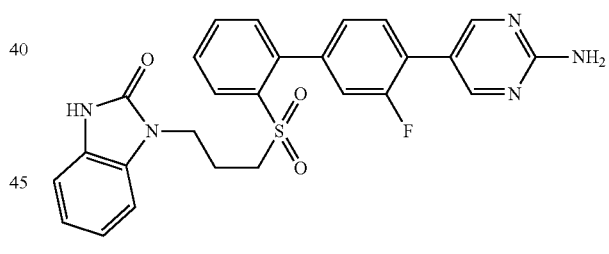

1-(3-((4'-(2-Aminopyrimidin-5-yl)-3'-fluoro-[1,1'-biphenyl]-2-yl)sulfonyl)propyl)-1H-benzo[d]imidazol-2(3H)-one The title compound was prepared using analogous conditions to those described in Example 6 utilizing 5-(2-fluoro-4-(4,4,5,5-tetramethyl-1,3,2-dioxaborolan-2-yl)phenyl)-pyrimidin-2-amine and 1-(3-((2-bromophenyl)sulfonyl) propyl)-1H-benzo[d]imidazol-2(3H)-one. MS (ESI): mass calcd. for $C_{26}H_{22}FN_5O_3S$, 503.14; m/z found, 503.9 [M+H]$^+$. $^1$H NMR (500 MHz, DMSO-d$_6$) δ 10.85 (s, 1H), 8.45 (s, 2H), 8.12-8.03 (d, J=7.8, 1H), 7.83-7.75 (m, 1H), 7.75-7.66 (m, 1H), 7.45-7.30 (m, 2H), 7.27-7.19 (d, J=11.5, 1H), 7.09-6.88 (m, 6H), 3.79-3.72 (t, J=6.5, 2H), 2.97-2.88 (dd, J=9.7, 6.3, 2H), 1.79-1.68 (m, 2H).

Example 319

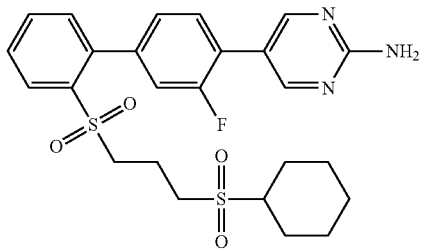

5-(2'-{[3-Cyclohexylsulfonyl)propyl]sulfonyl}-3-fluorobiphenyl-4-yl)pyrimidin-2-amine The title compound was prepared in a manner similar to that described in Example 88 using 1-bromo-2-((3-(cyclohexylsulfonyl)propyl)sulfonyl)benzene and 5-(2-fluoro-4-(4,4,5,5-tetramethyl-1,3,2-dioxaborolan-2-yl)phenyl)pyrimidin-2-amine. MS (ESI): mass calcd. for $C_{25}H_{28}FN_3O_4S_2$, 517.15; m/z found, 518.1 [M+H]$^+$. $^1$H NMR (500 MHz, CD$_3$OD) δ 8.59-8.51 (d, J=1.4, 2H), 8.20-8.14 (dd, J=8.0, 1.3, 1H), 7.82-7.76 (m, 1H), 7.72-7.67 (m, 1H), 7.59-7.52 (m, 1H), 7.51-7.46 (dd, J=7.7, 1.3, 1H), 7.38-7.31 (m, 2H), 3.16-3.08 (t, J=7.5, 2H), 3.08-3.01 (t, J=7.3, 2H), 2.94-2.82 (m, 1H), 2.07-1.97 (m, 4H), 1.91-1.80 (m, 2H), 1.79-1.62 (d, J=13.0, 1H), 1.48-1.35 (m, 2H), 1.35-1.25 (m, 2H), 1.24-1.12 (m, 1H).

Example 320

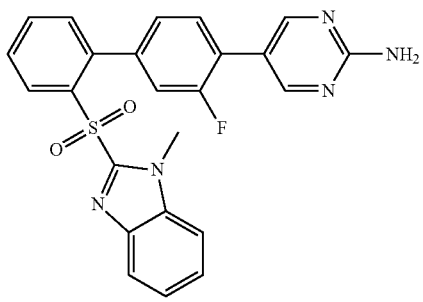

5-{3-Fluoro-2'-[(1-methyl-1H-benzimidazol-2-yl)sulfonyl]biphenyl-4-yl}primidin-2-amine The title compound was prepared in a manner similar to that described in Example 88 using 2-((2-bromophenyl)sulfonyl)-1-methyl-1H-benzo[d]imidazole and 5-(2-fluor-4-(4,4,5,5-tetramethyl-1,3,2-dioxaborolan-2-yl)phenyl)pyrimidin-2-amine. MS (ESI): mass calcd. for $C_{24}H_{18}FN_5O_2S$, 459.12; m/z found, 460.0 [M+H]$^+$. $^1$H NMR (500 MHz, CD$_3$OD) δ 7.03-6.96 (dd, J=7.8, 1.5, 1H), 6.88-6.86 (d, J=1.4, 2H), 6.43-6.28 (m, 1.5, 2H), 6.15-6.09 (d, J=8.2, 1H), 6.08-5.99 (m, 2H), 5.97-5.86 (m, 2H), 5.64-5.53 (m, 1H), 5.34-5.30 (dd, J=7.8, 1.7, 1H), 5.30-5.23 (dd, J=11.3, 1.7, 1H), 2.22 (s, 3H).

Example 321

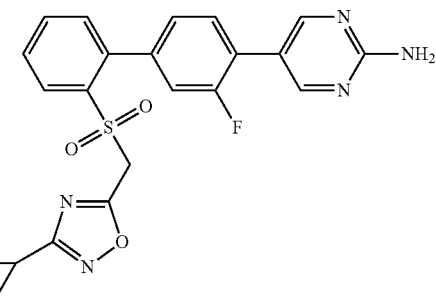

5-(2'-{[(3-Cyclopropyl-1,2,4-oxadiazol-5-yl)methyl]sulfonyl}-3-fluorobiphenyl-4-yl)pyrimidin-2-amine The title compound was prepared in a manner similar to that described in Example 88 using 5-(((2-bromophenyl)sulfonyl)methyl)-3-cyclopropyl-1,2,4-oxadiazole and 5-(2-fluoro-4-(4,4,5,5-tetramethyl-1,3,2-dioxaborolan-2-yl)phenyl)-pyrimidin-2-amine. MS (ESI): mass calcd. for $C_{22}H_{18}FN_5O_3S$, 451.11: m/z found, 452.1 [M+H]$^+$. $^1$H NMR (500 MHz, CD$_3$OD) δ 8.56 (s, 1H), 7.98-7.94 (m, 1H), 7.85-7.77 (dd, J=8.2, 6.9, 1H), 7.67-7.61 (m, 1H), 7.61-7.57 (m, 1H), 7.52-7.46 (d, J=7.6, 1H), 7.39-7.35 (dd, J=7.9, 1.6, 1H), 7.35-7.31 (m, 1H), 2.05-1.94 (m, 1H), 1.04-0.94 (m, 1H), 0.79-0.72 (m, 1H).

Example 322

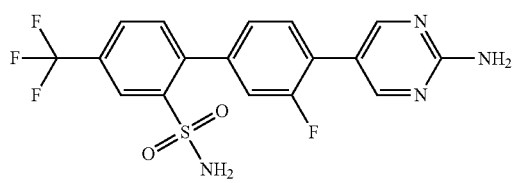

4'-(2-Aminopyrimidin-5-yl)-3'-fluoro-4-(trifluoromethyl)biphenyl-2-sulfonamide

The title compound was prepared in a manner similar to that described in Example 88 using 2-bromo-5-(trifluoromethyl)benzenesulfonamide and 5-(2-fluoro-4-(4,4,5,5-tetramethyl-1,3,2-dioxaborolan-2-yl)phenyl)pyrimidin-2-amine. MS (ESI): mass calcd. for $C_{17}H_{12}F_4N_4O_2S$, 412.06; m/z found, 413.0 [M+H]$^+$. $^1$H NMR (500 MHz, CD$_3$OD) δ 8.56-8.53 (d, J=1.4, 2H), 8.43-8.40 (m, 1H), 7.98-7.92 (d, J=7.7, 1H), 7.63-7.58 (d, J=8.0, 1H), 7.58-7.52 (m, 1H), 7.37-7.35 (m, 1H), 7.35-7.32 (m, 1H).

Example 323

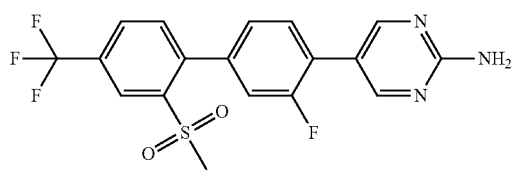

5-[3-Fluoro-2'-(methylsulfonyl)-4'-(trifluoromethyl)biphenyl-4-yl]pyrimidin-2-amine The title compound was prepared in a manner similar to that described in Example 88 using 1-bromo-2-(methylsulfonyl)-4-(trifluoromethyl)benzene and 5-(2-fluoro-4-(4,4,5,5-tetramethyl-1,3,2-dioxaborolan-2-yl)phenyl)pyrimidin-2-amine. MS (ESI): mass calcd. for $C_{18}H_{13}F_4N_3O_2S$, 411.07; m/z found, 412.0 [M+H]$^+$. $^1$H NMR (500 MHz, CD$_3$OD) δ 8.61-8.51 (d, J=1.4, 2H), 8.44 (s, 1H), 8.11-8.05 (d, J=7.5, 1H), 7.72-7.66 (d, J=8.0, 1H), 7.66-7.59 (m, 1H), 7.45-7.35 (m, 2H), 2.89 (s, 3H).

Example 324

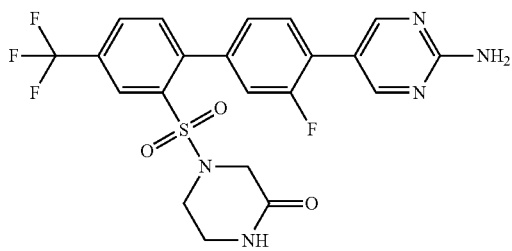

4-{[4'-(2-Aminopyrimidin-5-yl)-3'-fluoro-4-(trifluoromethyl)biphenyl-2-yl]sulfonyl}-piperazin-2-one The title compound was prepared in a manner similar to that described in Example 88 using 4-((2-bromo-5-(trifluoromethyl)phenyl)-sulfonyl)-piperazin-2-one and 5-(2-fluoro-4-(4,4,5,5-tetramethyl-1,3,2-dioxaborolan-2-yl)phenyl)-pyrimidin-2-amine. MS (ESI): mass calcd. for $C_{21}H_{17}F_4N_5O_3S$, 495.10; m/z found, 496.0 [M+H]$^+$. $^1$H NMR (500 MHz, CD$_3$OD) δ 8.70-8.61 (d, J=1.2, 2H), 8.40 (s, 1H), 8.10-8.03 (d, J=7.7, 1H), 7.71-7.64 (d, J=7.9, 1H), 7.64-7.58 (m, 1H), 7.39-7.37 (m, 1H), 7.36 (s, 1H), 3.34 (s, 2H), 3.22-3.17 (m, 2H), 3.17-3.12 (m, 2H).

Example 325

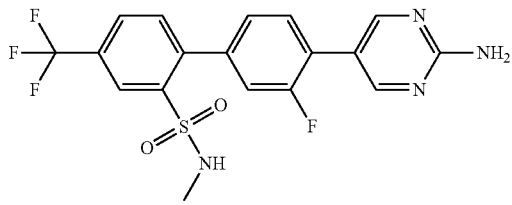

4'-(2-Aminopyrimidin-5-yl)-3'-fluoro-N-methyl-4-(trifluoromethyl)biphenyl-2-sulfonamide The title compound was prepared in a manner similar to that described in Example 88 using 2-bromo-N-methyl-5-(trifluoromethyl)benzenesulfonamide and 5-(2-fluoro-4-(4,4,5,5-tetramethyl-1,3,2-dioxaborolan-2-yl)phenyl)pyrimidin-2-amine. MS (ESI): mass calcd. for $C_{18}H_{14}F_4N_4O_2S$, 426.08; m/z found, 427.0 [M+H]$^+$. $^1$H NMR (500 MHz, CD$_3$OD) δ 8.57-8.52 (d, J=1.4, 2H), 8.33-8.27 (m, 1H), 8.02-7.94 (m, 1H), 7.66-7.60 (d, J=7.9, 1H), 7.60-7.52 (m, 1H), 7.38-7.31 (m, 2H), 2.46 (s, 3H).

Example 326

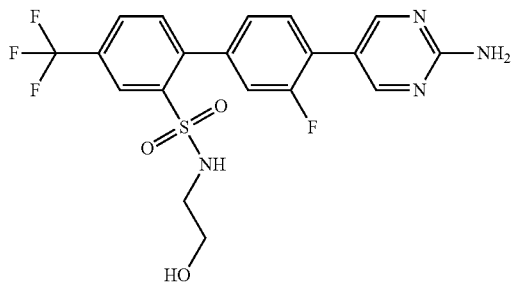

4'-(2-Aminopyrimidin-5-yl)-3'-fluoro-N-(2-hydroxyethyl)-4-(trifluoromethyl)biphenyl-2-sulfonamide The title compound was prepared in a manner similar to that described in Example 88 using 2-bromo-N-(2-hydroxyethyl)-5-(trifluoromethyl)benzenesulfonamide and 5-(2-fluoro-4-(4,4,5,5-tetramethyl-1,3,2-dioxaborolan-2-yl)phenyl)-pyrimidin-2-amine. MS (ESI): mass calcd. for $C_{19}H_{16}F_4N_4O_3S$, 456.09; m/z found, 457.0 [M+H]$^+$. $^1$H NMR (500 MHz, CD$_3$OD) δ 8.57-8.53 (d, J=1.4, 2H), 8.38-8.35 (m, 1H), 8.00-7.96 (dd, J=8.1, 1.5, 1H), 7.63-7.60 (d, J=8.0, 1H), 7.59-7.54 (m, 1H), 7.38-7.36 (dd, J=6.1, 1.6, 1H), 7.36-7.34 (m, 1H), 3.51-3.45 (t, J=5.9, 2H), 2.95-2.86 (t, J=5.9, 2H).

Example 327

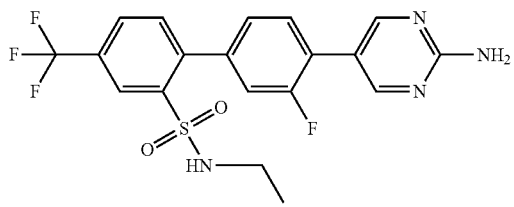

4'-(2-Aminopyrimidin-5-yl)-N-ethyl-3'-fluoro-4-trifluoromethyl)biphenyl-2-sulfonamide The title compound was prepared in a manner similar to that described in Example 88 using 2-bromo-N-ethyl-5-(trifluoromethyl)benzenesulfonamide and 5-(2-fluoro-4-(4,4,5,5-tetramethyl-1,3,2-dioxaborolan-2-yl)phenyl)pyrimidin-2-amine. MS (ESI): mass calcd. for $C_{19}H_{16}F_4N_4O_2S$, 440.09; m/z found, 441.0 [M+H]$^+$. $^1$H NMR (500 MHz, CD$_3$OD) δ 8.56-8.53 (d, J=1.4, 2H), 8.34-8.31 (m, 1H), 7.99-7.95 (m, 1H), 7.63-7.59 (d, J=8.0, 1H), 7.59-7.53 (m, 1H), 7.36-7.34 (dd, J=7.1, 1.6, 1H), 7.34-7.32 (m, 1H), 2.97-2.71 (q, J=7.2, 2H), 1.15-0.84 (t, J=7.2, 3H).

Example 328

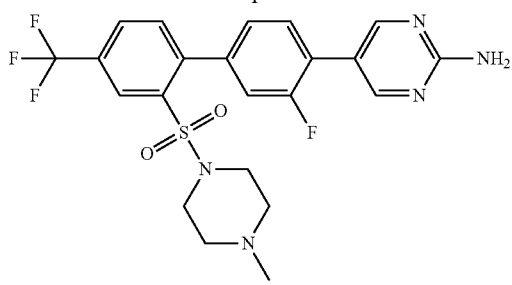

5-{3-Fluoro-2'-[(4-methylpiperazin-1-yl)sulfonyl]-4'-(trifluoromethyl)biphenyl-4-yl}pyrimidin-2-amine The title compound was prepared in a manner similar to that described in Example 88 using 1-((2-bromo-5-(trifluoromethyl)phenyl)sulfonyl)-4-methylpiperazine and 5-(2-fluoro-4-(4,4,5,5-tetramethyl-1,3,2-dioxaborolan-2-yl)phenyl)pyrimidin-2-amine. MS (ESI): mass calcd. for $C_{22}H_{21}F_4N_5O_2S$, 495.14; m/z found, 496.0 [M+H]+. 1H NMR (500 MHz, $CD_3OD$) δ 8.63-8.61 (d, J=1.4, 2H), 8.40-8.37 (d, J=1.4, 1H), 8.10-8.05 (m, 1H), 7.70-7.67 (d, J=8.0, 1H), 7.67-7.63 (m, 1H), 7.46-7.30 (m, 2H), 2.86 (s, 3H), 3.83-2.53 (br m, 8H).

Example 329

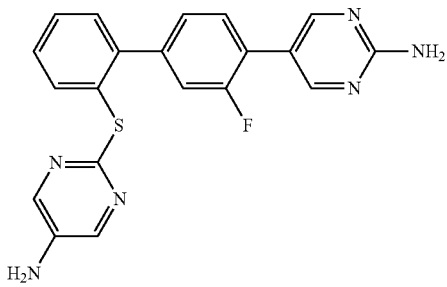

5-{2'-[(5-Aminopyrimidin-2-yl)sulfanyl]-3-fluorobiphenyl-4-yl}pyrimidin-2-amine formate salt The title compound was prepared using analogous conditions to those described in Example 213 utilizing 4'-(2-aminopyrimidin-5-yl)-3'-fluoro-[1,1'-biphenyl]-2-thiol and 5-amino-2-chloropyrimidine. MS (ESI): mass calcd. for $C_{20}H_{15}FN_6S$, 390.11; m/z found, 391.0 [M+H]+. 1H NMR (400 MHz, DMSO-$d_6$) δ 8.47 (d, J=1.4, 2H), 7.95 (s, 2H), 7.66-7.59 (m, 1H), 7.55-7.48 (m, 2H), 7.46-7.41 (m, 2H), 7.27-7.20 (m, 2H), 6.89 (s, 2H), 5.45 (s, 2H).

Example 330

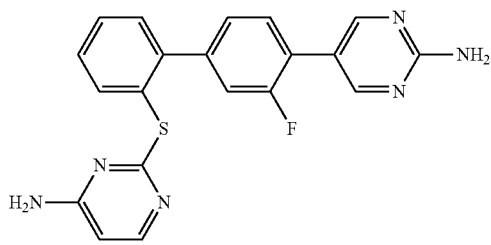

5-{2'-[(4-Aminopyrimidin-2-yl)sulfanyl]-3-fluorobiphenyl-4-yl}pyrimidin-2-amine formate salt The title compound was prepared using analogous conditions to those described in Example 213 4'-(2-aminopyrimidin-5-yl)-3'-fluoro-[1,1'-biphenyl]-2-thiol and 4-amino-2-chloropyrimidine. MS (ESI): mass calcd. for $C_{20}H_{15}FN_6S$, 390.11; m/z found, 390.9 [M+H]+. 1H NMR (400 MHz, DMSO-$d_6$) δ 8.47 (d, J=1.4, 2H), 7.80 (d, J=5.8, 1H), 7.73-7.66 (m, 1H), 7.57-7.50 (m, 2H), 7.48-7.44 (m, 2H), 7.32-7.23 (m, 2H), 6.90-6.88 (m, 4H), 6.11 (d, J=5.8, 1H).

Example 331

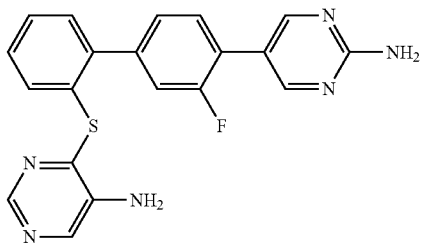

5-{2'-[(5-Aminopyrimidin-4-yl)sulfanyl]-3-fluorobiphenyl-4-yl}pyrimidin-2-amine formate salt The title compound was prepared using analogous conditions to those described in Example 213 utilizing 4'-(2-aminopyrimidin-5-yl)-3'-fluoro-[1,1'-biphenyl]-2-thiol and 5-amino-4-chloropyrimidine. MS (ESI): mass calcd. for $C_{20}H_5FN_6S$, 390.11; m/z found, 391.1 [M+H]+. 1H NMR (400 MHz, DMSO-$d_6$) δ 8.46 (d, J=1.4, 2H), 8.16 (s, 1H), 7.92 (s, 1H), 7.59-7.49 (m, 3H), 7.49-7.44 (m, 2H), 7.30-7.20 (m, 2H), 6.89 (s, 2H), 5.44 (s, 2H).

Example 332

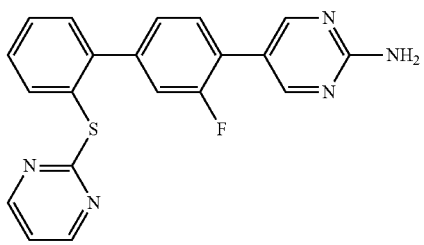

5-[3-Fluoro-2'-(pyrimidin-2-ylsufanyl)biphenyl-4-yl]pyrimidin-2-amine hyrochloride The title compound was prepared using analogous conditions to those described in Example 213 utilizing 4'-(2-aminopyrimidin-5-yl)-3'-fluoro-[1,1'-biphenyl]-2-thiol and and 2-chloropyrimidine. MS (ESI): mass calcd. for $C_{20}H_{14}FN_5S$, 375.10; m/z found, 375.9 [M+H]+. 1H NMR (400 MHz, DMSO-$d_6$) δ 8.66 (s, 2H), 8.56 (d, J=4.9, 2H), 7.79-7.73 (m, 1H), 7.63-7.56 (m, 2H), 7.55-7.48 (m, 2H), 7.33-7.24 (m, 2H), 7.21 (m, 1H), 6.23 (s, 2H).

Example 333

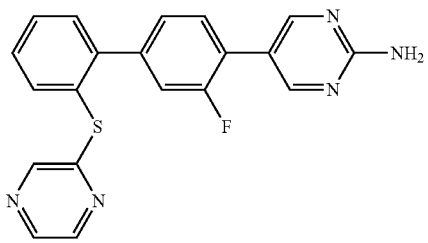

5-[3-Fluoro-2'-(pyrazin-2-ylsulfanyl)biphenyl-4-yl]pyrimidin-2-amine hydrochloride The title compound was prepared using analogous conditions to those described in Example 213 utilizing 4'-(2-aminopyrimidin-5-yl)-3'-fluoro-[1,1'-biphenyl]-2-thiol and 2-chloropyrazine. MS (ESI): mass calcd. for $C_2H_{14}FN_5S$, 375.10; m/z found, 375.9 [M+H]$^+$. $^1$H NMR (400 MHz, DMSO-$d_6$) δ 8.70-8.57 (m, 2H), 8.41 (dd, J=2.5, 1.6, 1H), 8.35 (d, J=2.6, 1H), 8.27 (d. J=1.5, 1H), 7.72 (dd. J=8.0, 1.2, 1H), 7.64-7.57 (m, 2H), 7.56-7.50 (m, 2H), 7.34 (d, J=11.8, 1H), 7.27 (d, J=8.0, 1H), 6.01 (s, 2H).

Example 334

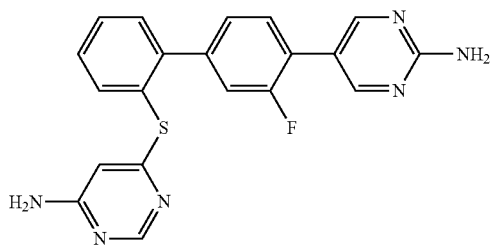

5-{2'-[(6-Aminopyrimidin-4-yl)sulfanyl]-3-fluorobiphenyl-4-yl}pyrimidin-2-amine formate salt The title compound was prepared using analogous conditions to those described in Example 213 utilizing 4'-(2-aminopyrimidin-5-yl)-3'-fluoro-[1,1'-biphenyl]-2-thiol and 4-amino-6-chloropyrimidine. MS (ESI): mass calcd. for $C_{20}H_{15}FN_6S$, 390.11; m/z found, 390.9 [M+H]$^+$. $^1$H NMR (400 MHz, DMSO-d) δ 8.48 (d, J=1.4, 2H), 8.06 (s, 1H), 7.77-7.71 (m, 1H), 7.68-7.61 (m, 1H), 7.60-7.52 (m, 3H), 7.29 (dd, J=11.9, 1.5, 1H), 7.25 (dd, J=7.9, 1.7, 1H), 6.88 (s, 2H), 6.78 (s, 2H), 5.78 (d, J=0.9, 1H).

Example 335

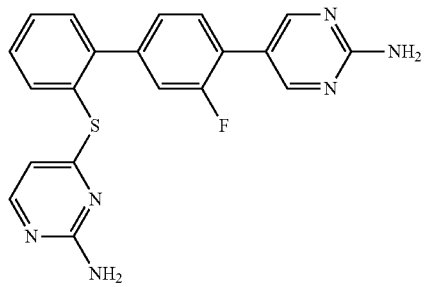

4-{4'-[(2-Aminopyrimidin-5-yl)-3'-fluorobiphenyl-2-yl]sulfanyl}pyrimidin-2-amine formate salt The title compound was prepared using analogous conditions to those described in Example 213 utilizing 4'-(2-aminopyrimidin-5-yl)-3'-fluoro-[1,1'-biphenyl]-2-thiol and 2-amino-4-chloropyrimidine. MS (ESI): mass calcd. for $C_{20}H_{15}FN_6S$, 390.11; m/z found, 390.9 [M+H]$^+$. $^1$H NMR (400 MHz, DMSO-$d_6$) δ 8.47 (d, J=1.3, 2H), 7.90 (d, J=5.3, 1H), 7.78-7.71 (m, 1H), 7.68-7.61 (m, 1H), 7.59-7.51 (m, 3H), 7.30 (dd. J=11.8, 1.6, 1H), 7.25 (dd, J=7.9, 1.7, 1H), 6.89 (s, 2H), 6.64 (s, 2H), 5.86 (d, J=5.3, 1H).

Example 336

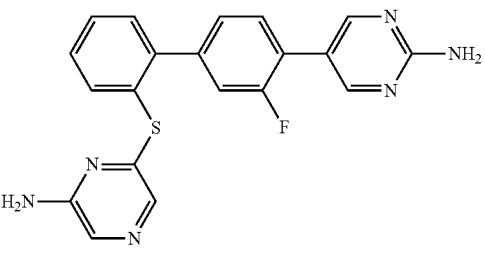

5-{2'-[(6-Aminopyrimidin-2-yl)sulfanyl]-3-fluorobiphenyl-4-yl}pyrimidin-2-amine formate salt The title compound was prepared using analogous conditions to those described in Example 6 utilizing 4'-(2-aminopyrimidin-5-yl)-3'-fluoro-[1,1'-biphenyl]-2-thiol and 2-amino-6-chloropyrazine. MS (ESI): mass calcd. for $C_{20}H_{15}FN_6S$, 390.11; m/z found, 391.0 [M+H]$^+$. $^1$H NMR (400 MHz, DMSO-$d_6$) δ 8.47 (d, J=1.3, 2H), 7.67-7.60 (m, 1H), 7.59-7.51 (m, 3H), 7.49-7.46 (m, 2H), 7.31 (dd, J=11.9, 1.5, 1H), 7.26 (dd, J=7.9, 1.7, 1H), 7.18 (s, 1H), 6.90 (s, 2H), 6.57 (s, 2H).

Example 337

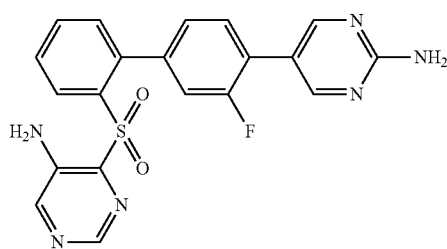

5-{2'-[(5-Aminopyrimidin-4-yl)sulfanyl]-3-fluorobiphenyl-4-yl}pyrimidin-2-amine hydrochloride To a solution of 5-{2'-[(5-aminopyrimidin-4-yl)sulfanyl]-3-fluorobiphenyl-4-yl}-pyrimidin-2-amine (200 mg, 0.51 mmol) in MeCN/DCM/H$_2$O (5 mL/5 mL/5 mL) were added NaIO$_4$ (326 mg, 1.50 mmol) and RuCl$_3$ (16 mg, 0.075 mmol). The reaction mixture was stirred at rt for 10 hours then poured into water (50 mL) and extracted with EtOAc (30 mL×3). The combined organic extracts were concentrated and purified by HPLC to give the title compound as a white solid. MS (ESI): mass calcd. for $C_{20}H_{15}FN_6O_2S$, 422.10; m/z found, 423.1 [M+H]$^+$. $^1$H NMR (400 MHz, DMSO-$d_6$) δ 8.57 (s, 2H), 8.30-8.25 (m, 2H), 8.22 (s, 1H), 7.83 (m, 1H), 7.77 (m, 1H), 7.44-7.33 (m, 2H), 6.88 (d, J=9.5, 2H), 6.29 (s, 2H).

Example 338

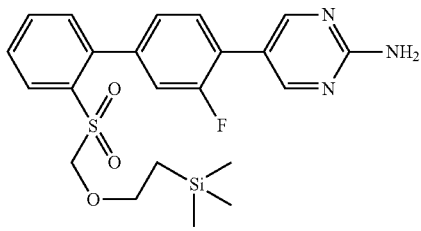

5-[3-Fluoro-2'-({[2-(trimethylsilyl)ethoxy]methyl}sulfonyl)biphenyl-4-yl]pyrimidin-2-amine formate salt The title compound was prepared using analogous conditions to those described in Example 337 utilizing 5-[3-fluoro-2'-({[2-(trimethylsilyl)-ethoxy]methyl}-sulfanyl)-biphenyl-4-yl]pyrimidin-2-amine. MS (ESI): mass calcd. for $C_{22}H_{26}FN_3O_3SSi$, 459.14; m/z found, 460.0 [M+H]$^+$. $^1$H NMR (400 MHz, CD$_3$OD) δ 8.63 (s, 2H), 8.19 (dd, J=7.9, 1.4, 1H), 7.79 (m, 1H), 7.70 (m, 1H), 7.59 (m, 1H), 7.46 (dd, J=7.5, 1.3, 1H), 7.34-7.31 (m, 2H), 4.36 (s, 2H), 3.80-3.68 (m, 2H), 0.87-0.76 (m, 2H), 0.08 (s, 9H).

Example 339

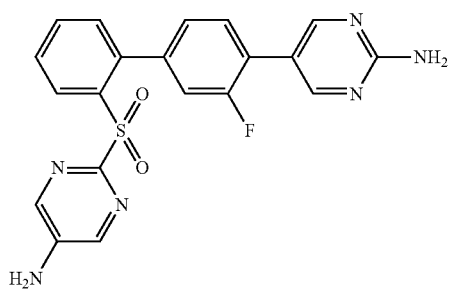

5-{2'-[(5-Aminopyrimidin-2-yl)sulfonyl]-3-fluorobiphenyl-4-yl}pyrimidin-2-amine hydrochloride The title compound was prepared using analogous conditions to those described in Example 337 utilizing 5-{2'-[(5-Aminopyrimidin-2-yl)sulfanyl]-3-fluorobiphenyl-4-yl}pyrimidin-2-amine formate salt MS (ESI): mass calcd. for $C_{20}H_{15}FN_6O_2S$, 422.10; m/z found, 423.1 [M+H]$^+$. $^1$H NMR (400 MHz, CD$_3$OD) δ 8.83 (s, 2H), 8.34 (dd, J=7.7, 1.5, 1H), 7.94 (s, 2H), 7.79-7.69 (m, 2H), 7.44 (m, 1H), 7.34 (dd, J=7.3, 1.4, 1H), 6.93 (dd, J=7.9, 1.6, 1H), 6.88 (dd, J=11.5, 1.5, 1H).

Example 340

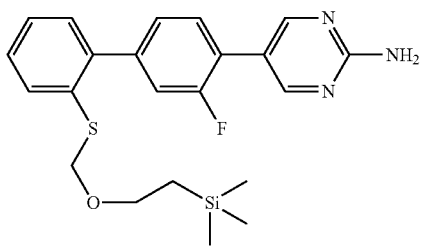

5-[3-Fluoro-2'-({[2-(trimethylsilyl)ethoxy]methyl}sulfanyl)biphenyl-4-yl]pyrimidin-2-amine The title compound was prepared using analogous conditions to those described in Example 6 utilizing utilizing 5-(2-fluoro-4-(4,4,5,5-tetramethyl-1,3,2-dioxaborolan-2-yl)phenyl)pyrimidin-2-amine and (2-(((2-bromophenyl)thio)methoxy)ethyl)trimethylsilane. MS (ESI): mass calcd. for $C_{22}H_{26}FN_3OSSi$, 427.16; m/z found, 428.0 [M+H]$^+$. $^1$H NMR (400 MHz, CD$_3$OD) δ 8.47 (d, J=1.4, 2H), 7.69 (dd, J=7.7, 1.1, 1H), 7.44 (m, 1H), 7.34-7.15 (m, 5H), 4.86 (s, 2H), 3.60-3.47 (m, 2H), 0.88-0.76 (m, 2H), 0.06 (s, 9H)

Example 341

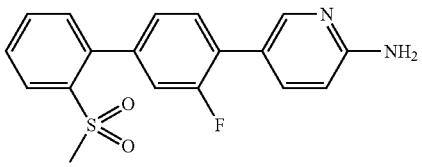

5-(3-Fluoro-2'-(methylsulfonyl)-[1,1'-biphenyl]-4-yl)pyridin-2-amine

Step A: 5-(4-Chloro-2-fluorophenyl)pyridin-2-amine

Solid 4-chloro-2-fluorobenzeneboronic acid (10.0 g, 57.4 mmol), 2-amino-5-bromopyridine (9.92 g, 57.4 mmol), palladium (II) trifluoroacetate (0.381 g, 1.15 mmol), and triphenylphosphine (0.602 g, 2.29 mmol) were combined in a 1 L flask under nitrogen, then toluene (150 mL), EtOH (150 mL), and 2 M Na$_2$CO$_3$ (100 mL) were added. The mixture was sparged with nitrogen for 30 min using a gas dispersion tube, then heated at 80° Celsius for 20 hours with vigorous stirring. The mixture was cooled to rt, diluted with EtOAc (200 mL), and transferred to a separatory funnel. The aqueous phase was removed, and the organic phase washed with brine. The combined aqueous phases were extracted with an equal volume of EtOAc, and the combined organic phases were dried and concentrated to dryness. The residue was subjected to FCC to provide 5-(4-chloro-2-fluorophenyl)pyridin-2-amine (9.10 g, 71%). MS (CI): mass calcd. for $C_{11}H_8CFN_2$, 222.04; m/z found, 223.1 [M+H]$^+$. $^1$H NMR (500 MHz, DMSO-d$_6$) δ 8.54-8.22 (s, 2H), 8.22-8.18 (d, J=2.1, 1H), 8.15-8.10 (m, 1H), 7.68-7.58 (m, 2H), 7.48-7.38 (m, 1H), 7.16-7.06 (d, J=9.3, 1H).

Step B: 5-(3-Fluoro-2'-(methylsulfonyl)-[1,1'-biphenyl]-4-yl)pyridin-2-amine 5-(4-Chloro-2-fluorophenyl)pyridin-2-amine (100 mg, 0.449 mmol), 2-(methylsulfonyl)phenylboronic acid (112 mg, 0.561 mmol), and chloro(2-dicyclohexyl-phosphino-2', 4',6'-triisopropyl-1,1'-biphenyl)[2-(2-aminoethyl)phenyl)]palladium(II) (33 mg, 0.045 mmol) were placed in a sealable reaction tube under nitrogen. THF (2 mL, sparged with nitrogen) and K$_3$PO$_4$ (2 mL, 0.5 M sparged with nitrogen) were added, and the reaction vessel was sealed and heated at 60° Celsius for 16 hours with vigorous stirring. The mixture was cooled to rt, diluted with EtOAc, and washed with 2 M K$_2$CO$_3$, then dried and concentrated to dryness. The residue was subjected to FCC to provide the title compound (45 mg, 29%). MS (CI): mass calcd. for $C_{18}H_{15}FN_2O_2S$, 342.08; m/z found, 343.0 [M+H]$^+$. $^1$H NMR (500 MHz, CDCl$_3$) δ 8.38-8.31 (s, 1H), 8.29-8.22 (m, 1H), 7.77-7.71 (m, 1H), 7.71-7.65 (m, 1H), 7.64-7.57 (m, 1H), 7.52-7.45 (m, 1H). 7.42-7.37 (m, 1H), 7.36-7.27 (m, 2H), 6.64-6.59 (m, 1H), 4.66-4.51 (s, 2H), 2.81-2.69 (s, 2H).

Example 342

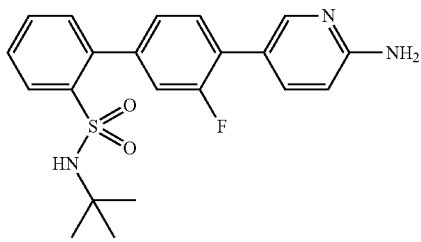

4'-(6-Aminopyridin-3-yl)-N-(tert-butyl)-3'-fluoro-[1,1'-biphenyl]-2-sulfonamide

The title compound was prepared in a manner similar to that described in Example 341, using (2-(N-(tert-butyl)sulfamoyl)phenyl)boronic acid in Step B. MS (CI): mass calcd. for $C_{21}H_{22}FN_3O_2S$, 399.14; m/z found, 400.2 [M+H]$^+$. $^1$H NMR (500 MHz, DMSO-d$_6$) δ 8.22-8.13 (s, 1H), 8.10-8.03 (d, J=7.8, 1H), 7.67-7.57 (m, 3H), 7.53-7.48 (m, 1H), 7.40-7.36 (d, J=7.4, 1H), 7.31-7.22 (m, 2H), 6.94-6.89 (s, 1H), 6.60-6.52 (d, J=8.6, 1H), 6.24-6.11 (s, 2H), 1.07-0.99 (s, 9H).

Example 343

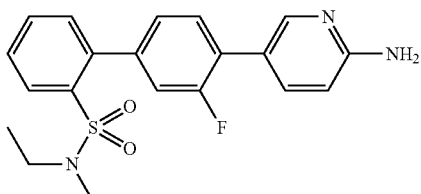

4'-(6-Aminopyridin-3-yl)-N,N-diethyl-3'-fluoro-[1,1'-biphenyl]-2-sulfonamide

The title compound was prepared in a manner similar to that described in Example 341, using (2-(N,N-diethylsulfamoyl)phenyl)boronic acid in Step B. MS (CI): mass calcd. for $C_{21}H_{22}FN_3O_2S$, 399.14; m/z found, 400.2 [M+H]$^+$. $^1$H NMR (500 MHz, DMSO-d$_6$) δ 8.28-8.22 (d, J=1.9, 1H), 8.18-8.12 (d, J=9.3, 1H), 8.12-7.88 (m, 1H), 7.76-7.69 (m, 1H), 7.68-7.59 (m, 2H), 7.43-7.38 (dd, J=7.5, 1.1, 1H), 7.37-7.32 (m, 1H), 7.32-7.27 (m, 1H), 7.09-7.04 (d, J=9.2, 1H), 2.99-2.90 (m, 3H), 1.00-0.90 (m, 4H).

The title compound was prepared in a manner similar to that described in

Example 344

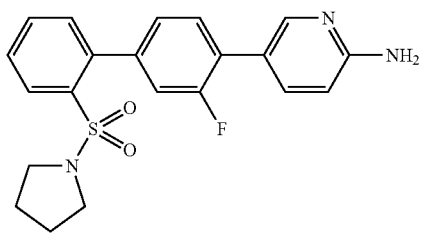

5-(3-Fluoro-2'-(pyrrolidin-1-ylsulfonyl)-[1,1'-biphenyl]-4-yl)pyridin-2-amine

The title compound was prepared in a manner similar to that described in Example 341, using (2-(pyrrolidin-1-ylsulfonyl)phenyl)boronic acid in Step B. MS (CI): mass calcd. for $C_{21}H_{20}FN_3O_2S$, 397.13; m/z found, 398.1 [M+H]$^+$. $^1$H NMR (500 MHz, DMSO-d$_6$) δ 8.37-8.11 (m, 4H), 8.01-7.95 (m, 1H), 7.77-7.71 (m, 1H), 7.69-7.61 (m, 2H), 7.44-7.36 (m, 2H), 7.35-7.30 (m, 1H), 7.15-7.10 (d, J=9.3, 1H), 2.99-2.80 (m, 4H), 1.77-1.62 (m, 4H).

Example 345

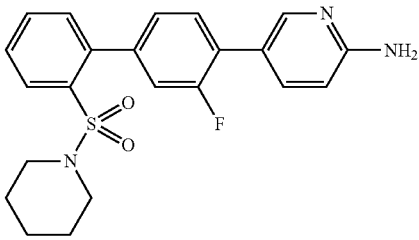

5-(3-Fluoro-2'-(piperidin-1-ylsulfonyl)-[1,1'-biphenyl]-4-yl)pyridin-2-amine

The title compound was prepared in a manner similar to that described in Example 341, using (2-(piperidin-1-ylsulfonyl)phenyl)boronic acid in Step B. MS (CI): mass calcd. for $C_{22}H_{22}FN_3O_2S$, 411.14; m/z found, 412.2 [M+H]$^+$. $^1$H NMR (500 MHz, DMSO-d) δ 8.47-8.16 (m, 4H), 8.02-7.96 (m, 1H), 7.79-7.72 (m, 1H), 7.71-7.60 (m, 2H), 7.46-7.36 (m, 2H), 7.35-7.29 (m, 1H), 7.16-7.11 (d, J=9.3, 1H), 2.86-2.74 (m, 4H), 1.45-1.27 (m, 6H).

Example 346

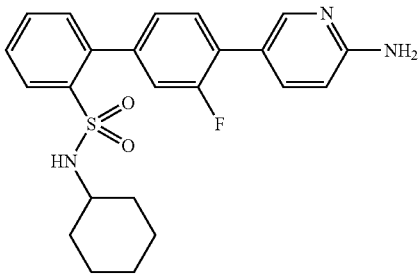

4'-(6-Aminopyridin-3-yl)-N-cyclohexyl-3'-fluoro-[1,1'-biphenyl]-2-sulfonamide

Step A: (4-(6-Aminopyridin-3-yl)-3-fluorophenyl)boronic acid 5-(4-Chloro-2-fluorophenyl)pyridin-2-amine (2.0 g, 9.0 mmol), 4,4,4',4',5,5,5',5'-octamethyl-2,2'-bi(1,3,2-dioxaborolane) (2.9 g, 11.0 mmol), chloro(2-dicyclohexyl-phosphino-2',4',6'-triisopropyl-1,1'-biphenyl)[2-(2'-amino-1,1'-biphenyl)]palladium(II) (0.14 g, 0.18 mmol), and KOAc (2.7 g, 27 mmol) were combined in a sealable reaction vessel under nitrogen, and then treated with anhydrous 1,4-dioxane (100 mL, sparged with nitrogen). The vessel was sealed and then heated at 80° Celsius for 16 hours. The mixture was cooled to rt, HCl (1 m, 50 mL) was added and the mixture stirred for 20 min. The mixture was then diluted with EtOAc (200 mL) and the aqueous phase was collected. The organic phase was extracted with 1 M HCl (2×75 mL). The combined aqueous phases were cooled in an icebath and the pH was adjusted to ca. 7 using solid sodium bicarbonate. The resulting precipitate was collected by filtration, washed well with water, and dried to provide the title compound (2.1 g, 98%). MS (CI): mass calcd. for $C_{11}H_{10}BFN_2O_2$, 232.08; m/z found, 233.1 [M+H]$^+$. $^1$H NMR (500 MHz, DMSO-d$_6$) δ 8.29-8.20 (s, 2H), 8.18-8.13 (s, 1H), 7.80-7.72 (m, 1H), 7.69-7.63 (m, 1H), 7.63-7.57 (m, 1H), 7.51-7.44 (m, 1H), 6.84-6.57 (m, 3H).

Step B: 4'-(6-Aminopyridin-3-yl)-N-cyclohexyl-3'-fluoro-[1,1'-biphenyl]-2-sulfonamide A mixture of (4-(6-aminopyridin-3-yl)-3-fluorophenyl) boronic acid (75 mg, 0.32 mmol), 2-bromo-N-cyclohexyl-benzenesulfonamide (0.11 g, 0.36 mmol), 1,1'-bis[di-tert-butylphosphino)ferrocene]palladium(II) chloride (11 mg, 0.016 mmol), K$_2$CO$_3$ (2 M, 1.6 mL, sparged with nitrogen) and THF (2 mL, sparged with nitrogen) were combined in a sealed vessel under nitrogen. The mixture was vigorously stirred at rt for 16 hours, then diluted with EtOAc. The aqueous phase was removed and the organic layer was dried and concentrated. The residue was subjected to FCC to provide the title compound (15 mg, 11%). MS (CI): mass calcd. for $C_{23}H_{24}FN_3O_2S$, 425.16; m/z found, 426.1 [M+H]$^+$. $^1$H NMR (500 MHz, DMSO-d$_6$) δ 8.20-8.14 (s, 1H), 8.05-7.96 (m, 1H), 7.70-7.57 (m, 3H), 7.55-7.47 (m, 1H), 7.44-7.35 (m, 2H), 7.30-7.20 (m, 2H), 6.59-6.52 (d, J=8.6, 1H), 6.23-6.11 (s, 2H), 2.83-2.69 (d, J=7.4, 1H), 1.68-1.52 (m, 4H), 1.49-1.38 (s, 1H), 1.19-0.92 (m, 6H).

Example 347

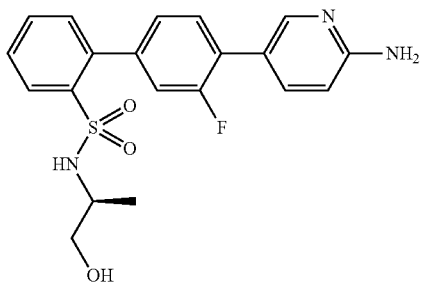

(S)-4'-(6-Aminopyridin-3-yl)-3'-fluoro-N-(1-hydroxypropan-2-yl)-[1,1'-biphenyl]-2-sulfonamide A mixture of (4-(6-aminopyridin-3-yl)-3-fluorophenyl) boronic acid (100 mg, 0.43 mmol), (S)-2-bromo-N-(1-hydroxypropan-2-yl)benzenesulfonamide (160 mg, 0.54 mmol), Pd(dppf)Cl$_2$.CH$_2$Cl$_2$ (18 mg, 0.022 mmol), K$_2$CO$_3$ (340 mg, 2.4 mmol), and DMSO (3 mL) was sparged with nitrogen, then the reaction vessel was sealed and heated at 80° Celsius for 16 hours. The mixture was cooled to rt, then filtered, and subjected to HPLC purification to provide the title compound. MS (CI): mass calcd. for $C_{20}H_{20}FN_3O_3S$, 401.12; m/z found, 402.1 [M+H]$^+$. $^1$H NMR (500 MHz, DMSO-d$_6$) δ 8.31-7.93 (m, 5H), 7.72-7.57 (m, 3H), 7.42-7.25 (m, 4H), 7.11-7.04 (d, J=9.2, 1H), 3.34-3.25 (s, 1H), 3.18-3.00 (m, 2H), 1.00-0.91 (d, J=6.5, 3H).

Example 348

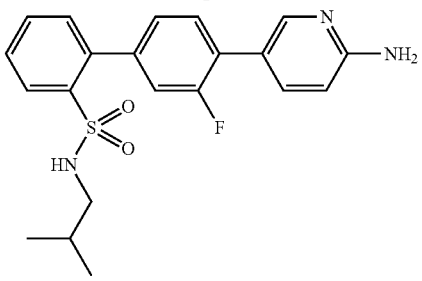

4'-(6-Aminopyridin-3-yl)-3'-fluoro-N-iso-butyl-[1,1'-biphenyl]-2-sulfonamide

The title compound was prepared in a manner similar to that described in Example 347 using 2-bromo-N-iso-butyl-benzenesulfonamide. MS (CI): mass calcd. for $C_{21}H_{22}FN_3O_2S$, 399.14; m/z found, 400.0 [M+H]$^+$. $^1$H NMR (500 MHz, DMSO-d$_5$) δ 8.26-8.19 (d, J=2.1, 1H), 8.18-8.11 (d, J=9.2, 1H), 8.08-7.79 (m, 3H), 7.72-7.53 (m, 4H), 7.43-7.30 (m, 3H), 7.08-7.00 (d, J=9.2, 1H), 2.57-2.52 (m, 2H), 1.66-1.56 (m, 1H), 0.82-0.75 (d, J=6.7, 6H).

Example 349

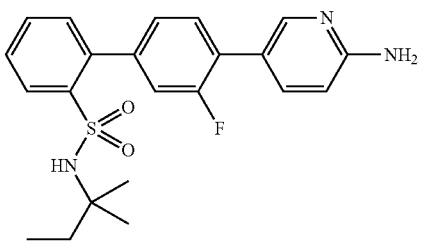

4'-(6-Aminopyridin-3-yl)-3'-fluoro-N-(tert-pentyl)-[1,1'-biphenyl]-2-sulfonamide The title compound was prepared in a manner similar to that described in Example 347 using 2-bromo-N-(tert-pentyl)benzenesulfonamide. MS (CI): mass calcd. for $C_{22}H_{24}FN_3O_2S$, 413.16; m/z found, 414.2 [M+H]$^+$. $^1$H NMR (500 MHz, DMSO-d$_6$) δ 8.23-8.19 (d, J=2.0, 1H), 8.19-8.11 (d, J=9.0, 1H), 8.10-8.05 (m, 1H), 8.05-7.79 (s, 2H), 7.69-7.57 (m, 3H), 7.40-7.29 (m, 3H), 7.09-7.02 (d, J=9.2, 1H), 6.98-6.91 (s, 1H), 1.48-1.36 (m, 2H), 1.04-0.91 (s, 6H), 0.79-0.67 (m, 3H).

Example 350

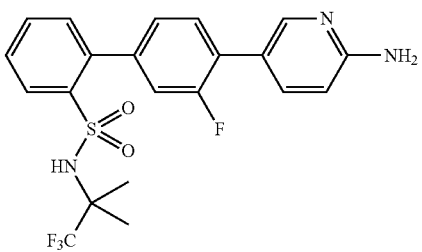

4'-(6-Aminopyridin-3-yl)-3'-fluoro-N-(1,1,1-trifluoro-2-methylpropan-2-yl)-[1,1'-biphenyl]-2-sulfonamide The title compound was prepared in a manner similar to that described in Example 347 using 2-bromo-N-(1,1,1-trifluoro-2-methylpropan-2-yl)benzenesulfonamide. MS (CI): mass calcd. for $C_{21}H_{19}F_4N_3O_2S$, 453.11; m/z found, 454.0 [M+H]$^+$. $^1$H NMR (500 MHz, DMSO-d$_6$) δ 8.28-8.19 (m, 2H), 8.17-8.11 (d, J=9.1, 1H), 8.07-8.02 (m, 1H), 8.03-7.80 (s, 2H), 7.74-7.65 (m, 2H), 7.64-7.58 (m, 1H), 7.43-7.39 (m, 1H), 7.38-7.32 (m, 1H), 7.32-7.28 (dd, J=7.9, 1.7, 1H), 7.07-7.00 (d, J=9.2, 1H), 1.29-1.17 (s, 6H).

Example 351

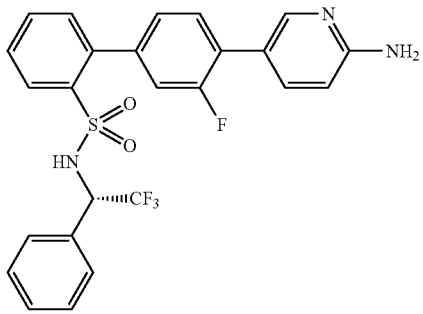

(S)-4'-(6-Aminopyridin-3-yl)-3'-fluoro-N-(2,2,2-trifluoro-1-phenylethyl)-[1,1'-biphenyl]-2-sulfonamide The title compound was prepared in a manner similar to that described in Example 347 using (S)-2-bromo-N-(2,2,2-trifluoro-1-phenylethyl)benzenesulfonamide. MS (CI): mass calcd. for $C_{25}H_{19}F_4N_3O_2S$, 501.11; m/z found, 502.1 [M+H]$^+$. $^1$H NMR (500 MHz, DMSO-d$_6$) δ 9.32-9.24 (d, J=10.1, 1H), 8.24-8.20 (d, J=2.1, 1H), 8.20-8.11 (d, J=9.2, 1H), 8.11-7.90 (s, 2H), 7.90-7.85 (m, 1H), 7.64-7.58 (m, 1H), 7.57-7.51 (m, 1H), 7.49-7.40 (m, 3H), 7.40-7.31 (m, 3H), 7.29-7.24 (dd, J=7.6, 1.2, 1H), 7.15-7.03 (m, 3H), 5.22-4.90 (m, 1H).

Example 352

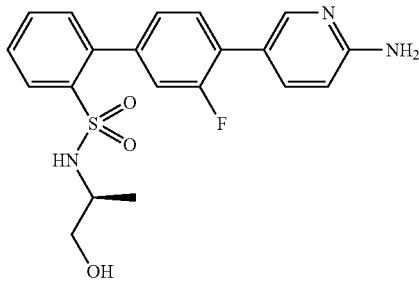

(R)-4'-(6-Aminopyridin-3-yl)-3'-fluoro-N-(1-hydroxypropan-2-yl)-[1,1'-biphenyl]-2-sulfonamide The title compound was prepared in a manner similar to that described in Example 347 using (R)-2-bromo-N-(1-hydroxypropan-2-yl)benzenesulfonamide. MS (CI): mass calcd. for $C_{20}H_{20}FN_3O_3S$, 401.12; m/z found, 402.0 [M+H]$^+$. $^1$H NMR (500 MHz, DMSO-d$_6$) δ 8.26-8.20 (d, J=2.1, 1H), 8.19-8.11 (d, J=9.2, 1H), 8.09-8.05 (m, 1H), 8.05-7.84 (s, 2H), 7.72-7.58 (m, 3H), 7.41-7.35 (m, 2H), 7.35-7.27 (m, 2H), 7.08-7.02 (d, J=9.2, 1H), 5.05-4.29 (m, 1H), 3.34-3.27 (dd, J=10.3, 5.0, 1H), 3.14-3.02 (m, 2H), 1.00-0.93 (d, J=6.5, 3H).

Example 353

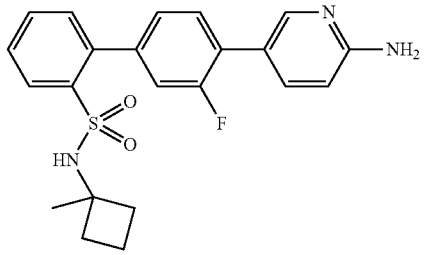

4'-(6-Aminopyridin-3-yl)-3'-fluoro-N-(1-methylcyclobutyl)-[1,1'-biphenyl]-2-sulfonamide The title compound was prepared in a manner similar to that described in Example 347 using 2-bromo-N-(1-methylcyclobutyl)benzenesulfonamide. MS (CI): mass calcd. for $C_{22}H_{22}FN_3O_2S$, 411.14; m/z found, 412.1 [M+H]$^+$. $^1$H NMR (500 MHz, DMSO-d$_6$) δ 8.24-8.20 (s, 1H), 8.20-8.15 (d, J=9.5, 1H), 8.15-7.90 (m, 3H), 7.70-7.58 (m, 3H), 7.55-7.51 (s, 1H), 7.41-7.28 (m, 3H), 7.10-7.05 (d. J=9.2, 1H), 2.15-2.05 (m, 2H), 1.71-1.51 (m, 4H), 1.26-1.18 (s, 3H).

Example 354

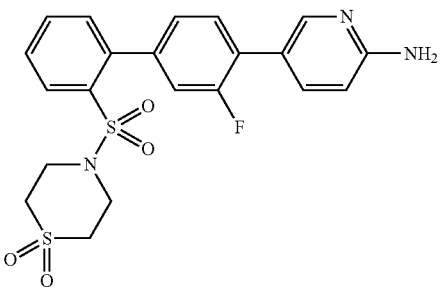

4-((4'-(6-Aminopyridin-3-yl)-3'-fluoro-[1,1'-biphenyl]-2yl)-sulfonyl)thiomorpholine 1,1-dioxide The title compound was prepared in a manner similar to that described in Example 347 using 4-((2-bromophenyl)sulfonyl)thiomorpholine 1,1-dioxide. MS (CI): mass calcd. for $C_{21}H_{20}FN_3O_4S_2$, 461.09; m/z found, 462.0 [M+H]$^+$. $^1$H NMR (500 MHz, DMSO-d$_6$) δ 8.27-8.21 (d, J=2.0, 1H), 8.20-8.14 (d, J=9.1, 1H), 8.13-7.88 (m, 3H), 7.82-7.76 (m, 1H), 7.72-7.62 (m, 2H), 7.48-7.39 (m, 2H), 7.37-7.31 (m, 1H), 7.10-7.02 (d, J=9.2, 1H), 3.12-3.04 (m, 4H), 3.34-3.26 (m, 4H).

Example 355

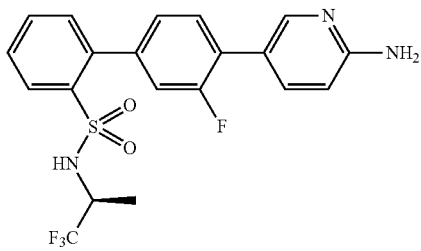

(S)-4'-(6-Aminopyridin-3-yl)-3'-fluoro-N-(1,1,1-trifluoropropan-2-yl)-[1,1'-biphenyl]-2-sulfonamide The title compound was prepared in a manner similar to that described in Example 347 using (S)-2-bromo-N-(1,1,1-trifluoropropan-2-yl)benzenesulfonamide. MS (CI): mass calcd. for $C_{20}H_{17}F_4N_3O_2S$, 439.10; m/z found, 440.1 [M+H]+. $^1$H NMR (500 MHz, DMSO-$d_6$) δ 8.56-8.49 (d, J=8.9, 1H), 8.26-8.20 (s, 1H), 8.20-8.12 (d, J=9.5, 1H), 8.09-7.82 (m, 3H), 7.74-7.59 (m, 3H), 7.42-7.37 (m, 1H), 7.36-7.27 (m, 2H), 7.09-7.01 (d, J=9.1, 1H), 3.98-3.86 (m, 1H), 1.22-1.11 (d, J=7.0, 3H).

Example 356

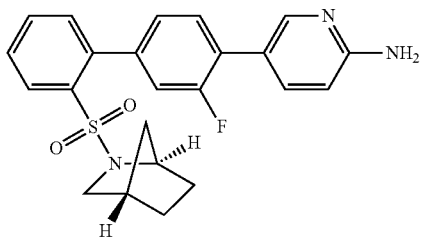

5-(2'-((1S,4S)-2-Oxa-5-azabicyclo[2.2.1]heptan-5-ylsulfonyl)-3-fluoro-[1,1'-biphenyl]-4-yl)pyridin-2-amine The title compound was prepared in a manner similar to that described in Example 347 using (1S,4S)-5-((2-bromophenyl)sulfonyl)-2-oxa-5-azabicyclo[2.2.1]heptane. MS (CI): mass calcd. for $C_{22}H_{20}FN_3O_3S$, 425.12; m/z found, 426.0 [M+H]+. $^1$H NMR (500 MHz, DMSO-$d_6$) δ 8.27-8.23 (d, J=2.0, 1H), 8.20-8.15 (d, J=9.2, 1H), 8.15-7.89 (m, 3H), 7.79-7.74 (m, 1H), 7.70-7.62 (m, 2H), 7.47-7.38 (m, 2H), 7.37-7.32 (m, 1H), 7.10-7.03 (d, J=9.2, 1H), 4.53-4.47 (s, 1H), 4.01-3.96 (s, 1H), 3.63-3.30 (m, 2H), 2.99-2.87 (m, 2H), 1.72-1.61 (d, J=10.0, 1H), 1.47-1.36 (m, 1H).

Example 357

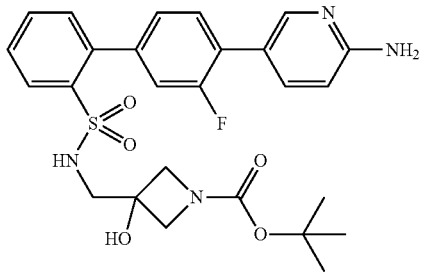

tert-Butyl 3-((4'-(6-aminopyridin-3-yl)-3'-fluoro-[1,1'-biphenyl]-2-ylsulfonamido)methyl)-3-hydroxyazetidine-1-carboxylate The title compound was prepared in a manner similar to that described in Example 347 using tert-butyl 3-((2-bromophenylsulfonamido)methyl)-3-hydroxyazetidine-1-carboxylate. MS (CI): mass calcd. for $C_{26}H_{29}FN_4O_5S$, 528.18; m/z found, 529.0 [M+H]+. $^1$H NMR (500 MHz, DMSO-$d_6$) δ 8.26-8.21 (d, J=2.0, 1H), 8.20-8.13 (d, J=9.4, 1H), 8.11-7.86 (m, 3H), 7.86-7.80 (m, 1H), 7.74-7.67 (m, 1H), 7.67-7.58 (m, 2H), 7.44-7.31 (m, 3H), 7.09-7.02 (d, J=9.1, 1H), 3.79-3.73 (m, 2H), 3.55-3.52 (m, 2H), 2.93-2.86 (d, J=6.5, 2H), 1.40-1.28 (s, 9H).

Example 358

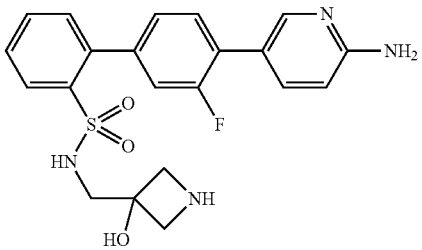

4'-(6-Aminopyridin-3-yl)-3'-fluoro-N-((3-hydroxyazetidin-3-yl)methyl)-[1,1'-biphenyl]-2-sulfonamide A mixture of tert-butyl 3-((2-bromophenylsulfonamido)methyl)-3-hydroxyazetidine-1-carboxylate (15 mg, 0.028 mmol), TFA (1 mL), and MeOH (1 mL) was maintained at rt for 2 hours, then concentrated to dryness. The residue was purified by HPLC to provide the title compound (8.0 mg, 52%) MS (CI): mass calcd. for $C_{21}H_{21}FN_4O_3S$, 428.13; m/z found, 429.0 [M+H]+. $^1$H NMR (500 MHz, DMSO-$d_6$) δ 8.84-8.70 (s, 1H), 8.68-8.52 (s, 1H), 8.26-8.19 (d, J=2.1, 1H), 8.13-8.03 (d, J=7.4, 1H), 8.01-7.94 (m, 1H), 7.94-7.88 (m, 1H), 7.74-7.71 (m, 1H), 7.69-7.65 (m, 1H), 7.63-7.59 (m, 1H), 7.48-7.42 (m, 1H), 7.42-7.31 (m, 2H), 7.05-6.91 (d, J=8.8, 1H), 6.33-6.17 (s, 1H), 3.94-3.87 (m, 2H), 3.76-3.69 (m, 2H), 3.05-3.00 (d, J=6.5, 2H).

Example 359

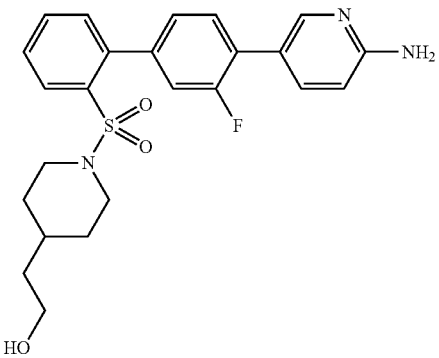

2-(1-(((4'-(6-Aminopyridin-3-yl)-3'-fluoro-[1,1'-biphenyl]-2-yl)sulfonyl)piperidin-4-yl)ethanol The title compound was prepared in a manner similar to that described in Example 347 using 2-(1-((2-bromophenyl)sulfonyl)piperidin-4-yl)ethanol. MS (CI): mass calcd. for $C_{24}H_{26}FN_3O_3S$, 455.17; m/z found, 456.3 [M+H]+. $^1$H NMR (500 MHz, DMSO-d$_6$) δ 8.24-8.20 (d, J=2.2, 1H), 8.17-8.09 (d, J=9.1, 1H), 8.02-7.98 (m, 1H), 3.37-3.36 (m, 5H), 7.97-7.78 (s, 2H), 7.77-7.73 (m, 1H), 7.69-7.64 (m, 1H), 7.64-7.59 (m, 1H), 7.44-7.41 (m, 1H), 7.41-7.35 (m, 1H), 7.34-7.30 (dd, J=7.9, 1.7, 1H), 7.07-6.99 (d, J=9.2, 1H), 3.40-3.34 (m, 3H), 3.25-3.21 (d, J=12.3, 2H), 2.43-2.34 (m, 2H), 1.59-1.50 (d, J=10.7, 2H), 1.45-1.31 (s, 1H), 1.31-1.20 (m, 2H), 0.89-0.78 (m, 2H).

Example 360

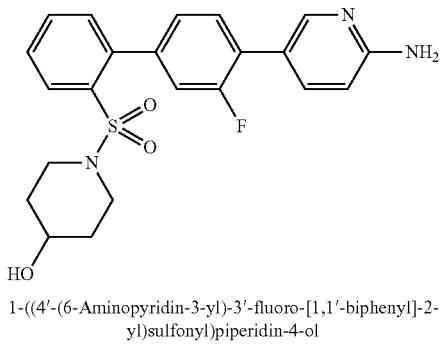 [SMILES: Nc1ccc(-c2ccc(-c3ccccc3S(=O)(=O)N3CCC(O)CC3)cc2F)cn1]

1-((4'-(6-Aminopyridin-3-yl)-3'-fluoro-[1,1'-biphenyl]-2-yl)sulfonyl)piperidin-4-ol The title compound was prepared in a manner similar to that described in Example 347 using 1-((2-bromophenyl)sulfonyl)piperidin-4-ol. MS (CI): mass calcd. for C$_{22}$H$_{22}$FN$_3$O$_3$S, 427.14; m/z found, 428.2 [M+H]$^+$. $^1$H NMR (500 MHz, DMSO-d$_6$) δ 8.26-8.22 (d, J=2.0, 1H), 8.19-8.15 (d, J=9.4, 1H), 8.14-7.92 (m, 3H), 7.78-7.73 (m, 1H), 7.69-7.65 (m, 1H), 7.65-7.60 (m, 1H), 7.45-7.40 (dd, J=7.6, 1.2, 1H), 7.40-7.35 (m, 1H), 7.33-7.28 (m, 1H), 7.09-7.04 (d, J=9.2, 1H), 3.54-3.52 (m, 2H), 3.09-3.01 (m, 2H), 2.69-2.61 (m, 2H), 1.64-1.53 (m, 2H), 1.28-1.17 (m, 2H).

Example 361

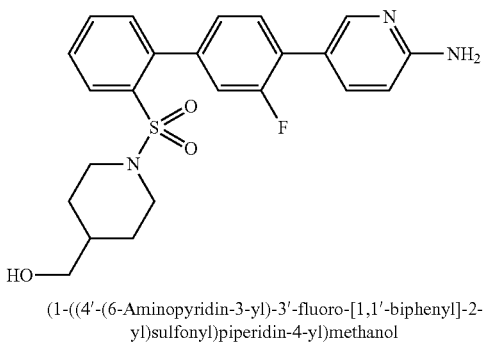 [SMILES: Nc1ccc(-c2ccc(-c3ccccc3S(=O)(=O)N3CCC(CO)CC3)cc2F)cn1]

(1-((4'-(6-Aminopyridin-3-yl)-3'-fluoro-[1,1'-biphenyl]-2-yl)sulfonyl)piperidin-4-yl)methanol The title compound was prepared in a manner similar to that described in Example 347 using (1-((2-bromophenyl)sulfonyl)piperidin-4-yl)methanol. MS (CI): mass calcd. for C$_{23}$H$_{24}$FN$_3$O$_3$S, 441.15; m/z found, 442.0 [M+H]$^+$. $^1$H NMR (500 MHz, DMSO-d$_6$) δ 8.26-7.94 (m, 5H), 7.78-7.72 (m, 1H), 7.70-7.60 (m, 2H), 7.45-7.36 (m, 2H), 7.34-7.30 (dd, J=8.0, 1.6, 1H), 7.10-7.04 (d, J=9.2, 1H), 3.29-3.24 (d, J=12.4, 2H), 3.19-3.14 (d, J=6.3, 2H), 2.45-2.36 (m, 2H), 1.60-1.52 (d, J=10.7, 2H), 1.41-1.29 (s, 1H), 0.94-0.78 (m, 2H).

Example 362

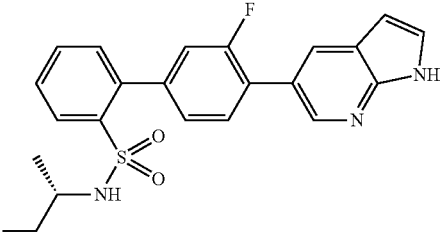

3'-Fluoro-N-[(1S)-2-hydroxy-1-methylethyl]-4'-(1H-pyrrolo[2,3-b]pyridin-5-yl)biphenyl-2-sulfonamide The title compound was prepared using methods analogous to those described in Example 376 using 5-(2-fluoro-4-(4,4,5,5-tetramethyl-1,3,2-dioxaborolan-2-yl)phenyl)-1H-pyrrolo[2,3-b]pyridine and (S)-2-bromo-N-(1-hydroxypropan-2-yl)benzenesulfonamide. MS (ESI): mass calcd. for C$_{22}$H$_{20}$FN$_3$O$_3$S, 425.12; m/z found, 426.0 [M+H]$^+$. $^1$H NMR (500 MHz, CDCl$_3$) δ 9.57 (s, 1H), 8.29-8.22 (m, 2H), 7.95-7.85 (m, 1H), 7.69-7.61 (m, 1H), 7.61-7.53 (m, 1H), 7.42-7.33 (m, 4H), 7.29 (d, J=7.8, 1H), 6.54-6.49 (m, 1H), 5.92 (d, J=6.7, 1H), 3.64-3.51 (m, 1H), 3.47-3.34 (m, 2H), 2.34 (s, 1H), 1.03 (d, J=6.5, 3H).

Example 363

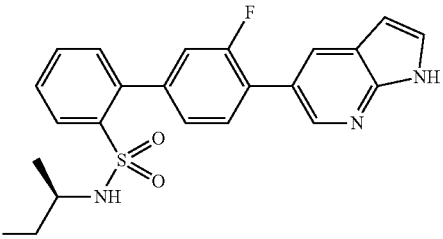

3'-Fluoro-N-[(1R)-2-hydroxy-1-methylethyl]-4'-(1H-pyrrolo[2,3-b]pyridin-5-yl)biphenyl-2-sulfonamide The title compound was prepared using methods analogous to those described in Example 376 using 5-(2-fluoro-4-(4,4,5,5-tetramethyl-1,3,2-dioxaborolan-2-yl)phenyl)-1H-pyrrolo[2,3-b]pyridine and (R)-2-bromo-N-(1-hydroxypropan-2-yl)benzenesulfonamide. MS (ESI): mass calcd. for C$_{22}$H$_{20}$FN$_3$O$_3$S, 425.12; m/z found, 426.0 [M+H]$^+$. $^1$H NMR (400 MHz, CDCl$_3$) δ 9.65 (s, 1H), 8.30-8.19 (m, 2H), 7.93-7.84 (m, 1H), 7.69-7.61 (m, 1H), 7.61-7.53 (m, 1H), 7.44-7.31 (m, 4H), 7.27 (d, J=7.8, 1H), 6.56-7.47 (m, 1H), 6.07 (d, J=6.5, 1H), 3.57 (t, J=7.0, 1H), 3.49-3.32 (m, 2H), 2.41 (s, 1H), 1.04 (d, J=6.4, 3H).

Example 364

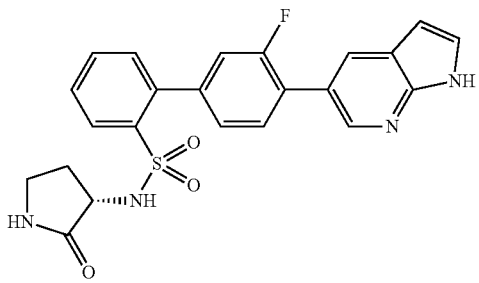

3'-Fluoro-N-[(3S)-2-oxopyrrolidin-3-yl]-4'-(1H-pyrrolo[2,3-b]pyridin-5-yl)biphenyl-2-sulfonamide The title compound was prepared using methods analogous to those described in Example 376 using 5-(2-fluoro-4-(4,4,5,5-tetramethyl-1,3,2-dioxaborolan-2-yl)phenyl)-1H-pyrrolo[2,3-b]pyridine and (S)-2-bromo-N-(1-hydroxypropan-2-yl)benzenesulfonamide. MS (ESI): mass calcd. for $C_{23}H_{19}FN_4O_3S$, 450.12; m/z found, 451.1 [M+H]+. $^1$H NMR (400 MHz, CDCl$_3$) δ Complex due to the presence of multiple conformations on the NMR time-scale, peaks listed for identification purposes only: δ 9.35 (s), 9.23 (s), 8.51-8.42 (m), 8.41-8.31 (m), 8.24-8.17 (m), 8.13-8.00 (m), 7.68-7.61 (m), 7.59-7.49 (m), 7.46-7.38 (m), 7.38-7.29 (m), 6.57-6.51 (m), 6.38 (s), 6.13 (s), 6.05 (s), 5.68 (s), 3.69-3.57 (m), 3.40-3.18 (m), 2.61-2.48 (m), 2.25-1.96 (m).

Example 365

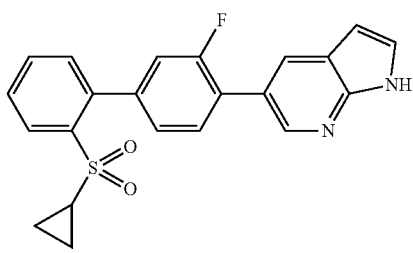

5-[2'-(Cyclopropylsulfonyl)-3-fluorobiphenyl-4-yl]-1H-pyrrolo[2,3-b]pyridine

The title compound was prepared using methods analogous to those described in Example 376 using 5-(2-fluoro-4-(4,4,5,5-tetramethyl-1,3,2-dioxaborolan-2-yl)phenyl)-1H-pyrrolo[2,3-b]pyridine and 1-bromo-2-(cyclopropylsulfonyl)benzene. MS (ESI): mass calcd. for $C_{22}H_{17}FN_2O_2S$, 392.10; m/z found, 393.0 [M+H]+. $^1$H NMR (400 MHz, CDCl$_3$) δ 9.26 (s, 1H), 8.62-8.52 (m, 1H), 8.24-8.12 (m, 2H), 7.71-7.63 (m, 1H), 7.62-7.53 (m, 2H), 7.45-7.31 (m, 4H), 6.64-6.55 (m, 1H), 2.19-2.08 (m, 1H), 1.18-1.08 (m, 2H), 0.93-0.82 (m, 2H).

Example 366

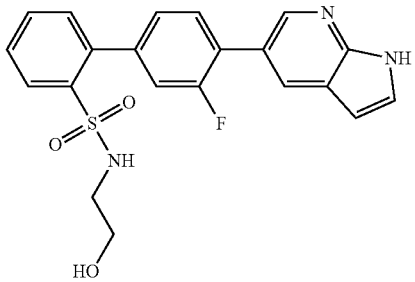

3'-Fluoro-N-(2-hydroxyethyl)-4'-(1H-pyrrolo[2,3-b]pyridin-5-yl)biphenyl-2-sulfonamide The title compound was prepared in a manner similar to that described in Example 88 using 5-bromo-1H-pyrrolo[2,3-b]pyridine and 3'-fluoro-N-(2-hydroxyethyl)-4'-(4,4,5,5-tetramethyl-1,3,2-dioxaborolan-2-yl)-[1,1'-biphenyl]-2-sulfonamide. MS (ESI): mass calcd. for $C_{21}H_{18}FN_3O_3S$, 411.11; m/z found, 412.0 [M+H]+. $^1$H NMR (500 MHz, CD$_3$OD) δ 8.44-8.41 (m, 1H), 8.24-8.21 (m, 1H), 8.14-8.05 (dd, J=8.0, 1.3, 1H), 7.71-7.64 (m, 1H), 7.63-7.55 (m, 2H), 7.46-7.44 (d, J=3.5, 1H), 7.44-7.41 (dd, J=7.6, 1.2, 1H), 7.36-7.34 (dd, J=3.8, 1.7, 1H), 7.34-7.31 (dd, J=7.3, 1.4, 1H), 6.59-6.55 (d, J=3.5, 1H), 3.52-3.47 (t, J=5.9, 2H), 2.92-2.87 (t. J=5.9, 2H).

Example 367

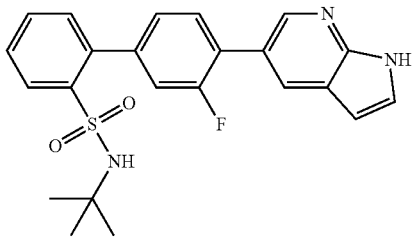

N-tert-Butyl-3'-fluoro-4'-(1H-pyrrolo[2,3-b]pyridin-5-yl)biphenyl-2-sulfonamide

The title compound was prepared in a manner similar to that described in Example 427 using 5-bromo-1H-pyrrolo[2,3-b]pyridine. MS (ESI): mass calcd. for $C_{23}H_{22}FN_3O_2S$, 423.14; m/z found, 424.1 [M+H]+. $^1$H NMR (500 MHz, CD$_3$OD) δ 8.56-8.45 (m, 2H), 8.18-8.11 (dd, J=8.0, 1.3, 1H), 7.70-7.61 (m, 2H), 7.61-7.55 (m, 3H), 7.44-7.35 (m, 3H), 6.76-6.69 (d, J=3.5, 1H), 1.09 (s, 9H).

Example 368

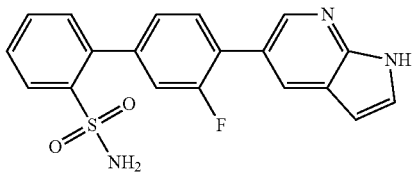

3'-Fluoro-4'-(1H-pyrrolo[2,3-b]pyridin-5-yl)biphenyl-2-sulfonamide

The title compound was prepared by forming N-tert-butyl-3'-fluoro-4'-(1H-pyrrolo[2,3-b]pyridin-5-yl)biphenyl-2-sulfonamide then removing the tert-butyl group by dissolving the crude N-tert-butyl-3'-fluoro-4'-(1H-pyrrolo[2,3-b]pyridin-5-yl)biphenyl-2-sulfonamide in 1 mL of trifluoroacetic acid and heating it at 60° Celsius for 2 hours, after which time the reaction was cooled, concentrated to dryness and purified using FCC. MS (ESI): mass calcd. for $C_{19}H_{14}FN_3O_2S$, 367.08; m/z found, 368.1 [M+H]$^+$. $^1$H NMR (500 MHz, CD$_3$OD) δ 8.43 (s, 1H), 8.26-8.22 (m, 1H), 8.17-8.12 (dd, J=8.0, 1.3, 1H), 7.69-7.62 (m, 1H), 7.62-7.55 (m, 2H), 7.47-7.44 (d, J=3.5, 1H), 7.44-7.40 (dd, J=7.6, 1.4, 1H), 7.38-7.30 (m, 2H), 6.60-6.56 (d, J=3.5, 1H).

Example 369

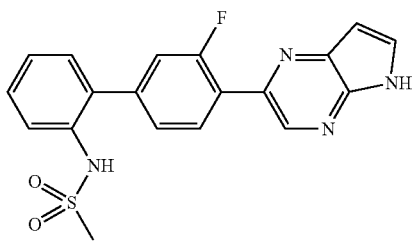

N-[3'-Fluoro-4'-(5H-pyrrolo[2,3-b]pyrazin-2-yl)biphenyl-2-yl]methanesulfonamide

Step A: 2-(4-Bromo-2-fluorphenyl)-5H-pyrrolo[2,3-b]pyrazine

To a 150 mL screw-cap vessel under nitrogen was added 5-bromo-4,7-diazaindole (1.0 g, 5.05 mmol), 4-bromo-2-fluorophenyl boronic acid (1.33 g, 6.06 mmol), Pd(dppf)Cl$_2$·CH$_2$Cl$_2$ (0.2 g, 0.24 mmol), K$_2$CO$_3$ (2.09 g, 15.2 mmol), 1,4-dioxane (35 mL) and water (13 mL). The mixture was sparged with nitrogen for 10 minutes, the vessel capped and the reaction heated at 95° Celsius for 24 hours. The reaction was then cooled to rt, diluted with ethyl acetate (200 mL) and washed with water (1×100 mL) and brine (1×100 mL). The organic layer was dried with Na$_2$SO$_4$ and evaporated to dryness. The crude product was purified by HPLC giving the title compound (515 mg, 35%). MS (ESI): mass calcd. for $C_{12}H_7BrFN_2$, 290.98; m/z found, 292.0 [M+H]$^+$.

Step B

To a mixture of 2-(4-bromo-2-fluorophenyl)-5H-pyrrolo[2,3-b]pyrazine (50 mg, 0.17 mmol), N-(2-(4,4,5,5-tetramethyl-1,3,2-dioxaborolan-2-yl)phenyl)-methane-sulfonamide (61 mg, 0.21 mmol) and Pd(dppf)Cl$_2$·CH$_2$Cl$_2$ (6.7 mg, 0.009 mmol) in a microwave vial were added acetonitrile (2.0 mL) and sat. NaHCO$_3$ (2.0 mL). The vial was sparged with nitrogen for 5 min then heated at 110° Celsius for 90 min via microwave irradiation. After cooling to rt, the reaction mixture was diluted with ethyl acetate (50 mL), washed with water (25 mL) and brine (25 mL), dried (Na$_2$SO$_4$) and concentrated to dryness. The crude product was purified by HPLC giving the title compound (45 mg, 69%). MS (ESI): mass calcd. for $C_{19}H_{15}FN_4O_2S$, 382.09; m/z found, 383.1 [M+H]$^+$. $^1$H NMR (400 MHz, CDCl$_3$) δ 10.38 (s, 1H), 8.78 (d, J=2.7, 1H), 8.20-8.12 (m, 1H), 7.71-7.64 (m, 2H), 7.48-7.39 (m, 1H), 7.37-7.31 (m, 2H), 7.28-7.21 (m, 2H), 6.91 (s, 1H), 6.81-6.75 (m, 1H), 2.93 (s, 3H).

Example 370

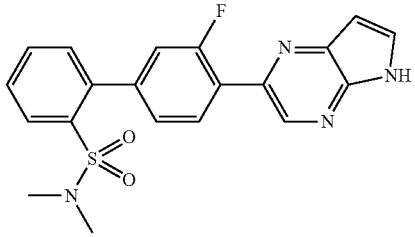

3'-Fluoro-N,N-dimethyl-4'-(5H-pyrrolo[2,3-b]pyrazin-2-yl)biphenyl-2-sulfonamide

The title compound was prepared using methods analogous to those described in Example 369 using N,N-dimethyl-2-(4,4,5,5-tetramethyl-1,3,2-dioxaborolan-2-yl)benzenesulfonamide in Step B. MS (ESI): mass calcd. for $C_{20}H_{17}FN_4O_2S$, 396.11; m/z found, 397.2 [M+H]$^+$. $^1$H NMR (400 MHz, CDCl$_3$) δ 10.57 (s, 1H), 8.79 (d, J=2.6, 1H), 8.15-8.04 (m, 2H), 7.69-7.59 (m, 2H), 7.58-7.51 (m, 1H), 7.41-7.31 (m, 3H), 6.81-6.74 (m, 1H), 2.48 (s, 6H).

Example 371

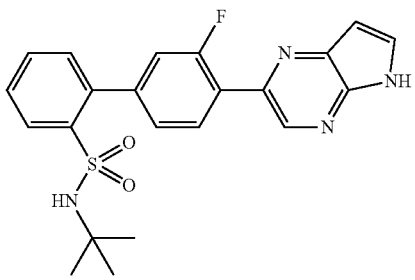

N-tert-Butyl-3'-fluoro-4'-(5H-pyrrolo[2,3-b]pyrazin-2-yl)biphenyl-2-sulfonamide

The title compound was prepared using methods analogous to those described in Example 369 using (2-(N-(tert-butyl)sulfamoyl)phenyl)boronic acid in Step B. MS (ESI): mass calcd. for $C_{22}H_{21}FN_4O_2S$, 424.14; m/z found, 425.1 [M+H]$^+$. $^1$H NMR (400 MHz, DMSO-d$_6$) δ 8.69 (d, J=2.6, 1H), 8.13-8.04 (m, 1H), 8.03-7.93 (m, 2H), 7.74-7.55 (m, 2H), 7.47-7.32 (m, 3H), 7.02 (s, 1H), 6.73 (d, J=3.6, 1H), 1.04 (s, 9H).

Example 372

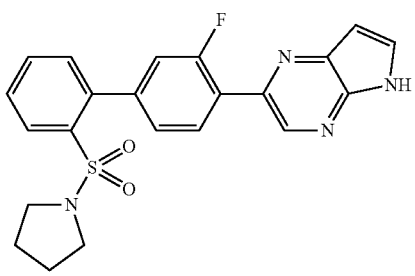

2-[3-Fluoro-2'-(pyrrolidin-1-ylsulfonyl)biphenyl-4-yl]-5H-pyrrolo[2,3-b]pyrazine The title compound was prepared using methods analogous to those described in Example 369 using (2-(pyrrolidin-1-ylsulfonyl)phenyl)boronic acid in Step B. MS (ESI): mass calcd. for $C_{22}H_{19}FN_4O_2S$, 422.12; m/z found, 423.1 $[M+H]^+$. $^1$H NMR (400 MHz, CDCl$_3$) δ 9.22 (br s, 1H), 8.83 (d, J=2.5, 1H), 8.24 (d, J=2.5, 1H), 8.19-8.13 (m, 1H), 8.14-8.07 (m, 1H), 7.96-7.90 (m, 1H), 7.72-7.65 (m, 1H), 7.65-7.58 (m, 1H), 7.57-7.49 (m, 1H), 7.49-7.30 (m, 1H), 6.88-6.79 (m, 1H), 3.02-2.90 (m, 3H), 1.77-1.66 (m, 3H), 1.59 (s, 2H).

Example 373

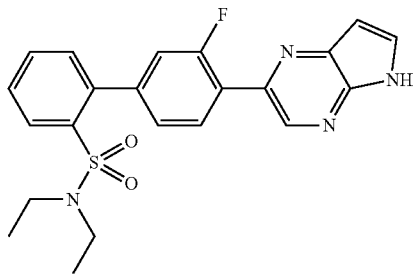

N,N-Diethyl-3'-fluoro-4'-(5H-pyrrolo[2,3-b]pyrazin-2-yl)biphenyl-2-sulfonamide

The title compound was prepared using methods analogous to those described in Example 369 using (2-(N,N-diethylsulfamoyl)phenyl)boronic acid in Step B. MS (ESI): mass calcd. for $C_{22}H_{21}FN_4O_2S$, 424.14; m/z found, 425.1 $[M+H]^+$. $^1$H NMR (400 MHz, CDCl$_3$) δ 9.23 (s, 1H), 8.83 (d, J=2.5, 1H), 8.15-8.05 (m, 2H), 7.71-7.66 (m, 1H), 7.63-7.56 (m, 1H), 7.55-7.48 (m, 1H), 7.39-7.30 (m, 3H), 6.86-6.82 (m, 1H), 3.03-2.88 (m, 4H), 1.00 (t, J=7.15, 6H).

Example 374

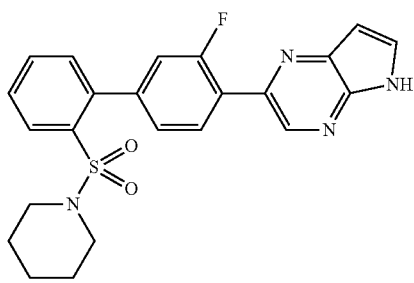

2-[3-Fluoro-2'-(piperidin-1-ylsulfonyl)biphenyl-4-yl]-5H-pyrrolo[2,3-b]pyrazine

The title compound was prepared using methods analogous to those described in Example 369 using (2-(piperidin-1-ylsulfonyl)phenyl)boronic acid in Step B. MS (ESI): mass calcd. for $C_{23}H_{21}FN_4O_2S$, 436.14; m/z found, 437.1 $[M+H]^+$. $^1$H NMR (400 MHz, CDCl$_3$) δ 9.20 (s, 1H), 8.83 (d, J=2.5, 1H), 8.18-8.03 (m, 2H), 7.71-7.65 (m, 1H), 7.65-7.58 (m, 1H), 7.57-7.51 (m, 1H), 7.41-7.32 (m, 3H), 6.87-6.82 (m, 1H), 2.93-2.81 (m, 4H), 1.46-1.36 (m, 6H).

Example 375

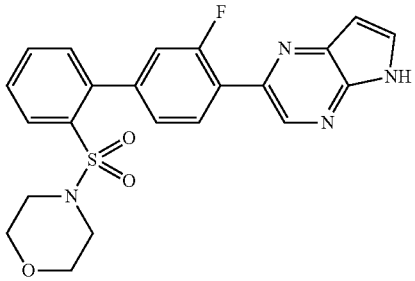

2-[3-Fluoro-2'-(morpholin-4-ylsulfonyl)biphenyl-4-yl]-5H-pyrrolo[2,3-b]pyrazine

The title compound was prepared using methods analogous to those described in Example 369 using (2-(morpholinosulfonyl)phenyl)boronic acid in Step B. MS (ESI): mass calcd. for $C_{22}H_{19}FN_4O_3S$, 438.12; m/z found, 439.1 $[M+H]^+$. $^1$H NMR (400 MHz, CDCl$_3$) δ 10.69 (s, 1H), 8.79 (d, J=2.6, 1H), 8.17-8.06 (m, 2H), 7.71-7.61 (m, 2H), 7.61-7.53 (m, 1H), 7.44-7.33 (m, 3H), 6.80-6.74 (m, 1H), 3.54-3.45 (m, 4H), 2.94-2.83 (m, 4H).

Example 376

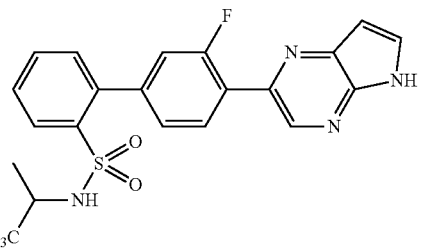

racemic 3'-Fluoro-4'-(5H-pyrrolo[2,3-b]pyrazin-2-yl)-N-(2,2,2-trifluoro-1-methylethyl)biphenyl-2-sulfonamide To a mixture of 2-(2-fluoro-4-(4,4,5,5-tetramethyl-1,3,2-dioxaborolan-2-yl)phenyl)-5H-pyrrolo[2,3-b]pyrazine (32 mg, 0.09 mmol), racemic 2-bromo-N-(1,1,1-trifluoropropan-2-yl)benzenesulfonamide (38 mg, 0.11 mmol) and Pd(dppf)Cl$_2$.CH$_2$Cl$_2$ (6 mg, 0.007 mmol) in a microwave vial were added acetonitrile (2.0 mL) and sat. NaHCO$_3$ (2.0 mL). The mixture was sparged with nitrogen for 5 min and then the vial capped and heated at 110° Celsius for 90 min. After cooling, the reaction mixture was diluted with ethyl acetate (50 mL) and washed with water (25 mL) and brine (25 mL). The organic layer was dried (Na$_2$SO$_4$) and concentrated to dryness. The crude product was purified by HPLC to give the title compound (28 mg, 64%). MS (ESI): mass calcd. $C_{21}H_{16}F_4N_4O_2S$, 464.09; m/z found, 465.1 $[M+H]^+$. $^1$H NMR (400 MHz, CDCl$_3$) δ 9.81 (s, 1H), 8.47 (s, 1H), 8.27-8.17 (m, 1H), 7.75-7.41 (m, 5H), 7.40-7.32 (m, 2H), 7.20 (d, J=12.6, 1H), 6.74-6.67 (m, 1H), 4.12-3.94 (m, 1H), 1.39-1.19 (m, 3H).

Example 377

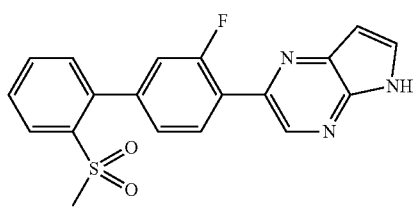

2-[3-Fluoro-2'-(methylsulfonyl)biphenyl-4-yl]-5H-pyrrolo[2,3-b]pyrazine

Step A: 2-[3-Fluoro-2'-(methylsulfanyl)biphenyl-4-yl]-5H-pyrrolo[2,3-b]pyrazine The title compound was prepared using methods analogous to those described in Example 369 using (2-(methylthio)phenyl)boronic acid in Step B. MS (ESI): mass calcd. for $C_{19}H_{14}FN_3S$., 335.09; m/z found, 336.1 [M+H]$^+$. $^1$H NMR (400 MHz, CDCl$_3$) δ 8.97 (s, 1H), 8.81 (d, J=2.5, 1H), 8.11-8.01 (m, 1H), 7.69-7.63 (m, 1H), 7.44-7.19 (m, 6H), 6.87-6.82 (m, 1H), 2.41 (s, 3H).

Step B

To a 10 mL round bottomed flask under nitrogen at rt were added 2-[3-fluoro-2'-(methylsulfanyl)biphenyl-4-yl]-5H-pyrrolo[2,3-b]pyrazine (32 mg, 0.07 mmol), m-CPBA (0.33 mg, 0.19 mmol) and DCM (1 mL). The mixture was stirred at rt for 2 hours. An additional 0.5 equivalents of mCPBA was added at this time and the reaction stirred an additional 1 hour. The reaction was then poured into sat. NaHCO$_3$ and extracted with DCM (×2). The solvent was then removed and the crude product purified by HPLC to give the title compound (12 mg, 35%). MS (ESI): mass calcd. for $C_{19}H_{14}FN_3O_2S$, 481.08; m/z found, 368.1 [M+H]$^+$. $^1$H NMR (400 MHz, CDCl$_3$) δ 9.48 (s, 1H), 8.82 (s, 1H), 8.27 (d, J=8.0, 1H), 8.18-8.09 (m, 1H), 7.77-7.67 (m, 2H), 7.66-7.57 (m, 1H), 7.48-7.36 (m, 3H), 6.89-6.83 (m, 1H), 2.76 (s, 3H).

Example 378

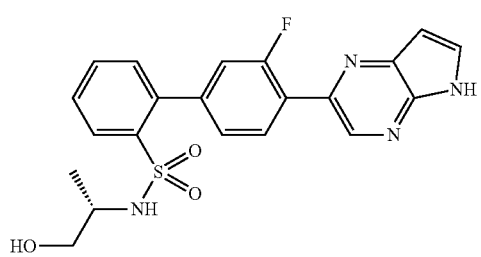

3'-Fluoro-N-[(1R)-2-hydroxy-1-methylethyl]-4'-(5H-pyrrolo[2,3-b]pyrazin-2-yl)biphenyl-2-sulfonamide The title compound was prepared using methods analogous to those described in Example 376 using (R)-2-bromo-N-(1-hydroxypropan-2-yl)benzenesulfonamide. MS (ESI): mass calcd. $C_{21}H_{19}FN_4O_3S$, 426.12; m/z found, 427.1 [M+H]$^+$. $^1$H NMR (400 MHz, CDCl$_3$) δ 9.40 (s, 1H), 8.74 (d, J=2.7, 1H), 8.60 (s, 1H), 8.29-8.20 (m, 1H), 7.83-7.74 (m, 1H), 7.71-7.62 (m, 2H), 7.61-7.50 (m, 1H), 7.47-7.36 (m, 2H), 7.35-7.16 (m, 1H), 5.50 (s, 1H), 3.65-3.49 (m, 1H), 3.48-3.28 (m, 2H), 2.16-1.94 (m, 1H), 1.04 (d, J=6.6, 3H).

Example 379

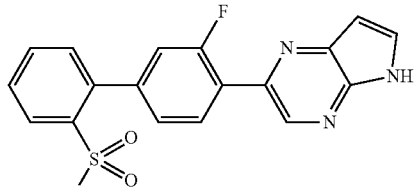

3'-Fluoro-N-methyl-4'-(5H-pyrrolo[2,3-b]pyrazin-2-yl)biphenyl-2-sulfonamide

The title compound was prepared using methods analogous to those described in Example 376 using 2-bromo-N-methylbenzenesulfonamide. MS (ESI): mass calcd. $C_{19}H_{15}FN_4O_2S$, 382.09; m/z found, 383.1 [M+H]$^+$. $^1$H NMR (400 MHz, CDCl$_3$) δ 9.35 (s, 1H), 8.67 (d, J=2.2, 1H), 8.29-8.18 (m, 1H), 8.03-7.83 (m, 1H), 7.71-7.55 (m, 3H), 7.47-7.29 (m, 3H), 6.83-6.73 (m, 1H), 4.85 (s, 1H), 2.56 (d, J=5.2, 3H).

Example 380

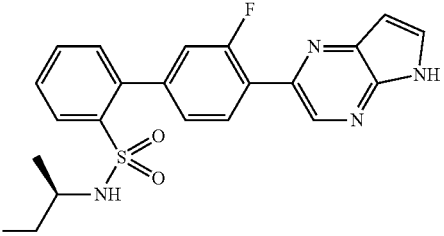

3'-Fluoro-N-[(1S)-2-hydroxy-1-methylethyl]-4'-(5H-pyrrolo[2,3-b]pyrazin-2-yl)biphenyl-2-sulfonamide The title compound was prepared using methods analogous to those described in Example 376 using (S)-2-bromo-N-(1-hydroxypropan-2-yl)benzenesulfonamide. MS (ESI): mass calcd. $C_{21}H_{19}FN_4O_3S$, 426.12; m/z found, 427.1 [M+H]$^+$. $^1$H NMR (400 MHz, CDCl$_3$) δ 9.40 (s, 1H), 8.74 (d, J=2.7, 1H), 8.60 (s, 1H), 8.29-8.20 (m, 1H), 7.83-7.74 (m, 1H), 7.71-7.62 (m, 2H), 7.61-7.50 (m, 1H), 7.47-7.36 (m, 2H), 7.35-7.16 (m, 1H), 5.50 (s, 1H), 3.65-3.49 (m, 1H), 3.48-3.28 (m, 2H), 2.16-1.94 (m, 1H), 1.04 (d, J=6.6, 3H).

Example 381

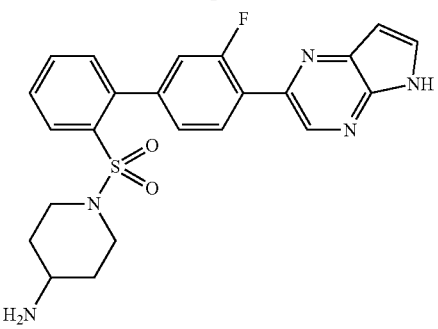

1-{[3-Fluoro-4'-(5H-pyrrolo[2,3-b]pyrazin-2-yl)biphenyl-2-yl]sulfonyl}piperidin-4-amine Step A: tert-Butyl (1-((3'-fluoro-4'-(1H-pyrrolo[2,3-b]pyridin-5-yl)-[1,1'-biphenyl]-2-yl)-sulfonyl)piperidin-4-yl)carbamate The title compound was prepared using methods analogous to those described in Example 376 using 5-(2-fluoro-4-(4,4,5,5-tetramethyl-1,3,2-dioxaborolan-2-yl)phenyl)-1H-pyrrolo[2,3-b]pyridine and tert-butyl (1-((2-bromophenyl)sulfonyl)piperidin-4-yl)carbamate. MS (ESI): mass calcd. for $C_{28}H_{30}FN_5O_4S$, 551.20; m/z found, 552.2 [M+H]$^+$. $^1$H NMR (400 MHz, CDCl$_3$) δ 9.04 (s, 1H), 8.81 (d, J=2.4, 1H), 8.18-8.04 (m, 2H), 7.69-7.59 (m, 2H), 7.60-7.48 (m, 1H), 7.48-7.30 (m, 4H), 6.85 (dd, J=3.7, 1.9, 1H), 4.44 (d, J=8.2, 1H), 3.79 (d, J=13.2, 1H), 3.49-3.27 (m, 3H), 2.91 (t, J=11.7, 1H), 2.47 (t, J=12.2, 2H), 1.98 (d, J=13.4, 1H), 1.79 (d, J=11.8, 2H), 1.42 (d, J=9.5, 12H), 1.31-1.10 (m, 3H).

Step B

The title compound was prepared as described in the preparation of Example 247 using tert-butyl (1-((3'-fluoro-4'-(1H-pyrrolo[2,3-b]pyridin-5-yl)-[1,1'-biphenyl]-2-yl)sulfonyl)piperidin-4-yl)carbamate. MS (ESI): mass calcd. for $C_{23}H_{22}FN_5O_2S$, 451.15; m/z found, 452.1 [M+H]$^+$. $^1$H NMR (400 MHz, CDCl$_3$) δ 9.66 (s, 1H), 8.82 (d, J=2.5, 1H), 8.20-8.04 (m, 2H), 7.69 (d, J=3.7, 1H), 7.66-7.59 (m, 1H), 7.58-7.51 (m, 1H), 7.42-7.32 (m, 3H), 6.83 (d, J=3.7, 1H), 3.43-3.30 (m, 2H), 2.70-2.59 (m, 1H), 2.55-2.40 (m, 2H), 1.75-1.65 (m, 2H), 1.56 (br s, 2H), 1.24-1.07 (m, 2H).

Example 382

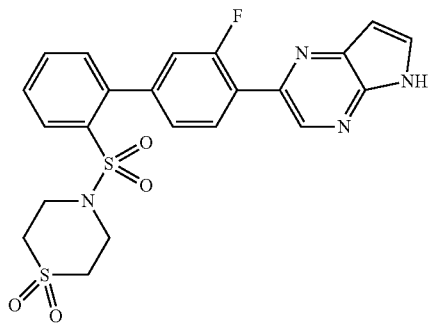

2-{2'-[(1,1-Dioxidothiomorpholin-4-yl)sulfonyl]-3-fluorobiphenyl-4-yl}-5H-pyrrolo[2,3-b]pyrazine The title compound was prepared using methods analogous to those described in Example 376 using 4-((2-bromophenyl)sulfonyl)thiomorpholine 1,1-dioxide. MS (ESI): mass calcd. for $C_{22}H_{19}FN_4O_4S_2$, 486.08; m/z found, 487.0 [M+H]$^+$. $^1$H NMR (400 MHz, CDCl$_3$) δ 9.19 (s, 1H), 8.83 (d, J=2.5, 1H), 8.22-8.11 (m, 2H), 7.75-7.65 (m, 2H), 7.64-7.55 (m, 1H), 7.43-7.37 (m, 1H), 7.34-7.21 (m, 2H), 6.88-6.80 (m, 1H), 3.45-3.26 (m, 4H), 3.09-2.94 (m, 4H).

Example 383

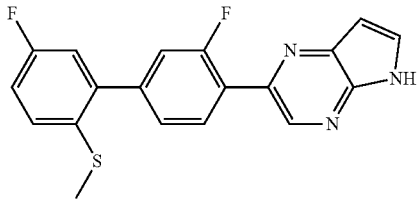

2-[3,5'-Difluoro-2'-(methylsulfanyl)biphenyl-4-yl]-5H-pyrrolo[2,3-b]pyrazine

The title compound was prepared using methods analogous to those described in Example 369 using (5-fluoro-2-(methylthio)phenyl)boronic acid in Step B. MS (ESI): mass calcd. for $C_{19}H_{13}F_2N_3S$, 353.08; m/z found, 354.1 [M+H]$^+$. $^1$H NMR (400 MHz, CDCl$_3$) δ 8.98 (s, 1H), 8.82 (d, J=2.6, 1H), 8.14-8.05 (m, 1H), 7.70-7.63 (m, 1H), 7.41-7.28 (m, 3H), 7.13-7.01 (m, 2H), 6.87-6.80 (m, 1H), 2.36 (s, 3H).

Example 384

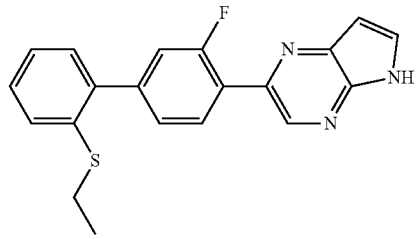

2-[2'-(Ethylsulfanyl)-3-fluorobiphenyl-4-yl]-5H-pyrrolo[2,3-b]pyrazine

The title compound was prepared using methods analogous to those described in Example 369 using (2-(ethylthio)phenyl)boronic acid in Step B. MS (ESI): mass calcd. for $C_{20}H_{16}FN_3S$, 349.10: m/z found, 350.1 [M+H]$^+$. $^1$H NMR (400 MHz, CDCl$_3$) δ 9.12 (s, 1H), 8.83 (d, J=2.6, 1H), 8.11-8.02 (m, 1H), 7.69-7.63 (m, 1H), 7.44-7.21 (m, 6H), 6.86-6.81 (m, 1H), 2.85 (q, J=7.4, 2H), 1.26 (t, J=7.4, 3H).

Example 385

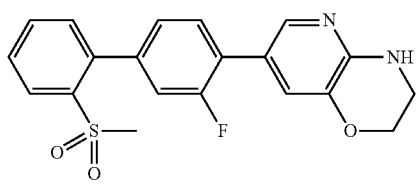

7-[3-Fluoro-2'-(methylsulfonyl)biphenyl-4-yl]-3,4-dihydro-2H-pyrido[3,2-b][1,4]oxazine The title compound was prepared in a manner similar to that described in Example 444 using 7-(2-fluoro-4-(4,4,5,5-tetramethyl-1,3-dioxolan-2-yl)phenyl)-3,4-dihydro-2H-pyrido[3,2-b][1,4]oxazine and 1-bromo-2-(methylsulfonyl)benzene. MS (ESI): mass calcd. for $C_{20}H_{17}FN_2O_3S$, 384.09; m/z found, 385.1 $[M+H]^+$. $^1H$ NMR (400 MHz, $CDCl_3$) δ 8.27-8.24 (m, 1H), 7.99-7.93 (m, 1H), 7.71-7.65 (m, 1H), 7.63-7.57 (m, 1H), 7.47 (m, 1H), 7.41-7.38 (m, 1H), 7.33-7.27 (m, 3H), 4.32-4.24 (m, 2H), 3.67-3.59 (m, 2H), 2.76 (s, 3H).

Example 386

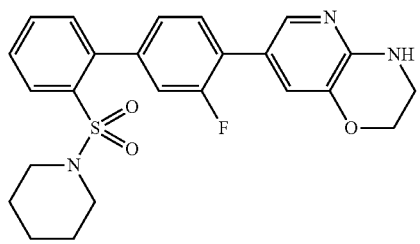

7-[3-Fluoro-2'-(piperidin-1-ylsulfonyl)biphenyl-4-yl]-3,4-dihydro-2H-pyrido[3,2-b][1,4]oxazine The title compound was prepared in a manner similar to that described in Example 444 using 7-(2-fluoro-4-(4,4,5,5-tetramethyl-1,3-dioxolan-2-yl)phenyl)-3,4-dihydro-2H-pyrido[3,2-b][1,4]oxazine and 1-((2-bromophenyl)sulfonyl)piperidine. MS (ESI): mass calcd. for $C_{24}H_{24}FN_3O_3S$, 453.15; m/z found, 454.2 $[M+H]^+$. $^1H$ NMR (400 MHz, $CD_3OD$) δ 8.07-8.03 (m, 1H), 7.82 (d, J=1.0, 1H), 7.73-7.67 (m, 2H), 7.65-7.55 (m, 2H), 7.42-7.39 (m, 1H), 7.36-7.30 (m, 2H), 4.41-4.32 (m, 2H), 3.74-3.71 (m, 2H), 2.91-2.79 (m, 4H), 1.49-1.37 (m, 6H).

Example 387

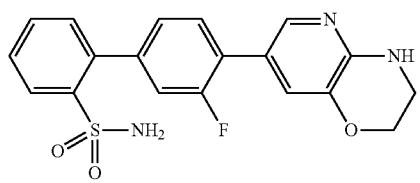

4'-(3,4-Dihydro-2H-pyrido[3,2-b][1,4]oxazin-7-yl)-3'-fluorobiphenyl-2-sulfonamide The title compound was prepared in a manner similar to that described in Example 444 using 7-(2-fluoro-4-(4,4,5,5-tetramethyl-1,3-dioxolan-2-yl)phenyl)-3,4-dihydro-2H-pyrido[3,2-b][1,4]oxazine and 2-bromobenzenesulfonamide. MS (ESI): mass calcd. for $C_{19}H_{16}FN_3O_3S$, 385.09; m/z found, 386.2 $[M+H]^+$. $^1H$ NMR (400 MHz, $CD_3OD$) δ 8.14-8.11 (m, 1H), 7.80 (d, J=1.0, 1H), 7.73-7.71 (m, 1H), 7.68-7.62 (m, 1H), 7.61-7.52 (m, 2H), 7.39-7.31 (m, 3H), 4.40-4.34 (m, 2H), 3.75-3.69 (m, 2H).

Example 388

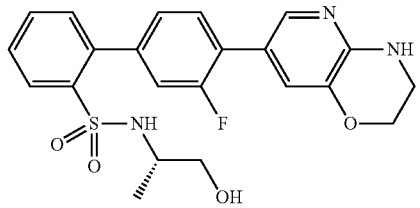

4'-(3,4-Dihydro-2H-pyrido[3,2-b][1,4]oxazin-7-yl)-3'-fluoro-N-[(1S)-2-hydroxy-1-methylethyl]biphenyl-2-sulfonamide The title compound was prepared in a manner similar to that described in Example 444 using 7-(2-fluoro-4-(4,4,5,5-tetramethyl-1,3-dioxolan-2-yl)phenyl)-3,4-dihydro-2H-pyrido[3,2-b][1,4]oxazine and (S)-2-bromo-N-(1-hydroxypropan-2-yl)benzenesulfonamide. MS (ESI): mass calcd. for $C_{22}H_{22}FN_3O_4S$, 443.13; m/z found, 444.1 $[M+H]^+$. $^1H$ NMR (400 MHz, $CD_3OD$) δ 8.15-8.12 (m, 1H), 7.80 (m, 1H), 7.72 (d, J=1.3, 1H), 7.69-7.64 (m, 1H), 7.62-7.52 (m, 2H), 7.40-7.33 (m, 3H), 4.37 (t, J=4.6, 2H), 3.76-3.69 (m, 2H), 3.43-3.36 (m, 1H), 3.30-3.26 (m, 1H), 3.24-3.16 (m, 1H), 1.04-1.01 (m, 3H).

Example 389

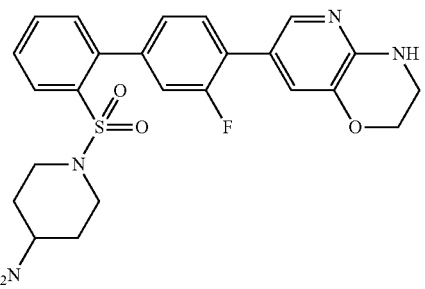

1-{[4'-(3,4-Dihydro-2H-pyrido[3,2-b][1,4]oxazin-7-yl)-3'-fluorobiphenyl-2-yl]sulfonyl}piperidin-4-amine The title compound was prepared in a manner similar to that described in Example 444 using 7-(2-fluoro-4-(4,4,5,5-tetramethyl-1,3-dioxolan-2-yl)phenyl)-3,4-dihydro-2H-pyrido[3,2-b][1,4]oxazine and 1-((2-bromophenyl)sulfonyl)piperidin-4-amine. MS (ESI): mass calcd. for $C_{24}H_{25}FN_4O_3S$, 468.16; m/z found, 469.1 $[M+H]^+$. $^1H$ NMR (400 MHz, $CD_3OD$) δ 8.09-8.05 (m, 1H), 7.83 (d, J=1.1, 1H), 7.75-7.68 (m, 2H), 7.66-7.55 (m, 2H), 7.43-7.39 (m, 1H), 7.34-7.26 (m, 2H), 4.39-4.35 (m, 2H), 3.76-3.68 (m, 2H), 3.47 (d, J=13.4, 2H), 3.21-3.11 (m, 1H), 2.60-2.50 (m, 2H), 1.96-1.87 (m, 2H), 1.56-1.43 (m, 2H).

Example 390

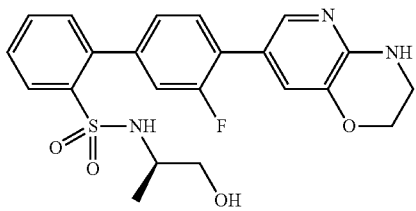

4'-(3,4-Dihydro-2H-pyrido[3,2-b][1,4]oxazin-7-yl)-3'-fluoro-N-[(1R)-2-hydroxy-1-methylethyl]biphenyl-2-sulfonamide The title compound was prepared in a manner similar to that described in Example 444 using 7-(2-fluoro-4-(4,4,5,5-tetramethyl-1,3-dioxolan-2-yl)phenyl)-3,4-dihydro-2H-pyrido[3,2-b][1,4]oxazine and (R)-2-bromo-N-(1-hydroxypropan-2-yl)benzenesulfonamide. MS (ESI): mass calcd. for $C_{22}H_{22}FN_3O_4S$, 443.13; m/z found, 444.1 [M+H]+. $^1$H NMR (400 MHz, CD$_3$OD) δ 8.16-8.10 (m, 1H), 7.82-7.79 (m, 1H), 7.74-7.71 (m, 1H), 7.70-7.64 (m, 1H), 7.61-7.57 (m, 1H), 7.54-7.46 (m, 1H), 7.40-7.33 (m, 3H), 4.40-4.36 (m, 2H), 3.75-3.69 (m, 2H), 3.48-3.33 (m, 2H), 3.24-3.16 (m, 1H), 1.05-1.01 (m, 3H).

Example 391

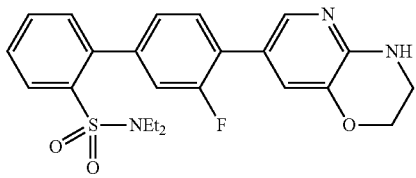

4'-(3,4-Dihydro-2H-pyrido[3,2-b][1,4]oxazin-7-yl)-N,N-diethyl-3'-fluorobiphenyl-2-sulfonamide The title compound was prepared in a manner similar to that described in Example 444 using 7-(2-fluoro-4-(4,4,5,5-tetramethyl-1,3-dioxolan-2-yl)phenyl)-3,4-dihydro-2H-pyrido[3,2-b][1,4]oxazine and 2-bromo-N,N-diethylbenzenesulfonamide. MS (ESI): mass calcd. for $C_{23}H_{24}FN_3O_3S$, 441.15; m/z found, 442.2 [M+H]+. $^1$H NMR (400 MHz, CD$_3$OD) δ 8.03-8.00 (m, 1H), 7.82 (d, J=1.0, 1H), 7.73-7.65 (m, 2H), 7.62-7.55 (m, 2H), 7.40-7.36 (m, 1H), 7.31 (s, 1H), 7.30-7.28 (m, 1H), 4.39-4.35 (m, 2H), 3.74-3.70 (m, 2H), 2.99 (q, J=7.1, 4H), 1.01 (t. J=7.1, 6H).

Example 392

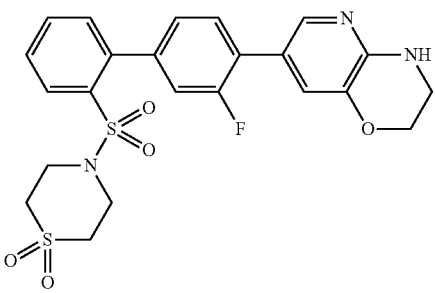

7-{2'-[(1,1-Dioxidothiomorpholin-4-yl)sulfonyl]-3-fluorobiphenyl-4-yl}-3,4-dihydro-2H-pyrido[3,2-b][1,4]oxazine

Step A: 7-(4-Chloro-2-fluorophenyl-3,4-dihydro-2H-pyrido[3,2-b][1,4]oxazine

Prepared in a manner similar to that found in Example 1 using of 7-bromo-3,4-dihydro-2H-pyrido[3,2-b][1,4]oxazine with (4-chloro-2-fluorophenyl)boronic acid. $^1$H NMR (400 MHz, CDCl$_3$) δ 7.84 (m, 1H), 7.35-7.28 (m, 1H), 7.20-7.14 (m, 3H), 4.29-4.25 (m, 2H), 3.64-3.58 (m, 2H).

Step B: 7-(2-Fluoro-4-(4,4,5,5-tetramethyl-1,3-dioxolan-2-yl)phenyl)-3,4-dihydro-2H-pyrido[3,2-b][1,4]oxazine Into a 100 mL flask were added 7-(4-chloro-2-fluorophenyl)-3,4-dihydro-2H-pyrido[3,2-b][1,4]oxazine (1.25 g, 4.72 mmol), 4,4,4',4',5,5,5',5'-octamethyl-2,2'-bi(1,3,2-dioxaborolane) 4,4,4',4',5,5,5',5'-octamethyl-2,2'-bi(1,3,2-dioxaborolane) (1.5 g, 5.9 mmol), KOAc (1.39 g, 14.2 mmol). Chloro(2-dicyclohexylphosphino-2',4',6'-triisopropyl-1,1'-biphenyl)[2-(2'-amino-1,1'-biphenyl)]palladium(II), 186 g, 0.236 mmol), and a stir bar. The flask was sealed with a rubber septum and sparged with N$_2$. The flask was charged with freshly sparged 1,4-dioxane (25 mL) and heated at 80° Celsius for 16 hours. The reaction was cooled to rt and concentrated to dryness. The crude product was purified by FCC to give 7-(2-fluoro-4-(4,4,5,5-tetramethyl-1,3-dioxolan-2-yl)phenyl)-3,4-dihydro-2H-pyrido[3,2-b][1,4]oxazine (1.208 g, 71%). $^1$H NMR (500 MHz, CDCl$_3$) δ 7.86-7.84 (m, 1H), 7.61-7.59 (m, 1H), 7.56-7.53 (m, 1H), 7.38 (m, 1H), 7.27-7.24 (m, 1H), 4.27-4.22 (m, 2H), 3.61-3.58 (m, 2H), 2.09 (s, 1H), 1.35 (s, 12H).

Step C

7-{2'-[(1,1-Dioxidothiomorpholin-4-yl)sulfonyl]-3-fluorobiphenyl-4-yl}-3,4-dihydro-2H-pyrido[3,2-b]-b][1,4]oxazine. Prepared in a manner similar to that found in Example 444 using 7-(2-fluoro-4-(4,4,5,5-tetramethyl-1,3-dioxolan-2-yl)phenyl)-3,4-dihydro-2H-pyrido[3,2-b]-b][1,4]oxazine with 4-((2-bromophenyl)sulfonyl)thiomorpholine 1,1-dioxide. MS (ESI): mass calcd. for $C_{23}H_{22}FN_3O_5S_2$, 503.10; m/z found, 504.1 [M+H]+. $^1$H NMR (400 MHz, CD$_3$OD) δ 8.16-8.13 (m, 1H), 7.85-7.83 (m, 1H), 7.78-7.72 (m, 2H), 7.69-7.60 (m, 2H), 7.45-7.41 (m, 1H), 7.37-7.30 (m, 2H), 4.41-4.35 (m, 2H), 3.76-3.68 (m, 2H), 3.38-3.33 (m, 4H), 3.06-2.98 (m, 4H).

Example 393

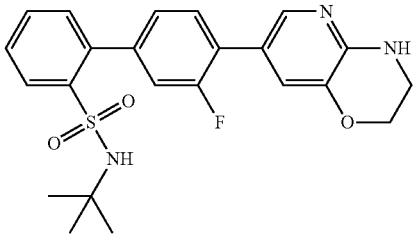

N-tert-Butyl-4'-(3,4-dihydro-2H-pyrido[3,2-b][1,4]oxazin-7-yl)-3'-fluorobiphenyl-2-sulfonamide The title compound was prepared in a manner similar to that described in Example 444 using N-(tert-butyl)-3'-fluoro-4'-(4,4,5,5-tetramethyl-1,3,2-dioxaborolan-2-yl)-[1, 1'-biphenyl]-2-sulfonamide and 7-bromo-3,4-dihydro-2H-pyrido[3,2-b][1,4]oxazine. MS (ESI): mass calcd. for $C_{23}H_{24}FN_3O_3S$, 441.15; m/z found, 442.2 [M+H]$^+$. $^1$H NMR (400 MHz, CD$_3$OD) δ 8.15-8.12 (m, 1H), 7.80 (d, J=0.9, 1H), 7.72-7.69 (m, 1H), 7.68-7.62 (m, 1H), 7.60-7.54 (m, 2H), 7.39-7.33 (m, 3H), 4.42-4.33 (m, 2H), 3.75-3.69 (m, 2H), 1.09 (s, 9H).

Example 394

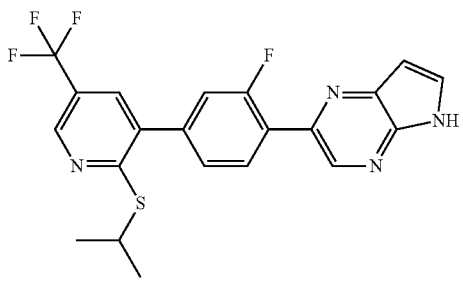

2-(2-Fluoro-4-{2-[(1-methylethyl)sulfanyl]-5-(trifluoromethyl)pyridin-3-yl}phenyl)-5H-pyrrolo[2,3-b]pyrazine The title compound was prepared using methods analogous to those described in Example 369 using (2-(isopropylthio)-5-(trifluoromethyl)pyridine-3-yl)boronic acid in Step B. MS (ESI): mass calcd. for $C_{21}H_{16}F_4N_4S$, 432.10; m/z found, 433.1 [M+H]$^+$. $^1$H NMR (400 MHz, CDCl$_3$) δ 9.12 (s, 1H), 8.83 (d, J=2.6, 1H), 8.74-8.68 (m, 1H), 8.19-8.10 (m, 1H), 7.71-7.66 (m, 1H), 7.62 (d, J=1.9, 1H), 7.42-7.37 (m, 1H), 7.33 (dd, J=1.7, 11.52, 1H), 6.87-6.82 (m, 1H), 4.19-4.03 (m, 1H), 1.40 (d, J=6.8, 6H).

Example 395

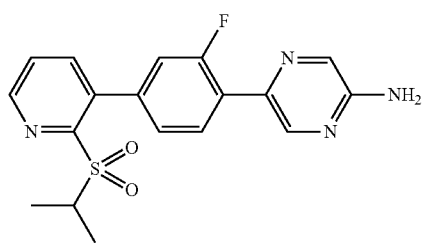

5-(2-Fluoro-4-{2-[(1-methylethyl)sulfonyl]pyridin-3-yl}phenyl)pyrazin-2-amine

Step A: 3-Bromo-2-(isopropylthio)pyridine

3-Bromopyridine-2-thiol (500 mg, 2.63 mmol) was added drop-wise to a suspension of sodium hydride in mineral oil (60%, 126 mg, 3.16 mmol) in DMF (5.0 mL) at 0° Celsius. The mixture was then stirred at 0° Celsius for 30 min followed by removal of the ice bath and stirring at rt for an additional 30 min. 2-Iodopropane (537 mg, 3.16 mmol) was then added and the reaction stirred at 60° Celsius for 18 hours. The reaction was cooled to rt, carefully diluted with water (100 mL), and extracted with ethyl acetate (2×100 mL). The combined organic extracts were dried with Na$_2$SO$_4$, filtered and concentrated to dryness. The crude product was purified by FCC giving 453 mg (74%) of the target thioether. MS (ESI): mass calcd. for $C_8H_{10}BrNS$, 230.97; m/z found, 232.1 [M+H]$^+$.

Step B: 3-Bromo-2-(isopropylsulfonyl)pyridine

3-Bromo-2-(isopropylthio)pyridine (100 mg, 0.43 mmol) was dissolved in DCM (6.0 mL) and m-CPBA (198 mg, 1.15 mmol) added. The reaction was stirred for 1.5 hours, and then treated with additional m-CPBA (100 mg, 0.058 mmol). Once complete conversion was achieved, the mixture was poured into sat. NaHCO$_3$ (50 mL) and extracted with DCM (2×50 mL). The combined extracts were concentrated to dryness and the crude product (112 mg, 98%) was used in next step without further purification.

Step C

The title compound was prepared using methods analogous to those described in Example 376 using 5-(2-fluoro-4-(4,4,5,5-tetramethyl-1,3,2-dioxaborolan-2-yl)phenyl)pyrazin-2-amine and 3-bromo-2-(isopropylsulfonyl)pyridine yielding 52 mg (88%) of the title compound. MS (ESI): mass calcd. for $C_{18}H_{17}FN_4O_2S$, 372.11; m/z found, 373.0 [M+H]$^+$. $^1$H NMR (400 MHz, CDCl$_3$) δ 8.69 (dd, J=4.6, 1.7, 1H), 8.60 (dd, J=2.1, 1.5, 1H), 8.10 (d, J=1.5, 1H), 8.08-7.98 (m, 1H), 7.81 (dd, J=7.8, 1.6, 1H), 7.58 (dd, J=7.8, 4.6, 1H), 7.38 (dd, J=8.0, 1.8, 1H), 7.32 (dd, J=11.7, 1.7, 1H), 4.71 (s, 2H), 4.19 (hept, J=6.8, 1H), 1.31 (d, J=6.9, 6H).

Example 396

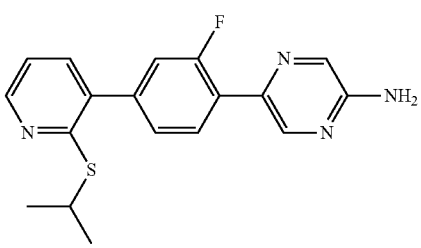

5-(2-Fluoro-4-{2-[(1-methylethyl)sulfanyl]pyridin-3-yl}phenyl)pyrazin-2-amine

The title compound was prepared using methods analogous to those described in Example 376 using 5-(2-fluoro-4-(4,4,5,5-tetramethyl-1,3,2-dioxaborolan-2-yl)phenyl)pyrazin-2-amine and 3-bromo-2-(isopropylthio)pyridine. MS (ESI): mass calcd. for $C_{18}H_{17}FN_4S$, 340.12; m/z found, 341.1 [M+H]$^+$. $^1$H NMR (400 MHz, CDCl$_3$) δ 8.62-8.57 (m, 1H), 8.49-8.43 (m, 1H), 8.12 (d, J=1.5, 1H), 8.04-7.93 (m, 1H), 7.45-7.39 (m, 1H), 7.34-7.30 (m, 1H), 7.29-7.22 (m, 1H), 7.11-7.03 (m, 1H), 4.69 (s, 2H), 4.17-4.00 (m, 1H), 1.37 (d, J=6.8, 6H).

Example 397

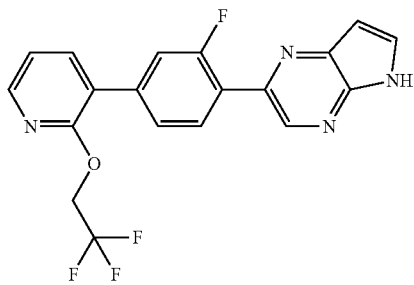

2-{2-Fluoro-4-[2-(2,2,2-trifluoroethoxy)pyridin-3-yl]phenyl}-5H-pyrrolo[2,3-b]pyrazine The title compound was prepared using methods analogous to those described in Example 369 using (2-((2,2,2-trifluoroethoxy)pyridine-3-yl)boronic acid in Step B. MS (ESI): mass calcd. for $C_{19}H_{12}F_4N_4O$, 388.09; m/z found, 389.1 [M+H]$^+$. $^1$H NMR (400 MHz, CDCl$_3$) δ 9.10 (s, 1H), 8.83 (d, J=2.5, 1H), 8.21-8.16 (m, 1H), 8.16-8.07 (m, 1H), 7.82-7.76 (m, 1H), 7.71-7.64 (m, 1H), 7.57-7.52 (m, 1H), 7.51-7.44 (m, 1H), 7.16-7.09 (m, 1H), 6.87-6.82 (m, 1H), 4.95-4.79 (m, 2H).

Example 398

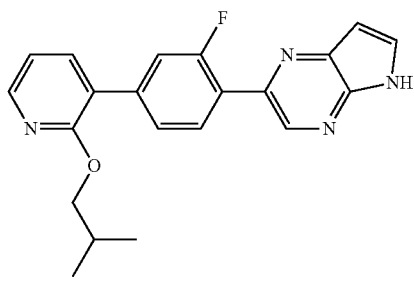

2-{2-Fluoro-4-[2-(2-methoxypropoxy)pyridin-3-yl]phenyl}-5H-pyrrolo[2,3-b]pyrazine The title compound was prepared using methods analogous to those described in Example 369 using (2-isobutoxypyridin-3-yl)boronic acid in Step B. MS (ESI): mass calcd. for $C_{21}H_{19}FN_4O$, 362.15; m/z found, 363.1 [M+H]$^+$. $^1$H NMR (400 MHz, CDCl$_3$) δ 9.26 (s, 1H), 8.84 (d, J=2.5, 1H), 8.23-8.15 (m, 1H), 8.14-8.04 (m, 1H), 7.74-7.65 (m, 2H), 7.59-7.48 (m, 2H), 7.03-6.96 (m, 1H), 6.88-6.81 (m, 1H), 4.17 (d, J=6.6, 2H), 2.33-1.99 (m, 1H), 1.02 (d, J=6.7, 6H).

Example 399

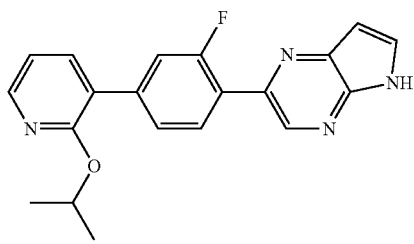

2-{2-Fluoro-4-[2-(1-methylethoxy)pyridin-3-yl]phenyl}-5H-pyrrolo[2,3-b]pyrazine

The title compound was prepared using methods analogous to those described in Example 369 using (2-isopropoxypyridin-3-yl)boronic acid in Step B. MS (ESI): mass calcd. for $C_{20}H_{17}FN_4O$, 348.14; m/z found, 349.1 [M+H]$^+$. $^1$H NMR (400 MHz, CDCl$_3$) δ 9.22 (s, 1H), 8.83 (d, J=2.5, 1H), 8.17 (dd, J=1.9, 4.9, 1H), 8.11-8.01 (m, 1H), 7.72-7.64 (m, 2H), 7.57-7.46 (m, 2H), 6.96 (dd, J=5.0, 7.3, 1H), 6.87-6.80 (m, 1H), 5.52-5.37 (m, 1H), 1.38 (d, J=6.2, 6H).

Example 400

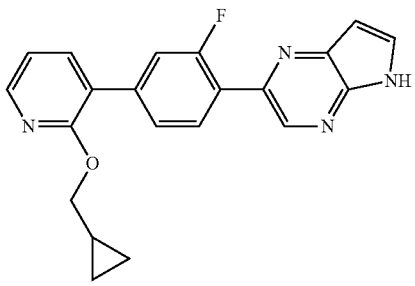

2-{4-[2-(Cyclopropylmethoxy)pyridin-3-yl]-2-fluorophenyl}-5H-pyrrolo[2,3-b]pyrazine The title compound was prepared using methods analogous to those described in Example 369 using (2-(cyclopropylmethoxy)pyridin-3-yl)boronic acid in Step B. MS (ESI): mass calcd. for $C_{21}H_{17}FN_4O$, 360.14; m/z found, 361.1 [M+H]$^+$. $^1$H NMR (400 MHz, CDCl$_3$) G 9.28 (s, 1H), 8.83 (d, J=2.5, 1H), 8.19-8.14 (m, 1H), 8.13-8.04 (m, 1H), 7.74-7.64 (m, 2H), 7.61-7.53 (m, 2H), 6.99 (dd, J=5.0, 7.4, 1H), 6.84 (dd, J=1.9, 3.7, 1H), 4.25 (d, J=7.0, 2H), 1.39-1.23 (m, 1H), 0.67-0.57 (m, 2H), 0.41-0.31 (m, 2H).

Example 401

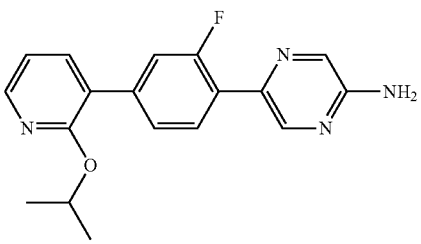

5-{2-Fluoro-4-[2-(1-methylethoxy)pyridin-3-yl]phenyl}pyrazin-2-amine

The title compound was prepared using methods analogous to those described in Example 369 using (2-isopropoxypyridin-3-yl)boronic acid and 5-(4-bromo-2-fluorophenyl)pyrazin-2-amine in Step B. MS (ESI): mass calcd. for $C_{18}H_{17}FN_4O$, 324.14; m/z found, 325.1 [M+H]$^+$. $^1$H NMR (400 MHz, CDCl$_3$) δ 8.63-8.57 (m, 1H), 8.18-8.13 (m, 1H), 8.12 (d, J=1.4, 1H), 7.99-7.90 (m, 1H), 7.69-7.62 (m, 1H), 7.58-7.41 (m, 2H), 6.98-6.91 (m, 1H), 5.49-5.35 (m, 1H), 4.68 (s, 2H), 1.37 (d, J=6.2, 6H).

Example 402

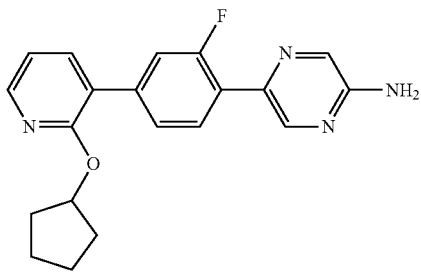

5-{4-[2-(Cyclopentyloxy)pyridin-3-yl]-2-fluorophenyl}pyrazin-2-amine

The title compound was prepared using methods analogous to those described in Example 369 using (2-(cyclopentyloxy)pyridin-3-yl)boronic acid and 5-(4-bromo-2-fluorophenyl)pyrazin-2-amine in Step B. MS (ESI): mass calcd. for $C_{20}H_{19}FN_4O$, 350.15; m/z found, 351.1 [M+H]$^+$. $^1$H NMR (400 MHz, CDCl$_3$) δ 8.62-8.58 (m, 1H), 8.19-8.15 (m, 1H), 8.12 (d, J=1.5, 1H), 8.00-7.90 (m, 1H), 7.69-7.63 (m, 1H), 7.48-7.40 (m, 2H), 6.98-6.92 (m, 1H), 5.59-5.50 (m, 1H), 4.68 (s, 2H), 2.03-1.89 (m, 2H), 1.89-1.70 (m, 4H), 1.71-1.55 (m, 2H).

Example 403

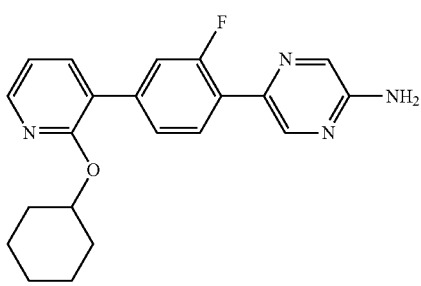

5-{4-[2-(Cyclohexyloxy)pyridin-3-yl]-2-fluorophenyl}pyrazin-2-amine

The title compound was prepared using methods analogous to those described in Example 369 using (2-(cyclohexyloxy)pyridin-3-yl)boronic acid and 5-(4-bromo-2-fluorophenyl)pyrazin-2-amine in Step B. MS (ESI): mass calcd. for $C_{21}H_{21}FN_4O$, 364.17; m/z found, 365.2 [M+H]$^+$. $^1$H NMR (400 MHz, CDCl$_3$) δ 8.64-8.57 (m, 1H), 8.18-8.10 (m, 2H), 8.00-7.92 (m, 1H), 7.70-7.63 (m, 1H), 7.52-7.43 (m, 2H), 6.94 (dd, J=5.0, 7.4, 1H), 5.26-5.16 (m, 1H), 4.66 (s, 2H), 2.05-1.91 (m, 2H), 1.82-1.68 (m, 2H), 1.66-1.24 (m, 6H).

Example 404

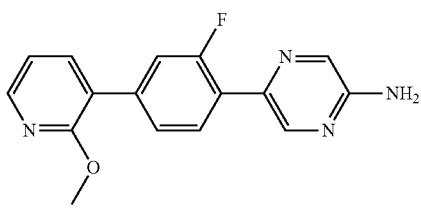

5-[2-Fluoro-4-(2-methoxypyridin-3-yl)phenyl]pyrazin-2-amine

The title compound was prepared using methods analogous to those described in Example 369 using (2-(methoxy)pyridin-3-yl)boronic acid and 5-(4-bromo-2-fluorophenyl)pyrazin-2-amine in Step B. MS (ESI): mass calcd. for $C_{16}H_{13}FN_4O$, 296.11; m/z found, 297.1 [M+H]$^+$. $^1$H NMR (400 MHz, CDCl$_3$) δ 8.62-8.56 (m, 1H), 8.19 (dd, J=1.9, 5.0, 1H), 8.12 (d, J=1.5, 1H), 8.01-7.94 (m, 1H), 7.70-7.65 (m, 1H), 7.48-7.41 (m, 2H), 7.00 (dd, J=5.0, 7.31, 1H), 4.66 (s, 2H), 4.00 (s, 3H).

Example 405

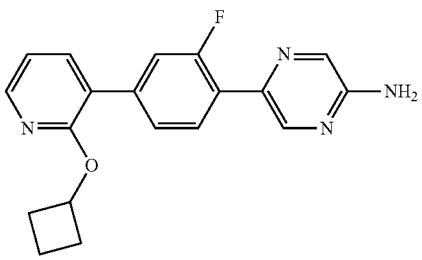

5-{4-[2-(Cyclobutyloxy)pyridin-3-yl]-2-fluorophenyl}pyrazin-2-amine

The title compound was prepared using methods analogous to those described in Example 369 using (2-(cyclobutoxy)pyridin-3-yl)boronic acid and 5-(4-bromo-2-fluorophenyl)pyrazin-2-amine in Step B. MS (ESI): mass calcd. for $C_{19}H_{17}FN_4O$, 336.14; m/z found, 337.1 [M+H]$^+$. $^1$H NMR (400 MHz, CDCl$_3$) δ 8.63-8.57 (m, 1H), 8.17-8.10 (m, 2H), 8.01-7.92 (m, 1H), 7.66 (dd, J=1.9, 7.4, 1H), 7.52-7.43 (m, 2H), 7.00-6.93 (m, 1H), 5.38-5.22 (m, 1H), 4.67 (s, 2H), 2.57-2.37 (m, 2H), 2.26-2.05 (m, 2H), 1.90-1.61 (m, 2H).

Example 406

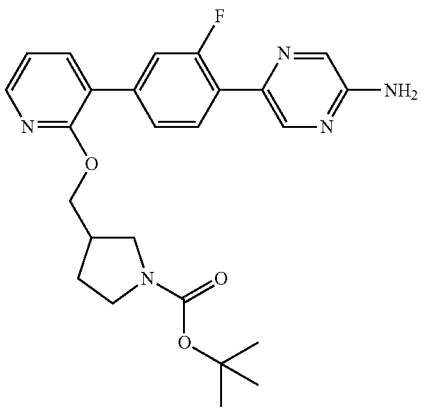

tert-Butyl 3-[({3-[4-(5-aminopyrazin-2-yl)-3-fluorophenyl]pyridin-2-yl}oxy)methyl]pyrrolidine-1-carboxylate The title compound was prepared using methods analogous to those described in Example 369 using tert-butyl 3-(((3-(4,4,5,5-tetramethyl-1,3,2-dioxaborolan-2-yl)pyridine-2-yl)oxy)methyl)pyrrolidine-1-carboxylate and 5-(4-bromo-2-fluorophenyl)pyrazin-2-amine in Step B. MS (ESI): mass calcd. for $C_{25}H_{28}FN_5O_3$, 465.22; m/z found, 466.2 [M+H]$^+$. $^1$H NMR (400 MHz, CDCl$_3$) δ 8.63-8.58 (m, 1H), 8.18-8.09 (m, 2H), 8.03-7.94 (m, 1H), 7.73-7.64 (m, 1H), 7.48-7.36 (m, 2H), 7.05-6.96 (m, 1H), 4.70 (s, 2H), 4.47-4.22 (m, 2H), 3.68-3.26 (m, 3H), 3.25-3.09 (m, 1H), 2.77-2.60 (m, 1H), 2.14-1.98 (m, 1H), 1.84-1.68 (m, 1H), 1.44 (s, 9H).

Example 407

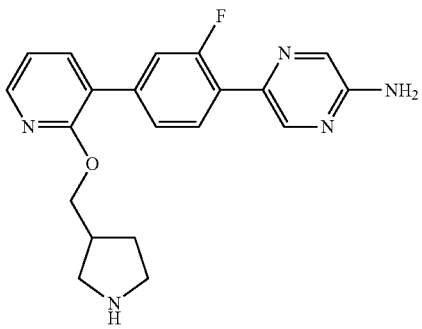

5-{2-Fluoro-4-[2-(pyrrolidin-3-ylmethoxy)pyridin-3-yl]phenyl}pyrazin-2-amine

Step A: Tert-butyl 3-(((3-(4-(5-aminopyrazin-2-yl)-3-fluorophenyl)pyridine-2-yl)oxy)methyl)pyrrolidine-1-carboxylate The title compound was prepared using methods analogous to those described in Example 369 using 5-(2-fluoro-4-(4,4,5,5-tetramethyl-1,3,2-dioxaborolan-2-yl)phenyl)pyrazin-2-amine and tert-butyl 3-(((3-bromopyridin-2-yl)oxy)methyl)pyrrolidine-1-carboxylate yielding the title compound (47 mg, 54%). MS (ESI): mass calcd. for $C_{25}H_{28}FN_5O_3$, 465.22; m/z found, 466.2 [M+H]+. $^1$H NMR (400 MHz, CDCl$_3$) δ 8.63-8.58 (m, 1H), 8.18-8.09 (m, 2H), 8.03-7.94 (m, 1H), 7.73-7.64 (m, 1H), 7.48-7.36 (m, 2H), 7.05-6.96 (m, 1H), 4.70 (s, 2H), 4.47-4.22 (m, 2H), 3.68-3.26 (m, 3H), 3.25-3.09 (m, 1H), 2.77-2.60 (m, 1H), 2.14-1.98 (m, 1H), 1.84-1.68 (m, 1H), 1.44 (s, 9H).

Step B

The title compound was prepared as described in the preparation of Example 249 using tert-butyl 3-(((3-(4-(5-aminopyrazin-2-yl)-3-fluorophenyl)pyridine-2-yl)oxy)methyl)pyrrolidine-1-carboxylate to give the title compound (15 mg, 41%). MS (ESI): mass calcd. for $C_{20}H_{20}FN_5O$, 365.17; m/z found, 366.2 [M+H]+. $^1$H NMR (400 MHz, CDCl$_3$) δ 8.63-8.57 (m, 1H), 8.20-8.13 (m, 1H), 8.12 (d, J=1.5, 1H), 8.02-7.93 (m, 1H), 7.72-7.65 (m, 1H), 7.49-7.38 (m, 2H), 7.03-6.96 (m, 1H), 4.69 (s, 2H), 4.40-4.20 (m, 2H), 3.09 (dd, J=11.2, 7.7, 1H), 3.04-2.83 (m, 2H), 2.76 (dd, J=11.2, 6.1, 1H), 2.66-2.49 (m, 1H), 2.06-1.89 (m, 1H), 1.61-1.49 (m, 2H).

Example 408

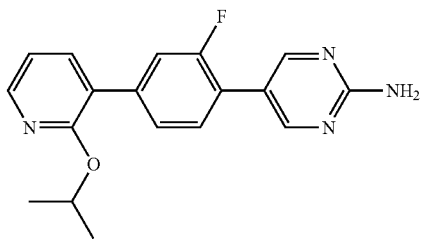

5-{2-Fluoro-4-[2-(1-methylethoxy)pyridin-3-yl]phenyl}pyrimidin-2-amine

To a microwave vial the following were added 5-(4-chloro-2-fluorophenyl)-pyrimidin-2-amine (50 mg, 0.22 mmol), (2-isopropoxypyridin-3-yl)boronic acid (51 mg, 0.28 mmol) and X-Phos precatalyst (4 mg, 0.005 mmol). The vial was flushed with nitrogen and then THF (0.5 mL) and 0.5 M K$_3$PO$_4$ (0.9 mL) were added. Both THF and the K$_3$PO$_4$ solution were sparged separately for 30 min prior to use. The resulting biphasic mixture was stirred at rt overnight. The reaction mixture was then poured into sat. NaHCO$_3$ (50 mL) and extracted with ethyl acetate (2×50 mL). The combined organic extracts were washed with water (1×50 mL) and brine (1×50 mL), dried (Na$_2$SO$_4$) and concentrated to dryness. The crude product was purified by HPLC to give the title compound (35 mg, 48%). MS (ESI): mass calcd. for $C_{18}H_{17}FN_4O$, 324.14; m/z found, 325.1 [M+H]+. $^1$H NMR (400 MHz, CDCl$_3$) δ 8.57 (d, J=1.4, 2H), 8.21-8.13 (m, 1H), 7.68-7.60 (m, 1H), 7.50-7.36 (m, 3H), 6.99-6.91 (m, 1H), 5.51-5.37 (m, 1H), 5.15 (s, 2H), 1.38 (d, J=6.2, 6H).

Example 409

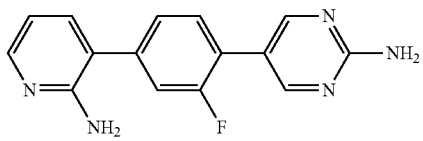

5-[4-(2-Aminopyridin-3-yl)-2-fluorophenyl]pyrimidin-2-amine

The title compound was prepared in a manner similar to that described in Example 88 using 3-bromopyridin-2-amine and 5-(2-fluoro-4-(4,4,5,5-tetramethyl-1,3,2-dioxaborolan-2-yl)phenyl)pyrimidin-2-amine. MS (ESI): mass calcd. for $C_{15}H_{12}FN_5$, 281.11; m/z found, 282.1 [M+H]+. $^1$H NMR (500 MHz, CD$_3$OD) δ 8.64-8.54 (m, 1H), 8.00-7.89 (m, 1H), 7.74-7.64 (m, 1H), 7.46-7.36 (m, 1H), 7.09-7.03 (m, 1H).

Example 410

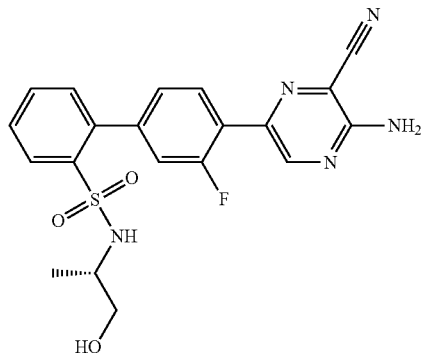

4'-(5-amino-6-cyanopyrazin-2-yl)-3'-fluoro-N-[(1R)-2-hydroxy-1-methylethyl]biphenyl-2-sulfonamide The title compound was prepared in manner similar to that described in Example 88 using (S)-2-bromo-N-(1-hydroxypropan-2-yl)benzenesulfonamide and 3-amino-6-(2-fluoro-4-(4,4,5,5-tetramethyl-1,3,2-dioxaborolan-2-yl)phenyl)pyrazine-2-carbonitrile. MS (ESI): mass calcd. for $C_{20}H_{18}FN_5O_3S$, 427.11; m/z found, 428.1 [M+H]$^+$. $^1$H NMR (400 MHz. CD$_3$OD) δ8.73 (d, J=2.1, 1H), 8.16 (dd. J=7.9, 1.4, 1H), 7.93 (m, 1H), 7.69 (m, 1H), 7.60 (m, 1H), 7.45-7.28 (m, 3H), 3.47-3.36 (m, 1H), 3.34-3.18 (m, 2H), 1.03 (d. J=6.6, 3H).

Example 411

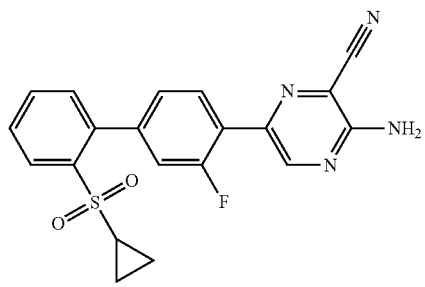

3-Amino-6-[2'-(cyclopropylsulfonyl)-3-fluorobiphenyl-4-yl]pyrazine-2-carbonitrile The title compound was prepared in manner similar to that described in Example 88 using 1-bromo-2-(cyclopropylsulfonyl)benzene and 3-amino-6-(2-fluoro-4-(4,4,5,5-tetramethyl-1,3,2-dioxaborolan-2-yl)phenyl)pyrazine-2-carbonitrile. MS (ESI): mass calcd. for $C_{20}H_{15}FN_4O_2S$, 394.09; m/z found, 395.1 [M+H]$^+$. $^1$H NMR (500 MHz, CDCl$_3$) δ 8.84 (d, J=1.8, 1H), 8.14 (dd, J=8.0, 1.4, 1H), 8.01 (m, 1H), 7.66 (m, 1H), 7.58 (m, 1H), 7.39-7.35 (m, 3H), 5.34 (s, 2H), 2.13-2.05 (m, 1H), 1.13-1.06 (m, 2H), 0.88-0.82 (m, 2H).

Example 412

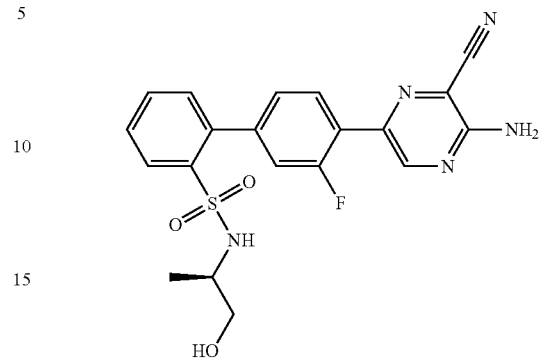

4'-(5-Amino-6-cyanopyrazin-2-yl)-3'-fluoro-N-[(1S)-2-hydroxy-1-methylethyl]biphenyl-2-sulfonamide The title compound was prepared in manner similar to that described in Example 88 using (S)-2-bromo-N-(1-hydroxypropan-2-yl)benzenesulfonamide and 3-amino-6-(2-fluoro-4-(4,4,5,5-tetramethyl-1,3,2-dioxaborolan-2-yl)phenyl)pyrazine-2-carbonitrile. MS (ESI): mass calcd. for $C_{20}H_{18}FN_5O_3S$, 427.11; m/z found, 428.1 [M+H]$^+$. $^1$H NMR (500 MHz, CDCl$_3$) δ 8.78 (d, J=1.6, 1H), 8.18 (dd, J=7.9, 1.4, 1H), 8.01 (m, 1H), 7.63 (m, 1H), 7.56 (m, 1H), 7.40-7.32 (m, 3H), 5.43 (s, 2H), 4.46-4.36 (m, 1H), 3.55-3.46 (m, 1H), 3.43-3.28 (m, 2H), 1.76 (t, J=5.7, 1H), 0.99 (d, J=6.6, 3H).

Example 413

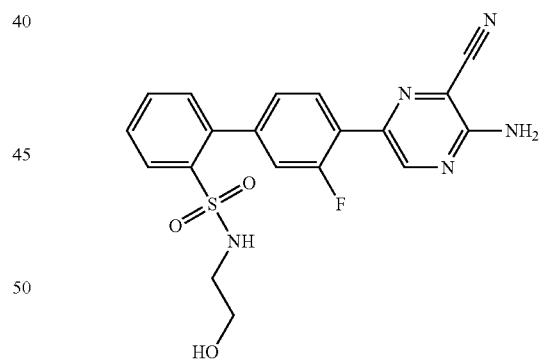

4'-(5-Amino-6-cyanopyrazin-2-yl)-3'-fluoro-N-(2-hydroxyethyl)biphenyl-2-sulfonamide The title compound was prepared in manner similar to that described in Example 88 using 2-bromo-N-(2-hydroxyethyl)benzenesulfonamide and 3-amino-6-(2-fluoro-4-(4,4,5,5-tetramethyl-1,3,2-dioxaborolan-2-yl)phenyl)pyrazine-2-carbonitrile. MS (ESI): mass calcd. for $C_{19}H_{16}FN_5O_3S$, 413.10; m/z found, 414.0 [M+H]$^+$. $^1$H NMR (500 MHz, CDCl$_3$) δ 8.81 (d, J=1.8, 1H), 8.17 (dd, J=8.0, 1.4, 1H), 8.02 (m, 1H), 7.64 (m, 1H), 7.56 (m, 1H), 7.40-7.31 (m, 3H), 5.38 (s, 2H), 4.35 (s, 1H), 3.64-3.58 (m, 2H), 2.95-2.87 (m, 2H), 1.64 (t, J=5.2, 1H).

Example 414

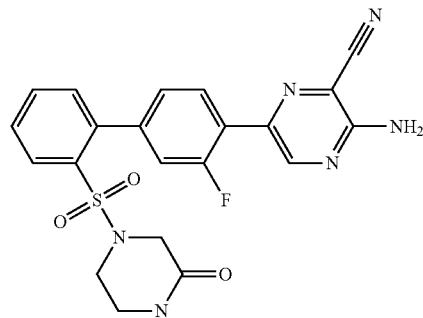

3-Amino-6-{3-fluoro-2'-[(3-oxopiperazin-1-yl)sulfonyl]biphenyl-4-yl}pyrazine-2-carbonitrile The title compound was prepared in a manner similar to that described in Example 88 using 4-((2-bromophenyl)sulfonyl)piperazin-2-one and 3-amino-6-(2-fluoro-4-(4,4,5,5-tetramethyl-1,3,2-dioxaborolan-2-yl)phenyl)pyrazine-2-carbonitrile. MS (ESI): mass calcd. for $C_{21}H_{17}FN_6O_3S$, 452.11; m/z found, 453.0 [M+H]$^+$. $^1$H NMR (500 MHz, CD$_3$OD) δ 8.65 (d. J=2.1, 1H), 8.05 (dd. J=8.1, 1.3, 1H), 7.85 (m, 1H), 7.65 (m, 1H), 7.55 (m, 1H), 7.36 (dd, J=7.6, 1.3, 1H), 7.26-7.17 (m, 2H), 3.29 (s, 2H), 3.04 (s, 4H).

Example 415

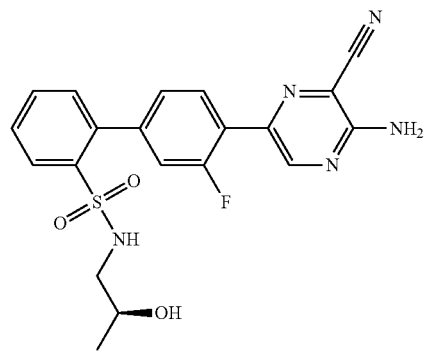

4'-(5-Amino-6-cyanopyrazin-2-yl)-3'-fluoro-N-[(2R)-2-hydroxypropyl]biphenyl-2-sulfonamide The title compound was prepared in a manner similar to that described in Example 88 using (R)-2-bromo-N-(2-hydroxypropyl)benzenesulfonamide and 3-amino-6-(2-fluoro-4-(4,4,5,5-tetramethyl-1,3,2-dioxaborolan-2-yl)phenyl)pyrazine-2-carbonitrile. MS (ESI): mass calcd. for $C_{20}H_{18}FN_5O_3S$, 427.11; m/z found, 428.1 [M+H]$^+$. $^1$H NMR (500 MHz, CD$_3$OD) δ 8.75 (d, J=2.1, 1H), 8.09 (dd, J=8.0, 1.3, 1H), 7.95 (m, 1H), 7.70 (m, 1H), 7.62 (m, 1H), 7.43 (dd, J=7.6, 1.4, 1H), 7.39-7.31 (m, 2H), 3.74-3.62 (m, 1H), 2.80-2.67 (m, 2H), 1.07 (d, J=6.3, 3H).

Example 416

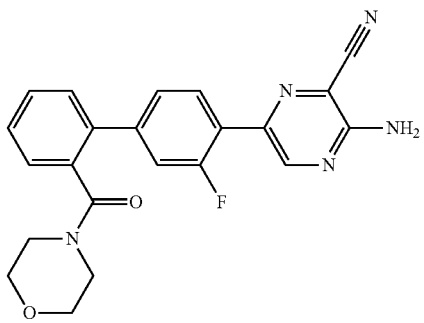

3-Amino-6-[3-fluoro-2'-(morpholin-4-ylcarbonyl)biphenyl-4-yl]pyrazine-2-carbonitrile The title compound was prepared in a manner similar to that described in Example 88 using (2-bromophenyl)(morpholino)methanone and 3-amino-6-(2-fluoro-4-(4,4,5,5-tetramethyl-1,3,2-dioxaborolan-2-yl)phenyl)pyrazine-2-carbonitrile. MS (ESI): mass calcd. for $C_{22}H_{18}FN_5O_2$, 403.14; m/z found, 404.1 [M+H]$^+$. $^1$H NMR (500 MHz, CD$_3$OD) δ 7.45 (d, J=2.1, 1H), 6.71 (m, 1H), 6.32-6.21 (m, 3H), 6.17-6.10 (m, 2H), 6.07 (dd, J=12.4, 1.8, 1H), 2.40-2.22 (m, 3H), 2.13-2.03 (m, 2H), 1.86-1.77 (m, 1H), 1.62-1.49 (m, 2H).

Example 417

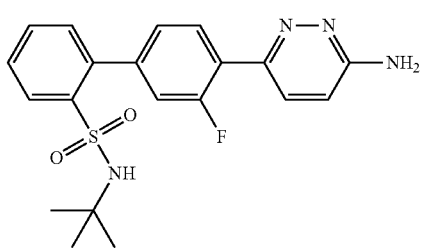

4'-(6-Aminopyridazin-3-yl)-N-tert-butyl-3'-fluorobiphenyl-2-sulfonamide

The title compound was prepared in a manner similar to that described in Example 444 using N-(tert-butyl)-3'-fluoro-4'-(4,4,5,5-tetramethyl-1,3,2-dioxaborolan-2-yl)-[1,1'-biphenyl]-2-sulfonamide and 6-chloropyridazin-3-amine. MS (ESI): mass calcd. for $C_{20}H_{21}FN_4O_2S$, 400.14; m/z found, 401.2 [M+H]$^+$. $^1$H NMR (400 MHz, CD$_3$OD) δ 8.26-8.22 (m, 1H), 8.16-8.13 (m, 1H), 7.91-7.85 (m, 1H), 7.69-7.64 (m, 1H), 7.63-7.56 (m, 2H), 7.44-7.37 (m, 3H), 1.09 (s, 9H).

Example 418

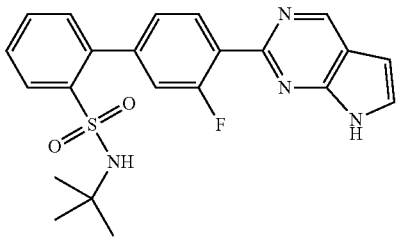

N-tert-Butyl-3'-fluoro-4'-(7H-pyrrolo[2,3-d]
pyrimidin-2-yl)biphenyl-2-sulfonamide The title compound was prepared in a manner similar to that described in Example 444 using N-(tert-butyl)-3'-fluoro-4'-(4,4,5,5-tetramethyl-1,3,2-dioxaborolan-2-yl)-[1,1'-biphenyl]-2-sulfonamide and 2-bromo-7H-pyrrolo[2,3-d]pyrimidine. MS (ESI): mass calcd. for $C_{22}H_{21}FN_4O_2S$, 424.14; m/z found, 425.2 [M+H]$^+$. $^1$H NMR (400 MHz, CD$_3$OD) δ 9.31 (s, 1H), 8.82 (s, 1H), 8.15 (m, 1H), 7.90 (d, J=3.6, 1H), 7.68 (d, J=7.5, 1H), 7.63 (d, J=6.3, 1H), 7.50 (s, 1H), 7.42 (d, J=7.1, 1H), 7.02 (d, J=3.6, 1H), 6.66 (d, J=3.6, 1H), 1.12 (s, 9H).

Example 419

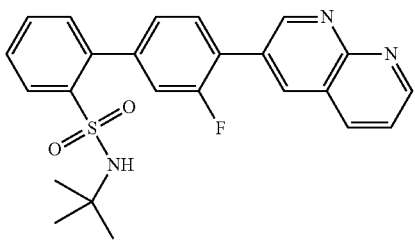

N-tert-Butyl-3'-fluoro-4'-(1,8-naphthyridin-3-yl)biphenyl-2-sulfonamide

The title compound was prepared in a manner similar to that described in Example 444 using N-(tert-butyl)-3'-fluoro-4'-(4,4,5,5-tetramethyl-1,3,2-dioxaborolan-2-yl)-[1,1'-biphenyl]-2-sulfonamide and 3-bromo-1,8-naphthyridine. MS (ESI): mass calcd. for $C_{24}H_{22}FN_3O_2S$, 435.14; m/z found, 436.1 [M+H]$^+$. $^1$H NMR (400 MHz, CD$_3$OD) δ 9.46 (s, 1H), 9.23 (s, 1H), 8.89 (s, 1H), 8.85 (d, J=7.2, 1H), 8.18-8.14 (m, 1H), 7.94-7.90 (m, 1H), 7.80 (m, 1H), 7.70-7.65 (m, 1H), 7.62-7.57 (m, 1H), 7.49-7.40 (m, 3H), 1.11 (s, 9H).

Example 420

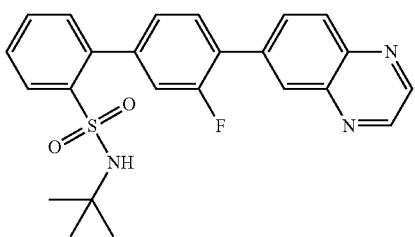

N-tert-Butyl-3'-fluoro-4'-quinoxalin-6-ylbiphenyl-2-sulfonamide

Step A: 4'-Bromo-N-(tert-butyl)-3'-fluoro-[1,1'-biphenyl]-2-sulfonamide

1-Bromo-2-fluoro-4-iodobenzene (117 mg, 0.389 mmol) and (2-(N-(tert-butyl)sulfamoyl)phenyl) boronic acid (100 mg, 0.389 mmol) were added to a 5 mL sealable vial equipped with a stir bar. 1,4-Dioxane (1 mL) and 2 M Na$_2$CO$_3$ (1 mL) solution were added. Argon was bubbled through the solvent while it was rapidly stirred for 10 min then Pd(dppf)Cl$_2$.CH$_2$Cl$_2$ (14 mg, 0.019 mmol) was added. The mixture was then stirred for 15 hours at 80° Celsius under an argon atmosphere. The reaction was diluted with 2 mL of ethyl acetate and 2 mL of water and the aqueous layer was extracted with ethyl acetate (3×10 mL). The combined organic extracts were then dried with Na$_2$SO$_4$ and concentrated to dryness. The crude product was purified by FCC to give the title compound. $^1$H NMR (500 MHz, CDCl$_3$) δ 8.20-8.15 (dd, J=7.9, 1.4, 1H), 7.64-7.59 (dd, J=8.2, 7.1, 1H), 7.60-7.55 (m, 1H), 7.54-7.49 (m, 1H), 7.31-7.27 (m, 2H), 7.21-7.16 (dd, J=8.5, 2.2, 1H), 3.65 (s, 1H), 1.07 (s, 9H).

Step B: N-tert-Butyl-3'-fluoro-4'-quinoxalin-6-ylbiphenyl-2-sulfonamide

4'-Bromo-N-(tert-butyl)-3'-fluoro-[1,1'-biphenyl]-2-sulfonamide (30 mg, 0.078 mmol) and 6-(4,4,5,5-tetramethyl-1,3,2-dioxaborolan-2-yl)quinoxaline (12 mg, 0.085 mmol) were added to a 5 mL sealable vial equipped with a stir bar. Dioxane (0.2 mL) and 2 M Na$_2$CO$_3$ (0.2 mL) were added. Argon was bubbled through the solvent while it was rapidly stirred for 10 min then Pd(dppf)Cl$_2$.CH$_2$Cl$_2$ (3 mg, 0.004 mmol) was added, and the mixture heated for 15 hours at 80° Celsius under an argon atmosphere. The reaction was diluted with 2 mL of ethyl acetate and 2 mL of water and the aqueous layer was extracted with ethyl acetate (3×10 mL). The combined organic extracts were then dried with Na$_2$SO$_4$ and concentrated to dryness. The crude product was purified by HPLC to give the title compound. MS (ESI): mass calcd. for $C_{24}H_{22}FN_3O_2S$, 435.14; m/z found, 436.4 [M+H]$^+$. $^1$H NMR (500 MHz, CDCl$_3$) δ 8.93-8.91 (d, J=1.8, 1H), 8.91-8.89 (d, J=1.8, 1H), 8.37-8.34 (m, 1H), 8.24-8.22 (m, 1H), 8.22-8.20 (m, 1H), 8.09-8.04 (m, 1H), 7.71-7.66 (m, 1H), 7.65-7.59 (m, 1H), 7.58-7.52 (m, 1H), 7.51-7.44 (dd, J=7.9, 1.8, 1H), 7.44-7.40 (dd, J=11.3, 1.7, 1H), 7.40-7.36 (dd, J=7.5, 1.4, 1H), 3.74 (s, 1H), 1.10 (s, 9H).

Example 421

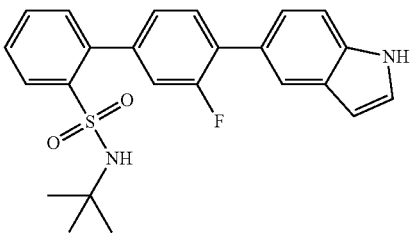

N-tert-Butyl-3'-fluoro-4'-(1H-indol-5-yl)biphenyl-2-sulfonamide

The title compound was prepared in a manner similar to that described in Example 420 using tert-butyl 5-(4,4,5,5-tetramethyl-1,3,2-dioxaborolan-2-yl)-1H-indole-1-carboxylate in Step B. After work up, the Boc group was then removed by treatment with trifluoroacetic acid (0.3 mL) in dichloromethane (1 mL) at rt followed by concentration and purification by HPLC to give the title compound. MS (ESI): mass calcd. for $C_{24}H_{23}FN_2O_2S$, 422.15; m/z found, 423.3 [M+H]$^+$. $^1$H NMR (500 MHz, CDCl$_3$) δ 8.27 (s, 1H), 8.23-8.17 (dd, J=8.0, 1.3, 1H), 7.91-7.85 (m, 1H), 7.63-7.56 (m, 2H), 7.55-7.49 (m, 2H), 7.48-7.43 (m, 1H), 7.42-7.36 (m, 2H), 7.36-7.31 (dd, J=11.3, 1.8, 1H), 7.31-7.27 (dd, J=3.2, 2.4, 1H), 6.67-6.61 (m, 1H), 3.72 (s, 1H), 1.06 (s, 9H).

Example 422

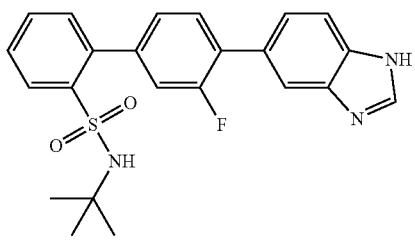

4'-(1H-Benzimidazol-5-yl)-
N-tert-butyl-3'-fluorobiphenyl-2-sulfonamide

The title compound was prepared in a manner similar to that described in Example 420 using 5-(4,4,5,5-tetramethyl-1,3,2-dioxaborolan-2-yl)-1H-benzo[d]imidazole in Step B. MS (ESI): mass calcd. for $C_{23}H_{22}FN_3O_2S$, 423.14; m/z found, 424.0 [M+H]$^+$. $^1$H NMR (500 MHz, CD$_3$OD) δ 9.32-9.21 (d, J=6.0, 1H), 8.18-8.12 (dd, J=8.0, 1.3, 1H), 8.04 (s, 1H), 7.96-7.89 (m, 1H), 7.89-7.82 (m, 1H), 7.69-7.55 (m, 3H), 7.45-7.33 (m, 3H), 1.11 (s, 9H).

Example 423

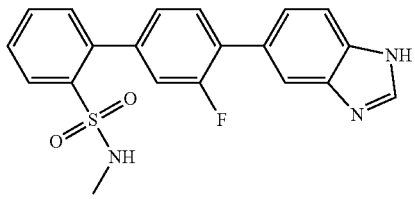

4'-(1H-Benzimidazol-5-yl)-3'-fluoro-
N-methylbiphenyl-2-sulfonamide

The title compound was prepared in a manner similar to that described in Example 420 using (2-(N-methylsulfamoyl)phenyl)boronic acid in Step A and 5-(4,4,5,5-tetramethyl-1,3,2-dioxaborolan-2-yl)-1H-benzo[d]imidazole in Step B. MS (ESI): mass calcd. for $C_{20}H_{16}FN_3O_2S$, 381.09; m/z found, 382.1 [M+H]$^+$. $^1$H NMR (500 MHz, CD$_3$OD) δ 9.35 (s, 1H), 8.06 (s, 1H), 8.05-8.03 (dd, J=8.0, 1.3, 1H), 7.96-7.92 (m, 1H), 7.91-7.86 (m, 1H), 7.72-7.67 (m, 1H), 7.65-7.60 (m, 2H), 7.46-7.43 (dd, J=7.5, 1.4, 1H), 7.38-7.32 (m, 2H), 2.50 (s, 3H).

Example 424

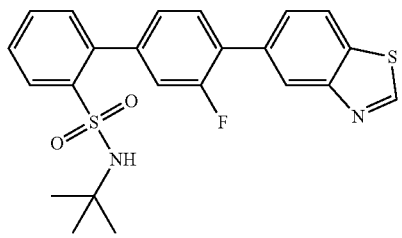

4'-(1,3-Benzothiazol-5-yl)-N-tert-butyl-3'-
fluorobiphenyl-2-sulfonamide

The title compound was prepared in a manner similar to that described in Example 420 using 5-(4,4,5,5-tetramethyl-1,3,2-dioxaborolan-2-yl)-benzo[d]thiazole in Step B. MS (ESI): mass calcd. for $C_{23}H_{21}FN_2O_2S_2$, 440.10; m/z found, 441.2 [M+H]$^+$. $^1$H NMR (500 MHz, CDCl$_3$) δ 9.07 (s, 1H), 8.39-8.35 (m, 1H), 8.24-8.19 (dd, J=8.0, 1.3, 1H), 8.10-8.05 (dd, J=8.4, 0.6, 1H), 7.75-7.69 (m, 1H), 7.65-7.62 (m, 1H), 7.62-7.58 (m, 1H), 7.57-7.51 (m, 1H), 7.45-7.42 (dd, J=7.8, 1.8, 1H), 7.41-7.38 (dd, J=4.1, 1.5, 1H), 7.38-7.36 (d, J=1.6, 1H), 3.73 (s, 1H), 1.08 (s, 9H).

Example 425

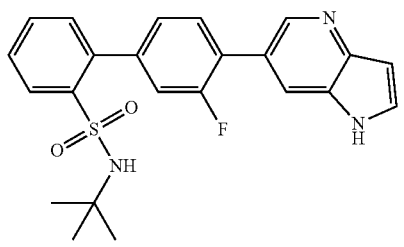

N-tert-Butyl-3'-fluoro-4'-(1H-pyrrolo[3,2-b]pyridin-6-yl)
biphenyl-2-sulfonamide The title compound was prepared in a manner similar to that described in Example 420 using 6-(4,4,5,5-tetramethyl-1,3,2-dioxaborolan-2-yl)-1H-pyrrolo[3,2-b]pyridine in Step B. MS (ESI): mass calcd. for $C_{23}H_{22}FN_3O_2S$, 423.14; m/z found, 424.1 [M+H]$^+$. $^1$H NMR (500 MHz, CD$_3$OD) δ 8.87-8.81 (m, 1H), 8.77-8.70 (d, J=1.5, 1H), 8.20-8.17 (d, J=3.3, 1H), 8.17-8.12 (dd, J=8.0, 1.3, 1H), 7.78-7.71 (m, 1H), 7.71-7.65 (m, 1H), 7.65-7.58 (m, 1H), 7.47-7.44 (dd, J=4.9, 1.5, 1H), 7.44 (s, 1H), 7.43-7.40 (dd, J=7.5, 1.4, 1H), 6.95-6.89 (dd, J=3.2, 0.9, 1H), 1.12 (s, 9H).

Example 426

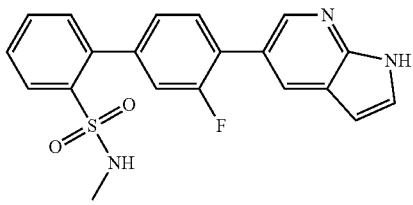

3'-Fluoro-N-methyl-4'-(1H-pyrrolo[2,3-b]pyridin-
5-yl)biphenyl-2-sulfonamide

The title compound was prepared in a manner similar to that described in Example 420 using (2-(N-methylsulfamoyl)phenyl)boronic acid in Step A and 5-(4,4,5,5-tetramethyl-1,3,2-dioxaborolan-2-yl)-1H-pyrrolo[2,3-b]pyridine in Step B. MS (ESI): mass calcd. for $C_{20}H_{16}FN_3O_2S$, 381.09; m/z found, 382.1 [M+H]$^+$. $^1$H NMR (500 MHz, CD$_3$OD) δ 8.49 (s, 1H), 8.46-8.37 (m, 1H), 8.13-7.97 (dd, J=7.9, 1.3, 1H), 7.74-7.66 (m, 1H), 7.66-7.57 (m, 2H), 7.57-7.52 (d, J=3.5, 1H), 7.46-7.40 (dd, J=7.7, 1.4, 1H), 7.38-7.30 (m, 2H), 6.72-6.63 (d, J=3.5, 1H), 2.48 (s, 3H).

Example 427

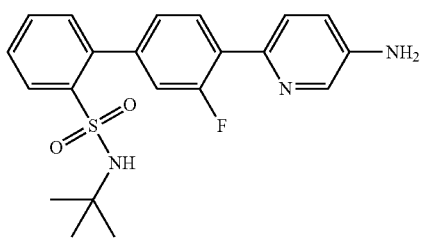

4'-(5-Aminopyridin-2-yl)-N-tert-butyl-3'-fluorobiphenyl-2-sulfonamide

N-(tert-Butyl)-3'-fluoro-4'-(4,4,5,5-tetramethyl-1,3,2-dioxaborolan-2-yl)-[1,1'-biphenyl]-2-sulfonamide (37 mg, 0.085 mmol) and 6-bromopyridin-3-amine (22 mg, 0.13 mmol) were added to a 5 mL sealable vial equipped with a stir bar. 1,4-Dioxane (0.2 mL) and 2 M Na$_2$CO$_3$ (0.2 mL) were added. Argon was bubbled through the solvent while it was rapidly stirred for 10 min then Pd(dppf)Cl$_2$·CH$_2$Cl$_2$ (3 mg, 0.004 mmol) was added, and the mixture stirred for 15 hours at 80° Celsius under an argon atmosphere. The reaction was diluted with 2 mL of ethyl acetate and 2 mL of water and the aqueous layer was extracted with ethyl acetate (3×10 mL). The combined organic extracts were then dried with Na$_2$SO$_4$ and concentrated to dryness. The crude product was purified by HPLC to give the title compound. MS (ESI): mass calcd. for $C_{21}H_{22}FN_3O_2S$, 399.14; m/z found, 400.2 [M+H]$^+$. $^1$H NMR (400 MHz, CDCl$_3$) δ 8.66 (s, 1H), 8.25-8.16 (dd, J=8.0, 1.4, 1H), 7.83-7.76 (dd, J=8.8, 1.7, 1H), 7.77-7.68 (m, 1H), 7.66-7.58 (m, 1H), 7.58-7.48 (m, 2H), 7.46-7.39 (m, 2H), 7.37-7.30 (dd, J=7.4, 1.5, 1H), 4.31 (s, 1H), 1.09 (s, 9H).

Example 428

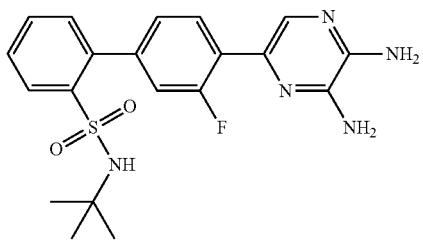

N-tert-Butyl-4'-(5,6-diaminopyrazin-2-yl)-3'-fluorobiphenyl-2-sulfonamide

The title compound was prepared in a manner similar to that described in Example 427 using 5-bromopyrazine-2,3-diamine. MS (ESI): mass calcd. for $C_{20}H_{22}FN_5O_2S$, 415.15; m/z found, 416.1 [M+H]$^+$. $^1$H NMR (500 MHz, CD$_3$OD) δ 8.16-8.11 (dd, J=8.0, 1.3, 1H), 8.11-8.06 (m, 1H), 7.66 (s, 1H), 7.66-7.62 (m, 1H), 7.60-7.54 (m, 1H), 7.40-7.35 (dd, J=7.5, 1.4, 1H), 7.35-7.34 (m, 1H), 7.34-7.31 (dd, J=7.7, 1.6, 1H), 1.07 (s, 9H).

Example 429

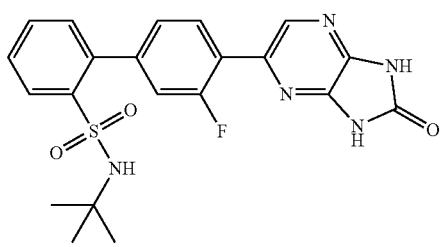

N-tert-Butyl-3'-fluoro-4'-(2-oxo-2,3-dihydro-1H-imidazo[4,5-b]pyrazin-5-yl)biphenyl-2-sulfonamide The title compound was prepared in a manner similar to that described in Example 427 using 5-bromo-1H-imidazo[4,5-b]pyrazin-2(3H)-one. MS (ESI): mass calcd. for $C_{21}H_{20}FN_5O_3S$, 441.13; m/z found, 442.2 [M+H]$^+$. $^1$H NMR (500 MHz, CD$_3$OD) δ 8.45-8.39 (d, J=1.7, 1H), 8.17-8.10 (m, 1H), 8.06-7.98 (m, 1H), 7.70-7.60 (m, 1H), 7.60-7.52 (m, 1H), 7.42-7.38 (dd, J=7.4, 1.3, 1H), 7.38-7.33 (m, 2H), 1.07 (s, 9H).

Example 430

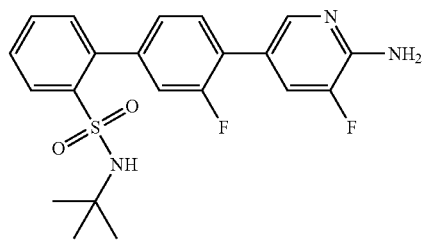

4'-(6-Amino-5-fluoropyridin-3-yl)-N-tert-butyl-3'-fluorobiphenyl-2-sulfonamide

The title compound was prepared in a manner similar to that described in Example 427 using 5-bromo-3-fluoropyridin-2-amine. MS (ESI): mass calcd. for $C_{21}H_{21}F_2N_3O_2S$, 417.13; m/z found, 418.2 [M+H]$^+$. $^1$H NMR (500 MHz, CD$_3$OD) δ 8.16-8.11 (dd, J=8.0, 1.3, 1H), 8.04-7.97 (m, 2H), 7.69-7.62 (m, 1H), 7.61-7.53 (m, 2H), 7.39-7.32 (m, 3H), 1.24-0.86 (s, 9H).

Example 431

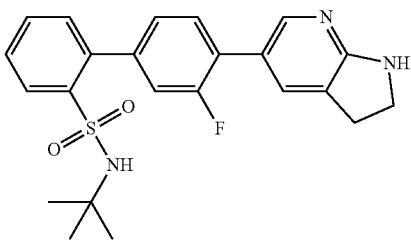

N-tert-Butyl-4'-(2,3-dihydro-1H-pyrrolo[2,3-b]pyridin-5-yl)-3'-fluorobiphenyl-2-sulfonamide The title compound was prepared in a manner similar to that described in Example 427 using 5-bromo-2,3-dihydro-1H-pyrrolo[2,3-b]pyridine. MS (ESI): mass calcd. for $C_{23}H_{24}FN_3O_2S$, 425.16; m/z found, 426.2 [M+H]$^+$. $^1$H NMR (500 MHz, CD$_3$OD) δ 8.18-8.06 (dd, J=7.9, 1.3, 1H), 7.95-7.85 (m, 1H), 7.76 (s, 1H), 7.68-7.62 (m, 1H), 7.61-7.49 (m, 2H), 7.43-7.30 (m, 3H), 4.03-3.92 (dd, J=8.8, 7.8, 2H), 3.37-3.32 (m, 2H), 1.10 (s, 9H).

Example 432

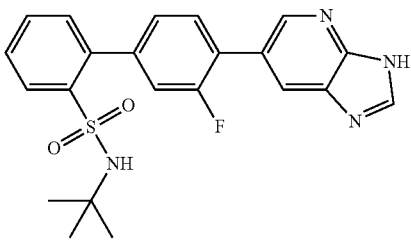

N-tert-Butyl-3'-fluoro-4'-(3H-imidazo[4,5-b]pyridin-6-yl)biphenyl-2-sulfonamide

The title compound was prepared in a manner similar to that described in Example 427 using 6-bromo-3H-imidazo[4,5-b]pyridine. MS (ESI): mass calcd. for $C_{22}H_{21}FN_4O_2S$, 424.14; m/z found, 425.1 [M+H]$^+$. $^1$H NMR (500 MHz, CD$_3$OD) δ 8.92 (s, 1H), 8.84-8.74 (m, 1H), 8.40 (s, 1H), 8.21-8.08 (dd, J=8.1, 1.3, 1H), 7.70-7.63 (m, 2H), 7.62-7.55 (m, 1H), 7.46-7.36 (m, 3H), 1.10 (s, 9H).

Example 433

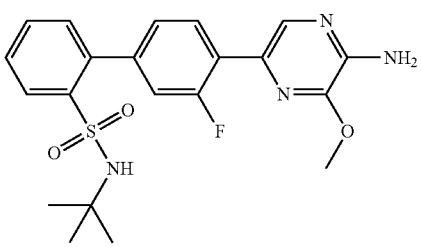

4'-(5-Amino-6-methoxypyrazin-2-yl)-N-tert-butyl-3'-fluorobiphenyl-2-sulfonamide

The title compound was prepared in a manner similar to that described in Example 427 using 5-bromo-3-methoxypyrazin-2-amine. MS (ESI): mass calcd. for $C_{21}H_{23}FN_4O_3S$, 430.15; m/z found, 431.1 [M+H]$^+$. $^1$H NMR (500 MHz, CD$_3$OD) δ 8.18-8.10 (m, 2H), 7.95 (s, 1H), 7.68-7.62 (m, 1H), 7.60-7.54 (m, 1H), 7.40-7.35 (m, 2H), 7.35-7.32 (dd, J=12.9, 1.6, 1H), 4.19 (s, 3H), 1.07 (s, 9H).

Example 434

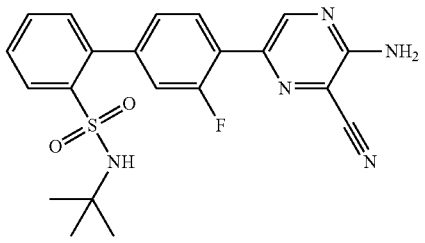

4'-(5-Amino-6-cyanopyrazin-2-yl)-N-tert-butyl-3'-fluorobiphenyl-2-sulfonamide

The title compound was prepared in a manner similar to that described in Example 427 using 3-amino-6-bromopyrazine-2-carbonitrile. MS (ESI): mass calcd. for $C_{21}H_{20}FN_5O_2S$, 425.13; m/z found, 426.2 [M+H]$^+$. $^1$H NMR (500 MHz, CD$_3$OD) δ 8.76-8.69 (d, J=2.1, 1H), 8.18-8.10 (dd, J=8.0, 1.3, 1H), 7.96-7.89 (m, 1H), 7.68-7.62 (m, 1H), 7.61-7.53 (m, 1H), 7.40-7.37 (dd, J=7.6, 1.4, 1H), 7.37-7.36 (m, 1H), 7.36-7.33 (dd, J=4.4, 1.6, 1H), 1.07 (s, 9H).

Example 435

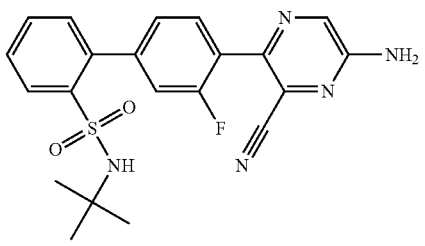

4'-(5-Amino-3-cyanopyrazin-2-yl)-N-tert-butyl-3'-fluorobiphenyl-2-sulfonamide

The title compound was prepared using analogous conditions to those described in Example 6 utilizing 6-amino-3-(4-bromo-2-fluorophenyl)pyrazine-2-carbonitrile and (2-(N-(tert-butyl)sulfamoyl)phenyl)boronic acid. MS (ESI): mass calcd. for $C_{21}H_{20}FN_5O_2S$, 425.13; m/z found, 426.1 [M+H]$^+$. $^1$H NMR (600 MHz, CDCl$_3$) δ 8.25 (s, 1H), 8.19 (dd, J=8.0, 1.4, 1H), 7.64-7.56 (m, 2H), 7.54-7.49 (m, 1H), 7.47 (dd, J=7.9, 1.7, 1H), 7.40-7.33 (m, 2H), 1.04 (s, 9H).

Example 436

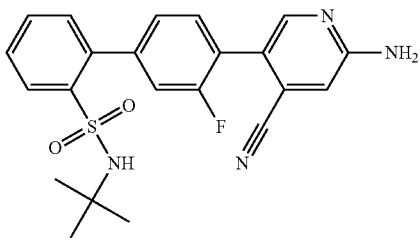

4'-(6-Amino-4-cyanopyridin-3-yl)-N-tert-butyl-3'-fluorobiphenyl-2-sulfonamide

The title compound was prepared using analogous conditions to those described in Example 6 utilizing 2-amino-5-(4-bromo-2-fluorophenyl)pyridine-4-carbonitrile and (2-(N-(tert-butyl)sulfamoyl)phenyl)boronic acid. MS (ESI): mass calcd. for $C_{22}H_{21}FN_4O_2S$, 424.14; m/z found, 425.1 [M+H]$^+$. $^1$H NMR (600 MHz, CDCl$_3$) δ 8.18 (d, J=7.8, 1H), 8.01 (s, 1H), 7.64-7.58 (m, 1H), 7.57-7.51 (m, 1H), 7.46-7.28 (m, 4H), 3.91 (s, 1H), 1.04 (s, 9H).

Example 437

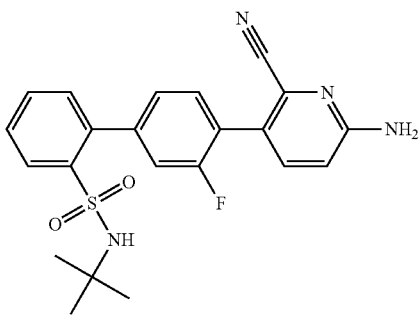

4'-(6-Amino-2-cyanopyridin-3-yl)-N-(tert-butyl)-3'-fluoro-[1,1'-biphenyl]-2-sulfonamide The title compound was prepared using analogous conditions to those described in Example 6 utilizing N-(tert-butyl)-3'-fluoro-4'-(4,4,5,5-tetramethyl-1,3,2-dioxaborolan-2-yl)-[1,1'-biphenyl]-2-sulfonamide and 6-amino-3-bromo-2-cyanopyridine. MS (ESI): mass calcd. for $C_{22}H_{21}FN_4O_2S$, 424.14; m/z found, 424.9 [M+H]$^+$. $^1$H NMR (500 MHz, DMSO-d$_6$) δ 8.11-8.04 (d, J=7.9, 1H), 7.71-7.64 (m, 1H), 7.64-7.58 (m, 2H), 7.54-7.48 (m, 1H), 7.45-7.36 (dd, J=19.2, 9.2, 2H), 7.36-7.30 (dd, J=7.9, 1.6, 1H), 6.89-6.83 (d, J=8.7, 1H), 6.83-6.75 (d, J=10.0, 3H), 1.03 (s, 9H).

Example 438

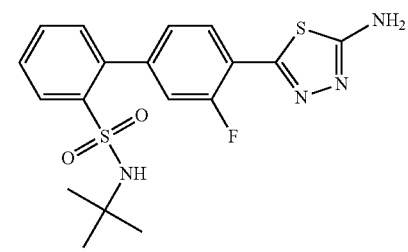

4'-(5-Amino-1,3,4-thiadiazol-2-yl)-N-(tert-butyl)-3'-fluoro-[1,1'-biphenyl]-2-sulfonamide The title compound was prepared using analogous conditions to those described in Example 6 utilizing 5-(2-fluoro-4-(4,4,5,5-tetramethyl-1,3,2-dioxaborolan-2-yl)phenyl)-1,3,4-thiadiazol-2-amine and 2-bromo-N-(tert-butyl)benzenesulfonamide. MS (ESI): mass calcd. for $C_{18}H_{19}FN_4O_2S_2$, 406.09; m/z found, 407.1 [M+H]$^+$. $^1$H NMR (300 MHz, CD$_3$OD) δ 8.20-8.10 (m, 2H), 7.69-7.56 (m, 2H), 7.46-7.36 (m, 3H), 1.08 (s, 9H).

Example 439

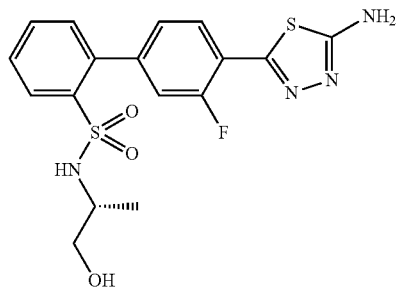

(R)-4'-(5-Amino-1,3,4-thiadiazol-2-yl)-3'-fluoro-N-(1-hydroxypropan-2-yl)-[1,1'-biphenyl]-2-sulfonamide The title compound was prepared using analogous conditions to those described in Example 6 utilizing 5-(2-fluoro-4-(4,4,5,5-tetramethyl-1,3,2-dioxaborolan-2-yl)phenyl)-1,3,4-thiadiazol-2-amine and (R)-2-bromo-N-(1-hydroxypropan-2-yl)benzenesulfonamide. MS (ESI): mass calcd. for $C_{17}H_{17}FN_4O_3S_2$, 408.07; m/z found, 409.1 [M+H]$^+$. $^1$H NMR (300 MHz, CD$_3$OD) δ 8.15-8.12 (m, 2H), 7.68 (m, 1H), 7.61 (m, 1H), 7.44-7.38 (m, 3H), 3.42-3.38 (m, 1H), 3.30-3.25 (m, 1H), 3.22-3.18 (m, 1H), 1.02 (d, J=6.6, 3H).

Example 440

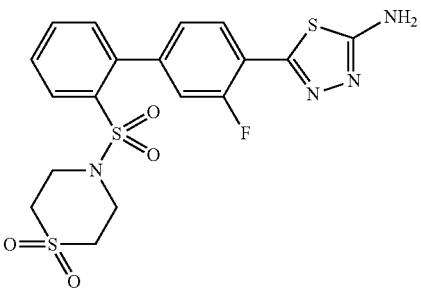

4-((4'-(5-Amino-1,3,4-thiadiazol-2-yl)-3'-fluoro-[1,1'-biphenyl]-2-yl)sulfonyl)thiomorpholine 1,1-dioxide The title compound was prepared using analogous conditions to those described in Example 6 utilizing 5-(2-fluoro-4-(4,4,5,5-tetramethyl-1,3,2-dioxaborolan-2-yl)phenyl)-1,3,4-thiadiazol-2-amine and 4-((2-bromophenyl)sulfonyl)thiomorpholine 1,1-dioxide. MS (ESI): mass calcd. for $C_{18}H_{17}FN_4O_4S_2$, 468.04; m/z found, 469.0 [M+H]$^+$. $^1$H NMR (300 MHz, CD$_3$OD) δ 8.19 (m, 1H), 8.15 (dd, J=8.0, 1.1, 1H), 7.76 (m, 1H), 7.67 (m, 1H), 7.45 (dd, J=7.6, 1.2, 1H), 7.39 (dd, J=11.9, 1.4, 1H), 7.36 (dd, J=8.1, 1.6, 1H), 3.42-3.33 (m, 4H), 3.09-3.02 (m, 4H).

Example 441

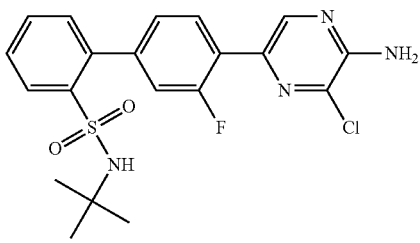

4'-(5-Amino-6-chloropyrazin-2-yl)-N-tert-butyl-3'-fluorobiphenyl-2-sulfonamide

To a 25 mL round-bottomed flask were added a stirbar, 52 mg (0.13 mmol) 4'-(5-aminopyrazin-2-yl)-N-tert-butyl-3'-fluorobiphenyl-2-sulfonamide, 27 mg (0.20 mmol) N-chlorosuccinamide, and dry DMF (2.0 mL). The flask was sparged with nitrogen and heated at 60° Celsius for 18 hours before cooling to rt and subjecting the reaction mixture (after syringe filtration) to HPLC purification to give the title compound (29.6 mg, 52%). MS (ESI): mass calcd. for $C_{20}H_{20}ClFN_4O_2S$, 434.10; m/z found, 435.1 [M+H]$^+$. $^1$H NMR (600 MHz, DMSO-$d_6$) δ 8.44 (d, J=2.0, 1H), 8.06 (dd, J=8.1, 1.5, 1H), 7.85 (dd, J=9.4, 6.8, 1H), 7.70-7.64 (m, 1H), 7.64-7.57 (m, 1H), 7.43-7.27 (m, 3H), 7.13 (s, 2H), 6.98 (d, J=3.7, 1H), 1.02 (s, 9H).

Example 442

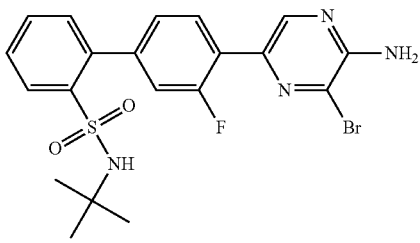

4'-(5-Amino-6-bromopyrazin-2-yl)-N-tert-butyl-3'-fluorobiphenyl-2-sulfonamide

To a 25 mL round-bottomed flask were added a stirbar, (55 mg, 14 mmol) 4'-(5-aminopyrazin-2-yl)-N-tert-butyl-3'-fluorobiphenyl-2-sulfonamide (32 mg, 0.18 mmol) NBS, and dry DMF (2.0 mL). The flask was sparged with nitrogen and stirred at rt for 18 hours before subjecting the reaction mixture (after syringe filtration) to HPLC purification to give the title compound (46 mg, 70%). MS (ESI): mass calcd. for $C_{20}H_{20}BrFN_4O_2S$, 479.05; m/z found, 479.0 [M+H]$^+$. $^1$H NMR (600 MHz, DMSO-$d_6$) δ 8.45 (d, J=1.8, 1H), 8.06 (dd, J=7.9, 1.4, 1H), 7.88-7.81 (m, 1H), 7.69-7.64 (m, 1H), 7.64-7.58 (m, 1H), 7.37 (dd, J=7.6, 1.4, 1H), 7.35-7.29 (m, 2H), 7.05 (s, 2H), 6.98 (s, 1H), 1.02 (s, 9H).

Example 443

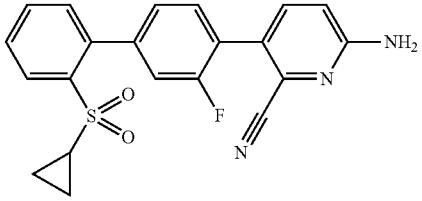

6-Amino-3-(2'-(cyclopropylsulfonyl)-3-fluoro-[1,1'-biphenyl]-4-yl)picolinonitrile The title compound was prepared using analogous conditions to those described in Example 6 2-(2'-(cyclopropylsulfonyl)-3-fluoro-[1,1'-biphenyl]-4-yl)-4,4,5,5-tetramethyl-1,3,2-dioxaborolane and 6-amino-3-bromo-2-cyanopyridine. MS (ESI): mass calcd. for $C_{21}H_{16}FN_3O_2S$, 393.09; m/z found, 393.9 [M+H]$^+$. $^1$H NMR (500 MHz, DMSO-$d_6$) δ 8.07 (d, J=7.9, 1H), 7.71-7.64 (m, 1H), 7.64-7.58 (m, 2H), 7.54-7.48 (m, 1H), 7.40 (dd, J=19.2, 9.2, 2H), 7.33 (dd, J=7.9, 1.6, 1H), 6.86 (d, J=8.7, 1H), 6.79 (d, J=10.0, 3H), 1.03 (s, 9H).

Example 444

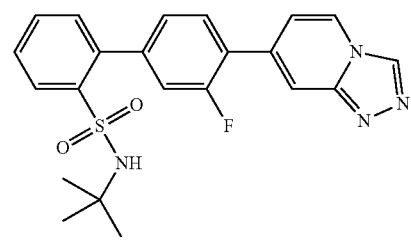

N-tert-Butyl-3'-fluoro-4'-[1,2,4]triazolo[4,3-a]pyridin-7-ylbiphenyl-2-sulfonamide To a 20 mL vial were added N-(tert-butyl)-3'-fluoro-4'-(4,4,5,5-tetramethyl-1,3,2-dioxaborolan-2-yl)-[1,1'-biphenyl]-2-sulfonamide (45 mg, 0.10 mmol), 7-bromo-[1,2,4]triazolo[4,3-a]pyridine (21 mg, 0.10 mmol) $K_2CO_3$ (29 mg, 0.21 mmol), Pd(dppf)Cl$_2$.CH$_2$Cl$_2$ (4 mg, 0.005 mmol), and a stir bar. The vial was sealed with a teflon lined cap and the vial sparged with $N_2$. The vial was then charged with freshly sparged DMSO (2 mL) and stirred for 16 hours at 80° Celsius. The reaction mixture was then cooled to rt, filtered, and purified by HPLC to give the title compound (30 mg, 53%). MS (ESI): mass calcd. for $C_{22}H_{21}FN_4O_2S$, 424.14; m/z found, 425.1 [M+H]$^+$. $^1$H NMR (400 MHz, CD$_3$OD) δ 9.40 (s, 1H), 8.79 (s, 1H), 8.20-8.11 (m, 2H), 7.77 (m, 1H), 7.70-7.57 (m, 3H), 7.47-7.38 (m, 3H), 1.10 (s, 9H).

Example 445

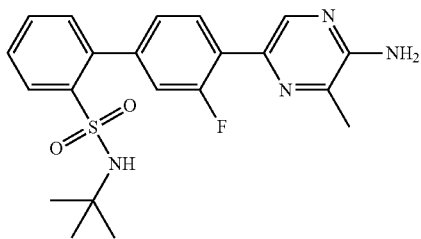

4'-(5-Amino-6-methylpyrazin-2-yl)-N-tert-butyl-3'-fluorobiphenyl-2-sulfonamide

The title compound was prepared in a manner similar to that described in Example 427 using 5-bromo-3-methylpyrazin-2-amine. MS (ESI): mass calcd. for $C_{21}H_{23}FN_4O_2S$, 414.15; m/z found, 415.2 [M+H]$^+$. $^1$H NMR (500 MHz, CD$_3$OD) δ 8.31-8.24 (m, 1H), 8.17-8.12 (dd, J=8.2, 1.3, 1H), 7.97-7.91 (m, 1H), 7.68-7.61 (m, 1H), 7.59-7.53 (m, 1H), 7.43-7.36 (dd, J=7.5, 1.3, 1H), 7.36-7.28 (m, 2H), 2.59-2.35 (m, 3H), 1.06 (s, 9H).

Example 446

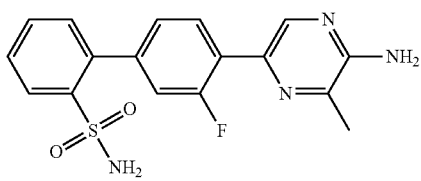

4'-(5-Amino-6-methylpyrazin-2-yl)-3'-fluorobiphenyl-2-sulfonamide

The title compound was prepared by forming 4'-(5-Amino-6-methylpyrazin-2-yl)-N-tert-butyl-3'-fluorobiphenyl-2-sulfonamide then removing the tert-butyl group by dissolving the crude 4'-(5-Amino-6-methylpyrazin-2-yl)-N-tert-butyl-3'-fluorobiphenyl-2-sulfonamide in 1 mL of trifluoroacetic acid and heating it to 60° Celsius for 2 hours, after which time the reaction was cooled to rt, concentrated to dryness and purified using FCC. MS (ESI): mass calcd. for $C_{17}H_{15}FN_4O_2S$, 358.09; m/z found, 359.1 [M+H]$^+$. $^1$H NMR (500 MHz, CD$_3$OD) δ 8.22 (s, 1H), 8.16-8.10 (dd, J=7.7, 1.3, 1H), 8.03-7.97 (m, 1H), 7.68-7.62 (m, 1H), 7.61-7.54 (m, 1H), 7.41-7.37 (dd, J=7.7, 1.4, 1H), 7.36-7.33 (dd, J=8.0, 1.7, 1H), 7.33-7.29 (dd, J=12.3, 1.6, 1H), 2.66-2.43 (m, 3H).

Example 447

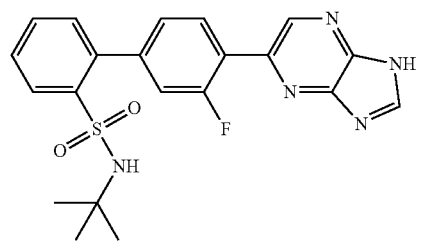

N-tert-Butyl-3'-fluoro-4'-(1H-imidazo[4,5-b]pyrazin-5-yl)biphenyl-2-sulfonamide

The title compound was prepared in a manner similar to that described in Example 427 using 5-bromo-1H-imidazo[4,5-b]pyrazine. MS (ESI): mass calcd. for $C_{21}H_{20}FN_5O_2S$, 425.13; m/z found, 426.2 [M+H]$^+$. $^1$H NMR (500 MHz, CD$_3$OD) δ 9.06-8.88 (d, J=2.1, 1H), 8.80 (s, 1H), 8.18-8.11 (dd, J=8.1, 1.3, 1H), 8.13-8.04 (m, 1H), 7.71-7.64 (m, 1H), 7.63-7.54 (m, 1H), 7.48-7.39 (m, 3H), 1.09 (s, 9H).

Example 448

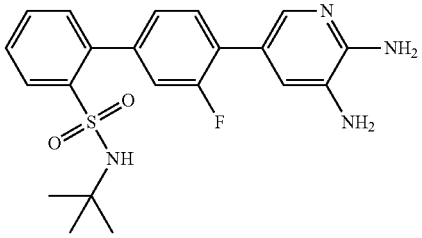

N-tert-Butyl-4'-(5,6-diaminopyridin-3-yl)-3'-fluorobiphenyl-2-sulfonamide

The title compound was prepared in a manner similar to that described in Example 427 using 5-bromopyridine-2,3-diamine. MS (ESI): mass calcd. for $C_{21}H_{23}FN_4O_2S$, 414.15; m/z found, 415.1 [M+H]$^+$. $^1$H NMR (500 MHz, CD$_3$OD) δ 8.18-8.06 (m, 1H), 7.69-7.62 (m, 1H), 7.61-7.56 (m, 1H), 7.56-7.50 (m, 2H), 7.47-7.42 (m, 1H), 7.40-7.30 (m, 3H), 1.104 (s, 9H).

Example 449

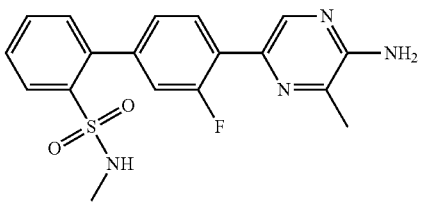

4'-(5-Amino-6-methylpyrazin-2-yl)-3'-fluoro-N-methylbiphenyl-2-sulfonamide

The title compound was prepared in a manner similar to that described in Example 427 using 5-bromo-3-methylpyrazin-2-amine and 3'-fluoro-N-methyl-4'-(4,4,5,5-tetramethyl-1,3,2-dioxaborolan-2-yl)-[1,1'-biphenyl]-2-sulfonamide. MS (ESI): mass calcd. for $C_{18}H_{17}FN_4O_2S$, 372.11; m/z found, 373.1 [M+H]$^+$. $^1$H NMR (500 MHz, CD$_3$OD) δ 8.27 (s, 1H), 8.09-8.00 (d, J=7.9, 1H), 7.96-7.87 (m, 1H), 7.71-7.63 (m, 1H), 7.63-7.55 (m, 1H), 7.44-7.38 (d, J=7.5, 1H), 7.34-7.21 (m, 2H), 2.46 (s, 3H), 2.44 (s, 3H).

Example 450

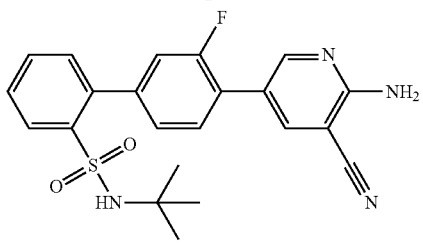

4'-(6-Amino-5-cyanopyridin-3-yl)-N-tert-butyl-3'-fluorobiphenyl-2-sulfonamide trifluoroacetic acid salt The title compound was prepared using analogous conditions to those described in Example 1 using N-(tert-butyl)-3'-fluoro-4'-(4,4,5,5-tetramethyl-1,3,2-dioxaborolan-2-yl)-[1,1'-biphenyl]-2-sulfonamide and 2-amino-5-bromonicotinonitrile. MS (ESI): mass calcd. for $C_{22}H_{21}FN_4O_2S$, 424.14; m/z found, 425.1 [M+H]$^+$. $^1$H NMR (500 MHz, DMSO-d$_6$) δ 8.49-8.44 (m, 1H), 8.12 (d, J=1.8, 1H), 8.06 (dd, J=7.9, 1.3, 1H), 7.66 (m, 1H), 7.63-7.56 (m, 2H), 7.38 (dd, J=7.5, 1.3, 1H), 7.33 (dd, J=11.9, 1.6, 1H), 7.27 (dd, J=7.9, 1.7, 1H), 7.18 (s, 2H), 6.90 (s, 1H), 1.03 (s, 9H).

Example 451

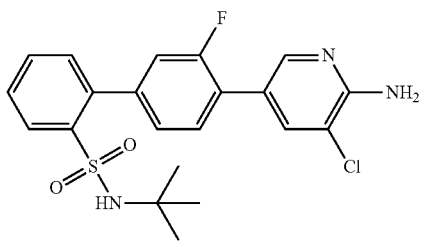

4'-(6-Amino-5-chloropyridin-3-yl)-N-tert-butyl-3'-fluorobiphenyl-2-sulfonamide trifluoroacetic acid salt The title compound was prepared using analogous conditions to those described in Example 1 using N-(tert-butyl-3'-fluoro-4'-(4,4,5,5-tetramethyl-1,3,2-dioxaborolan-2-yl)-[1,1'-biphenyl]-2-sulfonamide and 5-bromo-3-chloropyridin-2-amine. MS (ESI): mass calcd. for $C_{21}H_{21}ClFN_3O_2S$, 433.10; m/z found, 434.1 [M+H]$^+$. $^1$H NMR (500 MHz, DMSO-d$_6$) δ 8.20 (s, 1H), 8.06 (dd, J=7.9, 1.2, 1H), 7.85 (s, 1H), 7.66 (m, 1H), 7.62-7.54 (m, 2H), 7.37 (m, 1H), 7.31 (dd, J=11.9, 1.6, 1H), 7.26 (dd, J=7.9, 1.7, 1H), 6.89 (s, 1H), 6.62 (s, 2H), 1.03 (s, 9H).

Example 452

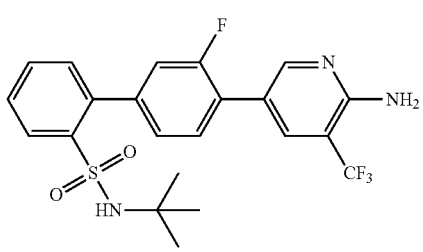

4'-[6-Amino-5-(trifluoromethyl)pyridin-3-yl]-N-tert-butyl-3'-fluorobiphenyl-2-sulfonamide trifluoroacetic acid salt The title compound was prepared using analogous conditions to those described in Example 1 using N-(tert-butyl)-3'-fluoro-4'-(4,4,5,5-tetramethyl-1,3,2-dioxaborolan-2-yl)-[1,1'-biphenyl]-2-sulfonamide and 5-bromo-3-(trifluoromethyl)pyridin-2-amine. MS (ESI): mass calcd. for $C_{22}H_{21}F_4N_3O_2S$, 467.13; m/z found, 468.1 [M+H]$^+$. $^1$H NMR (500 MHz, DMSO-d$_6$) δ 8.47 (s, 1H), 8.07 (dd, J=7.9, 1.2, 1H), 7.96 (s, 1H), 7.66 (m, 1H), 7.63-7.55 (m, 2H), 7.38 (dd, J=7.5, 1.3, 1H), 7.33 (dd, J=11.9, 1.6, 1H), 7.27 (dd, J=7.9, 1.7, 1H), 6.88 (s, 1H), 6.76 (s, 2H), 1.02 (s, 9H).

Example 453

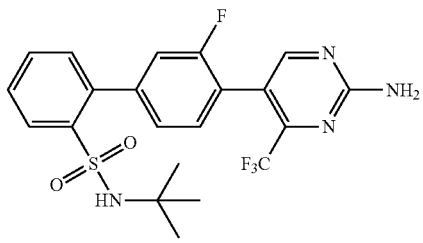

4'-[2-Amino-4-(trifluoromethyl)pyrimidin-5-yl]-N-tert-butyl-3'-fluorobiphenyl-2-sulfonamide trifluoroacetic acid salt The title compound was prepared using analogous conditions to those described in Example 1 using N-(tert-butyl-3'-fluoro-4'-(4,4,5,5-tetramethyl-1,3,2-dioxaborolan-2-yl)-[1,1'-biphenyl]-2-sulfonamide and 5-bromo-4-(trifluoromethyl)pyrimidin-2-amine. MS (ESI): mass calcd. for $C_{21}H_{20}F_4N_4O_2S$, 468.12; m/z found, 469.1 [M+H]$^+$. $^1$H NMR (400 MHz, DMSO-d$_6$) δ 8.45 (s, 1H), 8.07 (dd, J=7.8, 1.4, 1H), 7.67 (m, 1H), 7.62 (m, 1H), 7.53 (s, 2H), 7.45-7.38 (m, 2H), 7.37-7.29 (m, 2H), 6.74 (s, 1H), 1.01 (s, 9H).

Example 454

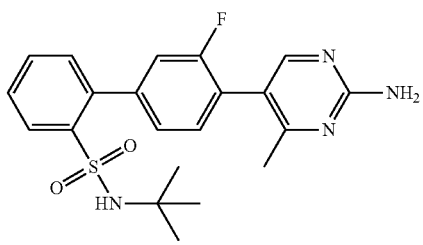

4'-(2-Amino-4-methylpyrimidin-5-yl)-N-tert-butyl-3'-fluorobiphenyl-2-sulfonamide trifluoroacetic acid salt The title compound was prepared using analogous conditions to those described in Example 1 using N-(tert-butyl)-3'-fluoro-4'-(4,4,5,5-tetramethyl-1,3,2-dioxaborolan-2-yl)-[1,1'-biphenyl]-2-sulfonamide and 5-bromo-4-methylpyrimidin-2-amine. MS (ESI): mass calcd. for $C_{21}H_{23}FN_4O_2S$, 414.15; m/z found, 415.1 [M+H]$^+$. $^1$H NMR (600 MHz, DMSO-d$_6$) δ 8.17 (s, 1H), 8.08 (dd, J=8.0, 1.2, 1H), 7.67 (m, 1H), 7.64-7.58 (m, 1H), 7.43-7.38 (m, 2H), 7.36 (dd, J=10.9, 1.6, 1H), 7.30 (dd, J=7.8, 1.7, 1H), 7.13 (s, 2H), 6.86 (s, 1H), 2.25 (d, J=0.8, 3H), 1.00 (s, 9H).

Intermediate HC

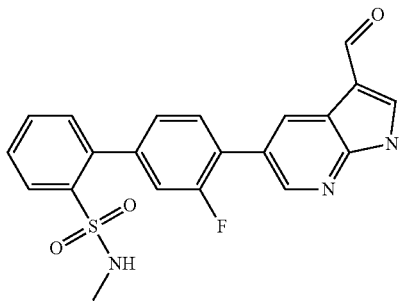

3'-fluoro-4'-(3-formyl-1H-pyrrolo[2,3-b]pyridin-5-yl)-N-methyl-[1,1'-biphenyl]-2-sulfonamide

Step A:
5-Bromo-1H-pyrrolo[2,3-b]pyridine-3-carbaldehyde

Hexamethylenetetramine (1.08 g, 7.61 mmol) was added to a solution of 5-bromo-1H-pyrrolo[2,3-b]pyridine (1 g, 5 mol) in HOAc (6.34 mL). The mixture was heated at 100° Celsius for 6 hours. The reaction mixture was then cooled to rt and diluted with water. The mixture was extracted with EtOAc, dried (Na$_2$SO$_4$), filtered and concentrated to dryness. The residue was purified by FCC to provide the title compound (379 mg, 33%). $^1$H NMR (500 MHz, CDCl$_3$) δ 10.02 (s, 1H), 8.77 (d, J=2.2, 1H), 8.48 (d, J=2.2, 1H), 7.99 (d, J=2.7, 1H).

Step B

The title compound was prepared using analogous conditions to those described in Example 88 using 5-bromo-1H-pyrrolo[2,3-b]pyridine-3-carbaldehyde and 3'-fluoro-N-methyl-4'-(4,4,5,5-tetramethyl-1,3,2-dioxaborolan-2-yl)-[1,1'-biphenyl]-2-sulfonamide. MS (ESI): mass calcd. for C$_{21}$H$_{16}$FN$_3$O$_3$S, 409.09; m/z found, 410.2 [M+H]$^+$.

Intermediate HD

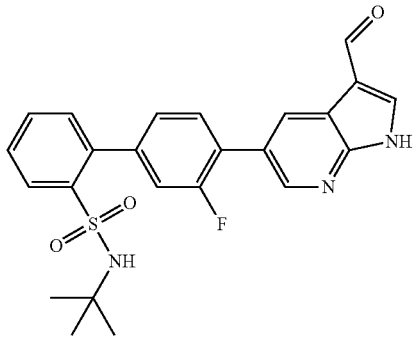

N-(tert-butyl)-3'-fluoro-4'-(3-formyl-1H-pyrrolo[2,3-b]pyridin-5-yl)-[1,1'-biphenyl]-2-sulfonamide The title compound was prepared using analogous conditions to those described in Example 88 using 5-bromo-1H-pyrrolo[2,3-b]pyridine-3-carbaldehyde and N-(tert-butyl)-3'-fluoro-4'-(4,4,5,5-tetramethyl-1,3,2-dioxaborolan-2-yl)-[1,1'-biphenyl]-2-sulfonamide. MS (ESI): mass calcd. for C$_{24}$H$_{22}$FN$_3$O$_3$S, 451.14; m/z found, 452.2 [M+H]$^+$.

Intermediate HE

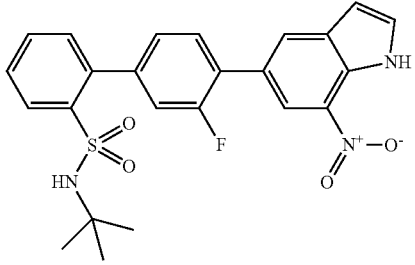

N-(tert-butly)-3'-fluoro-4'-(7-nitro-1H-indol-5-yl)-1,1'-biphenyl]-2-sulfonamide The title compound was prepared using analogous conditions to those described in Example 88 using 5-bromo-7-nitroindole and N-(tert-butyl)-3'-fluoro-4'-(4,4,5,5-tetramethyl-1,3,2-dioxaborolan-2-yl)-[1,1'-biphenyl]-2-sulfonamide. $^1$H NMR (400 MHz, CDCl$_3$) δ 8.42 (s, 1H), 8.27-8.18 (m, 2H), 7.65-7.58 (m, 2H), 7.58-7.50 (m, 1H), 7.50-7.35 (m, 4H), 6.83-6.77 (m, 1H), 1.17-1.03 (m, 9H).

Example 455

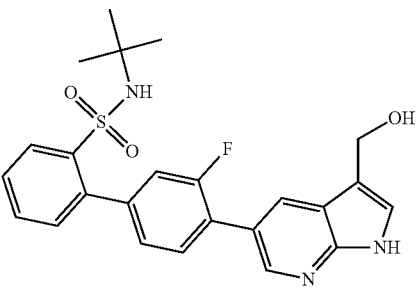

N-tert-Butyl-3'-fluoro-4'-[3-(hydroxymethyl)-1H-pyrrolo[2,3-b]pyridin-5-yl]biphenyl-2-sulfonamide The title compound was prepared using similar methods to those described in Example 457 using N-(tert-butyl)-3'-fluoro-4'-(3-formyl-1H-pyrrolo[2,3-b]pyridin-5-yl)-[1,1'-biphenyl]-2-sulfonamide. MS (ESI): mass calcd. for C$_{24}$H$_{24}$FN$_3$O$_3$S, 453.15; m/z found, 454.2 [M+H]$^+$. $^1$H NMR (500 MHz, CDCl$_3$) δ 8.50 (s, 1H), 8.26-8.20 (m, 2H), 7.63-7.58 (m, 1H), 7.56-7.48 (m, 3H), 7.44-7.39 (m, 1H), 7.39-7.34 (m, 3H), 4.92 (s, 2H), 1.11 (d, J=12.1, 9H).

Example 456

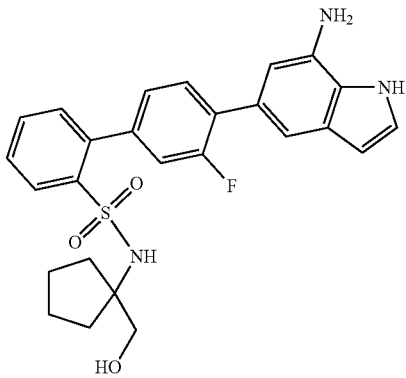

4'-(7-Amino-1H-indol-5-yl)-3'-fluoro-N-[1-(hydroxymethyl)cyclopentyl]biphenyl-2-sulfonamide The title compound was prepared in a manner similar to that described in Example 571 using 5-(2-fluoro-4-(4,4,5,5-tetramethyl-1,3,2-dioxaborolan-2-yl)phenyl)-1H-indol-7-amine and 2-bromo-N-(1-(hydroxymethyl)-cyclopentyl) benzenesulfonamide in Step B. MS (ESI): mass calcd. for $C_{26}H_{26}FN_3O_3S$, 479.17; m/z found, 480.3 [M+H]+. 1H NMR (500 MHz, CDCl3) δ 8.18 (dd, J=8.1, 1.4, 1H), 8.13 (s, 1H), 7.65-7.50 (m, 3H), 7.42 (s, 1H), 7.41-7.31 (m, 3H), 6.87 (m, 1H), 6.61 (dd, J=3.1, 2.0, 1H), 4.05 (s, 1H), 3.48 (s, 2H), 1.50-1.34 (m, 4H), 1.37-1.22 (m, 2H), 0.93-0.73 (m, 2H).

Example 457

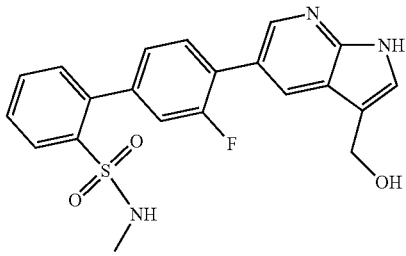

3'-Fluoro-4'-[3-(hydroxymethyl)-1H-pyrrolo[2,3-b]pyridin-5-yl]-N-methylbiphenyl-2-sulfonamide NaBH4 (4.45 mg, 0.13 mmol) was added to 3'-fluoro-4'-(3-formyl-1H-pyrrolo[2,3-b]pyridin-5-yl)-N-methyl-[1,1'-biphenyl]-2-sulfonamide (18 mg, 0.044 mmol) in MeOH (0.52 mL). The mixture was stirred at rt for 1 h and then concentrated to dryness. The residue was subjected to FCC purification to give the title compound. MS (ESI): mass calcd. for $C_{21}H_{18}FN_3O_3S$, 411.11; m/z found, 412.2 [M+H]+. 1H NMR (500 MHz, CDCl3) δ 9.36 (s, 1H), 8.34 (s, 1H), 8.23 (dd, J=7.9, 1.2, 1H), 8.12 (s, 1H), 7.68-7.61 (m, 1H), 7.61-7.54 (m, 1H), 7.42-7.30 (m, 5H), 5.21 (s, 1H), 4.88 (s, 2H), 2.52 (dd, J=13.9, 5.3, 3H).

Example 458

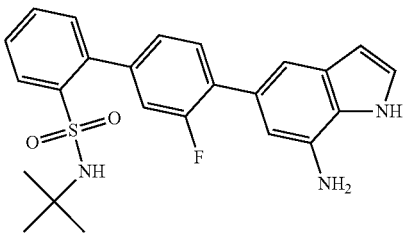

4'-(7-Amino-1H-indol-5-yl)-N-tert-butyl-3'-fluorobiphenyl-2-sulfonamide

Zn dust (123 mg, 1.88 mmol) was added to a solution of N-(tert-butyl)-3'-fluoro-4'-(7-nitro-1H-indol-5-yl)-[1,1'-biphenyl]-2-sulfonamide (23 mg, 0.19 mmol) and NH4Cl (101 mg, 1.88 mmol) in water (0.75 mL) and acetone (3.76 mL). The mixture was stirred at rt for 1 hour and then filtered through Celite. The resulting filtrate was concentrated to dryness and then taken up in water and extracted with EtOAc. The organic extract was dried (Na2SO4), filtered and concentrated to dryness to give the title compound (23 mg, 28%). MS (ESI): mass calcd. for $C_{24}H_{24}FN_3O_2S$, 437.16: m/z found, 438.2 [M+H]+. 1H NMR (400 MHz, CDCl3) δ 8.20 (dd, J=8.0, 1.3, 1H), 8.17-8.10 (m, 1H), 7.63-7.56 (m, 2H), 7.54-7.48 (m, 1H), 7.42 (s, 1H), 7.38 (dd, J=7.8, 1.7, 2H), 7.32 (dd, J=11.4, 1.8, 1H), 6.86 (m, 1H), 6.62 (dd, J=3.2, 2.0, 1H), 3.78-3.68 (m, 2H), 1.05 (s, 9H).

Example 459

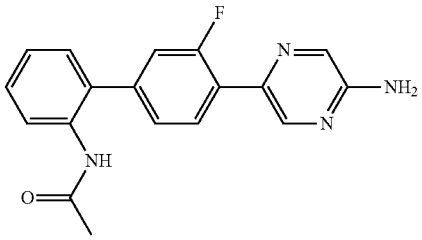

N-[4'-(5-Aminopyrazin-2-yl)-3'-fluorobiphenyl-2-yl]acetamide

The title compound was prepared using analogous conditions to those described in Example 1 utilizing 5-(2-fluoro-4-(4,4,5,5-tetramethyl-1,3,2-dioxaborolan-2-yl)phenyl) pyrazin-2-amine and N-(2-bromophenyl)acetamide. MS (ESI): mass calcd. for $C_{18}H_{15}FN_4O$, 322.12; m/z found, 322.9 [M+H]+. 1H NMR (400 MHz, DMSO-d6) δ 9.40 (s, 1H), 8.38 (s, 1H), 8.02 (s, 1H), 7.91 (m, 1H), 7.53-7.21 (m, 6H), 6.73 (s, 2H), 1.92 (s, 3H).

Example 460

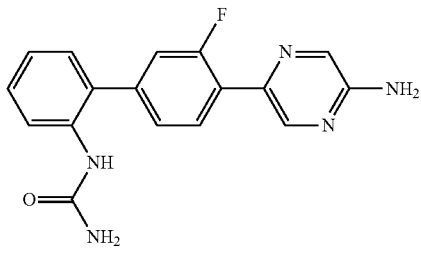

1-[4'-(5-Aminopyrazin-2-yl)-3'-fluorobiphenyl-2-yl]urea

The title compound was prepared using analogous conditions to those described in Example 1 utilizing 5-(2-fluoro-4-(4,4,5,5-tetramethyl-1,3,2-dioxaborolan-2-yl)phenyl)pyrazin-2-amine and 1-(2-bromophenyl)urea. MS (ESI): mass calcd. for $C_{17}H_{14}FN_5O$, 323.12; m/z found, 323.9 [M+H]$^+$. $^1$H NMR (400 MHz, DMSO-$d_6$) δ 8.38 (s, 1H), 8.02 (s, 1H), 7.95 (m, 1H), 7.86 (d, J=8.9, 1H), 7.56 (s, 1H), 7.36-7.19 (m, 4H), 7.08 (m, 1H), 6.73 (s, 2H), 6.01 (s, 2H).

Intermediate HF

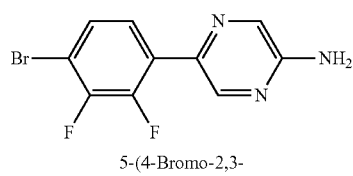

5-(4-Bromo-2,3-difluorophenyl)pyrazin-2-amine

A mixture of (4-bromo-2,3-difluorophenyl)boronic acid (400 mg, 1.69 mmol) and 5-bromopyrazin-2-amine (588 mg, 3.38 mmol was suspended in EtOH (5.6 ml) and toluene (5.7 mL) The resulting mixture was treated with aqueous $Na_2CO_3$ (2.0 N, 4.2 mL, 8.45 mmol). The resulting mixture was then sparged with nitrogen through the mixture for 10 min, and then Pd(PPh$_3$)$_4$ (98 mg, 0.085 mmol) was added. The reaction vessel was sealed and heated at 80° Celsius for 17 hours. The reaction mixture was cooled to rt and then partitioned between saturated aqueous NH$_4$Cl and EtOAc. The organic layer was dried over MgSO$_4$ and concentrated to dryness. The residue was suspended in DCM and the solid isolated by filtration to afford the title compound (160 mg, 33%), which was used without further purification. MS (ESI): mass calcd. for $C_{10}H_6BrF_2N_3$. 284.97; m/z found, 286.0 [M+H]$^+$. $^1$H NMR (400 MHz, DMSO-$d_6$) δ 8.36 (s, 1H), 8.01 (d, J=1.2, 1H), 7.68-7.56 (m, 2H), 6.87 (s, 2H).

Example 461

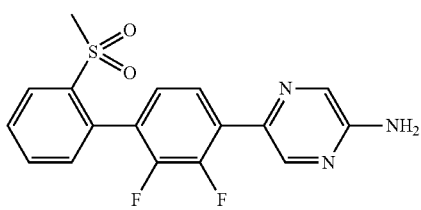

5-[2,3-Difluoro-2'-(methylsulfonyl)biphenyl-4-yl]pyrazin-2-amine

Nitrogen sparged DMSO (0.73 ml) was added to a mixture of 5-(4-bromo-2,3-difluorophenyl)pyrazin-2-amine (50 mg, 0.18 mmol), (2-(methylsulfonyl)phenyl)boronic acid (35 mg, 0.18 mmol), $K_2CO_3$ (73 mg, 0.532 mmol) and PdCl$_2$(dppf).CH$_2$Cl$_2$ (13 mg, 0.018 mmol) and heated at 80° Celsius for 2.5 hours. The mixture was cooled to rt and partitioned between sat. NaHCO$_3$ and EtOAc. The organic layer was isolated, dried over MgSO$_4$, and concentrated to dryness. Purification by FCC afforded the title compound (26 mg, 41%). MS (ESI): mass calcd. for $C_{17}H_{13}F_2N_3O_2S$, 361.07; m/z found, 362.0 [M+H]$^+$. $^1$H NMR (400 MHz, DMSO-$d_6$) δ 8.44-8.41 (m, 1H), 8.14 (dd, J=7.9, 1.4, 1H), 8.04 (d, J=1.5, 1H), 7.84 (m, 1H), 7.78 (m, 1H), 7.75-7.66 (m, 1H), 7.53 (dd, J=7.5, 1.3, 1H), 7.30 (dd, J=11.6, 4.9, 1H), 6.85 (s, 2H), 3.06 (s, 3H).

Example 462

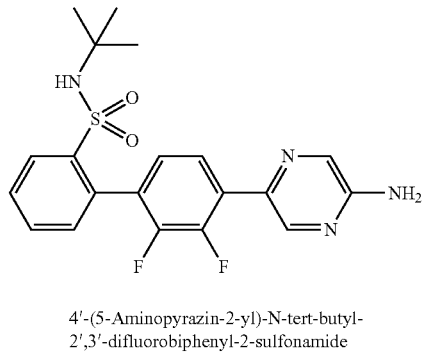 [SMILES: CC(C)(C)NS(=O)(=O)c1ccccc1-c1ccc(-c2cnc(N)cn2)c(F)c1F]

4'-(5-Aminopyrazin-2-yl)-N-tert-butyl-2',3'-difluorobiphenyl-2-sulfonamide

The title compound was prepared by methods analogous to Example 461 using (2-(N-(tert-butyl)sulfamoyl)phenyl)boronic acid. MS (ESI): mass calcd. for $C_{20}H_{20}F_2N_4O_2S$, 418.13; m/z found, 419.1 [M+H]$^+$. $^1$H NMR (500 MHz, CDCl$_3$) δ 8.36 (s, 1H), 8.25 (dd, J=7.9, 1.3, 1H), 7.94 (d, J=1.4, 1H), 7.71-7.66 (m, 1H), 7.60 (m, 1H), 7.55 (m, 1H), 7.34 (dd, J=7.4, 1.1, 1H), 7.33-7.28 (m, 1H), 5.47 (s, 1H), 5.19 (s, 2H), 1.20 (s, 9H).

Example 463

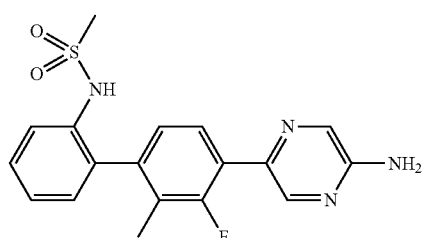

N-[4'-(5-Aminopyrazin-2-yl)-3'-fluoro-2'-methylbiphenyl-2-yl]methanesulfonamide

Step A: 5-(4-chloro-2-fluoro-3-methylphenyl)pyrazin-2-amine

The title compound was prepared by methods analogous to Intermediate HF using (4-chloro-2-fluoro-3-methylphenyl)boronic acid. MS (ESI): mass calcd. for C₁₁H₉ClFN₃, 237.05; m/z found, 238.0 [M+H]⁺.

Step B

To a mixture of 5-(4-chloro-2-fluoro-3-methylphenyl)pyrazin-2-amine (75 mg, 0.32 mmol), (2-(methylsulfonamido)phenyl)boronic acid (85 mg, 0.39 mmol) and chloro(2-dicyclohexylphosphino-2',4',6'-triisopropyl-1,1'-biphenyl)[2-(2'-amino-1,1'-biphenyl)]palladium(II) (5.0 mg, 0.006 mmol) in a sealed tube flushed with N₂ were added N₂ sparged K₃PO₄ (1.26 ml, 0.5 N) followed by N₂ sparged THF (0.63 ml). The reaction mixture was stirred at rt for 18 hours. The reaction mixture was then partitioned between EtOAc and brine. The organic layer was isolated, dried over MgSO₄, filtered and concentrated to dryness. Purification by FCC afforded the title compound (100 mg, 85%). MS (ESI): mass calcd. for C₁₈H₁₇FN₄O₂S, 372.10; m/z found, 373.1 [M+H]⁺. ¹H NMR (500 MHz, DMSO-d₆) δ 8.81 (s, 1H), 8.39-8.35 (m, 1H), 8.02 (d, J=1.5, 1H), 7.70 (m, 1H), 7.47 (dd, J=8.1, 1.0, 1H), 7.45-7.39 (m, 1H), 7.29 (m, 1H), 7.21 (dd, J=7.6, 1.5, 1H), 7.07 (d, J=8.0, 1H), 6.67 (s, 2H), 2.87 (s, 3H), 2.01 (d, J=2.5, 3H).

Example 464

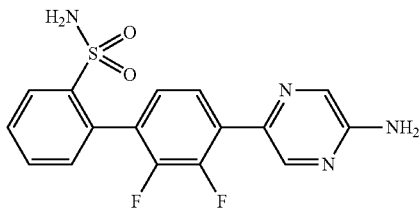

4'-(5-Aminopyrazin-2-yl)-2,3'-difluorobiphenyl-2-sulfonamide

A suspension of 4'-(5-aminopyrazin-2-yl)-N-tert-butyl-2',3'-difluorobiphenyl-2-sulfonamide (168 mg, 0.40 mmol) in TFA (3 mL) was heated at 50° Celsius for 3 hours. The reaction was then cooled to rt and carefully partitioned between NaHCO₃ and EtOAc. The organic layer was isolated, dried over MgSO₄, and concentrated to dryness. Purification by FCC afforded the title compound (140 mg, 96%). MS (ESI): mass calcd. for C₁₆H₁₂F₂N₄O₂S, 362.06; m/z found, 363.1 [M+H]⁺. ¹H NMR (500 MHz, DMSO-d₆) δ 8.40 (s, 1H), 8.12-8.01 (m, 2H), 7.72-7.61 (m, 3H), 7.45-7.36 (m, 3H), 7.19 (m, 1H), 6.81 (s, 2H).

Intermediate HG

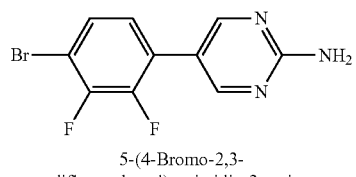

5-(4-Bromo-2,3-difluorophenyl)pyrimidin-2-amine

The title compound was prepared using analogous conditions to those described in 5-(4-chloro-2-fluorophenyl)pyrazin-2-amine using (4-bromo-2,3-difluorophenyl)boronic acid and 5-bromopyrimidin-2-amine. MS (ESI): mass calcd. for C₁₀H₆BrF₂N₃, 284.97; m/z found, 286.0 [M+H]⁺.

Example 465

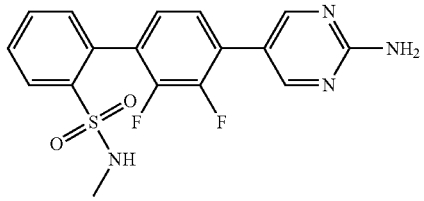

4'-(2-Aminopyrimidin-5-yl)-2',3'-difluoro-N-methylbiphenyl-2-sulfonamide trifluoroacetic acid salt The title compound was prepared using analogous conditions to those described in Example 1 using 5-(4-bromo-2,3-difluorophenyl)pyrimidin-2-amine and (2-(N-methylsulfamoyl)phenyl)boronic acid. MS (ESI): mass calcd. for C₁₇H₁₄F₂N₄O₂S, 376.08; m/z found, 377.1 [M+H]⁺. ¹H NMR (600 MHz, DMSO-d₆) δ 8.56 (s, 2H), 7.98 (dd, J=7.7, 1.6, 1H), 7.72 (m, 2H), 7.45 (dd, J=7.3, 1.6, 1H), 7.41 (m, 1H), 7.35 (m, 1H), 7.19 (m, 1H), 7.12 (s, 2H), 2.40 (d, J=4.9, 3H).

Example 466

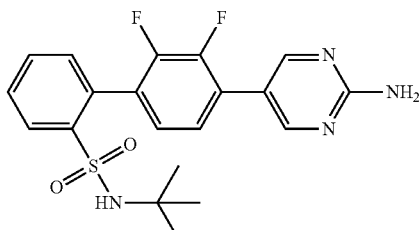

4'-(2-Aminopyrimidin-5-yl)--N-tert-butyl-2',3'-difluorobiphenyl-2-sulfonamide trifluoroacetic acid salt The title compound was prepared using analogous conditions to those described in Example 1 using 5-(4-bromo-2,3-difluorophenyl)pyrimidin-2-amine and (2-(N-(tert-butyl)sulfamoyl)phenyl)boronic acid. MS (ESI): mass calcd. for C₂₀H₂₀F₂N₄O₂S, 418.13; m/z found, 419.1 [M+H]⁺. ¹H NMR (600 MHz, CD₃OD) δ 8.63 (d, J=0.9, 2H), 8.15 (dd, J=7.9, 1.2, 1H), 7.67 (m, 1H), 7.63-7.58 (m, 1H), 7.38 (dd, J=7.5, 1.3, 1H), 7.35-7.29 (m, 1H), 7.27-7.18 (m, 1H), 1.13 (s, 9H).

Example 467

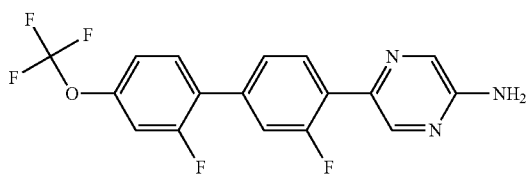

5-[2',3-Difluoro-4'-(trifluoromethoxy)biphenyl-4-yl]pyrazin-2-amine

The title compound was prepared using analogous conditions to those described in Example 1 utilizing 5-(2-fluoro-4-(4,4,5,5-tetramethyl-1,3,2-dioxaborolan-2-yl)phenyl)pyrazin-2-amine and 2-fluoro-4-(trifluoromethoxy)bromobenzene. MS (ESI): mass calcd. for $C_{17}H_{10}F_5N_3O$, 367.07; m/z found, 368.0 [M+H]$^+$. $^1$H NMR (400 MHz, DMSO-d$_6$) δ 8.40 (s, 1H), 8.03-7.96 (m, 2H), 7.78 (m, 1H), 7.56-7.49 (m, 3H), 7.37 (d, J=8.2, 1H), 6.75 (s, 2H).

Example 468

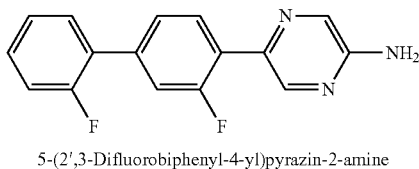

5-(2',3-Difluorobiphenyl-4-yl)pyrazin-2-amine

The title compound was prepared using analogous conditions to those described in Example 1 utilizing 5-(2-fluoro-4-(4,4,5,5-tetramethyl-1,3,2-dioxaborolan-2-yl)phenyl)pyrazin-2-amine and 2-bromofluorobenzene. MS (ESI): mass calcd. for $C_{16}H_{11}F_2N_3$, 283.09; m/z found, 284.1 [M+H]$^+$. $^1$H NMR (600 MHz, CDCl$_3$) δ 8.63-8.54 (m, 1H), 8.13 (d, J=1.4, 1H), 8.00 (m, 1H), 7.52-7.31 (m, 4H), 7.24-7.12 (m, 2H), 4.72 (s, 2H).

Example 469

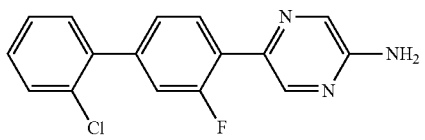

5-(2'-Chloro-3-fluorobiphenyl-4-yl)pyrazin-2-amine

The title compound was prepared using analogous conditions to those described in Example 1 utilizing 5-(2-fluoro-4-(4,4,5,5-tetramethyl-1,3,2-dioxaborolan-2-yl)phenyl)pyrazin-2-amine and 2-bromochlorobenzene. MS (ESI): mass calcd. for $C_{16}H_{11}ClFN_3$, 299.06; m/z found, 300.1 [M+H]$^+$. $^1$H NMR (600 MHz, CDCl$_3$) δ 8.60 (s, 1H), 8.12 (s, 1H), 7.98 (m, 1H), 7.54-7.44 (m, 1H), 7.41-7.23 (m, 5H), 4.68 (s, 2H).

Example 470

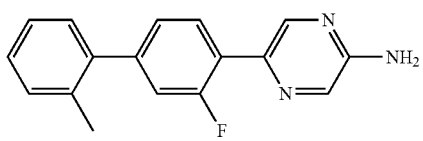

5-(3-Fluoro-2'-methylbiphenyl-4-yl)pyrazin-2-amine

The title compound was prepared using analogous conditions to those described in Example 1 utilizing 5-(2-fluoro-4-(4,4,5,5-tetramethyl-1,3,2-dioxaborolan-2-yl)phenyl)pyrazin-2-amine and 2-bromotoluene. MS (ESI): mass calcd. for $C_{17}H_{14}FN_3$, 279.12; m/z found, 280.1 [M+H]$^+$. $^1$H NMR (400 MHz, CDCl$_3$) 8.59 (s, 1H), 8.12 (s, 1H), 7.95 (m, 1H), 7.28-7.12 (m, 6H), 4.66 (s, 2H), 2.32 (s, 3H).

Example 471

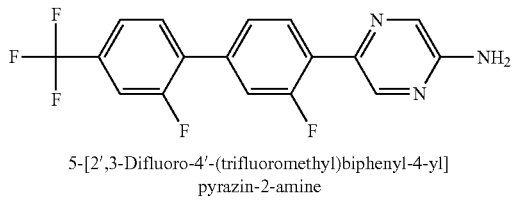 [SMILES: Nc1cnc(-c2ccc(-c3ccc(C(F)(F)F)cc3F)cc2F)cn1]

5-[2',3-Difluoro-4'-(trifluoromethyl)biphenyl-4-yl]pyrazin-2-amine

The title compound was prepared using analogous conditions to those described in Example 1 utilizing 5-(2-fluoro-4-(4,4,5,5-tetramethyl-1,3,2-dioxaborolan-2-yl)phenyl)pyrazin-2-amine and 2-fluoro-4-(trifluoromethyl)bromobenzene. MS (ESI): mass calcd. for $C_{17}H_{10}F_5N_3$, 351.08; m/z found, 351.9 [M+H]$^+$. $^1$H NMR (400 MHz, DMSO-d$_6$) δ 8.42 (s, 1H), 8.11-7.97 (m, 2H), 7.90-7.83 (m, 2H), 7.71 (d, J=8.1, 1H), 7.61-7.54 (m, 2H), 6.78 (s, 2H).

Example 472

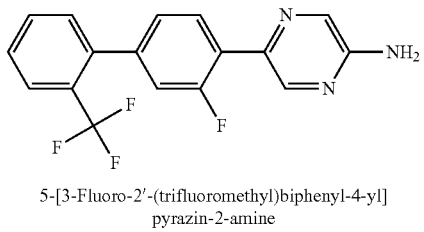 [SMILES: Nc1cnc(-c2ccc(-c3ccccc3C(F)(F)F)cc2F)cn1]

5-[3-Fluoro-2'-(trifluoromethyl)biphenyl-4-yl]pyrazin-2-amine

The title compound was prepared using analogous conditions to those described in Example 1 utilizing 5-(2-fluoro-4-(4,4,5,5-tetramethyl-1,3,2-dioxaborolan-2-yl)phenyl)pyrazin-2-amine and 2-trifluoromethylbromobenzene. MS (ESI): mass calcd. for $C_{17}H_{11}F_4N_3$, 333.09; m/z found, 334.1 [M+H]$^+$. $^1$H NMR (400 MHz, CD$_3$OD) δ 8.40 (s, 1H), 8.09 (s, 1H), 7.91 (m, 1H), 7.81 (d, J=7.6, 1H), 7.69 (m, 1H), 7.59 (m, 1H), 7.44 (d, J=7.8, 1H), 7.23 (d, J=8.7, 1H), 7.17 (d, J=11.8, 1H).

Example 473

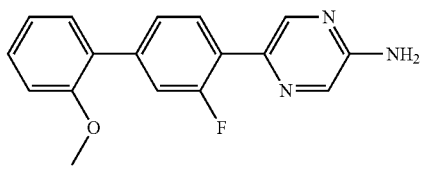

5-(3-Fluoro-2'-methoxybiphenyl-4-yl)pyrazin-2-amine

The title compound was prepared using analogous conditions to those described in Example 1 utilizing 5-(2-fluoro-4-(4,4,5,5-tetramethyl-1,3,2-dioxaborolan-2-yl)phenyl)pyrazin-2-amine and 2-methoxybromobenzene. MS (ESI): mass calcd. for $C_{17}H_{14}FN_3O$, 295.11; m/z found, 296.1

[M+H]⁺. ¹H NMR (400 MHz, CD₃OD) δ 8.38 (s, 1H), 8.08 (s, 1H), 7.85 (m, 1H), 7.45-7.29 (m, 4H), 7.14-7.00 (m, 2H), 3.84 (s, 3H).

Example 474

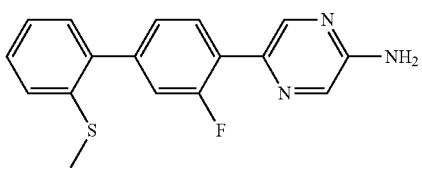

5-[3-Fluoro-2'-(methylsulfanyl)biphenyl-4-yl]
pyrazin-2-amine

The title compound was prepared using analogous conditions to those described in Example 1 utilizing 5-(2-fluoro-4-(4,4,5,5-tetramethyl-1,3,2-dioxaborolan-2-yl)phenyl)pyrazin-2-amine and 2-thiomethylbromobenzene. MS (ESI): mass calcd. for C₁₇H₁₄FN₃S, 311.09; m/z found, 312.0 [M+H]⁺. ¹H NMR (400 MHz, DMSO-d) δ 8.37 (s, 1H), 8.02 (d, J=1.2, 1H), 7.90 (m, 1H), 7.44-7.32 (m, 2H), 7.30 (s, 1H), 7.27-7.18 (m, 3H), 6.71 (s, 2H), 2.40 (s, 3H).

Example 475

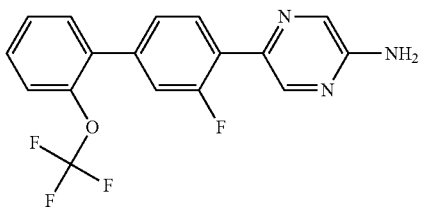

5-[3-Fluoro-2'-(trifluoromethoxy)biphenyl-4-yl]
pyrazin-2-amine

The title compound was prepared using analogous conditions to those described in Example 1 utilizing 5-(2-fluoro-4-(4,4,5,5-tetramethyl-1,3,2-dioxaborolan-2-yl)phenyl)pyrazin-2-amine and 2-(trifluoromethoxy)bromobenzene. MS (ESI): mass calcd. for C₁₇H₁₁F₄N₃O, 349.08; m/z found, 350.0 [M+H]⁺. ¹H NMR (400 MHz, DMSO-d₆) δ 8.39 (s, 1H), 8.02 (s, 1H), 7.96 (m, 1H), 7.65-7.47 (m, 4H), 7.42 (d, J=5.1, 1H), 7.39 (s, 1H), 6.73 (s, 2H).

Example 476

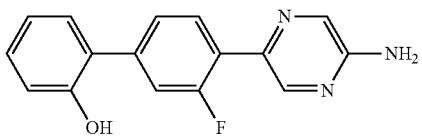

4'-(5-Aminopyrazin-2-yl)-3'-fluorobiphenyl-2-ol

The title compound was prepared using analogous conditions to those described in Example 1 utilizing 5-(2-fluoro-4-(4,4,5,5-tetramethyl-1,3,2-dioxaborolan-2-yl)phenyl)pyrazin-2-amine and 2-bromophenol. MS (ESI): mass calcd. for C₁₆H₁₂FN₃O, 281.10; m/z found, 282.0 [M+H]⁺. ¹H NMR (400 MHz, DMSO-d) δ 9.72 (s, 1H), 8.36 (s, 1H), 8.01 (d, J=1.4, 1H), 7.87 (m, 1H), 7.49 (dd, J=4.4, 1.3, 1H), 7.45 (s, 1H), 7.34 (dd, J=7.4, 1.3, 1H), 7.19 (m, 1H), 6.95 (d, J=7.3, 1H), 6.89 (m, 1H), 6.68 (s, 2H).

Example 477

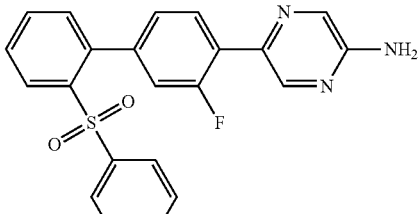

5-[3-Fluoro-2'-(phenylsulfonyl)biphenyl-4-yl]
pyrazin-2-amine

The title compound was prepared using analogous conditions to those described in Example 1 utilizing 5-(2-fluoro-4-(4,4,5,5-tetramethyl-1,3,2-dioxaborolan-2-yl)phenyl)pyrazin-2-amine and 1-bromo-2-(phenylsulfonyl)benzene. MS (ESI): mass calcd. for C₂₂H₁₆FN₃O₂S, 405.09; m/z found, 406.0 [M+H]⁺. ¹H NMR (400 MHz, DMSO-d₆) δ 8.35 (s, 1H), 8.29 (dd, J=6.7, 2.5, 1H), 8.03 (d, J=1.4, 1H), 7.80-7.66 (m, 3H), 7.58 (m, 1H), 7.41-7.28 (m, 5H), 6.84 (dd, J=8.0, 1.6, 1H), 6.78-6.66 (m, 3H).

Example 478

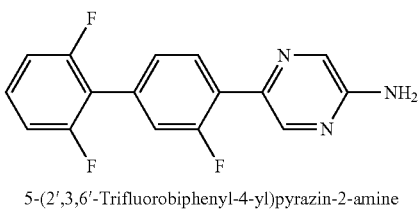 [SMILES: Nc1cnc(-c2ccc(-c3c(F)cccc3F)cc2F)cn1]

5-(2',3,6'-Trifluorobiphenyl-4-yl)pyrazin-2-amine

The title compound was prepared using analogous conditions to those described in Example 1 utilizing 5-(2-fluoro-4-(4,4,5,5-tetramethyl-1,3,2-dioxaborolan-2-yl)phenyl)pyrazin-2-amine and 2,6-difluorobromobenzene. MS (ESI): mass calcd. for C₁₆H₁₀F₃N₃, 301.08; m/z found, 302.0 [M+H]⁺. ¹H NMR (400 MHz, DMSO-d₆) δ 8.39 (s, 1H), 8.02 (s, 1H), 7.97 (m, 1H), 7.56-7.47 (m, 1H), 7.43 (d, J=12.5, 1H), 7.37 (d, J=7.9, 1H), 7.25 (m, 2H), 6.76 (s, 2H).

Example 479

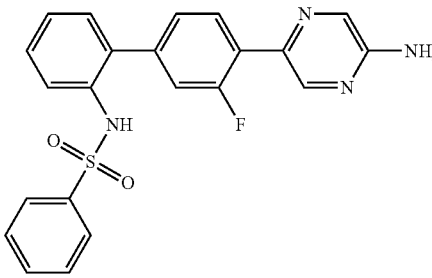

N-[4'-(5-Aminopyrazin-2-yl)-3'-fluorobiphenyl-2-yl]
benzenesulfonamide

The title compound was prepared using analogous conditions to those described in Example 1 utilizing 5-(2-fluoro-4-(4,4,5,5-tetramethyl-1,3,2-dioxaborolan-2-yl)phenyl)pyrazin-2-amine and N-(2-bromophenyl)benzenesulfonamide. MS (ESI): mass calcd. for $C_{22}H_{17}FN_4O_2S$, 420.11; m/z found, 421.1 [M+H]$^+$. $^1$H NMR (400 MHz, DMSO-d$_6$) δ 9.73 (s, 1H), 8.38 (s, 1H), 8.04 (s, 1H), 7.85-7.75 (m, 1H), 7.59-7.46 (m, 5H), 7.29-7.10 (m, 6H), 6.71 (s, 2H).

Example 480

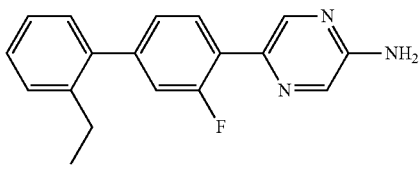

5-(2'-Ethyl-3-fluorobiphenyl-4-yl)pyrazin-2-amine

The title compound was prepared using analogous conditions to those described in Example 1 utilizing 5-(2-fluoro-4-(4,4,5,5-tetramethyl-1,3,2-dioxaborolan-2-yl)phenyl)pyrazin-2-amine and 2-ethylbromobenzene. MS (ESI): mass calcd. for $C_{18}H_{16}FN_3$, 293.13; m/z found, 294.0 [M+H]$^+$. $^1$H NMR (400 MHz, DMSO-d$_6$) δ 8.39 (s, 1H), 8.03 (d, J=1.3, 1H), 7.92 (m, 1H), 7.36 (d, J=3.9, 2H), 7.32-7.19 (m, 4H), 6.71 (s, 2H), 2.60 (q, J=7.5, 2H), 1.06 (t, J=7.5, 3H).

Example 481

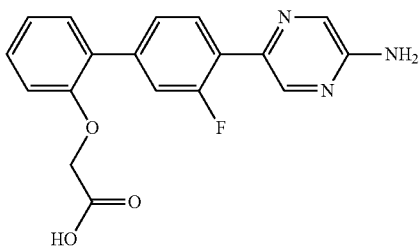

{[4'-(5-Aminopyrazin-2-yl)-3'-fluorobiphenyl-2-yl]oxy}acetic acid

Step A: Methyl 2-((4'-(5-aminopyrazin-2-yl)-3'-fluoro-[1,1'-biphenyl]-2-yl)oxy)acetate To a solution consisting of 4'-(5-aminopyrazin-2-yl)-5'-fluorobiphenyl-2-ol Example 476 (50 mg, 0.18 mmol) and DMF (1 mL) was added Cs$_2$CO$_3$ (116 mg, 0.36 mmol). The mixture was stirred at rt for 30 min. Methyl 2-bromoacetate (30 mg, 0.19 mmol) was added and the resultant mixture stirred at rt for 1 hour and then poured into 15 mL of water. The precipitate was collected and washed with water and air dried to give methyl 2-((4'-(5-aminopyrazin-2-yl)-3'-fluoro-[1,1'-biphenyl]-2-yl)oxy)acetate (50 mg, 72%). MS (ESI): mass calcd. for $C_{19}H_{16}FN_3O_3$, 353.12; m/z found, 354.0 [M+H]$^+$. $^1$H NMR (300 MHz, DMSO-d$_6$) δ 8.38 (s, 1H), 8.03 (s, 1H), 7.93 (m, 1H), 7.57 (d, J=13.0, 1H), 7.54 (d, J=9.2, 1H), 7.50 (d, J=7.4, 1H), 7.34 (m, 1H), 7.10-7.02 (m, 2H), 6.70 (s, 2H), 4.89 (s, 2H), 3.71 (s, 3H).

Step B

To a solution of methyl 2-(4'-(5-aminopyrazin-2-yl)-5'-fluorobiphenyl-2-yloxy)acetate (50 mg, 0.14 mmol) in THF (2 mL) were added LiOH.H$_2$O (63 mg, 1.5 mmol) and H$_2$O (2 mL). The mixture was stirred at rt for 14 hours. The THF was removed under reduced pressure, and the residue diluted with 15 mL of water, washed with DCM (5 mL×2), and then acidified with 1 N HCl to pH=7. The precipitate was collected and washed with water and dried under high vacuum to give the title compound (40 mg, 95% yield). MS (ESI): mass calcd. for $C_{18}H_{14}FN_3O_3$, 339.10; m/z found, 340.1 [M+H]$^+$. $^1$H NMR (400 MHz, DMSO-d$_6$) δ 13.02 (s, 1H), 8.36 (s, 1H), 8.01 (s, 1H), 7.88 (m, 1H), 7.55 (d, J=13.0, 1H), 7.48 (d, J=9.2, 1H), 7.40 (d, J=7.4, 1H), 7.33 (m, 1H), 7.08-7.00 (m, 2H), 6.69 (s, 2H), 4.76 (s, 2H).

Example 482

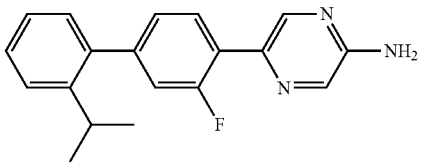

5-[3-Fluoro-2'-(1-methylethyl)biphenyl)-4-yl]pyrazin-2-amine

The title compound was prepared using analogous conditions to those described in Example 1 utilizing 5-(2-fluoro-4-(4,4,5,5-tetramethyl-1,3,2-dioxaborolan-2-yl)phenyl)pyrazin-2-amine and 2-isopropylbromobenzene. MS (ESI): mass calcd. for $C_{19}H_{18}FN_3$, 307.15; m/z found, 308.1 [M+H]$^+$. $^1$H NMR (400 MHz, DMSO-d$_6$) δ 8.39 (s, 1H), 8.03 (s, 1H), 7.91 (m, 1H), 7.49-7.34 (m, 2H), 7.27-7.17 (m, 4H), 6.71 (s, 2H), 3.06-2.97 (m, 1H), 1.14 (d, J=6.8, 6H).

Example 483

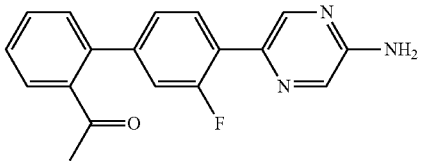

1-[4'-(5-Aminopyrazin-2-yl)-3'-fluorobiphenyl-2-yl]ethanone

The title compound was prepared using analogous conditions to those described in Example 1 utilizing 5-(4-bromo-2-fluorophenyl)pyrazin-2-amine and (2-acetylphenyl)boronic acid. MS (ESI): mass calcd. for $C_{18}H_{14}FN_3O$, 307.11; m/z found, 307.9 [M+H]$^+$. $^1$H NMR (400 MHz, DMSO-d$_6$) δ 8.39 (s, 1H), 8.03 (d, J=1.2, 1H), 7.91 (m, 1H), 7.69 (d, J=7.5, 1H), 7.61 (m, 1H), 7.53 (d, J=7.5, 1H), 7.48 (d, J=8.2, 1H), 7.26 (d, J=12.4, 1H), 7.19 (dd, J=8.0, 1.3, 1H), 6.75 (s, 2H), 2.31 (s, 3H).

Example 484

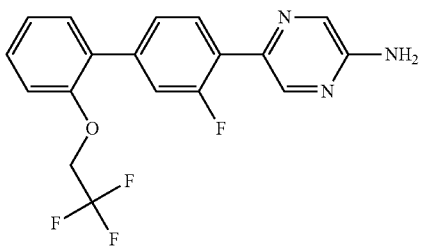

5-[3-Fluoro-2'-(2,2,2-trifluoroethoxy)biphenyl)-4-yl]pyrazin-2-amine

The title compound was prepared using analogous conditions to those described in Example 1 utilizing what 5-(2-fluoro-4-(4,4,5,5-tetramethyl-1,3,2-dioxaborolan-2-yl)phenyl)pyrazin-2-amine and 2-(2,2,2-trifluoroethoxy)bromobenzene. MS (ESI): mass calcd. for $C_{18}H_{13}F_4N_3O$, 363.10; m/z found, 363.9 [M+H]$^+$. $^1$H NMR (400 MHz, DMSO-$d_6$) δ 8.39 (s, 1H), 8.03 (s, 1H), 7.91 (m, 1H), 7.56-7.34 (m, 4H), 7.25 (d, J=8.0, 1H), 7.16 (m, 1H), 6.71 (s, 2H), 4.82 (q. J=8.8, 2H).

Example 485

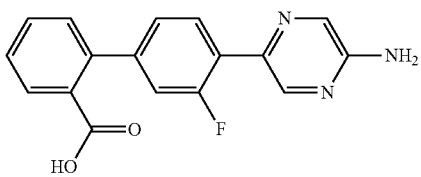

4'-(5-Aminopyrazin-2-yl)-3'-fluorobiphenyl-2-carboxylic acid

The title compound was prepared using analogous conditions to those described in Example 1 utilizing 5-(2-fluoro-4-(4,4,5,5-tetramethyl-1,3,2-dioxaborolan-2-yl)phenyl)pyrazin-2-amine and 2-bromobenzoic acid. MS (ESI): mass calcd. for $C_{17}H_{12}FN_3O_2$, 309.09; m/z found, 310.1 [M+H]$^+$. $^1$H NMR (400 MHz, DMSO-$d_6$) δ 12.88 (s, 1H), 8.36 (s, 1H), 8.02 (s, 1H), 7.87 (m, 1H), 7.76 (d, J=7.5, 1H), 7.60 (m, 1H), 7.50 (d, J=7.2, 1H), 7.44 (d, J=8.2, 1H), 7.25 (d, J=5.1, 1H), 7.22 (s, 1H), 6.70 (s, 2H).

Example 486

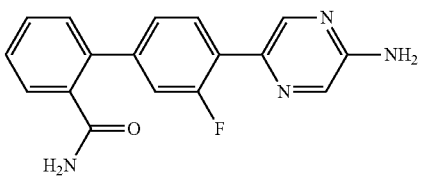

4'-(5-Aminopyrazin-2-yl)-3'-fluorobiphenyl-2-carboxamide

The title compound was prepared using analogous conditions to those described in Example 1 utilizing 5-(2-fluoro-4-(4,4,5,5-tetramethyl-1,3,2-dioxaborolan-2-yl)phenyl)pyrazin-2-amine and 2-bromobenzamide. MS (ESI): mass calcd. for $C_{17}H_{13}FN_4O$, 308.11; m/z found, 309.0 [M+H]$^+$. $^1$H NMR (400 MHz, DMSO-$d_6$) δ 8.35 (s, 1H), 8.01 (s, 1H), 7.86 (m, 1H), 7.75 (s, 1H), 7.55-7.26 (m, 7H), 6.70 (s, 2H).

Example 487

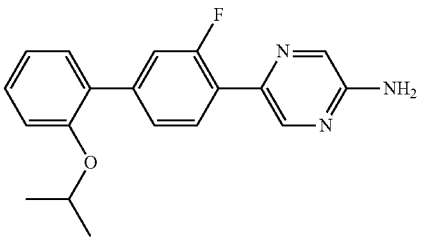

5-[3-Fluoro-2'-(1-methylethoxy)biphenyl)-4-yl]pyrazin-2-amine

The title compound was prepared using methods analogous to those described in Example 369 3 using (2-isopropoxyphenyl)boronic acid and 5-(4-bromo-2-fluorophenyl)pyrazin-2-amine in Step B. MS (ESI): mass calcd. for $C_{19}H_{18}FN_3O$, 323.14; m/z found, 324.1 [M+H]$^+$. $^1$H NMR (400 MHz, CDCl$_3$) δ 8.63-8.57 (m, 1H), 8.12 (d, J=1.4, 1H), 7.97-7.87 (m, 1H), 7.48-7.42 (m, 1.5H), 7.42-7.34 (m, 1.5H), 7.34-7.28 (m, 1H), 7.07-6.97 (m, 2H), 4.65 (s, 2H), 4.59-4.44 (m, 1H), 1.29 (d, J=6.1, 6H).

Example 488

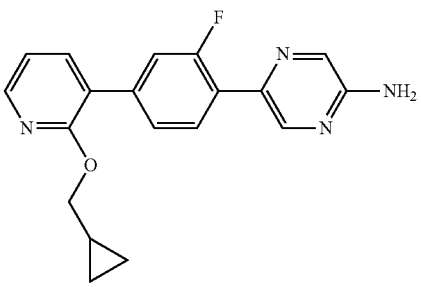

5-{4-[2-(Cyclopropylmethoxy)pyridin-3-yl]-2-fluorophenyl}pyrazin-2-amine

The title compound was prepared using methods analogous to those described in Example 369 using (2-(cyclopropylmethoxy)pyridin-3-yl)boronic and 5-(4-bromo-2-fluorophenyl)pyrazin-2-amine in Step B. MS (ESI): mass calcd. for $C_{19}H_{17}FN_4O$, 336.14; m/z found, 337.1 [M+H]$^+$. $^1$H NMR (400 MHz, CDCl$_3$) δ 8.64-8.59 (m, 1H), 8.17-8.09 (m, 2H), 8.02-7.93 (m, 1H), 7.72-7.66 (m, 1H), 7.54-7.48 (m, 2H), 7.01-6.95 (m, 1H), 4.67 (s, 2H), 4.24 (d, J=7.0, 2H), 1.37-1.22 (m, 1H), 0.66-0.54 (m, 2H), 0.42-0.31 (m, 2H).

Example 489

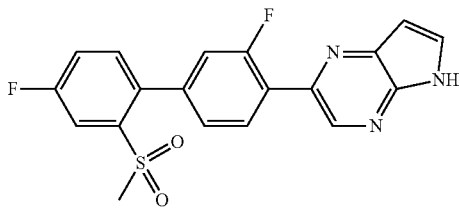

2-[3,4'-Difluoro-2'-(methylsulfonyl)biphenyl-4-yl]-
5H-pyrrolo[2,3-b]pyrazine

The title compound was prepared using methods analogous to those described in Step B of Example 377 using 2-[3,4'-difluoro-2'-(methylthio)-[1,1'-biphenyl-4-yl]-5H-pyrrolo[2,3-b]pyrazine. MS (ESI): mass calcd. for $C_{19}H_{13}F_2N_3O_2S$, 385.07; m/z found, 386.1 $[M+H]^+$. $^1H$ NMR (400 MHz, CDCl$_3$) δ 9.48 (s, 1H), 8.82 (s, 1H), 8.27 (d, J=8.0, 1H), 8.18-8.09 (m, 1H), 7.77-7.67 (m, 2H), 7.66-7.57 (m, 1H), 7.48-7.36 (m, 2H), 6.89-6.83 (m, 1H), 2.76 (s, 3H).

Example 490

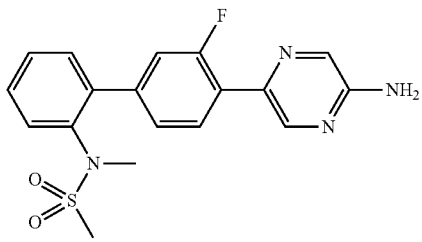

N-[4'-(5-Aminopyrazin-2-yl)-3'-fluorobiphenyl-2-yl]-
N-methylmethanesulfonmide

Step A: N-(2-(4,4,5,5-Tetramethyl-1,3,2-dioxaborolan-2-yl)phenyl)methanesulfonamide To a solution of 2-(4,4,5,5-tetramethyl-1,3,2-dioxaborolan-2-yl)aniline (1 g, 5 mmol) in pyridine (20 mL) was added methanesulfonyl chloride (627 mg, 5.5 mmol) and the mixture stirred at rt for 24 hours. The solvent was then removed under reduced pressure, and the resulting residue redissolved in DCM (200 mL), washed with 1 N HCl (1×100 mL) and 20% NaHCO$_3$ (1×100 mL). The organic layer was then isolated, dried (Na$_2$SO$_4$) and concentrated to dryness. The crude product was purified by crystallization from DCM/hexanes to give the title compound (700 mg, 52%). $^1H$ NMR (400 MHz, CDCl$_3$) δ 8.43 (s, 1H), 7.82-7.77 (m, 1H), 7.59 (d, J=8.2, 1H), 7.51-7.43 (m, 1H), 7.17-7.10 (m, 1H), 2.95 (s, 3H), 1.37 (s, 12H).

Step B: —N-Methyl-N-(2-(4,4,5,5-tetramethyl-1,3,2-dioxaborolan-2-yl)phenyl)-methane-sulfonamide To a round bottom flask under nitrogen were added N-(2-(4,4,5,5-tetramethyl-1,3,2-dioxaborolan-2-yl)phenyl) methanesulfonamide (250 mg, 0.84 mmol), K$_2$CO$_3$ (140 mg, 1.01 mmol) and acetone (5.0 mL). Iodomethane (0.06 mL, 1 mmol) was then added to the mixture dropwise and the reaction stirred for 18 hours at rt. The reaction was then diluted with ethyl acetate (100 mL), washed with water (2×) and brine (1×), dried (Na$_2$SO$_4$) and concentrated to dryness. The crude product was purified by FCC providing the title compound (230 mg, 88%). $^1H$ NMR (400 MHz, CDCl$_3$) δ 7.82 (dd, J=7.3, 1.8, 1H), 7.51-7.43 (m, 1H), 7.40-7.29 (m, 2H), 3.32 (s, 3H), 2.93 (s, 3H), 1.36 (s, 12H).

Step C

The title compound was prepared using methods analogous to those described in Example 369 using N-methyl-N-(2-(4,4,5,5,-tetramethyl-1,3,2-dioxaborolan-2-yl)phenyl) methanesulfonamide and 5-(4-bromo-2-fluorophenyl) pyrazin-2-amine in Step B. MS (ESI): mass calcd. for $C_{18}H_{17}FN_4O_2S$, 372.11; m/z found, 373.1 $[M+H]^+$. $^1H$ NMR (400 MHz, CDCl$_3$) 8.61-8.58 (m, 1H), 8.12 (d, J=1.5, 1H), 7.47-7.39 (m, 5H), 7.37-7.31 (m, 1H), 7.30-7.23 (m, 1H), 4.75 (s, 2H), 3.17 (s, 3H), 2.76 (s, 3H).

Example 491

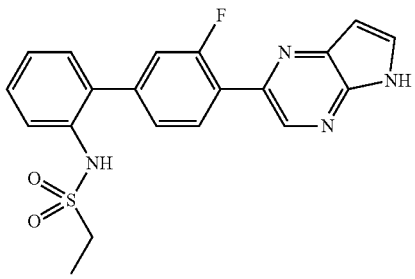

N-[3-Fluoro-4'-(5H-pyrrolo[2,3-b]pyrazin-2-yl)biphenyl-2-yl]
ethanesulfonamide

Step A: N-(2-(4,4,5,5-Tetramethyl-1,3,2-dioxaborolan-2-yl)phenyl)ethanesulfonamide The title compound was prepared using methods analogous to those described in Step A of Example 490 using 2-(4,4,5,5-tetramethyl-1,3,2-dioxaborolan-2-yl)aniline for 2-(4,4,5,5-tetramethyl-1,3,2-dioxaborolan-2-yl)aniline and ethanesulfonyl chloride. $^1H$ NMR (400 MHz, CDCl$_3$) δ 8.52 (s, 1H), 7.82-7.74 (m, 1H), 7.64 (d, J=8.3, 1H), 7.49-7.41 (m, 1H), 7.14-7.06 (m, 1H), 3.12 (q, J=7.4, 2H), 1.37 (s, 12H), 1.32 (t, J=7.4, 3H).

Step B

The title compound was prepared using methods analogous to those described in Step C of Example 490 using N-(2-(4,4,5,5-tetramethyl-1,3,2-dioxaborolan-2-yl)phenyl) ethanesulfonamide and 2-(4-bromo-2-fluorophenyl)-5H-pyrrolo[2,3-b]pyrazine. MS (ESI): mass calcd. for $C_{20}H_{17}FN_4O_2S$, 396.11; m/z found, 397.1 $[M+H]^+$. $^1H$ NMR (400 MHz, CDCl$_3$) δ 9.16 (s, 1H), 8.78 (d, J=2.6, 1H), 8.20-8.11 (m, 2H), 7.75-7.66 (m, 2H), 7.47-7.37 (m, 1H), 7.36-7.28 (m, 2H), 7.27-7.20 (m, 1H), 6.87-6.79 (m, 1H), 6.59 (s, 1H), 3.11 (q, J=7.4, 2H), 1.33-1.18 (m, 3H).

Example 492

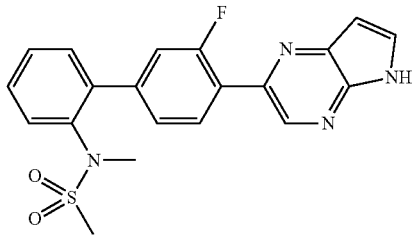

N-[3'-Fluoro-4'-(5H-pyrrolo[2,3-b]pyrazin-2-yl)biphenyl-2-yl]-
N-methylmethanesulfonamide The title compound was prepared using methods analogous to those described in Step C of Example 490 using 2-(4-bromo-2-fluorophenyl)-5H-pyrrolo[2,3-b]pyrazine. MS (ESI): mass calcd. $C_{20}H_{17}FN_4O_2S$, 396.11; m/z found, 397.1 [M+H]$^+$. $^1$H NMR (400 MHz, DMSO-d) δ 8.69 (d, J=2.6, 1H), 8.05-7.99 (m, 1H), 7.97 (d, J=3.6, 1H), 7.67-7.61 (m, 1H), 7.57-7.48 (m, 3H), 7.46-7.39 (m, 2H), 6.72 (d, J=3.6, 1H), 4.75 (s, 1H), 3.14 (s, 3H), 2.99 (s, 3H).

Example 493

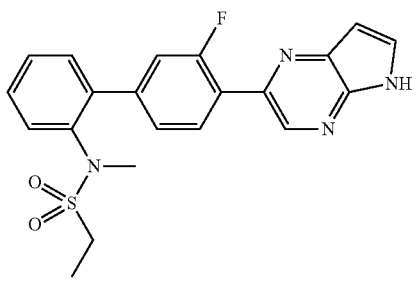

N-[3'-Fluoro-4'-(5H-pyrrolo[2,3-b]pyrazin-2-yl)biphenyl-2-yl]-
N-methylmethanesulfonamide The title compound was prepared using methods analogous to those described in Step C of Example 490 using 2-(4-bromo-2-fluorophenyl)-5H-pyrrolo[2,3-b]pyrazine. MS (ESI): mass calcd. $C_{21}H_{19}FN_4O_2S$, 410.12: m/z found, 411.1 [M+H]$^+$. $^1$H NMR (400 MHz, CDCl$_3$) δ 11.04 (s, 1H), 8.77 (d, J=2.7, 1H), 8.13-8.05 (m, 1H), 7.70-7.63 (m, 1H), 7.53-7.42 (m, 4H), 7.40-7.30 (m, 2H), 6.78-6.71 (m, 1H), 3.17 (s, 3H), 2.99-2.88 (m, 2H), 1.27 (t, J=7.4, 3H).

Example 494

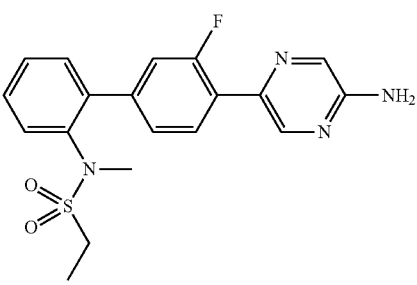

N-[4'-(5-Aminopyrazin-2-yl)-3'-fluorophenyl-2-yl]-
N-methylmethanesulfonamide

The title compound was prepared using methods analogous to those described in Example 369 using N-methyl-N-(2-(4,4,5,5,-tetramethyl-1,3,2-dioxaborolan-2-yl)phenyl)ethanesulfonamide and 5-(4-bromo-2-fluorophenyl)pyrazin-2-amine in Step B. MS (ESI): mass calcd. $C_{19}H_{19}FN_4O_2S$, 386.12; m/z found, 387.1 [M+H]$^+$. $^1$H NMR (400 MHz, CDCl$_3$) δ 8.63-8.57 (m, 1H), 8.13-8.09 (d, J=1.5, 1H), 8.04-7.95 (m, 1H), 7.72-7.62 (m, 0.75H), 7.59-7.51 (m, 0.25H), 7.50-7.39 (m, 3.75H), 7.37-7.32 (m, 1H), 7.31-7.28 (m, 0.25H), 4.69 (s, 2H), 3.16 (s, 3H), 2.89 (q, J=7.4, 2H), 1.25 (t, J=7.4, 3H).

Example 495

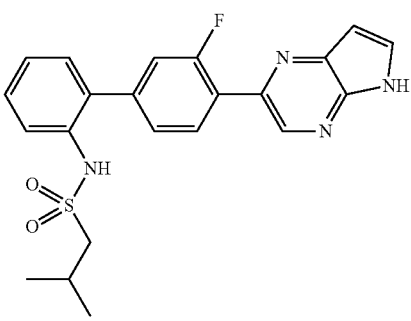

N-[3'-Fluoro-4'-(5H-pyrrolo[2,3-b]pyrazin-2-yl)biphenyl-2-yl]-
2-methylpropane-1-sulfonamide Step A: N-(2-(4,4,5,5-Tetramethyl-1,3,2-dioxaborolan-2-yl)phenyl)-2-methylpropanesulfonamide The title compound was prepared using methods analogous to those described in Step B of Example 490 using 2-(4,4,5,5-tetramethyl-1,3,2-dioxaborolan-2-yl)aniline and isobutylsulfonyl chloride. $^1$H NMR (400 MHz, CDCl$_3$) δ 8.48 (s, 1H), 7.81-7.75 (m, 1H), 7.63-7.58 (m, 1H), 7.49-7.41 (m, 1H), 7.14-7.06 (m, 1H), 2.96 (d, J=10.1, 2H), 2.39-2.19 (m, 1H), 1.37 (s, 12H), 1.11-0.99 (m, 6H).

Step B

The title compound was prepared using methods analogous to those described in Step C of Example 490 using N-(2-(4,4,5,5-tetramethyl-1,3,2-dioxaborolan-2-yl)phenyl)isobutylsulfonamide and 2-(4-bromo-2-fluorophenyl)-5H-pyrrolo[2,3-b]pyrazine. MS (ESI): mass calcd. $C_{22}H_{21}FN_4O_2S$, 424.14; m/z found, 425.1 [M+H]$^+$. $^1$H NMR (400 MHz, CDCl$_3$) δ 9.09 (s, 1H), 8.78 (d, J=2.6, 1H), 8.20-8.11 (m, 1H), 7.73-7.65 (m, 2H), 7.46-7.37 (m, 1H), 7.34-7.29 (m, 2H), 7.26-7.19 (m, 2H), 6.87-6.79 (m, 1H), 6.59 (s, 1H), 2.97 (d, J=6.6, 2H), 2.31-2.13 (m, 1H), 1.05 (d, J=6.7, 6H).

Example 496

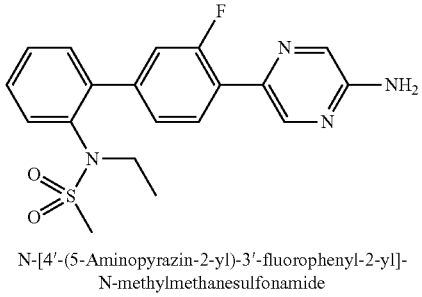 [SMILES: CCN(c1ccccc1-c1ccc(-c2cnc(N)cn2)c(F)c1)S(C)(=O)=O]

N-[4'-(5-Aminopyrazin-2-yl)-3'-fluorophenyl-2-yl]-
N-methylmethanesulfonamide

Step A: —N-Ethyl-N-(2-(4,4,5,5-tetramethyl-1,3,2-dioxaborolan-2-yl)phenyl)methane-sulfonamide The title compound was prepared using methods analogous to those described in Step B of Example 490 using iodoethane. $^1$H NMR (400 MHz, CDCl$_3$) δ 7.87-7.82 (m, 1H), 7.50-7.44 (m, 1H), 7.40-7.31 (m, 2H), 3.72 (q, J=7.1, 2H), 2.93 (s, 3H), 1.35 (s, 12H), 1.21-1.10 (m, 3H).

Step B

The title compound was prepared using methods analogous to those described in Step B of Example 369 by using N-ethyl-N-(2-(4,4,5,5,-tetramethyl-1,3,2-dioxaborolan-2-yl)phenyl)methanesulfonamide and 5-(4-bromo-2-fluoro-phenyl)pyrazin-2-amine. MS (ESI): mass calcd. C$_{19}$H$_{19}$FN$_4$O$_2$S.C$_2$HF$_3$O$_2$, 386.12; m/z found, 387.1 [M+H]$^+$. $^1$H NMR (400 MHz, CDCl$_3$) δ 8.44 (d, J=1.2, 1H), 8.33 (d, J=1.2, 1H), 8.14-8.04 (m, 1H), 7.51-7.33 (m, 6H), 3.46 (s, 2H), 2.95 (s, 3H), 1.05 (t, J=7.2, 3H).

Example 497

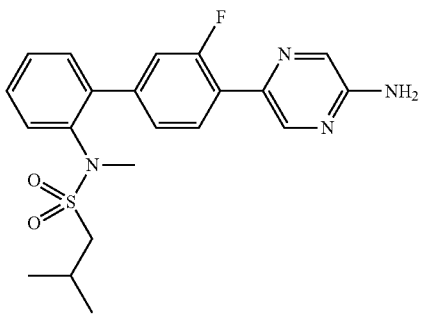

N-[4'-(5-Aminopyrazin-2-yl)-3'-fluorobiphenyl-2-yl]-N,2-dimethylpropane-1-sulfonamide

Step A: —N-Methyl-N-(2-(4,4,5,5-tetramethyl-1,3,2-dioxaborolan-2-yl)phenyl)-2-methylpropanesulfonamide The title compound was prepared using methods analogous to those described in Step B of Example 490 using N-(2-(4,4,5,5-tetramethyl-1,3,2-dioxaborolan-2-yl)phenyl)-2-methylpropanesulfonamide. $^1$H NMR (400 MHz, CDCl$_3$) δ 7.83-7.78 (m, 1H), 7.49-7.43 (m, 1H), 7.38-7.29 (m, 2H), 3.30 (s, 3H), 2.97-2.91 (m, 2H), 2.38-2.23 (m, 1H), 1.36 (s, 12H), 1.12-1.04 (m, 6H).

Step B

The title compound was prepared using methods analogous to those described in Step B of Example 369 using N-methyl-N-(2-(4,4,5,5,-tetramethyl-1,3,2-dioxaborolan-2-yl)phenyl)-2-methylpropanesulfonamide and 5-(4-bromo-2-fluoro-phenyl)pyrazin-2-amine yielding the title compound after purification by HPLC (32 mg, 41%). MS (ESI): mass calcd. C$_{21}$H$_{23}$FN$_4$O$_2$S, 414.15; m/z found, 415.1 [M+H]$^+$. $^1$H NMR (400 MHz, CDCl$_3$) δ 8.59 (s, 1H), 8.11 (d, J=1.3, 1H), 8.04-7.94 (m, 1H), 7.47-7.37 (m, 4H), 7.36-7.31 (m, 1H), 7.30-7.24 (m, 1H), 4.69 (s, 2H), 3.13 (s, 3H), 2.70 (d, J=6.6, 2H), 2.26-2.11 (m, 1H), 1.00 (d, J=6.7, 6H).

Example 498

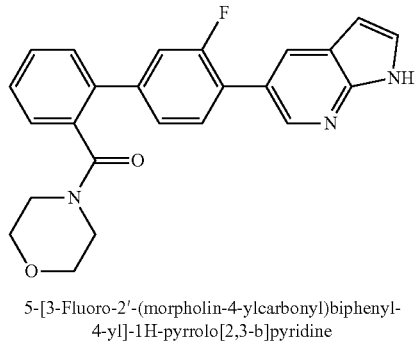 [SMILES: O=C(c1ccccc1-c1ccc(-c2cnc3[nH]ccc3c2)c(F)c1)N1CCOCC1]

5-[3-Fluoro-2'-(morpholin-4-ylcarbonyl)biphenyl-4-yl]-1H-pyrrolo[2,3-b]pyridine

The title compound was prepared using methods analogous to those described in Example 369 using 5-(2-fluoro-4-(4,4,5,5-tetramethyl-1,3,2-dioxaborolan-2-yl)phenyl)-1H-pyrrolo[2,3-b]pyridine and (2-bromophenyl)(morpholino)methanone. MS (ESI): mass calcd. for C$_{24}$H$_{20}$FN$_3$O$_2$, 401.15; m/z found, 402.1 [M+H]$^+$. $^1$H NMR (400 MHz, CDCl$_3$) δ 9.16 (s, 1H), 8.58-8.48 (m, 1H), 8.21-8.13 (m, 1H), 7.61-7.30 (m, 8H), 6.63-6.57 (m, 1H), 3.78-3.56 (m, 3H), 3.48-3.33 (m, 2H), 3.14-3.00 (m, 1H), 2.94-2.75 (m, 2H).

Example 499

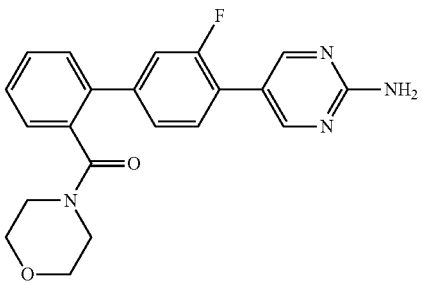

5-[3-Fluoro-2'-(morpholin-4-ylcarbonyl)biphenyl-4-yl]pyrimidin-2-amine

The title compound was prepared using methods analogous to those described in Example 369 using 5-(2-fluoro-4-(4,4,5,5-tetramethyl-1,3,2-dioxaborolan-2-yl)phenyl)pyrimidin-2-amine and (2-bromophenyl)(morpholino)methanone. MS (ESI): mass calcd. for $C_{21}H_{19}FN_4O_2$, 378.15; m/z found, 379.2 [M+H]$^+$. $^1$H NMR (400 MHz, CDCl$_3$) δ 8.56 (d, J=1.4, 2H), 7.54-7.41 (m, 5H), 7.36 (dd. J=8.0, 1.8, 1H), 7.32 (dd, J=11.5, 1.8, 1H), 5.20 (s, 2H), 3.74-3.58 (m, 3H), 3.49-3.30 (m, 2H), 3.15-3.01 (m, 1H), 2.94-2.77 (m, 2H).

Example 500

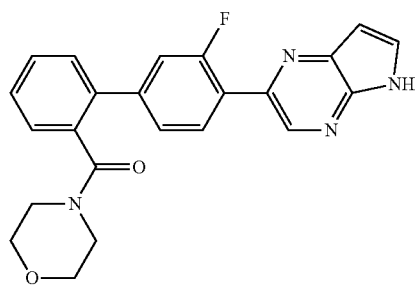

2-[3-Fluoro-2'-(morpholin-4-ylcarbonyl)biphenyl-4-yl]-5H-pyrrolo[2,3-b]pyrazine

The title compound was prepared using methods analogous to those described in Example 369 using (2-bromophenyl)(morpholino)methanone. MS (ESI): mass calcd. for $C_{23}H_{19}FN_4O_2$, 402.15; m/z found, 403.0 [M+H]$^+$. $^1$H NMR (400 MHz, CDCl$_3$) δ 9.12 (s, 1H), 8.82 (d, J=2.5, 1H), 8.19-8.09 (m, 1H), 7.71-7.65 (m, 1H), 7.55-7.34 (m, 6H), 6.87-6.80 (m, 1H), 3.74-3.57 (m, 3H), 3.51-3.30 (m, 2H), 3.15-3.01 (m, 1H), 2.97-2.77 (m, 2H).

Example 501

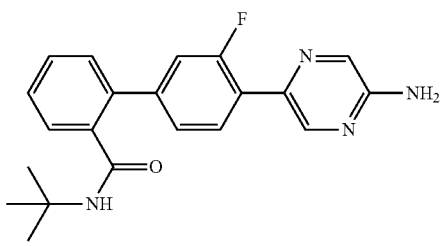

4'-(5-Aminopyrazin-2-yl)-N-tert-butyl-3'-fluorobiphenyl-2-carboxamide

The title compound was prepared using methods analogous to those described in Example 369 using 5-(2-fluoro-4-(4,4,5,5-tetramethyl-1,3,2-dioxaborolan-2-yl)phenyl)-pyrazin-2-amine and 2-bromo-N-(tert-butyl)benzamide. MS (ESI): mass calcd. for $C_{21}H_{21}FN_4O$, 364.17; m/z found, 365.1 [M+H]$^+$. $^1$H NMR (400 MHz, CDCl$_3$) δ 8.55-8.50 (m, 1H), 8.13 (d, J=1.4, 1H), 8.04-7.95 (m, 1H), 7.64-7.58 (m, 1H), 7.51-7.44 (m, 1H), 7.43-7.37 (m, 2H), 7.36-7.31 (m, 1H), 7.29-7.22 (m, 1H), 5.69 (s, 1H), 5.45 (s, 2H), 2.65-2.54 (m, 1H), 1.24 (m, 9H).

Example 502

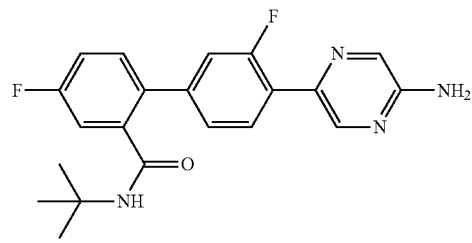

4'-(5-Aminopyrazin-2-yl)-N-tert-butyl-3',4-difluorobiphenyl-2-carboxamide

The title compound was prepared using methods analogous to those described in Example 369 using 5-(2-fluoro-4-(4,4,5,5-tetramethyl-1,3,2-dioxaborolan-2-yl)phenyl)pyrazin-2-amine and 2-bromo-N-(tert-butyl)-5-fluorobenzamide. MS (ESI): mass calcd. for $C_{21}H_{20}F_2N_4O$, 382.16; m/z found, 383.2 [M+H]$^+$.

Example 503

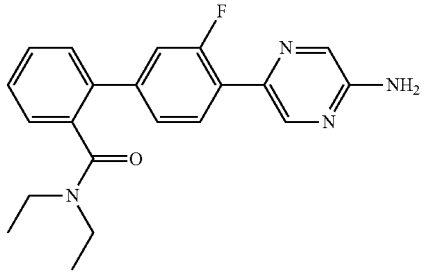

4'-(5-Aminopyrazin-2-yl)-N,N-diethyl-3'-fluorobiphenyl-2-carboxamide

The title compound was prepared using methods analogous to those described in Example 369 using 5-(2-fluoro-4-(4,4,5,5-tetramethyl-1,3,2-dioxaborolan-2-yl)phenyl)-pyrazin-2-amine and 2-bromo-N,N-diethylbenzamide. MS (ESI): mass calcd. for $C_{21}H_{21}FN_4O$, 364.17; m/z found, 365.2 [M+H]$^+$. $^1$H NMR (400 MHz, CDCl$_3$) δ 8.59-8.54 (m, 1H), 8.11 (d, J=1.5, 1H), 8.00-7.90 (m, 1H), 7.50-7.36 (m, 5H), 7.36-7.29 (m, 1H), 4.69 (s, 2H), 3.87-3.69 (m, 1H), 3.17-2.92 (m, 2H), 2.85-2.66 (m, 1H), 0.99 (t, J=7.1, 3H), 0.81 (t, J=7.1, 3H).

Example 504

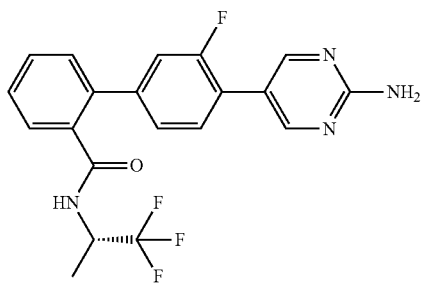

4'-(2-Aminopyrimidin-5-yl)-3'-fluoro-N-[(1S)-2,2,2-trifluoro-1-methylethyl]biphenyl-2-carboxamide Step A: Methyl 4'-(2-aminopyrimidin-5-yl)-3'-fluoro-[1,1'-biphenyl]-2-carboxylate A mixture of methyl 2-bromobenzoate (155 mg, 0.72 mmol), 5-(2-fluoro-4-(4,4,5,5-tetramethyl-1,3,2-dioxaborolan-2-yl)phenyl)pyrazin-2-amine (250 mg, 0.79 mmol), Pd(dppf)Cl$_2$·CH$_2$Cl$_2$ (31 mg, 0.036 mmol) and K$_2$CO$_3$ (2 mL, 2 N) in 1,4-dioxane (10 mL) was stirred at 60° Celsius under N$_2$ for 3 hours. The solvent was removed and the crude product was purified by FCC to afford the desired product (218 mg, 93%). MS (ESI): mass calcd. for C$_{18}$H$_{14}$FN$_3$O$_2$, 323.11; m/z found, 323.9 [M+H]$^+$.

Step B: 4'-(2-Aminopyrimidin-5-yl)-3'-fluoro-[1,1'-biphenyl]-2-carboxylic acid

A solution of methyl 4'-(2-aminopyrimidin-5-yl)-3'-fluoro-[1,1'-biphenyl]-2-carboxylate (218 mg, 0.67 mmol) in NaOH (8 mL, 2 N) and THF (8 mL) was stirred at 80° Celsius for 48 hours, and then concentrated to dryness. The residue was acidified with 2 N HCl. The precipitate was collected by filtration and washed with water several times, and dried in vacuo to afford the desired product (220 mg, 106%). The crude product was used without further purification. MS (ESI): mass calcd. for C$_{17}$H$_{12}$FN$_3$O$_2$, 309.09; m/z found, 309.9 [M+H]$^+$.

Step C:

To a solution of DIPEA (47 mg, 0.36 mmol) in DMF (2 mL) were added 4'-(2-aminopyrimidin-5-yl)-3'-fluoro-[1,1'-biphenyl]-2-carboxylic acid (75 mg, 0.24 mmol), (S)-1,1,1-trifluoropropan-2-amine (30 mg, 0.27 mmol) and HATU (110 mg, 0.290 mmol). The reaction mixture was stirred at rt overnight. The solvent was removed and the residue was purified by FCC to afford the title compound (41 mg, 41%). MS (ESI): mass calcd. for C$_{20}$H$_{16}$F$_4$N$_4$O, 404.13; m/z found, 404.9 [M+H]$^+$. $^1$H NMR (400 MHz, DMSO-d$_6$) δ 8.87 (d, J=8.9, 1H), 8.44 (d, J=1.4, 2H), 7.58-7.50 (m, 2H), 7.49-7.40 (m, 3H), 7.26-7.19 (m, 2H), 6.86 (s, 2H), 4.60 (dd, J=15.7, 7.8, 1H), 1.15 (d, J=7.0, 3H).

Example 505

4'-(5-Aminopyrazin-2-yl)-3'-fluoro-N-[(1S)-2,2,2-trifluoro-1-methylethyl]biphenyl-2-carboxamide The title compound was prepared using methods analogous to those described in Step C of Example 504 using 4'-(2-aminopyrazin-5-yl)-3'-fluoro-[1,1'-biphenyl]-2-carboxylic acid. MS (ESI): mass calcd. for C$_{20}$H$_{16}$F$_4$N$_4$O, 404.13; m/z found, 405.1 [M+H]$^+$. $^1$H NMR (400 MHz, DMSO-d$_6$) δ 8.91 (d, J=8.9, 1H), 8.01 (d, J=1.4, 1H), 7.90-7.80 (m, 1H), 7.57-7.52 (m, 1H), 7.50-7.41 (m, 3H), 7.28-7.20 (m, 2H), 6.69 (s, 2H), 4.66-4.57 (m, 1H), 1.16 (d, J=7.0, 3H).

Example 506

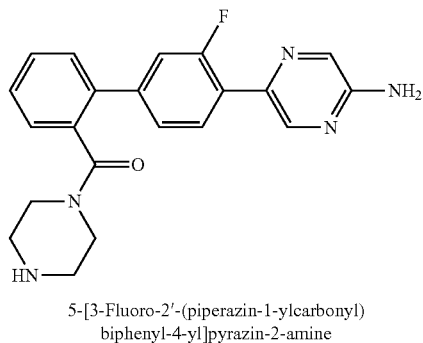 [SMILES: Nc1cnc(-c2ccc(-c3ccccc3C(=O)N3CCNCC3)cc2F)cn1]

5-[3-Fluoro-2'-(piperazin-1-ylcarbonyl)biphenyl-4-yl]pyrazin-2-amine

The title compound was prepared using methods analogous to those described in Step C of Example 504 using 4'-(2-aminopyrazin-5-yl)-3'-fluoro-[1,1'-biphenyl]-2-carboxylic acid and piperazine. MS (ESI): mass calcd. for C$_{21}$H$_{20}$FN$_5$O, 377.17; m/z found, 378.2 [M+H]$^+$. $^1$H NMR (400 MHz, CDCl$_3$) δ 8.64-8.56 (m, 1H), 8.11 (d, J=1.5, 1H), 8.04-7.93 (m, 1H), 7.53-7.40 (m, 4H), 7.37 (dd, J=8.1, 1.8, 1H), 7.30 (dd, J=12.2, 1.7, 1H), 4.77 (s, 2H), 3.72 (d, J=25.1, 2H), 3.14 (s, 1H), 2.92 (s, 2H), 2.65 (s, 2H), 2.05 (s, 1H).

Example 507

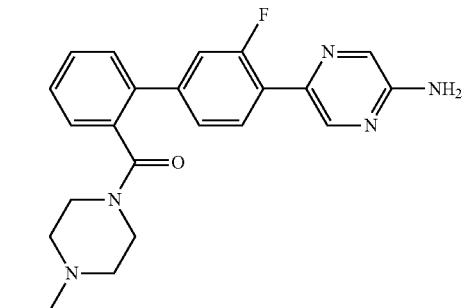

5-{2'-[(4-Acetylpiperazin-1-yl)carbonyl]-3-fluorobiphenyl-4-yl}pyrazin-2-amine

The title compound was prepared using methods analogous to those described in Step C of Example 504 using 4'-(2-aminopyrazin-5-yl)-3'-fluoro-[1,1'-biphenyl]-2-carboxylic acid for and 1-(piperazin-1-yl)ethanone. MS (ESI): mass calcd. for C$_{23}$H$_{22}$FN$_5$O$_2$, 419.18; m/z found, 420.1 [M+H]$^+$. $^1$H NMR (400 MHz, CDCl$_3$) δ 8.65-8.56 (m, 1H), 8.11 (d, J=1.5, 1H), 8.02 (dd, J=10.4, 5.8, 1H), 7.55-7.41 (m, 4H), 7.42-7.32 (m, 1H), 7.34-7.28 (m, 1H), 4.71 (s, 2H), 3.65 (s, 2H), 3.51-2.93 (m, 4H), 2.79 (s, 2H), 1.99 (d, J=3H).

Example 508

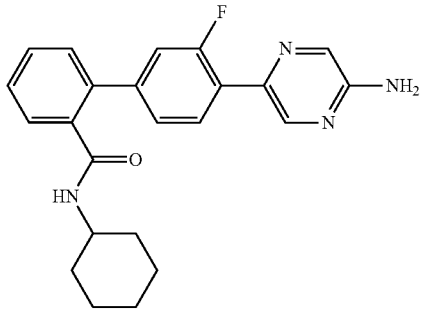

4′-(5-Aminopyrazin-2-yl)-N-cyclohexyl-3′-fluorobiphenyl-2-carboxamide

The title compound was prepared using methods analogous to those described in Step C of Example 504 using 4′-(2-aminopyrazin-5-yl)-3′-fluoro-[1,1′-biphenyl]-2-carboxylic acid and cyclohexanamine. MS (ESI): mass calcd. for $C_{23}H_{23}FN_4O$, 390.19; m/z found, 391.4 [M+H]$^+$. $^1$H NMR (400 MHz, CDCl$_3$) δ 8.60-8.53 (m, 1H), 8.11 (d, J=1.5, 1H), 8.03-7.93 (m, 1H), 7.74-7.62 (m, 1H), 7.54-7.37 (m, 3H), 7.32 (dd, J=8.0, 1.7, 1H), 7.30-7.20 (m, 1H), 5.24 (d, J=8.3, 1H), 4.72 (s, 2H), 3.93-3.73 (m, 1H), 1.78-1.67 (m, 2H), 1.61-1.44 (m, 3H), 1.39-1.27 (m, 2H), 1.14-0.98 (m, 1H), 0.97-0.81 (m, 2H).

Example 509

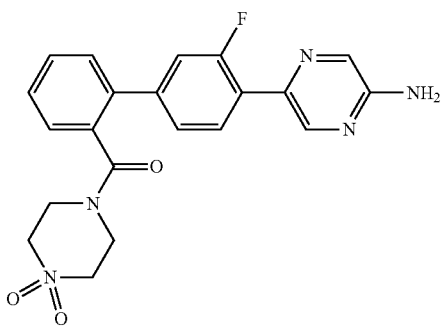

5-{2′-[(1,1-Dioxidothiomorpholin-4-yl)carbonyl]-3-fluorobiphenyl-4-yl}pyrazin-2-amine The title compound was prepared using methods analogous to those described in Step C of Example 504 using 4′-(2-aminopyrazin-5-yl)-3′-fluoro-[1,1′-biphenyl]-2-carboxylic acid and thiomorpholine 1,1-dioxide. MS (ESI): mass calcd. for $C_{21}H_{19}FN_4O_3S$, 426.12; m/z found, 427.0 [M+H]$^+$. $^1$H NMR (400 MHz, CDCl$_3$) δ 8.60 (s, 1H), 8.11 (s, 1H), 8.11-8.02 (m, 1H), 7.58-7.47 (m, 3H), 7.43 (d, J=7.5, 1H), 7.37 (dd, J=8.1, 1.8, 1H), 7.32 (dd, J=12.1, 1.7, 1H), 4.74 (s, 2H), 4.23 (s, 1H), 4.05 (s, 1H), 3.57-3.48 (m, 1H), 3.38 (s, 1H), 3.01 (s, 1H), 2.85 (s, 1H), 2.62 (s, 1H), 2.05 (s, 1H).

Example 510

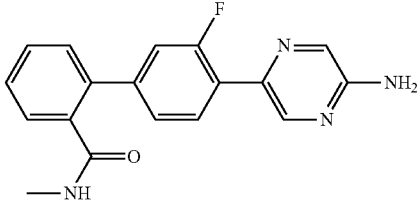

4′-(5-Aminopyrazin-2-yl)-3′-fluoro-N-methylbiphenyl-2-carboxamide

The title compound was prepared using methods analogous to those described in Step C of Example 504 using 4′-(2-aminopyrazin-5-yl)-3′-fluoro-[1,1′-biphenyl]-2-carboxylic acid and methylamine. MS (ESI): mass calcd. for $C_{18}H_{15}FN_4O$, 322.12; m/z found, 323.1 [M+H]$^+$. $^1$H NMR (400 MHz, DMSO-d$_6$) δ 8.35 (dd, J=2.3, 1.6, 1H), 8.15 (d, J=4.7, 1H), 8.00 (d, J=1.5, 1H), 7.84 (d, J=8.1, 1H), 7.52-7.41 (m, 4H), 7.27 (s, 1H), 7.24 (dd, J=5.5, 1.7, 1H), 6.68 (s, 2H), 2.59 (d, J=4.6, 3H).

Example 511

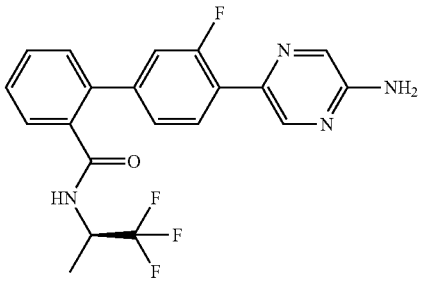

4′-(5-Aminopyrazin-2-yl)-3′-fluoro-N-[(1R)-2,2,2-trifluoro-1-methylethyl]biphenyl-2-carboxamide The title compound was prepared using methods analogous to those described in Step C of Example 504 using 4′-(2-aminopyrazin-5-yl)-3′-fluoro-[1,1′-biphenyl]-2-carboxylic acid and (R)-1,1,1-trifluoropropan-2-amine. MS (ESI): mass calcd. for $C_{20}H_{16}F_4N_4O$, 404.13: m/z found, 405.1 [M+H]$^+$. $^1$H NMR (400 MHz, DMSO-d$_6$) δ 8.91 (d, J=8.8, 1H) 8.34 (s, 1H), 8.01 (d, J=1.2, 1H), 7.90-7.80 (m, 1H), 7.58-7.40 (m, 4H), 7.29-7.18 (m, 2H), 6.69 (s, 2H), 4.68-4.56 (m, 1H), 1.16 (d, J=7.0, 3H).

Example 512

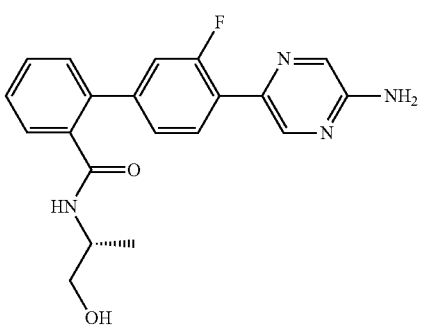

4′-(5-Aminopyrazin-2-yl)-3′-fluoro-N-[(1R)-2-hydroxy-1-methylethyl]biphenyl-2-carboxamide The title compound was prepared using methods analogous to those described in Step C of Example 504 using 4'-(2-aminopyrazin-5-yl)-3'-fluoro-[1,1'-biphenyl]-2-carboxylic acid and (R)-2-aminopropan-1-ol. MS (ESI): mass calcd. for $C_{20}H_{19}FN_4O_2$, 366.15; m/z found, 367.1 [M+H]$^+$. $^1$H NMR (400 MHz, DMSO-d$_6$) δ 8.37 (s, 1H), 8.15-7.97 (m, 2H), 7.94-7.82 (m, 1H), 7.55-7.39 (m, 4H), 7.37-7.26 (m, 2H), 6.71 (s, 2H), 4.64 (s, 1H), 3.92-3.73 (m, 1H), 3.26-3.10 (m, 2H), 0.98 (d, J=6.1, 3H).

Example 513

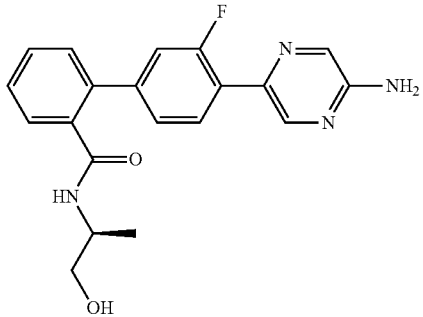

4'-(5-Aminopyrazin-2-yl)-3'-fluoro-N-[(1S)-2-hydroxy-1-methylethyl]biphenyl-2-carboxamide The title compound was prepared using methods analogous to those described in Step C of Example 504 using 4'-(2-aminopyrazin-5-yl)-3'-fluoro-[1,1'-biphenyl]-2-carboxylic acid and (S)-2-aminopropan-1-ol for (S)-1,1,1-trifluoropropan-2-amine. MS (ESI): mass calcd. for $C_{20}H_{19}FN_4O_2$, 366.15; m/z found, 367.1 [M+H]$^+$. $^1$H NMR (400 MHz, DMSO-d$_6$) δ 8.37 (s, 1H), 8.05 (d, J=5.1, 2H), 7.93-7.83 (m, 1H), 7.54-7.43 (m, 3H), 7.37-7.28 (m, 2H), 6.72 (s, 2H), 4.66 (t, J=5.6, 1H), 3.82 (d, J=7.0, 1H), 3.35 (s, 1H), 3.16 (d, J=10.4, 2H), 0.98 (d, J=6.6, 3H).

Example 514

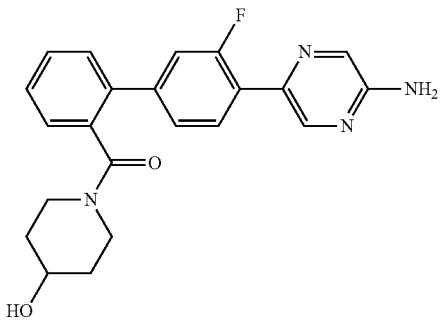

1-{[4'-(5-Aminopyrazin-2-yl)-3'-fluorobiphenyl-2-yl]carbonyl}piperidin-4-ol

The title compound was prepared using methods analogous to those described in Step C of Example 504 using 4'-(2-aminopyrazin-5-yl)-3'-fluoro-[1,1'-biphenyl]-2-carboxylic acid and piperidin-4-ol. MS (ESI): mass calcd. for $C_{22}H_{21}FN_4O_2$, 392.16; m/z found, 393.1 [M+H]$^+$. $^1$H NMR (400 MHz, CDCl$_3$) Complex due to the presence of multiple conformations on the NMR time-scale, peaks listed for identification purposes only: δ 8.54 (d, J=13.9), 8.11-8.05 (m), 7.98-7.83 (m), 7.47-7.27 (m), 6.72 (s), 4.68 (s), 4.24-4.05 (m), 3.76-3.53 (m), 3.27-3.18 (m), 2.91-2.80 (m), 2.62-2.51 (m), 1.82 (m), 1.69 (m), 1.51-1.45 (m), 1.26-1.18 (m), 0.48-0.41 (m).

Example 515

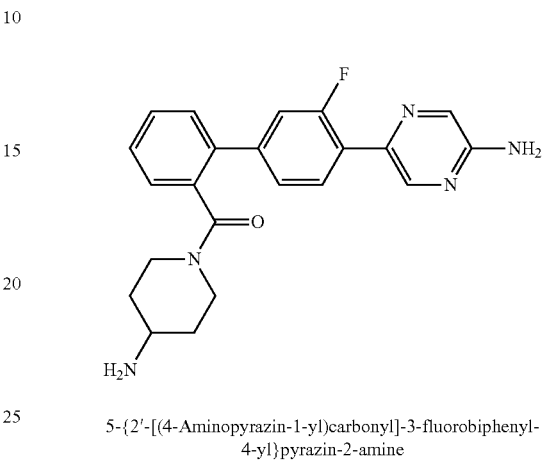

5-{2'-[(4-Aminopyrazin-1-yl)carbonyl]-3-fluorobiphenyl-4-yl}pyrazin-2-amine

The title compound was prepared using methods analogous to those described in Step C of Example 504 using 4'-(2-aminopyrazin-5-yl)-3'-fluoro-[1,1'-biphenyl]-2-carboxylic acid and piperidin-4-amine. MS (ESI): mass calcd. for $C_{22}H_{22}FN_5O$, 391.18; m/z found, 392.1 [M+H]$^+$. $^1$H NMR (400 MHz, DMSO-d$_6$) δ 8.34 (s, 1H), 7.99 (s, 1H), 7.88 (s, 1H), 7.48 (d, J=14.8, 3H), 7.35-7.20 (m, 3H), 6.69 (s, 2H), 4.31 (s, 1H), 3.08-2.50 (m, 6H), 1.75 (t, J=80.9, 2H), 1.38-0.86 (m, 2H).

Example 516

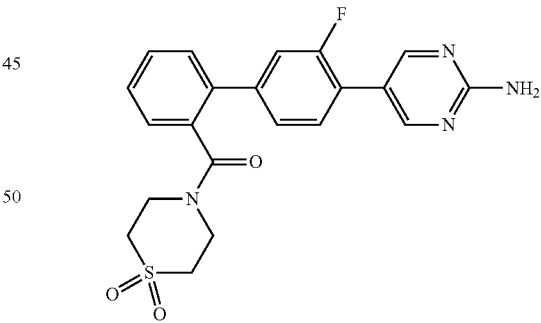

5-{2'-[(1,1-Dioxidothiomorpholin-4-yl)carbonyl]-3-fluorobiphenyl-4-yl}pyrazin-2-amine The title compound was prepared using methods analogous to those described in Step C of Example 504 using thiomorpholine 1,1-dioxide. MS (ESI): mass calcd. for $C_{21}H_{19}FN_4O_3S$, 426.12; m/z found, 426.9 [M+H]$^+$. $^1$H NMR (400 MHz, DMSO-d$_6$) δ 8.43 (s, 2H), 7.63 (s, 1H), 7.52 (d, J=20.5, 4H), 7.30 (dd, J=16.9, 9.9, 2H), 6.89 (s, 2H), 3.97 (s, 1H), 3.84 (s, 1H), 3.46 (s, 1H), 3.32 (s, 1H), 3.02 (s, 1H), 2.85 (s, 1H), 2.47 (s, 1H), 2.11 (s, 1H).

Example 517

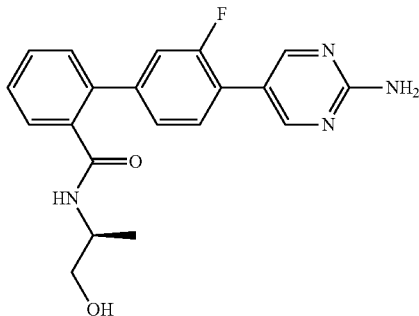

4'-(2-Aminopyrazin-5-yl)-3'-fluoro-N-[(1S)-2-hydroxy-1-methylethyl]biphenyl-2-carboxamide The title compound was prepared using methods analogous to those described in Step C of Example 504 using (S)-2-aminopropan-1-ol. MS (ESI): mass calcd. for $C_{20}H_{19}FN_4O_2$, 366.15; m/z found, 366.9 [M+H]$^+$. $^1$H NMR (400 MHz, DMSO-d$_6$) δ 8.46 (s, 2H), 8.00 (d, J=8.1, 1H), 7.62-7.50 (m, 1H), 7.48 (d, J=4.1, 1H), 7.43 (d, J=7.3, 3H), 7.34-7.23 (m, 2H), 6.88 (s, 2H), 4.61 (s, 1H), 3.87-3.75 (m, 1H), 3.38 (s, 1H), 3.14 (s, 1H), 0.96 (d, J=6.6, 3H).

Example 518

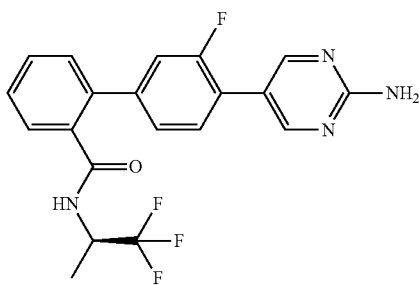

4'-(2-Aminopyrimidin-5-yl)-3'-fluoro-N-[(1R)-2,2,2-trifluoro-1-methylethyl]biphenyl-2-carboxamide The title compound was prepared using methods analogous to those described in Step C of Example 504 using (R)-1,1,1-trifluoropropan-2-amine. MS (ESI): mass calcd. for $C_{20}H_{16}F_4N_4O$, 404.13; m/z found, 404.9 [M+H]$^+$. $^1$H NMR (400 MHz, CDCl$_3$) δ 8.52 (d, J=1.0, 2H), 7.68 (dd, J=7.6, 1.4, 1H), 7.60-7.49 (m, 1H), 7.48-7.38 (m, 3H), 7.28-7.25 (m, 1H), 7.22 (dd, J=11.1, 1.7, 1H), 5.39 (d, J=9.6, 1H), 5.18 (s, 2H), 4.73 (m, 1H), 1.12 (d, J=7.0, 3H).

Example 519

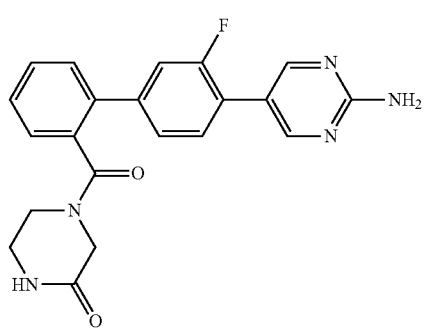

4-{[4'-(5-Aminopyrazin-2-yl)-3'-fluorobiphenyl-2-yl]carbonyl}piperidin-2-one

The title compound was prepared using methods analogous to those described in Step C of Example 504 using 4'-(2-aminopyrazin-5-yl)-3'-fluoro-[1,1-biphenyl]-2-carboxylic acid and piperazin-2-one. MS (ESI): mass calcd. for $C_{21}H_{18}FN_5O_2$, 391.14; m/z found, 392.1 [M+H]$^+$. $^1$H NMR (400 MHz, CDCl$_3$) Complex due to the presence of multiple conformations on the NMR time-scale, peaks listed for identification purposes only: δ 8.58-8.55 (m), 8.50-8.40 (m), 8.10 (d, J=1.5), 8.04-7.98 (m), 7.56-7.41 (m), 7.37-7.27 (m), 6.75 (s), 6.43 (s), 5.06 (s), 4.83 (s), 4.45 (d, J=19.2), 4.05-3.95 (m), 3.72-3.46 (m), 3.27 (s), 3.14 (s), 2.97 (s), 2.67 (s).

Example 520

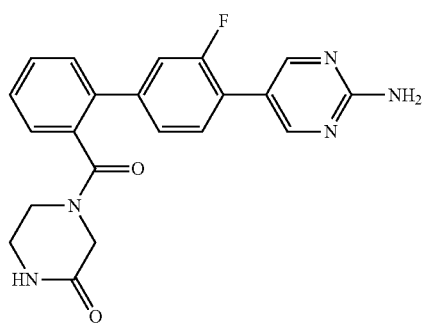

4-{[4'-(2-Aminopyrazin-5-yl)-3'-fluorobiphenyl-2-yl]carbonyl}piperidin-2-one

The title compound was prepared using methods analogous to those described in Step C of Example 504 using piperazin-2-one. MS (ESI): mass calcd. for $C_{21}H_{18}FN_5O_2$, 391.14; m/z found, 391.9 [M+H]$^+$. $^1$H NMR (400 MHz, CDCl$_3$) Complex due to the presence of multiple conformations on the NMR time-scale, peaks listed for identification purposes only: δ 8.47 (d, J=1.2), 8.41 (d, J=1.2), 7.49-7.34 (m), 7.29-7.19 (m), 6.68 (s), 6.35 (s), 5.45 (s), 5.25 (s), 4.38 (d, J=18.7), 4.03 (s), 3.59-3.50 (m), 3.31-2.88 (m), 2.64 (s).

705
Intermediate HH

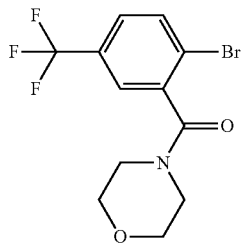

(2-Bromo-5-(trifluoromethyl)
phenyl)
(morpholino)methanone

2-Bromo-5-(trifluoromethyl)benzoic acid (200 mg, 0.74 mmol) was dissolved in DMF (4.65 mL) and HATU (424 mg, 1.12 mmol) added to the resultant mixture at rt. The solution was stirred for 10 min then treated with N,N-diisopropylethylamine (0.51 mL, 3.0 mmol) and morpholine (0.096 mL, 1.1 mmol). The reaction was stirred for 15 hours then quenched by the addition of saturated NH$_4$Cl (5 mL) and EtOAc (5 mL). The aqueous phase was extracted with ethyl acetate (3×10 mL) and the combined organic extracts washed with brine, dried over Na$_2$SO$_4$ and concentrated to dryness. The crude product was purified by FCC to give the title compound. $^1$H NMR (500 MHz, CDCl$_3$) δ 7.76-7.71 (m, 1H), 7.55-7.49 (m, 2H), 3.92-3.86 (m, 1H), 3.83-3.69 (m, 4H), 3.66-3.58 (m, 1H), 3.32-3.24 (m, 1H), 3.25-3.17 (m, 1H).

Example 521

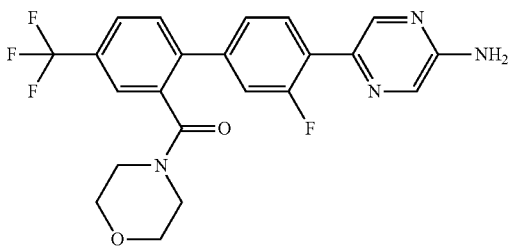

5-[3-Fluoro-2'-(morpholine-4-ylcarbonyl)-4'-
(trifluoromethyl)biphenyl-4-yl]pyrazin-2-amine The title compound was prepared in a manner similar to that described in Example 88 using (2-bromo-5-(trifluoromethyl)phenyl)(morpholino)-methanone. MS (ESI): mass calcd. for C$_{22}$H$_{18}$F$_4$N$_4$O$_2$, 446.14; m/z found, 447.0 [M+H]$^+$. $^1$H NMR (500 MHz, CD$_3$OD) δ 8.40 (s, 1H), 8.18 (s, 1H), 8.10-8.01 (m, 1H), 7.90-7.82 (d, J=7.9, 1H), 7.78-7.69 (m, 2H), 7.47-7.35 (m, 2H), 3.72-3.60 (m, J=10.0, 4.2, 2H), 3.58-3.49 (m, 1H), 3.44-3.36 (m, 1H), 3.15-3.04 (m, 1H), 2.90-2.80 (dd, J=13.4, 5.2, 1H), 2.80-2.72 (m, 1H).

706
Example 522

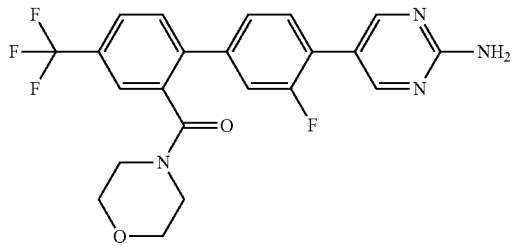

5-[3-Fluoro-2'-(morpholine-4-ylcarbonyl)-4'-
(trifluoromethyl)biphenyl-
4-yl]pyrazin-2-amine The title compound was prepared in a manner similar to that described in Example 88 using (2-bromo-5-(trifluoromethyl)phenyl)(morpholino)methanone and 5-(2-fluoro-4-(4,4,5,5-tetramethyl-1,3,2-dioxaborolan-2-yl)phenyl)pyrimidin-2-amine. MS (ESI): mass calcd. for C$_{22}$H$_{18}$F$_4$N$_4$O$_2$, 446.14; m/z found, 447.0 [M+H]$^+$. $^1$H NMR (500 MHz, CD$_3$OD) δ 8.65-8.58 (d, J=1.3, 2H), 7.91-7.85 (dd, J=8.3, 1.9, 1H), 7.78-7.76 (m, 1H), 7.76-7.73 (d, J=8.1, 1H), 7.71-7.63 (m, 1H), 7.46-7.43 (dd, J=2.7, 1.8, 1H), 7.43-7.41 (dd, J=6.2, 1.7, 1H), 3.72-3.60 (m, 2H), 3.60-3.52 (m, 1H), 3.46-3.39 (m, 1H), 3.37-3.33 (m, 1H), 3.16-3.09 (m, 1H), 2.92-2.77 (m, 2H).

Example 523

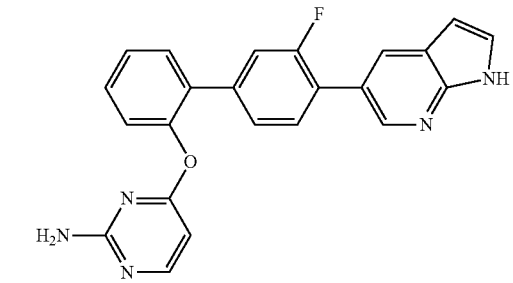

4-{[3'-Fluro-4'-(1H-pyrrolo[2,3-b]pyridin-
5-yl)biphenyl-2-yl]oxy}pyrimidin-2-amine The title compound was prepared using methods analogous to those described in Example 376 using 5-(2-fluoro-4-(4,4,5,5-tetramethyl-1,3,2-dioxaborolan-2-yl)phenyl)-1H-pyrrolo[2,3-b]pyridine and 4-(2-bromophenoxy)pyrimidin-2-amine. MS (ESI): mass calcd. for C$_{23}$H$_{16}$FN$_5$O, 397.13; m/z found, 398.1 [M+H]$^+$. $^1$H NMR (400 MHz, CDCl$_3$) δ 9.30 (s, 1H), 8.55-8.45 (m, 1H), 8.18-8.08 (m, 1H), 8.07 (d, J=5.7, 1H), 7.55-7.28 (m, 8H), 7.22 (dd, J=8.0, 1.4, 1H), 6.08 (d, J=5.7, 1H), 4.95 (s, 2H).

Example 524

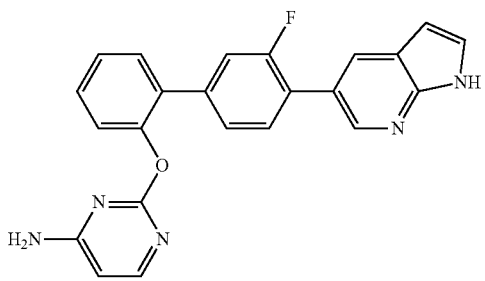

2-{[3'-Fluro-4'-(1H-pyrrolo[2,3-b]pyridin-5-yl)biphenyl-2-yl]oxy}pyrimidin-4-amine The title compound was prepared using methods analogous to those described in Example 376 using 5-(2-fluoro-4-(4,4,5,5-tetramethyl-1,3,2-dioxaborolan-2-yl)phenyl)-1H-pyrrolo[2,3-b]pyridine and 2-(2-bromophenoxy)pyrimidin-4-amine. MS (ESI): mass calcd. for $C_{23}H_{16}FN_5O$, 397.13; m/z found, 398.1 [M+H]$^+$. $^1$H NMR (400 MHz, CDCl$_3$) δ 8.94 (s, 1H), 8.47 (s, 1H), 8.11 (d, J=2.1, 1H), 7.96 (d, J=5.7, 1H), 7.54-7.30 (m, 9H), 6.07 (d, J=5.7, 1H), 4.96-4.85 (m, 2H).

Example 525

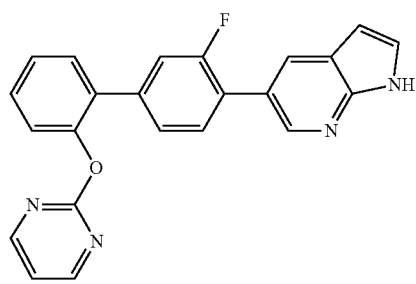

5-[3-Fluro-2'-(pyrimidin-2-yloxy)biphenyl-4-yl]-1H-pyrrolo[2,3-b]pyridine

The title compound was prepared using methods analogous to those described in Example 376 using 5-(2-fluoro-4-(4,4,5,5-tetramethyl-1,3,2-dioxaborolan-2-yl)phenyl)-1H-pyrrolo[2,3-b]pyridine and 2-(2-bromophenoxy)pyrimidine. MS (ESI): mass calcd. for $C_{23}H_{15}FN_4O$, 382.12: m/z found, 383.1 [M+H]$^+$. $^1$H NMR (400 MHz, CDCl$_3$) δ 9.24 (s, 1H), 8.51-8.42 (m, 3H), 8.14-8.05 (m, 1H), 7.57-7.28 (m, 8H), 6.99-6.89 (m, 1H), 6.55 (dd, J=3.6, 1.8, 1H).

Intermediate HI

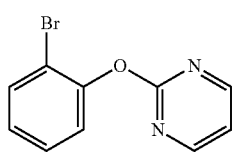

2-(2-Bromophenoxy)pyrimidine

To a 48 mL pressure tube containing a stirbar were added 2-chloropyrimidine (1.69 g, 14.7 mmol), 2-bromophenol (1.63 mL, 14.0 mmol), Cs$_2$CO$_3$ (5.49 g, 16.8 mmol) and DMSO (30 mL). The vial was sealed and heated at 120° Celsius for 15 hours. The reaction was then diluted with 100 mL of ethyl acetate and extracted with brine (2×50 mL). The organic layer was isolated, dried and concentrated to dryness to provide the crude product which was subsequently purified FCC to provide the title compound. $^1$H NMR (500 MHz, CDCl$_3$) δ 8.57 (s, 1H), 8.56 (s, 1H), 7.72-7.60 (dd, J=8.0, 1.6, 1H), 7.45-7.34 (m, 1H), 7.32-7.23 (m, 1H), 7.23-7.11 (m, 1H), 7.10-7.01 (t, J=4.8, 1H).

Intermediate HJ

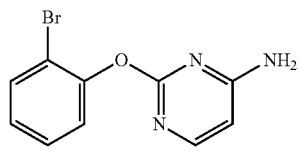

2-(2-Bromophenoxy)pyrimidin-4-amine

The title compound was prepared in a manner similar to that described for Intermediate HI using 2-chloropyrimidin-4-amine. $^1$H NMR (500 MHz, CDCl$_3$) δ 8.04-7.94 (d, J=5.7, 1H), 7.66-7.58 (dd, J=8.0, 1.5, 1H), 7.41-7.30 (m, 1H), 7.30-7.20 (m, 1H), 7.18-7.05 (m, 1H), 6.20-6.09 (d, J=5.7, 1H), 5.19 (s, 2H).

Intermediate HK

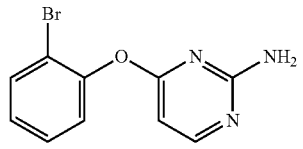

4-(2-Bromophenoxy)pyrimidin-2-amine

The title compound was prepared in a manner similar to that described for Intermediate HI using 4-chloropyrimidin-2-amine. $^1$H NMR (500 MHz, CDCl$_3$) δ 8.15-8.12 (d, J=5.6, 1H), 7.65-7.61 (dd, J=8.0, 1.6, 1H), 7.37-7.32 (m, 1H), 7.20-7.16 (dd, J=8.1, 1.5, 1H), 7.16-7.09 (m, 1H), 6.19-6.14 (d, J=5.7, 1H), 5.21 (s, 2H).

Intermediate HL

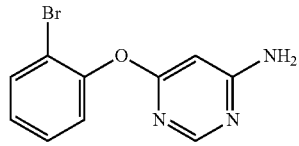

6-(2-Bromophenoxy)pyrimidin-4-amine

The title compound was prepared in a manner similar to that described for Intermediate HI using 6-chloropyrimidin-4-amine. $^1$H NMR (500 MHz, DMSO-d) δ 7.95 (d, J=0.8, 1H), 7.67-7.62 (m, 1H), 7.38 (m, 1H), 7.20-7.14 (m, 2H), 6.75 (s, 2H), 5.77 (d, J=0.9, 1H).

Intermediate HM

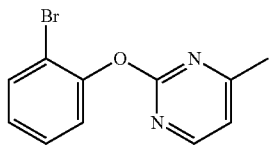

2-(2-Bromophenoxy)-4-methylpyrimidine

The title compound was prepared in a manner similar to that described for Intermediate HI using 2-chloro-4-methylpyrimidine. $^1$H NMR (500 MHz, DMSO-d$_6$) δ 8.44 (d, J=5.1, 1H), 7.72 (dd, J=8.0, 1.6, 1H), 7.49-7.43 (m, 1H), 7.34 (dd, J=8.0, 1.6, 1H), 7.26-7.20 (m, 1H), 7.17-7.14 (m, 1H), 2.41 (s, 3H).

Intermediate HN

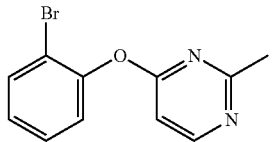

4-(2-Bromophenoxy)-2-methylpyrimidine

The title compound was prepared in a manner similar to that described for Intermediate HI using 4-chloro-2-methylpyrimidine. $^1$H NMR (500 MHz, CDCl$_3$) δ 8.47 (d, J=5.8, 1H), 7.64 (dd, J=8.0, 1.5, 1H), 7.42-7.33 (m, 1H), 7.23-7.10 (m, 2H), 6.64 (d, J=5.7, 1H), 2.55 (s, 3H).

Intermediate HO

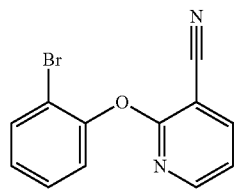

2-(2-Bromophenoxy)nicotinonitrile

The title compound was prepared in a manner similar to that described for Intermediate HI using 2-chloronicotinonitrile. $^1$H NMR (500 MHz, CDCl$_3$) δ 8.32-8.21 (dd, J=5.0, 1.9, 1H), 8.09-7.95 (dd, J=7.6, 1.9, 1H), 7.68-7.60 (dd, J=8.0, 1.5, 1H), 7.45-7.36 (m, 1H), 7.29-7.23 (dd, J=8.1, 1.5, 1H), 7.21-7.16 (m, 1H), 7.15-7.09 (dd, J=7.6, 5.0, 1H).

Intermediate HP

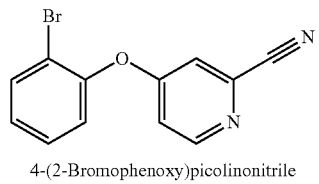 [SMILES: N#Cc1cc(Oc2ccccc2Br)ccn1]

4-(2-Bromophenoxy)picolinonitrile

The title compound was prepared in a manner similar to that described for Intermediate HI using 4-chloropicolinonitrile. $^1$H NMR (500 MHz, DMSO-d$_6$) δ 8.60-8.55 (m, 1H), 7.82-7.77 (m, 1H), 7.73-7.66 (m, 1H), 7.51 (m, 1H), 7.42-7.36 (m, 1H), 7.34-7.27 (m, 1H), 7.11-7.06 (m, 1H).

Intermediate HQ

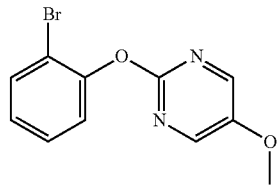

2-(2-Bromophenoxy)-5-methoxypyrimidine

The title compound was prepared in a manner similar to that described for Intermediate HI using 2-chloro-5-methoxypyrimidine. $^1$H NMR (500 MHz, DMSO-d$_6$) δ 8.41 (d, J=0.6, 2H), 7.73 (d, J=8.0, 1H), 7.46 (m, 1H), 7.33 (d, J=8.1, 1H), 7.23 (m, 1H), 3.87 (d, J=0.5, 3H).

Intermediate HR

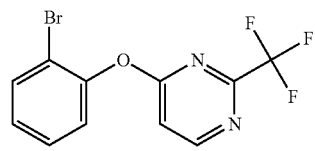

4-(2-Bromophenoxy)-2-(trifluoromethyl)pyrimidine

The title compound was prepared in a manner similar to that described for Intermediate HI using 4-chloro-2-(trifluoromethyl)pyrimidine. $^1$H NMR (500 MHz, DMSO-d) δ 8.92 (d, J=5.8, 1H), 7.76 (dd, J=8.0, 1.5, 1H), 7.53-7.40 (m, 3H), 7.29 (m, 1H).

Intermediate HS

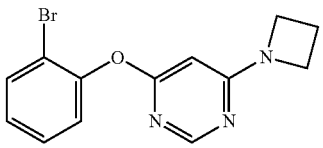

4-(Azetidin-1-yl)-6-(2-bromophenoxy)pyrimidine

The title compound was prepared in a manner similar to that described for Intermediate HI using 4-(azetidin-1-yl)-6-chloropyrimidine. ¹H NMR (400 MHz, DMSO-d₆) δ 8.10 (d, J=0.8, 1H), 7.70 (dd, J=8.0, 1.5, 1H), 7.43 (m, 1H), 7.30-7.18 (m, 2H), 5.84 (d, J=0.8, 1H), 4.06-3.97 (m, 4H), 2.41-2.30 (m, 2H).

Intermediate HT

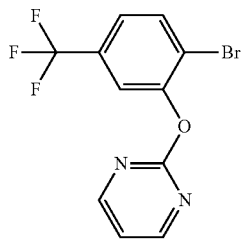

2-(2-Bromo-5-(trifluoromethyl)phenoxy)pyrimidine

The title compound was prepared in a manner similar to that described for Intermediate HI using 2-bromo-5-(trifluoromethyl)phenol. ¹H NMR (500 MHz, CDCl₃) δ 8.62-8.49 (d, J=4.8, 2H), 7.82-7.75 (dd, J=8.4, 0.9, 1H), 7.54-7.51 (d, J=2.0, 1H), 7.44-7.40 (m, 1H), 7.13-7.08 (m, 1H).

Intermediate HU

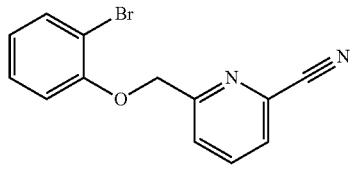

6-((2-Bromophenoxy)methyl)picolinonitrile

To a sealable 4 mL vial, containing 6-(chloromethyl)picolinonitrile (100 mg, 0.66 mmol) and 2-bromophenol (113 mg, 0.66 mmol), were added Cs₂CO₃ (320 mg, 0.98 mmol) and acetonitrile (1.7 mL). The vial was then heated at 80° Celsius for 15 hours. The reaction was then diluted with ethyl acetate, filtered through a celite plug and concentrated to dryness. The material was used without further purification. ¹H NMR (500 MHz, CDCl₃) δ 8.02-7.93 (m, 1H), 7.93-7.85 (m, 1H), 7.65-7.59 (dd, J=7.7, 1.1, 1H), 7.58-7.53 (dd, J=7.9, 1.6, 1H), 7.29-7.22 (m, 1H), 6.93-6.90 (dd, J=8.3, 1.3, 1H), 6.90-6.86 (m, 1H), 5.23 (s, 2H).

Intermediate HV

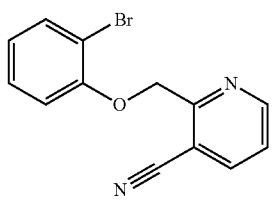

2-((2-Bromophenoxy)methyl)nicotinonitrile

The title compound was prepared in a manner similar to that described for Intermediate HI using 2-(chloromethyl)nicotinonitrile. ¹H NMR (500 MHz, CDCl₃) δ 8.83-8.74 (dd, J=4.9, 1.7, 1H), 8.02-7.97 (dd, J=7.9, 1.7, 1H), 7.57-7.49 (dd, J=7.9, 1.6, 1H), 7.42-7.35 (dd, J=7.9, 4.9, 1H), 7.27-7.20 (m, 1H), 7.08-7.01 (dd, J=8.2, 1.3, 1H), 6.91-6.83 (m, 1H), 5.37 (s, 2H).

Example 526

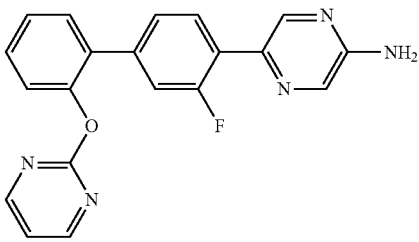

5-[3-Fluoro-2'-(pyrimidin-2-yloxy)biphenyl-4-yl]pyrazin-2-amine

The title compound was prepared in a manner similar to that described in Example 88 using 2-(2-bromophenoxy)pyrimidine. MS (ESI): mass calcd. for C₂₀H₁₄FN₅O, 359.12; m/z found, 360.1 [M+H]⁺. ¹H NMR (500 MHz, DMSO-d₆) δ 8.56 (d, J=4.8, 2H), 8.35-8.30 (m, 1H), 7.99 (d, J=1.5, 1H), 7.82 (m, 1H), 7.58 (dd, J=7.6, 1.7, 1H), 7.52-7.46 (m, 1H), 7.42-7.28 (m, 4H), 7.17 (t, J=4.8, 1H), 6.70 (s, 2H).

Example 527

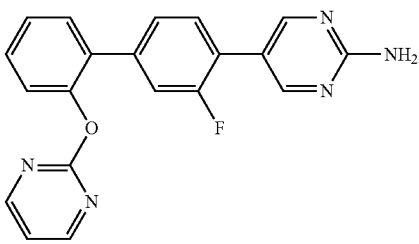

5-[3-Fluoro-2'-(pyrimidin-2-yloxy)biphenyl-4-yl]pyrimidin-2-amine

The title compound was prepared in a manner similar to that described in Example 88 using 2-(2-bromophenoxy)pyrimidine and 5-(2-fluoro-4-(4,4,5,5-tetramethyl-1,3,2-dioxaborolan-2-yl)phenyl)pyrimidin-2-amine. MS (ESI): mass calcd. for C₂₀H₁₄FN₅O, 359.12; m/z found, 360.1 [M+H]⁺. ¹H NMR (500 MHz, DMSO-d₆) δ 8.58 (d, J=4.8, 2H), 8.43 (d, J=1.4, 2H), 7.58-7.46 (m, 3H), 7.42-7.27 (m, 4H), 7.20 (t, J=4.8, 1H), 6.88 (s, 2H).

Example 528

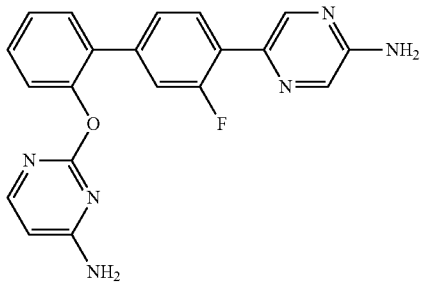

2-{[4'-(5-Aminopyrazin-2-yl)-3'-fluorobiphenyl-2-yl]oxy}pyrimidin-4-amine

The title compound was prepared in a manner similar to that described in Example 88 using 2-(2-bromophenoxy)pyrimidin-4-amine. MS (ESI): mass calcd. for C$_{20}$H$_{15}$FN$_{6}$O, 374.13; m/z found, 375.2 [M+H]$^{+}$. $^1$H NMR (500 MHz, CD$_3$OD) δ 8.35-8.28 (dd, J=2.1, 1.5, 1H), 8.08-8.00 (d, J=1.5, 1H), 7.84-7.77 (m, 1H), 7.77-7.71 (d, J=5.9, 1H), 7.52-7.47 (dd, J=7.6, 1.7, 1H), 7.46-7.40 (m, 1H), 7.38-7.32 (m, 2H), 7.32-7.27 (dd, J=12.6, 1.7, 1H), 7.23-7.16 (dd, J=8.1, 1.2, 1H), 6.11-6.09 (d, J=5.9, 1H).

Example 529

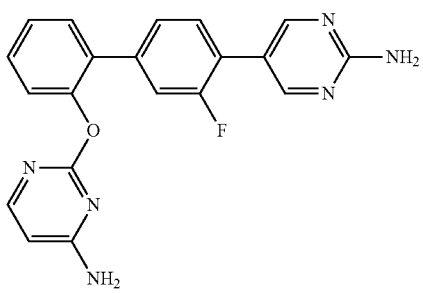

5-{2'-[(4-Aminopyrimidin-2-yl)oxy]-3-fluorobiphenyl-4-yl}pyrimidin-2-amine

The title compound was prepared in a manner similar to that described in Example 88 using 2-(2-bromophenoxy)pyrimidin-4-amine and 5-(2-fluoro-4-(4,4,5,5-tetramethyl-1,3,2-dioxaborolan-2-yl)phenyl)pyrimidin-2-amine. MS (ESI): mass calcd. for C$_{20}$H$_{15}$FN$_{6}$O, 374.13; m/z found, 375.1 [M+H]$^{+}$. $^1$H NMR (500 MHz, CD$_3$OD) δ 8.49-8.43 (d, J=1.4, 2H), 7.79-7.72 (d, J=5.9, 1H), 7.51-7.47 (dd, J=7.6, 1.7, 1H), 7.47-7.41 (m, 2H), 7.39-7.28 (m, 3H), 7.22-7.17 (dd, J=8.1, 1.2, 1H), 6.16-6.05 (d, J=5.9, 1H).

Example 530

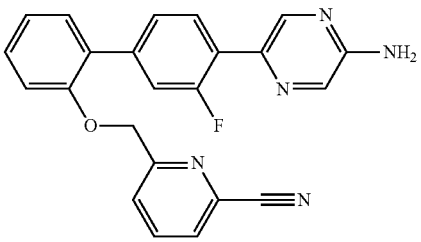

6-({[4'-(5-Aminopyrazin-2-yl)-3'-fluorobiphenyl-2-yl]oxy}methyl)pyridine-2-carbonitrile The title compound was prepared in a manner similar to that described in Example 88 using 6-((2-bromophenoxy)methyl)picolinonitrile. MS (ESI): mass calcd. for C$_{23}$H$_{16}$FN$_{5}$O, 397.13; m/z found, 398.1 [M+H]$^{+}$. $^1$H NMR (500 MHz, CD$_3$OD) δ 8.38-8.29 (d, J=1.5, 1H), 8.24 (s, 1H), 8.01-7.90 (m, 2H), 7.83-7.73 (m, 1H), 7.72-7.64 (dd, J=8.2, 1.0, 1H), 7.52-7.48 (dd, J=8.1, 1.6, 1H), 7.48-7.44 (m, 1H), 7.44-7.40 (dd, J=7.6, 1.7, 1H), 7.40-7.34 (m, 1H), 7.19-7.15 (dd, J=8.3, 1.1, 1H), 7.14-7.07 (m, 1H), 5.26 (s, 2H).

Example 531

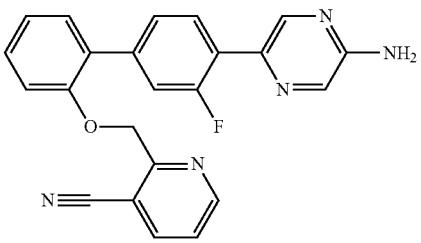

2-({[4'-(5-Aminopyrazin-2-yl)-3'-fluorobiphenyl-2-yl]oxy}methyl)pyridine-3-carbonitrile The title compound was prepared in a manner similar to that described in Example 88 using 2-((2-bromophenoxy)methyl)nicotinonitrile. MS (ESI): mass calcd. for C$_{23}$H$_{16}$FN$_{5}$O, 397.13; m/z found, 398.1 [M+H]$^{+}$. $^1$H NMR (500 MHz, CD$_3$OD) δ 8.80-8.73 (dd, J=5.0, 1.7, 1H), 8.32-8.27 (m, 1H), 8.24-8.22 (d, J=1.4, 1H), 8.22-8.15 (dd, J=7.9, 1.7, 1H), 7.89-7.82 (m, 1H), 7.57-7.49 (dd, J=7.9, 5.0, 1H), 7.45 (s, 1H), 7.44-7.42 (dd, J=4.4, 1.6, 1H), 7.41-7.35 (m, 2H), 7.26-7.22 (dd, J=8.2, 1.0, 1H), 7.14-7.09 (m, 1H), 5.34 (s, 2H).

Example 532

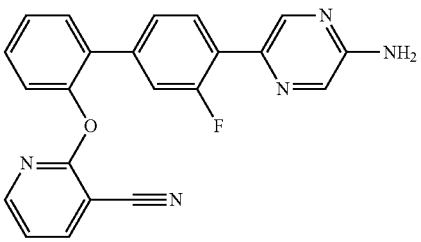

2-{[4'-(5-Aminopyrazin-2-yl)-3'-fluorobiphenyl-2-yl]oxy}methyl)pyridine-3-carbonitrile The title compound was prepared in a manner similar to that described in Example 88 using 2-(2-bromophenoxy) nicotinonitrile. MS (ESI): mass calcd. for $C_{22}H_{14}FN_5O$, 383.12; m/z found, 384.2 [M+H]$^+$. $^1$H NMR (500 MHz, CD$_3$OD) δ 8.28-8.25 (m, 1H), 8.22-8.18 (d, J=1.4, 1H), 8.17-8.13 (dd. J=5.0, 1.9, 1H), 8.10-8.04 (dd, J=7.6, 1.9, 1H), 7.89-7.82 (m, 1H), 7.57-7.53 (dd, J=7.6, 1.7, 1H), 7.53-7.47 (m, 1H), 7.45-7.41 (m, 1H), 7.41-7.37 (dd, J=8.1, 1.7, 1H), 7.34-7.28 (m, 2H), 7.12-7.04 (dd, J=7.6, 5.0, 1H).

Example 533

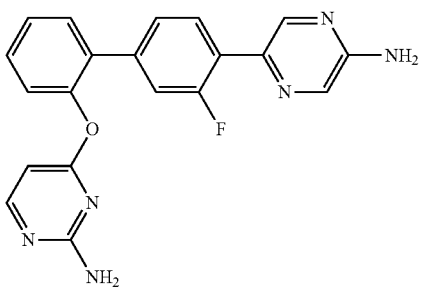

4-{[4'-(5-Aminopyrazin-2-yl)-3'-fluorobiphenyl-2-yl]oxy}pyrimidin-2-amine

The title compound was prepared in a manner similar to that described in Example 88 using 4-(2-bromophenoxy) pyrimidin-2-amine. MS (ESI): mass calcd. for $C_{20}H_{15}FN_6O$, 374.13; m/z found, 375.2 [M+H]$^+$. $^1$H NMR (500 MHz, CD$_3$OD) δ 8.35-8.29 (m, 1H), 8.12-8.07 (d, J=1.5, 1H), 8.05-8.00 (d, J=7.0, 1H), 7.92-7.85 (m, 1H), 7.59-7.55 (dd, J=7.5, 1.8, 1H), 7.55-7.49 (m, 1H), 7.49-7.43 (m, 1H), 7.36-7.33 (dd, J=8.1, 1.7, 1H), 7.33-7.31 (dd, J=8.0, 1.3, 1H), 7.31-7.27 (dd, J=12.5, 1.7, 1H), 6.72-6.42 (d, J=7.0, 1H).

Example 534

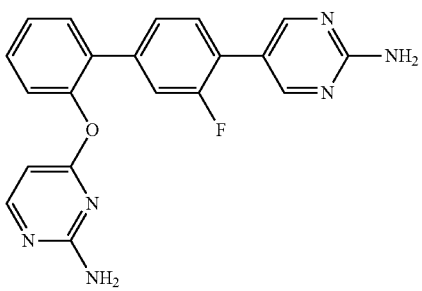

4-{[4'-(2-Aminopyrimidin-5-yl)-3'-fluorobiphenyl-2-yl]oxy}pyrimidin-2-amine

The title compound was prepared in a manner similar to that described in Example 88 using 4-(2-bromophenoxy) pyrimidin-2-amine and 5-(2-fluoro-4-(4,4,5,5-tetramethyl-1,3,2-dioxaborolan-2-yl)phenyl)pyrimidin-2-amine. MS (ESI): mass calcd. for $C_{20}H_{15}FN_6O$, 374.13; m/z found, 375.1 [M+H]$^+$. $^1$H NMR (500 MHz, CD$_3$OD) δ 8.46 (s, 2H), 7.98-7.94 (d, J=5.8, 1H), 7.53-7.49 (d, J=7.6, 1H), 7.49-7.42 (m, 2H), 7.41-7.36 (m, 1H), 7.36-7.32 (d, J=8.2, 1H), 7.32-7.27 (m, 1H), 7.26-7.14 (d, J=8.0, 1H), 6.13-6.04 (d, J=5.8, 1H).

Example 535

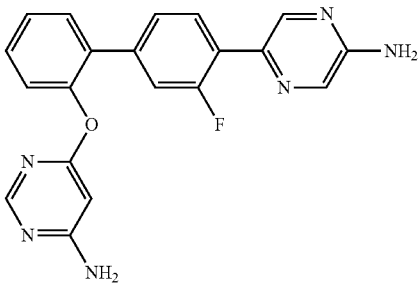

6-{[4'-(5-Aminopyrazin-2-yl)-3'-fluorobiphenyl-2-yl]oxy}pyrimidin-4-amine

The title compound was prepared in a manner similar to that described in Example 88 using 6-(2-bromophenoxy) pyrimidin-4-amine. MS (ESI): mass calcd. for $C_{20}H_{15}FN_6O$, 374.13; m/z found, 375.0 [M+H]$^+$. $^1$H NMR (500 MHz, DMSO-d$_6$) δ 8.24 (s, 1H), 7.97 (d, J=1.4, 1H), 7.90 (s, 1H), 7.74 (m, 1H), 7.50 (dd, J=7.6, 1.7, 1H), 7.42 (m, 1H), 7.36-7.29 (m, 2H), 7.28-7.22 (m, 1H), 7.13 (d, J=8.1, 1H), 6.65 (s, 2H), 6.52 (s, 2H), 5.67 (s, 1H).

Example 536

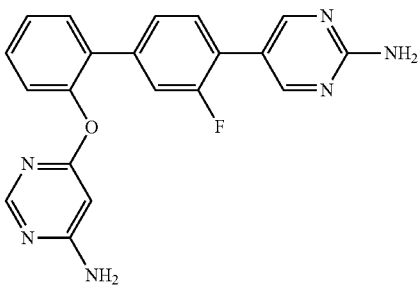

5-{2'-[(6-Aminopyrimidin-4-yl)oxy]-3-fluorobiphenyl-4-yl}pyrimidin-2-amine

The title compound was prepared in a manner similar to that described in Example 88 using 6-(2-bromophenoxy) pyrimidin-4-amine and 5-(2-fluoro-4-(4,4,5,5-tetramethyl-1,3,2-dioxaborolan-2-yl)phenyl)pyrimidin-2-amine. MS (ESI): mass calcd. for $C_{20}H_{15}FN_6O$, 374.13; m/z found, 375.0 [M+H]$^+$. $^1$H NMR (500 MHz, DMSO-d$_6$) δ 8.38 (s, 2H), 7.92 (s, 1H), 7.47 (m, 2H), 7.40 (d, J=6.4, 1H), 7.36-7.23 (m, 3H), 7.11 (d, J=7.7, 1H), 6.68 (br, 4H), 5.68 (s, 1H).

Example 537

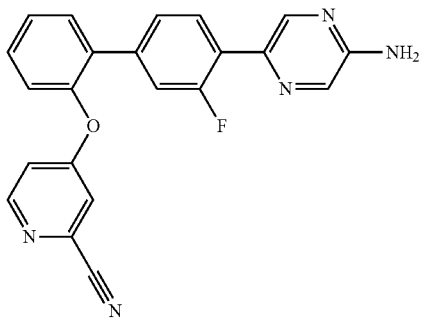

4-{[4'-(5-Aminopyrazin-2-yl)-3'-fluorobiphenyl-2-yl]oxy}pyridine-2-carbonitrile

The title compound was prepared in a manner similar to that described in Example 88 using 4-(2-bromophenoxy)picolinonitrile. MS (ESI): mass calcd. for $C_{22}H_{14}FN_5O$, 383.12; m/z found, 384.0 [M+H]$^+$. $^1$H NMR (500 MHz, DMSO-d$_6$) δ 8.47 (d, J=5.1, 1H), 8.29 (s, 1H), 7.96 (s, 1H), 7.81 (s, 1H), 7.66-7.56 (m, 2H), 7.48 (dd, J=20.1, 7.3, 2H), 7.39-7.20 (m, 3H), 7.07 (s, 1H), 6.68 (s, 2H).

Example 538

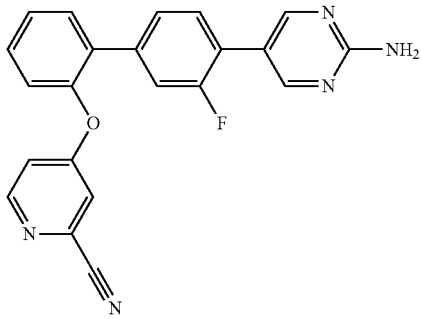

4-{[4'-(2-Aminopyrimidin-5-yl)-3'-fluorobiphenyl-2-yl]oxy}pyridine-2-carbonitrile The title compound was prepared in a manner similar to that described in Example 88 using 4-(2-bromophenoxy)picolinonitrile and 5-(2-fluoro-4-(4,4,5,5-tetramethyl-1,3,2-dioxaborolan-2-yl)phenyl)pyrimidin-2-amine. MS (ESI): mass calcd. for $C_{22}H_{14}FN_5O$, 383.12; m/z found, 384.0 [M+H]$^+$. $^1$H NMR (500 MHz, DMSO-d$_6$) δ 8.50 (d, J=5.7, 1H), 8.40 (d, J=1.3, 2H), 7.61 (dd, J=7.9, 2.0, 2H), 7.53 (dd, J=11.1, 5.0, 2H), 7.48-7.42 (m, 1H), 7.36 (dd, J=12.1, 1.5, 1H), 7.31 (dd, J=11.5, 5.0, 2H), 7.11 (dd, J=5.7, 2.5, 1H), 6.86 (s, 2H).

Example 539

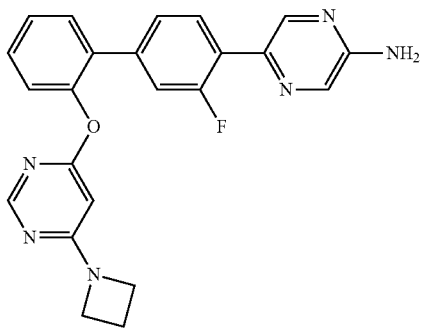

5-{2'-[(6-Azetidin-1-ylpyrimidin-4-yl)oxy]-3-fluorobiphenyl-4-yl}pyrazin-2-amine The title compound was prepared in a manner similar to that described in Example 88 using 4-(azetidin-1-yl)-6-(2-bromophenoxy)pyrimidine. MS (ESI): mass calcd. for $C_{23}H_{19}FN_6O$, 414.16; m/z found, 415.1 [M+H]$^+$. $^1$H NMR (400 MHz, DMSO-d$_6$) δ 8.39-8.31 (m, 1H), 8.08 (d, J=0.9, 1H), 8.02 (d, J=1.5, 1H), 7.85 (m, 1H), 7.55 (dd, J=7.6, 1.7, 1H), 7.51-7.42 (m, 1H), 7.40-7.29 (m, 3H), 7.18 (dd, J=8.0, 1.2, 1H), 6.71 (s, 2H), 5.71 (d, J=0.9, 1H), 3.96 (t, J=7.5, 4H), 2.39-2.24 (m, 2H).

Example 540

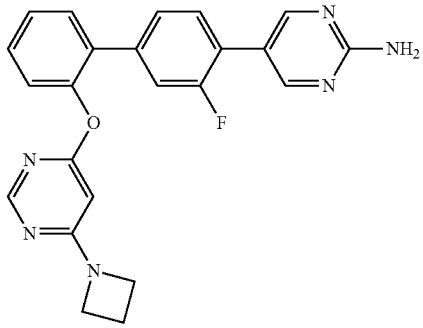

5-{2'-[(6-Azetidin-1-ylpyrimidin-4-yl)oxy]-3-fluorobiphenyl-4-yl}pyrimidin-2-amine The title compound was prepared in a manner similar to that described in Example 88 using 4-(azetidin-1-yl)-6-(2-bromophenoxy)pyrimidine and 5-(2-fluoro-4-(4,4,5,5-tetramethyl-1,3,2-dioxaborolan-2-yl)phenyl)pyrimidin-2-amine. MS (ESI): mass calcd. for $C_{23}H_{19}FN_6O$, 414.16; m/z found, 415.1 [M+H]$^+$. $^1$H NMR (400 MHz, DMSO-d$_6$) δ 8.46 (d, J=1.5, 2H), 8.11 (d, J=0.9, 1H), 7.60-7.52 (m, 2H), 7.50-7.41 (m, 1H), 7.41-7.31 (m, 3H), 7.17 (dd, J=8.1, 1.2, 1H), 6.89 (s, 2H), 5.73 (d, J=0.9, 1H), 3.98 (t, J=7.5, 4H), 2.41-2.27 (m, 2H).

Example 541

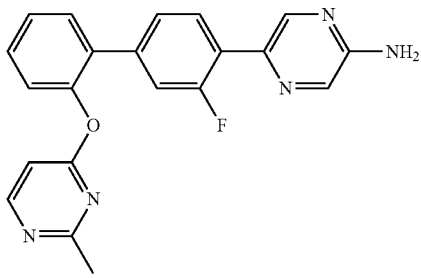

5-{3-Fluoro-2'-[(2-methylpyrimidin-4-yl)oxy]biphenyl-4-yl}pyrazin-2-amine

The title compound was prepared in a manner similar to that described in Example 88 using 4-(2-bromophenoxy)-2-methylpyrimidine. MS (ESI): mass calcd. for $C_{21}H_{16}FN_5O$, 373.13; m/z found, 374.1 [M+H]$^+$. $^1$H NMR (500 MHz, CDCl$_3$) δ 8.53 (s, 1H), 8.35 (d, J=5.8, 1H), 8.08 (d, J=1.3, 1H), 7.87 (m, 1H), 7.51 (dd, J=7.5, 1.9, 1H), 7.45 (m, 1H), 7.38 (dd, J=7.8, 6.9, 1H), 7.33 (dd, J=7.9, 1.6, 1H), 7.26 (m, 1H), 7.21 (d, J=8.1, 1H), 6.49 (d, J=5.8, 1H), 4.73 (s, 2H), 2.51 (s, 3H).

Example 542

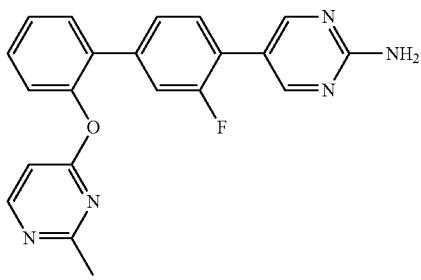

5-{3-Fluoro-2'-[(2-methylpyrimidin-4-yl)oxy]biphenyl-4-yl}pyrimidin-2-amine

The title compound was prepared in a manner similar to that described in Example 88 using 4-(2-bromophenoxy)-2-methylpyrimidine and 5-(2-fluoro-4-(4,4,5,5-tetramethyl-1,3,2-dioxaborolan-2-yl)phenyl)pyrimidin-2-amine. MS (ESI): mass calcd. for $C_{21}H_{16}FN_5O$, 373.13; m/z found, 374.1 [M+H]$^+$. $^1$H NMR (500 MHz, CDCl$_3$) δ 8.50 (s, 2H), 8.38 (d, J=5.8, 1H), 7.53-7.28 (m, 6H), 7.21 (d, J=7.9, 1H), 6.51 (d, J=5.7, 1H), 5.30 (s, 2H), 2.52 (s, 3H).

Example 543

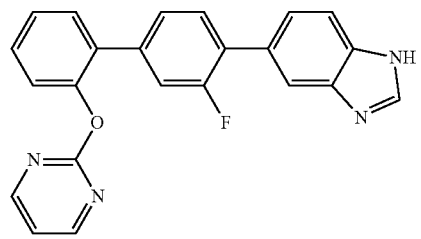

5-[3-Fluoro-2'-(pyrimidin-2-yloxy)biphenyl-4-yl]-1H-benzimidazole

The title compound was prepared in a manner similar to that described in Example 88 using 5-bromo-1H-benzo[d]imidazole and 2-((3'-fluoro-4'-(4,4,5,5-tetramethyl-1,3,2-dioxaborolan-2-yl)-[1,1'-biphenyl]-2-yl)oxy)pyrimidine. MS (ESI): mass calcd. for $C_{23}H_{15}FN_4O$, 382.12; m/z found, 383.1 [M+H]$^+$. $^1$H NMR (500 MHz, CD$_3$OD) δ 9.31 (s, 1H), 8.52-8.45 (d, J=4.9, 2H), 7.95 (s, 1H), 7.92-7.87 (d, J=8.6, 1H), 7.79-7.70 (d, J=8.6, 1H), 7.59-7.55 (dd, J=7.7, 1.7, 1H), 7.55-7.47 (m, 2H), 7.45-7.39 (m, 2H), 7.38-7.32 (dd, J=12.0, 1.7, 1H), 7.30-7.23 (dd, J=8.1, 1.2, 1H), 7.13-7.08 (t, J=4.8, 1H).

Example 544

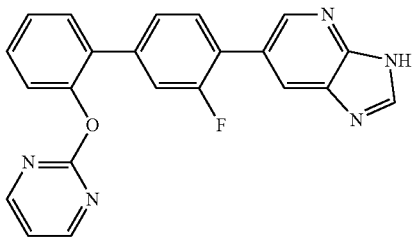

6-[3-Fluoro-2'-(pyrimidin-2-yloxy)biphenyl-4-yl]-3H-imidazo[4,5-b]pyridine

The title compound was prepared in a manner similar to that described in Example 88 using 6-bromo-3H-imidazo[4,5-b]pyridine and 2-((3'-fluoro-4'-(4,4,5,5-tetramethyl-1,3,2-dioxaborolan-2-yl)-[1,1'-biphenyl]-2-yl)oxy)pyrimidine. MS (ESI): mass calcd. for $C_{22}H_{14}FN_5O$, 383.12; m/z found, 384.1 [M+H]$^+$. $^1$H NMR (500 MHz, CD$_3$OD) δ 8.55-8.52 (m, 1H), 8.51-8.47 (d, J=4.9, 2H), 8.43 (s, 1H), 8.19-8.14 (t, J=1.7, 1H), 7.59-7.55 (dd, J=7.7, 1.8, 1H), 7.55-7.47 (m, 2H), 7.46-7.40 (m, 2H), 7.39-7.33 (dd, J=11.9, 1.7, 1H), 7.30-7.25 (dd, J=8.0, 1.2, 1H).

Example 545

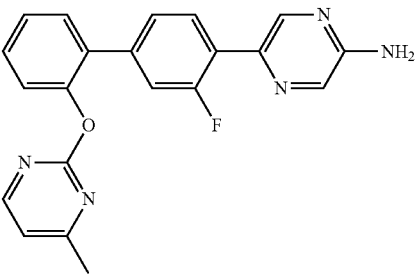

5-{3-Fluoro-2'-[(4-methylpyrimidin-2-yl)oxy]biphenyl-4-yl}pyrazin-2-amine

The title compound was prepared in a manner similar to that described in Example 88 using 2-(2-bromophenoxy)-4-methylpyrimidine. MS (ESI): mass calcd. for $C_{21}H_{16}FN_5O$, 373.13; m/z found, 374.1 [M+H]$^+$. $^1$H NMR (500 MHz, DMSO-d$_6$) δ 8.37 (d, J=5.1, 1H), 8.32 (d, J=1.6, 1H), 8.00 (d, J=1.6, 1H), 7.82 (m, 1H), 7.56 (dd, J=7.5, 1.7, 1H), 7.51-7.44 (m, 1H), 7.41-7.24 (m, 4H), 7.05 (d, J=5.1, 1H), 6.70 (s, 2H), 2.34 (s, 3H).

Example 546

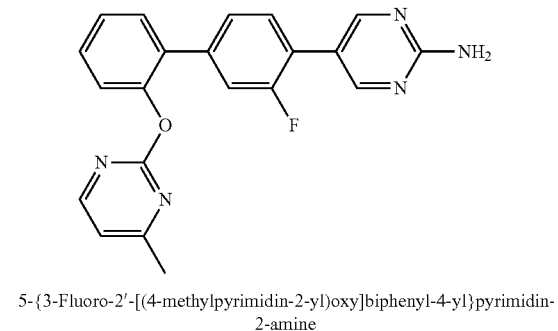 [SMILES: Cc1ccnc(Oc2ccccc2-c2ccc(-c3cnc(N)nc3)c(F)c2)n1]

5-{3-Fluoro-2'-[(4-methylpyrimidin-2-yl)oxy]biphenyl-4-yl}pyrimidin-2-amine

The title compound was prepared in a manner similar to that described in Example 88 using 2-(2-bromophenoxy)-4-methylpyrimidine and 5-(2-fluoro-4-(4,4,5,5-tetramethyl-1,3,2-dioxaborolan-2-yl)phenyl)pyrimidin-2-amine. MS (ESI): mass calcd. for $C_{21}H_{16}FN_5O$, 373.13; m/z found, 374.1 [M+H]$^+$. $^1$H NMR (500 MHz, DMSO-d$_6$) δ 8.44 (s, 2H), 8.39 (d, J=5.1, 1H), 7.57-7.44 (m, 3H), 7.41-7.31 (m, 3H), 7.25 (d, J=7.2, 1H), 7.07 (d, J=4.9, 1H), 6.89 (s, 2H), 2.35 (s, 3H).

Example 547

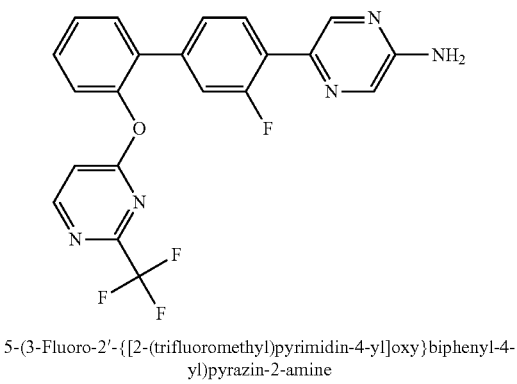 [SMILES: Nc1cnc(-c2ccc(-c3ccccc3Oc3ccnc(C(F)(F)F)n3)cc2F)cn1]

5-(3-Fluoro-2'-{[2-(trifluoromethyl)pyrimidin-4-yl]oxy}biphenyl-4-yl)pyrazin-2-amine The title compound was prepared in a manner similar to that described in Example 88 using 4-(2-bromophenoxy)-2-(trifluoromethyl)pyrimidine. MS (ESI): mass calcd. for $C_{21}H_{13}F_4N_5O$, 427.11; m/z found, 428.1 [M+H]$^+$. $^1$H NMR (500 MHz, DMSO-d$_6$) δ 8.76 (d, J=5.8, 1H), 8.29-8.24 (m, 1H), 7.95 (d, J=1.5, 1H), 7.78 (m, 1H), 7.58 (dd, J=7.5, 1.8, 1H), 7.54-7.48 (m, 1H), 7.45 (m, 1H), 7.39 (dd, J=8.0, 1.3, 1H), 7.27 (m, 3H), 6.66 (s, 2H).

Example 548

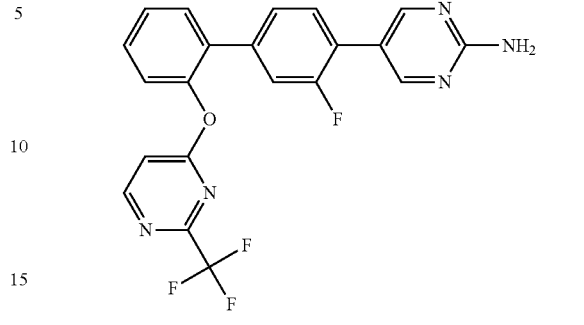

5-(3-Fluoro-2'-{[2-(trifluoromethyl)pyrimidin-4-yl]oxy}biphenyl-4-yl)pyrimidin-2-amine The title compound was prepared in a manner similar to that described in Example 88 using 4-(2-bromophenoxy)-2-(trifluoromethyl)pyrimidine and 5-(2-fluoro-4-(4,4,5,5-tetramethyl-1,3,2-dioxaborolan-2-yl)phenyl)pyrimidin-2-amine. MS (ESI): mass calcd. for $C_{21}H_{13}F_4N_5O$, 427.11; m/z found, 428.1 [M+H]$^+$. $^1$H NMR (500 MHz, DMSO-d$_6$) δ 8.78 (d, J=5.7, 1H), 8.37 (m, 2H), 7.57 (dd, J=7.5, 1.8, 1H), 7.48 (m, 3H), 7.39 (dd, J=8.0, 1.3, 1H), 7.33-7.22 (m, 3H), 6.85 (s, 2H).

Example 549

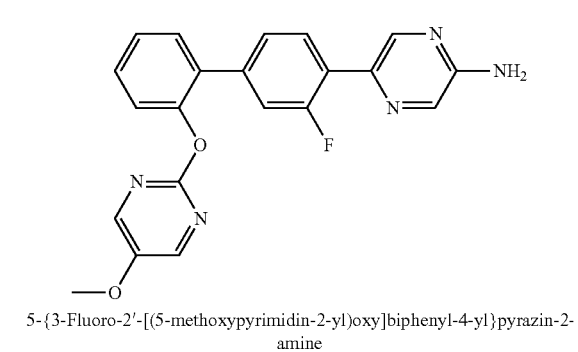 [SMILES: COc1cnc(Oc2ccccc2-c2ccc(-c3cnc(N)cn3)c(F)c2)nc1]

5-{3-Fluoro-2'-[(5-methoxypyrimidin-2-yl)oxy]biphenyl-4-yl}pyrazin-2-amine

The title compound was prepared in a manner similar to that described in Example 88 using 2-(2-bromophenoxy)-5-methoxypyrimidine. MS (ESI): mass calcd. for $C_{21}H_{16}FN_5O_2$, 389.13; m/z found, 390.1 [M+H]$^+$. $^1$H NMR (500 MHz, DMSO-d$_6$) δ 8.45 (s, 1H), 8.35 (s, 1H), 7.55 (m, 2H), 7.46 (m, 1H), 7.42-7.32 (m, 3H), 7.22 (d, J=8.0, 1H), 6.89 (s, 2H), 3.83 (s, 3H).

Example 550

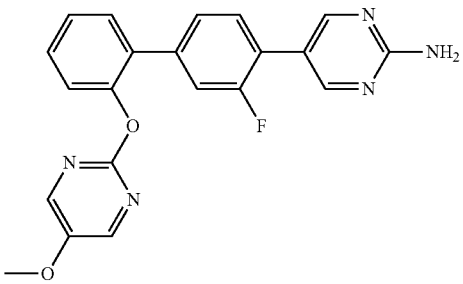

5-{3-Fluoro-2'-[(5-methoxypyrimidin-2-yl)oxy]biphenyl-4-yl}pyrimidin-2-amine

The title compound was prepared in a manner similar to that described in Example 88 using 2-(2-bromophenoxy)-5-methoxypyrimidine and 5-(2-fluoro-4-(4,4,5,5-tetramethyl-1,3,2-dioxaborolan-2-yl)phenyl)pyrimidin-2-amine. MS (ESI): mass calcd. for $C_{21}H_{16}FN_5O_2$, 389.13; m/z found, 390.1 [M+H]$^+$. $^1$H NMR (500 MHz, DMSO-d$_6$) δ 8.30-8.26 (m, 3H), 7.96 (d, J=1.5, 1H), 7.78 (m, 1H), 7.52 (dd, J=7.6, 1.7, 1H), 7.46-7.39 (m, 1H), 7.37-7.26 (m, 3H), 7.19 (dd, J=8.1, 1.2, 1H), 6.66 (s, 2H), 3.76 (d, J=1.9, 3H).

Example 551

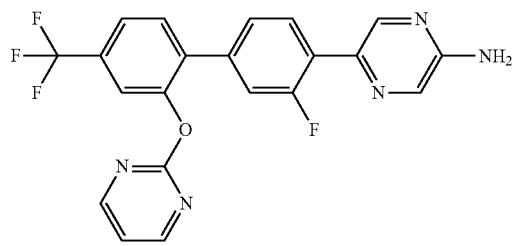

5-[3-Fluoro-2'-(pyrimidin-2-yloxy)-4'-(trifluoromethyl)biphenyl-4-yl]pyrazin-2-amine The title compound was prepared in a manner similar to that described in Example 88 using 2-(2-bromo-5-(trifluoromethyl)phenoxy)pyrimidine. MS (ESI): mass calcd. for $C_{21}H_{13}F_4N_5O$, 427.11; m/z found, 428.1 [M+H]$^+$. $^1$H NMR (500 MHz, CD$_3$OD) δ 8.49 (s, 1H), 8.48 (s, 1H), 8.30-8.27 (d, J=1.7, 1H), 8.13-8.10 (d, J=1.4, 1H), 7.89-7.84 (m, 1H), 7.77-7.73 (m, 1H), 7.73-7.68 (m, 1H), 7.63-7.59 (d, J=2.0, 1H), 7.42-7.38 (dd, J=8.1, 1.7, 1H), 7.37-7.33 (dd, J=12.4, 1.7, 1H), 7.14-7.07 (t, J=4.9, 1H).

Example 552

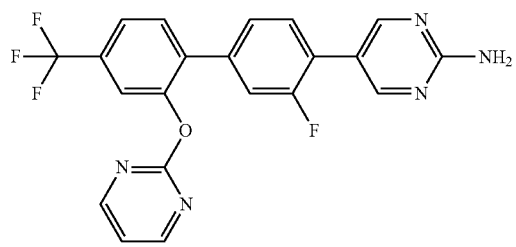

5-[3-Fluoro-2'-(pyrimidin-2-yloxy)-4'-(trifluoromethyl)biphenyl-4-yl]pyrimidin-2-amine The title compound was prepared in a manner similar to that described in Example 88 using 2-(2-bromo-5-(trifluoromethyl)phenoxy)pyrimidine. MS (ESI): mass calcd. for $C_{21}H_{13}F_4N_5O$, 427.11; m/z found, 428.0 [M+H]$^+$. $^1$H NMR (500 MHz, CD$_3$OD) δ 8.50 (s, 1H), 8.49 (s, 1H), 8.45-8.43 (d, J=1.4, 2H), 7.76-7.73 (m, 1H), 7.73-7.69 (m, 1H), 7.62-7.60 (d, J=1.6, 1H), 7.49-7.44 (m, 1H), 7.41-7.38 (m, 1H), 7.38-7.34 (dd, J=11.9, 1.7, 1H), 7.14-7.11 (t, J=4.8, 1H).

Example 553

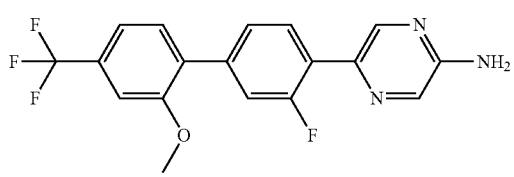

5-[3-Fluoro-2'-methoxy-4'-(trifluoromethyl)biphenyl-4-yl]pyrazin-2-amine

The title compound was prepared in a manner similar to that described in Example 88 using 1-bromo-2-methoxy-4-(trifluoromethyl)benzene. MS (ESI): mass calcd. for $C_{18}H_{13}F_4N_3O$, 363.10; m/z found, 364.0 [M+H]$^+$. $^1$H NMR (500 MHz, CD$_3$OD) δ 8.39-8.37 (m, 1H), 8.11-8.08 (d, J=1.5, 1H), 7.93-7.87 (m, 1H), 7.55-7.52 (m, 1H), 7.45-7.37 (m, 2H), 7.36-7.31 (m, 2H), 3.90 (s, 3H).

Example 554

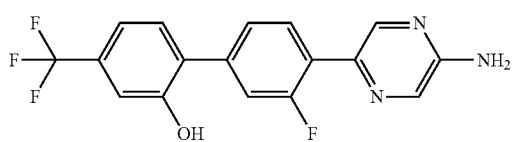

4'-(5-Aminopyrazin-2-yl)-3'-fluoro-4-(trifluoromethyl)biphenyl-2-ol

To a stirred solution of 5-[3-fluoro-2'-methoxy-4'-(trifluoromethyl)biphenyl-4-yl]pyrazin-2-amine (370 mg, 1.02 mmol) in dry dichloromethane (9.8 mL) at −78° Celsius, was added a boron tribromide in dichloromethane (3.1 mL, 1 M). The flask was slowly warmed to rt and stirred overnight. The reaction was poured into sat. NH$_4$Cl and the pH adjusted to 8 with saturated NaHCO$_3$. The resultant mixture was extracted with DCM (3×30 mL) and the combined extracts dried over Na$_2$SO$_4$, filtered and concentrated to dryness. The crude product was purified by HPLC to give the title compound. MS (ESI): mass calcd. for $C_{17}H_{11}F_4N_3O$, 349.08; m/z found, 350.1 [M+H]$^+$. $^1$H NMR (500 MHz, CD$_3$OD) δ 8.41-8.35 (m, 1H), 8.17-8.10 (d, J=1.5, 1H), 7.99-7.88 (m, 1H), 7.56-7.46 (m, 3H), 7.22-7.19 (m, 1H), 7.19-7.17 (d, J=1.7, 1H).

Example 555

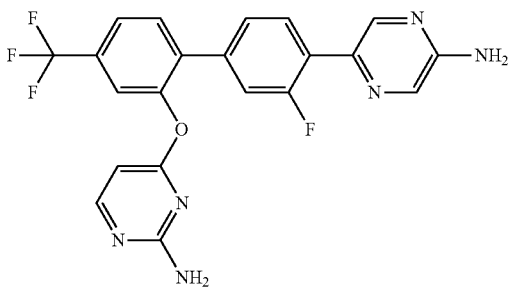

4'-{[4'-(5-Aminopyrazin-2-yl)-3'-fluoro-4-(trifluoromethyl)biphenyl-2-yl]oxy}pyrimidin-2-amine To a 5 mL vial were added a stir bar, 4'-(5-aminopyrazin-2-yl)-3'-fluoro-4-(trifluoromethyl)biphenyl-2-ol (40 mg, 0.12 mmol), 4-chloropyrimidin-2-amine (17.8 mg, 0.14 mmol), DMSO (1 mL) and $Cs_2CO_3$ (52 mg, 0.16 mmol). The vial was flushed with nitrogen and heated for 15 hours at 120° Celsius. The reaction was diluted with 5 mL of ethyl acetate and 5 mL of brine. The aqueous layer was then extracted with ethyl acetate (3×10 mL), the combined organic extracts dried over $Na_2SO_4$, and concentrated to dryness. The crude product was purified by HPLC to give the title compound. MS (ESI): mass calcd. for $C_{21}H_{14}F_4N_6O$, 442.12; m/z found, 443.1 [M+H]$^+$. $^1$H NMR (500 MHz, $CD_3OD$) δ 8.34 (s, 1H), 8.09-8.07 (d, J=1.4, 1H), 8.07-8.05 (d, J=7.0, 1H), 7.96-7.88 (m, 1H), 7.82-7.74 (d, J=1.6, 2H), 7.71 (s, 1H), 7.41-7.37 (dd, J=8.1, 1.7, 1H), 7.37-7.32 (dd, J=12.4, 1.7, 1H), 6.64-6.56 (d, J=7.0, 1H).

Example 556

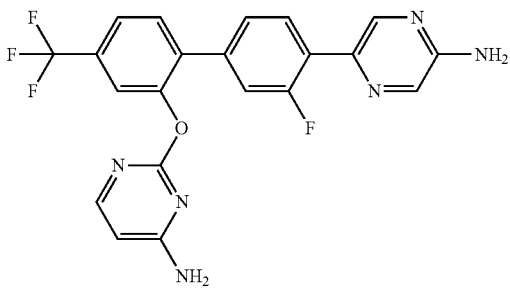

2-{[4'-(5-Aminopyrazin-2-yl)-3'-fluoro-4-(trifluoromethyl)biphenyl-2-yl]oxy}pyrimidin-4-amine The title compound was prepared in a manner similar to that described in Example 555 using 2-chloropyrimidin-4-amine. MS (ESI): mass calcd. for $C_{21}H_{14}F_4N_6O$, 442.12; m/z found, 443.1 [M+H]$^+$. $^1$H NMR (500 MHz, $CD_3OD$) δ 8.38-8.32 (m, 1H), 8.10-8.04 (d, J=1.5, 1H), 7.98-7.90 (m, 1H), 7.89-7.84 (d, J=6.9, 1H), 7.78 (s, 3H), 7.40-7.37 (dd, J=8.1, 1.8, 1H), 7.37-7.33 (dd, J=12.4, 1.7, 1H), 6.36-6.26 (d, J=6.9, 1H).

Example 557

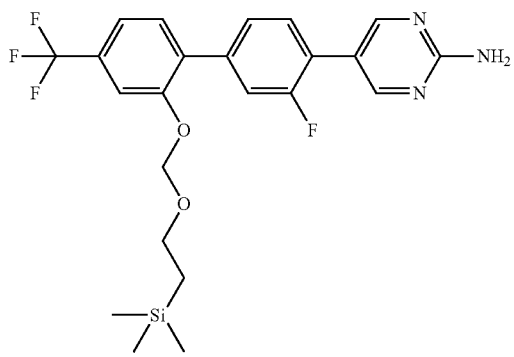

5-[3-Fluoro-4'-(trifluoromethyl)-2'-{[2-(trimethylsilyl)ethoxy]methoxy}biphenyl-4-yl]-pyrimidin-2-amine The title compound was prepared in a manner similar to that described in Example 88 using (2-((2-bromo-5-(trifluoromethyl)phenoxy)methoxy)ethyl)trimethylsilane and 5-(2-fluoro-4-(4,4,5,5-tetramethyl-1,3,2-dioxaborolan-2-yl)phenyl)-pyrimidin-2-amine. MS (ESI): mass calcd. for $C_{23}H_{25}F_4N_3O_2Si$, 479.17; m/z found, 480.0 [M+H]$^+$. $^1$H NMR (500 MHz, $CD_3OD$) δ 8.55-8.48 (m, 2H), 7.60-7.51 (m, 3H), 7.48-7.36 (m, 3H), 5.33-5.29 (d, J=1.0, 2H), 3.73-3.66 (m, 2H), 0.93-0.84 (t, J=8.0, 2H), −0.03--0.07 (m, 9H).

Example 558

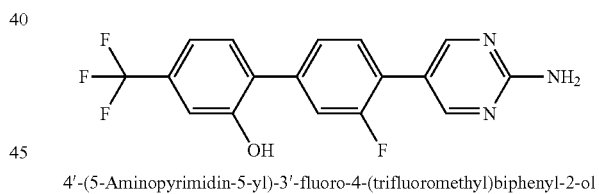

4'-(5-Aminopyrimidin-5-yl)-3'-fluoro-4-(trifluoromethyl)biphenyl-2-ol

To a stirred solution of 5-[3-fluoro-4'-(trifluoromethyl)-2'-{[2-(trimethylsilyl)ethoxy]-methoxy}-biphenyl-4-yl]pyrimidin-2-amine in 14 mL of THF were added water (1.40 mL), acetic acid (1.40 mL) and hydrochloric acid (0.43 mL, 6 N). The reaction was stirred overnight at 65° Celsius, before diluting with ethyl acetate (20 mL) and water (20 mL). The aqueous layer was extracted with ethyl acetate (3×30 mL) and the combined organic extracts dried over $Na_2SO_4$, and concentrated to dryness. The crude product was purified by FCC to provide the title compound. MS (ESI): mass calcd. for $C_{17}H_{11}F_4N_3O$, 349.08; m/z found, 350.1 [M+H]$^+$. $^1$H NMR (500 MHz, $CD_3OD$) δ 8.61 (s, 2H), 7.61-7.48 (m, 4H), 7.23-7.19 (dd, J=8.3, 1.8, 1H), 7.19-7.17 (d, J=1.6, 1H).

Example 559

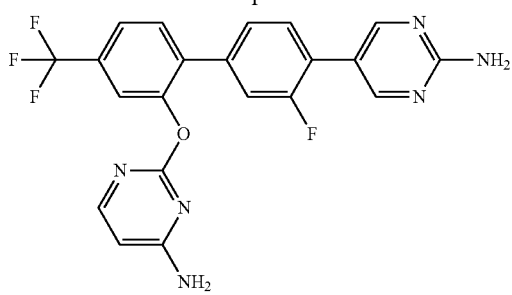

5-{2'-[(4-(Aminopyrimidin-2-yl)oxy]-3-fluoro-4'-(trifluoromethyl)biphenyl-4-yl}pyrimidin-2-amine The title compound was prepared in a manner similar to that described in Example 555 using 2-chloropyrimidin-4-amine and 4'-(2-aminopyrimidin-5-yl)-3'-fluoro-4-(trifluoromethyl)biphenyl-2-ol. MS (ESI): mass calcd. for $C_{21}H_{14}F_4N_6O$, 442.12; m/z found, 443.0 [M+H]$^+$. $^1$H NMR (500 MHz, CD$_3$OD) δ 8.46 (s, 2H), 7.80-7.74 (m, 1H), 7.74-7.67 (m, 1H), 7.67-7.62 (m, 1H), 7.52 (s, 1H), 7.51-7.44 (m, 1H), 7.44-7.31 (dd, J=17.9, 10.0, 2H), 6.20-6.08 (dd, J=6.0, 1.4, 1H).

Example 560

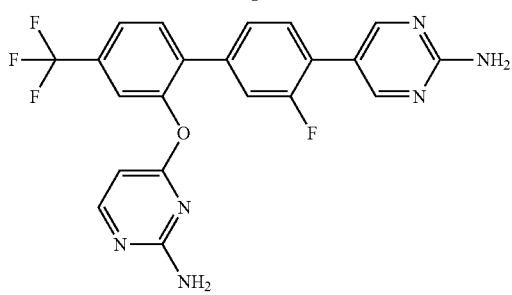

4-{[4'(2-Aminopyrimidin-5-yl)-3'-fluoro-4-(trifluoromethyl)biphenyl-2-yl]oxy}pyrimidin-2-amine The title compound was prepared in a manner similar to that described in Example 555 using 4-chloropyrimidin-2-amine and 4'-(2-aminopyrimidin-5-yl)-3'-fluoro-4-(trifluoromethyl)biphenyl-2-ol. MS (ESI): mass calcd. for $C_{21}H_{14}F_4N_6O$, 442.12; m/z found, 443.0 [M+H]$^+$. $^1$H NMR (500 MHz, CD$_3$OD) δ 8.51-8.43 (d, J=1.3, 2H), 8.06-7.94 (d, J=5.7, 1H), 7.72-7.69 (m, 1H), 7.69-7.66 (m, 1H), 7.55 (s, 1H), 7.52-7.47 (m, 1H), 7.39-7.31 (m, 2H), 6.31-6.03 (d, J=5.7, 1H).

Example 561

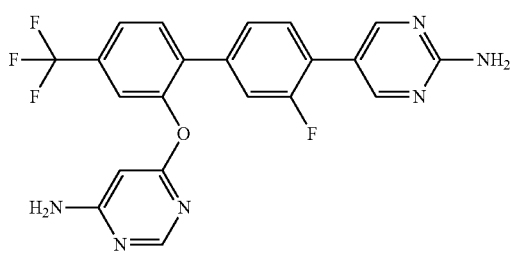

5-{2'-[(6-Aminopyrimidin-4-yl)-oxy]-3-fluoro-4'-(trifluoromethyl)biphenyl-4-yl}pyrimidin-2-amine The title compound was prepared in a manner similar to that described in Example 555 using 6-chloropyrimidin-4-amine and 4'-(2-aminopyrimidin-5-yl)-3'-fluoro-4-(trifluoromethyl)biphenyl-2-ol. MS (ESI): mass calcd. for $C_{21}H_{14}F_4N_6O$, 442.12; m/z found, 443.0 [M+H]$^+$. $^1$H NMR (400 MHz, CD$_3$OD) δ 8.60-8.54 (d, J=1.3, 2H), 8.11-8.07 (d, J=0.9, 1H), 7.82-7.69 (m, 2H), 7.60 (s, 1H), 7.59-7.52 (m, 1H), 7.47-7.36 (m, 2H), 5.95-5.88 (d, J=0.9, 1H).

Example 562

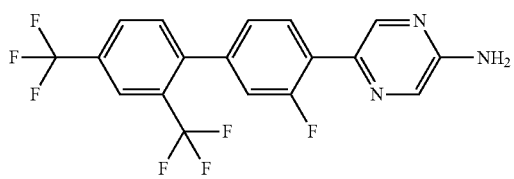

5-[3-Fluoro-2',4'-bis(trifluoromethyl)biphenyl-4-yl]pyrazin-2-amine

The title compound was prepared in a manner similar to that described in Example 88 using 1-((2-bromo-5-(trifluoromethyl)phenyl)sulfonyl)-4-methylpiperazine. MS (ESI): mass calcd. for $C_{18}H_{10}F_7N_3$, 401.08; m/z found, 402.0 [M+H]$^+$. $^1$H NMR (500 MHz, CD$_3$OD) δ 8.43-8.39 (m, 1H), 8.11-8.07 (m, 2H), 8.04-8.00 (d, J=8.2, 1H), 7.99-7.93 (m, 1H), 7.71-7.65 (d, J=8.0, 1H), 7.29-7.25 (d, J=8.2, 1H), 7.25-7.20 (d, J=11.6, 1H).

Example 563

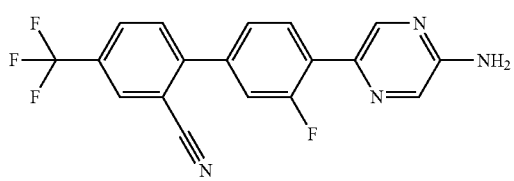

4'-(5-Aminopyrazin-2-yl)-3'-fluoro-4-(trifluoromethyl)biphenyl-2-carbonitrile

The title compound was prepared in a manner similar to that described in Example 88 using 2-bromo-5-(trifluoromethyl)benzonitrile. MS (ESI): mass calcd. for $C_{18}H_{10}F_4N_4$, 358.08; m/z found, 359.0 [M+H]$^+$. $^1$H NMR (500 MHz, CD$_3$OD) δ 8.45 (s, 1H), 8.23 (s, 1H), 8.11-8.08 (m, 1H), 8.08-8.03 (m, 2H), 7.91-7.84 (d, J=8.2, 1H), 7.58-7.49 (m, 2H).

Intermediate HW

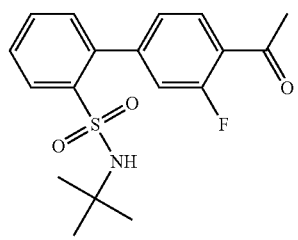

4'-Acetyl-N-tert-butyl-3'-fluorobiphenyl-2-sulfonamide

The title compound was prepared using conditions analogous to those described in Example 1 using (2-(N-(tert-butyl)sulfamoyl)phenyl)boronic acid and 1-(4-bromo-2-fluorophenyl)ethanone. $^1$H NMR (500 MHz, CDCl$_3$) δ 8.19 (dd, J=7.9, 1.3, 1H), 7.95 (m, 1H), 7.63-7.57 (m, 1H), 7.57-7.52 (m, 1H), 7.38-7.30 (m, 2H), 7.28 (dd, J=7.5, 1.3, 1H), 2.70 (d, J=4.9, 3H), 1.05 (m, 9H).

Intermediate HX

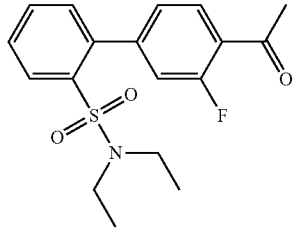

4'-Acetyl-N,N-diethyl-3'-fluorobiphenyl-2-sulfonamide

The title compound was prepared using conditions analogous to those described in Example 1 using (4-acetyl-3-fluorophenyl)boronic acid and 2-bromo-N,N-diethylbenzenesulfonamide. MS (ESI): mass calcd. for C$_{18}$H$_{20}$FNO$_3$S, 349.11; m/z found, 350.1 [M+H]$^+$. $^1$H NMR (500 MHz, CDCl$_3$) δ 8.05 (dd, J=7.9, 1.2, 1H), 7.92 (m, 1H), 7.61-7.56 (m, 1H), 7.55-7.49 (m, 1H), 7.29-7.27 (m, 2H), 7.25-7.24 (m, 1H), 2.95 (q, J=7.1, 4H), 2.69 (d, J=4.9, 3H), 1.01 (t, J=7.1, 6H).

Intermediate HY

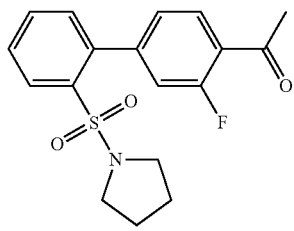

1-[3-Fluoro-2'-(pyrrolidin-1-ylsulfonyl)biphenyl-4-yl]ethanone

The title compound was prepared using conditions analogous to those described in Example 1 using (4-acetyl-3-fluorophenyl)boronic acid and 1-(2-bromo-phenylsulfonyl)pyrrolidine. MS (ESI): mass calcd. for C$_{18}$H$_{18}$FNO$_3$S, 347.10; m/z found, 348.0 [M+H]$^+$. $^1$H NMR (500 MHz, CDCl$_3$) δ 8.10 (dd, J=7.9, 1.3, 1H), 7.95-7.89 (m, 1H), 7.63-7.58 (m, 1H), 7.58-7.51 (m, 1H), 7.30-7.27 (m, 2H), 7.26-7.25 (m, 1H), 2.98-2.90 (m, 4H), 2.69 (d, J=4.9, 3H), 1.76-1.67 (m, 4H).

Example 564

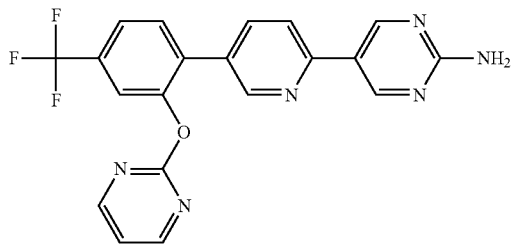

5-{5-[2-(Pyrimidin-2-yloxy)-4-(trifluoromethyl)phenyl]pyridin-2-yl}pyrimidin-2-amine The title compound was prepared in a manner similar to that described in Example 88 using 2-(2-bromo-5-(trifluoromethyl)phenoxy)pyrimidine and 5-(5-(4,4,5,5-tetramethyl-1,3,2-dioxaborolan-2-yl)pyridin-2-yl)pyrimidin-2-amine. MS (ESI): mass calcd. for C$_{20}$H$_{13}$F$_3$N$_6$O, 410.11; m/z found, 411.1 [M+H]$^+$. $^1$H NMR (400 MHz, CD$_3$OD) δ 8.98 (s, 2H), 8.73 (d, J=2.3, 1H), 8.50 (d, J=4.8, 2H), 8.04 (dd, J=8.3, 2.4, 1H), 7.85 (d, J=8.4, 1H), 7.81-7.72 (m, 2H), 7.66 (d, J=1.7, 1H), 7.13 (t, J=4.8, 1H).

Example 565

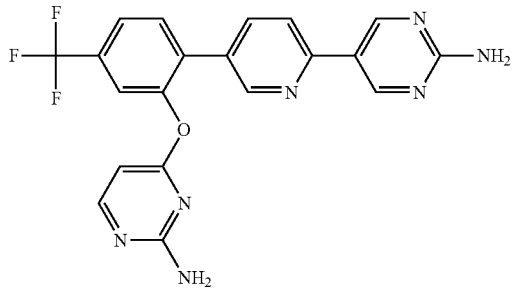

4-{2-[6-(2-Aminopyrimidin-5-yl)pyridin-3-yl]-5-(trifluoromethyl)phenoxy}pyrimidin-2-amine The title compound was prepared in a manner similar to that described in Example 88 using 4-(2-bromo-5-(trifluoromethyl)phenoxy)pyrimidin-2-amine and 5-(5-(4,4,5,5-tetramethyl-1,3,2-dioxaborolan-2-yl)pyridin-2-yl)pyrimidin-2-amine. MS (ESI): mass calcd. for C$_{20}$H$_{14}$F$_3$N$_7$O, 425.12; m/z found, 426.0 [M+H]$^+$. $^1$H NMR (400 MHz, CD$_3$OD) δ 8.89 (s, 2H), 8.67 (dd, J=2.3, 0.8, 1H), 7.99 (d, J=5.6, 1H), 7.95 (dd, J=8.3, 2.3, 1H), 7.81 (dd. J=8.2, 0.9, 1H), 7.76-7.69 (m, 2H), 7.59 (s, 1H), 6.18 (d. J=5.8, 1H).

Example 566

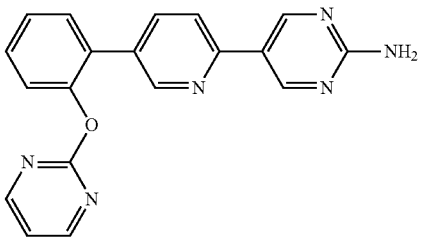

5-{5-[2-(Pyrimidin-2-yloxy)phenyl]pyridin-2-yl}pyrimidin-2-amine

The title compound was prepared in a manner similar to that described in Example 88 using 2-(2-bromophenoxy)

pyrimidine and 5-(5-(4,4,5,5-tetramethyl-1,3,2-dioxaborolan-2-yl)pyridin-2-yl)pyrimidin-2-amine. MS (ESI): mass calcd. for $C_{19}H_{14}N_6O$, 342.12; m/z found, 343.1 [M+H]$^+$. $^1$H NMR (400 MHz, CD$_3$OD) δ 8.97 (s, 2H), 8.70 (dd, J=2.3, 0.8, 1H), 8.48 (d, J=4.8, 2H), 8.06 (dd, J=8.3, 2.3, 1H), 7.85 (dd, J=8.3, 0.9, 1H), 7.58 (dd, J=7.6, 1.8, 1H), 7.56-7.50 (m, 1H), 7.48-7.41 (m, 1H), 7.30 (dd. J=8.0, 1.2, 1H), 7.10 (t, J=4.8, 1H).

Example 567

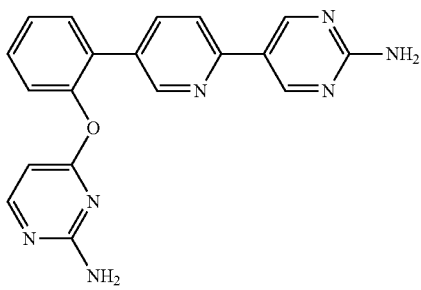

4-{2-[6-(2-Aminopyrimidin-5-yl)pyridin-3-yl]phenoxy}pyrimidin-2-amine

The title compound was prepared in a manner similar to that described in Example 88 using 4-(2-bromophenoxy)pyrimidin-2-amine and 5-(5-(4,4,5,5-tetramethyl-1,3,2-dioxaborolan-2-yl)pyridin-2-yl)pyrimidin-2-amine. MS (ESI): mass calcd. for $C_{19}H_{15}N_7O$, 357.13; m/z found, 358.1 [M+H]$^+$. $^1$H NMR (500 MHz, CD$_3$OD) δ 8.91 (s, 2H), 8.68-8.59 (m, 1H), 8.03 (dd, J=6.9, 0.9, 1H), 7.97-7.89 (m, 1H), 7.83 (d, J=8.3, 1H), 7.60-7.53 (m, 2H), 7.52-7.44 (m, 1H), 7.35 (d, J=7.9, 1H), 6.53 (dd, J=6.9, 0.9, 1H).

Example 568

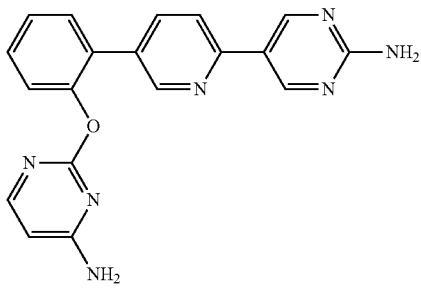

5-(5-{2-[(4-Aminopyrimidin-2-yl)oxy]phenyl}pyridin-2-yl)pyrimidin-2-amine

The title compound was prepared in a manner similar to that described in Example 88 using 2-(2-bromophenoxy)pyrimidin-4-amine and 5-(5-(4,4,5,5-tetramethyl-1,3,2-dioxaborolan-2-yl)pyridin-2-yl)pyrimidin-2-amine. MS (ESI): mass calcd. for $C_{19}H_5N_7O$, 357.13; m/z found, 358.0 [M+H]$^+$. $^1$H NMR (400 MHz, CD$_3$OD) δ 8.86 (s, 2H), 8.64 (dd, J=2.3, 0.8, 1H), 7.95 (dd, J=8.3, 2.3, 1H), 7.78-7.72 (m, 2H), 7.53-7.45 (m, 2H), 7.38 (m, 1H), 7.23 (dd, J=8.1, 1.2, 1H), 6.11 (d, J=5.9, 1H).

Example 569

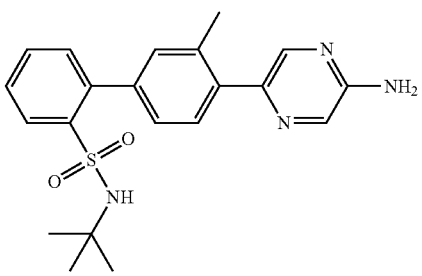

4'-(5-Aminopyrazin-2-yl)-N-tert-butyl-3'-methylbiphenyl-2-sulfonamide

The title compound was prepared in a manner similar to that described in Example 571 using (4-bromo-2-methylphenyl)boronic acid in Step A. MS (ESI): mass calcd. for $C_{21}H_{24}N_4O_2S$, 396.16; m/z found, 397.2 [M+H]$^+$. $^1$H NMR (500 MHz, CDCl$_3$) δ 8.21-8.17 (dd, J=8.0, 1.3, 1H), 8.13-8.07 (m, 2H), 7.61-7.54 (m, 1H), 7.52-7.47 (m, 1H), 7.47-7.39 (m, 3H), 7.36-7.31 (dd, J=7.5, 1.4, 1H), 4.82 (s, 2H), 4.16-4.09 (m, 1H), 2.41 (s, 3H), 1.05 (s, 9H).

Example 570

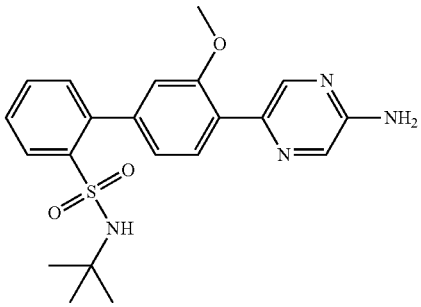

4'-(5-Aminopyrazin-2-yl)-N-tert-butyl-3'-methoxybiphenyl-2-sulfonamide

The title compound was prepared in a manner similar to that described in Example 571 using (4-bromo-2-methoxyphenyl)boronic acid in Step A. MS (ESI): mass calcd. for $C_{21}H_{24}N_4O_3S$, 412.16; m/z found, 413.3 [M+H]$^+$. $^1$H NMR (500 MHz, CD$_3$OD) δ 8.51-8.45 (d, J=1.6, 1H), 8.21-8.16 (d, J=1.5, 1H), 8.16-8.11 (dd, J=8.0, 1.3, 1H), 7.84-7.78 (d, J=7.9, 1H), 7.67-7.61 (m, 1H), 7.58-7.54 (m, 1H), 7.45-7.38 (dd, J=7.6, 1.4, 1H), 7.32-7.25 (d, J=1.6, 1H), 7.15-7.09 (dd, J=7.9, 1.6, 1H), 3.92 (s, 3H), 1.04 (s, 9H).

Example 571

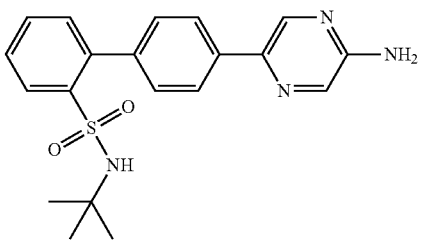

4'-(5-Aminopyrazin-2-yl)-N-tert-butylbiphenyl-2-sulfonamide

Step A: 5-(4-Bromophenyl)pyrazin-2-amine (4-Bromophenyl)boronic acid (100 mg, 0.498 mmol) and 5-bromopyrazin-2-amine (173 mg, 0.996 mmol) were added to a 5 mL sealable vial equipped with a stir bar. To this vial was added toluene (1.5 mL), ethanol (1.5 mL) and K$_2$CO$_3$ (0.7 mL, 2 M). The solvent was sparged with argon for 10 min before adding Pd(PPh$_3$)$_4$ (17 mg, 0.004 mmol), the vial sealed and the mixture stirred at 50° Celsius for 15 hours. The reaction was cooled to rt and then diluted with ethyl acetate (50 mL) and water (50 mL) and the layers separated. The aqueous layer was further extracted with ethyl acetate (3×50 mL). The combined organic extracts were dried with Na$_2$SO$_4$ and concentrated to dryness. The crude material was purified FCC to give 5-(4-bromophenyl)pyrazin-2-amine. $^1$H NMR (500 MHz, CDCl$_3$) δ 8.52-8.31 (d, J=1.5, 1H), 8.08-7.95 (d, J=1.6, 1H), 7.86-7.71 (d, J=8.4, 2H), 7.63-7.49 (d, J=8.6, 2H), 4.70 (s, 2H).

Step B: 4'-(5-Aminopyrazin-2-yl)-N-tert-butylbiphenyl-2-sulfonamide

To a 5 mL sealable vial equipped with a stir bar were added 5-(4-bromophenyl)pyrazin-2-amine (40 mg, 0.16 mmol), (2-(N-(tert-butyl)sulfamoyl)phenyl)-boronic acid (62 mg, 0.24 mmol), K$_2$CO$_3$ (66 mg, 0.48 mmol) and Pd(dppf)Cl$_2$.CH$_2$Cl$_2$ (12 mg, 0.016 mmol). The vial was then sealed, evacuated, backfilled with argon and charged with argon sparged DMSO (0.64 mL). The vial was heated at 70° Celsius for 15 hours. The reaction mixture was cooled to rt diluted with ethyl acetate (2 mL) and water (2 mL), the layers separated and the aqueous layer further extracted with ethyl acetate (3×10 mL). The combined organic extracts were then dried with Na$_2$SO$_4$ and concentrated to dryness. The crude product was purified by HPLC to give the title compound. MS (ESI): mass calcd. for C$_{20}$H$_{22}$N$_4$O$_2$S, 382.15; m/z found, 383.1 [M+H]$^+$. $^1$H NMR (400 MHz, CDCl$_3$) δ 8.48-8.39 (d, J=1.5, 1H), 8.23-8.18 (dd, J=8.0, 1.4, 1H), 8.18-8.15 (d, J=1.4, 1H), 7.99-7.95 (d, J=8.4, 1H), 7.65-7.61 (m, 2H), 7.61-7.55 (m, 1H), 7.55-7.46 (m, 1H), 7.38-7.31 (dd, J=7.5, 1.4, 1H), 3.70 (s, 1H), 1.25 (s, 1H), 1.03 (s, 9H).

Example 572

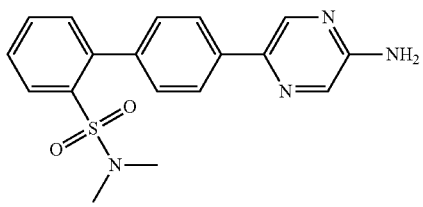

4'-(5-Aminopyrazin-2-yl)-N,N-dimethylbiphenyl-2-sulfonamide

The title compound was prepared in a manner similar to that described in Example 571 using (2-(N,N-dimethylsulfamoyl)phenyl)boronic acid in Step B. MS (ESI): mass calcd. for C$_{18}$H$_{18}$N$_4$O$_2$S, 354.12; m/z found, 355.2 [M+H]$^+$. $^1$H NMR (400 MHz, CD$_3$OD) δ 8.60-8.32 (d, J=1.5, 1H), 8.09-8.05 (dd, J=8.0, 1.4, 1H), 8.05-8.02 (d, J=1.5, 1H), 7.95-7.86 (m, 2H), 7.72-7.62 (m, 1H), 7.61-7.53 (m, 1H), 7.48-7.41 (m, 2H), 7.41-7.35 (dd, J=7.6, 1.4, 1H), 2.40 (s, 6H).

Example 573

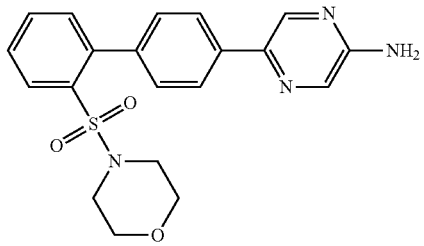

5-[2'-(Morpholin-4-ylsulfonyl)biphenyl-4-yl]pyrazin-2-amine

The title compound was prepared in a manner similar to that described in Example 571 using (2-(morpholinosulfonyl)phenyl)boronic acid in in Step B. MS (ESI): mass calcd. for C$_{20}$H$_{20}$N$_4$O$_3$S, 396.13; m/z found, 397.2 [M+H]$^+$. $^1$H NMR (500 MHz, DMSO-d$_6$) δ 8.60-8.55 (d, J=1.4, 1H), 8.05-8.00 (dd, J=8.0, 1.3, 1H), 8.00-7.94 (m, 3H), 7.78-7.73 (m, 1H), 7.69-7.62 (m, 1H), 7.49-7.39 (m, 3H), 6.61 (s, 2H), 2.76-2.68 (t. J=4.7, 3H).

Example 574

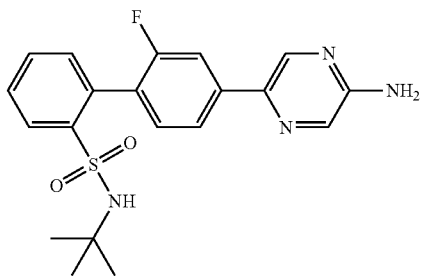

4'-(5-Aminopyrazin-2-yl)-N-tert-butyl-2'-fluorobiphenyl-2-sulfonamide

The title compound was prepared in a manner similar to that described in Example 571 using (4-bromo-3-fluorophenyl)boronic acid in Step A. MS (ESI): mass calcd. for C$_{20}$H$_{21}$FN$_4$O$_2$S, 400.14; m/z found, 401.1 [M+H]$^+$. $^1$H NMR (500 MHz, CD$_3$OD) δ 8.50-8.43 (d, J=1.5, 1H), 8.18-8.12 (dd, J=8.0, 1.4, 1H), 8.05-8.02 (d, J=1.5, 1H), 7.74-7.67 (m, 2H), 7.66-7.61 (m, 1H), 7.60-7.53 (m, 1H), 7.47-7.39 (m, 1H), 7.39-7.32 (dd, J=7.5, 1.5, 1H), 1.11 (s, 9H).

Example 575

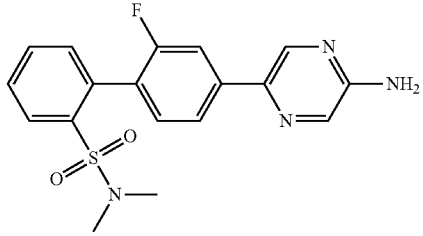

4'-(5-Aminopyrazin-2-yl)-2'-fluoro-N,N-dimethylbiphenyl-2-sulfonamide

The title compound was prepared in a manner similar to that described in Example 571 using (4-bromo-3-fluorophenyl)boronic acid in Step A and using (2-(N,N-dimethylsulfamoyl)phenyl)boronic acid in Step B. MS (ESI): mass calcd. for $C_{18}H_{17}FN_4O_2S$, 372.11; m/z found, 373.2 [M+H]$^+$. $^1$H NMR (500 MHz, CD$_3$OD) δ 8.51-8.41 (d, J=1.5, 1H), 8.10-8.06 (dd, J=8.0, 1.4, 1H), 8.06-8.02 (d, J=1.5, 1H), 7.75-7.67 (m, 3H), 7.67-7.59 (m, 1H), 7.43-7.39 (m, 1H), 7.39-7.34 (m, 1H), 2.49 (s, 6H).

The title

Example 576

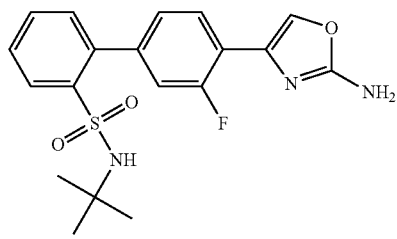

4'-(2-Amino-1,3-oxazol-4-yl)-N-tert-butyl-3'-fluorobiphenyl-2-sulfonamide

Step A: 4-(4-Bromo-2-fluorophenyl)oxazol-2-amine

A solution of 2-bromo-1-(4-bromo-2-fluorophenyl)ethanone (53 mg, 0.18 mmol) and urea (10.6 mg, 0.18 mmol) in CH$_3$CN (0.7 mL) was heated at 80° Celsius for 18 hours. The mixture was cooled to rt and made basic with NaOH (2 N). The resulting solution was extracted with EtOAc and the extract was dried (Na$_2$SO$_4$), filtered, and concentrated to dryness. The residue was purified using FCC to give 4-(4-bromo-2-fluorophenyl)oxazol-2-amine (37 mg, 82%). MS (ESI): mass calcd. for $C_9H_6BrFN_2O$, 255.96; m/z found, 257.1 [M+H]$^+$. $^1$H NMR (500 MHz, CDCl$_3$) δ 7.78 (m, 1H), 7.58 (d, J=4.3, 1H), 7.36-7.32 (m, 1H), 7.28 (dd, J=10.5, 1.9, 1H), 4.60 (s, 2H).

Step B

The title compound was prepared using methods described in Example 427 using 4-(4-bromo-2-fluorophenyl)oxazol-2-amine and (2-(N-(tert-butyl)sulfamoyl)phenyl)boronic acid. MS (ESI): mass calcd. for $C_{19}H_{20}FN_3O_3S$, 389.12; m/z found, 390.2 [M+H]$^+$. $^1$H NMR (500 MHz, CDCl$_3$) δ 8.18 (dd, J=7.9, 1.4, 1H), 7.98 (m, 1H), 7.66 (d, J=4.2, 1H), 7.57 (m, 1H), 7.54-7.48 (m, 1H), 7.38-7.30 (m, 3H), 4.63 (s, 2H), 3.64 (s, 1H), 1.03 (s, 9H).

Example 577

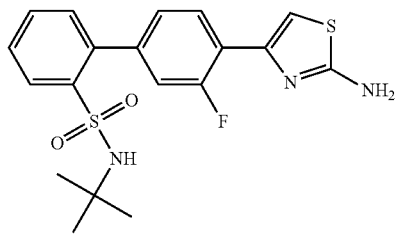

4'-(2-Amino-1,3-thiazol-4-yl)-N-tert-butyl-3'-fluorobiphenyl-2-sulfonamide

A solution of 4'-acetyl-N-tert-butyl-3'-fluorobiphenyl-2-sulfonamide (100 mg, 0.29 mmol), iodine (94.6 mg, 0.37 mmol), thiourea (44.01, 0.57 mmol) in EtOH (1.1 mL) was heated at 100 Celcius for 48 h. The reaction mixture was cooled to rt and the precipitate collected by filtration thus providing the title compound. MS (ESI): mass calcd. for $C_{19}H_{20}FN_3O_2S_2$, 405.10; m/z found, 406.2 [M+H]$^+$. $^1$H NMR (500 MHz, CDCl$_3$) δ 8.71 (s, 2H), 8.19 (d, J=7.9, 1H), 7.94 (m, 1H), 7.59 (m, 1H), 7.54 (dd, J=11.6, 3.8, 1H), 7.44 (dd, J=12.1, 1.6, 1H), 7.38 (dd, J=8.1, 1.7, 1H), 7.33 (dd, J=7.5, 1.3, 1H), 6.96 (d, J=1.3, 1H), 1.08 (s, 9H).

Example 578

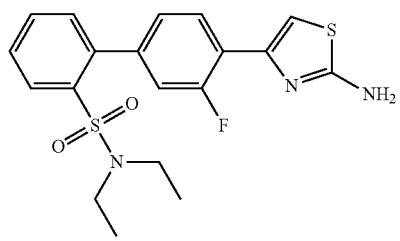

4'-(2-Amino-1,3-thiazol-4-yl)-N,N-diethyl-3'-fluorobiphenyl-2-sulfonamide

The title compound was prepared using methods analogous to those described in Example 577 using 4'-acetyl-N,N-diethyl-3'-fluorobiphenyl-2-sulfonamide. MS (ESI): mass calcd. for $C_{19}H_{20}FN_3O_2S_2$, 405.10; m/z found, 406.1 [M+H]$^+$. $^1$H NMR (500 MHz, CDCl$_3$) δ 8.64 (s, 2H), 8.06 (dd, J=7.9, 1.2, 1H), 7.93 (m, 1H), 7.59 (td, J=7.5, 1.4, 1H), 7.52 (m, 1H), 7.39-7.28 (m, 3H), 6.95 (d, J=1.1, 1H), 2.97 (q, J=7.2, 4H), 1.02 (t, J=7.1, 6H).

Example 579

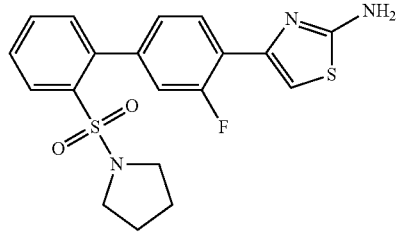

4-[3-Fluoro-2'-(pyrrolidin-1-ylsulfonyl)biphenyl-4-yl]-1,3-thiazol-2-amine

The title compound was prepared using methods analogous to those described in Example 577 using 1-[3-fluoro-2'-(pyrrolidin-1-ylsulfonyl)biphenyl-4-yl]ethanone. MS (ESI): mass calcd. for $C_{19}H_{18}FN_3O_2S_2$, 403.08; m/z found, 404.0 [M+H]$^+$. $^1$H NMR (500 MHz, CDCl$_3$) δ 8.11 (d, J=6.7, 1H), 7.91 (m, 1H), 7.61 (td, J=7.5, 1.4, 1H), 7.54 (m, 1H), 7.41-7.28 (m, 3H), 6.94 (d, J=1.2, 1H), 2.95 (t, J=6.7, 4H), 1.85-1.64 (m, 4H).

Example 580

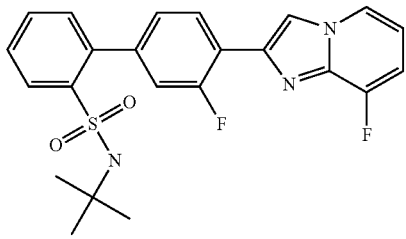

N-tert-Butyl-3'-fluoro-4'-(8-fluoroimidazo[1,2-a]pyridin-2-yl)biphenyl-2-sulfonamide The title compound was prepared using methods analogous to those described in Example 577 using 3-fluoropyridin-2-amine. MS (ESI): mass calcd. for $C_{23}H_{21}F_2N_3O_2S$, 441.13; m/z found, 442.2 [M+H]$^+$. $^1$H NMR (500 MHz, CDCl$_3$) δ 8.60-8.51 (m, 1H), 8.51-8.45 (m, 2H), 8.20 (d, J=6.6, 1H), 7.68-7.53 (m, 3H), 7.53-7.48 (m, 2H), 7.38 (d, J=7.6, 2H), 1.16-1.08 (m, 9H).

Example 581

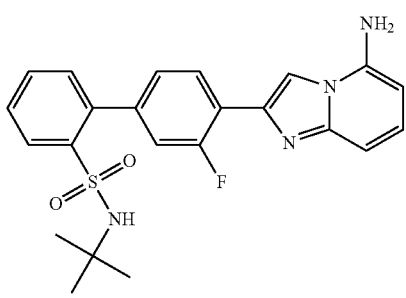

4'-(5-Aminoimidazo[1,2-a]pyridin-2-yl)-N-tert-butyl-3'-fluorobiphenyl-2-sulfonamide The title compound was prepared using methods analogous to those described in Example 577 using pyridine-2,3-diamine. MS (ESI): mass calcd. for $C_{23}H_{23}FN_4O_2S$, 438.15; m/z found, 439.2 [M+H]$^+$. $^1$H NMR (500 MHz, CDCl$_3$) δ 8.19-8.11 (m, 2H), 7.99-7.95 (m, 1H), 7.61 (dd, J=8.1, 6.8, 1H), 7.55 (m, 1H), 7.38-7.32 (m, 3H), 7.20-7.12 (m, 2H), 6.36 (d, J=8.5, 1H), 1.13 (s, 9H).

Example 582

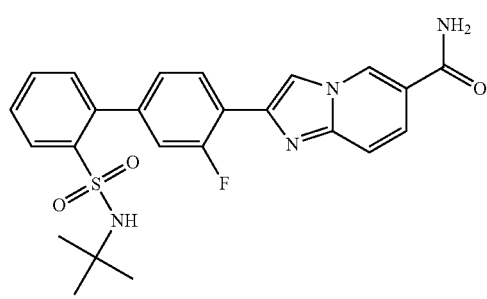

2-[2'-(tert-Butylsulfamoyl)-3-fluorobiphenyl-4-yl]imidazo[1,2-a]pyridine-6-carboxamide The title compound was prepared using methods analogous to those described in Example 577 using 6-aminonicotinamide. MS (ESI): mass calcd. for $C_{24}H_{23}FN_4O_3S$, 466.15; m/z found, 467.2 [M+H]$^+$. $^1$H NMR (500 MHz, CDCl$_3$) δ 8.91 (s, 1H), 8.24 (d, J=6.5, 1H), 8.14-8.03 (m, 2H), 7.93-7.84 (m, 2H), 7.64-7.52 (m, 3H), 7.49-7.42 (m, 1H), 7.35 (d, J=11.7, 1H), 6.49-6.40 (m, 1H), 1.28-1.20 (m, 9H).

Example 583

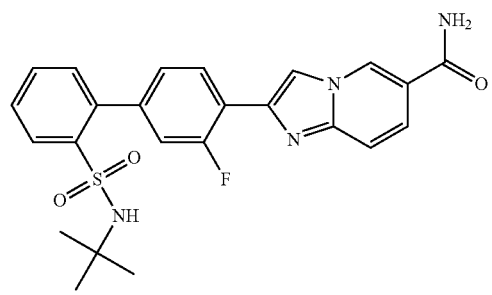

2-[2'-(tert-Butylsulfamoyl)-3-fluorobiphenyl-4-yl]imidazo[1,2-a]pyridine-6-carboxamide The title compound was prepared using methods analogous to those described in Example 577 using 6-aminonicotinamide. MS (ESI): mass calcd. for $C_{24}H_{23}FN_4O_3S$, 466.15; m/z found, 467.2 [M+H]$^+$. $^1$H NMR (500 MHz, CDCl$_3$) δ 8.91 (s, 1H), 8.24 (d, J=6.5, 1H), 8.14-8.03 (m, 2H), 7.93-7.84 (m, 2H), 7.64-7.52 (m, 3H), 7.49-7.42 (m, 1H), 7.35 (d, J=11.7, 1H), 6.49-6.40 (m, 1H), 1.28-1.20 (m, 9H).

Example 584

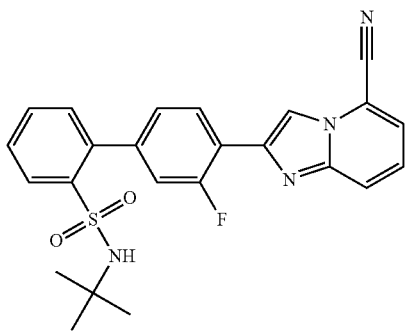

N-tert-Butyl-4'-(5-cyanoimidazo[1,2-a]pyridin-2-yl)-3'-fluorobiphenyl-2-sulfonamide The title compound was prepared using methods analogous to those described in Example 577 using 2-amino-4-cyanopyridine. MS (ESI): mass calcd. for $C_{24}H_{21}FN_4O_2S$, 448.14; m/z found, 449.2 [M+H]$^+$. $^1$H NMR (500 MHz, CDCl$_3$) δ 8.38-8.33 (m, 2H), 8.32-8.25 (m, 2H), 8.20 (dd, J=8.0, 1.2, 1H), 7.61 (m, 1H), 7.54 (td, J=7.8, 1.4, 1H), 7.51-7.45 (m, 1H), 7.42 (dd, J=8.0, 1.7, 1H), 7.35 (dd, J=7.5, 1.3, 1H), 7.16 (dd, J=7.0, 1.6, 1H), 1.07 (s, 9H).

Example 585

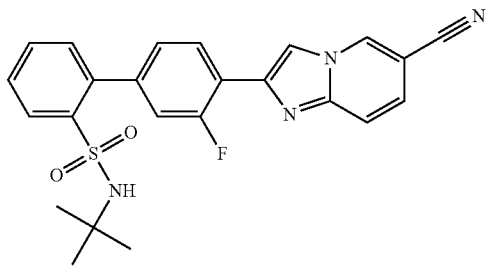

N-tert-Butyl-4'-(6-cyanoimidazo[1,2-a]pyridin-2-yl)-3'-fluorobiphenyl-2-sulfonamide The title compound was prepared using methods analogous to those described in Example 577 using 2-amino-5-cyanopyridine. MS (ESI): mass calcd. for $C_{24}H_{21}FN_4O_2S$, 448.14; m/z found, 449.2 [M+H]$^+$. $^1$H NMR (500 MHz, CDCl$_3$) δ 8.70 (s, 1H), 8.28 (m, 1H), 8.25-8.19 (m, 2H), 8.14 (d, J=9.4, 1H), 7.61 (m, 1H), 7.58-7.52 (m, 2H), 7.51-7.47 (m, 1H), 7.43 (dd, J=8.0, 1.7, 1H), 7.35 (dd, J=7.5, 1.3, 1H), 1.07 (s, 9H).

Example 586

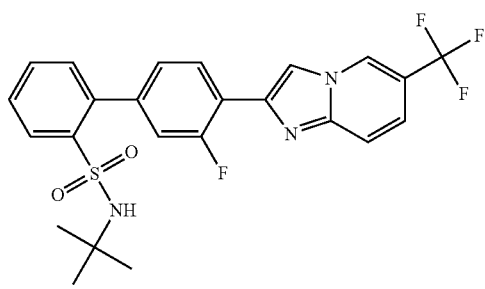

N-tert-Butyl-3'-fluoro-4'-[6-(trifluoromethyl)imidazo[1,2-a]pyridin-2-yl]biphenyl-2-sulfonamide The title compound was prepared using methods analogous to those described in Example 577 using 2-amino-5-(trifluoromethyl)pyridine. MS (ESI): mass calcd. for $C_{24}H_{21}F_4N_3O_2S$, 491.13; m/z found, 492.2 [M+H]$^+$. $^1$H NMR (500 MHz, CDCl$_3$) δ 8.68 (s, 1H), 8.31 (dd, J=16.6, 8.7, 2H), 8.25 (d, J=2.8, 1H), 8.20 (dd, J=8.0, 1.2, 1H), 7.72-7.66 (m, 1H), 7.65-7.59 (m, 1H), 7.59-7.49 (m, 2H), 7.43 (dd, J=8.0, 1.7, 1H), 7.35 (dd, J=7.5, 1.2, 1H), 1.05 (m, 9H).

Example 587

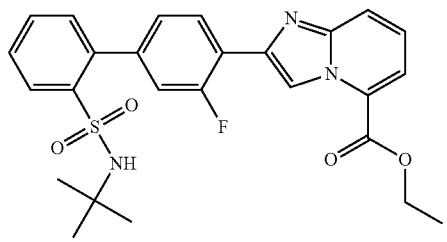

Ethyl 2-[2'-(tert-butylsulfamoyl)-3-fluorobiphenyl-4-yl]imidazol[1,2-a]pyridine-5-carboxylate The title compound was prepared using methods analogous to those described in Example 577 using 2-aminonicotinic acid. The ethyl ester was formed as a result of carrying out the reaction in EtOH. MS (ESI): mass calcd. for $C_{26}H_{26}FN_3O_4S$, 495.16; m/z found, 496.3 [M+H]$^+$. $^1$H NMR (500 MHz, CDCl$_3$) δ 8.62-8.55 (m, 1H), 8.36 (d, J=6.5, 1H), 8.23-8.18 (m, 2H), 8.01 (d, J=7.3, 1H), 7.62-7.55 (m, 1H), 7.55-7.49 (m, 1H), 7.44-7.33 (m, 3H), 6.91 (m, 1H), 4.54 (dd, J=14.2, 7.1, 2H), 1.51 (t, J=7.2, 3H), 1.03 (s, 9H).

Example 588

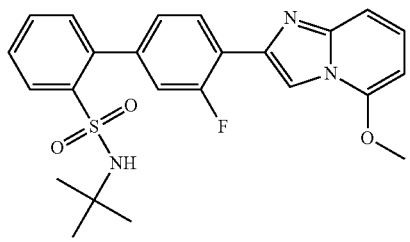

N-tert-Butyl-3'-fluoro-4'-(5-methoxyimidazo[1,2-a]pyridin-2-yl)biphenyl-2-sulfonamide Step A: 2-(4-Bromo-2-fluorophenyl)-5-methoxyimidazo[1,2-a]pyridine A solution of 2-bromo-1-(4-bromo-2-fluorophenyl)ethanone (100 mg, 0.34 mmol) and 2-amino-3-methoxypyridine (42 mg, 0.34 mmol) in EtOH (0.8 mL) was heated at 90° Celsius for 24 hours. The reaction mixture was cooled to rt and diluted with water. The resultant precipitate was collected by filtration to provide 2-(4-bromo-2-fluorophenyl)-5-methoxyimidazo[1,2-a]pyridine (35 mg, 32%) which was used without further purification.

Step B

The title compound was prepared using methods analogous to those described in Example 88 using 2-(4-bromo-2-fluorophenyl)-5-methoxyimidazo[1,2-a]pyridine and 2-(tert-butylamino)sulfonylphenylboronic acid. MS (ESI): mass calcd. for $C_{24}H_{24}FN_3O_3S$, 453.15; m/z found, 454.4 [M+H]$^+$. $^1$H NMR (500 MHz, CDCl$_3$) δ 8.58 (m, 1H), 8.19 (dd, J=8.0, 1.4, 1H), 8.10 (d, J=3.9, 1H), 7.81 (dd, J=6.7, 0.9, 1H), 7.60-7.55 (m, 1H), 7.54-7.48 (m, 1H), 7.43 (dd, J=12.1, 1.7, 1H), 7.38-7.32 (m, 2H), 6.73 (dd, J=7.6, 6.7, 1H), 6.50 (d, J=7.6, 1H), 4.07 (s, 3H), 3.68 (s, 1H), 1.02 (s, 9H).

Intermediate HZ

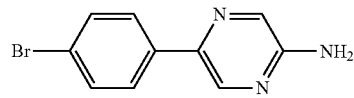

5-(4-Bromophenyl)pyrazin-2-amine

5-Bromopyrazin-2-amine (173 mg, 0.99 mmol) and (4-bromophenyl)boronic acid (100 mg, 0.490 mmol) were placed in a sealable vial followed by toluene (1.5 mL), ethanol (1.5 mL), and K₂CO₃ (0.7 mL, 2 M). The resultant mixture was then sparged with argon for 10 minutes before adding tetrakis(triphenylphosphine)palladium(0) (17 mg, 0.15 mmol), and heating at 50° Celsius. Reaction progress was monitored by LCMS. Once the reaction was complete, the reaction mixture was cooled to rt, diluted with EtOAc, filtered through Celite, and the resultant filtrate concentrated to dryness. The crude product was purified by FCC to provide the title compound. $^1$H NMR (500 MHz, CDCl₃) δ 8.52-8.31 (d, J=1.5, 1H), 8.08-7.95 (d, J=1.6, 1H), 7.86-7.71 (d, J=8.4, 2H), 7.63-7.49 (d, J=8.6, 2H), 4.81-4.61 (s, 2H).

Intermediate IA

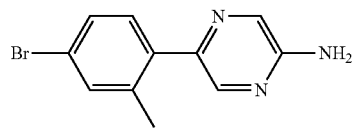

5-(4-Bromo-2-methylphenyl)pyrazin-2-amine

The title compound was prepared in a manner similar to that described for Intermediate HZ using (4-bromo-2-methylphenyl)boronic acid. $^1$H NMR (500 MHz, CD₃OD) δ 8.01-7.97 (m, 2H), 7.47 (dd, J=1.9, 0.9, 1H), 7.43-7.38 (m, 1H), 7.23 (d, J=8.2, 1H), 2.31 (s, 3H).

Intermediate IB

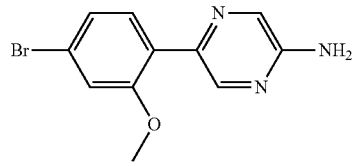

5-(4-Bromo-2-methoxyphenyl)pyrazin-2-amine

The title compound was prepared in a manner similar to that described Intermediate HZ using (4-bromo-2-methoxyphenyl)boronic acid.

Example 589

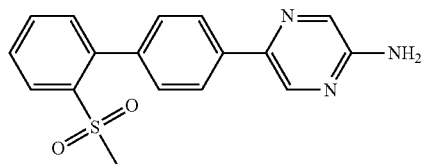

5-[2'-(Methylsulfonyl)biphenyl-4-yl]pyrazin-2-amine.

5-(4-Bromophenyl)pyrazin-2-amine (51 mg, 0.20 mmol), (2-(methylsulfonyl)phenyl) boronic acid (61 mg, 0.31 mmol), K₂CO₃ (85 mg, 0.61 mmol) and Pd(dppf)Cl₂·CH₂Cl₂ (15 mg, 0.020 mmol) were weighed into a sealable vial containing a stir-bar. The vial was sealed and evacuated before backfilling with argon and adding deoxygenated DMSO (0.8 mL). The vial was heated at 70° Celsius for 3 hours by which point the starting material had been consumed. The vial was cooler to rt, diluted with MeOH (1 mL), filtered with a syringe filter, and the filtrate subjected to HPLC purification to provide the title compound. MS (ESI): mass calcd. for C₁₇H₁₅N₃O₂S, 325.39; m/z found, 326.1 [M+H]⁺. $^1$H NMR (400 MHz, CDCl₃) δ 8.32 (dd, J=8.1, 1.4, 2H), 8.26 (dd, J=8.0, 1.4, 1H), 8.00-7.90 (m, 2H), 7.74-7.64 (m, 1H), 7.64-7.56 (m, 3H), 7.41 (dd, J=7.5, 1.4, 1H), 2.70 (s, 3H).

Example 590

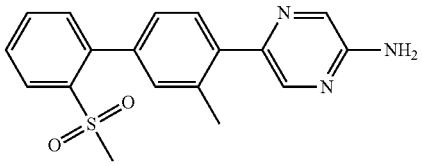

5-[3-Methyl-2'-(methylsulfonyl)biphenyl-4-yl]pyrazin-2-amine.

The title compound was prepared in a manner similar to that described in Example 589 using 5-(4-bromo-2-methylphenyl)pyrazin-2-amine. MS (ESI): mass calcd. for C₁₈H₁₇N₃O₂S, 339.42; m/z found, 340.2 [M+H]⁺. $^1$H NMR (500 MHz, CDCl₃) δ 8.25 (dd, J=8.0, 1.4, 1H), 8.20 (d, J=1.5, 1H), 8.11 (d, J=1.6, 1H), 7.70-7.63 (m, 1H), 7.60-7.54 (m, 1H), 7.49-7.45 (m, 1H), 7.43-7.36 (m, 3H), 4.75 (s, 2H), 2.71 (s, 3H), 2.45 (s, 3H).

Example 591

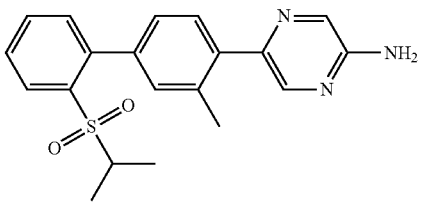

4'-(5-Aminopyrazin-2-yl)-N,N,3'-trimethylbiphenyl-2-sulfonamide.

The title compound was prepared in a manner similar to that described in Example 589 using 5-(4-bromo-2-methylphenyl)pyrazin-2-amine and (2-(N,N-dimethylsulfamoyl)phenyl)boronic acid. MS (ESI): mass calcd. for C₁₉H₂₀N₄O₂S, 368.46; m/z found, 369.1 [M+H]⁺. $^1$H NMR (500 MHz, CDCl₃) δ 8.16 (d, J=1.5, 1H), 8.12 (dd, J=8.0, 1.3, 1H), 8.10 (d, J=1.5, 1H), 7.60-7.55 (m, 1H), 7.52-7.47 (m, 1H), 7.43 (d, J=7.8, 1H), 7.35-7.29 (m, 3H), 4.77 (s, 2H), 2.44 (s, 3H), 2.42 (s, 6H).

Example 592

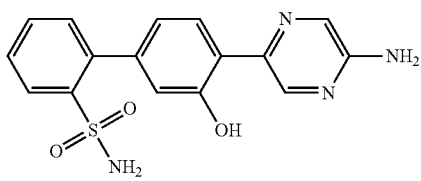

4'-(5-Aminopyrazin-2-yl)-3'-hydroxybiphenyl-2-sulfonamide.

The title compound was prepared in a manner similar to that described in Example 589 using (2-(N-(tert-butyl)sulfamoyl)phenyl)boronic acid and 5-(4-bromo-2-methoxyphenyl)pyrazin-2-amine. After the coupling, the tert-butyl group and methyl group were removed by treating a solution consisting of 4'-(5-aminopyrazin-2-yl)-N-(tert-butyl)-3'-methoxy-[1,1'-biphenyl]-2-sulfonamide (48 mg, 0.12 mmol) and DCM (2 mL), with BBr$_3$ (0.14 mL, 1 M in DCM) at −78° Celsius. The reaction mixture was warmed to room temperature. After the starting material was consumed the reaction mixture was poured into saturated NH$_4$Cl (10 mL) and extracted with DCM (3×10 mL). The combined organic extracts were dried with sodium sulfate, filtered, and concentrated to dryness. The resultant residue was subjected to HPLC purification to provide the title compound. MS (ESI): mass calcd. for C$_{16}$H$_{14}$N$_4$O$_3$S, 342.38; m/z found, 343.2 [M+H]$^+$. $^1$H NMR (500 MHz, CDCl$_3$) δ 8.71 (s, 1H), 8.18 (dd, J=7.9, 1.4, 1H), 7.93 (d, J=1.4, 1H), 7.80 (d, J=8.2, 1H), 7.64-7.57 (m, 1H), 7.57-7.48 (m, 1H), 7.39 (dd, J=7.6, 1.3, 1H), 7.12 (dd, J=8.1, 1.9, 1H), 7.09-7.03 (m, 1H), 4.38 (s, 2H).

Example 593

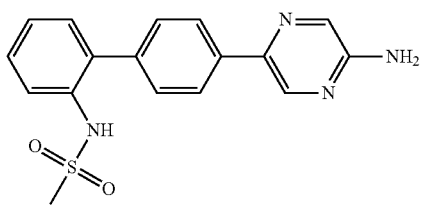

N-[4'-(5-Aminopyrazin-2-yl)biphenyl-2-yl]methaneslfonamide.

The title compound was prepared in a manner similar to that described in Example 589 using (2-(methylsulfonamido)phenyl)boronic acid. MS (ESI): mass calcd. for C$_{17}$H$_{16}$N$_4$O$_2$S, 340.41; m/z found, 341.1 [M+H]$^+$. $^1$H NMR (500 MHz, CDCl$_3$) δ 8.38 (d, J=1.4, 1H), 8.26 (d, J=1.5, 1H), 8.03-7.94 (m, 2H), 7.67 (dd, J=8.2, 1.1, 1H), 7.46 (d, J=8.3, 2H), 7.45-7.40 (m, 1H), 7.33-7.29 (m, 1H), 7.26-7.23 (m, 1H), 6.49 (s, 1H), 2.93 (s, 3H).

Example 594

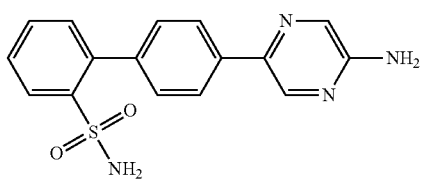

4'-(5-Aminopyrazin-2-yl)biphenyl-2-sulfonamide.

The title compound was prepared in a manner similar to that described in Example 589 using (2-sulfamoylphenyl)boronic acid. MS (ESI): mass calcd. for C$_{16}$H$_{14}$N$_4$O$_2$S, 326.38; m/z found, 327.1 [M+H]$^+$. $^1$H NMR (500 MHz, CD$_3$OD) δ 8.40 (d. J=1.5, 1H), 8.22 (d, J=1.4, 1H), 8.13 (dd, J=8.0, 1.3, 1H), 7.93 (d, J=8.3, 2H), 7.67-7.59 (m, 1H), 7.59-7.50 (m, 3H), 7.37 (dd, J=7.6, 1.4, 1H).

Example 595

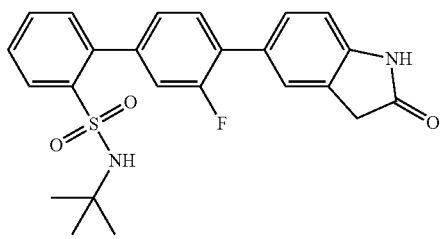

N-tert-Butyl-3'-fluoro-4'-(2-oxo-2,3-dihydro-1H-indol-5-yl)biphenyl-2-sulfonamide.

The title compound was prepared in a manner similar to that described in Example 427 using 5-bromoindolin-2-one. MS (ESI): mass calcd. for C$_{24}$H$_{23}$FN$_2$O$_3$S, 438.52; m/z found, 439.2 [M+H]$^+$. $^1$H NMR (500 MHz, CDCl$_3$) δ 8.20 (dd, J=7.9, 1.4, 1H), 8.09 (s, 1H), 7.63-7.56 (m, 1H), 7.56-7.50 (m, 1H), 7.50-7.41 (m, 3H), 7.39-7.36 (m, 1H), 7.35 (dd, J=7.6, 1.4, 1H), 7.32 (dd, J=11.4, 1.8, 1H), 6.97 (d, J=7.9, 1H), 3.90 (s, 1H), 3.61 (s, 2H), 1.08 (s, 9H).

Example 596

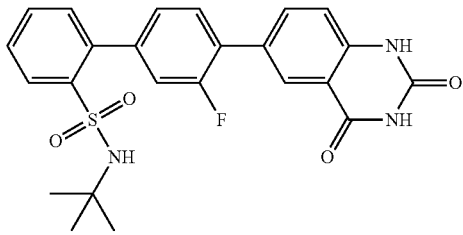

N-tert-Butyl-4'-(2,4-dioxo-1,2,3,4-tetrahydroquinazolin-6-yl)-3'-fluorobiphenyl-2-sulfonamide.

The title compound was prepared in a manner similar to that described in Example 427 using 6-bromoquinazoline-2,4(1H, 3H)-dione. MS (ESI): mass calcd. for C$_{24}$H$_{22}$FN$_3$O$_4$S, 467.52; m/z found, 468.2 [M+H]$^+$. $^1$H NMR (500 MHz, CD$_3$OD) δ 8.30-8.21 (m, 1H), 8.14 (dd, J=8.1, 1.4, 1H), 7.97-7.88 (m, 1H), 7.68-7.62 (m, 1H), 7.62-7.52 (m, 2H), 7.40 (dd, J=7.6, 1.4, 1H), 7.36 (s, 1H), 7.35-7.32 (m, 1H), 7.29 (d, J=8.5, 1H), 1.08 (s, 9H).

Example 597

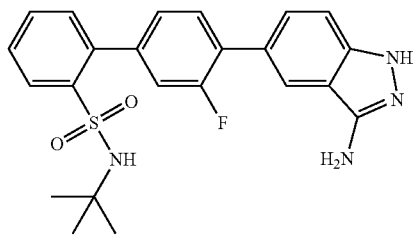

4'-(3-Amino-1H-inadazol-5-yl)-N-tert-butyl-3'-fluorobiphenyl-2-sulfonamide.

The title compound was prepared in a manner similar to that described in Example 427 using 5-bromo-1H-indazol-3-amine. MS (ESI): mass calcd. for C$_{23}$H$_{23}$FN$_4$O$_2$S, 438.53; m/z found, 439.1 [M+H]$^+$. $^1$H NMR (500 MHz, CD$_3$OD) δ 8.15 (dd, J=8.0, 1.3, 1H), 8.11 (s, 1H), 7.80 (d, J=8.6, 1H), 7.69-7.63 (m, 1H), 7.63-7.55 (m, 2H), 7.49 (dd, J=8.8, 0.9, 1H), 7.40 (dd, J=7.6, 1.4, 1H), 7.37-7.35 (m, 1H), 7.34 (dd, J=6.0, 1.6, 1H), 1.10 (s, 9H).

Example 598

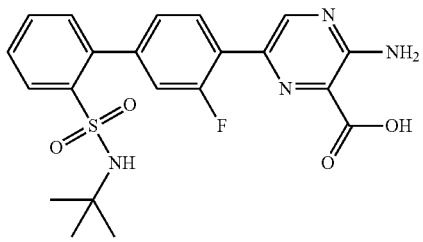

3-Amino-6-[2'-(tert-butylsulfamoyl)-3-fluorobiphenyl-4-yl] pyrazine-2-carboxylic acid.

The title compound was prepared in a manner similar to that described in Example 427 using 3-amino-6-bromopyrazine-2-carboxylic acid. MS (ESI): mass calcd. for C$_{21}$H$_{21}$FN$_4$O$_4$S, 444.49; m/z found, 445.0 [M+H]$^+$. $^1$H NMR (500 MHz, CD$_3$OD) δ 8.50 (s, 1H), 8.13 (dd, J=8.0, 1.3, 1H), 7.89 (s, 1H), 7.65 (td, J=7.5, 1.4, 1H), 7.56 (td, J=7.8, 1.4, 1H), 7.43 (d, J=7.4, 1H), 7.37-7.22 (m, 2H), 1.07 (s, 8H).

Intermediate IC

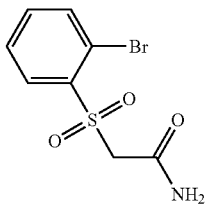

2-((2-Bromophenyl)sulfonyl)acetamide

Step A: 2-((2-Bromophenyl)thio)acetamide

To a 20 mL vial were added a stir-bar 2-chloroacetamide (783 mg, 8.37 mmol) 2-bromothiophenol (1.00 mL, 8.32 mmol) N,N-diisopropylethyl amine (1.5 ml, 8.7 mmol), and dry THF (5 mL). The reaction mixture was stirred for 4 days before concentrating and subjecting the crude product to FCC to afford the title compound. $^1$H NMR (600 MHz, DMSO-d$_6$) δ 7.65 (s, 1H), 7.60 (dd, J=7.9, 1.4, 1H), 7.41-7.30 (m, 2H), 7.25 (s, 1H), 7.13-7.06 (m, 1H), 3.69 (s, 2H).

Step B: 2-((2-Bromophenyl)sulfonyl)acetamide

To a 40 mL vial were added 2-((2-bromophenyl)thio) acetamide (1.00 g, 4.06 mmol), Oxone (7.51 g, 12.2 mmol), methanol (12 mL) and water (15 mL). The reaction mixture was stirred for 21 hours at which point it was diluted with ethyl acetate (25 mL) and washed with aqueous Na$_2$S$_2$O$_3$ (25 mL). The organic and water layers were separated and the aqueous phase further extracted with ethyl acetate (3×25 mL). The combined organic extracts were dried over magnesium sulfate, filtered, and concentrated to dryness. The crude product was subjected to FCC to provide the title compound. $^1$H NMR (600 MHz, DMSO-d$_6$) δ 8.04-7.95 (m, 1H), 7.93-7.87 (m, 1H), 7.72 (s, 1H), 7.68-7.60 (m, 2H), 7.39 (s, 1H), 4.41 (s, 2H).

Intermediate ID

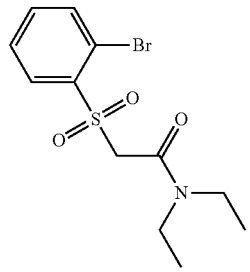

2-((2-Bromophenyl)sulfonyl)-N,N-diethylacetamide

The title compound was prepared in a manner similar to that described for 2-((2-bromophenyl)sulfonyl)acetamide using 2-chloro-N,N-diethylacetamide in Step A. $^1$H NMR (600 MHz, DMSO-d$_6$) δ 8.01-7.97 (m, 1H), 7.91-7.87 (m, 1H), 7.66-7.60 (m, 2H), 4.75 (s, 2H), 3.47-3.39 (q, J=7.1, 2H), 3.25-3.14 (q, J=7.0, 2H), 1.18-1.09 (t, J=7.1, 3H), 0.99-0.87 (t, J=7.0, 3H).

Intermediate 1E

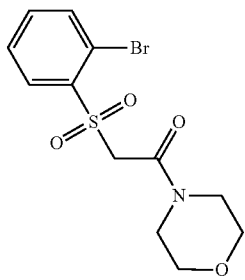

2-((2-Bromophenyl)sulfonyl)-1-morpholinoethanone

The title compound was prepared in a manner similar to that described for 2-((2-bromophenyl)sulfonyl)acetamide using 2-chloro-1-morpholinoethanone in Step A. $^1$H NMR (600 MHz, DMSO-d$_6$) δ 8.06-8.01 (m, 1H), 7.93-7.88 (m, 1H), 7.68-7.60 (m, 2H), 4.84 (s, 2H), 3.63-3.55 (m, 4H), 3.53-3.48 (dd, J=5.6, 4.0, 2H), 3.42-3.37 (d, J=5.2, 2H).

Example 599

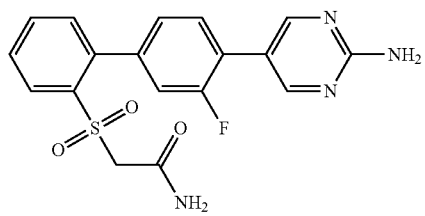

2-{[4'-(2-Aminopyrimidin-5-yl)-3'-fluorobiphenyl-2-yl]sulfonyl}acetamide.

The title compound was prepared using analogous conditions to those described in Example 6 utilizing 5-(2-fluoro-4-(4,4,5,5-tetramethyl-1,3,2-dioxaborolan-2-yl)phenyl)pyrimidin-2-amine and 2-((2-bromophenyl)sulfonyl)acetamide. MS (ESI): mass calcd. for C$_{18}$H$_{15}$FN$_4$O$_3$S, 386.41; m/z found, 387.1 [M+H]$^+$. $^1$H NMR (500 MHz, CD$_3$OD) δ 8.55 (d, J=1.4, 2H), 8.15 (dd, J=7.9, 1.2, 1H), 7.80-7.72 (m, 1H), 7.69-7.61 (m, 1H), 7.59-7.53 (m, 1H), 7.43 (dd, J=7.5, 1.3, 1H), 7.39-7.30 (m, 2H).

Example 600

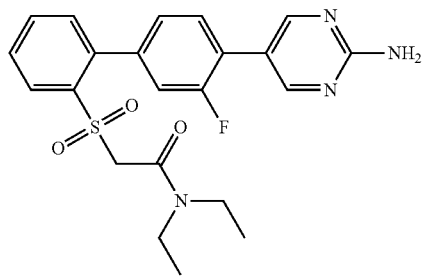

2-{[4'-(2-Aminopyrimidin-5-yl)-3'-fluorobiphenyl-2-yl]sulfonyl}-N,N-diethylacetamide.

The title compound was prepared using analogous conditions to those described in Example 6 utilizing 5-(2-fluoro-4-(4,4,5,5-tetramethyl-1,3,2-dioxaborolan-2-yl)phenyl)pyrimidin-2-amine and 2-((2-bromophenyl)sulfonyl)-N,N-diethylacetamide. MS (ESI): mass calcd. for C$_{22}$H$_{23}$FN$_4$O$_3$S, 442.52; m/z found, 443.1 [M+H]$^+$. $^1$H NMR (500 MHz, CD$_3$OD) δ 8.55 (d, J=1.4, 2H), 8.13 (dd, J=8.0, 1.3, 1H), 7.81-7.73 (m, 1H), 7.71-7.63 (m, 1H), 7.62-7.55 (m, 1H), 7.44 (dd, J=7.6, 1.3, 1H), 7.39 (dd, J=4.5, 1.7, 1H), 7.37 (dd, J=8.0, 1.3, 1H), 3.29-3.27 (m, 4H), 1.07 (t, J=7.2, 3H), 1.04 (t, J=7.2, 3H).

Example 601

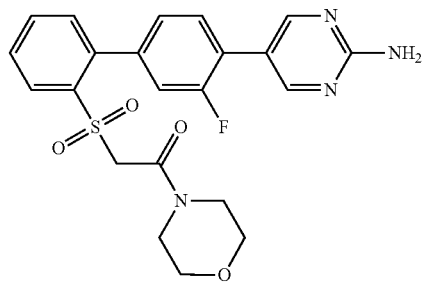

5-{3-Fluoro-2''-[(2-morpholin-4-yl-2-oxoethyl)sulfonyl]biphenyl-4-yl}pyrimidin-2-amine.

The title compound was prepared using analogous conditions to those described in Example 6 utilizing 5-(2-fluoro-4-(4,4,5,5-tetramethyl-1,3,2-dioxaborolan-2-yl)phenyl)pyrimidin-2-amine and 2-((2-bromophenyl)sulfonyl)-1-morpholinoethanone. MS (ESI): mass calcd. for C$_{22}$H$_{21}$FN$_4$O$_4$S, 456.5; m/z found, 457.0 [M+H]$^+$. $^1$H NMR (500 MHz, CD$_3$OD) δ 8.55 (d, J=1.4, 2H), 8.15 (dd, J=7.7, 1.3, 1H), 7.83-7.72 (m, 1H), 7.72-7.63 (m, 1H), 7.58 (dd, J=8.5, 7.7, 1H), 7.45 (dd, J=7.2, 1.2, 1H), 7.42-7.31 (m, 2H), 3.67-3.55 (m, 4H), 3.48 (t, J=4.8, 2H), 3.39 (t, J=4.8, 2H).

Example 602

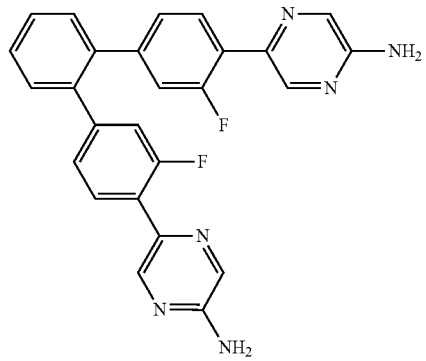

5,5'-(3,3''-Difluoro-1,1':2',1''-terphenyl-4,4''-diyl)dipyrazin-2-amine.

The title compound was prepared using analogous conditions to those described in Example 6 utilizing 1-bromo-2-iodobenzene. MS (ESI): mass calcd. for C$_{26}$H$_{18}$F$_2$N$_6$, 452.47; m/z found, 453.0 [M+H]$^+$. $^1$H NMR (500 MHz, CD₃OD) δ 8.35-8.30 (m, 2H), 8.02 (d, J=1.6, 2H), 7.78-7.70 (m, 2H), 7.49 (s, 4H), 7.07 (dd, J=8.1, 1.7, 2H), 7.04 (dd, J=12.4, 1.7, 2H).

Example 603

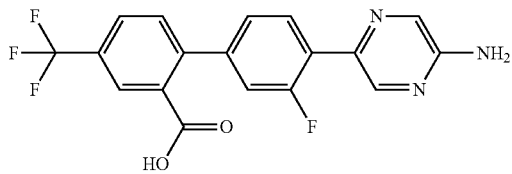

4'-(5-Aminopyrazin-2-yl)-3'-fluoro-4-(trifluoromethyl)biphenyl-2-carboxylic acid.

The title compound was prepared using analogous conditions to those described in Example 6 utilizing 2-bromo-5-(trifluoromethyl)benzoic acid. MS (ESI): mass calcd. for $C_{18}H_{11}F_4N_3O_2$, 377.3; m/z found, 378.0 [M+H]⁺. ¹H NMR (500 MHz, CD₃OD) δ 8.39 (s, 1H), 8.13 (s, 1H), 8.10 (s, 1H), 8.00-7.84 (m, 2H), 7.65 (d, J=8.0, 1H), 7.28 (d, J=8.1, 1H), 7.24 (d, J=12.6, 1H).

Example 604

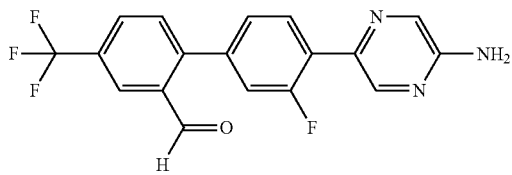

4'-(5-Aminopyrazin-2-yl)-3'-fluoro-4-(trifluoromethyl)biphenyl-2-carbaldehyde.

The title compound was prepared using analogous conditions to those described in Example 6 utilizing 2-bromo-5-(trifluoromethyl)benzaldehyde. MS (ESI): mass calcd. for $C_{18}H_{11}F_4N_3O$, 361.3; m/z found, 362.1 [M+H]⁺. The title compound can exist as either the aldehyde or the hydrate (gem-diol). Hydrate: ¹H NMR (400 MHz, CD₃OD) δ 8.39 (s, 1H), 8.15 (d, J=1.5, 1H), 8.10-8.02 (m, 2H), 7.70 (d, J=7.7, 1H), 7.49 (d, J=8.0, 1H), 7.36-7.27 (m, 2H), 5.47 (s, 1H). Aldehyde: ¹H NMR (400 MHz, CD₃OD) δ 10.04 (s, 1H), 8.43 (s, 1H), 8.39 (s, 1H), 8.26 (s, 1H), 8.02-7.94 (m, 2H), 7.77 (d, J=8.2, 1H), 7.44-7.36 (m, 2H).

Intermediate IF

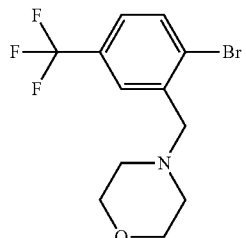

4-(2-Bromo-5-(trifluoromethyl)benzyl)morpholine

2-Bromo-5-(trifluoromethyl)benzaldehyde (266 mg, 1.05 mmol) and morpholine (0.10 mL, 1.2 mmol) were dissolved in DCM (2 mL), stirred for 20 minutes, and then treated with NaBH₄ (79 mg, 2.1 mmol). The reaction was stirred overnight at rt, after which time, the reaction was quenched by the slow addition of water (10 mL). The aqueous layer was further extracted with DCM (3×10 mL), dried over sodium sulfate, filtered, and concentrated to dryness. The crude product was purified by FCC to provide the title compound. ¹H NMR (500 MHz, CDCl₃) δ 7.77 (s, 1H), 7.67 (d, J=8.3, 1H), 7.37 (d, J=8.3, 1H), 3.80-3.69 (m, 4H), 3.63 (d, J=1.7, 2H), 2.59-2.49 (m, 4H).

Intermediate IG

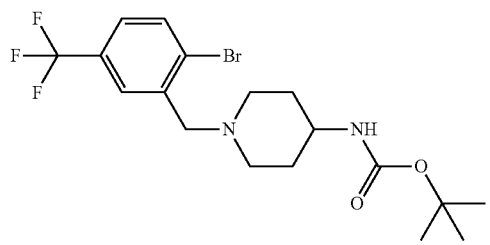

tert-Butyl (1-2-bromo-5-(trifluoromethyl)benzyl)piperidin-4-yl)carbamate

The title compound was prepared using analogous conditions to those described in Intermediate IF utilizing tert-butyl piperidin-4-ylcarbamate. ¹H NMR (500 MHz, CDCl₃) δ 7.82 (s, 1H), 7.71-7.59 (m, 1H), 7.41 (d, J=8.3, 1H), 4.80 (s, 2H) 4.44 (s, 1H), 3.52 (s, 1H), 3.14-2.89 (m, 2H), 2.65 (t, J=12.0, 2H), 1.93 (d, J=12.0, 2H), 1.45 (s, 9H), 1.36-1.16 (m, 2H).

Example 605

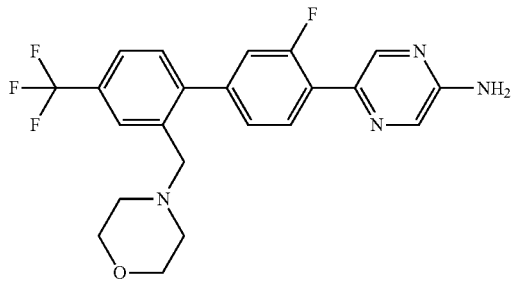

5-[3-Fluoro-2'-(2-morpholin-4-ylmethyl)-4'-(trifluoromethyl)biphenyl-4-yl]pyrazin-2-amine.

The title compound was prepared using analogous conditions to those described in Example 6 utilizing 4-(2-bromo-5-(trifluoromethyl)benzyl)morpholine. MS (ESI): mass calcd. for $C_{22}H_{20}F_4N_4O$, 432.42; m/z found, 433.0 [M+H]⁺. ¹H NMR (400 MHz, MeOD) δ 8.43 (s, 1H), 8.21-8.11 (m, 2H), 8.11-8.04 (m, 1H), 7.90 (dd, J=8.2, 1.8, 1H), 7.67 (d, J=8.1, 1H), 7.40-7.27 (m, 2H), 4.54 (s, 2H), 3.78 (s, 4H), 3.07 (s, 4H).

Example 606

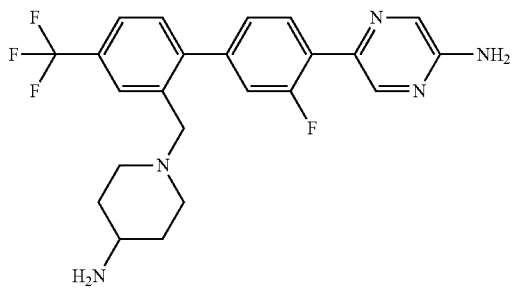

5-{2'-[(4-Aminopiperidin-1-yl)methyl]-3-fluoro-4'-(trifluoromethyl)biphenyl-4-yl}pyrazin-2-amine.

The title compound was prepared using analogous conditions to those described in Example 6 utilizing tert-butyl (1-(2-bromo-5-(trifluoromethyl)benzyl)piperidin-4-yl)carbamate, followed by removal of the Boc group.

Removal of Boc group: To a stirred solution of tert-butyl (1-((4'-(5-aminopyrazin-2-yl)-3'-fluoro-4-(trifluoromethyl)-[1,1'-biphenyl]-2-yl)methyl)piperidin-4-yl)carbamate (83 mg, 0.15 mmol) in DCM (2.4 mL) was added TFA (0.64 mL, 8.4 mmol) at room temperature. When the reaction had gone to completion, as followed by LCMS, the stir-bar was removed and the reaction mixture concentrated to dryness and the resultant residue subjected to HPLC purification to provide the title compound. MS (ESI): mass calcd. for $C_{23}H_{23}F_4N_5$, 445.47; m/z found, 446.1 [M+H]$^+$. $^1$H NMR (500 MHz, CD$_3$OD) δ 8.44-8.40 (m, 1H), 8.13 (d, J=1.5, 1H), 8.10-8.08 (m, 1H), 8.08-8.03 (m, 1H), 7.87 (d, J=8.2, 1H), 7.65 (d, J=8.1, 1H), 7.35 (dd, J=11.8, 1.7, 1H), 7.31 (dd, J=8.0, 1.7, 1H), 4.41 (s, 2H), 3.42-3.35 (m, 2H), 3.29-3.26 (m, 1H), 2.82-2.69 (m, 2H), 2.14-2.06 (m, 2H), 1.87-1.72 (m, 2H).

Example 607

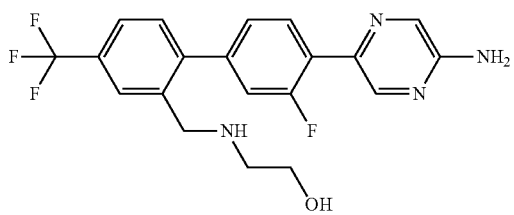

2-({[4'-[(5-Aminopiperidin-2-yl)-3'-fluoro-4-(trifluoromethyl)biphenyl-2-yl]methyl}amino)ethanol.

The title compound was prepared using analogous conditions to those described in Intermediate IF using 4'-(5-Aminopyrazin-2-yl)-3'-fluoro-4-(trifluoromethyl)biphenyl-2-carboxylic acid and ethanolamine. MS (ESI): mass calcd. for $C_{20}H_{18}F_4N_4O$, 406.39; m/z found, 407.1 [M+H]$^+$. $^1$H NMR (400 MHz, CD$_3$OD) δ 8.41 (s, 1H), 8.18 (s, 1H), 8.12-8.01 (m, 2H), 7.86 (dd, J=8.1, 1.7, 1H), 7.65 (d, J=8.1, 1H), 7.34 (dd, J=3.5, 1.6, 1H), 7.33-7.31 (m, 1H), 4.38 (s, 2H), 3.78-3.63 (m, 2H), 3.09-3.00 (m, 2H).

Intermediate IH

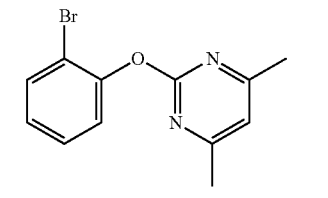

2-(2-Bromophenoxy)-4,6-dimethylpyrimidine

The title compound was prepared in a manner similar to that described for Intermediate HI using 2-chloro-4,6-dimethylpyrimidine. $^1$H NMR (400 MHz, DMSO-d$_6$) δ 7.72 (dd, J=8.0, 1.4, 1H), 7.48-7.41 (m, 1H), 7.31 (dd, J=8.0, 1.6, 1H), 7.25-7.19 (m, 1H), 7.02 (s, 1H), 2.32 (s, 6H).

Intermediate ZZ

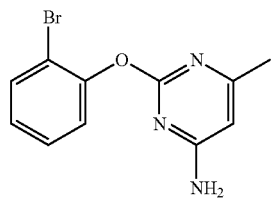

2-(2-Bromophenoxy)-6-methylpyrimidin-4-amine

The title compound was prepared in a manner similar to that described for Intermediate HI using 2-chloro-6-methylpyrimidin-4-amine. $^1$H NMR (400 MHz, DMSO-d$_6$) δ 7.63 (dd, J=8.0, 1.6, 1H), 7.40-7.34 (m, 1H), 7.21 (dd, J=8.0, 1.6, 1H), 7.15-7.09 (m, 1H), 6.83 (s, 2H), 5.99 (s, 1H), 2.07 (s, 3H).

Intermediate II

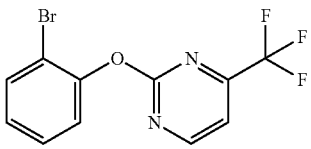

2-(2-Bromophenoxy)-4-(trifluoromethyl)pyrimidine

The title compound was prepared in a manner similar to that described for Intermediate HI using 2-chloro-4-(trifluoromethyl)pyrimidine. $^1$H NMR (400 MHz, DMSO-d) δ 9.03 (d, J=4.9, 1H), 7.86-7.73 (m, 2H), 7.55-7.42 (m, 2H), 7.32-7.24 (m, 1H).

Intermediate IJ

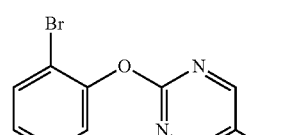

2-(2-bromophenoxy)pyrimidin-5-amine

The title compound was prepared in a manner similar to that described for Intermediate HI using 2-chloropyrimidin- 5-amine. $^1$H NMR (400 MHz, DMSO-$d_6$) δ d 7.98-7.94 (m, 2H), 7.71-7.66 (m, 1H), 7.45-7.37 (m, 1H), 7.24-7.20 (m, 1H), 7.17-7.12 (m, 1H), 5.22 (s, 2H).

Intermediate IK

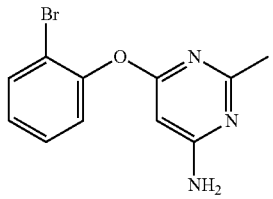

6-(2-Bromophenoxy)-2-methylpyrimidin-4-amine

The title compound was prepared in a manner similar to that described for Intermediate HI using 6-chloro-2-methylpyrimidin-4-amine. $^1$H NMR (400 MHz, DMSO-$d_6$) δ 7.64 (dd, J=8.3, 1.5, 1H), 7.47-7.33 (m, 1H), 7.17 (ddd, J=7.2, 3.8, 1.3, 2H), 6.54 (s, 2H), 5.46 (s, 1H), 2.14 (s, 3H).

Intermediate IL

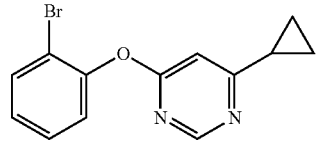

4-(2-Bromophenoxy)-6-cyclopropylpyrimidine

The title compound was prepared in a manner similar to that described for Intermediate HI using 4-chloro-6-cyclopropylpyrimidine. $^1$H NMR (400 MHz, DMSO-$d_6$) δ 8.48 (s, 1H), 7.81-7.64 (m, 1H), 7.47-7.41 (m, 1H), 7.36-7.28 (m, 1H), 7.26-7.21 (m, 1H), 7.14-7.09 (m, 1H), 2.16-2.08 (m, 1H), 1.06-0.99 (m, 4H).

Intermediate IM

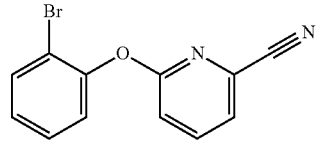

6-(2-Bromophenoxy)picolinonitrile

The title compound was prepared in a manner similar to that described for Intermediate HI using 6-chloropicolinonitrile. $^1$H NMR (400 MHz, DMSO-$d_6$) δ 8.13 (dd, J=8.5, 7.3, 1H), 7.82 (dd, J=7.3, 0.7, 1H), 7.77 (dd, J=8.0, 1.5, 1H), 7.53-7.47 (m, 2H), 7.38 (dd, J=8.1, 1.6, 1H), 7.32-7.25 (m, 1H).

Intermediate IN

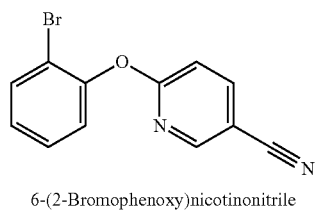 [SMILES: N#Cc1ccc(Oc2ccccc2Br)nc1]

6-(2-Bromophenoxy)nicotinonitrile

The title compound was prepared in a manner similar to that described for Intermediate HI using 6-chloronicotinonitrile. $^1$H NMR (400 MHz, DMSO-$d_6$) δ 8.71-8.56 (m, 1H), 8.39-8.34 (m, 1H), 7.78-7.74 (m, 1H), 7.51-7.46 (m, 1H), 7.39-7.33 (m, 2H), 7.30-7.24 (m, 1H).

Intermediate IO

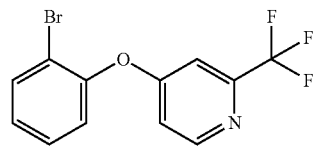

4-(2-Bromophenoxy)-2-(trifluoromethyl)pyrimidine

The title compound was prepared in a manner similar to that described for Intermediate HI using 4-chloro-2-(trifluoromethyl)pyridine. $^1$H NMR (400 MHz, DMSO-$d_6$) δ 8.60 (d, J=5.7, 1H), 7.80 (dd, J=8.0, 1.5, 1H), 7.55-7.48 (m, 1H), 7.43-7.36 (m, 2H), 7.31 (m 1H), 7.03 (dd, J=5.7, 2.4, 1H).

Intermediate IP

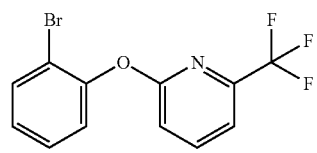

2-(2-Bromophenoxy)-6-(trifluoromethyl)pyridine

The title compound was prepared in a manner similar to that described for Intermediate HI using 2-chloro-6-(trifluoromethyl)pyridine. $^1$H NMR (400 MHz, DMSO-$d_6$) 8.18-8.12 (m, 1H), 7.80-7.74 (m, 1H), 7.65 (d, J=7.4, 1H), 7.51-7.46 (m, 1H), 7.40-7.35 (m, 2H), 7.29-7.24 (m, 1H).

Intermediate IQ

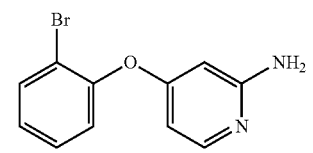

4-(2-Bromophenoxy)pyridin-2-amine

The title compound was prepared in a manner similar to that described for Intermediate HI using 4-chloropyridin-2-amine. $^1$H NMR (400 MHz, DMSO-d$_6$) δ 8.14 (s, 1H), 7.82-7.72 (m, 2H), 7.50-7.41 (m, 1H), 7.29-7.18 (m, 2H), 6.11 (dd, J=5.9, 2.3, 1H), 6.02 (s, 2H), 5.73 (d, J=2.3, 1H).

Intermediate IR

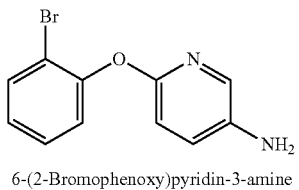 [SMILES: Nc1ccc(Oc2ccccc2Br)nc1]

6-(2-Bromophenoxy)pyridin-3-amine

The title compound was prepared in a manner similar to that described for Intermediate HI using 6-chloropyridin-3-amine. $^1$H NMR (400 MHz, DMSO-d) δ 7.63 (dd, J=8.0, 1.6, 1H), 7.40-7.34 (m, 1H), 7.21 (dd, J=8.0, 1.6, 1H), 7.15-7.09 (m, 1H), 6.83 (s, 2H), 5.99 (s, 1H), 2.07 (s, 3H).

Example 608

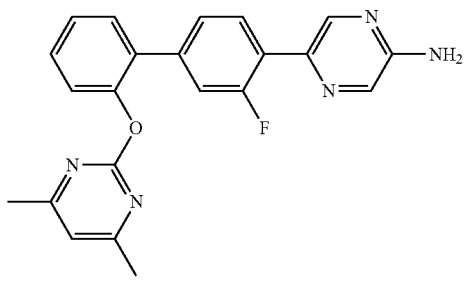

5-{2'-[(4,6-Dimethylpyrimidin-2-yl)oxy]-3-fluorobiphenyl-4-yl}pyrazin-2-amine.

The title compound was prepared in a manner similar to that described in Example 88 using 2-(2-bromophenoxy)-4,6-dimethylpyrimidine. MS (ESI): mass calcd. for C$_{22}$H$_{18}$FN$_5$O, 387.15; m/z found, 388.1 [M+H]$^+$. $^1$H NMR (400 MHz, DMSO-d$_6$) δ 8.28 (s, 1H), 7.96 (s, 1H), 7.78 (m, 1H), 7.50 (d, J=7.6, 1H), 7.42 (m 1H), 7.35-7.23 (m, 3H), 7.19 (d, J=7.8, 1H), 6.88 (s, 1H), 6.66 (s, 2H), 2.22 (s, 6H).

Example 609

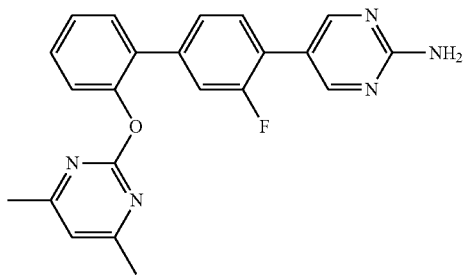

5-{2'-[(4,6-Dimethylpyrimidin-2-yl)oxy]-3-fluorobiphenyl-4-yl}pyrimidin-2-amine.

The title compound was prepared in a manner similar to that described in Example 88 using 2-(2-bromophenoxy)-4,6-dimethylpyrimidine and 5-(2-fluoro-4-(4,4,5,5-tetramethyl-1,3,2-dioxaborolan-2-yl)phenyl)pyrimidin-2-amine. MS (ESI): mass calcd. for C$_{22}$H$_{18}$FN$_5$O, 387.15; m/z found, 388.1 [M+H]$^+$. $^1$H NMR (400 MHz, DMSO-d$_6$) δ d 8.40 (s, 2H), 7.52-7.46 (m, 2H), 7.44-7.39 (m, 1H), 7.35-7.25 (m, 3H), 7.18 (d, J=8.0, 1H), 6.90 (s, 1H), 6.85 (s, 2H), 2.24 (s, 6H).

Example 610

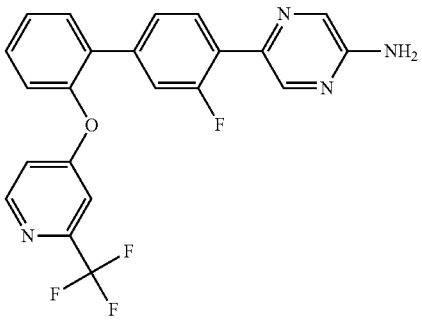

5-(3-Fluoro-2'-{[2-(trifluoromethyl)pyridin-4-yl]oxy}biphenyl-4-yl)pyrazin-2-amine.

The title compound was prepared in a manner similar to that described in Example 88 using 4-(2-bromophenoxy)-2-(trifluoromethyl)pyridine. MS (ESI): mass calcd. for C$_{22}$H$_{14}$F$_4$N$_4$O, 426.11; m/z found, 426.9 [M+H]$^+$. $^1$H NMR (400 MHz, DMSO-d$_6$) δ 8.51 (d, J=5.7, 1H), 8.30-8.25 (m, 1H), 7.96 (d, J=1.5, 1H), 7.81 (m, 1H), 7.64 (dd, J=7.6, 1.8, 1H), 7.50 (m, 2H), 7.39-7.29 (m, 4H), 7.04 (dd, J=5.7, 2.4, 1H), 6.68 (s, 2H).

Example 611

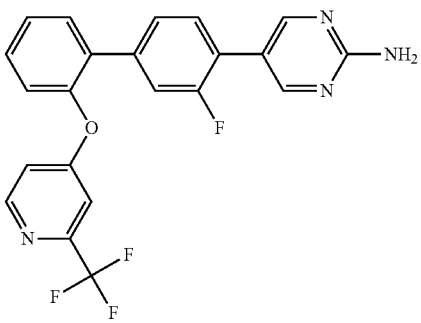

5-(3-Fluoro-2'-{[2-(trifluoromethyl)pyridin-4-yl]oxy}biphenyl-4-yl)pyrimidin-2-amine.

The title compound was prepared in a manner similar to that described in Example 88 using 4-(2-bromophenoxy)-2-(trifluoromethyl)pyridine and 5-(2-fluoro-4-(4,4,5,5-tetramethyl-1,3,2-dioxaborolan-2-yl)phenyl)pyrimidin-2-amine. MS (ESI): mass calcd. for C$_{22}$H$_{14}$F$_4$N$_4$O, 426.11; m/z found, 426.9 [M+H]$^+$. $^1$H NMR (400 MHz, DMSO-d$_6$) δ 8.51 (d, J=5.7, 1H), 8.38 (d, J=1.5, 2H), 7.62 (dd, J=7.6, 1.8, 1H), 7.56-7.42 (m, 3H), 7.38-7.30 (m, 4H), 7.04 (dd, J=5.6, 2.4, 1H), 6.84 (s, 2H).

Example 612

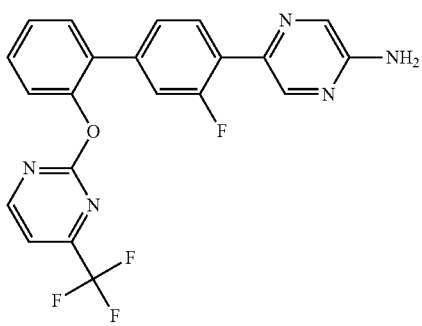

5-(3-Fluoro-2'-{[4-(trifluoromethyl)pyrimidin-2-yl]oxy}biphenyl-4-yl)pyrazin-2-amine.

The title compound was prepared in a manner similar to that described in Example 88 using 2-(2-bromophenoxy)-4-(trifluoromethyl)pyrimidine. MS (ESI): mass calcd. for $C_{21}H_{13}F_4N_5O$, 427.11; m/z found, 428.0 $[M+H]^+$. $^1H$ NMR (400 MHz, DMSO): δ 8.91 (d, J=4.9, 1H), 8.34-8.28 (m, 1H), 8.00 (d, J=1.4, 1H), 7.82 (m, 1H), 7.67 (d, J=4.9, 1H), 7.61-7.58 (m, 1H), 7.55-7.50 (m, 1H), 7.47-7.39 (m, 2H), 7.34-7.29 (m, 2H), 6.70 (s, 2H).

Example 613

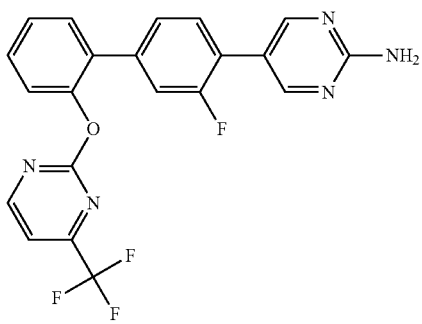

5-(3-Fluoro-2'-{[4-(trifluoromethyl)pyrimidin-2-yl]oxy}biphenyl-4-yl)pyrimidin-2-amine.

The title compound was prepared in a manner similar to that described in Example 88 using 2-(2-bromophenoxy)-4-(trifluoromethyl)pyrimidine and 5-(2-fluoro-4-(4,4,5,5-tetramethyl-1,3,2-dioxaborolan-2-yl)phenyl)pyrimidin-2-amine. MS (ESI): mass calcd. for $C_{21}H_{13}F_4N_5O$, 427.11; m/z found, 428.0 $[M+H]^+$. $^1H$ NMR (400 MHz, DMSO-$d_6$) δ 8.93 (d, J=4.9, 1H), 8.41 (d, J=1.4, 2H), 7.69 (d, J=4.9, 1H), 7.60-7.57 (m, 1H), 7.55-7.50 (m, 2H), 7.46-7.38 (m, 2H), 7.35-7.29 (m, 2H), 6.88 (s, 2H).

Example 614

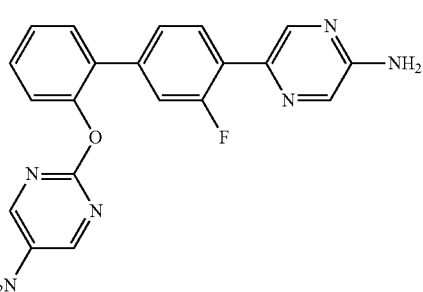

2-{[4'-(5-Aminopyrazin-2-yl)-3'-fluorobiphenyl-2-yl]oxy}pyrimidin-5-amine.

The title compound was prepared in a manner similar to that described in Example 88 using 2-(2-bromophenoxy)pyrimidin-5-amine. MS (ESI): mass calcd. for $C_2H_{15}FN_6O$, 374.13; m/z found, 375.0 $[M+H]^+$. $^1H$ NMR (400 MHz, DMSO-d) δ 8.35-8.31 (m, 1H), 8.01 (m, 1H), 7.92-7.89 (m, 2H), 7.83 (m, 1H), 7.53 (dd, J=7.6, 1.7, 1H), 7.44-7.26 (m, 4H), 7.13 (dd, J=8.1, 1.2, 1H), 6.68 (s, 2H), 5.16 (s, 2H).

Example 615

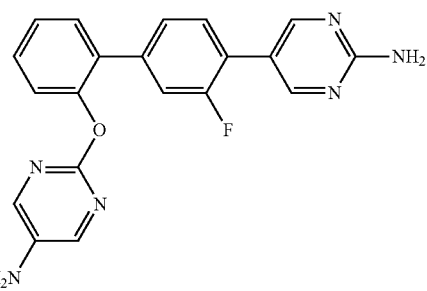

5-{2'-[(5-Aminopyrimidin-2-yl)oxy]-3-fluorobiphenyl-4-yl}pyrimidin-2-amine.

The title compound was prepared in a manner similar to that described in Example 88 using 2-(2-bromophenoxy)pyrimidin-5-amine and 5-(2-fluoro-4-(4,4,5,5-tetramethyl-1,3,2-dioxaborolan-2-yl)phenyl)pyrimidin-2-amine. MS (ESI): mass calcd. for $C_{20}H_{15}FN_6O$, 374.13; m/z found, 374.9 $[M+H]^+$. $^1H$ NMR (400 MHz, DMSO-$d_6$) δ 8.45 (d, J=1.5, 2H), 7.95-7.90 (m, 2H), 7.57-7.50 (m, 2H), 7.44-7.39 (m, 1H), 7.38-7.37 (m, 1H), 7.36-7.34 (m, 1H), 7.33-7.28 (m, 1H), 7.11 (dd, J=8.1, 1.2, 1H), 6.86 (s, 2H), 5.19 (s, 2H).

Example 616

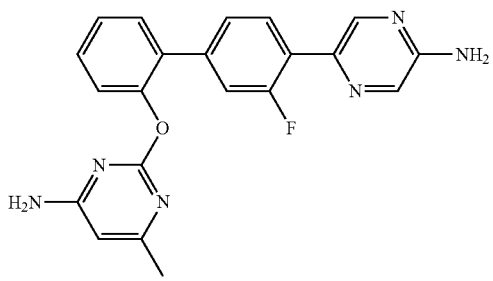

2-{[4'-(5-Aminopyrazin-2-yl)-3'-fluorobiphenyl-2-yl]oxy}-6-methylpyrimidin-4-amine.

The title compound was prepared in a manner similar to that described in Example 88 using 2-(2-bromophenoxy)-6-methylpyrimidin-4-amine. MS (ESI): mass calcd. for $C_{21}H_{17}FN_6O$, 388.15; m/z found, 389.0 [M+H]$^+$. $^1$H NMR (400 MHz, DMSO-d$_6$) δ 8.31 (s, 1H), 7.98 (s, 1H), 7.82 (m, 1H), 7.47 (d, J=7.6, 1H), 7.42-7.25 (m, 4H), 7.13 (d, J=8.0, 1H), 6.80 (s, 2H), 6.66 (s, 2H), 5.92 (s, 1H), 2.03 (s, 3H).

Example 617

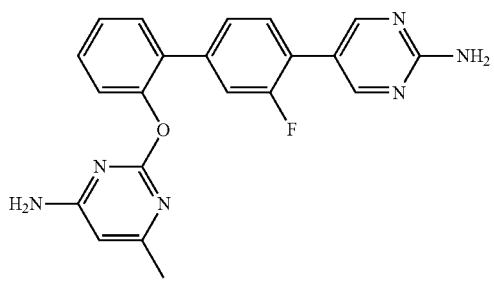

5-[2'-[(4-Amino-6-methylpyrimidin-2-yl)oxy]-3-fluorobiphenyl-4-yl}pyrimidin-2-amine.

The title compound was prepared in a manner similar to that described in Example 88 2-(2-bromophenoxy)-6-methylpyrimidin-4-amine and 5-(2-fluoro-4-(4,4,5,5-tetramethyl-1,3,2-dioxaborolan-2-yl)phenyl)pyrimidin-2-amine. MS (ESI): mass calcd. for $C_{21}H_{17}FN_6O$, 388.15; m/z found, 389.0 [M+H]$^+$. $^1$H NMR (400 MHz, DMSO-d$_6$) δ 8.43 (d, J=1.2, 2H), 7.53 (t, J=8.2, 1H), 7.49-7.44 (m, 1H), 7.41-7.36 (m, 1H), 7.34 (s, 1H), 7.33-7.30 (m, 1H), 7.29-7.25 (m, 1H), 7.12 (d, J=8.0, 1H), 6.85 (s, 2H), 6.82 (s, 2H), 5.94 (s, 1H), 2.04 (s, 3H).

Example 618

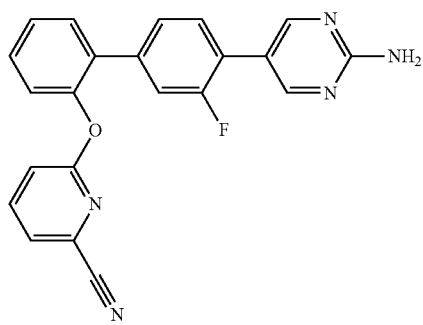

6-{[4'-(2-Aminopyrimidin-5-yl)-3'-fluorobiphenyl-2-yl]oxy}pyridine-2-carbonitrile.

The title compound was prepared in a manner similar to that described in Example 88 using 6-(2-bromophenoxy)picolinonitrile and 5-(2-fluoro-4-(4,4,5,5-tetramethyl-1,3,2-dioxaborolan-2-yl)phenyl)pyrimidin-2-amine. MS (ESI): mass calcd. for $C_{22}H_{14}FN_5O$, 383.12; m/z found, 383.9 [M+H]$^+$. $^1$H NMR (400 MHz, DMSO-d$_6$) δ 8.40 (d, J=1.4, 2H), 7.99 (dd, J=8.5, 7.4, 1H), 7.71-7.67 (m, 1H), 7.56 (dd, J=7.6, 1.7, 1H), 7.55-7.46 (m, 2H), 7.42-7.37 (m, 1H), 7.35-7.25 (m, 4H), 6.85 (s, 2H).

Example 619

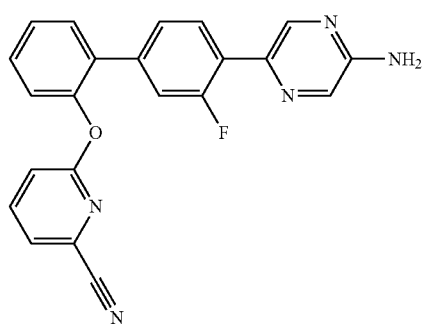

6-{[4'-(2-Aminopyrazin-2-yl)-3'-fluorobiphenyl-2-yl]oxy}pyridine-2-carbonitrile.

The title compound was prepared in a manner similar to that described in Example 88 using 6-(2-bromophenoxy)picolinonitrile. MS (ESI): mass calcd. for $C_{22}H_{14}FN_5O$, 383.12; m/z found, 383.9 [M+H]$^+$. $^1$H NMR (400 MHz, DMSO-d$_6$) δ 8.30-8.27 (m, 1H), 8.00-7.94 (m, 2H), 7.83-7.77 (m, 1H), 7.68-7.64 (m, 1H), 7.57 (dd, J=7.6, 1.7, 1H), 7.52-7.45 (m, 1H), 7.43-7.36 (m, 1H), 7.34-7.32 (m, 1H), 7.32-7.27 (m, 3H), 6.67 (s, 2H).

Example 620

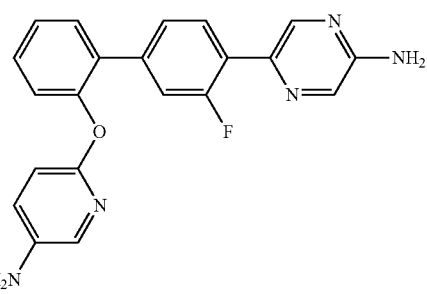

5-{2'-[(5-Aminopyridin-2-yl)oxy]-3-fluorobiphenyl-4-yl}pyrazin-2-amine.

The title compound was prepared in a manner similar to that described in Example 88 using 6-(2-bromophenoxy)pyridin-3-amine. MS (ESI): mass calcd. for $C_{21}H_{16}FN_5O$, 373.14; m/z found, 373.9 [M+H]$^+$. $^1$H NMR (400 MHz, DMSO-d$_6$) δ 8.31 (s, 1H), 7.98 (d, J=1.2, 1H), 7.83 (m, 1H), 7.51-7.45 (m, 2H), 7.42-7.31 (m, 3H), 7.23-7.18 (m, 1H), 7.03-6.99 (m, 1H), 6.94-6.90 (m, 1H), 6.71 (d, J=8.6, 1H), 6.66 (s, 2H), 5.01 (s, 2H).

Example 621

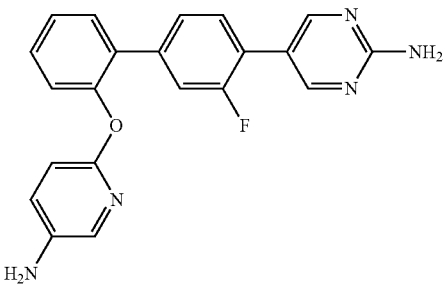

5-{2'-[(5-Aminopyridin-2-yl)oxy]-3-fluorobiphenyl-4-yl}pyrimidin-2-amine.

The title compound was prepared in a manner similar to that described in Example 88 using 6-(2-bromophenoxy)pyridin-3-amine and 5-(2-fluoro-4-(4,4,5,5-tetramethyl-1,3,2-dioxaborolan-2-yl)phenyl)pyrimidin-2-amine. MS (ESI): mass calcd. for $C_{21}H_{16}FN_5O$, 373.14; m/z found, 373.9 [M+H]$^+$. $^1$H NMR (400 MHz, DMSO-d$_6$) δ 8.44 (s, 2H), 7.53 (m, 1H), 7.50-7.45 (m, 2H), 7.44-7.38 (m, 2H), 7.36-7.30 (m, 1H), 7.20 (t, J=7.4, 1H), 7.06-7.00 (m, 1H), 6.91 (d, J=8.0, 1H), 6.85 (s, 2H), 6.72 (d, J=8.6, 1H), 5.03 (s, 2H).

Example 622

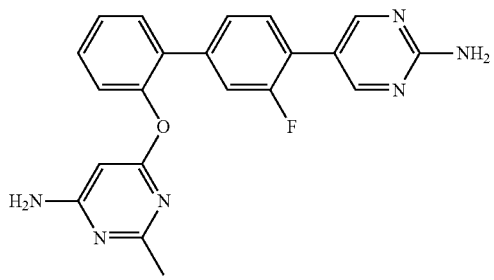

5-{2'-[(6-Amino-2-methylpyrimidin-4-yl)oxy]-3-fluorobiphenyl-4-yl}pyrimidin-2-amine.

The title compound was prepared in a manner similar to that described in Example 88 using 6-(2-bromophenoxy)-2-methylpyrimidin-4-amine and 5-(2-fluoro-4-(4,4,5,5-tetramethyl-1,3,2-dioxaborolan-2-yl)phenyl)pyrimidin-2-amine. MS (ESI): mass calcd. for $C_{21}H_{17}FN_6O$, 388.14; m/z found, 389.0 [M+H]$^+$. $^1$H NMR (400 MHz, CD$_3$OD) δ 8.45 (d, J=1.4, 2H), 7.54 (dd, J=7.6, 1.7, 1H), 7.50-7.42 (m, 2H), 7.42-7.29 (m, 3H), 7.20 (dd, J=8.0, 1.2, 1H), 5.43-5.31 (m, 1H), 2.25 (s, 3H).

Example 623

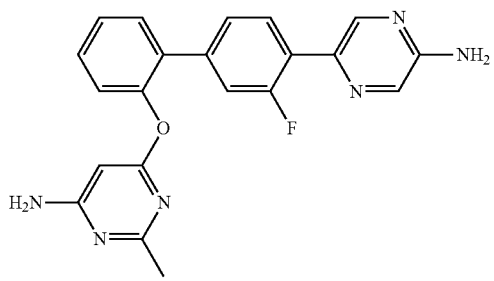

6-{[4'-(5-Aminopyrazin-2-yl)-3'-fluorobiphenyl-2-yl]oxy}-2-methylpyrimidin-4-amine.

The title compound was prepared in a manner similar to that described in Example 88 using 6-(2-bromophenoxy)-2-methylpyrimidin-4-amine. MS (ESI): mass calcd. for $C_{21}H_{17}FN_6O$, 388.14; m/z found, 389.0 [M+H]$^+$. $^1$H NMR (400 MHz, CD$_3$OD) δ 8.31 (dd, J=2.1, 1.6, 1H), 8.02 (d, J=1.5, 1H), 7.81 (m, 1H), 7.55 (dd, J=7.5, 1.8, 1H), 7.49-7.44 (m, 1H), 7.42-7.33 (m, 3H), 7.30 (dd, J=12.6, 1.7, 1H), 7.21 (dd, J=8.0, 1.2, 1H), 5.39 (s, 1H), 2.25 (s, 3H).

Example 624

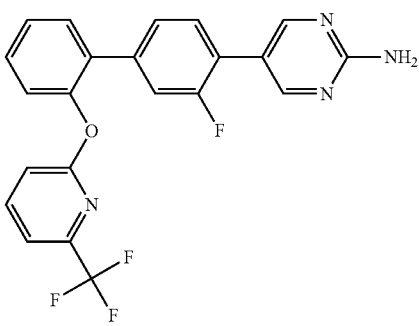

5-(3-Fluoro-2'-{[6-(trifluoromethyl)pyridin-2-yl]oxy}biphenyl-4-yl)pyrimidin-2-amine.

The title compound was prepared in a manner similar to that described in Example 88 using 2-(2-bromophenoxy)-6-(trifluoromethyl)pyridine and 5-(2-fluoro-4-(4,4,5,5-tetramethyl-1,3,2-dioxaborolan-2-yl)phenyl)pyrimidin-2-amine. MS (ESI): mass calcd. for $C_{22}H_{14}F_4N_4O$, 426.11; m/z found, 427.1 [M+H]$^+$. $^1$H NMR (400 MHz, DMSO-d$_6$) δ 8.42 (s, 2H), 8.04 (m, 1H), 7.59-7.48 (m, 4H), 7.41 (m, 1H), 7.35-7.24 (m, 4H), 6.89 (s, 2H).

Example 625

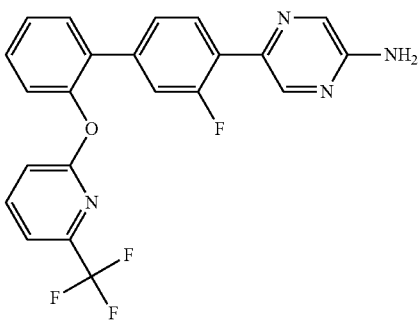

5-(3-Fluoro-2'-{[6-(trifluoromethyl)pyridin-2-yl]oxy}biphenyl-4-yl)pyrazin-2-amine.

The title compound was prepared in a manner similar to that described in Example 88 using 2-(2-bromophenoxy)-6-(trifluoromethyl)pyridine. MS (ESI): mass calcd. for $C_{22}H_{14}F_4N_4O$, 426.11; m/z found, 427.0 [M+H]$^+$. $^1$H NMR (400 MHz, DMSO-d$_6$) δ 8.33-8.27 (m, 1H), 8.05-7.98 (m, 2H), 7.81 (m, 1H), 7.62-7.56 (m, 1H), 7.54-7.47 (m, 2H), 7.44-7.38 (m, 1H), 7.35-7.23 (m, 4H), 6.70 (s, 2H).

Example 626

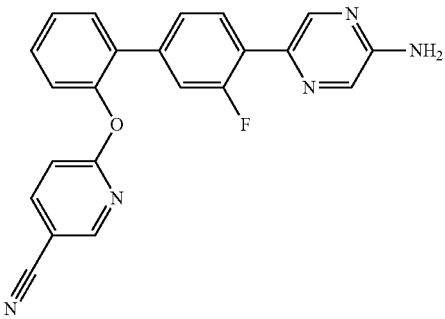

6-{[4'-(5-Aminopyrazin-2-yl)-3'-fluorobiphenyl-2-yl]oxy}pyridine-3-carbonitrile.

The title compound was prepared in a manner similar to that described in Example 88 using 6-(2-bromophenoxy) nicotinonitrile. MS (ESI): mass calcd. for $C_{22}H_{14}FN_5O$, 383.12; m/z found, 384.0 [M+H]$^+$. $^1$H NMR (400 MHz, DMSO-d$_6$) δ 8.57 (dd, J=2.3, 0.8, 1H), 8.34-8.31 (m, 1H), 8.24 (dd, J=8.8, 2.3, 1H), 7.99 (d, J=1.4, 1H), 7.83 (m, 1H), 7.60 (dd, J=7.6, 1.6, 1H), 7.53-7.47 (m, 1H), 7.45-7.40 (m, 1H), 7.35-7.28 (m, 3H), 7.19 (dd, J=8.6, 0.6, 1H), 6.70 (s, 2H).

Example 627

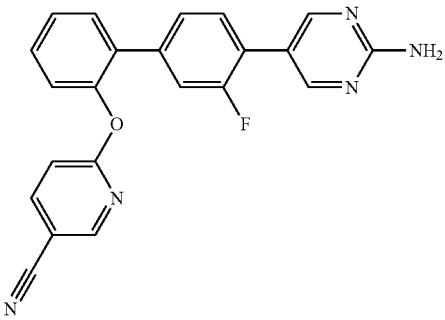

6-{[4'-(2-Aminopyrimidin-5-yl)-3'fluorobiphenyl-2-yl]oxy}pyridine-3-carbonitrile.

The title compound was prepared in a manner similar to that described in Example 88 using 6-(2-bromophenoxy) nicotinonitrile and 5-(2-fluoro-4-(4,4,5,5-tetramethyl-1,3,2-dioxaborolan-2-yl)phenyl)pyrimidin-2-amine. MS (ESI): mass calcd. for $C_{22}H_{14}FN_5O$, 383.12; m/z found, 384.0 [M+H]$^+$. $^1$H NMR (400 MHz, DMSO-d$_6$) δ 8.60 (dd, J=2.3, 0.8, 1H), 8.44 (d, J=1.6, 2H), 8.26 (dd, J=8.6, 2.3, 1H), 7.59 (dd, J=7.6, 1.8, 1H), 7.56-7.48 (m, 2H), 7.45-7.39 (m, 1H), 7.36-7.27 (m, 3H), 7.21 (dd, J=8.7, 0.7, 1H), 6.89 (s, 2H).

Example 628

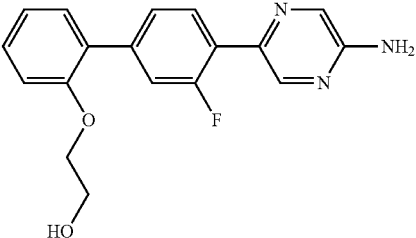

2-{[4'-(5-Aminopyrimidin-2-yl)-3'fluorobiphenyl-2-yl]oxy}ethanol.

The title compound was prepared in a manner similar to that described in Example 88 using 2-(2-bromophenoxy) ethanol. MS (ESI): mass calcd. for $C_{18}H_{16}FN_3O_2$, 325.12; m/z found, 326.1 [M+H]$^+$. $^1$H NMR (400 MHz, DMSO-d$_6$) δ 8.35 (s, 1H), 8.00 (d, J=1.2, 1H), 7.86 (m, 1H), 7.55-7.45 (m, 2H), 7.40-7.36 (m, 1H), 7.35-7.29 (m, 1H), 7.11 (d, J=8.2, 1H), 7.02 (m, 1H), 6.66 (s, 2H), 4.81 (s, 1H), 4.04 (t, J=5.0, 2H), 3.73-3.63 (m, 2H).

Example 629

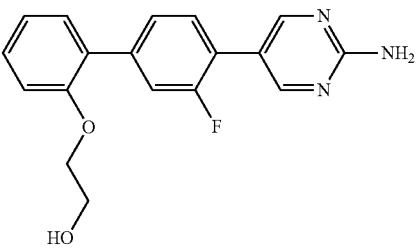

2-{[4'-(2-Aminopyrimidin-5-yl)-3'fluorobiphenyl-2-yl]oxy}ethanol.

The title compound was prepared in a manner similar to that described in Example 88 using 2-(2-bromophenoxy) ethanol and 5-(2-fluoro-4-(4,4,5,5-tetramethyl-1,3,2-dioxaborolan-2-yl)phenyl)pyrimidin-2-amine. MS (ESI): mass calcd. for $C_{18}H_{16}FN_3O_2$, 325.12; m/z found, 326.1 [M+H]$^+$. $^1$H NMR (400 MHz, DMSO-d$_6$) δ 8.48 (d, J=1.0, 2H), 7.57-7.51 (m, 2H), 7.48-7.44 (m, 1H), 7.38-7.30 (m, 2H), 7.12 (d. J=8.4, 1H), 7.02 (m, 1H), 6.90 (s, 2H), 4.05 (t, J=5.0, 2H), 3.68 (t, J=5.0, 2H).

Example 630

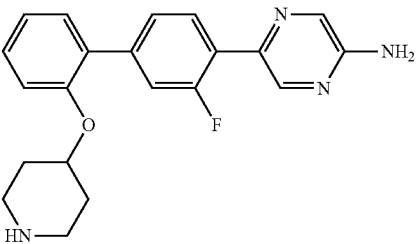

5-[3-Fluoro-2'-(piperidin-4-yloxy)biphenyl-4-yl]pyrazin-2-amine.

The title compound was prepared in a manner similar to that described in Example 88 using 4-(2-bromophenoxy)piperidine. MS (ESI): mass calcd. for $C_{21}H_{21}FN_4O$, 364.17; m/z found, 365.0 [M+H]$^+$. $^1$H NMR (400 MHz, DMSO-d$_6$) δ 8.36 (s, 1H), 8.29 (s, 1H), 8.01 (s, 1H), 7.89 (m, 1H), 7.46-7.31 (m, 4H), 7.19 (d, J=8.2, 1H), 7.05 (m, 1H), 6.68 (s, 2H), 4.68-4.59 (m, 1H), 2.97-2.87 (m, 4H), 2.07-1.93 (m, 2H), 1.82-1.54 (m, 2H).

Example 631

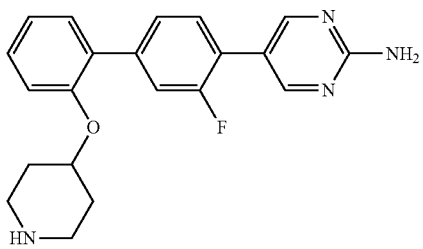

5-[3-Fluoro-2'-(piperidin-4-yloxy)biphenyl-4-yl]pyrimidin-2-amine.

The title compound was prepared in a manner similar to that described in Example 88 using 4-(2-bromophenoxy)piperidine and 5-(2-fluoro-4-(4,4,5,5-tetramethyl-1,3,2-dioxaborolan-2-yl)phenyl)pyrimidin-2-amine. MS (ESI): mass calcd. for $C_{21}H_{21}FN_4O$, 364.17; m/z found, 365.0 [M+H]$^+$. $^1$H NMR (400 MHz, DMSO-d$_6$) δ 8.48 (s, 2H), 8.29 (s, 1H), 7.56 (m, 1H), 7.46-7.31 (m, 4H), 7.20 (d, J=8.4, 1H), 7.05 (m, 1H), 6.86 (s, 2H), 4.62-4.66 (m, 1H), 2.91-2.93 (m, 4H), 2.07-1.96 (m, 2H), 1.77-1.65 (m, 2H).

Example 632

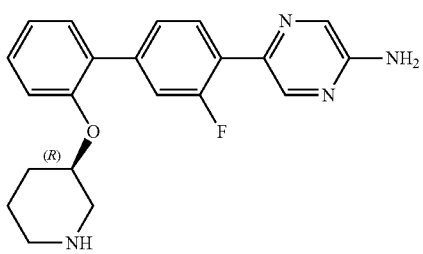

5-[3-Fluoro-2'-[(3R)-piperidin-4-yloxy]biphenyl-4-yl]pyrazin-2-amine.

The title compound was prepared in a manner similar to that described in Example 88 using (R)-3-(2-bromophenoxy)piperidine. MS (ESI): mass calcd. for $C_{21}H_{21}FN_4O$, 364.17; m/z found, 365.0 [M+H]$^+$. $^1$H NMR (400 MHz, DMSO-d$_6$) δ 8.38 (dd, J=2.1, 1.6, 1H), 8.08 (d, J=1.5, 1H), 7.94-7.90 (m, 1H), 7.48-7.37 (m, 4H), 7.23-7.13 (m, 2H), 4.52-4.40 (m, 1H), 3.30-3.24 (m, 2H), 3.20-3.06 (m, 2H), 2.01-1.69 (m, 4H).

Example 633

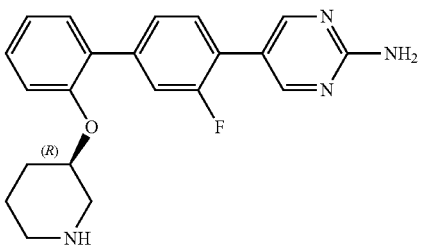

5-{3-Fluoro-2'-[(3R)-piperidin-3-yloxy)biphenyl-4-yl}pyrimidin-2-amine.

The title compound was prepared in a manner similar to that described in Example 88 using (R)-3-(2-bromophenoxy)piperidine and 5-(2-fluoro-4-(4,4,5,5-tetramethyl-1,3,2-dioxaborolan-2-yl)phenyl)pyrimidin-2-amine. MS (ESI): mass calcd. for $C_{21}H_{21}FN_4O$, 364.17; m/z found, 365.0 [M+H]$^+$. $^1$H NMR (400 MHz, DMSO-d$_6$) δ 8.48-8.45 (m, 2H), 7.60-7.48 (m, 2H), 7.46-7.34 (m, 3H), 7.23 (d, J=8.0, 1H), 7.13-7.06 (m, 1H), 6.87 (s, 2H), 4.68-4.56 (m, 1H), 3.35-3.30 (m, 1H), 3.11-2.99 (m, 2H), 2.98-2.89 (m, 1H), 2.03-1.93 (m, 1H), 1.88-1.77 (m, 1H), 1.72-1.58 (m, 2H).

Example 634

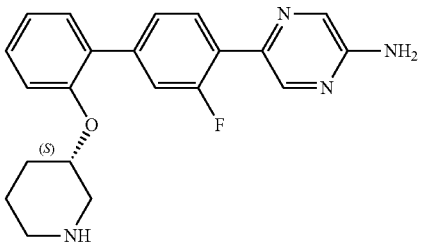

5-{3-Fluoro-2'-[(3S)-piperidin-3-yloxy)biphenyl-4-yl}pyrazin-2-amine.

The title compound was prepared in a manner similar to that described in Example 88 using (S)-3-(2-bromophenoxy)piperidine. MS (ESI): mass calcd. for $C_{21}H_{21}FN_4O$, 364.17; m/z found, 365.0 [M+H]$^+$. $^1$H NMR (400 MHz, DMSO-d$_6$) δ 8.37 (s, 1H), 8.02 (s, 1H), 7.91-7.87 (m, 1H), 7.52-7.45 (m, 2H), 7.42 (d, J=7.4, 1H), 7.36 (d, J=7.1, 1H), 7.22 (d, J=8.3, 1H), 7.12-7.08 (m, 1H), 6.69 (s, 2H), 4.57 (br m, 1H), 3.09-3.04 (m, 3H), 2.98-2.92 (m, 1H), 2.02-1.90 (m, 1H), 1.87-1.75 (m, 1H), 1.70-1.58 (m, 2H).

Example 635

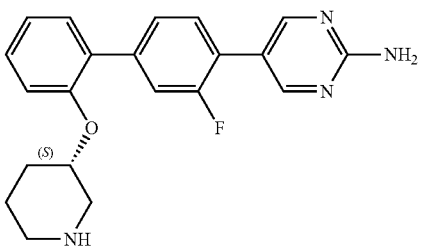

5-{3-Fluoro-2'-[(3S)-piperidin-3-yloxy)biphenyl-4-yl}pyrimidin-2-amine.

The title compound was prepared in a manner similar to that described in Example 88 using (S)-3-(2-bromophenoxy)piperidine and 5-(2-fluoro-4-(4,4,5,5-tetramethyl-1,3,2-dioxaborolan-2-yl)phenyl)pyrimidin-2-amine. MS (ESI): mass calcd. for $C_{21}H_{21}FN_4O$, 364.17; m/z found, 365.0 [M+H]$^+$. $^1$H NMR (400 MHz, DMSO-$d_6$) δ 8.48 (s, 2H), 7.59-7.48 (m, 2H), 7.44 (d, J=8.1, 1H), 7.40-7.35 (m, 2H), 7.24 (d, J=8.3, 1H), 7.11-7.07 (m, 1H), 6.87 (s, 2H), 4.73-4.53 (m, 1H), 3.38-3.30 (m, 1H), 3.12-2.86 (m, 3H), 2.04-1.94 (m, 1H), 1.80-1.71 (m, 2H), 1.65-1.54 (m, 1H).

Example 636

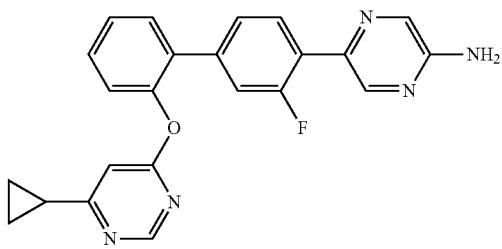

5-{2'-[(6-Cyclopropylpyrimidin-4-yl)oxy]-3-fluorobiphenyl-4-yl}pyrazin-2-amine.

The title compound was prepared in a manner similar to that described in Example 88 using 4-(2-bromophenoxy)-6-cyclopropylpyrimidine. MS (ESI): mass calcd. for $C_{23}H_{18}FN_5O$, 399.15; m/z found, 399.9 [M+H]$^+$. $^1$H NMR (400 MHz, DMSO-$d_6$) δ 8.43 (s, 1H), 8.30 (s, 1H), 7.97 (s, 1H), 7.81 (m, 1H), 7.58-7.54 (m, 1H), 7.49-7.43 (m, 1H), 7.41-7.35 (m, 1H), 7.33-7.23 (m, 3H), 6.98 (s, 1H), 6.68 (s, 2H), 2.09-2.01 (m, 1H), 1.02-0.89 (m, 4H).

Example 637

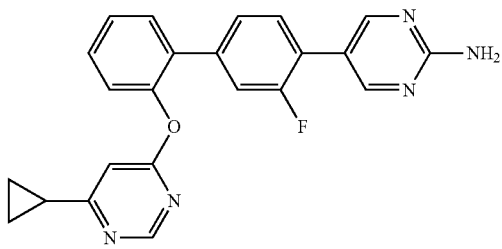

5-{2'-[(6-Cyclopropylpyrimidin-4-yl)oxy]-3-fluorobiphenyl-4-yl}pyrimidin-2-amine.

The title compound was prepared in a manner similar to that described in Example 88 using 4-(2-bromophenoxy)-6-cyclopropylpyrimidine and 5-(2-fluoro-4-(4,4,5,5-tetramethyl-1,3,2-dioxaborolan-2-yl)phenyl)pyrimidin-2-amine. MS (ESI): mass calcd. for $C_{23}H_{18}FN_5O$, 399.15; m/z found, 399.9 [M+H]$^+$. $^1$H NMR (400 MHz, DMSO-$d_6$) δ 8.45 (s, 1H), 8.42 (s, 2H), 7.56-7.50 (m, 2H), 7.48-7.43 (m, 1H), 7.41-7.36 (m, 1H), 7.33-7.23 (m, 3H), 6.99 (s, 1H), 6.86 (s, 2H), 2.09-2.01 (m, 1H), 1.02-0.92 (m, 4H).

Example 638

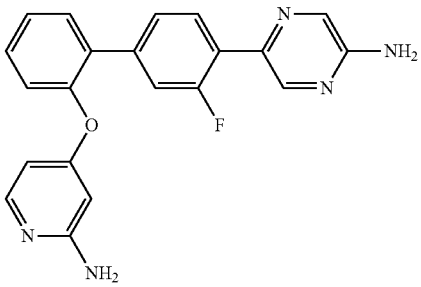

5-{2'-[(2-Aminopyridin-4-yl)oxy]-3-fluorobiphenyl-4-yl}pyrazin-2-amine.

The title compound was prepared in a manner similar to that described in Example 88 using 4-(2-bromophenoxy)pyridin-2-amine. MS (ESI): mass calcd. for $C_{21}H_{16}FN_5O$, 373.13; m/z found, 374.2 [M+H]$^+$. $^1$H NMR (400 MHz, DMSO-$d_6$) δ 8.36-8.30 (m, 1H), 7.99 (d, J=1.4, 1H), 7.90-7.82 (m, 1H), 7.76 (d. J=6.5, 1H), 7.63 (dd, J=7.7, 1.7, 1H), 7.57-7.48 (m, 1H), 7.46-7.40 (m, 1H), 7.39-7.31 (m, 2H), 7.27 (d, J=8.0, 1H), 6.70 (s, 2H), 6.55 (s, 2H), 6.23 (dd, J=6.4, 2.2, 1H), 5.86 (d, J=2.3, 1H).

Example 639

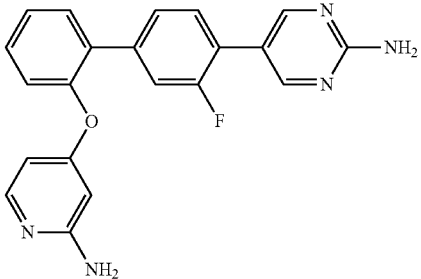

5-{2'-[(2-Aminopyridin-4-yl)oxy]-3-fluorobiphenyl-4-yl}pyrimidin-2-amine.

The title compound was prepared in a manner similar to that described in Example 88 using 4-(2-bromophenoxy)pyridin-2-amine and 5-(2-fluoro-4-(4,4,5,5-tetramethyl-1,3,2-dioxaborolan-2-yl)phenyl)pyrimidin-2-amine. MS (ESI): mass calcd. for $C_{21}H_{16}FN_5O$, 373.13; m/z found, 374.2 [M+H]$^+$. $^1$H NMR (400 MHz, DMSO-$d_6$) δ 8.44 (s, 2H), 7.77 (d, J=6.3, 1H), 7.65-7.48 (m, 3H), 7.45-7.32 (m, 3H), 7.25 (d, J=8.0, 1H), 6.88 (s, 2H), 6.52 (s, 2H), 6.23 (dd, J=6.3, 2.2, 1H), 5.87 (d, J=2.2, 1H).

Example 640

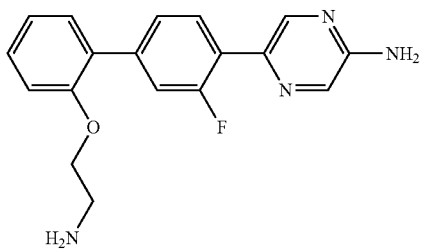

5-[2'-(2-Aminoethoxy)-3-fluorobiphenyl-4-yl]
pyrazin-2-amine.

The title compound was prepared in a manner similar to that described in Example 88 using 2-(2-bromophenoxy)ethanamine. MS (ESI): mass calcd. for $C_{18}H_{17}FN_4O$, 324.14; m/z found, 325.0 [M+H]$^+$. $^1$H NMR (400 MHz, DMSO-d$_6$) δ 8.36 (s, 1H), 8.31 (s, 1H), 8.01 (d, J=1.3, 1H), 7.90-7.86 (m, 1H), 7.50-7.45 (m, 2H), 7.41-7.33 (m, 2H), 7.14 (d, J=8.1, 1H), 7.08-7.05 (m, 1H), 6.67 (s, 2H), 4.10 (t, J=5.4, 2H), 3.01 (t, J=5.4, 2H).

Example 641

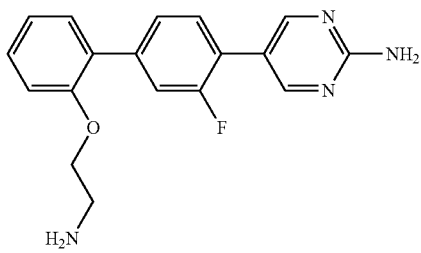

5-[2'-(2-Aminoethoxy)-3-fluorobiphenyl-4-yl]
pyrimidin-2-amine.

The title compound was prepared in a manner similar to that described in Example 88 using 2-(2-bromophenoxy)ethanamine and 5-(2-fluoro-4-(4,4,5,5-tetramethyl-1,3,2-dioxaborolan-2-yl)phenyl)pyrimidin-2-amine. MS (ESI): mass calcd. for $C_{18}H_{17}FN_4O$, 324.14; m/z found, 325.0 [M+H]$^+$. $^1$H NMR (400 MHz, DMSO-d$_6$) δ 8.47 (d, J=0.9, 2H), 8.29 (s, 1H), 7.58-7.54 (m, 1H), 7.53-7.49 (m, 1H), 7.45 (dd, J=8.0, 1.4, 1H), 7.39-7.34 (m, 2H), 7.15 (d, J=8.1, 1H), 7.09-7.05 (m, 1H), 6.86 (s, 2H), 4.13 (t J=5.4, 2H), 3.05 (t, J=5.4, 2H).

Example 642

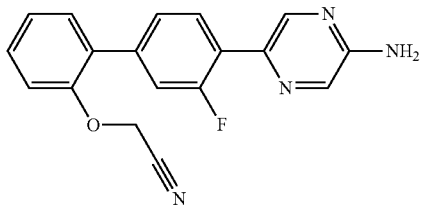

{[4'-(5-Aminopyrazin-2-yl)-3'-fluorobiphenyl-2-yl]
oxy}acetonitrile.

The title compound was prepared in a manner similar to that described in Example 88 using 2-(2-bromophenoxy)acetonitrile. MS (ESI): mass calcd. for $C_{18}H_{13}FN_4O$, 320.11; m/z found, 320.9 [M+H]$^+$. $^1$H NMR (400 MHz, DMSO-d$_6$) δ 8.40-8.33 (m, 1H), 8.01 (d, J=1.4, 1H), 7.91-7.87 (m, 1H), 7.45-7.39 (m, 3H), 7.37 (s, 1H), 7.30-7.24 (m, 1H), 7.18-7.15 (m, 1H), 6.68 (s, 2H), 5.18 (s, 2H).

Example 643

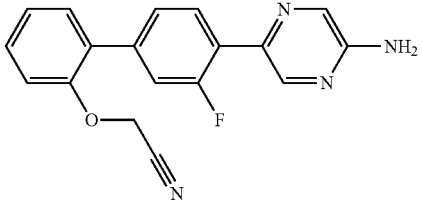

{[4'-(2-Aminopyrimidin-5-yl)-3'-fluorobiphenyl-2-yl]oxy}
acetonitrile.

The title compound was prepared in a manner similar to that described in Example 88 using 2-(2-bromophenoxy)acetonitrile and 5-(2-fluoro-4-(4,4,5,5-tetramethyl-1,3,2-dioxaborolan-2-yl)phenyl)pyrimidin-2-amine. MS (ESI): mass calcd. for $C_{18}H_{13}FN_4O$, 320.11; m/z found, 320.9 [M+H]$^+$. $^1$H NMR (400 MHz, DMSO-d$_6$) δ 8.47 (d, J=1.5, 2H), 7.60-7.56 (m, 1H), 7.46-7.34 (m, 4H), 7.26 (d. J=8.0, 1H), 7.18-7.14 (m, 1H), 6.87 (s, 2H), 5.18 (s, 2H).

Example 644

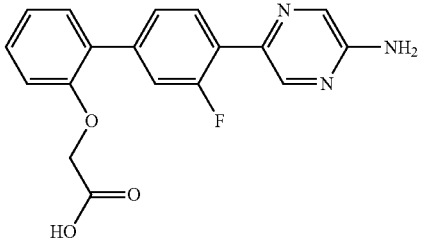

{[4'-(2-Aminopyrimidin-5-yl)-3'-fluorobiphenyl-2-yl]oxy}
acetic acid.

The title compound was prepared in a manner similar to that described in Example 88 using 2-(2-bromophenoxy)acetic acid and 5-(2-fluoro-4-(4,4,5,5-tetramethyl-1,3,2-dioxaborolan-2-yl)phenyl)pyrimidin-2-amine. MS (ESI): mass calcd. for $C_{18}H_{14}FN_3O_3$, 339.10; m/z found, 339.9 [M+H]$^+$. $^1$H NMR (400 MHz, DMSO-d$_6$) δ 8.46 (d, J=1.4, 2H), 7.71 (d, J=13.3, 1H), 7.51 (d, J=5.7, 2H), 7.29 (dd, J=7.5, 1.7, 1H), 7.25-7.17 (m, 1H), 6.92-6.89 (m, 1H), 6.88-6.80 (m, 3H), 4.14 (s, 2H).

Intermediate IS

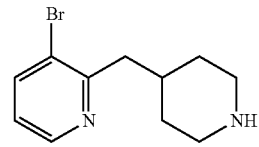

3-Bromo-2-(piperidin-4-yloxy)pyridine

Step A: tert-Butyl 4-((3-bromopyridin-2-yl)oxy)piperidine-1-carboxylate

A suspension of 2-bromophenol (2.0 g, 10 mmol), tert-butyl 4-hydroxypiperidine-1-carboxylate (2.09 g, 10.4 mmol), and cesium carbonate (6.8 g, 21 mmol) in dimethylsulfoxide (10 mL) was heated at 130° Celsius overnight. The reaction mixture was then cooled to rt, diluted with water (20 mL), and extracted with ethyl acetate (3×20 mL). The combined organic extracts were washed with water (3×10 mL) and dried over anhydrous magnesium sulfate. The solvent was removed in vacuo, and the residue purified by FCC to provide the title compound.

Step B: 3-Bromo-2-(piperidin-4-yloxy)pyridine

To a solution of tert-butyl 4-((3-bromopyridin-2-yl)oxy)piperidine-1-carboxylate in MeOH (10 mL) was added HCl (2 mL, 1 N). The reaction mixture was stirred at rt for 2 h before adjusting the pH to ~9 with NH$_4$OH. The mixture was then concentrated to dryness and the crude product purified by FCC to provide the title compound. $^1$H NMR (400 MHz, DMSO-d$_6$) δ 8.17 (dd, J=4.8, 1.7, 1H), 8.06 (dd, J=7.7, 1.7, 1H), 6.98 (dd, J=7.7, 4.9, 1H), 5.31 (m, 1H), 3.18-3.07 (m, 4H), 2.22-2.05 (m, 2H), 1.92 (m, 2H).

Intermediate IT

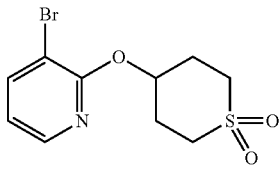

4-((3-Bromopyridin-2-yl)oxy)tetrahydro-2H-thiopyran 1,1-dioxide

Step A: 3-Bromo-2-((tetrahydro-2H-thiopyran-4-yl)oxy)pyridine

To a 100 mL reaction tube, equipped with a reflux condenser and under a nitrogen atmosphere, was added a solution consisting of tetrahydro-2H-thiopyran-4-ol (1.04 g, 8.78 mmol) in DMF (2 mL). The mixture was cooled to the 0° Celsius, and then treated with NaH (0.540 g, 60% dispersion in mineral oil, 13.5 mmol). When the addition was complete, the reaction was warmed to rt and stirred 30 min before adding 3-bromo-2-chloropyridine (1.3 g, 6.8 mmol), and heating at 130° Celsius for 10 hours. The reaction mixture was cooled to rt and carefully quenched with H$_2$O, concentrated to remove the solvent, and extracted with water (20 mL) and EtOAc (3×20 mL). The combined organic extracts were dried over Na$_2$SO$_4$, filtered, and concentrated to dryness. The crude material was purified by FCC to provide the title compound.

Step B: 4-((3-Bromopyridin-2-yl)oxy)tetrahydro-2H-thiopyran 1,1-dioxide

To a 100 mL round-bottomed flask, was added a solution, consisting of 3-bromo-2-(tetrahydro-2H-thiopyran-4-yloxy)pyridine (1.6 g, 5.8 mmol) and DCM (25 mL), under a nitrogen atmosphere. The mixture was cooled to the 0° Celsius and m-CPBA (3.63 g, 14.6 mmol, 77%) was added in portions. When the addition was complete, the reaction was warmed to rt and stirred for 3 h. The reaction was quenched by adding H$_2$O (10 mL) and the organic layer isolated. The aqueous phase was extracted with DCM (3×20 mL) and the combined organic extracts were washed with saturated NaHCO$_3$, dried over sodium sulfate, filtered, and concentrated to dryness. The crude product was purified by FCC to provide the title compound. $^1$H NMR (400 MHz, DMSO-d$_6$) δ 8.17 (dd, J=4.9, 1.6, 1H), 8.07 (dd, J=7.8, 1.6, 1H), 6.99 (dd, J=7.7, 4.9, 1H), 5.43-5.36 (m, 1H), 3.23-3.19 (m, 2H), 3.15 (dd, J=14.3, 7.3, 2H), 2.31-2.25 (m, 4H).

Intermediate IU

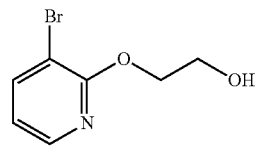

2-((3-Bromopyrdin-2-yl)oxy)ethanol

Sodium hydride (1.6 g, 42 mmol) was added to cooled (ice-water bath) ethane-1,2-diol (5 mL) and the resulting mixture stirred at rt for 30 min before adding 3-bromo-2-chloropyridine (2.0 g, 100 mmol). The mixture was then heated at 130° Celsius under a N$_2$ atmosphere overnight before cooling to rt and subjecting the reaction mixture to FCC purification to afford the title compound. $^1$H NMR (400 MHz, CDCl$_3$) δ 8.05 (dd, J=4.9, 1.7, 1H), 7.82 (dd, J=7.6, 1.7, 1H), 6.80 (dd, J=7.6, 4.9, 1H), 4.54-4.50 (m, 2H), 3.97 (dd, J=8.8, 5.5, 2H), 3.18 (t, J=5.8, 1H).

Intermediate IV

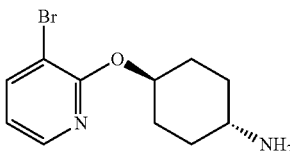

trans-4-((3-Bromopyridin-2-yl)oxy)cyclohexanamine

To a cooled (0° C.) 150 mL reaction tube equipped with reflux condenser and under a nitrogen atmosphere, were added trans-4-aminocyclohexanol (2.0 g, 17 mmol), NaH (2.08 g, 60% dispersion in mineral oil, 52.1 mmol), and DMF (25 mL) to give a colorless solution. After stirring for 1 h, 3-bromo-2-chloropyridine (3.34 g, 17.4 mmol) was added to the mixture And the resulting mixture heated at 60° Celsius for 5 h. After the starting material was consumed, the reaction was cooled to room temperature and quenched with H$_2$O (2 mL). The reaction mixture was concentrated to dryness and the resultant residue purified by FCC to provide the title compound. $^1$H NMR (400 MHz, DMSO-d$_6$) δ 8.11 (dd, J=4.8, 1.6, 1H), 7.98 (dd, J=7.7, 1.6, 1H), 6.89 (dd, J=7.7, 4.8, 1H), 4.92 (dd, J=9.4, 5.2, 1H), 2.98 (s, 1H), 2.05 (m, 2H), 1.95 (m, 2H), 1.53-1.38 (m, 4H)

Intermediate IW

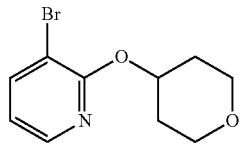

3-Bromo-2-((tetrahydro-2H-pyran-4-yl)oxy)pyridine

The title compound was prepared in a manner similar to that described in Step A for the synthesis of 4-((3-bromopyridin-2-yl)oxy)tetrahydro-2H-thiopyran1,1-dioxide using tetrahydro-2H-pyran-4-ol. $^1$H NMR (400 MHz, DMSO-d) 68.11 (dd, J=4.8, 1.7, 1H), 7.99 (dd, J=7.7, 1.7, 1H), 6.90 (dd, J=7.7, 4.8, 1H), 5.22 (m, 1H), 3.86-3.77 (m, 2H), 3.49 (m, 2H), 1.95 (m, 2H), 1.61 (m, 2H).

Intermediate IX

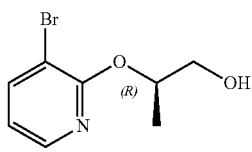

(R)-2-((3-Bromopyridin-2-yl)oxy)propan-1-ol

Step A: (R)-2-((1-(Benzyloxy)propan-2-yl)oxy)-3-bromopyridine

To a stirred solution of (R)-1-(benzyloxy)propan-2-ol (2.0 g, 12 mmol) in dry DMF (5 mL) was added NaH (1.5 g, 36 mmol) at 0 Celsius. The reaction mixture was then stirred for 30 min before adding 3-bromo-2-chloropyridine (2.3 g, 12 mmol) and stirring continued for another 4 h. The reaction was quenched by slow addition of water (10 mL) and the resultant mixture extracted with ethyl acetate (3×10 mL). The combined organic extracts were dried over Na$_2$SO$_4$, filtered, concentrated to dryness, and the crude product purified by FCC to provide the title compound.

Step B: (R)-2-((3-Bromopyridin-2-yl)oxy)propan-1-ol

To a stirred solution of (R)-2-((1-(benzyloxy)propan-2-yl)oxy)-3-bromopyridine (2.4 g, 7.5 mmol) in dry DCM (10 mL) was added BBr$_3$ (7.5 mL, 22 mmol, 3 M in DCM) at −78 Celsius in a drop-wise manner and stirring continued for 3 h. The reaction mixture was warmed to rt and the pH adjusted to ~7-8 with sat. NaHCO$_3$ (30 mL). The mixture was extracted with DCM (2×10 mL), and the combined extracts dried over Na$_2$SO$_4$, filtered, concentrated to dryness. The crude product was purified by FCC to provide the title compound. $^1$H NMR (400 MHz, CDCl$_3$) δ 8.05-7.99 (m, 1H), 7.84-7.75 (m, 1H), 6.83-6.71 (m, 1H), 5.25-5.12 (m, 1H), 3.78 (d, J=5.1, 2H), 3.29 (s, 1H), 1.37 (d, J=6.4, 3H).

Intermediate IY

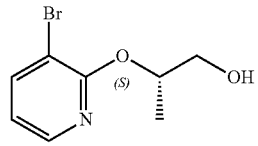

(S)-2-((3-Bromopyridin-2-yl)oxy)propan-1-ol

The title compound was prepared in a manner similar to that described for (R)-2-((3-bromopyridin-2-yl)oxy)propan-1-ol using (S)-1-(benzyloxy)propan-2-ol. $^1$H NMR (400 MHz, CDCl$_3$) δ 8.07-7.97 (m, 1H), 7.79 (m, 1H), 6.76 (m, 1H), 5.26-5.12 (m, 1H), 3.77 (t, J=6.1, 2H), 3.35 (s, 1H), 1.36 (d, J=6.3, 3H).

Example 645

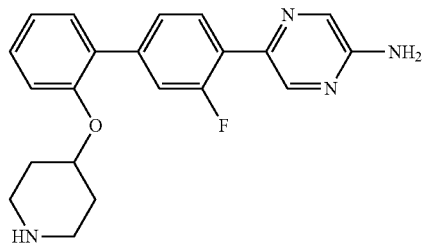

5-{2-Fluoro-4-[2-(piperidin-4-yloxy)pyridin-3-yl]phenyl} pyrazin-2-amine.

The title compound was prepared in a manner similar to that described in Example 88 using 3-bromo-2-(piperidin-4-yloxy)pyridine. MS (ESI): mass calcd. for C$_{20}$H$_{20}$FN$_5$O, 365.17; m/z found, 366.0 [M+H]$^+$. $^1$H NMR (400 MHz, DMSO-d$_6$) δ 8.40 (dd, J=2.3, 1.5, 1H), 8.20 (dd, J=4.9, 1.9, 1H), 8.04 (d, J=1.5, 1H), 8.00-7.88 (m, 2H), 7.60-7.52 (m, 2H), 7.15 (dd, J=7.4, 4.9, 1H), 6.73 (s, 2H), 5.45-5.32 (m, 1H), 3.11 (t, J=5.9, 4H), 2.23-2.06 (m, 2H), 2.04-1.83 (m, 2H).

Example 646

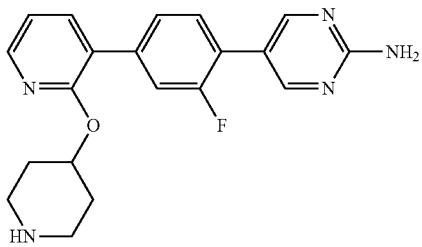

5-{2-Fluoro-4-[2-(piperidin-4-yloxy)pyridin-3-yl]phenyl}pyrimidin-2-amine.

The title compound was prepared in a manner similar to that described in Example 88 using 3-bromo-2-(piperidin-4-yloxy)pyridine and 5-(2-fluoro-4-(4,4,5,5-tetramethyl-1,3,2-dioxaborolan-2-yl)phenyl)pyrimidin-2-amine. MS (ESI): mass calcd. for $C_{20}H_{20}FN_5O$, 365.17; m/z found, 366.0 [M+H]$^+$. $^1$H NMR (400 MHz, DMSO-d$_6$) δ 8.51 (d, J=1.5, 2H), 8.20 (dd, J=4.9, 1.9, 1H), 7.89 (dd, J=7.4, 1.9, 1H), 7.68-7.51 (m, 3H), 7.14 (dd, J=7.4, 4.9, 1H), 6.90 (s, 2H), 5.36 (s, 1H), 3.06 (d, J=11.3, 4H), 2.13 (s, 2H), 1.86 (s, 2H).

Example 647

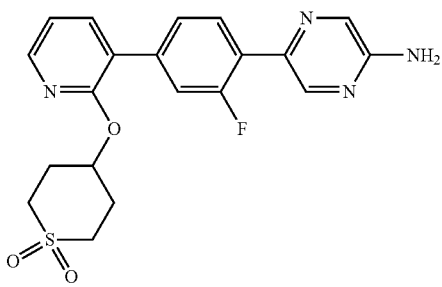

5-(4-{2-[(1,1-Dioxidotetrahydro-2H-thiopyran-4-yl)oxy]pyridin-3-yl}-2-fluorophenyl)pyrazin-2-amine.

The title compound was prepared in a manner similar to that described in Example 88 using 4-((3-bromopyridin-2-yl)oxy)tetrahydro-2H-thiopyran 1,1-dioxide. MS (ESI): mass calcd. for $C_{20}H_{19}FN_4O_3S$, 414.12; m/z found, 415.0 [M+H]$^+$. $^1$H NMR (400 MHz, DMSO-d$_6$) δ 8.40 (s, 1H), 8.21 (dd, J=4.8, 1.6, 1H), 8.04 (s, 1H), 7.99-7.88 (m, 2H), 7.61-7.51 (m, 2H), 7.16 (dd, J=7.4, 5.0, 1H), 6.71 (s, 2H), 5.49-5.38 (m, 1H), 3.21-3.15 (m, 2H), 3.10-2.99 (m, 2H), 2.30 (d, J=5.1, 4H).

Example 648

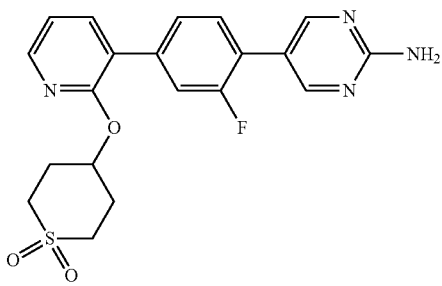

5-(4-[2[(1,1-Dioxidotetrahydro-2H-thiopyran-4-yl)oxy]pyridin-3-yl)-2-fluorophenyl)pyrimidin-2-amine.

The title compound was prepared in a manner similar to that described in Example 88 using 4-((3-bromopyridin-2-yl)oxy)tetrahydro-2H-thiopyran 1,1-dioxide and 5-(2-fluoro-4-(4,4,5,5-tetramethyl-1,3,2-dioxaborolan-2-yl)phenyl)pyrimidin-2-amine. MS (ESI): mass calcd. for $C_{20}H_{19}FN_4O_3S$, 414.12; m/z found, 415.0 [M+H]$^+$. $^1$H NMR (400 MHz, DMSO-d$_6$) b 8.51 (d, J=1.3, 2H), 8.21 (dd, J=4.9, 1.8, 1H), 7.90 (dd, J=7.4, 1.8, 1H), 7.64 (m, 1H), 7.58 (dd, J=12.4, 1.5, 1H), 7.53 (dd, J=8.0, 1.7, 1H), 7.16 (dd, J=7.4, 4.9, 1H), 6.89 (s, 2H), 5.42 (dd, J=6.3, 3.0, 1H), 3.21 (dd, J=14.5, 8.0, 2H), 3.09-3.01 (m, 2H), 2.34-2.24 (m, 4H).

Example 649

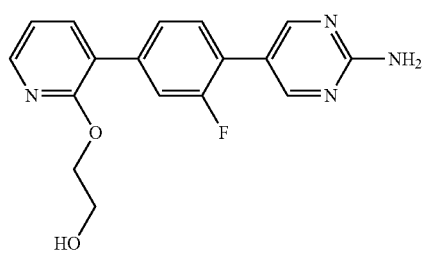

2-({3-[4-(2-Aminopyrimidin-5-yl)-3-fluorophenyl]pyridin-2-yl}oxy)ethanol.

The title compound was prepared in a manner similar to that described in Example 88 using 2-((3-bromopyridin-2-yl)oxy)ethanol and 5-(2-fluoro-4-(4,4,5,5-tetramethyl-1,3,2-dioxaborolan-2-yl)phenyl)pyrimidin-2-amine. MS (ESI): mass calcd. for $C_{17}H_{15}FN_4O_2$, 326.12; m/z found, 326.9 [M+H]$^+$. $^1$H NMR (400 MHz, DMSO-d$_6$) δ 8.47 (d, J=1.3, 2H), 8.15 (dd, J=4.9, 1.8, 1H), 7.84 (dd, J=7.4, 1.8, 1H), 7.65-7.52 (m, 3H), 7.08 (dd. J=7.4, 5.0, 1H), 6.87 (s, 2H), 4.80 (s, 1H), 4.40-4.32 (m, 2H), 3.70 (t, J=5.0, 2H).

Example 650

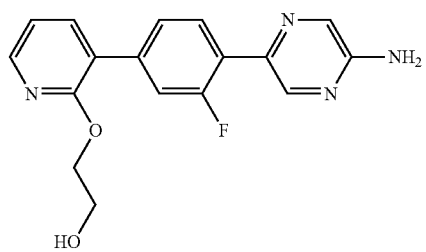

2-({3-[4-(5-Aminopyrazin-2-yl)-3-fluorophenyl]pyridin-2-yl}oxy)ethanol.

The title compound was prepared in a manner similar to that described in Example 88 using 2-((3-bromopyridin-2-yl)oxy)ethanol. MS (ESI): mass calcd. for $C_{17}H_{15}FN_4O_2$, 326.12; m/z found, 327.0 [M+H]$^+$. $^1$H NMR (400 MHz, DMSO-d$_6$) δ 8.36 (d, J=1.6, 1H), 8.15 (dd, J=4.9, 1.8, 1H), 8.00 (d, J=1.4, 1H), 7.93-7.83 (m, 2H), 7.58 (m, 2H), 7.08 (dd, J=7.4, 4.9, 1H), 6.68 (s, 2H), 4.80 (s, 1H), 4.39-4.34 (m, 2H), 3.70 (d, J=4.5, 2H).

Example 651

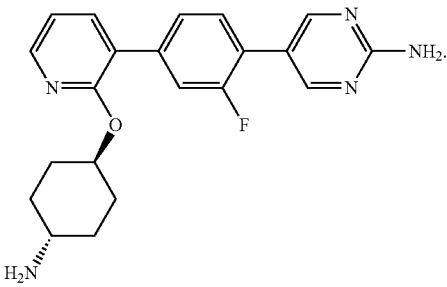

5-(4-{2-[(trans-4-Aminocyclohexyl)oxy]pyridin-3-yl}-2-fluorophenyl)pyrimidin-2-amine The title compound was prepared in a manner similar to that described in Example 88 using trans-4-((3-bromopyridin-2-yl)oxy)cyclohexanamine and 5-(2-fluoro-4-(4,4,5,5-tetramethyl-1,3,2-dioxaborolan-2-yl)phenyl)pyrimidin-2-amine. MS (ESI): mass calcd. for $C_{21}H_{22}FN_5O$, 379.18; m/z found, 380.1 [M+H]$^+$. $^1$H NMR (400 MHz, DMSO-d$_6$) δ 8.47 (d, J=1.1, 2H), 8.15 (dd, J=4.9, 1.7, 1H), 7.81 (dd, J=7.4, 1.7, 1H), 7.53 (m, 3H), 7.05 (dd, J=7.4, 5.0, 1H), 6.87 (s, 2H), 5.02 (m, 1H), 2.63 (m, 1H), 2.05 (m, 2H), 1.77 (m, 2H), 1.39 (m, 2H), 1.18 (m, 4H).

Example 652

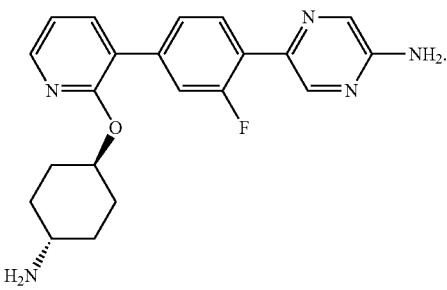

5-(4-{2-[(trans-4-Aminocyclohexyl)oxy]pyridin-3-yl}-2-fluorophenyl)pyrazin-2-amine formic acid salt The title compound was prepared in a manner similar to that described in Example 88 using trans-4-((3-bromopyridin-2-yl)oxy)cyclohexanamine. MS (ESI): mass calcd. for $C_{21}H_{22}FN_5O$, 379.18; m/z found, 380.1 [M+H]$^+$. $^1$H NMR (400 MHz, DMSO-d$_6$) δ 8.42 (s, 1H), 8.36 (d, J=1.9, 1H), 8.15 (dd, J=4.9, 1.8, 1H), 8.00 (d, J=1.4, 1H), 7.88 (m, 1H), 7.83 (dd, J=7.4, 1.9, 1H), 7.53-7.49 (m, 1H), 7.48 (s, 1H), 7.06 (dd, J=7.4, 4.9, 1H), 6.70 (s, 2H), 5.02 (m, 1H), 2.89 (s, 1H), 2.10 (m, 2H), 1.89 (m, 2H), 1.45-1.33 (m, 4H).

Example 653

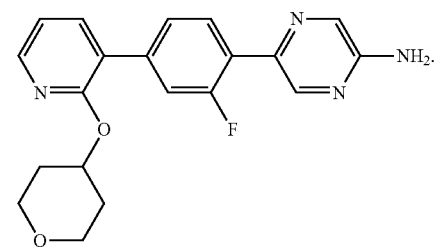

5-{2-Fluoro-4-[2-tetrahydro-2H-pyran-4-yloxy)pyridin-3-yl]phenyl}pyrazin-2-amine The title compound was prepared in a manner similar to that described in Example 88 using 3-bromo-2-((tetrahydro-2H-pyran-4-yl)oxy)pyridine. MS (ESI): mass calcd. for $C_{20}H_{19}FN_4O_2$, 366.15; m/z found, 367.1 [M+H]$^+$. $^1$H NMR (400 MHz, DMSO-d$_6$) δ 8.38-8.31 (m, 1H), 8.15 (dd, J=4.9, 1.9, 1H), 8.00 (d, J=1.5, 1H), 7.94-7.83 (m, 2H), 7.57-7.48 (m, 2H), 7.07 (dd, J=7.4, 4.9, 1H), 6.68 (s, 2H), 5.38-5.23 (m, 1H), 3.83-3.68 (m, 2H), 3.50 (m, 2H), 1.98 (d, J=7.5, 2H), 1.71-1.54 (m, 2H).

Example 654

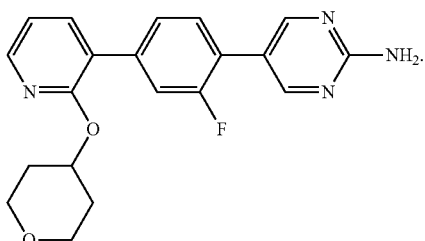

5-{2-Fluoro-4-[2-tetrahydro-2H-pyran-4-yloxy)pyridin-3-yl]phenyl}pyrimidin-2-amine The title compound was prepared in a manner similar to that described in Example 88 using 3-bromo-2-((tetrahydro-2H-pyran-4-yl)oxy)pyridine and 5-(2-fluoro-4-(4,4,5,5-tetramethyl-1,3,2-dioxaborolan-2-yl)phenyl)pyrimidin-2-amine. MS (ESI): mass calcd. for $C_{20}H_{19}FN_4O_2$, 366.15; m/z found, 367.1 [M+H]$^+$. $^1$H NMR (400 MHz, DMSO-d$_6$) b 8.47 (d, J=1.5, 2H), 8.15 (dd, J=4.9, 1.9, 1H), 7.84 (dd, J=7.4, 1.9, 1H), 7.64-7.48 (m, 3H), 7.07 (dd, J=7.4, 4.9, 1H), 6.86 (s, 2H), 5.30 (m, 1H), 3.81-3.72 (m, 2H), 3.49 (m, 2H), 1.98 (m, 2H), 1.70-1.55 (m, 2H).

Example 655

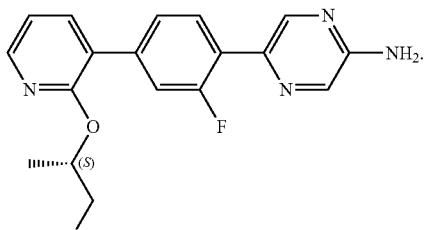

(2R)-2-({3-[4-(5-Aminopyrazin-2-yl)-3-fluorophenyl]pyridin-2-yl}oxy)propan-1-ol

The title compound was prepared in a manner similar to that described in Example 88 using (R)-2-((3-bromopyridin-2-yl)oxy)propan-1-ol. MS (ESI): mass calcd. for $C_{18}H_{17}FN_4O_2$, 340.13; m/z found, 341.0 [M+H]$^+$. $^1$H NMR (400 MHz, DMSO-d$_6$) δ 8.41-8.35 (m, 1H), 8.17 (dd, J=4.9, 1.8, 1H), 8.03 (d, J=1.4, 1H), 7.94-7.84 (m, 2H), 7.66-7.55 (m, 2H), 7.09 (dd, J=7.4, 4.9, 1H), 6.71 (s, 2H), 5.35-5.23 (m, 1H), 4.86 (t, J=5.4, 1H), 3.62-3.51 (m, 2H), 1.25 (d, J=6.3, 3H).

Example 656

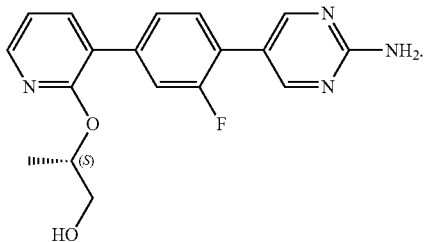

(2R)-2-({3-[4-(2-Aminopyrimidin-5-yl)-3-fluorophenyl]pyridin-2-yl}oxy)propan-1-ol The title compound was prepared in a manner similar to that described in Example 88 using (R)-2-((3-bromopyridin-2-yl)oxy)propan-1-ol and 5-(2-fluoro-4-(4,4,5,5-tetramethyl-1,3,2-dioxaborolan-2-yl)phenyl)pyrimidin-2-amine. MS (ESI): mass calcd. for $C_{18}H_{17}FN_4O_2$, 340.13; m/z found, 340.9 [M+H]$^+$. $^1$H NMR (400 MHz, DMSO-d$_6$) b 8.50 (d, J=1.4, 2H), 8.17 (dd, J=4.9, 1.9, 1H), 7.85 (dd, J=7.4, 1.9, 1H), 7.67-7.54 (m, 3H), 7.09 (dd, J=7.4, 4.9, 1H), 6.89 (s, 2H), 5.35-5.23 (m, 1H), 4.86 (t, J=5.4, 1H), 3.62-3.51 (m, 2H), 1.25 (d, J=6.3, 3H).

Example 657

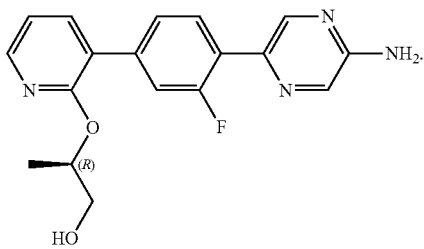

(2S)-2-({3-[4-(5-Aminopyrazin-2-yl)-3-fluorophenyl]pyridin-2-yl}oxy)propan-1-ol

The title compound was prepared in a manner similar to that described in Example 88 using (S)-2-((3-bromopyridin-2-yl)oxy)propan-1-ol. MS (ESI): mass calcd. for $C_{18}H_{17}FN_4O_2$, 340.13; m/z found, 341.0 [M+H]$^+$. $^1$H NMR (400 MHz, DMSO-d$_6$) δ 8.38-8.32 (m, 1H), 8.14 (dd. J=4.9, 1.9, 1H), 8.00 (d, J=1.5, 1H), 7.91-7.80 (m, 2H), 7.64-7.52 (m, 2H), 7.05 (dd, J=7.4, 4.9, 1H), 6.68 (s, 2H), 5.32-5.22 (m, 1H), 4.82 (t, J=5.3, 1H), 3.58-3.48 (m, 2H), 1.22 (d, J=6.3, 3H).

Example 658

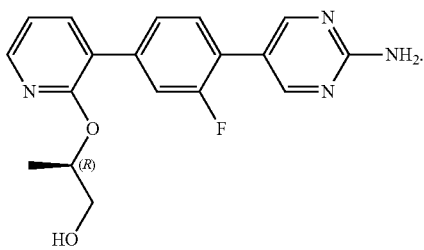

(2I)-2-({3-[4-(2-Aminopyrimidin-5-yl)-3-fluorophenyl]pyridin-2-yl}oxy)propan-1-ol The title compound was prepared in a manner similar to that described in Example 88 using (S)-2-((3-bromopyridin-2-yl)oxy)propan-1-ol and 5-(2-fluoro-4-(4,4,5,5-tetramethyl-1,3,2-dioxaborolan-2-yl)phenyl)pyrimidin-2-amine. MS (ESI): mass calcd. for $C_{18}H_{17}FN_4O_2$, 340.13; m/z found, 341.0 [M+H]$^+$. $^1$H NMR (400 MHz, DMSO-d$_6$) b 8.47 (d, J=1.2, 2H), 8.14 (dd, J=4.9, 1.8, 1H), 7.82 (dd, J=7.4, 1.8, 1H), 7.64-7.52 (m, 3H), 7.05 (dd, J=7.4, 4.9, 1H), 6.86 (s, 2H), 5.34-5.21 (m, 1H), 4.83 (s, 1H), 3.58-3.47 (m, 2H), 1.22 (d, J=6.3, 3H).

Example 659

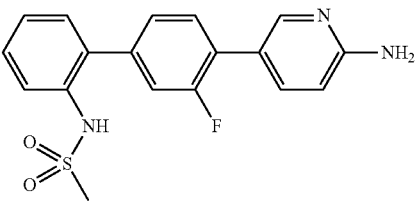

N-(4'-(6-Aminopyridin-3-yl)-3'-fluoro-[1,1'-biphenyl]-2-yl)methanesulfonamide

The title compound was prepared in a manner similar to that described in Example 341 using (2-(methylsulfonamido)phenyl)boronic acid in Step B. MS (Cl): mass calcd. for $C_{18}H_{16}FN_3O_2S$, 357.09; m/z found, 358.2 [M+H]$^+$. $^1$H NMR (500 MHz, DMSO-d$_6$) δ 14.69-13.78 (m, 1H), 9.21-9.14 (s, 1H), 8.52-8.10 (m, 5H), 7.72-7.63 (m, 1H), 7.52-7.36 (m, 10H), 7.18-7.10 (d, J=9.3, 1H), 2.90-2.80 (s, 3H).

Example 660

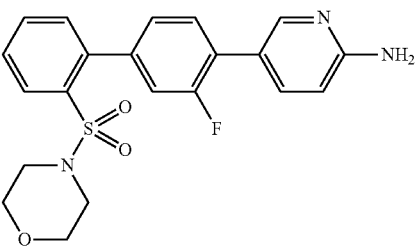

5-(3-Fluoro-2'-(morpholinosulfonyl)-[1,1'-biphenyl]-4-yl)pyridin-2-amine

The title compound was prepared in a manner similar to that described in Example 341 using (2-(morpholinosulfonyl)phenyl)boronic acid in Step B. MS (Cl): mass calcd. for $C_{21}H_{20}FN_3O_3S$, 413.12; m/z found, 414.1 [M+H]$^+$. $^1$H NMR (500 MHz, DMSO-d$_6$) δ 8.20-8.13 (s, 1H), 8.05-7.98 (m, 1H), 7.81-7.73 (m, 1H), 7.70-7.60 (m, 3H), 7.57-7.50 (m, 1H), 7.49-7.45 (dd, J=7.6, 1.2, 1H), 7.36-7.29 (dd, J=12.0, 1.6, 1H), 7.29-7.24 (m, 1H), 6.59-6.52 (d, J=8.5, 1H), 6.26-6.14 (s, 2H), 3.44-3.36 (m, 5H), 2.82-2.72 (m, 5H).

Example 661

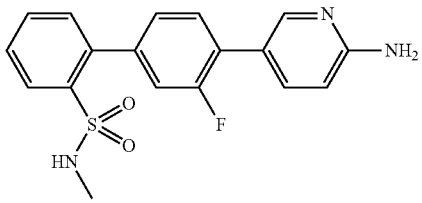

4'-(6-Aminopyridin-3-yl)-3'-fluoro-N-methyl-[1,1'-biphenyl]-2-sulfonamide

The title compound was prepared in a manner similar to that described in Example 341 using (2-(N-methylsulfamoyl)phenyl)boronic acid in Step B. MS (CI): mass calcd. for $C_{18}H_{16}FN_3O_2S$, 357.09; m/z found, 358.0 [M+H]$^+$. $^1$H NMR (500 MHz, acetone-d$_6$) δ 8.29-8.20 (s, 1H), 7.73-7.28 (m, 9H), 6.72-6.65 (m, 1H), 5.74-5.53 (d, J=8.2, 2H), 3.01-2.93 (s, 3H).

Example 662

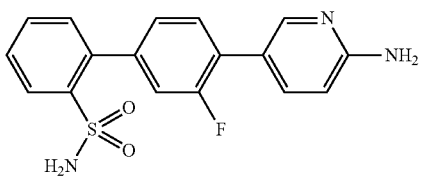

4'-(6-Aminopyridin-3-yl)-3'-fluoro-[1,1'-biphenyl]-2-sulfonamide trifluoroacetate A mixture of 4'-(6-aminopyridin-3-yl)-N-(tert-butyl)-3'-fluoro-[1,1'-biphenyl]-2-sulfonamide (55 mg, 0.14 mmol) and TFA (1 mL) was heated to 50° Celsius for 1.5 h. The mixture was cooled to rt and diluted with ether (10 mL. The resulting precipitate was collected via filtration and dried to provide the title compound. MS (CI): mass calcd. for $C_{17}H_{14}FN_3O_2S$, 343.08; m/z found, 344.1 [M+H]$^+$. $^1$H NMR (500 MHz, DMSO-d$_6$) δ 8.29-7.90 (m, 4H), 7.70-7.58 (m, 4H), 7.46-7.30 (m, 6H), 7.14-7.04 (d, J=9.2, 1H).

Example 663

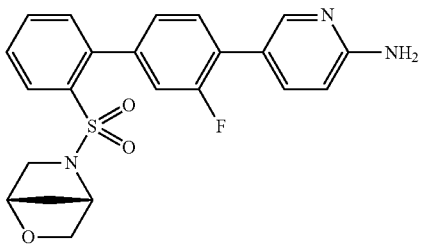

5-(2'-((1S,4S)-2-Oxa-5-azabicyclo[2.2.1]heptan-5-ylsulfonyl)-3-fluoro-[1,1'-biphenyl]-4-yl)pyridin-2-amine The title compound was prepared in a manner similar to that described in Example 347 using (1S,4S)-5-((2-bromophenyl)sulfonyl-2-oxa-5-azabicyclo[2.2.1]heptane. MS (CI): mass calcd. for $C_{21}H_{19}FN_4O_3S$, 426.12; m/z found, 427.0 [M+H]$^+$. $^1$H NMR (500 MHz, DMSO-d) δ 8.20-8.13 (s, 1H), 8.05-7.98 (m, 1H), 7.81-7.73 (m, 1H), 7.70-7.60 (m, 3H), 7.57-7.50 (m, 1H), 7.49-7.45 (dd, J=7.6, 1.2, 1H), 7.36-7.29 (dd, J=12.0, 1.6, 1H), 7.29-7.24 (m, 1H), 6.59-6.52 (d, J=8.5, 1H), 6.26-6.14 (s, 2H), 3.44-3.36 (m, 5H), 2.82-2.72 (m, 5H).

Example 664

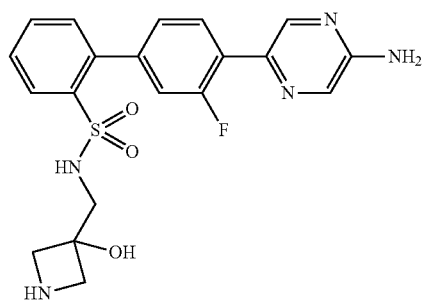

4'-(6-Aminopyrazin-2-yl)-3'-fluoro-N-((3-hydroxyazetidin-3-yl)methyl)-[1,1'-biphenyl]-2-sulfonamide The title compound was prepared in a manner similar to that described in Example 347 using 2-bromo-N-((3-hydroxyazetidin-3-yl)methyl)benzenesulfonamide. MS (CI): mass calcd. for $C_{20}H_{20}FN_5O_3S$, 429.13; m/z found, 430.0 [M+H]$^+$. $^1$H NMR (500 MHz, DMSO-d$_6$) δ 8.79-8.64 (s, 1H), 8.63-8.51 (s, 1H), 8.43-8.37 (m, 1H), 8.06-8.02 (d, J=1.5, 1H), 8.00-7.94 (m, 1H), 7.94-7.87 (m, 1H), 7.84-7.77 (m, 1H), 7.75-7.69 (m, 1H), 7.69-7.63 (m, 1H), 7.49-7.43 (m, 1H), 7.36-7.27 (m, 2H), 6.89-6.55 (s, 2H), 6.36-6.08 (s, 1H), 3.93-3.88 (m, 2H), 3.72-3.70 (m, 2H), 3.04-2.97 (d, J=6.5, 2H).

Example 665

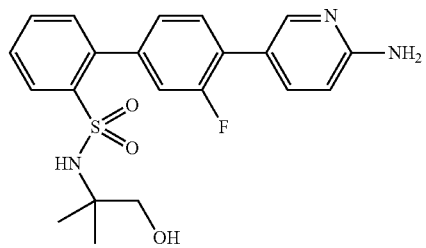

4'-(6-Aminopyridin-3-yl)-3'-fluoro-N-(1-hydroxy-2-methylpropan-2-yl)-[1,1'-biphenyl]-2-sulfonamide The title compound was prepared in a manner similar to that described in Example 347 using 2-bromo-N-(1-hydroxy-2-methylpropan-2-yl)benzenesulfonamide. MS (CI): mass calcd. for $C_{21}H_{22}FN_3O_3S$, 415.14; m/z found, 418.0 (off) [M+H]$^+$. $^1$H NMR (400 MHz, DMSO-d$_6$) δ 8.30-7.97 (m, 5H), 7.71-7.57 (m, 3H), 7.42-7.29 (m, 3H), 7.12-7.06 (d, J=9.2, 1H), 6.70-6.63 (s, 1H), 3.20-3.13 (s, 2H), 1.00-0.92 (s, 6H).

Example 666

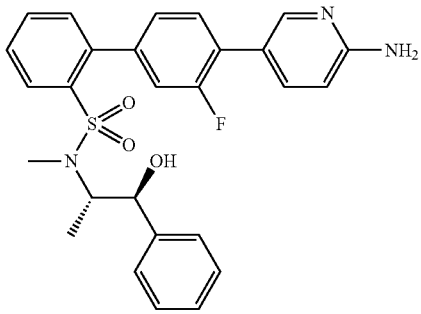

4'-(6-Aminopyridin-3-yl)-3'-fluoro-N-((1S,2S)-1-hydroxy-1-phenylpropan-2-yl)-N-methyl-[1-1'-biphenyl]-2-sulfonamide The title compound was prepared in a manner similar to that described in Example 347 using 2-bromo-N-((1S,2S)-1-hydroxy-1-phenylpropan-2-yl)-N-methylbenzenesulfonamide. MS (Cl): mass calcd. for $C_{21}H_{22}FN_3O_3S$, 494.17; m/z found, 494.1 [M+H]$^+$. $^1$H NMR (500 MHz, CD$_3$OD) δ 8.27-8.21 (d, J=9.5, 1H), 8.17-8.10 (m, 2H), 7.72-7.65 (m, 1H), 7.65-7.54 (m, 2H), 7.41-7.34 (m, 3H), 7.33-7.24 (m, 5H), 7.19-7.12 (d, J=9.3, 1H), 4.57-4.49 (d, J=8.4, 1H), 3.97-3.86 (m, 1H), 2.63-2.52 (s, 3H), 0.94-0.61 (d, J=6.9, 3H).

Example 667

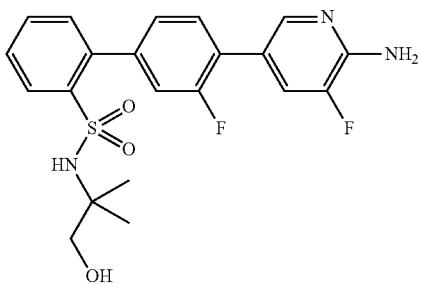

4'-(6-Amino-5-fluoropyridin-3-yl)-3'-fluoro-N-(1-hydroxy-2-methylpropan-2-yl)-[1-1'-biphenyl]-2-sulfonamide

Step A: (4-(6-Amino-5-fluoropyridin-3-yl)-3-fluorophenyl)boronic acid

A mixture of 4-chloro-2-fluorophenylboronic acid (820 mg, 4.70 mmol), 2-amino-3-fluoro-5-bromopyrazine (900 mg, 4.70 mmol), palladium trifluoroacetate (31 mg, 0.094 mmol), triphenylphosphine (49 mg, 0.19 mmol), toluene (15 mL), EtOH (15 mL), and Na$_2$CO$_3$ (9 mL, 2 M) was deoxygenated by sparging with nitrogen. The mixture was then heated at 50° Celsius while stirring for 16 h. The mixture was then cooled to rt and diluted with EtOAc. The mixture was filtered and the filtrate transferred to a separatory funnel. The organic phase was isolated, and the aqueous phase extracted with EtOAc. The combined organic extracts were washed with brine, dried over Na$_2$SO$_4$, concentrated to dryness, and subjected to FCC to give 5-(4-chloro-2-fluorophenyl)-3-fluoropyridin-2-amine (980 mg). This material was combined with bis(pinacolato)diboron (1.03 g, 4.94 mmol) and chloro(2-dicyclohexylphosphino-2',4',6'-triisopropyl-1,1'-biphenyl)[2-(2-aminoethyl)phenyl)]palladium (II) (62 mg, 0.079 mmol) and anhydrous potassium acetate (1.06 g, 11.8 mmol) in a sealable vessel under nitrogen. Deoxygenated 1,4-dioxane (150 mL) was added, and the reaction vessel sealed and heated at 60° Celsius for 16 h. The mixture was cooled to rt, diluted with EtOAc, and filtered through a pad of silica gel, and concentrated to give a brown residue. This material was taken up in HCl (40 mL, 1 M) and MeOH (ca. 5 mL), and any insoluble material was removed by filtration. The resulting solution was treated with solid NaHCO$_3$ to achieve pH 7. The precipitate was collected and dried to give 4-(6-amino-5-fluoropyridin-3-yl)-3-fluorophenyl)boronic acid (968 mg, 84%). MS (Cl): mass calcd. for $C_{11}H_9BF_2N_2O_2$, 250.01; m/z found, 252.0 [M+H]$^+$.

Step B: 4'-(6-Amino-5-fluoropyridin-3-yl)-3'-fluoro-N-(1-hydroxy-2-methylpropan-2-yl)-[1,1'-biphenyl]-2-sulfonamide, trifluoroacetate salt A mixture of 4-(6-amino-5-fluoropyridin-3-yl)-3-fluorophenyl)boronic acid (80 mg, 0.32 mmol), 2-bromo-N-(1-hydroxy-2-methylpropan-2-yl)benzenesulfonamide (118 mg, 0.380 mmol), Pd(dppf)Cl$_2$·CH$_2$Cl$_2$ (12 mg, 0.016 mmol), K$_2$CO$_3$ (0.80 mL, 1.6 mmol, 2 M), and 1,4-dioxane (2 mL) was deoxygenated by sparging with nitrogen for 10 min, then heated at 80° Celsius for 16 h. The mixture was filtered using a syringe filter and directly subjected to HPLC purification to provide the title compound (74 mg, 42%). MS (Cl): mass calcd. for $C_{21}H_{21}F_2N_3O_3S$, 433.13; m/z found, 435.0 [M+H]$^+$. $^1$H NMR (500 MHz, DMSO-do) δ 8.13-8.04 (m, 2H), 7.80-7.73 (d, J=12.3, 1H), 7.69-7.64 (m, 1H), 7.64-7.56 (m, 2H), 7.40-7.36 (m, 1H), 7.36-7.31 (m, 1H), 7.31-7.26 (m, 1H), 6.62-6.55 (s, 1H), 3.19-3.11 (s, 2H), 1.01-0.87 (s, 6H).

Example 668

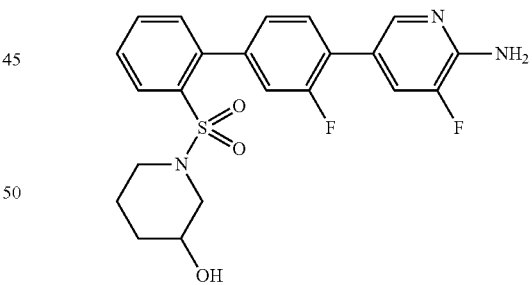

(racemic)-1-((4'-(6-Amino-5-fluoropyridin-3-yl)-3'-fluoro-[1,1'-biphenyl]-2-yl)sulfonyl)piperidin-3-ol The title compound was prepared in a manner similar to that described in Example 676 using (racemic)-1-((2-bromophenyl)sulfonyl)piperidin-3-ol in Step B. MS (Cl): mass calcd. for $C_{22}H_{21}F_2N_3O_3S$, 445.13; m/z found, 448.0 [M+H]$^+$. $^1$H NMR (500 MHz, CD$_3$OD) δ 8.11-8.06 (m, 1H), 8.06-7.98 (m, 2H), 7.74-7.68 (m, 1H), 7.66-7.55 (m, 2H), 7.44-7.39 (m, 1H), 7.36-7.29 (m, 2H), 3.45-3.36 (m, 1H), 1.71-1.62 (m, 1H), 3.30-3.23 (m, 1H), 3.17-3.09 (d, J=12.7, 1H), 2.52-2.42 (m, 1H), 2.30-2.21 (dd, J=12.0, 9.1, 1H), 1.91-1.81 (m, 1H), 1.43-1.31 (m, 1H), 1.28-1.17 (m, 1H).

Example 669

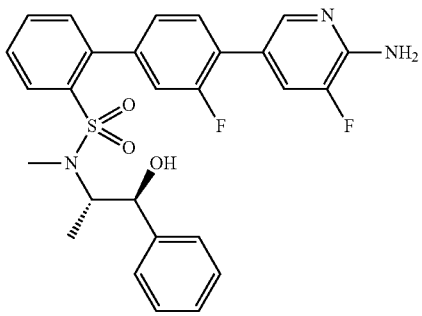

4'-(6-Amino-5-fluoropyridin-3-yl)-3'-fluoro-N-((1S,2S)-1-hydroxy-1-phenylpropan-2-yl)-N-methyl-[1,1'-biphenyl]-2-sulfonamide The title compound was prepared in a manner similar to that described in Example 676 using 2-bromo-N-((1S,2S)-1-hydroxy-1-phenylpropan-2-yl)-N-methylbenzenesulfonamide in Step B. MS (CI): mass calcd. for $C_{27}H_{25}F_2N_3O_3S$, 509.16; m/z found, 510.0 [M+H]$^+$. $^1$H NMR (500 MHz, CD$_3$OD) δ 8.15-8.09 (m, 1H), 8.04-7.95 (m, 2H), 7.69-7.63 (m, 1H), 7.62-7.52 (m, 2H), 7.38-7.22 (m, 8H), 4.55-4.45 (d, J=8.4, 1H), 3.95-3.81 (m, 1H), 2.59-2.49 (s, 3H), 0.79-0.70 (d, J=6.9, 3H).

Example 670

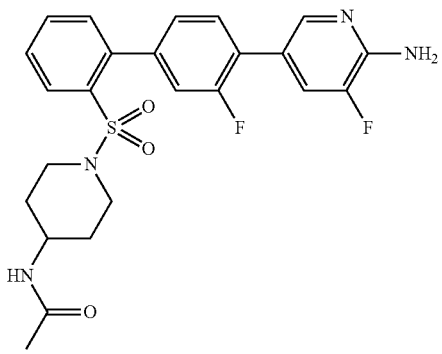

N-(1-((4'-(6-Amino-5-fluoropyridin-3-yl)-3'-fluoro-[1,1'-biphenyl]-2-yl)sulfonyl)piperidin-4-yl)acetamide The title compound was prepared in a manner similar to that described in Example 676 using N-(1-((2-bromophenyl)sulfonyl)piperidin-4-yl)acetamide in Step B. MS (CI): mass calcd. for $C_{24}H_{24}F_2N_4O_3S$, 486.15; m/z found, 487.1 [M+H]$^+$. $^1$H NMR (500 MHz, CD$_3$OD) δ 8.11-8.01 (m, 3H), 7.74-7.67 (m, 1H), 7.65-7.57 (m, 2H), 7.43-7.38 (m, 1H), 7.36-7.28 (m, 2H), 3.68-3.57 (m, 1H), 3.38-3.32 (d, J=13.1, 2H), 2.58-2.48 (m, 2H), 1.90-1.86 (s, 3H), 1.78-1.69 (m, 2H), 1.38-1.25 (m, 2H).

Example 671

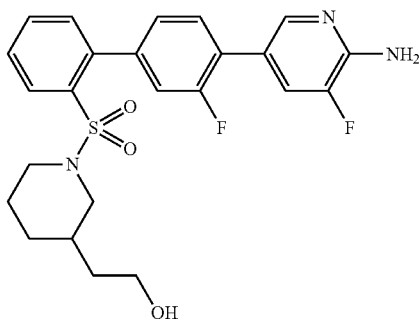

racemic 2-(1-((4'-(6-Amino-5-fluoropyridin-3-yl)-3'-fluoro-[1,1'-biphenyl]-2-yl)sulfonyl)piperidin-3-yl)ethanol.

The title compound was prepared in a manner similar to that described in Example 676 using racemic 2-(1-((2-bromophenyl)sulfonyl)piperidin-3-yl)ethanol in Step B. MS (CI): mass calcd. for $C_{24}H_{25}F_2N_3O_3S$, 473.16; m/z found, 474.1 [M+H]$^+$. $^1$H NMR (500 MHz, CD$_3$OD) δ 8.12-7.99 (m, 3H), 7.73-7.67 (m, 1H), 7.65-7.55 (m, 2H), 7.43-7.38 (m, 1H), 7.38-7.30 (m, 2H), 3.51-3.45 (m, 2H), 3.28-3.21 (m, 2H), 2.48-2.40 (m, 1H), 2.18-2.10 (m, 1H), 1.78-1.69 (m, 1H), 1.65-1.55 (m, 1H), 1.54-1.43 (m, 1H), 1.42-1.27 (m, 3H), 1.04-0.89 (m, 1H).

Example 672

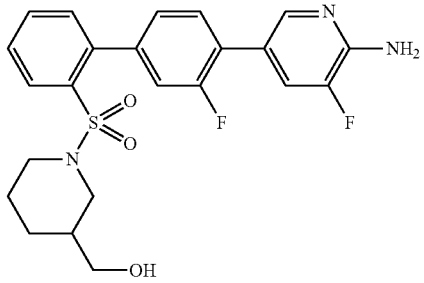

racemic (1-((4'-(6-Amino-5-fluoropyridin-3-yl)-3'-fluoro-[1,1'-biphenyl]-2-yl)sulfonyl)piperidin-3-yl)methanol.

The title compound was prepared in a manner similar to that described in Example 676 using racemic 2-(1-((2-bromophenyl)sulfonyl)piperidin-3-yl)methanol in Step B. MS (CI): mass calcd. for $C_{23}H_{23}F_2N_3O_3S$, 459.14; m/z found, 460.1 [M+H]$^+$. $^1$H NMR (500 MHz, CD$_3$OD) δ 8.11-8.00 (m, 3H), 7.73-7.68 (m, 1H), 7.66-7.55 (m, 2H), 7.45-7.30 (m, 3H), 3.45-3.39 (m, 1H), 3.38-3.34 (dd, J=11.0, 5.2, 1H), 3.29-3.24 (d, J=11.7, 1H), 3.24-3.18 (dd, J=11.0, 7.7, 1H), 2.47-2.38 (m, 1H), 2.23-2.14 (m, 1H), 1.68-1.56 (m, 2H), 1.55-1.43 (m, 1H), 1.39-1.26 (m, 1H), 1.04-0.92 (m, 1H).

Example 673

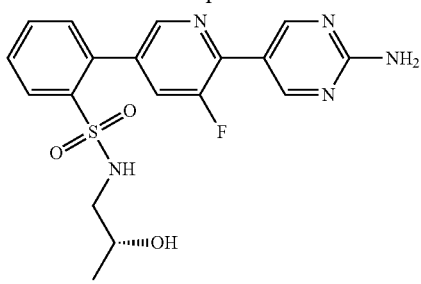

2-[6-(2-Aminopyrimidin-5-yl)-5-fluoropyridin-3-yl]-N-[(2R)-2-hydroxypropyl]benzenesulfonamide.

The title compound was prepared in a manner similar to that described in Example 427 using (6-(2-aminopyrimidin-5-yl)-5-fluoropyridin-3-yl)boronic acid and (R)-2-bromo-N-(2-hydroxypropyl)benzenesulfonamide. MS (ESI): mass calcd. for $C_{18}H_{18}FN_5O_3S$, 403.11; m/z found, 404.1 [M+H]+. 1H NMR (500 MHz, CD3OD) δ 9.02 (d, J=0.8, 2H), 8.52-8.47 (m, 1H), 8.09 (dd, J=7.9, 1.4, 1H), 7.81 (dd, J=11.9, 1.8, 1H), 7.72 (m, 1H), 7.66 (m, 1H), 7.46 (dd, J=7.5, 1.4, 1H), 3.74-3.59 (m, 1H), 2.84-2.66 (m, 2H), 1.06 (d, J=6.3, 3H).

Example 674

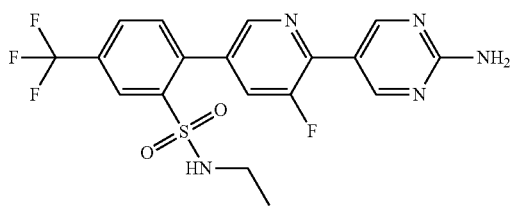

2-[6-(2-Aminopyrimidin-5-yl)-5-fluoropyridin-3-yl]-N-ethyl-5-(trifluoromethyl)benzenesulfonamide.

The title compound was prepared in a manner similar to that described in Example 427 using (6-(2-aminopyrimidin-5-yl)-5-fluoropyridin-3-yl)boronic acid and 2-bromo-N-ethyl-5-(trifluoromethyl)benzenesulfonamide. MS (ESI): mass calcd. for $C_{18}H_{15}F_4N_5O_2S$, 441.09; m/z found, 442.0 [M+H]+. 1H NMR (400 MHz, CD3OD) δ 8.94 (d, J=1.1, 2H), 8.51-8.46 (m, 1H), 8.37-8.31 (m, 1H), 8.03 (dd, J=8.1, 1.9, 1H), 7.81 (dd, J=11.9, 1.8, 1H), 7.68 (d, J=7.9, 1H), 2.86 (q, J=7.3, 2H), 1.02 (t, J=7.2, 3H).

Example 675

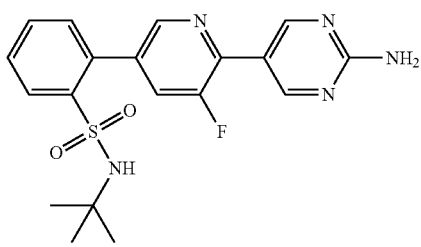

2-[6-(2-Aminopyrimidin-5-yl)-5-fluoropyridin-3-yl]-N-tert-butylbenzenesulfonamide.

The title compound was prepared in a manner similar to that described in Example 427 using (2-(N-(tert-butyl)sulfamoyl)phenyl)boronic acid and 5-(5-chloro-3-fluoropyridin-2-yl)pyrimidin-2-amine. MS (ESI): mass calcd. for $C_{19}H_{20}FN_5O_2S$, 401.13; m/z found, 402.1 [M+H]+. 1H NMR (400 MHz, CD3OD) δ 8.97 (d, J=1.1, 2H), 8.50-8.44 (m, 1H), 8.17 (dd, J=8.0, 1.3, 1H), 7.79 (dd, J=12.0, 1.8, 1H), 7.70 (m, 1H), 7.63 (m, 1H), 7.43 (dd, J=7.5, 1.5, 1H), 1.09 (s, 9H).

Example 676

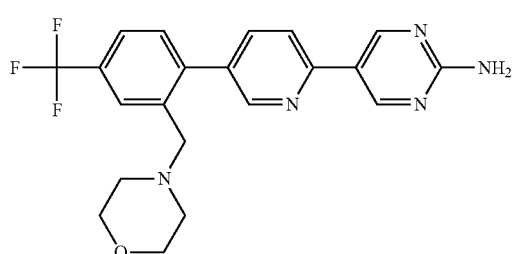

5-{5-[2-(Morpholin-4-ylmethyl)-4-(trifluoromethyl)phenyl]pyridin-2-yl}pyrimidin-2-amine.

The title compound was prepared in a manner similar to that described in Example 427 using 5-(5-(4,4,5,5-tetramethyl-1,3,2-dioxaborolan-2-yl)pyridin-2-yl)pyrimidin-2-amine and 4-(2-bromo-5-(trifluoromethyl)benzyl)morpholine. MS (ESI): mass calcd. for $C_{21}H_{20}F_3N_5O$, 415.16; m/z found, 416.0 [M+H]+. 1H NMR (500 MHz, CD3OD) δ 8.96 (s, 2H), 8.67 (dd, J=2.3, 0.9, 1H), 7.97 (dd, J=8.2, 2.3, 1H), 7.89 (dd, J=8.2, 0.9, 1H), 7.86-7.84 (m, 1H), 7.72-7.65 (m, 1H), 7.52 (d, J=7.9, 1H), 3.63-3.58 (m, 4H), 3.54-3.48 (m, 2H), 2.41-2.28 (m, 4H).

Example 677

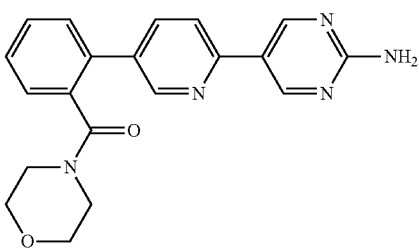

5-{5-[2-(Morpholin-4-ylcarbonyl)phenyl]pyridin-2-yl}pyrimidin-2-amine.

The title compound was prepared in a manner similar to that described in Example 427 using 5-(5-(4,4,5,5-tetramethyl-1,3,2-dioxaborolan-2-yl)pyridin-2-yl)pyrimidin-2-amine and (2-bromophenyl)(morpholino)methanone. MS (ESI): mass calcd. for $C_{20}H_{19}N_5O_2$, 361.15; m/z found, 362.1 [M+H]+. 1H NMR (500 MHz, CD3OD) δ 8.96 (s, 2H), 8.69-8.64 (m, 1H), 7.95-7.87 (m, 2H), 7.64-7.59 (m, 1H), 7.58-7.51 (m, 2H), 7.49-7.42 (m, 1H), 3.69-3.54 (m, 3H), 3.48-3.33 (m, 2H), 3.20-3.07 (m, 1H), 2.97-2.80 (m, 2H).

Example 678

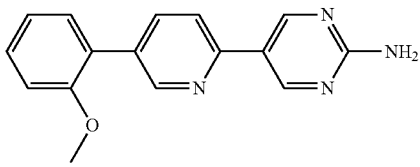

5-[5-(2-Methoxyphenyl)pyridin-2-yl]pyrimidin-2-amine.

The title compound was prepared in a manner similar to that described in Example 427 using 5-(5-(4,4,5,5-tetramethyl-1,3,2-dioxaborolan-2-yl)pyridin-2-yl)pyrimidin-2-amine and 1-bromo-2-methoxybenzene. MS (ESI): mass calcd. for $C_{16}H_{14}N_4O \cdot C_2HF_3O_2$, 278.12; m/z found, 279.1 [M+H]$^+$. $^1$H NMR (400 MHz, CD$_3$OD) δ 9.00 (s, 2H), 8.81 (d, J=2.2, 1H), 8.28 (dd, J=8.4, 2.2, 1H), 8.02 (d, J=8.4, 1H), 7.48-7.41 (m, 2H), 7.16 (d, J=8.4, 1H), 7.11 (m, 1H), 3.87 (s, 3H).

Example 679

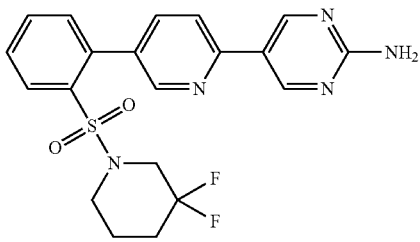

5-(5-{2-[(3,3-Difluoropiperidin-1-yl)sulfonyl]phenyl}pyridin-2-yl)pyrimidin-2-amine trifluoroacetic acid salt.

The title compound was prepared in a manner similar to that described in Example 427 using 5-(5-(4,4,5,5-tetramethyl-1,3,2-dioxaborolan-2-yl)pyridin-2-yl)pyrimidin-2-amine and 1-((2-bromophenyl)sulfonyl)-3,3-difluoropiperidine. MS (ESI): mass calcd. for $C_{20}H_{19}F_2N_5O_2S$, 431.12; m/z found, 432.0 [M+H]$^+$. $^1$H NMR (400 MHz, CD$_3$OD) δ 9.06 (s, 2H), 8.62 (dd, J=2.1, 1.1, 1H), 8.12 (dd, J=8.0, 1.3, 1H), 8.00-7.91 (m, 2H), 7.77 (m, 1H), 7.68 (m, 1H), 7.46 (dd, J=7.6, 1.4, 1H), 3.07 (t, J=11.3, 2H), 2.98-2.90 (m, 2H), 1.99-1.80 (m, 2H), 1.70-1.55 (m, 2H).

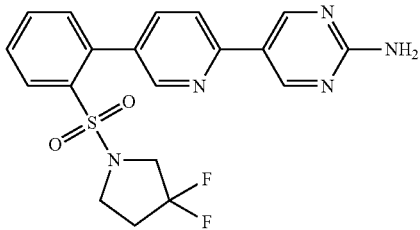

5-(5-{2-[(3,3-Difluoropyrrolidin-1-yl)sulfonyl]phenyl}pyridin-2-yl)pyrimidin-2-amine trifluoroacetic acid salt.

The title compound was prepared in a manner similar to that described in Example 427 using 5-(5-(4,4,5,5-tetramethyl-1,3,2-dioxaborolan-2-yl)pyridin-2-yl)pyrimidin-2-amine and 1-((2-bromophenyl)sulfonyl)-3,3-difluoropyrrolidine. MS (ESI): mass calcd. for $C_{19}H_{17}F_2N_5O_2S$, 417.11; m/z found, 418.0 [M+H]$^+$. $^1$H NMR (400 MHz, CD$_3$OD) δ 9.06 (s, 2H), 8.63 (m, 1H), 8.13 (dd, J=8.0, 1.3, 1H), 7.99-7.92 (m, 2H), 7.78 (m, 1H), 7.69 (m, 1H), 7.48 (dd, J=7.6, 1.4, 1H), 3.30-3.25 (m, 2H), 3.18 (t, J=7.3, 2H), 2.35-2.06 (m, 2H).

Example 681

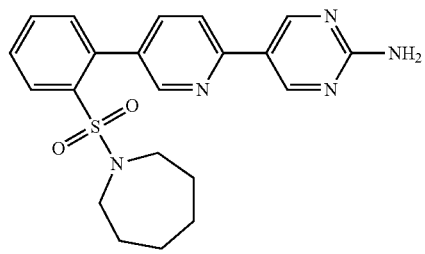

5-(5-[2-(Azepan-1-ylsulfonyl)phenyl]pyridin-2-yl}pyrimidin-2-amine trifluoroacetic acid salt.

The title compound was prepared in a manner similar to that described in Example 427 using 5-(5-(4,4,5,5-tetramethyl-1,3,2-dioxaborolan-2-yl)pyridin-2-yl)pyrimidin-2-amine and 1-((2-bromophenyl)sulfonyl)azepane. MS (ESI): mass calcd. for $C_{21}H_{23}N_5O_2S$, 409.16; m/z found, 410.1 [M+H]$^+$. $^1$H NMR (400 MHz, CD$_3$OD) δ 9.05 (s, 2H), 8.62 (m, 1H), 8.01 (dd. J=7.8, 1.4, 1H), 7.98-7.92 (m, 2H), 7.71 (m, 1H), 7.64 (m, 1H), 7.43 (dd, J=7.5, 1.4, 1H), 3.01-2.91 (m, 4H), 1.65-1.51 (m, 8H).

Example 682

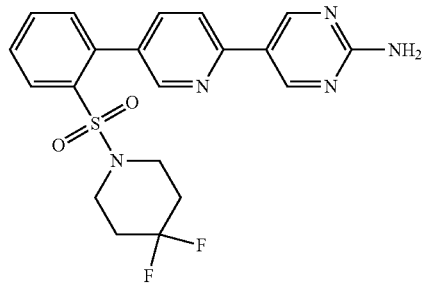

5-(5-{2-[(4,4-Difluoropiperidin-1-yl)sulfonyl]phenyl}pyridin-2-yl)pyridimidin-2-amine trifluoroacetic acid salt.

The title compound was prepared in a manner similar to that described in Example 427 using 5-(5-(4,4,5,5-tetramethyl-1,3,2-dioxaborolan-2-yl)pyridin-2-yl)pyrimidin-2-amine and 1-((2-bromophenyl)sulfonyl)-4,4-difluoropiperidine. MS (ESI): mass calcd. for $C_{20}H_{19}F_2N_5O_2S$, 431.12: m/z found, 432.0 [M+H]$^+$. $^1$H NMR (400 MHz, CD$_3$OD) δ 9.08 (s, 2H), 8.63 (m, 1H), 8.13 (dd, J=8.0, 1.3, 1H), 7.96 (d, J=2.0, 2H), 7.77 (m, 1H), 7.68 (m, 1H), 7.47 (dd, J=7.5, 1.4, 1H), 3.09-2.95 (m, 4H), 1.97-1.71 (m, 4H).

Example 683

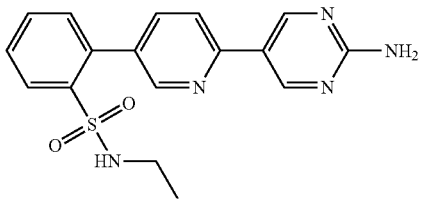

2-[6-(2-Aminopyrimidin-5-yl)pyridin-3-yl]-N-ethylbenzenesulfonamide trifluoroacetic acid salt.

The title compound was prepared in a manner similar to that described in Example 427 using 5-(5-(4,4,5,5-tetramethyl-1,3,2-dioxaborolan-2-yl)pyridin-2-yl)pyrimidin-2-amine and 2-bromo-N-ethylbenzenesulfonamide. MS (ESI): mass calcd. for $C_1H_{17}N_5O_2S$, 355.11; m/z found, 356.1 [M+H]$^+$. $^1$H NMR (400 MHz, CD$_3$OD) δ 9.06 (s, 2H), 8.66 (dd, J=2.3, 0.9, 1H), 8.08 (dd, J=7.9, 1.4, 1H), 8.05 (dd, J=8.3, 2.3, 1H), 7.97 (dd, J=8.3, 0.9, 1H), 7.72 (m, 1H), 7.65 (m, 1H), 7.44 (dd, J=7.5, 1.4, 1H), 2.86 (q, J=7.2, 2H), 1.02 (t, J=7.2, 3H).

Example 684

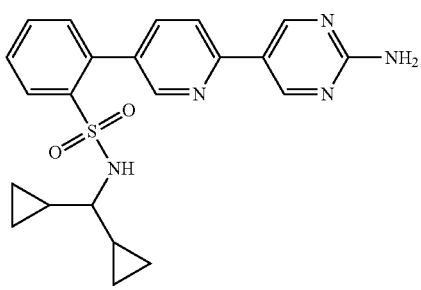

Example 14: 2-[6-(2-Aminopyrimidin-5-yl)pyridin-3-yl]-N-(dicyclopropylmethyl)benzenesulfonamide trifluoroacetic acid salt.

The title compound was prepared in a manner similar to that described in Example 427 using 5-(5-(4,4,5,5-tetramethyl-1,3,2-dioxaborolan-2-yl)pyridin-2-yl)pyrimidin-2-amine and 2-bromo-N-(dicyclopropylmethyl)benzenesulfonamide. MS (ESI): mass calcd. for $C_{22}H_{23}N_5O_2S$, 421.16; m/z found, 422.1 [M+H]$^+$. $^1$H NMR (400 MHz, CD$_3$OD) δ 8.99 (s, 2H), 8.65 (dd, J=2.3, 0.8, 1H), 8.16 (dd, J=7.9, 1.3, 1H), 8.03 (dd, J=8.3, 2.3, 1H), 7.93 (dd, J=8.3, 0.8, 1H), 7.70 (td, J=7.5, 1.4, 1H), 7.61 (m, 1H), 7.40 (dd, J=7.5, 1.3, 1H), 2.07 (t, J=8.3, 1H), 0.89-0.75 (m, 2H), 0.49-0.36 (m, 2H), 0.30-0.13 (m, 4H), 0.00--0.09 (m, 2H).

Example 685

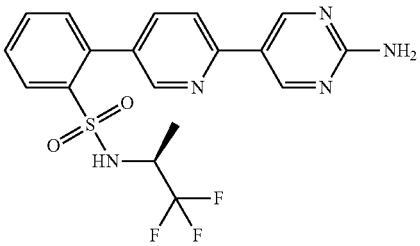

2-[6-(2-Aminopyrimidin-5-yl)pyridin-3-yl]-N-[(1S)-2,2,2-trifluoro-1-methylethyl]benzenesulfonamide trifluoroacetic acid salt.

The title compound was prepared in a manner similar to that described in Example 427 using 5-(5-(4,4,55-tetramethyl-1,3,2-dioxaborolan-2-yl)pyridin-2-yl)pyrimidin-2-amine and (S)-2-bromo-N-(1,1,1-trifluoropropan-2-yl)benzenesulfonamide. MS (ESI): mass calcd. for $C_{18}H_{16}F_3N_5O_2S$ $C_{18}H_{16}F_3N_5O_2S$, 423.10; m/z found, 424.0 [M+H]$^+$. $^1$H NMR (500 MHz, CD$_3$OD) δ 9.06 (s, 2H), 8.64 (dd, J=2.2, 0.9, 1H), 8.15 (dd, J=8.0, 1.3, 1H), 8.04 (dd, J=8.2, 2.2, 1H), 7.99 (dd, J=8.2, 0.9, 1H), 7.73 (m, 1H), 7.66 (m, 1H), 7.43 (dd, J=7.6, 1.3, 1H), 3.96-3.71 (m, 1H), 1.23 (d, J=7.0, 3H).

Example 686

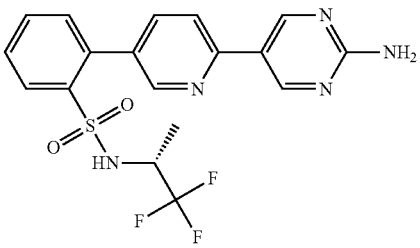

2-[6-(2-Aminopyrimidin-5-yl)pyridin-3-yl]-N-[(1R)-2,2,2-trifluoro-1-methylethyl]benzenesulfonamide trifluoroacetic acid salt.

The title compound was prepared in a manner similar to that described in Example 427 using 5-(5-(4,4,5,5-tetramethyl-1,3,2-dioxaborolan-2-yl)pyridin-2-yl)pyrimidin-2-amine and (R)-2-bromo-N-(1,1,1-trifluoropropan-2-yl)benzenesulfonamide. MS (ESI): mass calcd. for $C_{18}H_{16}F_3N_5O_2S$ $C_{18}H_{16}F_3N_5O_2S$, 423.10; m/z found, 424.0 [M+H]$^+$. $^1$H NMR (500 MHz, CD$_3$OD) δ 9.05 (d, J=0.9, 2H), 8.63 (m, 1H), 8.15 (dd, J=8.0, 1.3, 1H), 8.03-7.99 (m, 1H), 7.97 (m, 1H), 7.73 (m, 1H), 7.65 (m, 1H), 7.42 (dd, J=7.5, 1.3, 1H), 3.91-3.81 (m, 1H), 1.23 (d, J=7.0, 3H).

Example 687

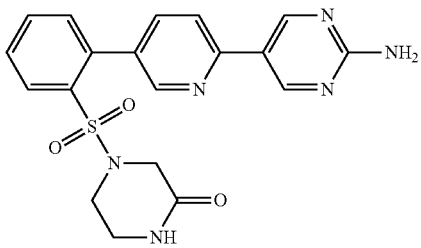

4-({2-[6-(2-Aminopyrimidin-5-yl)
pyridin-3-yl]phenyl}sulfonyl)piperazin-2-one.

The title compound was prepared in a manner similar to that described in Example 427 using 5-(5-(4,4,5,5-tetramethyl-1,3,2-dioxaborolan-2-yl)pyridin-2-yl)pyrimidin-2-amine and 4-((2-bromophenyl)sulfonyl)piperazin-2-one. MS (ESI): mass calcd. for $C_{19}H_{18}N_6O_3S$, 410.12; m/z found, 411.1 [M+H]$^+$. $^1$H NMR (500 MHz, CD$_3$OD) δ 8.97 (s, 2H), 8.60 (dd, J=2.2, 0.9, 1H), 8.18 (dd, J=8.0, 1.3, 1H), 7.91 (dd, J=8.2, 2.2, 1H), 7.87 (dd, J=8.2, 1.0, 1H), 7.80 (m, 1H), 7.70 (m, 1H), 7.50 (dd, J=7.5, 1.3, 1H), 3.42 (s, 2H), 3.15 (s, 4H).

Example 688

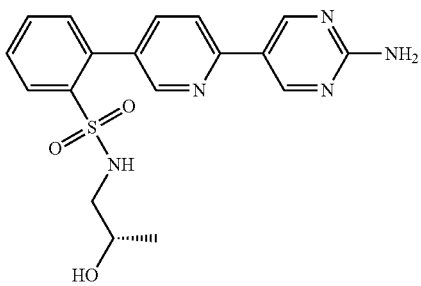

2-[6-(2-Aminopyrimidin-5-yl)
pyridin-3-yl]-N-[(2S)-2-hydroxypropyl]benzenesulfonamide.

The title compound was prepared in a manner similar to that described in Example 427 using 5-(5-(4,4,5,5-tetramethyl-1,3,2-dioxaborolan-2-yl)pyridin-2-yl)pyrimidin-2-amine and (S)-2-bromo-N-(2-hydroxypropyl)benzenesulfonamide. MS (ESI): mass calcd. for $C_{18}H_{19}N_5O_3S$, 385.12; m/z found, 386.1 [M+H]$^+$. $^1$H NMR (500 MHz, CD$_3$OD) δ 8.92 (s, 2H), 8.61-8.57 (m, 1H), 8.09 (d, J=8.0, 1H), 7.91 (dd, J=8.2, 2.3, 1H), 7.82 (d, J=8.2, 1H), 7.70 (m, 1H), 7.62 (m, 1H), 7.41 (d, J=6.8, 1H), 3.70-3.61 (m, 1H), 2.79-2.66 (m, 2H), 1.04 (d, J=6.3, 3H).

Example 689

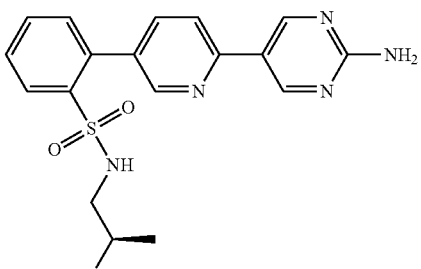

2-[6-(2-Aminopyrimidin-5-yl)
pyridin-3-yl]-N-[(2R)-2-hydroxypropyl]benzenesulfonamide.

The title compound was prepared in a manner similar to that described in Example 427 using 5-(5-(4,4,5,5-tetramethyl-1,3,2-dioxaborolan-2-yl)pyridin-2-yl)pyrimidin-2-amine and (R)-2-bromo-N-(2-hydroxypropyl)benzenesulfonamide. MS (ESI): mass calcd. for $C_{18}H_{19}N_5O_3S$, 385.12; m/z found, 386.1 [M+H]$^+$. $^1$H NMR (500 MHz, CD$_3$OD) δ 8.92 (s, 2H), 8.60 (dd, J=2.3, 0.8, 1H), 8.09 (dd, J=8.0, 1.3, 1H), 7.91 (dd, J=8.2, 2.3, 1H), 7.82 (dd, J=8.2, 0.9, 1H), 7.70 (m, 1H), 7.62 (m, 1H), 7.41 (dd, J=7.6, 1.4, 1H), 3.70-3.59 (m, 1H), 2.79-2.67 (m, 2H), 1.04 (d, J=6.3, 3H).

Example 690

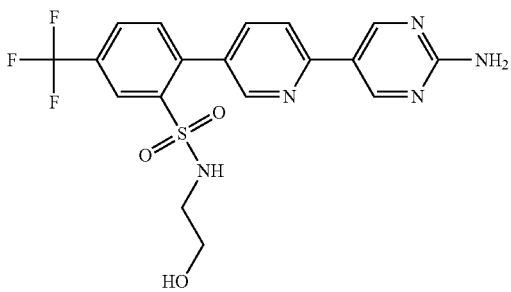

2-[6-(2-Aminopyrimidin-5-yl)
pyridin-3-yl]-N-(2-hydroxyethyl)-5-
(trifluoromethyl)benzenesulfonamide.

The title compound was prepared in a manner similar to that described in Example 427 using 5-(5-(4,4,5,5-tetramethyl-1,3,2-dioxaborolan-2-yl)pyridin-2-yl)pyrimidin-2-amine and 2-bromo-N-(2-hydroxyethyl)-5-(trifluoromethyl)benzenesulfonamide. MS (ESI): mass calcd. for $C_{18}H_{16}F_3N_5O_3S$, 439.09; m/z found, 440.0 [M+H]$^+$. $^1$H NMR (500 MHz, CD$_3$OD) δ 8.96 (s, 2H), 8.64 (d, J=1.7, 1H), 8.39 (s, 1H), 8.01 (d, J=8.0, 1H), 7.95 (dd, J=8.2, 2.3, 1H), 7.87 (d, J=8.3, 1H), 7.64 (d, J=8.0, 1H), 3.46 (t, J=5.9, 2H), 2.91 (t, J=5.9, 2H).

Example 691

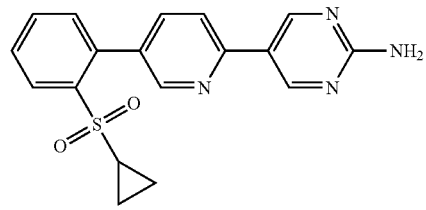

5-{5-[2-(Cyclopropylsulfonyl)phenyl]pyridin-2-yl}pyrimidin-2-amine trifluoroacetic acid salt.

The title compound was prepared in a manner similar to that described in Example 427 using 5-(5-(4,4,5,5-tetramethyl-1,3,2-dioxaborolan-2-yl)pyridin-2-yl)pyrimidin-2-amine and 1-bromo-2-(cyclopropylsulfonyl)benzene. MS (ESI): mass calcd. for $C_{18}H_{16}N_4O_2S$, 352.10; m/z found, 353.1 [M+H]$^+$. $^1$H NMR (500 MHz, CD$_3$OD) δ 7.80 (s, 2H), 7.41-7.36 (m, 1H), 6.86 (dd, J=8.0, 1.2, 1H), 6.74-6.70 (m, 1H), 6.69-6.64 (m, 1H), 6.50 (m, 1H), 6.42 (m, 1H), 6.20 (dd, J=7.5, 1.2, 1H), 1.08-0.98 (m, 1H), −0.28--0.39 (m, 4H).

Example 692

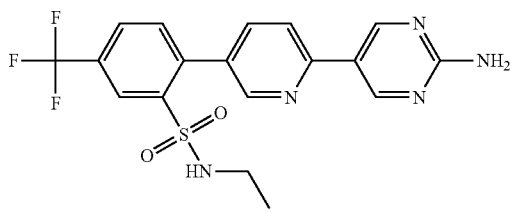

2-[6-(2-Aminopyrimidin-5-yl)pyridin-3-yl]-N-ethyl-5-(trifluoromethyl)benzenesulfonamide trifluoroacetic acid salt.

The title compound was prepared in a manner similar to that described in Example 427 using 5-(5-(4,4,5,5-tetramethyl-1,3,2-dioxaborolan-2-yl)pyridin-2-yl)pyrimidin-2-amine and 2-bromo-N-ethyl-5-(trifluoromethyl)benzenesulfonamide. MS (ESI): mass calcd. for $C_{18}H_{16}F_3N_5O_2S$, 423.10; m/z found, 424.1 [M+H]$^+$. $^1$H NMR (500 MHz, CD$_3$OD) δ 8.95 (s, 2H), 8.62 (d, J=2.0, 1H), 8.35 (s, 1H), 8.01 (d, J=9.9, 1H), 7.93 (dd, J=8.2, 2.3, 1H), 7.87 (d, J=8.2, 1H), 7.64 (d, J=7.9, 1H), 2.84 (q, J=7.2, 2H), 1.01 (t, J=7.2, 3H).

Example 693

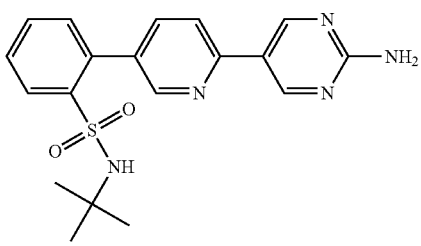

2-[6-(2-Aminopyrimidin-5-yl)pyridin-3-yl]-N-tert-benzenesulfonamide.

The title compound was prepared in a manner similar to that described in Example 427 using 5-(5-(4,4,5,5-tetramethyl-1,3,2-dioxaborolan-2-yl)pyridin-2-yl)pyrimidin-2-amine and 2-bromo-N-(tert-butyl)benzenesulfonamide. MS (ESI): mass calcd. for $C_{19}H_{21}N_5O_2S$, 383.14; m/z found, 384.1 [M+H]$^+$. $^1$H NMR (400 MHz, CD$_3$OD) δ 8.96 (s, 2H), 8.62 (dd, J=2.3, 0.9, 1H), 8.34 (d, J=1.8, 1H), 8.01 (dd, J=8.0, 1.6, 1H), 7.94 (dd, J=8.2, 2.3, 1H), 7.87 (dd, J=8.2, 0.9, 1H), 7.65 (d, J=7.9, 1H), 2.84 (q, J=7.2, 2H), 1.01 (t, J=7.2, 3H).

Example 694

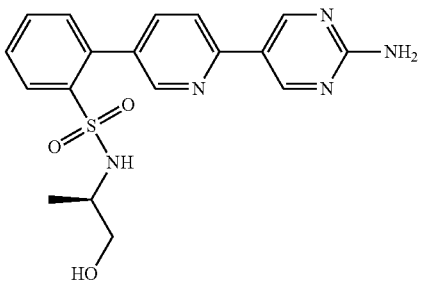

2-[6-(2-Aminopyrimidin-5-yl)pyridin-3-yl]-N-[(1R)-2-hydroxy-1-methylethyl]benzenesulfonamide.

The title compound was prepared in a manner similar to that described in Example 427 using 5-(5-(4,4,5,5-tetramethyl-1,3,2-dioxaborolan-2-yl)pyridin-2-yl)pyrimidin-2-amine and (R)-2-bromo-N-(1-hydroxypropan-2-yl)benzenesulfonamide. MS (ESI): mass calcd. for $C_{18}H_{19}N_5O_3S$, 385.12; m/z found, 386.1 [M+H]$^+$. $^1$H NMR (400 MHz, CD$_3$OD) δ 8.92 (s, 2H), 8.66-8.56 (m, 1H), 8.19 (dd, J=8.0, 1.4, 1H), 7.95 (dd, J=8.2, 2.3, 1H), 7.83 (dd, J=8.2, 0.9, 1H), 7.72 (m, 1H), 7.64 (m, 1H), 7.43 (dd, J=7.5, 1.4, 1H), 3.43-3.16 (m, 4H), 1.03 (d, J=6.6, 3H).

Example 695

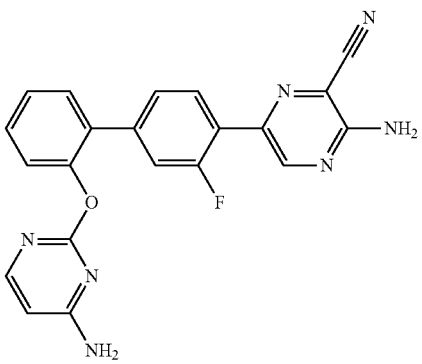

3-Amino-6-{2'-[(4-aminopyrimidin-2-yl)oxy]-3-fluorobiphenyl-4-yl}pyrazine-2-carbonitrile trifluoroacetic acid salt.

The title compound was prepared in a manner similar to that described in Example 427 using 5-(5-(4,4,5,5-tetramethyl-1,3,2-dioxaborolan-2-yl)pyridin-2-yl)pyrimidin-2-amine and 2-(2-bromophenoxy)pyrimidin-4-amine. MS (ESI): mass calcd. for $C_{21}H_{14}FN_7O$, 399.12; m/z found, 400.0 [M+H]⁺. ¹H NMR (500 MHz, CD₃OD) δ 8.73-8.70 (m, 1H), 7.89-7.81 (m, 2H), 7.51-7.43 (m, 2H), 7.41-7.35 (m, 4H), 7.23 (m, 1H).

Example 696

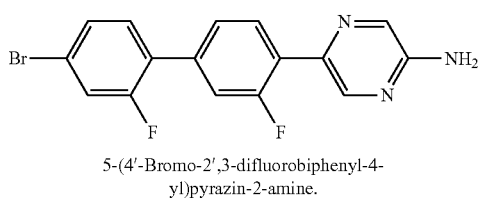 [SMILES: Nc1cnc(-c2ccc(-c3ccc(Br)cc3F)cc2F)cn1]

5-(4'-Bromo-2',3-difluorobiphenyl-4-yl)pyrazin-2-amine.

The title compound was prepared in a manner similar to that described for Intermediate D with DME as a solvent, heating at 100° Celsius for 16 hours and using 2-amino-5-bromopyrazine and 4-bromo-2-fluorobenzeneboronic acid. MS (ESI): mass calcd. for $C_{16}H_{10}BrF_2N_3$, 361.00; m/z found, 362.0, 364.0 [M+H]⁺. ¹H NMR (400 MHz, CDCl₃) δ 8.47 (s, 1H), 8.30 (d, J=1.4, 1H), 8.12-8.02 (m, 1H), 7.49-7.32 (m, 5H), 6.37-5.94 (m, 1H), 6.15 (s, 2H).

Example 697

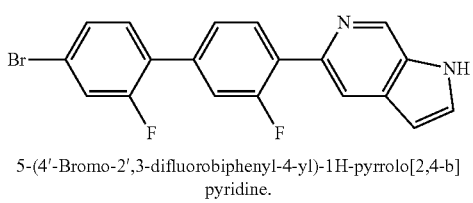 [SMILES: Fc1cc(Br)ccc1-c1ccc(-c2cc3cc[nH]c3cn2)c(F)c1]

5-(4'-Bromo-2',3-difluorobiphenyl-4-yl)-1H-pyrrolo[2,4-b]pyridine.

The title compound was prepared in a manner similar to that described for Intermediate HF heating at 90° Celsius for 16 hours and using 5-bromo-1H-pyrrolo[2,3-b]pyridine and 4-bromo-2-fluorobenzeneboronic acid. MS (ESI): mass calcd. for $C_{19}H_{11}BrF_2N_2$, 384.01; m/z found, 385.0, 387.0 [M+H]⁺. ¹H NMR (400 MHz, CDCl₃) δ 12.29 (s, 1H), 8.47 (s, 2H), 7.60-7.50 (m, 2H), 7.50-7.34 (m, 5H), 6.73 (s, 1H).

Example 698

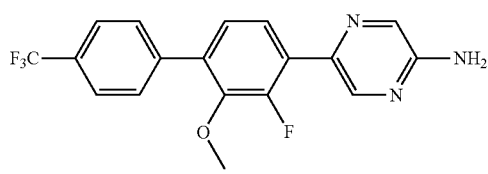

5-(3-fluoro-2-methoxy-4'-(trifluoromethyl)-[1,1'-biphenyl]-4-yl)pyrazin-2-amine.

The title compound was prepared in a manner similar to that described for Example 850 using 5-(4-bromo-2-fluoro-3-methoxyphenyl)pyrazin-2-amine and 4-(trifluoromethyl)phenylboronic acid. MS (ESI): mass calcd. for $C_{18}H_{13}F_4N_3O$, 363.10; m/z found, 363.9 [M+H]⁺. ¹H NMR (400 MHz, CDCl₃) δ 8.61-8.56 (m, 1H), 8.12 (d, J=1.5, 1H), 7.72-7.66 (m, 4H), 7.22 (dd, J=8.3, 1.4, 1H), 7.28-7.24 (m, 1H), 4.73 (s, 2H), 3.77 (d, J=1.2, 3H).

Example 699

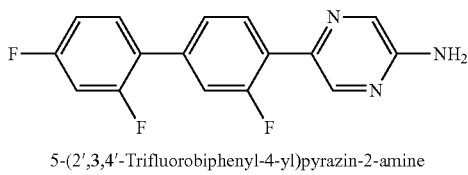

5-(2',3,4'-Trifluorobiphenyl-4-yl)pyrazin-2-amine

The title compound was prepared using conditions analogous to those used to make Example 6 utilizing 5-(4-bromo-2-fluorophenyl)pyrazin-2-amine and (2,4-difluorophenyl)boronic acid. MS (ESI): mass calcd. for $C_{16}H_{10}F_3N_3$, 301.08; m/z found, 302.0 [M+H]⁺. ¹H NMR (400 MHz, DMSO-d₆) δ 8.43-8.35 (m, 1H), 8.03 (d, J=1.4, 1H), 7.97 (m, 1H), 7.73-7.65 (m, 1H), 7.54-7.35 (m, 3H), 7.26-7.20 (m, 1H), 6.74 (s, 2H).

Example 700

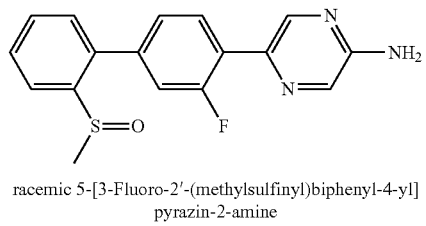 [SMILES: CS(=O)c1ccccc1-c1ccc(-c2cnc(N)cn2)c(F)c1]

racemic 5-[3-Fluoro-2'-(methylsulfinyl)biphenyl-4-yl]pyrazin-2-amine

The title compound was prepared using conditions analogous to those used to make Intermediate EB utilizing 5-(3-fluoro-2'-(methylsulfinyl)-[1,1'-biphenyl]-4-yl)pyrazin-2-amine. MS (ESI): mass calcd. for $C_{17}H_{14}FN_3OS$, 327.08; m/z found, 328.1 [M+H]⁺. ¹H NMR (400 MHz, DMSO-d₆) δ 8.41 (s, 1H), 8.10-7.89 (m, 3H), 7.79-7.58 (m, 2H), 7.51-7.28 (m, 3H), 6.75 (s, 2H), 2.49 (s, 3H).

Example 701

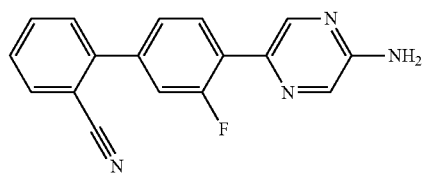

4'-(5-Aminopyrazin-2-yl)-3'-fluorobiphenyl-2-carbonitrile

The title compound was prepared using conditions analogous to those used to make Example 6 utilizing 5-(4-bromo-2-fluorophenyl)pyrazin-2-amine and (2-cyanophenyl)boronic acid. MS (ESI): mass calcd. for $C_{17}H_{11}FN_4$, 290.10; m/z found, 291.1 [M+H]⁺. ¹H NMR (400 MHz, DMSO-d₆) δ 8.42 (s, 1H), 8.05-7.98 (m, 3H), 7.83 (m, 1H), 7.71 (d, J=7.6, 1H), 7.66-7.47 (m, 3H), 6.77 (s, 2H).

Intermediate IZ

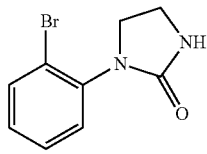

1-(2-Bromophenyl)imidazolidin-2-one

To a solution of imidazolidin-2-one (86 mg, 1.0 mmol) in 1,4-dioxane (5 mL) was added $Cs_2CO_3$ (651 mg, 2.00 mmol) and $Pd(OAc)_2$ (15 mg, 0.050 mmol). The mixture was purged with $N_2$ several times. XantPhos (43 mg, 0.075 mmol) and 1-bromo-2-iodobenzene 4 (280 mg, 1.00 mmol) were added and the reaction mixture was stirred at 100° Celsius for 14 hours under an $N_2$ atmosphere. After cooling to rt, the mixture was concentrated to dryness and the residue purified by FCC to give the title compound (60 mg, 25% yield). MS (ESI): mass calcd. for $C_9H_9N_2OBr$ 239.99, m/z found 240.1 [M+H]$^+$; $^1$H NMR (300 MHz, CDCl$_3$) δ 7.65-7.61 (m, 1H), 7.38-7.34 (m, 2H), 7.25-7.19 (m, 1H), 3.94-3.89 (m, 2H), 3.66-3.61 (m, 2H).

Example 702

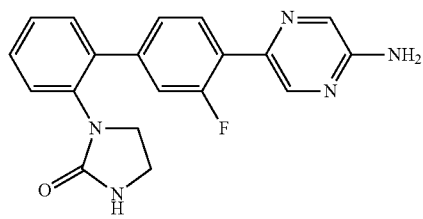

1-(4'-(5-Aminopyrazin-2-yl)-3'-fluoro-[1,1'-biphenyl]-2-yl)imidazolidin-2-one

The title compound was prepared using conditions analogous to those used to make Example 6 utilizing 5-(2-fluor-4-(4,4,5,5-tetramethyl-1,3,2-dioxaborolan-2-yl)phenyl)pyrazin-2-amine and 1-(2-bromophenyl)imidazolidin-2-one. MS (ESI): mass calcd. for $C_{19}H_{16}FN_5O$, 349.13; m/z found, 350.0 [M+H]$^+$. $^1$H NMR (400 MHz, CD$_3$OD) δ 8.41 (s, 1H), 8.10 (s, 1H), 7.94 (m, 1H), 7.81-7.77 (m, 1H), 7.51-7.46 (m, 5H), 3.51 (t, J=6.2, 2H), 3.37 (t, J=6.2, 2H).

Example 703

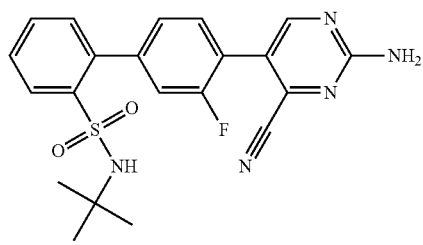

4'-(2-Amino-4-cyanopyrimidin-5-yl)-N-tert-butyl-3'-fluorobiphenyl-2-sulfonamide

The title compound was prepared using conditions analogous to those used to make Example 6 utilizing (2'-(N-(tert-butyl)sulfamoyl)-3-fluoro-[1,1'-biphenyl]-4-yl)boronic acid and 2-amino-5-bromo-4-cyanopyrimidine. MS (ESI): mass calcd. for $C_{21}H_{20}FN_5O_2S$, 327.08; m/z found, 328.1 [M+H]$^+$. $^1$H NMR (600 MHz, DMSO-d$_6$) δ 8.64-8.59 (m, 1H), 8.07 (dd, J=7.9, 1.4, 1H), 7.71-7.65 (m, 1H), 7.65-7.59 (m, 2H), 7.57 (s, 2H), 7.45-7.39 (m, 2H), 7.36 (dd, J=7.8, 1.7, 1H), 6.89 (s, 1H), 1.02 (s, 9H).

Example 704

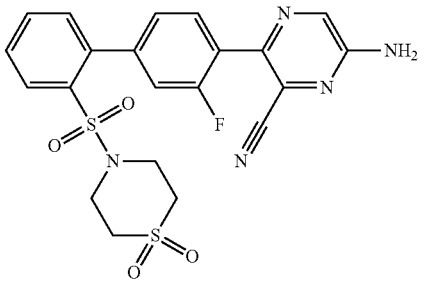

6-Amino-3-{2'-[(1,1-dioxidothiomorpholin-4-yl)sulfonyl]-3-fluorobiphenyl-4-yl}pyrazine-2-carbonitrile The title compound was prepared using conditions analogous to those used to make Example 6 utilizing 6-amino-3-(2-fluoro-4-(4,4,5,5-tetramethyl-1,3,2-dioxaborolan-2-yl)phenyl)pyrazine-2-carbonitrile and 4-((2-bromophenyl)sulfonyl)thiomorpholine 1,1-dioxide. MS (ESI): mass calcd. for $C_{21}H_{18}FN_5O_4S_2$, 487.08: m/z found, 488.1 [M+H]$^+$. $^1$H NMR (600 MHz, DMSO-δ$_6$) δ 8.26 (s, 1H), 8.08 (dd, J=8.0, 1.3, 1H), 7.83-7.77 (m, 1H), 7.73-7.68 (m, 1H), 7.68-7.63 (m, 1H), 7.51 (dd, J=7.6, 1.3, 1H), 7.44 (dd, J=10.9, 1.7, 1H), 7.40 (s, 2H), 7.35 (dd, J=7.9, 1.6, 1H), 3.31-3.23 (m, 4H), 3.11-3.04 (m, 4H).

Example 705

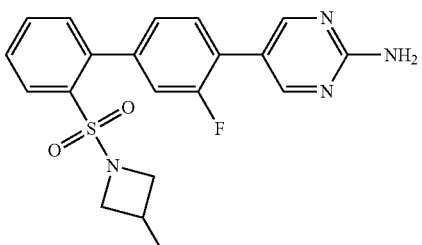

1-{[4'-(2-Aminopyrimidin-5-yl)-3'-fluorobiphenyl-2-yl]sulfonyl}-N-methylazetidine-3-carboxamide The title compound was prepared using conditions analogous to those used to make Example 6 5-(2-fluoro-4-(4,4,5,5-tetramethyl-1,3,2-dioxaborolan-2-yl)phenyl)pyrimidin-2-amine and 1-((2-bromophenyl)sulfonyl)-N-methylazetidine-3-carboxamide. MS (ESI): mass calcd. for $C_{21}H_{20}FN_5O_3S$, 441.13; m/z found, 441.9 [M+H]$^+$. $^1$H NMR (500 MHz, DMSO-δ$_6$) δ 8.52 (s, 2H), 8.02 (d, J=7.9, 1H), 7.84 (d, J=4.8, 1H), 7.79-7.72 (m, 1H), 7.69-7.63 (m, 1H), 7.61-7.55 (m, 1H), 7.45 (d, J=7.5, 1H), 7.33 (d, J=11.7, 1H), 7.27 (d, J=7.8, 1H), 6.89 (s, 2H), 3.70 (t, J=7.0, 2H), 3.63 (t, J=8.0, 2H), 3.19-3.08 (m, 1H), 2.56 (d, J=4.4, 3H).

Example 706

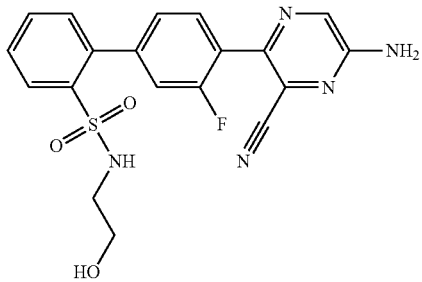

4'-(5-Amino-3-cyanopyrazin-2-yl)-3'-fluoro-N-(2-hydroxyethyl)biphenyl-2-sulfonamide The title compound was prepared using conditions analogous to those used to make Example 6 utilizing 6-amino-3-(2-fluoro-4-(4,4,5,5-tetramethyl-1,3,2-dioxaborolan-2-yl)phenyl)pyrazine-2-carbonitrile and 2-bromo-N-(2-hydroxyethyl)benzenesulfonamide. MS (ESI): mass calcd. for $C_{19}H_{16}FN_5O_3S$, 413.10; m/z found, 414.0 [M+H]$^+$. $^1$H NMR (500 MHz, DMSO-$\delta_6$) δ 8.26 (s, 1H), 7.99 (dd, J=7.9, 1.4, 1H), 7.72-7.59 (m, 3H), 7.47-7.41 (m, 2H), 7.41-7.31 (m, 4H), 4.70-4.64 (t, J=5.5, 1H), 3.45-3.27 (m, 2H), 2.85-2.78 (m, 2H).

Example 707

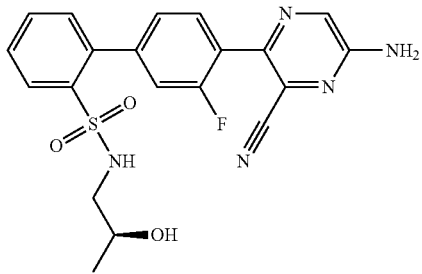

4'-(5-Amino-3-cyanopyrazin-2-yl)-3'-fluoro-N-[(2S)-2-hydroxypropyl]biphenyl-2-sulfonamide The title compound was prepared using conditions analogous to those used to make Example 6 utilizing 6-amino-3-(2-fluoro-4-(4,4,5,5-tetramethyl-1,3,2-dioxaborolan-2-yl)phenyl)pyrazine-2-carbonitrile and S-2-bromo-N-(2-hydroxypropyl)benzenesulfonamide. MS (ESI): mass calcd. for $C_{20}H_{18}FN_5O_3S$, 427.11; m/z found, 428.0 [M+H]$^+$. $^1$H NMR (500 MHz, DMSO-$\delta_6$) δ 8.26 (s, 1H), 7.97 (dd, J=7.9, 1.4, 1H), 7.72-7.59 (m, 3H), 7.49-7.43 (m, 2H), 7.41-7.33 (m, 4H), 4.71 (d, J=4.7, 1H), 3.61-3.53 (m, 1H), 3.17 (d, J=5.3, 1H), 2.73-2.59 (m, 2H), 0.98 (d, J=6.2, 3H).

Example 708

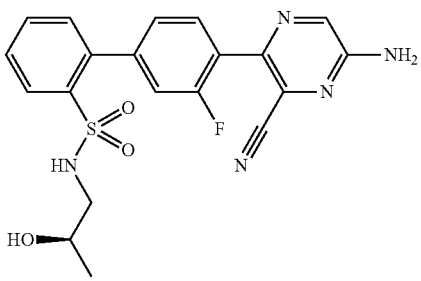

4'-(5-Amino-3-cyanopyrazin-2-yl)-3'-fluoro-N-[(2R)-2-hydroxypropyl]biphenyl-2-sulfonamide The title compound was prepared using conditions analogous to those used to make Example 6 utilizing 6-amino-3-(2-fluoro-4-(4,4,5,5-tetramethyl-1,3,2-dioxaborolan-2-yl)phenyl)pyrazine-2-carbonitrile and R-2-bromo-N-(1-hydroxypropan-2-yl)benzenesulfonamide. Characterization data were identical to the enantiomer (Example X).

Example 709

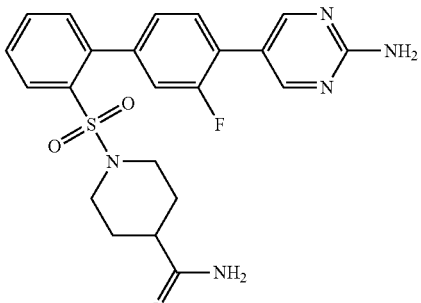

1-((4'-(2-Aminopyrimidin-5-yl)-3'-fluoro-[1,1'-biphenyl]-2-yl)sulfonyl)piperidine-4-carboxamide The title compound was prepared using conditions analogous to those used to make Example 6 utilizing 5-(2-fluoro-4-(4,4,5,5-tetramethyl-1,3,2-dioxaborolan-2-yl)phenyl)pyrimidin-2-amine and 1-((2-bromophenyl)sulfonyl)piperidine-4-carboxamide. MS (ESI): mass calcd. for $C_{22}H_{22}FN_5O_3S$, 455.14; m/z found, 455.9 [M+H]$^+$. $^1$H NMR (500 MHz, DMSO-$\delta_6$) δ 8.51 (d, J=1.4, 2H), 8.02 (dd, J=8.0, 1.3, 1H), 7.78-7.71 (m, 1H), 7.69-7.63 (m, 1H), 7.61-7.54 (m, 1H), 7.45 (dd, J=7.6, 1.4, 1H), 7.32 (dd, J=11.8, 1.7, 1H), 7.26 (dd, J=7.9, 1.8, 1H), 7.17 (s, 1H), 6.88 (s, 2H), 6.73 (s, 1H), 3.26-3.19 (m, 2H), 2.47-2.38 (m, 2H), 2.13-2.02 (m, 1H), 1.59 (dd, J=13.9, 3.8, 2H), 1.31-1.17 (m, 2H).

Example 710

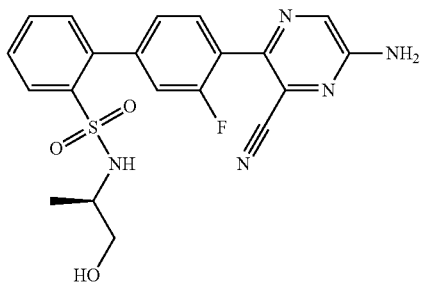

4'-(5-Amino-3-cyanopyrazin-2-yl)-3'-fluoro-N-[(1R)-2-hydroxy-1-methylethyl]biphenyl-2-sulfonamide The title compound was prepared using conditions analogous to those used to make Example 6 utilizing 6-amino-3-(2-fluoro-4-(4,4,5,5-tetramethyl-1,3,2-dioxaborolan-2-yl)phenyl)pyrazine-2-carbonitrile and R-2-bromo-N-(1-hydroxypropan-2-yl)benzenesulfonamide. MS (ESI): mass calcd. for $C_{20}H_{18}FN_5O_3S$, 426.11; m/z found, 427.9 $[M+H]^+$. $^1$H NMR (400 MHz, $CD_3OD$) δ 8.22 (s, 1H), 8.15 (dd, J=8.0, 1.4, 1H), 7.72-7.64 (m, 1H), 7.64-7.56 (m, 2H), 7.46-7.33 (m, 3H), 3.46-3.36 (m, 1H), 3.30-3.25 (m, 1H), 3.25-3.14 (m, 1H), 1.02 (d, J=6.6, 3H).

Example 711

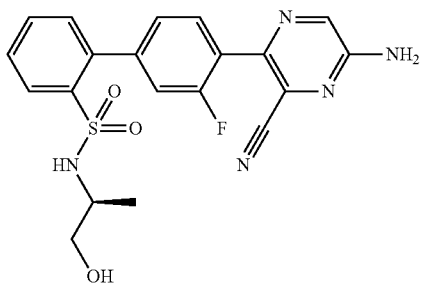

4'-(5-Amino-3-cyanopyrazin-2-yl)-3'-fluoro-N-[(1S)-2-hydroxy-1-methylethyl]biphenyl-2-sulfonamide The title compound was prepared using conditions analogous to those used to make Example 6 utilizing 6-amino-3-(2-fluoro-4-(4,4,5,5-tetramethyl-1,3,2-dioxaborolan-2-yl)phenyl)pyrazine-2-carbonitrile and S-2-bromo-N-(1-hydroxypropan-2-yl)benzenesulfonamide. Characterization data were identical to the enantiomer (Example X).

Example 712

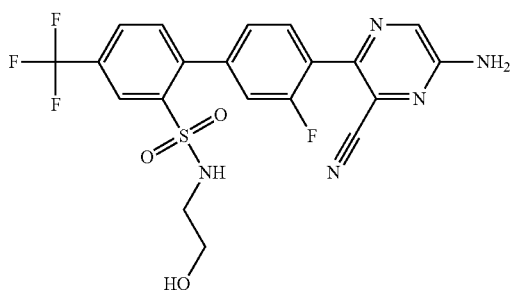

4'-(5-Amino-3-cyanopyrazin-2-yl)-3'-fluoro-N-(2-hydroxyethyl)-4-(trifluoromethyl)biphenyl-2-sulfonamide The title compound was prepared using conditions analogous to those used to make Example 6 utilizing 6-amino-3-(2-fluoro-4-(4,4,5,5-tetramethyl-1,3,2-dioxaborolan-2-yl)phenyl)pyrazine-2-carbonitrile and 2-bromo-N-(2-hydroxyethyl)-5-(trifluoromethyl)benzenesulfonamide. MS (ESI): mass calcd. for $C_{20}H_{15}F_4N_5O_3S$, 481.08; m/z found, 482.1 $[M+H]^+$. $^1$H NMR (600 MHz, DMSO-$d_6$) δ 8.35-8.31 (m, 1H), 8.26 (s, 1H), 8.10-8.05 (m, 1H), 7.91-7.86 (m, 1H), 7.71 (d, J=7.9, 1H), 7.68-7.63 (m, 1H), 7.46 (dd, J=10.9, 1.7, 1H), 7.43-7.36 (m, 3H), 4.75 (t, J=5.4, 1H), 3.40-3.33 (m, 2H), 2.88-2.78 (m, 2H).

Example 713

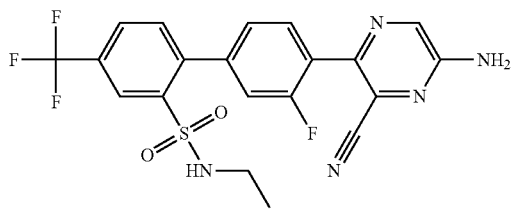

4'-(5-Amino-3-cyanopyrazin-2-yl)-N-ethyl-3'-fluoro-4-(trifluoromethyl)-[1,1'-biphenyl]-2-sulfonamide The title compound was prepared using conditions analogous to those used to make Example 6 utilizing 6-amino-3-(2-fluoro-4-(4,4,5,5-tetramethyl-1,3,2-dioxaborolan-2-yl)phenyl)pyrazine-2-carbonitrile and 2-bromo-N-ethyl-5-(trifluoromethyl)benzenesulfonamide. MS (ESI): mass calcd. for $C_{20}H_{15}F_4N_5O_2S$, 465.09; m/z found, 465.8 $[M+H]^+$. $^1$H NMR (600 MHz, DMSO-$d_6$) δ 8.26 (s, 2H), 8.11-8.07 (m, 1H), 7.87-7.81 (m, 1H), 7.72 (d, J=7.9, 1H), 7.69-7.63 (m, 1H), 7.45 (dd, J=10.8, 1.7, 1H), 7.43-7.36 (m, 3H), 2.78 (qd, J=7.2, 5.5, 2H), 0.97 (t, J=7.2, 3H).

Example 714

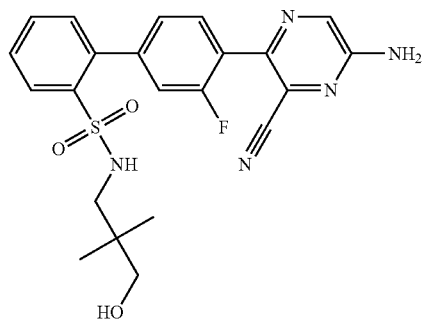

4'-(5-Amino-3-cyanopyrazin-2-yl)-3'-fluoro-N-(3-hydroxy-2,2-dimethylpropyl)biphenyl-2-sulfonamide The title compound was prepared using conditions analogous to those used to make Example 6 utilizing 6-amino-3-(2-fluoro-4-(4,4,5,5-tetramethyl-1,3,2-dioxaborolan-2-yl)phenyl)pyrazine-2-carbonitrile and 2-bromo-N-(3-hydroxy-2,2-dimethylpropyl)benzenesulfonamide. MS (ESI): mass calcd. for $C_{22}H_{22}FN_5OS$, 455.14; m/z found, 456.0 $[M+H]^+$. $^1$H NMR (600 MHz, DMSO-$d_6$) δ 8.26 (s, 1H), 7.93 (dd, J=7.8, 1.5, 1H), 7.72-7.60 (m, 3H), 7.47 (dd, J=7.4, 1.5, 1H), 7.43-7.34 (m, 5H), 4.49 (t, J=5.4, 1H), 3.08 (d, J=5.4, 2H), 2.62 (d, J=6.5, 2H), 0.73 (s, 6H).

Example 715

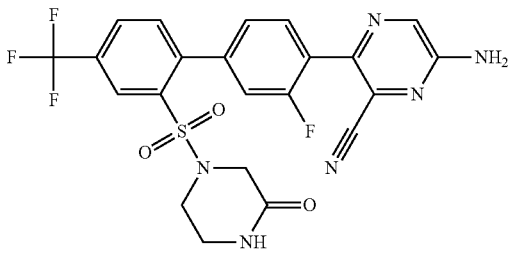

6-Amino-3-{3-fluoro-2'-[(3-oxopiperazin-1-yl)sulfonyl]-4'-(trifluoromethyl)biphenyl-4-yl}pyrazine-2-carbonitrile The title compound was prepared using conditions analogous to those used to make Example 6 utilizing 6-amino-3-(2-fluoro-4-(4,4,5,5-tetramethyl-1,3,2-dioxaborolan-2-yl)phenyl)pyrazine-2-carbonitrile and 4-((2-bromo-5-(trifluoromethyl)phenyl)sulfonyl)piperazin-2-one. MS (ESI): mass calcd. for $C_{22}H_{16}F_4N_6O_3S$, 520.09; m/z found, 520.8 [M+H]$^+$. $^1$H NMR (600 MHz, DMSO-$d_6$) δ 8.29 (d, J=1.9, 1H), 8.26 (s, 1H), 8.19 (dd, J=8.2, 1.9, 1H), 8.07-8.01 (m, 1H), 7.77 (d, J=7.9, 1H), 7.70-7.64 (m, 1H), 7.49 (dd, J=10.8, 1.7, 1H), 7.44-7.36 (m, 3H), 3.39 (s, 2H), 3.07-2.96 (m, 4H).

Example 716

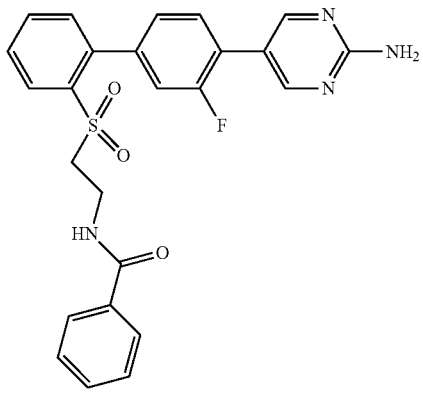

N-(2-{[4'-(2-Aminopyrimidin-5-yl)-3'-fluorobiphenyl-2-yl]sulfonyl}ethyl)benzamide The title compound was prepared using conditions analogous to those used to make Example 337 utilizing N-(2-((4'-(2-aminopyrimidin-5-yl)-3'-fluoro-[1,1'-biphenyl]-2-yl)thio)ethyl)benzamide. MS (ESI): mass calcd. for $C_{25}H_{21}FN_4O_3S$, 476.13; m/z found, 477.0 [M+H]$^+$. $^1$H NMR (600 MHz, DMSO) δ 8.52-8.46 (m, 3H), 8.11 (dd, J=7.8, 1.4, 1H), 7.74-7.68 (m, 1H), 7.68-7.61 (m, 3H), 7.61-7.56 (m, 1H), 7.52-7.47 (m, 1H), 7.43-7.38 (m, 3H), 7.36 (dd, J=11.7, 1.7, 1H), 7.30 (dd, J=7.9, 1.7, 1H), 6.93 (s, 2H), 3.47-3.40 (m, 2H), 3.30-3.24 (t, J=6.7, 2H).

Example 717

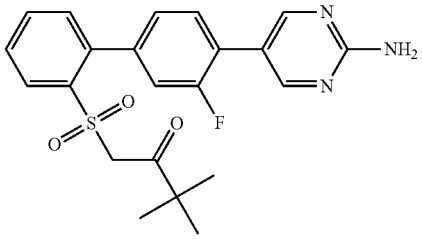

1-{[4'-(2-Aminopyrimidin-5-yl)-3'-fluorobiphenyl-2-yl]sulfonyl}-3,3-dimethylbutan-2-one The title compound was prepared using conditions analogous to those used to make Example 6 5-(2-fluoro-4-(4,4,5,5-tetramethyl-1,3,2-dioxaborolan-2-yl)phenyl)pyrimidin-2-amine and 1-((2-bromophenyl)sulfonyl)-3,3-dimethylbutan-2-one. MS (ESI): mass calcd. for $C_{22}H_{22}FN_3O_3S$, 427.14; m/z found, 428.0 [M+H]$^+$. $^1$H NMR (600 MHz, DMSO-$d_6$) δ 8.51 (d, J=1.5, 2H), 8.09 (dd, J=8.0, 1.3, 1H), 7.82-7.76 (m, 1H), 7.75-7.69 (m, 1H), 7.68-7.62 (m, 1H), 7.44 (dd, J=7.6, 1.3, 1H), 7.39-7.34 (dd, J=11.6, 1.8, 1H), 7.29 (dd, J=7.9, 1.7, 1H), 6.96 (s, 2H), 4.44 (s, 2H), 0.94 (s, 9H).

Example 718

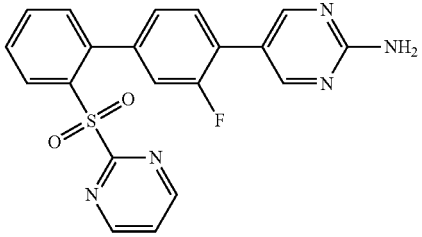

5-[3-Fluoro-2'-(pyrimidin-2-ylsulfonyl)biphenyl-4-yl]pyrimidin-2-amine

Step A: Ethyl 3-(4'-(2-aminopyrimidin-5-yl)-5'-fluorobiphenyl-2-ylthio)propanoate A mixture of ethyl 3-((2-bromophenyl)thio)propanoate (5.8 g, 20 mmol), 5-(2-fluoro-4-(4,4,5,5-tetramethyl-1,3,2-dioxaborolan-2-yl)phenyl)pyrimidin-2-amine (6.95 g, 22.1 mmol), Pd(dppf)Cl$_2$.CH$_2$Cl$_2$ (1.7 g, 2.0 mmol), Na$_2$CO$_3$ (4.25 g, 40.1 mmol) and 1,4-dioxane/water (80 mL/10 mL) was stirred at 90° C. overnight under N$_2$. The reaction mixture was cooled to rt, filtered, and the filtrate concentrated to dryness. The resultant residue was subjected to FCC to give the title compound (6.5 g, 82%). MS (ESI): mass calcd. for $C_{21}H_{20}FN_3O_2S$, 397.13; m/z found, 397.9 [M+H]$^+$.

Step B: 4'-(2-Aminopyrimidin-5-yl)-5'-fluorobiphenyl-2-thiol

To a solution of ethyl 3-(4'-(2-aminopyrimidin-5-yl)-5'-fluorobiphenyl-2-ylthio)propanoate (6.5 g, 16 mmol) in THF (70 mL) was added t-BuOK (3.68 g, 32.8 mmol) under a N₂ atmosphere. After stirring for 10 min, methanol (5 mL) was added and the resulting mixture purified by FCC to give the title compound (4.8 g, 16 mmol, 98%). MS (ESI): mass calcd. for $C_{16}H_{12}FN_3S$, 297.07; m/z found, 298.1 [M+H]⁺.

Step C: 5-(3-Fluoro-6'-(pyrimidin-2-ylthio)biphenyl-4-yl)pyrimidin-2-amine

A solution of 4'-(2-aminopyrimidin-5-yl)-5'-fluorobiphenyl-2-thiol (300 mg, 1.00 mmol), 2-chloropyrimidine (229 mg, 2.00 mmol), PPh₃ (262 mg, 1.00 mmol) and TEA (0.38 mL) in DMF (10 mL) was stirred at 120° C. under a N₂ atmosphere over-night. The reaction mixture was then cooled to rt, concentrated to dryness, and the residue subjected to FCC purification to give the title compound (170 mg, 45%). MS (ESI): mass calcd. for $C_{20}H_{14}FN_5S$, 375.10; m/z found, 375.9 [M+H]⁺. ¹H NMR (400 MHz, DMSO-d₆) δ 8.66 (s, 2H), 8.56 (d, J=4.9, 2H), 7.79-7.73 (m, 1H), 7.63-7.56 (m, 2H), 7.55-7.48 (m, 2H), 7.33-7.24 (m, 2H), 7.21 (t, J=4.9, 1H), 6.23 (s, 2H).

Step D: 5-[3-Fluoro-2'-(pyrimidin-2-ylsulfonyl)biphenyl-4-yl]pyrimidin-2-amine

To a rt solution of 5-(3-fluoro-6'-(pyrimidin-2-ylthio)biphenyl-4-yl)pyrimidin-2-amine (100 mg, 0.270 mmol), NaIO₄ (170 mg, 0.810 mmol) in CH₃CN/DCM/H₂O (5 mL/5 mL/5 mL) was added RuCl₃ (6 mg, 0.03 mmol). The resultant mixture was stirred for 3 h before diluting with saturated NaHCO₃ (15 mL). The organic solvent was removed in vacuo, and the resultant solid isolated by filtration. The filter cake was washed with water, dried under vacuum and then subjected to HPLC purification to give the title compound (12 mg, 11%). MS (ESI): mass calcd. for $C_{20}H_{14}FN_5O_2S$, 407.09; m/z found, 408.0 [M+H]⁺. ¹H NMR (400 MHz, DMSO-d₆) δ 8.87 (d, J=4.8, 2H), 8.42 (s, 2H), 8.33 (d, J=7.6, 1H), 7.86 (m, 1H), 7.80 (t, J=7.6, 1H), 7.74 (m, 1H), 7.43 (d, J=7.1, 1H), 7.30 (m, 1H), 6.93 (s, 2H), 6.80 (d, J=11.7, 1H), 6.75 (d, J=8.0, 1H).

Example 719

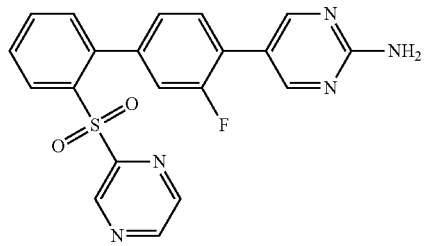

5-[3-Fluoro-2'-(pyrazin-2-ylsulfonyl)biphenyl-4-yl]pyrimidin-2-amine

The title compound was prepared using conditions analogous to those used to make Example 718. MS (ESI): mass calcd. for $C_{20}H_{14}FN_5O_2S$, 407.09; m/z found, 408.1 [M+H]⁺. ¹H NMR (400 MHz, DMSO-d) δ 8.88 (d, J=2.3, 1H), 8.71 (dd, J=2.3, 1.5, 1H), 8.55 (d, J=1.3, 1H), 8.44 (d, J=1.4, 2H), 8.35 (dd, J=7.8, 1.4, 1H), 7.85 (m, 1H), 7.81 (m, 1H), 7.41 (dd, J=7.4, 1.3, 1H), 7.34 (m, 1H), 6.95 (s, 2H), 6.80 (dd, J=7.9, 1.7, 1H), 6.75 (dd. J=11.4, 1.6, 1H).

Example 720

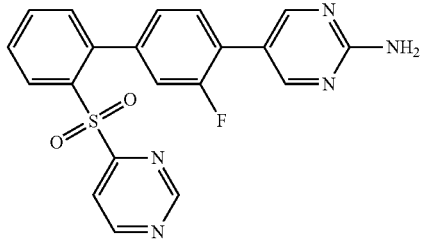

5-[3-Fluoro-2'-(pyrimidin-2-ylsulfonyl)biphenyl-4-yl]pyrimidin-2-amine

The title compound was prepared using conditions analogous to those used to make Example 718. MS (ESI): mass calcd. for $C_{20}H_{14}FN_5O_2S$, 407.09; m/z found, 408.1 [M+H]⁺. ¹H NMR (400 MHz, DMSO-d₆) δ 9.28 (d, J=1.3, 1H), 8.96 (d, J=5.1, 1H), 8.57 (s, 2H), 8.35 (dd, J=7.8, 1.3, 1H), 7.88 (m, 1H), 7.83 (m, 1H), 7.58 (dd, J=5.1, 1.3, 1H), 7.44 (dd, J=7.4, 1.2, 1H), 7.36 (m, 1H), 6.86-6.81 (m, 2H).

Example 721

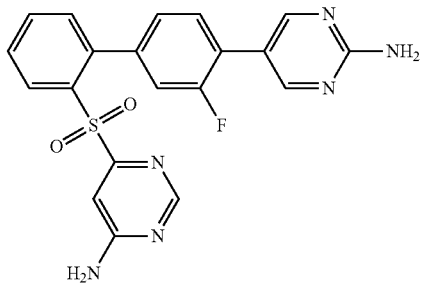

5-{2'-[(6-Aminopyrimidin-4-yl)sulfonyl]-3-fluorobiphenyl-4-yl}pyrimidin-2-amine

The title compound was prepared using conditions analogous to those used to make Example 718. MS (ESI): mass calcd. for $C_{20}H_{15}FN_6O_2S$, 422.10; m/z found, 423.1 [M+H]⁺. ¹H NMR (400 MHz, DMSO-d₅) δ 8.64 (s, 2H), 8.27-8.25 (m, 2H), 7.83 (m, 1H), 7.78 (m, 1H), 7.56-7.35 (m, 4H), 6.97-6.87 (m, 2H), 6.45 (s, 1H).

Example 722

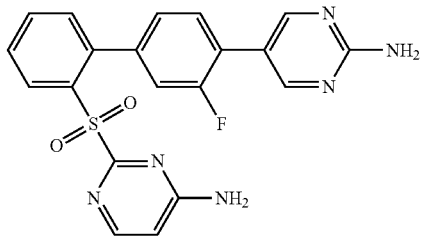

5-{2'-[(Aminopyrimidin-2-yl)sulfonyl]-3-fluorobiphenyl-4-yl}pyrimidin-2-amine

The title compound was prepared using conditions analogous to those used to make Example 718. MS (ESI): mass calcd. for $C_{20}H_{15}FN_6O_2S$, 422.10; m/z found, 423.0 [M+H]$^+$. $^1$H NMR (400 MHz, DMSO-d$_6$) δ 8.46 (s, 2H), 8.22 (d, J=7.7, 1H), 7.98 (d, J=5.8, 1H), 7.80 (m, 1H), 7.74 (m, 1H), 7.53 (s, 2H), 7.41 (d, J=7.3, 1H), 7.36 (m, 1H), 7.01 (s, 2H), 6.89-6.84 (m, 2H), 6.43 (d, J=5.9, 1H).

Example 723

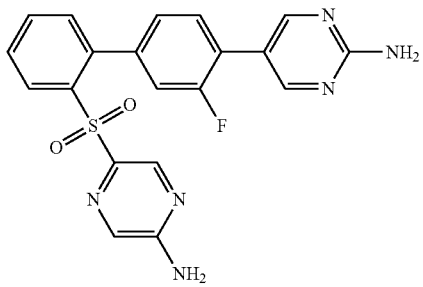

5-{2'-[(5-Aminopyrazin-2-yl)sulfonyl]-3-fluorobiphenyl-4-yl}pyrimidin-2-amine

The title compound was prepared using conditions analogous to those used to make Example 718. MS (ESI): mass calcd. for $C_{20}H_{15}FN_6O_2S$, 422.10; m/z found, 423.1 [M+H]$^+$. $^1$H NMR (400 MHz, CD$_3$OD) δ 8.88 (s, 2H), 8.34 (dd, J=7.8, 1.5, 1H), 7.88 (d, J=1.2, 1H), 7.79-7.68 (m, 3H), 7.51 (m, 1H), 7.34 (dd, J=7.3, 1.4, 1H), 7.04 (dd, J=7.9, 1.6, 1H), 6.98 (dd, J=11.4, 1.5, 1H).

Example 724

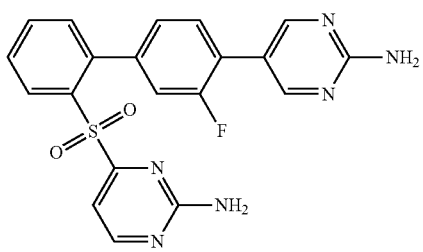

4-{[4'-(2-Aminopyrimidin-5-yl)-3'-fluorobiphenyl-2-yl]sulfonyl}pyrimidin-2-amine The title compound was prepared using conditions analogous to those used to make Example 718. MS (ESI): mass calcd. for $C_{20}H_{15}FN_6O_2S$, 422.10; m/z found, 423.1 [M+H]$^+$. $^1$H NMR (400 MHz, DMSO-d$_6$) δ 8.43 (s, 2H), 8.28 (d, J=4.8, 1H), 8.24 (d, J=7.6, 1H), 7.86-7.79 (m, 1H), 7.76 (m, 1H), 7.43 (d, J=6.1, 1H), 7.36 (m, 1H), 7.25 (s, 2H), 6.98-6.83 (m, 4H), 6.50 (d, J=4.8, 1H).

Example 725

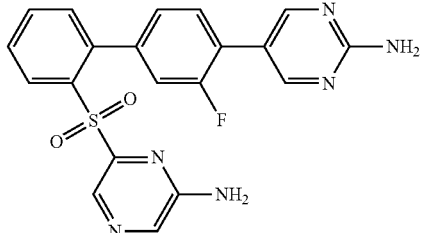

5-{2'-[(6-Aminopyrazin-2-yl)sulfonyl]-3-fluorobiphenyl-4-yl}pyrimidin-2-amine

The title compound was prepared using conditions analogous to those used to make Example 718. MS (ESI): mass calcd. for $C_{20}H_{15}FN_6O_2S$, 422.10; m/z found, 423.0 [M+H]$^+$. $^1$H NMR (400 MHz, CD$_3$OD) δ 8.84 (s, 2H), 8.36 (dd, J=7.8, 1.3, 1H), 7.96 (s, 1H), 7.80 (m, 1H), 7.75 (m, 1H), 7.61 (s, 1H), 7.47 (m, 1H), 7.38 (dd, J=7.4, 1.2, 1H), 7.03 (dd, J=7.9, 1.6, 1H), 6.96 (dd, J=11.4, 1.5, 1H).

Example 726

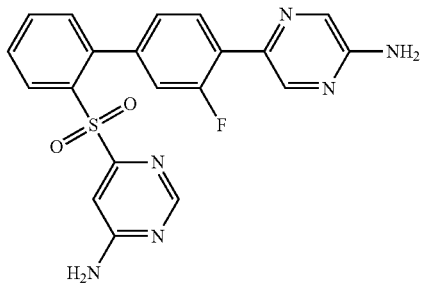

6-{[4'-(5-Aminopyrazin-2-yl)-3'-fluorobiphenyl-2-yl]sulfonyl}pyrimidin-4-amine

The title compound was prepared using conditions analogous to those used to make Example 718. MS (ESI): mass calcd. for $C_{20}H_{15}FN_6O_2S$, 422.10; m/z found, 423.0 [M+H]$^+$. $^1$H NMR (400 MHz, DMSO-d$_6$) δ 8.37 (s, 1H), 8.25-8.22 (m, 2H), 8.02 (s, 1H), 7.85-7.71 (m, 2H), 7.65 (m, 1H), 7.42-7.39 (m, 3H), 6.88 (s, 1H), 6.84 (d, J=7.2, 1H), 6.47 (s, 1H).

Example 727

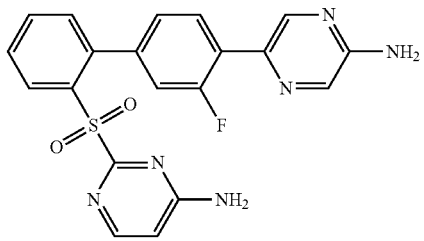

2-{[4'-(5-Aminopyrazin-2-yl)-3'-fluorobiphenyl-2-yl]sulfonyl}pyrimidin-4-amine

811

The title compound was prepared using conditions analogous to those used to make Example 718. MS (ESI): mass calcd. for $C_{20}H_{15}FN_6O_2S$, 422.10; m/z found, 423.1 [M+H]$^+$. $^1$H NMR (400 MHz, DMSO-d$_6$) δ 8.31 (s, 1H), 8.20 (d, J=7.2, 1H), 8.02 (s, 1H), 7.97 (d, J=5.7, 1H), 7.83-7.61 (m, 3H), 7.51 (s, 2H), 7.41 (d, J=7.5, 1H), 6.89-6.82 (m, 2H), 6.43 (d, J=5.9, 1H).

Example 728

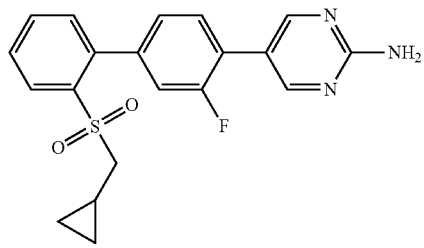

5-{2'-[(Cyclopropylmethyl)sulfonyl]-3-fluorobiphenyl-4-yl}pyrimidin-2-amine

The title compound was prepared using conditions analogous to those used to make Example 6 5-(2-fluoro-4-(4,4,5,5-tetramethyl-1,3,2-dioxaborolan-2-yl)phenyl)pyrimidin-2-amine and 1-bromo-2-((cyclopropylmethyl)sulfonyl)benzene. MS (ESI): mass calcd. for $C_2H_{18}FN_3O_2S$, 383.11; m/z found, 384.2 [M+H]$^+$. $^1$H NMR (400 MHz, DMSO-d$_6$) δ 8.53 (d, J=1.5, 2H), 8.11 (dd, J=7.9, 1.2, 1H), 7.80 (m, 1H), 7.72 (m, 1H), 7.62 (m, 1H), 7.46 (dd, J=7.6, 1.1, 1H), 7.37 (dd, J=11.8, 1.7, 1H), 7.28 (dd, J=7.9, 1.7, 1H), 6.93 (s, 2H), 2.91 (d, J=7.2, 2H), 0.78-0.69 (m, 1H), 0.45-0.37 (m, 2H), 0.13-0.05 (m, 2H).

Example 729

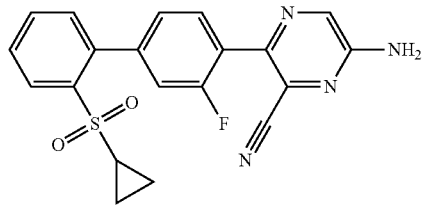

6-Amino-3-[2'-(cyclopropylsulfonyl)-3-fluorobiphenyl-4-yl]pyrazine-2-carbonitrile The title compound was prepared using conditions analogous to those used to make Example 6 utilizing 6-amino-3-(2-fluoro-4-(4,4,5,5-tetramethyl-1,3,2-dioxaborolan-2-yl)phenyl)pyrazine-2-carbonitrile and 1-bromo-2-(cyclopropylsulfonyl)benzene. MS (ESI): mass calcd. for $C_{20}H_{15}FN_4O_2S$, 394.09; m/z found, 395.0 [M+H]$^+$. $^1$H NMR (600 MHz, DMSO-d$_6$) δ 8.26 (s, 1H), 8.07 (dd, J=8.0, 1.3, 1H), 7.82-7.77 (m, 1H), 7.74-7.69 (m, 1H), 7.66-7.62 (m, 1H), 7.52 (dd, J=7.6, 1.3, 1H), 7.44 (dd, J=10.8, 1.7, 1H), 7.41-7.36 (m, 3H), 2.47-2.41 (m, 1H), 0.99-0.91 (m, 2H), 0.90-0.83 (m, 2H).

812

Intermediate JA

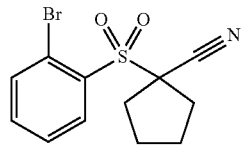

1-((2-Bromophenyl)sulfonyl)cyclopentanecarbonitrile

Step A: 2-(2-Bromophenylthio)acetonitrile

A mixture of 2-bromobenzenethiol (6.3 mL, 53 mmol), K$_2$CO$_3$ (13.8 g, 100 mmol) and 2-chloroacetonitrile (3.2 mL, 50 mmol) in DMF (50 mL) was stirred at 25° C. for 6 h, poured into water (700 mL), and extracted with petroleum ether (300 mL) followed by DCM (2×200 mL). The combined DCM extracts were concentrated to dryness, and re-dissolved in petroleum ether/ethyl acetate (10:1, 600 mL). The organic solution was washed with water (250 mL) and brine (250 mL), dried over Na$_2$SO$_4$, filtered and concentrated to dryness to give the title compound (11 g, 85%). $^1$H NMR (300 MHz, CDCl$_3$) δ 7.67 (dd, J=7.8, 1.5, 1H), 7.60 (dd, J=7.8, 1.5, 1H), 7.41 (m, 1H), 7.25 (m, 1H), 3.68 (s, 2H).

Step B: 2-(2-Bromophenylsulfonyl)acetonitrile

A mixture of 2-(2-bromophenylthio)acetonitrile (10.8 g, 47.4 mmol), NaIO$_4$ (30.4 g, 142 mmol) and RuCl$_3$ (4 mg) in DCM/ACN/H$_2$O (1:1:1, 300 mL) was stirred at rt for 18 h, and then filtered. The filtrate was diluted with water (600 mL), extracted with DCM (3×200 mL). The combined organic extracts were washed with brine (200 mL), dried over Na$_2$SO$_4$, filtered through a pad of silica gel, and concentrated to dryness to give the title compound (10.4 g, 84%). $^1$HNMR (400 MHz, CDCl$_3$) δ 8.30-8.24 (m, 1H), 7.88-7.82 (m, 1H), 7.11-7.62 (m, 2H), 4.48 (s, 2H).

Step C: 1-((2-Bromophenyl)sulfonyl)cyclopentanecarbonitrile

A mixture of 2-(2-bromophenylsulfonyl)acetonitrile (4.4 g, 17 mmol), tetrabutylammonium bromide (0.82 g, 2.6 mmol), 1,4-dibromobutane (3.85 g, 17.8 mmol) and NaOH (14 mL, 5 N) in DCM (30 mL) was stirred at rt for 5 h, before diluting with DCM (200 mL), washing with water (2×80 mL) and brine (60 mL), drying over Na$_2$SO$_4$, filtering, and concentrating to dryness. The residue was treated with IPA (20 mL) and sonicated before isolating the title compound (2.2 g) via vacuum filtration. The filtrate was concentrated to dryness and the resultant residue subjected to FCC to give additional title compound. MS (ESI): mass calcd. for $C_{12}H_{12}BrFN_3O_2S$, 312.98; m/z found, 314.0 [M+H]$^+$. $^1$HNMR (300 MHz, CDCl$_3$) δ 8.28 (dd, J=7.5, 1.5, 1H), 7.85 (dd, J=7.5, 1.5, 1H), 7.62-7.51 (m, 2H), 2.80-2.68 (m, 2H), 2.34-2.22 (m, 2H), 2.02-1.81 (m, 4H).

Intermediate JB

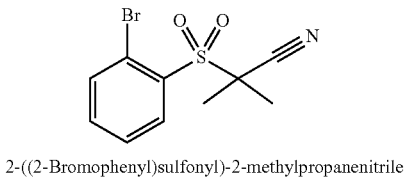

2-((2-Bromophenyl)sulfonyl)-2-methylpropanenitrile

The title compound was prepared using conditions analogous to those used to make 1-((2-bromophenyl)sulfonyl)cyclopentanecarbonitrile utilizing MeI in Step A.

Intermediate JC

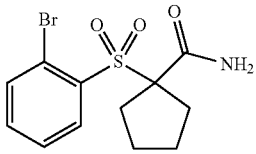

1-(2-Bromophenylsulfonyl)cyclopentanecarboxamide

A 30% $H_2O_2$ solution (1.6 mL) was added drop-wise at rt to a mixture of 1-(2-bromophenylsulfonyl)cyclopentanecarbonitrile (1.6 g, 5.1 mmol), $K_2CO_3$ (2.1 g, 15 mmol), and DMSO (5 mL). The mixture was stirred for 30 min before diluting with water (40 mL) and isolating the precipitate via vacuum filtration. The precipitate was washed with water and air-dried to give the title compound (1.5 g, 89%). MS (ESI): mass calcd. for $C_{12}H_{19}NO_3S$, 330.99; m/z found, 331.9 [M+H]$^+$. $^1$H NMR (400 MHz, DMSO-d$_6$) δ 7.99-7.95 (m, 1H), 7.89-7.84 (m, 1H), 7.64-7.51 (m, 4H), 2.41-2.25 (m, 4H), 1.78-1.66 (m, 2H), 1.58-1.45 (m, 2H).

Intermediate JD

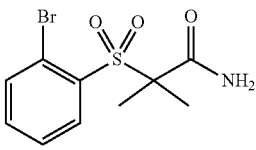

2-((2-Bromophenyl)sulfonyl)-2-methylpropanamide

The title compound was prepared using conditions analogous to those used to make 1-(2-bromophenylsulfonyl)cyclopentanecarboxamide starting with 2-((2-bromophenyl)sulfonyl)-2-methylpropanenitrile.

Example 730

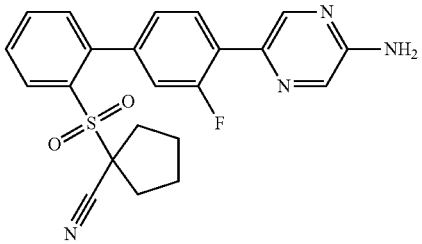

1-{[4'-(5-Aminopyrazin-2-yl)-3'-fluorobiphenyl-2-yl]sulfonyl}cyclopentanecarbonitrile The title compound was prepared using conditions analogous to those used to make Example 6 utilizing 5-(2-fluoro-4-(4,4,5,5-tetramethyl-1,3,2-dioxaborolan-2-yl)phenyl)pyrazin-2-amine and 1-((2-bromophenyl)sulfonyl)cyclopentanecarbonitrile. MS (ESI): mass calcd. for $C_{22}H_{19}FN_4O_2S$, 422.12; m/z found, 423.1 [M+H]$^+$. $^1$H NMR (400 MHz, DMSO-d) δ 8.40 (s, 1H), 8.21 (dd, J=8.0, 1.0, 1H), 8.03 (d, J=1.4, 1H), 7.92 (m, 1H), 7.88-7.80 (m, 2H), 7.53 (d, J=7.6, 1H), 7.35 (dd, J=12.3, 1.5, 1H), 7.29 (dd, J=8.0, 1.6, 1H), 6.74 (s, 2H), 2.21-2.04 (m, 4H), 1.71-1.67 (m, 4H).

Example 731

1-{[4'-(5-Aminopyrazin-2-yl)-3'-fluorobiphenyl-2-yl]sulfonyl}cyclopentanecarboxamide The title compound was prepared using conditions analogous to those used to make Example 6 utilizing 5-(2-fluoro-4-(4,4,5,5-tetramethyl-1,3,2-dioxaborolan-2-yl)phenyl)pyrazin-2-amine and 1-(2-bromophenylsulfonyl)cyclopentanecarboxamide. MS (ESI): mass calcd. for $C_{22}H_{21}FN_4O_3S$, 440.13; m/z found, 441.1 [M+H]$^+$. $^1$H NMR (400 MHz, DMSO-d$_6$) δ 8.40 (s, 1H), 8.05 (s, 1H), 7.98 (d, J=7.8, 1H), 7.86 (m, 1H), 7.76 (m, 1H), 7.65 (m, 1H), 7.46 (s, 1H), 7.37 (d, J=7.4, 2H), 7.26-7.23 (m, 2H), 6.77 (s, 2H), 2.20 (s, 2H), 2.05-1.88 (m, 2H), 1.56 (s, 2H), 1.43 (s, 2H).

Example 732

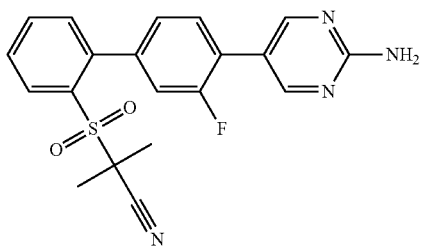

2-{[4'-(2-Aminopyrimidin-5-yl)-3'-fluorobiphenyl-2-yl]sulfonyl}-2-methylpropaneitrile The title compound was prepared using conditions analogous to those used to make Example 6 5-(2-fluoro-4-(4,4,5,5-tetramethyl-1,3,2-dioxaborolan-2-yl)phenyl)pyrimidin-2-amine and 2-((2-bromophenyl)sulfonyl)-2-methylpropanenitrile. MS (ESI): mass calcd. for $C_{20}H_{17}FN_4O_2S$, 396.11; m/z found, 397.1 [M+H]$^+$. $^1$H NMR (400 MHz, DMSO-$d_6$) δ 8.62 (s, 2H), 8.19 (d, J=7.9, 1H), 7.94 (m, 1H), 7.84 (m, 1H), 7.59 (m, 1H), 7.52 (d, J=7.5, 1H), 7.40 (dd, J=11.8, 1.1, 1H), 7.31 (dd, J=7.9, 1.4, 1H), 1.51 (s, 6H).

Example 733

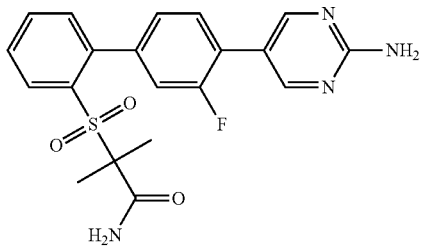

2-{[4'-(2-Aminopyrimidin-5-yl)-3'-fluorobiphenyl-2-yl]sulfonyl}-2-methylpropanamide The title compound was prepared using conditions analogous to those used to make Example 6 5-(2-fluoro-4-(4,4,5,5-tetramethyl-1,3,2-dioxaborolan-2-yl)phenyl)pyrimidin-2-amine and 2-((2-bromophenyl)sulfonyl)-2-methylpropanamide. MS (ESI): mass calcd. for $C_{20}H_{19}FN_4O_3S$, 414.12; m/z found, 415.1 [M+H]$^+$. $^1$H NMR (400 MHz, DMSO-$d_6$) δ 8.68 (s, 2H), 7.97 (d, J=7.9, 1H), 7.79 (m, 1H), 7.68 (m, 1H), 7.58 (m, 1H), 7.41 (s, 1H), 7.36 (d, J=7.5, 1H), 7.32-7.29 (m, 2H), 7.26 (d, J=7.9, 1H), 1.32 (s, 6H).

Example 734

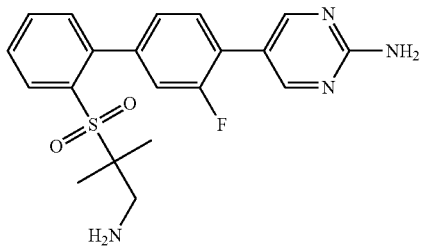

5-[2'-[(2-Amino-1,1-dimethylethyl)sulfonyl]-3-fluorobiphenyl-4-yl}pyrimidin-2-amine

Step A: 2-(2-Bromophenylsulfonyl)-2-methylpropan-1-amine

BH$_3$.THF (4 mL, 1 M in THF) was added drop-wise to a solution of 2-((2-bromophenyl)sulfonyl)-2-methylpropanenitrile (258 mg, 1.00 mmol) in THF (1 mL) at rt. The mixture was refluxed for 4 hours and then cooled to rt. Aqueous HCl (5 mL, 6 N) was added and stirring continued for an additional 1 hour. The mixture was basified to pH=9 by addition of NaOH (6 N), diluted with water (20 mL), and extracted with DCM (3×20 mL). The combined extracts were washed with water (2×30 mL) and brine (60 mL), dried over Na$_2$SO$_4$, filtered, and concentrated to dryness to give the crude title compound (203 mg, 70%), which was used in the subsequent step without further purification. MS (ESI): mass calcd. for $C_{10}H_{14}NO_2S$, 290.99; m/z found, 292.1 [M+H]$^+$.

Step B: tert-Butyl 2-(2-bromophenylsulfonyl)-2-methylpropylcarbamate

A mixture of 2-(2-bromophenylsulfonyl)-2-methylpropan-1-amine (203 mg, 0.700 mmol) and di-tert-butyl dicarbonate (152 mg, 0.700 mmol) in MeOH (10 mL) was stirred at 50° C. for 6 hours, cooled to rt, and then concentrated to dryness. The resulting residue was subjected to FCC purification to give the title compound (180 mg, 65%). MS (ESI): mass calcd. for $C_{15}H_{22}NO_4S$, 391.05; m/z found, 291.8 [M-Boc+H]$^+$. $^1$H NMR (400 MHz, CDCl$_3$) δ 8.05 (dd, J=7.8, 1.7, 1H), 7.80 (dd, J=7.7, 1.0, 1H), 7.56-7.50 (m, 1H), 7.52-7.42 (m, 1H), 5.51 (s, 1H), 3.52 (d, J=6.4, 2H), 1.45 (s, 9H), 1.37 (s, 6H).

Step C: tert-Butyl 2-(4'-(5-aminopyrazin-2-yl)-5'-fluorobiphenyl-2-ylsulfonyl)-2-methylpropyl carbamate A mixture of K$_2$CO (55 mg, 0.40 mmol) and dry DMF (5 mL) was sparged with N$_2$ for 2 minutes and then treated with tert-butyl 2-(2-bromophenylsulfonyl)-2-methylpropylcarbamate (78 mg, 0.20 mmol), 5-(2-fluoro-4-(4,4,5,5-tetramethyl-1,3,2-dioxaborolan-2-yl)phenyl)pyrazin-2-amine (66 mg, 0.21 mmol), t-BuXphos (14 mg, 0.020 mmol) and Pd$_2$(dba)$_3$ (18 mg, 0.020 mmol). The resulting mixture was purged with N$_2$ several times, and then stirred at 80° C. overnight. The reaction mixture was cooled to rt, diluted with EtOAc (20 mL), and filtered. The filtrate was concentrated to dryness and subjected to FCC to give the title compound (52 mg, 52%). MS (ESI): mass calcd. for $C_{25}H_{29}N_4O_4S$, 500.19; m/z found, 501.1 [M+H]$^+$.

Step D: 5-(6'-(1-Amino-2-methylpropan-2-ylsulfonyl)-3-fluorobiphenyl-4-yl)pyrazin-2-amine To a solution of tert-butyl 2-(4'-(5-aminopyrazin-2-yl)-5'-fluorobiphenyl-2-ylsulfonyl)-2-methylpropyl carbamate (52 mg, 0.10 mmol) in DCM (5 mL) was added TFA (2 mL). The resulting mixture was stirred at rt overnight then concentrated to dryness. The residue was basified to pH~7-8 by addition of saturated NaHCO$_3$. The resulting mixture was diluted with water (30 mL), extracted with DCM (3×10 mL), and the combined extracts washed with brine (20 mL), concentrated to dryness, and the resultant crude product purified by HPLC to give the title compound. MS (ESI): mass calcd. for $C_{20}H_{21}FN_4O_2S$, 400.14; m/z found, 401.1 [M+H]$^+$. $^1$H NMR (400 MHz, CD$_3$OD) δ 8.88 (s, 2H), 8.18 (d, J=7.9, 1H), 7.90-7.86 (m, 1H), 7.80-7.76 (m, 1H), 7.68-7.64 (m, 1H), 7.50 (d, J=7.6, 1H), 7.40 (d, J=3.1, 1H), 7.38 (s, 1H), 3.18 (s, 2H), 1.22 (s, 6H).

Example 735

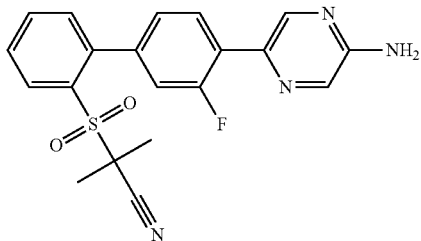

2-{[4'-(2-Aminopyrazin-2-yl)-3'-fluorobiphenyl-2-yl]sulfonyl}-2-methylpropanenitrile The title compound was prepared using conditions analogous to those used to make Example 6 utilizing 5-(2-fluor-4-(4,4,5,5-tetramethyl-1,3,2-dioxaborolan-2-yl)phenyl)pyrazin-2-amine and 2-((2-bromophenyl)sulfonyl)-2-methylpropanenitrile. MS (ESI): mass calcd. for $C_{20}H_{17}FN_4O_2S$, 396.11; m/z found, 397.0 [M+H]$^+$. $^1$H NMR (400 MHz, DMSO-d$_6$) δ 8.39 (s, 1H), 8.18 (d, J=8.0, 1H), 8.12 (d, J=1.2, 1H), 7.94 (m, 1H), 7.88-7.82 (m, 2H), 7.54 (d, J=7.6, 1H), 7.37 (dd, J=12.4, 1.4, 1H), 7.29 (dd, J=8.1, 1.6, 1H), 1.50 (s, 6H).

Example 736

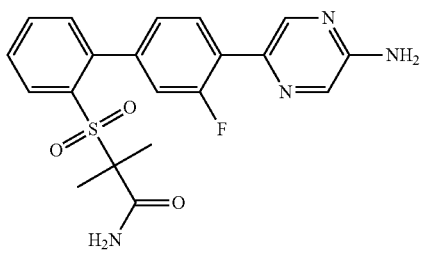

2-{[4'-(5-Aminopyrazin-2-yl)-3'-fluorobiphenyl-2-yl]sulfonyl}-2-methylpropanamide The title compound was prepared using conditions analogous to those used to make Example 6 utilizing 5-(2-fluoro-4-(4,4,5,5-tetramethyl-1,3,2-dioxaborolan-2-yl)phenyl)pyrazin-2-amine and 2-((2-bromophenyl)sulfonyl)-2-methylpropanamide. MS (ESI): mass calcd. for $C_{20}H_{19}FN_4O_3S$, 414.12; m/z found, 415.0 [M+H]$^+$. $^1$H NMR (400 MHz, DMSO-d$_6$) δ 8.38 (s, 1H), 8.16 (d, J=1.2, 1H), 7.96 (dd, J=8.0, 0.9, 1H), 7.85 (m, 1H), 7.78 (m, 1H), 7.72-7.64 (m, 1H), 7.44 (s, 1H), 7.37 (dd, J=7.6, 0.9, 1H), 7.34 (s, 1H), 7.27 (dd, J=6.4, 1.3, 1H), 7.24 (s, 1H), 1.31 (s, 6H).

Example 737

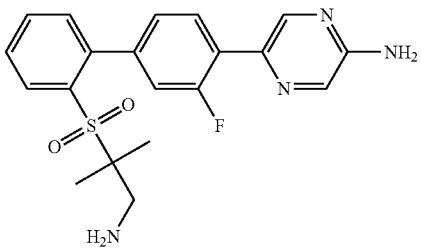

5-{2'-[(2-Amino-1,1-dimethylethyl)sulfonyl]-3-fluorobiphenyl-4-yl}pyrazin-2-amine The title compound was prepared using conditions analogous to those used to make Example 6 using -(2-fluoro-4-(4,4,5,5-tetramethyl-1,3,2-dioxaborolan-2-yl)phenyl)pyrazin-2-amine and 2-((2-bromophenyl)sulfonyl)-2-methylpropan-1-amine. MS (ESI): mass calcd. for $C_{20}H_{21}FN_4O_2S$, 400.14; m/z found, 401.1 [M+H]$^+$. $^1$H NMR (400 MHz, CD$_3$OD) δ 8.40 (s, 1H), 8.11 (d, J=6.9, 1H), 8.08 (d, J=1.4, 1H), 7.89-7.85 (m, 1H), 7.82-7.78 (m, 1H), 7.72-7.68 (m, 1H), 7.47 (d, J=6.5, 1H), 7.30-7.26 (m, 2H), 2.77 (s, 2H), 1.12 (s, 6H).

Example 738

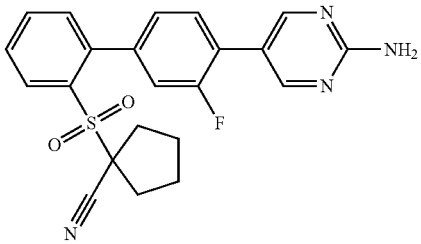

1-{[4'-(2-Aminopyrimidin-5-yl)-3'-fluorobiphenyl-2-yl]sulfonyl}cyclopentanecarbonitrile The title compound was prepared using conditions analogous to those used to make Example 6 5-(2-fluoro-4-(4,4,5,5-tetramethyl-1,3,2-dioxaborolan-2-yl)phenyl)pyrimidin-2-amine and 1-((2-bromophenyl)sulfonyl)cyclopentanecarbonitrile. MS (ESI): mass calcd. for $C_{22}H_{19}FN_4O_2S$, 422.12; m/z found, 423.1 [M+H]$^+$. $^1$H NMR (400 MHz, DMSO-d$_6$) δ 8.52 (s, 2H), 8.21 (d, J=8.0, 1H), 7.91 (m, 1H), 7.86-7.79 (m, 1H), 7.57 (m, 1H), 7.52 (d, J=7.6, 1H), 7.37 (dd, J=11.8, 1.4, 1H), 7.29 (dd, J=8.0, 1.6, 1H), 6.92 (s, 2H), 2.22-2.07 (m, 4H), 1.72-1.68 (m, 4H).

Example 739

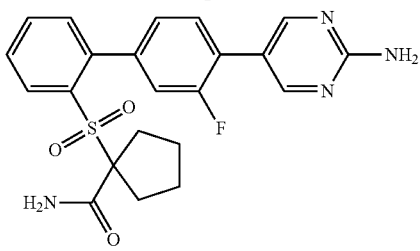

1-{[4'-(2-Aminopyrimidin-5-yl)-3'-fluorobiphenyl-2-yl]sulfonyl}cyclopentanecarboxamide The title compound was prepared using conditions analogous to those used to make Example 6 5-(2-fluoro-4-(4,4,5,5-tetramethyl-1,3,2-dioxaborolan-2-yl)phenyl)pyrimidin-2-amine and 1-(2-bromophenylsulfonyl)cyclopentanecarboxamide. MS (ESI): mass calcd. for $C_{22}H_{21}FN_4O_3S$, 440.13; m/z found, 441.1 [M+H]$^+$. $^1$H NMR (400 MHz, DMSO-d$_6$) δ 8.52 (s, 2H), 7.98 (d, J=7.7, 1H), 7.75 (m, 1H), 7.65 (m, 1H), 7.54 (m, 1H), 7.42 (s, 1H), 7.36-7.34 (m, 2H), 7.28-7.22 (m, 2H), 6.93 (s, 2H), 2.27-2.16 (m, 2H), 2.04-1.91 (m, 2H), 1.57 (s, 2H), 1.49-1.35 (m, 2H).

Example 740

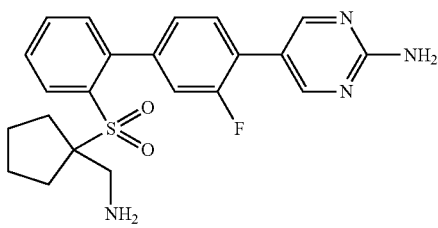

5-(2'-{[1-(Aminomethyl)cyclopentyl]sulfonyl}-3-fluorobiphenyl-4-yl)pyrimidin-2-amine The title compound was prepared using conditions analogous to those used to make Example 6 5-(2-fluoro-4-(4,4,5,5-tetramethyl-1,3,2-dioxaborolan-2-yl)phenyl)pyrimidin-2-amine and (1-((2-bromophenyl)sulfonyl)cyclopentyl)methanamine. MS (ESI): mass calcd. for $C_{22}H_{23}FN_5O_2S$, 426.15; m/z found, 427.1 [M+H]$^+$. $^1$H NMR (400 MHz, CD$_3$OD) δ 8.54 (d, J=1.3, 2H), 8.20 (dd, J=7.9, 1.2, 1H), 7.83 (m, 1H), 7.73 (m, 1H), 7.57-7.46 (m, 2H), 7.35-7.32 (m, 2H), 2.92 (s, 2H), 2.13-1.99 (m, 2H), 1.65-1.42 (m, 6H).

Example 741

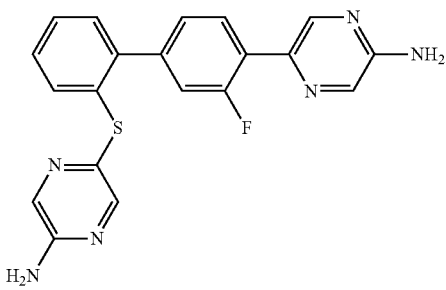

5-{[4'-(5-Aminopyrazin-2-yl)-3'-fluorobiphenyl-2-yl]sulfanyl}pyrazin-2-amine

The title compound was prepared using conditions analogous to those used to make Example 718, Steps A-C using 5-(2-fluoro-4-(4,4,5,5-tetramethyl-1,3,2-dioxaborolan-2-yl)phenyl)pyrazin-2-amine in Step A and 2-amino-5-chloropyrazine in Step C. MS (ESI): mass calcd. for $C_{19}H_{16}FN_5O_3S$, 390.11; m/z found, 391.1 [M+H]$^+$. $^1$H NMR (400 MHz, DMSO-d$_6$) δ 8.37 (s, 1H), 8.05 (s, 1H), 7.94-7.86 (m, 3H), 7.33-7.28 (m, 5H), 7.12-7.06 (m, 1H).

Example 742

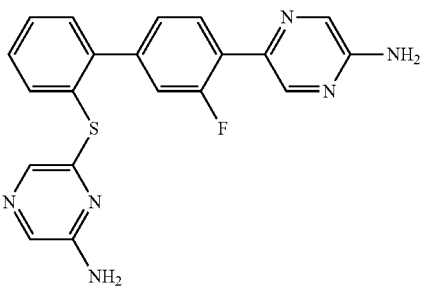

5-[2'-[(6-Aminopyrazin-2-yl)sulfanyl]-3-fluorobiphenyl-4-yl}pyrazin-2-amine

The title compound was prepared using conditions analogous to those used to make Example 718, Steps A-C using 5-(2-fluoro-4-(4,4,5,5-tetramethyl-1,3,2-dioxaborolan-2-yl)phenyl)pyrazin-2-amine in Step A and 2-amino-6-chloropyrazine in Step C. MS (ESI): mass calcd. for $C_{20}H_{15}FN_6S$, 390.11; m/z found, 391.1 [M+H]$^+$. $^1$H NMR (400 MHz, CD$_3$OD) δ 8.28 (s, 1H), 8.21 (s, 1H), 7.84 (m, 1H), 7.73-7.65 (m, 1H), 7.58-7.41 (m, 5H), 7.28-7.21 (m, 2H), 7.20-7.10 (m, 2H).

Example 743

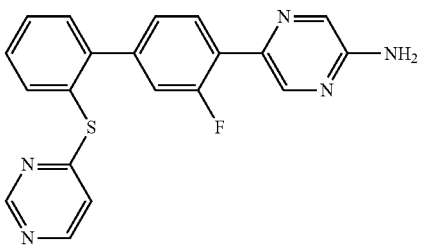

5-(3-Fluoro-2'-(pyrimidin-4-ylthio)-[1,1'-biphenyl]-4-yl)pyrazin-2-amine

The title compound was prepared using conditions analogous to those used to make Example 718, Steps A-C using 5-(2-fluoro-4-(4,4,5,5-tetramethyl-1,3,2-dioxaborolan-2-yl)phenyl)pyrazin-2-amine in Step A and 4-chloropyrimidine in Step C. MS (ESI): mass calcd. for $C_{20}H_{14}FN_5S$, 375.10; m/z found, 375.9 [M+H]$^+$. $^1$H NMR (400 MHz, CD$_3$OD) δ 8.73 (s, 1H), 8.32 (d, J=5.7, 1H), 8.28 (m, 1H), 8.19 (d, J=1.4, 1H), 7.85 (m, 1H), 7.81-7.74 (m, 1H), 7.72-7.63 (m, 1H), 7.63-7.53 (m, 2H), 7.31-7.18 (m, 2H), 6.90 (dd, J=5.6, 1.3, 1H).

Example 744

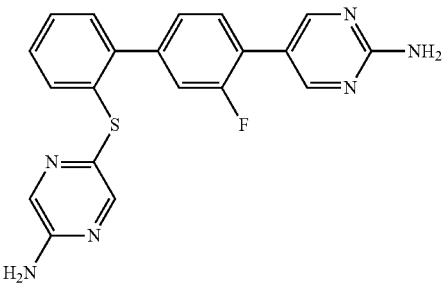

5-{2'-[(5-Aminopyrazin-2-yl)sulfanyl]-3-fluorobiphenyl-4-yl}pyrimidin-2-amine

The title compound was prepared using conditions analogous to those used to make Example 718, Steps A-C using 2-amino-5-chloropyrazine in Step C. MS (ESI): mass calcd. for $C_2H_{15}FN_6S$, 390.11; m/z found, 391.1 [M+H]$^+$. $^1$H NMR (400 MHz, CD$_3$OD) δ 8.51 (d, J=1.4, 2H), 7.79 (d, J=1.4, 1H), 7.72 (d, J=1.4, 1H), 7.47 (m, 1H), 7.32-7.17 (m, 6H).

Example 745

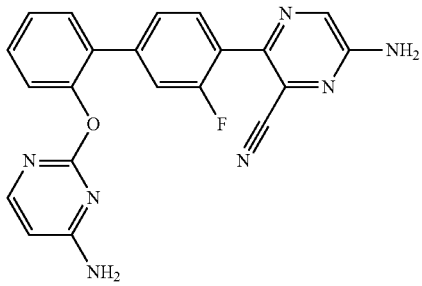

6-Amino-3-{2'-[(4-aminopyrimidin-2-yl)oxy]-3-fluorobiphenyl-4-yl}pyrazine-2-carbonitrile The title compound was prepared using conditions analogous to those used to make Example 6 utilizing 6-amino-3-(2-fluoro-4-(4,4,5,5-tetramethyl-1,3,2-dioxaborolan-2-yl)phenyl)pyrazine-2-carbonitrile and 2-(2-bromophenoxy)pyrimidin-4-amine. MS (ESI): mass calcd. for $C_{21}H_{14}FN_7OS_2$, 399.12; m/z found, 400.2 [M+H]$^+$. $^1$H NMR (600 MHz, DMSO-$d_6$) δ 8.22 (s, 1H), 7.79 (d, J=5.8, 1H), 7.62-7.51 (m, 2H), 7.49-7.38 (m, 3H), 7.38-7.30 (m, 3H), 7.20 (dd, J=8.0, 1.2, 1H), 7.01 (s, 2H), 6.10 (d, J=5.8, 1H).

Example 746

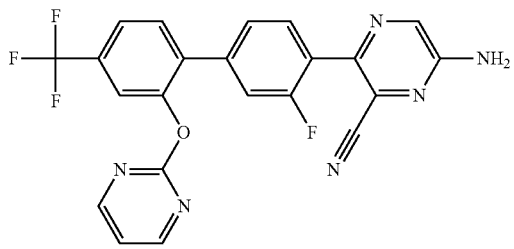

6-Amino-3-[3-fluoro-2'-(pyrimidin-2-yloxy)-4'-(trifluoromethyl)biphenyl-4-yl]pyrazine-2-carbonitrile The title compound was prepared using conditions analogous to those used to make Example 6 utilizing 6-amino-3-(2-fluoro-4-(4,4,5,5-tetramethyl-1,3,2-dioxaborolan-2-yl)phenyl)pyrazine-2-carbonitrile and 2-(2-bromo-5-(trifluoromethyl)phenoxy)pyrimidine. MS (ESI): mass calcd. for $C_{22}H_{12}F_4N_6O$, 452.10; m/z found, 453.1 [M+H]$^+$. $^1$H NMR (600 MHz, DMSO-$d_6$) δ 8.56 (d, J=4.8, 2H), 8.20 (s, 1H), 7.89-7.81 (m, 2H), 7.81-7.75 (m, 1H), 7.61-7.54 (m, 1H), 7.48 (dd, J=11.1, 1.7, 1H), 7.43 (dd, J=8.1, 1.7, 1H), 7.37 (s, 2H), 7.22-7.17 (m, 1H).

Example 747

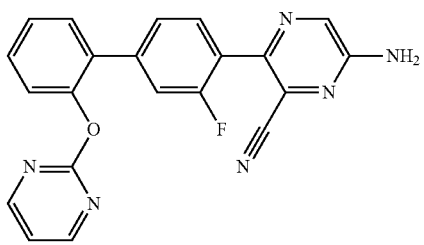

6-Amino-3-[3-fluoro-2'-(pyrimidin-2-yloxy)biphenyl-4-yl]pyrazine-2-carbonitrile

The title compound was prepared using conditions analogous to those used to make Example 6 utilizing 6-amino-3-(2-fluoro-4-(4,4,5,5-tetramethyl-1,3,2-dioxaborolan-2-yl)phenyl)pyrazine-2-carbonitrile and 2-(2-bromophenoxy)pyrimidine. MS (ESI): mass calcd. for $C_{21}H_{13}FN_6O$, 384.11; m/z found, 385.0 [M+H]$^+$. $^1$H NMR (600 MHz, DMSO-$d_6$) δ 8.55 (d, J=4.8, 2H), 8.20 (s, 1H), 7.61 (dd, J=7.7, 1.7, 1H), 7.57-7.49 (m, 2H), 7.44-7.37 (m, 3H), 7.35 (s, 2H), 7.32 (dd, J=8.1, 1.2, 1H), 7.19-7.15 (m, 1H).

Example 748

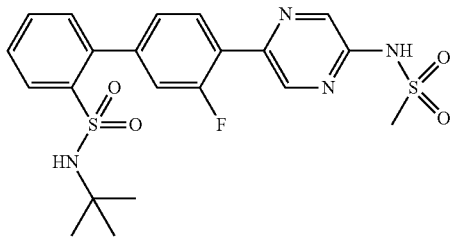

N-(tert-Butyl)-3'-fluoro-4'-(5-(methylsulfonamido)pyrazin-2-yl)-[1,1'-biphenyl]-2-sulfonamide Step A: N-(tert-Butyl)-3'-fluoro-4'-(5-(N-(methylsulfonyl)methylsulfonamido)pyrazin-2-yl)-[1,1'-biphenyl]-2-sulfonamide To a 20 mL vial were added a stir-bar, 4'-(5-aminopyrazin-2-yl)-N-(tert-butyl)-3'-fluoro-[1,1'-biphenyl]-2-sulfonamide (49 mg, 0.12 mmol), dry DCM (2.0 mL), DIPEA, (0.10 mL, 0.58 mmol), and methanesulfonyl chloride (0.020 mL, 0.25 mmol). The mixture was stirred at rt for 17.25 h before subjecting it to FCC to give impure title compound. The product was used in the next step without further purification.

Step B: N-(tert-Butyl)-3'-fluoro-4'-(5-(methylsulfonamido)pyrazin-2-yl)-[1,1'-biphenyl]-2-sulfonamide To a 20 mL vial containing N-(tert-butyl)-3'-fluoro-4'-(5-(N-(methylsulfonyl)methylsulfonamido)pyrazin-2-yl)-[1,1'-biphenyl]-2-sulfonamide (38 mg, 0.068 mmol) were added a stir-bar and DMSO (1 mL). The mixture was sonicated until homogeneous, and then treated with NaOH (0.23 mL, 0.23 mmol, 1.0 N). The mixture was stirred at rt for 18.7 h before passing it through a syringe filter and subjecting it to HPLC purification thus yielding the title compound (28 mg, 86%). MS (ESI): mass calcd. for $C_{21}H_{23}FN_4O_4S_2$, 478.11; m/z found, 479.1 $[M+H]^+$. $^1H$ NMR (600 MHz, DMSO-$d_6$) δ 11.29 (s, 1H), 8.82-8.72 (m, 1H), 8.46 (d, J=1.5, 1H), 8.07 (dd, J=7.9, 1.4, 1H), 7.98-7.91 (m, 1H), 7.71-7.65 (m, 1H), 7.65-7.58 (m, 1H), 7.43-7.32 (m, 3H), 7.05 (s, 1H), 3.41 (s, 3H), 1.03 (s, 9H).

Example 749

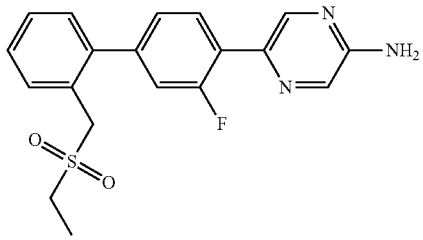

5-{2'-[(Ethylsulfonyl)methyl]-3-fluorobiphenyl-4-yl}pyrazin-2-amine hydrogen chloride salt

Step A: 5-(6'-(Chloromethyl)-3-fluorobiphenyl-4-yl)pyrazin-2-amine

A mixture of (4'-(5-aminopyrazin-2-yl)-3'-fluoro-[1,1'-biphenyl]-2-yl)methanol (1.8 g, 6.1 mmol) and $SOCl_2$ (6 mL) in DCM (20 mL) was stirred at 70° C. for 4 h. The reaction mixture was cooled to rt and concentrated to dryness to give the title compound (1.86 g, 98%). $^1H$ NMR (300 MHz, DMSO-$d_6$) δ 8.40 (s, 1H), 8.04 (s, 1H), 7.96 (m, 1H), 7.66-7.57 (m, 1H), 7.51-7.42 (m, 2H), 7.40-7.30 (m, 3H), 6.89-6.62 (m, 2H), 4.73 (s, 2H).

Step B: S-(4'-(5-Aminopyrazin-2-yl)-5'-fluorobiphenyl-2-yl)methyl ethanethioate A mixture of 5-(6'-(chloromethyl)-3-fluorobiphenyl-4-yl)pyrazin-2-amine (1.86 g, 5.94 mmol) and KSAc (0.81 g, 7.1 mmol) in 1,4-dioxane/$H_2O$ (30 mL/6 mL) was stirred at rt for 2 h. The solvent was then removed in vacuo and the residue purified by FCC to give the title compound (1.42 g, 68%). MS (ESI): mass calcd. for $C_{19}H_{16}FN_3OS$, 353.10; m/z found, 353.9 $[M+H]^+$.

Step C: 5-(2'-(Ethylthiomethyl)-3-fluorobiphenyl-4-yl)pyrazin-2-amine

To a solution of S-(4'-(5-aminopyrazin-2-yl)-5'-fluorobiphenyl-2-yl)methyl ethanethioate (100 mg, 0.280 mmol) in $CH_3OH$ (30 mL) were added $Ph_3P$ (150 mg, 0.560 mmol), $K_2CO_3$ (78 mg, 0.56 mmol), and bromoethane [drop-wise addition (60 mg, 0.56 mmol)] at rt. The reaction mixture was stirred at rt for 16 h, before removing the solvent in vacuo. The crude product was purified first by preparative-TLC followed by HPLC to give the title compound (70 mg HCOOH salt, 73%).

Step D: 5-{2'-[(Ethylsulfonyl)methyl]-3-fluorobiphenyl-4-yl}pyrazin-2-amine A mixture of 5-(2'-(ethylthiomethyl)-3-fluorobiphenyl-4-yl)pyrazin-2-amine (70 mg, 0.21 mmol), m-CPBA (107 mg, 0.618 mmol) and TFA (0.2 mL) in dry DCM (20 mL) was stirred at rt for 5 h, and then the solvent was removed under vacuum. The residue was purified by HPLC to give the title compound (40 mg, 52%). MS (ESI): mass calcd. for $C_{19}H_{18}FN_3O_2S$, 371.11; m/z found, 371.9 $[M+H]^+$. $^1H$ NMR (300 MHz, $CD_3OD$) 8.68 (d, J=1.2, 1H), 8.26 (d, J=1.3, 1H), 8.15 (m, 1H), 7.70-7.61 (m, 1H), 7.53-7.31 (m, 5H), 4.43 (s, 2H), 2.97 (q, J=7.4, 2H), 1.20 (t, J=7.4, 3H).

Example 750

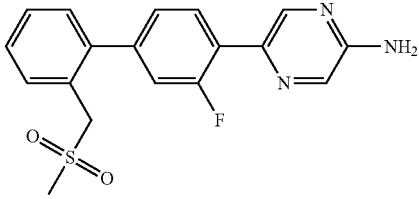

5-{3-Fluoro-2'-[(methylsulfonyl)methyl]biphenyl-4-yl}pyrazin-2-amine

The title compound was prepared using conditions analogous to those used to make Example 749 utilizing 2-iodomethane in Step C. MS (ESI): mass calcd. for $C_{18}H_{16}FN_3O_2S$, 357.09; m/z found, 357.9 $[M+H]^+$. $^1H$ NMR (400 MHz, $CD_3OD$) δ 8.66 (d, J=1.4, 1H), 8.26 (d, J=1.3, 1H), 8.14 (m, 1H), 7.70-7.61 (m, 1H), 7.54-7.45 (m, 2H), 7.43-7.32 (m, 3H), 4.49 (s, 2H), 2.83 (s, 3H).

Example 751

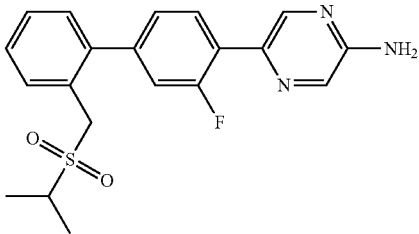

5-(3-Fluoro-2'-{[(1-methylethyl)sulfonyl]methyl}biphenyl-4-yl)pyrazin-2-amine

The title compound was prepared using conditions analogous to those used to make Example 749 utilizing 2-iodopropane in Step C. MS (ESI): mass calcd. for $C_{20}H_{20}FN_5O_3S$, 385.13; m/z found, 386.1 $[M+H]^+$. $^1H$ NMR (400 MHz, $CD_3OD$) δ 8.72-8.61 (m, 1H), 8.24 (s, 1H), 8.13 (m, 1H), 7.70-7.59 (m, 1H), 7.54-7.28 (m, 5H), 4.40 (s, 2H), 3.18-3.07 (m, 1H), 1.23 (d, J=6.8, 6H).

Example 752

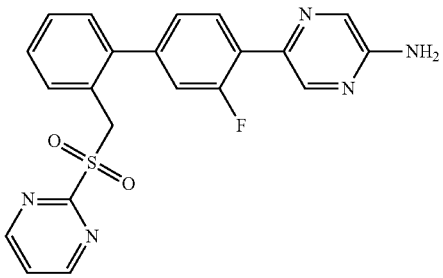

5-{3-Fluoro-2'-[(pyrimidin-2-ylsulfonyl)methyl]biphenyl-4-yl}pyrazin-2-amine

The title compound was prepared using conditions analogous to those used to make Example 749 utilizing 5-(3-fluoro-2'-((pyrimidin-2-ylthio)methyl)-[1,1'-biphenyl]-4-yl)pyrazin-2-amine in Step D. MS (ESI): mass calcd. for $C_{21}H_{16}FN_5O_2S$, 421.10; m/z found, 422.1 [M+H]$^+$. $^1$H NMR (400 MHz, CD$_3$OD) δ 8.91 (d, J=4.9, 2H), 8.41 (s, 1H), 8.11 (d, J=1.3, 1H), 7.90 (t, J=8.1, 1H), 7.71 (m, 1H), 7.66-7.59 (m, 1H), 7.52-7.40 (m, 2H), 7.34 (dd, J=7.3, 1.5, 1H), 7.27-7.14 (m, 2H), 5.02 (s, 2H).

Example 753

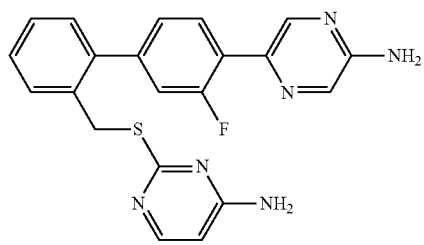

2-({[4'-(5-Aminopyrazin-2-yl)-3'-fluorobiphenyl-2-yl]methyl}sulfanyl)pyrimidin-4-amine The title compound was prepared using conditions analogous to those used to make Example 749, Steps A-C utilizing 4-amino-2-chloropyrimidine. MS (ESI): mass calcd. for $C_{21}H_{17}FN_6S$, 404.12; m/z found, 405.1 [M+H]$^+$. $^1$H NMR (400 MHz, CD$_3$OD) δ 8.63 (d, J=1.1, 1H), 8.25 (d, J=1.2, 1H), 8.10 (m, 1H), 7.86 (d, J=7.2, 1H), 7.68-7.58 (m, 1H), 7.51-7.39 (m, 2H), 7.37-7.23 (m, 3H), 6.40 (d, J=7.2, 1H), 4.62 (s, 2H).

Example 754

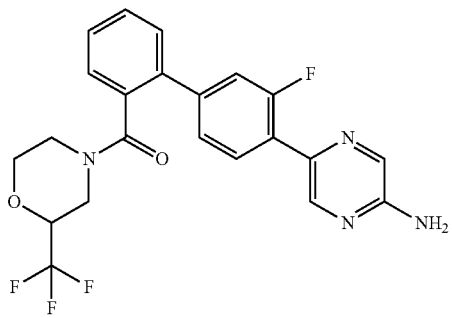

racemic 5-(3-Fluoro-2'-{[2-(trifluoromethyl)morpholin-4-yl]carbonyl}biphenyl-4-yl)pyrazin-2-amine The title compound was prepared as described in Step C of Example 504 utilizing racemic 2-(trifluoromethyl)morpholine. MS (ESI): mass calcd. for $C_{22}H_{18}F_4N_4O_2$, 446.14; m/z found, 447.1 [M+H]$^+$. $^1$H NMR (400 MHz, CDCl$_3$) Complex due to the presence of multiple conformations on the NMR time-scale, peaks listed for identification purposes only: δ 8.61 (s), 8.18-7.95 (m), 7.59-7.29 (m), 4.88-4.41 (m), 4.11-3.51 (m), 3.32 (m), 3.17-3.00 (m), 3.00-2.84 (m), 2.68-2.41 (m), 2.37-2.16 (m).

Example 755

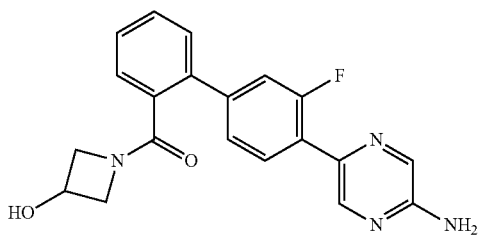

1-{[4'-(5-Aminopyrazin-2-yl)-3'-fluorobiphenyl-2-yl]carbonyl}azetidin-3-ol

The title compound was prepared as described in Step C of Example 504 utilizing 3-hydroxyazetidine. MS (ESI): mass calcd. for $C_{20}H_{17}FN_4O_2$, 364.13; m/z found, 364.9 [M+H]$^+$. $^1$H NMR (400 MHz, DMSO-d$_6$) δ 8.37 (s, 1H), 8.02 (s, 1H), 7.93-7.89 (m, 1H), 7.55-7.38 (m, 4H), 7.36-7.24 (m, 2H), 6.67 (s, 2H), 5.64 (s, 1H), 4.28 (s, 1H), 4.08-4.01 (m, 1H), 3.79-3.75 (m, 1H), 3.58-3.54 (m, 1H), 3.15 (s, 1H).

Example 756

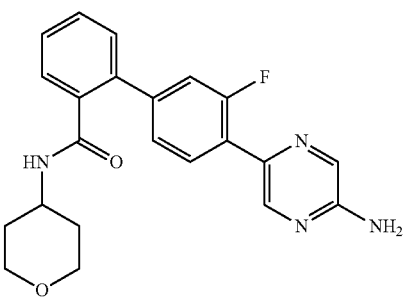

4'-(5-Aminopyrazin-2-yl)-3'-fluoro-N-(tetrahydro-2H-pyran-4-yl)biphenyl-2-carboxamide The title compound was prepared as described in Step C of Example 504 utilizing tetrahydro-2H-pyran-4-amine. MS (ESI): mass calcd. for $C_{22}H_{21}FN_4O_2$, 392.16; m/z found, 392.9 [M+H]$^+$. $^1$H NMR (400 MHz, DMSO-d$_6$) δ 8.33 (s, 1H), 8.22 (d, J=7.7, 1H), 8.01 (d, J=1.1, 1H), 7.86-7.82 (m, 1H), 7.54-7.38 (m, 4H), 7.29-7.25 (m, 2H), 6.65 (s, 2H), 3.86-3.77 (m, 1H), 3.73-3.70 (m, 2H), 3.26 (s, 2H), 1.61-1.59 (m, 2H), 1.38-1.28 (m, 2H).

Example 757

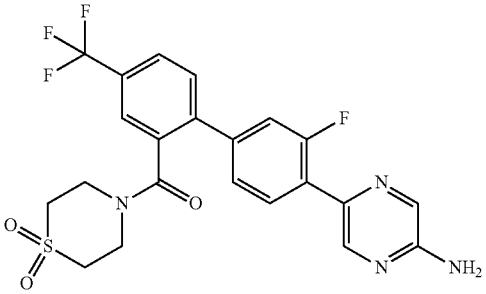

5-{2'-[(1,1-Dioxidothiomorpholin-4-yl)carbonyl]-3-fluoro-4'-(trifluoromethyl)biphenyl-4-yl}pyrazin-2-amine The title compound was prepared as described in Step C of Example 504 utilizing thiomorpholine 1,1-dioxide. MS (ESI): mass calcd. for $C_{22}H_{18}F_4N_4O_3S$, 494.10; m/z found, 494.7 [M+H]$^+$. $^1$H NMR (400 MHz, DMSO-d$_6$) δ 8.36 (s, 1H), 8.02-7.90 (m, 4H), 7.78-7.76 (m, 1H), 7.36-7.29 (m, 2H), 6.75 (s, 2H), 4.35-4.20 (m, 1H), 3.59-3.46 (m, 2H), 3.31-3.12 (m, 4H), 3.04-2.90 (m, 1H).

Example 758

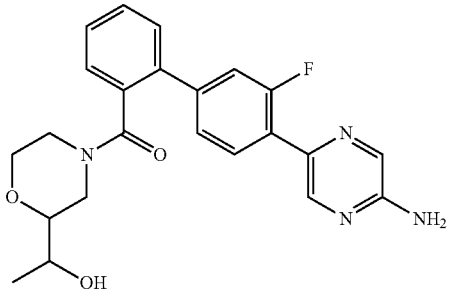

1-(4-{[4'-(5-Aminopyrazin-2-yl)-3'-fluorobiphenyl-2-yl]carbonyl}morpholin-2-yl)ethanol (diastereomeric mixture).

The title compound was prepared as described in Step C of Example 504 utilizing a diastereomeric mixture of 1-(piperidin-3-yl)ethanolgiving the title compound. MS (ESI): mass calcd. for $C_{23}H_{23}FN_4O_3$, 422.18; m/z found, 422.9 [M+H]$^+$. $^1$H NMR (400 MHz, CD$_3$OD) δ Complex due to the presence of multiple conformations on the NMR time-scale and diastereoisomers, peaks listed for identification purposes only: 8.30 (s), 8.01-7.80 (m), 7.53-7.14 (m), 4.55-4.49 (m), 4.33-4.25 (m), 3.90-3.66 (m), 3.61-3.31 (m), 3.25 (s), 3.16-2.85 (m), 2.84-2.12 (m), 1.07-0.76 (m).

Example 759

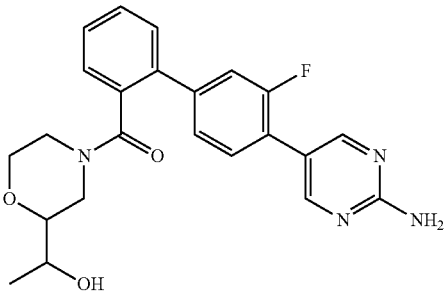

1-(4-{[4'-(2-Aminopyrimidin-5-yl)-3'-fluorobiphenyl-2-yl]carbonyl}morpholin-2-yl)ethanol (diastereomeric mixture).

The title compound was prepared as described in Step C of Example 504 utilizing a diastereomeric mixture of 1-(piperidin-3-yl)ethanol. MS (ESI): mass calcd. for $C_{23}H_{23}FN_4O_3$, 422.18; m/z found, 422.9 [M+H]$^+$. $^1$H NMR (400 MHz, CD$_3$OD) Complex due to the presence of multiple conformations on the NMR time-scale and diastereoisomers, peaks listed for identification purposes only: δ 8.43 (s), 7.57-7.17 (m), 4.55-4.49 (m), 4.32-4.26 (m), 3.89-3.70 (m), 3.61-3.33 (m), 3.33-3.23 (m), 3.12-2.86 (m), 2.85-2.12 (m), 1.10-0.77 (m).

Example 760

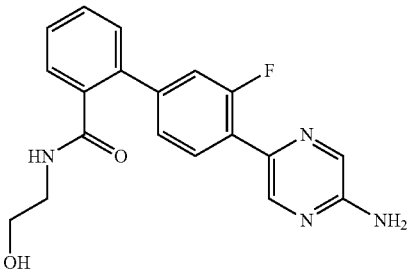

4'-(5-Aminopyrazin-2-yl)-3'-fluoro-N-(2-hydroxyethyl)biphenyl-2-carboxamide

The title compound was prepared as described in Step C of Example 504 utilizing ethanolamine. MS (ESI): mass calcd. for $C_{19}H_{17}FN_4O_2$, 352.13; m/z found, 352.9 [M+H]$^+$. $^1$H NMR (400 MHz, CD$_3$OD) δ 8.37 (s, 1H), 8.06 (d, J=1.2, 1H), 7.94-7.83 (m, 1H), 7.59-7.39 (m, 4H), 7.38-7.22 (m, 2H), 3.51 (t, J=6.1, 2H), 3.35-3.31 (m, 2H).

Example 761

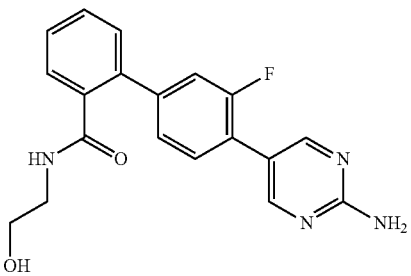

4'-(2-Aminopyrimidin-5-yl)-3'-fluoro-N-(2-hydroxyethyl)biphenyl-2-carboxamide

The title compound was prepared as described in Step C of Example 504 utilizing ethanolamine. MS (ESI): mass calcd. for C$_{19}$H$_{17}$FN$_4$O$_2$, 352.13; m/z found, 352.9 [M+H]$^+$. $^1$H NMR (400 MHz, CD$_3$OD) δ 8.51 (s, 2H), 7.57-7.42 (m, 5H), 7.34-7.27 (m, 5H), 3.52 (t, J=6.0, 2H), 3.35-3.31 (m, 2H).

Example 762

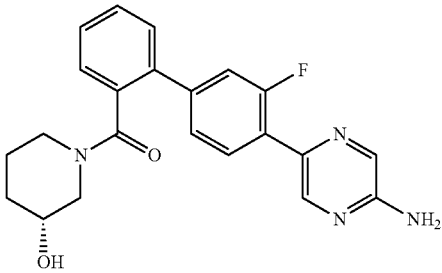

(3R)-1-{[4'-(5-Aminopyrazin-2-yl)-3'-fluorobiphenyl-2-yl]carbonyl}piperidin-3-ol The title compound was prepared as described in Step C of Example 504 utilizing (R)-3-hydroxypiperidine. MS (ESI): mass calcd. for C$_{22}$H$_{21}$FN$_4$O$_2$, 392.16; m/z found, 393.0 [M+H]$^+$. $^1$H NMR (400 MHz, CDCl$_3$) Complex due to the presence of multiple conformations on the NMR time-scale, peaks listed for identification purposes only: δ 8.37 (s), 8.09 (br s), 8.03-7.87 (m), 7.65-7.45 (m), 7.45-7.23 (m), 4.34-4.20 (m), 4.13-4.09 (m), 3.94-3.80 (m), 3.68-3.31 (m), 3.21-2.84 (m), 2.79-2.48 (m), 1.94-1.65 (m), 1.39-1.08 (m).

Example 763

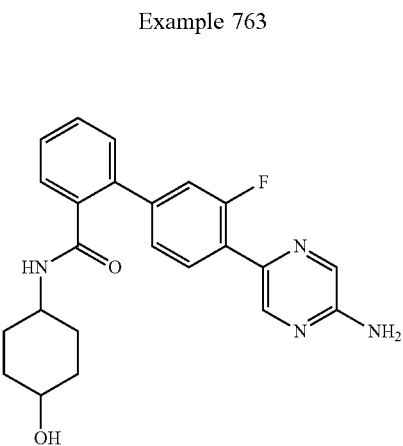

(cis/trans) 4'-(5-Aminopyrazin-2-yl)-3'-fluoro-N-(4-hydroxycyclohexyl)biphenyl-2-carboxamide The title compound was prepared as described in Step C of Example 504 utilizing (cis/trans) 4-aminocyclohexanol. MS (ESI): mass calcd. for C$_{23}$H$_{23}$FN$_4$O$_2$, 406.18; m/z found, 407.0 [M+H]$^+$. $^1$H NMR (400 MHz, CDCl$_3$) δ 8.36 (s, 1H), 8.07-8.04 (m, 1H), 7.88 (m, 1H), 7.57-7.40 (m, 4H), 7.33-7.24 (m, 2H), 3.69-3.62 (m, 1H), 3.46-3.39 (m, 4H), 3.34 (br s, 1H), 1.87-1.76 (m, 4H), 1.33-1.26 (m, 2H), 1.18-1.08 (m, 2H).

Example 764

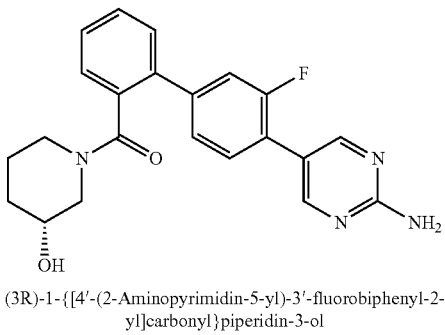 [SMILES: Nc1ncc(-c2ccc(-c3ccccc3C(=O)N3CCC[C@@H](O)C3)cc2F)cn1]

(3R)-1-{[4'-(2-Aminopyrimidin-5-yl)-3'-fluorobiphenyl-2-yl]carbonyl}piperidin-3-ol The title compound was prepared as described in Step C of Example 504 utilizing (R)-piperidin-3-ol. MS (ESI): mass calcd. for C$_{22}$H$_{21}$FN$_4$O$_2$, 392.16; m/z found, 393.0 [M+H]$^+$. $^1$H NMR (400 MHz, CDCl$_3$) Complex due to the presence of multiple conformations on the NMR time-scale, peaks listed for identification purposes only: δ 8.52-8.51 (m), 7.59-7.47 (m), 7.44-7.28 (m), 4.30-4.04 (m), 3.93-3.81 (m), 3.69-3.32 (m), 3.17-2.89 (m), 2.83-2.57 (m), 1.96-1.67 (m), 1.53-1.15 (m).

Example 765

(cis/trans) 4'-(2-Aminopyrimidin-5-yl)-3'-fluoro-N-(4-hydroxycyclohexyl)biphenyl-2-carboxamide The title compound was prepared as described in Step C of Example 504 utilizing (cis/trans) 4-aminocyclohexanol. MS (ESI): mass calcd. for C$_{23}$H$_{23}$FN$_4$O$_2$, 406.18; m/z found, 407.0 [M+H]$^+$. $^1$H NMR (400 MHz, CD$_3$OD) δ 8.49 (d, J=1.2, 2H), 7.58-7.40 (m, 5H), 7.33-7.26 (m, 2H), 3.69-3.61 (m, 1H), 3.51-3.38 (m, 1H), 3.33 (br s, 1H), 1.88-1.76 (m, 4H), 1.35-1.27 (m, 2H), 1.14 (m, 2H).

Example 766

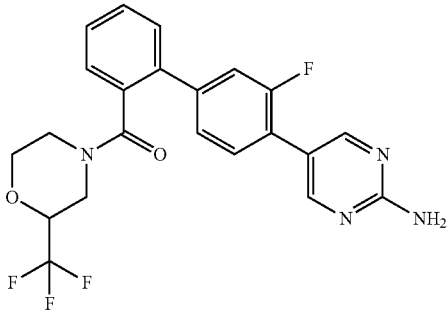

racemic 5-(3-Fluoro-2'-{[2-(trifluoromethyl)morpholin-4-yl]carbonyl}biphenyl-4-yl)pyrimidin-2-amine The title compound was prepared as described in Step C of Example 504 utilizing racemic 2-(trifluoromethyl)morpholine. MS (ESI): mass calcd. for $C_{22}H_{18}F_4N_4O_2$, 446.14; m/z found, 447.1 [M+H]$^+$. $^1$H NMR (400 MHz, CDCl$_3$) Complex due to the presence of multiple conformations on the NMR time-scale, peaks listed for identification purposes only: δ 8.57 (s), 7.62-7.27 (m), 5.21 (s), 4.74 (dd), 4.52 (d), 4.12-3.73 (m), 3.65 (d), 3.48-3.21 (m), 3.21-3.01 (m), 2.94 (m), 2.60 (m), 2.35 (s), 2.16 (s).

Example 767

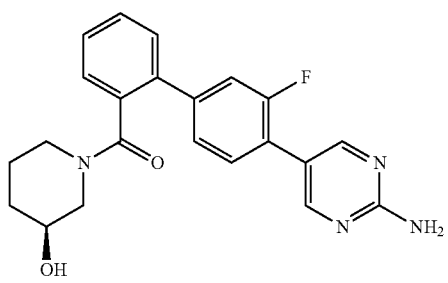

(3S)-1-{[4'-(2-Aminopyrimidin-5-yl]-3'-fluorobiphenyl-2-yl]carbonyl}piperidin-3-ol The title compound was prepared as described in Step C of Example 504 utilizing (S)-piperidin-3-ol. MS (ESI): mass calcd. for $C_{22}H_{21}FN_4O_2$, 392.16; m/z found, 393.0 [M+H]$^+$. $^1$H NMR (400 MHz, CD$_3$OD) Complex due to the presence of multiple conformations on the NMR time-scale, peaks listed for identification purposes only: δ 8.51 (d), 7.64-7.45 (m), 7.43-7.29 (m), 4.31-4.03 (m), 3.94-3.80 (m), 3.69-3.58 (m), 3.51-3.35 (m), 3.34 (s), 3.22-2.84 (m), 2.84-2.56 (m), 2.44 (dd), 2.10-1.55 (m), 1.52-1.15 (m).

Example 768

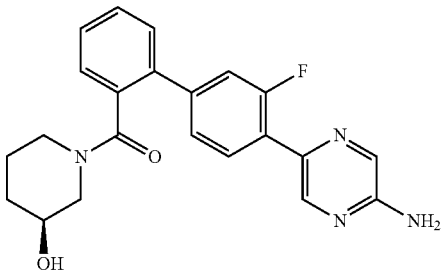

(3S)-1-{[4'-(5-Aminopyrazin-2-yl)-3'-fluorobiphenyl-2-yl]carbonyl}piperidin-3-ol The title compound was prepared as described in Step C of Example 504 utilizing (S)piperidin-3-ol. MS (ESI): mass calcd. for $C_{22}H_{21}FN_4O_2$, 392.16; m/z found, 393.0 [M+H]$^+$. $^1$H NMR (400 MHz, CD$_3$OD) Complex due to the presence of multiple conformations on the NMR time-scale, peaks listed for identification purposes only: δ 8.38 (s), 8.07 (s), 7.97-7.87 (m), 7.59-7.45 (m), 7.44-7.25 (m), 4.30-4.27 (m), 4.11 (dd), 4.30-4.27 (m), 3.66-3.56 (m), 3.49-3.32 (m), 3.20-2.83 (m), 2.79-2.50 (m), 2.36 (dd), 2.04-1.58 (m), 1.50-1.13 (m).

Example 769

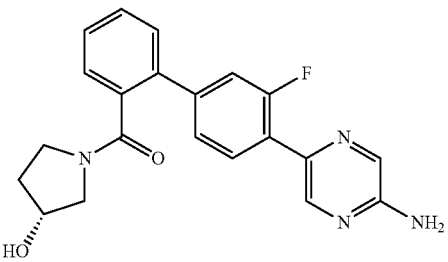

(3R)-1-{[4'-(5-Aminopyrazin-2-yl)-3'-fluorobiphenyl-2-yl]carbonyl}pyrrolidin-3-ol The title compound was prepared as described in Step C of Example 504 utilizing (R)-pyrrolidin-3-ol. MS (ESI): mass calcd. for $C_{21}H_{19}FN_4O_2$, 378.15; m/z found, 379.0 [M+H]$^+$. $^1$H NMR (400 MHz, CDCl$_3$) Complex due to the presence of multiple conformations on the NMR time-scale, peaks listed for identification purposes only: δ 8.39 (s), 8.00 (s), 7.89-7.79 (m), 7.45-7.22 (m), 5.13 (m), 4.30 (m), 4.14 (m), 3.70-3.36 (m), 3.02-2.96 (m), 2.59 (m), 1.90-1.55 (m).

Example 770

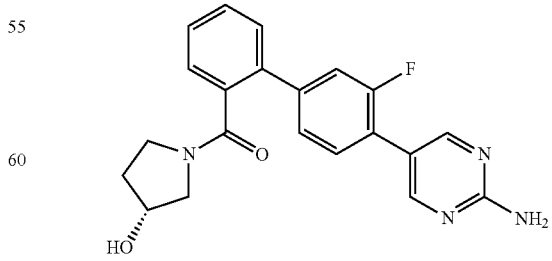

(3R)-1-{[4'-(2-Aminopyrimidin-5-yl)-3'-fluorobiphenyl-2-yl]carbonyl}pyrrolidin-3-ol The title compound was prepared as described in Step C of Example 504 utilizing (R)-pyrrolidin-3-ol. MS (ESI): mass calcd. for $C_{21}H_{19}FN_4O_2$, 378.15; m/z found, 379.0 $[M+H]^+$. $^1H$ NMR (400 MHz, $CDCl_3$) Complex due to the presence of multiple conformations on the NMR time-scale, peaks listed for identification purposes only: δ 8.46 (d), 7.46-7.23 (m), 5.47 (m), 4.31 (m), 4.16 (m), 3.65-3.37 (m), 3.13-2.86 (m), 2.81 (m), 1.86-1.60 (m).

Example 771

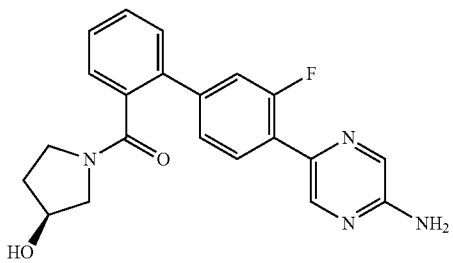

(3S)-1-{[4'-(5-Aminopyrazin-2-yl)-3'-fluorobiphenyl-2-yl]carbonyl}pyrrolidin-3-ol The title compound was prepared as described in Step C of Example 504 utilizing (S)-pyrrolidin-3-ol. MS (ESI): mass calcd. for $C_{21}H_{19}FN_4O_2$, 378.15; m/z found, 378.9 $[M+H]^+$. $^1H$ NMR (400 MHz, $CDCl_3$) Complex due to the presence of multiple conformations on the NMR time-scale, peaks listed for identification purposes only: δ 8.28 (s), 7.96 (s), 7.87-7.78 (m), 7.51-7.18 (m), 4.25-4.16 (m), 4.05 (m), 3.58-3.29 (m), 3.20 (m), 3.11-2.77 (m), 1.73 (m), 1.60 (m).

Example 772

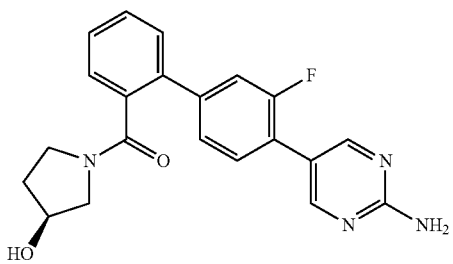

(3S)-1-{[4'-(2-Aminopyrimidin-5-yl)-3'-fluorobiphenyl-2-yl]carbonyl}pyrrolidin-3-ol The title compound was prepared as described in Step C of Example 504 utilizing (S)-pyrrolidin-3-ol. MS (ESI): mass calcd. for $C_{21}H_{19}FN_4O_2$, 378.15; m/z found, 379.0 $[M+H]^+$. $^1H$ NMR (400 MHz, $CDCl_3$) Complex due to the presence of multiple conformations on the NMR time-scale, peaks listed for identification purposes only: δ 8.45 (d), 7.45-7.23 (m), 5.19 (m), 4.33 (m), 4.17 (m), 3.63-3.56 (m), 3.50 (d), 3.06-2.87 (m), 1.79 (m), 1.67 (m).

Example 773

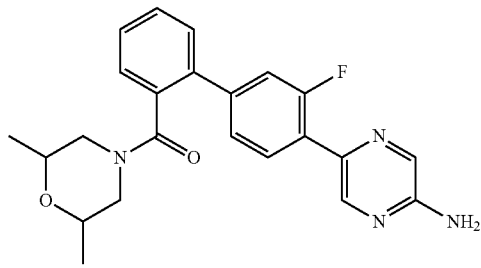

6-{2'-{[2'-6-Dimethylmorpholin-4-yl)carbonyl]-3-fluorobiphenyl-4-yl}pyrazin-2-amine (diastereoisomeric mixture).

The title compound was prepared as described in Step C of Example 504 utilizing a diastereoisomeric mixture of 2,6-dimethylmorpholine. MS (ESI): mass calcd. for $C_{23}H_{23}FN_4O_2$, 406.18; m/z found, 407.0 $[M+H]^+$. $^1H$ NMR (400 MHz, $CDCl_3$) Complex due to the presence of multiple diastereoisomers and conformations on the NMR time-scale, peaks listed for identification purposes only: δ 8.58 (d), 8.11 (s), 8.09-8.00 (m), 7.55-7.29 (m), 4.77 (br s), 4.52 (d), 3.64-3.30 (m), 3.10-3.00 (m), 2.58-2.47 (m), 2.44-2.33 (m), 2.18-2.01 (m), 1.14 (dd), 0.97-0.84 (m).

Example 774

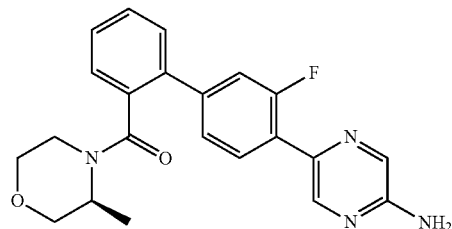

5-(3-Fluoro-2'-{[(3S)-3-methylmorpholin-4-yl]carbonyl}biphenyl-4-yl)pyrazin-2-amine The title compound was prepared as described in Step C of Example 504 utilizing (S)-3-methylmorpholine. MS (ESI): mass calcd. for $C_{22}H_{21}FN_4O_2$, 392.16; m/z found, 393.0 $[M+H]^+$. $^1H$ NMR (400 MHz, DMSO-$d_6$) δ 8.38 (d, J=9.6, 1H), 8.04 (s, 1H), 8.00-7.91 (m, 1H), 7.61-7.45 (m, 3H), 7.45-7.20 (m, 3H), 6.75 (d, J=5.1, 2H), 4.54-4.01 (m, 1H), 3.77-3.39 (m, 2H), 3.25-3.15 (m, 1H), 3.05-2.85 (m, 1H), 2.85-2.63 (m, 1H), 2.22-1.95 (m, 1H), 1.20 (d, J=6.9, 3H).

Example 775

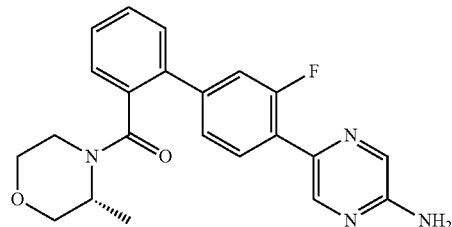

5-(3-Fluoro-2'-{[(3R)-3-methylmorpholin-4-yl]carbonyl}biphenyl-4-yl)pyrazin-2-amine The title compound was prepared as described in Step C of Example 504 utilizing (R)-3-methylmorpholine. MS (ESI): mass calcd. for $C_{22}H_{21}FN_4O_2$, 392.16; m/z found, 393.0 [M+H]$^+$. $^1$H NMR (400 MHz, DMSO-d$_6$) δ 8.38 (d, J=9.6, 1H), 8.04 (s, 1H), 8.01-7.89 (m, 1H), 7.61-7.46 (m, 3H), 7.45-7.19 (m, 3H), 6.75 (d, J=5.1, 2H), 4.53-4.03 (m, 1H), 3.73-3.58 (m, 1H), 3.54-3.41 (m, 1H), 3.25-3.15 (m, 1H), 3.05-2.86 (m, 1H), 2.84-2.64 (m, 1H), 2.23-1.88 (m, 1H), 1.20 (d, J=6.9, 3H).

Example 776

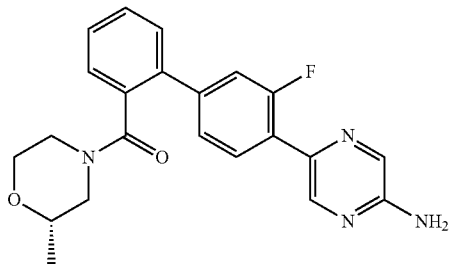

5-(3-Fluoro-2'-{[(2S)-2-methylmorpholin-4-yl]carbonyl}biphenyl-4-yl)pyrazin-2-amine The title compound was prepared as described in Step C of Example 504 utilizing (S)-2-methylmorpholine. MS (ESI): mass calcd. for $C_{22}H_{21}FN_4O_2$, 392.16; m/z found, 393.0 [M+H]$^+$. $^1$H NMR (400 MHz, DMSO-d) δ 8.39 (s, 1H), 8.04 (s, 1H), 7.97-7.95 (m, 1H), 7.65-7.46 (m, 3H), 7.45-7.24 (m, 3H), 6.76 (s, 2H), 4.27 (dd, J=23.7, 13.0, 1H), 3.87-3.38 (m, 2H), 3.13-2.70 (m, 2H), 2.63-2.42 (m, 1H), 2.19-1.90 (m, 1H), 1.04 (d, J=6.0, 3H).

Example 777

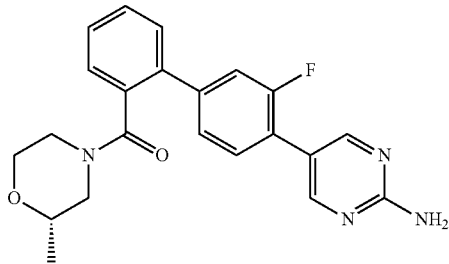

5-(3-Fluoro-2'-{[(2S)-2-methylmorpholin-4-yl]carbonyl}biphenyl-4-yl)pyrimidin-2-amine The title compound was prepared as described in Step C of Example 504 utilizing (S)-2-methylmorpholine. MS (ESI): mass calcd. for $C_{22}H_{21}FN_4O_2$, 392.16; m/z found, 393.0 [M+H]$^+$. $^1$H NMR (400 MHz, DMSO-d$_6$) δ 8.50 (d, J=5.2, 2H), 7.76-7.60 (m, 1H), 7.60-7.46 (m, 3H), 7.46-7.22 (m, 3H), 6.76 (s, 2H), 4.27 (dd, J=20.9, 12.6, 1H), 3.88-3.52 (m, 1H), 3.43 (m, 1H), 3.17-2.82 (m, 2H), 2.81-2.52 (m, 1H), 2.31-1.97 (m, 1H), 1.05 (d, J=5.9, 3H).

Example 778

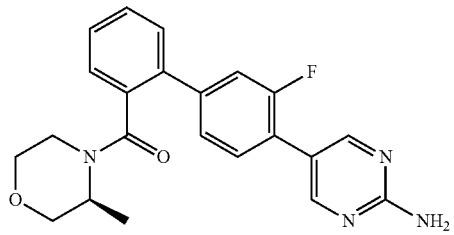

5-(3-Fluoro-2'-{[(3S)-3-methylmorpholin-4-yl]carbonyl}biphenyl-4-yl)pyrimidin-2-amine The title compound was prepared as described in Step C of Example 504 utilizing (S)-3-methylmorpholine. MS (ESI): mass calcd. for $C_{22}H_{21}FN_4O_2$, 392.16; m/z found, 393.0 [M+H]$^+$. $^1$H NMR (400 MHz, DMSO-d$_6$): δ 8.54-8.45 (m, 2H), 7.72-7.60 (m, 1H), 7.57-7.47 (m, 3H), 7.42-7.21 (m, 3H), 6.94 (d, J=6.0, 2H), 4.48 (s, 1H), 3.90 (dd, J=13.9, 11.2, 1H), 3.60 (d, J=11.4, 1H), 3.16 (s, 1H), 3.01-2.68 (m, 2H), 2.27-1.96 (m, 1H), 1.20 (d, J=6.8, 3H)

Example 779

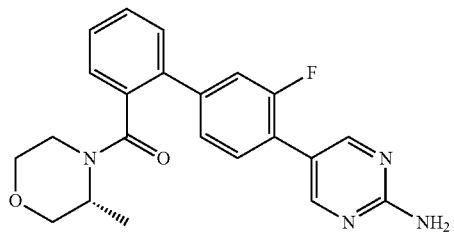

5-(3-Fluoro-2'-{[(3R)-3-methylmorpholin-4-yl]carbonyl}biphenyl-4-yl)pyrimidin-2-amine The title compound was prepared as described in Step C of Example 504 utilizing (R)-3-methylmorpholine. MS (ESI): mass calcd. for $C_{22}H_{21}FN_4O_2$, 392.16; m/z found, 393.0 [M+H]$^+$. $^1$H NMR (400 MHz, DMSO-d$_6$) δ 8.46 (d, J=11.5, 2H), 7.69-7.58 (m, 1H), 7.56-7.42 (m, 3H), 7.40-7.18 (m, 3H), 6.91 (d. J=5.8, 2H), 4.41 (d. J=21.0, 1H), 3.87 (dd, J=13.5, 11.0, 1H), 3.56 (d, J=11.2, 1H), 3.15 (dd, J=8.0, 5.6, 1H), 3.00-2.66 (m, 2H), 2.12 (m, 1H), 1.17 (d, J=6.8, 3H).

Example 780

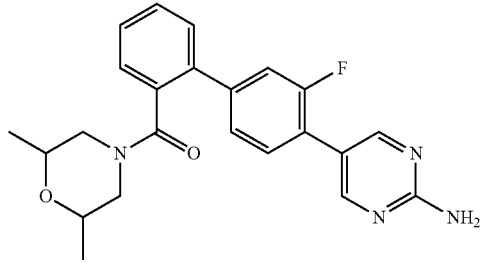

5-{2'-{[2,6-Dimethylmorpholin-4-yl)carbonyl]-3-fluorobiphenyl-4-yl}pyrazin-2-amine
(diastereoisomeric mixture)

The title compound was prepared as described in Step C of Example 504 utilizing a diastereoisomeric mixture of 2,6-dimethylmorpholine. MS (ESI): mass calcd. for $C_{23}H_{23}FN_4O_2$, 406.18; m/z found, 407.0 [M+H]$^+$. $^1$H NMR (400 MHz, DMSO-$d_6$) δ 8.47 (d, J=9.3, 2H), 7.68-7.59 (m, 1H), 7.54-7.45 (m, 3H), 7.36-7.26 (m, 3H), 6.91 (d, J=10.5, 2H), 4.29 (d, J=12.6, 2H), 3.00 (dd, J=31.3, 12.7, 1H), 2.59-2.50 (m, 1H), 2.40-2.26 (m, 1H), 2.17-2.07 (m, 1H), 1.12-0.96 (m, 3H), 0.89-0.72 (m, 3H).

Example 781

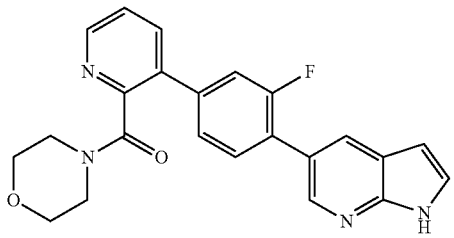

5-(2-Fluoro-4-[2-(morpholin-4-ylcarbonyl)pyridin-3-yl]phenyl}-1H-pyrrolo[2,3-b]pyridine The title compound was prepared as described in Example 376 utilizing 5-(2-fluoro-4-(4,4,5,5-tetramethyl-1,3,2-dioxaborolan-2-yl)phenyl)-1H-pyrrolo[2,3-b]pyridine. MS (ESI): mass calcd. for $C_{23}H_{19}FN_4O_2$, 402.15; m/z found, 403.0 [M+H]$^+$. $^1$H NMR (400 MHz, CDCl$_3$) δ 9.34 (s, 1H), 8.73-8.64 (m, 1H), 8.55 (s, 1H), 8.18 (m, 1H), 7.88-7.79 (m, 1H), 7.60 (m, 1H), 7.51-7.41 (m, 1H), 7.43-7.32 (m, 3H), 6.65-6.55 (m, 1H), 3.73 (dd, J=5.8, 4.0, 2H), 3.63 (dd, J=5.7, 4.2, 2H), 3.34 (dd, J=5.6, 4.1, 2H), 3.18-3.06 (m, 2H).

Intermediate JE

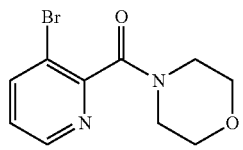

(3-Bromopyridin-2-yl)(morpholino)methanone

To a round-bottomed flask that had been purged with nitrogen, were added 3-bromopicolinic acid (500 mg, 2.50 mmol), morpholine (259 mg, 3.00 mmol), EDCl (712 mg, 3.70 mmol), HOBT (501 mg, 3.70 mmol), triethylamine (1.0 mL, 7.4 mmol) and DMF (12 mL). The mixture was stirred at rt for 24 h, before diluting with water (100 mL) and extracting with ethyl acetate (2×100 mL). The combined organic extracts were washed with saturated bicarbonate (1×50 mL), water (2×50 mL), dried with sodium sulfate, and concentrated to dryness. The crude product was purified by FCC to provide the title compound. MS (ESI): mass calcd. for $C_{10}H_{11}BrN_2O_2$, 270.00; m/z found, 271.0 [M+H]$^+$. $^1$H NMR (500 MHz, CDCl$_3$) δ 8.57 (dd, J=4.7, 1.4, 1H), 7.93 (dd, J=8.2, 1.4, 1H), 7.23 (dd, J=8.2, 4.7, 1H), 3.90-3.77 (m, 4H), 3.74-3.62 (m, 2H), 3.30-3.15 (m, 2H).

Example 782

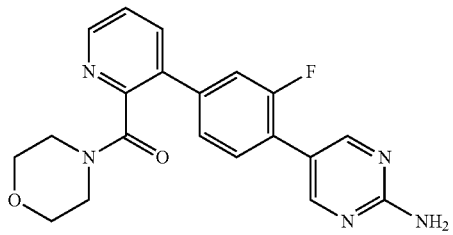

5-{2-Fluoro-4-[2-(moropholin-4-ylcarbonyl)pyridin-3-yl]phenyl}pyrimidin-2-amine

The title compound was prepared as described in Example 376 utilizing 5-(2-fluoro-4-(4,4,5,5-tetramethyl-1,3,2-dioxaborolan-2-yl)phenyl)pyrimidin-2-amine. MS (ESI): mass calcd. for $C_{20}H_{18}FN_5O_2$, 379.14; m/z found, 380.1 [M+H]$^+$. $^1$H NMR (400 MHz, CDCl$_3$) δ 8.72-8.63 (m, 1H), 8.56 (d, J=1.4, 2H), 7.85-7.75 (m, 1H), 7.53-7.42 (m, 2H), 7.39-7.28 (m, 2H), 5.17 (s, 2H), 3.71 (dd, J=5.6, 3.8, 2H), 3.63 (dd, J=5.6, 3.8, 2H), 3.37 (dd, J=5.6, 4.2, 2H), 3.18-3.06 (m, 2H).

Example 783

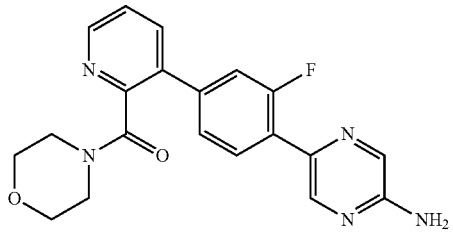

5-{2-Fluoro-4-[2-(morpholin-4-ylcarbonyl)pyridin-3-yl]phenyl}pyrazin-2-amine

The title compound was prepared as described in Example 376 utilizing 5-(2-fluoro-4-(4,4,5,5-tetramethyl-1,3,2-dioxaborolan-2-yl)phenyl)pyrazin-2-amine. MS (ESI): mass calcd. for $C_{20}H_{18}FN_5O_2$, 379.14; m/z found, 380.1 [M+H]$^+$. $^1$H NMR (400 MHz, CDCl$_3$) δ 8.67 (dd, J=4.8, 1.6, 1H), 8.61 (m, 1H), 8.12 (d, J=1.4, 1H), 8.06 (m, 1H), 7.81 (dd, J=7.9, 1.6, 1H), 7.44 (dd, J=7.9, 4.8, 1H), 7.38 (dd, J=8.1, 1.8, 1H), 7.32 (dd, J=12.1, 1.8, 1H), 4.72 (s, 2H), 3.69 (dd, J=5.6, 3.9, 2H), 3.60 (dd, J=5.7, 4.1, 2H), 3.30 (dd, J=5.6, 4.1, 2H), 3.07 (dd. J=5.5, 4.1, 2H).

Example 784

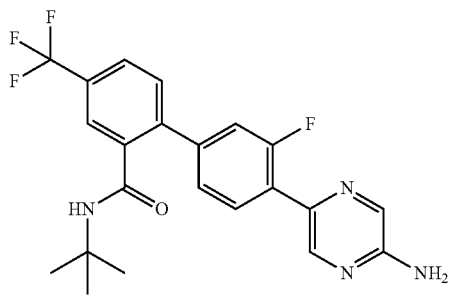

2-[4-(5-Aminopyrazin-2-yl)-3-fluoro-phenyl]-N-tert-butyl-5-(trifluoromethyl)benzamide The title compound was prepared as described in Step C of Example 504 utilizing t-butylamine. MS (ESI): mass calcd. for $C_{22}H_{20}F_4N_4O$, 432.16; m/z found, 432.9 [M+H]$^+$. $^1$H NMR (400 MHz, DMSO-d$_6$) δ 8.37-8.32 (m, 1H), 8.06-8.00 (m, 2H), 7.92-7.88 (m, 1H), 7.83 (d, J=8.2, 1H), 7.68-7.65 (m, 2H), 7.38-7.35 (m, 2H), 6.68 (s, 2H), 1.21 (s, 9H).

Example 785

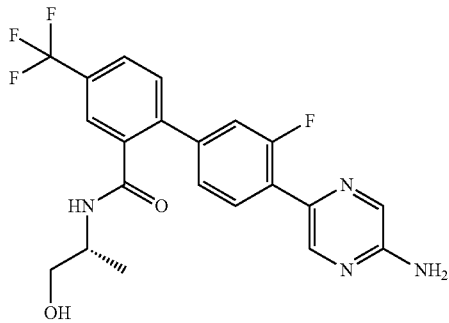

2-[4-(5-Aminopyrazin-2-yl)-3-fluoro-phenyl]-N-[(1R)-2-hydroxy-1-methyl-ethyl]-5-(trifluoromethyl)benzamide The title compound was prepared as described in Step C of Example 504 utilizing (R)-2-aminopropan-1-ol. MS (ESI): mass calcd. for $C_{21}H_{18}F_4N_4O_2$, 434.14; m/z found, 434.9 [M+H]$^+$. $^1$H NMR (400 MHz, DMSO-d$_6$) δ 8.38 (s, 1H), 8.29 (d, J=7.9, 1H), 8.05 (s, 1H), 7.97-7.84 (m, 2H), 7.77 (s, 1H), 7.71 (d, J=7.9, 1H), 7.37 (d, J=9.4, 2H), 6.71 (s, 2H), 4.70 (s, 1H), 3.93-3.78 (m, 1H), 3.25-3.15 (m, 2H), 1.00 (d, J=6.2, 3H).

Example 786

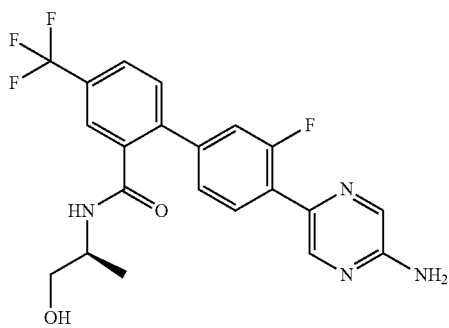

2-[4-(5-Aminopyrazin-2-yl)-3-fluoro-phenyl]-N-[(1S)-2-hydroxy-1-methyl-ethyl]-5-(trifluoromethyl)benzamide The title compound was prepared as described in Step C of Example 504 utilizing (S)-2-aminopropan-1-ol. MS (ESI): mass calcd. for $C_{21}H_{18}F_4N_4O_2$, 434.14; m/z found, 434.9 [M+H]$^+$. $^1$H NMR (400 MHz, DMSO-d) δ 8.42-8.39 (m, 1H), 8.31 (d, J=8.1, 1H), 8.07 (d, J=1.5, 1H), 7.96-7.89 (m, 2H), 7.79 (s, 1H), 7.74 (d, J=8.0, 1H), 7.41 (s, 1H), 7.38 (dd, J=4.5, 1.6, 1H), 6.74 (s, 2H), 4.72 (t, J=5.7, 1H), 3.92-3.83 (m, 1H), 3.25-3.19 (m, 2H), 1.02 (d, J=6.7, 3H).

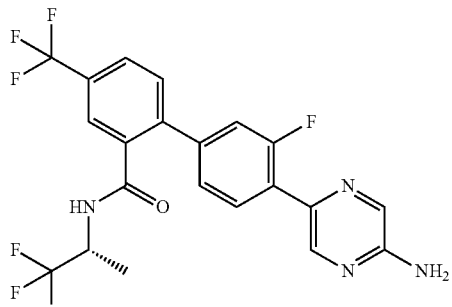

2-[4-(5-Aminopyrazin-2-yl)-3-fluoro-phenyl]-5-(trifluoromethyl)-N-[(1R)-2,2,2-trifluoro-1-methyl-ethyl]benzamide The title compound was prepared as described in Step C of Example 504 utilizing (R)-1,1,1-trifluoropropan-2-amine. MS (ESI): mass calcd. for $C_{21}H_{15}F_7N_4O$, 472.11; m/z found, 472.8 [M+H]$^+$. $^1$H NMR (400 MHz, DMSO-d$_6$) δ 9.11 (d, J=8.8, 1H), 8.41-8.35 (m, 1H), 8.04 (d, J=1.4, 1H), 7.94-7.90 (m, 2H), 7.80-7.72 (m, 2H), 7.36-7.28 (m, 2H), 6.72 (s, 2H), 4.70-4.60 (m, 1H), 1.22 (d, J=7.0, 3H).

Example 788

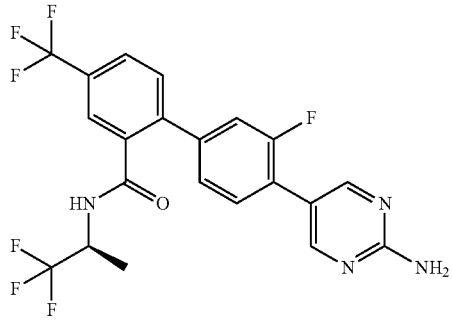

2-[4-(2-Aminopyrimidin-5-yl)-3-fluoro-phenyl]-5-(trifluoromethyl)-N-[(1S)-2,2,2-trifluoro-1-methyl-ethyl]benzamide The title compound was prepared as described in Step C of Example 504 utilizing (S)-1,1,1-trifluoropropan-2-amine. MS (ESI): mass calcd. for $C_{21}H_{15}F_7N_4O$, 472.11; m/z found, 472.9 [M+H]$^+$. $^1$H NMR (400 MHz, DMSO-d$_6$) δ 9.10 (d, J=8.8, 1H), 8.48 (s, 2H), 7.94 (d, J=8.1, 1H), 7.80-7.72 (m, 2H), 7.65-7.61 (m, 1H), 7.34-7.30 (m, 2H), 6.90 (s, 2H), 4.69-4.60 (m, 1H), 1.22 (d, J=7.0, 3H).

Example 789

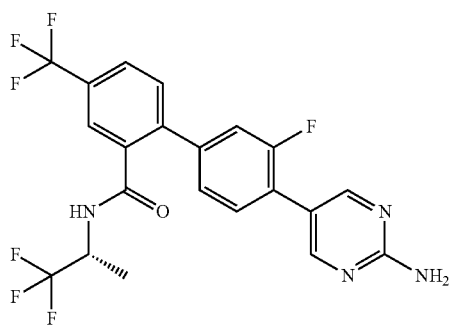

2-[4-(2-Aminopyrimidin-5-yl)-3-fluoro-phenyl]-5-(trifluoromethyl)-N-[(1R)-2,2,2-trifluoro-1-methyl-ethyl]benzamide The title compound was prepared as described in Step C of Example 504 utilizing (R)-1,1,1-trifluoropropan-2-amine. MS (ESI): mass calcd. for $C_{21}H_{15}F_7N_4O$, 472.11; m/z found, 472.8 [M+H]$^+$. $^1$H NMR (400 MHz, DMSO-d$_6$) δ 9.10 (d, J=8.8, 1H), 8.48 (s, 2H), 7.93 (d, J=8.0, 1H), 7.81-7.71 (m, 2H), 7.65-7.61 (m, 1H), 7.37-7.26 (m, 2H), 6.91 (s, 2H), 4.68-4.62 (m, 1H), 1.22 (d, J=7.0, 3H).

Example 790

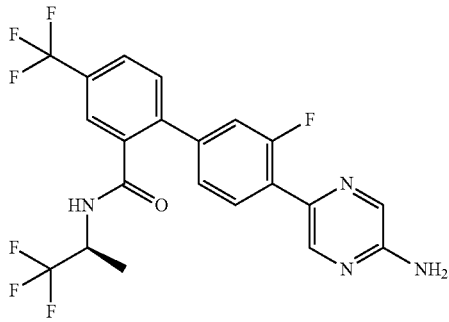

2-[4-(5-Aminopyrazin-2-yl)-3-fluoro-phenyl]-5-(trifluoromethyl)-N-[(1S)-2,2,2-trifluoro-1-methyl-ethyl]benzamide The title compound was prepared as described in Step C of Example 504 utilizing (S)-1,1,1-trifluoropropan-2-amine. MS (ESI): mass calcd. for $C_{21}H_{15}F_7N_4O$, 472.11; m/z found, 472.8 [M+H]$^+$. $^1$H NMR (400 MHz, DMSO-d$_6$) δ 9.13 (d. J=8.8, 1H), 8.43-8.35 (m, 1H), 8.06 (d, J=1.4, 1H), 7.96-7.91 (m, 2H), 7.77 (d, J=8.8, 2H), 7.37-7.29 (m, 2H), 6.73 (s, 2H), 4.71-4.61 (m, 1H), 1.23 (d, J=7.0, 3H).

Example 791

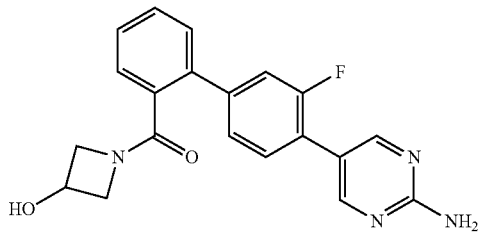

[2-[4-(2-Aminopyrimidin-5-yl)-3-fluoro-phenyl]phenyl]-(3-hydroxyazetidin-1-yl)methanone The title compound was prepared as described in Step C of Example 504 utilizing azetidin-3-. MS (ESI): mass calcd. for $C_{20}H_{17}FN_4O_2$, 364.13; m/z found, 364.9 [M+H]$^+$. $^1$H NMR (400 MHz, DMSO-d$_6$) δ 8.51 (s, 2H), 7.65-7.61 (m, 1H), 7.57-7.40 (m, 4H), 7.35-7.30 (m, 2H), 6.88 (s, 2H), 5.65 (d, J=4.8, 1H), 4.31 (s, 1H), 4.11-4.04 (m, 1H), 3.81 (t, J=7.9, 1H), 3.60 (dd, J=10.2, 4.4, 1H), 3.39 (dd, J=9.1, 4.4, 1H).

Example 792

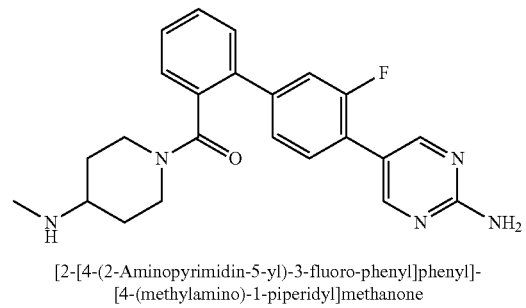 [SMILES: CNC1CCN(C(=O)c2ccccc2-c2ccc(-c3cnc(N)nc3)c(F)c2)CC1]

[2-[4-(2-Aminopyrimidin-5-yl)-3-fluoro-phenyl]phenyl]-[4-(methylamino)-1-piperidyl]methanone The title compound was prepared as described in Step C of Example 504 utilizing N-methylpiperidin-4-amine. MS (ESI): mass calcd. for $C_{23}H_{24}FN_5O$, 405.20; m/z found, 405.9 [M+H]$^+$. $^1$H NMR (400 MHz, CD$_3$OD) δ 8.61 (d, J=10.6, 2H), 7.71-7.55 (m, 4H), 7.54-7.32 (m, 3H), 4.57 (d, J=12.6, 1H), 3.45-3.43 (m, 1H), 3.05-2.90 (m, 1H), 2.75-2.63 (m, 1H), 2.59-2.54 (m, 1H), 2.35 (m, 3H), 2.02-1.92 (m, 1H), 1.73-1.62 (m, 1H), 1.41-1.16 (m, 1H), 1.08-0.44 (m, 1H).

Example 793

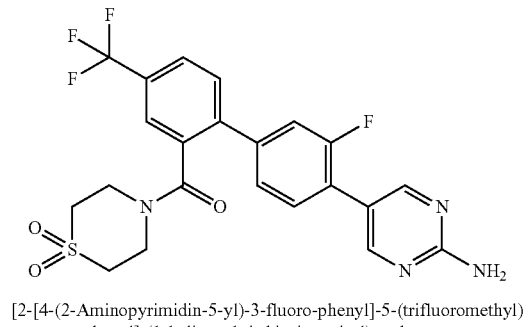

[2-[4-(2-Aminopyrimidin-5-yl)-3-fluoro-phenyl]-5-(trifluoromethyl)phenyl]-(1,1-dioxo-1,4-thiazinan-4-yl)methanone The title compound was prepared as described in Step C of Example 504 utilizing thiomorpholine 1,1-dioxide. MS (ESI): mass calcd. for $C_{22}H_{18}F_4N_4O_3S$, 494.10; m/z found, 494.8 [M+H]$^+$. $^1$H NMR (400 MHz, DMSO-d) δ 8.49 (s, 2H), 8.03 (s, 1H), 7.94 (d, J=8.2H, 1H), 7.80 (d, J=8.1, 1H), 7.72-7.68 (m, 1H), 7.40 (d, J=11.7, 1H), 7.34 (d, J=7.6, 1H), 6.92 (s, 2H), 4.25-4.10 (m, 1H), 3.68-3.65 (m, 1H), 3.59-3.48 (m, 1H), 3.26-3.11 (m, 3H), 3.03-2.92 (m, 1H), 2.42-2.28 (m, 1H).

Example 794

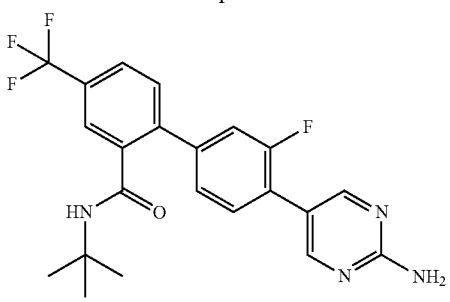

2-[4-(2-Aminopyrimidin-5-yl)-3-fluoro-phenyl]-N-tert-butyl-5-(trifluoromethyl)benzamide The title compound was prepared as described in Step C of Example 504 utilizing t-butyl amine. MS (ESI): mass calcd. for $C_{22}H_{20}F_4N_4O$, 432.16: m/z found, 432.8 [M+H]$^+$. $^1$H NMR (400 MHz, DMSO-d) δ 8.46 (s, 2H), 8.04 (s, 1H), 7.83 (d, J=8.0, 1H), 7.71-7.58 (m, 3H), 7.41-7.32 (m, 2H), 6.87 (s, 2H), 1.22 (s, 9H).

Example 795

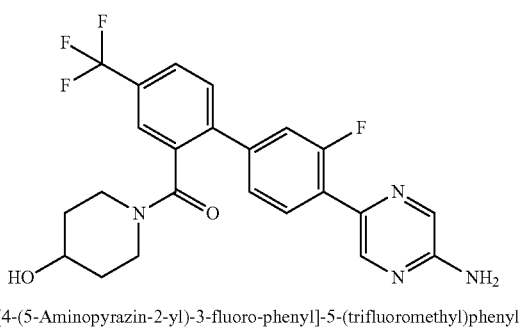

[2-[4-(5-Aminopyrazin-2-yl)-3-fluoro-phenyl]-5-(trifluoromethyl)phenyl]-(4-hydroxy-1-piperidyl)methanone The title compound was prepared as described in Step C of Example 504 utilizing piperidin-4-ol. MS (ESI): mass calcd. for $C_{23}H_{20}F_4N_4O_2$, 460.15; m/z found, 460.8 [M+H]$^+$. $^1$H NMR (400 MHz, DMSO-d) δ 8.39-8.33 (m, 1H), 8.03 (s, 1H), 7.98-7.91 (m, 1H), 7.86 (d, J=8.2, 1H), 7.75 (dd, J=8.1, 3.2, 1H), 7.70 (d, J=6.3, 1H), 7.40-7.32 (m, 2H), 6.72 (s, 2H), 4.69-4.61 (m, 1H), 3.99-3.73 (m, 1H), 3.53-3.50 (m, 1H), 3.17-2.59 (m, 3H), 1.66-1.34 (m, 2H), 1.17-0.45 (m, 2H).

Example 796

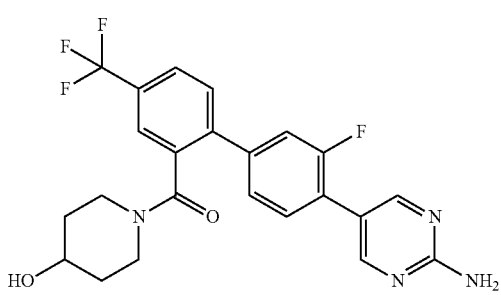

[2-[4-(2-Aminopyrimidin-5-yl)-3-fluoro-phenyl]-5-(trifluoromethyl)phenyl]-(4-hydroxy-1-piperidyl)methanone The title compound was prepared as described in Step C of Example 504 utilizing piperidin-4-ol. MS (ESI): mass calcd. for $C_{23}H_{20}F_4N_4O_2$, 460.15; m/z found, 460.9 [M+H]$^+$. $^1$H NMR (400 MHz, DMSO-d$_6$) δ 8.49 (d, J=7.1, 2H), 7.89 (d, J=8.2, 1H), 7.83-7.65 (m, 3H), 7.48-7.33 (m, 2H), 6.91 (s, 2H), 4.05-4.02 (m, 1H), 3.91-3.76 (m, 1H), 3.64-3.48 (m, 1H), 3.23-3.18 (m, 1H), 3.05-2.63 (m, 2H), 1.72-1.40 (m, 2H), 1.20-0.97 (m, 2H).

Example 797

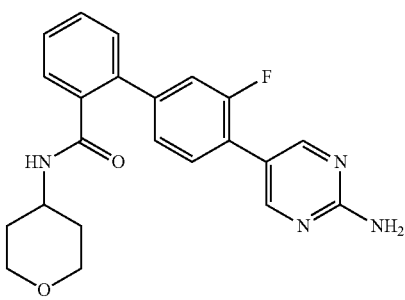

2-[4-(2-Aminopyrimidin-5-yl)-3-fluoro-phenyl]-N-tetrahydropyran-4-yl-benzamide

The title compound was prepared as described in Step C of Example 504 utilizing tetrahydro-2H-pyran-4-amine. MS (ESI): mass calcd. for $C_{22}H_{21}FN_4O_2$, 392.16; m/z found, 392.9 [M+H]$^+$. $^1$H NMR (400 MHz, DMSO-d$_6$) δ 8.47 (d, J=1.1, 2H), 8.24 (d, J=7.8, 1H), 7.61-7.49 (m, 2H), 7.48-7.41 (m, 3H), 7.32-7.29 (m, 2H), 6.87 (s, 2H), 3.89-3.79 (m, 1H), 3.76-3.73 (m, 2H), 3.34 (s, 2H), 1.64-1.61 (m, 2H), 1.41-1.29 (m, 2H).

Example 798

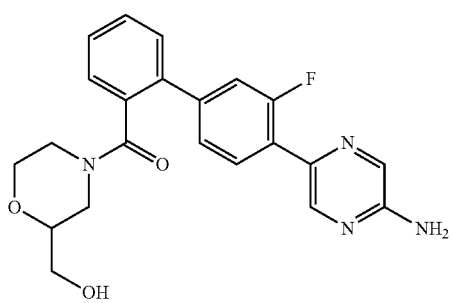

racemic [2-[4-(5-Aminopyrazin-2-yl)-3-fluoro-phenyl]-[2-(hydroxymethyl)morpholin-4-yl]methanone The title compound was prepared as described in Step C of Example 504 utilizing morpholin-2-ylmethanol. MS (ESI): mass calcd. for $C_{22}H_{21}FN_4O_3$, 408.16; m/z found, 408.9 [M+H]$^+$. $^1$H NMR (400 MHz, CD$_3$OD) δ 8.39 (s, 1H), 8.07 (s, 1H), 7.97-7.91 (m, 1H), 7.58-7.25 (m, 6H), 4.51-4.31 (m, 1H), 3.95-3.56 (m, 1H), 3.55-3.43 (m, 2H), 3.40-3.33 (m, 1H), 3.26-2.96 (m, 2H), 2.90-2.63 (m, 1H), 2.60-2.19 (m, 1H).

Example 799

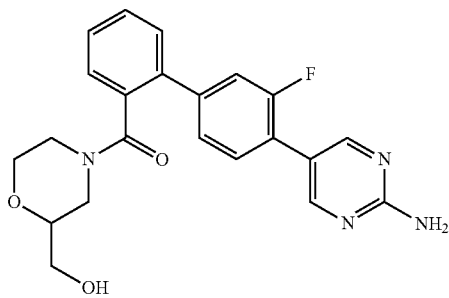

racemic [2-[4-(2-Aminopyrimidin-5-yl)-3-fluoro-phenyl]phenyl]-[2-(hydroxymethyl)morpholin-4-yl]methanone The title compound was prepared as described in Step C of Example 504 utilizing racemic morpholin-2-ylmethanol. MS (ESI): mass calcd. for $C_{22}H_{21}FN_4O_3$, 408.16; m/z found, 409.0 [M+H]$^+$. $^1$H NMR (400 MHz, CD$_3$OD) δ 8.52 (s, 2H), 7.67-7.25 (m, 7H), 4.49-4.33 (m, 1H), 3.96-3.56 (m, 1H), 3.56-3.43 (m, 2H), 3.41-3.31 (m, 1H), 3.23-2.95 (m, 2H), 2.89-2.53 (m, 1H), 2.52-2.13 (m, 1H).

Intermediate JF

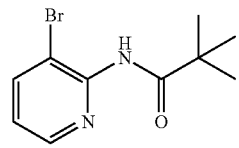

N-(3-Bromopyridin-2-yl)pivalamide

3-Bromopyridin-2-amine (500 mg, 2.89 mmol) and pivaloyl chloride (420 mg, 3.48 mmol) were added to a 50 mL round-bottomed flask. Pyridine (10 mL) was then added and the mixture stirred and heated at 80° C. for 4 h. The reaction was then cooled to rt and stirred overnight. The reaction mixture was then concentrated to dryness and the resultant residue subjected to FCC to provide the title compound. MS (ESI): mass calcd. for $C_{10}H_{13}BrN_2O$, 256.02; m/z found, 257.1 [M+H]$^+$.

Example 800

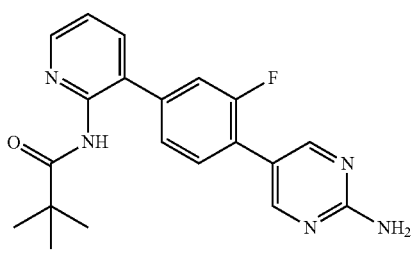

N-{3-[4-(2-Aminopyrimidin-5-yl)-3-fluorophenyl]pyridin-2-yl}-2,2-dimethylpropanamide The title compound was prepared as described in Example 376 using 5-(2-fluoro-4-(4,4,5,5-tetramethyl-1,3,2-dioxaboralan-2-yl)phenyl)pyrimidin-2-amine and N-(3-bromopyridin-2-yl)pivalamide. MS (ESI): mass calcd. for $C_{20}H_{20}FN_5O$, 365.17; m/z found, 366.15 [M+H]$^+$. $^1$H NMR (400 MHz, DMSO-d$_6$) δ 9.65 (s, 1H), 8.52-8.43 (m, 3H), 7.93-7.83 (m, 1H), 7.56-7.64 (m, 1H), 7.47-7.68 (m, 1H), 7.38-7.26 (m, 2H), 6.93 (s, 2H), 1.05 (s, 9H).

Example 801

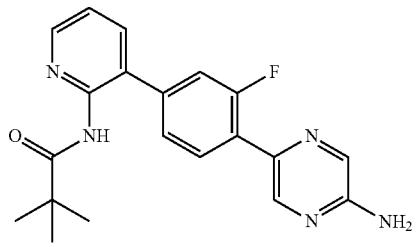

N-{3-[4-(5-Aminopyrazin-2-yl)-3-fluorophenyl]pyridin-2-yl}-2,2-dimethylpropanamide The title compound was prepared as described in Example 376 using 5-(2-fluoro-4-(4,4,5,5-tetramethyl-1,3,2-dioxaboralan-2-yl)phenyl)pyrazin-2-amine and N-(3-bromopyridin-2-yl)pivalamide. MS (ESI): mass calcd. for $C_{20}H_{20}FN_5O$, 365.17; m/z found, 366.2 [M+H]$^+$. $^1$H NMR (400 MHz, DMSO-d) δ 9.66 (s, 1H), 8.52-8.42 (m, 1H), 8.40-8.30 (m, 1H), 8.03 (d, J=1.4, 1H), 7.95-7.82 (m, 2H), 7.47-7.38 (m, 1H), 7.39-7.30 (m, 1H), 6.73 (s, 2H), 1.05 (s, 9H).

Example 802

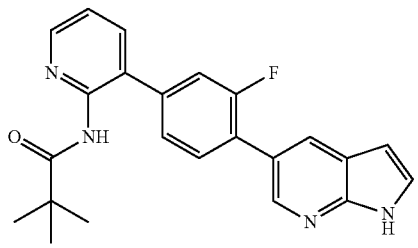

N-{3-[3-Fluoro-4-(1H-pyrrolo[2,3-b]pyridin-5-yl)phenyl]pyridin-2-yl}-2,2-dimethylpropanamide The title compound was prepared as described in Example 376 using 5-(2-fluoro-4-(4,4,5,5-tetramethyl-1,3,2-dioxaboralan-2-yl)phenyl)-1H-pyrrolo[2,3-b]pyridine and N-(3-bromopyridin-2-yl)pivalamide. MS (ESI): mass calcd. for $C_{23}H_{21}FN_4O$, 388.17; m/z found, 389.1 [M+H]$^+$. $^1$H NMR (400 MHz, DMSO-d$_6$) δ 11.81 (s, 1H), 9.67 (s, 1H), 8.54-8.46 (m, 1H), 8.42-8.33 (m, 1H), 8.18-8.09 (m, 1H), 7.96-7.87 (m, 1H), 7.71-7.62 (m, 1H), 7.55 (d, J=3.5, 1H), 7.50-7.40 (m, 1H), 7.41-7.31 (m, 2H), 6.54 (d, J=3.5, 1H), 1.07 (s, 9H).

Example 803

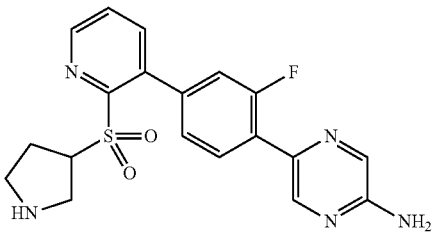

racemic 5-(2-Fluoro-4-(2-(pyrrolidin-3-ylsulfonyl)pyridin-3-yl)phenyl)pyrazin-2-amine hydrochloride

Step A: 3-Bromopyridine-2-thiol

A mixture of 3-bromo-2-chloropyridine (10 g, 0.050 mol) and Na$_2$S (12 g, 0.15 mol) in DMF (150 mL) was stirred at 120° C. for 16 h. and the reaction mixture was cooled to rt and then concentrated to dryness. The resultant residue was diluted with water (80 mL), acidified to pH=5-6 with conc. HCl, and then extracted with ethyl acetate (3×50 mL). The combined organic extracts were dried over Na$_2$SO$_4$ and concentrated to dryness to give the title compound (6.4 g, crude). MS (ESI): mass calcd. For C$_5$H$_4$BrNS 188.92; m/z found, 191.9 [M+H]$^+$.

Step B: tert-Butyl 3-(3-bromopyridin-2-ylthio)pyrrolidine-1-carboxylate

A mixture of 3-bromopyridine-2-thiol (0.30 g, 1.6 mmol), tert-butyl 3-bromopyrrolidine-1-carboxylate (0.79 g, 3.2 mmol) and K$_2$CO$_3$ (438 mg, 3.20 mmol) in DMF (12 mL) was stirred at rt for 4 h. The reaction mixture was concentrated to dryness and the residue subjected to FCC purification to give partially purified title compound (1.05 g, 63% purity).

Step C: tert-Butyl 3-(3-bromopyridin-2-ylsulfonyl)pyrrolidine-1-carboxylate

To a solution of tert-butyl 3-(3-bromopyridin-2-ylthio)pyrrolidine-1-carboxylate (0.9 g, 63% purity, 1.6 mmol) in DCM/CH$_3$CN (20 mL/20 mL) were added NaIO$_4$ (1.6 g, 7.6 mmol), H$_2$O (20 mL), and RuCl$_3$ (10 mg, 0.070 mmol). The mixture was stirred at rt for 10 minutes and then concentrated to dryness. The resultant residue was diluted with water (50 mL) and extracted with DCM (3×40 mL). The combined extracts were dried over MgSO$_4$, concentrated to dryness to give impure title compound (1.0 g, 60% purity) which was used for next step without any further purification.

Step D: tert-Butyl 3-(3-(4-(5-aminopyrazin-2-yl)-3-fluorophenyl)pyridin-2-ylsulfonyl)pyrrolidine-1-carboxylate A mixture of tert-butyl 3-(3-bromopyridin-2-ylsulfonyl)pyrrolidine-1-carboxylate (205 mg, 60% purity, 0.320 mmol), 5-(2-fluoro-4-(4,4,5,5-tetramethyl-1,3,2-dioxaborolan-2-yl)phenyl)pyrazin-2-amine (100 mg, 0.320 mmol), Pd(dppf)Cl$_2$·CH$_2$Cl$_2$ (23 mg, 0.030 mmol), and Na$_2$CO$_3$ (101 mg, 0.950 mmol) in DMF (6 mL) was stirred at 100° C. for 16 h under N$_2$ before cooling to rt and concentrating it to dryness. The resultant residue was subjected to FCC followed by HPLC purification to give the title compound (150 mg, 99%). MS (ESI): mass calcd. For C$_{24}$H$_{26}$FN$_5$O$_4$S 499.17; m/z found, 521.9 [M+Na]$^+$.

Step E: 5-(2-Fluoro-4-(2-(pyrrolidin-3-ylsulfonyl)pyridin-3-yl)phenyl)pyrazin-2-amine hydrochloride.

To a solution consisting of tert-butyl 3-(3-(4-(5-aminopyrazin-2-yl)-3-fluorophenyl)pyridin-2-ylsulfonyl)pyrrolidine-1-carboxylate (150 mg, 0.300 mmol) and DCM (10 mL) was added HCl/EtOH (5 N, 10 mL). The mixture was stirred at rt for 2 h, concentrated to dryness, and the resultant residue subjected to HPLC purification to give the title compound (67 mg, 52%). MS (ESI): mass calcd. For C$_{19}$H$_{18}$FN$_5$O$_2$S·HCl 399.12; m/z found, 400.1 [M+H]$^+$. $^1$H NMR (300 MHz, DMSO-d$_6$) δ 9.79 (br s, 1H), 9.42 (br s, 1H), 8.79 (d, J=4.6, 1H), 8.51-8.30 (m, 1H), 8.20-7.78 (m, 3H), 7.51-7.02 (m, 3H), 4.81 (dd, J=14.1, 7.6, 1H), 3.72 (s, 1H), 3.49-3.14 (m, 3H), 2.44-2.20 (m, 2H).

Example 804

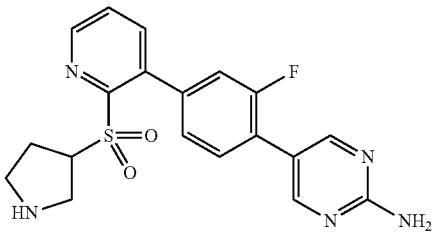

5-(2-Fluoro-4-(2-(pyrrolidin-3-ylsulfonyl)pyridin-3-yl)phenyl)pyrimidin-2-amine formic acid salt.

The title compound was prepared as described in step E of Example 803 using tert-butyl 3-(3-(4-(5-aminopyrimidin-2-yl)-3-fluorophenyl)pyridin-2-ylsulfonyl)pyrrolidine-1-carboxylate. MS (ESI): mass calcd. for C$_{19}$H$_{18}$FN$_5$O$_2$S, 399.12; m/z found, 400.1 [M+H]$^+$. $^1$H NMR (300 MHz, CD$_3$OD) δ 8.71 (dd, J=4.7, 1.6, 1H), 8.52 (d, J=1.4, 2H), 8.41 (br s, 1H), 8.03 (dd, J=7.9, 1.5, 1H), 7.78 (dd, J=7.9, 4.7, 1H), 7.58 (m, 1H), 7.49-7.35 (m, 2H), 4.95-4.90 (m, 1H), 3.81 (dd, J=13.3, 8.9, 1H), 3.66 (dd, J=13.3, 5.4, 1H), 3.44-3.33 (m, 2H), 2.52-2.38 (m, 2H).

Example 805

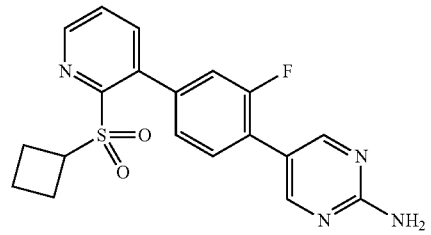

5-(4-(2-(Cyclobutylsulfonyl)pyridin-3-yl)-2-fluorophenyl)pyrimidin-2-amine hydrochloride.

The title compound was prepared as described in step D of Example 803 using 3-bromo-2-(cyclobutylsulfonyl)pyridine and 5-(2-fluoro-4-(4,4,5,5-tetramethyl-1,3,2-dioxaboralan-2-yl)phenyl)pyrimidin-2-. MS (ESI): mass calcd. for $C_{19}H_{17}FN_4O_2S.HCl$, 384.11; m/z found, 385.1 [M+H]$^+$. $^1$H NMR (400 MHz, CD$_3$OD) δ 8.80 (d, J=0.8, 2H), 8.70 (dd, J=4.7, 1.6, 1H), 7.99 (dd, J=7.8, 1.6, 1H), 7.74 (dd, J=7.8, 4.7, 1H), 7.69 (m, 1H), 7.53-7.46 (m, 2H), 4.80-4.69 (m, 1H), 2.54-2.41 (m, 2H), 2.41-2.30 (m, 2H), 2.20-2.07 (m, 1H), 2.05-1.94 (m, 1H).

Example 806

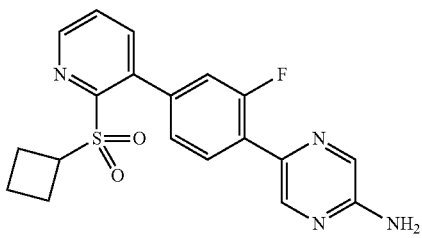

5-(4-(2-(Cyclobutylsulfonyl)pyridin-3-yl)-2-fluorophenyl)pyrazin-2-amine hydrochloride The title compound was prepared as described in step D of Example 803 using 3-bromo-2-(cyclobutylsulfonyl)pyridine. MS (ESI): mass calcd. for $C_{19}H_{17}FN_4O_2S.HCl$, 384.11; m/z found, 385.1 [M+H]$^+$. $^1$H NMR (400 MHz, CD$_3$OD) δ 8.69 (dd, J=4.7, 1.5, 1H), 8.52 (s, 1H), 8.33 (s, 1H), 8.12 (m, 1H), 7.99 (dd, J=7.8, 1.5, 1H), 7.74 (dd, J=7.8, 4.7, 1H), 7.49 (d, J=2.7, 1H), 7.46 (s, 1H), 4.80-4.70 (m, 1H), 2.54-2.42 (m, 2H), 2.40-2.30 (m, 2H), 2.21-2.07 (m, 1H), 2.04-1.94 (m, 1H).

Example 807

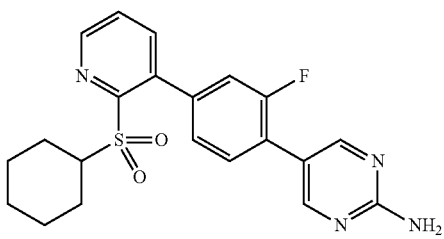

5-(4-(2-(Cyclohexlsulfonyl)pyridin-3-yl)-2-fluorophenyl)pyrimidin-2-amine hydrochloride The title compound was prepared as described in step D of Example 803 using 3-bromo-2-(cyclohexylsulfonyl)pyridine and 5-(2-fluoro-4-(4,4,5,5-tetramethyl-1,3,2-dioxaboralan-2-yl)phenyl)pyrimidin-2-amine. MS (ESI): mass calcd. for $C_{21}H_{21}FN_4O_2S.HCl$, 412.14; m/z found, 413.1 [M+H]$^+$. $^1$H NMR (300 MHz, CD$_3$OD) δ 8.74 (dd, J=4.6, 1.6, 1H), 8.56 (s, 2H), 7.96 (dd, J=7.9, 1.6, 1H), 7.74 (dd, J=7.9, 4.7, 1H), 7.57 (m, 1H), 7.37 (dd, J=3.6, 1.3, 1H), 7.34 (s, 1H), 3.97-3.83 (m, 1H), 2.01-1.63 (m, 5H), 1.52-1.13 (m, 5H).

Example 808

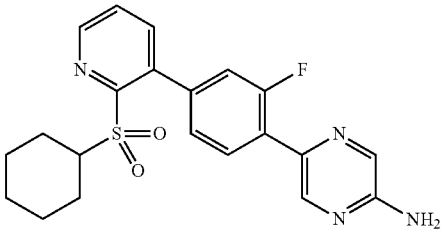

5-(4-(2-(Cyclohexylsulfonyl)pyridin-3-yl)-2-fluorophenyl)pyrazin-2-amine hydrochloride The title compound was prepared as described in step D of Example 803 using 3-bromo-2-(cyclohexylsulfonyl)pyridine. MS (ESI): mass calcd. for $C_{21}H_{21}FN_4O_2S.HCl$, 412.14; m/z found, 413.1 [M+H]$^+$. $^1$H NMR (300 MHz, DMSO-d$_6$) δ 8.78 (d, J=4.4, 1H), 8.39 (s, 1H), 8.02 (d, J=6.3, 2H), 7.90 (m, 1H), 7.80 (dd, J=7.8, 4.6, 1H), 7.35 (dd, J=14.8, 10.8, 2H), 6.75 (s, 2H), 3.98-3.80 (m, 1H), 1.80 (d, J=14.9, 4H), 1.62 (d, J=12.3, 1H), 1.39-1.07 (m, 5H).

Example 809

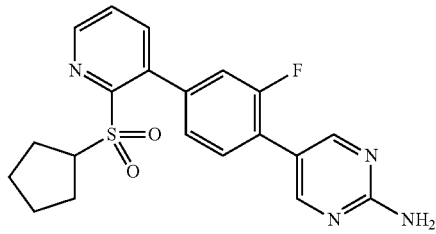

5-(4-(2-(Cyclopentylsulfonyl)pyridin-3-yl)-2-fluorophenyl)pyrimidine-2-amine hydrochloride The title compound was prepared as described in step D of Example 803 using 3-bromo-2-(cyclopentylsulfonyl)pyridine and 5-(2-fluoro-4-(4,4,5,5-tetramethyl-1,3,2-dioxaboralan-2-yl)phenyl)pyrimidin-2-amine. MS (ESI): mass calcd. for $C_{20}H_{19}FN_4O_2S.HCl$, 398.12; m/z found, 399.1 [M+H]$^+$. $^1$H NMR (300 MHz, CD$_3$OD) δ 8.88 (s, 2H), 8.73 (dd, J=4.6, 1.5, 1H), 7.96 (dd, J=7.8, 1.5, 1H), 7.80-7.62 (m, 2H), 7.55-7.41 (m, 2H), 4.56-4.40 (m, 1H), 2.09-1.79 (m, 4H), 1.69 (d, J=4.7, 4H).

Example 810

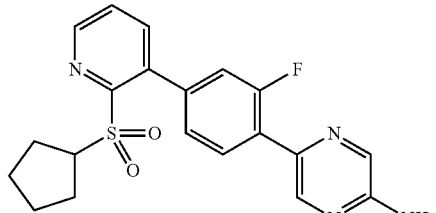

5-(4-(2-(Cyclopentylsulfonyl)pyridin-3-yl)-2-fluorophenyl)pyrazin-2-amine hydrochloride The title compound was prepared as described in step D of Example 803 using 3-bromo-2-(cyclopentylsulfonyl)pyridine. MS (ESI): mass calcd. for $C_{20}H_{19}FN_4O_2S \cdot HCl$, 398.12; m/z found, 399.10 [M+H]$^+$. 1H NMR (300 MHz, $CD_3OD$) δ 8.80-8.68 (m, 2H), 8.25 (d, J=1.1, 1H), 8.13 (m, 1H), 7.96 (dd, J=7.8, 1.5, 1H), 7.73 (dd, J=7.8, 4.6, 1H), 7.43 (d, J=10.3, 2H), 4.52-4.39 (m, 1H), 2.10-1.80 (m, 4H), 1.68 (d, J=5.4, 4H).

Example 811

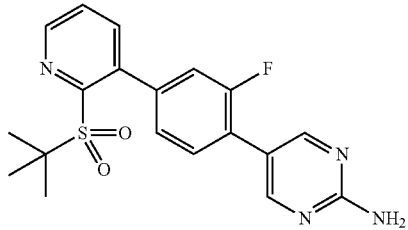

5-(4-(2-(tert-Butylsulfonyl)pyridin-3-yl)-2-fluorophenyl)pyrimidin-2-amine formic acid salt.

The title compound was prepared as described in step D of Example 803 using 3-bromo-2-(tert-butylsulfonyl)pyridine and 5-(2-fluoro-4-(4,4,5,5-tetramethyl-1,3,2-dioxaboralan-2-yl)phenyl)pyrimidin-2-amine. MS (ESI): mass calcd. for $C_{19}H_{19}FN_4O_2S$, 386.12; m/z found, 387.0 [M+H]$^+$. $^1$H NMR (300 MHz, CDCl$_3$) δ 8.73 (dd, J=4.6, 1.7, 1H), 8.56 (d, J=1.4, 2H), 7.73 (dd, J=7.8, 1.7, 1H), 7.56 (dd, J=7.8, 4.6, 1H), 7.41 (m, 1H), 7.28 (dd, J=7.9, 1.8, 1H), 7.21 (d, J=1.7, 1H), 5.29 (s, 2H), 1.48 (s, 9H).

Example 812

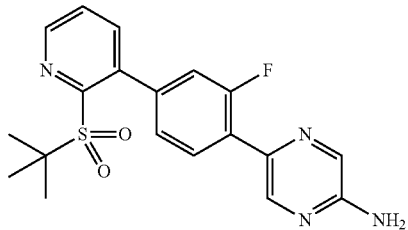

5-(4-(2-(tert-Butylsulfonyl)pyridin-3-yl)-2-fluorophenyl)pyrazin-2-amine formic acid salt.

The title compound was prepared as described in step D of Example 803 using 3-bromo-2-(tert-butylsulfonyl)pyridine. MS (ESI): mass calcd. for $C_{19}H_{19}FN_4O_2S$, 386.12; m/z found, 387.0 [M+H]$^+$. $^1$H NMR (300 MHz, CDCl$_3$) δ 8.73 (dd, J=4.5, 1.7, 1H), 8.54 (s, 1H), 8.12 (s, 1H), 7.98 (m, 1H), 7.74 (dd, J=7.8, 1.7, 1H), 7.56 (dd, J=7.8, 4.6, 1H), 7.28 (d, J=1.7, 1H), 7.20 (d, J=1.7, 1H), 5.01 (s, 2H), 1.45 (s, 9H).

Example 813

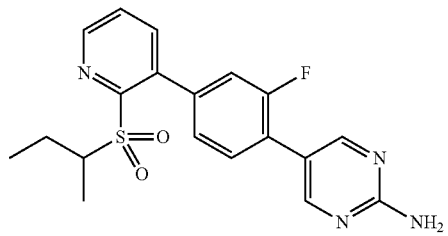

racemic 5-(4-(2-(sec-Butylsulfonyl)pyridin-3-yl)-2-fluorophenyl)pyrimidin-2-amine formate The title compound was prepared as described in step D of Example 803 using racemic 3-bromo-2-(sec-butylsulfonyl)pyridine and 5-(2-fluoro-4-(4,4,5,5-tetramethyl-1,3,2-dioxaboralan-2-yl)phenyl)pyrimidin-2-amine. MS (ESI): mass calcd. for $C_{19}H_{19}FN_4O_2S$, 386.12; m/z found, 387.0 [M+H]$^+$. $^1$H NMR (300 MHz, CD$_3$OD) δ 8.73 (dd, J=4.6, 1.6, 1H), 8.53 (d, J=1.4, 2H), 7.96 (dd, J=7.8, 1.6, 1H), 7.73 (dd, J=7.8, 4.6, 1H), 7.56 (m, 1H), 7.40-7.32 (m, 2H), 4.00-3.89 (m, 1H), 1.95-1.81 (m, 1H), 1.53-1.43 (m, 1H), 1.23 (d, J=8.3, 3H), 1.01 (t, J=7.5, 3H).

Example 814

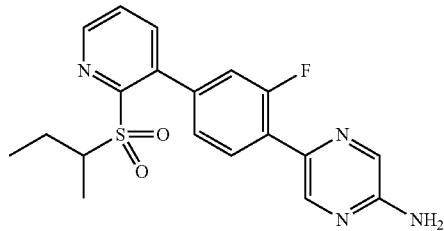

racemic 5-(4-(2-(sec-Butylsulfonyl)pyridin-3-yl)-2-fluorophenyl)pyrazin-2-amine formate The title compound was prepared as described in step D of Example 803 using racemic 3-bromo-2-(sec-butylsulfonyl)pyridine. MS (ESI): mass calcd. for $C_{19}H_{19}FN_4O_2S$, 386.12; m/z found, 387.0 [M+H]$^+$. $^1$H NMR (300 MHz, CD$_3$OD) δ 8.73 (dd, J=4.6, 1.6, 1H), 8.41-8.35 (m, 1H), 8.20 (d, J=1.4, 1H), 8.03-7.94 (m, 2H), 7.74 (dd, J=7.8, 4.6, 1H), 7.40-7.32 (m, 2H), 3.90 (s, 1H), 1.92-1.82 (m, 1H), 1.53-1.42 (m, 1H), 1.24 (d, J=6.9, 3H), 1.00 (t, J=7.5, 3H).

Example 815

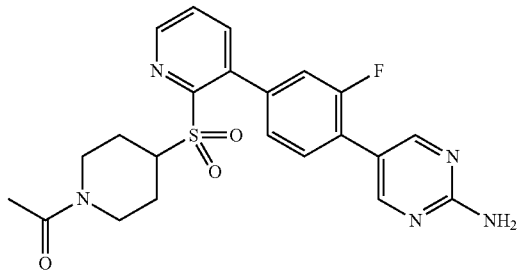

1-((3-(4-(2-Aminopyrimidin-5-yl)-3-fluorophenyl)pyridine-2-yl)sulfonyl)piperidin-1-yl)ethanone The title compound was prepared as described in step D of Example 803 using 1-(4-((3-bromopyridin-2-yl)sulfonyl)piperidin-1-yl)ethanone and 5-(2-fluoro-4-(4,4,5,5-tetramethyl-1,3,2-dioxaboralan-2-yl)phenyl)pyrimidin-2-amine. MS (ESI): mass calcd. for $C_{22}H_{22}FN_5O_3S \cdot HCl$, 455.14; m/z found, 456.1 [M+H]$^+$. $^1$H NMR (400 MHz, CD$_3$OD) δ 8.76 (dd, J=4.6, 1.6, 1H), 8.56 (d, J=1.3, 2H), 8.00 (dd, J=7.9, 1.6, 1H), 7.78 (dd, J=7.9, 4.7, 1H), 7.59 (m, 1H), 7.40 (dd, J=4.3, 1.4, 1H), 7.38 (s, 1H), 4.61 (d, J=13.4, 1H), 4.35 (m, 1H), 4.06 (d, J=14.0, 1H), 3.24 (d, J=13.0, 2.8, 1H), 2.76 (m, 1H), 2.11 (s, 3H), 2.09-1.97 (m, 2H), 1.74 (m, 1H), 1.61 (m, 1H).

Example 816

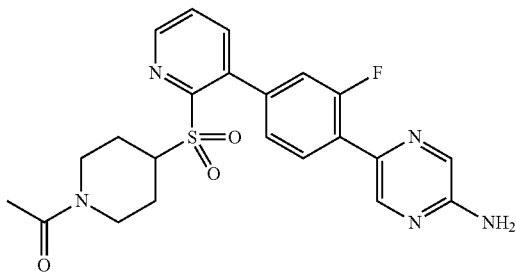

1-((3-(4-(2-Aminopyrazin-5-yl)-3-fluorophenyl)pyridine-2-yl)sulfonyl)piperidin-1-yl)ethanone hydrogen chloride salt The title compound was prepared as described in step D of Example 803 using 1-(4-((3-bromopyridin-2-yl)sulfonyl)piperidin-1-yl)ethanone. MS (ESI): mass calcd. for $C_{22}H_{22}FN_5O_3S \cdot HCl$, 455.14; m/z found, 456.0 [M+H]$^+$. $^1$H NMR (400 MHz, CD$_3$OD): δ 8.76 (dd, J=4.6, 1.6, 1H), 8.46-8.39 (m, 1H), 8.10 (d, J=1.4, 1H), 8.01 (dd, J=7.9, 1.6, 1H), 7.96 (m, 1H), 7.78 (dd, J=7.9, 4.7, 1H), 7.39 (s, 1H), 7.37 (dd, J=4.4, 1.5, 1H), 4.60 (d, J=13.5, 1H), 4.37-4.26 (m, 1H), 4.05 (d, J=14.0, 1H), 3.23 (m, 1H), 2.75 (m, 1H), 2.10 (s, 3H), 2.07-1.97 (m, 2H), 1.74 (m, 1H), 1.61 (m, 1H).

Example 817

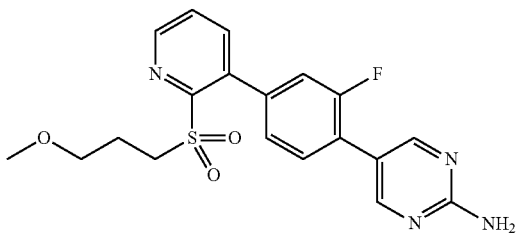

5-(2-Fluoro-4-(2-((3-methoxypropyl)sulfonyl)pyridine-3-yl)phenyl)pyrimidin-2-amine hydrogen chloride salt.

The title compound was prepared as described in step D of Example 803 using 3-bromo-2-((3-methoxypropyl)sulfonyl)pyridine and 5-(2-fluoro-4-(4,4,5,5-tetramethyl-1,3,2-dioxaboralan-2-yl)phenyl)pyrimidin-2-amine. MS (ESI): mass calcd. for $C_{19}H_{19}FN_4O_3S$, 402.12; m/z found, 403.1 [M+H]$^+$. $^1$H NMR (400 MHz, CD$_3$OD) δ 8.74 (dd, J=4.6, 1.5, 1H), 8.61 (s, 2H), 7.99 (dd, J=7.8, 1.5, 1H), 7.76 (dd, J=7.8, 4.7, 1H), 7.60 (m, 1H), 7.42 (dd, J=3.9, 1.3, 1H), 7.40 (s, 1H), 3.70-3.62 (m, 2H), 3.48 (m, 2H), 3.32 (s, 3H), 2.03-1.94 (m, 2H).

Example 818

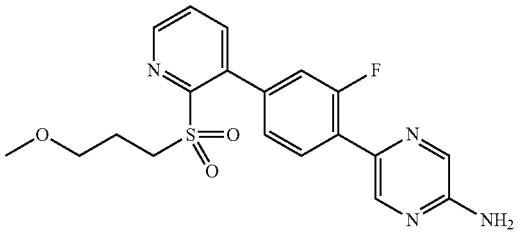

5-(2-Fluoro-4-(2-((3-methoxypropyl)sulfonyl)pyridine-3-yl)phenyl)pyrazin-2-amine hydrogen chloride salt.

The title compound was prepared as described in step D of Example 803 using 3-bromo-2-((3-methoxypropyl)sulfonyl)pyridine. MS (ESI): mass calcd. for $C_{19}H_{19}FN_4O_3S$, 402.12; m/z found, 403.1 [M+H]$^+$. $^1$H NMR (300 MHz, CD$_3$OD) δ 8.69 (d, J=3.5, 1H), 8.35 (s, 1H), 8.21 (s, 1H), 8.04-7.90 (m, 2H), 7.72 (dd, J=7.8, 4.7, 1H), 7.39 (s, 1H), 7.35 (d, J=2.0, 1H), 3.68-3.56 (m, 2H), 3.45 (m, 2H), 3.29 (s, 3H), 2.04-1.89 (m, 2H).

Example 819

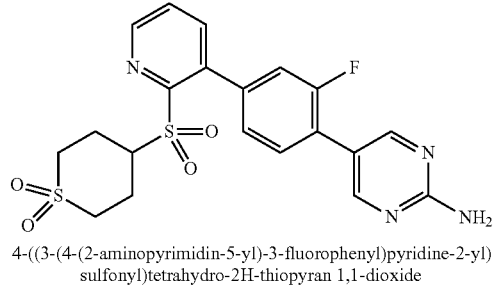 [SMILES: Nc1ncc(-c2ccc(-c3cccnc3S(=O)(=O)C3CCS(=O)(=O)CC3)cc2F)cn1]

4-((3-(4-(2-aminopyrimidin-5-yl)-3-fluorophenyl)pyridine-2-yl)sulfonyl)tetrahydro-2H-thiopyran 1,1-dioxide The title compound was prepared as described in step D of Example 803 using 4-((3-bromopyridin-2-yl)sulfonyl)tetrahydro-2H-thiopyran 1,1-dioxide and 5-(2-fluoro-4-(4,4,5,5-tetramethyl-1,3,2-dioxaboralan-2-yl)phenyl)pyrimidin-2-amine giving the target molecule after purification by HPLC. MS (ESI): mass calcd. for $C_{20}H_{19}FN_4O_4S_2 \cdot HCOOH$, 462.08; m/z found, 463.00 [M+H]$^+$. $^1$H NMR (300 MHz, CDCl$_3$) δ 8.67 (d, J=4.1, 1H), 8.58 (s, 2H), 7.87 (d, J=7.3, 1H), 7.72-7.59 (m, 1H), 7.56-7.44 (m, 1H), 7.42-7.29 (d, J=14.6, 2H), 5.22 (s, 2H), 4.52-4.48 (m, 1H), 3.43-3.23 (m, 2H), 3.03 (s, 2H), 2.68-2.47 (m, 4H).

Example 820

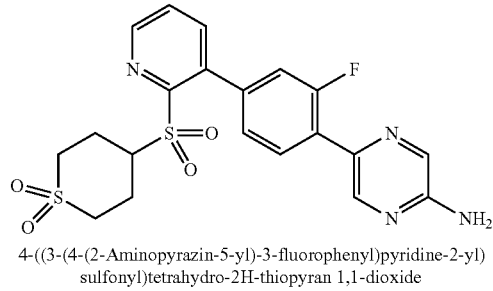 [SMILES: Nc1cnc(-c2ccc(-c3cccnc3S(=O)(=O)C3CCS(=O)(=O)CC3)cc2F)cn1]

4-((3-(4-(2-Aminopyrazin-5-yl)-3-fluorophenyl)pyridine-2-yl)sulfonyl)tetrahydro-2H-thiopyran 1,1-dioxide The title compound was prepared as described in step D of Example 803 using 4-((3-bromopyridin-2-yl)sulfonyl)tetrahydro-2H-thiopyran 1,1-dioxide giving the target molecule after purification by HPLC. MS (ESI): mass calcd. for $C_{20}H_{19}FN_4O_4S_2$·HCOOH, 462.08; m/z found, 463.00 [M+H]$^+$. $^1$H NMR (300 MHz, CDCl$_3$): δ 8.66 (dd, J=4.6, 1.6, 1H), 8.63-8.59 (m, 1H), 8.11 (d, J=1.5, 1H), 8.06 (m, 1H), 7.86 (dd, J=7.8, 1.6, 1H), 7.63 (dd, J=7.8, 4.6, 1H), 7.37 (dd, J=8.1, 1.8, 1H), 7.31 (dd, J=11.6, 1.7, 1H), 4.77 (s, 2H), 4.42-4.28 (m, 1H), 3.45-3.27 (m, 2H), 3.10-2.94 (m, 2H), 2.67-2.48 (m, 4H).

Example 821

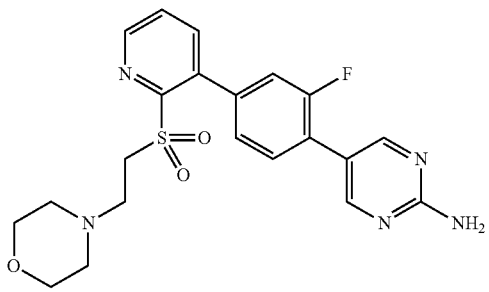

5-(2-Fluoro-4-(2-((2-morpholinoethyl)sulfonyl)pyridine-3-yl)phenyl)pyrimidin-2-amine formic acid salt.

The title compound was prepared as described in step D of Example 803 using 4-(2-((3-bromopyridin-2-yl)sulfonyl)ethyl)morpholine and 5-(2-fluoro-4-(4,4,5,5-tetramethyl-1,3,2-dioxaboralan-2-yl)phenyl)pyrimidin-2-amine. MS (ESI): mass calcd. for $C_{21}H_{22}FN_5O_3S$·HCOOH, 443.14; m/z found, 444.10 [M+H]$^+$. $^1$H NMR (300 MHz. CDCl$_3$) δ 8.65 (dd, J=4.7, 1.6, 1H), 8.56 (s, 2H), 7.82 (dd, J=7.8, 1.6, 1H), 7.61 (dd, J=7.9, 4.7, 1H), 7.47 (m, 1H), 7.39 (dd, J=8.0, 1.7, 1H), 7.33 (dd, J=11.0, 1.7, 1H), 5.52 (s, 2H), 3.85 (t, J=9, 2H), 3.63 (s, 4H), 2.93 (t, J=9, 2H), 2.54 (s, 4H).

Example 822

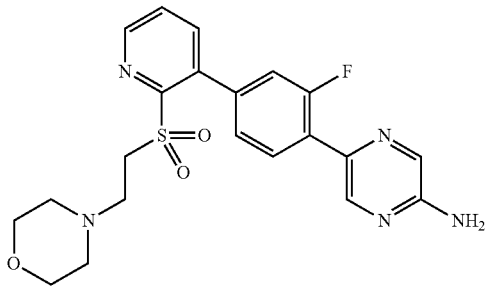

5-(2-Fluoro-4-(2-((2-morpholinoethyl)sulfonyl)pyridine-3-yl)phenyl)pyrazin-2-amine The title compound was prepared as described in step D of Example 803 using 4-(2-((3-bromopyridin-2-yl)sulfonyl)ethyl)morpholine giving the target molecule after purification by HPLC. MS (ESI): mass calcd. for $C_{21}H_{22}FN_5O_3S$·HCOOH, 443.14; m/z found, 444.10 [M+H]$^+$. $^1$H NMR (300 MHz, CDCl$_3$): δ 8.65 (dd, J=4.6, 1.6, 1H), 8.51 (s, 1H), 8.14 (d, J=1.5, 1H), 8.04 (m, 1H), 7.83 (dd, J=7.8, 1.6, 1H), 7.61 (dd, J=7.8, 4.7, 1H), 7.43-7.30 (m, 2H), 5.28 (m, 2H), 3.98-3.84 (m, 2H), 3.80-3.58 (m, 4H), 3.09-2.96 (m, 2H), 2.78-2.54 (m, 4H).

Example 823

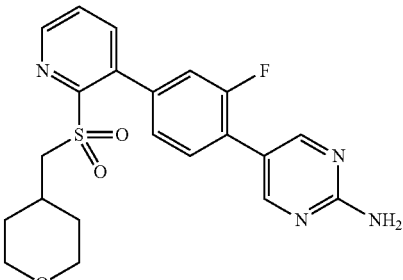

5-(2-Fluoro-4-(2-(((tetrahydro-2H-pyran-4-yl)methyl)sulfonyl)pyridine-3-yl)pyrimidin-2-amine formic acid salt.

The title compound was prepared as described in step D of Example 803 using 3-bromo-2-(((tetrahydro-2H-pyran-4-yl)methyl)sulfonyl)pyridine. MS (ESI): mass calcd. for $C_{21}H_{21}FN_4O_3S$, 428.13; m/z found, 429.1 [M+H]$^+$. $^1$H NMR (300 MHz, CD$_3$OD) δ 8.71 (dd, J=4.6, 1.5, 1H), 8.53 (d, J=1.3, 2 H), 7.97 (dd, J=7.8, 1.6, 1H), 7.74 (dd, J=7.9, 4.6, 1H), 7.57 (m, 1H), 7.44-7.35 (m, 2H), 3.96-3.78 (m, 2H), 3.57 (d, J=6.3, 2H), 3.47-3.37 (m, 2H), 2.25-2.10 (m, 1H), 1.85-1.69 (m, 2H), 1.54-1.36 (m, 2H).

Example 824

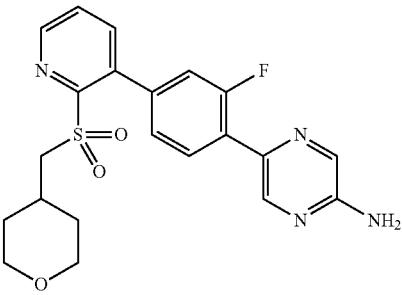

5-(2-Fluoro-4-(2-(((tetrahydro-2H-pyran-4-yl)methyl)sulfonyl)pyridine-3-yl)pyrazin-2-amine formic acid salt.

The title compound was prepared as described in step D of Example 803 using 3-bromo-2-(((tetrahydro-2H-pyran-4-yl)methyl)sulfonyl)pyridine. MS (ESI): mass calcd. for $C_{21}H_{21}FN_4O_3S$, 428.13; m/z found, 429.1 [M+H]$^+$. $^1$H NMR (300 MHz, CDCl$_3$) δ 8.65 (dd, J=4.6, 1.6, 1H), 8.60 (s, 1H), 8.10 (s, 1H), 8.04 (m, 1H), 7.82 (dd, J=7.8, 1.6, 1H), 7.59 (dd, J=7.8, 4.7, 1H), 7.40 (dd, J=8.0, 1.7, 1H), 7.34 (dd, J=11.8, 1.6, 1H), 4.76 (s, 2H), 3.92 (dd, J=10.6, 3.2, 2H), 3.56 (d, J=6.4, 2H), 3.39 (m, 2H), 2.40-2.26 (m, 1H), 1.84 (d, J=11.0, 2H), 1.49 (m, 2H).

Example 825

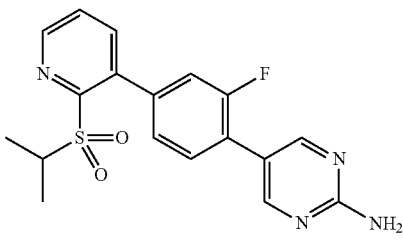

5-(2-Fluoro-4-{2-[(1-methylethyl)sulfonyl]pyridin-3-yl}phenyl)pyrimidin-2-amine

The title compound was prepared as described in step D of Example 803 using 5-(2-fluoro-4-(4,4,5,5-tetramethyl-1,3,2-dioxaborolan-2-yl)phenyl)pyrimidin-2-amine and 3-bromo-2-(isopropylsulfonyl)pyridine. MS (ESI): mass calcd. for $C_{18}H_{17}FN_4O_2S$, 372.11; m/z found, 373.0 $[M+H]^+$. 1H NMR (400 MHz, $CDCl_3$) δ 8.69 (dd, J=4.7, 1.7, 1H), 8.57 (d, J=1.4, 2H), 7.80 (dd, J=7.8, 1.6, 1H), 7.59 (dd, J=7.8, 4.6, 1H), 7.46 (m, 1H), 7.39 (dd, J=7.9, 1.8, 1H), 7.32 (dd, J=11.1, 1.7, 1H), 5.17 (s, 2H), 4.26 (hept, J=6.9, 1H), 1.32 (d, J=6.9, 6H).

Example 826

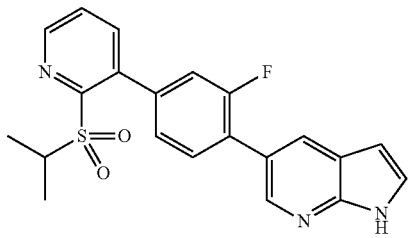

5-(2-Fluoro-4-(2-(isopropylsulfonyl)pyridine-3-yl)phenyl)-1H-pyrrolo[2,3-b]pyridine The title compound was prepared as described in step D of Example 803 using 5-(2-fluoro-4-(4,4,5,5-tetramethyl-1,3,2-dioxaborolan-2-yl)phenyl)-1H-pyrrolo[2,3-b]pyridine and 3-bromo-2-(isopropylsulfonyl)pyridine. MS (ESI): mass calcd. for $C_{21}H_{18}FN_4O_2S$, 395.11; m/z found, 396.1 $[M+H]^+$. $^1H$ NMR (400 MHz, $CDCl_3$) δ 9.45 (s, 1H), 8.70 (dd, J=4.6, 1.6, 2H), 8.25-8.17 (m, 1H), 7.84 (dd, J=7.8, 1.7, 1H), 7.64-7.54 (m, 2H), 7.46-7.32 (m, 3H), 6.61 (s, 1H), 4.26 (hept, J=6.8, 1H), 1.34 (d, J=6.9, 6H).

Example 827

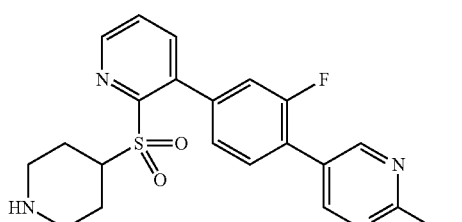

5-{2-Fluoro-4-[2-piperidine-4-ylsulfonyl)pyridin-3-yl]phenyl}pyrimidin-2-amine formic acid salt.

The title compound was prepared as described in step D of Example 803 using 5-(2-fluoro-4-(4,4,5,5-tetramethyl-1,3,2-dioxaboralan-2-yl)phenyl)pyrimidin-2-amine. MS (ESI): mass calcd. for $C_{20}H_{20}FN_5O_2S$, 413.13; m/z found, 414.1 $[M+H]^+$. $^1H$ NMR (300 MHz, $CDCl_3$) δ 8.91 (s, 2H), 8.78 (m, 1H), 8.03 (m, 1H), 7.82 (m, 1H), 7.75-7.71 (m, 1H), 7.50-7.42 (m, 2H), 4.52-4.46 (m, 1H), 3.57-3.54 (m, 2H), 3.24-3.17 (m, 2H), 2.31-2.28 (m, 2H), 2.13-1.96 (m, 2H).

Example 828

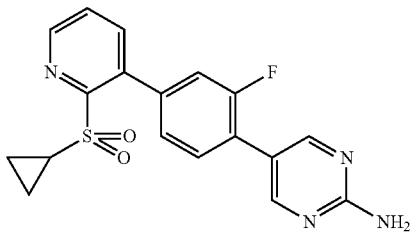

5-{4-[2-(Cyclopropylsulfonyl)pyridin-3-yl]-2-fluorophenyl}pyrimidin-2-amine formic acid salt.

Step A: 3-Bromo-2-((3-chloropropyl)thiopyridine

A mixture of 3-bromopyridine-2-thiol (0.04 g, 0.2 mmol), 1-bromo-3-chloropropane in DMF (0.424 mmol/mL, 2.0 mL), and $K_2CO_3$ (60 mg, 0.424 mmol) in DMF (2.0 mL) was stirred at rt for 10 minutes. The reaction mixture was then concentrated to dryness and the resultant residue diluted with water (10 mL) and extracted with ethyl acetate (3×10 mL). The combined organic extracts were dried over $Na_2SO_4$ and concentrated to dryness to give the title compound (0.05 g, 89% purity). MS (ESI): mass calcd. for $C_8H_9BrClNS$, 264.93; m/z found, 265.8 $[M+H]^+$.

Step B: 3-Bromo-2-((3-chloropropyl)sulfonyl)pyridine

To a solution of 3-bromo-2-((3-chloropropyl)thio)pyridine (0.05 g, 89% purity, 0.2 mmol) in DCM/$CH_3CN$ (3.0 mL/3.0 mL) were added $NaIO_4$ (0.121 g, 0.567 mmol), $H_2O$ (3.0 mL), and $RuCl_3$ (2.0 mg, 0.014 mmol). The mixture was stirred at rt. for 10 minutes and concentrated to dryness. The residue was diluted with water (10 mL) and extracted with ethyl acetate (3×10 mL). The combined organic extracts were dried over $MgSO_4$, and concentrated to dryness to give the title compound (0.05 g, 89% purity), which was used in next step without any further purification. MS (ESI): mass calcd. for $C_8H_9BrClNO_2S$, 296.92; m/z found, 297.9 $[M+H]^+$.

Step C: 3-Bromo-2-(cyclopropylsulfonyl)pyridine

To a solution of 3-bromo-2-((chloropropyl)sulfonyl)pyridine (0.05 g, 89% purity, 0.2 mmol) in THF (20 mL) was added t-BuOK (0.047 g, 0.42 mmol) at −38° C. and the mixture was stirred for an additional 30 minutes. The reaction was quenched by adding saturated $NH_4Cl$ aqueous solution (2.5 mL) and concentrated to dryness. The resultant residue was diluted with water (10 mL) and extracted with DCM (2×10 mL). The combined organic extracts were dried over $MgSO_4$, and concentrated to dryness to give the title compound (0.08 g, crude), which was used in the next step without further purification. MS (ESI): mass calcd. for C₈H₈BrNO₂S, 260.95; m/z found, 262.0 [M+H]⁺.

Step D: 5-{4-[2-(Cyclopropylsulfonyl)pyridin-3-yl]-2-fluorophenyl}pyrimidin-2-amine The title compound was prepared as described in step D of Example 803 using 5-(2-fluoro-4-(4,4,5,5-tetramethyl-1,3,2-dioxaborolan-2-yl)phenyl)pyrimidin-2-amine and 3-bromo-2-(cyclopropylsulfonyl). MS (ESI): mass calcd. for C₁₈H₁₅FN₄O₂S.HCOOH, 370.09; m/z found, 370.9 [M+H]⁺. ¹H NMR (300 MHz, CDCl₃) δ 8.67 (m, 1H), 8.55 (s, 2H), 7.76 (m, 1H), 7.55 (m, 1H), 7.49-7.27 (m, 3H), 5.37 (s, 2H), 3.23-3.08 (m, 1H), 1.25-1.01 (m, 4H).

Example 829

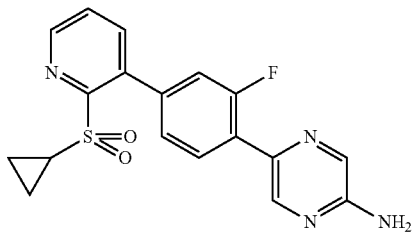

5-{4-[2-(Cyclopropylsulfonyl)pyridin-3-yl]-2-fluorophenyl}pyrazin-2-amine formic acid salt.

The title compound was prepared as described in step D of Example 803 using 5-(2-fluoro-4-(4,4,5,5-tetramethyl-1,3,2-dioxaborolan-2-yl)phenyl)pyrazin-2-amine and 3-bromo-2-(cyclopropylsulfonyl)pyridine. MS (ESI): mass calcd. for C₁₈H₁₅FN₄O₂S, 370.09; m/z found, 370.9 [M+H]⁺; ¹H NMR (300 MHz, CDCl₃) δ 8.66 (m, 1H), 8.55 (s, 1H), 8.06 (d, J=1.4, 1H), 8.02-7.96 (m, 1H), 7.77 (m, 1H), 7.54 (m, 1H), 7.36 (m, 1H), 7.30 (m, 1H), 4.70 (s, 2H), 3.12-3.01 (m, 1H), 1.25-0.97 (m, 4H).

Example 830

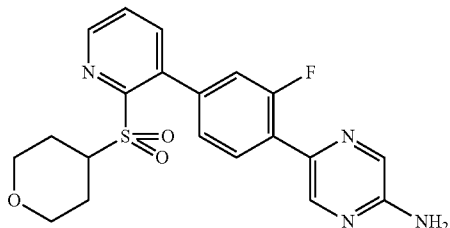

5-{2-Fluoro-4-[2-(tetrahydro-2H-pyran-4-ylsulfonyl)pyridin-3-yl]phenyl}pyrazin-2-amine hydrochloride The title compound was prepared as described in step D of Example 803 using 5-(2-fluoro-4-(4,4,5,5-tetramethyl-1,3,2-dioxaborolan-2-yl)phenyl)pyrazin-2-amine and 3-bromo-2-((tetrahydro-2H-pyran-4-yl)sulfonyl)pyridine. MS (ESI): mass calcd. for C₂₀H₁₉FN₄O₃S.HCl, 414.12; m/z found, 415.1 [M+H]⁺; ¹H NMR (300 MHz, CDCl₃) δ 8.78 (d, J=4.6, 1H), 8.40 (s, 1H), 8.13-7.99 (m, 2H), 7.95-7.89 (m, 1H), 7.87-7.78 (m, 1H), 7.38 (m, 2H), 6.76 (s, 2H), 4.33-4.20 (m, 1H), 3.92 (dd, J=11.1, 3.7, 2H), 3.50-3.35 (m, 2H), 1.85-1.69 (m, 2H), 1.69-1.48 (m, 2H).

Example 831

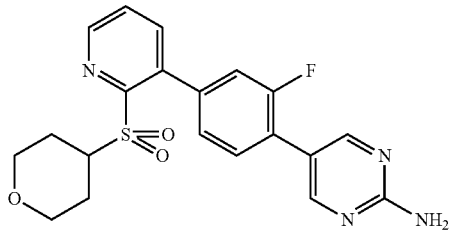

5-{2-Fluoro-4-[2-(tetrahydro-2H-pyran-4-ylsulfonyl)pyridin-3-yl]phenyl}pyrimidin-2-amine formic acid salt.

The title compound was prepared as described in step D of Example 803 using 5-(2-fluoro-4-(4,4,5,5-tetramethyl-1,3,2-dioxaborolan-2-yl)phenyl)pyrimidin-2-amine and 3-bromo-2-((tetrahydro-2H-pyran-4-yl)sulfonyl)pyridine. MS (ESI): mass calcd. for C₂₀H₁₉FN₄O₃S, 414.12; m/z found, 415.1 [M+H]⁺; ¹H NMR (300 MHz, CD₃OD) δ 8.78 (m, 1H), 8.52 (d, J=1.4, 2H), 8.04 (m, 1H), 7.82 (m, 1H), 7.67-7.61 (m, 1H), 7.43 (m, 1H), 7.36 (m, 1H), 6.95 (s, 2H), 4.29-4.24 (m, 1H), 3.94-3.89 (m, 2H), 3.45-3.35 (m, 2H), 1.77-1.73 (m, 2H), 1.77-1.52 (m, 2H).

Example 832

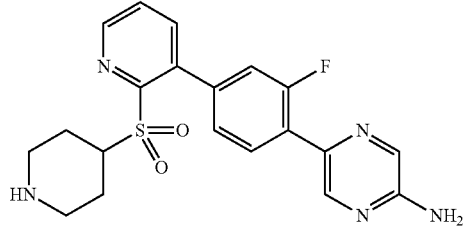

5-{2-Fluoro-4-[2-(piperidin-4-ylsulfonyl)pyridin-3-yl]phenyl}pyrazin-2-amine hydrochloride The title compound was prepared as described in step D of Example 803 using 5-(2-fluoro-4-(4,4,5,5-tetramethyl-1,3,2-dioxaborolan-2-yl)phenyl)pyrazin-2-amine. MS (ESI): mass calcd. for C₂₀H₂₀FN₅O₂S, 413.13; m/z found, 414.1 [M+H]⁺. ¹H NMR (300 MHz, CD₃OD) δ 8.81-8.69 (m, 1H), 8.54 (s, 1H), 8.29 (s, 1H), 8.11-8.06 (m, 1H), 8.01 (m, 1H), 7.78 (m, 1H), 7.42 (s, 1H), 7.39 (d, J=2.1, 1H), 4.55-4.38 (m, 1H), 3.54-3.50 (m, 2H), 3.19-3.12 (m, 2H), 2.30-2.26 (m, 2H), 2.09-1.88 (m, 2H).

Example 833

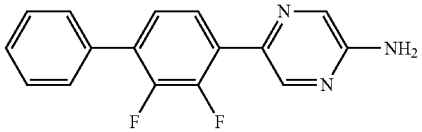

5-(2,3-Difluorobiphenyl-4-yl)pyrazin-2-amine.

The title compound was prepared by a method analogous to Example 461 using phenylboronic acid. MS (ESI): mass calcd. for $C_{16}H_{11}F_2N_3$, 283.09; m/z found, 284.1 [M+H]$^+$. $^1$H NMR (500 MHz, DMSO-d$_6$) δ 8.43-8.40 (m, 1H), 8.04 (d, J=1.5, 1H), 7.78-7.72 (m, 1H), 7.65-7.60 (m, 2H), 7.55-7.50 (m, 2H), 7.50-7.41 (m, 2H), 6.83 (s, 2H).

Intermediate JF

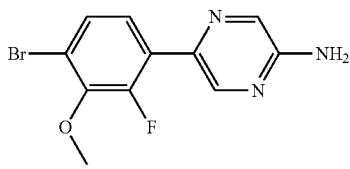

5-(4-Bromo-2-fluoro-3-methoxyphenyl)pyrazin-2-amine.

Step A:
(4-Bromo-2-fluoro-3-methoxyphenyl)boronic acid

A solution of 2,2',6,6'-tetramethylpiperidine (0.98 ml, 5.8 mmol) in THF (9.8 ml) was cooled to −78° C. under a N$_2$ atmosphere. To the solution was then added n-BuLi (2.21 N in hexanes, 2.45 ml, 5.41 mmol) drop-wise over a couple of minutes, and then the mixture warmed to 0° C. for 20-30 min. The mixture was then cooled back to −78° Celsius and treated with triisopropyl borate (1.25 ml, 5.41 mmol). After 5 minutes 1-bromo-3-fluoro-2-methoxybenzene (1.0 g, 4.9 mmol) was slowly added and the reaction stirred at −78° Celsius for 1.5 h before warming to rt The reaction mixture was then treated with AcOH (2.8 ml, 49 mmol), diluted with water, and extracted with EtOAc. The EtOAc extract was dried over MgSO$_4$, filtered, and concentrated to dryness. The crude product was used without purification.

Step B: 5-(4-Bromo-2-fluoro-3-methoxyphenyl)pyrazin-2-amine

A mixture of (4-bromo-2-fluoro-3-methoxyphenyl)boronic acid (940 mg, 1.69 mmol) and 5-bromopyrazin-2-amine (1.31 g, 7.56 mmol) was treated with EtOH (12.4 ml), toluene (12.8 ml), and aqueous Na$_2$CO$_3$ (2.0 N, 9.44 ml, 18.9 mmol), and the resulting mixture deoxygenated by sparging with for 10 minutes. Pd(PPh$_3$)$_4$ (218 mg, 0.189 mmol) was then added, and the mixture heated at 80° Celsius for 17 h. The reaction was cooled to rt and then partitioned between saturated aqueous NH$_4$Cl and EtOAc. The organic layer was isolated, dried over MgSO$_4$, and concentrated to dryness. The resultant residue was suspended in DCM and the title compound isolated by filtration (300 mg, 27%), which was used without further purification. Additional product was obtained by concentrating the filtrate to dryness and subjecting the residue to FCC (560 mg, 50%). MS (ESI): mass calcd. for $C_{11}H_9BrFN_3O$, 296.99; m/z found, 298.0 [M+H]$^+$. $^1$H NMR (500 MHz, DMSO-d) δ 8.34 (dd, J=2.6, 1.5, 1H), 8.00 (d, J=1.5, 1H), 7.54-7.49 (m, 2H), 6.78 (s, 2H), 3.90 (d, J=0.6, 3H).

Example 834

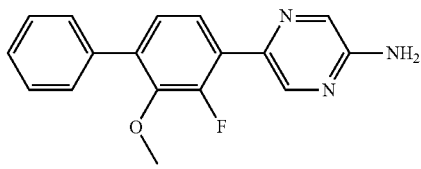

5-(3-Fluoro-2-methoxybiphenyl-4-yl)pyrazin-2-amine.

The title compound was prepared by a method analogous to Example 461 using phenylboronic acid and 5-(4-bromo-2-fluoro-3-methoxyphenyl)pyrazin-2-amine. MS (ESI): mass calcd. for $C_{17}H_{14}FN_3O$, 295.11; m/z found, 296.1 [M+H]$^+$. $^1$H NMR (500 MHz, CDCl$_3$) δ 8.58-8.55 (m, 1H), 8.12 (d, J=1.5, 1H), 7.65 (dd, J=8.1, 7.5, 1H), 7.61-7.54 (m, 2H), 7.48-7.42 (m, 2H), 7.41-7.34 (m, 1H), 7.23 (dd, J=8.2, 1.4, 1H), 4.69 (s, 2H), 3.74 (d, J=0.9, 3H).

Example 835

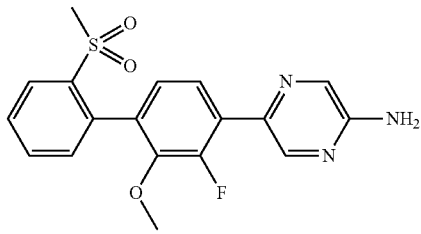

5-[3-Fluoro-2-methoxy-2'-(methylsulfonyl)biphenyl-4-yl]pyrazin-2-amine.

The title compound was prepared by a method analogous to Example 461 using 5-(4-bromo-2-fluoro-3-methoxyphenyl)pyrazin-2-amine. MS (ESI): mass calcd. for $C_{18}H_{16}FN_3O_3S$, 373.09; m/z found, 374.1 [M+H]$^+$. $^1$H NMR (500 MHz, CDCl$_3$) δ 8.58-8.53 (m, 1H), 8.21 (dd, J=8.0, 1.3, 1H), 8.11 (d, J=1.5, 1H), 7.71-7.58 (m, 3H), 7.35 (dd, J=7.5, 1.2, 1H), 7.13 (dd, J=8.1, 1.3, 1H), 4.74 (s, 2H), 3.82 (d, J=1.9, 3H), 2.96 (s, 3H).

Example 836

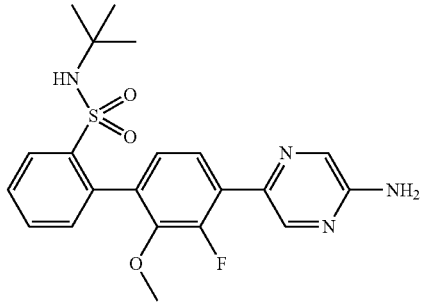

4'-(5-Aminopyrazin-2-yl)-N-tert-butyl-3'-fluoro-2'-methoxybiphenyl-2-sulfonamide.

The title compound was prepared by a method analogous to Example 461 using (2-(N-(tert-butyl)sulfamoyl)phenyl) boronic acid and 5-(4-bromo-2-fluoro-3-methoxyphenyl)pyrazin-2-amine. MS (ESI): mass calcd. for $C_{21}H_{23}FN_4O_3S$, 430.15; m/z found, 431.1 [M+H]$^+$. $^1$H NMR (400 MHz, CDCl$_3$) δ 8.53-8.48 (m, 1H), 8.19 (dd, J=7.9, 1.4, 1H), 8.08 (d, J=1.5, 1H), 7.64-7.55 (m, 2H), 7.52 (m, 1H), 7.29 (dd, J=7.4, 1.4, 1H), 7.18 (dd, J=8.2, 1.4, 1H), 4.80 (s, 2H), 4.42 (s, 1H), 3.85 (d, J=1.8, 3H), 1.21 (s, 9H).

Example 837

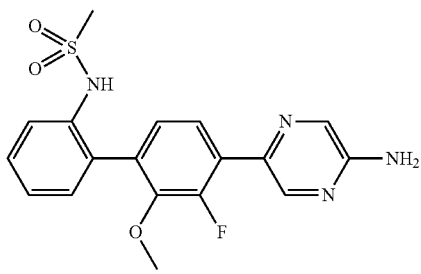

N-[4′-(5-Aminopyrazin-2-yl)-3′-fluoro-2′-methoxybiphenyl-2-yl]methanesulfonamide.

The title compound was prepared by a method analogous to Example 461 using (2-(methylsulfonamido)phenyl)boronic acid and 5-(4-bromo-2-fluoro-3-methoxyphenyl)pyrazin-2-amine. MS (ESI): mass calcd. for $C_{18}H_{17}FN_4O_3S$, 388.10; m/z found, 389.1 [M+H]$^4$. $^1$H NMR (400 MHz, CDCl$_3$) δ 8.59 (dd, J=2.3, 1.6, 1H), 8.12 (d, J=1.5, 1H), 7.75 (dd, J=8.2, 7.2, 1H), 7.69 (d, J=8.0, 1H), 7.46 (m, 1H), 7.37-7.32 (m, 2H), 7.15 (dd, J=8.2, 1.5, 1H), 7.10 (s, 1H), 4.77 (s, 2H), 3.73 (d, J=1.1, 3H), 2.58 (s, 3H).

Example 838

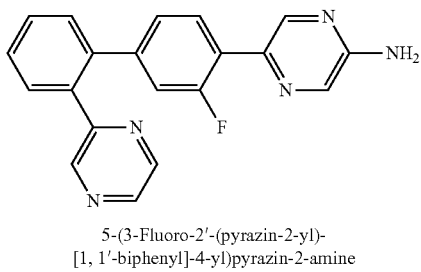 [SMILES: Nc1cnc(-c2ccc(-c3ccccc3-c3cnccn3)cc2F)cn1]

5-(3-Fluoro-2′-(pyrazin-2-yl)-[1,1′-biphenyl]-4-yl)pyrazin-2-amine

Step A: 2-(2-Chlorophenyl)pyrazine

2-Bromopyrazine (100 mg, 0.630 mmol) and ((2-chlorophenyl)boronic acid (103 mg, 0.660 mmol) were added to a 5 mL sealable vial equipped with a stir-bar. A solution consisting of 1,4-dioxane (3 mL) and Na$_2$CO$_3$ (1.6 mL, 2 M) was added and the mixture sparged with argon for 10 minutes before adding Pd(ddp)Cl$_2$.CH$_2$Cl$_2$ (23 mg, 0.031 mmol) and heating at 80° Celsius for 15 hours. The reaction was then cooled to rt, diluted with 5 mL of ethyl acetate and 5 mL of water, and the mixture extracted with ethyl acetate (3×20 mL). The combined organic extracts were then dried with sodium sulfate and concentrated to dryness. The resultant residue was subjected to FCC to provide the title compound. $^1$H NMR (500 MHz, CDCl$_3$) δ 8.98-8.96 (d, J=1.6, 1H), 8.70-8.68 (dd, J=2.5, 1.6, 1H), 8.58-8.56 (d, J=2.6, 1H), 7.66-7.58 (m, 1H), 7.54-7.50 (m, 1H), 7.43-7.39 (m, 2H).

Step B: 5-(3-Fluoro-2′-pyrazin-2-ylbiphenyl-4-yl)pyrazin-2-amine 2-(2-Chlorophenyl)pyrazine (58 mg, 0.31 mmol), 5-(2-fluoro-4-(4,4,5,5-tetramethyl-1,3,2-dioxaborolan-2-yl)phenyl)pyrazin-2-amine (88 mg, 0.28 mmol) and chloro(2-dicyclohexylphosphino-2′,4′,6′-triisopropyl-1,1′-biphenyl)[2-(2′-amino-1,1′-biphenyl)]palladium(II) (4.4 mg, 0.0060 mmol) were placed into a sealable 5 mL vial equipped with a stir-bar. The vial was sealed, evacuated and backfilled with argon three times. To this vial was added separately deoxygenated THF (0.56 mL) and K$_3$PO$_4$ (1.1 mL, 0.5 M). The vial was then heated at 45° Celsius for 1 hour before cooling to rt diluting with brine (5 mL), and extracting with EtOAc (1×5 mL, 3×10 mL). The combined organic extracts were then dried with sodium sulfate, filtered, and concentrated to dryness. The crude product was purified via FCC to provide the title compound. MS (ESI): mass calcd. for $C_{20}H_{14}FN_5$, 343.12; m/z found, 344.1 [M+H]$^+$. $^1$H NMR (500 MHz, CD$_3$OD) δ 8.65-8.59 (dd, J=2.6, 1.6, 1H), 8.47-8.42 (d, J=2.6, 1H), 8.33-8.31 (dd, J=2.2, 1.4, 1H), 8.31-8.29 (d, J=1.5, 1H), 8.04-8.02 (d, J=1.5, 1H), 7.79-7.73 (m, 1H), 7.72-7.69 (m, 1H), 7.64-7.53 (m, 3H), 7.11-6.87 (m, 2H).

Example 839

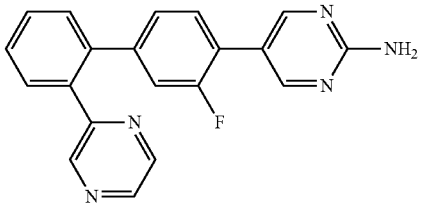

5-(3-Fluoro-2′-pyrazin-2-ylbiphenyl-4-yl)pyrimidin-2-amine.

The title compound was prepared in a manner similar to that described in Example 838 using 5-(2-fluoro-4-(4,4,5,5-tetramethyl-1,3,2-dioxaborolan-2-yl)phenyl)pyrimidin-2-amine in Step B. MS (ESI): mass calcd. for $C_{20}H_{14}FN_5$, 343.12; m/z found, 344.1 [M+H]$^+$. $^1$H NMR (500 MHz, CD$_3$OD) δ 8.61 (s, 1H), 8.56 (s, 2H), 8.47-8.40 (d, J=2.6, 1H), 8.31 (s, 1H), 7.74-7.67 (d, J=7.3, 1H), 7.65-7.57 (m, 1H), 7.57-7.54 (d, J=7.3, 1H), 7.46-7.41 (m, 1H), 7.08-7.04 (d, J=11.8, 1H), 7.04-7.00 (d, J=8.0, 1H).

Example 840

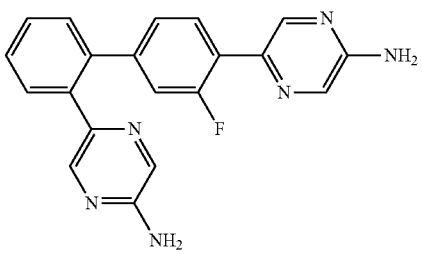

5,5′-(3′-Fluorobiphenyl-2,4′-diyl)dipyrazin-2-amine.

The title compound was prepared in a manner similar to that described in Example 847 using 5-bromopyrazin-2-amine in Step A. MS (ESI): mass calcd. for C$_{20}$H$_{15}$FN, 358.13; m/z found, 359.1 [M+H]$^+$. $^1$H NMR (500 MHz, CD$_3$OD) δ 8.37-8.29 (m, 1H), 8.06-8.02 (d, J=1.5, 1H), 7.93-7.90 (d, J=1.5, 1H), 7.82-7.73 (m, 1H), 7.63-7.55 (m, 2H), 7.53-7.44 (m, 3H), 7.05-6.97 (m, 2H).

Example 841

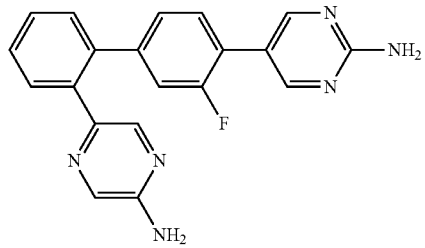

5-[2'-(5-Aminopyrazin-2-yl)-3'-fluorobiphenyl-4-yl]pyrimidin-2-amine.

The title compound was prepared in a manner similar to that described in Example 838 using 5-bromopyrazin-2-amine in Step A and 5-(2-fluoro-4-(4,4,5,5-tetramethyl-1,3,2-dioxaborolan-2-yl)phenyl)pyrimidin-2-amine in Step B. MS (ESI): mass calcd. for C$_{20}$H$_{15}$FN$_6$, 358.13; m/z found, 359.1 [M+H]$^+$. $^1$H NMR (500 MHz, CD$_3$OD) δ 8.50-8.44 (d, J=1.4, 2H), 7.95-7.90 (d, J=1.5, 1H), 7.63-7.55 (m, 2H), 7.52-7.44 (m, 3H), 7.43-7.38 (m, 1H), 7.06-7.03 (m, 1H), 7.03-7.01 (dd, J=6.2, 1.6, 1H).

Example 842

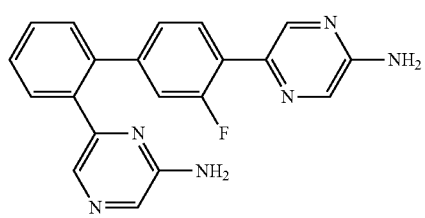

5-[2'-(6-Aminopyrazin-2-yl)-3'-fluorobiphenyl-4-yl]pyrazin-2-amine.

The title compound was prepared in a manner similar to that described in Example 838 using 6-bromopyrazin-2-amine in Step A. MS (ESI): mass calcd. for C$_{20}$H$_{15}$FN$_6$, 358.13; m/z found, 359.1 [M+H]$^+$. $^1$H NMR (500 MHz, CD$_3$OD) δ 8.34-8.25 (m, 1H), 8.15-8.08 (d, J=1.5, 1H), 7.86-7.78 (m, 1H), 7.77 (s, 1H), 7.66-7.59 (m, 1H), 7.59-7.48 (m, 3H), 7.40 (s, 1H), 7.10-7.00 (m, 2H).

Example 843

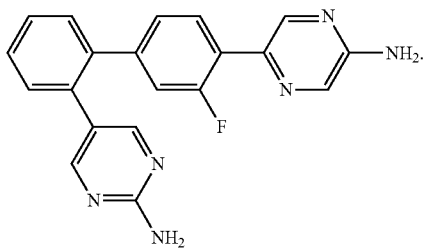

5-[4'-(5-Aminopyrazin-2-yl)-3'-fluorobiphenyl-2-yl]pyrimidin-2-amine

The title compound was prepared in a manner similar to that described in Example 838 using 5-bromopyrimidin-2-amine in Step A. MS (ESI): mass calcd. for C$_{20}$H$_{15}$FN$_6$, 358.13; m/z found, 359.1 [M+H]$^+$. $^1$H NMR (500 MHz, CD$_3$OD) δ 8.33 (s, 1H), 8.19-8.14 (m, 2H), 8.12-8.08 (d, J=1.9, 1H), 7.90-7.80 (dd, J=8.8, 7.2, 1H), 7.57-7.41 (m, 4H), 7.12 (s, 1H), 7.10 (s, 1H).

Example 844

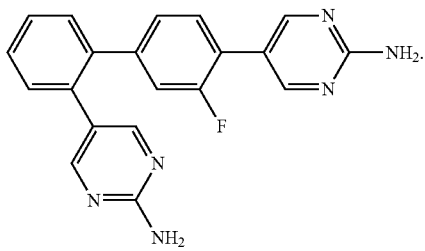

5,5'-(3'-Fluorobiphenyl-2,4'-diyl)dipyrimidin-2-amine

The title compound was prepared in a manner similar to that described in Example 838 using 5-bromopyrimidin-2-amine in Step A and 5-(2-fluoro-4-(4,4,5,5-tetramethyl-1,3,2-dioxaborolan-2-yl)phenyl)pyrimidin-2-amine in Step B. MS (ESI): mass calcd. for C$_{20}$H$_{15}$FN$_6$, 358.13; m/z found, 359.1 [M+H]$^+$. $^1$H NMR (500 MHz, CD$_3$OD) δ 8.57 (s, 2H), 8.16 (d, J=2.0, 2H), 7.57-7.45 (m, 5H), 7.14 (t, J=10.3, 2H).

Example 845

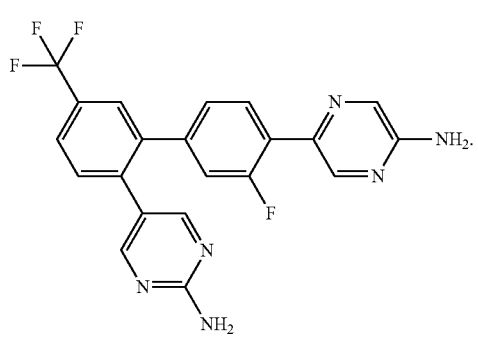

5-[4'-(5-Aminopyrazin-2-yl)-3'-fluoro-5-(trifluoromethyl)biphenyl-2-yl]pyrimidin-2-amine The title compound was prepared in a manner similar to that described in Example 838 using 5-(2-fluoro-4-(4,4,5,5-tetramethyl-1,3,2-dioxaborolan-2-yl)phenyl)pyrazin-2-amine and 2-bromo-1-chloro-4-(trifluoromethyl)benzene in Step A and 5-(4,4,5,5-tetramethyl-1,3,2-dioxaborolan-2-yl)pyrimidin-2-amine in Step B. MS (ESI): mass calcd. for $C_{21}H_{14}F_4N_6$, 426.12; m/z found, 427.0 [M+H]$^+$. $^1$H NMR (500 MHz, CD$_3$OD) δ 8.36 (dd, J=2.1, 1.5, 1H), 8.10 (s, 2H), 8.05 (d, J=1.5, 1H), 7.90-7.85 (m, 1H), 7.81-7.77 (m, 1H), 7.74 (d, J=1.8, 1H), 7.66 (d, J=8.0, 1H), 7.13 (dd, J=2.6, 1.7, 1H), 7.11 (dd, J=6.5, 1.6, 1H).

Example 846

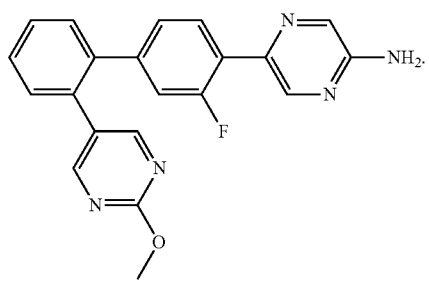

5-[3-Fluoro-2'-(2-methoxypyrimidin-5-yl)biphenyl-4-yl]pyrazin-2-amine

The title compound was prepared in a manner similar to that described in Example 838 using 5-bromo-2-methoxypyrimidine in Step A. MS (ESI): mass calcd. for $C_{21}H_{16}FN_5O$, 373.13; m/z found, 374.1 [M+H]$^+$. $^1$H NMR (500 MHz, CD$_3$OD) δ 8.36 (s, 2H), 8.34 (dd, J=2.1, 1.4, 1H), 8.04 (d, J=1.5, 1H), 7.84-7.74 (m, 1H), 7.56-7.44 (m, 4H), 7.12-6.97 (m, 2H), 3.98 (s, 3H).

Example 847

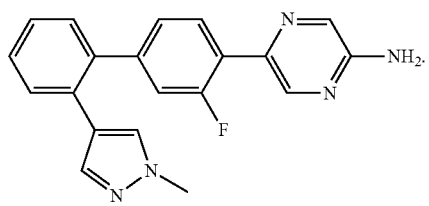

5-[3-Fluoro-2'-(1-methyl-1H-pyrazol-4-yl)biphenyl-4-yl]pyrazin-2-amine

The title compound was prepared in a manner similar to that described in Example 838 using 4-bromo-1-methyl-1H-pyrazole in Step A. MS (ESI): mass calcd. for $C_{20}H_{16}FN_5$, 345.14; m/z found, 346.2 [M+H]$^+$. $^1$H NMR (500 MHz, CD$_3$OD) δ 8.38-8.35 (m, 1H), 8.06 (d, J=1.5, 1H), 7.85-7.79 (m, 1H), 7.51-7.46 (m, 1H), 7.42-7.37 (m, 1H), 7.37-7.32 (m, 3H), 7.15-7.11 (m, 2H), 7.05 (dd. J=12.2, 1.7, 1H), 3.80 (s, 3H).

Example 848

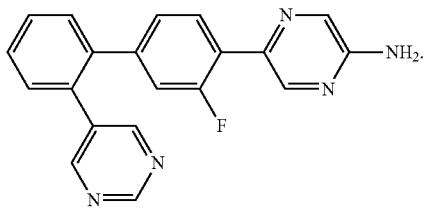

5-(3-Fluoro-2'-pyrimidin-5-ylbiphenyl-4-yl)pyrazin-2-amine

The title compound was prepared in a manner similar to that described in Example 838 using 5-bromopyrimidine in Step A. MS (ESI): mass calcd. for $C_{20}H_{14}FN_5$, 343.12; m/z found, 344.1 [M+H]$^+$. $^1$H NMR (500 MHz, CD$_3$OD) δ 9.01 (s, 1H), 8.61 (s, 2H), 8.32-8.27 (m, 1H), 8.17 (d, J=1.4, 1H), 7.88-7.78 (m, 1H), 7.63-7.50 (m, 4H), 7.11-7.00 (m, 2H).

Example 849

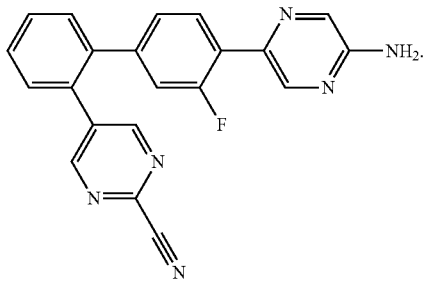

5-[4'-(5-Aminopyrazin-2-yl)-3'-fluorobiphenyl-2-yl]pyrimidine-2-carbonitrile

The title compound was prepared in a manner similar to that described in Example 838 using 5-bromopyrimidine-2-carbonitrile in Step A. MS (ESI): mass calcd. for $C_{21}H_{13}FN_6$, 368.12; m/z found, 369.1 [M+H]$^+$. $^1$H NMR (500 MHz, CD$_3$OD) 8.73 (s, 2H), 8.37-8.33 (m, 1H), 8.04 (d, J=1.5, 1H), 7.80 (m, J=8.1, 1H), 7.68-7.55 (m, 4H), 7.11 (dd, J=12.1, 1.7, 1H), 7.01 (dd, J=8.1, 1.7, 1H).

Example 850

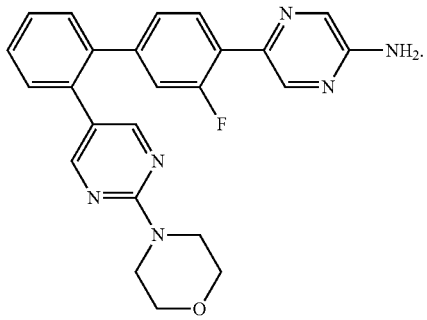

5-[3-Fluoro-2'-(2-morpholin-4-ylpyrimidin-5-yl)biphenyl-4-yl]pyrazin-2-amine

The title compound was prepared in a manner similar to that described in Example 838 using 4-(5-bromopyrimidin-

Example 851

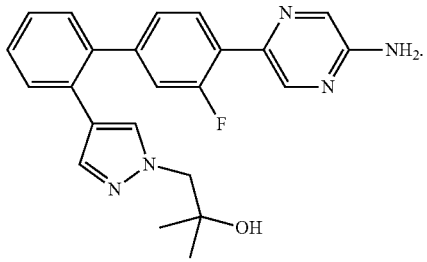

1-{4-[4'-(5-Aminopyrazin-2-yl)-3'-
fluorobiphenyl-2-yl]-1H-
pyrazol-1-yl}-2-methylpropan-2-ol The title compound was prepared in a manner similar to that described in Example 838 using 1-(4-bromo-1H-pyrazol-1-yl)-2-methylpropan-2-ol in Step A. MS (ESI): mass calcd. for $C_{23}H_{22}FN_5O$, 403.18; m/z found, 404.1 [M+H]$^+$. $^1$H NMR (500 MHz, CD$_3$OD) δ 8.37-8.32 (m, 1H), 8.07 (d, J=1.5, 1H), 7.85-7.78 (m, 1H), 7.53-7.48 (m, 1H), 7.44-7.37 (m, 1H), 7.35 (dd, J=5.0, 1.1, 2H), 7.32 (d, J=0.9, 1H), 7.25 (d, J=0.8, 1H), 7.15 (dd, J=8.0, 1.7, 1H), 7.04 (dd, J=12.3, 1.7, 1H), 3.98 (s, 2H), 1.07 (s, 6H).

Example 852

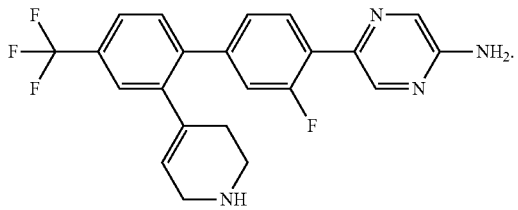

5-[3-Fluoro-2'-(1,2,3,6-tetrahydropyridin-4-yl)-4'-
(trifluoromethyl)biphenyl-4-yl]pyrazin-2-amine The title compound was prepared in a manner similar to that described in Example 838 using tert-butyl 4-(4,4,5,5-tetramethyl-1,3,2-dioxaborolan-2-yl)-5,6-dihydropyridine-1(2H)-carboxylate and 2-bromo-1-chloro-4-(trifluoromethyl)benzene in Step A, followed by removal of the Boc group. To a stirred solution of tert-butyl 4-(4'-(5-aminopyrazin-2-yl)-3'-fluoro-4-(trifluoromethyl)-[1,1'-biphenyl]-2-yl)-5,6-dihydropyridine-1(2H)-carboxylate (68 mg, 0.13 mmol) in DCM (2 mL) was added TFA (0.56 mL, 7.3 mmol) at room temperature. When analysis by LCMS indicated the reaction was complete, the stir-bar was removed, the reaction mixture concentrated to dryness, and the residue subjected to HPLC purification to provide the title compound. MS (ESI): mass calcd. for $C_{22}H_{18}F_4N_4$, 414.15; m/z found, 415.0 [M+H]$^+$. $^1$H NMR (500 MHz, CD$_3$OD) δ 8.41-8.37 (m, 1H), 8.13 (d, J=1.5, 1H), 8.03-7.96 (m, 1H), 7.78-7.72 (m, 1H), 7.64 (d, J=1.8, 1H), 7.61 (d, J=8.0, 1H), 7.37 (dd, J=8.0, 1.7, 1H), 7.33 (dd, J=12.1, 1.7, 1H), 5.89 (m, 1H), 3.85-3.75 (m, 2H), 3.19 (t, J=6.0, 2H), 2.33-2.22 (m, 2H).

Example 853

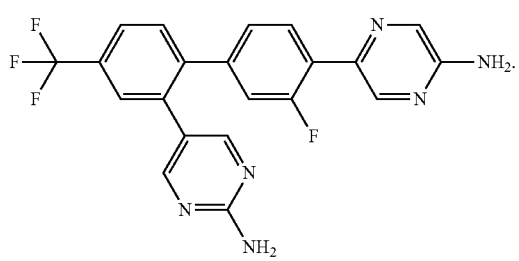

5-[4'-(5-Aminopyrazin-2-yl)-3'-fluoro-4-
(trifluoromethyl)biphenyl-2-yl]pyrimidin-2-amine The title compound was prepared in a manner similar to that described in Example 838 using 5-(4,4,5,5-tetramethyl-1,3,2-dioxaborolan-2-yl)pyrimidin-2-amine and 2-bromo-1-chloro-4-(trifluoromethyl)benzene in Step A. MS (ESI): mass calcd. for $C_{21}H_{14}F_4N_6$, 426.12; m/z found, 427.0 [M+H]$^+$. $^1$H NMR (500 MHz, CD$_3$OD) δ 8.34 (s, 1H), 8.16 (d, J=1.2, 2H), 8.10 (s, 1H), 7.92-7.86 (m, 1H), 7.80 (d, J=8.3, 1H), 7.78 (d, J=1.7, 1H), 7.69 (d, J=8.0, 1H), 7.23-7.08 (m, 2H).

Example 854

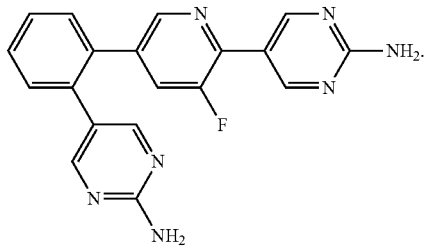

5-{2-[6-(2-Aminopyrimidin-5-yl)-5-fluoropyridin-3-yl]
phenyl}pyrimidin-2-amine

The title compound was prepared in a manner similar to that described in Example 427 using (6-(2-aminopyrimidin-5-yl)-5-fluoropyridin-3-yl)boronic acid and 5-(2-chlorophenyl)pyrimidin-2-amine. MS (ESI): mass calcd. for $C_{19}H_{14}FN_7$, 359.13; m/z found, 360.1 [M+H]$^+$. $^1$H NMR (500 MHz, CD$_3$OD) δ 8.93 (s, 2H), 8.31-8.28 (m, 1H), 8.19 (s, 2H), 7.64 (dd, J=12.0, 1.9, 1H), 7.59-7.51 (m, 4H).

Example 855

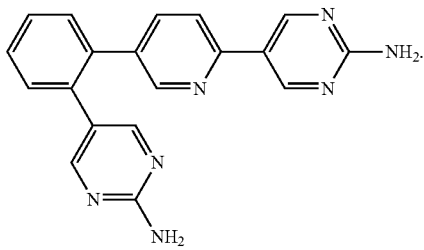

5-{5-[2-(2-Aminopyrimidin-5-yl)phenyl]pyridin-2-yl}pyrimidin-2-amine

The title compound was prepared in a manner similar to that described in Example 427 using 5-(5-(4,4,5,5-tetramethyl-1,3,2-dioxaborolan-2-yl)pyridin-2-yl)pyrimidin-2-amine and 5-(2-bromophenyl)pyrimidin-2-amine. MS (ESI): mass calcd. for $C_{19}H_{15}N_7$, 341.14; m/z found, 342.1 [M+H]$^+$. $^1$H NMR (500 MHz, CD$_3$OD) δ 8.97 (s, 2H), 8.47 (dd, J=2.3, 0.9, 1H), 8.16 (s, 2H), 7.86 (dd, J=8.2, 0.9, 1H), 7.80 (dd, J=8.2, 2.3, 1H), 7.59-7.49 (m, 4H).

Example 856

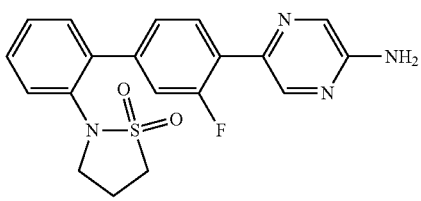

5-[2'-(1,1-Dioxidoisothiazolidin-2-yl)-3-fluorobiphenyl-4-yl]pyrazin-2-amine

Title compound was prepared using conditions analogous to those described in Example 1 using 5-(2-fluoro-4-(4,4,5,5-tetramethyl-1,3,2-dioxaborolan-2-yl)phenyl)-pyrazin-2-amine and 2-(2-bromophenyl)isothiazolidine 1,1-dioxide. MS (ESI): mass calcd. for $C_{19}H_7FN_4O_2S$, 384.11; m/z found, 385.2 [M+H]$^+$. $^1$H NMR (500 MHz, CDCl$_3$) δ 8.62-8.58 (m, 1H), 8.12 (d, J=1.5, 1H), 7.99 (m, 1H), 7.76-7.71 (m, 1H), 7.49-7.45 (m, 1H), 7.46-7.38 (m, 4H), 4.69 (s, 2H), 3.30-3.04 (m, 4H), 2.39-2.11 (m, 2H).

Example 857

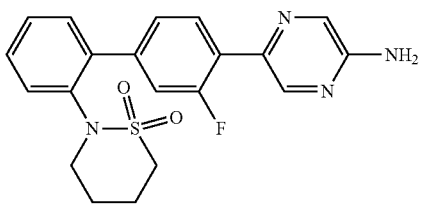

5-[2'-(1,1-Dioxido-1,2-thiazinan-2-yl)-3-fluorobiphenyl-4-yl]pyrazin-2-amine

Title compound was prepared using conditions analogous to those described in Example 1 using 5-(2-fluoro-4-(4,4,5,5-tetramethyl-1,3,2-dioxaborolan-2-yl)phenyl)pyrazin-2-amine and 2-(2-bromophenyl)-1,2-thiazinane 1,1-dioxide. MS (ESI): mass calcd. for $C_{20}H_{19}FN_4O_2S$, 398.12; m/z found, 399.2 [M+H]$^+$. $^1$H NMR (500 MHz, CDCl$_3$) δ 8.48-8.43 (m, 1H), 8.38-8.33 (m, 1H), 8.08-8.02 (m, 1H), 7.62 (m, 1H), 7.45-7.39 (m, 4H), 7.34 (dd, J=12.5, 1.7, 1H), 3.76-3.65 (m, 2H), 3.24-3.10 (m, 2H), 3.00-2.89 (m, 2H), 2.35-2.23 (m, 2H), 2.22-2.10 (m, 2H).

Example 858

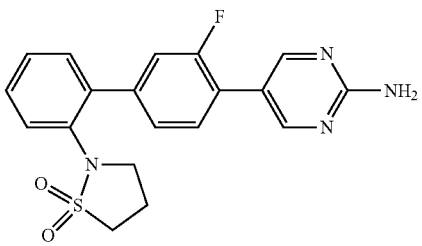

5-[2'-(1,1-Dioxidoisothiazolidin-2-yl)-3-fluorobiphenyl-4-yl]pyrimidin-2-amine

Title compound was prepared using methods analogous to those described in Example 384 using 5-(2-fluoro-4-(4,4,5,5-tetramethyl-1,3,2-dioxaborolan-2-yl)phenyl)pyrimidin-2-amine and 2-(2-bromophenyl)isothiazolidine 1,1-dioxide. MS (ESI): mass calcd. for $C_{19}H_{17}FN_4O_2S$, 384.11; m/z found, 385.0 [M+H]$^+$. $^1$H NMR (400 MHz, CDCl$_3$) δ 8.58 (d, J=1.4, 2H), 7.78-7.71 (m, 1H), 7.69-7.58 (m, 1H), 7.50-7.32 (m, 4H), 7.29-7.20 (m, 1H), 5.21 (s, 2H), 3.77 (t, J=6.8, 1H), 3.43-3.17 (m, 2H), 2.67-2.47 (m, 1H), 2.42-2.17 (m, 2H).

Example 859

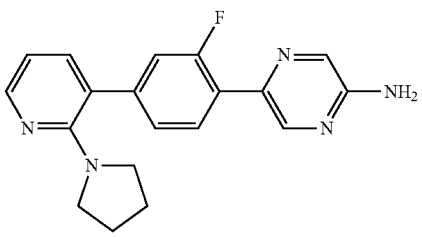

5-[2-Fluoro-4-(2-pyrrolidin-1-ylpyridin-3-yl)phenyl]pyrazin-2-amine

Title compound was prepared using methods analogous to those described in Example 377 using (2-(pyrrolidin-1-yl)pyridine-3-yl)boronic acid and 5-(4-bromo-2-fluorophenyl)pyrazin-2-amine in Step B. MS (ESI): mass calcd. for $C_{19}H_{18}FN_5$, 335.15; m/z found, 336.1 [M+H]$^+$. $^1$H NMR (400 MHz, CDCl$_3$) δ 8.61-8.56 (m, 1H), 8.22-8.17 (m, 1H), 8.12 (s, 1H), 7.97-7.88 (m, 1H), 7.45-7.38 (m, 1H), 7.29-7.23 (m, 1H), 7.21-7.14 (m, 1H), 6.75-6.67 (m, 1H), 4.67 (s, 2H), 3.28-3.10 (m, 4H), 1.87-1.73 (m, 4H).

Example 860

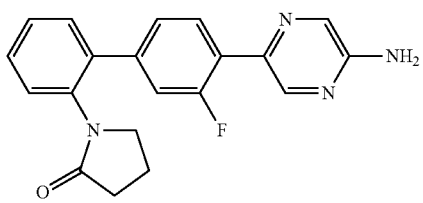

1-[4'-(5-Aminopyrazin-2-yl)-3'-fluorobiphenyl-2-yl]pyrrolidin-2-one

Title compound was prepared using analogous conditions to those described in Example 1 utilizing 5-(2-fluoro-4-(4,4,5,5-tetramethyl-1,3,2-dioxaborolan-2-yl)phenyl)pyrazin-2-amine and 1-(2-bromophenyl)pyrrolidin-2-one. MS (ESI): mass calcd. for $C_{20}H_{17}FN_4O$, 348.14; m/z found, 349.0 [M+H]$^+$. $^1$H NMR (400 MHz, DMSO-$d_6$) δ 8.39 (s, 1H), 8.03 (s, 1H), 7.91 (m, 1H), 7.54-7.14 (m, 6H), 6.72 (s, 2H), 3.44 (t, J=6.7, 2H), 2.26 (t, J=7.9, 2H), 1.97-1.87 (m, 2H).

Intermediate JF

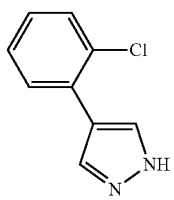

4-(2-Chlorophenyl)-1H-pyrazole

To a mixture of 2-chlorophenylboronic acid (16.6 g, 106 mmol), tert-butyl 4-bromo-1H-pyrazole-1-carboxylate (17.4 g, 71 mmol) and $K_2CO_3$ (14.7 g, 142 mmol) in a 1 L round-bottomed flask were added Pd(dppf)Cl$_2$-DCM (0.58 g, 0.71 mmol), 1,4-dioxane (200 mL) and $H_2O$ (50 mL). The mixture was sparged with $N_2$ for 15 min then stirred at 80° C. for 16 h. The reaction mixture was cooled to RT, filtered, and concentrated to dryness. The resulting residue was diluted with water (100 mL), and then extracted with EtOAc (3×100 mL). The combined organic extracts were washed with brine (100 mL), dried over $Na_2SO_4$, concentrated to dryness, and the resulting residue was purified by FCC to give the title compound (9.2 g, 73%). MS (ESI): mass calcd. for $C_9H_7ClN_2$, 178.03; m/z found 179.0 [M+H]$^+$. $^1$H NMR (400 MHz, CDCl$_3$) δ 8.80 (s, 1H), 8.59 (s, 1H), 7.52-7.46 (m, 1H), 7.45-7.39 (m, 1H), 7.36-7.25 (m, 2H).

Intermediate JG

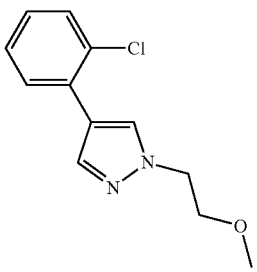

4-(2-Chlorophenyl)-1-(2-methoxyethyl)-1H-pyrazole

To a 50 mL round-bottomed flask, were added 4-(2-chlorophenyl)-1H-pyrazole (1.0 g, 5.6 mmol), 1-bromo-2-methoxyethane (1.17 g, 8.4 mmol), $Cs_2CO_3$ (3.64 g, 11.2 mmol) and DMF (10 mL). The mixture was stirred at RT for 16 h and diluted with water (100 mL). The resulting mixture was extracted with EtOAc (3×50 mL). The combined organic extracts were washed with brine (3×50 mL), dried over $Na_2SO_4$, concentrated to dryness and purified by FCC to afford the title compound (890 mg, 67%). MS (ESI): mass calcd. for $C_{12}H_{13}ClN_2O$, 236.07; m/z found 237.1 [M+H]$^+$. $^1$H NMR (400 MHz, CDCl$_3$) δ 7.93 (s, 1H), 7.87 (s, 1H), 7.47-7.43 (m, 2H), 7.29-7.27 (m, 1H), 7.21-7.17 (m, 1H), 4.39 (t, J=5.2 Hz, 2H), 3.81 (t, J=5.2 Hz, 2H), 3.36 (s, 3H).

Intermediate JH

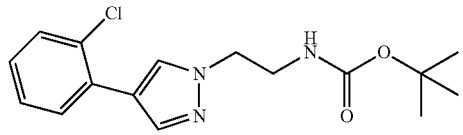

tert-butyl (2-(4-(2-Chlorophenyl)-1H-pyrazol-1-yl)ethyl)carbamate

The title compound was prepared using analogous conditions to those described for 4-(2-chlorophenyl)-1-(2-methoxyethyl)-1H-pyrazole using tert-butyl(2-bromoethyl)carbamate. MS (ESI): mass calcd. for $C_{16}H_{20}ClN_3O_2$, 321.12; m/z found 322.1 [M+H]$^+$. $^1$H NMR (300 MHz, CDCl$_3$) δ 7.82 (d, J=2.2 Hz, 2H), 7.46-7.42 (m, 2H), 7.32-7.13 (m, 2H), 4.95 (s, 1H), 4.29 (t, J=5.5 Hz, 2H), 3.61 (d, J=5.2 Hz, 2H), 1.44 (s, 9H).

Intermediate JI

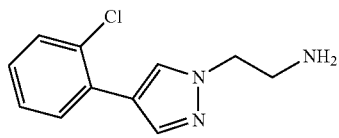

2-(4-(2-Chlorophenyl)-1H-pyrazol-1-yl)ethanamine hydrochloride

A mixture of tert-Butyl 2-(4-(2-chlorophenyl)-1H-pyrazol-1-yl)ethylcarbamate (1.0 g, 3.1 mmol) and HCl (20 mL, 30% solution in EtOH) was stirred at RT for 16 h. Precipitated solid was collected by filtration and washed with ethyl ether (10 mL) to give the title compound (670 mg, 84%). MS (ESI): mass calcd. for $C_{11}H_{12}ClN_3$, 221.07; m/z found 222.1 $[M+H]^+$. $^1$H NMR (400 MHz, DMSO-$d_6$) δ 8.31 (s, 1H), 8.22 (s, 3H), 7.97 (s, 1H), 7.62 (dd, J=7.7, 1.4 Hz, 1H), 7.52 (d, J=8.0 Hz, 1H), 7.39-7.35 (m, 1H), 7.32-7.24 (m, 1H), 4.46 (t, J=6.2 Hz, 2H), 3.35-3.23 (m, 2H).

Intermediate JJ

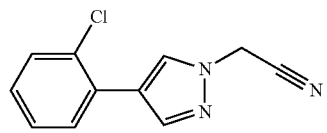

2-(4-(2-Chlorophenyl)-1H-pyrazol-1-yl)acetonitrile

A mixture of 4-(2-chlorophenyl)-1H-pyrazole (1.0 g, 5.6 mmol), 2-bromoacetonitrile (1.0 g, 8.4 mmol) and $Cs_2CO_3$ (3.64 g, 11.2 mmol) and DMF (10 mL) in a 50 mL round-bottomed flask was stirred at 50° C. After 16 h, additional 2-bromoacetonitrile (1 g, 8.4 mmol) was added. The resulting mixture was stirred at 100° C. for 8 h, cooled to RT and diluted with water (100 mL). The resulting mixture was extracted with EtOAc (3×50 mL). The combined organic extracts were washed with brine (3×50 mL), dried over $Na_2SO_4$, concentrated to dryness and the resulting residue was purified by FCC to give the title compound (600 mg, 49%). MS (ESI): mass calcd. for $C_{11}H_8ClN_3$, 217.04; m/z found 218.1 $[M+H]^+$. $^1$H NMR (400 MHz, CDCl$_3$) δ 7.96 (s, 1H), 7.88 (s, 1H), 7.47-7.44 (m, 2H), 7.32-7.28 (m, 1H), 7.26-7.21 (m, 1H), 5.14 (s, 2H).

Intermediate JK

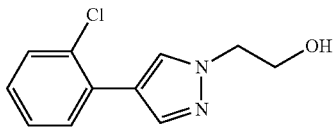

2-(4-(2-Chlorophenyl)-1H-pyrazol-1-yl)ethanol

To a 50 mL round-bottomed flask were added 4-(2-chlorophenyl)-1H-pyrazole (1.0 g, 5.6 mmol), 2-bromoethanol (1.05 g, 8.4 mmol), $Cs_2CO_3$ (3.64 g, 11.2 mmol) and DMF (10 mL). The reaction mixture was stirred at 80° C. for 16 h, then treated with additional of 2-bromoethanol (1.05 g, 8.4 mmol) was added. The resulting mixture was stirred at 100° C. for an additional 8 h, cooled to RT and diluted with water (100 mL). The resulting mixture was extracted with EtOAc (3×50 mL). The combined organic extracts were washed with brine (3×50 mL), dried over $Na_2SO_4$, concentrated to dryness and the resulting residue was purified by FCC to give the title compound (800 mg, 64%). MS (ESI): mass calcd. for $C_{11}H_{11}ClN_2O$, 222.06; m/z found 223.1 $[M+H]^+$. $^1$H NMR (400 MHz, CDCl$_3$) δ 7.91 (s, 1H), 7.87 (s, 1H), 7.49-7.45 (m, 2H), 7.32-7.29 (m, 1H), 7.24-7.20 (m, 1H), 4.46-4.23 (m, 2H), 4.19-3.99 (m, 2H), 3.31 (s, 1H).

Intermediate JL

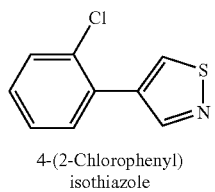 [SMILES: Clc1ccccc1-c1cnsc1]

4-(2-Chlorophenyl)isothiazole

Step A: (Z)—N-(2-(2-Chlorophenyl)-3-(dimethylamino)allylidene)-N-methyl methanaminium chloride DMF (27 mL, 0.4 mol) was added drop wise to POCl$_3$ (28 mL, 0.3 mol) in a 250 mL round-bottomed flask at 0° C. After the addition was complete, the resulting mixture was stirred at 0° C. for 20 min, followed by the addition of 2-(2-chlorophenyl)acetic acid (17 g, 0.1 mol). The reaction mixture was stirred at 85° C. for 2 h, cooled to RT and poured into ice water (400 mL). The resulting mixture was extracted with CH$_2$Cl$_2$ (3×150 mL). The combined organic extracts were washed with water (200 mL), dried over Na$_2$SO$_4$, concentrated to dryness and the resulting residue was purified by FCC to give the title compound (26.2 g, 96%). MS (ESI): mass calcd. for $C_{13}H_{18}ClN_2+$, 237.12; m/z found 237.0 $[M]^+$. $^1$H NMR (300 MHz, CDCl$_3$) δ 8.94 (s, 2H), 7.43-7.38 (m, 1H), 7.36-7.30 (m, 1H), 7.29-7.22 (m, 2H), 3.39 (s, 6H), 2.44 (s, 6H).

Step B: 2-(2-Chlorophenyl)malonaldehyde

To a solution consisting of (Z)—N-(2-(2-chlorophenyl)-3-(dimethylamino)allylidene)-N-methyl methanaminium chloride (8.0 g, 29 mmol) and EtOH (40 mL) in a 250 mL round-bottomed flask was added aqueous NaOH (25%, 40 mL). The resulting mixture was refluxed for 1 h and then cooled to RT. The EtOH was removed by evaporation under vacuum and the aqueous mixture was diluted with ice water (100 mL), acidified to pH=1 by adding HCl (1 N) and then extracted with EtOAc (3×100 mL). The combined organic extracts were washed with brine (100 mL), dried over Na$_2$SO$_4$ and concentrated to dryness to give the title compound (5.37 g, 100%). MS (ESI): mass calcd. for $C_9H_7ClO_2$, 182.01; m/z found 182.9 $[M+H]^+$. $^1$H NMR (300 MHz, DMSO-$d_6$) δ 12.05 (s, 1H), 8.58 (s, 2H), 7.47-7.43 (m, 1H), 7.36-7.25 (m, 2H), 7.18-7.10 (m, 1H).

Step C: (Z)-3-Chloro-2-(2-chlorophenyl)acrylaldehyde

To a 0° C. solution consisting of 2-(2-chlorophenyl)malonaldehyde (2.82 g, 15.5 mmol) and CH$_2$Cl$_2$ (20 mL) in a 50 mL round-bottomed flask was added SOCl$_2$ (10 mL, 138 mmol). The resulting mixture was stirred at 0° C. for 30 min, concentrated to dryness and purified by FCC to give the title compound (2.37 g, 76%). $^1$H NMR (300 MHz, CDCl$_3$) δ 9.66 (s, 1H), 7.51 (s, 1H), 7.51-7.46 (m, 1H), 7.40-7.31 (m, 2H), 7.20-7.13 (m, 1H).

Step D: 4-(2-Chlorophenyl)isothiazole

To a 25 mL round-bottomed flask containing a solution consisting of (Z)-3-chloro-2-(2-chlorophenyl)acryl aldehyde (2.37 g, 11.8 mmol) and DMF (8 mL), was added NH$_4$SCN (3.58 g, 47.2 mmol). The reaction mixture was stirred at 70° C. for 16 h before cooling to RT and diluting with brine (100 mL). The resulting mixture was extracted with ethyl ether (3×100 mL). The combined organic extracts were washed with brine (3×100 mL), dried over Na$_2$SO$_4$, concentrated to dryness and the resulting residue was purified by FCC to provide the title compound (980 mg, 43%). MS (ESI): mass calcd. for C$_9$H$_6$ClNS, 194.99; m/z found 195.9 [M+H]$^+$. $^1$H NMR (400 MHz, CDCl$_3$) δ 8.78 (s, 1H), 8.69 (s, 1H), 7.54-7.46 (m, 1H), 7.46-7.38 (m, 1H), 7.37-7.27 (m, 2H).

Example 861

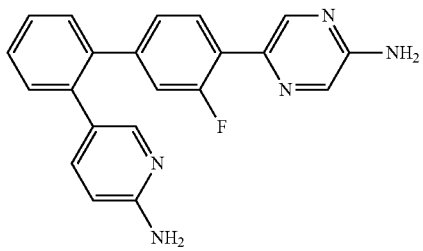

5-[2'-(6-Aminopyridin-3-yl)-3-fluorobiphenyl-4-yl]pyrazin-2-amine.

The title compound was prepared in a manner similar to that described in Example 838 using 5-bromopyridin-2-amine in Step A. MS (ESI): mass calcd. for C$_{21}$H$_{16}$FN$_5$, 357.14; m/z found, 358.2 [M+H]$^+$. $^1$H NMR (400 MHz, CD$_3$OD) δ 8.34 (s, 1H), 8.06 (s, 1H), 7.80-7.76 (m, 1H), 7.70 (d, J=2.0 Hz, 1H), 7.51-7.39 (m, 4H), 7.28 (dd, J=8.6, 2.2 Hz, 1H), 7.07 (d, J=8.1 Hz, 1H), 7.02 (d. J=12.5 Hz, 1H), 6.51 (d, J=8.6 Hz, 1H).

Example 862

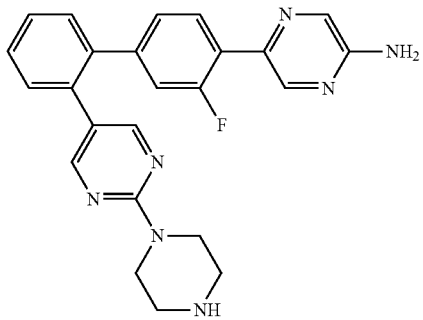

5-[3-Fluoro-2'-(2-piperazin-1-ylpyrimidin-5-yl)biphenyl-4-yl]pyrazin-2-amine.

The title compound was prepared in a manner similar to that described in Example 838 using 5-bromo-2-(piperazin-1-yl)pyrimidine in Step A. MS (ESI): mass calcd. for C$_{24}$H$_{22}$FN$_7$, 427.19; m/z found, 427.8 [M+H]$^+$. $^1$H NMR (400 MHz, DMSO-d$_6$) δ 8.34 (s, 1H), 8.22 (s, 2H), 8.06 (d, J=1.3 Hz, 1H), 7.82-7.76 (m, 1H), 7.54-7.47 (m, 4H), 7.17 (d, J=12.6 Hz, 1H), 7.07 (dd, J=8.0, 1.6 Hz, 1H), 4.00-3.83 (m, 4H), 3.21-3.09 (m, 4H).

Example 863

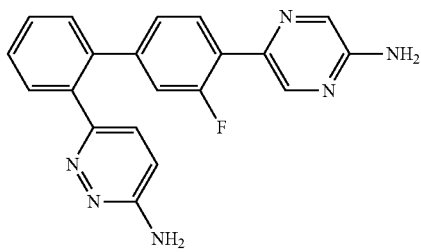

6-[4'-(5-Aminopyrazin-2-yl)-3'-fluorobiphenyl-2-yl]pyridazin-3-amine. #55495609#

The title compound was prepared in a manner similar to that described in Example 838 using 6-bromopyridazin-3-amine in Step A. MS (ESI): mass calcd. for C$_{20}$H$_{15}$FN$_6$, 358.13; m/z found, 358.8 [M+H]$^+$. $^1$H NMR (400 MHz, DMSO-d$_6$) δ 8.35 (s, 1H), 8.17 (s, 1H), 7.88-7.82 (m, 1H), 7.74-7.57 (m, 4H), 7.51 (d, J=9.6 Hz, 1H), 7.39 (dd, J=9.6, 1.9 Hz, 1H), 7.27 (d, J=12.4 Hz, 1H), 7.05 (d, J=8.0 Hz, 1H).

Example 864

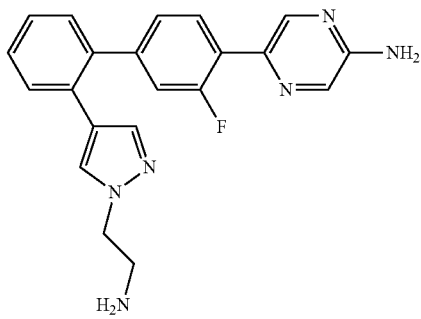

5-{2'[1-(2-Aminoethyl)-1H-pyrazol-4-yl]-3-fluorobiphenyl-4-yl}pyrazin-2-amine. #55510962#

The title compound was prepared using analogous conditions to those described in Example 287 using 5-(2-fluoro-4-(4,4,5,5-tetramethyl-1,3,2-dioxaborolan-2-yl)phenyl)pyrazin-2-amine and 2-(4-(2-chlorophenyl)-1H-pyrazol-1-yl)ethanamine hydrochloride. MS (ESI): mass calcd. for C$_{21}$H$_{19}$FN$_6$, 374.17; m/z found, 375.2 [M+H]$^+$. $^1$H NMR (400 MHz, CD$_3$OD) δ 8.73 (d, J=1.3 Hz, 1H), 8.23 (d, J=1.3 Hz, 1H), 8.08-8.04 (m, 1H), 7.60 (s, 1H), 7.56-7.51 (m, 1H), 7.47-7.34 (m, 3H), 7.26 (s, 1H), 7.23 (dd, J=8.1, 1.6 Hz, 1H), 7.17 (dd, J=12.7, 1.6 Hz, 1H), 4.41 (t. J=5.8 Hz, 2H), 3.38 (t, J=5.8 Hz, 2H).

Example 865

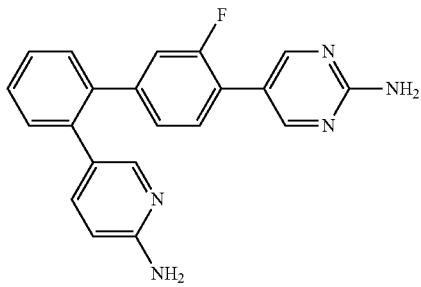

5-[2'-(6-Aminopyridin-3-yl)-3-fluorobiphenyl-4-yl]pyrimidin-2-amine.

The title compound was prepared in a manner similar to that described in Example 838 using 5-bromopyridin-2-amine in Step A and 5-(2-fluoro-4-(4,4,5,5-tetramethyl-1,3,2-dioxaborolan-2-yl)phenyl)pyrimidin-2-amine in Step B. MS (ESI): mass calcd. for $C_{21}H_{16}FN_5$, 357.14; m/z found, 358.1 [M+H]$^+$. $^1$H NMR (400 MHz, DMSO-d$_6$) δ 8.46 (d, J=1.3 Hz, 2H), 7.71 (d, J=2.0 Hz, 1H), 7.53-7.36 (m, 5H), 7.14 (dd, J=8.5, 2.5 Hz, 1H), 7.09 (dd, J=12.1, 1.5 Hz, 1H), 7.03 (dd, J=8.0, 1.7 Hz, 1H), 6.89 (s, 2H), 6.34 (d, J=8.6 Hz, 1H), 5.94 (s, 2H).

Example 866

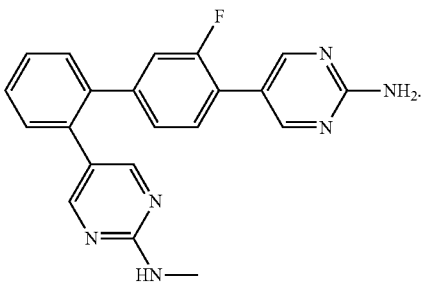

5-[4'-(2-Aminopyrimidin-5-yl)-3'-fluorobiphenyl-2-yl]-N-methylpyrimidin-2-amine

The title compound was prepared in a manner similar to that described in Example 838 using 5-bromo-N-methylpyrimidin-2-amine in Step A and 5-(2-fluoro-4-(4,4,5,5-tetramethyl-1,3,2-dioxaborolan-2-yl)phenyl)pyrimidin-2-amine in Step B. MS (ESI): mass calcd. for $C_{21}H_{17}FN_6$, 372.15; m/z found, 373.1 [M+H]$^+$. $^1$H NMR (400 MHz, DMSO-d$_6$) δ 8.47 (d, J=1.1 Hz, 2H), 8.06 (s, 2H), 7.57-7.40 (m, 5H), 7.19-7.13 (m, 2H), 7.06 (dd, J=8.0, 1.5 Hz, 1H), 6.90 (s, 2H), 2.77 (d, J=4.8 Hz, 3H).

Example 867

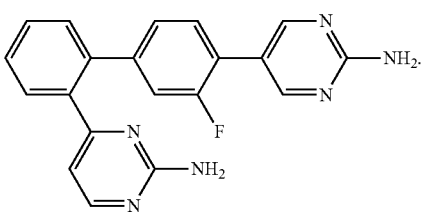

4-[4'-(2-Aminopyrimidin-5-yl)-3'-fluorobiphenyl-2-yl]pyrimidin-2-amine

The title compound was prepared in a manner similar to that described in Example 838 using 4-bromopyrimidin-2-amine in Step A and 5-(2-fluoro-4-(4,4,5,5-tetramethyl-1,3,2-dioxaborolan-2-yl)phenyl)pyrimidin-2-amine in Step B. MS (ESI): mass calcd. for $C_{20}H_{15}FN_6$, 358.13; m/z found, 359.0 [M+H]$^+$. $^1$H NMR (400 MHz, DMSO-d) δ 8.46 (d, J=1.1 Hz, 2H), 8.04 (d, J=5.0 Hz, 1H), 7.63-7.45 (m, 5H), 7.16 (dd, J=12.0, 1.4 Hz, 1H), 7.04 (dd, J=8.0, 1.6 Hz, 1H), 6.90 (s, 2H), 6.66 (s, 2H), 6.19 (d, J=5.0 Hz, 1H).

Example 868

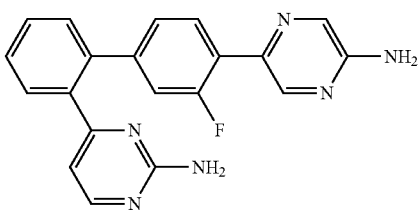

4-[4'-(5-Aminopyrazin-2-yl)-3'-fluorobiphenyl-2-yl]pyrimidin-2-amine.

The title compound was prepared in a manner similar to that described in Example 838 using 4-bromopyrimidin-2-amine in Step A. MS (ESI): mass calcd. for $C_{20}H_{15}FN$, 358.13; m/z found, 359.1 [M+H]$^+$. $^1$H NMR (400 MHz, DMSO-d$_6$) δ 8.35 (s, 1H), 8.03 (d, J=5.0 Hz, 1H), 8.00 (s, 1H), 7.81-7.77 (m, 1H), 7.63-7.46 (m, 4H), 7.13 (d, J=12.5 Hz, 1H), 7.05 (d, J=8.7 Hz, 1H), 6.71 (s, 2H), 6.65 (s, 2H), 6.17 (d, J=5.1 Hz, 1H).

Example 869

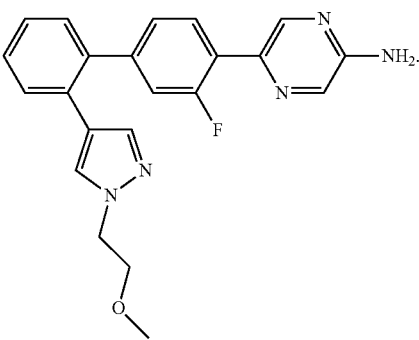

5-{3-Fluoro-2'-[1-(2-methoxyethyl)-1H-pyrazol-4-yl]biphenyl-4-yl}pyrazin-2-amine The title compound was prepared using analogous conditions to those described in Example 287 using 5-(2-fluoro-4-(4,4,5,5-tetramethyl-1,3,2-dioxaborolan-2-yl)phenyl)pyrazin-2-amine and 4-(2-chlorophenyl)-1-(2-methoxyethyl)-1H-pyrazole. MS (ESI): mass calcd. for $C_{22}H_{20}FN_5O$, 389.17; m/z found, 390.1 [M+H]$^+$. $^1$H NMR (400 MHz, CD$_3$OD) δ 8.37 (s, 1H), 8.32 (s, 1H), 7.98-7.94 (m, 1H), 7.53 (d, J=7.4 Hz, 1H), 7.47-7.34 (m, 4H), 7.25 (s, 1H), 7.19 (d, J=8.1 Hz, 1H), 7.10 (d, J=12.5 Hz, 1H), 4.21 (t, J=4.9 Hz, 2H), 3.65 (t, J=4.8 Hz, 2H), 3.25 (s, 3H).

Example 870

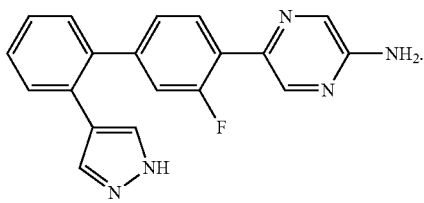

5-[3-Fluoro-2'-(1H-pyrazol-4-yl]biphenyl-4-yl]pyrazin-2-amine

The title compound was prepared in a manner similar to that described in Example 838 using tert-butyl 4-bromo-1H-pyrazole-1-carboxylate in Step A. MS (ESI): mass calcd. for $C_{19}H_{14}FN_5$, 331.12; m/z found, 332.1 [M+H]$^+$. $^1$H NMR (400 MHz, DMSO-d$_6$) b 12.77 (s, 1H), 8.37 (s, 1H), 8.02 (s, 1H), 7.86-7.82 (m, 1H), 7.54 (d, J=7.6 Hz, 1H), 7.47 (s, 1H), 7.44-7.31 (m, 3H), 7.17 (s, 1H), 7.12 (d, J=5.4 Hz, 1H), 7.10 (s, 1H), 6.71 (s, 2H).

Example 871

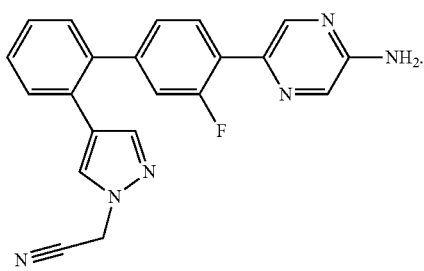

{4[4'-(5-Aminopyrazin-2-yl)-3'-fluorobiphenyl-2-yl]-1H-pyrazol-1-yl}acetonitrile The title compound was prepared using analogous conditions to those described in Example 287 using 5-(2-fluoro-4-(4,4,5,5-tetramethyl-1,3,2-dioxaborolan-2-yl)phenyl)pyrazin-2-amine and 2-(4-(2-chlorophenyl)-1H-pyrazol-1-yl)acetonitrile. MS (ESI): mass calcd. for $C_{21}H_{15}FN_6$, 370.13; m/z found, 370.8 [M+H]$^+$. $^1$H NMR (400 MHz, DMSO-d$_6$) δ 8.37 (s, 1H), 8.02 (d, J=1.3 Hz, 1H), 7.87-7.82 (m, 1H), 7.62 (s, 1H), 7.52 (d, J=7.1 Hz, 1H), 7.47-7.33 (m, 3H), 7.30 (s, 1H), 7.15-7.09 (m, 2H), 6.72 (s, 2H), 5.42 (s, 2H).

Example 872

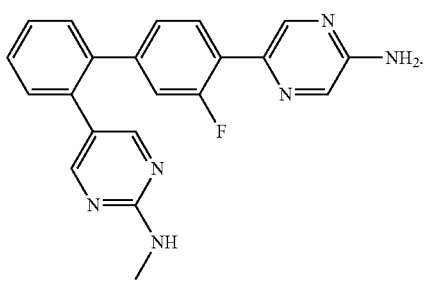

5-[4'-(5-Aminopyrazin-2-yl)-3'-fluorobiphenyl-2-yl]-N-methylpyrimidin-2-amine

The title compound was prepared in a manner similar to that described in Example 838 using 5-bromo-N-methylpyrimidin-2-amine in Step A. MS (ESI): mass calcd. for $C_{21}H_{17}FN_6$, 372.15; m/z found, 373.1 [M+H]$^+$. $^1$H NMR (400 MHz, CD$_3$OD) δ 8.36 (s, 1H), 8.09-8.06 (m, 3H), 7.85-7.81 (m, 1H), 7.55-7.44 (m, 4H), 7.13-7.05 (m, 2H), 2.90 (s, 3H).

Example 873

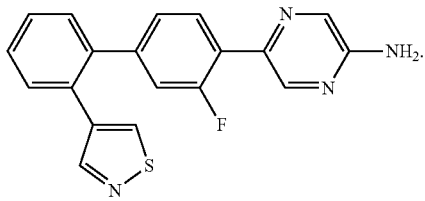

5-(3-Fluoro-2'-isothiazol-4-ylbiphenyl-4-yl)pyrazin-2-amine

The title compound was prepared using analogous conditions to those described in Example 287 using 5-(2-fluoro-4-(4,4,5,5-tetramethyl-1,3,2-dioxaborolan-2-yl)phenyl)pyrazin-2-amine and 4-(2-chlorophenyl)isothiazole. MS (ESI): mass calcd. for $C_{19}H_{13}FN_4S$, 348.08; m/z found, 349.0 [M+H]$^+$. $^1$H NMR (400 MHz, CDCl$_3$) δ 8.53 (s, 1H), 8.30 (s, 1H), 8.23 (s, 1H), 8.10 (d, J=1.4 Hz, 1H), 7.87-7.82 (m, 1H), 7.53-7.39 (m, 4H), 7.03 (dd, J=8.0, 1.7 Hz, 1H), 6.98 (dd, J=12.1, 1.6 Hz, 1H), 4.76 (s, 2H).

Example 874

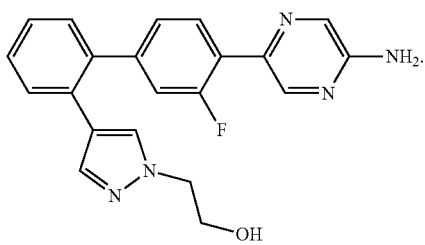

2-{4-[4'-(5-Aminopyrazin-2-yl)-3'-fluorobiphenyl-2-yl]-1H-pyrazol-1-yl}ethanol

The title compound was prepared using analogous conditions to those described in Example 287 using 5-(2-fluoro-4-(4,4,5,5-tetramethyl-1,3,2-dioxaborolan-2-yl)phenyl)pyrazin-2-amine and 2-(4-(2-chlorophenyl)-1H-pyrazol-1-yl)ethanol. MS (ESI): mass calcd. for $C_{21}H_{18}FN_5O$, 375.15; m/z found, 376.1 [M+H]$^+$. $^1$H NMR (400 MHz, DMSO-d$_6$) δ 8.40-8.35 (m, 1H), 8.02 (d, J=1.5 Hz, 1H), 7.86-7.82 (m, 1H), 7.53-7.50 (m, 2H), 7.45-7.38 (m, 1H), 7.34-7.33 (m, 2H), 7.15-7.11 (m, 2H), 7.08 (d, J=0.6 Hz, 1H), 6.72 (s, 2H), 4.84 (t, J=5.3 Hz, 1H), 4.04 (t, J=5.7 Hz, 2H), 3.66-3.62 (m, 2H).

Example 875

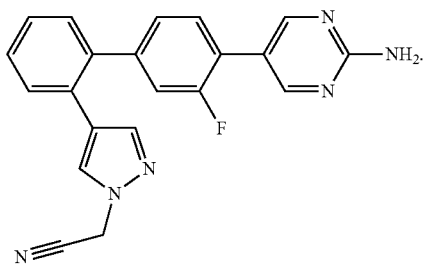

{4-[4'-(2-Aminopyrimidin-5-yl)-3'-fluorobiphenyl-2-yl]-1H-pyrazol-1-yl}acetonitrile The title compound was prepared using analogous conditions to those described in Example 287 using 2-(4-(2-chlorophenyl)-1H-pyrazol-1-yl)acetonitrile. MS (ESI): mass calcd. for $C_{21}H_{15}FN_6$, 370.13; m/z found, 371.1 [M+H]$^+$. $^1$H NMR (400 MHz, DMSO-d$_6$) δ 8.49 (d, J=1.0 Hz, 2H), 7.61-7.50 (m, 3H), 7.48-7.31 (m, 4H), 7.16 (dd, J=11.8, 1.3 Hz, 1H), 7.09 (dd, J=7.9, 1.5 Hz, 1H), 6.92 (s, 2H), 5.43 (s, 2H).

Example 876

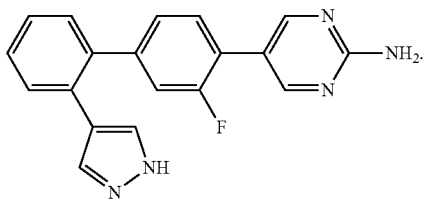

5-[3-Fluoro-2'-(1H-pyrazol-4-yl)biphenyl-4-yl]pyrimidin-2-amine

The title compound was prepared in a manner similar to that described in Example 838 using tert-butyl 4-bromo-1H-pyrazole-1-carboxylate in Step A and 5-(2-fluoro-4-(4,4,5,5-tetramethyl-1,3,2-dioxaborolan-2-yl)phenyl)pyrimidin-2-amine in Step B. MS (ESI): mass calcd. for $C_{19}H_{14}FN_5$, 331.12; m/z found, 332.1 [M+H]$^+$. $^1$H NMR (400 MHz, DMSO-d$_6$) δ 12.79 (s, 1H), 8.49 (s, 2H), 7.60-7.47 (m, 3H), 7.45-7.39 (m, 1H), 7.39-7.30 (m, 2H), 7.26-7.07 (m, 3H), 6.91 (s, 2H).

Intermediate JM

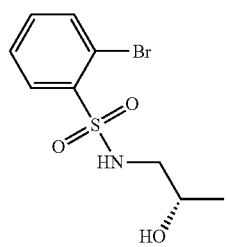

(S)-2-Bromo-N-(2-hydroxypropyl)benzenesulfonamide

The title compound was prepared using analogous conditions to those described in Intermediate AU using (S)-1-aminopropan-2-ol. MS (ESI): mass calcd. for $C_9H_{12}BrNO_3S$, 292.97; m/z found, 294.0 [M+H]$^+$. $^1$H NMR (400 MHz, CDCl$_3$) δ 8.14 (dd, J=7.7, 1.8 Hz, 1H), 7.75 (dd, J=7.7, 1.4 Hz, 1H), 7.53-7.46 (m, 1H), 7.46-7.40 (m, 1H), 5.62 (s, 1H), 3.98-3.78 (m, 1H), 3.02 (d, J=12.9 Hz, 1H), 2.74 (dd, J=13.0, 8.1 Hz, 1H), 2.01 (d, J=4.1 Hz, 1H), 1.16 (d, J=6.3 Hz, 3H).

Intermediate JN

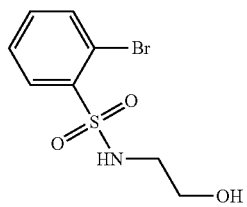

2-Bromo-N-(2-hydroxyethyl)benzenesulfonamide

The title compound was prepared using analogous conditions to those described in Intermediate AU using 2-aminoethanol. MS (ESI): mass calcd. for $C_8H_{10}BrNO_3S$, 278.96; m/z found, 279.9 [M+H]$^+$. $^1$H NMR (500 MHz, CDCl$_3$) δ 8.17-8.11 (dd, J=7.8, 1.8 Hz, 1H), 7.79-7.72 (dd, J=7.8, 1.3 Hz, 1H), 7.52-7.46 (m, 1H), 7.46-7.40 (m, 1H), 5.79-5.66 (t, J=5.7 Hz, 1H), 3.73-3.65 (dd, J=5.6, 4.6 Hz, 2H), 3.13-3.03 (ddd, J=6.0, 5.1, 4.4 Hz, 2H), 2.22-2.10 (s, 1H).

Intermediate JO

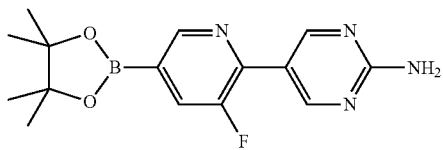

5-(3-Fluoro-5-(4,4,5,5-tetramethyl-1,3,2-dioxaborolan-2-yl)pyridin-2-yl)pyrimidin-2-amine

Step A:
5-(5-Chloro-3-fluoropyridin-2-yl)pyrimidin-2-amine

A solution consisting of (2-aminopyrimidin-5-yl)boronic acid (3.4 g, 25 mmol), 2-bromo-5-chloro-3-fluoropyridine (5.4 g, 25 mmol), palladium(II)acetate/1,1'-bis(di-t-butylphosphino)ferrocene/potassium phosphate admixture (1.1 g, 1.0 mmol), Na$_2$CO$_3$ (122 mL, 245 mmol, 2 M) and THF (122 mL) was stirred at RT. After 1 h, the THF was removed in vacuo and the residue was diluted with CH$_2$Cl$_2$ (200 mL). The organic extracts were isolated and the aqueous mixture was further extracted with CH$_2$Cl$_2$ (2×200 mL). The combined organic extracts were, concentrated to dryness and triturated with EtOAc to afford the title compound (5.5 g, 44%). MS (ESI): mass calcd. for $C_9H_6ClFN_4$, 224.03; m/z found, 225.0 [M+H]$^+$. $^1$H NMR (500 MHz, DMSO-d$_6$) δ 8.76 (d, J=1.4 Hz, 2H), 8.57 (m, 1H), 8.18 (dd, J=11.1, 2.0 Hz, 1H), 7.18 (s, 2H).

Step B: 5-(3-Fluoro-5-(4,4,5,5-tetramethyl-1,3,2-dioxaborolan-2-yl)pyridin-2-yl)pyrimidin-2-amine To a 200 mL round-bottomed flask were added a stirbar, 5-(5-chloro-3-fluoropyridin-2-yl)pyrimidin-2-amine (2.4 g, 11 mmol), 4,4,4',4',5,5,5',5'-octamethyl-2,2'-bi(1,3,2-dioxaborolane) (3.4 g, 13 mmol), chloro(2-dicyclohexylphosphino-2',4',6'-tri-i-propyl-1,1'-biphenyl)(2'-amino-1,1'-biphenyl-2-yl)palladium(II) (161 mg, 0.214 mmol), KOAc (3.1 g, 32 mmol) and 1,4-dioxane (100 mL). The flask was fitted with a septum, sparged with $N_2$ for 10 min and heated at 80° C. for 5 h. The resulting reaction mixture was cooled to RT and then filtered through a Büchner funnel. The filter paper was washed with $CH_2Cl_2$ (50 mL) and the filtrate was concentrated directly onto silica and subjected to FCC to give the title compound (2.4 g, 71%). $C_{15}H_{18}BFN_4O_2$, 316.15; m/z found, 235.0 [M-pinacol]$^+$. $^1$H NMR (600 MHz, DMSO-d$_6$) δ 8.83 (d, J=1.2 Hz, 2H), 8.64-8.59 (m, 1H), 7.80 (dd, J=11.7, 1.3 Hz, 1H), 7.19 (s, 2H), 1.32 (s, 12H).

Example 877

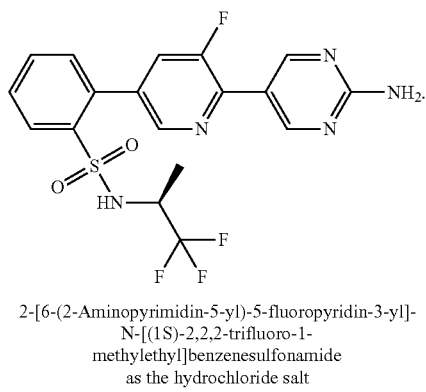 [SMILES: C[C@H](NS(=O)(=O)c1ccccc1-c1cnc(-c2cnc(N)nc2)c(F)c1)C(F)(F)F]

2-[6-(2-Aminopyrimidin-5-yl)-5-fluoropyridin-3-yl]-N-[(1S)-2,2,2-trifluoro-1-methylethyl]benzenesulfonamide as the hydrochloride salt A mixture of 5-(3-fluoro-5-(4,4,5,5-tetramethyl-1,3,2-dioxaborolan-2-yl)pyridin-2-yl)pyrimidin-2-amine (420 mg, 1.32 mmol), (S)-2-bromo-N-(1,1,1-trifluoropropan-2-yl)benzenesulfonamide (480 mg, 1.46 mmol), chloro(2-dicyclohexylphosphino-2',4',6'-triisopropyl-1,1'-biphenyl)[2-(2'-amino-1,1'-biphenyl)]palladium(II) (100 mg, 10%), THF (4 mL) and aqueous $K_3PO_4$ (0.5 M, 4 mL) in a 25 mL sealed tube was sparged with $N_2$ for 10 minutes and then stirred at 70° C. for 16 h. The resulting reaction mixture was cooled to RT and concentrated to dryness. The resulting residue was dissolved in $CH_2Cl_2$ (35 mL) and washed with water (3×10 mL). The organic phase was isolated and dried over $Na_2SO_4$, concentrated to dryness and the resulting residue was purified by prep-HPLC to give title compound (35 mg hydrochloride, 6%). MS (ESI): mass calcd. for $C_{18}H_{15}F_4N_5O_2S$, 441.09; m/z found 442.0 [M+H]$^+$. $^1$H NMR (400 MHz, CD$_3$OD) δ 9.24 (s, 2H), 8.50 (s, 1H), 8.13 (d, J=7.7 Hz, 1H), 7.81-7.66 (m, 3H), 7.44 (d, J=6.7 Hz, 1H), 3.94-3.85 (m, 1H), 1.25 (d, J=6.9 Hz, 3H).

Example 878

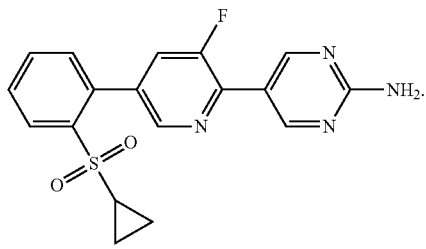

5-{5-[2-(Cyclopropylsulfonyl)phenyl]-3-fluoropyridin-2-yl}pyrimidin-2-amine

The title compound was prepared using analogous conditions to those described in Example 877 using 1-bromo-2-(cyclopropylsulfonyl)benzene. MS (ESI): mass calcd. for $C_{18}H_{15}FN_4O_2S$, 370.09; m/z found, 371.1 [M+H]$^+$. $^1$H NMR (400 MHz, DMSO-d$_6$) δ 10.55 (s, 2H), 9.03 (s, 2H), 8.54 (s, 1H), 8.11 (d, J=7.8 Hz, 1H), 7.98 (d, J=12.0 Hz, 1H), 7.86-7.83 (m, 1H), 7.79-7.75 (m, 1H), 7.55 (d, J=7.4 Hz, 1H), 2.63-2.55 (m, 1H), 1.04-0.95 (m, 2H), 0.95-0.88 (m, 2H).

Example 879

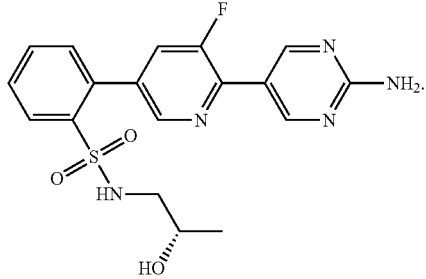

2-[6-(2-Aminopyrimidin-5-yl)-5-fluoropyridin-3-yl]-N-[(2S)-2-hydroxypropyl]benzenesulfonamide The title compound was prepared using analogous conditions to those described in Example 877 using (S)-2-bromo-N-(2-hydroxypropyl)benzenesulfonamide. MS (ESI): mass calcd. for $C_{18}H_{18}FN_5O_3S$, 403.11; m/z found, 404.0 [M+H]$^+$. $^1$H NMR (300 MHz, CD$_3$OD) δ 9.24 (s, 2H), 8.61-8.53 (m, 1H), 8.09 (dd, J=7.7, 1.5 Hz, 1H), 7.90 (dd, J=11.8, 1.7 Hz, 1H), 7.80-7.59 (m, 2H), 7.47 (dd, J=7.3, 1.6 Hz, 1H), 3.76-3.61 (m, 1H), 2.87-2.69 (m, 2H), 1.08 (d, J=6.3 Hz, 3H).

Example 880

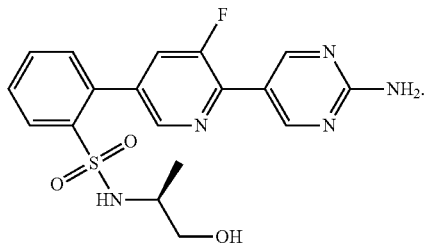

2-[6-(2-Aminopyrimidin-5-yl)-5-fluoropyridin-3-yl]-N-[(1S)-2-hydroxy-1-methylethyl]benzenesulfonamide The title compound was prepared using analogous conditions to those described in Example 877 using (S)-2-bromo-N-(1-hydroxypropan-2-yl)benzenesulfonamide. MS (ESI): mass calcd. for $C_{18}H_{18}FN_5O_3S$, 403.11; m/z found, 404.1 [M+H]$^+$. $^1$H NMR (300 MHz, CD$_3$OD): δ 9.24 (s, 2H), 8.57-8.56 (m, 1H), 8.17 (dd, J=7.7, 1.3 Hz, 1H), 7.90 (dd, J=12.0, 1.6 Hz, 1H), 7.78-7.61 (m, 2H), 7.45 (dd, J=7.3, 1.3 Hz, 1H), 3.42-3.36 (m, 1H), 3.28-3.18 (m, 2H), 1.05 (d, J=6.5 Hz, 3H).

Example 881

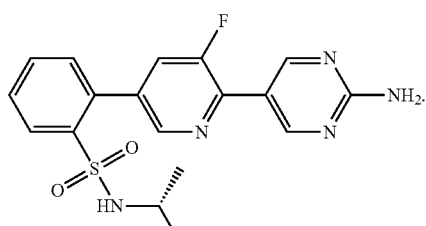

2-[6-(2-Aminopyrimidin-5-yl)-5-fluoropyridin-3-yl]-N-[(1R)-2-hydroxy-1-methylethyl]benzenesulfonamide The title compound was prepared using analogous conditions to those described in Example 877 using (R)-2-bromo-N-(1-hydroxypropan-2-yl)benzenesulfonamide. MS (ESI): mass calcd. for $C_{18}H_{18}FN_5O_3S$, 403.11; m/z found, 404.1 [M+H]$^+$. $^1$H NMR (300 MHz, CD$_3$OD) δ 9.24 (s, 2H), 8.57-8.56 (m, 1H), 8.17 (dd, J=7.7, 1.3 Hz, 1H), 7.90 (dd, J=12.0, 1.6 Hz, 1H), 7.78-7.61 (m, 2H), 7.45 (dd, J=7.3, 1.3 Hz, 1H), 3.42-3.36 (m, 1H), 3.28-3.18 (m, 2H), 1.05 (d, J=6.5 Hz, 3H).

Example 882

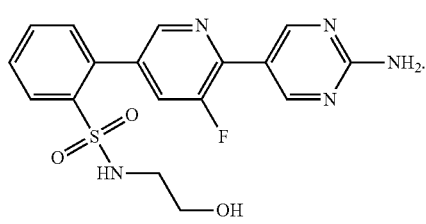

2-[6-(2-Aminopyrimidin-5-yl)-5-fluoropyridin-3-yl]-N-(2-hydroxyethyl)benzenesulfonamide The title compound was prepared using analogous conditions to those described in Example 877 using 2-bromo-N-(2-hydroxyethyl)benzenesulfonamide. MS (ESI): mass calcd. for $C_{17}H_{16}FN_5O_3S$, 389.10; m/z found, 390.1 [M+H]$^+$. $^1$H NMR (300 MHz, CD$_3$OD) b 9.23 (s, 2H), 8.55 (s, 1H), 8.10 (d, J=7.6 Hz, 1H), 7.87 (d, J=11.9 Hz, 1H), 7.75-7.64 (m, 2H), 7.45 (d, J=7.2 Hz, 1H), 3.49 (t, J=5.8 Hz, 2H), 2.95 (t, J=5.6 Hz, 2H).

Example 883

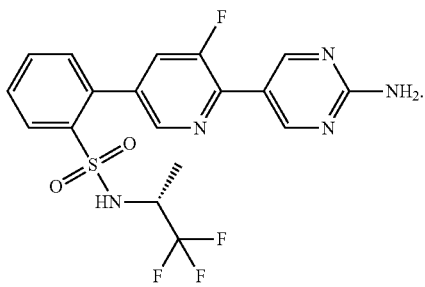

2-[6-(2-Aminopyrimidin-5-yl)-5-fluoropyridin-3-yl]-N-[(1R)-2,2,2-trifluoro-1-methylethyl]benzenesulfonamide The title compound was prepared using analogous conditions to those described in Example 877 using (R)-2-bromo-N-(1,1,1-trifluoropropan-2-yl)benzenesulfonamide. MS (ESI): mass calcd. for $C_{18}H_{15}F_4N_5O_2S$, 441.09; m/z found, 442.1 [M+H]$^+$. $^1$H NMR (400 MHz, CD$_3$OD) δ 9.08 (s, 2H), 8.47 (s, 1H), 8.14 (dd, J=7.8, 1.3 Hz, 1H), 7.77-7.63 (m, 3H), 7.44 (dd, J=7.5, 1.3 Hz, 1H), 3.94-3.85 (m, 1H), 1.25 (d, J=7.0 Hz, 3H).

Intermediate JP

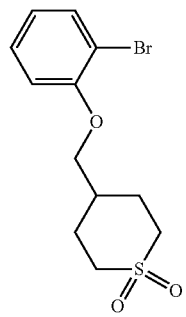

4-((2-Bromophenoxy)methyl)tetrahydro-2H-thiopyran 1,1-dioxide

Step A:
4-((2-Bromophenoxy)methyl)tetrahydro-2H-thiopyran

To a solution consisting of 1-bromo-2-fluorobenzene (1.3 g, 7.4 mmol) and DMF (10 mL) were added (tetrahydro-2H-thiopyran-4-yl)methanol (1.0 g, 7.4 mmol), NaH (0.6 g, 14.9 mmol) at 0° C. Then the mixture was stirred at 60° C. under N$_2$ overnight. After which time the reaction mixture was cooled to RT, poured into ice-water, and extracted with ethyl acetate (3×20 mL). The combined organic extracts were washed with brine (20 mL), dried over MgSO$_4$, filtered and concentrated to dryness to give the title compound, which was used in next step without further purification.

Step B:
4-((2-Bromophenoxy)methyl)tetrahydro-2H-thiopyran 1,1-dioxide

To a 0° C. solution consisting of 4-((2-bromophenoxy)methyl)tetrahydro-2H-thiopyran and CH$_2$Cl$_2$ (15 mL) was slowly added meta-chloroperoxybenzoic acid (3.4 g, 14.9 mmol). The resulting reaction mixture was stirred at RT overnight, then diluted with Na$_2$S$_2$O$_3$ (20 mL, 10% aq.) and extracted with CH$_2$Cl$_2$ (3×20 mL). The combined organic extracts were washed with brine (20 mL), dried over MgSO$_4$, filtered and concentrated to dryness. The crude product was recrystallized from ethyl acetate to afford the title compound (1.6 g, 67%). $^1$H NMR (400 MHz, CDCl$_3$) δ 7.54 (dd, J=8.2, 1.6, 1H), 7.28-7.24 (m, 1H), 6.86 (dd, J=7.5, 6.6, 2H), 3.92 (d, J=5.8, 2H), 3.23-3.12 (m, 2H), 3.05 (dd, J=17.5, 8.9, 2H), 2.37 (d, J=11.2, 2H), 2.09 (m, 3H).

Intermediate JQ

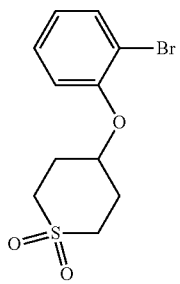

4-(2-Bromophenoxy)tetrahydro-2H-thiopyran 1,1-dioxide

Step A:
4-(2-bromophenoxy)tetrahydro-2H-thiopyran

To a 0° C. solution consisting of 1-bromo-2-fluorobenzene (1.3 g, 7.5 mmol) in DMF (10 mL) was added tetrahydro-2H-thiopyran-4-ol (740 mg, 6.3 mmol) and NaH (750 mg, 18.8 mmol). The mixture was stirred at 60° C. under a N$_2$ atmosphere. After 12 h, the reaction mixture was cooled to RT, poured into ice-water and extracted with ethyl acetate (3×30 mL). The combined organic extracts were washed with brine (30 mL), dried over MgSO$_4$, filtered and concentrated to dryness to give the title compound, which was used without further purification.

Step B:
4-(2-Bromophenoxy)tetrahydro-2H-thiopyran 1,1-dioxide

To a 0° C. solution consisting of 4-(2-bromophenoxy)tetrahydro-2H-thiopyran and CH$_2$Cl$_2$ (20 mL), was slowly added meta-chloroperoxybenzoic acid (3.7 g, 16.5 mmol). The reaction mixture was stirred at RT overnight. After which time the mixture was diluted with Na$_2$S$_2$O$_3$ (20 mL, 10% aq.), basified with NaOH (2 N) to pH=8 and extracted with CH$_2$Cl$_2$ (3×15 mL). The combined organic extracts were concentrated to dryness and the resulting residue was purified by FCC to give the title compound (650 mg, 38%). $^1$H NMR (400 MHz, CDCl$_3$) 57.58-7.56 (m, 1H), 7.31-7.25 (m, 1H), 6.98-6.85 (m, 2H), 4.72 (s, 1H), 3.62-3.46 (m, 2H), 2.97-2.87 (m, 2H), 2.52-2.43 (m, 2H), 2.41-2.34 (m, 2H).

Intermediate JR

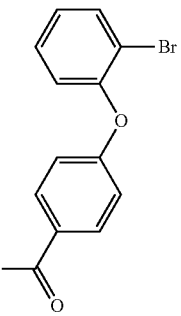

4-(2-Bromophenoxy)benzoic acid

Step A: Methyl 4-(2-bromophenoxy)benzoate

A mixture of methyl 4-fluorobenzoate (3.0 g, 19.5 mmol), 2-bromophenol (6.7 g, 39 mmol), Cs$_2$CO$_3$ (12.7 g, 39 mmol) and DMSO (30 mL) was stirred at RT for 36 h, and then diluted with water (30 mL). The aqueous mixture was extracted with EtOAc (3×50 mL). The combined organic extracts were dried over Na$_2$SO$_4$, filtered and concentrated to dryness. The crude residue was purified by FCC to give the title compound (3.6 g, 60%).

Step B: 4-(2-Bromophenoxy)benzoic acid

To a solution consisting of methyl 4-(2-bromophenoxy)benzoate (3.5 g, 11.4 mmol), MeOH (30 mL) and water (10 mL) was added NaOH (910 mg, 22.8 mmol). The reaction mixture was stirred for 10 h at RT. The MeOH was removed by evaporation and the resulting mixture was acidified with HCl (1 N) to pH=7. The resulting solid was isolated by filtration, washed with water, and then dried in a vacuum to provide the title compound (2.9 g, 87%). MS (ESI): mass calcd. for C$_{13}$H$_9$BrO$_3$, 291.97; m/z found, 293.1 [M+H]$^+$. $^1$H NMR (400 MHz, DMSO-d$_6$) δ 7.93 (d, J=8.6 Hz, 2H), 7.76 (d, J=8.2 Hz, 1H), 7.50-7.41 (m, 1H), 7.27-7.17 (m, 2H), 6.98-6.85 (m, 2H).

Intermediate JS

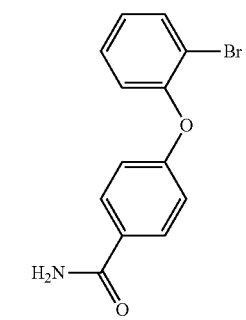

4-(2-Bromophenoxy)benzamide

To a 100 mL round-bottomed flask, were added SOCl$_2$ (20 mL, 276 mmol) followed by 4-(2-bromophenoxy)benzoic acid (1.8 g, 6.1 mmol) and the reaction mixture was refluxed for 2 h. The reaction mixture was cooled to RT and then concentrated to dryness. The resulting residue was dissolved in THF (30 mL) and treated with NH₄OH (10 mL). The reaction mixture was stirred overnight, and then concentrated to dryness to give a solid residue. The resulting residue was collected by filtration washed with water and dried under vacuum to afford the title compound which was used without further purification (1.4 g, 78%). ¹H NMR (400 MHz, DMSO-$d_6$) δ 7.92-7.84 (m, 3H), 7.78-7.73 (m, 1H), 7.47-7.41 (m, 1H), 7.26 (s, 1H), 7.23-7.15 (m, 2H), 6.91 (d, J=8.8 Hz, 2H).

Intermediate JT

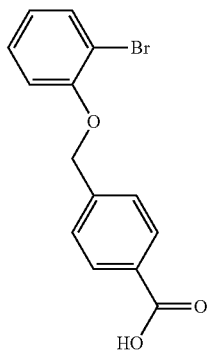

4-((2-Bromophenoxy)methyl)benzoic acid

Step A: Methyl 4-((2-bromophenoxy)methyl)benzoate

To a 10 mL reaction tube equipped with reflux condenser, under N₂, were added 2-bromophenol (1.5 g, 8.6 mmol), methyl 4-(bromomethyl)benzoate (2.0 g, 8.6 mmol), K₂CO₃ (2.4 g, 17.3 mmol) and MeCN (5 mL). The resulting mixture was heated at reflux for 3 h before it was cooled to RT and EtOAc (30 mL) was added and the resulting mixture was filtered then washed with EtOAc (2×10 mL). The combined organic extracts were concentrated to dryness and the residue was purified by FCC to provide the title compound (2.5 g, 90%).

Step B: 4-((2-bromophenoxy)methyl)benzoic acid

To a 150 mL round-bottomed flask, under a N₂ atmosphere, were added methyl 4-((2-bromophenoxy)methyl) benzoate (2.5 g, 7.8 mmol), NaOH (0.6 g, 15.6 mmol) and MeOH (50 mL). The resulting mixture was stirred at RT for 10 h. After which time, water (50 mL) was added and the mixture was concentrated in vacuo to remove the MeOH. The aqeuous mixture was adjusted to pH=4 with 1 M HCl, which resulted in formation of a solid that was collected by filtration. The solid was dried under vacuum to obtain the title compound (2.2 g, 92%). MS (ESI): mass calcd. for C₁₄H₁₁BrO₃, 305.99; m/z found, 328.2 [M+Na]⁺. ¹H NMR (400 MHz, DMSO-$d_6$) δ 12.94 (s, 1H), 7.95 (d, J=8.1, 2H), 7.61-7.48 (m, 3H), 7.35-7.28 (m, 1H), 7.16 (d. J=8.3, 1H), 6.89 (m, 1H), 5.28 (s, 2H).

Intermediate JU

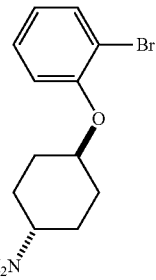

trans 4-(2-Bromophenoxy)cyclohexanamine

To a 150 mL round-bottomed flask equipped with a reflux condenser under a N₂ atmosphere, were added trans-4-aminocyclohexanol (2.3 g, 20 mmol), NaH (2.4 g, 60% purity, 60 mmol) and DMF (25 mL) at 0° C. After 1 h, 1-bromo-2-fluorobenzene (2.051 mL, 19.97 mmol) was added to the solution. The resulting mixture was heated at 60° C. for 5 h. The reaction mixture was cooled to RT, quenched with H₂O (2 mL) and concentrated to dryness. The resulting residue was purified using FCC to provide the title compound (1.8 g, 33.4%). MS (ESI): mass calcd. for C₁₂H₁₆BrNO, 269.04; m/z found, 269.9 [M+H]⁺. ¹H NMR (400 MHz, DMSO-$d_6$) δ 8.41 (s, 1H), 7.53 (dd, J=7.9, 1.6 Hz, 1H), 7.32-7.24 (m, 1H), 7.17 (dd, J=8.4, 1.4 Hz, 1H), 6.88-6.81 (m, 1H), 4.37-4.25 (m, 1H), 3.00-2.90 (m, 1H), 2.09-2.01 (m, 2H), 1.96-1.88 (m, 2H), 1.50-1.34 (m, 4H).

Example 884

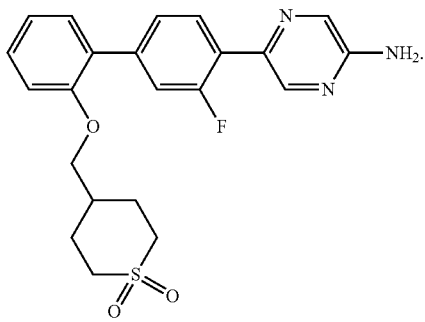

5-{2'-[(1,1-Dioxidotetrahydro-2H-thiopyran-4-yl)methoxy]-3-fluorobiphenyl-4-yl}pyrazin-2-amine The title compound was prepared in a manner similar to that described in Example 88 using 4-((2-bromophenoxy) methyl)tetrahydro-2H-thiopyran 1,1-dioxide. MS (ESI): mass calcd. for C₂₂H₂₂FN₃O₃S, 427.14; m/z found, 427.9 [M+H]⁺. ¹H NMR (400 MHz, DMSO-$d_6$) δ 8.36 (d, J=1.5 Hz, 1H), 8.01 (d, J=1.3 Hz, 1H), 7.90-7.86 (m, 1H), 7.44-7.32 (m, 4H), 7.13 (d, J=8.3 Hz, 1H), 7.06-7.02 (m, 1H), 6.67 (s, 2H), 3.94 (d, J=5.7 Hz, 2H), 3.17-3.08 (m, 2H), 3.03-3.00 (m, 2H), 2.10-2.00 (m, 3H), 1.79-1.73 (m, 2H).

Example 885

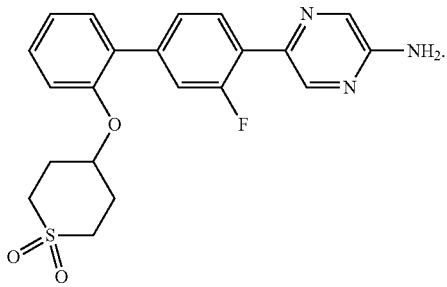

5-{2'-[(1,1-Dioxidotetrahydro-2H-thiopyran-4-yl)oxy]-3-fluorobiphenyl-4-yl}pyrazin-2-amine The title compound was prepared in a manner similar to that described in Example 88 using 4-(2-bromophenoxy) tetrahydro-2H-thiopyran 1,1-dioxide. MS (ESI): mass calcd. for $C_{21}H_{20}FN_3O_3S$, 413.12; m/z found, 413.9 [M+H]$^+$. $^1$H NMR (400 MHz, DMSO-d$_6$) δ 8.39 (s, 1H), 8.04 (s, 1H), 7.95-7.91 (m, 1H), 7.51-7.35 (m, 4H), 7.25 (d, J=8.3 Hz, 1H), 7.13-7.09 (m, 1H), 6.68 (s, 2H), 4.82-4.67 (m, 1H), 3.09-3.06 (m, 2H), 2.92-2.87 (m, 2H), 2.19-2.15 (m, 4H).

Example 886

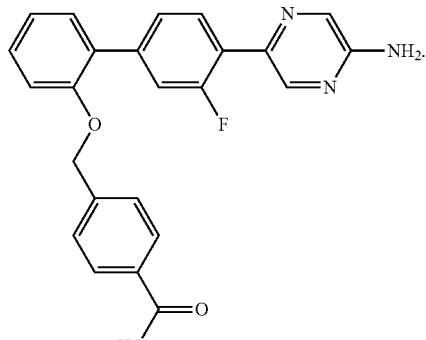

4-({[4'-(5-Aminopyrazin-2-yl)-3'-fluorobiphenyl-2-yl]oxy}methyl)benzoic acid

The title compound was prepared in a manner similar to that described in Example 88 using 4-((2-bromophenoxy) methyl)benzoic acid. MS (ESI): mass calcd. for $C_{24}H_{18}FN_3O_3$, 415.13; m/z found, 415.9 [M+H]$^+$. $^1$H NMR (400 MHz, DMSO-d$_6$) δ 8.35 (s, 1H), 8.02 (d, J=1.4 Hz, 1H), 7.89-7.84 (m, 1H), 7.79 (d, J=8.1 Hz, 2H), 7.49-7.43 (m, 2H), 7.40 (dd, J=7.5, 1.6 Hz, 1H), 7.37-7.31 (m, 1H), 7.26 (d, J=8.1 Hz, 2H), 7.20 (d, J=8.1 Hz, 1H), 7.06-7.03 (m, 1H), 6.68 (s, 2H), 5.13 (s, 2H).

Example 887

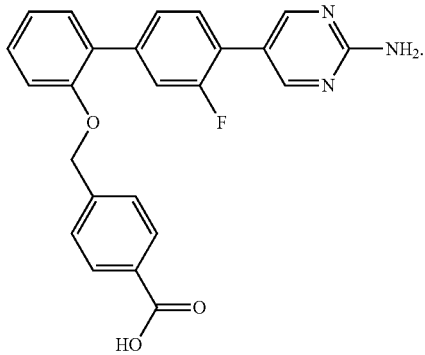

4-({[4'-(2-Aminopyrimidin-5-yl)-3'-fluorobiphenyl-2-yl]oxy}methyl)benzoic acid

The title compound was prepared in a manner similar to that described in Example 88 using 4-((2-bromophenoxy) methyl)benzoic acid and 5-(2-fluoro-4-(4,4,5,5-tetramethyl-1,3,2-dioxaborolan-2-yl)phenyl)pyrimidin-2-amine. MS (ESI): mass calcd. for $C_{24}H_{18}FN_3O_3$, 415.13; m/z found, 415.9 [M+H]$^+$. $^1$H NMR (400 MHz, DMSO-d$_6$) δ 8.47 (d, J=1.2 Hz, 2H), 7.79 (d, J=8.0 Hz, 2H), 7.58-7.54 (m, 1H), 7.50-7.43 (m, 2H), 7.40-7.31 (m, 2H), 7.25 (d, J=8.0 Hz, 2H), 7.19 (d, J=8.3 Hz, 1H), 7.06-7.02 (m, 1H), 6.85 (s, 2H), 5.14 (s, 2H).

Example 888

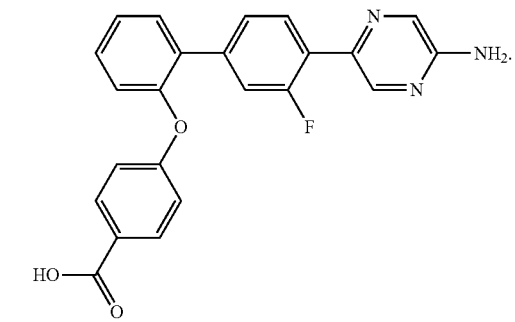

4-{[4'-(5-Aminopyrazin-2-yl)-3'-fluorobiphenyl-2-yl]oxy}benzoic acid

The title compound was prepared in a manner similar to that described in Example 88 using 4-(2-bromophenoxy) benzoic acid. MS (ESI): mass calcd. for $C_{23}H_{16}FN_3O_3$, 401.12; m/z found, 402.4 [M+H]$^+$. $^1$H NMR (400 MHz, DMSO-d$_6$) δ 8.31 (s, 1H), 7.97 (s, 1H), 7.89-7.79 (m, 3H), 7.64-7.58 (m, 1H), 7.50-7.44 (m, 1H), 7.43-7.35 (m, 3H), 7.19-7.14 (m, 1H), 6.98-6.89 (m, 2H), 6.67 (s, 2H).

Example 889

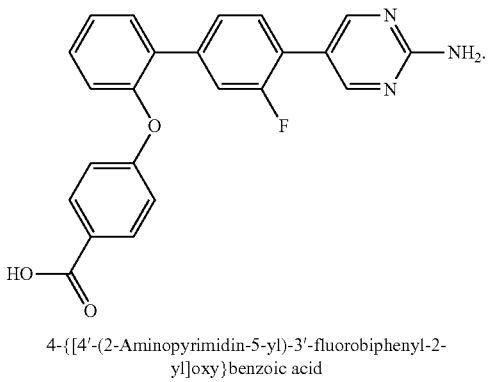 [SMILES: Nc1ncc(-c2ccc(-c3ccccc3Oc3ccc(C(=O)O)cc3)cc2F)cn1]

4-{[4'-(2-Aminopyrimidin-5-yl)-3'-fluorobiphenyl-2-yl]oxy}benzoic acid

The title compound was prepared in a manner similar to that described in Example 88 using 4-(2-bromophenoxy)benzoic acid and 5-(2-fluoro-4-(4,4,5,5-tetramethyl-1,3,2-dioxaborolan-2-yl)phenyl)pyrimidin-2-amine. MS (ESI): mass calcd. for $C_{23}H_{18}FN_3O_3$, 401.12; m/z found, 401.9 [M+H]$^+$. $^1$H NMR (400 MHz, DMSO-d$_6$) δ 8.45-8.39 (m, 2H), 7.89-7.85 (m, 2H), 7.61-7.58 (m, 1H), 7.57-7.51 (m, 1H), 7.49-7.44 (m, 1H), 7.43-7.34 (m, 3H), 7.16-7.12 (m, 1H), 6.98-6.93 (m, 2H), 6.86 (s, 2H).

Example 890

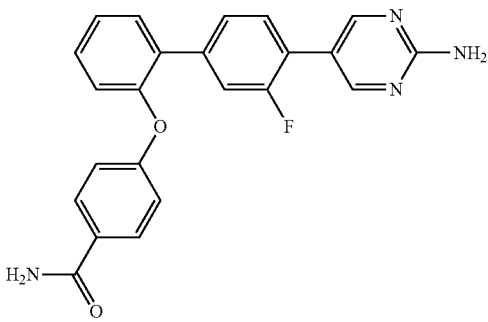

4-{[4'-(2-Aminopyrimidin-5-yl)-3'-fluorobiphenyl-2-yl]oxy}benzamide.

The title compound was prepared in a manner similar to that described in Example 88 using 4-(2-bromophenoxy)benzamide and 5-(2-fluoro-4-(4,4,5,5-tetramethyl-1,3,2-dioxaborolan-2-yl)phenyl)pyrimidin-2-amine. MS (ESI): mass calcd. for $C_{23}H_{17}FN_4O_2$, 400.13; m/z found, 400.9 [M+H]$^+$. $^1$H NMR (400 MHz, DMSO-d$_6$) δ 8.43 (s, 2H), 7.88-7.79 (m, 3H), 7.62-7.50 (m, 2H), 7.48-7.38 (m, 3H), 7.37-7.31 (m, 1H), 7.23 (s, 1H), 7.09 (d, J=7.8 Hz, 1H), 6.94 (d, J=8.8 Hz, 2H), 6.85 (s, 2H).

Example 891

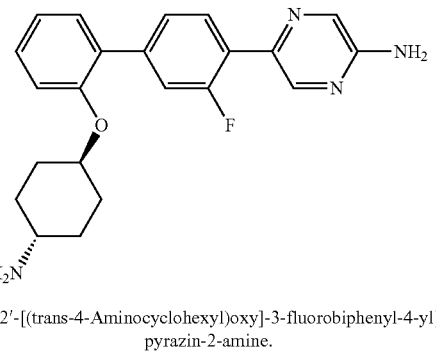

5-{2'-[(trans-4-Aminocyclohexyl)oxy]-3-fluorobiphenyl-4-yl}pyrazin-2-amine.

The title compound was prepared in a manner similar to that described in Example 88 using trans 4-(2-bromophenoxy)cyclohexanamine. MS (ESI): mass calcd. for $C_{22}H_{23}FN_4O$, 378.19; m/z found, 379.2 [M+H]$^+$. $^1$H NMR (400 MHz, DMSO-d$_6$) δ 8.42 (s, 1H), 8.35 (s, 1H), 8.01 (d, J=1.4 Hz, 1H), 7.89-7.83 (m, 1H), 7.43-7.35 (m, 3H), 7.34-7.29 (m, 1H), 7.17 (d, J=8.2 Hz, 1H), 7.05-6.98 (m, 1H), 6.67 (s, 2H), 4.34-4.24 (m, 1H), 2.91-2.83 (m, 1H), 2.08-2.01 (m, 2H), 1.89-1.83 (m, 2H), 1.40-1.29 (m, 4H).

Example 892

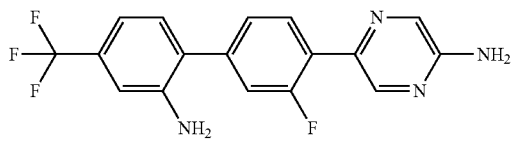

5-[2'-Amino-3-fluoro-4'-(trifluoromethyl)biphenyl-4-yl]pyrazin-2-amine.

The title compound was prepared using analogous conditions to those described in Example 1 using 2-bromo-5-(trifluoromethyl)aniline. MS (ESI): mass calcd. for $C_{17}H_{12}F_4N_4$, 348.10; m/z found, 349.0 [M+H]$^+$. $^1$H NMR (500 MHz, CDCl$_3$) δ 8.59-8.57 (m, 1H), 8.12 (d, J=1.5 Hz, 1H), 8.02 (m, 1H), 7.36-7.33 (m, 1H), 7.31-7.22 (m, 3H), 7.08-7.05 (m, 1H), 7.01-6.99 (m, 1H), 4.75 (s, 2H), 4.00 (s, 2H).

Intermediate JV

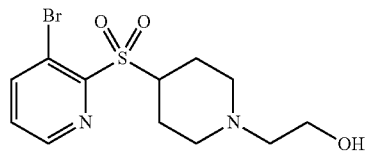

2-(4-((3-Bromopyridin-2-yl)sulfonyl)piperidin-1-yl)ethanol

Step A: tert-Butyl 4-(3-bromopyridin-2-ylthio)piperidine-1-carboxylate

To a 250 mL round-bottomed flask were added, 3-bromopyridine-2-thiol (3.0 g, 16 mmol), tert-butyl 4-bromopiperidine-1-carboxylate (5.0 g, 19 mmol), K$_2$CO$_3$ (4.3 g, 31 mmol) and DMF (30 mL). The reaction mixture was stirred at RT for 4 h and then concentrated to dryness. The residue was purified by FCC to give the title compound (3.2 g, 54% purity). MS (ESI): mass calcd. for C$_{15}$H$_{21}$BrN$_2$O$_2$S, 372.05; m/z found, 373.1 [M+H]$^+$.

Step B: tert-Butyl 4-(3-bromopyridin-2-ylsulfonyl)piperidine-1-carboxylate

To a 250 mL round bottom flask was added, tert-butyl 4-(3-bromopyridin-2-ylthio)piperidine-1-carboxylate (3.0 g, 8.0 mmol, 54% purity), NaIO$_4$ (5.0 g, 24.0 mmol), RuCl$_3$ (10 mg, 0.05 mmol) and H$_2$O/DCM/CH$_3$CN (15 mL/15 mL/15 mL). The reaction mixture was stirred at RT for 1 h and then concentrated to dryness. The residue was diluted with water (50 mL) and extracted with DCM (3×50 mL). The combined organic extracts were dried over Na$_2$SO$_4$, filtered, concentrated to dryness and the resultant residue was purified by FCC to give the title compound (1.61 g, 50%). MS (ESI): mass calcd. for C$_{15}$H$_{21}$BrN$_2$O$_4$S, 404.04; m/z found, 405.3 [M+H]$^+$.

Step C: 3-Bromo-2-(piperidin-4-ylsulfonyl)pyridine hydrochloride

To a 100 mL round-bottomed flask were added, tert-butyl 4-(3-bromopyridin-2-ylsulfonyl)piperidine-1-carboxylate (242 mg, 0.6 mmol), MeOH (20 mL) and HCl (4 mL, 6 N in EtOH). The mixture was stirred at RT for 3 h and then concentrated to dryness to give the title compound (210 mg) which was used without further purification. MS (ESI): mass calcd. for C$_{10}$H$_{14}$BrClN$_2$O$_2$S, 303.99; m/z found, 304.4 [M+H]$^+$.

Step D: 2-(4-(3-Bromopyridin-2-ylsulfonyl)piperidin-1-yl)ethanol

To a 100 mL round-bottomed flask were added, 3-bromo-2-(piperidin-4-ylsulfonyl)pyridine hydrochloride (500 mg, 1.47 mmol), 1-bromoethan-2-ol (204 mg, 1.5 mmol), K$_2$CO$_3$ (304 mg, 2.2 mmol) and CH$_3$CN (20 mL). The mixture was stirred at 60° C. for 16 h, cooled to RT, concentrated to dryness and the resulting residue was purified by FCC to give the title compound (370 mg, 69%). MS (ESI): mass calcd. for C$_{12}$H$_{17}$BrN$_2$O$_3$S, 348.01; m/z found, 349.3 [M+H]$^+$.

Intermediate JW

3-Chloro-2-phenylpyridine

To a microwave vial were added phenyl boronic acid (76 mg, 0.62 mmol), 2-bromo-3-chloropyridine (100 mg, 0.52 mmol), Pd(dppf)Cl$_2$·CH$_2$Cl$_2$ (20 mg, 0.025 mmol), acetonitrile (2.0 mL) and sat. aq. NaHCO$_3$ (1.5 mL). Nitrogen was bubbled through the biphasic mixture for 2 minutes before the vial was sealed. The reaction vessel was then placed in the microwave and heated at 110° C. for 1.5 h. The resulting reaction mixture was cooled to RT, diluted with ethyl acetate (50 mL), washed with water (1×25 mL), brine (1×25 mL), dried with Na$_2$SO$_4$ and concentrated to dryness. The resultant residue was subjected to prep-HPLC to afford the title compound (48 mg, 49%). MS (ESI): mass calcd. for C$_{11}$H$_8$ClN, 189.03; m/z found, 190.0 [M+H]$^+$.

Example 893

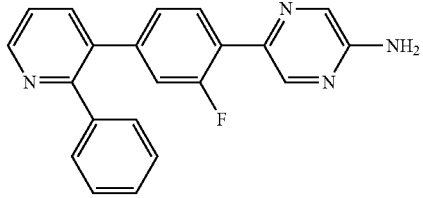

5-[2-Fluoro-4-(2-phenylpyridin-3-yl)phenyl]pyrazin-2-amine.

The title compound was prepared in a manner similar to that described in Step B of Example 838 using 3-chloro-2-phenylpyridine and 5-(2-fluoro-4-(4,4,5,5-tetramethyl-1,3,2-dioxaborolan-2-yl)phenyl)pyrazin-2-amine. MS (ESI): mass calcd. for C$_{21}$H$_{15}$FN$_4$, 342.13; m/z found, 343.0 [M+H]$^+$. $^1$H NMR (400 MHz, DMSO-d$_6$) δ 8.70 (dd, J=4.8, 1.7 Hz, 1H), 8.45 (d, J=1.5 Hz, 2H), 7.90 (dd, J=7.7, 1.7 Hz, 1H), 7.55-7.44 (m, 2H), 7.41-7.26 (m, 5H), 7.16 (dd, J=11.9, 1.8 Hz, 1H), 7.05 (dd, J=8.0, 1.8 Hz, 1H), 6.92 (s, 2H).

Intermediate JX

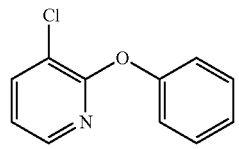

3-Chloro-2-phenoxypyridine

To a 50 mL round-bottomed flask under nitrogen were added 2-bromo-3-chloropyridine (250 mg, 1.3 mmol), phenol (145 mg, 1.5 mmol), cesium carbonate (502 mg, 1.5 mmol) and DMSO (5 mL). The mixture was then heated at 60° C. for 24 h. The resulting reaction mixture was then cooled to RT, diluted with ethyl acetate (100 mL), washed with sat. aq. NaHCO$_3$ (1×75 mL), water (1×75 mL). The organic extracts were dried over Na$_2$SO$_4$ and concentrated to dryness. The resultant residue was then purified by FCC to provide the title compound (205 mg, 77%). MS (ESI): mass calcd. for C$_{11}$H$_8$ClNO, 189.03; m/z found, 190.0 [M+H]$^+$.

Example 894

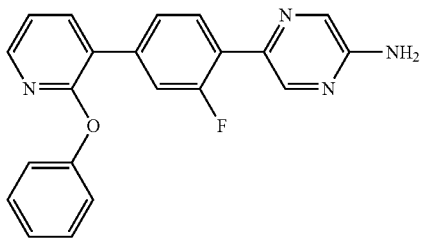

5-[2-Fluoro-4-(2-phenoxypyridin-3-yl)phenyl]pyrazin-2-amine.

The title compound was prepared in a manner similar to that described in Step B of Example 838 using 3-chloro-2-phenoxypyridine and 5-(2-fluoro-4-(4,4,5,5-tetramethyl-1,3,2-dioxaborolan-2-yl)phenyl)pyrazin-2-amine. MS (ESI): mass calcd. for $C_{21}H_{15}FN_4O$, 358.12; m/z found, 359.1 [M+H]$^+$. $^1$H NMR (400 MHz, DMSO-d$_8$) δ 8.39 (dd, J=2.4, 1.5 Hz, 1H), 8.14 (dd, J=4.9, 1.9 Hz, 1H), 8.07-8.00 (m, 2H), 8.00-7.92 (m, 1H), 7.70-7.60 (m, 2H), 7.46-7.37 (m, 2H), 7.27 (dd, J=7.5, 4.8 Hz, 1H), 7.24-7.13 (m, 3H), 6.74 (s, 2H).

Example 895

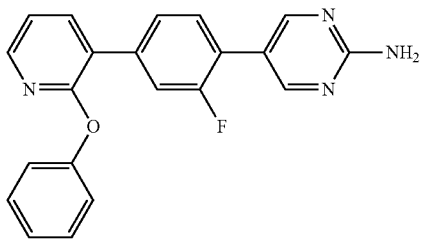

5-[2-Fluoro-4-(2-phenoxypyridin-3-yl)phenyl]pyrimidin-2-amine.

The title compound was prepared in a manner similar to that described in Step B of Example 838 using 3-chloro-2-phenoxypyridine and 5-(2-fluoro-4-(4,4,5,5-tetramethyl-1,3,2-dioxaboralan-2-yl)phenyl)pyrimidin-2-amine. MS (ESI): mass calcd. for $C_{21}H_{15}FN_4O$, 358.12; m/z found, 359.1 [M+H]$^+$. $^1$H NMR (400 MHz, DMSO-d$_6$) δ 8.50 (d, J=1.5 Hz, 2H), 8.14 (dd, J=4.8, 1.9 Hz, 1H), 8.02 (dd, J=7.5, 1.9 Hz, 1H), 7.70-7.59 (m, 3H), 7.46-7.38 (m, 2H), 7.30-7.13 (m, 4H), 6.93 (s, 2H).

Intermediate JY

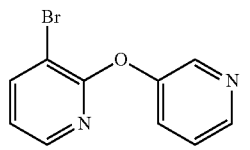

3-Bromo-2-(pyridine-3-yloxy)pyridine

To a screw-capped vial was added 3-bromo-2-chloropyridine (250 mg, 1.3 mmol), 3-hydroxy pyridine (150 mg, 1.6 mmol), cesium carbonate (510 mg, 1.6 mmol) and DMSO (5.0 mL). The vial was capped and the mixture was stirred at 60° C. for 24 h. The resulting reaction mixture was cooled to RT, poured into water (100 mL) and extracted with ethyl acetate (2×50 mL). The combined organic extracts were washed with water (1×50 mL) and brine (1×50 mL). The organic extracts were concentrated to dryness and purified by FCC to provide the title compound (214 mg, 66%). MS (ESI): mass calcd. for $C_{10}H_7BrN_2O$, 249.97; m/z found, 250.9 [M+H]$^+$.

Example 896

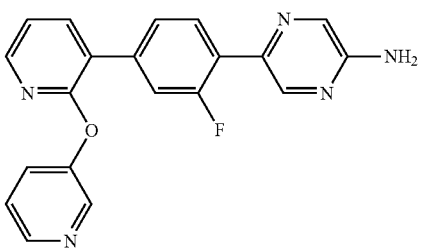

5-{2-Fluoro-4-[2-(pyridin-3-yloxy)pyridin-3-yl]phenyl}pyrazin-2-amine.

The title compound was prepared in a manner similar to that described in Step D of Example 803 using 3-bromo-2-(pyridine-3-yloxy)pyridine. MS (ESI): mass calcd. for $C_{20}H_{14}FN_5O$, 359.12; m/z found, 360.1 [M+H]$^-$ $^1$H NMR (400 MHz, DMSO-d$_6$) δ 8.51 (d, J=2.7 Hz, 1H), 8.44 (dd, J=4.6, 1.4 Hz, 1H), 8.45-8.35 (m, 1H), 8.14 (dd, J=4.9, 1.8 Hz, 1H), 8.09-8.01 (m, 2H), 7.81-7.92 (m, 1H), 7.74-7.62 (m, 3H), 7.48 (dd, J=8.3, 4.7 Hz, 1H), 7.31 (dd, J=7.5, 4.9 Hz, 1H).

Example 897

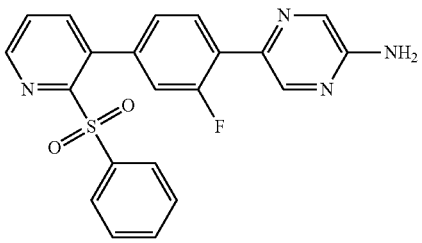

5-{2-Fluoro-4-[2-(phenylsulfonyl)pyridin-3-yl]phenyl}pyrazin-2-amine.

The title compound was prepared in a manner similar to that described in Step D of Example 803 using 3-bromo-2-(phenylsulfonyl)pyridine. MS (ESI): mass calcd. for $C_{21}H_{15}FN_4O_2S$, 406.09; m/z found, 406.9 [M+H]$^+$. $^1$H NMR (400 MHz, CD$_3$OD) δ 8.63 (dd, J=4.7, 1.6 Hz, 1H), 8.44 (s, 1H), 8.12 (d, J=1.4 Hz, 1H), 7.94-7.88 (m, 2H), 7.74-7.64 (m, 4H), 7.54-7.48 (m, 2H), 7.23 (dd, J=8.0, 1.7 Hz, 1H), 7.17 (dd, J=12.0, 1.6 Hz, 1H).

Example 898

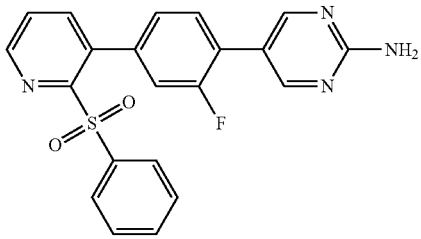

5-{2-Fluoro-4-[2-(phenylsulfonyl)pyridin-3-yl]phenyl}pyrimidin-2-amine.

Step A: 3-Bromo-2-(phenylthio)pyridine

The intermediate was prepared in a manner similar to that for Intermediate JZ using thiophenol. MS (ESI): mass calcd. for $C_{11}H_8BrNS$ 264.96, m/z found 265.8 [M+H]$^+$.

Step B: 3-Bromo-2-(phenylsulfonyl)pyridine

The intermediate was prepared in a manner similar to that described in Step B of Intermediate JV using 3-bromo-2-(phenylthio)pyridine. MS (ESI): mass calcd. for $C_{11}H_8BrNO_2S$ 296.95, m/z found 298.1 [M+H]$^+$.

Step C: 5-{2-Fluoro-4-[2-(phenylsulfonyl)pyridin-3-yl]phenyl}pyrimidin-2-amine The title compound was prepared in a manner similar to that described in Step D of Example 803 using 3-bromo-2-(phenylsulfonyl)pyridine and 5-(2-fluoro-4-(4,4,5,5-tetramethyl-1,3,2-dioxaboralan-2-yl)phenyl)pyrimidin-2-amine. MS (ESI): mass calcd. for $C_{21}H_{15}FN_4O_2S$, 406.09; m/z found, 407.0 [M+H]$^+$. $^1$H NMR (400 MHz, CD$_3$OD) δ 8.73 (s, 2H), 8.62 (dd, J=4.6, 1.5 Hz, 1H), 7.92 (dd, J=7.8, 1.5 Hz, 1H), 7.77-7.73 (m, 2H), 7.73-7.67 (m, 2H), 7.64-7.59 (m, 1H), 7.57-7.52 (m, 2H), 7.33-7.25 (m, 2H).

Intermediate JZ

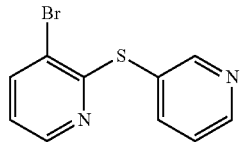

3-Bromo-2-(pyridine-3-ylthio)pyridine

To a 100 mL round-bottomed flask were added 3-bromo-2-chloropyridine (500 mg, 2.6 mmol), pyridine-3-thiol (291 mg, 2.6 mmol), Cs$_2$CO$_3$ (2.4 g, 7.8 mmol) and DMSO (15 mL). The reaction mixture was stirred at 100° C. for 5 h. After which time the reaction mixture was cooled to RT, concentrated to dryness and the resultant residue was purified by FCC to give the title compound (400 mg, 58%). MS (ESI): mass calcd. for $C_{10}H_7BrN_2S$, 265.95; m/z found, 267.1 [M+H]$^+$.

Example 899

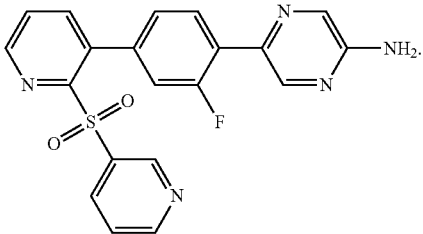

5-{2-Fluoro-4-[2-(pyridin-3-ylsulfonyl)pyridin-3-yl]phenyl}pyrazin-2-amine.

Step A: 3-Bromo-2-(pyridin-3-ylsulfonyl)pyridine

The intermediate was prepared in a manner similar to that described in Step B of Intermediate JV using 3-bromo-2-(pyridin-3-ylthio)pyridine. MS (ESI): mass calcd. for $C_{10}H_7BrN_2O_2S$, 297.94, m/z found 298.6 [M+H]$^+$.

Step B: 5-{2-Fluoro-4-[2-(pyridin-3-ylsulfonyl)pyridin-3-yl]phenyl}pyrazin-2-amine The title compound was prepared in a manner similar to that described in Step D of Example 803 using 3-bromo-2-(pyridin-3-ylsulfonyl)pyridine. MS (ESI): mass calcd. for $C_{20}H_{14}FN_5O_2S$, 407.09; m/z found, 408.0 [M+H]$^+$. $^1$H NMR (400 MHz, CD$_3$OD) δ 8.90 (dd, J=2.3, 0.6 Hz, 1H), 8.81 (dd, J=4.9, 1.6 Hz, 1H), 8.56 (dd, J=4.6, 1.6 Hz, 1H), 8.48-8.42 (m, 1H), 8.21-8.18 (m, 1H), 8.11 (d, J=1.5 Hz, 1H), 8.01-7.94 (m, 2H), 7.70 (dd, J=7.8, 4.7 Hz, 1H), 7.63-7.59 (m, 1H), 7.38-7.29 (m, 2H).

Example 900

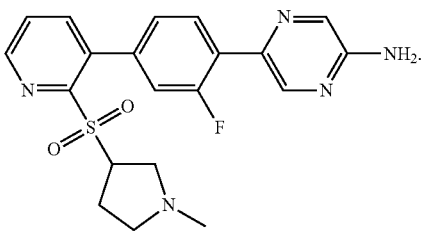

5-(2-Fluoro-4-{2-[(1-methylpyrrolidin-3-yl)sulfonyl]pyridin-3-yl}phenyl)pyrazin-2-amine

Step A: tert-Butyl 3-(3-bromopyridin-2-ylthio)pyrrolidine-1-carboxylate

The intermediate was prepared in a manner similar to that described in Step A of Intermediate JV using tert-butyl 3-bromopyrrolidine-1-carboxylate. MS (ESI): mass calcd. for $C_{14}H_{19}BrN_2O_2S$, 358.04, m/z found 381.0 [M+Na]$^+$.

Step B: tert-Butyl 3-(3-bromopyridin-2-ylsulfonyl)pyrrolidine-1-carboxylate

The intermediate was prepared in a manner similar to that described in Step B of Intermediate JV using tert-butyl 3-(3-bromopyridin-2-ylthio)pyrrolidine-1-carboxylate. MS (ESI): mass calcd. for $C_{14}H_{19}BrN_2O_4S$, 390.02, m/z found 335.0 $[M-Me_3C]^+$.

Step C: 3-Bromo-2-(pyrrolidin-3-ylsulfonyl)pyridine

To a 100 mL round-bottomed flask were added, tert-butyl 3-(3-bromopyridin-2-ylsulfonyl)pyrrolidine-1-carboxylate (1.8 g, 4.2 mmol) and DCM (20 mL). A solution of HCl (20 mL, 6 N in EtOH) was then added and the mixture was stirred at RT for 2 h followed by concentration to dryness. The residue was diluted with sat. aq. $NaHCO_3$ (50 mL) and extracted with DCM (6×40 mL). The combined organic extracts were dried over $MgSO_4$ and concentrated to dryness to provide the title compound (1 g, 83%). MS (ESI): mass calcd. for $C_9H_{11}BrN_2O_2S$, 289.97, m/z found 291.0 $[M+H]^+$.

Step D: 3-Bromo-2-(1-methylpyrrolidin-3-ylsulfonyl)pyridine

To a 100 mL round-bottomed flask was added, 3-bromo-2-(pyrrolidin-3-ylsulfonyl)pyridine (1.0 g, 3.4 mmol) and DCM (20 mL). An aqueous solution of formaldehyde (37%, 280 mg, 10.3 mmol), AcOH (0.5 mL) and $NaBH(AcO)_3$ (2.2 g, 10.3 mmol) were then added. The resulting mixture was stirred at RT for 1 h. then concentrated to dryness. The residue was purified by FCC to give the title compound (240 mg, 23%). MS (ESI): mass calcd. for $C_{10}H_{13}BrN_2O_2S$, 303.99, m/z found 305.0 $[M+H]^+$.

Step E: 5-(2-Fluoro-4-{2-[(1-methylpyrrolidin-3-yl)sulfonyl]pyridin-3-yl}phenyl)pyrazin-2-amine The title compound was prepared in a manner similar to that described in Step D of Example 803 using 3-bromo-2-(1-methylpyrrolidin-3-ylsulfonyl)pyridine. MS (ESI): mass calcd. for $C_{20}H_{20}FN_5O_2S$, 413.13; m/z found, 414.1 $[M+H]^+$. $^1H$ NMR (400 MHz, $CD_3OD$) δ 8.63 (d, J=3.2 Hz, 1H), 8.61 (s, 1H), 8.12 (s, 1H), 8.11-8.07 (m, 1H), 7.89 (d, J=6.7 Hz, 1H), 7.65 (dd, J=7.8, 4.7 Hz, 1H), 7.42-7.35 (m, 2H), 4.89-4.85 (m, 1H), 4.80 (s, 2H), 4.31-4.21 (m, 1H), 3.63-3.59 (m, 1H), 3.29-3.24 (m, 1H), 3.05-2.98 (m, 1H), 2.81 (s, 3H), 2.77-2.58 (m, 2H).

Example 901

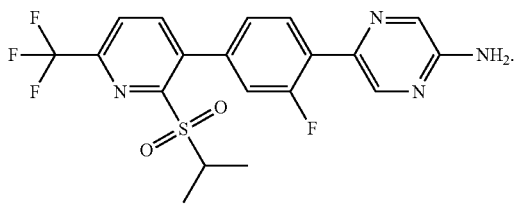

5-(2-Fluoro-4-{2-[(1-methylethyl)sulfonyl]-6-(trifluoromethyl)pyridin-3-yl}phenyl)pyrazin-2-amine Step A: 3-Bromo-6-(trifluoromethyl)pyridine-2-thiol To a 100 mL round-bottomed flask were added, 3-bromo-2-chloro-6-(trifluoromethyl)pyridine (1.0 g, 3.8 mmol), $Na_2S.9H_2O$ (2.8 g, 11.5 mmol) and DMSO (15 mL). The reaction mixture was stirred at 100° C. for 48 h, then cooled to RT and filtered. The filtrate was used in the next step without purification.

Step B: 3-Bromo-2-(iso-propylthio-6-(trifluoromethyl)pyridine

The intermediate was prepared in a manner similar to that described in Step A of Intermediate JV using 3-bromo-6-(trifluoromethyl)pyridine-2-thiol and 2-bromopropane. MS (ESI): mass calcd. for $C_9H_9BrF_3NS$, 298.96; m/z found, 300.0 $[M+H]^+$.

Step C: 3-Bromo-2-(iso-propylsulfonyl)-6-(trifluoromethyl)pyridine

The intermediate was prepared in a manner similar to that described in Step B of Intermediate JV using 3-bromo-2-(isopropylthio)-6-(trifluoromethyl)pyridine. MS (ESI): mass calcd. for $C_9H_9BrF_3NO_2S$, 330.95; m/z found, 331.9 $[M+H]^+$.

Step D: 5-(2-Fluoro-4-{2-[(1-methylethyl)sulfonyl]-6-(trifluoromethyl)pyridin-3-yl}phenyl)pyrazin-2-amine The title compound was prepared in a manner similar to that described in Step D of Example 803 using 3-bromo-2-(isopropylsulfonyl)-6-(trifluoromethyl)pyridine. MS (ESI): mass calcd. for $C_{19}H_{16}F_4N_4O_2S$, 440.09; m/z found, 441.1 $[M+H]^+$. $^1H$ NMR (400 MHz, $CD_3OD$) δ 8.71 (d, J=1.3 Hz, 1H), 8.33-8.25 (m, 2H), 8.22-8.18 (m, 2H), 7.57-7.49 (m, 2H), 4.37-4.17 (m, 1H), 1.34 (d, J=6.9 Hz, 6H).

Example 902

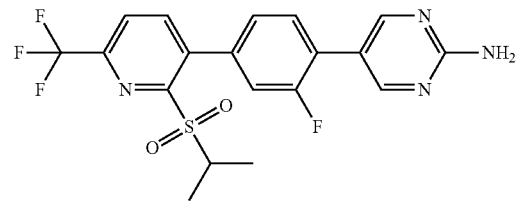

5-(2-Fluoro-4-{2-[(1-methylethyl)sulfonyl]-6-(trifluoromethyl)pyridin-3-yl}phenyl)pyrimidin-2-amine.

The title compound was prepared in a manner similar to that described in Step D of Example 803 using 3-bromo-2-(isopropylsulfonyl)-6-(trifluoromethyl)pyridine and 5-(2-fluoro-4-(4,4,5,5-tetramethyl-1,3,2-dioxaboralan-2-yl)phenyl)pyrimidin-2-amine. MS (ESI): mass calcd. for $C_{19}H_{16}F_4N_4O_2S$, 440.09; m/z found, 441.1 $[M+H]^+$. $^1H$ NMR (400 MHz, $CD_3OD$) δ 8.90 (s, 2H), 8.26 (d, J=8.1 Hz, 1H), 8.19 (d, J=8.1 Hz, 1H), 7.76-7.72 (m, 1H), 7.58-7.49 (m, 2H), 4.30-4.20 (m, 1H), 1.33 (d, J=6.9 Hz, 6H).

Example 903

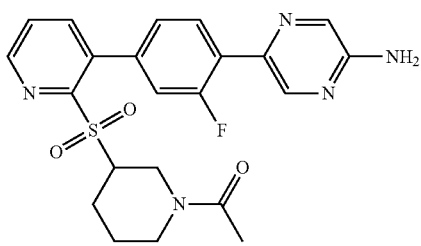

5-(4-{2-[(1-Acetylpiperidin-3-yl)sulfonyl]pyridin-3-yl}-2-fluorophenyl)pyrazin-2-amine.

Step A: tert-Butyl 3-(3-bromopyridin-2-ylthio)piperidine-1-carboxylate

To a 250 mL round-bottomed flask was added, 3-bromopyridine-2-thiol (1.0 g, 5.3 mmol), tert-butyl 3-(tosyloxy)cyclohexanecarboxylate (1.2 g, 3.7 mmol), $K_2CO_3$ (720 mg, 5.3 mmol) and DMF (15 mL). The reaction mixture was stirred at 60° C. for 16 h then cooled to RT. The resulting mixture was concentrated to dryness and purified by FCC to give the title compound (300 mg, 21% purity). MS (ESI): mass calcd. for, $C_{15}H_{21}BrN_2O_2S$, 372.05; m/z found, 373.1 $[M+H]^+$.

Step B: tert-Butyl 3-(3-bromopyridin-2-ylsulfonyl)piperidine-1-carboxylate

The intermediate was prepared in a manner similar to that described in Step B of Intermediate JV using tert-butyl 3-(3-bromopyridin-2-ylthio)piperidine-1-carboxylate. MS (ESI): mass calcd. for, $C_{15}H_{21}BrN_2O_4S$, 404.04; m/z found, 405.1 $[M+H]^+$.

Step C: 3-Bromo-2-(piperidin-3-ylsulfonyl)pyridine

The intermediate was prepared in a manner similar to that described in Step C of Intermediate JV using tert-butyl 3-(3-bromopyridin-2-ylsulfonyl)piperidine-1-carboxylate. MS (ESI): mass calcd. for $C_{10}H_{13}BrN_2O_2S$, 303.99; m/z found, 305.0 $[M+H]^+$.

Step D: 1-(3-(3-Bromopyridin-2-ylsulfonyl)piperidin-1-yl)ethanone

To a 100 mL round-bottomed flask were added 3-bromo-2-(piperidin-3-ylsulfonyl)pyridine hydrochloride (150 mg, 0.44 mmol), acetyl chloride (52 mg, 0.66 mmol), $CH_2Cl_2$ (20 mL) and $Et_3N$ (90 mg, 0.88 mmol). The mixture was stirred at RT for 1 h then neutralized to pH=7 by adding sat. aq. $NaHCO_3$ and extracted with DCM (3×10 mL). The combined organic extracts were dried over $Na_2SO_4$ and concentrated to dryness to give the title compound (160 mg) which was used in the next step without further purification. MS (ESI): mass calcd. for $C_{12}H_{15}BrN_2O_3S$, 346.00; m/z found, 346.9 $[M+H]^+$.

Step E: 5-(4-{2-[(1-Acetylpiperidin-3-yl)sulfonyl]pyridin-3-yl}-2-fluorphenyl)pyrazin-2-amine The title compound was prepared in a manner similar to that described in Step D of Example 803 using 1-(3-(3-bromopyridin-2-ylsulfonyl)piperidin-1-yl)ethanone. MS (ESI): mass calcd. for $C_{22}H_{22}FN_5O_3S$, 455.14; m/z found, 455.9 $[M+H]^+$. $^1$H NMR (400 MHz, $CD_3OD$) δ 8.78 (s, 1H), 8.69-8.58 (m, 1H), 8.30 (s, 1H), 8.17-8.11 (m, 1H), 8.03 (dd, J=11.5, 7.9 Hz, 1H), 7.83-7.78 (m, 1H), 7.48-7.43 (m, 2H), 4.67-3.78 (m, 3H), 3.58-3.17 (m, 1H), 3.07-2.92 (m, 1H), 2.19 (s, 1H), 2.13 (m, 3H), 1.99-1.78 (m, 2H), 1.68-1.50 (m, 1H).

Example 904

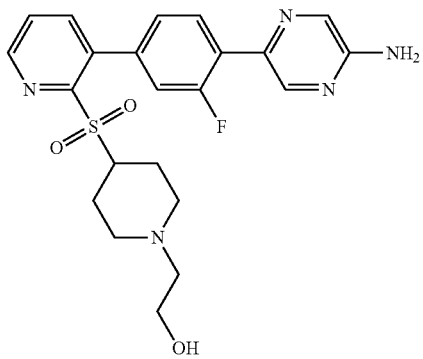

2-[4-({3-[4-(5-Aminopyrazin-2-yl)-3-fluorophenyl]pyridin-2-yl}sulfonyl)piperidin-1-yl]ethanol.

The title compound was prepared in a manner similar to that described in Step D of Example 803 using 2-(4-(3-bromopyridin-2-ylsulfonyl)piperidin-1-yl)ethanol. MS (ESI): mass calcd. for $C_{22}H_{24}FN_5O_3S$, 457.16; m/z found, 458.1 $[M+H]^+$. $^1$H NMR (300 MHz, $CD_3OD$) δ 8.80-8.74 (m, 1H), 8.72 (d, J=1.1 Hz, 1H), 8.25 (d, J=1.2 Hz, 1H), 8.20-8.11 (m, 1H), 8.03 (dd, J=7.8, 1.4 Hz, 1H), 7.79 (dd, J=7.9, 4.6 Hz, 1H), 7.50-7.40 (m, 2H), 4.56-4.42 (m, 1H), 3.96-3.72 (m, 4H), 3.54-3.45 (m, 1H), 3.30-3.11 (m, 4H), 2.39-2.28 (m, 2H), 2.20-2.00 (m, 2H).

Example 905

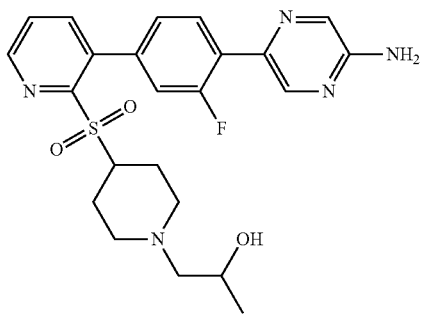

(racemic)-1-[4-({3-[4-(5-Aminopyrazin-2-yl)-3-fluorophenyl]pyridin-2-yl}sulfonyl)piperidin-1-yl]propan-2-ol.

Step A: 1-(4-(3-Bromopyridin-2-ylsulfonyl)piperidin-1-yl)propan-2-ol

To a 100 mL round-bottomed flask were added, 3-bromo-2-(piperidin-4-ylsulfonyl)pyridine hydrochloride (500 mg, 1.47 mmol), 1-bromopropan-2-ol (204 mg, 1.47 mmol), K₂CO₃ (304 mg, 2.2 mmol) and CH₃CN (20 mL). The mixture was stirred at 60° C. for 16 h. The resulting mixture was cooled to RT, concentrated to dryness and the resultant residue was purified by FCC to give the title compound (370 mg, 69%). MS (ESI): mass calcd. for $C_{13}H_{19}BrN_2O_3S$, 362.03; m/z found, 363.3 [M+H]⁺.

Step B: 1-[4-({3-[4-(5-Aminopyrazin-2-yl)-3-fluorophenyl]pyridin-2-yl}sulfonyl)piperidin-1-yl]propan-2-ol The title compound was prepared in a manner similar to that described in Step D of Example 803 using 1-(4-(3-bromopyridin-2-ylsulfonyl)piperidin-1-yl)propan-2-ol. MS (ESI): mass calcd. for $C_{23}H_{26}FN_5O_3S$, 471.17; m/z found, 472.1 [M+H]⁺. ¹H NMR (300 MHz, CD₃OD) δ 8.78-8.73 (m, 1H), 8.72-8.66 (m, 1H), 8.26 (s, 1H), 8.15 (m, 1H), 8.05-8.00 (m, 1H), 7.79 (dd, J=7.9, 4.6 Hz, 1H), 7.48-7.40 (m, 2H), 4.59-4.42 (m, 1H), 4.26-4.11 (m, 1H), 3.79 (t, J=11.4 Hz, 2H), 3.52-3.41 (m, 1H), 3.23-2.94 (m, 4H), 2.39-2.25 (m, 2H), 2.22-2.01 (m, 2H), 1.23 (d, J=6.1 Hz, 3H).

Example 906

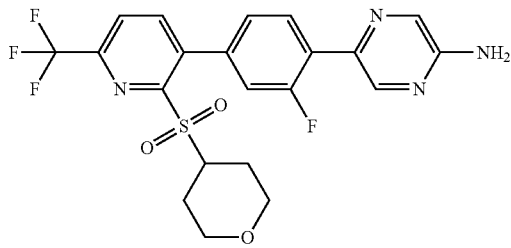

5-{2-Fluoro-4-[2-(tetrahydro-2H-pyran-4-ylsulfonyl)-6-(trifluoromethyl)pyridin-3-yl]phenyl}pyrazin-2-amine.

Step A: 3-Bromo-2-(tetrahydro-2H-pyran-4-ylthio)-6-(trifluoromethyl)pyridine

The intermediate was prepared in a manner similar to that described in Step A of Intermediate JV using 3-bromo-6-(trifluoromethyl)pyridine-2-thiol and 4-bromotetrahydro-2H-pyran. MS (ESI): mass calcd. for $C_{11}H_{11}BrF_3NOS$, 340.97; m/z found, 342.0 [M+H]⁺.

Step B: 3-Bromo-2-(tetrahydro-2H-pyran-4-ylsulfonyl)-6-(trifluoromethyl)pyridine The intermediate was prepared in a manner similar to that described in Step B of Intermediate JV using 3-bromo-2-(tetrahydro-2H-pyran-4-ylthio)-6-(trifluoromethyl)pyridine. MS (ESI): mass calcd. for $C_{11}H_{11}BrF_3NO_3S_2$, 372.96; m/z found, 373.6 [M+H]⁺.

Step C: 5-{2-Fluoro-4-[2-(tetrahydro-2H-pyran-4-ylsulfonyl)-6-(trifluoromethyl)pyridin-3-yl]phenyl}pyrazin-2-amine The title compound was prepared in a manner similar to that described in Step D of Example 803 using 3-bromo-2-(tetrahydro-2H-pyran-4-ylsulfonyl)-6-(trifluoromethyl)pyridine. MS (ESI): mass calcd. for $C_{21}H_{18}F_4N_4O_3S$, 482.10; m/z found, 483.1 [M+H]⁺. ¹H NMR (400 MHz, CD₃OD) δ 8.44 (s, 1H), 8.29 (d, J=8.0 Hz, 1H), 8.20 (d, J=8.1 Hz, 1H), 8.15 (s, 1H), 8.05-8.01 (m, 1H), 7.48 (d, J=4.1 Hz, 1H), 7.46 (s, 1H), 4.38-4.32 (m, 1H), 4.08-4.04 (m, 2H), 3.54-3.49 (m, 2H), 1.96-1.93 (m, 2H), 1.89-1.79 (m, 2H).

Example 907

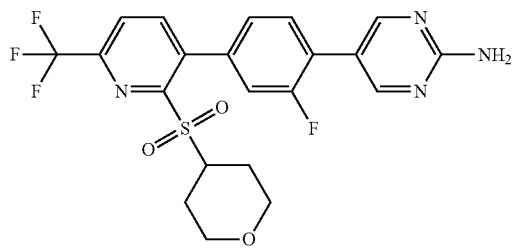

5-{2-Fluoro-4-[2-(tetrahydro-2H-pyran-4-ylsulfonyl)-6-(trifluoromethyl)pyridin-3-yl]phenyl}pyrimidin-2-amine.

The title compound was prepared in a manner similar to that described in Step D of Example 803 using 3-bromo-2-(tetrahydro-2H-pyran-4-ylsulfonyl)-6-(trifluoromethyl)pyridine and 5-(2-fluoro-4-(4,4,5,5-tetramethyl-1,3,2-dioxaborolan-2-yl)phenyl)pyrimidin-2-amine. MS (ESI): mass calcd. for $C_{21}H_{18}F_4N_4O_3S$, 482.10; m/z found, 483.1 [M+H]⁺. ¹H NMR (400 MHz, CD₃OD) δ 8.74 (d, J=0.8 Hz, 2H), 8.27 (d, J=8.1 Hz, 1H), 8.20 (d, J=8.1 Hz, 1H), 7.70-7.66 (m, 1H), 7.53-7.48 (m, 2H), 4.39-4.34 (m, 1H), 4.07-4.03 (m, 2H), 3.54-3.47 (m, 2H), 1.95-1.92 (m, 2H), 1.87-1.78 (m, 2H).

Example 908

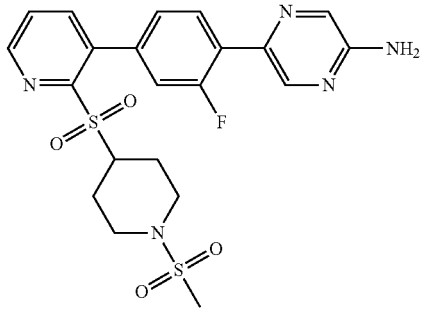

5-[2-Fluoro-4-(2-{[1-(methylsulfonyl)piperidin-4-yl]sulfonyl}pyridin-3-yl)phenyl]pyrazin-2-amine.

Step A: 3-Bromo-2-(1-(methylsulfonyl)piperidin-4-ylsulfonyl)pyridine

The intermediate was prepared in a manner similar to that described in Step D of Intermediate JV using methanesulfonyl chloride. MS (ESI): mass calcd. for $C_{11}H_{15}BrN_2O_4S_2$, 381.97; m/z found, 382.7 [M+H]⁺.

Step B: 5-[2-Fluoro-4-(2-{[1-(methylsulfonyl)piperidin-4-yl]sulfonyl}pyridin-3-yl)phenyl]pyrazin-2-amine The title compound was prepared in a manner similar to that described in Step D of Example 803 using 3-bromo-2-

(1-(methylsulfonyl)piperidin-4-ylsulfonyl)pyridine. MS (ESI): mass calcd. for $C_{21}H_{22}FN_5O_4S_2$, 491.11; m/z found, 492.1 [M+H]$^+$. $^1$H NMR (400 MHz, CD$_3$OD) δ 8.75 (dd, J=4.7, 1.5 Hz, 1H), 8.65 (d, J=1.2 Hz, 1H), 8.26 (d, J=1.2 Hz, 1H), 8.15-8.11 (m, 1H), 8.00 (dd, J=7.9, 1.5 Hz, 1H), 7.77 (dd, J=7.9, 4.7 Hz, 1H), 7.44-7.42 (m, 2H), 4.26-4.21 (m, 1H), 3.84-3.81 (m, 2H), 2.91-2.83 (m, 5H), 2.11-2.08 (m, 2H), 1.83-1.73 (m, 2H).

Example 909

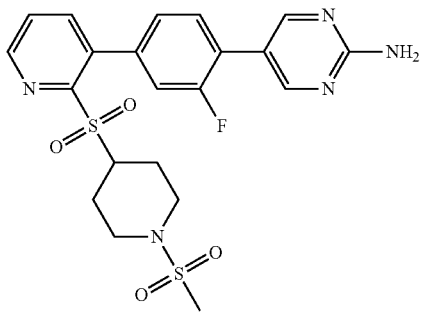

5-[2-Fluoro-4-(2-{[1-(methylsulfonyl)piperidin-4-yl]sulfonyl}pyridin-3-yl)phenyl]pyrimidin-2-amine.

The title compound was prepared in a manner similar to that described in Step D of Example 803 using 3-bromo-2-(1-(methylsulfonyl)piperidin-4-ylsulfonyl)pyridine and 5-(2-fluoro-4-(4,4,5,5-tetramethyl-1,3,2-dioxaboralan-2-yl)phenyl)pyrimidin-2-amine. MS (ESI): mass calcd. for $C_{21}H_{22}FN_5O_4S_2$, 491.11; m/z found, 492.1 [M+H]$^+$. $^1$H NMR (400 MHz, DMSO-d$_6$) δ 8.88 (s, 2H), 8.76 (dd, J=4.6, 1.5 Hz, 1H), 7.99 (dd, J=7.9, 1.5 Hz, 1H), 7.78 (dd, J=7.9, 4.7 Hz, 1H), 7.71-7.67 (m, 1H), 7.46 (dd, J=7.0, 1.4 Hz, 1H), 7.44-7.43 (m, 1H), 4.29-4.23 (m, 1H), 3.84-3.81 (m, 2H), 2.91-2.85 (m, 5H), 2.12-2.09 (m, 2H), 1.83-1.72 (m, 2H).

Example 910

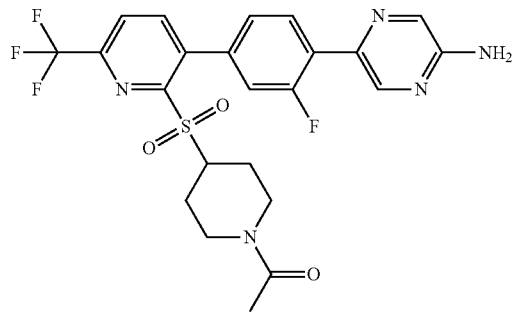

5-(4-{2-[(1-Acetylpiperidin-4-yl)sulfonyl]-6-(trifluoromethyl)pyridin-3-yl}-2-fluorophenyl)pyrazin-2-amine.

Step A: 1-(4-(3-Bromo-6-(trifluoromethyl)pyridin-2-ylsulfonyl)piperidin-1-yl)ethanone The intermediate was prepared in a manner similar to that described in Step D of Example 903 using 3-bromo-2-(piperidin-4-ylsulfonyl)-6-(trifluoromethyl)pyridine hydrochloride. MS (ESI): mass calcd. for $C_{13}H_{14}BrF_3N_2O_3S$ 413.99; m/z found, 414.6 [M+H]$^+$.

Step B: 5-(4-{2-[(1-Acetylpiperidin-4-ylsulfonyl]-6-(trifluoromethyl)pyridin-3-yl}-2-fluorophenyl)pyrazin-2-amine The title compound was prepared in a manner similar to that described in Step D of Example 803 using 1-(4-(3-bromo-6-(trifluoromethyl)pyridin-2-ylsulfonyl)piperidin-1-yl)ethanone. MS (ESI): mass calcd. for $C_{23}H_{21}F_4N_5O_3S$, 523.13; m/z found, 524.1 [M+H]$^+$. $^1$H NMR (400 MHz, CD$_3$OD) δ 8.73 (d, J=1.2 Hz, 1H), 8.32-8.29 (m, 2H), 8.25-8.18 (m, 2H), 7.58-7.50 (m, 2H), 4.64-4.61 (m, 1H), 4.42-4.36 (m, 1H), 4.10-4.07 (m, 1H), 3.29-3.23 (m, 1H), 2.83-2.76 (m, 1H), 2.18-2.15 (m, 1H), 2.12-2.07 (m, 4H), 1.81-1.75 (m, 1H), 1.73-1.59 (m, 1H).

Example 911

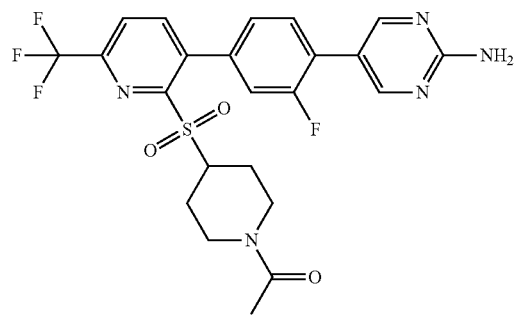

5-(4-{2-[(1-Acetylpiperidin-4-yl)sulfonyl]-6-(trifluoromethyl)pyridin-3-yl}-2-fluorophenyl)pyrimidin-2-amine.

The title compound was prepared in a manner similar to that described in Step D of Example 803 using 1-(4-(3-bromo-6-(trifluoromethyl)pyridin-2-ylsulfonyl)piperidin-1-yl) ethanone and 5-(2-fluoro-4-(4,4,5,5-tetramethyl-1,3,2-dioxaboralan-2-yl)phenyl)pyrimidin-2-amine. MS (ESI): mass calcd. for $C_{23}H_{21}F_4N_5O_3S$, 523.13; m/z found, 524.1 [M+H]$^+$. $^1$H NMR (400 MHz, CD$_3$OD) δ 8.93 (s, 2H), 8.30 (d, J=8.1 Hz, 1H), 8.23 (d, J=8.1 Hz, 1H), 7.79-7.75 (m, 1H), 7.61-7.51 (m, 2H), 4.64-4.61 (m, 1H), 4.45-4.34 (m, 1H), 4.11-4.07 (m, 1H), 3.33-3.26 (m, 1H), 2.84-2.78 (m, 1H), 2.23-2.05 (m, 5H), 1.85-1.76 (m, 1H), 1.71-1.61 (m, 1H).

Example 912

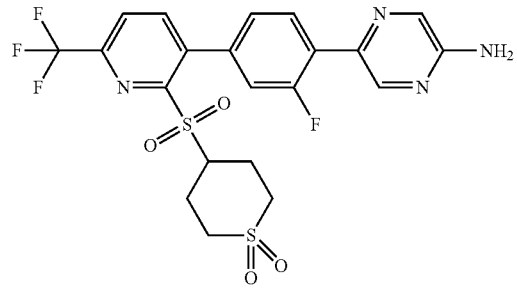

5-(4-{2-[(1,1-Dioxidotetrahydro-2H-thiopyran-4-yl)sulfonyl]-6-(trifluoromethyl)pyridin-3-yl}-2-fluorophenyl)pyrazin-2-amine.

Step A: 4-((3-Bromo-6-(trifluoromethyl)pyridin-2-yl)thio)tetrahydro-2H-thiopyran 1,1-dioxide The intermediate was prepared in a manner similar to that described in Step A of Intermediate JV using 3-bromo-6-(trifluoromethyl)pyridine-2-thiol and 4-iodotetrahydro-2H-thiopyran 1,1-dioxide. MS (ESI): mass calcd. for $C_{11}H_{11}BrF_3NO_2S_2$, 388.94; m/z found, 389.5 [M+H]$^+$.

Step B: 4-((3-Bromo-6-(trifluoromethyl)pyridin-2-yl)sulfonyl)tetrahydro-2H-thiopyran 1,1-dioxide The intermediate was prepared in a manner similar to that described in Step B of Intermediate JV using 4-((3-bromo-6-(trifluoromethyl)pyridin-2-yl)thio)tetrahydro-2H-thiopyran 1,1-dioxide. MS (ESI): mass calcd. for $C_{11}H_{11}BrF_3NO_4S_2$, 420.93; m/z found, 421.5 [M+H]$^+$.

Step C: 5-(4-{2-[(1,1-Dioxidotetrahydro-2H-thiopyran-4-yl)sulfonyl]-6-(trifluoromethyl)pyridin-3-yl}-2-fluorophenyl)pyrazin-2-amine The title compound was prepared in a manner similar to that described in Step D of Example 803 using 4-((3-bromo-6-(trifluoromethyl)pyridin-2-yl)sulfonyl)tetrahydro-2H-thiopyran 1,1-dioxide. MS (ESI): mass calcd. for $C_{21}H_{18}F_4N_4O_4S_2$, 530.07; m/z found, 531.0 [M+H]$^+$. $^1$H NMR (400 MHz, DMSO-d) δ 8.42-8.37 (m, 3H), 8.06 (s, 1H), 8.00-7.95 (m, 1H), 7.50 (dd, J=12.1, 1.5 Hz, 1H), 7.43 (dd, J=8.1, 1.7 Hz, 1H), 6.83 (s, 2H), 4.33-4.27 (m, 1H), 3.41-3.34 (m, 2H), 3.22-3.19 (m, 2H), 2.38-2.35 (m, 2H), 2.13-2.04 (m, 2H).

Example 913

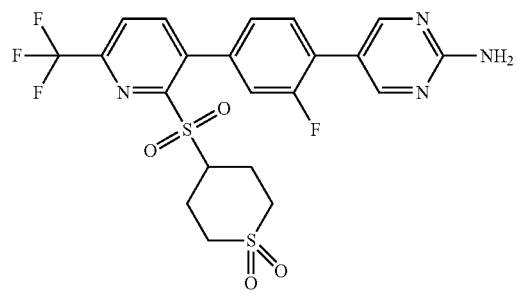

5-(4-{2-[(1,1-Dioxidotetrahydro-2H-thiopyran-4-yl)sulfonyl]-6-(trifluoromethyl)pyridin-3-yl}-2-fluorophenyl)pyrimidin-2-amine.

The title compound was prepared in a manner similar to that described in Step D of Example 803 using 4-((3-bromo-6-(trifluoromethyl)pyridin-2-yl)sulfonyl)tetrahydro-2H-thiopyran 1,1-dioxide and 5-(2-fluoro-4-(4,4,5,5-tetramethyl-1,3,2-dioxaboralan-2-yl)phenyl)pyrimidin-2-amine. MS (ESI): mass calcd. for $C_{21}H_{18}F_4N_4O_4S_2$, 530.07; m/z found, 531.0 [M+H]$^+$. $^1$H NMR (400 MHz, DMSO-d$_6$) δ 8.65-8.62 (m, 2H), 8.39 (s, 2H), 7.75-7.71 (m, 1H), 7.54 (d, J=11.6 Hz, 1H), 7.44 (d, J=8.0 Hz, 1H), 5.10 (s, 2H), 4.34-4.28 (m, 1H), 3.40-3.34 (m, 2H), 3.22-3.19 (m, 2H), 2.38-2.35 (m, 2H), 2.13-2.04 (m, 2H).

The following Examples 1-13 summarized in Table 4 are prophetic and unless otherwise specified, can be readily synthesized by a person skilled in the art utilizing the above described reaction schemes or by synthesis routes generally known to a person skilled in the art. One skilled in the art based on presently disclosed compounds would conclude the following prophetic compounds to be active against FLAP.

TABLE 4

Prophetic Examples

| STRUCTURE | No. | NAME |
|---|---|---|
| 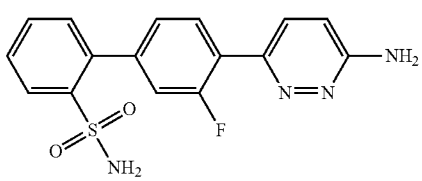 [SMILES: Nc1ccc(-c2ccc(-c3ccccc3S(N)(=O)=O)cc2F)nn1] | 1 | 4'-(6-Aminopyridazin-3-yl)-3'-fluorobiphenyl-2-sulfonamide |
| 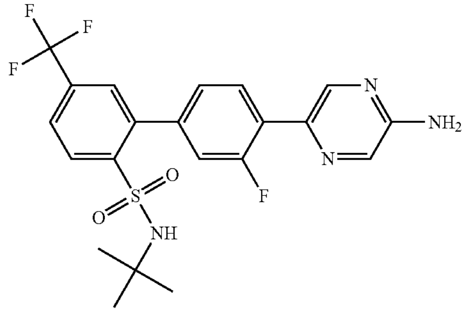 [SMILES: CC(C)(C)NS(=O)(=O)c1ccc(C(F)(F)F)cc1-c1ccc(-c2cnc(N)cn2)c(F)c1] | 2 | 4'-(5-Aminopyrazin-2-yl)-N-tert-butyl-3'-fluoro-5-(trifluoromethyl)biphenyl-2-sulfonamide |

TABLE 4-continued

Prophetic Examples

| STRUCTURE | No. | NAME |
|---|---|---|
| 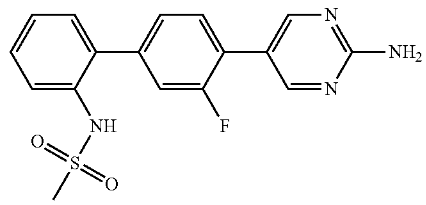 | 4 | N-[4'-(2-Aminopyrimidin-5-yl)-3'-fluorobiphenyl-2-yl]methanesulfonamide |
| 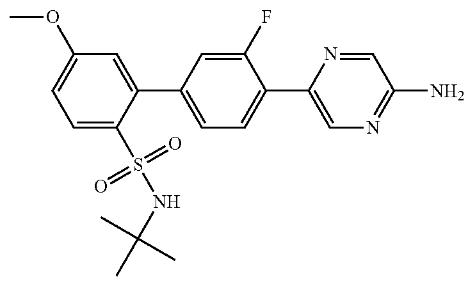 [SMILES: COc1ccc(S(=O)(=O)NC(C)(C)C)c(-c2ccc(-c3cnc(N)cn3)c(F)c2)c1] | 5 | 4'-(5-Aminopyrazin-2-yl)-N-tert-butyl-3'-fluoro-5-methoxybiphenyl-2-sulfonamide |
| 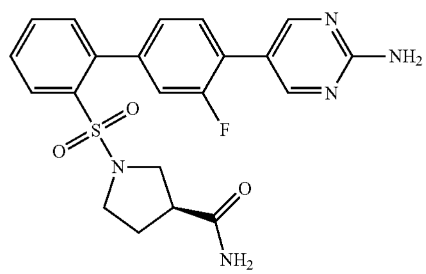 [SMILES: NC(=O)[C@H]1CCN(S(=O)(=O)c2ccccc2-c2ccc(-c3cnc(N)nc3)c(F)c2)C1] | 6 | (3S)-1-{[4'-(2-Aminopyrimidin-5-yl)-3'-fluorobiphenyl-2-yl]sulfonyl}pyrrolidine-3-carboxamide |
| 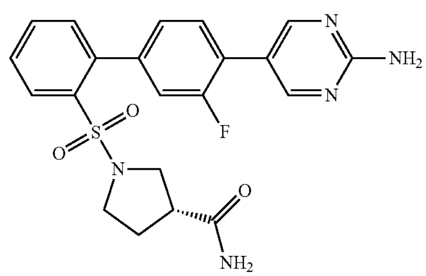 [SMILES: NC(=O)[C@@H]1CCN(S(=O)(=O)c2ccccc2-c2ccc(-c3cnc(N)nc3)c(F)c2)C1] | 7 | (3R)-1-{[4'-(2-Aminopyrimidin-5-yl)-3'-fluorobiphenyl-2-yl]sulfonyl}pyrrolidine-3-carboxamide |
| 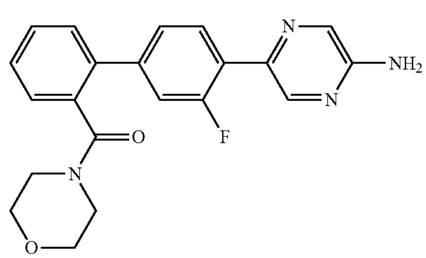 [SMILES: Nc1cnc(-c2ccc(-c3ccccc3C(=O)N3CCOCC3)cc2F)cn1] | 8 | 5-[3-Fluoro-2'-(morpholin-4-ylcarbonyl)biphenyl-4-yl]pyrazin-2-amine |
| 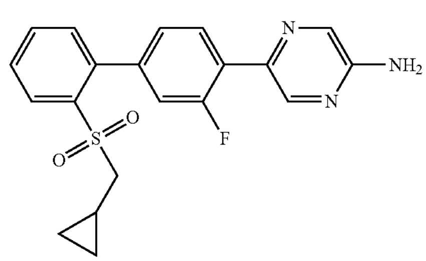 [SMILES: Nc1cnc(-c2ccc(-c3ccccc3S(=O)(=O)CC3CC3)cc2F)cn1] | 9 | 5-{2'-[(Cyclopropylmethyl)sulfonyl]-3-fluorobiphenyl-4-yl}pyrazin-2-amine |

TABLE 4-continued

Prophetic Examples

| STRUCTURE | No. | NAME |
|---|---|---|
| (structure) | 10 | 1-{[4'-(2-Aminopyrimidin-5-yl)-3'-fluorobiphenyl-2-yl]sulfonyl}-4-(pentafluoroethyl)piperidin-4-ol |
| (structure) | 11 | tert-Butyl (1-{[3'-fluoro-4'-(5H-pyrrolo[2,3-b]pyrazin-2-yl)biphenyl-2-yl]sulfonyl}piperidin-4-yl)carbamate |
| (structure) | 12 | 4'-(5-Aminopyrazin-2-yl)-N-tert-butyl-3',4-difluorobiphenyl-2-sulfonamide |
| (structure) | 13 | 4'-(5-Aminopyrazin-2-yl)-N-tert-butyl-3'-fluoro-4-(trifluoromethyl)biphenyl-2-sulfonamide |

D) General Administration, Formulation, and Dosages

The present invention provides substituted heteroaryl ketone compounds which are useful as FLAP modulators.

The invention features a method for treating a subject in need thereof with an FLAP-mediated disease and/or disorder, said method comprising administering to the subject a therapeutically effective amount of a compound of the invention. In particular, the invention also provides a method for treating or inhibiting the progression of an FLAP-mediated disease and/or disorder, or associated symptoms or complications thereof in a subject afflicted with such a disease and/or disorder, wherein the method comprises administering to the subject a therapeutically effective amount of a compound of the invention.

Embodiments of the present invention include a method wherein the compound of Formula (I) is a FLAP modulator.

Embodiments of the present invention include a use of the compound of Formula (I) in the manufacture of a medicament for treating an FLAP-mediated disease and/or disorder.

Embodiments of the present invention include a use of the compound of Formula (I) as a medicine.

The compounds of Formula (I) have an FLAP-modulating effect and are useful as therapeutic agents for various FLAP-mediated disorders and/or disorders, or associated symptoms or complications, for example, respiratory disorders, cardiac and cardiovascular diseases, autoimmune disorders, carcinogenesis, and associated symptoms or complications thereof.

The compounds of Formula (I) may be administered orally or parenterally, and after formulation into preparations suitable for the intended administration route, they can be used as therapeutic agents for treating an FLAP-mediated disease and/or disorder. FLAP-mediated diseases and/or disorders include, but are not limited, diseases and/or disorders that are related to leukotriene synthesis pathway, and therefore may be treated, controlled or in some cases prevented, by treatment with the compounds of this invention.

One aspect of the present invention provides a method for the treatment of diseases and/or disorders, or associated symptoms or complications thereof, responsive to the modulation of FLAP in a subject in need thereof which comprises administering to the subject a therapeutically or prophylactically effective amount of a compound of Formula (I) or a form thereof.

Another aspect of the present invention provides a method for the treatment of a disease and/or disorder selected from the group consisting of respiratory diseases and/or disorders, cardiac and cardiovascular diseases and/or disorders, autoimmune diseases and/or disorders, carcinogenesis, and associated symptoms or complications thereof, in a subject in need thereof which comprises administering to the subject a therapeutically or prophylactically effective amount of a compound of Formula (I) or a form thereof.

More specifically, this invention is directed to a method of treating exacerbations, non-allergic asthma, aspirin exacerbated respiratory disease, pulmonary arterial hypertension, fibrotic lung diseases, acute respiratory distress syndrome, obstructive sleep apnea and chronic obstructive pulmonary disease, or associated symptoms or complications thereof, in a subject afflicted with such a disease and/or disorder, wherein the method comprises administering to the subject a therapeutically or prophylactically effective amount of a compound of Formula (I) or a form thereof.

Furthermore, this invention is directed to a method of treating myocardial infarction, atherosclerosis and coronary artery disease, stroke, aortic aneurisms, atherosclerosis, or associated symptoms or complications thereof, in a subject afflicted with such a disease and/or disorder, wherein the method comprises administering to the subject a therapeutically or prophylactically effective amount of a compound of Formula (I) or a form thereof.

Yet, this invention is also directed to a method of treating rheumatoid arthritis, inflammatory bowel disease, nephritis, spondyloarthritis, polymyositis, dermatomyositis, gouty effusions, systemic lupus erythematosus, systemic sclerosis, Alzheimer's disease, multiple sclerosis, allergic rhinitis, chronic sinusitis, allergic dermatitis and asthma, wherein the method comprises administering to the subject a therapeutically or prophylactically effective amount of a compound of Formula (I) or a form thereof.

Finally, this invention is also directed to a method of treating tumor cell proliferation, differentiation, and apoptosis, tumor-associated angiogenesis, as well as the migration and invasion of carcinoma cells, wherein the method comprises administering to the subject a therapeutically or prophylactically effective amount of a compound of Formula (I) or a form thereof.

Another aspect of the present invention provides a pharmaceutical composition comprising at least one compound of Formula (I) or a form thereof, and a pharmaceutically acceptable carrier.

The invention also features a method for treating a subject in need thereof with an FLAP-mediated disease and/or disorder, said method comprising administering to the subject a therapeutically effective amount of a pharmaceutical composition comprising at least one compound of the invention.

Yet another aspect of the present invention relates to the use of a compound of Formula (I) or a form thereof, for the manufacture of a medicament useful for the treatment of an FLAP-mediated disease and/or disorder in a subject in need thereof.

In a clinical use of the compounds of the invention, pharmaceutically-acceptable additives may be added thereto to formulate various preparations in accordance with the intended administration route thereof, and the preparations may be administered.

Various additives generally used in the field of pharmaceutical compositions may be used herein, including, for example, gelatin, lactose, sucrose, titanium oxide, starch, crystalline cellulose, methyl cellulose, hydroxypropylmethyl cellulose, carboxymethyl cellulose, corn starch, microcrystalline wax, white petrolatum, magnesium metasilicate aluminate, anhydrous calcium phosphate, citric acid, trisodium citrate, hydroxypropyl cellulose, sorbitol, sorbitan fatty acid ester, polysorbate, sucrose fatty acid ester, polyoxyethylene, hardened castor oil, polyvinylpyrrolidone, magnesium stearate, palmitoleic acid, light silicic acid anhydride, talc, vegetable oil, benzyl alcohol, gum arabic, propylene glycol, polyalkylene glycol, cyclodextrin, and hydroxypropylcyclodextrin.

Combined with such additives, the compound of the invention may be formulated into various forms of preparations, for example, solid preparations such as tablets, capsules, granules, powders and suppositories; and liquid preparations such as syrups, elixirs and injections. These preparations can be produced in any method known in the field of pharmaceutical compositions. The liquid preparations may be in such a form that is dissolved or suspended in water or in any other suitable medium before use. Especially for injections, the preparation may be dissolved or suspended, if desired, in a physiological saline or glucose solution, and a buffer and a preservative may be added thereto.

The compounds of the invention are effective for animals, including humans and other mammals. Any ordinary physician, veterinarian or clinician may readily determine the necessity, if any, of treatment with an instant compound.

Those of skill in the treatment of diseases and/or disorders, or associated symptoms or complications thereof, mediated by FLAP can determine the effective daily amount from the test results presented hereinafter and other information. The exact dosage and frequency of administration depends on the particular compound of invention used, the particular disease and/or disorder, or associated symptoms or complications thereof, being treated, the severity of the disease and/or disorder, or associated symptoms or complications thereof, being treated, the age, weight and general physical condition of the particular patient as well as other medication the patient may be taking, as is well known to those skilled in the art. Furthermore, it is evident that said effective daily amount may be lowered or increased depending on the response of the treated patient and/or depending on the evaluation of the physician prescribing the compounds of the instant invention. The effective daily amount ranges mentioned herein are therefore only guidelines in practicing the present invention.

Preferably, the method for the treatment of the FLAP diseases and/or disorders described in the present invention using any of the compounds as defined herein, the dosage form will contain a pharmaceutically acceptable carrier containing between from about 1 mg to about 1000 mg; particularly from about 0.5 mg to about 500 mg of the compound, and may be constituted into any form suitable for the mode of administration selected. The dosages, however, may be varied depending upon the requirement of the subjects, the severity of the disease and/or disorder, or associated symptoms or complications thereof, being treated and the compound being employed. The use of either daily administration or post-periodic dosing may be employed.

When the compound of the invention is, for example, put into clinical use, then its dose and its administration frequency may vary depending on the sex, the age, the body weight and the condition of the patient and on the type and the range of the necessary treatment with the compound. For oral administration, in general, the dose of the compound may be in a range of from about 0.01 mg/kg/day to about 100 mg/kg of body weight/day or in a range of from about 0.03 mg/kg/day to about 1 mg/kg/day. The oral administration frequency is preferably from one to a few times per day. For parenteral administration, the dose may be in a range of from about 0.001 mg/kg/day to about 10 mg/kg/day, in a range of from about 0.001 mg/kg/day to about 0.1 mg/kg/day or, in a range of from about 0.01 mg/kg/day to about 0.1 mg/kg/day. The parenteral administration frequency is preferably from one to a few times per day. For oral administration, the compositions are preferably provided in the form of tablets containing from about 1.0 mg to about 1000 mg of the active ingredient, particularly 1 mg, 5 mg, 10 mg, 15 mg, 20 mg, 25 mg, 50 mg, 75 mg, 100 mg, 150 mg, 200 mg, 250 mg, 300 mg, 400 mg, 500 mg, 600 mg, 750 mg, 800 mg, 900 mg, and 1000 mg of the active ingredient for the symptomatic adjustment of the dosage to the patient to be treated. The compounds may be administered on a regimen of 1 to 4 times per day, preferably once or twice per day.

Ordinary physicians, veterinarians and clinicians may readily determine the effective dose of the pharmaceutical compound necessary to treat, prevent, inhibit, retard or stop the intended disease, and may readily treat the diseased patient with the compound.

The pharmaceutical compositions herein will contain, per unit dosage unit, e.g., tablet, capsule, powder, injection, suppository, teaspoonful and the like, of from about 0.001 mg/kg/day to about 10 mg/kg/day (particularly from about 0.01 mg/kg/day to about 1 mg/kg/day; and, more particularly, from about 0.1 mg/kg/day to about 0.5 mg/kg/day) and may be given at a dosage of from about 0.001 mg/kg/day to about 30 mg/kg/day (particularly from about 0.01 mg/kg/day to about 2 mg/kg/day, more particularly from about 0.1 mg/kg/day to about 1 mg/kg/day and even more particularly from about 0.5 mg/kg/day to about 1 mg/kg/day).

Preferably these compositions are in unit dosage forms from such as tablets, pills, capsules, dry powders for reconstitution or inhalation, granules, lozenges, sterile parenteral solutions or suspensions, metered aerosol or liquid sprays, drops, ampoules, autoinjector devices or suppositories for administration by oral, intranasal, sublingual, intraocular, transdermal, parenteral, rectal, vaginal, dry powder inhaler or other inhalation or insufflation means. Alternatively, the composition may be presented in a form suitable for 1 to 4 times per day, preferably once or twice per day administration; for example, an insoluble salt of the active compound, such as the decanoate salt, may be adapted to provide a depot preparation for intramuscular injection.

The preparation may contain the compound of the invention in an amount in a range of from about 1.0 to about 100% by weight or, in a range of from about 1.0 to about 60% by weight of the preparation. The preparation may contain any other therapeutically-effective compound.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the subject. Conventional procedures for the selection and preparation of suitable prodrug derivatives are described, for example, in "*Design of Prodrugs*", ed. H. Bundgaard, Elsevier, 1985.

Some of the crystalline forms for the compounds may exist as polymorphs and as such are intended to be included in the present invention. In addition, some of the compounds may form solvates with water (i.e., hydrates) or common organic solvents, and such solvates are intended to be encompassed within the scope of this invention.

Where the processes for the preparation of the compounds according to the invention give rise to mixtures of stereoisomers, these isomers may be separated by conventional techniques such as preparative chromatography. The compounds may be prepared in racemic form or as individual enantiomers or diasteromers by either stereospecific synthesis or by resolution. The compounds may, for example, be resolved into their component enantiomers or diastereomers by standard techniques, such as the formation of stereoisomeric pairs by salt formation with an optically active base, followed by fractional crystallization and regeneration of the free acid. The compounds may also be resolved by formation of stereoisomeric esters or amides, followed by chromatographic separation and removal of the chiral auxiliary. Alliteratively, the compounds may be resolved using a chiral HPLC column. It is to be understood that all stereoisomers, racemic mixtures, diastereomers, cis-trans isomers, and enantiomers thereof are encompassed within the scope of the present invention.

E) Use

Dosages

For preparing pharmaceutical compositions such as tablets, the principal active ingredient is mixed with a pharmaceutical carrier, e.g. conventional tableting ingredients such as diluents, binders, adhesives, disintegrants, lubricants, antiadherents and gildants. Suitable diluents include, but are not limited to, starch (i.e. corn, wheat, or potato starch, which may be hydrolized), lactose (granulated, spray dried or anhydrous), sucrose, sucrose-based diluents (confectioner's sugar; sucrose plus about 7 to 10 weight percent invert sugar; sucrose plus about 3 weight percent modified dextrins; sucrose plus invert sugar, about 4 weight percent invert sugar, about 0.1 to 0.2 weight percent cornstarch and magnesium stearate), dextrose, inositol, mannitol, sorbitol, microcrystalline cellulose (i.e. AVICEL™ microcrystalline cellulose available from FMC Corp.), dicalcium phosphate, calcium sulfate dihydrate, calcium lactate trihydrate and the like. Suitable binders and adhesives include, but are not limited to *acacia* gum, guar gum, tragacanth gum, sucrose, gelatin, glucose, starch, and cellulosics (i.e. methylcellulose, sodium carboxymethylcellulose, ethylcellulose, hydroxypropylmethylcellulose, hydroxypropylcellulose, and the like), water soluble or dispersible binders (i.e. alginic acid and salts thereof, magnesium aluminum silicate, hydroxyethylcellulose [i.e. TYLOSE™ available from Hoechst Celanese], polyethylene glycol, polysaccharide acids, bentonites, polyvinylpyrrolidone, polymethacrylates and pregelatinized starch) and the like. Suitable disintegrants include, but are not limited to, starches (corn, potato, etc.), sodium starch glycolates, pregelatinized starches, clays (magnesium aluminum silicate), celluloses (such as crosslinked sodium carboxymethylcellulose and microcrystalline cellulose), alginates, pregelatinized starches (i.e. corn starch, etc.), gums (i.e. agar, guar, locust bean, karaya, pectin, and tragacanth gum), cross-linked polyvinylpyrrolidone and the like. Suitable lubricants and antiadherents include, but are not limited to, stearates (magnesium, calcium and sodium), stearic acid, talc waxes, stearowet, boric acid, sodium chloride, DL-leucine, carbowax 4000, carbowax 6000, sodium oleate, sodium benzoate, sodium acetate, sodium lauryl sulfate, magnesium lauryl sulfate and the like. Suitable gildants include, but are not limited to, talc, cornstarch, silica (i.e. CAB-O-SIL™ rusilica available from Cabot, SYLOID™ silica available from W.R. Grace/Davison, and AEROSIL™ silica available from Degussa) and the like. Sweeteners and flavorants may be added to chewable solid dosage forms to improve the palatability of the oral dosage form. Additionally, colorants and coatings may be added or applied to the solid dosage form for ease of identification of the drug or for aesthetic purposes. These carriers are formulated with the pharmaceutical active to provide an accurate, appropriate dose of the pharmaceutical active with a therapeutic release profile.

Generally these carriers are mixed with the pharmaceutical active to form a solid preformulation composition containing a homogeneous mixture of the pharmaceutical active form of the present invention, or a pharmaceutically acceptable salt thereof. Generally the preformulation will be formed by one of three common methods: (a) wet granulation, (b) dry granulation and (c) dry blending. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from about 0.1 mg to about 500 mg of the active ingredient of the present invention. The tablets or pills containing the novel compositions may also be formulated in multilayer tablets or pills to provide a sustained or provide dual-release products. For example, a dual release tablet or pill can comprise an inner dosage and an outer dosage component the latter being in the form of an envelope over the former. The two components can be separated by an enteric layer, which serves to resist disintegration in the stomach and permits the inner component to pass intact into the duodenum or to be delayed in release. A variety of materials can be used for such enteric layers or coatings, such materials including a number of polymeric materials such as shellac, cellulose acetate (i.e. cellulose acetate phthalate, cellulose acetate trimetllitate), polyvinyl acetate phthalate, hydroxypropyl methylcellulose phthalate, hydroxypropyl methylcellulose acetate succinate, methacrylate and ethylacrylate copolymers, methacrylate and methyl methacrylate copolymers and the like. Sustained release tablets may also be made by film coating or wet granulation using slightly soluble or insoluble substances in solution (which for a wet granulation acts as the binding agents) or low melting solids a molten form (which in a wet granulation may incorporate the active ingredient). These materials include natural and synthetic polymers waxes, hydrogenated oils, fatty acids and alcohols (i.e. beeswax, carnauba wax, cetyl alcohol, cetylstearyl alcohol, and the like), esters of fatty acids metallic soaps, and other acceptable materials that can be used to granulate, coat, entrap or otherwise limit the solubility of an active ingredient to achieve a prolonged or sustained release product.

The liquid forms in which the novel compositions of the present invention may be incorporated for administration orally or by injection include, but are not limited to aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable suspending agents for aqueous suspensions, include synthetic and natural gums such as, acacia, agar, alginate (i.e. propylene alginate, sodium alginate and the like), guar, karaya, locust bean, pectin, tragacanth, and xanthan gum, cellulosics such as sodium carboxymethylcellulose, methylcellulose, hydroxymethylcellulose, hydroxyethylcellulose, hydroxypropyl cellulose and hydroxypropyl methylcellulose, and combinations thereof, synthetic polymers such as polyvinyl pyrrolidone, carbomer (i.e. carboxypolymethylene), and polyethylene glycol; clays such as bentonite, hectorite, attapulgite or sepiolite; and other pharmaceutically acceptable suspending agents such as lecithin, gelatin or the like. Suitable surfactants include but are not limited to sodium docusate, sodium lauryl sulfate, polysorbate, octoxynol-9, nonoxynol-10, polysorbate 20, polysorbate 40, polysorbate 60, polysorbate 80, polyoxamer 188, polyoxamer 235 and combinations thereof. Suitable deflocculating or dispersing agents include pharmaceutical grade lecithins. Suitable flocculating agents include but are not limited to simple neutral electrolytes (i.e. sodium chloride, potassium, chloride, and the like), highly charged insoluble polymers and polyelectrolyte species, water soluble divalent or trivalent ions (i.e. calcium salts, alums or sulfates, citrates and phosphates (which can be used jointly in formulations as pH buffers and flocculating agents). Suitable preservatives include but are not limited to parabens (i.e. methyl, ethyl, n-propyl and n-butyl), sorbic acid, thimerosal, quaternary ammonium salts, benzyl alcohol, benzoic acid, chlorhexidine gluconate, phenylethanol and the like. There are many liquid vehicles that may be used in liquid pharmaceutical dosage forms; however, the liquid vehicle that is used in a particular dosage form must be compatible with the suspending agent(s). For example, nonpolar liquid vehicles such as fatty esters and oils liquid vehicles are best used with suspending agents such as low HLB (Hydrophile-Lipophile Balance) surfactants, stearalkonium hectorite, water insoluble resins, water insoluble film forming polymers and the like. Conversely, polar liquids such as water, alcohols, polyols and glycols are best used with suspending agents such as higher HLB surfactants, clays silicates, gums, water soluble cellulosics, water soluble polymers and the like. For parenteral administration, sterile suspensions and solutions are desired. Liquid forms useful for parenteral administration include sterile solutions, emulsions and suspensions.

Isotonic preparations which generally contain suitable preservatives are employed when intravenous administration is desired.

Furthermore, compounds of the present invention can be administered in an intranasal dosage form via topical use of suitable intranasal vehicles or via transdermal skin patches, the composition of which are well known to those of ordinary skill in that art. To be administered in the form of a transdermal delivery system, the administration of a therapeutic dose will, of course, be continuous rather than intermittent throughout the dosage regimen.

Compounds of the present invention can also be administered in the form of liposome delivery systems, such as small unilamellar vesicles, large unilamellar vesicles, multilamellar vesicles and the like. Liposomes can be formed from a variety of phospholipids, such as cholesterol, stearylamine, phosphatidylcholines and the like.

The daily dose of a pharmaceutical composition of the present invention may be varied over a wide range from about 0.1 mg to about 5000 mg; preferably, the dose will be in the range of from about 1 mg to about 100 mg per day for an average human. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 or 500 milligrams of the active ingredient for the symptomatic adjustment of the dosage to the subject to be treated. Advantageously, a compound of the present invention may be administered in a single daily dose or the total daily dosage may be administered in divided doses of two, three or four times daily.

It is also apparent to one skilled in the art that the therapeutically effective dose for active compounds of the invention or a pharmaceutical composition thereof will vary according to the desired effect. Therefore, optimal dosages to be administered may be readily determined by those skilled in the art, and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

Compounds of this invention may be administered in any of the foregoing compositions and dosage regimens or by means of those compositions and dosage regimens established in the art whenever use of the compounds of the invention as FLAP modulators is required for a subject in need thereof.

In their use, the compounds of the invention may be combined with any other therapeutic agents that are useful for the treatment of an FLAP-mediated disorder.

The combination includes not only the composition of compounds of the invention and one other active substance but also the composition of compounds of the invention and two or more other active substances or non-drug therapy. The scope of possible combinations of a compound of the invention and one, two or more active substances are within the knowledge of one skilled in the art for the treatment of an FLAP-mediated disorder.

Specifically, the combination of a FLAP modulator with prostaglandin modulators, cyclooxygenase-1 modulators, or cyclooxygenase-2 modulators might be used to treat inflammatory and autoimmune diseases and/or disorders as well as cardiovascular diseases and/or disorders, or vascular injury (Z. Yu et al., "Disruption of the 5-lipoxygenase pathway attenuates atherogenesis consequent to COX-2 deletion in mice," *Proc. Natl. Acad. Sci. USA,* 2012, 109(17), 6727-32; Z. Yu et al., "Myeloid Cell 5-Lipoxygenase Activating Protein Modulates the Response to Vascular Injury," *Circ. Res.,* 2012, Epub December 18). Due to the synergy of histamine and leukotrienes, the combination of a FLAP modulator and a histamine receptor 1 or 4 antagonist might have utility in treating respiratory, allergic, dermatological and autoimmune disorders (A. Reicin et al., "Montelukast, a leukotriene receptor antagonist, in combination with loratadine, a histamine receptor antagonist, in the treatment of chronic asthma," *Arch. Intern. Med.,* 2000, 160(16), 2418-88; S. Sanada et al., "The effectiveness of montelukast for the treatment of anti-histamine-resistant chronic urticaria," *Arch. Dermatol. Res.,* 2005, 297(3), 134-38).

Formulations

To prepare the pharmaceutical compositions of this invention, one or more compounds of Formula (I) or salt thereof as the active ingredient, is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients,* published by the American Pharmaceutical Association and the Pharmaceutical Society of Great Britain.

The compounds of the present invention may be formulated into various pharmaceutical forms for administration purposes. Methods of formulating pharmaceutical compositions have been described in numerous publications such as *Pharmaceutical Dosage Forms: Tablets. Second Edition. Revised and Expanded,* Volumes 1-3, edited by Lieberman et al; *Pharmaceutical Dosage Forms: Parenteral Medications,* Volumes 1-2, edited by Avis et al; and *Pharmaceutical Dosage Forms: Disperse Systems,* Volumes 1-2, edited by Lieberman et al; published by Marcel Dekker, Inc.

F) Biological Examples

The ability of the compounds of the present invention to treat a FLAP-mediated disease and/or disorder, or associated symptoms or complications thereof, was determined using the following procedures. Binding assay data represent the average value obtained from two different assay plates, with samples run in duplicate on each plate. Human whole blood assay data represent a single replicate on an assay plate using whole blood from at least one healthy donor. Certain FLAP binding and human whole blood assay data are presented in Table 5.

FLAP Binding Assay

The assay below is used to test the modulatory activity of compounds against FLAP. Human and mouse FLAP-encoding DNA was amplified by polymerase chain reaction and cloned into pFastBac1 (Invitrogen) with a NH2-terminal 6-His tag for expression in *Spodoptera frugiperda* (Sf-9) cells. FLAP-containing membranes were prepared as was a FITC-labeled FLAP modulator [5-[({2-(2-{3-[3-(tert-Butylsulfanyl)-1-(4-chlorobenzyl)-5-(quinolin-2-ylmethoxy)-1H-indol-2-yl]-2,2-dimethylpropanoyl}hydrazino)-2-oxoethyl]sulfanyl}acetyl)amino]-2-(6-hydroxy-3-oxo-3H-xanthen-9-yl)benzoic acid]. The FLAP binding assay is performed in HTRF format (homogeneous time resolved fluorescence). FLAP-containing membranes (1 µg/well final for human) are incubated in the presence of the HTRF ligand. [5-[({[2-(2-{3-[3-(tert-butylsulfanyl)-1-(4-chlorobenzyl)-5-(quinolin-2-ylmethoxy)-1H-indol-2-yl]-2,2-dimethylpropanoyl}hydrazino)-2-oxoethyl]sulfanyl}acetyl)amino]-2-(6-hydroxy-3-oxo-3H-xanthen-9-yl)benzoic acid] (25 nM final), a terbium labeled anti-His tag antibody (0.5 ng/well final, from Cisbio) and compounds. The reaction is allowed to proceed for two hours after which the plate is read on an Envision plate reader in HTRF mode. Data are expressed as a HTRF ratio.

For human FLAP binding assays, data are analyzed with 3DX Explorer software. A ratio is calculated with the relative light units at 520 nm over the relative light units at 495 nm. For analysis, data from multiple runs are averaged and each compound may be tested in 2 to 20 runs. Each run comprises two plates and each plate includes duplicates. Data from each plate is averaged and data are imported into 3DX. The data from multiple runs are aggregated as the average of duplicates of the calculated ratios in order to calculate $K_i$ and $IC_{50}$ values. It will be understood that a calculated value of 0.000 in Table 5 indicates that the $K_i$ is less than 1 nM. The letters ND and/or the absence of data in any of the boxes in Table 5 and Table 6 indicates that $K_i$ or $IC_{50}$ values were not determined.

Human Whole Blood Assay

An in vitro cellular assay was performed using human whole blood collected in heparin-containing tubes, which was used to test the ability of compounds to modulate the leukotriene pathway in human whole blood. The blood was diluted 1:1 in RPMI medium, pre-incubated for 15 min at 37° Celsius with test compounds at various concentrations, and then stimulated with calcium ionophore, A23187 (7 µg/mL), for 30 min at 37° Celsius. The samples were then centrifuged and plasma was removed. The plasma was diluted in assay buffer and $LTB_4$ levels were measured using a commercial kit (Enzo Life Sciences). The concentration of each compound that was required for half-maximal inhibition (modulation) of recombinant enzyme activity ($IC_{50}$) was calculated by a 4-parameter equation using the program GraphPad Prism (GraphPad software).

TABLE 5

FLAP binding and Human Whole Blood assay data

| Cmp No. | FLAP Binding wild type HTRF $K_i$ (µM) | Human Whole Blood LTB4 $IC_{50}$ 1:1 (µM) |
|---|---|---|
| 1 | 0.217 | 0.860 |
| 2 | 0.286 | 0.358 |
| 3 | >10 | |
| 4 | 0.001 | 0.018 |
| 5 | 0.035 | 0.370 |
| 6 | 0.001 | 0.033 |
| 7 | 0.002 | 0.014 |
| 8 | 0.001 | 0.012 |
| 9 | 0.003 | 0.060 |
| 10 | 0.003 | 0.053 |
| 11 | 0.002 | 0.015 |
| 12 | 0.002 | 0.021 |
| 13 | 0.001 | 0.018 |
| 14 | 0.003 | 0.032 |
| 15 | 0.010 | 0.059 |
| 16 | 0.006 | 0.018 |
| 17 | 0.002 | 0.025 |
| 18 | 0.002 | 0.070 |
| 19 | 0.002 | 0.050 |
| 20 | 0.001 | 0.009 |
| 21 | 0.002 | 0.035 |
| 22 | 0.002 | 0.048 |
| 23 | 0.001 | 0.013 |
| 24 | 0.002 | 0.048 |
| 25 | 0.003 | 0.023 |
| 26 | 0.001 | 0.026 |
| 27 | 0.029 | 10.000 |
| 28 | 0.090 | 0.325 |
| 29 | 0.059 | 0.030 |
| 30 | 0.095 | |
| 31 | 0.004 | 0.036 |
| 32 | 0.008 | 0.030 |
| 33 | 0.304 | |
| 34 | 0.031 | 0.334 |
| 35 | 0.036 | 0.094 |
| 36 | 0.010 | 0.120 |
| 37 | 0.030 | 0.676 |
| 38 | 0.033 | 0.177 |
| 39 | 0.008 | 0.075 |
| 40 | 0.014 | 0.112 |
| 41 | 0.014 | 2.687 |
| 42 | 0.011 | 0.149 |
| 43 | 0.002 | 0.111 |
| 44 | 0.007 | 0.058 |
| 45 | 0.003 | 0.010 |
| 46 | 0.057 | 0.194 |
| 47 | 0.001 | 0.017 |
| 48 | 0.011 | 0.158 |
| 49 | 0.002 | 0.021 |
| 50 | 0.001 | 0.015 |
| 51 | 0.004 | 0.042 |
| 52 | 0.004 | 0.155 |
| 53 | 0.003 | 0.238 |
| 54 | 0.020 | 0.023 |
| 55 | 0.001 | 1.232 |
| 56 | 0.011 | 3.516 |
| 57 | 0.015 | 0.252 |
| 58 | 0.005 | 0.991 |
| 59 | 0.020 | 1.017 |
| 60 | 0.028 | 0.464 |
| 61 | 0.011 | 0.117 |
| 62 | 0.142 | 0.111 |
| 63 | 0.006 | 0.028 |
| 64 | 0.002 | 0.006 |
| 65 | 0.049 | 0.322 |
| 66 | 0.021 | 0.069 |
| 67 | 0.003 | 0.012 |
| 68 | 0.001 | 0.006 |
| 69 | 0.001 | 0.008 |
| 70 | 0.002 | 0.010 |
| 71 | 0.002 | 0.023 |
| 72 | 0.111 | 0.168 |
| 73 | 0.062 | 0.077 |
| 74 | 0.006 | 0.061 |
| 75 | 0.012 | 0.185 |
| 76 | 0.002 | 0.027 |
| 77 | 0.003 | 0.342 |
| 78 | 0.001 | 0.166 |
| 79 | 0.005 | 0.150 |
| 80 | 0.004 | 0.088 |
| 81 | 0.006 | 0.152 |
| 82 | 0.001 | 0.018 |
| 83 | 0.001 | 0.019 |
| 84 | 0.003 | 0.097 |
| 85 | 0.002 | 0.020 |
| 86 | 0.003 | 0.027 |
| 87 | 0.003 | 0.075 |
| 88 | 0.007 | 0.036 |
| 89 | 0.006 | 0.043 |
| 90 | 0.001 | 0.012 |
| 91 | 0.005 | 0.028 |
| 92 | 0.325 | 0.222 |
| 93 | 0.127 | 0.128 |
| 94 | 0.076 | 0.235 |
| 95 | 0.010 | 0.053 |
| 96 | 0.354 | >10 |
| 97 | 0.008 | 0.042 |
| 98 | 0.008 | 0.039 |
| 99 | 0.002 | 0.030 |

TABLE 5-continued

FLAP binding and Human Whole Blood assay data

| Cmp No. | FLAP Binding wild type HTRF $K_i$ (µM) | Human Whole Blood LTB4 IC$_{50}$ 1:1 (µM) |
|---|---|---|
| 100 | 0.001 | 0.024 |
| 101 | 0.002 | 0.014 |
| 102 | 0.000 | 0.035 |
| 103 | 0.000 | 0.017 |
| 104 | 0.012 | >1 |
| 105 | 0.025 | 0.481 |
| 106 | 0.019 | >1 |
| 107 | 0.016 | 0.132 |
| 108 | 0.010 | 0.049 |
| 109 | 0.001 | 0.018 |
| 110 | 0.003 | 0.029 |
| 111 | 0.004 | 0.058 |
| 112 | 0.007 | 0.154 |
| 113 | 0.010 | 0.145 |
| 114 | 0.012 | 0.221 |
| 115 | 0.004 | 0.108 |
| 116 | 0.001 | 0.012 |
| 117 | 0.001 | 0.007 |
| 118 | 0.000 | 0.006 |
| 119 | 0.003 | 0.022 |
| 120 | 0.001 | 0.017 |
| 121 | 0.000 | 0.010 |
| 122 | 0.001 | 0.018 |
| 123 | 0.083 | 1.125 |
| 124 | 0.035 | 0.217 |
| 125 | 0.050 | >10 |
| 126 | 0.141 | 0.572 |
| 127 | 0.002 | 0.035 |
| 128 | 0.001 | 0.038 |
| 129 | 0.004 | 0.534 |
| 130 | 0.129 | 0.633 |
| 131 | 0.144 | 0.695 |
| 132 | 0.002 | 0.011 |
| 133 | 0.001 | 0.032 |
| 134 | 0.001 | >1 |
| 135 | 0.000 | 0.016 |
| 136 | 0.001 | 0.015 |
| 137 | 0.003 | 0.044 |
| 138 | 0.011 | 0.174 |
| 139 | 0.133 | 0.341 |
| 140 | 0.001 | 0.011 |
| 141 | 0.001 | 0.003 |
| 142 | 0.015 | 0.041 |
| 143 | 0.008 | 0.049 |
| 144 | 0.015 | 0.097 |
| 145 | 0.017 | 0.021 |
| 146 | 0.019 | 0.168 |
| 147 | 0.001 | 0.102 |
| 148 | 0.002 | 0.008 |
| 149 | 0.005 | 0.082 |
| 150 | 0.001 | 0.011 |
| 151 | 0.001 | 0.114 |
| 152 | 0.081 | 0.537 |
| 153 | 0.003 | 0.007 |
| 154 | 0.029 | 1.044 |
| 155 | 0.012 | 0.103 |
| 156 | 0.351 | >10 |
| 157 | 0.010 | 1.841 |
| 158 | 0.001 | 0.001 |
| 159 | 0.001 | 0.001 |
| 160 | 0.000 | 0.005 |
| 161 | 0.000 | 0.048 |
| 162 | 0.005 | 0.122 |
| 163 | 0.001 | 0.595 |
| 164 | 0.001 | 0.333 |
| 165 | 0.018 | 0.879 |
| 166 | 0.164 | 4.463 |
| 167 | 0.047 | 0.442 |
| 168 | 0.014 | 0.135 |
| 169 | 0.003 | 0.023 |
| 170 | 0.001 | 0.012 |
| 171 | 0.002 | 0.013 |
| 172 | 0.004 | 0.020 |
| 173 | 0.001 | 0.017 |
| 174 | 0.002 | 0.023 |
| 175 | 0.001 | 0.017 |
| 176 | 0.000 | 0.010 |
| 177 | 0.000 | 0.302 |
| 178 | 1.323 | |
| 179 | 0.000 | 0.002 |
| 180 | 0.002 | 0.037 |
| 181 | 0.007 | 0.240 |
| 182 | 0.020 | 0.217 |
| 183 | 0.034 | 0.130 |
| 184 | 0.009 | 0.021 |
| 185 | 0.010 | 0.051 |
| 186 | 0.019 | 0.021 |
| 187 | 0.066 | 0.069 |
| 188 | 0.201 | 1.185 |
| 189 | 0.173 | 1.649 |
| 190 | 0.058 | 0.471 |
| 191 | 0.658 | |
| 192 | 0.058 | 0.171 |
| 193 | 0.026 | 0.144 |
| 194 | 0.733 | |
| 195 | 0.003 | 0.093 |
| 196 | 0.010 | 0.104 |
| 197 | 0.010 | 0.083 |
| 198 | 0.083 | 0.375 |
| 199 | 0.039 | 0.250 |
| 200 | 0.035 | 0.176 |
| 201 | 0.021 | 0.358 |
| 202 | 0.072 | 0.172 |
| 203 | 0.005 | 0.052 |
| 204 | 0.004 | 0.128 |
| 205 | 0.008 | 0.066 |
| 206 | 0.002 | 0.043 |
| 207 | 0.017 | 0.205 |
| 208 | 0.000 | 0.014 |
| 209 | 0.001 | 0.034 |
| 210 | 0.000 | 0.020 |
| 211 | 0.001 | 0.006 |
| 212 | 0.001 | 0.005 |
| 213 | 0.002 | 0.025 |
| 214 | 0.012 | 0.138 |
| 215 | 0.002 | 0.012 |
| 216 | 0.002 | 0.016 |
| 217 | 0.001 | 0.009 |
| 218 | 0.003 | 0.029 |
| 219 | 0.005 | 0.031 |
| 220 | 0.205 | 0.219 |
| 221 | 0.300 | 0.854 |
| 222 | 0.118 | 0.638 |
| 223 | 0.663 | |
| 224 | 0.293 | 0.516 |
| 225 | 0.856 | |
| 226 | 0.211 | 0.329 |
| 227 | 0.670 | |
| 228 | 1.055 | |
| 229 | 1.067 | |
| 230 | 1.205 | 5.000 |
| 231 | 0.135 | 0.564 |
| 232 | 0.358 | |
| 233 | 0.637 | |
| 234 | 0.025 | 0.238 |
| 235 | 0.036 | 0.285 |
| 236 | 0.057 | 0.443 |
| 237 | 0.008 | 0.134 |
| 238 | 0.005 | 0.038 |
| 239 | 0.006 | |
| 240 | 0.002 | 0.021 |
| 241 | 0.015 | 0.061 |
| 242 | 0.001 | 0.004 |
| 243 | 0.003 | 0.120 |
| 244 | 0.029 | 0.211 |
| 245 | 0.045 | 0.233 |
| 246 | 0.199 | 0.302 |
| 247 | 0.089 | 0.197 |
| 248 | 0.050 | 0.124 |
| 249 | 0.059 | 0.094 |

TABLE 5-continued

FLAP binding and Human Whole Blood assay data

| Cmp No. | FLAP Binding wild type HTRF $K_i$ (μM) | Human Whole Blood LTB4 IC$_{50}$ 1:1 (μM) |
|---|---|---|
| 250 | 0.038 | 0.077 |
| 251 | 0.005 | 0.068 |
| 252 | 0.127 | 0.206 |
| 253 | 0.134 | 0.191 |
| 254 | 0.080 | 0.586 |
| 255 | 0.008 | 0.076 |
| 256 | 0.035 | 0.073 |
| 257 | 0.154 | 1.125 |
| 258 | 0.243 | 0.202 |
| 259 | 0.005 | 0.034 |
| 260 | 0.010 | 0.057 |
| 261 | 0.006 | 0.075 |
| 262 | 0.018 | 0.046 |
| 263 | 0.169 | 0.207 |
| 264 | 0.028 | 0.144 |
| 265 | 0.045 | 0.160 |
| 266 | 0.184 | 0.464 |
| 267 | 0.154 | 0.350 |
| 268 | 0.011 | 0.056 |
| 269 | 0.015 | 0.087 |
| 270 | 0.057 | 1.065 |
| 271 | 0.051 | 0.606 |
| 272 | 0.032 | 0.125 |
| 273 | 0.009 | 0.105 |
| 274 | | |
| 275 | 0.065 | 0.192 |
| 276 | 0.023 | 0.325 |
| 277 | 0.052 | >1 |
| 278 | 0.036 | 0.095 |
| 279 | 0.070 | 0.149 |
| 280 | 0.003 | 0.087 |
| 281 | 0.061 | 0.044 |
| 282 | 0.750 | 0.280 |
| 283 | 0.009 | 0.119 |
| 284 | 0.042 | 1.037 |
| 285 | 0.003 | 0.111 |
| 286 | 0.142 | 0.206 |
| 287 | 0.009 | 0.074 |
| 288 | 0.103 | 0.420 |
| 289 | 0.022 | 0.036 |
| 290 | 0.940 | |
| 291 | 0.007 | 0.421 |
| 292 | 0.012 | 1.029 |
| 293 | >10 | |
| 294 | 0.002 | 0.248 |
| 295 | 0.025 | 0.110 |
| 296 | 0.005 | 0.066 |
| 297 | 0.005 | 0.045 |
| 298 | 0.081 | 1.166 |
| 299 | 0.121 | |
| 300 | 0.013 | 0.120 |
| 301 | 0.013 | 0.204 |
| 302 | 2.500 | |
| 303 | 0.612 | |
| 304 | >10 | |
| 305 | 0.002 | 0.078 |
| 306 | 0.397 | |
| 307 | 0.004 | 0.416 |
| 308 | >10 | |
| 309 | 0.214 | 1.785 |
| 310 | 0.492 | |
| 311 | 0.747 | |
| 312 | 0.262 | 0.376 |
| 313 | 0.397 | 0.574 |
| 314 | 0.089 | 0.178 |
| 315 | 0.001 | 0.027 |
| 316 | 0.746 | |
| 317 | 0.335 | >10 |
| 318 | 0.689 | 2.001 |
| 319 | 0.204 | 3.263 |
| 320 | 0.129 | 1.084 |
| 321 | 0.505 | 8.486 |
| 322 | 0.032 | 0.138 |
| 323 | 0.770 | 6.644 |
| 324 | 0.019 | 0.101 |
| 325 | 0.004 | 0.091 |
| 326 | 0.003 | 0.029 |
| 327 | 0.002 | 0.039 |
| 328 | 0.015 | 0.119 |
| 329 | 0.012 | 0.066 |
| 330 | 0.012 | 0.088 |
| 331 | 0.014 | 0.062 |
| 332 | 0.065 | 0.125 |
| 333 | 0.045 | 0.671 |
| 334 | 0.012 | 0.067 |
| 335 | 0.002 | 0.037 |
| 336 | 0.004 | 0.065 |
| 337 | 2.500 | |
| 338 | 0.199 | 1.094 |
| 339 | 2.500 | |
| 340 | 0.104 | 0.321 |
| 341 | >10 | |
| 342 | 0.002 | 0.117 |
| 343 | 0.004 | 0.057 |
| 344 | 0.081 | >10 |
| 345 | 0.028 | 0.259 |
| 346 | 0.005 | 0.095 |
| 347 | 0.077 | 0.161 |
| 348 | 0.005 | 0.106 |
| 349 | 0.001 | 0.013 |
| 350 | 0.002 | 0.026 |
| 351 | 0.017 | 0.297 |
| 352 | 0.016 | 0.064 |
| 353 | 0.001 | 0.020 |
| 354 | 0.037 | 0.093 |
| 355 | 0.005 | 0.029 |
| 356 | 0.032 | 0.107 |
| 357 | 0.114 | 1.128 |
| 358 | 0.055 | >10 |
| 359 | 0.004 | 0.054 |
| 360 | 0.022 | 0.067 |
| 361 | 0.005 | 0.026 |
| 362 | 0.001 | 0.047 |
| 363 | 0.001 | 0.184 |
| 364 | 0.003 | 0.150 |
| 365 | 0.003 | 0.060 |
| 366 | 0.001 | 0.040 |
| 367 | 0.001 | 0.006 |
| 368 | 0.013 | 0.178 |
| 369 | 0.017 | 0.375 |
| 370 | 0.002 | 0.088 |
| 371 | 0.001 | 0.015 |
| 372 | 0.025 | 0.031 |
| 373 | 0.001 | 0.007 |
| 374 | 0.001 | 0.011 |
| 375 | 0.002 | 0.031 |
| 376 | 0.000 | 0.010 |
| 377 | 0.033 | 0.979 |
| 378 | 0.001 | 0.016 |
| 379 | 0.001 | 0.033 |
| 380 | 0.001 | 0.046 |
| 381 | 0.005 | 0.141 |
| 382 | 0.000 | 0.011 |
| 383 | 0.008 | 1.633 |
| 384 | 0.004 | 0.082 |
| 385 | 0.042 | 1.083 |
| 386 | 0.002 | 0.077 |
| 387 | 0.008 | 0.253 |
| 388 | 0.002 | 0.037 |
| 389 | 0.013 | 0.137 |
| 390 | 0.000 | 0.010 |
| 391 | 0.002 | 0.056 |
| 392 | 0.001 | 0.016 |
| 393 | 0.001 | 0.012 |
| 394 | >10 | |
| 395 | 0.009 | 0.032 |
| 396 | 0.008 | 0.137 |
| 397 | >10 | |
| 398 | 0.034 | 1.132 |
| 399 | 0.028 | 0.358 |

TABLE 5-continued

FLAP binding and Human Whole Blood assay data

| Cmp No. | FLAP Binding wild type HTRF $K_i$ (μM) | Human Whole Blood LTB4 $IC_{50}$ 1:1 (μM) |
|---|---|---|
| 400 | 0.014 | 0.729 |
| 401 | 0.158 | 0.538 |
| 402 | 0.092 | 0.522 |
| 403 | 0.070 | 0.389 |
| 404 | 0.155 | 1.490 |
| 405 | 0.100 | 2.708 |
| 406 | 0.135 | 4.314 |
| 407 | >10 | |
| 408 | 0.128 | 1.142 |
| 409 | >10 | |
| 410 | 0.004 | 0.088 |
| 411 | 0.036 | 1.968 |
| 412 | 0.019 | 0.509 |
| 413 | 0.019 | 0.448 |
| 414 | 0.065 | 0.120 |
| 415 | 0.011 | 0.037 |
| 416 | 1.249 | |
| 417 | 0.108 | 0.726 |
| 418 | 1.250 | |
| 419 | 1.369 | |
| 420 | 0.086 | 3.280 |
| 421 | 0.028 | >10 |
| 422 | 0.003 | 0.146 |
| 423 | 0.284 | 4.795 |
| 424 | 0.010 | >10 |
| 425 | 0.002 | 0.111 |
| 426 | 0.002 | 0.073 |
| 427 | 0.054 | 1.599 |
| 428 | 0.004 | 0.004 |
| 429 | 0.013 | 0.209 |
| 430 | 0.005 | 0.059 |
| 431 | 0.001 | 0.009 |
| 432 | 0.004 | 0.019 |
| 433 | 0.001 | 0.025 |
| 434 | 0.001 | 0.036 |
| 435 | 0.009 | 0.166 |
| 436 | 0.308 | 3.277 |
| 437 | 0.023 | 0.381 |
| 438 | 0.001 | 0.017 |
| 439 | 0.063 | 0.300 |
| 440 | 0.031 | 0.215 |
| 441 | 0.001 | 0.006 |
| 442 | 0.001 | 0.009 |
| 443 | 0.343 | 3.331 |
| 444 | 0.183 | >10 |
| 445 | 0.001 | 0.008 |
| 446 | 0.304 | 1.371 |
| 447 | 0.003 | 0.144 |
| 448 | 0.010 | 0.112 |
| 449 | 0.022 | 0.079 |
| 450 | 0.074 | 0.340 |
| 451 | 0.002 | 0.038 |
| 452 | 0.081 | 1.954 |
| 453 | >10 | >10 |
| 454 | 0.012 | 0.345 |
| 455 | 0.001 | 0.094 |
| 456 | 0.003 | 0.114 |
| 457 | 0.003 | 0.140 |
| 458 | 0.004 | 0.053 |
| 459 | >10 | |
| 460 | >10 | |
| 461 | 0.041 | 0.209 |
| 462 | 0.002 | 0.062 |
| 463 | 0.982 | |
| 464 | 0.121 | >10 |
| 465 | 0.186 | 0.957 |
| 466 | 0.254 | 0.990 |
| 467 | 0.250 | 2.827 |
| 468 | 0.620 | |
| 469 | 0.250 | 2.347 |
| 470 | 0.620 | |
| 471 | 0.250 | 3.395 |
| 472 | 0.145 | 2.524 |
| 473 | 0.113 | 1.411 |
| 474 | 0.021 | 2.653 |
| 475 | 0.750 | |
| 476 | 0.032 | 0.891 |
| 477 | 0.016 | 0.738 |
| 478 | 0.250 | |
| 479 | 0.006 | 0.571 |
| 480 | 0.354 | |
| 481 | 1.912 | |
| 482 | 0.120 | |
| 483 | 0.354 | |
| 484 | 0.078 | 3.465 |
| 485 | >10 | |
| 486 | 2.500 | |
| 487 | 0.054 | 0.444 |
| 488 | 0.097 | 1.653 |
| 489 | 0.020 | 0.307 |
| 490 | 0.354 | 0.269 |
| 491 | 0.015 | 0.215 |
| 492 | 0.015 | 0.155 |
| 493 | 0.007 | 0.303 |
| 494 | 0.032 | 0.099 |
| 495 | 0.004 | 0.509 |
| 496 | 0.019 | 0.165 |
| 497 | 0.025 | 0.510 |
| 498 | 0.016 | 0.111 |
| 499 | 0.433 | |
| 500 | 0.048 | 0.139 |
| 501 | 0.359 | |
| 502 | 0.083 | 0.363 |
| 503 | 0.014 | 0.092 |
| 504 | 0.768 | |
| 505 | 0.018 | 0.071 |
| 506 | >10 | |
| 507 | >10 | |
| 508 | 0.790 | |
| 509 | 0.147 | 0.093 |
| 510 | 1.939 | |
| 511 | 0.213 | 0.323 |
| 512 | 0.443 | 0.470 |
| 513 | >10 | |
| 514 | 0.132 | 0.148 |
| 515 | >10 | |
| 516 | >10 | |
| 517 | >10 | |
| 518 | >10 | |
| 519 | >10 | |
| 520 | >10 | |
| 521 | 0.005 | 0.013 |
| 522 | 0.348 | 0.393 |
| 523 | 0.001 | 0.025 |
| 524 | 0.001 | 0.018 |
| 525 | 0.003 | 0.036 |
| 526 | 0.008 | 0.019 |
| 527 | 0.074 | 0.183 |
| 528 | 0.005 | 0.034 |
| 529 | 0.036 | 0.090 |
| 530 | 0.034 | 1.112 |
| 531 | 0.008 | 0.323 |
| 532 | 0.006 | 0.032 |
| 533 | 0.005 | 0.023 |
| 534 | 0.012 | 0.069 |
| 535 | 0.001 | 0.017 |
| 536 | 0.021 | 0.068 |
| 537 | 0.003 | 0.042 |
| 538 | 0.020 | 0.330 |
| 539 | 0.002 | 0.052 |
| 540 | 0.016 | 0.085 |
| 541 | 0.012 | 0.066 |
| 542 | 0.107 | 0.311 |
| 543 | 0.444 | 4.165 |
| 544 | 0.028 | 1.652 |
| 545 | 0.012 | 0.050 |
| 546 | 0.148 | 0.253 |
| 547 | 0.035 | 0.104 |
| 548 | 0.467 | 0.741 |
| 549 | 0.009 | 0.123 |

TABLE 5-continued

FLAP binding and Human Whole Blood assay data

| Cmp No. | FLAP Binding wild type HTRF $K_i$ (μM) | Human Whole Blood LTB4 $IC_{50}$ 1:1 (μM) |
|---|---|---|
| 550 | 0.002 | 0.016 |
| 551 | 0.000 | 0.021 |
| 552 | 0.005 | 0.102 |
| 553 | 0.019 | 0.430 |
| 554 | 0.002 | 0.039 |
| 555 | 0.002 | 0.024 |
| 556 | 0.001 | 0.013 |
| 557 | 0.147 | 1.066 |
| 558 | 0.012 | 0.210 |
| 559 | 0.002 | 0.055 |
| 560 | 0.005 | 0.095 |
| 561 | 0.004 | 0.043 |
| 562 | 0.055 | 0.226 |
| 563 | 0.020 | 0.328 |
| 564 | 0.200 | 0.583 |
| 565 | 0.081 | 0.984 |
| 566 | >10 | |
| 567 | 1.135 | |
| 568 | 2.500 | |
| 569 | 0.070 | 0.335 |
| 570 | 0.035 | 1.183 |
| 571 | 0.002 | 0.091 |
| 572 | 0.370 | |
| 573 | 0.114 | |
| 574 | 0.015 | 0.494 |
| 575 | 0.750 | |
| 576 | 0.008 | 0.116 |
| 577 | 0.010 | 0.091 |
| 578 | 0.025 | 0.956 |
| 579 | 0.095 | 1.544 |
| 580 | 0.055 | 5.000 |
| 581 | 0.060 | 2.823 |
| 582 | >10 | |
| 583 | >10 | |
| 584 | >10 | |
| 585 | >10 | |
| 586 | >10 | |
| 587 | >10 | |
| 588 | 0.133 | >10 |
| 589 | >10 | |
| 590 | >10 | |
| 591 | ~2.49 | |
| 592 | >10 | |
| 593 | >10 | |
| 594 | >10 | |
| 595 | ~2.49 | |
| 596 | >10 | |
| 597 | ~2.49 | |
| 598 | >10 | |
| 599 | >10 | |
| 600 | >10 | |
| 601 | >10 | |
| 602 | 0.0006 | 0.0167 |
| 603 | 0.0276 | >10 |
| 604 | 0.0050 | 0.0894 |
| 605 | 0.0019 | 0.0978 |
| 606 | 0.0463 | 2.624 |
| 607 | 0.1384 | 0.1520 |
| 608 | 0.0287 | 0.0539 |
| 609 | 0.2464 | 0.7677 |
| 610 | 0.0274 | 0.1170 |
| 611 | 0.2489 | 0.5626 |
| 612 | 0.0146 | 0.0420 |
| 613 | 0.2146 | 0.5565 |
| 614 | | |
| 615 | | |
| 616 | | |
| 617 | | |
| 618 | 0.0146 | 0.2109 |
| 619 | 0.0034 | 0.0451 |
| 620 | 0.0019 | 0.0132 |
| 621 | 0.0050 | 0.1006 |
| 622 | 0.0461 | 0.3401 |
| 623 | 0.0049 | 0.0935 |
| 624 | | |
| 625 | 0.0078 | 0.1727 |
| 626 | 0.0062 | 0.0453 |
| 627 | 0.0437 | 0.3661 |
| 628 | 0.3362 | |
| 629 | 0.8358 | |
| 630 | 1.8950 | |
| 631 | >10 | |
| 632 | 1.2677 | |
| 633 | >10 | |
| 634 | 0.3108 | 1.470 |
| 635 | 1.0869 | |
| 636 | 0.0046 | 0.1072 |
| 637 | 0.0188 | 0.3975 |
| 638 | 0.0014 | 0.0148 |
| 639 | 0.0072 | 0.0670 |
| 640 | 1.3397 | |
| 641 | >10 | |
| 642 | 0.0788 | 0.9806 |
| 643 | 0.3225 | 4.2874 |
| 644 | >10 | |
| 645 | | |
| 646 | | |
| 647 | | |
| 648 | | |
| 649 | >10 | |
| 650 | 0.8316 | |
| 651 | 0.3062 | 1.5363 |
| 652 | 0.0627 | 0.8425 |
| 653 | 0.0173 | 0.5267 |
| 654 | 0.1303 | 1.0459 |
| 655 | 0.5034 | 1.8302 |
| 656 | 1.3957 | |
| 657 | 0.0735 | 2.3415 |
| 658 | 0.5717 | |
| 659 | ~0.7500 | |
| 660 | 0.0833 | >10 |
| 661 | ~2.49 | |
| 662 | ~1.22 | |
| 663 | 0.0058 | 0.0347 |
| 664 | 0.0050 | >1 |
| 665 | 0.0026 | 0.0224 |
| 666 | 0.0032 | 0.0361 |
| 667 | 0.0060 | 0.0396 |
| 668 | 0.0230 | 0.1897 |
| 669 | 0.0040 | 0.1064 |
| 670 | 0.0977 | 0.5255 |
| 671 | 0.0157 | 0.1645 |
| 672 | 0.0137 | 0.1964 |
| 673 | 0.1343 | 0.1013 |
| 674 | 0.0024 | 0.0174 |
| 675 | 0.0007 | 0.0551 |
| 676 | 0.2339 | 3.7145 |
| 677 | >10 | |
| 678 | >10 | |
| 679 | 0.1316 | 0.2054 |
| 680 | 0.6097 | 1.0502 |
| 681 | 0.0522 | 0.1057 |
| 682 | 0.2239 | 0.2638 |
| 683 | 0.6021 | 0.2800 |
| 684 | 0.0463 | 0.1342 |
| 685 | 0.0523 | 0.1148 |
| 686 | 0.3343 | 1.4900 |
| 687 | 0.7399 | 3.5456 |
| 688 | 0.6955 | 1.1844 |
| 689 | 0.4846 | 0.7872 |
| 690 | 0.1771 | 0.1175 |
| 691 | >10 | |
| 692 | 0.0533 | 0.1097 |
| 693 | 0.0495 | 0.1032 |
| 694 | 0.6762 | 1.0115 |
| 695 | 0.0084 | 0.3355 |
| 696 | ~0.2499 | 3.27492 |
| 697 | >10 | |
| 698 | 0.0087 | 0.1117 |
| 699 | | |

TABLE 5-continued

FLAP binding and Human Whole Blood assay data

| Cmp No. | FLAP Binding wild type HTRF $K_i$ (μM) | Human Whole Blood LTB4 $IC_{50}$ 1:1 (μM) |
|---|---|---|
| 700 | >10 | |
| 701 | ~1.41 | |
| 702 | ~0.3041 | |
| 703 | >10 | |
| 704 | 0.1025 | 0.1906 |
| 705 | 0.0869 | 0.2891 |
| 706 | 0.0796 | 0.3620 |
| 707 | 0.0327 | 0.1266 |
| 708 | 0.0235 | 0.1416 |
| 709 | 0.0054 | 0.2682 |
| 710 | 0.0137 | 0.05651 |
| 711 | 0.0417 | 0.1420 |
| 712 | 0.0019 | 0.05233 |
| 713 | 0.0017 | 0.05339 |
| 714 | 0.0024 | 0.03311 |
| 715 | 0.0082 | 0.1858 |
| 716 | >10 | |
| 717 | 1.0083 | |
| 718 | >10 | |
| 719 | >10 | |
| 720 | >10 | |
| 721 | >10 | |
| 722 | >10 | |
| 723 | >10 | |
| 724 | >10 | |
| 725 | 1.2960 | |
| 726 | 0.9041 | |
| 727 | 0.4838 | 1.1740 |
| 728 | 0.7813 | |
| 729 | 0.0647 | 0.8609 |
| 730 | 0.0067 | 0.1359 |
| 731 | 0.0147 | 0.05132 |
| 732 | 0.5571 | |
| 733 | >10 | |
| 734 | >10 | |
| 735 | 0.0320 | 0.2722 |
| 736 | 0.3303 | 0.4144 |
| 737 | 0.9842 | |
| 738 | 0.2400 | 2.9546 |
| 739 | 0.3701 | 1.1132 |
| 740 | >10 | |
| 741 | 0.0046 | 0.02633 |
| 742 | 0.0029 | 0.02572 |
| 743 | 0.0016 | 0.02165 |
| 744 | 0.0155 | 0.13173 |
| 745 | 0.0117 | 0.11073 |
| 746 | 0.0020 | 0.13699 |
| 747 | 0.0271 | 0.26224 |
| 748 | >10 | |
| 749 | 0.2455 | 0.46752 |
| 750 | 1.1582 | |
| 751 | 0.0809 | 1.05657 |
| 752 | 0.1352 | 0.29915 |
| 753 | 0.0044 | 0.02130 |
| 754 | 0.0699 | 0.37722 |
| 755 | 0.9395 | |
| 756 | >10 | |
| 757 | 0.0052 | 0.016206 |
| 758 | 0.5569 | |
| 759 | >10 | |
| 760 | 1.1559 | |
| 761 | >10 | |
| 762 | 0.1589 | 0.44177 |
| 763 | 1.1148 | |
| 764 | >10 | |
| 765 | >10 | |
| 766 | 1.9090 | |
| 767 | >10 | |
| 768 | 0.5728 | |
| 769 | 1.5449 | |
| 770 | >10 | |
| 771 | >10 | |
| 772 | >10 | |
| 773 | 0.2227 | 0.63899 |
| 774 | | |
| 775 | | |
| 776 | | |
| 777 | | |
| 778 | >10 | |
| 779 | ~2.49 | |
| 780 | >10 | |
| 781 | 0.7295 | |
| 782 | >10 | |
| 783 | >10 | |
| 784 | 0.0079 | 0.1105 |
| 785 | 0.0085 | 0.0575 |
| 786 | 0.0607 | 0.10485 |
| 787 | 0.0091 | 0.0979 |
| 788 | 0.0178 | 0.2715 |
| 789 | 0.1303 | 0.9392 |
| 790 | 0.0015 | 0.02533 |
| 791 | >10 | |
| 792 | >10 | |
| 793 | 0.2795 | 0.6419 |
| 794 | 0.0328 | 3.9355 |
| 795 | 0.0085 | 0.0686 |
| 796 | 0.3912 | |
| 797 | >10 | |
| 798 | 0.2573 | 0.220039 |
| 799 | >10 | |
| 800 | >10 | |
| 801 | >10 | |
| 802 | >10 | 0.000993574 |
| 803 | 0.1065 | 0.241268 |
| 804 | 0.6359 | |
| 805 | 0.0297 | 0.352777 |
| 806 | 0.0018 | 0.048395 |
| 807 | 0.0058 | 0.0721606 |
| 808 | 0.0004 | 0.00637236 |
| 809 | 0.0038 | 0.0376964 |
| 810 | 0.0006 | 0.00563897 |
| 811 | 0.3149 | 0.541252 |
| 812 | 0.0085 | 0.0120393 |
| 813 | 0.0339 | 0.0750585 |
| 814 | 0.0028 | 0.0209218 |
| 815 | 0.2555 | 0.128115 |
| 816 | 0.0218 | 0.0460044 |
| 817 | 0.4629 | |
| 818 | 0.0272 | 0.051606 |
| 819 | 0.0405 | 0.0474898 |
| 820 | 0.0033 | 0.041639 |
| 821 | >10 | |
| 822 | 0.2804 | 0.099106 |
| 823 | 0.1923 | 0.0950605 |
| 824 | 0.0103 | 0.0180053 |
| 825 | 0.2732 | 0.122321 |
| 826 | 0.0007 | 0.0199205 |
| 827 | >10 | |
| 828 | 0.1153 | 0.259777 |
| 829 | 0.0032 | 0.00596486 |
| 830 | 0.0029 | 0.00555393 |
| 831 | 0.1309 | 0.0791589 |
| 832 | 1.3119 | |
| 833 | ~0.500034 | |
| 834 | 0.0489 | 1.09069 |
| 835 | ~0.35359 | 0.417157 |
| 836 | 0.0255 | 0.595114 |
| 837 | ~1.74985 | |
| 838 | 0.0286 | 0.350106 |
| 839 | 0.8297 | 2.78805 |
| 840 | 0.0127 | 0.0995864 |
| 841 | 0.1458 | 0.369658 |
| 842 | 0.0053 | 0.061038 |
| 843 | 0.0156 | 0.0442792 |
| 844 | 0.5093 | 0.907193 |
| 845 | >10 | |
| 846 | 0.0105 | 0.0418215 |
| 847 | 0.0081 | 0.0991289 |
| 848 | 0.0968 | 0.321736 |
| 849 | 0.0356 | >1 |

TABLE 5-continued

FLAP binding and Human Whole Blood assay data

| Cmp No. | FLAP Binding wild type HTRF $K_i$ (μM) | Human Whole Blood LTB4 $IC_{50}$ 1:1 (μM) |
|---|---|---|
| 850 | 0.0377 | 0.195434 |
| 851 | 0.0326 | 0.359335 |
| 852 | 0.1179 | 1.34555 |
| 853 | 0.0047 | 0.0456037 |
| 854 | 1.2773 | |
| 855 | >10 | |
| 856 | 0.0605 | 0.083888 |
| 857 | 0.0280 | 0.205494 |
| 858 | 0.2097 | 0.369743 |
| 859 | ~1.249 | |
| 860 | ~1.479 | |

Certain compounds were tested in additional runs for the assays described above and the data is provided in Table 6.

TABLE 6

FLAP binding and Human Whole Blood assay data

| Cmp No. | FLAP Binding wild type HTRF $K_i$ (μM) | Human Whole Blood LTB4 $IC_{50}$ 1:1 (μM) |
|---|---|---|
| 1 | 0.3521 | 0.8596 |
| 2 | 0.1785 | 0.3582 |
| 3 | >10 | |
| 4 | 0.0004 | 0.0184 |
| 5 | 0.0366 | 0.3698 |
| 6 | 0.0011 | 0.0328 |
| 7 | 0.0008 | 0.0136 |
| 8 | 0.0013 | 0.0120 |
| 9 | 0.0015 | 0.0603 |
| 10 | 0.0027 | 0.0531 |
| 11 | 0.0016 | 0.0154 |
| 12 | 0.0019 | 0.0213 |
| 13 | 0.0012 | 0.0178 |
| 14 | 0.0035 | 0.0324 |
| 15 | 0.0111 | 0.0590 |
| 16 | 0.0050 | 0.0184 |
| 17 | 0.0017 | 0.0251 |
| 18 | 0.0018 | 0.0703 |
| 19 | 0.0022 | 0.0498 |
| 20 | 0.0009 | 0.0085 |
| 21 | 0.0021 | 0.0347 |
| 22 | 0.0021 | 0.0481 |
| 23 | 0.0012 | 0.0129 |
| 24 | 0.0023 | 0.0482 |
| 25 | 0.0032 | 0.0263 |
| 26 | 0.0009 | 0.0258 |
| 27 | 0.0263 | ~10 |
| 28 | 0.0822 | 0.3246 |
| 29 | 0.0632 | 0.0301 |
| 30 | 0.0950 | |
| 31 | 0.0040 | 0.0358 |
| 32 | 0.0062 | 0.0299 |
| 33 | ~0.3041 | |
| 34 | 0.0308 | 0.3340 |
| 35 | 0.0361 | 0.0944 |
| 36 | 0.0081 | 0.1366 |
| 37 | 0.0296 | 0.6761 |
| 38 | 0.0288 | 0.1773 |
| 39 | 0.0081 | 0.0751 |
| 40 | 0.0144 | 0.1118 |
| 41 | 0.0106 | 2.6866 |
| 42 | 0.0102 | 0.1493 |
| 43 | 0.0030 | 0.0381 |
| 44 | 0.0065 | 0.0582 |
| 45 | 0.0031 | 0.0102 |
| 46 | 0.0615 | 0.1774 |
| 47 | 0.0016 | 0.0166 |
| 48 | 0.0070 | 0.1583 |
| 49 | 0.0020 | 0.0211 |
| 50 | 0.0013 | 0.0154 |
| 51 | 0.0038 | 0.0424 |
| 52 | 0.0037 | 0.1551 |
| 53 | 0.0033 | 0.2377 |
| 54 | 0.0249 | 0.0413 |
| 55 | 0.0011 | 1.2317 |
| 56 | 0.0088 | 3.5164 |
| 57 | 0.0134 | 0.2517 |
| 58 | 0.0046 | 0.9911 |
| 59 | 0.0204 | 1.0170 |
| 60 | 0.0280 | 0.4638 |
| 61 | 0.0159 | 0.1173 |
| 62 | 0.1418 | 0.1111 |
| 63 | 0.0061 | 0.0284 |
| 64 | 0.0019 | 0.0131 |
| 65 | 0.0633 | 0.3224 |
| 66 | 0.0266 | 0.0689 |
| 67 | 0.0042 | 0.0168 |
| 68 | 0.0011 | 0.0109 |
| 69 | 0.0009 | 0.0081 |
| 70 | 0.0023 | 0.0100 |
| 71 | 0.0019 | 0.0227 |
| 72 | 0.1200 | 0.1682 |
| 73 | 0.0620 | 0.0769 |
| 74 | 0.0057 | 0.0610 |
| 75 | 0.0107 | 0.1851 |
| 76 | 0.0017 | 0.0267 |
| 77 | 0.0032 | 0.3416 |
| 78 | 0.0007 | 0.1663 |
| 79 | 0.0053 | 0.1498 |
| 80 | 0.0039 | 0.0881 |
| 81 | 0.0064 | 0.1518 |
| 82 | 0.0007 | 0.0181 |
| 83 | 0.0007 | 0.0191 |
| 84 | 0.0031 | 0.0975 |
| 85 | 0.0019 | 0.0199 |
| 86 | 0.0026 | 0.0266 |
| 87 | 0.0032 | 0.0752 |
| 88 | 0.0062 | 0.0364 |
| 89 | 0.0049 | 0.0432 |
| 90 | 0.0009 | 0.0125 |
| 91 | 0.0047 | 0.0383 |
| 92 | 0.2802 | 0.3092 |
| 93 | 0.0833 | 0.1275 |
| 94 | 0.0760 | 0.2347 |
| 95 | 0.0097 | 0.0515 |
| 96 | 0.3537 | >10 |
| 97 | 0.0066 | 0.0422 |
| 98 | 0.0061 | 0.0391 |
| 99 | 0.0016 | 0.0301 |
| 100 | 0.0008 | 0.0245 |
| 101 | 0.0018 | 0.0137 |
| 102 | 0.0004 | 0.0345 |
| 103 | 0.0003 | 0.0165 |
| 104 | 0.0117 | >1 |
| 105 | 0.0247 | 0.4805 |
| 106 | 0.0191 | >1 |
| 107 | 0.0164 | 0.1316 |
| 108 | 0.0095 | 0.0486 |
| 109 | 0.0015 | 0.0181 |
| 110 | 0.0026 | 0.0294 |
| 111 | 0.0042 | 0.0576 |
| 112 | 0.0069 | 0.1543 |
| 113 | 0.0105 | 0.1451 |
| 114 | 0.0120 | 0.2215 |
| 115 | 0.0041 | 0.1080 |
| 116 | 0.0007 | 0.0122 |
| 117 | 0.0007 | 0.0066 |
| 118 | 0.0004 | 0.0063 |
| 119 | 0.0027 | 0.0217 |
| 120 | 0.0011 | 0.0171 |
| 121 | 0.0005 | 0.0096 |
| 122 | 0.0007 | 0.0179 |
| 123 | 0.0827 | 1.1249 |
| 124 | 0.0353 | 0.2172 |
| 125 | 0.0497 | >10 |
| 126 | 0.1408 | 0.5717 |

TABLE 6-continued

FLAP binding and Human Whole Blood assay data

| Cmp No. | FLAP Binding wild type HTRF $K_i$ (μM) | Human Whole Blood LTB4 $IC_{50}$ 1:1 (μM) |
|---|---|---|
| 127 | 0.0020 | 0.0346 |
| 128 | 0.0008 | 0.0382 |
| 129 | 0.0039 | 0.5341 |
| 130 | 0.1295 | 0.6326 |
| 131 | 0.1438 | 0.6947 |
| 132 | 0.0024 | 0.0111 |
| 133 | 0.0010 | 0.0320 |
| 134 | 0.0013 | >1 |
| 135 | 0.0004 | 0.0161 |
| 136 | 0.0005 | 0.0155 |
| 137 | 0.0029 | 0.0438 |
| 138 | 0.0114 | 0.1737 |
| 139 | 0.1330 | 0.3409 |
| 140 | 0.0014 | 0.0106 |
| 141 | 0.0007 | 0.0033 |
| 142 | 0.0151 | 0.0406 |
| 143 | 0.0085 | 0.0488 |
| 144 | 0.0148 | 0.0971 |
| 145 | 0.0167 | 0.0209 |
| 146 | 0.0191 | 0.1684 |
| 147 | 0.0006 | 0.1021 |
| 148 | 0.0025 | 0.0083 |
| 149 | 0.0052 | 0.0824 |
| 150 | 0.0015 | 0.0113 |
| 151 | 0.0013 | 0.1140 |
| 152 | 0.0807 | 0.5365 |
| 153 | 0.0025 | 0.0069 |
| 154 | 0.0293 | 1.0445 |
| 155 | 0.0116 | 0.1025 |
| 156 | 0.3513 | >10 |
| 157 | 0.0098 | 1.8408 |
| 158 | 0.0006 | 0.0014 |
| 159 | 0.0008 | 0.0013 |
| 160 | 0.0004 | 0.0053 |
| 161 | 0.0004 | 0.0478 |
| 162 | 0.0051 | 0.1223 |
| 163 | 0.0005 | 0.5953 |
| 164 | 0.0008 | 0.3332 |
| 165 | 0.0184 | 0.8790 |
| 166 | 0.1645 | 4.4627 |
| 167 | 0.0468 | 0.4416 |
| 168 | 0.0143 | 0.1348 |
| 169 | 0.0029 | 0.0229 |
| 170 | 0.0013 | 0.0118 |
| 171 | 0.0020 | 0.0135 |
| 172 | 0.0036 | 0.0201 |
| 173 | 0.0008 | 0.0165 |
| 174 | 0.0024 | 0.0231 |
| 175 | 0.0014 | 0.0170 |
| 176 | 0.0005 | 0.0100 |
| 177 | 0.0005 | 0.3016 |
| 178 | ~1.3228 | |
| 179 | 0.0004 | 0.0021 |
| 180 | 0.0021 | 0.0369 |
| 181 | 0.0067 | 0.2397 |
| 182 | 0.0199 | 0.2171 |
| 183 | 0.0344 | 0.1300 |
| 184 | 0.0089 | 0.0206 |
| 185 | 0.0095 | 0.0507 |
| 186 | 0.0188 | 0.0207 |
| 187 | 0.0657 | 0.0689 |
| 188 | 0.2014 | 1.1849 |
| 189 | 0.0632 | 1.6493 |
| 190 | 0.0662 | 0.4710 |
| 191 | ~0.6579 | |
| 192 | 0.0483 | 0.1708 |
| 193 | 0.0309 | 0.1439 |
| 194 | 0.1558 | |
| 195 | 0.0023 | 0.0690 |
| 196 | 0.0078 | 0.0963 |
| 197 | 0.0071 | 0.0831 |
| 198 | 0.0721 | 0.8194 |
| 199 | 0.0386 | 0.2518 |
| 200 | 0.0349 | 0.1762 |
| 201 | 0.0207 | 0.3582 |
| 202 | 0.0716 | 0.1721 |
| 203 | 0.0050 | 0.0523 |
| 204 | 0.0045 | 0.1282 |
| 205 | 0.0076 | 0.0656 |
| 206 | 0.0020 | 0.0427 |
| 207 | 0.0171 | 0.2046 |
| 208 | 0.0004 | 0.0137 |
| 209 | 0.0010 | 0.0340 |
| 210 | 0.0004 | 0.0196 |
| 211 | 0.0005 | 0.0058 |
| 212 | 0.0008 | 0.0053 |
| 213 | 0.0024 | 0.0246 |
| 214 | 0.0116 | 0.1378 |
| 215 | 0.0024 | 0.0116 |
| 216 | 0.0022 | 0.0160 |
| 217 | 0.0012 | 0.0089 |
| 218 | 0.0033 | 0.0291 |
| 219 | 0.0048 | 0.0312 |
| 220 | 0.2052 | 0.2186 |
| 221 | 0.3001 | 0.8543 |
| 222 | 0.1176 | 0.6381 |
| 223 | 0.6628 | |
| 224 | 0.2926 | 0.5158 |
| 225 | 0.8561 | |
| 226 | 0.2108 | 0.3289 |
| 227 | 0.6699 | |
| 228 | 1.0554 | |
| 229 | 1.0673 | |
| 230 | 1.2050 | ~5.00034 |
| 231 | 0.1354 | 0.5639 |
| 232 | 0.3575 | |
| 233 | 0.6365 | |
| 234 | 0.0255 | 0.2382 |
| 235 | 0.0357 | 0.2848 |
| 236 | 0.0571 | 0.4431 |
| 237 | 0.0078 | 0.1338 |
| 238 | 0.0050 | 0.0379 |
| 239 | 0.0059 | |
| 240 | 0.0024 | 0.0215 |
| 241 | 0.0146 | 0.0605 |
| 242 | 0.0007 | 0.0039 |
| 243 | 0.0033 | 0.1199 |
| 244 | 0.0294 | 0.2109 |
| 245 | 0.0453 | 0.2330 |
| 246 | 0.1990 | 0.3017 |
| 247 | 0.0894 | 0.1968 |
| 248 | 0.0568 | 0.1237 |
| 249 | 0.0595 | 0.0940 |
| 250 | 0.0382 | 0.0774 |
| 251 | 0.0045 | 0.0678 |
| 252 | 0.1267 | 0.2055 |
| 253 | 0.1344 | 0.1906 |
| 254 | 0.0800 | 0.5856 |
| 255 | 0.0081 | 0.0761 |
| 256 | 0.0350 | 0.0734 |
| 257 | 0.1537 | 1.1249 |
| 258 | 0.2430 | 0.2021 |
| 259 | 0.0078 | 0.0340 |
| 260 | 0.0089 | 0.0566 |
| 261 | 0.0056 | 0.0749 |
| 262 | 0.0183 | 0.0456 |
| 263 | 0.1272 | 0.2074 |
| 264 | 0.0276 | 0.1439 |
| 265 | 0.0355 | 0.1600 |
| 266 | 0.1330 | 0.4639 |
| 267 | 0.1854 | 0.3504 |
| 268 | 0.0114 | 0.0559 |
| 269 | 0.0149 | 0.0873 |
| 270 | 0.0573 | 1.0654 |
| 271 | 0.0505 | 0.6062 |
| 272 | 0.0269 | 0.1246 |
| 273 | 0.0093 | 0.1047 |
| 274 | | |
| 275 | 0.0648 | 0.1921 |
| 276 | 0.0235 | 0.3248 |

TABLE 6-continued

FLAP binding and Human Whole Blood assay data

| Cmp No. | FLAP Binding wild type HTRF $K_i$ (µM) | Human Whole Blood LTB4 IC$_{50}$ 1:1 (µM) |
|---|---|---|
| 277 | 0.0516 | >1 |
| 278 | 0.0356 | 0.0945 |
| 279 | 0.0700 | 0.1176 |
| 280 | 0.0033 | 0.0872 |
| 281 | 0.0608 | 0.0445 |
| 282 | ~0.7500 | 0.2799 |
| 283 | 0.0090 | 0.1187 |
| 284 | 0.0423 | 1.0373 |
| 285 | 0.0033 | 0.1110 |
| 286 | 0.1419 | 0.2060 |
| 287 | 0.0085 | 0.0744 |
| 288 | 0.1028 | 0.4201 |
| 289 | 0.0216 | 0.0361 |
| 290 | ~0.9401 | |
| 291 | 0.0067 | 0.4205 |
| 292 | 0.0099 | 1.0294 |
| 293 | >10 | |
| 294 | 0.0024 | 0.2477 |
| 295 | 0.0200 | 0.1097 |
| 296 | 0.0031 | 0.0660 |
| 297 | 0.0032 | 0.0446 |
| 298 | 0.0806 | 1.1657 |
| 299 | 0.1212 | |
| 300 | 0.0128 | 0.1205 |
| 301 | 0.0126 | 0.2044 |
| 302 | ~2.4997 | |
| 303 | ~0.612351 | |
| 304 | >10 | |
| 305 | 0.0016 | 0.0776 |
| 306 | 0.3974 | |
| 307 | 0.0045 | 0.4158 |
| 308 | >10 | |
| 309 | 0.2143 | 1.7848 |
| 310 | 0.4919 | |
| 311 | 0.7466 | |
| 312 | 0.3226 | 0.3764 |
| 313 | 0.3877 | 0.5739 |
| 314 | 0.0888 | 0.1776 |
| 315 | 0.0013 | 0.0272 |
| 316 | 0.7456 | |
| 317 | 0.3346 | >10 |
| 318 | 0.6890 | 2.0012 |
| 319 | 0.2036 | 3.2629 |
| 320 | 0.1293 | 1.0839 |
| 321 | 0.5055 | 8.4859 |
| 322 | 0.0324 | 0.1382 |
| 323 | 0.7702 | 6.6435 |
| 324 | 0.0188 | 0.1014 |
| 325 | 0.0047 | 0.0908 |
| 326 | 0.0031 | 0.0287 |
| 327 | 0.0018 | 0.0386 |
| 328 | 0.0154 | 0.1187 |
| 329 | 0.0120 | 0.0658 |
| 330 | 0.0119 | 0.0883 |
| 331 | 0.0144 | 0.0619 |
| 332 | 0.0654 | 0.1245 |
| 333 | 0.0448 | 0.6710 |
| 334 | 0.0117 | 0.0672 |
| 335 | 0.0019 | 0.0370 |
| 336 | 0.0042 | 0.0651 |
| 337 | ~2.49977 | |
| 338 | 0.1992 | 1.0937 |
| 339 | ~2.49977 | |
| 340 | 0.1043 | 0.3210 |
| 341 | >10 | |
| 342 | 0.0018 | 0.1167 |
| 343 | 0.0043 | 0.0568 |
| 344 | 0.0812 | >10 |
| 345 | 0.0277 | 0.2591 |
| 346 | 0.0045 | 0.0946 |
| 347 | 0.0769 | 0.1612 |
| 348 | 0.0050 | 0.1059 |
| 349 | 0.0009 | 0.0128 |
| 350 | 0.0024 | 0.0259 |
| 351 | 0.0165 | 0.2966 |
| 352 | 0.0158 | 0.0642 |
| 353 | 0.0014 | 0.0198 |
| 354 | 0.0365 | 0.0930 |
| 355 | 0.0049 | 0.0294 |
| 356 | 0.0320 | 0.1066 |
| 357 | 0.1139 | 1.1282 |
| 358 | 0.0550 | >10 |
| 359 | 0.0043 | 0.0541 |
| 360 | 0.0216 | 0.0675 |
| 361 | 0.0052 | 0.0262 |
| 362 | 0.0012 | 0.0472 |
| 363 | 0.0006 | 0.1840 |
| 364 | 0.0025 | 0.1498 |
| 365 | 0.0029 | 0.0600 |
| 366 | 0.0010 | 0.0399 |
| 367 | 0.0009 | 0.0056 |
| 368 | 0.0132 | 0.1780 |
| 369 | 0.0173 | 0.3751 |
| 370 | 0.0019 | 0.0880 |
| 371 | 0.0007 | 0.0150 |
| 372 | ~0.0249977 | 0.0313 |
| 373 | 0.0008 | 0.0066 |
| 374 | 0.0012 | 0.0115 |
| 375 | 0.0021 | 0.0313 |
| 376 | 0.0005 | 0.0099 |
| 377 | 0.0330 | 0.9786 |
| 378 | 0.0006 | 0.0163 |
| 379 | 0.0013 | 0.0334 |
| 380 | 0.0011 | 0.0460 |
| 381 | 0.0048 | 0.1405 |
| 382 | 0.0005 | 0.0110 |
| 383 | 0.0079 | 1.6334 |
| 384 | 0.0039 | 0.0819 |
| 385 | 0.0419 | 1.0829 |
| 386 | 0.0018 | 0.0773 |
| 387 | 0.0080 | 0.2528 |
| 388 | 0.0017 | 0.0367 |
| 389 | 0.0131 | 0.1371 |
| 390 | 0.0004 | 0.0096 |
| 391 | 0.0020 | 0.0563 |
| 392 | 0.0009 | 0.0163 |
| 393 | 0.0010 | 0.0124 |
| 394 | >10 | |
| 395 | 0.0088 | 0.0269 |
| 396 | 0.0076 | 0.1372 |
| 397 | >10 | |
| 398 | 0.0344 | 1.1316 |
| 399 | 0.0285 | 0.3583 |
| 400 | 0.0141 | 0.7291 |
| 401 | 0.1581 | 0.5379 |
| 402 | 0.0921 | 0.5223 |
| 403 | 0.0698 | 0.3889 |
| 404 | 0.1547 | 1.4904 |
| 405 | 0.0998 | 2.7077 |
| 406 | 0.1347 | 4.3142 |
| 407 | >10 | |
| 408 | 0.1284 | 1.1424 |
| 409 | >10 | |
| 410 | 0.0037 | 0.0884 |
| 411 | 0.0360 | 1.9679 |
| 412 | 0.0193 | 0.5087 |
| 413 | 0.0186 | 0.4476 |
| 414 | 0.0655 | 0.1204 |
| 415 | 0.0109 | 0.0370 |
| 416 | 1.2485 | |
| 417 | 0.1082 | 0.7264 |
| 418 | ~1.2499 | |
| 419 | ~1.3693 | |
| 420 | 0.0856 | 3.2802 |
| 421 | 0.0283 | >10 |
| 422 | 0.0031 | 0.1460 |
| 423 | 0.2841 | 4.7951 |
| 424 | 0.0103 | >10 |
| 425 | 0.0023 | 0.1108 |
| 426 | 0.0020 | 0.0731 |

TABLE 6-continued

FLAP binding and Human Whole Blood assay data

| Cmp No. | FLAP Binding wild type HTRF $K_i$ (μM) | Human Whole Blood LTB4 $IC_{50}$ 1:1 (μM) |
|---|---|---|
| 427 | 0.0439 | 1.5992 |
| 428 | 0.0043 | 0.0044 |
| 429 | 0.0131 | 0.2089 |
| 430 | 0.0051 | 0.0592 |
| 431 | 0.0008 | 0.0094 |
| 432 | 0.0042 | 0.0188 |
| 433 | 0.0011 | 0.0254 |
| 434 | 0.0011 | 0.0362 |
| 435 | 0.0094 | 0.1657 |
| 436 | 0.3075 | 3.2772 |
| 437 | 0.0233 | 0.3809 |
| 438 | 0.0007 | 0.0166 |
| 439 | 0.0629 | 0.3005 |
| 440 | 0.0309 | 0.2155 |
| 441 | 0.0008 | 0.0065 |
| 442 | 0.0009 | 0.0090 |
| 443 | 0.3430 | 3.3312 |
| 444 | 0.1826 | >10 |
| 445 | 0.0005 | 0.0077 |
| 446 | 0.3044 | 1.3709 |
| 447 | 0.0031 | 0.1441 |
| 448 | 0.0101 | 0.1119 |
| 449 | 0.0216 | 0.0788 |
| 450 | ~0.0740 | 0.3398 |
| 451 | 0.0024 | 0.0385 |
| 452 | ~0.0805 | 1.9543 |
| 453 | >10 | >10 |
| 454 | 0.0115 | 0.3450 |
| 455 | 0.0007 | 0.0943 |
| 456 | 0.0026 | 0.1139 |
| 457 | 0.0027 | 0.1400 |
| 458 | 0.0042 | 0.0530 |
| 459 | >10 | |
| 460 | >10 | |
| 461 | 0.0405 | 0.2088 |
| 462 | 0.0023 | 0.0616 |
| 463 | ~0.9819 | |
| 464 | 0.1209 | >10 |
| 465 | 0.1860 | 0.9565 |
| 466 | ~0.2544 | 0.9901 |
| 467 | 0.0535 | 2.8275 |
| 468 | 0.3317 | |
| 469 | 0.1790 | 2.3469 |
| 470 | 0.3973 | |
| 471 | 0.0558 | 3.3947 |
| 472 | 0.1360 | 2.5241 |
| 473 | 0.0730 | 1.4109 |
| 474 | 0.0215 | 2.6534 |
| 475 | 0.0896 | 4.1812 |
| 476 | 0.0241 | 0.3500 |
| 477 | 0.0147 | 0.2678 |
| 478 | ~0.2499 | |
| 479 | 0.0077 | 0.5710 |
| 480 | ~0.3535 | |
| 481 | 1.9116 | |
| 482 | 0.0609 | 0.3203 |
| 483 | ~0.35359 | |
| 484 | 0.0759 | 3.4650 |
| 485 | >10 | |
| 486 | ~2.4997 | |
| 487 | 0.0543 | 0.4443 |
| 488 | 0.0975 | 1.6527 |
| 489 | 0.0196 | 0.3069 |
| 490 | ~0.3535 | 0.2691 |
| 491 | 0.0146 | 0.2147 |
| 492 | 0.0154 | 0.1555 |
| 493 | 0.0069 | 0.3030 |
| 494 | 0.0316 | 0.0993 |
| 495 | 0.0041 | 0.5091 |
| 496 | 0.0188 | 0.1653 |
| 497 | 0.0251 | 0.5103 |
| 498 | 0.0157 | 0.1113 |
| 499 | 0.4330 | |
| 500 | 0.0485 | 0.1386 |
| 501 | 0.3591 | |
| 502 | 0.0833 | 0.3626 |
| 503 | 0.0140 | 0.0923 |
| 504 | 0.7679 | |
| 505 | 0.0181 | 0.0705 |
| 506 | >10 | |
| 507 | >10 | |
| 508 | 0.7905 | |
| 509 | 0.1473 | 0.1598 |
| 510 | 1.9387 | |
| 511 | 0.2128 | 0.3231 |
| 512 | 0.4430 | 0.4699 |
| 513 | >10 | |
| 514 | 0.1319 | 0.1477 |
| 515 | >10 | |
| 516 | >10 | |
| 517 | >10 | |
| 518 | >10 | |
| 519 | >10 | |
| 520 | >10 | |
| 521 | 0.0054 | 0.0133 |
| 522 | 0.2861 | 0.2639 |
| 523 | 0.0013 | 0.0251 |
| 524 | 0.0007 | 0.0182 |
| 525 | 0.0030 | 0.0365 |
| 526 | 0.0083 | 0.0188 |
| 527 | 0.0743 | 0.1829 |
| 528 | 0.0055 | 0.0340 |
| 529 | 0.0362 | 0.0796 |
| 530 | 0.0344 | 1.1117 |
| 531 | 0.0085 | 0.3234 |
| 532 | 0.0060 | 0.0318 |
| 533 | 0.0045 | 0.0227 |
| 534 | 0.0118 | 0.0689 |
| 535 | 0.0015 | 0.0155 |
| 536 | 0.0214 | 0.0678 |
| 537 | 0.0030 | 0.0421 |
| 538 | 0.0202 | 0.3298 |
| 539 | 0.0016 | 0.0521 |
| 540 | 0.0163 | 0.0850 |
| 541 | 0.0118 | 0.0660 |
| 542 | 0.1070 | 0.3112 |
| 543 | 0.4438 | 4.1649 |
| 544 | 0.0282 | 1.6516 |
| 545 | 0.0115 | 0.0504 |
| 546 | 0.1480 | 0.2531 |
| 547 | 0.0348 | 0.1042 |
| 548 | 0.4672 | 0.7408 |
| 549 | 0.0094 | 0.1228 |
| 550 | 0.0017 | 0.0160 |
| 551 | 0.0004 | 0.0209 |
| 552 | 0.0055 | 0.1020 |
| 553 | 0.0193 | 0.4304 |
| 554 | 0.0021 | 0.0390 |
| 555 | 0.0016 | 0.0245 |
| 556 | 0.0007 | 0.0131 |
| 557 | 0.1471 | 1.0659 |
| 558 | 0.0120 | 0.2100 |
| 559 | 0.0015 | 0.0547 |
| 560 | 0.0052 | 0.0951 |
| 561 | 0.0044 | 0.0429 |
| 562 | 0.0548 | 0.2259 |
| 563 | 0.0197 | 0.3276 |
| 564 | 0.2001 | 0.5828 |
| 565 | 0.0813 | 0.9836 |
| 566 | >10 | |
| 567 | 1.1347 | |
| 568 | ~2.499 | |
| 569 | ~0.0700 | 0.3345 |
| 570 | 0.0355 | 1.1833 |
| 571 | 0.0017 | 0.0907 |
| 572 | ~0.3699 | |
| 573 | 0.1136 | |
| 574 | 0.0139 | 0.4942 |
| 575 | ~0.7500 | |
| 576 | 0.0079 | 0.1157 |

TABLE 6-continued

FLAP binding and Human Whole Blood assay data

| Cmp No. | FLAP Binding wild type HTRF $K_i$ (μM) | Human Whole Blood LTB4 $IC_{50}$ 1:1 (μM) |
|---|---|---|
| 577 | 0.0102 | 0.0907 |
| 578 | 0.0252 | 0.9557 |
| 579 | 0.0951 | 1.5442 |
| 580 | 0.0548 | ~5.00034 |
| 581 | 0.0596 | 2.8229 |
| 582 | >10 | |
| 583 | >10 | |
| 584 | >10 | |
| 585 | >10 | |
| 586 | >10 | |
| 587 | >10 | |
| 588 | 0.1333 | >10 |
| 589 | >10 | |
| 590 | >10 | |
| 591 | ~2.4997 | |
| 592 | >10 | |
| 593 | >10 | |
| 594 | >10 | |
| 595 | ~2.4997 | |
| 596 | >10 | |
| 597 | ~2.4997 | |
| 598 | >10 | |
| 599 | >10 | |
| 600 | >10 | |
| 601 | >10 | |
| 602 | 0.0006 | 0.0167 |
| 603 | 0.0276 | >10 |
| 604 | 0.0050 | 0.0895 |
| 605 | 0.0019 | 0.0979 |
| 606 | 0.0463 | 2.6242 |
| 607 | 0.1384 | 0.1521 |
| 608 | 0.0287 | 0.0539 |
| 609 | 0.2464 | 0.7677 |
| 610 | 0.0274 | 0.1171 |
| 611 | 0.2489 | 0.5626 |
| 612 | 0.0146 | 0.0420 |
| 613 | 0.2146 | 0.5565 |
| 614 | 0.0098 | |
| 615 | 0.0509 | |
| 616 | 0.0164 | |
| 617 | 0.1615 | |
| 618 | 0.0146 | 0.2109 |
| 619 | 0.0034 | 0.0451 |
| 620 | 0.0019 | 0.0132 |
| 621 | 0.0050 | 0.1007 |
| 622 | 0.0461 | 0.3402 |
| 623 | 0.0049 | 0.0935 |
| 624 | 0.0327 | |
| 625 | 0.0078 | 0.1727 |
| 626 | 0.0062 | 0.0454 |
| 627 | 0.0437 | 0.3662 |
| 628 | 0.3362 | |
| 629 | 0.8358 | |
| 630 | 1.8950 | |
| 631 | >10 | |
| 632 | 1.2677 | |
| 633 | >10 | |
| 634 | 0.3108 | 1.4706 |
| 635 | 1.0869 | |
| 636 | 0.0046 | 0.1073 |
| 637 | 0.0188 | 0.3976 |
| 638 | 0.0014 | 0.0148 |
| 639 | 0.0072 | 0.0671 |
| 640 | 1.3397 | |
| 641 | >10 | |
| 642 | 0.0788 | 0.9806 |
| 643 | 0.3225 | 4.2875 |
| 644 | >10 | |
| 645 | >10 | |
| 646 | >10 | |
| 647 | 0.2271 | |
| 648 | 0.8339 | |
| 649 | >10 | |
| 650 | 0.8316 | |
| 651 | 0.3062 | 1.5364 |
| 652 | 0.0627 | 0.8426 |
| 653 | 0.0173 | 0.5267 |
| 654 | 0.1303 | 1.0459 |
| 655 | 0.5034 | 1.8302 |
| 656 | 1.3957 | |
| 657 | 0.0735 | 2.3415 |
| 658 | 0.5717 | |
| 659 | ~0.7500 | |
| 660 | 0.0833 | >10 |
| 661 | ~2.4997 | |
| 662 | ~1.2246 | |
| 663 | 0.0058 | 0.0347 |
| 664 | 0.0050 | >1 |
| 665 | 0.0026 | 0.0224 |
| 666 | 0.0032 | 0.0361 |
| 667 | 0.0060 | 0.0396 |
| 668 | 0.0230 | 0.1897 |
| 669 | 0.0040 | 0.1064 |
| 670 | 0.0977 | 0.5255 |
| 671 | 0.0157 | 0.1646 |
| 672 | 0.0137 | 0.1965 |
| 673 | 0.1343 | 0.1013 |
| 674 | 0.0036 | 0.0133 |
| 675 | 0.0010 | 0.0551 |
| 676 | 0.2339 | 3.7145 |
| 677 | >10 | |
| 678 | >10 | |
| 679 | 0.1316 | 0.2054 |
| 680 | 0.6097 | 1.0503 |
| 681 | 0.0522 | 0.1058 |
| 682 | 0.2239 | 0.2638 |
| 683 | 0.6021 | 0.2800 |
| 684 | 0.0463 | 0.1343 |
| 685 | 0.0592 | 0.1150 |
| 686 | 0.3343 | 1.4900 |
| 687 | 0.7399 | 3.5457 |
| 688 | 0.6955 | 1.1844 |
| 689 | 0.4846 | 0.7872 |
| 690 | 0.1771 | 0.1175 |
| 691 | >10 | |
| 692 | 0.0533 | 0.1098 |
| 693 | 0.0495 | 0.1033 |
| 694 | 0.6762 | 1.0116 |
| 695 | 0.0084 | 0.3356 |
| 696 | 0.1410 | 3.2749 |
| 697 | >10 | |
| 698 | 0.0087 | 0.1117 |
| 699 | | |
| 700 | >10 | |
| 701 | 0.1318 | |
| 702 | ~0.3041 | |
| 703 | >10 | |
| 704 | 0.1025 | 0.1907 |
| 705 | 0.0869 | 0.2891 |
| 706 | 0.0796 | 0.3621 |
| 707 | 0.0327 | 0.1267 |
| 708 | 0.0235 | 0.1416 |
| 709 | 0.0054 | 0.2682 |
| 710 | 0.0137 | 0.0565 |
| 711 | 0.0417 | 0.1420 |
| 712 | 0.0019 | 0.0523 |
| 713 | 0.0017 | 0.0534 |
| 714 | 0.0024 | 0.0331 |
| 715 | 0.0082 | 0.1858 |
| 716 | >10 | |
| 717 | 1.0083 | |
| 718 | >10 | |
| 719 | >10 | |
| 720 | >10 | |
| 721 | >10 | |
| 722 | >10 | |
| 723 | >10 | |
| 724 | >10 | |
| 725 | 1.2960 | |
| 726 | 0.9041 | |

TABLE 6-continued

FLAP binding and Human Whole Blood assay data

| Cmp No. | FLAP Binding wild type HTRF $K_i$ (μM) | Human Whole Blood LTB4 IC$_{50}$ 1:1 (μM) |
|---|---|---|
| 727 | 0.4838 | 1.1741 |
| 728 | 0.7813 | |
| 729 | 0.0647 | 0.8610 |
| 730 | 0.0067 | 0.1359 |
| 731 | 0.0147 | 0.0513 |
| 732 | 0.5571 | |
| 733 | >10 | |
| 734 | >10 | |
| 735 | 0.0320 | 0.2723 |
| 736 | 0.3303 | 0.4145 |
| 737 | 0.9842 | |
| 738 | 0.2400 | 2.9546 |
| 739 | 0.3701 | 1.1133 |
| 740 | >10 | |
| 741 | 0.0046 | 0.0263 |
| 742 | 0.0029 | 0.0257 |
| 743 | 0.0016 | 0.0217 |
| 744 | 0.0155 | 0.1317 |
| 745 | 0.0117 | 0.1107 |
| 746 | 0.0020 | 0.1370 |
| 747 | 0.0271 | 0.2622 |
| 748 | >10 | |
| 749 | 0.2455 | 0.4675 |
| 750 | 1.1582 | |
| 751 | 0.0809 | 1.0566 |
| 752 | 0.1352 | 0.2992 |
| 753 | 0.0044 | 0.0213 |
| 754 | 0.0699 | 0.3772 |
| 755 | 0.9395 | |
| 756 | >10 | |
| 757 | 0.0052 | 0.0162 |
| 758 | 0.5569 | |
| 759 | >10 | |
| 760 | 1.1558 | |
| 761 | >10 | |
| 762 | 0.1589 | 0.4418 |
| 763 | 1.1148 | |
| 764 | >10 | |
| 765 | >10 | |
| 766 | 1.9090 | |
| 767 | >10 | |
| 768 | 0.5728 | |
| 769 | 1.5449 | |
| 770 | >10 | |
| 771 | >10 | |
| 772 | >10 | |
| 773 | 0.2227 | 0.6390 |
| 774 | 1.2975 | |
| 775 | 0.0304 | |
| 776 | 0.1497 | |
| 777 | 1.6211 | |
| 778 | >10 | |
| 779 | ~2.4997 | |
| 780 | >10 | |
| 781 | 0.7295 | |
| 782 | >10 | |
| 783 | >10 | |
| 784 | 0.0079 | 0.1105 |
| 785 | 0.0085 | 0.0576 |
| 786 | 0.0607 | 0.1049 |
| 787 | 0.0091 | 0.0980 |
| 788 | 0.0178 | 1.8026 |
| 789 | 0.1303 | 0.9386 |
| 790 | 0.0015 | 0.0253 |
| 791 | >10 | |
| 792 | >10 | |
| 793 | 0.2795 | 0.6419 |
| 794 | 0.0328 | 3.9355 |
| 795 | 0.0085 | 0.0686 |
| 796 | 0.3912 | |
| 797 | >10 | |
| 798 | 0.2573 | 0.2200 |
| 799 | >10 | |
| 800 | >10 | |
| 801 | >10 | |
| 802 | >10 | >1 |
| 803 | 0.1065 | 0.2413 |
| 804 | 0.6359 | |
| 805 | 0.0297 | 0.3528 |
| 806 | 0.0018 | 0.0484 |
| 807 | 0.0058 | 0.0722 |
| 808 | 0.0004 | 0.0064 |
| 809 | 0.0038 | 0.0377 |
| 810 | 0.0006 | 0.0056 |
| 811 | 0.3149 | 0.5413 |
| 812 | 0.0085 | 0.0120 |
| 813 | 0.0339 | 0.0751 |
| 814 | 0.0028 | 0.0209 |
| 815 | 0.2555 | 0.1281 |
| 816 | 0.0370 | 0.0610 |
| 817 | 0.4629 | |
| 818 | 0.0272 | 0.0516 |
| 819 | 0.0743 | 0.0475 |
| 820 | 0.0033 | 0.0416 |
| 821 | >10 | |
| 822 | 0.2804 | 0.0991 |
| 823 | 0.1923 | 0.0951 |
| 824 | 0.0103 | 0.0180 |
| 825 | 0.2732 | 0.1223 |
| 826 | 0.0007 | 0.0199 |
| 827 | >10 | |
| 828 | 0.1153 | 0.2598 |
| 829 | 0.0057 | 0.0090 |
| 830 | 0.0029 | 0.0056 |
| 831 | 0.1492 | 0.0725 |
| 832 | 1.3119 | |
| 833 | ~0.5000 | |
| 834 | 0.0489 | 1.0907 |
| 835 | ~0.35359 | 0.4172 |
| 836 | 0.0255 | 0.5951 |
| 837 | ~1.74985 | |
| 838 | 0.0286 | 0.3501 |
| 839 | 0.8297 | 2.7880 |
| 840 | 0.0127 | 0.0996 |
| 841 | 0.1458 | 0.3697 |
| 842 | 0.0053 | 0.0610 |
| 843 | 0.0156 | 0.0443 |
| 844 | 0.5093 | 0.9072 |
| 845 | >10 | |
| 846 | 0.0105 | 0.0418 |
| 847 | 0.0081 | 0.0991 |
| 848 | 0.0968 | 0.3217 |
| 849 | 0.0383 | 3.9030 |
| 850 | 0.0377 | 0.1954 |
| 851 | 0.0326 | 0.3593 |
| 852 | 0.1179 | 1.3456 |
| 853 | 0.0047 | 0.0456 |
| 854 | 1.2773 | |
| 855 | >10 | |
| 856 | 0.0605 | 0.0839 |
| 857 | 0.0280 | 0.2055 |
| 858 | 0.2097 | 0.3697 |
| 859 | ~1.2499 | |
| 860 | ~1.4791 | |
| 861 | 0.0040 | 0.0449 |
| 862 | 0.1221 | 0.1210 |
| 863 | 0.0411 | 0.1401 |
| 864 | 0.2164 | 0.4128 |
| 865 | 0.0962 | 0.1924 |
| 866 | 0.1705 | 0.5388 |
| 867 | 0.2463 | 0.7930 |
| 868 | 0.0215 | 0.3446 |
| 869 | 0.1412 | 0.8437 |
| 870 | 0.0143 | 0.0867 |
| 871 | 0.0250 | 0.3714 |
| 872 | 0.0083 | 0.0530 |
| 873 | 0.0231 | 0.3355 |
| 874 | 0.0511 | 0.3588 |
| 875 | 0.1699 | 0.8511 |
| 876 | 0.0803 | 1.0770 |

TABLE 6-continued

FLAP binding and Human Whole Blood assay data

| Cmp No. | FLAP Binding wild type HTRF $K_i$ (μM) | Human Whole Blood LTB4 $IC_{50}$ 1:1 (μM) |
|---|---|---|
| 877 | 0.0047 | 0.0105 |
| 878 | 0.2762 | 0.3202 |
| 879 | 0.1681 | 0.1064 |
| 880 | 0.0867 | 0.1796 |
| 881 | 0.0760 | 0.1282 |
| 882 | 0.1666 | 0.0688 |
| 883 | 0.0342 | 0.0695 |
| 884 | 0.2387 | 0.7055 |
| 885 | 0.0408 | 1.0573 |
| 886 | 0.0058 | >1 |
| 887 | 0.0304 | >1 |
| 888 | 0.0007 | 0.3666 |
| 889 | 0.0039 | 0.2358 |
| 890 | 0.0037 | 0.0623 |
| 891 | 0.0315 | 0.7516 |
| 892 | 0.0774 | 0.7311 |
| 893 | 0.0303 | 0.6027 |
| 894 | 0.0038 | 0.1411 |
| 895 | 0.0132 | 0.2220 |
| 896 | 0.0221 | 0.4664 |
| 897 | 0.0070 | 0.0903 |
| 898 | 0.0797 | 0.9281 |
| 899 | 0.0770 | 0.0873 |
| 900 | 0.0351 | 0.0408 |
| 901 | 0.0018 | 0.0016 |
| 902 | 0.0184 | 0.0886 |
| 903 | 0.0387 | 0.0634 |
| 904 | 0.2547 | 0.1046 |
| 905 | 0.0579 | 0.0529 |
| 906 | 0.0003 | 0.0020 |
| 907 | 0.0060 | 0.0120 |
| 908 | 0.0266 | 0.0437 |
| 909 | 0.2528 | 0.1166 |
| 910 | 0.0029 | 0.0092 |
| 911 | 0.1663 | 0.0287 |
| 912 | 0.0005 | 0.0088 |
| 913 | 0.0063 | 0.0119 |

Throughout this application, various publications are cited. The disclosure of these publications is hereby incorporated by reference into this application to describe more fully the state of the art to which this invention pertains.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

The invention claimed is:

1. A compound of Formula (I)

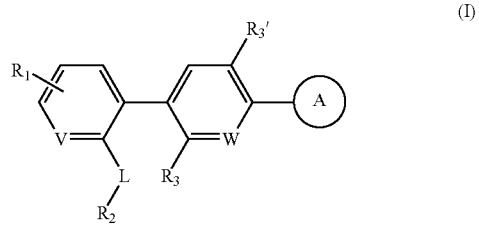

(I)

wherein

L is a bond, —CH$_2$—, —SO$_2$—, —CH$_2$—SO$_2$—, —SO$_2$—CH$_2$—, —SO$_2$—NR—, —SO$_2$—NR—CH$_2$—, —CH$_2$—SO$_2$—NR—, —NR—, —NR—SO$_2$—, —NR—SO$_2$—NR—, —S—, —S—CH$_2$—, —CH$_2$—S—,
—C(=O)—, —C(=O)—O—, —O—, —O—CH$_2$—, —NR—C(=O)—, —NR—C(=O)—NR—, or —C(=O)—NR—, wherein R is H, C$_{1-2}$alkyl, C$_{1-2}$alkyl-OH or cyclopropyl;

R$_1$ is H, halo, methyl, CF$_3$, —O—CF$_3$, or —O—CH$_3$;

R$_2$ is H, cyano, halo, —SO$_2$—CH$_3$, 2-(trimethylsilyl)ethoxy, phenyl, C$_{1-6}$alkyl, heteroaryl, heterocyclyl, C$_{3-9}$cycloalkyl, provided R$_2$ is not H if L is a bond, and wherein said phenyl, C$_{1-6}$alkyl, heteroaryl, heterocyclyl or C$_{3-9}$cycloalkyl is optionally and independently substituted with 1-4 substituents selected from the group consisting of:

methyl, ethyl, oxo, fluoro, hydroxyl, cyano, amino, methoxy, tert-butoxy, acetyl, cyclopropyl, cyclobutyl, cyclohexyl, phenyl, azetidin-1-yl, azetidin-3-yl, pyrrolidin-1-yl, 2,4-dihydro-3H-1,2,4-triazol-3-one-4-yl, 1H-imidazol-4-yl, pyrazin-2-yl, pyrimidin-2-yl, 1,3-oxazolidin-2-one-5-yl, N-benzamide, benzo[d]imidazol-2(3H)-one, 4-methylpiperazin-1-yl, morpholin-4-yl, CF$_3$, —SO$_2$—CH$_3$, —C(=O)-cyclopropyl, —SO$_2$-cyclohexyl, —NHCH$_3$, —N(CH$_3$)$_2$, —NHAc, —NHCO$_2$t-Bu, —CH$_2$—NH$_2$, —C(=O)—NH$_2$, —C(=O)—N(ethyl)$_2$, —NH—C(=O)—NH$_2$, —NH—C(=O)—CH$_3$, —C(=O)—(C$_1$-C$_4$alkyl), —C(=O)—OH, —C(=O)—NH(C$_1$-C$_4$alkyl)-(CH$_2$)$_n$—OH, and —(CH$_2$)$_n$—CN, wherein n is 1 or 2;

V is CH, CR', or N, wherein R' is methyl or F;

W is CR" or N, wherein R" is H, F, hydroxyl, amino, CH$_3$ or —O—CH$_3$;

ring A is selected from the group consisting of:

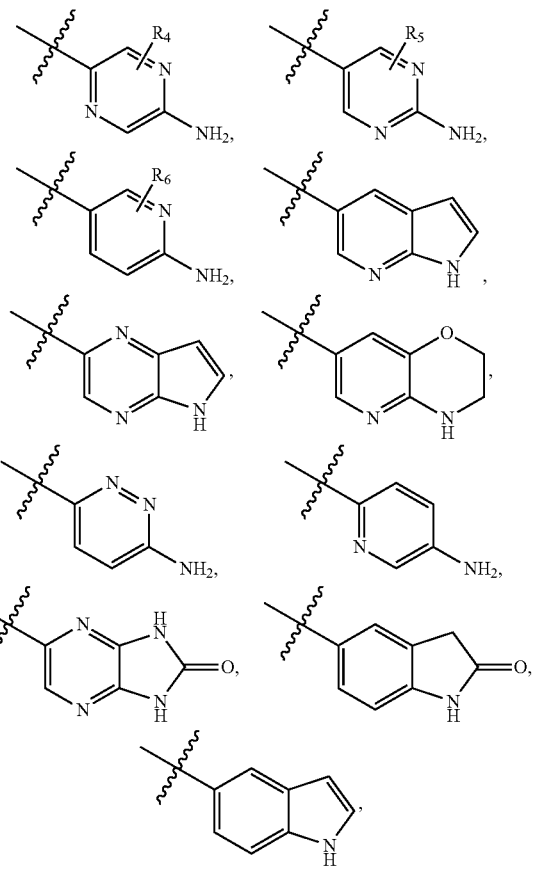

951

-continued

[structures]

$R_3$ is H, F, methyl, or —O—CH$_3$;
$R_3'$ is H or F;
$R_4$ is H, methyl, cyano, amino, halo, —COOH, or —O—CH$_3$;
$R_5$ is H, methyl, cyano, or —CF$_3$;
$R_6$ is H, cyano, amino, halo, or —CF$_3$; and
$R_7$ is halo, amino, —CONH$_2$, cyano, —O—CH$_3$, —CF$_3$, or —COO-ethyl;
or a pharmaceutically acceptable salt thereof.

2. The compound of claim 1, wherein
L is a bond, —O—, —SO$_2$—NH—, —NH—SO$_2$—, —SO$_2$—, —S—, —C(=O)—, fluoro or —C(=O)—NH—;

952

$R_1$ is H, bromo or CF$_3$;
$R_2$ is H, methyl, ethyl, propyl, isopropyl, tert-butyl, cyclopropyl, cyclohexyl, pyrrolidin-1-yl, pyrrolidin-3-yl, piperidin-1-yl, piperidin-2-yl, piperidin-3-yl, piperidin-4-yl, piperazin-1-yl, tetrahydro-2H-thiopyran-4-yl, morpholin-2-yl, morpholin-4-yl, thiomorpholin-4-yl, pyrazin-2-yl, pyrimidin-2-yl, or pyrimidin-4-yl, provided $R_2$ is not H if L is a bond, and wherein $R_2$ is optionally substituted with hydroxyl, fluoro, amino, oxo, methyl, or —CH$_2$—NH$_2$;
V is CH or N;
W is CR" or N, wherein R" is H or F;
ring A is

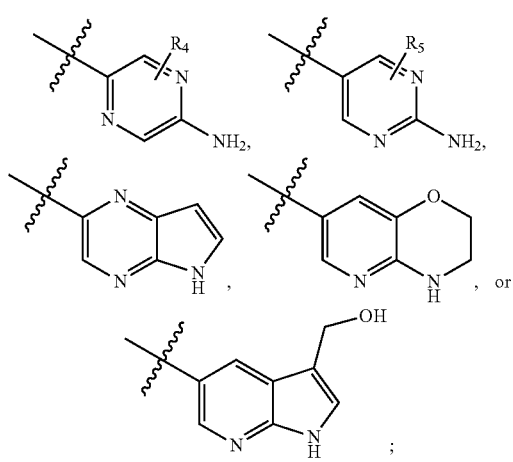

$R_3$ is H;
$R_3'$ is H;
$R_4$ is H or cyano; and
$R_5$ is H or cyano;
or a pharmaceutically acceptable salt thereof.

3. The compound of claim 1, wherein
L is a bond, —O—, —SO$_2$—NH—, —NH—SO$_2$—, —SO$_2$—, —S—, or —C(=O)—;
$R_1$ is H or CF$_3$;
$R_2$ is H, methyl, ethyl, propyl, isopropyl, tert-butyl, cyclopropyl, cyclohexyl, pyrrolidin-1-yl, pyrrolidin-3-yl, piperidin-1-yl, piperidin-2-yl, piperidin-3-yl, piperidin-4-yl, piperazin-1-yl, tetrahydro-2H-thiopyran-4-yl, morpholin-2-yl, morpholin-4-yl, thiomorpholin-4-yl, pyrazin-2-yl, pyrimidin-2-yl, or pyrimidin-4-yl, provided $R_2$ is not H if L is a bond, and wherein $R_2$ is optionally substituted with hydroxyl, fluoro, amino, oxo, methyl, or —CH$_2$—NH$_2$;
V is CH or N;
W is CR" or N, wherein R" is H or F;
ring A is

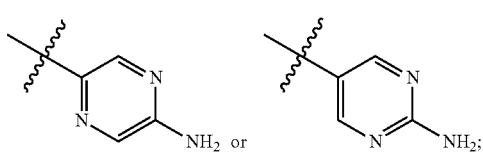 [SMILES: *c1cnc(N)cn1 ; *c1cnc(N)nc1]

$R_3$ is H; and
$R_3'$ is H;
or a pharmaceutically acceptable salt thereof.

4. The compound of claim 1, wherein the compound is selected from:

5-(3-fluoro-2'-(methylsulfonyl)-[1,1'-biphenyl]-4-yl)pyrazin-2-amine,
N-[4'-(5-Aminopyrazin-2-yl)-3'-fluorobiphenyl-2-yl]methanesulfonamide,
6-Amino-3-[3-fluoro-2'-(methylsulfonyl)biphenyl-4-yl]pyrazine-2-carbonitrile,
4'-(5-Aminopyrazin-2-yl)-N-tert-butyl-3'-fluorobiphenyl-2-sulfonamide,
4'-(5-aminopyrazin-2-yl)-3'-fluoro-[1,1'-biphenyl]-2-sulfonamide,
4'-(5-Aminopyrazin-2-yl)-N-cyclohexyl-3'-fluorobiphenyl-2-sulfonamide,
4'-(5-Aminopyrazin-2-yl)-3'-fluoro-N-(2-methylpropyl)biphenyl-2-sulfonamide,
4'-(5-Aminopyrazin-2-yl)-3'-fluoro-N-(2,2,2-trifluoro-1-methylethyl)biphenyl-2-sulfonamide (racemic),
4'-(5-Aminopyrazin-2-yl)-N-(cyclobutylmethyl)-3'-fluorobiphenyl-2-sulfonamide,
(endo)-4'-(5-Aminopyrazin-2-yl)-N-bicyclo[2.2.1]hept-2-yl-3'-fluorobiphenyl-2-sulfonamide (racemic),
4'-(5-Aminopyrazin-2-yl)-3'-fluoro-N-(1-methylcyclobutyl)biphenyl-2-sulfonamide,
4'-(5-Aminopyrazin-2-yl)-N-(1,1-dimethylpropyl)-3'-fluorobiphenyl-2-sulfonamide,
4'-(5-Aminopyrazin-2-yl)-3'-fluoro-N-(2,2,2-trifluoro-1,1-dimethylethyl)biphenyl-2-sulfonamide,
4'-(5-Aminopyrazin-2-yl)-N-cyclopentyl-3'-fluorobiphenyl-2-sulfonamide,
4'-(5-Aminopyrazin-2-yl)-3'-fluoro-N-methylbiphenyl-2-sulfonamide,
4'-(5-Aminopyrazin-2-yl)-N-ethyl-3'-fluorobiphenyl-2-sulfonamide,
4'-(5-Aminopyrazin-2-yl)-3'-fluoro-N-(2-phenylethyl)biphenyl-2-sulfonamide,
(R)-4'-(5-Aminopyrazin-2-yl)-3'-fluoro-N-[(1R)-2,2,2-trifluoro-1-phenylethyl]biphenyl-2-sulfonamide,
(S)-4'-(5-Aminopyrazin-2-yl)-3'-fluoro-N-[(1S)-2,2,2-trifluoro-1-phenylethyl]biphenyl-2-sulfonamide,
(S)-4'-(5-Aminopyrazin-2-yl)-3'-fluoro-N-[(1S)-2,2,2-trifluoro-1-methylethyl]biphenyl-2-sulfonamide,
4'-(5-Aminopyrazin-2-yl)-N-(2,3-dihydro-1H-inden-2-yl)-3'-fluorobiphenyl-2-sulfonamide,
(S)-4'-(5-Aminopyrazin-2-yl)-N-[(1S)-2,3-dihydro-1H-inden-1-yl]-3'-fluorobiphenyl-2-sulfonamide,
(R)-4'-(5-Aminopyrazin-2-yl)-N-[(1R)-2,3-dihydro-1H-inden-1-yl]-3'-fluorobiphenyl-2-sulfonamide,
(R)-4'-(5-Aminopyrazin-2-yl)-3'-fluoro-N-[(1R)-1-phenylethyl]biphenyl-2-sulfonamide,
(R)-4'-(5-Aminopyrazin-2-yl)-3'-fluoro-N-[(1R)-2-hydroxy-1-methylethyl]biphenyl-2-sulfonamide,
4'-(5-Aminopyrazin-2-yl)-3'-fluoro-N-phenylbiphenyl-2-sulfonamide,
(S)-4'-(5-Aminopyrazin-2-yl)-N-[(3S)-1-ethyl-2-oxoazepan-3-yl]-3'-fluorobiphenyl-2-sulfonamide,
(S)-4'-(5-Aminopyrazin-2-yl)-3'-fluoro-N-[(3S)-2-oxoazepan-3-yl]biphenyl-2-sulfonamide,
(S)-4'-(5-Aminopyrazin-2-yl)-3'-fluoro-N-[(3S)-1-methyl-2-oxoazepan-3-yl]biphenyl-2-sulfonamide,
4'-(5-Aminopyrazin-2-yl)-3'-fluoro-N-(1,2,2,6,6-pentamethylpiperidin-4-yl)biphenyl-2-sulfonamide,
4'-(5-Aminopyrazin-2-yl)-3'-fluoro-N-pyridin-3-ylbiphenyl-2-sulfonamide,
4'-(5-Aminopyrazin-2-yl)-3'-fluoro-N-[(1S)-2-hydroxy-1-methylethyl]biphenyl-2-sulfonamide,
N-[4'-(5-Aminopyrazin-2-yl)-3'-fluorobiphenyl-2-yl]sulfamide,
N-(4'-(5-aminopyrazin-2-yl)-3'-fluoro-[1,1'-biphenyl]-2-yl)propane-2-sulfonamide,
N-[4'-(5-Aminopyrazin-2-yl)-3'-fluorobiphenyl-2-yl]ethanesulfonamide,
N-[4'-(5-Aminopyrazin-2-yl)-3'-fluorobiphenyl-2-yl]propane-1-sulfonamide,
N-[4'-(5-Aminopyrazin-2-yl)-3'-fluorobiphenyl-2-yl]-2-methylpropane-1-sulfonamide,
N-(4'-(5-aminopyrazin-2-yl)-3'-fluoro-[1,1'-biphenyl]-2-yl)cyclopropanesulfonamide,
N-[4'-(5-Aminopyrazin-2-yl)-3'-fluorobiphenyl-2-yl]hexane-1-sulfonamide,
N-(4'-(5-aminopyrazin-2-yl)-3'-fluoro-[1,1'-biphenyl]-2-yl)cyclobutanesulfonamide,
N-[4'-(5-Aminopyrazin-2-yl)-3'-fluorobiphenyl-2-yl]-1,1,1-trifluoromethanesulfonamide,
4'-(5-Aminopyrazin-2-yl)-3'-fluoro-N,N-dimethylbiphenyl-2-sulfonamide,
5-[3-Fluoro-2'-(piperidin-1-ylsulfonyl)biphenyl-4-yl]pyrazin-2-amine,
5-[3-Fluoro-2'-(morpholin-4-ylsulfonyl)biphenyl-4-yl]pyrazin-2-amine,
5-{2'-[(1,1-Dioxidothiomorpholin-4-yl)sulfonyl]-3-fluorobiphenyl-4-yl}pyrazin-2-amine,
5-[3-Fluoro-2'-(piperazin-1-ylsulfonyl)biphenyl-4-yl]pyrazin-2-amine,
4'-(5-Aminopyrazin-2-yl)-N,N-diethyl-3'-fluorobiphenyl-2-sulfonamide,
5-[3-Fluoro-2'-(pyrrolidin-1-ylsulfonyl)biphenyl-4-yl]pyrazin-2-amine,
5-{2'-[(4,4-Difluoropiperidin-1-yl)sulfonyl]-3-fluorobiphenyl-4-yl}pyrazin-2-amine,
5-{2'-[(3,3-Difluoropiperidin-1-yl)sulfonyl]-3-fluorobiphenyl-4-yl}pyrazin-2-amine,
5-{2'-[(3,3-Difluoropyrrolidin-1-yl)sulfonyl]-3-fluorobiphenyl-4-yl}pyrazin-2-amine,
5-{2'-[(3,3-Difluoroazetidin-1-yl)sulfonyl]-3-fluorobiphenyl-4-yl}pyrazin-2-amine,
5-[2'-(Azepan-1-ylsulfonyl)-3-fluorobiphenyl-4-yl]pyrazin-2-amine,
5-{3-Fluoro-2'-[(4-methylpiperazin-1-yl)sulfonyl]biphenyl-4-yl}pyrazin-2-amine,
1-{[4'-(5-Aminopyrazin-2-yl)-3'-fluorobiphenyl-2-yl]sulfonyl}-4-(trifluoromethyl)piperidin-4-ol,
5-(3-Fluoro-2'-{[4-(methylsulfonyl)piperazin-1-yl]sulfonyl}biphenyl-4-yl)pyrazin-2-amine,
5-{2'-[(4-Acetylpiperazin-1-yl)sulfonyl]-3-fluorobiphenyl-4-yl}pyrazin-2-amine,
5-(2'-{[4-(Cyclopropylcarbonyl)piperazin-1-yl]sulfonyl}-3-fluorobiphenyl-4-yl)pyrazin-2-amine,
2-(4-{[4'-(5-Aminopyrazin-2-yl)-3'-fluorobiphenyl-2-yl]sulfonyl}piperazin-1-yl)ethanol,
5-{2'-[(4-Cyclopropylpiperazin-1-yl)sulfonyl]-3-fluorobiphenyl-4-yl}pyrazin-2-amine,
racemic 5-[3-Fluoro-2'-(hexahydropyrrolo[1,2-a]pyrazin-2(1H)-ylsulfonyl)biphenyl-4-yl]pyrazin-2-amine,
5-{2'-[(3,5-Dimethylpiperazin-1-yl)sulfonyl]-3-fluorobiphenyl-4-yl}pyrazin-2-amine,
racemic 1-{[4'-(5-Aminopyrazin-2-yl)-3'-fluorobiphenyl-2-yl]sulfonyl}piperidine-3-carbonitrile,
1-{[4'-(5-Aminopyrazin-2-yl)-3'-fluorobiphenyl-2-yl]sulfonyl}piperidine-4-carbonitrile,
5-{2'-[(4-Aminopiperidin-1-yl)sulfonyl]-3-fluorobiphenyl-4-yl}pyrazin-2-amine, 4-{[4'-(5-Aminopyrazin-2-yl)-3'-fluorobiphenyl-2-yl]sulfonyl}piperazin-2-one,
1-{[4'-(5-Aminopyrazin-2-yl)-3'-fluorobiphenyl-2-yl]sulfonyl}piperidin-4-ol,
(1-{[4'-(5-Aminopyrazin-2-yl)-3'-fluorobiphenyl-2-yl]sulfonyl}piperidin-4-yl)methanol,
2-(1-{[4'-(5-Aminopyrazin-2-yl)-3'-fluorobiphenyl-2-yl]sulfonyl}piperidin-4-yl)ethanol,
racemic 1-{[4'-(5-Aminopyrazin-2-yl)-3'-fluorobiphenyl-2-yl]sulfonyl}piperidin-3-ol,
racemic 2-(1-{[4'-(5-Aminopyrazin-2-yl)-3'-fluorobiphenyl-2-yl]sulfonyl}piperidin-3-yl)ethanol,
5-(3-Fluoro-2'-{[4-(methylamino)piperidin-1-yl]sulfonyl}biphenyl-4-yl)pyrazin-2-amine,
5-(2'-{[4-(Dimethylamino)piperidin-1-yl]sulfonyl}-3-fluorobiphenyl-4-yl)pyrazin-2-amine,
racemic 5-{2'-[(3-Aminopiperidin-1-yl)sulfonyl]-3-fluorobiphenyl-4-yl}pyrazin-2-amine,
N-(1-{[4'-(5-Aminopyrazin-2-yl)-3'-fluorobiphenyl-2-yl]sulfonyl}piperidin-4-yl)acetamide,
racemic (1-{[4'-(5-Aminopyrazin-2-yl)-3'-fluorobiphenyl-2-yl]sulfonyl}piperidin-3-yl)methanol,
racemic tert-Butyl (1-{[4'-(5-aminopyrazin-2-yl)-3'-fluorobiphenyl-2-yl]sulfonyl}piperidin-3-yl)carbamate,
4'-(5-Aminopyrazin-2-yl)-3'-fluoro-N-[(1S,2S)-2-hydroxy-1-(hydroxymethyl)-2-phenylethyl]biphenyl-2-sulfonamide,
4'-(5-Aminopyrazin-2-yl)-3'-fluoro-N-[(1S)-1-(hydroxymethyl)-3-methylbutyl]biphenyl-2-sulfonamide,
4'-(5-Aminopyrazin-2-yl)-3'-fluoro-N-(3-hydroxypropyl)biphenyl-2-sulfonamide,
4'-(5-Aminopyrazin-2-yl)-3'-fluoro-N-[(1S)-2-hydroxy-1-phenylethyl]biphenyl-2-sulfonamide,
4'-(5-Aminopyrazin-2-yl)-3'-fluoro-N-[(1R)-2-hydroxy-1-phenylethyl]biphenyl-2-sulfonamide,
4'-(5-Aminopyrazin-2-yl)-3'-fluoro-N-[(1S,2R)-2-hydroxy-1-methyl-2-phenylethyl]biphenyl-2-sulfonamide,
4'-(5-Aminopyrazin-2-yl)-3'-fluoro-N-[(1S,2S)-1-(hydroxymethyl)-2-methylbutyl]biphenyl-2-sulfonamide,
4'-(5-Aminopyrazin-2-yl)-3'-fluoro-N-[(1R,2R)-2-hydroxycyclohexyl]biphenyl-2-sulfonamide,
4'-(5-Aminopyrazin-2-yl)-3'-fluoro-N-[(1R)-1-(hydroxymethyl)propyl]biphenyl-2-sulfonamide,
4'-(5-Aminopyrazin-2-yl)-3'-fluoro-N-[(1R,2S)-2-hydroxycyclohexyl]biphenyl-2-sulfonamide,
4'-(5-Aminopyrazin-2-yl)-3'-fluoro-N-(2-hydroxyethyl)biphenyl-2-sulfonamide,
4'-(5-Aminopyrazin-2-yl)-N-cyclopropyl-3'-fluorobiphenyl-2-sulfonamide,
4'-(5-Aminopyrazin-2-yl)-N-(cyclopropylmethyl)-3'-fluorobiphenyl-2-sulfonamide,
(R)-(1-((4'-(5-aminopyrazin-2-yl)-3'-fluoro-[1,1'-biphenyl]-2-yl)sulfonyl)pyrrolidin-2-yl)methanol,
(R)-5-(2'-((3-aminopyrrolidin-1-yl)sulfonyl)-3-fluoro-[1,1'-biphenyl]-4-yl)pyrazin-2-amine,
(S)-5-(2'-((3-aminopyrrolidin-1-yl)sulfonyl)-3-fluoro-[1,1'-biphenyl]-4-yl)pyrazin-2-amine,
(R) 5-(2'-{[2-(Aminomethyl)pyrrolidin-1-yl]sulfonyl}-3-fluorobiphenyl-4-yl)pyrazin-2-amine,
(S)-(1-((4'-(5-aminopyrazin-2-yl)-3'-fluoro-[1,1'-biphenyl]-2-yl)sulfonyl)pyrrolidin-2-yl)methanol,
4'-(5-Aminopyrazin-2-yl)-3'-fluoro-N-(methylsulfonyl)biphenyl-2-sulfonamide,
(R)-4'-(5-aminopyrazin-2-yl)-3'-fluoro-N-(2-hydroxypropyl)-[1,1'-biphenyl]-2-sulfonamide,
(S)-4'-(5-aminopyrazin-2-yl)-3'-fluoro-N-(2-hydroxypropyl)-[1,1'-biphenyl]-2-sulfonamide,
4'-(5-Aminopyrazin-2-yl)-3'-fluoro-N-[(1-hydroxycyclohexyl)methyl]biphenyl-2-sulfonamide,
4'-(5-Aminopyrazin-2-yl)-3'-fluoro-N-(2-hydroxy-1,1-dimethylethyl)biphenyl-2-sulfonamide,
4'-(5-Aminopyrazin-2-yl)-3'-fluoro-N-(2-hydroxy-2-methylpropyl)biphenyl-2-sulfonamide,
4'-(5-Aminopyrazin-2-yl)-3'-fluoro-N-(3-hydroxy-1,1-dimethylpropyl)biphenyl-2-sulfonamide,
4'-(5-Aminopyrazin-2-yl)-3'-fluoro-N-(3-hydroxy-2,2-dimethylpropyl)biphenyl-2-sulfonamide,
(S)-4'-(5-aminopyrazin-2-yl)-N-(2,3-dihydroxypropyl)-3'-fluoro-[1,1'-biphenyl]-2-sulfonamide,
(R)-4'-(5-aminopyrazin-2-yl)-N-(2,3-dihydroxypropyl)-3'-fluoro-[1,1'-biphenyl]-2-sulfonamide,
(trans)-1-{[4'-(5-Aminopyrazin-2-yl)-3'-fluorobiphenyl-2-yl]sulfonyl}pyrrolidine-3,4-diol,
(S)-4'-(5-aminopyrazin-2-yl)-3'-fluoro-N-(2-oxopyrrolidin-3-yl)-[1,1'-biphenyl]-2-sulfonamide,
(S)-4'-(5-aminopyrazin-2-yl)-3'-fluoro-N-(2-oxopiperidin-3-yl)-[1,1'-biphenyl]-2-sulfonamide,
(R)-4'-(5-Aminopyrazin-2-yl)-3'-fluoro-N-[1-(hydroxymethyl)-2-methylpropyl]biphenyl-2-sulfonamide,
trans 4'-(5-Aminopyrazin-2-yl)-3'-fluoro-N-(4-hydroxycyclohexyl)biphenyl-2-sulfonamide,
(R)-(1-((4'-(5-aminopyrazin-2-yl)-3'-fluoro-[1,1'-biphenyl]-2-yl)sulfonyl)pyrrolidin-3-yl)methanol,
(S)-(1-{[4'-(5-Aminopyrazin-2-yl)-3'-fluorobiphenyl-2-yl]sulfonyl}pyrrolidin-3-yl)methanol,
(R)-4'-(5-Aminopyrazin-2-yl)-3'-fluoro-N-(2-oxopiperidin-3-yl)biphenyl-2-sulfonamide,
(R)-4'-(5-Aminopyrazin-2-yl)-3'-fluoro-N-methyl-N-piperidin-3-ylbiphenyl-2-sulfonamide,
(S)-4'-(5-Aminopyrazin-2-yl)-3'-fluoro-N-methyl-N-piperidin-3-ylbiphenyl-2-sulfonamide,
(S)-4'-(5-aminopyrazin-2-yl)-3'-fluoro-N-(1-hydroxy-3-phenylpropan-2-yl)-[1,1'-biphenyl]-2-sulfonamide,
(R)-4'-(5-aminopyrazin-2-yl)-3'-fluoro-N-(2-hydroxy-2-phenylethyl)-[1,1'-biphenyl]-2-sulfonamide,
4'-(5-aminopyrazin-2-yl)-3'-fluoro-N-((1S,2S)-1-hydroxy-1-phenylpropan-2-yl)-N-methyl-[1,1'-biphenyl]-2-sulfonamide,
1-{[4'-(5-Aminopyrazin-2-yl)-3'-fluorobiphenyl-2-yl]sulfonyl}azetidin-3-ol,
racemic (trans)-4'-(5-Aminopyrazin-2-yl)-3'-fluoro-N-(2-hydroxycyclohexyl)biphenyl-2-sulfonamide,
racemic (trans)-4'-(5-Aminopyrazin-2-yl)-3'-fluoro-N-[2-(hydroxymethyl)cyclohexyl]biphenyl-2-sulfonamide,
racemic (cis)-4'-(5-Aminopyrazin-2-yl)-3'-fluoro-N-[2-(hydroxymethyl)cyclohexyl]biphenyl-2-sulfonamide,
4'-(5-Aminopyrazin-2-yl)-3'-fluoro-N-piperidin-4-ylbiphenyl-2-sulfonamide,
5-(2'-{[3-(Aminomethyl)azetidin-1-yl]sulfonyl}-3-fluorobiphenyl-4-yl)pyrazin-2-amine,
4'-(5-Aminopyrazin-2-yl)-N-(azetidin-3-ylmethyl)-3'-fluorobiphenyl-2-sulfonamide,
(R)-5-(3-Fluoro-2'-{[3-(methylamino)pyrrolidin-1-yl]sulfonyl}biphenyl-4-yl)pyrazin-2-amine,
(R)-4'-(5-Aminopyrazin-2-yl)-3'-fluoro-N-(2,2,2-trifluoro-1-methylethyl)biphenyl-2-sulfonamide,
5-[3-Fluoro-2'-(1,4,6,7-tetrahydro-5H-pyrazolo[4,3-c]pyridin-5-ylsulfonyl)biphenyl-4-yl]pyrazin-2-amine,
4-(1-{[4'-(5-Aminopyrazin-2-yl)-3'-fluorobiphenyl-2-yl]sulfonyl}piperidin-4-yl)-2,4-dihydro-3H-1,2,4-triazol-3-one, 5-(2'-((1R,4R)-2,5-diazabicyclo[2.2.1]heptan-2-ylsulfonyl)-3-fluoro-[1,1'-biphenyl]-4-yl)pyrazin-2-amine,
5-(2'-((1S,4S)-2,5-diazabicyclo[2.2.1]heptan-2-ylsulfonyl)-3-fluoro-[1,1'-biphenyl]-4-yl)pyrazin-2-amine,
4'-(5-Aminopyrazin-2-yl)-3'-fluoro-N-(5-hydroxypentyl) biphenyl-2-sulfonamide,
4'-(5-Aminopyrazin-2-yl)-3'-fluoro-N-(6-hydroxyhexyl) biphenyl-2-sulfonamide,
N-(4-Aminocyclohexyl)-4'-(5-aminopyrazin-2-yl)-3'-fluorobiphenyl-2-sulfonamide,
(S)-(1-{[4'-(5-Aminopyrazin-2-yl)-3'-fluorobiphenyl-2-yl]sulfonyl}-2,3-dihydro-1H-indol-2-yl)methanol,
4'-(5-Aminopyrazin-2-yl)-N-cyclohexyl-3'-fluoro-N-(2-hydroxyethyl)biphenyl-2-sulfonamide,
(S)-5-{2'-[(3-Aminopiperidin-1-yl)sulfonyl]-3-fluorobiphenyl-4-yl}pyrazin-2-amine,
4'-(5-Aminopyrazin-2-yl)-3'-fluoro-N,N-bis(2-hydroxyethyl)biphenyl-2-sulfonamide,
1-{[4'-(5-Aminopyrazin-2-yl)-3'-fluorobiphenyl-2-yl]sulfonyl}azetidine-2-carboxamide,
4'-(5-Aminopyrazin-2-yl)-N-cyclopropyl-3'-fluoro-N-(tetrahydro-2H-pyran-4-yl)biphenyl-2-sulfonamide,
4'-(5-Aminopyrazin-2-yl)-3'-fluoro-N-(2-hydroxyethyl)-N-(1-methylethyl)biphenyl-2-sulfonamide,
racemic (4-{[4'-(5-Aminopyrazin-2-yl)-3'-fluorobiphenyl-2-yl]sulfonyl}morpholin-2-yl)methanol,
(1R,5S)-3-((4'-(5-aminopyrazin-2-yl)-3'-fluoro-[1,1'-biphenyl]-2-yl)sulfonyl)-3-azabicyclo[3.1.0]hexan-6-amine,
(S)-5-(3-fluoro-2'-((2-methylpiperazin-1-yl)sulfonyl)-[1,1'-biphenyl]-4-yl)pyrazin-2-amine,
(R)-5-(3-fluoro-2'-((2-methylpiperazin-1-yl)sulfonyl)-[1,1'-biphenyl]-4-yl)pyrazin-2-amine,
(R)-(1-((4'-(5-aminopyrazin-2-yl)-3'-fluoro-[1,1'-biphenyl]-2-yl)sulfonyl)piperazin-2-yl)methanol,
4'-(5-Aminopyrazin-2-yl)-3'-fluoro-N-[2-hydroxy-1-(hydroxymethyl)-1-methylethyl]biphenyl-2-sulfonamide,
(S)-4'-(5-aminopyrazin-2-yl)-3'-fluoro-N-(1-hydroxy-3-methyl butan-2-yl)-[1,1'-biphenyl]-2-sulfonamide,
(S)-4'-(5-aminopyrazin-2-yl)-3'-fluoro-N-(1-hydroxy-3,3-dimethylbutan-2-yl)-[1,1'-biphenyl]-2-sulfonamide,
(R)-4'-(5-aminopyrazin-2-yl)-3'-fluoro-N-(1-hydroxy-3,3-dimethylbutan-2-yl)-[1,1'-biphenyl]-2-sulfonamide,
tert-Butyl [2-({[4'-(5-aminopyrazin-2-yl)-3'-fluorobiphenyl-2-yl]sulfonyl}amino)ethyl]carbamate,
N-(2-Aminoethyl)-4'-(5-aminopyrazin-2-yl)-3'-fluorobiphenyl-2-sulfonamide,
(S)-4'-(5-aminopyrazin-2-yl)-3'-fluoro-N-(1-hydroxybutan-2-yl)-[1,1'-biphenyl]-2-sulfonamide,
(S)-4'-(5-aminopyrazin-2-yl)-3'-fluoro-N-(pyrrolidin-3-yl)-[1,1'-biphenyl]-2-sulfonamide,
N-[2-({[4'-(5-Aminopyrazin-2-yl)-3'-fluorobiphenyl-2-yl]sulfonyl}amino)ethyl]acetamide,
(S)-2-(4'-(5-aminopyrazin-2-yl)-3'-fluoro-[1,1'-biphenyl]-2-ylsulfonamido)propanoic acid,
4'-(5-Aminopyrazin-2-yl)-N-[2-(carbamoylamino)ethyl]-3'-fluorobiphenyl-2-sulfonamide,
4'-(5-aminopyrazin-2-yl)-3'-fluoro-N-((1S,2S)-2-hydroxy-2,3-dihydro-1H-inden-1-yl)-[1,1'-biphenyl]-2-sulfonamide,
4'-(5-aminopyrazin-2-yl)-3'-fluoro-N-((1R,2R)-2-hydroxy-2,3-dihydro-1H-inden-1-yl)-[1,1'-biphenyl]-2-sulfonamide,
4'-(5-aminopyrazin-2-yl)-3'-fluoro-N-((1S,2R)-2-hydroxy-2,3-dihydro-1H-inden-1-yl)-[1,1'-biphenyl]-2-sulfonamide,
4'-(5-aminopyrazin-2-yl)-3'-fluoro-N-((1R,2S)-2-hydroxy-2,3-dihydro-1H-inden-1-yl)-[1,1'-biphenyl]-2-sulfonamide,
4'-(5-aminopyrazin-2-yl)-3'-fluoro-N-((1S,2S)-2-hydroxycyclohexyl)-[1,1'-biphenyl]-2-sulfonamide,
4'-(5-Aminopyrazin-2-yl)-3'-fluoro-N-[6-(trifluoromethyl)pyridin-3-yl]biphenyl-2-sulfonamide,
5-(3-Fluoro-2'-{[4-(1H-imidazol-4-yl)piperidin-1-yl]sulfonyl}biphenyl-4-yl)pyrazin-2-amine,
N-[(4-Amino-2-methylpyrimidin-5-yl)methyl]-4'-(5-aminopyrazin-2-yl)-3'-fluorobiphenyl-2-sulfonamide,
4'-(5-Aminopyrazin-2-yl)-N-(2,6-dimethoxypyrimidin-4-yl)-3'-fluorobiphenyl-2-sulfonamide,
4'-(5-Aminopyrazin-2-yl)-3'-fluoro-N-(5-methylpyrazin-2-yl)biphenyl-2-sulfonamide,
(S)-2-(4'-(5-aminopyrazin-2-yl)-3'-fluoro-[1,1'-biphenyl]-2-ylsulfonamido)-4-methylpentanamide,
4'-(5-Aminopyrazin-2-yl)-N-(2-cyanoethyl)-3'-fluorobiphenyl-2-sulfonamide,
(R)-4'-(5-aminopyrazin-2-yl)-N-(1-cyanopropan-2-yl)-3'-fluoro-[1,1'-biphenyl]-2-sulfonamide,
(S)-4'-(5-aminopyrazin-2-yl)-N-(1-cyanopropan-2-yl)-3'-fluoro-[1,1'-biphenyl]-2-sulfonamide,
4'-(5-Aminopyrazin-2-yl)-N-(2-cyanoethyl)-N-cyclopropyl-3'-fluorobiphenyl-2-sulfonamide,
4'-(5-Aminopyrazin-2-yl)-3'-fluoro-N-(3-methyloxetan-3-yl)biphenyl-2-sulfonamide,
3-(4-{[4'-(5-Aminopyrazin-2-yl)-3'-fluorobiphenyl-2-yl]sulfonyl}piperazin-1-yl)propanenitrile,
(S)-4'-(5-aminopyrazin-2-yl)-3'-fluoro-N-(1-methoxypropan-2-yl)-[1,1'-biphenyl]-2-sulfonamide,
5-{3-Fluoro-2'-[(4-pyrazin-2-ylpiperazin-1-yl)sulfonyl]biphenyl-4-yl}pyrazin-2-amine,
5-{3-Fluoro-2'-[(4-pyrimidin-2-ylpiperazin-1-yl)sulfonyl]biphenyl-4-yl}pyrazin-2-amine,
5-(2'-Amino-3-fluorobiphenyl-4-yl)pyrazin-2-amine,
4'-(5-Aminopyrazin-2-yl)-3'-fluoro-N-[1-(hydroxymethyl)cyclopentyl]biphenyl-2-sulfonamide,
1-{[4'-(5-Aminopyrazin-2-yl)-3'-fluorobiphenyl-2-yl]sulfonyl}-3-phenylpyrrolidin-3-ol,
N-[4'-(5-Aminopyrazin-2-yl)-3'-fluorobiphenyl-2-yl]pyrrolidine-1-sulfonamide,
N'-[4'-(5-Aminopyrazin-2-yl)-3'-fluorobiphenyl-2-yl]-N,N-dimethylsulfamide,
N-[4'-(5-Aminopyrazin-2-yl)-3'-fluorobiphenyl-2-yl]morpholine-4-sulfonamide,
(3S)-1-{[4'-(5-Aminopyrazin-2-yl)-3'-fluorobiphenyl-2-yl]sulfonyl}pyrrolidin-3-ol,
(3R)-1-{[4'-(5-Aminopyrazin-2-yl)-3'-fluorobiphenyl-2-yl]sulfonyl}pyrrolidin-3-ol,
(3S,4S)-1'-{[4'-(5-Aminopyrazin-2-yl)-3'-fluorobiphenyl-2-yl]sulfonyl}-1,3'-bipyrrolidin-4'-ol,
(3S,4S)-1-{[4'-(5-Aminopyrazin-2-yl)-3'-fluorobiphenyl-2-yl]sulfonyl}-4-morpholin-4-ylpyrrolidin-3-ol,
(3S,4S)-1-{[4'-(5-Aminopyrazin-2-yl)-3'-fluorobiphenyl-2-yl]sulfonyl}-4-(4-methylpiperazin-1-yl)pyrrolidin-3-ol,
5-{3-Fluoro-2'-[(trifluoromethyl)-sulfanyl]biphenyl-4-yl}pyrazin-2-amine,
5-[2'-(tert-Butylsulfanyl)-3-fluorobiphenyl-4-yl]pyrazin-2-amine,
5-[2'-(Ethylsulfonyl)-3-fluorobiphenyl-4-yl]pyrazin-2-amine,
5-[3-Fluoro-2'-(propylsulfonyl)biphenyl-4-yl]pyrazin-2-amine,
5-{3-Fluoro-2'-[(2-methylpropyl)sulfonyl]biphenyl-4-yl}pyrazin-2-amine, 5-[2'-(tert-Butylsulfonyl)-3-fluorobiphenyl-4-yl]pyrazin-2-amine,
5-[2'-(Cyclopentylsulfonyl)-3-fluorobiphenyl-4-yl]pyrazin-2-amine,
5-[2'-(Cyclobutylsulfonyl)-3-fluorobiphenyl-4-yl]pyrazin-2-amine,
5-[2'-(Cyclopropylsulfonyl)-3-fluorobiphenyl-4-yl]pyrazin-2-amine,
5-{3-Fluoro-2'-[(1-methylethyl)sulfonyl]biphenyl-4-yl}pyrazin-2-amine,
5-{3-Fluoro-2'-[(trifluoromethyl)sulfonyl]biphenyl-4-yl}pyrazin-2-amine,
2-{[4'-(5-Aminopyrazin-2-yl)-3'-fluorobiphenyl-2-yl]sulfanyl}acetamide,
2-{[4'-(5-Aminopyrazin-2-yl)-3'-fluorobiphenyl-2-yl]sulfanyl}-N,N-diethylacetamide,
5-{3-Fluoro-2'-[(2-morpholin-4-yl-2-oxoethyl)sulfanyl]biphenyl-4-yl}pyrazin-2-amine,
(racemic) 5-({[4'-(5-Aminopyrazin-2-yl)-3'-fluorobiphenyl-2-yl]sulfanyl}methyl)-1,3-oxazolidin-2-one,
N-(2-{[4'-(5-Aminopyrazin-2-yl)-3'-fluorobiphenyl-2-yl]sulfanyl}ethyl)benzamide,
5-(3-Fluoro-2'-{[4-(methylsulfonyl)benzyl]sulfanyl}biphenyl-4-yl)pyrazin-2-amine,
4'-(5-Aminopyrazin-2-yl)-3'-fluoro-4-(trifluoromethyl)biphenyl-2-sulfonamide,
5-[3-Fluoro-2'-(methylsulfonyl)-4'-(trifluoromethyl)biphenyl-4-yl]pyrazin-2-amine,
4'-(5-Aminopyrazin-2-yl)-3'-fluoro-N-methyl-4-(trifluoromethyl)biphenyl-2-sulfonamide,
4-{[4'-(5-Aminopyrazin-2-yl)-3'-fluoro-4-(trifluoromethyl)biphenyl-2-yl]sulfonyl}piperazin-2-one,
4'-(5-aminopyrazin-2-yl)-3'-fluoro-N-(2-hydroxyethyl)-4-(trifluoromethyl)biphenyl-2-sulfonamide,
4'-(5-Aminopyrazin-2-yl)-N-ethyl-3'-fluoro-4-(trifluoromethyl)biphenyl-2-sulfonamide,
5-{3-Fluoro-2'-[(4-methylpiperazin-1-yl)sulfonyl]-4'-(trifluoromethyl)biphenyl-4-yl}pyrazin-2-amine,
5-[3-Fluoro-2'-(pyrimidin-2-ylsulfanyl)biphenyl-4-yl]pyrazin-2-amine hydrochloride,
5-[3-Fluoro-2'-(pyrimidin-4-ylsulfanyl)biphenyl-4-yl]pyrimidin-2-amine formate salt,
6-{[4'-(5-Aminopyrazin-2-yl)-3'-fluorobiphenyl-2-yl]sulfanyl}pyrimidin-4-amine hydrochloride,
2-{[4'-(5-Aminopyrazin-2-yl)-3'-fluorobiphenyl-2-yl]sulfanyl}pyrimidin-4-amine hydrochloride,
4-{[4'-(5-Aminopyrazin-2-yl)-3'-fluorobiphenyl-2-yl]sulfanyl}pyrimidin-5-amine hydrochloride,
5-[3-Fluoro-2'-(pyrazin-2-ylsulfanyl)biphenyl-4-yl]pyrazin-2-amine hydrochloride,
2-{[4'-(5-Aminopyrazin-2-yl)-3'-fluorobiphenyl-2-yl]sulfanyl}pyrimidin-5-amine hydrochloride,
1-[4'-(5-Aminopyrazin-2-yl)-3'-fluorobiphenyl-2-yl]-N-methyl methanesulfonamide formic acid salt,
1-[4'-(5-Aminopyrazin-2-yl)-3'-fluorobiphenyl-2-yl]-N-(2-hydroxyethyl)methanesulfonamide formic acid salt,
1-({[4'-(5-Aminopyrazin-2-yl)-3'-fluorobiphenyl-2-yl]methyl}sulfonyl)azetidin-3-ol formic acid salt,
4-({[4'-(5-Aminopyrazin-2-yl)-3'-fluorobiphenyl-2-yl]methyl}sulfonyl)piperazin-2-one formic acid salt,
(S)-1-(4'-(5-Aminopyrazin-2-yl)-3'-fluoro-[1,1'-biphenyl]-2-yl)-N-(1-hydroxypropan-2-yl)methanesulfonamide,
(R)-1-(4'-(5-Aminopyrazin-2-yl)-3'-fluoro-[1,1'-biphenyl]-2-yl)-N-(1-hydroxypropan-2-yl)methanesulfonamide hydrochloride,
1-[4'-(5-Aminopyrazin-2-yl)-3'-fluorobiphenyl-2-yl]-N-(trans-4-hydroxycyclohexyl)methanesulfonamide,
(S)-1-[4'-(5-Aminopyrazin-2-yl)-3'-fluorobiphenyl-2-yl]-N-[(2S)-2-hydroxypropyl]methanesulfonamide hydrochloride,
(R)-1-[4'-(5-Aminopyrazin-2-yl)-3'-fluorobiphenyl-2-yl]-N-[(2S)-2-hydroxypropyl]methanesulfonamide,
5-(2'-{[(4-Aminopiperidin-1-yl)sulfonyl]methyl}-3-fluorobiphenyl-4-yl)pyrazin-2-amine hydrochloride,
1-[4'-(5-Aminopyrazin-2-yl)-3'-fluorobiphenyl-2-yl]methanesulfonamide hydrochloride,
1-[4'-(5-Aminopyrazin-2-yl)-3'-fluorobiphenyl-2-yl]-N-ethylmethanesulfonamide formate salt,
1-[1-({[4'-(5-Aminopyrazin-2-yl)-3'-fluorobiphenyl-2-yl]methyl}sulfonyl)piperidin-4-yl]urea hydrochloride,
N-[1-({[4'-(5-Aminopyrazin-2-yl)-3'-fluorobiphenyl-2-yl]methyl}sulfonyl)piperidin-4-yl]acetamide formate salt,
5-{2'-[(Ethylsulfanyl)methyl]-3-fluorobiphenyl-4-yl}pyrazin-2-amine formate salt,
5-{3-Fluoro-2'-[(methylsulfanyl)methyl]biphenyl-4-yl}pyrazin-2-amine hydrochloride,
5-(3-Fluoro-2'-{[(1-methylethyl)sulfanyl]methyl}biphenyl-4-yl)pyrazin-2-amine hydrochloride,
2-(((4'-(5-Aminopyrazin-2-yl)-3'-fluoro-[1,1'-biphenyl]-2-yl)methyl)thio)pyrimidin-4-amine hydrochloride,
6-(((4'-(5-aminopyrazin-2-yl)-3'-fluoro-[1,1'-biphenyl]-2-yl)methyl)thio)pyrimidin-4-amine hydrochloride,
5-(3-fluoro-2'-((pyridazin-3-ylthio)methyl)-[1,1'-biphenyl]-4-yl)pyrazin-2-amine hydrochloride,
6-(((4'-(5-Aminopyrazin-2-yl)-3'-fluoro-[1,1'-biphenyl]-2-yl)methyl)thio)pyridazin-3-amine hydrochloride,
5-{2'-[(1,1-Dioxidotetrahydro-2H-thiopyran-4-yl)sulfonyl]-3-fluorobiphenyl-4-yl}pyrazin-2-amine,
4-{[4'-(5-Aminopyrazin-2-yl)-3'-fluorobiphenyl-2-yl]sulfanyl}pyrimidin-2-amine hydrochloride,
5-(3-fluoro-2'-((pyrimidin-4-ylthio)methyl)-[1,1'-biphenyl]-4-yl)pyrazin-2-amine hydrochloride,
5-[3-Fluoro-2'-({[2-(trimethylsilyl)ethoxy]methyl}sulfanyl)biphenyl-4-yl]pyrazin-2-amine,
5-[3-Fluoro-2'-({[2-(trimethylsilyl)ethoxy]methyl}sulfonyl)biphenyl-4-yl]pyrazin-2-amine hydrochloride,
5-(3-Fluoro-2'-{[3-(methylsulfonyl)propyl]sulfonyl}biphenyl-4-yl)pyrazin-2-amine hydrochloride,
5-(3-Fluoro-2'-{[(2R)-2-methylpiperazin-1-yl]sulfonyl}biphenyl-4-yl)pyrimidin-2-amine,
4'-(2-Aminopyrimidin-5-yl)-3'-fluoro-N-[(1S)-1-(hydroxymethyl)propyl]biphenyl-2-sulfonamide,
4'-(2-Aminopyrimidin-5-yl)-N-(2-cyanoethyl)-N-cyclopropyl-3'-fluorobiphenyl-2-sulfonamide,
4'-(2-Aminopyrimidin-5-yl)-N-(2-cyanoethyl)-3'-fluorobiphenyl-2-sulfonamide,
4'-(2-Aminopyrimidin-5-yl)-3'-fluoro-N-(3-hydroxy-2,2-dimethylpropyl)biphenyl-2-sulfonamide,
racemic (4-{[4'-(2-Aminopyrimidin-5-yl)-3'-fluorobiphenyl-2-yl]sulfonyl}morpholin-2-yl)methanol,
5-(3-Fluoro-2'-{[(2S)-2-methylpiperazin-1-yl]sulfonyl}biphenyl-4-yl)pyrimidin-2-amine,
5-[2'-(Cyclopropylsulfonyl)-3-fluorobiphenyl-4-yl]pyrimidin-2-amine,
4'-(2-Aminopyrimidin-5-yl)-3'-fluoro-N-[2-hydroxy-1-(hydroxymethyl)-1-methylethyl]biphenyl-2-sulfonamide,
4'-(2-aminopyrimidin-5-yl)-3'-fluoro-N-methyl-N-[(3S)-piperidin-3-yl]biphenyl-2-sulfonamide, 4'-(2-aminopyrimidin-5-yl)-3'-fluoro-N-methyl-N-[(3R)-piperidin-3-yl]biphenyl-2-sulfonamide,

[(2R)-1-{[4'-(2-Aminopyrimidin-5-yl)-3'-fluorobiphenyl-2-yl]sulfonyl}piperazin-2-yl]methanol, racemic cis 4'-(2-Aminopyrimidin-5-yl)-3'-fluoro-N-[(cis)-2-hydroxycyclohexyl]biphenyl-2-sulfonamide, racemis trans 4'-(2-Aminopyrimidin-5-yl)-3'-fluoro-N-[(trans)-2-hydroxycyclohexyl]biphenyl-2-sulfonamide, 4'-(2-Aminopyrimidin-5-yl)-3'-fluoro-N-(2-hydroxyethyl)-N-(1-methylethyl)biphenyl-2-sulfonamide, 4'-(2-Aminopyrimidin-5-yl)-3'-fluoro-N-(trans-4-hydroxycyclohexyl)biphenyl-2-sulfonamide, 4'-(2-Aminopyrimidin-5-yl)-3'-fluoro-N-[(3S)-2-oxopyrrolidin-3-yl]biphenyl-2-sulfonamide, 5-{2'-[(1,1-Dioxidothiomorpholin-4-yl)sulfonyl]-3-fluorobiphenyl-4-yl}pyrimidin-2-amine, 4'-(2-Aminopyrimidin-5-yl)-3'-fluoro-N-[(2R)-2-hydroxypropyl]biphenyl-2-sulfonamide, 1-{[4'-(2-Aminopyrimidin-5-yl)-3'-fluorobiphenyl-2-yl]sulfonyl}azetidin-3-ol trifluoroacetic acid salt, 4'-(2-Aminopyrimidin-5-yl)-3'-fluoro-N-[(3R)-2-oxopiperidin-3-yl]biphenyl-2-sulfonamide trifluoroacetic acid salt, 4'-(2-Aminopyrimidin-5-yl)-3'-fluoro-N-[(3S)-2-oxopiperidin-3-yl]biphenyl-2-sulfonamide trifluoroacetic acid salt, 4'-(2-Aminopyrimidin-5-yl)-3'-fluoro-N-[(1R)-2,2,2-trifluoro-1-methylethyl]biphenyl-2-sulfonamide trifluoroacetic acid salt, 4'-(2-Aminopyrimidin-5-yl)-3'-fluoro-N-[(1R)-1-(hydroxymethyl)-2,2-dimethylpropyl]biphenyl-2-sulfonamide trifluoroacetic acid salt, 4'-(2-Aminopyrimidin-5-yl)-3'-fluoro-N-[(1S)-1-(hydroxymethyl)-2,2-dimethylpropyl]biphenyl-2-sulfonamide trifluoroacetic acid salt, 4'-(2-Aminopyrimidin-5-yl)-3'-fluoro-N-[(1S)-1-(hydroxymethyl)-2-methylpropyl]biphenyl-2-sulfonamide trifluoroacetic acid salt, 4'-(2-Aminopyrimidin-5-yl)-3'-fluoro-N-(2-hydroxy-2-methylpropyl)biphenyl-2-sulfonamide trifluoroacetic acid salt, 4'-(2-Aminopyrimidin-5-yl)-3'-fluoro-N-[(1R)-1-(hydroxymethyl)-2-methylpropyl]biphenyl-2-sulfonamide trifluoroacetic acid salt, 4'-(2-Aminopyrimidin-5-yl)-N-[(2S)-2,3-dihydroxypropyl]-3'-fluorobiphenyl-2-sulfonamide trifluoroacetic acid salt, 4'-(2-Aminopyrimidin-5-yl)-3'-fluoro-N-(2-hydroxyethyl)biphenyl-2-sulfonamide trifluoroacetic acid salt,

[(2R)-1-{[4'-(2-Aminopyrimidin-5-yl)-3'-fluorobiphenyl-2-yl]sulfonyl}pyrrolidin-2-yl]methanol trifluoroacetic acid salt,

[(2S)-1-{[4'-(2-Aminopyrimidin-5-yl)-3'-fluorobiphenyl-2-yl]sulfonyl}pyrrolidin-2-yl]methanol trifluoroacetic acid salt, 4'-(2-Aminopyrimidin-5-yl)-3'-fluoro-N-[(2S)-2-hydroxypropyl]biphenyl-2-sulfonamide trifluoroacetic acid salt, 4'-(2-Aminopyrimidin-5-yl)-3'-fluoro-N-(2-hydroxy-1,1-dimethylethyl)biphenyl-2-sulfonamide trifluoroacetic acid salt, 5-{2'-[(4-Cyclopropylpiperazin-1-yl)sulfonyl]-3-fluorobiphenyl-4-yl}pyrimidin-2-amine trifluoroacetic acid salt, 2-(4-{[4'-(2-Aminopyrimidin-5-yl)-3'-fluorobiphenyl-2-yl]sulfonyl}piperazin-1-yl)ethanol trifluoroacetic acid salt, 4'-(2-Aminopyrimidin-5-yl)-N-(cyclopropylmethyl)-3'-fluorobiphenyl-2-sulfonamide trifluoroacetic acid, 4'-(2-Aminopyrimidin-5-yl)-N-cyclopropyl-3'-fluorobiphenyl-2-sulfonamide trifluoroacetic acid salt, 4'-(2-Aminopyrimidin-5-yl)-3'-fluoro-N-phenylbiphenyl-2-sulfonamide trifluoroacetic acid salt, 4'-(2-Aminopyrimidin-5-yl)-3'-fluoro-N-[(1S)-2-hydroxy-1-methylethyl]biphenyl-2-sulfonamide trifluoroacetic acid salt, 4'-(2-Aminopyrimidin-5-yl)-N-tert-butyl-3'-fluoro-3-methylbiphenyl-2-sulfonamide trifluoroacetic acid salt, 4'-(2-Aminopyrimidin-5-yl)-3'-fluoro-N-methylbiphenyl-2-sulfonamide trifluoroacetic acid salt, 4'-(2-Aminopyrimidin-5-yl)-3'-fluoro-N-[(1R)-2-hydroxy-1-methylethyl]biphenyl-2-sulfonamide trifluoroacetic acid salt, 5-[3-Fluoro-2'-(piperazin-1-ylsulfonyl)biphenyl-4-yl]pyrimidin-2-amine trifluoroacetic acid salt, 4'-(2-Aminopyrimidin-5-yl)-3'-fluoro-N-[(1R)-2,2,2-trifluoro-1-phenylethyl]biphenyl-2-sulfonamide trifluoroacetic acid salt, 4'-(2-Aminopyrimidin-5-yl)-3'-fluoro-N-[(1S)-2,2,2-trifluoro-1-phenylethyl]biphenyl-2-sulfonamide trifluoroacetic acid salt, 5-[2'-(tert-Butylsulfonyl)-3-fluorobiphenyl-4-yl]pyrimidin-2-amine trifluoroacetic acid salt, 4'-(2-Aminopyrimidin-5-yl)-3'-fluoro-N-(2-methylpropyl)biphenyl-2-sulfonamide trifluoroacetic acid salt, 4'-(2-Aminopyrimidin-5-yl)-N-ethyl-3'-fluorobiphenyl-2-sulfonamide trifluoroacetic acid salt, 4'-(2-Aminopyrimidin-5-yl)-3'-fluoro-N-(2,2,2-trifluoro-1,1-dimethylethyl)biphenyl-2-sulfonamide trifluoroacetic acid salt, 4'-(2-Aminopyrimidin-5-yl)-3'-fluoro-N-[(1S)-2,2,2-trifluoro-1-methylethyl]biphenyl-2-sulfonamide trifluoroacetic acid salt, 5-[3-Fluoro-2'-(pyrrolidin-1-ylsulfonyl)biphenyl-4-yl]pyrimidin-2-amine trifluoroacetic acid salt, 4'-(2-Aminopyrimidin-5-yl)-3'-fluoro-N,N-dimethylbiphenyl-2-sulfonamide trifluoroacetic acid salt, 4'-(2-Aminopyrimidin-5-yl)-N,N-diethyl-3'-fluorobiphenyl-2-sulfonamide trifluoroacetic acid salt, 5-[3-Fluoro-2'-(piperidin-1-ylsulfonyl)biphenyl-4-yl]pyrimidin-2-amine trifluoroacetic acid salt, 4'-(2-Aminopyrimidin-5-yl)-3'-fluorobiphenyl-2-sulfonamide trifluoroacetic acid salt, 5-[3-Fluoro-2'-(morpholin-4-ylsulfonyl)biphenyl-4-yl]pyrimidin-2-amine trifluoroacetic acid salt, 5-[3-Fluoro-2'-(methylsulfonyl)biphenyl-4-yl]pyrimidin-2-amine trifluoroacetic acid salt, 4'-(2-aminopyrimidin-5-yl)-N-(tert-butyl)-3'-fluoro-[1,1'-biphenyl]-2-sulfonamide trifluoroacetic acid salt, 4-{[4'-(2-Aminopyrimidin-5-yl)-3'-fluorobiphenyl-2-yl]sulfonyl}piperazin-2-one trifluoroacetic acid salt, tert-Butyl N-{[4'-(2-aminopyrimidin-5-yl)-3'-fluorobiphenyl-2-yl]sulfonyl}-L-alaninate, N-{[4'-(2-Aminopyrimidin-5-yl)-3'-fluorobiphenyl-2-yl]sulfonyl}-L-alanine, N-[4'-(2-Aminopyrimidin-5-yl)-3'-fluorobiphenyl-2-yl]pyrrolidine-1-sulfonamide, N-[4'-(2-Aminopyrimidin-5-yl)-3'-fluorobiphenyl-2-yl]morpholine-4-sulfonamide, N'-[4'-(2-Aminopyrimidin-5-yl)-3'-fluorobiphenyl-2-yl]-N,N-dimethylsulfamide, 5-(2'-(2-oxa-6-azaspiro[3.3]heptan-6-ylsulfony)-3-fluoro-[1,1'-biphenyl]-4-yl)pyrimidin-2-amine,
6-((4'-(2-aminopyrimidin-5-yl)-3'-fluoro-[1,1'-biphenyl]-2-yl)sulfonyl)-2-thia-6-azaspiro[3.3]heptane 2,2-dioxide,
1-((4'-(2-aminopyrimidin-5-yl)-3'-fluoro-[1,1'-biphenyl]-2-yl)sulfonyl)azetidine-3-carbonitrile,
1-((4'-(2-aminopyrimidin-5-yl)-3'-fluoro-[1,1'-biphenyl]-2-yl)sulfonyl)-3-(trifluoromethyl)azetidin-3-ol,
5-{2'-[(1,1-Dioxidotetrahydro-2H-thiopyran-4-yl)sulfonyl]-3-fluorobiphenyl-4-yl}pyrimidin-2-amine hydrochloride,
2-(((4'-(2-aminopyrimidin-5-yl)-3'-fluoro-[1,1'-biphenyl]-2-yl)sulfonyl)methyl)quinazolin-4(3H)-one,
1-(3-((4'-(2-aminopyrimidin-5-yl)-3'-fluoro-[1,1'-biphenyl]-2-yl)sulfonyl)propyl)-1H-benzo[d]imidazol-2(3H)-one,
5-(2'-{[3-(Cyclohexylsulfonyl)propyl]sulfonyl}-3-fluorobiphenyl-4-yl)pyrimidin-2-amine,
5-{3-Fluoro-2'-[(1-methyl-1H-benzimidazol-2-yl)sulfonyl]biphenyl-4-yl}pyrimidin-2-amine,
5-(2'-{[(3-Cyclopropyl-1,2,4-oxadiazol-5-yl)methyl]sulfonyl}-3-fluorobiphenyl-4-yl)pyrimidin-2-amine,
4'-(2-aminopyrimidin-5-yl)-3'-fluoro-4-(trifluoromethyl)biphenyl-2-sulfonamide,
5-[3-fluoro-2'-(methylsulfonyl)-4'-(trifluoromethyl)biphenyl-4-yl]pyrimidin-2-amine,
4-{[4'-(2-aminopyrimidin-5-yl)-3'-fluoro-4-(trifluoromethyl)biphenyl-2-yl]sulfonyl}piperazin-2-one,
4'-(2-aminopyrimidin-5-yl)-3'-fluoro-N-methyl-4-(trifluoromethyl)biphenyl-2-sulfonamide,
4'-(2-Aminopyrimidin-5-yl)-3'-fluoro-N-(2-hydroxyethyl)-4-(trifluoromethyl)biphenyl-2-sulfonamide,
4'-(2-Aminopyrimidin-5-yl)-N-ethyl-3'-fluoro-4-(trifluoromethyl)biphenyl-2-sulfonamide,
5-{3-Fluoro-2'-[(4-methylpiperazin-1-yl)sulfonyl]-4'-(trifluoromethyl)biphenyl-4-yl}pyrimidin-2-amine,
5-{2'-[(5-Aminopyrimidin-2-yl)sulfanyl]-3-fluorobiphenyl-4-yl}pyrimidin-2-amine formate salt,
5-{2'-[(4-Aminopyrimidin-2-yl)sulfanyl]-3-fluorobiphenyl-4-yl}pyrimidin-2-amine formate salt,
5-{2'-[(5-Aminopyrimidin-4-yl)sulfanyl]-3-fluorobiphenyl-4-yl}pyrimidin-2-amine formate salt,
5-[3-Fluoro-2'-(pyrimidin-2-ylsulfanyl)biphenyl-4-yl]pyrimidin-2-amine hydrochloride,
5-[3-Fluoro-2'-(pyrazin-2-ylsulfanyl)biphenyl-4-yl]pyrimidin-2-amine hydrochloride,
5-{2'-[(6-Aminopyrimidin-4-yl)sulfanyl]-3-fluorobiphenyl-4-yl}pyrimidin-2-amine formate salt,
4-{[4'-(2-Aminopyrimidin-5-yl)-3'-fluorobiphenyl-2-yl]sulfanyl}pyrimidin-2-amine formate salt,
5-{2'-[(6-Aminopyrazin-2-yl)sulfanyl]-3-fluorobiphenyl-4-yl}pyrimidin-2-amine formate salt,
5-{2'-[(5-Aminopyrimidin-4-yl)sulfonyl]-3-fluorobiphenyl-4-yl}pyrimidin-2-amine hydrochloride,
5-[3-Fluoro-2'-({[2-(trimethylsilyl)ethoxy]methyl}sulfonyl)biphenyl-4-yl]pyrimidin-2-amine formate salt,
5-{2'-[(5-Aminopyrimidin-2-yl)sulfonyl]-3-fluorobiphenyl-4-yl}pyrimidin-2-amine hydrochloride,
5-[3-Fluoro-2'-({[2-(trimethylsilyl)ethoxy]methyl}sulfanyl)biphenyl-4-yl]pyrimidin-2-amine,
5-(3-Fluoro-2'-(methylsulfonyl)-[1,1'-biphenyl]-4-yl)pyridin-2-amine,
4'-(6-aminopyridin-3-yl)-N-(tert-butyl)-3'-fluoro-[1,1'-biphenyl]-2-sulfonamide,
4'-(6-aminopyridin-3-yl)-N,N-diethyl-3'-fluoro-[1,1'-biphenyl]-2-sulfonamide,
5-(3-fluoro-2'-(pyrrolidin-1-ylsulfonyl)-[1,1'-biphenyl]-4-yl)pyridin-2-amine,
5-(3-fluoro-2'-(piperidin-1-ylsulfonyl)-[1,1'-biphenyl]-4-yl)pyridin-2-amine,
4'-(6-aminopyridin-3-yl)-N-cyclohexyl-3'-fluoro-[1,1'-biphenyl]-2-sulfonamide,
(S)-4'-(6-aminopyridin-3-yl)-3'-fluoro-N-(1-hydroxypropan-2-yl)-[1,1'-biphenyl]-2-sulfonamide,
4'-(6-aminopyridin-3-yl)-3'-fluoro-N-isobutyl-[1,1'-biphenyl]-2-sulfonamide,
4'-(6-aminopyridin-3-yl)-3'-fluoro-N-(tert-pentyl)-[1,1'-biphenyl]-2-sulfonamide,
4'-(6-aminopyridin-3-yl)-3'-fluoro-N-(1,1,1-trifluoro-2-methylpropan-2-yl)-[1,1'-biphenyl]-2-sulfonamide,
(S)-4'-(6-aminopyridin-3-yl)-3'-fluoro-N-(2,2,2-trifluoro-1-phenylethyl)-[1,1'-biphenyl]-2-sulfonamide,
(R)-4'-(6-aminopyridin-3-yl)-3'-fluoro-N-(1-hydroxypropan-2-yl)-[1,1'-biphenyl]-2-sulfonamide,
4'-(6-aminopyridin-3-yl)-3'-fluoro-N-(1-methylcyclobutyl)-[1,1'-biphenyl]-2-sulfonamide,
4-((4'-(6-aminopyridin-3-yl)-3'-fluoro-[1,1'-biphenyl]-2-yl)sulfonyl)thiomorpholine 1,1-dioxide,
(S)-4'-(6-aminopyridin-3-yl)-3'-fluoro-N-(1,1,1-trifluoropropan-2-yl)-[1,1'-biphenyl]-2-sulfonamide,
5-(2'-((1S,4S)-2-oxa-5-azabicyclo[2.2.1]heptan-5-ylsulfonyl)-3-fluoro-[1,1'-biphenyl]-4-yl)pyridin-2-amine,
tert-butyl 3-((4'-(6-aminopyridin-3-yl)-3'-fluoro-[1,1'-biphenyl]-2-ylsulfonamido)methyl)-3-hydroxyazetidine-1-carboxylate,
4'-(6-aminopyridin-3-yl)-3'-fluoro-N-((3-hydroxyazetidin-3-yl)methyl)-[1,1'-biphenyl]-2-sulfonamide,
2-(1-((4'-(6-aminopyridin-3-yl)-3'-fluoro-[1,1'-biphenyl]-2-yl)sulfonyl)piperidin-4-yl)ethanol,
1-((4'-(6-aminopyridin-3-yl)-3'-fluoro-[1,1'-biphenyl]-2-yl)sulfonyl)piperidin-4-ol,
(1-((4'-(6-aminopyridin-3-yl)-3'-fluoro-[1,1'-biphenyl]-2-yl)sulfonyl)piperidin-4-yl)methanol,
3'-Fluoro-N-[(1S)-2-hydroxy-1-methylethyl]-4'-(1H-pyrrolo[2,3-b]pyridin-5-yl)biphenyl-2-sulfonamide,
3'-Fluoro-N-[(1R)-2-hydroxy-1-methylethyl]-4'-(1H-pyrrolo[2,3-b]pyridin-5-yl)biphenyl-2-sulfonamide,
3'-Fluoro-N-[(3S)-2-oxopyrrolidin-3-yl]-4'-(1H-pyrrolo[2,3-b]pyridin-5-yl)biphenyl-2-sulfonamide,
5-[2'-(Cyclopropylsulfonyl)-3-fluorobiphenyl-4-yl]-1H-pyrrolo[2,3-b]pyridine,
3'-Fluoro-N-(2-hydroxyethyl)-4'-(1H-pyrrolo[2,3-b]pyridin-5-yl)biphenyl-2-sulfonamide,
N-tert-Butyl-3'-fluoro-4'-(1H-pyrrolo[2,3-b]pyridin-5-yl)biphenyl-2-sulfonamide,
3'-Fluoro-4'-(1H-pyrrolo[2,3-b]pyridin-5-yl)biphenyl-2-sulfonamide,
N-[3'-Fluoro-4'-(5H-pyrrolo[2,3-b]pyrazin-2-yl)biphenyl-2-yl]methanesulfonamide,
3'-Fluoro-N,N-dimethyl-4'-(5H-pyrrolo[2,3-b]pyrazin-2-yl)biphenyl-2-sulfonamide,
N-tert-Butyl-3'-fluoro-4'-(5H-pyrrolo[2,3-b]pyrazin-2-yl)biphenyl-2-sulfonamide,
2-[3-Fluoro-2'-(pyrrolidin-1-ylsulfonyl)biphenyl-4-yl]-5H-pyrrolo[2,3-b]pyrazine,
N,N-Diethyl-3'-fluoro-4'-(5H-pyrrolo[2,3-b]pyrazin-2-yl)biphenyl-2-sulfonamide,
2-[3-Fluoro-2'-(piperidin-1-ylsulfonyl)biphenyl-4-yl]-5H-pyrrolo[2,3-b]pyrazine,
2-[3-Fluoro-2'-(morpholin-4-ylsulfonyl)biphenyl-4-yl]-5H-pyrrolo[2,3-b]pyrazine, 3'-Fluoro-4'-(5H-pyrrolo[2,3-b]pyrazin-2-yl)-N-(2,2,2-trifluoro-1-methylethyl)biphenyl-2-sulfonamide,
2-[3-Fluoro-2'-(methylsulfonyl)biphenyl-4-yl]-5H-pyrrolo[2,3-b]pyrazine,
3'-Fluoro-N-[(1R)-2-hydroxy-1-methylethyl]-4'-(5H-pyrrolo[2,3-b]pyrazin-2-yl)biphenyl-2-sulfonamide,
3'-Fluoro-N-methyl-4'-(5H-pyrrolo[2,3-b]pyrazin-2-yl)biphenyl-2-sulfonamide,
3'-Fluoro-N-[(1S)-2-hydroxy-1-methylethyl]-4'-(5H-pyrrolo[2,3-b]pyrazin-2-yl)biphenyl-2-sulfonamide,
1-{[3'-Fluoro-4'-(5H-pyrrolo[2,3-b]pyrazin-2-yl)biphenyl-2-yl]sulfonyl}piperidin-4-amine,
2-{2'-[(1,1-Dioxidothiomorpholin-4-yl)sulfonyl]-3-fluorobiphenyl-4-yl}-5H-pyrrolo[2,3-b]pyrazine,
2-[3,5'-Difluoro-2'-(methylsulfanyl)biphenyl-4-yl]-5H-pyrrolo[2,3-b]pyrazine,
2-[2'-(Ethylsulfanyl)-3-fluorobiphenyl-4-yl]-5H-pyrrolo[2,3-b]pyrazine,
7-[3-Fluoro-2'-(methylsulfonyl)biphenyl-4-yl]-3,4-dihydro-2H-pyrido[3,2-b][1,4]oxazine,
7-[3-Fluoro-2'-(piperidin-1-ylsulfonyl)biphenyl-4-yl]-3,4-dihydro-2H-pyrido[3,2-b][1,4]oxazine,
4'-(3,4-Dihydro-2H-pyrido[3,2-b][1,4]oxazin-7-yl)-3'-fluorobiphenyl-2-sulfonamide,
4'-(3,4-Dihydro-2H-pyrido[3,2-b][1,4]oxazin-7-yl)-3'-fluoro-N-[(1S)-2-hydroxy-1-methylethyl]biphenyl-2-sulfonamide,
1-{[4'-(3,4-Dihydro-2H-pyrido[3,2-b][1,4]oxazin-7-yl)-3'-fluorobiphenyl-2-yl]sulfonyl}piperidin-4-amine,
4'-(3,4-Dihydro-2H-pyrido[3,2-b][1,4]oxazin-7-yl)-3'-fluoro-N-[(1R)-2-hydroxy-1-methylethyl]biphenyl-2-sulfonamide,
4'-(3,4-Dihydro-2H-pyrido[3,2-b][1,4]oxazin-7-yl)-N,N-diethyl-3'-fluorobiphenyl-2-sulfonamide,
7-{2'-[(1,1-Dioxidothiomorpholin-4-yl)sulfonyl]-3-fluorobiphenyl-4-yl}-3,4-dihydro-2H-pyrido[3,2-b][1,4]oxazine,
N-tert-Butyl-4'-(3,4-dihydro-2H-pyrido[3,2-b][1,4]oxazin-7-yl)-3'-fluorobiphenyl-2-sulfonamide,
2-(2-Fluoro-4-{2-[(1-methylethyl)sulfanyl]-5-(trifluoromethyl)pyridin-3-yl}phenyl)-5H-pyrrolo[2,3-b]pyrazine,
5-(2-Fluoro-4-{2-[(1-methylethyl)sulfonyl]pyridin-3-yl}phenyl)pyrazin-2-amine,
5-(2-Fluoro-4-{2-[(1-methylethyl)sulfanyl]pyridin-3-yl}phenyl)pyrazin-2-amine,
2-{2-Fluoro-4-[2-(2,2,2-trifluoroethoxy)pyridin-3-yl]phenyl}-5H-pyrrolo[2,3-b]pyrazine,
2-{2-Fluoro-4-[2-(2-methylpropoxy)pyridin-3-yl]phenyl}-5H-pyrrolo[2,3-b]pyrazine,
2-{2-Fluoro-4-[2-(1-methylethoxy)pyridin-3-yl]phenyl}-5H-pyrrolo[2,3-b]pyrazine,
2-{4-[2-(Cyclopropylmethoxy)pyridin-3-yl]-2-fluorophenyl}-5H-pyrrolo[2,3-b]pyrazine,
5-{2-Fluoro-4-[2-(1-methylethoxy)pyridin-3-yl]phenyl}pyrazin-2-amine,
5-{4-[2-(Cyclopentyloxy)pyridin-3-yl]-2-fluorophenyl}pyrazin-2-amine,
5-{4-[2-(Cyclohexyloxy)pyridin-3-yl]-2-fluorophenyl}pyrazin-2-amine,
5-[2-Fluoro-4-(2-methoxypyridin-3-yl)phenyl]pyrazin-2-amine,
5-{4-[2-(Cyclobutyloxy)pyridin-3-yl]-2-fluorophenyl}pyrazin-2-amine,
tert-Butyl 3-[({3-[4-(5-aminopyrazin-2-yl)-3-fluorophenyl]pyridin-2-yl}oxy)methyl]pyrrolidine-1-carboxylate,
5-{2-Fluoro-4-[2-(pyrrolidin-3-ylmethoxy)pyridin-3-yl]phenyl}pyrazin-2-amine,
5-{2-Fluoro-4-[2-(1-methylethoxy)pyridin-3-yl]phenyl}pyrimidin-2-amine,
5-[4-(2-Aminopyridin-3-yl)-2-fluorophenyl]pyrimidin-2-amine,
4'-(5-amino-6-cyanopyrazin-2-yl)-3'-fluoro-N-[(2R)-2-hydroxy-1-methylethyl]biphenyl-2-sulfonamide,
3-Amino-6-[2'-(cyclopropylsulfonyl)-3-fluorobiphenyl-4-yl]pyrazine-2-carbonitrile,
4'-(5-Amino-6-cyanopyrazin-2-yl)-3'-fluoro-N-[(1S)-2-hydroxy-1-methylethyl]biphenyl-2-sulfonamide,
4'-(5-Amino-6-cyanopyrazin-2-yl)-3'-fluoro-N-(2-hydroxyethyl)biphenyl-2-sulfonamide,
3-Amino-6-{3-fluoro-2'-[(3-oxopiperazin-1-yl)sulfonyl]biphenyl-4-yl}pyrazine-2-carbonitrile,
4'-(5-Amino-6-cyanopyrazin-2-yl)-3'-fluoro-N-[(2R)-2-hydroxypropyl]biphenyl-2-sulfonamide,
3-Amino-6-[3-fluoro-2'-(morpholin-4-ylcarbonyl)biphenyl-4-yl]pyrazine-2-carbonitrile,
4'-(6-Aminopyridazin-3-yl)-N-tert-butyl-3'-fluorobiphenyl-2-sulfonamide,
N-tert-Butyl-3'-fluoro-4'-(7H-pyrrolo[2,3-d]pyrimidin-2-yl)biphenyl-2-sulfonamide,
N-tert-Butyl-3'-fluoro-4'-(1,8-naphthyridin-3-yl)biphenyl-2-sulfonamide,
N-tert-Butyl-3'-fluoro-4'-quinoxalin-6-ylbiphenyl-2-sulfonamide,
N-tert-Butyl-3'-fluoro-4'-(1H-indol-5-yl)biphenyl-2-sulfonamide,
4'-(1H-Benzimidazol-5-yl)-N-tert-butyl-3'-fluorobiphenyl-2-sulfonamide,
4'-(1H-Benzimidazol-5-yl)-3'-fluoro-N-methylbiphenyl-2-sulfonamide,
4'-(1,3-Benzothiazol-5-yl)-N-tert-butyl-3'-fluorobiphenyl-2-sulfonamide,
N-tert-Butyl-3'-fluoro-4'-(1H-pyrrolo[3,2-b]pyridin-6-yl)biphenyl-2-sulfonamide,
3'-Fluoro-N-methyl-4'-(1H-pyrrolo[2,3-b]pyridin-5-yl)biphenyl-2-sulfonamide,
4'-(5-Aminopyridin-2-yl)-N-tert-butyl-3'-fluorobiphenyl-2-sulfonamide,
N-tert-Butyl-4'-(5,6-diaminopyrazin-2-yl)-3'-fluorobiphenyl-2-sulfonamide,
N-tert-Butyl-3'-fluoro-4'-(2-oxo-2,3-dihydro-1H-imidazo[4,5-b]pyrazin-5-yl)biphenyl-2-sulfonamide,
4'-(6-Amino-5-fluoropyridin-3-yl)-N-tert-butyl-3'-fluorobiphenyl-2-sulfonamide,
N-tert-Butyl-4'-(2,3-dihydro-1H-pyrrolo[2,3-b]pyridin-5-yl)-3'-fluorobiphenyl-2-sulfonamide,
N-tert-Butyl-3'-fluoro-4'-(3H-imidazo[4,5-b]pyridin-6-yl)biphenyl-2-sulfonamide,
4'-(5-Amino-6-methoxypyrazin-2-yl)-N-tert-butyl-3'-fluorobiphenyl-2-sulfonamide,
4'-(5-Amino-6-cyanopyrazin-2-yl)-N-tert-butyl-3'-fluorobiphenyl-2-sulfonamide,
4'-(5-Amino-3-cyanopyrazin-2-yl)-N-tert-butyl-3'-fluorobiphenyl-2-sulfonamide,
4'-(6-Amino-4-cyanopyridin-3-yl)-N-tert-butyl-3'-fluorobiphenyl-2-sulfonamide,
4'-(6-amino-2-cyanopyridin-3-yl)-N-(tert-butyl)-3'-fluoro-[1,1'-biphenyl]-2-sulfonamide,
4'-(5-Amino-6-chloropyrazin-2-yl)-N-tert-butyl-3'-fluorobiphenyl-2-sulfonamide,
4'-(5-Amino-6-bromopyrazin-2-yl)-N-tert-butyl-3'-fluorobiphenyl-2-sulfonamide, 6-amino-3-(2'-(cyclopropylsulfonyl)-3-fluoro-[1,1'-biphenyl]-4-yl)picolinonitrile,
N-tert-Butyl-3'-fluoro-4'-[1,2,4]triazolo[4,3-a]pyridin-7-ylbiphenyl-2-sulfonamide,
4'-(5-Amino-6-methylpyrazin-2-yl)-N-tert-butyl-3'-fluorobiphenyl-2-sulfonamide,
4'-(5-Amino-6-methylpyrazin-2-yl)-3'-fluorobiphenyl-2-sulfonamide,
N-tert-Butyl-3'-fluoro-4'-(1H-imidazo[4,5-b]pyrazin-5-yl)biphenyl-2-sulfonamide,
N-tert-Butyl-4'-(5,6-diaminopyridn-3-yl)-3'-fluorobiphenyl-2-sulfonamide,
4'-(5-Amino-6-methylpyrazin-2-yl)-3'-fluoro-N-methylbiphenyl-2-sulfonamide,
4'-(6-Amino-5-cyanopyridin-3-yl)-N-tert-butyl-3'-fluorobiphenyl-2-sulfonamide trifluoroacetic acid salt,
4'-(6-Amino-5-chloropyridin-3-yl)-N-tert-butyl-3'-fluorobiphenyl-2-sulfonamide trifluoroacetic acid salt,
4'-[6-Amino-5-(trifluoromethyl)pyridin-3-yl]-N-tert-butyl-3'-fluorobiphenyl-2-sulfonamide trifluoroacetic acid salt,
4'-[2-Amino-4-(trifluoromethyl)pyrimidin-5-yl]-N-tert-butyl-3'-fluorobiphenyl-2-sulfonamide trifluoroacetic acid salt,
4'-(2-Amino-4-methylpyrimidin-5-yl)-N-tert-butyl-3'-fluorobiphenyl-2-sulfonamide trifluoroacetic acid salt,
N-tert-Butyl-3'-fluoro-4'-[3-(hydroxymethyl)-1H-pyrrolo[2,3-b]pyridin-5-yl]biphenyl-2-sulfonamide,
4'-(7-Amino-1H-indol-5-yl)-3'-fluoro-N-[1-(hydroxymethyl)cyclopentyl]biphenyl-2-sulfonamide,
3'-Fluoro-4'-[3-(hydroxymethyl)-1H-pyrrolo[2,3-b]pyridin-5-yl]-N-methylbiphenyl-2-sulfonamide,
4'-(7-Amino-1H-indol-5-yl)-N-tert-butyl-3'-fluorobiphenyl-2-sulfonamide,
N-[4'-(5-Aminopyrazin-2-yl)-3'-fluorobiphenyl-2-yl]acetamide,
1-[4'-(5-Aminopyrazin-2-yl)-3'-fluorobiphenyl-2-yl]urea,
5-[2,3-Difluoro-2'-(methylsulfonyl)biphenyl-4-yl]pyrazin-2-amine,
4'-(5-Aminopyrazin-2-yl)-N-tert-butyl-2',3'-difluorobiphenyl-2-sulfonamide,
N-[4'-(5-Aminopyrazin-2-yl)-3'-fluoro-2'-methylbiphenyl-2-yl]methanesulfonamide,
4'-(5-Aminopyrazin-2-yl)-2',3'-difluorobiphenyl-2-sulfonamide,
4'-(2-Aminopyrimidin-5-yl)-2',3'-difluoro-N-methylbiphenyl-2-sulfonamide trifluoroacetic acid salt,
4'-(2-Aminopyrimidin-5-yl)-N-tert-butyl-2',3'-difluorobiphenyl-2-sulfonamide trifluoroacetic acid salt,
5-[2',3-Difluoro-4'-(trifluoromethoxy)biphenyl-4-yl]pyrazin-2-amine,
5-(2',3-Difluorobiphenyl-4-yl)pyrazin-2-amine,
5-(2'-Chloro-3-fluorobiphenyl-4-yl)pyrazin-2-amine,
5-(3-Fluoro-2'-methylbiphenyl-4-yl)pyrazin-2-amine,
5-[2',3-Difluoro-4'-(trifluoromethyl)biphenyl-4-yl]pyrazin-2-amine,
5-[3-Fluoro-2'-(trifluoromethyl)biphenyl-4-yl]pyrazin-2-amine,
5-(3-Fluoro-2'-methoxybiphenyl-4-yl)pyrazin-2-amine,
5-[3-Fluoro-2'-(methylsulfanyl)biphenyl-4-yl]pyrazin-2-amine,
5-[3-Fluoro-2'-(trifluoromethoxy)biphenyl-4-yl]pyrazin-2-amine,
4'-(5-Aminopyrazin-2-yl)-3'-fluorobiphenyl-2-ol,
5-[3-Fluoro-2'-(phenylsulfonyl)biphenyl-4-yl]pyrazin-2-amine,
5-(2',3,6'-Trifluorobiphenyl-4-yl)pyrazin-2-amine,
N-[4'-(5-Aminopyrazin-2-yl)-3'-fluorobiphenyl-2-yl]benzenesulfonamide,
5-(2'-Ethyl-3-fluorobiphenyl-4-yl)pyrazin-2-amine,
{[4'-(5-Aminopyrazin-2-yl)-3'-fluorobiphenyl-2-yl]oxy}acetic acid,
5-[3-Fluoro-2'-(1-methylethyl)biphenyl-4-yl]pyrazin-2-amine,
1-[4'-(5-Aminopyrazin-2-yl)-3'-fluorobiphenyl-2-yl]ethanone,
5-[3-Fluoro-2'-(2,2,2-trifluoroethoxy)biphenyl-4-yl]pyrazin-2-amine,
4'-(5-Aminopyrazin-2-yl)-3'-fluorobiphenyl-2-carboxylic acid,
4'-(5-Aminopyrazin-2-yl)-3'-fluorobiphenyl-2-carboxamide,
5-[3-Fluoro-2'-(1-methylethoxy)biphenyl-4-yl]pyrazin-2-amine,
5-{4-[2-(Cyclopropylmethoxy)pyridin-3-yl]-2-fluorophenyl}pyrazin-2-amine,
2-[3,4'-Difluoro-2'-(methylsulfonyl)biphenyl-4-yl]-5H-pyrrolo[2,3-b]pyrazine,
N-[4'-(5-Aminopyrazin-2-yl)-3'-fluorobiphenyl-2-yl]-N-methylmethanesulfonamide,
N-[3'-Fluoro-4'-(5H-pyrrolo[2,3-b]pyrazin-2-yl)biphenyl-2-yl]ethanesulfonamide,
N-[3'-Fluoro-4'-(5H-pyrrolo[2,3-b]pyrazin-2-yl)biphenyl-2-yl]-N-methylmethanesulfonamide,
N-[3'-Fluoro-4'-(5H-pyrrolo[2,3-b]pyrazin-2-yl)biphenyl-2-yl]-N-methylethanesulfonamide,
N-[4'-(5-Aminopyrazin-2-yl)-3'-fluorobiphenyl-2-yl]-N-methylethanesulfonamide,
N-[3'-Fluoro-4'-(5H-pyrrolo[2,3-b]pyrazin-2-yl)biphenyl-2-yl]-2-methylpropane-1-sulfonamide,
N-[4'-(5-Aminopyrazin-2-yl)-3'-fluorobiphenyl-2-yl]-N-ethylmethanesulfonamide,
N-[4'-(5-Aminopyrazin-2-yl)-3'-fluorobiphenyl-2-yl]-N,2-dimethylpropane-1-sulfonamide,
5-[3-Fluoro-2'-(morpholin-4-ylcarbonyl)biphenyl-4-yl]-1H-pyrrolo[2,3-b]pyridine,
5-[3-Fluoro-2'-(morpholin-4-ylcarbonyl)biphenyl-4-yl]pyrimidin-2-amine,
2-[3-Fluoro-2'-(morpholin-4-ylcarbonyl)biphenyl-4-yl]-5H-pyrrolo[2,3-b]pyrazine,
4'-(5-Aminopyrazin-2-yl)-N-tert-butyl-3'-fluorobiphenyl-2-carboxamide,
4'-(5-Aminopyrazin-2-yl)-N-tert-butyl-3',4-difluorobiphenyl-2-carboxamide,
4'-(5-Aminopyrazin-2-yl)-N,N-diethyl-3'-fluorobiphenyl-2-carboxamide,
4'-(2-Aminopyrimidin-5-yl)-3'-fluoro-N-[(1S)-2,2,2-trifluoro-1-methylethyl]biphenyl-2-carboxamide,
4'-(5-Aminopyrazin-2-yl)-3'-fluoro-N-[((1S)-2,2,2-trifluoro-1-methylethyl]biphenyl-2-carboxamide,
5-[3-Fluoro-2'-(piperazin-1-ylcarbonyl)biphenyl-4-yl]pyrazin-2-amine,
5-{2'-[(4-Acetylpiperazin-1-yl)carbonyl]-3-fluorobiphenyl-4-yl}pyrazin-2-amine,
4'-(5-Aminopyrazin-2-yl)-N-cyclohexyl-3'-fluorobiphenyl-2-carboxamide,
5-{2'-[(1,1-Dioxidothiomorpholin-4-yl)carbonyl]-3-fluorobiphenyl-4-yl}pyrazin-2-amine,
4'-(5-Aminopyrazin-2-yl)-3'-fluoro-N-methylbiphenyl-2-carboxamide,
4'-(5-Aminopyrazin-2-yl)-3'-fluoro-N-[((1R)-2,2,2-trifluoro-1-methylethyl]biphenyl-2-carboxamide,
4'-(5-Aminopyrazin-2-yl)-3'-fluoro-N-[(1R)-2-hydroxy-1-methylethyl]biphenyl-2-carboxamide, 4'-(5-Aminopyrazin-2-yl)-3'-fluoro-N-[(1S)-2-hydroxy-1-methylethyl]biphenyl-2-carboxamide,
1-{[4'-(5-Aminopyrazin-2-yl)-3'-fluorobiphenyl-2-yl]carbonyl}piperidin-4-ol,
5-{2'-[(4-Aminopiperidin-1-yl)carbonyl]-3-fluorobiphenyl-4-yl}pyrazin-2-amine,
5-{2'-[(1,1-Dioxidothiomorpholin-4-yl)carbonyl]-3-fluorobiphenyl-4-yl}pyrimidin-2-amine,
4'-(2-Aminopyrimidin-5-yl)-3'-fluoro-N-[(1S)-2-hydroxy-1-methylethyl]biphenyl-2-carboxamide,
4'-(2-Aminopyrimidin-5-yl)-3'-fluoro-N-[(1R)-2,2,2-trifluoro-1-methylethyl]biphenyl-2-carboxamide,
4-{[4'-(5-Aminopyrazin-2-yl)-3'-fluorobiphenyl-2-yl]carbonyl}piperazin-2-one,
4-{[4'-(2-Aminopyrimidin-5-yl)-3'-fluorobiphenyl-2-yl]carbonyl}piperazin-2-one,
5-[3-Fluoro-2'-(morpholin-4-ylcarbonyl)-4'-(trifluoromethyl)biphenyl-4-yl]pyrazin-2-amine,
5-[3-Fluoro-2'-(morpholin-4-ylcarbonyl)-4'-(trifluoromethyl)biphenyl-4-yl]pyrimidin-2-amine,
4-{[3'-Fluoro-4'-(1H-pyrrolo[2,3-b]pyridin-5-yl)biphenyl-2-yl]oxy}pyrimidin-2-amine,
2-{[3'-Fluoro-4'-(1H-pyrrolo[2,3-b]pyridin-5-yl)biphenyl-2-yl]oxy}pyrimidin-4-amine,
5-[3-Fluoro-2'-(pyrimidin-2-yloxy)biphenyl-4-yl]-1H-pyrrolo[2,3-b]pyridine,
5-[3-Fluoro-2'-(pyrimidin-2-yloxy)biphenyl-4-yl]pyrazin-2-amine,
5-[3-Fluoro-2'-(pyrimidin-2-yloxy)biphenyl-4-yl]pyrimidin-2-amine,
2-{[4'-(5-Aminopyrazin-2-yl)-3'-fluorobiphenyl-2-yl]oxy}pyrimidin-4-amine,
5-{2'-[(4-Aminopyrimidin-2-yl)oxy]-3-fluorobiphenyl-4-yl}pyrimidin-2-amine,
6-({[4'-(5-Aminopyrazin-2-yl)-3'-fluorobiphenyl-2-yl]oxy}methyl)pyridine-2-carbonitrile,
2-({[4'-(5-Aminopyrazin-2-yl)-3'-fluorobiphenyl-2-yl]oxy}methyl)pyridine-3-carbonitrile,
2-{[4'-(5-Aminopyrazin-2-yl)-3'-fluorobiphenyl-2-yl]oxy}pyridine-3-carbonitrile,
4-{[4'-(5-Aminopyrazin-2-yl)-3'-fluorobiphenyl-2-yl]oxy}pyrimidin-2-amine,
4-{[4'-(2-Aminopyrimidin-5-yl)-3'-fluorobiphenyl-2-yl]oxy}pyrimidin-2-amine,
6-{[4'-(5-Aminopyrazin-2-yl)-3'-fluorobiphenyl-2-yl]oxy}pyrimidin-4-amine,
5-{2'-[(6-Aminopyrimidin-4-yl)oxy]-3-fluorobiphenyl-4-yl}pyrimidin-2-amine,
4-{[4'-(5-Aminopyrazin-2-yl)-3'-fluorobiphenyl-2-yl]oxy}pyridine-2-carbonitrile,
4-{[4'-(2-Aminopyrimidin-5-yl)-3'-fluorobiphenyl-2-yl]oxy}pyridine-2-carbonitrile,
5-{2'-[(6-Azetidin-1-ylpyrimidin-4-yl)oxy]-3-fluorobiphenyl-4-yl}pyrazin-2-amine,
5-{2'-[(6-Azetidin-1-ylpyrimidin-4-yl)oxy]-3-fluorobiphenyl-4-yl}pyrimidin-2-amine,
5-{3-Fluoro-2'-[(2-methylpyrimidin-4-yl)oxy]biphenyl-4-yl}pyrazin-2-amine,
5-{3-Fluoro-2'-[(2-methylpyrimidin-4-yl)oxy]biphenyl-4-yl}pyrimidin-2-amine,
5-[3-Fluoro-2'-(pyrimidin-2-yloxy)biphenyl-4-yl]-1H-benzimidazole,
6-[3-Fluoro-2'-(pyrimidin-2-yloxy)biphenyl-4-yl]-3H-imidazo[4,5-b]pyridine,
5-{3-Fluoro-2'-[(4-methylpyrimidin-4-yl)oxy]biphenyl-4-yl}pyrazin-2-amine,
5-{3-Fluoro-2'-[(4-methylpyrimidin-2-yl)oxy]biphenyl-4-yl}pyrimidin-2-amine,
5-(3-Fluoro-2'-{[2-(trifluoromethyl)pyrimidin-4-yl]oxy}biphenyl-4-yl)pyrazin-2-amine,
5-(3-Fluoro-2'-{[2-(trifluoromethyl)pyrimidin-4-yl]oxy}biphenyl-4-yl)pyrimidin-2-amine,
5-{3-Fluoro-2'-[(5-methoxypyrimidin-2-yl)oxy]biphenyl-4-yl}pyrazin-2-amine,
5-{3-Fluoro-2'-[(5-methoxypyrimidin-2-yl)oxy]biphenyl-4-yl}pyrimidin-2-amine,
5-[3-Fluoro-2'-(pyrimidin-2-yloxy)-4'-(trifluoromethyl)biphenyl-4-yl]pyrazin-2-amine,
5-[3-Fluoro-2'-(pyrimidin-2-yloxy)-4'-(trifluoromethyl)biphenyl-4-yl]pyrimidin-2-amine,
5-[3-Fluoro-2'-methoxy-4'-(trifluoromethyl)biphenyl-4-yl]pyrazin-2-amine,
4'-(5-Aminopyrazin-2-yl)-3'-fluoro-4-(trifluoromethyl)biphenyl-2-ol,
4-{[4'-(5-Aminopyrazin-2-yl)-3'-fluoro-4-(trifluoromethyl)biphenyl-2-yl]oxy}pyrimidin-2-amine,
2-{[4'-(5-Aminopyrazin-2-yl)-3'-fluoro-4-(trifluoromethyl)biphenyl-2-yl]oxy}pyrimidin-4-amine,
5-[3-Fluoro-4'-(trifluoromethyl)-2'-{[2-(trimethylsilyl)ethoxy]methoxy}biphenyl-4-yl]pyrimidin-2-amine,
4'-(2-Aminopyrimidin-5-yl)-3'-fluoro-4-(trifluoromethyl)biphenyl-2-ol,
5-{2'-[(4-Aminopyrimidin-2-yl)oxy]-3-fluoro-4'-(trifluoromethyl)biphenyl-4-yl}pyrimidin-2-amine,
4-{[4'-(2-Aminopyrimidin-5-yl)-3'-fluoro-4-(trifluoromethyl)biphenyl-2-yl]oxy}pyrimidin-2-amine,
5-{2'-[(6-Aminopyrimidin-4-yl)oxy]-3-fluoro-4'-(trifluoromethyl)biphenyl-4-yl}pyrimidin-2-amine,
5-[3-Fluoro-2',4'-bis(trifluoromethyl)biphenyl-4-yl]pyrazin-2-amine,
4'-(5-Aminopyrazin-2-yl)-3'-fluoro-4-(trifluoromethyl)biphenyl-2-carbonitrile,
5-{5-[2-(Pyrimidin-2-yloxy)-4-(trifluoromethyl)phenyl]pyridin-2-yl}pyrimidin-2-amine,
4-{2-[6-(2-Aminopyrimidin-5-yl)pyridin-3-yl]-5-(trifluoromethyl) phenoxy}pyrimidin-2-amine,
5-{5-[2-(Pyrimidin-2-yloxy)phenyl]pyridin-2-yl}pyrimidin-2-amine,
4-{2-[6-(2-Aminopyrimidin-5-yl)pyridin-3-yl]phenoxy}pyrimidin-2-amine,
5-(5-{2-[(4-Aminopyrimidin-2-yl)oxy]phenyl}pyridin-2-yl)pyrimidin-2-amine,
4'-(5-Aminopyrazin-2-yl)-N-tert-butyl-3'-methylbiphenyl-2-sulfonamide,
4'-(5-Aminopyrazin-2-yl)-N-tert-butyl-3'-methoxybiphenyl-2-sulfonamide,
4'-(5-Aminopyrazin-2-yl)-N-tert-butylbiphenyl-2-sulfonamide,
4'-(5-Aminopyrazin-2-yl)-N,N-dimethylbiphenyl-2-sulfonamide,
5-[2'-(Morpholin-4-ylsulfonyl)biphenyl-4-yl]pyrazin-2-amine,
4'-(5-Aminopyrazin-2-yl)-N-tert-butyl-2'-fluorobiphenyl-2-sulfonamide,
4'-(5-Aminopyrazin-2-yl)-2'-fluoro-N,N-dimethylbiphenyl-2-sulfonamide,
4'-(2-Amino-1,3-oxazol-4-yl)-N-tert-butyl-3'-fluorobiphenyl-2-sulfonamide,
N-tert-Butyl-3'-fluoro-4'-(8-fluoroimidazo[1,2-a]pyridin-2-yl)biphenyl-2-sulfonamide,
4'-(5-Aminoimidazo[1,2-a]pyridin-2-yl)-N-tert-butyl-3'-fluorobiphenyl-2-sulfonamide, 2-[2'-(tert-Butylsulfamoyl)-3-fluorobiphenyl-4-yl]imidazo[1,2-a]pyridine-6-carboxamide,
2-[2'-(tert-Butylsulfamoyl)-3-fluorobiphenyl-4-yl]imidazo[1,2-a]pyridine-6-carboxamide,
N-tert-Butyl-4'-(5-cyanoimidazo[1,2-a]pyridin-2-yl)-3'-fluorobiphenyl-2-sulfonamide,
N-tert-Butyl-4'-(6-cyanoimidazo[1,2-a]pyridin-2-yl)-3'-fluorobiphenyl-2-sulfonamide,
N-tert-Butyl-3'-fluoro-4'-[6-(trifluoromethyl)imidazo[1,2-a]pyridin-2-yl]biphenyl-2-sulfonamide,
Ethyl 2-[2'-(tert-butylsulfamoyl)-3-fluorobiphenyl-4-yl]imidazo[1,2-a]pyridine-5-carboxylate,
N-tert-Butyl-3'-fluoro-4'-(5-methoxyimidazo[1,2-a]pyridin-2-yl)biphenyl-2-sulfonamide,
5-[2'-(Methylsulfonyl)biphenyl-4-yl]pyrazin-2-amine,
5-[3-Methyl-2'-(methylsulfonyl)biphenyl-4-yl]pyrazin-2-amine,
4'-(5-Aminopyrazin-2-yl)-N,N,3'-trimethylbiphenyl-2-sulfonamide,
4'-(5-Aminopyrazin-2-yl)-3'-hydroxybiphenyl-2-sulfonamide,
N-[4'-(5-Aminopyrazin-2-yl)biphenyl-2-yl]methanesulfonamide,
4'-(5-Aminopyrazin-2-yl)biphenyl-2-sulfonamide,
N-tert-Butyl-3'-fluoro-4'-(2-oxo-2,3-dihydro-1H-indol-5-yl)biphenyl-2-sulfonamide,
N-tert-Butyl-4'-(2,4-dioxo-1,2,3,4-tetrahydroquinazolin-6-yl)-3'-fluorobiphenyl-2-sulfonamide,
4'-(3-Amino-1H-indazol-5-yl)-N-tert-butyl-3'-fluorobiphenyl-2-sulfonamide,
3-Amino-6-[2'-(tert-butylsulfamoyl)-3-fluorobiphenyl-4-yl]pyrazine-2-carboxylic acid,
2-{[4'-(2-Aminopyrimidin-5-yl)-3'-fluorobiphenyl-2-yl]sulfonyl}acetamide,
2-{[4'-(2-Aminopyrimidin-5-yl)-3'-fluorobiphenyl-2-yl]sulfonyl}-N,N-diethylacetamide,
5-{3-Fluoro-2'-[(2-morpholin-4-yl-2-oxoethyl)sulfonyl]biphenyl-4-yl}pyrimidin-2-amine,
5,5'-(3,3''-Difluoro-1,1':2',1''-terphenyl-4,4''-diyl)dipyrazin-2-amine,
4'-(5-Aminopyrazin-2-yl)-3'-fluoro-4-(trifluoromethyl)biphenyl-2-carboxylic acid,
4'-(5-Aminopyrazin-2-yl)-3'-fluoro-4-(trifluoromethyl)biphenyl-2-carbaldehyde,
5-[3-Fluoro-2'-(morpholin-4-ylmethyl)-4'-(trifluoromethyl)biphenyl-4-yl]pyrazin-2-amine,
5-{2'-[(4-Aminopiperidin-1-yl)methyl]-3-fluoro-4'-(trifluoromethyl)biphenyl-4-yl}pyrazin-2-amine,
2-({[4'-(5-Aminopyrazin-2-yl)-3'-fluoro-4-(trifluoromethyl)biphenyl-2-yl]methyl}amino)ethanol,
5-{2'-[(4,6-Dimethylpyrimidin-2-yl)oxy]-3-fluorobiphenyl-4-yl}pyrazin-2-amine,
5-{2'-[(4,6-Dimethylpyrimidin-2-yl)oxy]-3-fluorobiphenyl-4-yl}pyrimidin-2-amine,
5-(3-Fluoro-2'-{[2-(trifluoromethyl)pyridin-4-yl]oxy}biphenyl-4-yl)pyrazin-2-amine,
5-(3-Fluoro-2'-{[2-(trifluoromethyl)pyridin-4-yl]oxy}biphenyl-4-yl)pyrimidin-2-amine,
5-(3-Fluoro-2'-{[4-(trifluoromethyl)pyrimidin-2-yl]oxy}biphenyl-4-yl)pyrazin-2-amine,
5-(3-Fluoro-2'-{[4-(trifluoromethyl)pyrimidin-2-yl]oxy}biphenyl-4-yl)pyrimidin-2-amine,
2-{[4'-(5-Aminopyrazin-2-yl)-3'-fluorobiphenyl-2-yl]oxy}pyrimidin-5-amine,
5-{2'-[(5-Aminopyrimidin-2-yl)oxy]-3-fluorobiphenyl-4-yl}pyrimidin-2-amine,
2-{[4'-(5-Aminopyrazin-2-yl)-3'-fluorobiphenyl-2-yl]oxy}-6-methylpyrimidin-4-amine,
5-{2'-[(4-Amino-6-methyl pyrimidin-2-yl)oxy]-3-fluorobiphenyl-4-yl}pyrimidin-2-amine,
6-{[4'-(2-Aminopyrimidin-5-yl)-3'-fluorobiphenyl-2-yl]oxy}pyridine-2-carbonitrile,
6-{[4'-(5-Aminopyrazin-2-yl)-3'-fluorobiphenyl-2-yl]oxy}pyridine-2-carbonitrile,
5-{2'-[(5-Aminopyridin-2-yl)oxy]-3-fluorobiphenyl-4-yl}pyrazin-2-amine,
5-{2'-[(5-Aminopyridin-2-yl)oxy]-3-fluorobiphenyl-4-yl}pyrimidin-2-amine,
5-{2'-[(6-Amino-2-methylpyrimidin-4-yl)oxy]-3-fluorobiphenyl-4-yl}pyrimidin-2-amine,
6-{[4'-(5-Aminopyrazin-2-yl)-3'-fluorobiphenyl-2-yl]oxy}-2-methylpyrimidin-4-amine,
5-(3-Fluoro-2'-{[6-(trifluoromethyl)pyridin-2-yl]oxy}biphenyl-4-yl)pyrimidin-2-amine,
5-(3-Fluoro-2'-{[6-(trifluoromethyl)pyridin-2-yl]oxy}biphenyl-4-yl)pyrazin-2-amine,
6-{[4'-(5-Aminopyrazin-2-yl)-3'-fluorobiphenyl-2-yl]oxy}pyridine-3-carbonitrile,
6-{[4'-(2-Aminopyrimidin-5-yl)-3'-fluorobiphenyl-2-yl]oxy}pyridine-3-carbonitrile,
2-{[4'-(5-Aminopyrazin-2-yl)-3'-fluorobiphenyl-2-yl]oxy}ethanol,
2-{[4'-(2-Aminopyrimidin-5-yl)-3'-fluorobiphenyl-2-yl]oxy}ethanol,
5-[3-Fluoro-2'-(piperidin-4-yloxy)biphenyl-4-yl]pyrazin-2-amine,
5-[3-Fluoro-2'-(piperidin-4-yloxy)biphenyl-4-yl]pyrimidin-2-amine,
5-{3-Fluoro-2'-[(3R)-piperidin-3-yloxy]biphenyl-4-yl}pyrazin-2-amine,
5-{3-Fluoro-2'-[(3R)-piperidin-3-yloxy]biphenyl-4-yl}pyrimidin-2-amine,
5-{3-Fluoro-2'-[(3S)-piperidin-3-yloxy]biphenyl-4-yl}pyrazin-2-amine,
5-{3-Fluoro-2'-[(3S)-piperidin-3-yloxy]biphenyl-4-yl}pyrimidin-2-amine,
5-{2'-[(6-Cyclopropylpyrimidin-4-yl)oxy]-3-fluorobiphenyl-4-yl}pyrazin-2-amine,
5-{2'-[(6-Cyclopropylpyrimidin-4-yl)oxy]-3-fluorobiphenyl-4-yl}pyrimidin-2-amine,
5-{2'-[(2-Aminopyridin-4-yl)oxy]-3-fluorobiphenyl-4-yl}pyrazin-2-amine,
5-{2'-[(2-Aminopyridin-4-yl)oxy]-3-fluorobiphenyl-4-yl}pyrimidin-2-amine,
5-[2'-(2-Aminoethoxy)-3-fluorobiphenyl-4-yl]pyrazin-2-amine,
5-[2'-(2-Aminoethoxy)-3-fluorobiphenyl-4-yl]pyrimidin-2-amine,
{[4'-(5-Aminopyrazin-2-yl)-3'-fluorobiphenyl-2-yl]oxy}acetonitrile,
{[4'-(2-Aminopyrimidin-5-yl)-3'-fluorobiphenyl-2-yl]oxy}acetonitrile,
{[4'-(2-Aminopyrimidin-5-yl)-3'-fluorobiphenyl-2-yl]oxy}acetic acid,
5-{2-Fluoro-4-[2-(piperidin-4-yloxy)pyridin-3-yl]phenyl}pyrazin-2-amine,
5-{2-Fluoro-4-[2-(piperidin-4-yloxy)pyridin-3-yl]phenyl}pyrimidin-2-amine,
5-(4-{2-[(1,1-Dioxidotetrahydro-2H-thiopyran-4-yl)oxy]pyridin-3-yl}-2-fluorophenyl)pyrazin-2-amine,
5-(4-{2-[(1,1-Dioxidotetrahydro-2H-thiopyran-4-yl)oxy]pyridin-3-yl}-2-fluorophenyl)pyrimidin-2-amine, 2-({3-[4-(2-Aminopyrimidin-5-yl)-3-fluorophenyl]pyridin-2-yl}oxy)ethanol,
2-({3-[4-(5-Aminopyrazin-2-yl)-3-fluorophenyl]pyridin-2-yl}oxy)ethanol,
5-(4-{2-[(trans-4-Aminocyclohexyl)oxy]pyridin-3-yl}-2-fluorophenyl)pyrimidin-2-amine,
5-(4-{2-[(trans-4-Aminocyclohexyl)oxy]pyridin-3-yl}-2-fluorophenyl)pyrazin-2-amine formic acid salt,
5-{2-Fluoro-4-[2-(tetrahydro-2H-pyran-4-yloxy)pyridin-3-yl]phenyl}pyrazin-2-amine,
5-{2-Fluoro-4-[2-(tetrahydro-2H-pyran-4-yloxy)pyridin-3-yl]phenyl}pyrimidin-2-amine,
(2R)-2-({3-[4-(5-Aminopyrazin-2-yl)-3-fluorophenyl]pyridin-2-yl}oxy)propan-1-ol,
(2R)-2-({3-[4-(2-Aminopyrimidin-5-yl)-3-fluorophenyl]pyridin-2-yl}oxy)propan-1-ol,
(2S)-2-({3-[4-(5-Aminopyrazin-2-yl)-3-fluorophenyl]pyridin-2-yl}oxy)propan-1-ol,
(2I)-2-({3-[4-(2-Aminopyrimidin-5-yl)-3-fluorophenyl]pyridin-2-yl}oxy)propan-1-ol,
N-(4'-(6-Aminopyridin-3-yl)-3'-fluoro-[1,1'-biphenyl]-2-yl)methanesulfonamide,
5-(3-Fluoro-2'-(morpholinosulfonyl)-[1,1'-biphenyl]-4-yl)pyridin-2-amine,
4'-(6-Aminopyridin-3-yl)-3'-fluoro-N-methyl-[1,1'-biphenyl]-2-sulfonamide,
4'-(6-Aminopyridin-3-yl)-3'-fluoro-[1,1'-biphenyl]-2-sulfonamide trifluoroacetate,
5-(2'-((1S,4S)-2-Oxa-5-azabicyclo[2.2.1]heptan-5-ylsulfonyl)-3-fluoro-[1,1'-biphenyl]-4-yl)pyridin-2-amine,
4'-(6-Aminopyrazin-2-yl)-3'-fluoro-N-((3-hydroxyazetidin-3-yl)methyl)-[1,1'-biphenyl]-2-sulfonamide,
4'-(6-Aminopyridin-3-yl)-3'-fluoro-N-(1-hydroxy-2-methylpropan-2-yl)-[1,1'-biphenyl]-2-sulfonamide,
4'-(6-Aminopyridin-3-yl)-3'-fluoro-N-((1S,2S)-1-hydroxy-1-phenylpropan-2-yl)-N-methyl-[1,1'-biphenyl]-2-sulfonamide,
4'-(6-Amino-5-fluoropyridin-3-yl)-3'-fluoro-N-(1-hydroxy-2-methylpropan-2-yl)-[1,1'-biphenyl]-2-sulfonamide,
(racemic)-1-((4'-(6-Amino-5-fluoropyridin-3-yl)-3'-fluoro-[1, 1'-biphenyl]-2-yl)sulfonyl)piperidin-3-ol,
4'-(6-Amino-5-fluoropyridin-3-yl)-3'-fluoro-N-((1S,2S)-1-hydroxy-1-phenylpropan-2-yl)-N-methyl-[1,1'-biphenyl]-2-sulfonamide,
N-(1-((4'-(6-Amino-5-fluoropyridin-3-yl)-3'-fluoro-[1,1'-biphenyl]-2-yl)sulfonyl)piperidin-4-yl)acetamide,
racemic 2-(1-((4'-(6-Amino-5-fluoropyridin-3-yl)-3'-fluoro-[1,1'-biphenyl]-2-yl)sulfonyl)piperidin-3-yl)ethanol,
racemic 1-((4'-(6-Amino-5-fluoropyridin-3-yl)-3'-fluoro-[1,1'-biphenyl]-2-yl)sulfonyl)piperidin-3-yl)methanol,
2-[6-(2-Aminopyrimidin-5-yl)-5-fluoropyridin-3-yl]-N-[(2R)-2-hydroxypropyl]benzenesulfonamide,
2-[6-(2-Aminopyrimidin-5-yl)-5-fluoropyridin-3-yl]-N-ethyl-5-(trifluoromethyl)benzenesulfonamide,
2-[6-(2-Aminopyrimidin-5-yl)-5-fluoropyridin-3-yl]-N-tert-butylbenzenesulfonamide,
5-{5-[2-(Morpholin-4-ylmethyl)-4-(trifluoromethyl)phenyl]pyridin-2-yl}pyrimidin-2-amine,
5-{5-[2-(Morpholin-4-ylcarbonyl)phenyl]pyridin-2-yl}pyrimidin-2-amine,
5-[5-(2-Methoxyphenyl)pyridin-2-yl]pyrimidin-2-amine,
5-(5-{2-[(3,3-Difluoropiperidin-1-yl)sulfonyl]phenyl}pyridin-2-yl)pyrimidin-2-amine trifluoroacetic acid salt,
5-(5-{2-[(3,3-Difluoropyrrolidin-1-yl)sulfonyl]phenyl}pyridin-2-yl)pyrimidin-2-amine trifluoroacetic acid salt,
5-{5-[2-(Azepan-1-ylsulfonyl)phenyl]pyridin-2-yl}pyrimidin-2-amine trifluoroacetic acid salt,
5-(5-{2-[(4,4-Difluoropiperidin-1-yl)sulfonyl]phenyl}pyridin-2-yl)pyrimidin-2-amine trifluoroacetic acid salt,
2-[6-(2-Aminopyrimidin-5-yl)pyridin-3-yl]-N-ethylbenzenesulfonamide trifluoroacetic acid salt,
2-[6-(2-Aminopyrimidin-5-yl)pyridin-3-yl]-N-(dicyclopropylmethyl)benzenesulfonamide trifluoroacetic acid salt,
2-[6-(2-Aminopyrimidin-5-yl)pyridin-3-yl]-N-[(1S)-2,2,2-trifluoro-1-methylethyl]benzenesulfonamide trifluoroacetic acid salt,
2-[6-(2-Aminopyrimidin-5-yl)pyridin-3-yl]-N-[(1R)-2,2,2-trifluoro-1-methylethyl]benzenesulfonamide trifluoroacetic acid salt,
4-({2-[6-(2-Aminopyrimidin-5-yl)pyridin-3-yl]phenyl}sulfonyl)piperazin-2-one,
2-[6-(2-Aminopyrimidin-5-yl)pyridin-3-yl]-N-[(2S)-2-hydroxypropyl]benzenesulfonamide,
2-[6-(2-Aminopyrimidin-5-yl)pyridin-3-yl]-N-[(2R)-2-hydroxypropyl]benzenesulfonamide,
2-[6-(2-Aminopyrimidin-5-yl)pyridin-3-yl]-N-(2-hydroxyethyl)-5-(trifluoromethyl)benzenesulfonamide,
5-{5-[2-(Cyclopropylsulfonyl)phenyl]pyridin-2-yl}pyrimidin-2-amine trifluoroacetic acid salt,
2-[6-(2-Aminopyrimidin-5-yl)pyridin-3-yl]-N-ethyl-5-(trifluoromethyl)benzenesulfonamide trifluoroacetic acid salt,
2-[6-(2-Aminopyrimidin-5-yl)pyridin-3-yl]-N-tert-butylbenzenesulfonamide,
2-[6-(2-Aminopyrimidin-5-yl)pyridin-3-yl]-N-[(1R)-2-hydroxy-1-methylethyl]benzenesulfonamide,
3-Amino-6-{2'-[(4-aminopyrimidin-2-yl)oxy]-3-fluorobiphenyl-4-yl}pyrazine-2-carbonitrile trifluoroacetic acid salt,
5-(4'-Bromo-2',3-difluorobiphenyl-4-yl)pyrazin-2-amine,
5-(4'-Bromo-2',3-difluorobiphenyl-4-yl)-1H-pyrrolo[2,3-b]pyridine,
5-(3-fluoro-2-methoxy-4'-(trifluoromethyl)-[1,1'-biphenyl]-4-yl)pyrazin-2-amine,
5-(2',3,4'-Trifluorobiphenyl-4-yl)pyrazin-2-amine,
racemic 5-[3-Fluoro-2'-(methylsulfinyl)biphenyl-4-yl]pyrazin-2-amine,
4'-(5-Aminopyrazin-2-yl)-3'-fluorobiphenyl-2-carbonitrile,
1-(4'-(5-Aminopyrazin-2-yl)-3'-fluoro-[1, 1'-biphenyl]-2-yl)imidazolidin-2-one,
4'-(2-Amino-4-cyanopyrimidin-5-yl)-N-tert-butyl-3'-fluorobiphenyl-2-sulfonamide,
6-Amino-3-{2'-[(1,1-dioxidothiomorpholin-4-yl)sulfonyl]-3-fluorobiphenyl-4-yl}pyrazine-2-carbonitrile,
1-{[4'-(2-Aminopyrimidin-5-yl)-3'-fluorobiphenyl-2-yl]sulfonyl}-N-methylazetidine-3-carboxamide,
4'-(5-Amino-3-cyanopyrazin-2-yl)-3'-fluoro-N-(2-hydroxyethyl)biphenyl-2-sulfonamide,
4'-(5-Amino-3-cyanopyrazin-2-yl)-3'-fluoro-N-[(2S)-2-hydroxypropyl]biphenyl-2-sulfonamide,
4'-(5-Amino-3-cyanopyrazin-2-yl)-3'-fluoro-N-[(2R)-2-hydroxypropyl]biphenyl-2-sulfonamide,
1-((4'-(2-Aminopyrimidin-5-yl)-3'-fluoro-[1,1'-biphenyl]-2-yl)sulfonyl)piperidine-4-carboxamide,
4'-(5-Amino-3-cyanopyrazin-2-yl)-3'-fluoro-N-[(1R)-2-hydroxy-1-methylethyl]biphenyl-2-sulfonamide, 4'-(5-Amino-3-cyanopyrazin-2-yl)-3'-fluoro-N-[(1S)-2-hydroxy-1-methylethyl]biphenyl-2-sulfonamide,
4'-(5-Amino-3-cyanopyrazin-2-yl)-3'-fluoro-N-(2-hydroxyethyl)-4-(trifluoromethyl)biphenyl-2-sulfonamide,
4'-(5-Amino-3-cyanopyrazin-2-yl)-N-ethyl-3'-fluoro-4-(trifluoromethyl)-[1,1'-biphenyl]-2-sulfonamide,
4'-(5-Amino-3-cyanopyrazin-2-yl)-3'-fluoro-N-(3-hydroxy-2,2-dimethylpropyl)biphenyl-2-sulfonamide,
6-Amino-3-{3-fluoro-2'-[(3-oxopiperazin-1-yl)sulfonyl]-4'-(trifluoromethyl)biphenyl-4-yl}pyrazine-2-carbonitrile,
N-(2-{[4'-(2-Aminopyrimidin-5-yl)-3'-fluorobiphenyl-2-yl]sulfonyl}ethyl)benzamide,
1-{[4'-(2-Aminopyrimidin-5-yl)-3'-fluorobiphenyl-2-yl]sulfonyl}-3,3-dimethylbutan-2-one,
5-[3-Fluoro-2'-(pyrimidin-2-ylsulfonyl)biphenyl-4-yl]pyrimidin-2-amine,
5-[3-Fluoro-2'-(pyrazin-2-ylsulfonyl)biphenyl-4-yl]pyrimidin-2-amine,
5-[3-Fluoro-2'-(pyrimidin-4-ylsulfonyl)biphenyl-4-yl]pyrimidin-2-amine,
5-{2'-[(6-Aminopyrimidin-4-yl)sulfonyl]-3-fluorobiphenyl-4-yl}pyrimidin-2-amine,
5-{2'-[(4-Aminopyrimidin-2-yl)sulfonyl]-3-fluorobiphenyl-4-yl}pyrimidin-2-amine,
5-{2'-[(5-Aminopyrazin-2-yl)sulfonyl]-3-fluorobiphenyl-4-yl}pyrimidin-2-amine,
4-{[4'-(2-Aminopyrimidin-5-yl)-3'-fluorobiphenyl-2-yl]sulfonyl}pyrimidin-2-amine,
5-{2'-[(6-Aminopyrazin-2-yl)sulfonyl]-3-fluorobiphenyl-4-yl}pyrimidin-2-amine,
6-{[4'-(5-Aminopyrazin-2-yl)-3'-fluorobiphenyl-2-yl]sulfonyl}pyrimidin-4-amine,
2-{[4'-(5-Aminopyrazin-2-yl)-3'-fluorobiphenyl-2-yl]sulfonyl}pyrimidin-4-amine,
5-{2'-[(Cyclopropylmethyl)sulfonyl]-3-fluorobiphenyl-4-yl}pyrimidin-2-amine,
6-Amino-3-[2'-(cyclopropylsulfonyl)-3-fluorobiphenyl-4-yl]pyrazine-2-carbonitrile,
1-{[4'-(5-Aminopyrazin-2-yl)-3'-fluorobiphenyl-2-yl]sulfonyl}cyclopentanecarbonitrile,
1-{[4'-(5-Aminopyrazin-2-yl)-3'-fluorobiphenyl-2-yl]sulfonyl}cyclopentanecarboxamide,
2-{[4'-(2-Aminopyrimidin-5-yl)-3'-fluorobiphenyl-2-yl]sulfonyl}-2-methylpropanenitrile,
2-{[4'-(2-Aminopyrimidin-5-yl)-3'-fluorobiphenyl-2-yl]sulfonyl}-2-methylpropanamide,
5-{2'-[(2-Amino-1,1-dimethylethyl)sulfonyl]-3-fluorobiphenyl-4-yl}pyrimidin-2-amine,
2-{[4'-(5-Aminopyrazin-2-yl)-3'-fluorobiphenyl-2-yl]sulfonyl}-2-methylpropanenitrile,
2-{[4'-(5-Aminopyrazin-2-yl)-3'-fluorobiphenyl-2-yl]sulfonyl}-2-methylpropanamide,
5-{2'-[(2-Amino-1,1-dimethylethyl)sulfonyl]-3-fluorobiphenyl-4-yl}pyrazin-2-amine,
1-{[4'-(2-Aminopyrimidin-5-yl)-3'-fluorobiphenyl-2-yl]sulfonyl}cyclopentanecarbonitrile,
1-{[4'-(2-Aminopyrimidin-5-yl)-3'-fluorobiphenyl-2-yl]sulfonyl}cyclopentanecarboxamide,
5-(2'-{[1-(Aminomethyl)cyclopentyl]sulfonyl}-3-fluorobiphenyl-4-yl)pyrimidin-2-amine,
5-{[4'-(5-Aminopyrazin-2-yl)-3'-fluorobiphenyl-2-yl]sulfanyl}pyrazin-2-amine,
5-{2'-[(6-Aminopyrazin-2-yl)sulfanyl]-3-fluorobiphenyl-4-yl}pyrazin-2-amine,
5-(3-Fluoro-2'-(pyrimidin-4-ylthio)-[1,1'-biphenyl]-4-yl)pyrazin-2-amine,
5-{2'-[(5-Aminopyrazin-2-yl)sulfanyl]-3-fluorobiphenyl-4-yl}pyrimidin-2-amine
6-Amino-3-{2'-[(4-aminopyrimidin-2-yl)oxy]-3-fluorobiphenyl-4-yl}pyrazine-2-carbonitrile,
6-Amino-3-[3-fluoro-2'-(pyrimidin-2-yloxy)-4'-(trifluoromethyl)biphenyl-4-yl]pyrazine-2-carbonitrile,
6-Amino-3-[3-fluoro-2'-(pyrimidin-2-yloxy)biphenyl-4-yl]pyrazine-2-carbonitrile,
N-(ter-Butyl)-3'-fluoro-4'-(5-(methylsulfonamido)pyrazin-2-yl)-[1,1'-biphenyl]-2-sulfonamide,
5-{2'-[(Ethylsulfonyl)methyl]-3-fluorobiphenyl-4-yl}pyrazin-2-amine hydrogen chloride salt,
5-{3-Fluoro-2'-[(methylsulfonyl)methyl]biphenyl-4-yl}pyrazin-2-amine,
5-(3-Fluoro-2'-{[(1-methylethyl)sulfonyl]methyl}biphenyl-4-yl)pyrazin-2-amine,
5-{3-Fluoro-2'-[(pyrimidin-2-ylsulfonyl)methyl]biphenyl-4-yl}pyrazin-2-amine,
2-({[4'-(5-Aminopyrazin-2-yl)-3'-fluorobiphenyl-2-yl]methyl}sulfanyl)pyrimidin-4-amine,
racemic 5-(3-Fluoro-2'-{[2-(trifluoromethyl)morpholin-4-yl]carbonyl}biphenyl-4-yl)pyrazin-2-amine,
1-{[4'-(5-Aminopyrazin-2-yl)-3'-fluorobiphenyl-2-yl]carbonyl}azetidin-3-ol,
4'-(5-Aminopyrazin-2-yl)-3'-fluoro-N-(tetrahydro-2H-pyran-4-yl)biphenyl-2-carboxamide,
5-{2'-[(1,1-Dioxidothiomorpholin-4-yl)carbonyl]-3-fluoro-4'-(trifluoromethyl)biphenyl-4-yl}pyrazin-2-amine,
1-(4-{[4'-(5-Aminopyrazin-2-yl)-3'-fluorobiphenyl-2-yl]carbonyl}morpholin-2-yl)ethanol (diastereomeric mixture),
1-(4-{[4'-(2-Aminopyrimidin-5-yl)-3'-fluorobiphenyl-2-yl]carbonyl}morpholin-2-yl)ethanol (diastereomeric mixture),
4'-(5-Aminopyrazin-2-yl)-3'-fluoro-N-(2-hydroxyethyl)biphenyl-2-carboxamide,
4'-(2-Aminopyrimidin-5-yl)-3'-fluoro-N-(2-hydroxyethyl)biphenyl-2-carboxamide,
(3R)-1-{[4'-(5-Aminopyrazin-2-yl)-3'-fluorobiphenyl-2-yl]carbonyl}piperidin-3-ol,
(cis/trans) 4'-(5-Aminopyrazin-2-yl)-3'-fluoro-N-(4-hydroxycyclohexyl)biphenyl-2-carboxamide,
(3R)-1-{[4'-(2-Aminopyrimidin-5-yl)-3'-fluorobiphenyl-2-yl]carbonyl}piperidin-3-ol,
(cis/trans) 4'-(2-Aminopyrimidin-5-yl)-3'-fluoro-N-(4-hydroxycyclohexyl)biphenyl-2-carboxamide,
racemic 5-(3-Fluoro-2'-{[2-(trifluoromethyl)morpholin-4-yl]carbonyl}biphenyl-4-yl)pyrimidin-2-amine,
(3S)-1-{[4'-(2-Aminopyrimidin-5-yl)-3'-fluorobiphenyl-2-yl]carbonyl}piperidin-3-ol,
(3S)-1-{[4'-(5-Aminopyrazin-2-yl)-3'-fluorobiphenyl-2-yl]carbonyl}piperidin-3-ol,
(3R)-1-{[4'-(5-Aminopyrazin-2-yl)-3'-fluorobiphenyl-2-yl]carbonyl}pyrrolidin-3-ol,
(3R)-1-{[4'-(2-Aminopyrimidin-5-yl)-3'-fluorobiphenyl-2-yl]carbonyl}pyrrolidin-3-ol,
(3S)-1-{[4'-(5-Aminopyrazin-2-yl)-3'-fluorobiphenyl-2-yl]carbonyl}pyrrolidin-3-ol,
(3S)-1-{[4'-(2-Aminopyrimidin-5-yl)-3'-fluorobiphenyl-2-yl]carbonyl}pyrrolidin-3-ol,
5-{2'-[(2,6-Dimethylmorpholin-4-yl)carbonyl]-3-fluorobiphenyl-4-yl}pyrazin-2-amine (diastereoisomeric mixture), 5-(3-Fluoro-2'-{[(3S)-3-methylmorpholin-4-yl]carbonyl}biphenyl-4-yl)pyrazin-2-amine,
5-(3-Fluoro-2'-{[(3R)-3-methylmorpholin-4-yl]carbonyl}biphenyl-4-yl)pyrazin-2-amine,
5-(3-Fluoro-2'-{[(2S)-2-methylmorpholin-4-yl]carbonyl}biphenyl-4-yl)pyrazin-2-amine,
5-(3-Fluoro-2'-{[(2S)-2-methylmorpholin-4-yl]carbonyl}biphenyl-4-yl)pyrimidin-2-amine,
5-(3-Fluoro-2'-{[(3S)-3-methylmorpholin-4-yl]carbonyl}biphenyl-4-yl)pyrimidin-2-amine,
5-(3-Fluoro-2'-{[(3R)-3-methylmorpholin-4-yl]carbonyl}biphenyl-4-yl)pyrimidin-2-amine,
5-{2'-[(2,6-Dimethylmorpholin-4-yl)carbonyl]-3-fluoro-biphenyl-4-yl}pyrimidin-2-amine (diastereoisomeric mixture),
5-{2-Fluoro-4-[2-(morpholin-4-ylcarbonyl)pyridin-3-yl]phenyl}-1H-pyrrolo[2,3-b]pyridine,
5-{2-Fluoro-4-[2-(morpholin-4-ylcarbonyl)pyridin-3-yl]phenyl}pyrimidin-2-amine,
5-{2-Fluoro-4-[2-(morpholin-4-ylcarbonyl)pyridin-3-yl]phenyl}pyrazin-2-amine,
2-[4-(5-Aminopyrazin-2-yl)-3-fluoro-phenyl]-N-tert-butyl-5-(trifluoromethyl)benzamide,
2-[4-(5-Aminopyrazin-2-yl)-3-fluoro-phenyl]-N-[(1R)-2-hydroxy-1-methyl-ethyl]-5-(trifluoromethyl)benzamide,
2-[4-(5-Aminopyrazin-2-yl)-3-fluoro-phenyl]-N-[(1S)-2-hydroxy-1-methyl-ethyl]-5-(trifluoromethyl)benzamide,
2-[4-(5-Aminopyrazin-2-yl)-3-fluoro-phenyl]-5-(trifluoromethyl)-N-[(1R)-2,2,2-trifluoro-1-methyl-ethyl]benzamide,
2-[4-(2-Aminopyrimidin-5-yl)-3-fluoro-phenyl]-5-(trifluoromethyl)-N-[(1S)-2,2,2-trifluoro-1-methyl-ethyl]benzamide,
2-[4-(2-Aminopyrimidin-5-yl)-3-fluoro-phenyl]-5-(trifluoromethyl)-N-[(1R)-2,2,2-trifluoro-1-methyl-ethyl]benzamide,
2-[4-(5-Aminopyrazin-2-yl)-3-fluoro-phenyl]-5-(trifluoromethyl)-N-[(1S)-2,2,2-trifluoro-1-methyl-ethyl]benzamide,
[2-[4-(2-Aminopyrimidin-5-yl)-3-fluoro-phenyl]phenyl]-(3-hydroxyazetidin-1-yl)methanone,
[2-[4-(2-Aminopyrimidin-5-yl)-3-fluoro-phenyl]phenyl]-[4-(methylamino)-1-piperidyl]methanone,
[2-[4-(2-Aminopyrimidin-5-yl)-3-fluoro-phenyl]-5-(trifluoromethyl)phenyl]-(1,1-dioxo-1,4-thiazinan-4-yl)methanone,
2-[4-(2-Aminopyrimidin-5-yl)-3-fluoro-phenyl]-N-tert-butyl-5-(trifluoromethyl)benzamide,
[2-[4-(5-Aminopyrazin-2-yl)-3-fluoro-phenyl]-5-(trifluoromethyl)phenyl]-(4-hydroxy-1-piperidyl)methanone,
[2-[4-(2-Aminopyrimidin-5-yl)-3-fluoro-phenyl]-5-(trifluoromethyl)phenyl]-(4-hydroxy-1-piperidyl)methanone,
2-[4-(2-Aminopyrimidin-5-yl)-3-fluoro-phenyl]-N-tetrahydropyran-4-yl-benzamide,
[2-[4-(5-Aminopyrazin-2-yl)-3-fluoro-phenyl]phenyl]-[2-(hydroxymethyl)morpholin-4-yl]methanone,
racemic [2-[4-(2-Aminopyrimidin-5-yl)-3-fluoro-phenyl]phenyl]-[2-(hydroxymethyl)morpholin-4-yl]methanone,
N-{3-[4-(2-Aminopyrimidin-5-yl)-3-fluorophenyl]pyridin-2-yl}-2,2-dimethylpropanamide,
N-{3-[4-(5-Aminopyrazin-2-yl)-3-fluorophenyl]pyridin-2-yl}-2,2-dimethylpropanamide,
N-{3-[3-Fluoro-4-(1H-pyrrolo[2,3-b]pyridin-5-yl)phenyl]pyridin-2-yl}-2,2-dimethylpropanamide,
racemic 5-(2-Fluoro-4-(2-(pyrrolidin-3-ylsulfonyl)pyridin-3-yl)phenyl)pyrazin-2-amine hydrochloride,
5-(2-Fluoro-4-(2-(pyrrolidin-3-ylsulfonyl)pyridin-3-yl)phenyl)pyrimidin-2-amine formic acid salt,
5-(4-(2-(Cyclobutylsulfonyl)pyridin-3-yl)-2-fluorophenyl)pyrimidin-2-amine hydrochloride,
5-(4-(2-(Cyclobutylsulfonyl)pyridin-3-yl)-2-fluorophenyl)pyrazin-2-amine hydrochloride,
5-(4-(2-(Cyclohexylsulfonyl)pyridin-3-yl)-2-fluorophenyl)pyrimidin-2-amine hydrochloride,
5-(4-(2-(Cyclohexylsulfonyl)pyridin-3-yl)-2-fluorophenyl)pyrazin-2-amine hydrochloride,
5-(4-(2-(Cyclopentylsulfonyl)pyridin-3-yl)-2-fluorophenyl)pyrimidine-2-amine hydrochloride,
5-(4-(2-(Cyclopentylsulfonyl)pyridin-3-yl)-2-fluorophenyl)pyrazin-2-amine hydrochloride,
5-(4-(2-(tert-Butylsulfonyl)pyridin-3-yl)-2-fluorophenyl)pyrimidin-2-amine formic acid salt,
5-(4-(2-(tert-Butylsulfonyl)pyridin-3-yl)-2-fluorophenyl)pyrazin-2-amine formic acid salt,
racemic 5-(4-(2-(sec-Butylsulfonyl)pyridin-3-yl)-2-fluorophenyl)pyrimidin-2-amine formate,
racemic 5-(4-(2-(sec-Butylsulfonyl)pyridin-3-yl)-2-fluorophenyl)pyrazin-2-amine formate,
1-((3-(4-(2-Aminopyrimidin-5-yl)-3-fluorophenyl)pyridine-2-yl)sulfonyl)piperidin-1-yl)ethanone,
1-((3-(4-(2-Aminopyrazin-5-yl)-3-fluorophenyl)pyridine-2-yl)sulfonyl)piperidin-1-yl)ethanone hydrogen chloride salt,
5-(2-Fluoro-4-(2-((3-methoxypropyl)sulfonyl)pyridine-3-yl)phenyl)pyrimidin-2-amine hydrogen chloride salt,
5-(2-Fluoro-4-(2-((3-methoxypropyl)sulfonyl)pyridine-3-yl)phenyl)pyrazin-2-amine hydrogen chloride salt,
4-((3-(4-(2-aminopyrimidin-5-yl)-3-fluorophenyl)pyridine-2-yl)sulfonyl)tetrahydro-2H-thiopyran 1,1-dioxide,
4-((3-(4-(2-Aminopyrazin-5-yl)-3-fluorophenyl)pyridine-2-yl)sulfonyl)tetrahydro-2H-thiopyran 1,1-dioxide,
5-(2-Fluoro-4-(2-((2-morpholinoethyl)sulfonyl)pyridine-3-yl)phenyl)pyrimidin-2-amine formic acid salt,
5-(2-Fluoro-4-(2-((2-morpholinoethyl)sulfonyl)pyridine-3-yl)phenyl)pyrazin-2-amine,
5-(2-Fluoro-4-(2-(((tetrahydro-2H-pyran-4-yl)methyl)sulfonyl)pyridine-3-yl)pyrimidin-2-amine formic acid salt,
5-(2-Fluoro-4-(2-(((tetrahydro-2H-pyran-4-yl)methyl)sulfonyl)pyridine-3-yl)pyrazin-2-amine formic acid salt,
5-(2-Fluoro-4-{2-[(1-methylethyl)sulfonyl]pyridin-3-yl}phenyl)pyrimidin-2-amine,
5-(2-Fluoro-4-(2-(isopropylsulfonyl)pyridine-3-yl)phenyl)-1H-pyrrolo[2,3-b]pyridine,
5-{2-Fluoro-4-[2-(piperidin-4-ylsulfonyl)pyridin-3-yl]phenyl}pyrimidin-2-amine formic acid salt,
5-{4-[2-(Cyclopropylsulfonyl)pyridin-3-yl]-2-fluorophenyl}pyrimidin-2-amine formic acid salt,
5-{4-[2-(Cyclopropylsulfonyl)pyridin-3-yl]-2-fluorophenyl}pyrazin-2-amine formic acid salt,
5-{2-Fluoro-4-[2-(tetrahydro-2H-pyran-4-ylsulfonyl)pyridin-3-yl]phenyl}pyrazin-2-aminehydrochloride
5-{2-Fluoro-4-[2-(tetrahydro-2H-pyran-4-ylsulfonyl)pyridin-3-yl]phenyl}pyrimidin-2-amine formic acid salt, 5-{2-Fluoro-4-[2-(piperidin-4-ylsulfonyl)pyridin-3-yl]
phenyl}pyrazin-2-aminehydrochloride,
5-(2,3-Difluorobiphenyl-4-yl)pyrazin-2-amine,
5-(3-Fluoro-2-methoxybiphenyl-4-yl)pyrazin-2-amine,
5-[3-Fluoro-2-methoxy-2'-(methylsulfonyl)biphenyl-4-
yl]pyrazin-2-amine,
4'-(5-Aminopyrazin-2-yl)-N-tert-butyl-3'-fluoro-2'-
methoxybiphenyl-2-sulfonamide,
N-[4'-(5-Aminopyrazin-2-yl)-3'-fluoro-2'-methoxybiphe-
nyl-2-yl]methanesulfonamide,
5-(3-Fluoro-2'-(pyrazin-2-yl)-[1,1'-biphenyl]-4-yl)
pyrazin-2-amine,
5-(3-Fluoro-2'-pyrazin-2-ylbiphenyl-4-yl)pyrimidin-2-
amine,
5,5'-(3'-Fluorobiphenyl-2,4'-diyl)dipyrazin-2-amine,
5-[2'-(5-Aminopyrazin-2-yl)-3-fluorobiphenyl-4-yl]py-
rimidin-2-amine,
5-[2'-(6-Aminopyrazin-2-yl)-3-fluorobiphenyl-4-yl]
pyrazin-2-amine,
5-[4'-(5-Aminopyrazin-2-yl)-3'-fluorobiphenyl-2-yl]py-
rimidin-2-amine,
5,5'-(3'-Fluorobiphenyl-2,4'-diyl)dipyrimidin-2-amine,
5-[4'-(5-Aminopyrazin-2-yl)-3'-fluoro-5-(trifluorom-
ethyl)biphenyl-2-yl]pyrimidin-2-amine,
5-[3-Fluoro-2'-(2-methoxypyrimidin-5-yl)biphenyl-4-yl]
pyrazin-2-amine,
5-[3-Fluoro-2'-(1-methyl-1H-pyrazol-4-yl)biphenyl-4-yl]
pyrazin-2-amine,
5-(3-Fluoro-2'-pyrimidin-5-ylbiphenyl-4-yl)pyrazin-2-
amine,
5-[4'-(5-Aminopyrazin-2-yl)-3'-fluorobiphenyl-2-yl]py-
rimidine-2-carbonitrile,
5-[3-Fluoro-2'-(2-morpholin-4-ylpyrimidin-5-yl)biphe-
nyl-4-yl]pyrazin-2-amine,
1-{4-[4'-(5-Aminopyrazin-2-yl)-3'-fluorobiphenyl-2-yl]-
1H-pyrazol-1-yl}-2-methylpropan-2-ol,
5-[3-Fluoro-2'-(1,2,3,6-tetrahydropyridin-4-yl)-4'-(trif-
luoromethyl)biphenyl-4-yl]pyrazin-2-amine,
5-[4'-(5-Aminopyrazin-2-yl)-3'-fluoro-4-(trifluorom-
ethyl)biphenyl-2-yl]pyrimidin-2-amine,
5-{2-[6-(2-Aminopyrimidin-5-yl)-5-fluoropyridin-3-yl]
phenyl}pyrimidin-2-amine,
5-{5-[2-(2-Aminopyrimidin-5-yl)phenyl]pyridin-2-
yl}pyrimidin-2-amine,
5-[2'-(1,1-Dioxidoisothiazolidin-2-yl)-3-fluorobiphenyl-
4-yl]pyrazin-2-amine,
5-[2'-(1,1-Dioxido-1,2-thiazinan-2-yl)-3-fluorobiphenyl-
4-yl]pyrazin-2-amine,
5-[2'-(1,1-Dioxidoisothiazolidin-2-yl)-3-fluorobiphenyl-
4-yl]pyrimidin-2-amine,
5-[2-Fluoro-4-(2-pyrrolidin-1-ylpyridin-3-yl)phenyl]
pyrazin-2-amine,
1-[4'-(5-Aminopyrazin-2-yl)-3'-fluorobiphenyl-2-yl]pyr-
rolidin-2-one,
5-(4'-Bromo-2',3-difluorobiphenyl-4-yl)-1H-pyrrolo[2,3-
b]pyridine,
5-(2',3,4'-Trifluorobiphenyl-4-yl)pyrazin-2-amine,
5-[3-Fluoro-2'-(methylsulfinyl)biphenyl-4-yl]pyrazin-2-
amine,
5-[2'-(Methylsulfonyl)biphenyl-4-yl]pyrazin-2-amine,
5-[3-Methyl-2'-(methylsulfonyl)biphenyl-4-yl]pyrazin-2-
amine,
4'-(5-Aminopyrazin-2-yl)-3'-hydroxybiphenyl-2-sulfona-
mide,
N-[4'-(5-Aminopyrazin-2-yl)biphenyl-2-yl]methanesul-
fonamide,
4'-(5-Aminopyrazin-2-yl)biphenyl-2-sulfonamide,
4'-(6-Aminopyridazin-3-yl)-3'-fluorobiphenyl-2-sulfona-
mide,
N-tert-Butyl-4'-(2,4-dioxo-1,2,3,4-tetrahydroquinazolin-
6-yl)-3'-fluorobiphenyl-2-sulfonamide,
3-Amino-6-[2'-(tert-butylsulfamoyl)-3-fluorobiphenyl-4-
yl]pyrazine-2-carboxylicacid,
4'-(5-Aminopyrazin-2-yl)-N-tert-butyl-3'-fluoro-5-(trif-
luoromethyl)biphenyl-2-sulfonamide,
5-{5-[2-(Cyclopropylsulfonyl)phenyl]pyridin-2-
yl}pyrimidin-2-amine,
2-{[4'-(2-Aminopyrimidin-5-yl)-3'-fluorobiphenyl-2-yl]
sulfonyl}acetamide,
2-{[4'-(2-Aminopyrimidin-5-yl)-3'-fluorobiphenyl-2-yl]
sulfonyl}-N,N-diethylacetamide,
5-{3-Fluoro-2'-[(2-morpholin-4-yl-2-oxoethyl)sulfonyl]
biphenyl-4-yl}pyrimidin-2-amine,
5-[5-(2-Methoxyphenyl)pyridin-2-yl]pyrimidin-2-amine,
5-{5-[2-(Morpholin-4-ylcarbonyl)phenyl]pyridin-2-
yl}pyrimidin-2-amine,
4'-(2-Amino-4-cyanopyrimidin-5-yl)-N-tert-butyl-3'-
fluorobiphenyl-2-sulfonamide,
5-[3-Fluoro-2'-(pyrimidin-2-ylsulfonyl)biphenyl-4-yl]py-
rimidin-2-amine,
5-[3-Fluoro-2'-(pyrazin-2-ylsulfonyl)biphenyl-4-yl]py-
rimidin-2-amine,
N-(2-{[4'-(2-Aminopyrimidin-5-yl)-3'-fluorobiphenyl-2-
yl]sulfonyl}ethyl)benzamide,
5-[3-Fluoro-2'-(pyrimidin-4-ylsulfonyl)biphenyl-4-yl]py-
rimidin-2-amine,
5-{2'-[(6-Aminopyrimidin-4-yl)sulfonyl]-3-fluorobiphe-
nyl-4-yl}pyrimidin-2-amine,
5-{2'-[(4-Aminopyrimidin-2-yl)sulfonyl]-3-fluorobiphe-
nyl-4-yl}pyrimidin-2-amine,
5-{2'-[(5-Aminopyrazin-2-yl)sulfonyl]-3-fluorobiphenyl-
4-yl}pyrimidin-2-amine,
5-(2-Fluoro-4-{2-[(2-morpholin-4-ylethyl)sulfonyl]pyri-
din-3-yl}phenyl)pyrimidin-2-amine,
5-[4'-(5-Aminopyrazin-2-yl)-3'-fluoro-5-(trifluorom-
ethyl)biphenyl-2-yl]pyrimidin-2-amine,
5-{5-[2-(2-Aminopyrimidin-5-yl)phenyl]pyridin-2-
yl}pyrimidin-2-amine,
4-{[4'-(2-Aminopyrimidin-5-yl)-3'-fluorobiphenyl-2-yl]
sulfonyl}pyrimidin-2-amine,
5-{2-Fluoro-4-[2-(morpholin-4-ylcarbonyl)pyridin-3-yl]
phenyl}pyrazin-2-amine,
5-{2-Fluoro-4-[2-(morpholin-4-ylcarbonyl)pyridin-3-yl]
phenyl}pyrimidin-2-amine,
5-(3-Fluoro-2'-{[(3S)-3-methylmorpholin-4-yl]
carbonyl}biphenyl-4-yl)pyrimidin-2-amine,
5-{2-Fluoro-4-[2-(piperidin-4-ylsulfonyl)pyridin-3-yl]
phenyl}pyrimidin-2-amine,
(3S)-1-{[4'-(2-Aminopyrimidin-5-yl)-3'-fluorobiphenyl-
2-yl]carbonyl}pyrrolidin-3-ol,
(3S)-1-{[4'-(5-Aminopyrazin-2-yl)-3'-fluorobiphenyl-2-
yl]carbonyl}pyrrolidin-3-ol,
(3R)-1-{[4'-(2-Aminopyrimidin-5-yl)-3'-fluorobiphenyl-
2-yl]carbonyl}pyrrolidin-3-ol,
2-({3-[4-(2-Aminopyrimidin-5-yl)-3-fluorophenyl]pyri-
din-2-yl}oxy)ethanol,
5-{2'-[(2,6-Dimethylmorpholin-4-yl)carbonyl]-3-fluoro-
biphenyl-4-yl}pyrimidin-2-amine,
(3S)-1-{[4'-(2-Aminopyrimidin-5-yl)-3'-fluorobiphenyl-
2-yl]carbonyl}piperidin-3-ol,
5-[3-Fluoro-2'-(piperidin-4-yloxy)biphenyl-4-yl]pyrimi-
din-2-amine,
2-{[4'-(2-Aminopyrimidin-5-yl)-3'-fluorobiphenyl-2-yl]
sulfonyl}-2-methylpropanamide, 5-{3-Fluoro-2'-[(3R)-piperidin-3-yloxy]biphenyl-4-yl}pyrimidin-2-amine,
5-(2'-{[1-(Aminomethyl)cyclopentyl]sulfonyl}-3-fluorobiphenyl-4-yl)pyrimidin-2-amine,
4'-(2-Aminopyrimidin-5-yl)-3'-fluoro-N-(4-hydroxycyclohexyl)biphenyl-2-carboxamide,
(3R)-1-{[4'-(2-Aminopyrimidin-5-yl)-3'-fluorobiphenyl-2-yl]carbonyl}piperidin-3-ol,
{[4'-(2-Aminopyrimidin-5-yl)-3'-fluorobiphenyl-2-yl]oxy}acetic acid,
4'-(2-Aminopyrimidin-5-yl)-3'-fluoro-N-(2-hydroxyethyl)biphenyl-2-carboxamide,
4'-(5-Aminopyrazin-2-yl)-3'-fluoro-N-(2-hydroxyethyl)biphenyl-2-carboxamide,
4'-(5-Aminopyrazin-2-yl)-3'-fluoro-N-(tetrahydro-2H-pyran-4-yl)biphenyl-2-carboxamide,
5-[2'-(2-Aminoethoxy)-3-fluorobiphenyl-4-yl]pyrazin-2-amine,
5-[2'-(2-Aminoethoxy)-3-fluorobiphenyl-4-yl]pyrimidin-2-amine,
2-[3,5'-Difluoro-2'-(methylsulfanyl)biphenyl-4-yl]-5H-pyrrolo[2,3-b]pyrazine,
N-[4'-(2-Aminopyrimidin-5-yl)-3'-fluorobiphenyl-2-yl]methanesulfonamide,
4'-(5-Aminopyrazin-2-yl)-N,N,3'-trimethylbiphenyl-2-sulfonamide,
4'-(6-Aminopyridin-3-yl)-3'-fluoro-N-methylbiphenyl-2-sulfonamide,
N-tert-Butyl-3'-fluoro-4'-(2-oxo-2,3-dihydro-1H-indol-5-yl)biphenyl-2-sulfonamide,
4'-(3-Amino-1H-indazol-5-yl)-N-tert-butyl-3'-fluorobiphenyl-2-sulfonamide,
5-(3-Fluoro-2'-{[(3R)-3-methylmorpholin-4-yl]carbonyl}biphenyl-4-yl)pyrimidin-2-amine,
5-(3-Fluoro-2'-{[2-(trifluoromethyl)morpholin-4-yl]carbonyl}biphenyl-4-yl)pyrimidin-2-amine,
5-[3-Fluoro-2'-(piperidin-4-yloxy)biphenyl-4-yl]pyrazin-2-amine,
N-[4'-(5-Aminopyrazin-2-yl)-3'-fluoro-2'-methoxybiphenyl-2-yl]methanesulfonamide,
1-{[4'-(5-Aminopyrazin-2-yl)-3'-fluorobiphenyl-2-yl]carbonyl}azetidin-3-ol,
(3R)-1-{[4'-(5-Aminopyrazin-2-yl)-3'-fluorobiphenyl-2-yl]carbonyl}pyrrolidin-3-ol,
4'-(5-Aminopyrazin-2-yl)-3'-fluorobiphenyl-2-carbonitrile,
(2R)-2-({3-[4-(2-Aminopyrimidin-5-yl)-3-fluorophenyl]pyridin-2-yl}oxy)propan-1-ol,
5-{2-Fluoro-4-[2-(piperidin-4-ylsulfonyl)pyridin-3-yl]phenyl}pyrazin-2-amine,
5-{2'-[(6-Aminopyrazin-2-yl)sulfonyl]-3-fluorobiphenyl-4-yl}pyrimidin-2-amine,
4'-(6-Aminopyridin-3-yl)-3'-fluorobiphenyl-2-sulfonamide,
5-{3-Fluoro-2'-[(methylsulfonyl)methyl]biphenyl-4-yl}pyrazin-2-amine,
5-{3-Fluoro-2'-[(3S)-piperidin-3-yloxy]biphenyl-4-yl}pyrimidin-2-amine,
4'-(5-Aminopyrazin-2-yl)-3'-fluoro-N-(4-hydroxycyclohexyl)biphenyl-2-carboxamide,
1-{[4'-(2-Aminopyrimidin-5-yl)-3'-fluorobiphenyl-2-yl]sulfonyl}-3,3-dimethylbutan-2-one,
6-{[4'-(5-Aminopyrazin-2-yl)-3'-fluorobiphenyl-2-yl]sulfonyl}pyrimidin-4-amine,
2-{[4'-(2-Aminopyrimidin-5-yl)-3'-fluorobiphenyl-2-yl]oxy}ethanol,
2-({3-[4-(5-Aminopyrazin-2-yl)-3-fluorophenyl]pyridin-2-yl}oxy)ethanol,
5-{2'-[(Cyclopropylmethyl)sulfonyl]-3-fluorobiphenyl-4-yl}pyrimidin-2-amine,
N-[4'-(6-Aminopyridin-3-yl)-3'-fluorobiphenyl-2-yl]methanesulfonamide,
4-({2-[6-(2-Aminopyrimidin-5-yl)pyridin-3-yl]phenyl}sulfonyl)piperazin-2-one,
5-{2-Fluoro-4-[2-(morpholin-4-ylcarbonyl)pyridin-3-yl]phenyl}-1H-pyrrolo[2,3-b]pyridine,
2-[6-(2-Aminopyrimidin-5-yl)pyridin-3-yl]-N-[(2S)-2-hydroxypropyl]benzenesulfonamide,
2-[6-(2-Aminopyrimidin-5-yl)pyridin-3-yl]-N-[(1R)-2-hydroxy-1-methylethyl]benzenesulfonamide,
5-{2-Fluoro-4-[2-(pyrrolidin-3-ylsulfonyl)pyridin-3-yl]phenyl}pyrimidin-2-amine,
5-(5-{2-[(3,3-Difluoropyrrolidin-1-yl)sulfonyl]phenyl}pyridin-2-yl)pyrimidin-2-amine,
2-[6-(2-Aminopyrimidin-5-yl)pyridin-3-yl]-N-ethylbenzenesulfonamide,
(3S)-1-{[4'-(5-Aminopyrazin-2-yl)-3'-fluorobiphenyl-2-yl]carbonyl}piperidin-3-ol,
(2S)-2-({3-[4-(2-Aminopyrimidin-5-yl)-3-fluorophenyl]pyridin-2-yl}oxy)propan-1-ol,
2-{[4'-(2-Aminopyrimidin-5-yl)-3'-fluorobiphenyl-2-yl]sulfonyl}-2-methylpropanenitrile,
(2R)-2-({3-[4-(5-Aminopyrazin-2-yl)-3-fluorophenyl]pyridin-2-yl}oxy)propan-1-ol,
2-[6-(2-Aminopyrimidin-5-yl)pyridin-3-yl]-N-[(2R)-2-hydroxypropyl]benzenesulfonamide,
2-{[4'-(5-Aminopyrazin-2-yl)-3'-fluorobiphenyl-2-yl]sulfonyl}pyrimidin-4-amine,
4'-(5-Aminopyrazin-2-yl)-N-tert-butyl-3'-fluoro-5-methoxybiphenyl-2-sulfonamide,
5-(2-Fluoro-4-{2-[(3-methoxypropyl)sulfonyl]pyridin-3-yl}phenyl)pyrimidin-2-amine,
1-{[4'-(2-Aminopyrimidin-5-yl)-3'-fluorobiphenyl-2-yl]sulfonyl}cyclopentanecarboxamide,
5-[3-Fluoro-2-methoxy-2'-(methylsulfonyl)biphenyl-4-yl]pyrazin-2-amine,
2-{[4'-(5-Aminopyrazin-2-yl)-3'-fluorobiphenyl-2-yl]oxy}ethanol,
2-[6-(2-Aminopyrimidin-5-yl)pyridin-3-yl]-N-[(1R)-2,2,2-trifluoro-1-methylethyl]benzenesulfonamide,
2-{[4'-(5-Aminopyrazin-2-yl)-3'-fluorobiphenyl-2-yl]sulfonyl}-2-methylpropanamide,
{[4'-(2-Aminopyrimidin-5-yl)-3'-fluorobiphenyl-2-yl]oxy}acetonitrile,
5-{4-[2-(tert-Butylsulfonyl)pyridin-3-yl]-2-fluorophenyl}pyrimidin-2-amine,
5-{3-Fluoro-2'-[(3S)-piperidin-3-yloxy]biphenyl-4-yl}pyrazin-2-amine,
5-(4-{2-[(trans-4-Aminocyclohexyl)oxy]pyridin-3-yl}-2-fluorophenyl)pyrimidin-2-amine,
5-(2-Fluoro-4-{2-[(2-morpholin-4-ylethyl)sulfonyl]pyridin-3-yl}phenyl)pyrazin-2-amine,
5-(2-Fluoro-4-{2-[(1-methylethyl)sulfonyl]pyridin-3-yl}phenyl)pyrimidin-2-amine,
5-(4-{2-[(1-Acetylpiperidin-4-yl)sulfonyl]pyridin-3-yl}-2-fluorophenyl)pyrimidin-2-amine,
5-(4'-Bromo-2',3-difluorobiphenyl-4-yl)pyrazin-2-amine,
5-(3-Fluoro-2'-{[2-(trifluoromethyl)pyridin-4-yl]oxy}biphenyl-4-yl)pyrimidin-2-amine,
5-{2'-[(4,6-Dimethylpyrimidin-2-yl)oxy]-3-fluorobiphenyl-4-yl}pyrimidin-2-amine,
5-{2'-[(Ethylsulfonyl)methyl]-3-fluorobiphenyl-4-yl}pyrazin-2-amine, 1-{[4'-(2-Aminopyrimidin-5-yl)-3'-fluorobiphenyl-2-yl]sulfonyl}cyclopentanecarbonitrile,
(3S)-1-{[4'-(2-Aminopyrimidin-5-yl)-3'-fluorobiphenyl-2-yl]sulfonyl}pyrrolidine-3-carboxamide,
5-{5-[2-(Morpholin-4-ylmethyl)-4-(trifluoromethyl)phenyl]pyridin-2-yl}pyrimidin-2-amine,
5-(5-{2-[(4,4-Difluoropiperidin-1-yl)sulfonyl]phenyl}pyridin-2-yl)pyrimidin-2-amine,
5-{2'-[(2,6-Dimethylmorpholin-4-yl)carbonyl]-3-fluorobiphenyl-4-yl}pyrazin-2-amine,
5-(3-Fluoro-2'-{[4-(trifluoromethyl)pyrimidin-2-yl]oxy}biphenyl-4-yl)pyrimidin-2-amine,
(3R)-1-{[4'-(2-Aminopyrimidin-5-yl)-3'-fluorobiphenyl-2-yl]sulfonyl}pyrrolidine-3-carboxamide,
5-(2-Fluoro-4-{2-[(tetrahydro-2H-pyran-4-ylmethyl)sulfonyl]pyridin-3-yl}phenyl)pyrimidin-2-amine,
2-[6-(2-Aminopyrimidin-5-yl)pyridin-3-yl]-N-(2-hydroxyethyl)-5-(trifluoromethyl)benzenesulfonamide,
(3R)-1-{[4'-(5-Aminopyrazin-2-yl)-3'-fluorobiphenyl-2-yl]carbonyl}piperidin-3-ol,
5-[3-Fluoro-2'-(morpholin-4-ylcarbonyl)biphenyl-4-yl]pyrazin-2-amine,
2-({[4'-(5-Aminopyrazin-2-yl)-3'-fluoro-4-(trifluoromethyl)biphenyl-2-yl]methyl}amino)ethanol,
5-{3-Fluoro-2'-[(pyrimidin-2-ylsulfonyl)methyl]biphenyl-4-yl}pyrazin-2-amine,
2-[6-(2-Aminopyrimidin-5-yl)-5-fluoropyridin-3-yl]-N-[(2R)-2-hydroxypropyl]benzenesulfonamide,
5-(5-{2-[(3,3-Difluoropiperidin-1-yl)sulfonyl]phenyl}pyridin-2-yl)pyrimidin-2-amine,
5-{2-Fluoro-4-[2-(tetrahydro-2H-pyran-4-ylsulfonyl)pyridin-3-yl]phenyl}pyrimidin-2-amine,
5-{2-Fluoro-4-[2-(tetrahydro-2H-pyran-4-yloxy)pyridin-3-yl]phenyl}pyrimidin-2-amine,
5-[3-Fluoro-2'-(1,2,3,6-tetrahydropyridin-4-yl)-4'-(trifluoromethyl)biphenyl-4-yl]pyrazin-2-amine,
5-{4-[2-(Cyclopropylsulfonyl)pyridin-3-yl]-2-fluorophenyl}pyrimidin-2-amine,
5-{2-Fluoro-4-[2-(pyrrolidin-3-ylsulfonyl)pyridin-3-yl]phenyl}pyrazin-2-amine,
6-Amino-3-{2'-[(1,1-dioxidothiomorpholin-4-yl)sulfonyl]-3-fluorobiphenyl-4-yl}pyrazine-2-carbonitrile,
N-(1-{[4'-(6-Amino-5-fluoropyridin-3-yl)-3'-fluorobiphenyl-2-yl]sulfonyl}piperidin-4-yl)acetamide,
1-{[4'-(2-Aminopyrimidin-5-yl)-3'-fluorobiphenyl-2-yl]sulfonyl}-N-methylazetidine-3-carboxamide,
5-[3-Fluoro-2'-(morpholin-4-ylsulfonyl)biphenyl-4-yl]pyridin-2-amine,
5-(3-Fluoro-2'-{[(1-methylethyl)sulfonyl]methyl}biphenyl-4-yl)pyrazin-2-amine,
4'-(5-Amino-3-cyanopyrazin-2-yl)-3'-fluoro-N-(2-hydroxyethyl)biphenyl-2-sulfonamide,
{[4'-(5-Aminopyrazin-2-yl)-3'-fluorobiphenyl-2-yl]oxy}acetonitrile,
(2S)-2-({3-[4-(5-Aminopyrazin-2-yl)-3-fluorophenyl]pyridin-2-yl}propan-1-ol,
6-Amino-3-[2'-(cyclopropylsulfonyl)-3-fluorobiphenyl-4-yl]pyrazine-2-carbonitrile,
5-(4-{2-[(trans-4-Aminocyclohexyl)oxy]pyridin-3-yl}-2-fluorophenyl)pyrazin-2-amine,
2-[6-(2-Aminopyrimidin-5-yl)pyridin-3-yl]-N-ethyl-5-(trifluoromethyl)benzenesulfonamide,
2-[6-(2-Aminopyrimidin-5-yl)pyridin-3-yl]-N-[(1S)-2,2,2-trifluoro-1-methylethyl]benzenesulfonamide,
5-{5-[2-(Azepan-1-ylsulfonyl)phenyl]pyridin-2-yl}pyrimidin-2-amine,
2-[6-(2-Aminopyrimidin-5-yl)pyridin-3-yl]-N-tert-butyl-benzenesulfonamide,
2-[6-(2-Aminopyrimidin-5-yl)pyridin-3-yl]-N-(dicyclopropylmethyl)benzenesulfonamide,
5-{2'-[(4-Aminopiperidin-1-yl)methyl]-3-fluoro-4'-(trifluoromethyl)biphenyl-4-yl}pyrazin-2-amine,
5-{2'-[(6-Amino-2-methyl pyrimidin-4-yl)oxy]-3-fluorobiphenyl-4-yl}pyrimidin-2-amine,
6-{[4'-(2-Aminopyrimidin-5-yl)-3'-fluorobiphenyl-2-yl]oxy}pyridine-3-carbonitrile,
4'-(5-Amino-3-cyanopyrazin-2-yl)-3'-fluoro-N-[(1S)-2-hydroxy-1-methylethyl]biphenyl-2-sulfonamide,
5-(4-{2-[(1,1-Dioxidotetrahydro-2H-thiopyran-4-yl)sulfonyl]pyridin-3-yl}-2-fluorophenyl)pyrimidin-2-amine,
5-(2-Fluoro-4-{2-[(1-methylpropyl)sulfonyl]pyridin-3-yl}phenyl)pyrimidin-2-amine,
4'-(5-Amino-3-cyanopyrazin-2-yl)-3'-fluoro-N-[(2S)-2-hydroxypropyl]biphenyl-2-sulfonamide,
2-{[4'-(5-Aminopyrazin-2-yl)-3'-fluorobiphenyl-2-yl]sulfonyl}-2-methylpropanenitrile,
5-{4-[2-(Cyclobutylsulfonyl)pyridin-3-yl]-2-fluorophenyl}pyrimidin-2-amine,
5-{2'-[(4,6-Dimethylpyrimidin-2-yl)oxy]-3-fluorobiphenyl-4-yl}pyrazin-2-amine,
5-{2'-[(Cyclopropylmethyl)sulfonyl]-3-fluorobiphenyl-4-yl}pyrazin-2-amine,
4'-(5-Aminopyrazin-2-yl)-3'-fluoro-4-(trifluoromethyl)biphenyl-2-carboxylic acid,
5-(3-Fluoro-2'-{[2-(trifluoromethyl)pyridin-4-yl]oxy}biphenyl-4-yl)pyrazin-2-amine,
5-(2-Fluoro-4-{2-[(3-methoxypropyl)sulfonyl]pyridin-3-yl}phenyl)pyrazin-2-amine,
6-Amino-3-[3-fluoro-2'-(pyrimidin-2-yloxy)biphenyl-4-yl]pyrazine-2-carbonitrile,
4'-(5-Aminopyrazin-2-yl)-N-tert-butyl-3'-fluoro-2'-methoxybiphenyl-2-sulfonamide,
4'-(5-Amino-3-cyanopyrazin-2-yl)-3'-fluoro-N-[(2R)-2-hydroxypropyl]biphenyl-2-sulfonamide,
1-{[4'-(6-Amino-5-fluoropyridin-3-yl)-3'-fluorobiphenyl-2-yl]sulfonyl}piperidin-3-ol,
5-(4-{2-[(1-Acetylpiperidin-4-yl)sulfonyl]pyridin-3-yl}-2-fluorophenyl)pyrazin-2-amine,
5-{2'-[(6-Cyclopropylpyrimidin-4-yl)oxy]-3-fluorobiphenyl-4-yl}pyrimidin-2-amine,
5-{2-Fluoro-4-[2-(tetrahydro-2H-pyran-4-yloxy)pyridin-3-yl]phenyl}pyrazin-2-amine,
2-(1-{[4'-(6-Amino-5-fluoropyridin-3-yl)-3'-fluorobiphenyl-2-yl]sulfonyl}piperidin-3-yl)ethanol,
5-{2'-[(5-Aminopyrazin-2-yl)sulfanyl]-3-fluorobiphenyl-4-yl}pyrimidin-2-amine
1-{[4'-(5-Aminopyrazin-2-yl)-3'-fluorobiphenyl-2-yl]sulfonyl}cyclopentanecarboxamide,
6-{[4'-(2-Aminopyrimidin-5-yl)-3'-fluorobiphenyl-2-yl]oxy}pyridine-2-carbonitrile,
5-(3-Fluoro-2'-{[4-(trifluoromethyl)pyrimidin-2-yl]oxy}biphenyl-4-yl)pyrazin-2-amine,
4'-(5-Amino-3-cyanopyrazin-2-yl)-3'-fluoro-N-[(1R)-2-hydroxy-1-methylethyl]biphenyl-2-sulfonamide,
(1-{[4'-(6-Amino-5-fluoropyridin-3-yl)-3'-fluorobiphenyl-2-yl]sulfonyl}piperidin-3-yl)methanol,
6-Amino-3-{2'-[(4-aminopyrimidin-2-yl)oxy]-3-fluorobiphenyl-4-yl}pyrazine-2-carbonitrile,
5-[3-Fluoro-2'-(2-methoxypyrimidin-5-yl)biphenyl-4-yl]pyrazin-2-amine,
5-(2-Fluoro-4-{2-[(tetrahydro-2H-pyran-4-ylmethyl)sulfonyl]pyridin-3-yl}phenyl)pyrazin-2-amine, 5-{4-[2-(tert-Butylsulfonyl)pyridin-3-yl]-2-fluorophenyl}pyrazin-2-amine
3-Amino-6-{2'-[(4-aminopyrimidin-2-yl)oxy]-3-fluorobiphenyl-4-yl}pyrazine-2-carbonitrile,
6-Amino-3-{3-fluoro-2'-[(3-oxopiperazin-1-yl)sulfonyl]-4'-(trifluoromethyl)biphenyl-4-yl}pyrazine-2-carbonitrile,
4'-(5-Aminopyrazin-2-yl)-N-tert-butyl-3'-fluoro-4-(trifluoromethyl)biphenyl-2-carboxamide,
5-(3-Fluoro-2'-{[6-(trifluoromethyl)pyridin-2-yl]oxy}biphenyl-4-yl)pyrazin-2-amine,
5-{2'-[(2-Aminopyridin-4-yl)oxy]-3-fluorobiphenyl-4-yl}pyrimidin-2-amine,
1-{[4'-(5-Aminopyrazin-2-yl)-3'-fluorobiphenyl-2-yl]sulfonyl}cyclopentanecarbonitrile,
6-{[4'-(5-Aminopyrazin-2-yl)-3'-fluorobiphenyl-2-yl]oxy}pyridine-3-carbonitrile,
4'-(6-Amino-5-fluoropyridin-3-yl)-3'-fluoro-N-(2-hydroxy-1,1-dimethylethyl)biphenyl-2-sulfonamide,
5-{4-[2-(Cyclohexylsulfonyl)pyridin-3-yl]-2-fluorophenyl}pyrimidin-2-amine,
5-{3-Fluoro-2'-[(1 S,4S)-2-oxa-5-azabicyclo[2.2.1]hept-5-ylsulfonyl]biphenyl-4-yl}pyrazin-2-amine,
1-{[4'-(2-Aminopyrimidin-5-yl)-3'-fluorobiphenyl-2-yl]sulfonyl}piperidine-4-carboxamide,
4'-(5-Aminopyrazin-2-yl)-3'-fluoro-4-(trifluoromethyl)biphenyl-2-carbaldehyde,
4'-(5-Aminopyrazin-2-yl)-3'-fluoro-N-[(3-hydroxyazetidin-3-yl)methyl]biphenyl-2-sulfonamide,
5-{2'-[(5-Aminopyridin-2-yl)oxy]-3-fluorobiphenyl-4-yl}pyrimidin-2-amine,
5-{[4'-(5-Aminopyrazin-2-yl)-3'-fluorobiphenyl-2-yl]sulfanyl}pyrazin-2-amine,
5-{2'-[(6-Cyclopropylpyrimidin-4-yl)oxy]-3-fluorobiphenyl-4-yl}pyrazin-2-amine,
2-({[4'-(5-Aminopyrazin-2-yl)-3'-fluorobiphenyl-2-yl]methyl}sulfanyl)pyrimidin-4-amine,
4'-(6-Amino-5-fluoropyridin-3-yl)-3'-fluoro-N-[(1S,2S)-2-hydroxy-1-methyl-2-phenylethyl]-N-methylbiphenyl-2-sulfonamide,
5-{4-[2-(Cyclopentylsulfonyl)pyridin-3-yl]-2-fluorophenyl}pyrimidin-2-amine,
2-[3-Fluoro-2'-(methylsulfanyl)biphenyl-4-yl]-5H-pyrrolo[2,3-b]pyrazine,
6-{[4'-(5-Aminopyrazin-2-yl)-3'-fluorobiphenyl-2-yl]oxy}pyridine-2-carbonitrile,
5-(4-{2-[(1,1-Dioxidotetrahydro-2H-thiopyran-4-yl)sulfonyl]pyridin-3-yl}-2-fluorophenyl)pyrazin-2-amine,
5-{4-[2-(Cyclopropylsulfonyl)pyridin-3-yl]-2-fluorophenyl}pyrazin-2-amine,
4'-(6-Aminopyridin-3-yl)-3'-fluoro-N-[(1S,2S)-2-hydroxy-1-methyl-2-phenylethyl]-N-methylbiphenyl-2-sulfonamide,
5-{2'-[(1,1-Dioxidothiomorpholin-4-yl)carbonyl]-3-fluoro-4'-(trifluoromethyl)biphenyl-4-yl}pyrazin-2-amine,
N,N-Diethyl-3'-fluoro-4'-(1H-pyrrolo[2,3-b]pyridin-5-yl)biphenyl-2-sulfonamide,
5-{2-Fluoro-4-[2-(tetrahydro-2H-pyran-4-ylsulfonyl)pyridin-3-yl]phenyl}pyrazin-2-amine,
5-{2'-[(6-Aminopyrazin-2-yl)sulfanyl]-3-fluorobiphenyl-4-yl}pyrazin-2-amine,
5-(2-Fluoro-4-{2-[(1-methylpropyl)sulfonyl]pyridin-3-yl}phenyl)pyrazin-2-amine,
4'-(6-Aminopyridin-3-yl)-3'-fluoro-N-(2-hydroxy-1,1-dimethylethyl)biphenyl-2-sulfonamide,
2-[6-(2-Aminopyrimidin-5-yl)-5-fluoropyridin-3-yl]-N-ethyl-5-(trifluoromethyl)benzenesulfonamide,
4'-(5-Amino-3-cyanopyrazin-2-yl)-3'-fluoro-N-(3-hydroxy-2,2-dimethylpropyl)biphenyl-2-sulfonamide,
6-Amino-3-[3-fluoro-2'-(pyrimidin-2-yloxy)-4'-(trifluoromethyl)biphenyl-4-yl]pyrazine-2-carbonitrile,
5-[3-Fluoro-2'-(morpholin-4-ylmethyl)-4'-(trifluoromethyl)biphenyl-4-yl]pyrazin-2-amine,
4'-(5-Amino-3-cyanopyrazin-2-yl)-3'-fluoro-N-(2-hydroxyethyl)-4
5-{2'-[(5-Aminopyridin-2-yl)oxy]-3-fluorobiphenyl-4-yl}pyrazin-2-amine,
5-{4-[2-(Cyclobutylsulfonyl)pyridin-3-yl]-2-fluorophenyl}pyrazin-2-amine,
4'-(5-Amino-3-cyanopyrazin-2-yl)-N-ethyl-3'-fluoro-4-(trifluoromethyl)biphenyl-2-sulfonamide,
5-[3-Fluoro-2'-(pyrimidin-4-ylsulfanyl)biphenyl-4-yl]pyrazin-2-amine,
1-{[4'-(2-Aminopyrimidin-5-yl)-3'-fluorobiphenyl-2-yl]sulfonyl}-4-(pentafluoroethyl)piperidin-4-ol,
5-{2'-[(2-Aminopyridin-4-yl)oxy]-3-fluorobiphenyl-4-yl}pyrazin-2-amine,
5-(2-Fluoro-4-{2-[(1-methylethyl)sulfonyl]pyridin-3-yl}phenyl)-1H-pyrrolo[2,3-b]pyridine,
2-[6-(2-Aminopyrimidin-5-yl)-5-fluoropyridin-3-yl]-N-tert-butylbenzenesulfonamide,
tert-Butyl (1-{[3'-fluoro-4'-(5H-pyrrolo[2,3-b]pyrazin-2-yl)biphenyl-2-yl]sulfonyl}piperidin-4-yl)carbamate,
5-{4-[2-(Cyclopentylsulfonyl)pyridin-3-yl]-2-fluorophenyl}pyrazin-2-amine,
4'-(5-Aminopyrazin-2-yl)-N-tert-butyl-3,3'-difluorobiphenyl-2-sulfonamide,
5-{4-[2-(Cyclohexylsulfonyl)pyridin-3-yl]-2-fluorophenyl}pyrazin-2-amine,
4'-(5-Aminopyrazin-2-yl)-N-tert-butyl-3',4-difluorobiphenyl-2-sulfonamide,
5-(3-Fluoro-2'-{[(2S)-2-methylmorpholin-4-yl]carbonyl}biphenyl-4-yl)pyrimidin-2-amine,
5-(3-Fluoro-2'-{[(2S)-2-methylmorpholin-4-yl]carbonyl}biphenyl-4-yl)pyrazin-2-amine,
2-{[4'-(5-Aminopyrazin-2-yl)-3'-fluorobiphenyl-2-yl]oxy}pyrimidin-5-amine,
5-{2'-[(5-Aminopyrimidin-2-yl)oxy]-3-fluorobiphenyl-4-yl}pyrimidin-2-amine,
5-(2-fluoro-4-(2-(piperidin-4-yloxy)pyridin-3-yl)phenyl)pyrazin-2-amine,
5-{2-Fluoro-4-[2-(piperidin-4-yloxy)pyridin-3-yl]phenyl}pyrimidin-2-amine,
2-{[4'-(5-Aminopyrazin-2-yl)-3'-fluorobiphenyl-2-yl]oxy}-6-methylpyrimidin-4-amine,
5-{2'-[(4-Amino-6-methylpyrimidin-2-yl)oxy]-3-fluorobiphenyl-4-yl}pyrimidin-2-amine,
5-(3-Fluoro-2'-{[(3R)-3-methylmorpholin-4-yl]carbonyl}biphenyl-4-yl)pyrazin-2-amine,
5-(4-{2-[(1,1-Dioxidotetrahydro-2H-thiopyran-4-yl)oxy]pyridin-3-yl}-2-fluorophenyl)pyrazin-2-amine,
5-(3-Fluoro-2'-{[(3S)-3-methylmorpholin-4-yl]carbonyl}biphenyl-4-yl)pyrazin-2-amine,
5-(4-{2-[(1,1-Dioxidotetrahydro-2H-thiopyran-4-yl)oxy]pyridin-3-yl}-2-fluorophenyl)pyrimidin-2-amine,
5-(3-Fluoro-2'-{[6-(trifluoromethyl)pyridin-2-yl]oxy}biphenyl-4-yl)pyrimidin-2-amine,
5-{3-Fluoro-2'-[(3R)-piperidin-3-yloxy]biphenyl-4-yl}pyrazin-2-amine,
1-(4-{[4'-(5-Aminopyrazin-2-yl)-3'-fluorobiphenyl-2-yl]carbonyl}morpholin-2-yl)ethanol, 1-(4-{[4'-(2-Aminopyrimidin-5-yl)-3'-fluorobiphenyl-2-yl]carbonyl}morpholin-2-yl)ethanol,
5-(3-Fluoro-2'-{[2-(trifluoromethyl)morpholin-4-yl]carbonyl}biphenyl-4-yl)pyrazin-2-amine,
N-{3-[4-(5-Aminopyrazin-2-yl)-3-fluorophenyl]pyridin-2-yl}-2,2-dimethylpropanamide,
N-{3-[4-(2-Aminopyrimidin-5-yl)-3-fluorophenyl]pyridin-2-yl}-2,2-dimethylpropanamide,
5-{2'-[(2-Amino-1,1-dimethylethyl)sulfonyl]-3-fluorobiphenyl-4-yl}pyrazin-2-amine,
5-{2'-[(2-Amino-1,1-dimethylethyl)sulfonyl]-3-fluorobiphenyl-4-yl}pyrimidin-2-amine,
N-{3-[3-Fluoro-4-(1H-pyrrolo[2,3-b]pyridin-5-yl)phenyl]pyridin-2-yl}-2,2-dimethylpropanamide,
4'-(5-Aminopyrazin-2-yl)-N-tert-butyl-3'-fluoro-4-(trifluoromethyl)biphenyl-2-sulfonamide,
5-[2'-Amino-3-fluoro-4'-(trifluoromethyl)biphenyl-4-yl]pyrazin-2-amine,
5-{2'-[(1,1-Dioxidotetrahydro-2H-thiopyran-4-yl)methoxy]-3-fluorobiphenyl-4-yl}pyrazin-2-amine,
5-{2'-[(1,1-Dioxidotetrahydro-2H-thiopyran-4-yl)oxy]-3-fluorobiphenyl-4-yl}pyrazin-2-amine,
4-({[4'-(5-Aminopyrazin-2-yl)-3'-fluorobiphenyl-2-yl]oxy}methyl)benzoic acid,
4-({[4'-(2-Aminopyrimidin-5-yl)-3'-fluorobiphenyl-2-yl]oxy}methyl)benzoic acid,
4-{[4'-(5-Aminopyrazin-2-yl)-3'-fluorobiphenyl-2-yl]oxy}benzoic acid,
4-{[4'-(2-Aminopyrimidin-5-yl)-3'-fluorobiphenyl-2-yl]oxy}benzoic acid,
2-[4-({3-[4-(5-Aminopyrazin-2-yl)-3-fluorophenyl]pyridin-2-yl}sulfonyl)piperidin-1-yl]ethanol,
4-[4'-(5-Aminopyrazin-2-yl)-3'-fluorobiphenyl-2-yl]pyrimidin-2-amine,
1-[4-({3-[4-(5-Aminopyrazin-2-yl)-3-fluorophenyl]pyridin-2-yl}sulfonyl)piperidin-1-yl]propan-2-ol,
5-[3-Fluoro-2'-(1H-pyrazol-4-yl)biphenyl-4-yl]pyrazin-2-amine,
5-[2'-(6-Aminopyridin-3-yl)-3-fluorobiphenyl-4-yl]pyrazin-2-amine,
5-{3-Fluoro-2'-[1-(2-methoxyethyl)-1H-pyrazol-4-yl]biphenyl-4-yl}pyrazin-2-amine,
5-{5-[2-(Cyclopropylsulfonyl)phenyl]-3-fluoropyridin-2-yl}pyrimidin-2-amine,
4-{[4'-(2-Aminopyrimidin-5-yl)-3'-fluorobiphenyl-2-yl]oxy}benzamide,
5-{2'-[(trans-4-Aminocyclohexyl)oxy]-3-fluorobiphenyl-4-yl}pyrazin-2-amine,
5-{2-Fluoro-4-[2-(phenylsulfonyl)pyridin-3-yl]phenyl}pyrazin-2-amine,
6-[4'-(5-Aminopyrazin-2-yl)-3'-fluorobiphenyl-2-yl]pyridazin-3-amine,
{4-[4'-(5-Aminopyrazin-2-yl)-3'-fluorobiphenyl-2-yl]-1H-pyrazol-1-yl}acetonitrile,
5-[4'-(5-Aminopyrazin-2-yl)-3'-fluorobiphenyl-2-yl]-N-methylpyrimidin-2-amine,
2-[6-(2-Aminopyrimidin-5-yl)-5-fluoropyridin-3-yl]-N-[(1S)-2,2,2-trifluoro-1-methylethyl]benzenesulfonamide,
5-{2-Fluoro-4-[2-(phenylsulfonyl)pyridin-3-yl]phenyl}pyrimidin-2-amine,
5-[3-Fluoro-2'-(2-piperazin-1-ylpyrimidin-5-yl)biphenyl-4-yl]pyrazin-2-amine,
5-{2'-[1-(2-Aminoethyl)-1H-pyrazol-4-yl]-3-fluorobiphenyl-4-yl}pyrazin-2-amine,
2-[6-(2-Aminopyrimidin-5-yl)-5-fluoropyridin-3-yl]-N-[(2S)-2-hydroxypropyl]benzenesulfonamide,
5-(3-Fluoro-2'-isothiazol-4-ylbiphenyl-4-yl)pyrazin-2-amine,
5-[2-Fluoro-4-(2-phenoxypyridin-3-yl)phenyl]pyrazin-2-amine,
5-[2-Fluoro-4-(2-phenoxypyridin-3-yl)phenyl]pyrimidin-2-amine,
2-{4-[4'-(5-Aminopyrazin-2-yl)-3'-fluorobiphenyl-2-yl]-1H-pyrazol-1-yl}ethanol,
5-(4-{2-[(1-Acetylpiperidin-3-yl)sulfonyl]pyridin-3-yl}-2-fluorophenyl)pyrazin-2-amine,
5-(4-{2-[(1-Acetylpiperidin-4-yl)sulfonyl]-6-(trifluoromethyl)pyridin-3-yl}-2-fluorophenyl)pyrazin-2-amine,
2-[6-(2-Aminopyrimidin-5-yl)-5-fluoropyridin-3-yl]-N-[(1S)-2-hydroxy-1-methylethyl]benzenesulfonamide,
2-[6-(2-Aminopyrimidin-5-yl)-5-fluoropyridin-3-yl]-N-[(1R)-2-hydroxy-1-methylethyl]benzenesulfonamide,
5-[2-Fluoro-4-(2-phenylpyridin-3-yl)phenyl]pyrazin-2-amine,
5-(2-Fluoro-4-{2-[(1-methylpyrrolidin-3-yl)sulfonyl]pyridin-3-yl}phenyl)pyrazin-2-amine,
5-{2-Fluoro-4-[2-(pyridin-3-ylsulfonyl)pyridin-3-yl]phenyl}pyrazin-2-amine,
5-(2-Fluoro-4-{2-[(1-methylethyl)sulfonyl]-6-(trifluoromethyl)pyridin-3-yl}phenyl)pyrazin-2-amine,
5-(4-{2-[(1-Acetylpiperidin-4-yl)sulfonyl]-6-(trifluoromethyl)pyridin-3-yl}-2-fluorophenyl)pyrimidin-2-amine,
5-[2'-(6-Aminopyridin-3-yl)-3-fluorobiphenyl-4-yl]pyrimidin-2-amine,
5-[4'-(2-Aminopyrimidin-5-yl)-3'-fluorobiphenyl-2-yl]-N-methylpyrimidin-2-amine,
5-(2-Fluoro-4-{2-[(1-methylethyl)sulfonyl]-6-(trifluoromethyl)pyridin-3-yl}phenyl)pyrimidin-2-amine,
{4-[4'-(2-Aminopyrimidin-5-yl)-3'-fluorobiphenyl-2-yl]-1H-pyrazol-1-yl}acetonitrile
5-[3-Fluoro-2'-(1H-pyrazol-4-yl)biphenyl-4-yl]pyrimidin-2-amine,
4-[4'-(2-Aminopyrimidin-5-yl)-3'-fluorobiphenyl-2-yl]pyrimidin-2-amine,
5-{2-Fluoro-4-[2-(pyridin-3-yloxy)pyridin-3-yl]phenyl}pyrazin-2-amine,
5-(4-{2-[(1,1-Dioxidotetrahydro-2H-thiopyran-4-yl)sulfonyl]-6-(trifluoromethyl)pyridin-3-yl}-2-fluorophenyl)pyrimidin-2-amine,
5-[2-Fluoro-4-(2-{[1-(methylsulfonyl)piperidin-4-yl]sulfonyl}pyridin-3-yl)phenyl]pyrazin-2-amine,
5-(4-{2-[(1,1-Dioxidotetrahydro-2H-thiopyran-4-yl)sulfonyl]-6-(trifluoromethyl)pyridin-3-yl}-2-fluorophenyl)pyrazin-2-amine,
5-{2-Fluoro-4-[2-(tetrahydro-2H-pyran-4-ylsulfonyl)-6-(trifluoromethyl)pyridin-3-yl]phenyl}pyrazin-2-amine,
5-{2-Fluoro-4-[2-(tetrahydro-2H-pyran-4-ylsulfonyl)-6-(trifluoromethyl)pyridin-3-yl]phenyl}pyrimidin-2-amine,
2-[6-(2-Aminopyrimidin-5-yl)-5-fluoropyridin-3-yl]-N-(2-hydroxyethyl)benzenesulfonamide,
2-[6-(2-Aminopyrimidin-5-yl)-5-fluoropyridin-3-yl]-N-[(1R)-2,2,2-trifluoro-1-methylethyl]benzenesulfonamide, and
5-[2-Fluoro-4-(2-{[1-(methylsulfonyl)piperidin-4-yl]sulfonyl}pyridin-3-yl)phenyl]pyrimidin-2-amine.

5. A pharmaceutical composition comprising at least one compound of claim 1 and at least one pharmaceutically acceptable carrier.

6. The pharmaceutical composition of claim 5 comprising at least one compound of claim 4.

7. A compound selected from the group consisting of:
5-(3-Fluoro-2'-(methylsulfonyl)-[1,1'-biphenyl]-4-yl)pyrazin-2-amine;
N-[4'-(5-Aminopyrazin-2-yl)-3'-fluorobiphenyl-2-yl]methanesulfonamide;
6-Amino-3-[3-fluoro-2'-(methylsulfonyl)biphenyl-4-yl]pyrazine-2-carbonitrile;
4'-(5-Aminopyrazin-2-yl)-N-tert-butyl-3'-fluorobiphenyl-2-sulfonamide;
4'-(5-Aminopyrazin-2-yl)-3'-fluoro-[1,1'-biphenyl]-2-sulfonamide;
4'-(5-Aminopyrazin-2-yl)-N-cyclohexyl-3'-fluorobiphenyl-2-sulfonamide;
4'-(5-Aminopyrazin-2-yl)-3'-fluoro-N-(2-methylbiphenyl-2-sulfonamide;
(racemic)-4'-(5-Aminopyrazin-2-yl)-3'-fluoro-N-(2,2,2-trifluoro-1-methylethyl)biphenyl-2-sulfonamide racemic;
4'-(5-Aminopyrazin-2-yl)-N-(cyclobutylmethyl)-3'-fluorobiphenyl-2-sulfonamide;
(racemic)-(endo)-4'-(5-Aminopyrazin-2-yl)-N-bicyclo[221]hept-2-yl-3'-fluorobiphenyl-2-sulfonamide racemic;
4'-(5-Aminopyrazin-2-yl)-3'-fluoro-N-(1-methylcyclobutyl)biphenyl-2-sulfonamide;
4'-(5-Aminopyrazin-2-yl)-N-(1,1-dimethylpropyl)-3'-fluorobiphenyl-2-sulfonamide;
4'-(5-Aminopyrazin-2-yl)-3'-fluoro-N-(2,2,2-trifluoro-1,1-dimethylethyl)biphenyl-2-sulfonamide;
4'-(5-Aminopyrazin-2-yl)-N-cyclopentyl-3'-fluorobiphenyl-2-sulfonamide;
4'-(5-Aminopyrazin-2-yl)-3'-fluoro-N-methylbiphenyl-2-sulfonamide;
4'-(5-Aminopyrazin-2-yl)-N-ethyl-3'-fluorobiphenyl-2-sulfonamide;
4'-(5-Aminopyrazin-2-yl)-3'-fluoro-N-(2-phenylethyl)biphenyl-2-sulfonamide;
(R)-4'-(5-Aminopyrazin-2-yl)-3'-fluoro-N-[(1R)-2,2,2-trifluoro-1-phenylethyl]biphenyl-2-sulfonamide;
(S)-4'-(5-Aminopyrazin-2-yl)-3'-fluoro-N-[(1S)-2,2,2-trifluoro-1-phenylethyl]biphenyl-2-sulfonamide;
(S)-4'-(5-Aminopyrazin-2-yl)-3'-fluoro-N-[(1S)-2,2,2-trifluoro-1-methylethyl]biphenyl-2-sulfonamide;
4'-(5-Aminopyrazin-2-yl)-N-(2,3-dihydro-1H-inden-2-yl)-3'-fluorobiphenyl-2-sulfonamide;
(S)-4'-(5-Aminopyrazin-2-yl)-N-[(1S)-2,3-dihydro-1H-inden-1-yl]-3'-fluorobiphenyl-2-sulfonamide;
(R)-4'-(5-Aminopyrazin-2-yl)-N-[(1R)-2,3-dihydro-1H-inden-1-yl]-3'-fluorobiphenyl-2-sulfonamide;
(R)-4'-(5-Aminopyrazin-2-yl)-3'-fluoro-N-[(1R)-1-phenylethyl]biphenyl-2-sulfonamide;
(R)-4'-(5-Aminopyrazin-2-yl)-3'-fluoro-N-[(1R)-2-hydroxy-1-methylethyl]biphenyl-2-sulfonamide;
4'-(5-Aminopyrazin-2-yl)-3'-fluoro-N-phenylbiphenyl-2-sulfonamide;
(S)-4'-(5-Aminopyrazin-2-yl)-N-[(3S)-1-ethyl-2-oxoazepan-3-yl]-3'-fluorobiphenyl-2-sulfonamide;
(S)-4'-(5-Aminopyrazin-2-yl)-3'-fluoro-N-[(3S)-2-oxoazepan-3-yl]biphenyl-2-sulfonamide;
(S)-4'-(5-Aminopyrazin-2-yl)-3'-fluoro-N-[(3S)-1-methyl-2-oxoazepan-3-yl]biphenyl-2-sulfonamide;
4'-(5-Aminopyrazin-2-yl)-3'-fluoro-N-(1,2,2,6,6-pentamethylpiperidin-4-yl)biphenyl-2-sulfonamide;
4'-(5-Aminopyrazin-2-yl)-3'-fluoro-N-pyridin-3-ylbiphenyl-2-sulfonamide;
4'-(5-Aminopyrazin-2-yl)-3'-fluoro-N-[(1S)-2-hydroxy-1-methylethyl]biphenyl-2-sulfonamide;
N-[4'-(5-Aminopyrazin-2-yl)-3'-fluorobiphenyl-2-yl]sulfamide;
N-(4'-(5-aminopyrazin-2-yl)-3'-fluoro-[1,1'-biphenyl]-2-yl)propane-2-sulfonamide;
N-[4'-(5-Aminopyrazin-2-yl)-3'-fluorobiphenyl-2-yl]ethanesulfonamide;
N-[4'-(5-Aminopyrazin-2-yl)-3'-fluorobiphenyl-2-yl]propane-1-sulfonamide;
N-[4'-(5-Aminopyrazin-2-yl)-3'-fluorobiphenyl-2-yl]-2-methylpropane-1-sulfonamide;
N-(4'-(5-Aminopyrazin-2-yl)-3'-fluoro-[1,1-biphenyl]-2-yl)cyclopropanesulfonamide;
N-[4'-(5-Aminopyrazin-2-yl)-3'-fluorobiphenyl-2-yl]hexane-1-sulfonamide;
N-(4'-(5-Aminopyrazin-2-yl)-3'-fluoro-[1,1'-biphenyl]-2-yl)cyclobutanesulfonamide;
N-[4'-(5-Aminopyrazin-2-yl)-3'-fluorobiphenyl-2-yl]-1,1,1-trifluoromethanesulfonamide;
4'-(5-Aminopyrazin-2-yl)-3'-fluoro-N,N-dimethylbiphenyl-2-sulfonamide;
5-[3-Fluoro-2'-(piperidin-1-ylsulfonyl)biphenyl-4-yl]pyrazin-2-amine;
5-[3-Fluoro-2'-(morpholin-4-ylsulfonyl)biphenyl-4-yl]pyrazin-2-amine;
5-{2'-[(1,1-Dioxidothiomorpholin-4-yl)sulfonyl]-3-fluorobiphenyl-4-yl}pyrazin-2-amine;
5-[3-Fluoro-2'-(piperazin-1-ylsulfonyl)biphenyl-4-yl]pyrazin-2-amine;
4'-(5-Aminopyrazin-2-yl)-N,N-diethyl-3'-fluorobiphenyl-2-sulfonamide;
5-8 3-Fluoro-2'-(pyrrolidin-1-ylsulfonyl)biphenyl-4-yl]pyrazin-2-amine;
5-{2'-[(4,4-Difluoropipenclin-1-yl)sulfonyl]-3-fluorobiphenyl-4-yl}pyrazin-2-amine;
5-{2'-[(3,3-Difluoropipenclin-1-yl)sulfonyl]-3-fluorobiphenyl-4-yl}pyrazin-2-amine;
5-{2'-[(3,3-Difluoropyrrolidin-1-yl)sulfonyl]-3-fluorobiphenyl-4-yl}pyrazin-2-amine;
5-{2'-[(3,3-Difluoroazetidin-1-yl)sulfonyl]-3-fluorobiphenyl-4-yl}pyrazin-2-amine;
5-[2'-(Azepan-1-ylsulfonyl)-3-fluorobiphenyl-4-yl]pyrazin-2-amine;
5-{3-Fluoro-2'-[(4-methylpiperazin-1-0)sulfonyl]phenyl-4-yl}pyrazin-2-amine;
1-{[4'-(5-Aminopyrazin-2-yl)-3'-fluorobiphenyl-2-yl]sulfonyl}-4-(trifluoromethyl)}pipendin-4-ol;
5-(3-Fluoro-2'-{[4-(methylsulfonyl)piperazin-1-yl]sulfonyl}biphenyl-4-0)pyrazin-2-amine;
5-{2'-[(4-Acetylpiperazin-1-yl)sulfonyl]-3-fluorobiphenyl-4-yl}pyrazin-2-amine;
5-(2'-{[4-(Cyclopropylcarbonyl)piperazin-1-yl]sulfonyl}-3-fluorobiphenyl-4-yl)pyrazin-2-amine;
2-(4-{[4'-(5-Aminopyrazin-2-yl)-3'-fluorobiphenyl-2-yl]sulfonyl}piperazin-1-yl)ethanol;
5-{2'-[(4-Cyclopropylpiperazin-1-yl)sulfonyl]-3-fluorobiphenyl-4-yl}pyrazin-2-amine;
(racemic) 5-[3-Fluoro-2'-(hexahydropyrrolo[1,2-a]pyrazin-2(1H)-ylsulfonyl)biphenyl-4-yl]pyrazin-2-amine;
5-{2'-[(3,5-Dimethylpiperazin-1-yl)sulfonyl]-3-fluorobiphenyl-4-yl}pyrazin-2-amine;
(racemic) 1-{[4'-(5-Aminopyrazin-2-yl)-3'-fluorobiphenyl-2-yl]sulfonyl}piperidine-3-carbonitrile;
1-{[4'-(5-Aminopyrazin-2-yl)-3'-fluorobiphenyl-2-yl]sulfonyl}piperidine-4-carbonitrile;
5-{2'-[(4-Aminopipenclin-1-yl)sulfonyl]-3-fluorobiphenyl-4-yl}pyrazin-2-amine;

4-{[4'-(5-Aminopyrazin-2-yl)-3'-fluorobiphenyl-2-yl]sulfonyl}piperazin-2-one;
1-{[4'-(5-Aminopyrazin-2-yl)-3'-fluorobiphenyl-2-yl]sulfonyl}piperidin-4-ol;
(1-{[4'-(5-Aminopyrazin-2-yl)-3'-fluorobiphenyl-2-yl]sulfonyl}piperidin-4-yl)methanol;
2-(1-{[4'-(5-Aminopyrazin-2-yl)-3'-fluorobiphenyl-2-yl]sulfonyl}piperidin-4-yl)pethanol;
(racemic) 1-{[4'-(5-Aminopyrazin-2-yl)-3'-fluorobiphenyl-2-yl]sulfonyl}piperidin-3-ol;
(racemic) 2-(1-{[4'-(5-Aminopyrazin-2-yl)-3'-fluorobiphenyl-2-yl]sulfonyl}piperidin-3-yl)ethanol;
5-(3-Fluoro-2'-{[4-(methylamino)piperidin-1-yl]sulfonyl}biphenyl-4-yl)pyrazin-2-amine;
5-(2'-{[4-(Dimethylamino)piperidin-1-yl]sulfonyl}-3-fluorobiphenyl-4-yl)pyrazin-2-amine;
(racemic) 5-{2'-[(3-Aminopiperidin-1-yl)sulfonyl]-3-fluorobiphenyl-4-yl}pyrazin-2-amine;
N-(1-{[4'-(5-Aminopyrazin-2-yl)-3'-fluorobiphenyl-2-yl]sulfonyl}piperidin-4-yl)acetamide;
(racemic) (1-{[4'-(5-Aminopyrazin-2-yl)-3'-fluorobiphenyl-2-yl]sulfonyl}piperidin-3-yl)methanol;
(racemic) tert-Butyl (1-{[4'-(5-aminopyrazin-2-yl)-3'-fluorobiphenyl-2-yl]sulfonyl}piperidin-3-yl)carbamate;
4'-(5-Aminopyrazin-2-yl)-3'-fluoro-N-[(1S,2S)-2-hydroxy-1-(hydroxymethyl)-2-phenylethyl]piphenyl-2-sulfonamide;
4'-(5-Aminopyrazin-2-yl)-3'-fluoro-N-[(1S)-1-(hydroxymethyl)-3-methylbutyl]biphenyl-2-sulfonamide;
4'-(5-Aminopyrazin-2-yl)-3'-fluoro-N-(3-hydroxypropyl)biphenyl-2-sulfonamide;
4'-(5-Aminopyrazin-2-yl)-3'-fluoro-N-[(1S)-2-hydroxy-1-phenylethyl]biphenyl-2-sulfonamide;
4'-(5-Aminopyrazin-2-yl)-3'-fluoro-N-[(1R)-2-hydroxy-1-phenylethyl]biphenyl-2-sulfonamide;
4'-(5-Aminopyrazin-2-yl)-3'-fluoro-N-[(1S,2R)-2-hydroxy-1-methyl-2-phenylethyl]piphenyl-2-sulfonamide;
4'-(5-Aminopyrazin-2-yl)-3'-fluoro-N-[(1S,2S)-1-(hydroxymethyl)-2-methylbutyl]biphenyl-2-sulfonamide;
4'-(5-Aminopyrazin-2-yl)-3'-fluoro-N-[(1R,2R)-2-hydroxycyclohexyl]biphenyl-2-sulfonamide;
4'-(5-Aminopyrazin-2-yl)-3'-fluoro-N-[(1R)-1-(hydroxymethyl)propyl]biphenyl-2-sulfonamide;
4'-(5-Aminopyrazin-2-yl)-3'-fluoro-N-[(1R,2S)-2-hydroxycyclohexyl]biphenyl-2-sulfonamide;
4'-(5-Aminopyrazin-2-yl)-3'-fluoro-N-(2-hydroxyethyl)biphenyl-2-sulfonamide;
4'-(5-Aminopyrazin-2-yl)-N-cyclopropyl-3'-fluorobiphenyl-2-sulfonamide;
4'-(5-Aminopyrazin-2-yl)-N-(cyclopropylmethyl)-3'-fluorobiphenyl-2-sulfonamide;
(R)-(1((4'-(5-Aminopyrazin-2-yl)-3'-fluoro1,1'-biphenyl]-2-yl)sulfonyl)pyrrolidin-2-yl)methanol;
(R)-5-(2'4(3-Aminopyrrolidin-1-yl)sulfonyl)-3-fluoro-[1,1 biphenyl]-4-yl)pyrazin-2-amine;
(S)-5-(2'4(3-Aminopyrrolidin-1-yl)sulfonyl)-3-fluoro-[1,1 biphenyl]-4-yl)pyrazin-2-amine;
(R) 5(2'-{[2-(Aminomethyl)pyrrolidin-1-yl]sulfonyl}-3-fluorobiphenyl-4-yl)pyrazin-2-amine;
(S)-(1-((4'-(5-Aminopyrazin-2-yl)-3'-fluoro41,1'-biphenyl]-2-yl)sulfonyl)pyrrolidin-2-yl)methanol;
4'-(5-Aminopyrazin-2-yl)-3'-fluoro-N-(methylsulfonyl)biphenyl-2-sulfonamide;
(R)-4'-(5-Aminopyrazin-2-yl)-3'-fluoro-N-(2-hydroxypropyl)41,1'-biphenyl]-2-sulfonamide;
(S)-4'-(5-Aminopyrazin-2-yl)-3'-fluoro-N-(2-hydroxypropyl)41,1'-biphenyl]-2-sulfonamide;
4'-(5-Aminopyrazin-2-yl)-3'-fluoro-N-[(1-hydroxycyclohexyl)methyl]biphenyl-2-sulfonamide;
4'-(5-Aminopyrazin-2-yl)-3'-fluoro-N-(2-hydroxy-1,1-dimethylethyl)biphenyl-2-sulfonamide;
4'-(5-Aminopyrazin-2-yl)-3'-fluoro-N-(2-hydroxy-2-methylpropyl)biphenyl-2-sulfonamide;
4'-(5-Aminopyrazin-2-yl)-3'-fluoro-N-(3-hydroxy-1,1-dimethylpropyl)biphenyl-2-sulfonamide;
4'-(5-Aminopyrazin-2-yl)-3'-fluoro-N-(3-hydroxy-2,2-dimethylpropyl)biphenyl-2-sulfonamide;
(S)-4'-(5-Aminopyrazin-2-yl)-N-(2,3-dihydroxypropyl)-3'-fluoro-[1,1'-biphenyl]-2-sulfonamide;
(R)-4'-(5-Aminopyrazin-2-yl)-N-(2,3-dihydroxypropyl)-3'-fluoro-[1,1'-biphenyl]-2-sulfonamide;
(trans)-1-{[4'-(5-Aminopyrazin-2-yl)-3'-fluorobiphenyl-2-yl]sulfonyl}pyrrolidine-3,4-diol;
(S)-4'-(5-Aminopyrazin-2-yl)-3'-fluoro-N-(2-oxopyrrolidin-3-yl)1,1'-biphenyl]-2-sulfonamide;
(S)-4'-(5-Aminopyrazin-2-yl)-3'-fluoro-N-(2-oxopiperidin-3-yl)-1,1'-biphenyl]-2-sulfonamide;
(R)-4'-(5-Aminopyrazin-2-yl)-3'-fluoro-N-[1-(hydroxymethyl)-2-methylpropyl]biphenyl-2-sulfonamide;
trans 4'-(5-Aminopyrazin-2-yl)-3'-fluoro-N-(4-hydroxycyclohexyl)biphenyl-2-sulfonamide;
(R)-(1-((4'-(5-Aminopyrazin-2-yl)-3'-fluoro-[1,1'-biphenyl]-2-yl)sulfonyl)pyrrolidin-3-yl)methanol;
(S)-(1-{[4'-(5-Aminopyrazin-2-yl)-3'-fluorobiphenyl-2-yl]sulfonyl})pyrrolidin-3-yl)methanol;
(R)-4'-(5-Aminopyrazin-2-yl)-3'-fluoro-N-(2-oxopiperidin-3-yl)biphenyl-2-sulfonamide;
(R)-4'-(5-Aminopyrazin-2-yl)-3'-fluoro-N-methyl-N-piperidin-3-yl)biphenyl-2-sulfonamide;
(S)-4'-(5-Aminopyrazin-2-yl)-3'-fluoro-N-methyl-N-piperidin-3-yl)biphenyl-2-sulfonamide;
(S)-4'-(5-Aminopyrazin-2-yl)-3'-fluoro-N-(1-hydroxy-3-phenylpropan-2-yl)-1,1'-biphenyl]-2-sulfonamide;
(R)-4'-(5-Aminopyrazin-2-yl)-3'-fluoro-N-(2-hydroxy-2-phenylethyl)-1,1'-biphenyl]-2-sulfonamide;
4'-(5-Aminopyrazin-2-yl)-3'-fluoro-N-((1S,2S)-1-hydroxy-1-phenylpropan-2-yl)-N-methyl-[1,1'-biphenyl]-2-sulfonamide;
1-{[4'-(5-Aminopyrazin-2-yl)-3'-fluorobiphenyl-2-yl]sulfonyl}azetidin-3-ol;
(racemic) (trans)-4'-(5-Aminopyrazin-2-yl)-3'-fluoro-N-(2-hydroxycyclohexyl)biphenyl-2-sulfonamide;
(racemic) (trans)-4'-(5-Aminopyrazin-2-yl)-3'-fluoro-N42-(hydroxymethyl)cyclohexyl]biphenyl-2-sulfonamide;
(racemic) (cis)-4'-(5-Aminopyrazin-2-yl)-3'-fluoro-N42-(hydroxymethyl)cyclohexyl]biphenyl-2-sulfonamide;
4'-(5-Aminopyrazin-2-yl)-3'-fluoro-N-piperidin-4-ylbiphenyl-2-sulfonamide;
5-(2'-{[3-(Aminomethyl)azetidin-1-yl]sulfonyl}-3-fluorobiphenyl-4-ly) pyrazin-2-amine;
4'-(5-Aminopyrazin-2-yl)-N-(azetidin-3-ylmethyl)-3'-fluorobiphenyl-2-sulfonamide;
(R)-5-(3-Fluoro-2'-{[3-(methylamino)pyrrolidin-1-yl]sulfonyl}biphenyl-4-yl)pyrazin-2-amine;
(R)-4'-(5-Aminopyrazin-2-yl)-3'-fluoro-N-(2,2,2-trifluoro-1-methylethyl)biphenyl-2-sulfonamide;
5-[3-Fluoro-2'-(1,4,6,7-tetrahydro-5H-pyrazolo[4,3-c]pyridin-5-ylsulfonyl)biphenyl-4-yl]pyrazin-2-amine;

4-(1-{[4'-(5-Aminopyrazin-2-yl)-3'-fluorobiphenyl-2-yl]
   sulfonyl}piperidin-4-yl)-2,4-dihydro-3H-1,2,4-triazol-
   3- one;
5-(2'-((1R,4R)-2,5-Diazabicyclo[221]heptan-2-ylsulfo-
   nyl)-3-fluoro-[1,1'-biphenyl]-4-yl)pyrazin-2-amine;
5-(2'-((1S,4S)-2,5-Diazabicyclo[221]heptan-2-ylsulfo-
   nyl)-3-fluoro-[1,1'-biphenyl]-4-yl)pyrazin-2-amine;
4'-(5-Aminopyrazin-2-yl)-3'-fluoro-N-(5-hydroxypentyl)
   biphenyl-2-sulfonamide;
4'-(5-Aminopyrazin-2-yl)-3'-fluoro-N-(6-hydroxyhexyl)
   biphenyl-2-sulfonamide;
N-(4-Aminocyclohexyl)-4'-(5-aminopyrazin-2-yl)-3'-
   fluorobiphenyl-2-sulfonamide;
(S)-(1-{[4'-(5-Aminopyrazin-2-yl)-3'-fluorobiphenyl-2-
   yl]sulfonyl}-2,3-dihydro-1H-indol-2-yl)methanol;
4'-(5-Aminopyrazin-2-yl)-N-cyclohexyl-3'-fluoro-N-(2-
   hydroxyethyl)biphenyl-2-sulfonamide;
(S)-5-{2'-[(3-Aminopiperidin-1-yl)sulfonyl]-3-fluorobi-
   phenyl-4-yl}pyrazin-2-amine;
4'-(5-Aminopyrazin-2-yl)-3'-fluoro-N, N-bis(2-hydroxy-
   ethyl)biphenyl-2-sulfonamide;
1-{[4'-(5-Aminopyrazin-2-yl)-3'-fluorobiphenyl-2-yl]
   sulfonyl}azetidine-2-carboxamide;
4'-(5-Aminopyrazin-2-yl)-N-cyclopropyl-3'-fluoro-N-
   (tetrahydro-2H-pyran-4-yl)biphenyl-2-sulfonamide;
4'-(5-Aminopyrazin-2-yl)-3'-fluoro-N-(2-hydroxyethyl)-
   N-(1-methylethyl)biphenyl-2-sulfonamide;
racemic    (4-{[4'-(5-Aminopyrazin-2-yl)-3'-fluorobiphe-
   nyl-2-yl]sulfonyl}morpholin-2-yl)methanol;
(1R,5S)-3-((4'-(5-Aminopyrazin-2-yl)-3'-fluoro- [1'-bi-
   phenyl]-2-yl)sulfonyl)-3-azabicyclo[310]hexan-6-
   amine;
(S)-5-(3-Fluoro-2'-((2-methylpiperazin-1  -yl)sulfonyl)1
   ,1 'biphenyl]-4-yl)pyrazin-2-amine;
(R)-5-(3-Fluoro-2'4(2-methylpiperazin-1-yl)sulfonyl)41
   ,1 -biphenyl]-4-yl)pyrazin-2-amine;
(R)-(1-((4'-(5-Aminopyrazin-2-yl)-3'-fluoro-[1,1'-biphe-
   nyl]-2-yl)sulfonyl)piperazin-2-yl)methanol;
4'-(5-Aminopyrazin-2-yl)-3'-fluoro-N-[2-hydroxy-1-(hy-
   droxymethyl)-1-methylethyl]biphenyl-2-sulfonamide;
(S)-4'-(5-Aminopyrazin-2-yl)-3'-fluoro-N-(1-hydroxy-3-
   methylbutan-2-yl)-1,1'-biphenyl]-2-sulfonamide;
(S)-4'-(5-Aminopyrazin-2-yl)-3'-fluoro-N-(1-hydroxy-3,
   3-dimethylbutan-2-yl)-[1, 1'-biphenyl]-2-sulfonamide;
(R)-4'-(5-Aminopyrazin-2-yl)-3'-fluoro-N-(1-hydroxy-3,
   3-dimethylbutan-2-yl)[1,1'-biphenyl]-2-sulfonamide;
tert-Butyl  [2-({[4'-(5-aminopyrazin-2-yl)-3'-fluorobiphe-
   nyl-2-yl]sulfonyl}amino)ethyl]carbamate;
N-(2-Aminoethyl)-4'-(5-aminopyrazin-2-yl)-3'-fluorobi-
   phenyl-2-sulfonamide;
(S)-4'-(5-Aminopyrazin-2-yl)-3'-fluoro-N-(1-hydroxybu-
   tan-2-yl)1,1'-biphenyl]-2-sulfonamide;
(S)-4'-(5-Aminopyrazin-2-yl)-3'-fluoro-N-(pyrrolidin-3-
   yl)1, 1-biphenyl]-2-sulfonamide;
N-[2-({[4'-(5-Aminopyrazin-2-yl)-3'-fluorobiphenyl-2-
   yl]sulfonyl}amino)ethyl]acetamide;
(S)-2-(4'-(5-Aminopyrazin-2-yl)-3'-fluoro1,1'-biphenyl]-
   2-ylsulfonamido)propanoic acid;
4'-(5-Aminopyrazin-2-yl)-N-[2-(carbamoylamino)ethyl]-
   3'-fluorobiphenyl-2-sulfonamide;
4'-(5-Aminopyrazin-2-yl)-3'-fluoro-N-((1S,2S)-2-hy-
   droxy-2,3-dihydro-1H-inden-1y1)1,1'-biphenyl]-2-
   sulfonamide;
4'-(5-Aminopyrazin-2-yl)-3'-fluoro-N-((1R,2R)-2-hy-
   droxy-2,3-dihydro-1H-inden-1-yl)[1,'-biphenyl]-2-sul-
   fonamide;
4'-(5-Aminopyrazin-2-yl)-3'-fluoro-N-((1S,2R)-2-hy-
   droxy-2,3-dihydro-1H-inden-1-yl)-[1, "-biphenyl]-2-
   sulfonamide;
4'-(5-Aminopyrazin-2-yl)-3'-fluoro-N-((1R,2S)-2-hy-
   droxy-2,3-dihydro-1H-inden-1-yl)'1 ,1-biphenyl]-2-
   sulfonamide;
4'-(5-Aminopyrazin-2-yl)-3'-fluoro-N-((1    S,2S)-2-hy-
   droxycyclohexyl)40 ,1-biphenyl]-2-sulfonamide;
4'-(5-Aminopyrazin-2-yl)-3'-fluoro-N-[6-(trifluorom-
   ethyl)pyridin-3-yl]biphenyl-2-sulfonamide;
5-(3-Fluoro-2'-{[4-(1H-imidazol-4yl)piperidin-1-yl]
   sulfonyl}biphenyl-4-yl)pyrazin-2-amine;
N-[(4-Amino-2-methylpyrimidin-5-yl)methyl]-4'-(5-
   aminopyrazin-2-yl)-3'-fluorobiphenyl-2-sulfonamide;
4'-(5-Aminopyrazin-2-yl)-N-(2,6-dimethoxypyrim idin-
   4-yl)-3'-fluorobiphenyl-2-sulfonamide;
4'-(5-Aminopyrazin-2-yl)-3'-fluoro-N-(5-methylpyrazin-
   2-yl)biphenyl-2-sulfonamide;
(S)-2-(4'-(5-Aminopyrazin-2-yl)-3'-fluoro-[1   ,1'-biphe-
   nyl]-2-ylsulfonamido)-4-methylpentanamide;
4'-(5-Aminopyrazin-2-yl)-N-(2-cyanoethyl)-3'-fluorobi-
   phenyl-2-sulfonamide;
(R)-4'-(5-Aminopyrazin-2-yl)-N-(1-cyanopropan-2-yl)-
   3'-fluoro-[1,1'-biphenyl]-2-sulfonamide;
(S)-4'-(5-Aminopyrazin-2-yl)-N-(1-cyanopropan-2-yl)-
   3'-fluoro-[1 , l-biphenyl]-2-sulfonamide;
4'-(5-Aminopyrazin-2-yl)-N-(2-cyanoethyl)-N-cyclopro-
   pyl-3'-fluorobiphenyl-2-sulfonamide;
4'-(5-Aminopyrazin-2-yl)-3'-fluoro-N-(3-methyloxetan-
   3-yl)biphenyl-2-sulfonamide;
3-(4-{[4'-(5-Aminopyrazin-2-yl)-3'-fluorobiphenyl-2-yl]
   sulfonyl}piperazin-1-yl)propanenitrile;
(S)-4'-(5-Aminopyrazin-2-yl)-3'-fluoro-N-(1-methoxy-
   propan-2-041 ,1'-biphenyl]-2-sulfonamide;
5-{3-Fluoro-2'-[(4-pyrazin-2-ylpiperazin-1-yl)sulfonyl]
   biphenyl-4-yl}pyrazin-2-amine;
5-{3-Fluoro-2'-[(4-pyrimidin-2-ylpiperazin-1-yl)sulfo-
   nyl]biphenyl-4-yl}pyrazin-2-amine;
5-(2'-Amino-3-fluorobiphenyl-4-yl)pyrazin-2-amine;
4'-(5-Aminopyrazin-2-yl)-3'-fluoro-N-[1   -(hydroxym-
   ethyl)cyclopentyl]biphenyl-2-sulfonamide;
1   -{[4'-(5-Aminopyrazin-2-0-3'-fluorobiphenyl-2-yl]sul-
   fonyl}-3-phenylpyrrolidin-3-ol;
N-[4'-(5-Aminopyrazin-2-yl)-3'-fluorobiphenyl-2-yl]pyr-
   rolidine-1-sulfonamide;
N-[4'-(5-Aminopyrazin-2-yl)-3'-fluorobiphenyl-2-yl]-N,
   N-dimethylsulfamide;
N-[4'-(5-Aminopyrazin-2-yl)-3'-fluorobiphenyl-2-yl]
   morpholine-4-sulfonamide;
(3S)-1-{[4'-(5-Aminopyrazin-2-yl)-3'-fluorobiphenyl-2-
   yl]sulfonyl}pyrrolidin-3-ol;
(3R)-1-{[4'-(5-Aminopyrazin-2-yl)-3'-fluorobiphenyl-2-
   yl]sulfonyl}pyrrolidin-3-ol;
(3'S,4'S)-1'-{[4'-(5-Aminopyrazin-2-0-3'-fluorobiphenyl-
   2-yl]sulfonyl}-1 ,3'-bipyrrolidin-4'-ol;
(3S,4S)-1-{[4'-(5-Aminopyrazin-2-0-3'-fluorobiphenyl-
   2-yl]sulfonyl}-4-morpholin-4-ylpyrrolidin-3-ol;
(3S,4S)-1-{[4'-(5-Aminopyrazin-2-yl)-3'-fluorobiphenyl-
   2-yl]sulfonyl}-4-(4-methylpiperazin-1)pyrrolidin-3-ol;
5-{3-Fluoro-2'-[(trifluoromethyl)-sulfanyl]biphenyl-4-
   yl}pyrazin-2-amine;
5[2'-(tert-Butylsulfanyl)-3-fluorobiphenyl-4-yl]pyrazin-
   2-amine;
5[2'-(Ethylsulfonyl)-3-fluorobiphenyl-4-yl]pyrazin-2-
   amine;
5[3-Fluoro-2'-(propylsulfonyl)biphenyl-4-yl]pyrazin-2-
   amine;

5-{3-Fluoro-2'-[(2-methylpropyl)sulfonyl]biphenyl-4-yl}pyrazin-2-amine;
5[2'-(tert-Butylsulfonyl)-3-fluorobiphenyl-4-yl]pyrazin-2-amine;
5[2'-(Cyclopentylsulfonyl)-3-fluorobiphenyl-4-yl]pyrazin-2-amine;
5[2'-(Cyclobutylsulfonyl)-3-fluorobiphenyl-4-yl]pyrazin-2-amine;
5[2'-(Cyclopropylsulfonyl)-3-fluorobiphenyl-4-yl]pyrazin-2-amine;
5[3-Fluoro-2'-(hexylsulfonyl)biphenyl-4-yl]pyrazin-2-amine;
5-{3-Fluoro-2'-[(1-methylethyl)sulfonyl]biphenyl-4-yl}pyrazin-2-amine;
2-{[4'-(5-Aminopyrazin-2-yl)-3'-fluorobiphenyl-2-yl]sulfanyl}acetamide;
2-{[4'-(5-Aminopyrazin-2-yl)-3'-fluorobiphenyl-2-yl]sulfanyl}-N, N-diethylacetamide;
5-{3-Fluoro-2'-[(2-morpholin-4-yl-2-oxoethyl)sulfanyl]biphenyl-4-yl}pyrazin-2-amine;
(racemic) 5-({[4'-(5-Aminopyrazin-2-yl)-3'-fluorobiphenyl-2-yl]sulfanyl}methyl)-1,3-oxazolidin-2-one;
N-(2-{[4'-(5-Aminopyrazin-2-yl)-3'-fluorobiphenyl-2-yl]sulfanyl}ethyl)benzamide;
5-(3-Fluoro-2'-{[4-(methylsulfonyl)benzyl]sulfanyl}biphenyl-4yl)pyrazin-2-amine;
4'-(5-Aminopyrazin-2-yl)-3'-fluoro-4-(trifluoromethyl)biphenyl-2-sulfonamide;
5[3-Fluoro-2'-(methylsulfonyl)-4'-(trifluoromethyl)biphenyl-4-yl]pyrazin-2-amine;
4'-(5-Aminopyrazin-2-yl)-3'-fluoro-N-methyl-4-(trifluoromethyl)biphenyl-2-sulfonamide;
4-{[4'-(5-Aminopyrazin-2-yl)-3'-fluoro-4-(trifluoromethyl)biphenyl-2-yl]sulfonyl}piperazin-2-one;
4'-(5-aminopyrazin-2-yl)-3'-fluoro-N-(2-hydroxyethyl)-4-(trifluoromethyl)biphenyl-2-sulfonamide;
4'-(5-Aminopyrazin-2-yl)-N-ethyl-3'-fluoro-4-(trifluoromethyl)biphenyl-2-sulfonamide;
5-{3-Fluoro-2'-[(4-methylpiperazin-1-yl)sulfonyl]-4'-(trifluoromethyl)biphenyl-4-yl}pyrazin-2-amine;
5[3-Fluoro-2'-(pyrimidin-2-ylsulfanyl)biphenyl-4-yl]pyrazin-2-amine;
5[3-Fluoro-2'-(pyrimidin-4-ylsulfanyl)biphenyl-4-yl]pyrimidin-2-amine;
6-{[4'-(5-Aminopyrazin-2-yl)-3'-fluorobiphenyl-2-yl]sulfanyl}pyrimidin-4-amine;
2-{[4'-(5-Aminopyrazin-2-yl)-3'-fluorobiphenyl-2-yl]sulfanyl}pyrimidin-4-amine;
4-{[4'-(5-Aminopyrazin-2-yl)-3'-fluorobiphenyl-2-yl]sulfanyl}pyrimidin-5-amine;
5[3-Fluoro-2'-(pyrazin-2-ylsulfanyl)biphenyl-4-yl]pyrazin-2-amine;
2-{[4'-(5-Aminopyrazin-2-yl)-3'-fluorobiphenyl-2-yl]sulfanyl}pyrimidin-5-amine;
1[4'-(5-Aminopyrazin-2-yl)-3'-fluorobiphenyl-2-yl]-N-methylmethanesulfonamide;
1[4'-(5-Aminopyrazin-2-yl)-3'-fluorobiphenyl-2-yl]-N-(2-hydroxyethyl)methanesulfonamide;
1-({[4'-(5-Aminopyrazin-2-yl)-3'-fluorobiphenyl-2-yl]methyl}sulfonyl)azetidin-3-ol;
4-({[4'-(5-Aminopyrazin-2-yl)-3'-fluorobiphenyl-2-yl]methyl}sulfonyl)piperazin-2-one;
(S)-1-(4'45-Aminopyrazin-2-yl)-3'-fluoro-[1,1'-biphenyl]-2-yl)-N-(1-hydroxypropan-2-yl)methanesulfonamide;
(R)-1-(4'-(5-Aminopyrazin-2-yl)-3'-fluoro-[1,1'-biphenyl]-2-yl)-N-(1-hydroxypropan-2-yl)methanesulfonamide;
1 -[4'-(5-Aminopyrazin-2-yl)-3'-fluorobiphenyl-2-yl]-N-(trans-4-hydroxycyclohexyl)methanesulfonamide;
(S)-1-[4'-(5-Aminopyrazin-2-yl)-3'-fluorobiphenyl-2-yl]-N-[(2S)-2-hydroxypropyl]methanesulfonamide;
(R)-1-[4'-(5-Aminopyrazin-2-yl)-3'-fluorobiphenyl-2-yl]-N-[(2S)-2-hydroxypropyl]methanesulfonamide;
5-(2'-{[(4-Aminopiperidin-1-yl)sulfonyl]methyl1-3-fluorobiphenyl-4-}pyrazin-2-amine;
1-[4'-(5-Aminopyrazin-2-yl)-3'-fluorobiphenyl-2-yl]methanesulfonamide;
1-[4'-(5-Aminopyrazin-2-yl)-3'-fluorobiphenyl-2-yl]-N-ethylmethanesulfonamide;
1-[1-({[4'-(5-Aminopyrazin-2-yl)-3'-fluorobiphenyl-2-yl]methyl}sulfonyl)piperidin-4-yl]urea;
N- [1-({[4'-(5-Aminopyrazin-2-yl)-3'-fluorobiphenyl-2-yl]methyl}sulfonyl)piperidin-4-yl]acetamide;
5-{2'-[(Ethylsulfanyl)methyl]-3-fluorobiphenyl-4-yl}pyrazin-2-amine;
5-{3-Fluoro-2'-[(methylsulfanyl)methyl]biphenyl-4-yl}pyrazin-2-amine;
5-(3-Fluoro-2'-{[(1-methylethyl)sulfanyl]methyl}biphenyl-4-yl)pyrazin-2-amine;
2-(((4'-(5-Aminopyrazin-2-yl)-3'-fluoro41,1'-biphenyl]-2-yl)methyl)thio)pyrimidin-4-amine;
6-(((4'-(5-Aminopyrazin-2-yl)-3'-fluoro41,1'-biphenyl]-2-yl)methyl)thio)pyrimidin-4-amine;
5-(3-Fluoro-2'-((pyridazin-3-ylthio)methyl)41,1'-biphenyl]-4-yl)pyrazin-2-amine;
6-(((4'-(5-Aminopyrazin-2-yl)-3'-fluoro41,1-biphenyl]-2-yl)methyl)thio)pyridazin-3-amine;
5-{2'-[(1,1-Dioxidotetrahydro-2H-thiopyran-4-yl)sulfonyl]-3-fluorobiphenyl-4-yl}pyrazin-2-amine;
4-{[4'-(5-Aminopyrazin-2-yl)-3'-fluorobiphenyl-2-yl]sulfanyl}pyrimidin-2-amine;
5-(3-Fluoro-2'-((pyrimidin-4-ylthio)methyl)41,1'-biphenyl]-4-yl)pyrazin-2-amine;
5[3-Fluoro-2'-({[2-(trimethylsily)ethoxy]methyl}sulfanyl)biphenyl-4-yl]pyrazin-2-amine;
5[3-Fluoro-2'-({[2-(trimethylsily)ethoxy]methyl}sulfonyl)biphenyl-4-yl]pyrazin-2-amine;
5-(3-Fluoro-2'-{[3-(methylsulfonyl)propyl]sulfonyl}biphenyl)-4-pyrazin-2-amine;
5-(3-Fluoro-2'-{[(2R)-2-methylpiperazin-1-yl]sulfonyl}biphenyl-4-yl)pyrimidin-2-amine;
4'-(2-Aminopyrimidin-5-yl)-3'-fluoro-N-[(1S)-1-(hydroxymethyl)propyl]biphenyl-2-sulfonamide;
4'-(2-Aminopyrimidin-5-yl)-N-(2-cyanoethyl)-N-cyclopropyl-3'-fluorobiphenyl-2-sulfonamide;
4'-(2-Aminopyrimidin-5-yl)-N-(2-cyanoethyl)-3'-fluorobiphenyl-2-sulfonamide;
4'-(2-Aminopyrimidin-5-yl)-3'-fluoro-N-(3-hydroxy-2,2-dimethylpropyl)biphenyl-2-sulfonamide;
(racemic) (4-{[4'-(2-Aminopyrimidin-5-yl)-3'-fluorobiphenyl-2-sulfonyl}morpholin-2-yl)methanol;
5-(3-Fluoro-2'-{[(2S)-2-methylpiperazin-1-yl]sulfonyll-biphenyl-4-Opyrimidin-2-amine;
5[2'-(Cyclopropylsulfonyl)-3-fluorobiphenyl-4-yl]pyrimidin-2-amine;
4'-(2-Aminopyrimidin-5-yl)-3'-fluoro-N-[2-hydroxy-1-(hydroxymethyl)-1-biphenyl-2-sulfonamide;
4'-(2-Aminopyrimidin-5-yl)-3'-fluoro-N-methyl-N-[(3S)-piperidin-3-yl]biphenyl-2-sulfonamide;
4'-(2-Aminopyrimidin-5-yl)-3'-fluoro-N-methyl-N-[(3R)-piperidin-3-yl]biphenyl-2-sulfonamide;

[(2R)-1-{[4'-(2-Aminopyrimidin-5-yl)-3'-fluorobiphenyl-2-yl]sulfonyl}piperazin-2-yl]methanol;
(racemic) (cis) 4'-(2-Aminopyrimidin-5-0-3'-fluoro-N-(cis)-2-hydroxycyclohexylpiphenyl-2- sulfonamide;
(racemic) (trans) 4'-(2-Aminopyrimidin-5-0-3'-fluoro-N-(trans)-2-hydroxycyclohexylpiphenyl-2-sulfonamide;
4'-(2-Aminopyrimidin-5-yl)-3'-fluoro-N-(2-hydroxyethyl)-N-(1-methylethyl)biphenyl-2-sulfonamide;
4'-(2-Aminopyrimidin-5-yl)-3'-fluoro-N-(trans-4-hydroxycyclohexyl)biphenyl-2-sulfonamide;
4'-(2-Aminopyrimidin-5-yl)-3'-fluoro-N-[(3S)-2-oxopyrolidin-3-yl]biphenyl-2-sulfonamide;
5-{2'-[(1,1-Dioxidothiomorpholin-4-yl)sulfonyl]-3-fluorobiphenyl-4-yl}pyrimidin-2-amine;
1-{[4'-(2-Aminopyrimidin-5-yl)-3'-fluorobiphenyl-2-yl]sulfonyl}azetidin-3-ol;
4'-(2-Aminopyrimidin-5-yl)-3'-fluoro-N-[(3R)-2-oxopiperidin-3-yl]biphenyl-2-sulfonamide;
4'-(2-Aminopyrimidin-5-yl)-3'-fluoro-N-[(3S)-2-oxopiperidin-3-yl]biphenyl-2-sulfonamide;
4'-(2-Aminopyrimidin-5-yl)-3'-fluoro-N-[(1 R)-2,2,2-trifluoro-1 -methylethyl]biphenyl-2-sulfonamide;
4'-(2-Aminopyrimidin-5-yl)-3'-fluoro-N-[(1 R)-1-(hydroxymethyl)-2,2-dimethylpropyl]piphenyl-2-sulfonamide;
4'-(2-Aminopyrimidin-5-yl)-3'-fluoro-N-[(1S)-1-(hydroxymethyl)-2,2-dimethylpropyl]piphenyl-2-sulfonamide;
4'-(2-Aminopyrimidin-5-yl)-3'-fluoro-N-[(1S)-1-(hydroxymethyl)-2-methylpropyl]biphenyl-2-sulfonamide;
4'-(2-Aminopyrimidin-5-yl)-3'-fluoro-N-(2-hydroxy-2-methylpropyl)biphenyl-2-sulfonamide;
4'-(2-Aminopyrimidin-5-yl)-3'-fluoro-N-[(1 R)-1-(hydroxymethyl)-2-methylpropyl]biphenyl-2-sulfonamide;
4'-(2-Aminopyrimidin-5-yl)-N-[(2S)-2, 3-dihydroxypropyl]-3'-fluorobiphenyl-2-sulfonamide;
4'-(2-Aminopyrimidin-5-yl)-3'-fluoro-N-(2-hydroxyethyl)biphenyl-2-sulfonamide;
[(2R)-1-{[4'-(2-Aminopyrimidin-5-yl)-3'-fluorobiphenyl-2-yl]sulfonyl}pyrrolidin-2-yl]methanol;
[(2S)-1 -{[4'-(2-Aminopyrimidin-5-yl)-3'-fluorobiphenyl-2-yl]sulfonyl}pyrrolidin-2-yl]methanol;
4'-(2-Aminopyrimidin-5-yl)-3'-fluoro-N-[(2R)-2-hydroxypropyl]biphenyl-2-sulfonamide;
4'-(2-Aminopyrimidin-5-yl)-3'-fluoro-N-[(2S)-2-hydroxypropyl]biphenyl-2-sulfonamide;
4'-(2-Aminopyrimidin-5-yl)-3'-fluoro-N-(2-hydroxy-1 ,1 -dimethylethyl)biphenyl-2-sulfonamide;
5-{2'-[(4-Cyclopropylpiperazin-1-yl)sulfonyl]-3-fluorobiphenyl-4-yl}pyrimidin-2-amine;
2-(4-{[4'-(2-Aminopyrimidin-5-yl)-3'-fluorobiphenyl-2-yl]sulfonyl}piperazin-1-yl)ethanol;
4'-(2-Aminopyrimidin-5-yl)-N-(cyclopropylmethyl)-3'-fluorobiphenyl-2-sulfonamide;
4'-(2-Aminopyrimidin-5-yl)-N-cyclopropyl-3'-fluorobiphenyl-2-sulfonamide;
4'-(2-Aminopyrimidin-5-yl)-3'-fluoro-N-phenylbiphenyl-2-sulfonamide;
4'-(2-Aminopyrimidin-5-yl)-3'-fluoro-N-[(1S)-2-hydroxy-1-methylethyl]biphenyl-2-sulfonamide;
4'-(2-Aminopyrimidin-5-yl)--N-tert-butyl-3'-fluoro-3-methylbiphenyl-2-sulfonamide;
4'-(2-Aminopyrimidin-5-yl)-3'-fluoro-N-methylbiphenyl-2-sulfonamide;
4'-(2-Aminopyrimidin-5-yl)-3'-fluoro-N-[(1 R)-2-hydroxy-1-methylethyl]biphenyl-2-sulfonamide;
5-[3-Fluoro-2'-(piperazin-1 -ylsulfonyl)biphenyl-4-yl]pyrimidin-2-amine;
4'-(2-Aminopyrimidin-5-yl)-3'-fluoro-N-[(1 R)-2,2,2-trifluoro-1-phenylethyl]biphenyl-2-sulfonamide;
4'-(2-Aminopyrimidin-5-yl)-3'-fluoro-N-[(1S)-2,2,2-trifluoro-1-phenylethyl]biphenyl-2-sulfonamide;
5[2'-(tert-Butylsulfonyl)-3-fluorobiphenyl-4-yl]pyrimidin-2-amine;
4'-(2-Aminopyrimidin-5-yl)-3'-fluoro-N-(2-methylpropyl)biphenyl-2-sulfonamide;
4'-(2-Aminopyrimidin-5-yl)-N-ethyl-3'-fluorobiphenyl-2-sulfonamide;
4'-(2-Aminopyrim idin-5-yl)-3'-fluoro-N-(2,2,2-trifluoro-1 ,1-dimethylethyl)biphenyl-2-sulfonamide;
4'-(2-Aminopyrimidin-5-yl)-3'-fluoro-N-[(1S)-2,2,2-trifluoro-1-methylethyl]biphenyl-2-sulfonamide;
5-[3-Fluoro-2'-(pyrrolidin-1 -ylsulfonyl)biphenyl-4-yl]pyrimidin-2-amine;
4'-(2-Aminopyrimidin-5-yl)-3'-fluoro-N,N-dimethyl)biphenyl-2-sulfonamide;
4'-(2-Aminopyrimidin-5-yl)-N,N-diethyl-3'-fluorobiphenyl-2-sulfonamide;
5-[3-Fluoro-2'-(piperidin-1 -ylsulfonyl)biphenyl-4-yl]pyrimidin-2-amine;
4'-(2-Aminopyrimidin-5-yl)-3'-fluorobiphenyl-2-sulfonamide;
5[3-Fluoro-2'-(morpholin-4-ylsulfonyl)biphenyl-4-yl]pyrimidin-2-amine;
5[3-Fluoro-2'-(methylsulfonyl)biphenyl-4-yl]pyrimidin-2-amine;
4'-(2-Aminopyrimidin-5-yl)-N-(tert-butyl)-3'-fluoro-[1,1'-biphenyl]-2-sulfonamide;
4-{[4'-(2-Aminopyrimidin-5-yl)-3'-fluorobiphenyl-2-yl]sulfonyl}piperazin-2-one;
tert-Butyl N-{[4'-(2-aminopyrimidin-5-yl)-3'-fluorobiphenyl-2-yl]sulfonyl}-L- alaninate;
N-{[4'-(2-Aminopyrimidin-5-yl)-3'-fluorobiphenyl-2-yl]sulfonyl}-L-alanine;
N-[4'-(2-Aminopyrimidin-5-yl)-3'-fluorobiphenyl-2-yl]pyrrolidine-1-sulfonamide;
N-[4'-(2-Aminopyrimidin-5-yl)-3'-fluorobiphenyl-2-yl]morpholine-4-sulfonamide;
N'-[4'-(2-Aminopyrimidin-5-yl)-3'-fluorobiphenyl-2-yl]-N,N-dimethylsulfamide;
5-(2'-(2-Oxa-6-azaspiro[33]heptan-6-ylsulfonyl)-3-fluoro-[1 ,1'-biphenyl]-4-yl)pyrimidin-2-amine;
6-((4'-(2-Aminopyrimidin-5-yl)-3'-fluoro-[1,1'-biphenyl]-2-yl)sulfonyl)-2-thia-6-azaspiro[33]heptane 2,2-dioxide;
1-((4'-(2-Aminopyrim ,1'-biphenyl]-2-yl)sulfonyl)azetidine-3-carbonitrile;
1-((4'-(2-Aminopyrimidin-5-yl)-3'-fluoro-[1 ,l-biphenyl]-2-yl)sulfonyl)-3-(trifluoromethyl)azetidin-3-ol;
5-{2'-[(1 ,1-Dioxidotetrahydro-2H-thiopyran-4-yl)sulfonyl]-3-fluorobiphenyl-4-yl}pyrimidin-2-amine;
2-(((4'-(2-Aminopyrimidin-5-yl)-3'-fluoro-[1,1'-biphenyl]-2-yl)sulfonyl)methyl)quinazolin-4(3H)-one;
1-(34(4'-(2-Aminopyrimidin-5-yl)-3'-fluoro-[1 ,1'-biphenyl]-2-yl)sulfonyl)propyl)-1H-benzo[d]imidazol-2(3H)-one;
5-(2'-{[3-(Cyclohexylsulfonyl)propyl]sulfonyl}1-3-fluorobiphenyl-4yl)pyrimidin-2-amine;
5-{3-Fluoro-2'-[(1-methyl-1H-benzimidazol-2-yl)sulfonyl]biphenyl-4-yl}pyrimidin-2-amine;

5-(2'-{[(3-Cyclopropyl-1,2,4-oxadiazol-5-yl)methyl]sulfonyl}-3-fluorobiphenyl-4-yl)pyrimidin-2-amine;
4'-(2-Aminopyrimidin-5-yl)-3'-fluoro-4-(trifluoromethyl)biphenyl-2-sulfonamide;
5[3-Fluoro-2'-(methylsulfonyl)-4'-(trifluoromethyl)biphenyl-4-yl]pyrimidin-2-amine;
4-{[4'-(2-Aminopyrimidin-5-yl)-3'-fluoro-4-(trifluoromethyl)biphenyl-2-yl]sulfonyl}piperazin-2-one;
4'-(2-Aminopyrimidin-5-yl)-3'-fluoro-N-methyl-4-(trifluoromethyl)biphenyl-2-sulfonamide;
4'-(2-Aminopyrimidin-5-yl)-3'-fluoro-N-(2-hydroxyethyl)-4-(trifluoromethyl)biphenyl-2-sulfonamide;
4'-(2-Aminopyrimidin-5-yl)-N-ethyl-3'-fluoro-4-(trifluoromethyl)biphenyl-2-sulfonamide;
5-{3-Fluoro-2'-[(4-methylpiperazin-1-yl)sulfonyl]-4'-(trifluoromethyl)biphenyl-4-yl}pyrimidin-2-amine;
5-{2'-[(5-Aminopyrimidin-2-yl)sulfanyl]-3-fluorobiphenyl-4-yl}pyrimidin-2-amine;
5-{2'-[(4-Aminopyrimidin-2-yl)sulfanyl]-3-fluorobiphenyl-4-yl}pyrimidin-2-amine;
5-{2'-[(5-Aminopyrimidin-4-yl)sulfanyl]-3-fluorobiphenyl-4-yl}pyrimidin-2-amine;
5[3-Fluoro-2'-(pyrimidin-2-ylsulfanyl)biphenyl-4-yl]pyrimidin-2-amine;
5[3-Fluoro-2'-(pyrazin-2-ylsulfanyl)biphenyl-4-yl]pyrimidin-2-amine;
5-{2'-[(6-Aminopyrimidin-4-yl)sulfanyl]-3-fluorobiphenyl-4-yl}pyrimidin-2-amine;
4-{['4'-(2-Aminopyrimidin-5-yl)-3'-fluorobiphenyl-2-yl]sulfanyl}pyrimidin-2-amine;
5-{2'-[(6-Aminopyrazin-2-yl)sulfanyl]-3-fluorobiphenyl-4-yl}pyrimidin-2-amine;
5-{2'-[(5-Aminopyrimidin-4-yl)sulfonyl]-3-fluorobiphenyl-4-yl}pyrimidin-2-amine;
5{3-Fluoro-2'-({[2-(trimethylsilyl)ethoxy]methyl}sulfonyl)biphenyl-4-yl}pyrimidin-2-amine;
5-{2'-[(5-Aminopyrimidin-2-yl)sulfonyl]-3-fluorobiphenyl-4-yl}pyrimidin-2-amine;
5{3-Fluoro-2'-({[2-(trimethylsilyl)ethoxy]methyl}sulfanyl)biphenyl-4-yl}pyrimidin-2-amine;
5-(3-Fluoro-2-(methylsulfonyl)41,1'-biphenyl]-4-yl)pyridin-2-amine;
4'-(6-Aminopyridin-3-yl)-N-(tert-butyl)-3'-fluoro-[1,1'-biphenyl]-2-sulfonamide;
4'-(6-Aminopyridin-3-yl)-N,N-diethyl-3'-fluoro-[1,1-biphenyl]-2-sulfonamide;
5-(3-Fluoro-2'-(pyrrolidin-1-ylsulfonyl)41,1'-biphenyl]-4-yl)pyridin-2-amine;
5-(3-Fluoro-2'-(piperidin-1-ylsulfonyl)41,1'-biphenyl]-4-yl)pyridin-2-amine;
4'-(6-Aminopyridin-3-yl)-N-cyclohexyl-3'-fluoro-[l,1'-biphenyl]-2-sulfonamide;
(S)-4'-(6-Aminopyridin-3-yl)-3-fluoro-N-(1-hydroxypropan-2yl)-1,1'-biphenyl]-2-sulfonamide;
4'-(6-Aminopyridin-3-yl)-3'-fluoro-N-isobutyl-[1,1'-biphenyl]-2-sulfonamide;
4'-(6-Aminopyridin-3-yl)-3'-fluoro-N-(tert-pentyl)-[1,1'-biphenyl]-2-sulfonamide;
4'-(6-Aminopyridin-3-yl)-3'-fluoro-N-(1,1,1-trifluoro-2-methylpropan-2-yl)41,t-biphenyl]-2-sulfonamide;
(S)-4'-(6-Aminopyridin-3-yl)-3'-fluoro-N-(2,2,2-trifluoro-1-phenylethyl)-[1,1'-biphenyl]-2-sulfonamide;
(R)-4'-(6-Aminopyridin-3-yl)-3'-fluoro-N-(1-hydroxypropan-2-yl)41,1'-biphenyl]-2-sulfonamide;
4'-(6-Aminopyridin-3-yl)-3'-fluoro-N-(1-methylcyclobutyl)-[1,1'-biphenyl]-2-sulfonamide;
4-((4'-(6-Aminopyridin-3-yl)-3'-fluoroql,1'-biphenyl]-2-yl)sulfonyl)thiomorpholine1,1-dioxide;
(S)-4'-(6-Aminopyridin-3-yl)-3'-fluoro-N-(1,1,1-trifluoropropan-2-yl)41,1'-biphenyl]-2-sulfonamide;
5-(2'-((1S,4S)-2-Oxa-5-azabicyclo[221]heptan-5-ylsulfonyl)-3-fluoro-[1,1'-biphenyl]-4-yl)pyridin-2-amine;
tert-Butyl 34(4'-(6-aminopyridin-3-yl)-3'-fluoro-[1,1'-biphenyl]-2-ylsulfonamido)methyl)-3-hydroxyazetidine-1-carboxylate;
4'-(6-Aminopyridin-3-yl)-3'-fluoro-N-((3-hydroxyazetidin-3-yl)methyl)-[1,1'-biphenyl]-2-sulfonamide;
2-(1-((4'-(6-Aminopyridin-3-yl)-3'-fluoro-[1,t-biphenyl]-2-yl)sulfonyl)piperidin-4-y1)ethanol;
1-((4'-(6-Aminopyridin-3-yl)-3'-fluoro-[1,1'-biphenyl]-2-yl)sulfonyl)piperidin-4-ol;
(1-((4'-(6-Aminopyridin-3-yl)-3'-fluoro-[1,1'-biphenyl]-2-yl)sulfonyl)piperidin-4-y1)methanol;
3'-Fluoro-N-[(1S)-2-hydroxy-1-methylethyl]-4'41H-pyrrolo[2,3-b]pyridin-5-yl)biphenyl-2-sulfonamide;
3'-Fluoro-N-[(1R)-2-hydroxy-1-methylethyl]-4'-(1H-pyrrolo[2,3-b]pyridin-5-yl)biphenyl-2-sulfonamide;
3'-Fluoro-N-[(3S)-2-oxopyrrolidin-3-yl]-4'-(1H-pyrrolo[2,3-b]pyridin-5-yl)biphenyl-2-sulfonamide;
5-[2'-(Cyclopropylsulfonyl)-3-fluorobiphenyl-4-yl]-1H-pyrrolo[2,3-b]pyridine;
3'-Fluoro-N-(2-hydroxyethyl)-4'-(1H-pyrrolo[2,3-b]pyridin-5-yl)biphenyl-2-sulfonamide;
N-tert-Butyl-3'-fluoro-4'-(1H-pyrrolo[2,3-b]pyridin-5-yl)biphenyl-2-sulfonamide;
3'-Fluoro-4'-(1H-pyrrolo[2,3-b]pyridin-5-yl)biphenyl-2-sulfonamide;
N-[3'-Fluoro-4'-(5H-pyrrolo[2,3-b]pyrazin-2-yl)biphenyl-2-yl]methanesulfonamide;
3'-Fluoro-N,N-dimethyl-4'-(5H-pyrrolo[2,3-b]pyrazin-2-yl)biphenyl-2-sulfonamide;
N-tert-Butyl-3'-fluoro-4'-(5H-pyrrolo[2,3-b]pyrazin-2-yl)biphenyl-2-sulfonamide;
2-[3-Fluoro-2'-(pyrrolidin-1-ylsulfonyl)biphenyl-4-yl]-5H-pyrrolo[2,3-b]pyrazine;
N,N-Diethyl-3'-fluoro-4'-(5H-pyrrolo[2,3-b]pyrazin-2-yl)biphenyl-2-sulfonamide;
2-[3-Fluoro-2'-(piperidin-1-ylsulfonyl)biphenyl-4-yl]-5H-pyrrolo[2,3-b]pyrazine;
2-[3-Fluoro-2'-(morpholin-4-ylsulfonyl)biphenyl-4-yl]-5H-pyrrolo[2,3-b]pyrazine;
3'-Fluoro-4'-(5H-pyrrolo[2,3-b]pyrazin-2-yl)N--N-(2,2,2-trifluoro-1-methylethyl)biphenyl-2-sulfonamide;
2-[3-Fluoro-2'-(methylsulfonyl)biphenyl-4-yl]-5H-pyrrolo[2,3-b]pyrazine;
3'-Fluoro-N-[(1R)-2-hydroxy-1-methylethyl]-4'-(5H-pyrrolo[2,3-b]pyrazin-2-yl)biphenyl-2-sulfonamide;
3'-Fluoro-N-methyl-4'-(5H-pyrrolo[2,3-b]pyrazin-2-yl)biphenyl-2-sulfonamide;
3'-Fluoro-N-[(1S)-2-hydroxy-1-methylethyl]-4'-(5H-pyrrolo[2,3-b]pyrazin-2-yl)biphenyl-2-sulfonamide;
1-{[3'-Fluoro-4'-(5H-pyrrolo[2,3-b]pyrazin-2-yl)biphenyl-2-yl]sulfonyl}piperidin-4-amine;
2-{2'-[(1,1-Dioxidothiomorpholin-4-yl)sulfonyl]-3-fluorobiphenyl-4-yl}-5H-pyrrolo[2,3-b]pyrazine;
2-[3,5'-Difluoro-2'-(methylsulfanyl)biphenyl-4-yl]-5H-pyrrolo[2,3-b]pyrazine;
2-[2'-(Ethylsulfanyl)-3-fluorobiphenyl-4-yl]-5H-pyrrolo[2,3-b]pyrazine;
7-[3-Fluoro-2'-(methylsulfonyl)biphenyl-4-yl]-3,4-dihydro-2H-pyrido[3,2-b][1,4]oxazine;
7-[3-Fluoro-2'-(piperidin-1-ylsulfonyl)biphenyl-4-yl]-3,4-dihydro-2H-pyrido[3,2-b][1,4]oxazine;

4'-(3,4-Dihydro-2H-pyrido[3,2-b][1,4]oxazin-7-yl)-3'-fluorobiphenyl-2-sulfonamide;
4'-(3,4-Dihydro-2H-pyrido[3,2-b][1,4]oxazin-7-yl)-3'-fluoro-N-[(1S)-2-hydroxy-1-methylethyl]biphenyl-2-sulfonamide;
1-{[4'-(3,4-Dihydro-2H-pyrido[3,2-b][1,4]oxazin-7-yl)-3'-fluorobiphenyl-2-yl]sulfonyl]piperidin-4-amine;
4'-(3,4-Dihydro-2H-pyrido[3,2-b][1,4]oxazin-7-yl)-3'-fluoro-N-[(1R)-2-hydroxy-1-methylethyl]biphenyl-2-sulfonamide;
4'-(3,4-Dihydro-2H-pyrido[3,2-b][1,4]oxazin-7-yl)-N,N-diethyl-3'-fluorobiphenyl-2-sulfonamide;
7-{2'-[(1,1-Dioxidothiomorpholin-4-yl)sulfonyl]-3-fluorobiphenyl-4-yl}-3,4-dihydro-2H-pyrido[3,2-b][1,4]oxazine;
N-tert-Butyl-4'-(3,4-dihydro-2H-pyrido[3,2-b][1,4]oxazin-7-yl)-3'-fluorobiphenyl-2-sulfonamide;
2-(2-Fluoro-4-{2-[(1-methylethyl)sulfanyl]-5-(trifluoromethyl)pyridin-3-yl}phenyl)-5H-pyrrolo[2,3-b]pyrazine;
5-(2-Fluoro-4-{2-[(1-methylethyl)sulfonyl]pyridin-3-yl}phenyl)pyrazin-2-amine;
5-(2-Fluoro-4-{2-[(1-methylethyl)sulfanyl]pyridin-3-yl}phenyl)pyrazin-2-amine;
2-{2-Fluoro-4[2-(2,2,2-trifluoroethoxy)pyridin-3-yl]phenyl}-5H-pyrrolo[2,3-b]pyrazine;
2-{2-Fluoro-4[2-(2-methylpropoxy)pyridin-3-yl]phenyl}-5H-pyrrolo[2,3-b]pyrazine;
2-{2-Fluoro-4[2-(1-methylethoxy)pyridin-3-yl]phenyl}-5H-pyrrolo[2,3-b]pyrazine;
2-{4-[2-(Cyclopropylmethoxy)pyridin-3-yl]-2-fluorophenyl}-5H-pyrrolo[2,3-b]pyrazine;
5-{4-[2-Fluoro-4-[2-(1-methylethoxy)pyridin-3-yl]phenyl}pyrazin-2-amine;
5-{4[2-(Cyclopentyloxy)pyridin-3-yl]-2-fluorophenyl}pyrazin-2-amine;
5-{2[2-(Cyclohexyloxy)pyridin-3-yl]-2-fluorophenyl}pyrazin-2-amine;
5-[2-Fluoro-4-(2-methoxypyridin-3-yl)phenyl]pyrazin-2-amine;
5-{4-[2-(Cyclobutyloxy)pyridin-3-yl]-2-fluorophenyl}pyrazin-2-amine;
tert-Butyl 3-[({3-[4-(5-aminopyrazin-2-yl)-3-fluorophenyl]pyridin-2-yl}oxy)methyl]pyrrolidine-1-carboxylate;
5-{2-Fluoro-4-[2-(pyrrolidin-3-ylmethoxy)pyridin-3-yl]phenyl}pyrazin-2-amine;
5-{2-Fluoro-4-[2-(1-methylethoxy)pyridin-3-yl]phenyl}pyrimidin-2-amine;
5-[4-(2-Aminopyridin-3-yl)-2-fluorophenyl]pyrimidin-2-amine;
4'-(5-Amino-6-cyanopyrazin-2-yl)-3'-fluoro-N-[(1R)-2-hydroxy-1-methylethyl]biphenyl-2-sulfonamide;
3-Amino-6[2'-(cyclopropylsulfonyl)-3-fluorobiphenyl-4-yl]pyrazine-2-carbonitrile;
4'-(5-Amino-6-cyanopyrazin-2-yl)-3'-fluoro-N-[(1S)-2-hydroxy-1-methylethyl]biphenyl-2-sulfonamide;
4'-(5-Amino-6-cyanopyrazin-2-yl)-3'-fluoro-N-(2-hydroxyethyl)biphenyl-2-sulfonamide;
3-Amino-6-{3-fluoro-2'-[(3-oxopiperazin-1-yl)sulfonyl]biphenyl-4-yl}pyrazine-2-carbonitrile;
4'-(5-Amino-6-cyanopyrazin-2-yl)-3'-fluoro-N-[(2R)-2-hydroxypropyl]biphenyl-2-sulfonamide;
3-Amino-6[3-fluoro-2'-(morpholin-4-ylcarbonyl)biphenyl-4-yl]pyrazine-2-carbonitrile;
4'-(6-Aminopyridazin-3-yl)-N-tert-butyl-3'-fluorobiphenyl-2-sulfonamide;
N-tert-Butyl-3'-fluoro-4'-(7H-pyrrolo[2,3-d]pyrimidin-2-yl)biphenyl-2-sulfonamide;
N-tert-Butyl-3'-fluoro-4'-(1,8-naphthyridin-3-yl)biphenyl-2-sulfonamide;
N-tert-Butyl-3'-fluoro-4'-quinoxalin-6-yl)biphenyl-2-sulfonamide;
N-tert-Butyl-3'-fluoro-4'-(1H-indol-5-yl)biphenyl-2-sulfonamide;
4'-(1H-Benzimidazol-5-yl)-N-tert-butyl-3'-fluorobiphenyl-2-sulfonamide;
4'-(1H-Benzimidazol-5-yl)-3'-fluoro-N-methylbiphenyl-2-sulfonamide;
4'-(1,3-Benzothiazol-5-yl)-N-tert-butyl-3'-fluorobiphenyl-2-sulfonamide;
N-tert-Butyl-3'-fluoro-4'-(1H-pyrrolo[3,2-b]pyridin-6-yl)biphenyl-2-sulfonamide;
3'-Fluoro-N-methyl-4'-(1H-pyrrolo[2,3-b]pyridin-5-yl)biphenyl-2-sulfonamide;
4'-(5-Aminopyridin-2-yl)-N-tert-butyl-3'-fluorobiphenyl-2-sulfonamide;
N-tert-Butyl-4'-(5,6-diaminopyrazin-2-yl)-3'-fluorobiphenyl-2-sulfonamide;
N-tert-Butyl-3'-fluoro-4'-(2-oxo-2,3-dihydro-1H-imidazo[4,5-b]pyrazin-5-yl)biphenyl-2-sulfonamide;
4'-(6-Amino-5-fluoropyridin-3-yl)-N-tert-butyl-3'-fluorobiphenyl-2-sulfonamide;
N-tert-Butyl-4'-(2,3-dihydro-1H-pyrrolo[2,3-b]pyridin-5-yl)-3'-fluorobiphenyl-2-sulfonamide;
N-tert-Butyl-3'-fluoro-4'-(3H-imidazo[4,5-b]pyridin-6-yl)biphenyl-2-sulfonamide;
4'-(5-Amino-6-methoxypyrazin-2-yl)-N-tert-butyl-3'-fluorobiphenyl-2-sulfonamide;
4'-(5-Amino-6-cyanopyrazin-2-yl)-N-tert-butyl-3'-fluorobiphenyl-2-sulfonamide;
4'-(5-Amino-3-cyanopyrazin-2-yl)-N-tert-butyl-3'-fluorobiphenyl-2-sulfonamide;
4'-(6-Amino-4-cyanopyridin-3-yl)-N-tert-butyl-3'-fluorobiphenyl-2-sulfonamide;
4'-(6-Amino-2-cyanopyridin-3-yl)-N-(tert-butyl)-3'-fluoro[1,1'-biphenyl]-2-sulfonamide;
4'-(5-Amino-1,3,4-thiadiazol-2-yl)-N-(tert-butyl)-3'-fluoro[1,1'-biphenyl]-2-sulfonamide;
(R)-4'-(5-Amino-1,3,4-thiadiazol-2-yl)-3'-fluoro-N-(1-hydroxypropan-2-yl)[1,1'-biphenyl]-2-sulfonamide;
4-((4'-(5-Amino-1,3,4-thiadiazol-2-yl)-3'-fluoro[1,1'-biphenyl]-2-yl)sulfonyl)thiomorpholine 1,1-dioxide;
4'-(5-Amino-6-chloropyrazin-2-yl)-N-tert-butyl-3'-fluorobiphenyl-2-sulfonamide;
4'-(5-Amino-6-bromopyrazin-2-yl)-N-tert-butyl-3'-fluorobiphenyl-2-sulfonamide;
6-Amino-3-(2'-(cyclopropylsulfonyl)-3-fluoro[1,1'-biphenyl]-4-yl)picolinonitrile;
N-tert-Butyl-3'-fluoro-4'[1,2,4]triazolo[4,3-a]pyridin-7-ylbiphenyl-2-sulfonamide;
4'-(5-Amino-6-methylpyrazin-2-yl)-N-tert-butyl-3'-fluorobiphenyl-2-sulfonamide;
4'-(5-Amino-6-methylpyrazin-2-yl)-3'-fluorobiphenyl-2-sulfonamide;
N-tert-Butyl-3'-fluoro-4'-(1H-imidazo[4,5-b]pyrazin-5-yl)biphenyl-2-sulfonamide;
N-tert-Butyl-4'-(5,6-diaminopyridin-3-yl)-3'-fluorobiphenyl-2-sulfonamide;
4'-(5-Amino-6-methylpyrazin-2-yl)-3'-fluoro-N-methylbiphenyl-2-sulfonamide;
4'-(6-Amino-5-cyanopyridin-3-yl)-N-tert-butyl-3'-fluorobiphenyl-2-sulfonamide;

4'-(6-Amino-5-chloropyridin-3-yl)--N-tert-butyl-3'-fluorobiphenyl-2-sulfonamide;
4'-[6-Amino-5-(trifluoromethyl)pyridin-3-yl]--N-tert-butyl-3'-fluorobiphenyl-2-sulfonamide;
4'-[2-Amino-4-(trifluoromethyl)pyrimidin-5-yl]-N-tert-butyl-3'-fluorobiphenyl-2-sulfonamide;
4'-(2-Amino-4-methylpyrimidin-5-yl)--N-tert-butyl-3'-fluorobiphenyl-2-sulfonamide;
N-tert-Butyl-3'-fluoro-4'-[3-(hydroxymethyl)-1H-pyrrolo[2,3-b]pyridin-5-yl]biphenyl-2-sulfonamide;
4'-(7-Amino-1 H-indol-5-yl)-3'-fluoro-N41 -(hydroxymethyl)cyclopentyl]biphenyl-2-sulfonamide;
3'-Fluoro-4'-[3-(hydroxymethyl)-1 H-pyrrolo[2,3-b]pyridin-5-yl]-N-methylbiphenyl-2-sulfonamide;
4'-(7-Amino-1 H-indol-5-yl)-N-tert-butyl-3'-fluorobiphenyl-2-sulfonamide;
N-[4'-(5-Aminopyrazin-2-yl)-3'-fluorobiphenyl-2-yl]acetamide;
1 44'-(5-Aminopyrazin-2-yl)-3'-fluorobiphenyl-2-yl]urea;
5-[2,3-D ifluoro-2'-(methylsulfonyl)biphenyl-4-yl]pyrazin-2-amine;
4'-(5-Aminopyrazin-2-yl)-N-tert-butyl-2',3'-difluorobiphenyl-2-sulfonamide;
N-[4'-(5-Am nopyrazin-2-yl)-3'-fluoro-2'-methylbiphenyl-2-yl]methanesulfonam ide;
4'-(5-Aminopyrazin-2-yl)-2',3'-difluorobiphenyl-2-sulfonamide;
4'-(2-Aminopyrimidin-5-yl)-2',3'-difluoro-N-methylbiphenyl-2-sulfonamide;
4'-(2-Aminopyrimidin-5-yl)--N-tert-butyl-2',3'-difluorobiphenyl-2-sulfonamide;
5 [2',3-Difluoro-4'-(trifluoromethoxy)biphenyl-4-yl]pyrazin-2-amine;
5-(2',3-Difluorobiphenyl-4-yl)pyrazin-2-amine;
5-(2'-Chloro-3-fluorobiphenyl-4-yl)pyrazin-2-amine;
5-(3-Fluoro-2'-methylbiphenyl-4-yl)pyrazin-2-amine;
5[2',3-Difluoro-4'-(trifluoromethyl)biphenyl-4-yl]pyrazin-2-amine;
5[3-Fluoro-2'-(trifluoromethyl)biphenyl-4-yl]pyrazin-2-amine;
5-(3-Fluoro-2'-methoxybiphenyl-4-yl)pyrazin-2-amine;
5-[3-Fluoro-2'-(methylsulfanyl)biphenyl-4-yl]pyrazin-2-amine;
5-[3-Fluoro-2'-(trifluoromethoxy)biphenyl-4-yl]pyrazin-2-amine;
4'-(5-Aminopyrazin-2-yl)-3'-fluorobiphenyl-2-ol;
5-[3-Fluoro-2'-(phenylsulfonyl)biphenyl-4-yl]pyrazin-2-amine;
5-(2',3,6'-Trifluorobiphenyl-4-yl)pyrazin-2-amine;
N-[4'-(5-Aminopyrazin-2-yl)-3'-fluorobiphenyl-2-yl]benzenesulfonamide;
5-(2'-Ethyl-3-fluorobiphenyl-4-yl)pyrazin-2-amine;
{[4'-(5-Aminopyrazin-2-yl)-3'-fluorobiphenyl-2-yl]oxy}acetic acid;
5-[3-Fluoro-2'-(1-methylethyl)biphenyl-4-yl]pyrazin-2-amine;
1-[4'-(5-Aminopyrazin-2-yl)-3'-fluorobiphenyl-2-yl]ethanone;
5-[3-Fluoro-2'-(2,2,2-trifluoroethoxy)biphenyl-4-yl]pyrazin-2-amine;
4'-(5-Aminopyrazin-2-yl)-3'-fluorobiphenyl-2-carboxylicacid;
4'-(5-Aminopyrazin-2-yl)-3'-fluorobiphenyl-2-carboxamide;
5-[3-Fluoro-2'-(1-methylethoxy)biphenyl-4-yl]pyrazin-2-amine;
5-{442-(Cyclopropylmethoxy)pyridin-3-yl]-2-fluorophenyl}pyrazin-2-amine;
2-[3,4'-Difluoro-2'-(methylsulfonyl)biphenyl-4-yl]-5H-pyrrolo[2,3-b]pyrazine;
N-[4'-(5-Aminopyrazin-2-yl)-3'-fluorobiphenyl-2-yl]-N-methylmethanesulfonmide;
N-[3'-Fluoro-4'-(5H-pyrrolo[2,3-b]pyrazin-2-yl)biphenyl-2-yl]ethanesulfonamide;
N-[3'-Fluoro-4'-(5H-pyrrolo[2,3-b]pyrazin-2-yl)biphenyl-2-yl]N--N-methylmethanesulfonamide;
N-[3'-Fluoro-4'-(5H-pyrrolo[2,3-b]pyrazin-2-yl)biphenyl-2-yl]-N-methylethanesulfonamide;
N-[4'-(5-Aminopyrazin-2-yl)-3'-fluorobiphenyl-2-yl]-N-methylethanesulfonam ide;
N-[3'-Fluoro-4'-(5H-pyrrolo[2,3-b]pyrazin-2-yl)biphenyl-2-yl]-2-methylpropane-1-sulfonamide;
N-[4'-(5-Aminopyrazin-2-yl)-3'-fluorobiphenyl-2-yl]-N-ethylmethanesulfonamide;
N-[4'-(5-Aminopyrazin-2-yl)-3'-fluorobiphenyl-2-yl]-N, 2-dimethylpropane-1 -sulfonamide;
5-[3-Fluoro-2'-(morpholin-4-ylcarbonyl)biphenyl-4-yl]-1 H-pyrrolo[2,3-b]pyridine;
5-[3-Fluoro-2'-(morpholin-4-ylcarbonyl)biphenyl-4-yl]pyrimidin-2-amine;
2-[3-Fluoro-2'-(morpholin-4-ylcarbonyl)biphenyl-4-yl]-5H-pyrrolo[2,3-b]pyrazine;
4'-(5-Aminopyrazin-2-yl)-N-tert-butyl-3'-fluorobiphenyl-2-carboxamide;
4'-(5-Aminopyrazin-2-yl)-N-tert-butyl-3',4-difluorobiphenyl-2-carboxamide;
4'-(5-Aminopyrazin-2-yl)-N, N-diethyl-3'-fluorobiphenyl-2-carboxamide;
4'-(2-Aminopyrimidin-5-yl)-3'-fluoro-N-[(1S)-2,2,2-trifluoro-1-methylethyl]biphenyl-2-carboxamide;
4'-(5-Aminopyrazin-2-yl)-3'-fluoro-N-[(1S)-2,2,2-trifluoro-1-methylethyl]biphenyl-2-carboxamide;
5-[3-Fluoro-2'-(piperazin-1 -ylcarbonyl)biphenyl-4-yl]pyrazin-2-amine;
5-{2'-[(4-Acetylpiperazin-1-yl)carbonyl]-3-fluorobiphenyl-4-yl}pyrazin-2-amine;
4'-(5-Aminopyrazin-2-yl)-N-cyclohexyl-3'-fluorobiphenyl-2-carboxamide;
5-{2'-[(1 ,1 -Dioxidothiomorpholin-4-yl)carbonyl]-3-fluorobiphenyl-4-yl}pyrazin-2-amine;
4'-(5-Aminopyrazin-2-yl)-3'-fluoro-N-methylbiphenyl-2-carboxamide;
4'-(5-Aminopyrazin-2-yl)-3'-fluoro-N-[(1R)-2,2,2-trifluoro-1-methylethyl]biphenyl-2-carboxamide;
4'-(5-Aminopyrazin-2-yl)-3'-fluoro-N-[(1R)-2-hydroxy-1-methylethyl]biphenyl-2-carboxamide;
4'-(5-Aminopyrazin-2-yl)-3'-fluoro-N-[(1S)-2-hydroxy-1-methylethyl]biphenyl-2-carboxamide;
1-{[4'-(5-Aminopyrazin-2-yl)-3'-fluorobiphenyl-2-yl]carbonyl}piperidin-4-ol;
5-{2'-[(4-Aminopiperidin-1 -yl)carbonyl]-3-fluorobiphenyl-4-yl}pyrazin-2-amine;
5-{2'-[(1 ,1 -Dioxidothiomorpholin-4-yl)carbonyl]-3-fluorobiphenyl-4-yl}pyrimidin-2-amine;
4'-(2-Aminopyrimidin-5-yl)-3'-fluoro-N-[(1S)-2-hydroxy-1-methylethyl]biphenyl-2-carboxamide;
4'-(2-Aminopyrimidin-5-yl)-3'-fluoro-N-[(1R)-2,2,2-trifluoro-1-methylethyl]biphenyl-2-carboxamide;
4-{[4'-(5-Aminopyrazin-2-yl)-3'-fluorobiphenyl-2-yl]carbonyl}piperazin-2-one;
4-{[4'-(2-Aminopyrimidin-5-yl)-3'-fluorobiphenyl-2-yl]carbonyl}piperazin-2-one;

5-[3-Fluoro-2'-(morpholin-4-ylcarbonyl)-4'-(trifluoromethyl)biphenyl-4-yl]pyrazin-2-amine;
5-[3-Fluoro-2'-(morpholin-4-ylcarbonyl)-4'-(trifluoromethyl)biphenyl-4-yl]pyrimidin-2-amine;
4-{[3'-Fluoro-4'-(1H-pyrrolo[2,3-b]pyridin-5-yl)biphenyl-2-yl]oxy}pyrimidin-2-amine;
2-{[3'-Fluoro-4'-(1H-pyrrolo[2,3-b]pyridin-5-yl)biphenyl-2-yl]oxy}pyrimidin-4-amine;
5-[3-Fluoro-2'-(pyrimidin-2-yloxy)biphenyl-4-yl]-1H-pyrrolo[2,3-b]pyridine;
5-[3-Fluoro-2'-(pyrimidin-2-yloxy)biphenyl-4-yl]pyrazin-2-amine;
5-[3-Fluoro-2'-(pyrimidin-2-yloxy)biphenyl-4-yl]pyrimidin-2-amine;
2-{[4'-(5-Aminopyrazin-2-yl)-3'-fluorobiphenyl-2-yl]oxy}pyrimidin-4-amine;
5-{2'-[(4-Aminopyrimidin-2-yl)oxy]-3-fluorobiphenyl-4-yl}pyrimidin-2-amine;
6-({[4'-(5-Aminopyrazin-2-yl)-3'-fluorobiphenyl-2-yl]oxy}methyl)pyridine-2-carbonitrile;
2-({[4'-(5-Aminopyrazin-2-yl)-3'-fluorobiphenyl-2-yl]oxy}methyl)pyridine-3-carbonitrile;
2-{[4'-(5-Aminopyrazin-2-yl)-3'-fluorobiphenyl-2-yl]oxy}pyridine-3-carbonitrile;
4-{[4'-(5-Aminopyrazin-2-yl)-3'-fluorobiphenyl-2-yl]oxy}pyrimidin-2-amine;
4-{[4'-(2-Aminopyrimidin-5-yl)-3'-fluorobiphenyl-2-yl]oxy}pyrimidin-2-amine;
6-{[4'-(5-Aminopyrazin-2-yl)-3'-fluorobiphenyl-2-yl]oxy}pyrimidin-4-amine;
5-{2'-[(6-Aminopyrimidin-4-yl)oxy]-3-fluorobiphenyl-4-yl}pyrimidin-2-amine;
4-{[4'-(5-Aminopyrazin-2-yl)-3'-fluorobiphenyl-2-yl]oxy}pyridine-2-carbonitrile;
4-{[4'-(2-Aminopyrimidin-5-yl)-3'-fluorobiphenyl-2-yl]oxy}pyridine-2-carbonitrile;
5-{2'-[(6-Azetidin-1-ylpyrimidin-4-yl)oxy]-3-fluorobiphenyl-4-yl}pyrazin-2-amine;
5-{2'-[(6-Azetidin-1-ylpyrimidin-4-yl)oxy]-3-fluorobiphenyl-4-yl}pyrimidin-2-amine;
5-{3-Fluoro-2'-[(2-methylpyrimidin-4-yl)oxy]biphenyl-4-yl}pyrazin-2-amine;
5-{3-Fluoro-2'-[(2-methylpyrimidin-4-yl)oxy]biphenyl-4-yl}pyrimidin-2-amine;
5-[3-Fluoro-2'-(pyrimidin-2-yloxy)biphenyl-4-yl]-1H-benzimidazole;
6-[3-Fluoro-2'-(pyrimidin-2-yloxy)biphenyl-4-yl]-3H-imidazo[4,5-b]pyridine;
5-{3-Fluoro-2'-[(4-methylpyrimidin-2-yl)oxy]biphenyl-4-yl}pyrazin-2-amine;
5-{3-Fluoro-2'-[(4-methylpyrimidin-2-yl)oxy]biphenyl-4-yl}pyrimidin-2-amine;
5-(3-Fluoro-2'-{[2-(trifluoromethyl)pyrimidin-4-yl]oxy}biphenyl-4-yl)pyrazin-2-amine;
5-(3-Fluoro-2'-{[2-(trifluoromethyl)pyrimidin-4-yl]oxy}biphenyl-4-yl)pyrimidin-2-amine;
5-{3-Fluoro-2'-[(5-methoxypyrimidin-2-yl)oxy]biphenyl-4-yl}pyrazin-2-amine;
5-{3-Fluoro-2'-[(5-methoxypyrimidin-2-yl)oxy]biphenyl-4-yl}pyrimidin-2-amine;
5-[3-Fluoro-2'-(pyrimidin-2-yloxy)-4'-(trifluoromethyl)biphenyl-4-yl]pyrazin-2-amine;
5-[3-Fluoro-2'-(pyrimidin-2-yloxy)-4'-(trifluoromethyl)biphenyl-4-yl]pyrimidin-2-amine;
5-[3-Fluoro-2'-methoxy-4'-(trifluoromethyl)biphenyl-4-yl]pyrazin-2-amine;
4'-(5-Aminopyrazin-2-yl)-3'-fluoro-4-(trifluoromethyl)biphenyl-2-ol;
4-{[4'-(5-Aminopyrazin-2-yl)-3'-fluoro-4-(trifluoromethyl)biphenyl-2-yl]oxy}pyrimidin-2-amine;
2-{[4'-(5-Aminopyrazin-2-yl)-3'-fluoro-4-(trifluoromethyl)biphenyl-2-yl]oxy}pyrimidin-4-amine;
5-[3-Fluoro-4'-(trifluoromethyl)-2'-{[2-(trimethylsilyl)ethoxy]methoxy}biphenyl-4-yl]pyrimidin-2-amine;
4'-(2-Aminopyrimidin-5-yl)-3'-fluoro-4-(trifluoromethyl)biphenyl-2-ol;
5-{2'-[(4-Aminopyrimidin-2-yl)oxy]-3-fluoro-4'-(trifluoromethyl)biphenyl-4-yl}pyrimidin-2-amine;
4-{[4'-(2-Aminopyrimidin-5-yl)-3'-fluoro-4-(trifluoromethyl)biphenyl-2-yl]oxy}pyrimidin-2-amine;
5-{2'-[(6-Aminopyrimidin-4-yl)oxy]-3-fluoro-4'-(trifluoromethyl)biphenyl-4-yl}pyrimidin-2-amine;
5-[3-Fluoro-2',4'-bis(trifluoromethyl)biphenyl-4-yl]pyrazin-2-amine;
4'-(5-Aminopyrazin-2-yl)-3'-fluoro-4-(trifluoromethyl)biphenyl-2-carbonitrile;
5-{5-[2-(Pyrimidin-2-yloxy)-4-(trifluoromethyl)phenyl]pyridin-2-yl}pyrimidin-2-amine;
4-{2-[6-(2-Aminopyrimidin-5-yl)pyridin-3-yl]-5-(trifluoromethyl)phenoxy}pyrimidin-2-amine;
5-{5-[2-(Pyrimidin-2-yloxy)phenyl]pyridin-2-yl}pyrimidin-2-amine;
4-{2-[6-(2-Aminopyrimidin-5-yl)pyridin-3-yl]phenoxy}pyrimidin-2-amine;
5-(5-{2-[(4-Aminopyrimidin-2-yl)oxy]phenyl}pyridin-2-yl)pyrimidin-2-amine;
4'-(5-Aminopyrazin-2-yl)-N-tert-butyl-3'-methylbiphenyl-2-sulfonamide;
4'-(5-Aminopyrazin-2-yl)-N-tert-butyl-3'-methoxybiphenyl-2-sulfonamide;
4'-(5-Aminopyrazin-2-yl)-N-tert-butylbiphenyl-2-sulfonamide;
4'-(5-Aminopyrazin-2-yl)-N,N-dimethylbiphenyl-2-sulfonamide;
5[2'-(Morpholin-4-ylsulfonyl)biphenyl-4-yl]pyrazin-2-amine;
4'-(5-Aminopyrazin-2-yl)-N-tert-butyl-2'-fluorobiphenyl-2-sulfonamide;
4'-(5-Aminopyrazin-2-yl)-2'-fluoro-N,N-dimethylbiphenyl-2-sulfonamide;
4'-(2-Amino-1,3-oxazol-4-yl)-N-tert-butyl-3'-fluorobiphenyl-2-sulfonamide;
4'-(2-Amino-1,3-thiazol-4-yl)-N-tert-butyl-3'-fluorobiphenyl-2-sulfonamide;
4'-(2-Amino-1,3-thiazol-4-yl)-N,N-diethyl-3'-fluorobiphenyl-2-sulfonamide;
4-[3-Fluoro-2'-(pyrrolidin-1-ylsulfonyl)biphenyl-4-yl]-1,3-thiazol-2-amine;
N-tert-Butyl-3'-fluoro-4'-(8-fluoroimidazo[1,2-a]pyridin-2-yl)biphenyl-2-sulfonamide;
4'-(5-Aminoimidazo[1,2-a]pyridin-2-yl)-N-tert-butyl-3'-fluorobiphenyl-2-sulfonamide;
2-[2'-(tert-Butylsulfamoyl)-3-fluorobiphenyl-4-yl]imidazo[1,2-a]pyridine-6-carboxamide;
2-[2'-(tert-Butylsulfamoyl)-3-fluorobiphenyl-4-yl]imidazo[1,2-a]pyridine-6-carboxamide;
N-tert-Butyl-4'-(5-cyanoimidazo[1,2-a]pyridin-2-yl)-3'-fluorobiphenyl-2-sulfonamide;
N-tert-Butyl-4'-(6-cyanoimidazo[1,2-a]pyridin-2-yl)-3'-fluorobiphenyl-2-sulfonamide;
N-tert-Butyl-3'-fluoro-4'46-(trifluoromethyl)imidazo[1,2-a]pyridin-2-yl]biphenyl-2-sulfonamide;

Ethyl 2-[2'-(tert-butylsulfamoyl)-3-fluorobiphenyl-4-yl]imidazo[1,2-a]pyridine-5-carboxylate;
N-tert-Butyl-3'-fluoro-4'-(5-methoxyimidazo[1,2-a]pyridin-2-yl)biphenyl-2-sulfonamide;
5[2'-(Methylsulfonyl)biphenyl-4-yl]pyrazin-2-amine;
5[3-Methyl-2'-(methylsulfonyl)biphenyl-4-yl]pyrazin-2-amine;
4'-(5-Aminopyrazin-2-yl)-N,N,3'-trimethylbiphenyl-2-sulfonamide;
4'-(5-Aminopyrazin-2-yl)-3'-hydroxybiphenyl-2-sulfonamide;
N-[4'-(5-Aminopyrazin-2-yl)biphenyl-2-yl]methanesulfonamide;
4'-(5-Aminopyrazin-2-yl)biphenyl-2-sulfonamide;
N-tert-Butyl-3'-fluoro-4'-(2-oxo-2,3-dihydro-1 H-indol-5-yl)biphenyl-2-sulfonamide;
N-tert-Butyl-4'-(2,4-dioxo-1,2,3,4-tetrahydroquinazolin-6-yl)-3'-fluorobiphenyl-2-sulfonamide;
4'-(3-Amino-1 H-indazol-5-yl)-N-tert-butyl-3'-fluorobiphenyl-2-sulfonamide;
3-Amino-6-[2'-(tert-butylsulfamoyl)-3-fluorobiphenyl-4-yl]pyrazine-2-carboxylic acid;
2-{[4'-(2-Aminopyrimidin-5-yl)-3'-fluorobiphenyl-2-yl]sulfonyl}acetamide;
2-{[4'-(2-Aminopyrimidin-5-0-3'-fluorobiphenyl-2-yl]sulfonyl}-N,N-diethylacetamide;
5-{3-Fluoro-2'-[(2-morpholin-4-yl-2-oxoethyl)sulfonyl]biphenyl-4-yl}pyrimidin-2-amine;
5,5'-(3,3''-Difluoro-1,1':2',1''-terphenyl-4,4''-diyl)dipyrazin-2-amine;
4'-(5-Aminopyrazin-2-yl)-3'-fluoro-4-(trifluoromethyl)biphenyl-2-carboxylic acid;
4'-(5-Aminopyrazin-2-yl)-3'-fluoro-4-(trifluoromethyl)biphenyl-2-carbaldehyde;
5-[3-Fluoro-2'-(morpholin-4-ylmethyl)-4'-(trifluoromethyl)biphenyl-4-yl]pyrazin-2-amine;
5-{2'-[(4-Aminopiperidin-1-yl)methyl]-3-fluoro-4'-(trifluoromethyl)biphenyl-4-yl}pyrazin-2-amine;
2-({[4'-(5-Aminopyrazin-2-yl)-3'-fluoro-4-(trifluoromethyl)biphenyl-2-yl]methyl}amino)ethanol;
5-{2'-[(4,6-Dimethylpyrimidin-2-yl)oxy]-3-fluorobiphenyl-4-yl]pyrazin-2-amine;
5-{2'-[(4,6-Dimethylpyrimidin-2-yl)oxy]-3-fluorobiphenyl-4-yl]pyrimidin-2-amine;
5-(3-Fluoro-2'-{[2-(trifluoromethyl)pyridin-4-yl]oxy}biphenyl-4-Opyrazin-2-amine;
5-(3-Fluoro-2'-{[2-(trifluoromethyl)pyridin-4-yl]oxy}biphenyl-4-Opyrimidin-2-amine;
5-(3-Fluoro-2'-{[4-(trifluoromethyl)pyrimidin-2-yl]oxy}biphenyl-4-Opyrazin-2-amine;
5-(3-Fluoro-2'-{[4-(trifluoromethyl)pyrimidin-2-yl]oxy}biphenyl-4-Opyrimidin-2-amine;
2-{[4'-(5-Aminopyrazin-2-yl)-3'-fluorobiphenyl-2-yl]oxy}pyrimidin-5-amine;
5-{2'-[(5-Aminopyrimidin-2-yl)oxy]-3-fluorobiphenyl-4-yl}pyrimidin-2-amine;
2-{[4'-(5-Aminopyrazin-2-yl)-3'-fluorobiphenyl-2-yl]oxy}-6-methylpyrim idin-4-amine;
5-{2'-[(4-Amino-6-methylpyrimidin-2-yl)oxy]-3-fluorobiphenyl-4-yl}pyrimidin-2-amine;
6-{[4'-(2-Aminopyrimidin-5-yl)-3'-fluorobiphenyl-2-yl]oxy}pyridine-2-carbonitrile;
6-{[4'-(5-Aminopyrazin-2-yl)-3'-fluorobiphenyl-2-yl]oxy}pyridine-2-carbonitrile;
5-{2'-[(5-Aminopyridin-2-yl)oxy]-3-fluorobiphenyl-4-yl}pyrazin-2-amine;
5-{2'-[(5-Aminopyridin-2-yl)oxy]-3-fluorobiphenyl-4-yl}pyrimidin-2-amine;
5-{2'-[(6-Amino-2-methylpyrimidin-4-yl)oxy]-3-fluorobiphenyl-4-yl}pyrimidin-2-amine;
6-{[4'-(5-Aminopyrazin-2-yl)-3'-fluorobiphenyl-2-yl]oxy}-2-methylpyrim idin-4-amine;
5-(3-Fluoro-2'-{[6-(trifluoromethyl)pyridin-2-yl]oxy}biphenyl-4-yl)pyrimidin-2-amine;
5-(3-Fluoro-2'-{[6-(trifluoromethyl)pyridin-2-yl]oxy}biphenyl-4-yl)pyrazin-2-amine;
6-{[4'-(5-Aminopyrazin-2-yl)-3'-fluorobiphenyl-2-yl]oxy}pyridine-3-carbonitrile;
6-{[4'-(2-Aminopyrimidin-5-yl)-3'-fluorobiphenyl-2-yl]oxy}pyridine-3-carbonitrile;
2-{[4'-(5-Aminopyrazin-2-yl)-3'-fluorobiphenyl-2-yl]oxy}ethanol;
2-{[4'-(2-Aminopyrimidin-5-yl)-3'-fluorobiphenyl-2-yl]oxy}ethanol;
5(3-Fluoro-2'-(piperidin-4-yloxy)biphenyl-4-yl]pyrazin-2-amine;
5(3-Fluoro-2'-(piperidin-4-yloxy)biphenyl-4-yl]pyrimidin-2-amine;
5-{3-Fluoro-2'-[(3R)-piperidin-3-yloxy]biphenyl-4-yl}pyrazin-2-amine;
5-{3-Fluoro-2'-[(3R)-piperidin-3-yloxy]biphenyl-4-yl}pyrimidin-2-amine;
5-{3-Fluoro-2'-[(3S)-piperidin-3-yloxy]biphenyl-4-yl}pyrazin-2-amine;
5-{3-Fluoro-2'-[(3S)-piperidin-3-yloxy]biphenyl-4-yl}pyrimidin-2-amine;
5-{2'-[(6-Cyclopropylpyrimidin-4-yl)oxy]-3-fluorobiphenyl-4-yl}pyrazin-2-amine;
5-{2'-[(6-Cyclopropylpyrimidin-4-yl)oxy]-3-fluorobiphenyl-4-yl}pyrimidin-2-amine;
5-{2'-[(2-Aminopyridin-4-yl)oxy]-3-fluorobiphenyl-4-yl}pyrazin-2-amine;
5-{2'-[(2-Aminopyridin-4-yl)oxy]-3-fluorobiphenyl-4-yl}pyrimidin-2-amine;
5-[2'-(2-Aminoethoxy)-3-fluorobiphenyl-4-yl]pyrazin-2-amine;
5-[2'-(2-Aminoethoxy)-3-fluorobiphenyl-4-yl]pyrimidin-2-amine;
{[4'-(5-Aminopyrazin-2-yl)-3'-fluorobiphenyl-2-yl]oxy}acetonitrile;
{[4'-(2-Aminopyrimidin-5-yl)-3'-fluorobiphenyl-2-yl]oxy}acetonitrile;
{[4'-(2-Aminopyrimidin-5-yl)-3'-fluorobiphenyl-2-yl]oxy}acetic acid;
5-{2-Fluoro-4-[2-(piperidin-4-yl]oxy)pyridin-3-yl]phenyl}pyrazin-2-amine;
5-{2-Fluoro-4-[2-(piperidin-4-yloxy)pyridin-3-yl]phenyl}pyrimidin-2-amine;
5-(4-{2-[(1,1-Dioxidotetrahydro-2H-thiopyran-4-yl)oxy]pyridin-3-yl]-2-fluorophenyl)pyrazin-2-amine;
5-(4-{2-[(1,1-Dioxidotetrahydro-2H-thiopyran-4-yl)oxy]pyridin-3-yl]-2-fluorophenyl)pyrimidin-2-amine;
2-({3-[4-(2-Aminopyrimidin-5-yl)-3-fluorophenyl]pyridin-2-yl}oxy)ethanol;
2-({3-[4-(5-Aminopyrazin-2-yl)-3-fluorophenyl]pyridin-2-yl}oxy)ethanol;
5-(4-{2-[(trans-4-Aminocyclohexyl)oxy]pyridin-3-yl1-2-fluorophenyl)pyrim idin-2-amine;
5-(4-{2-[(trans-4-Aminocyclohexyl)oxy]pyridin-3-yl}-2-fluorophenyl)pyrazin-2-amine;
5-{2-Fluoro-4-[2-(tetrahydro-2H-pyran-4-yloxy)pyridin-3-yl]phenyl}pyrazin-2-amine;

5-{2-Fluoro-4-[2-(tetrahydro-2H-pyran-4-yloxy)pyridin-3-yl]phenyl}pyrimidin-2-amine;
(2R)-2-({3-[4-(5-Aminopyrazin-2-yl)-3-fluorophenyl]pyridin-2-yl}oxy)propan-1-ol;
(2R)-2-({344-(2-Aminopyrimidin-5-yl)-3-fluorophenyl]pyridin-2-yl}oxy)propan-1-01;
(2S)-2-({3-[4-(5-Aminopyrazin-2-yl)-3-fluorophenyl]pyridin-2-yl}oxy)propan-1-ol;
(21)-2-({344-(2-Aminopyrimidin-5-yl)-3-fluorophenyl]pyridin-2-yl}oxy)propan-1-01;
N-(4'-(6-Aminopyridin-3-yl)-3'-fluoro41,1'-biphenyl]-2-yl)methanesulfonamide;
5-(3-Fluoro-2'-(morpholinosulfonyl)41,t-biphenyl]-4-yl)pyridin-2-amine;
4'-(6-Aminopyridin-3-yl)-3'-fluoro-N-methyl41,1'-biphenyl]-2-sulfonamide;
4'-(6-Aminopyridin-3-yl)-3'-fluoroql,1'-biphenyl]-2-sulfonamide;
5-(2'-((1S,4S)-2-Oxa-5-azabicyclo[221]heptan-5-ylsulfonyl)-3-fluoro-[1,1'-biphenyl]-4-yl)pyridin-2-amine;
4'-(6-Aminopyrazin-2-yl)-3'-fluoro-N-((3-hydroxyazetidin-3-yl)methyl)41,1'-biphenyl]-2-sulfonamide;
4'-(6-Aminopyridin-3-yl)-3'-fluoro-N-(1-hydroxy-2-methylpropan-2-yl)41,t-biphenyl]-2-sulfonamide;
4'-(6-Aminopyridin-3-yl)-3'-fluoro-N-((1S,2S)-1-hydroxy-1-phenylpropan-2-yl)-N-methyl-[1,1'-biphenyl]-2-sulfonamide;
4'-(6-Amino-5-fluoropyridin-3-yI)-3'-fluoro-N-(1-hydroxy-2-methylpropan-2-yI)-[1,t-biphenyl]-2-sulfonamide;
(racemic)-1-((4'-(6-Amino-5-fluoropyridin-3-yl)-3'-fluoro-[1,1'-biphenyl]-2-y1)sulfonyl)piperidin-3-ol;
4'-(6-Amino-5-fluoropyridin-3-yl)-3'-fluoro-N-((1S,2S)-1-hydroxy-1-phenylpropan-2-yl)-N-methyl-[1,1'-biphenyl]-2-sulfonamide;
N-(1-((4'-(6-Amino-5-fluoropyridin-3-yl)-3'-fluoro41,1'-biphenyI]-2-yl)sulfonyl)piperidin-4-yl)acetamide;
racemic 2-[1-((4'-(6-Amino-5-fluoropyridin-3-yl)-3'-fluoroql,t-biphenyl]-2-yl)sulfonyl)piperidin-3-yl)ethanol;
racemic 1-((4'-(6-Amino-5-fluoropyridin-3-yl)-3'-fluoro-[1,1'-biphenyI]-2-yl)sulfonyl)piperidin-3-yl)methanol;
2-[6-(2-Aminopyrimidin-5-yl)-5-fluoropyridin-3-yl]-N-[(2R)-2-hydroxypropyl]benzenesulfonamide;
2-[6-(2-Aminopyrimidin-5-yl)-5-fluoropyridin-3-yl]-N-ethyl-5-(trifluoromethyl)benzenesulfonamide;
2-[6-(2-Aminopyrimidin-5-yl)-5-fluoropyridin-3-yl]-N-tert-butylbenzenesulfonamide;
5-{5-[2-(Morpholin-4-ylmethyl)-4-(trifluoromethyl)phenyl]pyridin-2-yl}pyrimidin-2-amine;
5-{5-[2-(Morpholin-4-ylcarbonyl)phenyl]pyridin-2-yl}pyrimidin-2-amine;
5-[5-(2-Methoxyphenyl)pyridin-2-yl]pyrimidin-2-amine;
5-(5-{2-[(3,3-Difluoropiperidin-1-yl)sulfonyl]phenyl}pyridin-2-yl)pyrimidin-2-amine;
5-(5-{2-[(3,3-Difluoropyrrolidin-1-yl)sulfonyl]phenyl}pyridin-2-yl)pyrimidin-2-amine;
5-{5-[2-(Azepan-1-yl)sulfonyl]phenyl]pyridin-2-yl}pyrimidin-2-amine;
5-(5-{2-[(4,4-Difluoropiperidin-1-yl)sulfonyl]phenyl}pyridin-2-yl)pyrimidin-2-amine;
2-[6-(2-Aminopyrimidin-5-yl)pyridin-3-yl]-N-ethylbenzenesulfonamide;
2-[6-(2-Aminopyrimidin-5-yl)pyridin-3-yl]-N-(dicyclopropylmethyl)benzenesulfonamide;
2-[6-(2-Aminopyrimidin-5-yl)pyridin-3-yl]-N-[(1S)-2,2,2-trifluoro-1-methylethyl]benzenesulfonamide;
2-[6-(2-Aminopyrimidin-5-yl)pyridin-3-yl]-N-[(1R)-2,2,2-trifluoro-1-methylethyl]benzenesulfonamide;
4-({2-[6-(2-Aminopyrimidin-5-yl)pyridin-3-yl]phenyl}sulfonyl)piperazin-2-one;
2-[6-(2-Aminopyrimidin-5-yl)pyridin-3-yl]-N-[(2S)-2-hydroxypropyl]benzenesulfonamide;
2-[6-(2-Aminopyrimidin-5-yl)pyridin-3-yl]-N-[(2R)-2-hydroxypropyl]benzenesulfonamide;
2-[6-(2-Aminopyrimidin-5-yl)pyridin-3-yl]-N-(2-hydroxyethyl)-5-(trifluoromethyl)benzenesulfonamide;
5-{5-[2-(Cyclopropylsulfonyl)phenyl]pyridin-2-yl}pyrimidin-2-amine;
2-[6-(2-Aminopyrimidin-5-yl)pyridin-3-yl]-N-ethyl-5-(trifluoromethyl)benzenesulfonamide;
2-[6-(2-Aminopyrimidin-5-yl)pyridin-3-yl]-N-tert-butylbenzenesulfonamide;
2-[6-(2-Aminopyrimidin-5-yl)pyridin-3-yl]-N-[(1R)-2-hydroxy-1-methylethyl]benzenesulfonamide;
3-Amino-6-{2'-[(4-aminopyrimidin-2-yl)oxy]-3-fluorobiphenyl-4-yl}pyrazine-2-carbonitrile;
5-(4'-Bromo-2',3-difluorobiphenyl-4-yl)pyrazin-2-amine;
5-(4'-Bromo-2',3-difluorobiphenyl-4-yl)-1H-pyrrolo[2,3-b]pyridine;
5-(3-fluoro-2-methoxy-4'-(trifluoromethyl)41,t-biphenyl]-4-yl)pyrazin-2-amine;
5-(2',3,4'-Trifluorobiphenyl-4-yl)pyrazin-2-amine;
(racemic) 5-[3-Fluoro-2'-(methylsulfinyl)biphenyl-4-yl]pyrazin-2-amine;
4'-(5-Aminopyrazin-2-yl)-3'-fluorobiphenyl-2-carbonitrile;
1-(4'-(5-Aminopyrazin-2-yl)-3'-fluoro41,1'-biphenyl]-2-yl)imidazolidin-2-one;
4'-(2-Amino-4-cyanopyrimidin-5-yl)-N-tert-butyl-3'-fluorobiphenyl-2-sulfonamide;
6-Amino-3-{2'-[(1,1-dioxidothiomorpholin-4-yl)sulfonyl]-3-fluorobiphenyl-4-yllpyrazine-2-carbonitrile;
1-{[4'-(2-Aminopyrimidin-5-0-3'-fluorobiphenyl-2-yl]sulfonyl}-N-methylazetidine-3-carboxamide;
4'-(5-Amino-3-cyanopyrazin-2-yl)-3'-fluoro-N-(2-hydroxyethyl)biphenyl-2-sulfonamide;
4'-(5-Amino-3-cyanopyrazin-2-yl)-3'-fluoro-N-[(2S)-2-hydroxypropyl]biphenyl-2-sulfonamide;
4'-(5-Amino-3-cyanopyrazin-2-yl)-3'-fluoro-N-[(2R)-2-hydroxypropyl]biphenyl-2-sulfonamide;
1-((4'-(2-Aminopyrimidin-5-yl)-3'-fluoro41,1 Lbiphenyl]-2-yl)sulfonyl)piperidine-4-carboxamide;
4'-(5-Amino-3-cyanopyrazin-2-yl)-3'-fluoro-N-[(1R)-2-hydroxy-1-methylethyl]biphenyl-2-sulfonamide;
4'-(5-Amino-3-cyanopyrazin-2-yl)-3'-fluoro-N-[(1S)-2-hydroxy-1-methylethyl]biphenyl-2-sulfonamide;
4'-(5-Amino-3-cyanopyrazin-2-yl)-3'-fluoro-N-(2-hydroxyethyl)-4-(trifluoromethyl)biphenyl-2-sulfonamide;
4'-(5-Amino-3-cyanopyrazin-2-yl)-N-ethyl-3'-fluoro-4-(trifluoromethyl)41,1'-biphenyl]-2-sulfonamide;
4'-(5-Amino-3-cyanopyrazin-2-yI)-3'-fluoro-N-(3-hydroxy-2,2-dimethylpropyl)biphenyl-2-sulfonamide;
6-Amino-3-{3-fluoro-2'-[(3-oxopiperazin-1-yl)sulfonyI]-4'-(trifluoromethyl)biphenyl-4-yl}pyrazine-2-carbonitrile;
N-(2-{[4'-(2-Aminopyrimidin-5-yl)-3'-fluorobiphenyl-2-yl]sulfonyl}ethyl)benzamide;
b 1-{[4'-(2-Aminopyrimidin-5-0-3'-fluorobiphenyl-2-yl]sulfonyl1-3,3-dimethylbutan-2-one;
5-[3-Fluoro-2'-(pyrimidin-2-ylsulfonyl)biphenyl-4-yl]pyrimidin-2-amine;

5-[3-Fluoro-2'-(pyrazin-2-ylsulfonyl)biphenyl-4-yl]pyrimidin-2-amine;
5-[3-Fluoro-2'-(pyrimidin-4-ylsulfonyl)biphenyl-4-yl]pyrimidin-2-amine;
5-{2'-[(6-Aminopyrimidin-4-yl)sulfonyl]-3-fluorobiphenyl-4-yl}pyrimidin-2-amine;
5-{2'-[(4-Aminopyrimidin-2-yl)sulfonyl]-3-fluorobiphenyl-4-yl}pyrimidin-2-amine;
5-{2'-[(5-Aminopyrazin-2-yl)sulfonyl]-3-fluorobiphenyl-4-yl}pyrimidin-2-amine;
4-{[4'-(2-Aminopyrimidin-5-yl)-3'-fluorobiphenyl-2-yl]sulfonyl}pyrimidin-2-amine;
5-{2'-[(6-Aminopyrazin-2-yl)sulfonyl]-3-fluorobiphenyl-4-yl}pyrimidin-2-amine;
6-{[4'-(5-Aminopyrazin-2-yl)-3'-fluorobiphenyl-2-yl]sulfonyl}pyrimidin-4-amine;
2-{[4'-(5-Aminopyrazin-2-yl)-3'-fluorobiphenyl-2-yl]sulfonyl}pyrimidin-4-amine;
5-{2'-[(Cyclopropylmethyl)sulfonyl]-3-fluorobiphenyl-4-yl}pyrimidin-2-amine;
6-Amino-3 42'-(cyclopropylsulfonyl)-3-fluorobiphenyl-4-yl]pyrazine-2-carbonitrile;
1-{[4'-(5-Aminopyrazin-2-yl)-3'-fluorobiphenyl-2-yl]sulfonyl}cyclopentanecarbonitrile;
1-{[4'-(5-Aminopyrazin-2-yl)-3'-fluorobiphenyl-2-yl]sulfonyl}cyclopentanecarboxamide;
2-{[4'-(2-Aminopyrimidin-5-0-3'-fluorobiphenyl-2-yl]sulfonyl}2-methylpropanenitrile;
2-{[4'-(2-Aminopyrimidin-5-yl)-3'-fluorobiphenyl-2-yl]sulfonyl}-2-methylpropanamide;
5-{2'-[(2-Amino-1,1-dimethylethyl)sulfonyl]-3-fluorobiphenyl-4-yl}pyrimidin-2-amine;
2-{[4'-(5-Aminopyrazin-2-0-3'-fluorobiphenyl-2-yl]sulfonyl1-2-methylpropanenitrile;
2-{[4'-(5-Aminopyrazin-2-yl)-3'-fluorobiphenyl-2-yl]sulfonyl}-2-methylpropanamide;
5-{2'-[(2-Amino-1,1-dimethylethyl)sulfonyl]-3-fluorobiphenyl-4-yl}pyrazin-2-amine;
1-{[4'-(2-Aminopyrimidin-5-yl)-3'-fluorobiphenyl-2-yl]sulfonyl}cyclopentanecarbonitrile;
1-{[4'-(2-Aminopyrimidin-5-yl)-3'-fluorobiphenyl-2-yl]sulfonyl}cyclopentanecarboxamide;
5-(2'-{[1-(Aminomethyl)cyclopentyl]sulfonyl1-3-fluorobiphenyl-4-yl)pyrimidin-2-amine;
5-{[4'-(5-Aminopyrazin-2-yl)-3'-fluorobiphenyl-2-yl]sulfanyl}pyrazin-2-amine;
5-{2'-[(6-Aminopyrazin-2-yl)sulfanyl]-3-fluorobiphenyl-4-yl}pyrazin-2-amine;
5-(3-Fluoro-2'-(pyrimidin-4-ylthio)-[1,1'-biphenyl]-4-yl)pyrazin-2-amine;
5-{2'-[(5-Aminopyrazin-2-yl)sulfanyl]-3-fluorobiphenyl-4-yl}pyrimidin-2-amine;
6-Amino-3-{2'-[(4-aminopyrimidin-2-yl)oxy]-3-fluorobiphenyl-4-yl}pyrazine-2-carbonitrile;
6-Amino-3-[3-fluoro-2'-(pyrimidin-2-yloxy)-4'-(trifluoromethyl)biphenyl-4-yl]pyrazine-2-carbonitrile;
6-Amino-3'-fluoro-2'-(pyrimidin-2-yloxy)biphenyl-4-yl]pyrazine-2-carbonitrile;
N-(tert-Butyl)-3'-fluoro-4'-(5-(methylsulfonamido)pyrazin-2-yl)41,1'-biphenyl]-2-sulfonamide;
5-{2'-[(Ethylsulfonyl)methyl]-3-fluorobiphenyl-4-yl}pyrazin-2-amine;
5-{3-Fluoro-2'-[(methylsulfonyl)methypiphenyl-4-yl}pyrazin-2-amine;
5-(3-Fluoro-2'-{[(1-methylethyl)sulfonyl]methyllbiphenyl-4-yl)pyrazin-2-amine;
5-{3-Fluoro-2'-[(pyrimidin-2-ylsulfonyl)methypiphenyl-4-yl}pyrazin-2-amine;
2-({[4'-(5-Aminopyrazin-2-yl)-3'-fluorobiphenyl-2-yl]methyl}sulfanyl)pyrimidin-4-amine;
(racemic) 5-(3-Fluoro-2'-{[2-(trifluoromethyl)morpholin-4-yl]carbonyl}biphenyl-4-yl)pyrazin-2-amine;
1-{[4'-(5-Aminopyrazin-2-yl)-3'-fluorobiphenyl-2-yl]carbonyl}azetidin-3-ol;
4'-(5-Aminopyrazin-2-yl)-3'-fluoro-N-(tetrahydro-2H-pyran-4-yl)biphenyl-2-carboxamide;
5-{2'-[(1,1-Dioxidothiomorpholin-4-yl)carbonyl]-3-fluoro-4'-(trifluoromethyl)biphenyl-4-yllpyrazin-2-amine;
1-(4-{[4'-(5-Aminopyrazin-2-yl)-3'-fluorobiphenyl-2-yl]carbonyl}morpholin-2-ypethanol (diastereomeric mixture);
1-(4-{[4'-(2-Aminopyrimidin-5-yl)-3'-fluorobiphenyl-2-yl]carbonyl}morpholin-2-yl)ethanol (diastereomeric mixture);
4'-(5-Aminopyrazin-2-yl)-3'-fluoro-N-(2-hydroxyethyl)biphenyl-2-carboxamide;
4'-(2-Aminopyrimidin-5-yl)-3'-fluoro-N-(2-hydroxyethyl)biphenyl-2-carboxamide;
(3R)-1-{[4'-(5-Aminopyrazin-2-yl)-3'-fluorobiphenyl-2-yl]carbonyl}piperidin-3-ol;
(cis/trans) 4'-(5-Aminopyrazin-2-yl)-3'-fluoro-N-(4-hydroxycyclohexyl)biphenyl-2-carboxamide;
(3R)-1-{[4'-(2-Aminopyrimidin-5-yl)-3'-fluorobiphenyl-2-yl]carbonyl}piperidin-3-ol;
(cis/trans) 4'-(2-Aminopyrimidin-5-yl)-3'-fluoro-N-(4-hydroxycyclohexyl}biphenyl-2-carboxamide;
(racemic) 5-(3-Fluoro-2'-{[2-(trifluoromethyl)morpholin-4-yl]carbonyl}biphenyl-4-yl)pyrimidin-2-amine;
(3S)-1-{[4'-(2-Aminopyrimidin-5-yl)-3'-fluorobiphenyl-2-yl]carbonyl}piperidin-3-ol;
(3S)-1-{[4'-(5-Aminopyrazin-2-yl)-3'-fluorobiphenyl-2-yl]carbonyl}piperidin-3-ol;
(3R)-1-{[4'-(5-Aminopyrazin-2-yl)-3'-fluorobiphenyl-2-yl]carbonyl}pyrrolidin-3-ol;
(3R)-1-{[4'-(2-Aminopyrimidin-5-yl)-3'-fluorobiphenyl-2-yl]carbonyl}pyrrolidin-3-ol;
(3S)-1-{[4'-(5-Aminopyrazin-2-yl)-3'-fluorobiphenyl-2-yl]carbonyl}pyrrolidin-3-ol;
(3S)-1-{[4'-(2-Aminopyrimidin-5-yl)-3'-fluorobiphenyl-2-yl]carbonyl}pyrrolidin-3-ol;
5-{2'-[(2,6-Dimethylmorpholin-4-yl)carbonyl]-3-fluorobiphenyl-4-yl}pyrazin-2-amine (diastereoisomeric mixture);
5-(3-Fluoro-2'-{[(3S)-3-methylmorpholin-4-yl]carbonyl}biphenyl-4-yl)pyrazin-2-amine;
5-(3-Fluoro-2'-{[(3R)-3-methylmorpholin-4-yl]carbonyl}biphenyl-4-yl)pyrazin-2-amine;
5-(3-Fluoro-2'-{[(2S)-2-methylmorpholin-4-yl]carbonyl}piphenyl-4-yl)pyrazin-2-amine;
5-(3-Fluoro-2'-{[(2S)-2-methylmorpholin-4-yl]carbonyl}piphenyl-4-yl)pyrimidin-2-amine;
5-(3-Fluoro-2'-{[(3S)-3-methylmorpholin-4-yl]carbonyl}piphenyl-4-yl)pyrimidin-2-amine;
5-(3-Fluoro-2'-{[(3R)-3-methylmorpholin-4-yl]carbonyl}biphenyl-4-yl)pyrimidin-2-amine;
5-{2'-[(2,6-Dimethylmorpholin-4-yl)carbonyl]-3-fluorobiphenyl-4-yl}pyrimidin-2-amine (diastereoisomeric mixture);
5-{2-{Amino-4-[2-(morpholin-4-ylcarbonyl)pyridin-3-yl]phenyl}-1H-pyrrolo[2,3-1D]pyridine;
5-{2-Fluoro-442-(morpholin-4-ylcarbonyl)pyridin-3-yl]phenyl}pyrimidin-2-amine;

5-{2-Fluoro-442-(morpholin-4-ylcarbonyl)pyridin-3-yl]phenyl}pyrazin-2-amine;
2-[4-(5-Aminopyrazin-2-yl)-3-fluoro-phenyl]-N-tert-butyl-5-(trifluoromethyl)benzamide;
2-[4-(5-Aminopyrazin-2-yl)-3-fluoro-phenyl]-N-[(1R)-2-hydroxy-1-methyl-ethyl]-5-(trifluoromethyl)benzamide;
2-[4-(5-Aminopyrazin-2-yl)-3-fluoro-phenyl]-N-[(1S)-2-hydroxy-1-methyl-ethyl]-5-(trifluoromethyl)benzamide;
2-[4-(5-Aminopyrazin-2-yl)-3-fluoro-phenyl]-5-(trifluoromethyl)-N-[(1 R)-2,2,2-trifluoro-1-methyl-ethyl]benzamide;
2-[4-(2-Aminopyrimidin-5-yl)-3-fluoro-phenyl]-5-(trifluoromethyl)-N-[(1 S)-2,2,2-trifluoro-1-methyl-ethyl]benzamide;
2-[4-(2-Aminopyrimidin-5-yl)-3-fluoro-phenyl]-5-(trifluoromethyl)-N-[(1 R)-2,2,2-trifluoro-1-methyl-ethyl]benzamide;
2-[4-(5-Aminopyrazin-2-yl)-3-fluoro-phenyl]-5-(trifluoromethyl)-N-[(1 S)-2,2,2-trifluoro-1-methyl-ethyl]benzamide;
[2-[4-(2-Aminopyrimidin-5-yl)-3-fluoro-phenyl]phenyl]-(3-hydroxyazetidin-1 -yl)methanone;
[2-[4-(2-Aminopyrimidin-5-yl)-3-fluoro-phenyl]phenylH4-(methylamino)-1-piperidyl]methanone;
[2-[4-(2-Aminopyrimidin-5-yl)-3-fluoro-phenyl]-5-(trifluoromethyl)phenyl]-(1 ,1-dioxo-1 ,4-thiazinan-4-yl)methanone;
2-[4-(2-Aminopyrimidin-5-yl)-3-fluoro-phenyl]-N-tert-butyl-5-(trifluoromethyl)benzamide;
[2-[4-(5-Aminopyrazin-2-yl)-3-fluoro-phenyl]-5-(trifluoromethyl)phenyl]-(4-hydroxy-1 -piperidyl)methanone;
[2-[4-(2-Aminopyrimidin-5-yl)-3-fluoro-phenyl]-5-(trifluoromethyl)phenyl]-(4-hydroxy-1-piperidyl)methanone;
2-[4-(2-Aminopyrimidin-5-yl)-3-fluoro-phenyl]-N-tetrahydropyran-4-yl-benzam ide;
(racemic) [2-[4-(5-Aminopyrazin-2-yl)-3-fluoro-phenyl]phenyl-2-(hydroxymethyl)morpholin-4-yl]methanone;
(racemic)[2-[4-(2-Aminopyrimidin-5-yl)-3-fluoro-phenyl]phenyl]-[2-(hydroxymethyl)morpholin-4-yl]methanone;
N-{3-[4-(2-Aminopyrimidin-5-0-3-fluorophenyl]pyridin-2-}-2,2-dimethylpropanamide;
N-{3-[4-(5-Aminopyrazin-2-0-3-fluorophenyl]pyridin-2-}-2,2-dimethylpropanamide;
N-{3-[3-Fluoro-4-(1H-pyrrolo[2,3-b]pyridin-5-yl)phenyl]pyridin-2yl}-2,2-dimethylpropanamide;
(racemic) 5-(2-Fluoro-4-(2-(pyrrolidin-3-ylsulfonyl)pyridin-3-yl)phenyl)pyrazin-2-amine;
5-(2-Fluoro-4-(2-(pyrrolidin-3-ylsulfonyl)pyridin-3-yl)phenyl)pyrimidin-2-amine;
5-(4-(2-(Cyclobutylsulfonyl)pyridin-3-yl)-2-fluorophenyl)pyrimidin-2-amine;
5-(4-(2-(Cyclobutylsulfonyl)pyridin-3-yl)-2-fluorophenyl)pyrazin-2-amine;
5-(4-(2-(CyclohexIsulfonyl)pyridin-3-yl)-2-fluorophenyl)pyrimidin-2-amine;
5-(4-(2-(Cyclohexylsulfonyl)pyridin-3-yl)-2-fluorophenyl)pyrazin-2-amine;
5-(4-(2-(Cyclopentylsulfonyl)pyridin-3-yl)-2-fluorophenyl)pyrimidine-2-amine;
5-(4-(2-(Cyclopentylsulfonyl)pyridin-3-yl)-2-fluorophenyl)pyrazin-2-amine;
5-(4-(2-(tert-Butylsulfonyl)pyridin-3-yl)-2-fluorophenyl)pyrimidin-2-amine;
5-(4-(2-(tert-Butylsulfonyl)pyridin-3-yl)-2-fluorophenyl)pyrazin-2-amine;
(racemic) 5-(4-(2-(sec-Butylsulfonyl)pyridin-3-yl)-2-fluorophenyl)pyrimidin-2-amine;
(racemic)5-(4-(2-(sec-Butylsulfonyl)pyridin-3-yl)-2-fluorophenyl)pyrazin-2-amine;
1-((3-(4-(2-Aminopyrimidin-5-yl)-3-fluorophenyl)pyridine-2-yl)sulfonyl)piperidin-1-yl)ethanone;
1-((3-(4-(2-Aminopyrazin-5-yl)-3-fluorophenyl)pyridine-2-yl)sulfonyl)piperidin-1-yl)ethanone;
5-(2-Fluoro-4-(2-((3-methoxypropyl)sulfonyl)pyridine-3-yl)phenyl)pyrimidin-2-amine;
5-(2-Fluoro-4-(2-((3-methoxypropyl)sulfonyl)pyridine-3-yl)phenyl)pyrazin-2-amine;
4-((3-(4-(2-Aminopyrimidin-5-yl)-3-fluorophenyl)pyridine-2-yl)sulfonyl)tetrahydro-2H-thiopyran 1,1-dioxide;
4-((3-(4-(2-Aminopyrazin-5-yl)-3-fluorophenyl)pyridine-2-yl)sulfonyl)tetrahydro-2H-thiopyran 1,1-dioxide;
5-(2-Fluoro-4-(2-((2-morpholinoethyl)sulfonyl)pyridine-3-yl)phenyl)pyrimidin-2-amine;
5-(2-Fluoro-4-(2-((2-morpholinoethyl)sulfonyl)pyridine-3-yl)phenyl)pyrazin-2-amine;
5-(2-Fluoro-4-(2-(((tetrahydro-2H-pyran-4-yl)methyl)sulfonyl)pyridine-3-yl)pyrimidin-2-amine;
5-(2-Fluoro-4-(2-(((tetrahydro-2H-pyran-4-yl)methyl)sulfonyl)pyridine-3-yl)pyrazin-2-amine;
5-(2-Fluoro-4-{2-[(1 -methylethyl)sulfonyl]pyridin-3-ylphenyl)pyrimidin-2-amine;
5-(2-Fluoro-4-(2-(isopropylsulfonyl)pyridine-3-yl)phenyl)-1 H-pyrrolo[2,3-b]pyridine;
5-{2-Fluoro-442-(piperidin-4-ylsulfonyl)pyridin-3-yl]phenyllpyrimidin-2-amine;
5-{4-[2-(Cyclopropylsulfonyl)pyridin-3-yl]-2-fluorophenyl}pyrimidin-2-amine;
5-{4-[2-(Cyclopropylsulfonyl)pyridin-3-yl]-2-fluorophenyl}pyrazin-2-amine;
5-{2-Fluoro-4-[2-(tetrahydro-2H-pyran-4-ylsulfonyl)pyridin-3-yl]phenyl}pyrazin-2-amine;
5-{2-Fluoro-4-[2-(tetrahydro-2H-pyran-4-ylsulfonyl)pyridin-3-yl]phenyl}pyrimidin-2-amine;
5-{2-Fluoro-4-[2-(piperidin-4-ylsulfonyl)pyridin-3-yl]phenyl}pyrazin-2-amine;
5-(2,3-Difluorobiphenyl-4-yl)pyrazin-2-amine;
5-(3-Fluoro-2-methoxybiphenyl-4-yl)pyrazin-2-amine;
5-[3-Fluoro-2-methoxy-2'-(methylsulfonyl)biphenyl-4-yl]pyrazin-2-amine;
4'-(5-Aminopyrazin-2-yl)-N-tert-butyl-3'-fluoro-2'-methoxybiphenyl-2-sulfonamide;
N-[4'-(5-Aminopyrazin-2-yl)-3'-fluoro-2'-methoxybiphenyl-2-yl]methanesulfonamide;
5-(3-Fluoro-2'-(pyrazin-2-yl)41 ,t-biphenyl]-4-yl)pyrazin-2-amine;
5-(3-Fluoro-2'-pyrazin-2-ylbiphenyl-4-yl)pyrimidin-2-amine;
5,5'-(3'-Fluorobiphenyl-2,4'-diyl)dipyrazin-2-amine;
5-[2'-(5-Aminopyrazin-2-yl)-3-fluorobiphenyl-4-yl]pyrimidin-2-amine;
5-[2'-(6-Aminopyrazin-2-yl)-3-fluorobiphenyl-4-yl]pyrazin-2-amine;
5-[4'-(5-Aminopyrazin-2-yl)-3'-fluorobiphenyl-2-yl]pyrimidin-2-amine;
5,5'-(3'-Fluorobiphenyl-2,4'-diyl)dipyrimidin-2-amine;
5-[4'-(5-Aminopyrazin-2-yl)-3'-fluoro-5-(trifluoromethyl)biphenyl-2-yl]pyrimidin-2-amine;

5-[3-Fluoro-2'-(2-methoxypyrimidin-5-yl)biphenyl-4-yl]pyrazin-2-amine;
5-[3-Fluoro-2'-(1-methyl-1 H-pyrazol-4-yl)biphenyl-4-yl]pyrazin-2-amine;
5-(3-Fluoro-2'-pyrimidin-5-ylbiphenyl-4-yl)pyrazin-2-amine;
5-[4'-(5-Aminopyrazin-2-yl)-3'-fluorobiphenyl-2-yl]pyrimidine-2-carbonitrile;
5-[3-Fluoro-2'-(2-morpholin-4-ylpyrimidin-5-yl)biphenyl-4-yl]pyrazin-2-amine;
1-{4-[4'-(5-Aminopyrazin-2-yl)-3'-fluorobiphenyl-2-yl]-1 H-pyrazol-l-yl}-2-methylpropan-2-ol;
5-[3-Fluoro-2'-(1,2,3,6-tetrahydropyridin-4-yl)-4'-(trifluoromethyl)biphenyl-4-yl]pyrazin-2-amine;
5-[4'-(5-Aminopyrazin-2-yl)-3'-fluoro-4-(trifluoromethyl)biphenyl-2-yl]pyrimidin-2-amine;
5-{2-[6-(2-Aminopyrimidin-5-yl)-5-fluoropyridin-3-yl]phenyl}pyrimidin-2-amine;
5-{5-[2-(2-Aminopyrimidin-5-yl)phenyl]pyridin-2-yl}pyrimidin-2-amine;
5-[2'41,1-Dioxidoisothiazolidin-2-yl)-3-fluorobiphenyl-4-yl]pyrazin-2-amine;
5-[2'41,1-Dioxido-1,2-thiazinan-2-yl)-3-fluorobiphenyl-4-yl]pyrazin-2-amine;
5-[2'41,1-Dioxidoisothiazolidin-2-yl)-3-fluorobiphenyl-4-yl]pyrimidin-2-amine;
5-[2-Fluoro-4-(2-pyrrolidin-1-ylpyridin-3-yl)phenyl]pyrazin-2-amine;
1-[4'-(5-Aminopyrazin-2-yl)-3'-fluorobiphenyl-2-yl]pyrrolidin-2-one;
(2S)-2-({344-(2-Aminopyrimidin-5-yl)-3-fluorophenyl]pyridin-2-ylloxy)propan-1-ol;
(3S)-1-{[4'-(2-Aminopyrimidin-5-yl)-3'-fluorobiphenyl-2-yl]sulfonyl}pyrrolidine-3-carboxamide;
(3R)-1-{[4'-(2-Aminopyrimidin-5-yl)-3'-fluorobiphenyl-2-yl]sulfonyl}pyrrolidine-3-carboxamide;
5-{3-Fluoro-2'-[(1 S,4S)-2-oxa-5-azabicyclo[2.2.1]hept-5-ylsulfonyl]biphenyl-4-yl}pyrazin-2-amine;
4'-(6-Amino-5-fluoropyridin-3-yl)-3'-fluoro-N-[(1S,2S)-2-hydroxy-1-methyl-2-phenylethyl]-N-methylbiphenyl-2-sulfonamide;
4'-(6-Aminopyridin-3-yl)-3'-fluoro-N-[(1S,2S)-2-hydroxy-1-methyl-2-phenylethyl]-N-methylbiphenyl-2-sulfonamide;
4'-(6-Aminopyridazin-3-yl)-3'-fluorobiphenyl-2-sulfonamide;
4'-(5-Aminopyrazin-2-yl)-N-tert-butyl-3'-fluoro-5-(trifluoromethyl)biphenyl-2-sulfonamide;
N4'-(2-Aminopyrimidin-5-yl)-3'-fluorobiphenyl-2-yl]methanesulfonamide;
4'-(5-Aminopyrazin-2-yl)-N-tert-butyl-3'-fluoro-5-methoxybiphenyl-2-sulfonamide;
(3S)-1-{[4'-(2-Aminopyrimidin-5-yl)-3'-fluorobiphenyl-2-yl]sulfonyl}pyrrolidine-3-carboxamide;
(3R)-1-{[4'-(2-Aminopyrimidin-5-yl)-3'-fluorobiphenyl-2-yl]sulfonyl}pyrrolidine-3-carboxamide;
5-[3-Fluoro-2'-(morpholin-4-ylcarbonyl)biphenyl-4-yl]pyrazin-2-amine;
5-{2'-[(Cyclopropylmethyl)sulfonyl]-3-fluorobiphenyl-4-yllpyrazin-2-amine;
1-{[4'-(2-Am inopyrimidin-5-yl)-3'-fluorobiphenyl-2-yl]sulfonyl}-4-(pentafluoroethyl)piperidin-4-ol;
4'-(5-Aminopyrazin-2-yl)-N-tert-butyl-3'-fluoro-4-(trifluoromethyl)biphenyl-2-sulfonamide;
4'-(5-Aminopyrazin-2-yl)-N-tert-butyl-3'-fluoro-4-(trifluoromethyl)biphenyl-2-sulfonamide;
4'-(5-Aminopyrazin-2-yl)-N-tert-butyl-3',4-difluorobiphenyl-2-sulfonamide;
2-[3-Fluoro-2'-(methylsulfanyl)biphenyl-4-yl]-5H-pyrrolo[2,3-b]pyrazine;
N,N-Diethyl-3'-fluoro-4'-(1H-pyrrolo[2,3-b]pyridin-5-yl)biphenyl-2-sulfonamide;
4'-(5-Aminopyrazin-2-yl)-N-tert-butyl-3, 3'-difluorobiphenyl-2-sulfonamide;
5-2'-Amino-3-fluoro-4'-(trifluoromethyl)biphenyl-4-yl]pyrazin-2-amine;
5-{2'-[(1,1-Dioxidotetrahydro-2H-thiopyran-4-yl)methoxy]-3-fluorobiphenyl-4-yl}pyrazin-2-amine;
5-{2'-[(1,1-Dioxidotetrahydro-2H-thiopyran-4-yl)oxy]-3-fluorobiphenyl-4-yl}pyrazin-2-amine;
4-({[4'-(5-Aminopyrazin-2-yl)-3'-fluorobiphenyl-2-yl]oxylmethyl)benzoic acid;
4-({[4'-(2-Aminopyrimidin-5-yl)-3'-fluorobiphenyl-2-yl]oxylmethyl)benzoic acid;
4-{[4'-(5-Aminopyrazin-2-yl)-3'-fluorobiphenyl-2-yl]oxy}benzoic acid;
4-{[4'-(2-Aminopyrimidin-5-yl)-3'-fluorobiphenyl-2-yl]oxy}benzoic acid;
2-[4-({3-[4-(5-Aminopyrazin-2-yl)-3-fluorophenyl]pyridin-2-yl}sulfonyl)piperidin-1-yl]ethanol;
4-[4'-(5-Aminopyrazin-2-yl)-3'-fluorobiphenyl-2-yl]pyrimidin-2-amine;
1-[4{3-[4-(5-Aminopyrazin-2-yl)-3-fluorophenyl]pyridin-2-yl}sulfonyl)pipendin-1-yl]propan-2-ol;
5-[3-Fluoro-2'-(1 H-pyrazol-4-yl)biphenyl-4-yl]pyrazin-2-amine;
5-[2'-(6-Aminopyridin-3-yl)-3-fluorobiphenyl-4-yl]pyrazin-2-amine;
5-{3-Fluoro-2'41-(2-methoxyethyl)-1 H-pyrazol-4-yl]biphenyl-4-yl}pyrazin-2-amine;
5-{5-[2-(Cyclopropylsulfonyl)phenyl]-3-fluoropyridin-2-yl}pyrimidin-2-amine;
4-{[4'-(2-Aminopyrimidin-5-yl)-3'-fluorobiphenyl-2-yl]oxylbenzamide;
5-{2'-[(trans-4-Aminocyclohexyl)oxy]-3-fluorobiphenyl-4-yl}pyrazin-2-amine;
5-{2-Fluoro-4-[2-(phenylsulfonyl)pyridin-3-yl]phenyl}pyrazin-2-amine;
6-[4'-(5-Aminopyrazin-2-yl)-3'-fluorobiphenyl-2-yl]pyridazin-3-amine;
{4-[4'-(5-Aminopyrazin-2-yl)-3'-fluorobiphenyl-2-yl]-1H-pyrazol-1-yl}acetonitrile;
5-[4'-(5-Aminopyrazin-2-yl)-3'-fluorobiphenyl-2-yl]-N-methylpyrimidin-2-amine;
2-[6-(2-Aminopyrimidin-5-yl)-5-fluoropyridin-3-yl]-N-[(1S)-2,2,2-trifluoro-1-methylethyl]benzenesulfonamide;
5-{2-Fluoro-4-[2-(phenylsulfonyl)pyridin-3-yl]phenyl}pyrimidin-2-amine;
5-[3-Fluoro-2'-(2-piperazin-1-ylpyrimidin-5-yl)biphenyl-4-yl]pyrazin-2-amine;
5-{2'-[1-(2-Aminoethyl)-1H-pyrazol-4-yl]-3-fluorobiphenyl-4-yl}pyrazin-2-amine;
2-[6-(2-Aminopyrimidin-5-yl)-5-fluoropyridin-3-yl]-N-[(2S)-2-hydroxypropyl]benzenesulfonamide;
5-(3-Fluoro-2'-isothiazol-4-ylbiphenyl-4-yl)pyrazin-2-amine;
5-[2-Fluoro-4-(2-phenoxypyridin-3-yl)phenyl]pyrazin-2-amine;
5-[2-Fluoro-4-(2-phenoxypyridin-3-yl)phenyl]pyrimidin-2-amine;
2-{4-[4'-(5-Aminopyrazin-2-yl)-3'-fluorobiphenyl-2-yl]-1H-pyrazol-1-yl}ethanol;

5-(4-{2-[(1-Acetylpipendin-3-yl)sulfonyl]pyridin-3-yl]-2-fluorophenyl)pyrazin-2-amine;
5-(4-{2-[(1-Acetylpipendin-4-yl)sulfonyl]-6-(trifluoromethyl)pyridin-3-yl]-2-fluorophenyl)pyrazin-2-amine;
2-[6-(2-Aminopyrimidin-5-yl)-5-fluoropyridin-3-yl]-N-[(1S)-2-hydroxy-1-methylethyl]benzenesulfonamide;
2-[6-(2-Aminopyrimidin-5-yl)-5-fluoropyridin-3-yl]-N-[(1R)-2-hydroxy-1-methylethyl]benzenesulfonamide;
5-[2-Fluoro-4-(2-phenyl]pyridin-3-yl)phenyl]pyrazin-2-amine;
5-(2-Fluoro-4-{2-[(1-methylpyrrolidin-3-yl)sulfonyl]pyridin-3-yl}phenyl)pyrazin-2-amine;
5-{2-Fluoro-4-[2-(pyridin-3-ylsulfonyl)pyridin-3-yl]phenyl}pyrazin-2-amine;
5-(2-Fluoro-4-{2-[(1-methylethyl)sulfonyl]-6-(trifluoromethyl)pyridin-3-yl}phenyl)pyrazin-2-amine;
5-(4-{2-[(1-Acetylpiperidin-4-yl)sulfonyl]-6-(trifluoromethyl)pyridin-3-01-2-fluorophenyl)pyrimidin-2-amine;
5-[2'-(6-Aminopyridin-3-yl)-3-fluorobiphenyl-4-yl]pyrimidin-2-amine;
5-[4'-(2-Aminopyrimidin-5-yl)-3'-fluorobiphenyl-2-yl]-N-methylpyrimidin-2-amine;
5-(2-Fluoro-4-{2-[(1-methylethyl)sulfonyl]-6-(trifluoromethyl)pyridin-3-yl}phenyl)pyrimidin-2-amine;
{4-[4'-(2-Aminopyrimidin-5-yl)-3'-fluorobiphenyl-2-yl]-1H-pyrazol-1-yl}acetonitrile;
5-[3-Fluoro-2'-(1H-pyrazol-4-yl)biphenyl-4-yl]pyrimidin-2-amine;
4-[4'-(2-Aminopyrimidin-5-yl)-3'-fluorobiphenyl-2-yl]pyrim din-2-amine;
5-{2-Fluoro-4-[2-(pyridin-3-yloxy)pyridin-3-yl]phenyl}pyrazin-2-amine;
5-(4-{2-[(1,1-Dioxidotetrahydro-2H-thiopyran-4-yl)sulfonyl]-6-(trifluoromethyl)pyridin-3-01-2-fluorophenyl)pyrimidin-2-amine;
5-[2-Fluoro-4-(2-{[1-(methylsulfonyl)piperidin-4-yl]sulfonyl}pyridin-3-yl)phenyl]pyrazin-2-amine;
5-(4-{2-[(1,1-Dioxidotetrahydro-2H-thiopyran-4-yl)sulfonyl]-6-(trifluoromethyl)pyridin-3-01-2-fluorophenyl)pyrazin-2-amine;
5-{2-Fluoro-4-[2-(tetrahydro-2H-pyran-4-ylsulfonyl)-6-(trifluoromethyl)pyridin-3-yl]phenyl}pyrazin-2-amine;
5-{2-Fluoro-4-2-(tetrahydro-2H-pyran-4-ylsulfonyl)-6-(trifluoromethyl)pyridin-3-yl]phenyl}pyrimidin-2-amine;
2-[6-(2-Aminopyrimidin-5-yl)-5-fluoropyridin-3-yl]-N-(2-hydroxyethyl)benzenesulfonamide;
2-[6-(2-Aminopyrimidin-5-yl)-5-fluoropyridin-3-yl]-N-[(1R)-2,2,2-trifluoro-1-methylethyl]benzenesulfonamide; and
5-[2-Fluoro-4-(2-{[1-(methylsulfonyl)piperidin-4-yl]sulfonyl]pyridin-3-yl)phenyl]pyrimidin-2-amine;

and pharmaceutically acceptable salts thereof.

8. The pharmaceutical composition of claim 5 comprising at least one compound of claim 7.

9. A method of treating a subject suffering from or diagnosed with a disease, disorder, or medical condition medicated by FLAP activity, comprising administering to the subject a therapeutically effective amount of at least one compound of claim 1.

10. The method according to claim 9, wherein the disease, disorder, or medical condition is selected from the group consisting of respiratory disorders, cardiac and cardiovascular diseases, autoimmune and allergic disorders, and carcinogenesis disorders.

11. The method according to claim 10, wherein respiratory disorder is selected from the group consisting of non-allergic asthma, fibrotic lung diseases, acute respiratory distress syndrome and chronic obstructive pulmonary disease.

12. The method according to claim 10, wherein the cardiac and cardiovascular disease is selected from the group consisting of myocardial infarction, atherosclerosis and stroke aortic aneurisms, and atherosclerosis.

13. The method according to claim 10, wherein the autoimmune and allergic disease is selected from the group consisting of rheumatoid arthritis, inflammatory bowel disease, nephritis, spondyloarthritis, polymyositis, dermatomyositis, gouty effusions, systemic lupus erythematosus, systemic sclerosis, Alzheimer's disease, multiple sclerosis, allergic rhinitis, allergic dermatitis and asthma.

14. The method according to claim 10, wherein the carcinogenesis disorder is selected from the group consisting of tumor cell proliferation, tumor cell differentiation, apoptosis, tumor-associated angiogenesis, and the migration or invasion of carcinoma cells.

15. The method of claim 9, wherein the therapeutically effective amount of the compound of Formula (I) is from about 0.1 mg/dose to about 5 g/dose.

16. A process for making a pharmaceutical composition comprising admixing any of the compounds according to claim 1 and a pharmaceutically acceptable carrier.

* * * * *